(12) United States Patent
Yang et al.

(10) Patent No.: US 12,226,424 B2
(45) Date of Patent: Feb. 18, 2025

(54) TARGET PROTEIN DEGRADATION COMPOUNDS, THEIR ANTI-TUMOR USE, THEIR INTERMEDIATES AND USE OF INTERMEDIATES

(71) Applicant: ShanghaiTech University, Shanghai (CN)

(72) Inventors: Xiaobao Yang, Shanghai (CN); Biao Jiang, Shanghai (CN); Renhong Sun, Shanghai (CN); Chaowei Ren, Shanghai (CN); Ning Sun, Shanghai (CN); Ying Kong, Shanghai (CN); Yan Li, Shanghai (CN); Jinju Chen, Shanghai (CN); Qianqian Yin, Shanghai (CN); Xiaoling Song, Shanghai (CN); Quanju Zhao, Shanghai (CN); Xing Qiu, Shanghai (CN)

(73) Assignee: ShanghaiTech University, Shanghai (CN)

( * ) Notice: Subject to any disclaimer, the term of this patent is extended or adjusted under 35 U.S.C. 154(b) by 556 days.

(21) Appl. No.: 17/046,690

(22) PCT Filed: Apr. 9, 2019

(86) PCT No.: PCT/CN2019/081840
§ 371 (c)(1),
(2) Date: Oct. 9, 2020

(87) PCT Pub. No.: WO2019/196812
PCT Pub. Date: Oct. 17, 2019

(65) Prior Publication Data
US 2022/0117982 A1    Apr. 21, 2022

(30) Foreign Application Priority Data

Apr. 9, 2018 (CN) .......................... 201810312040.8

(51) Int. Cl.
*A61K 31/675* (2006.01)
*A61K 31/138* (2006.01)
(Continued)

(52) U.S. Cl.
CPC .......... *A61K 31/675* (2013.01); *A61K 31/138* (2013.01); *A61K 31/454* (2013.01);
(Continued)

(58) Field of Classification Search
CPC .. A61K 31/675; A61K 31/138; A61K 31/454; A61K 31/496; A61K 31/5025;
(Continued)

(56) References Cited

U.S. PATENT DOCUMENTS

2018/0099940 A1* 4/2018 Crew .................. C07D 211/76

FOREIGN PATENT DOCUMENTS

CA     3038979 A1    4/2018
CA     3047784 A1    6/2018
(Continued)

OTHER PUBLICATIONS

STN transcript excerpt for US 2018/0099940 A1 (Year: 2022).*
(Continued)

*Primary Examiner* — Jeffrey H Murray
(74) *Attorney, Agent, or Firm* — Osha Bergman Watanabe & Burton LLP

(57) ABSTRACT

The present disclosure relates to compounds of formula (I) and their anti-tumor uses, and their intermediates of formula (III), intermediates of formula (IV), and uses of the intermediates. The compound of formula (I) has a degrading effect on a specific target protein, which is mainly composed of three parts. The first part is a small molecule compound (SMBP, Small Molecules Binding Protein) that can bind to a protein, the second part LIN is a linker, and the three-part ULM is a ubiquitin ligand (ULM, Ubiquitin Ligase Binding Moiety), wherein SMBP is covalently bound to LIN, and LIN is covalently bound to ULM. A series of compounds designed and synthesized in the present disclosure have a wide range of pharmacological activities, including the functions of degrading specific proteins and/or inhibiting activities of specific proteins, and thus can be used in related tumor treatments.

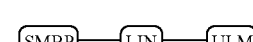

Formula (I)

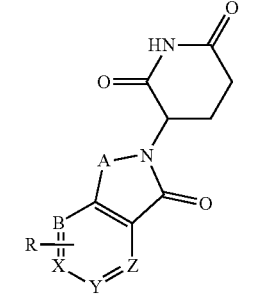

Formula (III)

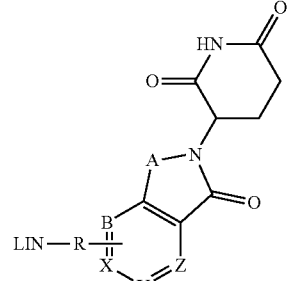

Formula (IV)

17 Claims, 4 Drawing Sheets

(51) Int. Cl.
    *A61K 31/454* (2006.01)
    *A61K 31/496* (2006.01)
    *A61K 31/5025* (2006.01)
    *A61K 31/506* (2006.01)
    *A61K 31/519* (2006.01)
    *A61K 31/5517* (2006.01)
    *A61K 45/06* (2006.01)
    *A61K 47/54* (2017.01)
    *A61K 47/60* (2017.01)
    *A61P 35/00* (2006.01)

(52) U.S. Cl.
    CPC ........ *A61K 31/496* (2013.01); *A61K 31/5025* (2013.01); *A61K 31/506* (2013.01); *A61K 31/519* (2013.01); *A61K 31/5517* (2013.01); *A61K 45/06* (2013.01); *A61K 47/545* (2017.08); *A61K 47/60* (2017.08); *A61P 35/00* (2018.01)

(58) Field of Classification Search
    CPC ................ A61K 31/506; A61K 31/519; A61K 31/5517; A61K 45/06; A61K 47/545; A61K 47/60; A61K 31/55; A61K 31/551; C07D 237/32; C07D 401/04; C07D 401/14; C07D 405/14; C07D 417/14; C07D 471/04; C07D 487/04; C07D 487/06; C07D 495/14; A61P 35/00; A61P 35/02
    USPC ........................................................ 514/299
    See application file for complete search history.

(56) References Cited

FOREIGN PATENT DOCUMENTS

| | | | |
|---|---|---|---|
| CN | 103396397 A | 11/2013 | |
| CN | 103787802 A | 5/2014 | |
| CN | 106458993 A | 2/2017 | |
| CN | 110506039 A | 11/2019 | |
| JP | H02-184659 A | 7/1990 | |
| JP | 2006-519827 A | 8/2006 | |
| JP | 2008-513538 A | 5/2008 | |
| JP | 2010-515715 A | 5/2010 | |
| JP | 2010-535798 A | 11/2010 | |
| JP | 2011-523646 A | 8/2011 | |
| JP | 2013-534221 A | 9/2013 | |
| JP | 2013-539765 A | 10/2013 | |
| JP | 2017513862 A | 6/2017 | |
| WO | WO2008115516 * | 9/2008 | ........... C07D 403/04 |
| WO | 2009/008371 A1 | 1/2009 | |
| WO | 2010/143664 A1 | 12/2010 | |
| WO | 2016197032 A1 | 12/2016 | |
| WO | 2017079267 A1 | 5/2017 | |
| WO | 2017/176957 A1 | 10/2017 | |
| WO | 2017/185031 A1 | 10/2017 | |
| WO | WO-2017176958 A1 * | 10/2017 | ............. A61P 35/00 |
| WO | 2017/197056 A1 | 11/2017 | |
| WO | 2017197051 A1 | 11/2017 | |
| WO | 2018/052945 A1 | 3/2018 | |
| WO | 2018052949 A1 | 3/2018 | |
| WO | 2018071606 A1 | 4/2018 | |
| WO | 2018/102067 A2 | 6/2018 | |
| WO | 2018/102725 A1 | 6/2018 | |
| WO | 2018/119448 A1 | 6/2018 | |
| WO | 2018119441 A1 | 6/2018 | |
| WO | 2018/140809 A1 | 8/2018 | |
| WO | 2019/133531 A1 | 7/2019 | |
| WO | 2019195609 A2 | 10/2019 | |
| WO | 2020173426 A1 | 9/2020 | |

OTHER PUBLICATIONS

Turk, et al., Proceedings of the National Academy of Sciences of the United States of America (1996), 93(15), 7552-7556. (Year: 1996).*
Lai, et al., "Modular PROTAC Design for the Degradation of Oncogenic BCR-ABL," Angewandte Chemie, International Edition ,2016 , 55(2), 807-810, 4 pages.
Zhang, et al., "Proteolysis Targeting Chimeras (PROTACS) of Anaplastic Lymphoma Kinase (ALK)," European Journal of Medicinal Chemistry, 2018, 151, 304 to 314, 36 Pages.
Shoey et al., "Translation Termination Factor GSPT1 Is a Phenotypically Relevant Off / Target of Heterobifunctional Phthalimide Degraders," ACS Chemical Biology, 2018, 13 (3), 553 to 560, 22 pages.
Office Action Issued in Corresponding Japanese Application No. 2020-555408, dated Mar. 25, 2022, 19 pages.
Extended European Search Report issued in corresponding EP Application No. 19786024.0 dated Nov. 23, 2021 (9 pages).
Examination Report issued in corresponding AU Application No. 2019251151 dated Sep. 15, 2021 (6 pages).
Office Action issued in corresponding CA Application No. 3,096,790 dated Dec. 3, 2021 (8 pages).
Office Action issued in corresponding CN Application No. 201910279248.9 with English translation dated Mar. 12, 2021 (15 pages).
Li, Yiming et al. "A Highly Efficient Cu-Catalyzed S-Transfer Reaction: From Amine to Sulfide" Organic Letters, vol. 16. No. 10. May 6, 2014 (May 6, 2014). pp. 2692-2695. and p. 2694. table 4 (4 pages).
International Search Report issued in International Application No. PCT/CN2019/081840 dated Jul. 9, 2019 (4 pages).
Written Opinion issued in International Application No. PCT/CN2019/081840 dated Jul. 9, 2019 (8 pages).

* cited by examiner

SIAIS151072

TARGET PROTEIN DEGRADATION COMPOUNDS, THEIR ANTI-TUMOR USE, THEIR INTERMEDIATES AND USE OF INTERMEDIATES

CROSS REFERENCE TO A RELATED APPLICATION

This application is a National Phase Patent Application of International Patent Application Number PCT/CN2019/081840, filed on Apr. 9, 2019, which claims priority of CN Patent Application Number 201810312040.8, filed on Apr. 9, 2018.

TECHNICAL FIELD

The present disclosure relates to target protein degradation compounds, their anti-tumor uses, their intermediates and use of the intermediates.

BACKGROUND

PROTAD (Proteolysis targeting drug) is a ternary complex, in which the first part is small molecule which can bind to specifical protein of interest; the second part is linker with different length; and the third part is E3 ligase ligand with ubiquitination function. The designed PROTAD small molecule compounds can target specific proteins and recruit E3 ubiquitination ligase through the E3 ligase ligand, so that the target protein is connected to the E3 ubiquitination ligase through the PROTAD small molecule, and ubiquitinated by the E3 ligase, thereby being degraded under the action of the proteasome.

The ligands of E3 Cereblon (CRBN)/Cullin4A ligase have a phthalimide skeleton, namely thalidomide and its analogs pomalidomide and lenalidomide. However, the currently published E3 CRBN ligands use thalidomide, pomalidomide and lenalidomide to covalently bond with the linking unit through carbon-nitrogen bonds. So far, there have been no reports and related studies that thalidomide, pomalidomide and lenalidomide are covalently bonded to the linking unit through carbon-sulfur bonds. Therefore, it is of great significance to design different heteroatom E3 ubiquitinated ligase ligands to study its ability to bind to the receptor and its strength of action, and then design a new sulfur-containing E3 ligase ligand and apply it to PROTAD small molecule drugs.

Based on the above reasons, we proposed and designed a new sulfur-containing E3 ligase ligand and applied it to the design of PROTAD small molecule drugs.

SUMMARY

In one aspect, the present disclosure provides a compound of formula (I):

Formula (I)

or salts, enantiomers, stereoisomers, solvates, or polymorphs thereof, wherein SMBP, LIN, ULM and all substituents are as defined in the detailed description of the invention.

The present disclosure also provides a pharmaceutical composition comprising the compound of formula (I) or a pharmaceutically acceptable salt thereof, and at least one pharmaceutically acceptable carrier.

The present disclosure also provides a compound of formula (I), or a pharmaceutically acceptable salt thereof for use as a medicament:

Formula (I)

The present disclosure also provides the compound of formula (I), or a pharmaceutically acceptable salt thereof for use in the prevention and/or treatment of a cancer.

The present disclosure further provides the use of the compound of formula (I), or a pharmaceutically acceptable salt thereof for preparing a medicament for preventing and/or treating a cancer.

The present disclosure also provides a method for treating or preventing a cancer, comprising administering to a subject in need a therapeutically effective amount of the compound of formula (I), or a pharmaceutically acceptable salt thereof, or the pharmaceutical composition according to the present invention.

In another aspect, the present disclosure provides a compound of formula (III):

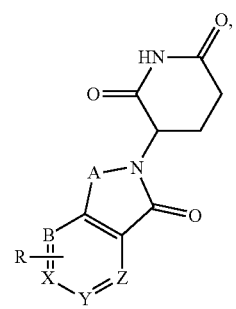

Formula (III)

or salts, enantiomers, stereoisomers, solvates, or polymorphs thereof, wherein A, B, X, Y, Z and substituent R are as defined in the detailed description of the invention.

In another aspect, the present disclosure provides a compound of formula (IV):

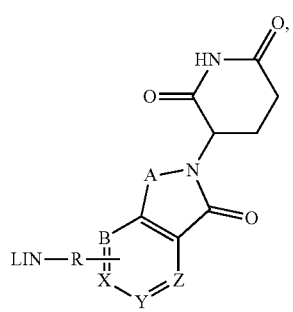

Formula (IV)

or salts, enantiomers, stereoisomers, solvates, or polymorphs thereof, wherein A, B, X, Y, Z, R, LIN and all substituents are as defined in the detailed description of the invention.

The present disclosure further provides the use of the compound of formula (III) or a salt, enantiomer, stereoisomer, solvate, or polymorph thereof for preparing the compound of formula (I) as described above.

The present disclosure further provides the use of the compound of formula (IV) or a salt, enantiomer, stereoisomer, solvate, or polymorph thereof for preparing the compound of formula (I) as described above.

The present disclosure further provides the compound of formula (IV), or a pharmaceutically acceptable salt thereof for use as a medicament.

The present disclosure further provides the compound of formula (IV), or a pharmaceutically acceptable salt thereof, for use in the prevention and/or treatment of a cancer.

The present disclosure further provides the use of the compound of formula (IV) or a pharmaceutically acceptable salt thereof for preparing a medicament for preventing and/or treating a cancer.

The present disclosure further provides a method for treating or preventing a cancer, comprising administering to a subject in need a therapeutically effective amount of the compound of formula (IV), or a pharmaceutically acceptable salt thereof, or the pharmaceutical composition.

DETAILED DESCRIPTION

Figure 1:
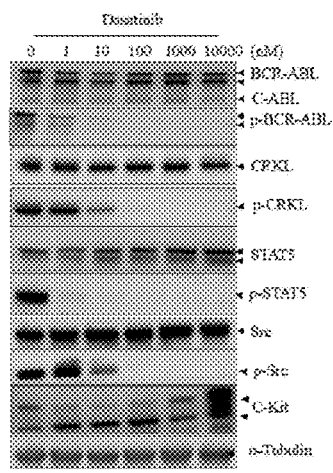
FIGS. 1-14 show the Western-blot detection of the series of PROTAD compounds according to the present disclosure prepared from the newly designed E3 ligase ligand according to the present disclosure. As compared to the commercial parent inhibitors Dasatinib and Bosutinib, the PROTAD compounds according to the present disclosure can effectively degrade BCR-ABL and c-ABL proteins.
Figure 2:
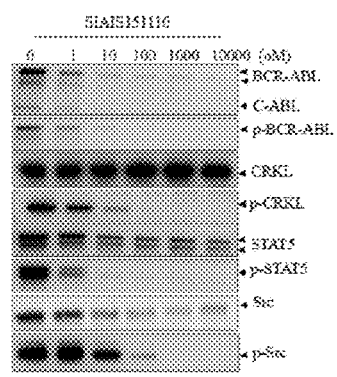
Figure 3:
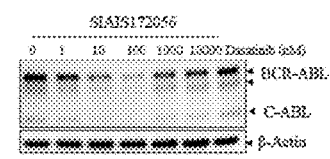
Figure 4:
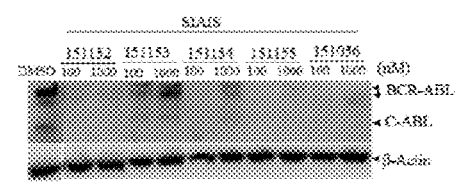
Figure 5:
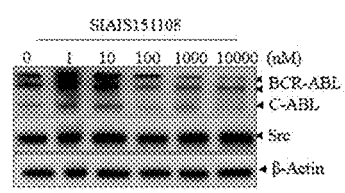
Figure 6:
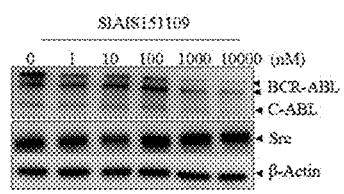
Figure 7:
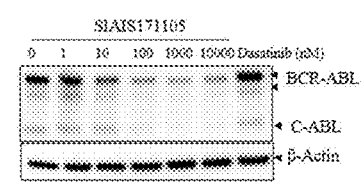
Figure 8:
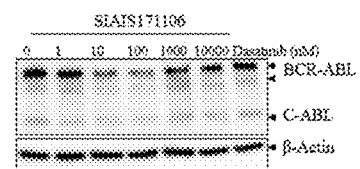
Figure 9:
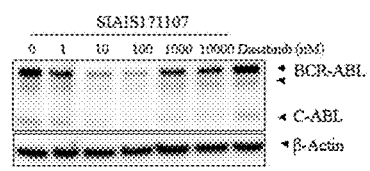
Figure 10:
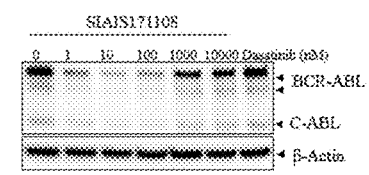
Figure 11:
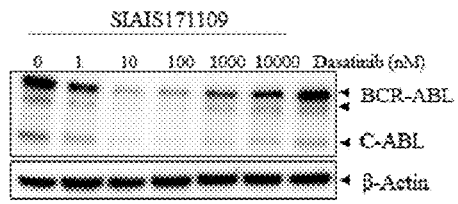
Figure 13:
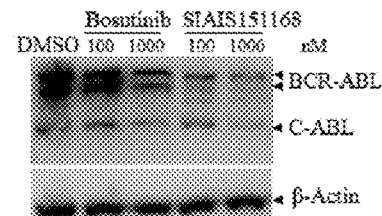
Figure 12:
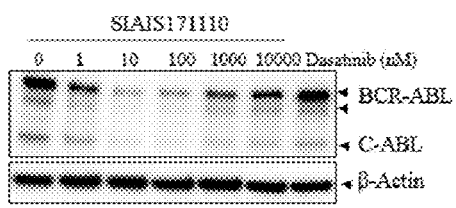
Figure 14:
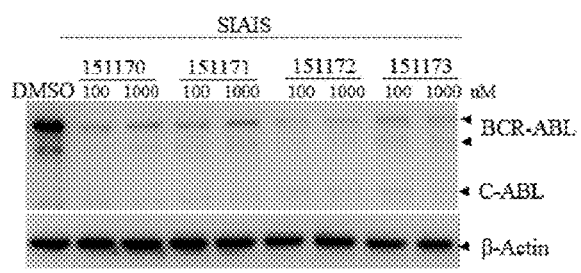

Therefore, in one aspect, the present disclosure provides a compound of formula (I):

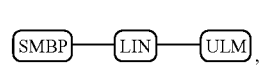

Formula (I)

wherein SMBP is covalently bonded to ULM through a linking group LIN;

wherein SMBP represents a small molecule compound or its derivative capable of binding protein; LIN-ULM represents the chemical structure of the following formula (II):

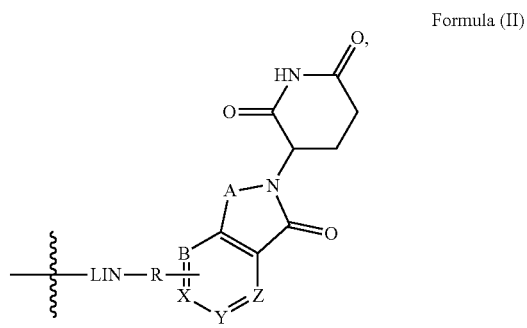

Formula (II)

wherein,
A represents $CH_2$ or CO, B, X, Y, and Z are the same or different and each independently represent CH or N, and R represents S, SO, $SO_2$ or piperazinylene; and LIN is a linking group and represents —U-alkylene-, wherein
the alkylene group is a linear or branched alkylene group optionally interrupted one or more times by one or more groups selected from the group consisting of O, CONH, NHCO, NH, alkynylene, alkenylene, cycloalkylene, arylene, heterocyclylene, heteroarylene, or any combination thereof, wherein the linear or branched alkylene group is optionally substituted with one or more substituents, and the group U represents CO or NH, or the group U is absent;

or its salts, enantiomers, stereoisomers, solvates, polymorphs.

Herein, LIN represents —U-alkylene-, wherein one of the two ends of the —U-alkylene- (for example, the group U) can link to SMBP, and the other end (alkylene group) can bind to ULM; or one of the two ends of the —U-alkylene group (for example, the alkylene group) may link to SMBP, and the other end (the group U) can link to ULM.

In an embodiment of the present disclosure, the SMBP is a small molecule drug that targets CDK4/6, ALK, Bcr-abl, PARP, ER or BET.

In an embodiment of the present disclosure, the SMBP represents:

Rebosini, Abemaciclib, Palbociclib, Crizotinib, Ceritinib, Brigatinib, Alectinib, Ensartinib, TAE684, ASP3026, GSK1838705A, AZD3463, Imatinib, Dasatinib, Bosutinib, Ponatinib, Olaparib, Niraparib, Rucaparib, Toremifene, Tamoxifen, 4-Hydroxyltamoxifen, JQ-1, I-BET762 or their derivatives.

In an embodiment of the present disclosure, the SMBP represents a fragment of the following general formula:

(Ia) 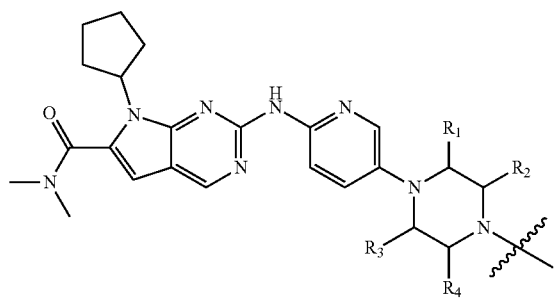,
(Ib) 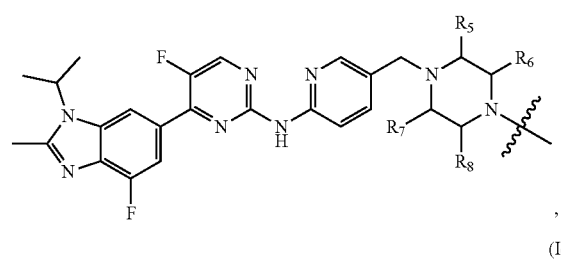,
(Ic) 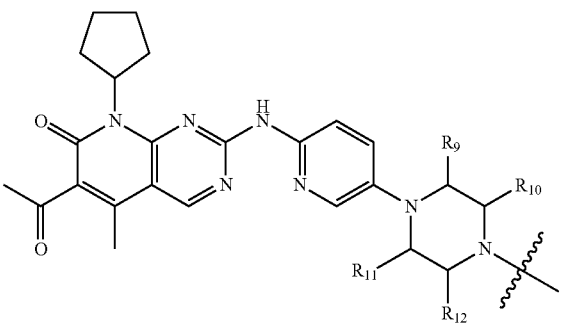,
(Id) 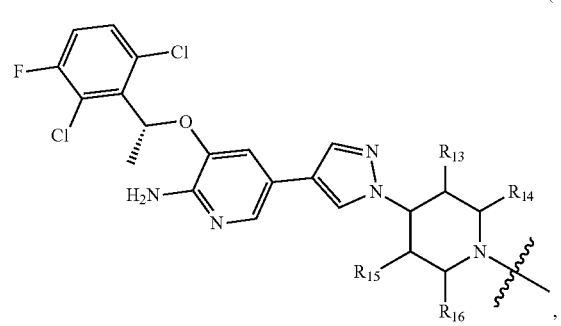,
(Ie) 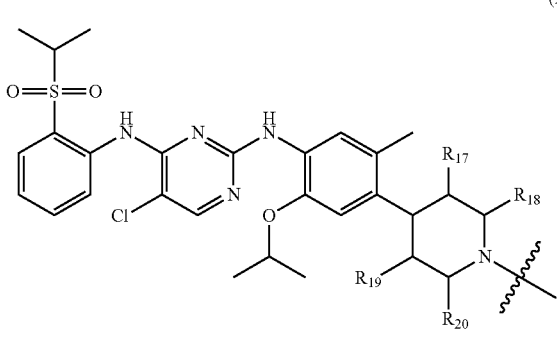,
(If) 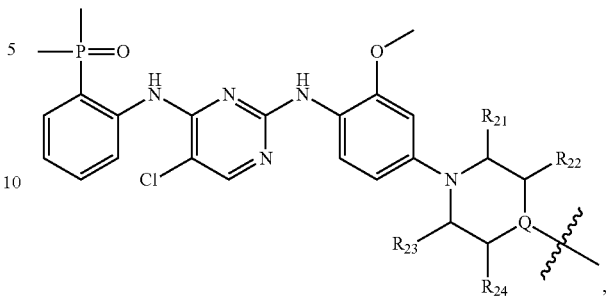,
(Ig) 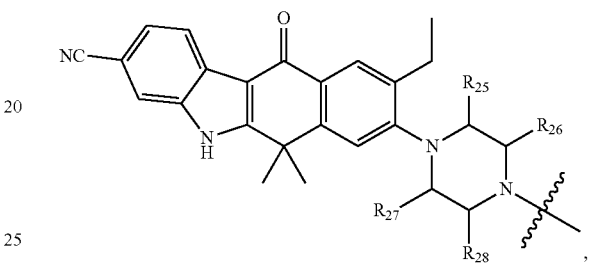,
(Ih) 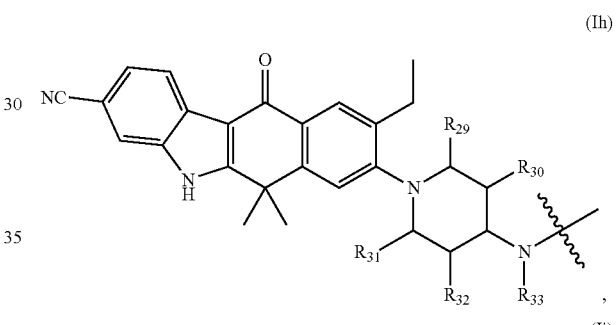,
(Ii) 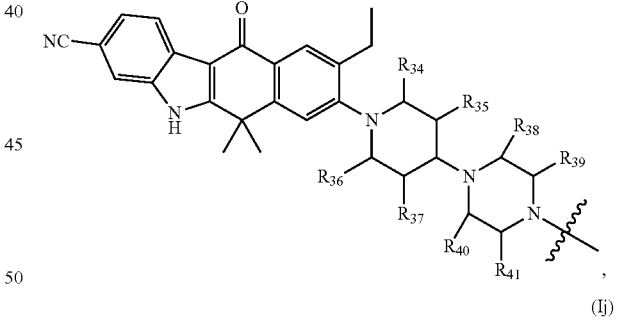,
(Ij) 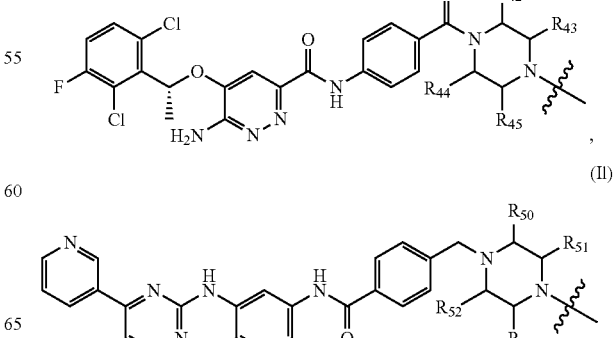,
(Il) 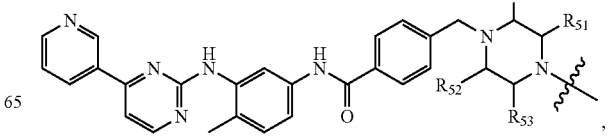, -continued
(Im)
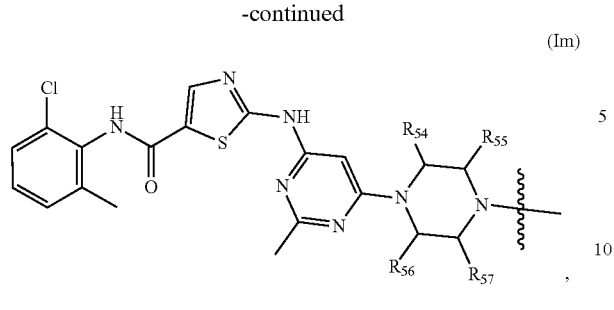
(In)
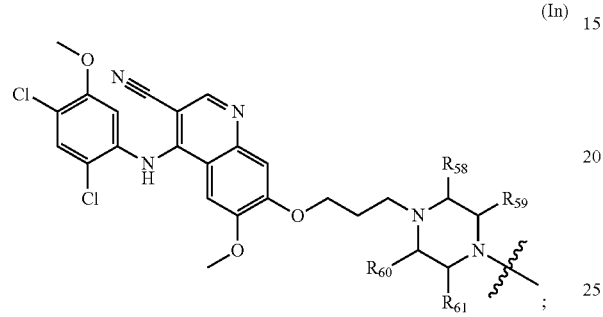
(Io)
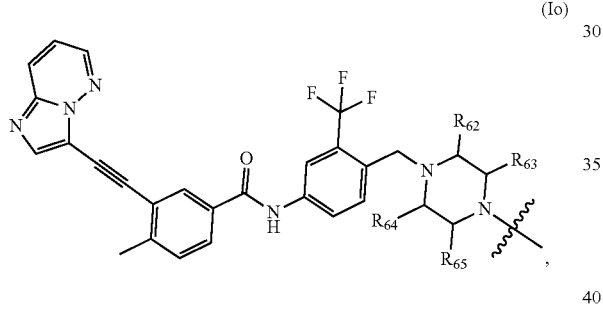
(Ip)
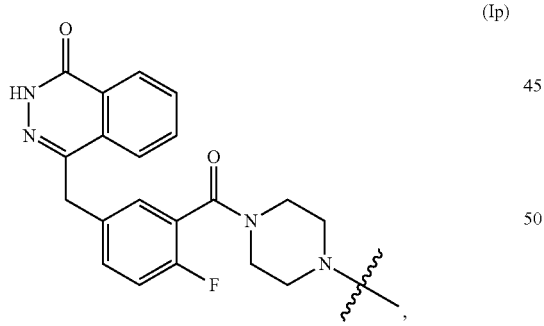
(Iq)
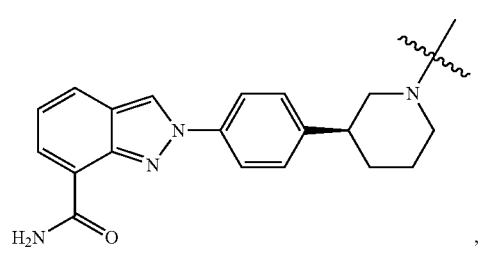
-continued
(Ir)
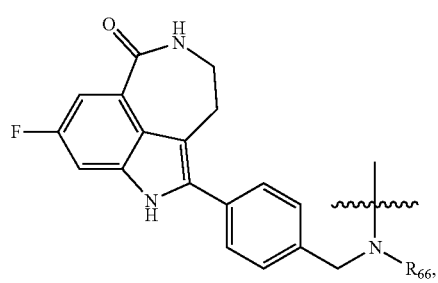
(Is)
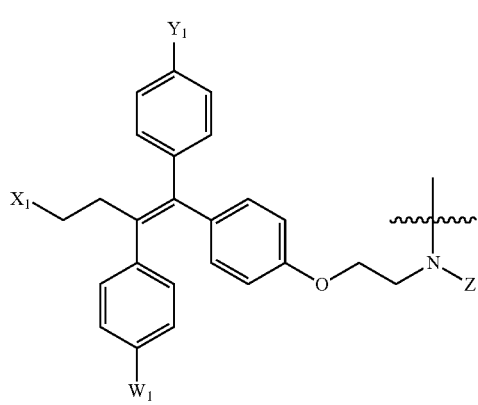
(It)
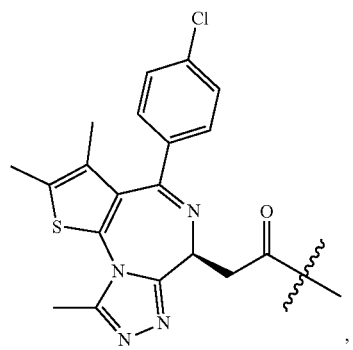
(Iu)
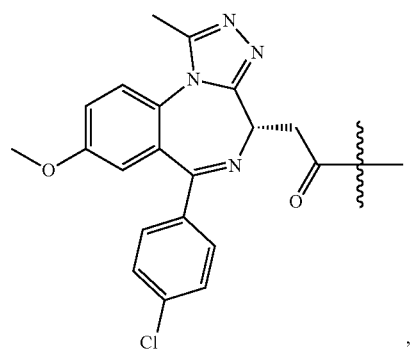

-continued (Iv)
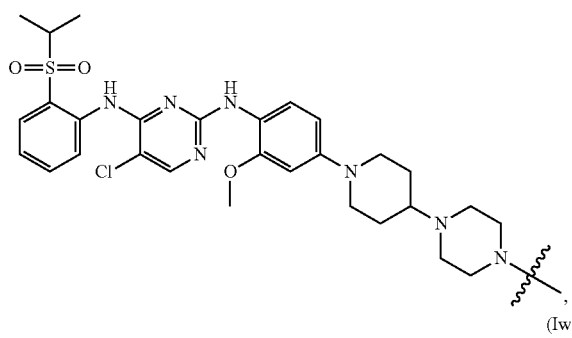

(Iw)
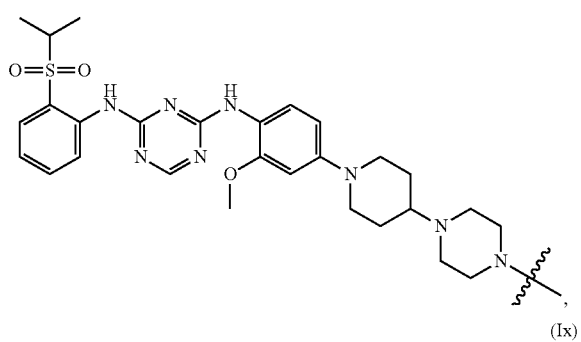

(Ix)
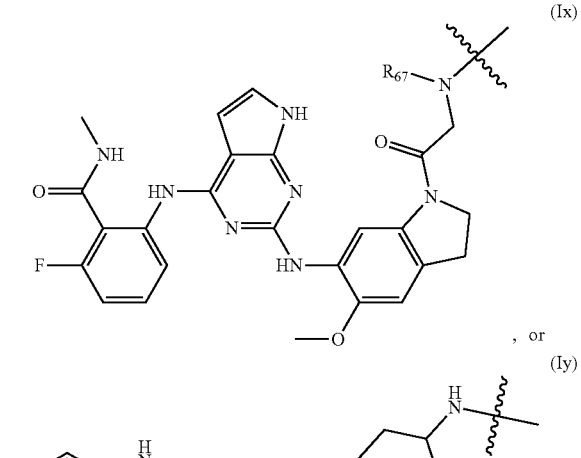

, or (Iy)
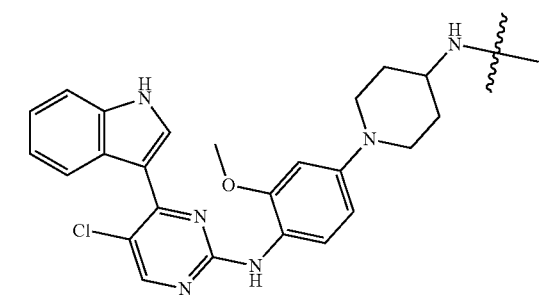

;

wherein, $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{34}$, $R_{35}$, $R_{36}$, $R_{37}$, $R_{38}$, $R_{39}$, $R_{40}$, $R_{41}$, $R_{42}$, $R_{43}$, $R_{44}$, $R_{45}$, $R_{50}$, $R_{51}$, $R_{52}$, $R_{53}$, $R_{54}$, $R_{55}$, $R_{56}$, $R_{57}$, $R_{58}$, $R_{59}$, $R_{60}$, $R_{61}$, $R_{62}$, $R_{63}$, $R_{64}$, $R_{65}$, and $R_{66}$ are each independently H or methyl, and $R_{33}$ and $R_{67}$ each independently represent H, methyl or ethyl; and wherein in formula (If), Q is N or CH, wherein CH is further linked to the group LIN through NH or piperazinylene; and wherein in formula (Is), $X_1$ is Cl or H, $Y_1$ is H or OH, $Z_1$ is H or methyl, and $W_1$ is H; or in an embodiment of the present disclosure, $X_1$ is Cl or H, $Y_1$ is H or OH, $Z_1$ is H or methyl, and $W_1$ is OH.

In an embodiment of the present disclosure, in formula (Is), $X_1$ is Cl, $Y_1$ is H, $Z_1$ is H or methyl, and $W_1$ is H. In an embodiment of the present disclosure, in formula (Is), $X_1$ is Cl, $Y_1$ is OH, $Z_1$ is H or methyl, and $W_1$ is H. In an embodiment of the present disclosure, in formula (Is), $X_1$ is H, $Y_1$ is H, $Z_1$ is H or methyl, and $W_1$ is H. In an embodiment of the present disclosure, in formula (Is), $X_1$ is H, $Y_1$ is OH, $Z_1$ is H or methyl, and $W_1$ is H. In an embodiment of the present disclosure, in formula (Is), $X_1$ is H, $Y_1$ is OH, $Z_1$ is H or methyl, and $W_1$ is OH.

In an embodiment of the present disclosure, in formula (II), A represents $CH_2$ or CO, B, X, Y, and Z are the same and all represent CH, and R represents S, SO, $SO_2$ Or piperazinylene. In a sub-embodiment of the present disclosure, in formula (II), A represents $CH_2$ or CO, B, X, Y, and Z are the same and all represent CH, and R represents S. In a sub-embodiment of the present disclosure, in formula (II), A represents $CH_2$ or CO, B, X, Y, and Z are the same and all represent CH, and R represents SO. In a sub-embodiment of the present disclosure, in formula (II), A represents $CH_2$ or CO, B, X, Y, and Z are the same and all represent CH, and R represents $SO_2$. In a sub-embodiment of the present disclosure, in formula (II), A represents $CH_2$ or CO, B, X, Y, and Z are the same and all represent CH, and R represents piperazinylene.

In an embodiment of the present disclosure, formula (II) is also the following structural formula:

Formula (II-1)
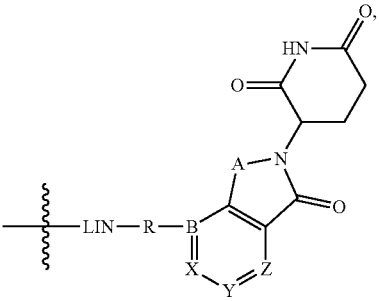

wherein the groups LIN, R, A, B, X, Y, Z are as defined above.

In an embodiment of the present disclosure, formula (II) is also the following structural formula:

Formula (II-2)
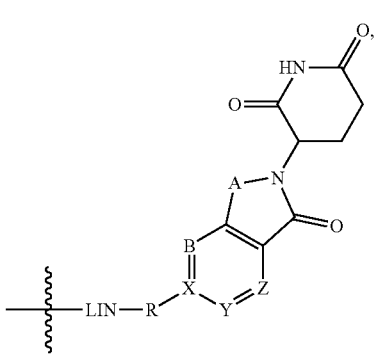

wherein the groups LIN, R, A, B, X, Y, Z are as defined above.

In an embodiment of the present disclosure, formula (II) is also the following structural formula:

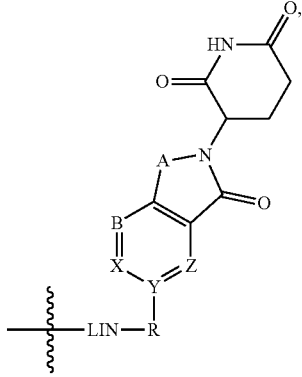

Formula (II-3)

wherein the groups LIN, R, A, B, X, Y, Z are as defined above.

In an embodiment of the present disclosure, formula (II) is also the following structural formula:

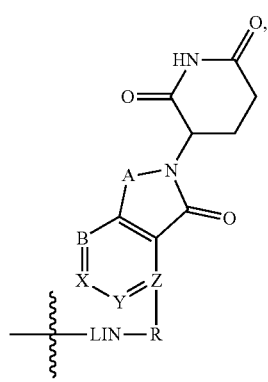

Formula (II-4)

wherein the groups LIN, R, A, B, X, Y, Z are as defined above.

In an embodiment of the present disclosure, formula (II) is also the following structural formula:

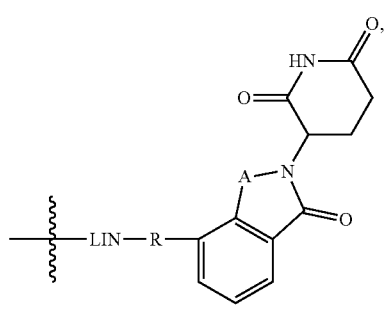

Formula (II-5)

wherein the groups LIN, R, A are as defined above.

In an embodiment of the present disclosure, the LIN represents: —U—$C_{1-30}$ alkylene-, —U—$(CH_2)_{n1}$—(O$(CH_2)_{n2})_{m1}$—, —U—$(CH_2)_{n1}$—(O$(CH_2)_{n2})_{m1}$—(O$(CH_2))_{n3})_{m2}$—, —U—$(CR_{a1}R_{a2})_{n1}$—(O$(CR_{a3}R_{a4})_{n2})_{m1}$—, —U—$(CR_{a5}R_{a6})_{n1}$—(O$(CR_{a7}R_{a8})_{n2})_{m1}$—(O$(CR_{a9}R_{a10})_{n3})_{m2}$—, —U—$(CH_2)_{n1}$—(CONH—$(CH_2)_{n2})_{m1}$—, —U—$(CH_2)_{n1}$—(CONH—$(CH_2)_{n2})_{m1}$—(O$(CH_2)_{n3})_{m2}$—, —U—$(CH_2)_{n1}$—(O$(CH_2)_{n2})_{m1}$—O—$(CH_2)_{n3}$—CONH—$(CH_2)_{n4}$—(O$(CH_2)_{n5})_{m2}$—O—$(CH_2)_{n6}$—, —U—$(CR_{a11}R_{a12})_{n1}$—(O$(CR_{a13}R_{a14})_{n2})_{m1}$—O—$(CR_{a15}R_{a16})_{n3}$—CONH—$(CR_{a17}R_{a18})_{n4}$—(O$(CR_{a19}R_{a20})_{n5})_{m2}$—O—$(CR_{a21}R_{a22})_{n6}$—, —U—$(CR_{a23}R_{a24})_{n1}$—CONH—(O$(CR_{a25}R_{a26})_{n2})_{m1}$—, —U—$(CH_2)_{n1}$—(NHCO—$(CH_2)_{n2})_{m1}$—, —U—$(CH_2)_{n1}$—(NHCO—$(CH_2)_{n2})_{m1}$—(O$(CH_2)_{n3})_{m2}$—, a straight or branched —U-alkylene-interrupted one or more times by one or more of alkynylene, alkenylene, cycloalkylene, arylene, heterocyclylene or heteroarylene or any combination thereof, or —U—$(CH_2)_{n1}$—(O$(CH_2)_{n2})_{m1}$— whose backbone carbon chain is interrupted one or more times by one or more of arylene or heterocyclylene or heteroarylene or any combination thereof;

$R_{a1}$, $R_{a2}$, $R_{a3}$, $R_{a4}$, $R_{a5}$, $R_{a6}$, $R_{a7}$, $R_{a8}$, $R_{a9}$, $R_{a10}$, $R_{a11}$, $R_{a12}$, $R_{a13}$, $R_{a14}$, $R_{a15}$, $R_{a16}$, $R_{a17}$, $R_{a18}$, $R_{a19}$, $R_{a20}$, $R_{a21}$, $R_{a22}$, $R_{a23}$, $R_{a24}$, $R_{a25}$, $R_{a26}$ each independently represent H, linear or branched $C_1$-$C_{10}$ alkyl or $C_3$-$C_{10}$ cycloalkyl, wherein in the same group LIN, $R_{a1}$, $R_{a2}$, $R_{a3}$, and $R_{a4}$ are not H at the same time, $R_{a5}$, $R_{a6}$, $R_{a7}$, $R_{a8}$, $R_{a9}$, and $R_{a10}$ are not H at the same time, $R_{a11}$, $R_{a12}$, $R_{a13}$, $R_{a14}$, $R_{a15}$, $R_{a16}$, $R_{a17}$, $R_{a18}$, $R_{a19}$, $R_{a20}$, $R_{a21}$, and $R_{a22}$ are not H at the same time, or $R_{a23}$, $R_{a24}$, $R_{a25}$, and $R_{a26}$ are not H at the same time;

n1, n2, n3, n4, n5, n6, m1, m2 each independently represent an integer of 1, 2, 3, 4, 5, 6, 7, 8, 9, 10, 11, 12, 13, 14, 15, 16, 17, 18, 19, or 20; and wherein the group U represents CO or NH, or the group U is absent.

In an embodiment of the present disclosure, the LIN is preferably —U—$C_{1-30}$ alkylene-. In an embodiment of the present disclosure, the LIN is preferably —U-methylene- or —U—$C_{2-30}$ alkylene-, wherein the $C_{2-30}$ alkylene group is a linear or branched $C_{2-30}$ alkylene (preferably $C_2$-$C_{29}$ alkylene chain, $C_2$-$C_{28}$ alkylene chain, $C_2$-$C_{27}$ alkylene chain, $C_2$-$C_{26}$ alkylene chain, $C_2$-$C_{25}$ alkylene chain, $C_2$-$C_{24}$ alkylene chain, $C_2$-$C_{23}$ alkylene chain, $C_2$-$C_{22}$ alkylene chain, $C_2$-$C_{21}$ alkylene chain, $C_2$-$C_{20}$ alkylene chain, $C_2$-$C_{19}$ alkylene chain, $C_2$-$C_{18}$ alkylene chain Chain, $C_2$-$C_{17}$ alkylene chain, $C_2$-$C_{16}$ alkylene chain, $C_2$-$C_{18}$ alkylene chain, $C_2$-$C_{14}$ alkylene chain, $C_2$-$C_{13}$ alkylene chain, $C_2$-$C_{12}$ alkylene chain, $C_2$-$C_{11}$ alkylene chain, $C_2$-$C_{10}$ alkylene chain, $C_2$-$C_9$ alkylene chain, $C_2$-$C_8$ alkylene chain, $C_2$-$C_7$ alkylene chain, $C_2$-$C_6$ alkylene chain, $C_2$-$C_5$ alkylene chain, $C_2$-$C_4$ alkylene chain, or $C_2$-$C_3$ alkylene chain), and the group U represents CO or NH, or the group U is absent.

In an embodiment of the present disclosure, preferably, the LIN represents: —U—$CH_2$—; —U—$(CH_2)_2$—; —U—$(CH_2)_3$—; —U—$(CH_2)_4$—; —U—$(CH_2)_5$—; —U—$(CH_2)_6$—; —U—$(CH_2)_7$—; —U—$(CH_2)_8$—; —U—$(CH_2)_9$—; —U—$(CH_2)_{10}$—; —U—$(CH_2)_{11}$—; —U—$(CH_2)_{12}$—; —U—$(CH_2)_{13}$—; —U—$(CH_2)_{14}$—; —U—$(CH_2)_{15}$—; —U—$(CH_2)_{16}$—; —U—$(CH_2)_{17}$—; —U—$(CH_2)_{18}$—; —U—$(CH_2)_{19}$—; —U—$(CH_2)_{20}$—; —U—$(CH_2)_{21}$—; —U—$(CH_2)_{22}$—; —U—$(CH_2)_{23}$—; —U—$(CH_2)_{24}$—; —U—$(CH_2)_{25}$—; —U—$(CH_2)_{26}$—; —U—$(CH_2)_{27}$—; —U—$(CH_2)_{28}$—; —U—$(CH_2)_{29}$—, or —U—$(CH_2)_{30}$—;

wherein the group U represents CO or NH, or the group U is absent.

In an embodiment of the present disclosure, the LIN is preferably —U—$C_{2-40}$ alkylene-(preferably —U—$C_{2-30}$ alkylene-), wherein the alkylene group is optionally interrupted one or more times by one or more of O, CONH, NHCO, NH, alkynylene, alkenylene, cycloalkylene, arylene, heterocyclylene, or heteroarylene or any combination thereof, and the group U represents CO or NH, or the group U is absent.

In an embodiment of the present disclosure, the LIN represents: —U—CH$_2$—O—(CH$_2$)$_2$—, —U—CH$_2$—(O(CH$_2$)$_2$)$_2$—, —U—CH$_2$—(O(CH$_2$)$_2$)$_3$—, —U—CH$_2$—(O(CH$_2$)$_2$)$_4$—, —U—CH$_2$—(O(CH$_2$)$_2$)$_5$—, —U—CH$_2$—(O(CH$_2$)$_2$)$_6$—, —U—CH$_2$—(O(CH$_2$)$_2$)$_7$—, —U—CH$_2$—(O(CH$_2$)$_2$)$_8$—, —U—CH$_2$—(O(CH$_2$)$_2$)$_9$—, —U—CH$_2$—(O(CH$_2$)$_2$)$_{10}$—, —U—(CH$_2$)$_2$—O—(CH$_2$)$_2$—, —U—(CH$_2$)$_2$—(O(CH$_2$)$_2$)$_2$—, —U—(CH$_2$)$_2$—(O(CH$_2$)$_2$)$_3$—, —U—(CH$_2$)$_2$—(O(CH$_2$)$_2$)$_4$—, —U—(CH$_2$)$_2$—(O(CH$_2$)$_2$)$_5$—, —U—(CH$_2$)$_2$—(O(CH$_2$)$_2$)$_6$—, —U—(CH$_2$)$_2$—(O(CH$_2$)$_2$)$_7$—, —U—(CH$_2$)$_2$—(O(CH$_2$)$_2$)$_8$—, —U—(CH$_2$)$_2$—(O(CH$_2$)$_2$)$_9$—, —U—(CH$_2$)$_2$—(O(CH$_2$)$_2$)$_{10}$—, —U—(CH$_2$)$_3$—O—(CH$_2$)$_2$—, —U—(CH$_2$)$_3$—(O(CH$_2$)$_2$)$_2$—, —U—(CH$_2$)$_3$—(O(CH$_2$)$_2$)$_3$—, —U—(CH$_2$)$_3$—(O(CH$_2$)$_2$)$_4$—, —U—(CH$_2$)$_3$—(O(CH$_2$)$_2$)$_5$—, —U—(CH$_2$)$_3$—(O(CH$_2$)$_2$)$_6$—, —U—(CH$_2$)$_3$—(O(CH$_2$)$_2$)$_7$—, —U—(CH$_2$)$_3$—(O(CH$_2$)$_2$)$_8$—, —U—(CH$_2$)$_3$—(O(CH$_2$)$_2$)$_9$—, —U—(CH$_2$)$_3$—(O(CH$_2$)$_2$)$_{10}$—, —U—(CH$_2$)$_4$—O—(CH$_2$)$_2$—, —U—(CH$_2$)$_4$—(O(CH$_2$)$_2$)$_2$—, —U—(CH$_2$)$_4$—(O(CH$_2$)$_2$)$_3$—, —U—(CH$_2$)$_4$—(O(CH$_2$)$_2$)$_4$—, —U—(CH$_2$)$_4$—(O(CH$_2$)$_2$)$_5$—, —U—(CH$_2$)$_4$—(O(CH$_2$)$_2$)$_6$—, —U—(CH$_2$)$_4$—(O(CH$_2$)$_2$)$_7$—, —U—(CH$_2$)$_4$—(O(CH$_2$)$_2$)$_8$—, —U—(CH$_2$)$_4$—(O(CH$_2$)$_2$)$_9$—, —U—(CH$_2$)$_4$—(O(CH$_2$)$_2$)$_{10}$—, —U—CH$_2$—O—(CH$_2$)$_3$—, —U—CH$_2$—(O(CH$_2$)$_3$)$_2$—, —U—CH$_2$—(O(CH$_2$)$_3$)$_3$—, —U—CH$_2$—(O(CH$_2$)$_3$)$_4$—, —U—CH$_2$—(O(CH$_2$)$_3$)$_5$—, —U—CH$_2$—(O(CH$_2$)$_3$)$_6$—, —U—CH$_2$—(O(CH$_2$)$_3$)$_7$—, —U—CH$_2$—(O(CH$_2$)$_3$)$_8$—, —U—CH$_2$—(O(CH$_2$)$_3$)$_9$—, —U—CH$_2$—(O(CH$_2$)$_3$)$_{10}$—, —U—(CH$_2$)$_2$—O—(CH$_2$)$_3$—, —U—(CH$_2$)$_2$—(O(CH$_2$)$_3$)$_2$—, —U—(CH$_2$)$_2$—(O(CH$_2$)$_3$)$_3$—, —U—(CH$_2$)$_2$—(O(CH$_2$)$_3$)$_4$—, —U—(CH$_2$)$_2$—(O(CH$_2$)$_3$)$_5$—, —U—(CH$_2$)$_2$—(O(CH$_2$)$_3$)$_6$—, —U—(CH$_2$)$_2$—(O(CH$_2$)$_3$)$_7$—, —U—(CH$_2$)$_2$—(O(CH$_2$)$_3$)$_8$—, —U—(CH$_2$)$_2$—(O(CH$_2$)$_3$)$_9$—, —U—(CH$_2$)$_2$—(O(CH$_2$)$_3$)$_{10}$—, —U—(CH$_2$)$_3$—O—(CH$_2$)$_3$—, —U—(CH$_2$)$_3$—(O(CH$_2$)$_3$)$_2$—, —U—(CH$_2$)$_3$—(O(CH$_2$)$_3$)$_3$—, —U—(CH$_2$)$_3$—(O(CH$_2$)$_3$)$_4$—, —U—(CH$_2$)$_3$—(O(CH$_2$)$_3$)$_5$—, —U—(CH$_2$)$_3$—(O(CH$_2$)$_3$)$_6$—, —U—(CH$_2$)$_3$—(O(CH$_2$)$_3$)$_7$—, —U—(CH$_2$)$_3$—(O(CH$_2$)$_3$)$_8$—, —U—(CH$_2$)$_3$—(O(CH$_2$)$_3$)$_9$—, —U—(CH$_2$)$_3$—(O(CH$_2$)$_3$)$_{10}$—, —U—CH$_2$—O—(CH$_2$)$_2$—O—(CH$_2$)$_3$—, —U—CH$_2$—(O(CH$_2$)$_2$)$_2$—(O(CH$_2$)$_3$)$_2$—, —U—CH$_2$—(O(CH$_2$)$_2$)$_3$—(O(CH$_2$)$_3$)$_3$—, —U—CH$_2$—(O(CH$_2$)$_2$)$_4$—(O(CH$_2$)$_3$)$_4$—, —U—CH$_2$—(O(CH$_2$)$_2$)$_5$—(O(CH$_2$)$_3$)$_5$—, —U—CH$_2$—(O(CH$_2$)$_2$)$_6$—(O(CH$_2$)$_3$)$_6$—, —U—(CH$_2$)$_2$—O—(CH$_2$)$_2$—O—(CH$_2$)$_3$—, —U—(CH$_2$)$_2$—(O(CH$_2$)$_2$)$_2$—(O(CH$_2$)$_3$)$_2$—, —U—(CH$_2$)$_2$—(O(CH$_2$)$_2$)$_3$—(O(CH$_2$)$_3$)$_3$—, —U—(CH$_2$)$_2$—(O(CH$_2$)$_2$)$_4$—(O(CH$_2$)$_3$)$_4$—, —U—(CH$_2$)$_2$—(O(CH$_2$)$_2$)$_5$—(O(CH$_2$)$_3$)$_5$—, —U—(CH$_2$)$_2$—(O(CH$_2$)$_2$)$_6$—(O(CH$_2$)$_3$)$_6$—, —U—(CH$_2$)$_3$—O—(CH$_2$)$_2$—O—(CH$_2$)$_3$—, —U—(CH$_2$)$_3$—(O(CH$_2$)$_2$)$_2$—(O(CH$_2$)$_3$)$_2$—, —U—(CH$_2$)$_3$—(O(CH$_2$)$_2$)$_3$—(O(CH$_2$)$_3$)$_3$—, —U—(CH$_2$)$_3$—(O(CH$_2$)$_2$)$_4$—(O(CH$_2$)$_3$)$_4$—, —U—(CH$_2$)$_3$—(O(CH$_2$)$_2$)$_5$—(O(CH$_2$)$_3$)$_5$—, —U—(CH$_2$)$_3$—(O(CH$_2$)$_2$)$_6$—(O(CH$_2$)$_3$)$_6$—, —U—(CH$_2$)$_3$—O—(CH$_2$)$_3$—O—(CH$_2$)$_2$—, —U—(CH$_2$)$_3$—O—(CH$_2$)$_3$—O—(CH$_2$)$_2$)$_2$—, —U—(CH$_2$)$_3$—(O(CH$_2$)$_3$)$_2$—(O(CH$_2$)$_2$)$_2$—, —U—(CH$_2$)$_3$—(O(CH$_2$)$_3$)$_3$—(O(CH$_2$)$_2$)$_3$—, —U—(CH$_2$)$_3$—(O(CH$_2$)$_3$)$_4$—(O(CH$_2$)$_2$)$_4$—, —U—(CH$_2$)$_3$—(O(CH$_2$)$_3$)$_5$—(O(CH$_2$)$_2$)$_5$—, —U—(CH$_2$)$_3$—(O(CH$_2$)$_3$)$_6$—(O(CH$_2$)$_2$)$_6$—, —U—(CH$_2$)$_2$—O—(CH$_2$)$_2$—O—CH$_2$—, —U—(CH$_2$)$_2$—O—(CH$_2$)$_2$—O—CH$_2$—, —U—(CH$_2$)$_2$—(O(CH$_2$)$_2$)$_2$—O—(CH$_2$)$_3$—, —U—(CH$_2$)$_2$—(O(CH$_2$)$_2$)$_3$—O—(CH$_2$)$_3$—, —U—(CH$_2$)$_2$—(O(CH$_2$)$_2$)$_4$—O—(CH$_2$)$_3$—, —U—(CH$_2$)$_5$—(O(CH$_2$)$_2$)$_2$—O—(CH$_2$)$_5$—, or —U—(CH$_2$)$_5$—(O(CH$_2$)$_2$)$_2$—O—(CH$_2$)$_6$—;

wherein the group U represents CO or NH, or the group U is absent.

In an embodiment of the present disclosure, the LIN is —U-alkylene-, the alkylene (preferably a C$_{1-30}$ alkylene chain, particularly preferably a C$_2$-C$_{29}$ alkylene chain, C$_2$-C$_{28}$ alkylene chain, C$_2$-C$_{27}$ alkylene chain, C$_2$-C$_{26}$ alkylene chain, C$_2$-C$_{25}$ alkylene chain, C$_2$-C$_{24}$ alkylene chain, C$_2$-C$_{23}$ alkylene chain, C$_2$-C$_{22}$ alkylene chain, C$_2$-C$_{21}$ alkylene chain, C$_2$-C$_{20}$ alkylene chain, C$_2$-C$_{19}$ alkylene chain, C$_2$-C$_{18}$ alkylene chain, C$_2$-C$_{17}$ alkylene chain, C$_2$-C$_{16}$ alkylene chain, C$_2$-C$_{18}$ alkylene chain, C$_2$-C$_{14}$ alkylene chain, C$_2$-C$_{13}$ alkylene chain, C$_2$-C$_{12}$ alkylene chain, C$_2$-C$_{11}$ alkylene chain, C$_2$-C$_{10}$ alkylene chain, C$_2$-C$_9$ alkylene chain, C$_2$-C$_8$ alkylene chain, C$_2$-C$_7$ alkylene chain, C$_2$-C$_6$ alkylene chain, C$_2$-C$_5$ alkylene chain, C$_2$-C$_4$ alkylene chain, Or C$_2$-C$_3$ alkylene chain) is a linear or branched alkylene chain substituted one or more times by one or more substituents selected from hydroxyl, amino, mercapto, halogen or a combination thereof; wherein the group U represents CO or NH, or the group U is absent.

In an embodiment of the present disclosure, the LIN is preferably —U—C$_{1-30}$ alkylene-, and the C$_{1-30}$ alkylene group is a linear or branched C$_1$-C$_{30}$ alkylene chain (preferably C$_1$-C$_{29}$ alkylene chain, C$_1$-C$_{28}$ alkylene chain, C$_1$-C$_{27}$ alkylene chain, C$_1$-C$_{26}$ alkylene chain, C$_1$-C$_{25}$ alkylene chain, C$_1$-C$_{24}$ alkylene chain, C$_1$-C$_{23}$ alkylene chain, C$_1$-C$_{22}$ alkylene chain, C$_1$-C$_{21}$ alkylene chain, C$_1$-C$_{20}$ alkylene chain, C$_1$-C$_{19}$ alkylene chain, C$_1$-C$_{18}$ alkylene chain, C$_1$-C$_{17}$ alkylene chain, C$_1$-C$_{16}$ alkylene chain, C$_1$-C$_{15}$ alkylene chain, C$_1$-C$_{14}$ alkylene chain, C$_1$-C$_{13}$ alkylene chain, C$_1$-C$_{12}$ alkylene chain, C$_1$-C$_{11}$ alkylene chain, C$_1$-C$_{10}$ alkylene chain, C$_1$-C$_9$ alkylene chain, C$_1$-C$_8$ alkylene chain, C$_1$-C$_7$ alkylene chain, C$_1$-C$_6$ alkylene chain, C$_1$-C$_5$ alkylene chain, C$_1$-C$_4$ alkylene chain, C$_1$-C$_3$ alkylene chain, or C$_1$-C$_2$ alkylene chain) substituted by one or more substituents selected from hydroxyl, amino, mercapto, halogen or a combination thereof, wherein the group U represents CO or NH, or the group U is absent. In a sub-embodiment of the present disclosure, the number of the substituents can be, for example, 1-30, 1-25, 1-20, or 1-15, 1-10, 1-9, 1-8, 1-7, 1-6, 1-5, 1-4, 1-3, or 1-2, or 20, 19, 18, 17, 16, 15, 14, 13, 12, 11, 10, 9, 8, 7, 6, 5, 4, 3, 2 or 1.

In an embodiment of the present disclosure, the LIN represents: —U—(CH$_2$)$_{n11}$-triazolylene-(CH$_2$)$_{n12}$—, —U—(CH$_2$)$_{n11}$-triazolylene-(CH$_2$)$_{n12}$—(O(CH$_2$)$_{n13}$)$_{m11}$—, —U—(CH$_2$)$_{n11}$—(O(CH$_2$)$_{n12}$)$_{m11}$—O—(CH$_2$)$_{n13}$-triazolylene-(CH$_2$)$_{n14}$—(O(CH$_2$)$_{n15}$)$_{m12}$—O—(CH$_2$)$_{n16}$—, —U—(CH$_2$)$_{n11}$-triazolylene-(CH$_2$)$_{n12}$—(O(CH$_2$)$_{n13}$)$_{m11}$—O—(CH$_2$)$_{n14}$—, or —U—(CH$_2$)$_{n11}$—(O(CH$_2$)$_{n12}$)$_{m11}$—O—(CH$_2$)$_{n13}$-triazolylene-(CH$_2$)$_{n14}$—;

wherein n11, n12, n13, n14, n15, n16, m11, and m12 each independently represent an integer of 1, 2, 3, 4, 5, 6, 7, 8, 9, 10, 11, 12, 13, 14, 15, 16, 17, 18, 19, or 20;

wherein the group U represents CO or NH, or the group U is absent.

In an embodiment of the present disclosure, the LIN preferably represents: —U—(CH$_2$)$_3$-triazolylene-(CH$_2$)$_5$—, —U—(CH$_2$)$_2$-triazolylene-(CH$_2$))$_5$—, —U—CH$_2$-triazolylene-(CH$_2$)$_5$—, —U—(CH$_2$)$_2$-triazolylene-(CH$_2$)$_4$—, —U—(CH$_2$)$_3$-triazolylene-(CH$_2$)$_2$—O(CH$_2$)$_2$—, —U—(CH$_2$)$_2$-triazolylene-(CH$_2$)$_2$—O(CH$_2$)$_2$—, or —U—CH$_2$-triazolylene-(CH$_2$)$_2$—O(CH$_2$)$_2$—.

In an embodiment of the present disclosure, the LIN preferably represents:

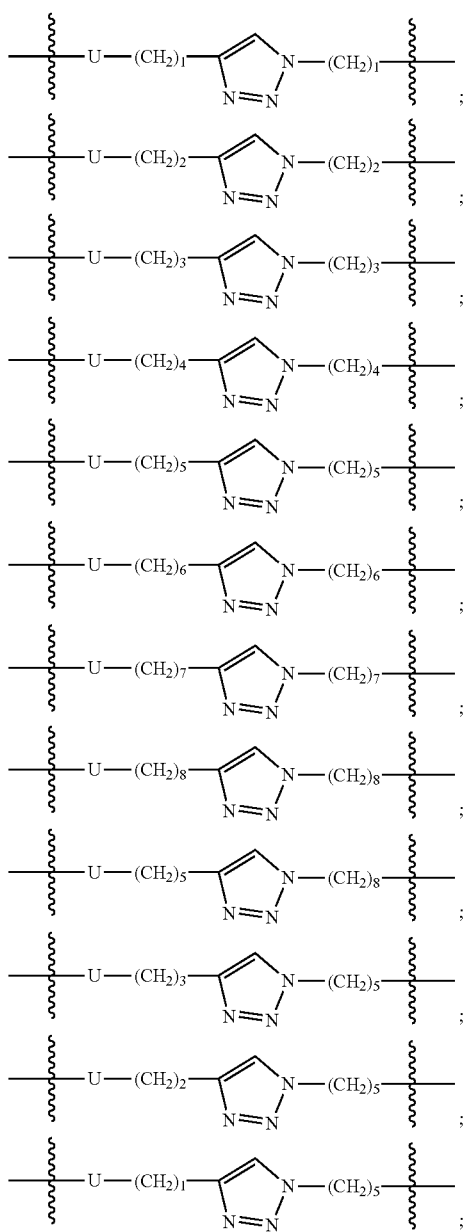

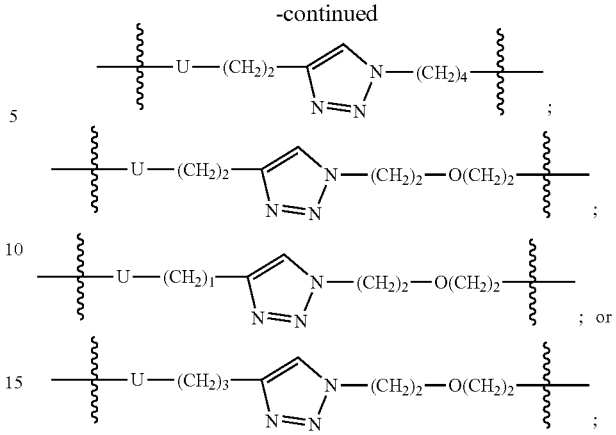

wherein the group U represents CO or NH, or the group U is absent.

In an embodiment of the present disclosure, the LIN preferably represents: —U—CH$_2$CONHCH$_2$—, —U—(CH$_2$)$_2$CONH(CH$_2$)$_2$—, —U—(CH$_2$)$_3$CONH(CH$_2$)$_3$—, —U—(CH$_2$)$_3$CONH(CH$_2$)$_4$—, —U—(CH$_2$)$_4$CONH(CH$_2$)$_4$—, —U—(CH$_2$)$_5$CONH(CH$_2$)$_5$—, —U—(CH$_2$)$_6$CONH(CH$_2$)$_7$—, —U—(CH$_2$)$_6$CONH(CH$_2$)$_6$—, —U—(CH$_2$)$_7$CONH(CH$_2$)$_7$—, —U—(CH$_2$)$_8$CONH(CH$_2$)$_8$, —U—(CH$_2$)$_9$CONH(CH$_2$)$_9$—, —U—(CH$_2$)$_{10}$CONH(CH$_2$)$_{10}$—, —U—(CH$_2$)$_2$CONH(CH$_2$)$_5$—, —U—(CH$_2$)$_2$CONH(CH$_2$)$_3$—, —U—(CH$_2$)$_2$CONH(CH$_2$)$_4$—, or —U—(CH$_2$)$_2$CONH(CH$_2$)$_2$—O—(CH$_2$)$_2$—;

wherein the group U represents CO or NH, or the group U is absent.

In an embodiment of the present disclosure, the LIN is preferably —U—CH$_2$NHCOCH$_2$—, —U—(CH$_2$)$_2$NHCO(CH$_2$)$_2$—, —U—(CH$_2$)$_3$NHCO(CH$_2$)$_3$—, —U—(CH$_2$)$_3$NHCO(CH$_2$)$_4$—, —U—(CH$_2$)$_4$NHCO(CH$_2$)$_4$—, —U—(CH$_2$)$_5$NHCO(CH$_2$)$_5$—, —U—(CH$_2$)$_6$NHCO(CH$_2$)$_7$—, —U—(CH$_2$)$_6$NHCO(CH$_2$)$_6$—, —U—(CH$_2$)$_7$NHCO(CH$_2$)$_7$—, —U—(CH$_2$)$_8$NHCO(CH$_2$)$_8$, —U—(CH$_2$)$_9$NHCO(CH$_2$)$_9$—, —U—(CH$_2$)$_{10}$NHCO(CH$_2$)$_{10}$—, —U—(CH$_2$)$_2$NHCO(CH$_2$)$_5$—, —U—(CH$_2$)$_2$NHCO(CH$_2$)$_3$—, —U—(CH$_2$)$_2$NHCO(CH$_2$)$_4$—, —U—(CH$_2$)$_4$NHCO(CH$_2$)$_8$—, or —U—(CH$_2$)$_2$NHCO(CH$_2$)$_2$—O—(CH$_2$)$_2$—;

wherein the group U represents CO or NH, or the group U is absent.

In an embodiment of the present disclosure, the compound of formula (I) is also the compound of formula (Ia-2):

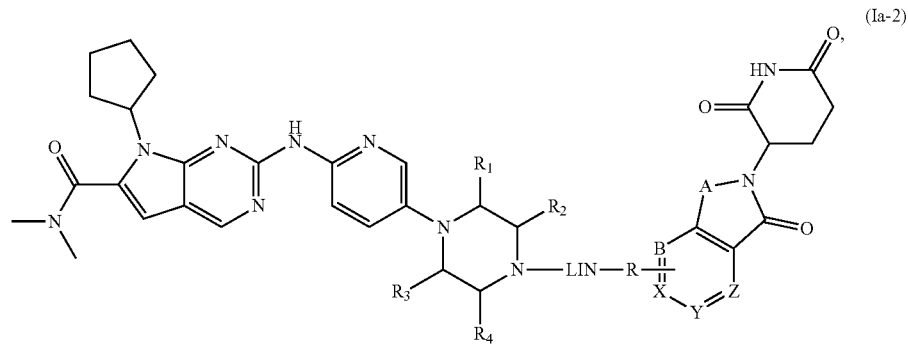

wherein, the groups LIN, R, A, B, X, Y and Z are as defined above, and the groups $R_1$, $R_2$, $R_3$ and $R_4$ are as defined above.

In ab embodiment of the present disclosure, the compound of formula (I) is also the compound of formula (Ia-3):

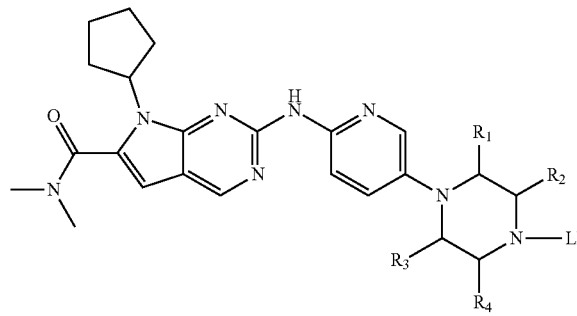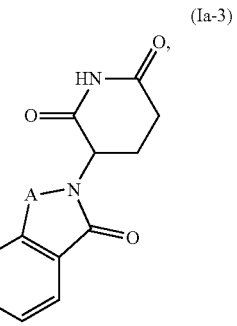

(Ia-3)

wherein, the groups LIN, R and A are as defined above, and the groups $R_1$, $R_2$, $R_3$, and $R_4$ are as defined above.

In a sub-embodiment of the compound of formula (Ia-3) of the present disclosure, the LIN represents —U—$C_{1-30}$ alkylene-; and the group U represents CO or NH, or the group U is absent. In a sub-embodiment of the compound of formula (Ia-3), the LIN represents: —U—$CH_2$—; —U—$(CH_2)_2$—; —U—$(CH_2)_3$—; —U—$(CH_2)_4$—; —U—$(CH_2)_5$—; —U—$(CH_2)_6$—; —U—$(CH_2)_7$—; —U—$(CH_2)_8$—; —U—$(CH_2)_9$—; —U—$(CH_2)_{10}$—; —U—$(CH_2)_{11}$—; —U—$(CH_2)_{12}$—; —U—$(CH_2)_{13}$—; —U—$(CH_2)_{14}$—; —U—$(CH_2)_{15}$—; —U—$(CH_2)_{16}$—; —U—$(CH_2)_{17}$—; —U—$(CH_2)_{18}$—; —U—$(CH_2)_{19}$—; —U—$(CH_2)_{20}$—; —U—$(CH_2)_{21}$—; —U—$(CH_2)_{22}$—; —U—$(CH_2)_{23}$—; —U—$(CH_2)_{24}$—; —U—$(CH_2)_{25}$—; —U—$(CH_2)_{26}$—; —U—$(CH_2)_{27}$—; —U—$(CH_2)_{28}$—; —U—$(CH_2)_{29}$—; or —U—$(CH_2)_{30}$—; wherein the group U represents CO or NH, or the group U is absent.

In a sub-embodiment of the compound of formula (Ia-3) of the present disclosure, the LIN is preferably —U—$C_{2-40}$ alkylene-(preferably —U—$C_{2-30}$ alkylene-), wherein the alkylene chain is optionally interrupted one or more times by one or more of O, CONH, NHCO, NH, alkynylene, alkenylene, cycloalkylene, arylene, heterocyclylene or heteroarylene or any combination thereof, and the group U represents CO or NH, or the group U is absent. In a sub-embodiment of the compound of formula (Ia-3), the LIN preferably represents: —U—$(CH_2)_{n1}$—(O$(CH_2)_{n2})_{m1}$— or —U—$(CH_2)_{n1}$—(O$(CH_2)_{n2})_{m1}$—(O$(CH_2)_{n3})_{m2}$—, wherein n1, n2, n3, m1 and m2 each independently represent an integer of 1, 2, 3, 4, 5, 6, 7, 8, 9, 10, 11, 12, 13, 14, 15, 16, 17, 18, 19 or 20; and wherein the group U represents CO or NH, or the group U is absent. In a sub-embodiment of the compound of formula (Ia-3), the LIN preferably represents: —U—$CH_2$—O—$(CH_2)_2$—, —U—$CH_2$—(O$(CH_2)_2)_2$—, —U—$CH_2$—(O$(CH_2)_2)_3$—, —U—$CH_2$—(O$(CH_2)_2)_4$—, —U—$CH_2$—(O$(CH_2)_2)_5$—, —U—$CH_2$—(O$(CH_2)_2)_6$—, —U—$CH_2$—(O$(CH_2)_2)_7$—, —U—$CH_2$—(O$(CH_2)_2)_8$—, —U—$CH_2$—(O$(CH_2)_2)_9$—, —U—$CH_2$—(O$(CH_2)_2)_{10}$—, —U—$(CH_2)_2$—O—$(CH_2)_2$—, —U—$(CH_2)_2$—(O$(CH_2)_2)_2$—, —U—$(CH_2)_2$—(O$(CH_2)_2)_3$—, —U—$(CH_2)_2$—(O$(CH_2)_2)_4$—, —U—$(CH_2)_2$—(O$(CH_2)_2)_5$—, —U—$(CH_2)_2$—(O$(CH_2)_2)_6$—, —U—$(CH_2)_2$—(O$(CH_2)_2)_7$—, —U—$(CH_2)_2$—(O$(CH_2)_2)_8$—, —U—$(CH_2)_2$—(O$(CH_2)_2)_9$—, —U—$(CH_2)_2$—(O$(CH_2)_2)_{10}$—, —U—$(CH_2)_3$—O—$(CH_2)_2$—, —U—$(CH_2)_3$—(O$(CH_2)_2)_2$—, —U—$(CH_2)_3$—(O$(CH_2)_2)_3$—, —U—$(CH_2)_3$—(O$(CH_2)_2)_4$—, —U—$(CH_2)_3$—(O$(CH_2)_2)_5$—, —U—$(CH_2)_3$—(O$(CH_2)_2)_6$—, —U—$(CH_2)_3$—(O$(CH_2)_2)_7$—, —U—$(CH_2)_3$—(O$(CH_2)_2)_8$—, —U—$(CH_2)_3$—(O$(CH_2)_2)_9$—, —U—$(CH_2)_3$—(O$(CH_2)_2)_{10}$—, —U—$(CH_2)_4$—O—$(CH_2)_2$—, —U—$(CH_2)_4$—(O$(CH_2)_2)_2$—, —U—$(CH_2)_4$—(O$(CH_2)_2)_3$—, —U—$(CH_2)_4$—(O$(CH_2)_2)_4$—, —U—$(CH_2)_4$—(O$(CH_2)_2)_5$—, —U—$(CH_2)_4$—(O$(CH_2)_2)_6$—, —U—$(CH_2)_4$—(O$(CH_2)_2)_7$—, —U—$(CH_2)_4$—(O$(CH_2)_2)_8$—, —U—$(CH_2)_4$—(O$(CH_2)_2)_9$—, —U—$(CH_2)_4$—(O$(CH_2)_2)_{10}$—, —U—$CH_2$—O—$(CH_2)_3$—, —U—$CH_2$—(O$(CH_2)_3)_2$—, —U—$CH_2$—(O$(CH_2)_3)_3$—, —U—$CH_2$—(O$(CH_2)_3)_4$—, —U—$CH_2$—(O$(CH_2)_3)_5$—, —U—$CH_2$—(O$(CH_2)_3)_6$—, —U—$CH_2$—(O$(CH_2)_3)_7$—, —U—$CH_2$—(O$(CH_2)_3)_8$—, —U—$CH_2$—(O$(CH_2)_3)_9$—, —U—$CH_2$—(O$(CH_2)_3)_{10}$—, —U—$(CH_2)_2$—O—$(CH_2)_3$—, —U—$(CH_2)_2$—(O$(CH_2)_3)_2$—, —U—$(CH_2)_2$—(O$(CH_2)_3)_3$—, —U—$(CH_2)_2$—(O$(CH_2)_3)_4$—, —U—$(CH_2)_2$—(O$(CH_2)_3)_5$—, —U—$(CH_2)_2$—(O$(CH_2)_3)_6$—, —U—$(CH_2)_2$—(O$(CH_2)_3)_7$—, —U—$(CH_2)_2$—(O$(CH_2)_3)_8$—, —U—$(CH_2)_2$—(O$(CH_2)_3)_9$—, —U—$(CH_2)_2$—(O$(CH_2)_3)_{10}$—, —U—$(CH_2)_3$—O—$(CH_2)_3$—, —U—$(CH_2)_3$—(O$(CH_2)_3)_2$—, —U—$(CH_2)_3$—(O$(CH_2)_3)_3$—, —U—$(CH_2)_3$—(O$(CH_2)_3)_4$—, —U—$(CH_2)_3$—(O$(CH_2)_3)_5$—, —U—$(CH_2)_3$—(O$(CH_2)_3)_6$—, —U—$(CH_2)_3$—(O$(CH_2)_3)_7$—, —U—$(CH_2)_3$—(O$(CH_2)_3)_8$—, —U—$(CH_2)_3$—(O$(CH_2)_3)_9$—, —U—$(CH_2)_3$—(O$(CH_2)_3)_{10}$—, —U—$CH_2$—O—$(CH_2)_2$—O—$(CH_2)_3$—, —U—$CH_2$—(O$(CH_2)_2)_2$—(O$(CH_2)_3)_2$—, —U—$CH_2$—(O$(CH_2)_2)_3$—(O$(CH_2)_2)_4$—(O$(CH_2)_3)_5$—, —U—$CH_2$—(O$(CH_2)_2)_5$—(O$(CH_2)_3)_5$—, —U—$CH_2$—(O$(CH_2)_2)_6$—(O$(CH_2)_3)_6$—, —U—$(CH_2)_2$—O—$(CH_2)_2$—O—$(CH_2)_3$—, —U—$(CH_2)_2$—(O$(CH_2)_2)_2$—(O$(CH_2)_2)_2$—, —U—$(CH_2)_2$—(O$(CH_2)_2)_3$—(O$(CH_2)_2)_3$—, —U—$(CH_2)_2$—(O$(CH_2)_2)_4$—(O$(CH_2)_3)_4$—, —U—$(CH_2)_2$—(O$(CH_2)_2)_5$—(O$(CH_2)_3)_5$—, —U—$(CH_2)_2$—(O$(CH_2)_2)_6$—(O$(CH_2)_3)_6$—, —U—$(CH_2)_3$—O—$(CH_2)_2$—O—$(CH_2)_3$—, —U—$(CH_2)_3$—(O$(CH_2)_2)_2$—(O$(CH_2)_2)_2$—, —U—$(CH_2)_3$—(O$(CH_2)_2)_3$—(O$(CH_2)_3)_3$—, —U—$(CH_2)_3$—(O$(CH_2)_2)_4$—(O$(CH_2)_3)_4$—, —U—$(CH_2)_3$—(O$(CH_2)_2)_5$—(O$(CH_2)_3)_5$—, —U—$(CH_2)_3$—(O$(CH_2)_2)_6$—(O$(CH_2)_3)_6$—, —U—$CH_2$—O—$(CH_2)_3$—O—$(CH_2)_2$—, —U—$CH_2$—(O$(CH_2)_3)_2$—(O$(CH_2)_2)_2$—, —U—$CH_2$—(O$(CH_2)_3)_3$—(O$(CH_2)_2)_3$—, —U—$CH_2$—(O$(CH_2)_3)_4$—(O$(CH_2)_2)_4$—, —U—$CH_2$—(O$(CH_2)_3)_5$—(O$(CH_2)_2)_5$—, —U—$CH_2$—(O$(CH_2)_3)_6$—(O$(CH_2)_2)_6$—, —U—$(CH_2)_2$—O—$(CH_2)_3$—O—$(CH_2)_2$—, —U—$(CH_2)_2$—(O$(CH_2)_3)_2$—(O$(CH_2)_2)_2$—, —U—$(CH_2)_2$—(O$(CH_2)_3)_3$—(O$(CH_2)_2)_3$—, —U—$(CH_2)_2$—(O$(CH_2)_3)_4$—(O $(CH_2)_2)_4$—, —U—$(CH_2)_2$—$(O(CH_2)_3)_5$—$(O(CH_2)_2)_5$—, —U—$(CH_2)_2$—$(O(CH_2)_3)_6$—$(O(CH_2)_2)_6$—, —U—$(CH_2)_3$—O—$(CH_2)_3$—O—$(CH_2)_2$—, —U—$(CH_2)_3$—$(O(CH_2)_3)_2$—$(O(CH_2)_2)_2$—, —U—$(CH_2)_3$—$(O(CH_2)_3)_3$—$(O(CH_2)_2)_3$—, —U—$(CH_2)_3$—$(O(CH_2)_3)_4$—$(O(CH_2)_2)_4$—, —U—$(CH_2)_3$—$(O(CH_2)_3)_5$—$(O(CH_2)_2)_5$—, —U—$(CH_2)_3$—$(O(CH_2)_3)_6$—$(O(CH_2)_2)_6$—, —U—$CH_2$—O—$(CH_2)_2$—O—$CH_2$—, —U—$(CH_2)_2$—O—$(CH_2)_2$—O—$CH_2$—, —U—$(CH_2)_2$—$(O(CH_2)_2)_2$—O—$(CH_2)_3$—, —U—$(CH_2)_2$—$(O(CH_2)_2)_3$—O—$(CH_2)_3$—, —U—$(CH_2)_2$—$(O(CH_2)_2)_4$—O—$(CH_2)_3$—, —U—$(CH_2)_5$—$(O(CH_2)_2)_2$—O—$(CH_2)_5$—, or —U—$(CH_2)_5$—$(O(CH_2)_2)_2$—O—$(CH_2)_6$—;

wherein the group U represents CO or NH, or the group U is absent.

In an embodiment of the present disclosure, the compound of formula (I) is also the compound of formula (Ib-2):

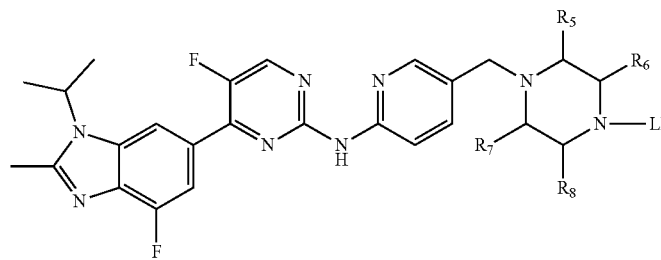

(Ib-2)

wherein, the groups LIN, R, A, B, X, Y and Z are as defined above, and the groups $R_5$, $R_6$, $R_7$ and $R_8$ are as defined above.

In an embodiment of the present disclosure, the compound of formula (I) is also the compound of formula (Ib-3):

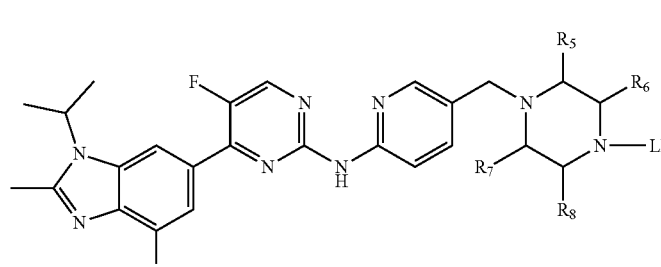

(Ib-3)

wherein, the groups LIN, R and A are as defined above, and the groups $R_5$, $R_6$, $R_7$ and $R_8$ are as defined above.

In a sub-embodiment of the compound of formula (Ib-3) of the present disclosure, the LIN represents —U—$C_{1-30}$ alkylene-; and the group U represents CO or NH, or the group U is absent. In a sub-embodiment of the compound of formula (Ib-3), the LIN represents: —U—$CH_2$—; —U—$(CH_2)_2$—; —U—$(CH_2)_3$—; —U—$(CH_2)_4$—; —U—$(CH_2)_5$—; —U—$(CH_2)_6$—; —U—$(CH_2)_7$—; —U—$(CH_2)_8$—; —U—$(CH_2)_9$—; —U—$(CH_2)_{10}$—; —U—$(CH_2)_{11}$—; —U—$(CH_2)_{12}$—; —U—$(CH_2)_{13}$—; —U—$(CH_2)_{14}$—; —U—$(CH_2)_{15}$—; —U—$(CH_2)_{16}$—; —U—$(CH_2)_{17}$—; —U—$(CH_2)_{18}$—; —U—$(CH_2)_{19}$—; —U—$(CH_2)_{20}$—; —U—$(CH_2)_{21}$—; —U—$(CH_2)_{22}$—; —U—$(CH_2)_{23}$—; —U—$(CH_2)_{24}$—; —U—$(CH_2)_{25}$—; —U—$(CH_2)_{26}$—; —U—$(CH_2)_{27}$—; —U—$(CH_2)_{28}$—; —U—$(CH_2)_{29}$—; or —U—$(CH_2)_{30}$—; wherein the group U represents CO or NH, or the group U is absent.

In a sub-embodiment of the compound of formula (Ib-3) of the present disclosure, the LIN is preferably —U—$C_{2-40}$ alkylene-(preferably —U—$C_{2-30}$ alkylene-), wherein the alkylene chain is optionally interrupted one or more times by one or more of O, CONH, NHCO, NH, alkynylene, alkenylene, cycloalkylene, arylene, heterocyclylene or heteroarylene or any combination thereof, and the group U represents CO or NH, or the group U is absent. In a sub-embodiment of the compound of formula (Ib-3), the LIN preferably represents: —U—$(CH_2)_{n1}$—$(O(CH_2)_{n2})_{m1}$— or —U—$(CH_2)_{n1}$—$(O(CH_2)_{n2})_{m1}$—$(O(CH_2)_{n3})_{m2}$—, wherein n1, n2, n3, m1 and m2 each independently represent an integer of 1, 2, 3, 4, 5, 6, 7, 8, 9, 10, 11, 12, 13, 14, 15, 16, 17, 18, 19 or 20; and wherein the group U represents CO or NH, or the group U is absent. In a sub-embodiment of the compound of formula (Ib-3), the LIN preferably represents: —U—$CH_2$—O—$(CH_2)_2$—, —U—$CH_2$—$(O(CH_2)_2)_2$—, —U—$CH_2$—$(O(CH_2)_2)_3$—, —U—CH₂—(O(CH₂)₂)₄—, —U—CH₂—(O(CH₂)₂)₅—, —U—CH₂—(O(CH₂)₂)₆—, —U—CH₂—(O(CH₂)₂)₇—, —U—CH₂—(O(CH₂)₂)₈—, —U—CH₂—(O(CH₂)₂)₉—, —U—CH₂—(O(CH₂)₂)₁₀—, —U—(CH₂)₂—O—(CH₂)₂—, —U—(CH₂)₂—(O(CH₂)₂)₂—, —U—(CH₂)₂—(O(CH₂)₂)₃—, —U—(CH₂)₂—(O(CH₂)₂)₄—, —U—(CH₂)₂—(O(CH₂)₂)₅—, —U—(CH₂)₂—(O(CH₂)₂)₆—, —U—(CH₂)₂—(O(CH₂)₂)₇—, —U—(CH₂)₂—(O(CH₂)₂)₈—, —U—(CH₂)₂—(O(CH₂)₂)₉—, —U—(CH₂)₂—(O(CH₂)₂)₁₀—, —U—(CH₂)₃—O—(CH₂)₂—, —U—(CH₂)₃—(O(CH₂)₂)₂—, —U—(CH₂)₃—(O(CH₂)₂)₃—, —U—(CH₂)₃—(O(CH₂)₂)₄—, —U—(CH₂)₃—(O(CH₂)₂)₅—, —U—(CH₂)₃—(O(CH₂)₂)₆—, —U—(CH₂)₃—(O(CH₂)₂)₇—, —U—(CH₂)₃—(O(CH₂)₂)₈—, —U—(CH₂)₃—(O(CH₂)₂)₉—, —U—(CH₂)₃—(O(CH₂)₂)₁₀—, —U—(CH₂)₄—O—(CH₂)₂—, —U—(CH₂)₄—(O(CH₂)₂)₂—, —U—(CH₂)₄—(O(CH₂)₂)₃—, —U—(CH₂)₄—(O(CH₂)₂)₄—, —U—(CH₂)₄—(O(CH₂)₂)₅—, —U—(CH₂)₄—(O(CH₂)₂)₆—, —U—(CH₂)₄—(O(CH₂)₂)₇—, —U—(CH₂)₄—(O(CH₂)₂)₈—, —U—(CH₂)₄—(O(CH₂)₂)₉—, —U—(CH₂)₄—(O(CH₂)₂)₁₀—, —U—CH₂—O—(CH₂)₃—, —U—CH₂—(O(CH₂)₃)₂—, —U—CH₂—(O(CH₂)₃)₃—, —U—CH₂—(O(CH₂)₃)₄—, —U—CH₂—(O(CH₂)₃)₅—, —U—CH₂—(O(CH₂)₃)₆—, —U—CH₂—(O(CH₂)₃)₇—, —U—CH₂—(O(CH₂)₃)₈—, —U—CH₂—(O(CH₂)₃)₉—, —U—CH₂—(O(CH₂)₃)₁₀—, —U—(CH₂)₂—O—(CH₂)₃—, —U—(CH₂)₂—(O(CH₂)₃)₂—, —U—(CH₂)₂—(O(CH₂)₃)₃—, —U—(CH₂)₂—(O(CH₂)₃)₄—, —U—(CH₂)₂—(O(CH₂)₃)₅—, —U—(CH₂)₂—(O(CH₂)₃)₆—, —U—(CH₂)₂—(O(CH₂)₃)₇—, —U—(CH₂)₂—(O(CH₂)₃)₈—, —U—(CH₂)₂—(O(CH₂)₃)₉—, —U—(CH₂)₂—(O(CH₂)₃)₁₀—, —U—(CH₂)₃—O—(CH₂)₃—, —U—(CH₂)₃—(O(CH₂)₃)₂—, —U—(CH₂)₃—(O(CH₂)₃)₃—, —U—(CH₂)₃—(O(CH₂)₃)₄—, —U—(CH₂)₃—(O(CH₂)₃)₅—, —U—(CH₂)₃—(O(CH₂)₃)₆—, —U—(CH₂)₃—(O(CH₂)₃)₇—, —U—(CH₂)₃—(O(CH₂)₃)₈—, —U—(CH₂)₃—(O(CH₂)₃)₉—, —U—(CH₂)₃—(O(CH₂)₃)₁₀—, —U—CH₂—O—(CH₂)₂—O—(CH₂)₃—, —U—CH₂—(O(CH₂)₂)₂—(O(CH₂)₃)₃—, —U—CH₂—(O(CH₂)₂)₃—(O(CH₂)₃)₃—, —U—CH₂—(O(CH₂)₂)₄—(O(CH₂)₃)₄—, —U—CH₂—(O(CH₂)₂)₅—(O(CH₂)₃)₅—, —U—CH₂—(O(CH₂)₂)₆—(O(CH₂)₃)₆—, —U—(CH₂)₂—O—(CH₂)₂—O—(CH₂)₃—, —U—(CH₂)₂—(O(CH₂)₂)₂—(O(CH₂)₃)₂—, —U—(CH₂)₂—(O(CH₂)₂)₃—(O(CH₂)₃)₃—, —U—(CH₂)₂—(O(CH₂)₂)₄—(O(CH₂)₃)₄—, —U—(CH₂)₂—(O(CH₂)₂)₅—(O(CH₂)₃)₅—, —U—(CH₂)₂—(O(CH₂)₂)₆—(O(CH₂)₃)₆—, —U—(CH₂)₃—O—(CH₂)₂—O—(CH₂)₃—, —U—(CH₂)₃—(O(CH₂)₂)₂—(O(CH₂)₃)₂—, —U—(CH₂)₃—(O(CH₂)₂)₃—(O(CH₂)₃)₃—, —U—(CH₂)₃—(O(CH₂)₂)₄—(O(CH₂)₃)₄—, —U—(CH₂)₃—(O(CH₂)₂)₅—(O(CH₂)₃)₅—, —U—(CH₂)₃—(O(CH₂)₂)₆—(O(CH₂)₃)₆—, —U—CH₂—O—(CH₂)₃—O—(CH₂)₂—, —U—CH₂—(O(CH₂)₃)₂—(O(CH₂)₂)₂—, —U—CH₂—(O(CH₂)₃)₃—(O(CH₂)₂)₃—, —U—CH₂—(O(CH₂)₃)₄—(O(CH₂)₂)₄—, —U—CH₂—(O(CH₂)₃)₅—(O(CH₂)₂)₅—, —U—CH₂—(O(CH₂)₃)₆—(O(CH₂)₂)₆—, —U—(CH₂)₂—O—(CH₂)₃—O—(CH₂)₂—, —U—(CH₂)₂—(O(CH₂)₃)₂—(O(CH₂)₂)₂—, —U—(CH₂)₂—(O(CH₂)₃)₃—(O(CH₂)₂)₃—, —U—(CH₂)₂—(O(CH₂)₃)₄—(O(CH₂)₂)₄—, —U—(CH₂)₂—(O(CH₂)₃)₅—(O(CH₂)₂)₅—, —U—(CH₂)₂—(O(CH₂)₃)₆—(O(CH₂)₂)₆—, —U—(CH₂)₃—O—(CH₂)₃—O—(CH₂)₂—, —U—(CH₂)₃—(O(CH₂)₃)₂—(O(CH₂)₂)₂—, —U—(CH₂)₃—(O(CH₂)₃)₃—(O(CH₂)₂)₃—, —U—(CH₂)₃—(O(CH₂)₃)₄—(O(CH₂)₂)₄—, —U—(CH₂)₃—(O(CH₂)₃)₅—(O(CH₂)₂)₅—, —U—(CH₂)₃—(O(CH₂)₃)₆—(O(CH₂)₂)₆—, —U—CH₂—O—(CH₂)₂—O—CH₂—, —U—(CH₂)₂—O—(CH₂)₂—O—CH₂—, —U—(CH₂)₂—O—(CH₂)₂—O—CH₂—, —U—(CH₂)₂—(O(CH₂)₂)₂—O—(CH₂)₃—, —U—(CH₂)₂—(O(CH₂)₂)₃—O—(CH₂)₃—, —U—(CH₂)₂—(O(CH₂)₂)₄—O—(CH₂)₃—, —U—(CH₂)₅—(O(CH₂)₂)₂—O—(CH₂)₅—, or —U—(CH₂)₅—(O(CH₂)₂)₂—O—(CH₂)₆—; wherein the group U represents CO or NH, or the group U is absent.

In an embodiment of the present disclosure, the compound of formula (I) is also the compound of formula (Ic-2):

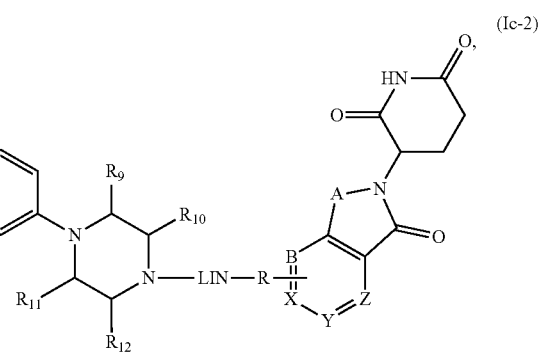

(Ic-2)

wherein, the groups LIN, R, A, B, X, Y and Z are as defined above, and the groups R₉, R₁₀, R₁₁ and R₁₂ are as defined above.

In an embodiment of the present disclosure, the compound of formula (I) is also the compound of formula (Ic-3):

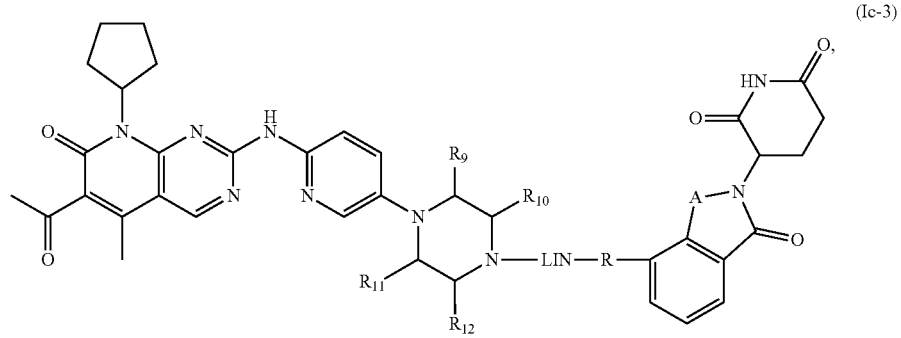

(Ic-3)

wherein, the groups LIN, R and A are as defined above, and the groups $R_9$, $R_{10}$, $R_{11}$ and $R_{12}$ are as defined above.

In a sub-embodiment of the compound of formula (Ic-3) of the present disclosure, the LIN represents —U—$C_{1-30}$ alkylene-; and the group U represents CO or NH, or the group U is absent. In a sub-embodiment of the compound of formula (Ic-3), the LIN represents: —U—$CH_2$—; —U—$(CH_2)_2$—; —U—$(CH_2)_3$—; —U—$(CH_2)_4$—; —U—$(CH_2)_5$—; —U—$(CH_2)_6$—; —U—$(CH_2)_7$—; —U—$(CH_2)_8$—; —U—$(CH_2)_9$—; —U—$(CH_2)_{10}$—; —U—$(CH_2)_{11}$—; —U—$(CH_2)_{12}$—; —U—$(CH_2)_{13}$—; —U—$(CH_2)_{14}$—; —U—$(CH_2)_{15}$—; —U—$(CH_2)_{16}$—; —U—$(CH_2)_{17}$—; —U—$(CH_2)_{18}$—; —U—$(CH_2)_{19}$—; —U—$(CH_2)_{20}$—; —U—$(CH_2)_{21}$—; —U—$(CH_2)_{22}$—; —U—$(CH_2)_{23}$—; —U—$(CH_2)_{24}$—; —U—$(CH_2)_{25}$—; —U—$(CH_2)_{26}$—; —U—$(CH_2)_{27}$—; —U—$(CH_2)_{28}$—; —U—$(CH_2)_{29}$—; or U—$(CH_2)_{30}$—; wherein the group U represents CO or NH, or the group U is absent.

In a sub-embodiment of the compound of formula (Ic-3) of the present disclosure, the LIN is preferably —U—$C_{2-40}$ alkylene-(preferably —U—$C_{2-30}$ alkylene-), wherein the alkylene chain is optionally interrupted one or more times by one or more of O, CONH, NHCO, NH, alkynylene, alkenylene, cycloalkylene, arylene, heterocyclylene or heteroarylene or any combination thereof, and the group U represents CO or NH, or the group U is absent. In a sub-embodiment of the compound of formula (Ic-3), the LIN preferably represents: —U—$(CH_2)_{n1}$—(O$(CH_2)_{n2})_{m1}$— or —U—$(CH_2)_{n1}$—(O$(CH_2)_{n2})_{n1}$—(O$(CH_2)_{n3})_{m2}$—, wherein n1, n2, n3, m1 and m2 each independently represent an integer of 1, 2, 3, 4, 5, 6, 7, 8, 9, 10, 11, 12, 13, 14, 15, 16, 17, 18, 19 or 20; and wherein the group U represents CO or NH, or the group U is absent. In a sub-embodiment of the compound of formula (Ic-3), the LIN preferably represents: —U—$CH_2$—O—$(CH_2)_2$—, —U—$CH_2$—(O$(CH_2)_2)_2$—, —U—$CH_2$—(O$(CH_2)_2)_3$—, —U—$CH_2$—(O$(CH_2)_2)_4$—, —U—$CH_2$—(O$(CH_2)_2)_5$—, —U—$CH_2$—(O$(CH_2)_2)_6$—, —U—$CH_2$—(O$(CH_2)_2)_7$—, —U—$CH_2$—(O$(CH_2)_2)_8$—, —U—$CH_2$—(O$(CH_2)_2)_9$—, —U—$CH_2$—(O$(CH_2)_2)_{10}$—, —U—$(CH_2)_2$—O—$(CH_2)_2$—, —U—$(CH_2)_2$—(O$(CH_2)_2)_2$—, —U—$(CH_2)_2$—(O$(CH_2)_2)_3$—, —U—$(CH_2)_2$—(O$(CH_2)_2)_4$—, —U—$(CH_2)_2$—(O$(CH_2)_2)_5$—, —U—$(CH_2)_2$—(O$(CH_2)_2)_6$—, —U—$(CH_2)_2$—(O$(CH_2)_2)_7$—, —U—$(CH_2)_2$—(O$(CH_2)_2)_8$—, —U—$(CH_2)_2$—(O$(CH_2)_2)_9$—, —U—$(CH_2)_2$—(O$(CH_2)_2)_{10}$—, —U—$(CH_2)_3$—O—$(CH_2)_2$—, —U—$(CH_2)_3$—(O$(CH_2)_2)_2$—, —U—$(CH_2)_3$—(O$(CH_2)_2)_3$—, —U—$(CH_2)_3$—(O$(CH_2)_2)_4$—, —U—$(CH_2)_3$—(O$(CH_2)_2)_5$—, —U—$(CH_2)_3$—(O$(CH_2)_2)_6$—, —U—$(CH_2)_3$—(O$(CH_2)_2)_7$—, —U—$(CH_2)_3$—(O$(CH_2)_2)_8$—, —U—$(CH_2)_3$—(O$(CH_2)_2)_9$—, —U—$(CH_2)_3$—(O$(CH_2)_2)_{10}$—, —U—$(CH_2)_4$—O—$(CH_2)_2$—, —U—$(CH_2)_4$—(O$(CH_2)_2)_2$—, —U—$(CH_2)_4$—(O$(CH_2)_2)_3$—, —U—$(CH_2)_4$—(O$(CH_2)_2)_4$—, —U—$(CH_2)_4$—(O$(CH_2)_2)_5$—, —U—$(CH_2)_4$—(O$(CH_2)_2)_6$—, —U—$(CH_2)_4$—(O$(CH_2)_2)_7$—, —U—$(CH_2)_4$—(O$(CH_2)_2)_8$—, —U—$(CH_2)_4$—(O$(CH_2)_2)_9$—, —U—$(CH_2)_4$—(O$(CH_2)_2)_{10}$—, —U—$CH_2$—O—$(CH_2)_3$—, —U—$CH_2$—(O$(CH_2)_3)_2$—, —U—$CH_2$—(O$(CH_2)_3)_3$—, —U—$CH_2$—(O$(CH_2)_3)_4$—, —U—$CH_2$—(O$(CH_2)_3)_5$—, —U—$CH_2$—(O$(CH_2)_3)_6$—, —U—$CH_2$—(O$(CH_2)_3)_7$—, —U—$CH_2$—(O$(CH_2)_3)_8$—, —U—$CH_2$—(O$(CH_2)_3)_9$—, —U—$CH_2$—(O$(CH_2)_3)_{10}$—, —U—$(CH_2)_2$—O—$(CH_2)_3$—, —U—$(CH_2)_2$—(O$(CH_2)_3)_2$—, —U—$(CH_2)_2$—(O$(CH_2)_3)_3$—, —U—$(CH_2)_2$—(O$(CH_2)_3)_4$—, —U—$(CH_2)_2$—(O$(CH_2)_3)_5$—, —U—$(CH_2)_2$—(O$(CH_2)_3)_6$—, —U—$(CH_2)_2$—(O$(CH_2)_3)_7$—, —U—$(CH_2)_2$—(O$(CH_2)_3)_8$—, —U—$(CH_2)_2$—(O$(CH_2)_3)_9$—, —U—$(CH_2)_2$—(O$(CH_2)_3)_{10}$—, —U—$(CH_2)_3$—O—$(CH_2)_3$—, —U—$(CH_2)_3$—(O$(CH_2)_3)_2$—, —U—$(CH_2)_3$—(O$(CH_2)_3)_3$—, —U—$(CH_2)_3$—(O$(CH_2)_3)_4$—, —U—$(CH_2)_3$—(O$(CH_2)_3)_5$—, —U—$(CH_2)_3$—(O$(CH_2)_3)_6$—, —U—$(CH_2)_3$—(O$(CH_2)_3)_7$—, —U—$(CH_2)_3$—(O$(CH_2)_3)_8$—, —U—$(CH_2)_3$—(O$(CH_2)_3)_9$—, —U—$(CH_2)_3$—(O$(CH_2)_3)_{10}$—, —U—$CH_2$—O—$(CH_2)_2$—O—$(CH_2)_3$—, —U—$CH_2$—(O$(CH_2)_2)_2$—(O$(CH_2)_3)_2$—, —U—$CH_2$—(O$(CH_2)_2)_3$—(O$(CH_2)_3)_3$—, —U—$CH_2$—(O$(CH_2)_2)_4$—(O$(CH_2)_3)_4$—, —U—$CH_2$—(O$(CH_2)_2)_5$—(O$(CH_2)_3)_5$—, —U—$CH_2$—(O$(CH_2)_2)_6$—(O$(CH_2)_3)_6$—, —U—$(CH_2)_2$—O—$(CH_2)_2$—O—$(CH_2)_3$—, —U—$(CH_2)_2$—(O$(CH_2)_2)_2$—(O$(CH_2)_3)_2$—, —U—$(CH_2)_2$—(O$(CH_2)_2)_3$—(O$(CH_2)_3)_3$—, —U—$(CH_2)_2$—(O$(CH_2)_2)_4$—(O$(CH_2)_3)_4$—, —U—$(CH_2)_2$—(O$(CH_2)_2)_5$—(O$(CH_2)_3)_5$—, —U—$(CH_2)_2$—(O$(CH_2)_2)_6$—(O$(CH_2)_3)_6$—, —U—$(CH_2)_3$—O—$(CH_2)_2$—O—$(CH_2)_3$—, —U—$(CH_2)_3$—(O$(CH_2)_2)_2$—(O$(CH_2)_3)_2$—, —U—$(CH_2)_3$—(O$(CH_2)_2)_3$—(O$(CH_2)_3)_3$—, —U—$(CH_2)_3$—(O$(CH_2)_2)_4$—(O$(CH_2)_3)_4$—, —U—$(CH_2)_3$—(O$(CH_2)_2)_5$—(O$(CH_2)_3)_5$—, —U—$(CH_2)_3$—(O$(CH_2)_2)_6$—(O$(CH_2)_3)_6$—, —U—$CH_2$—O—$(CH_2)_3$—O—$(CH_2)_2$—, —U—$CH_2$—(O$(CH_2)_3)_2$—(O$(CH_2)_2)_2$—, —U—$CH_2$—(O$(CH_2)_3)_3$—(O$(CH_2)_2)_3$—, —U—$CH_2$—(O$(CH_2)_3)_4$—(O$(CH_2)_2)_4$—, —U—$CH_2$—(O$(CH_2)_3)_5$—(O$(CH_2)_2)_5$—, —U—$CH_2$—(O$(CH_2)_3)_6$—(O$(CH_2)_2)_6$—, —U—$(CH_2)_2$—O—$(CH_2)_3$—O—$(CH_2)_2$—, —U—$(CH_2)_2$—(O$(CH_2)_3)_2$—(O$(CH_2)_2)_2$—, —U—$(CH_2)_2$—(O$(CH_2)_3)_3$—(O$(CH_2)_2)_3$—, —U—$(CH_2)_2$—(O$(CH_2)_3)_4$—(O$(CH_2)_2)_4$—, —U—$(CH_2)_2$—(O$(CH_2)_3)_5$—(O$(CH_2)_2)_5$—, —U—$(CH_2)_2$—(O$(CH_2)_3)_6$—(O$(CH_2)_2)_6$—, —U—$(CH_2)_3$—O—$(CH_2)_3$—O—$(CH_2)_2$—, —U—$(CH_2)_3$—(O$(CH_2)_3)_2$—(O$(CH_2)_2)_2$—, —U—$(CH_2)_3$—(O$(CH_2)_3)_3$—(O$(CH_2)_2)_3$—, —U—$(CH_2)_3$—(O$(CH_2)_3)_3$ $_4$—(O(CH$_2$)$_2$)$_4$—, —U—(CH$_2$)$_3$—(O(CH$_2$)$_3$)$_5$—(O(CH$_2$)$_2$)$_5$—, —U—(CH$_2$)$_3$—(O(CH$_2$)$_3$)$_6$—(O(CH$_2$)$_2$)$_6$—, —U—CH$_2$—O—(CH$_2$)$_2$—O—CH$_2$—, —U—(CH$_2$)$_2$—O—(CH$_2$)$_2$—O—CH$_2$—, —U—(CH$_2$)$_2$—(O(CH$_2$)$_2$)$_2$—O—(CH$_2$)$_3$—, —U—(CH$_2$)$_2$—(O(CH$_2$)$_2$)$_3$—O—(CH$_2$)$_3$—, —U—(CH$_2$)$_2$—(O(CH$_2$)$_2$)$_4$—O—(CH$_2$)$_3$—, —U—(CH$_2$)$_5$—(O(CH$_2$)$_2$)$_2$—O—(CH$_2$)$_5$—, or —U—(CH$_2$)$_5$—(O(CH$_2$)$_2$)$_2$—O—(CH$_2$)$_6$—; wherein the group U represents CO or NH, or the group U is absent.

In an embodiment of the present disclosure, the compound of formula (I) is also the compound of formula (Id-2):

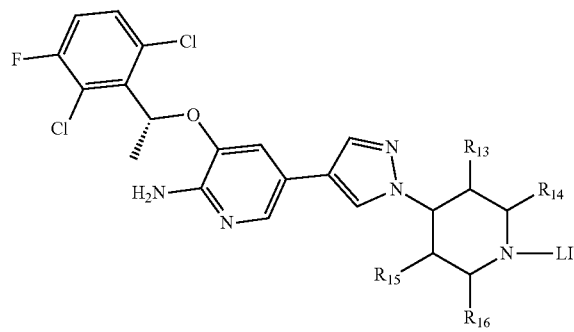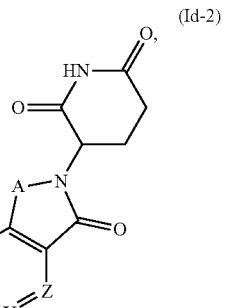

(Id-2)

wherein, the groups LIN, R, A, B, X, Y and Z are as defined above, and the groups R$_{13}$, R$_{14}$, R$_{15}$ and R$_{16}$ are as defined above.

In an embodiment of the present disclosure, the compound of formula (I) is also the compound of formula (Id-3):

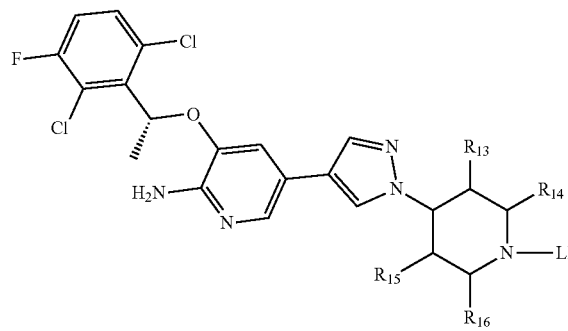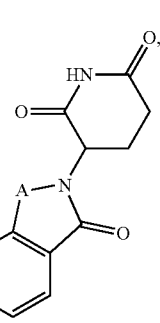

(Id-3)

wherein, the groups LIN, R and A are as defined above, and the groups R$_{13}$, R$_{14}$, R$_{15}$ and R$_{16}$ are as defined above.

In a sub-embodiment of the compound of formula (Id-3) of the present disclosure, the LIN represents —U—C$_{1-30}$ alkylene-; and the group U represents CO or NH, or the group U is absent. In a sub-embodiment of the compound of formula (Id-3), the LIN represents: —U—CH$_2$—; —U—(CH$_2$)$_2$—; —U—(CH$_2$)$_3$—; —U—(CH$_2$)$_4$—; —U—(CH$_2$)$_5$—; —U—(CH$_2$)$_6$—; —U—(CH$_2$)$_7$—; —U—(CH$_2$)$_8$—; —U—(CH$_2$)$_9$—; —U—(CH$_2$)$_{10}$—; —U—(CH$_2$)$_{11}$—; —U—(CH$_2$)$_{12}$—; —U—(CH$_2$)$_{13}$—; —U—(CH$_2$)$_{14}$—; —U—(CH$_2$)$_{15}$—; —U—(CH$_2$)$_{16}$—; —U—(CH$_2$)$_{17}$—; —U—(CH$_2$)$_{18}$—; —U—(CH$_2$)$_{19}$—; —U—(CH$_2$)$_{20}$—; —U—(CH$_2$)$_{21}$—; —U—(CH$_2$)$_{22}$—; —U—(CH$_2$)$_{23}$—; —U—(CH$_2$)$_{24}$—; —U—(CH$_2$)$_{25}$—; —U—(CH$_2$)$_{26}$—; —U—(CH$_2$)$_{27}$—; —U—(CH$_2$)$_{28}$—; —U—(CH$_2$)$_{29}$—; or —U—(CH$_2$)$_{30}$—; wherein the group U represents CO or NH, or the group U is absent.

In a sub-embodiment of the compound of formula (Id-3) of the present disclosure, the LIN is preferably —U—C$_{2-40}$ alkylene-(preferably —U—C$_{2-30}$ alkylene-), wherein the alkylene chain is optionally interrupted one or more times by one or more of O, CONH, NHCO, NH, alkynylene, alkenylene, cycloalkylene, arylene, heterocyclylene or heteroarylene or any combination thereof, and the group U represents CO or NH, or the group U is absent. In a sub-embodiment of the compound of formula (Id-3), the LIN preferably represents: —U—(CH$_2$)$_{n1}$—(O(CH$_2$)$_{n2}$)$_{m1}$— or —U—(CH$_2$)$_{n1}$—(O(CH$_2$)$_{n2}$)$_{m1}$—(O(CH$_2$)$_{n3}$)$_{m2}$—, wherein n1, n2, n3, m1, and m2 each independently represent an integer of 1, 2, 3, 4, 5, 6, 7, 8, 9, 10, 11, 12, 13, 14, 15, 16, 17, 18, 19 or 20; and wherein the group U represents CO or NH, or the group U is absent. In a sub-embodiment of the compound of formula (Id-3), the LIN preferably represents: —U—CH$_2$—O—(CH$_2$)$_2$—, —U—CH$_2$—(O(CH$_2$)$_2$)$_2$—, —U—CH$_2$—(O(CH$_2$)$_2$)$_3$—, —U—CH$_2$—(O(CH$_2$)$_2$)$_4$—, —U—CH$_2$—(O(CH$_2$)$_2$)$_5$—, —U—CH$_2$—(O(CH$_2$)$_2$)$_6$—, —U—CH$_2$—(O(CH$_2$)$_2$)$_7$—, —U—CH$_2$—(O(CH$_2$)$_2$)$_8$—, —U—CH$_2$—(O(CH$_2$)$_2$)$_9$—, —U—CH$_2$—(O(CH$_2$)$_2$)$_{10}$—, —U—(CH$_2$)$_2$—O—(CH$_2$)$_2$—, —U—(CH$_2$)$_2$—(O(CH$_2$)$_2$)$_2$—, —U—(CH$_2$)$_2$—(O(CH$_2$)$_2$)$_3$—, —U—(CH$_2$)$_2$—(O(CH$_2$)$_2$)$_4$—, —U—(CH$_2$)$_2$—(O(CH$_2$)$_2$)$_5$—, —U—(CH$_2$)$_2$—(O(CH$_2$)$_2$)$_6$—, —U—(CH$_2$)$_2$—(O(CH$_2$)$_2$)$_7$—, —U—(CH$_2$)$_2$—(O(CH$_2$)$_2$)$_8$—, —U—(CH$_2$)$_2$—(O(CH$_2$)$_2$)$_9$—, —U—(CH$_2$)$_2$—(O(CH$_2$)$_2$)$_{10}$—, —U—(CH$_2$)$_3$—O—(CH$_2$)$_2$—, —U—(CH$_2$)$_3$—(O(CH$_2$)$_2$)$_2$—, —U—(CH$_2$)$_3$—(O(CH$_2$)$_2$)$_3$—, —U—(CH$_2$)$_3$—(O(CH$_2$)$_2$)$_4$—, —U—(CH$_2$)$_3$—(O(CH$_2$)$_2$)$_5$—, —U—(CH$_2$)$_3$—(O(CH$_2$)$_2$)$_6$—, —U—(CH$_2$)$_3$—(O(CH$_2$)$_2$)$_7$—, —U—(CH$_2$)$_3$—(O(CH$_2$)$_2$)$_8$—, —U—(CH$_2$)$_3$—(O(CH$_2$)$_2$)$_9$—, —U—(CH$_2$)$_3$—(O(CH$_2$)$_2$)$_{10}$—, —U—(CH$_2$)$_4$—O—(CH$_2$)$_2$—, —U—

—(CH$_2$)$_4$—(O(CH$_2$)$_2$)$_2$—, —U—(CH$_2$)$_4$—(O(CH$_2$)$_2$)$_3$—, —U—(CH$_2$)$_4$—(O(CH$_2$)$_2$)$_4$—, —U—(CH$_2$)$_4$—(O(CH$_2$)$_2$)$_5$—, —U—(CH$_2$)$_4$—(O(CH$_2$)$_2$)$_6$—, —U—(CH$_2$)$_4$—(O(CH$_2$)$_2$)$_7$—, —U—(CH$_2$)$_4$—(O(CH$_2$)$_2$)$_8$—, —U—(CH$_2$)$_4$—(O(CH$_2$)$_2$)$_9$—, —U—(CH$_2$)$_4$—(O(CH$_2$)$_2$)$_{10}$—, —U—CH$_2$—O—(CH$_2$)$_3$—, —U—CH$_2$—(O(CH$_2$)$_3$)$_2$—, —U—CH$_2$—(O(CH$_2$)$_3$)$_3$—, —U—CH$_2$—(O(CH$_2$)$_3$)$_4$—, —U—CH$_2$—(O(CH$_2$)$_3$)$_5$—, —U—CH$_2$—(O(CH$_2$)$_3$)$_6$—, —U—CH$_2$—(O(CH$_2$)$_3$)$_7$—, —U—CH$_2$—(O(CH$_2$)$_3$)$_8$—, —U—CH$_2$—(O(CH$_2$)$_3$)$_9$—, —U—CH$_2$—(O(CH$_2$)$_3$)$_{10}$—, —U—(CH$_2$)$_2$—O—(CH$_2$)$_3$—, —U—(CH$_2$)$_2$—(O(CH$_2$)$_3$)$_2$—, —U—(CH$_2$)$_2$—(O(CH$_2$)$_3$)$_3$—, —U—(CH$_2$)$_2$—(O(CH$_2$)$_3$)$_4$—, —U—(CH$_2$)$_2$—(O(CH$_2$)$_3$)$_5$—, —U—(CH$_2$)$_2$—(O(CH$_2$)$_3$)$_6$—, —U—(CH$_2$)$_2$—(O(CH$_2$)$_3$)$_7$—, —U—(CH$_2$)$_2$—(O(CH$_2$)$_3$)$_8$—, —U—(CH$_2$)$_2$—(O(CH$_2$)$_3$)$_9$—, —U—(CH$_2$)$_2$—(O(CH$_2$)$_3$)$_{10}$—, —U—(CH$_2$)$_3$—O—(CH$_2$)$_3$—, —U—(CH$_2$)$_3$—(O(CH$_2$)$_3$)$_2$—, —U—(CH$_2$)$_3$—(O(CH$_2$)$_3$)$_3$—, —U—(CH$_2$)$_3$—(O(CH$_2$)$_3$)$_4$—, —U—(CH$_2$)$_3$—(O(CH$_2$)$_3$)$_5$—, —U—(CH$_2$)$_3$—(O(CH$_2$)$_3$)$_6$—, —U—(CH$_2$)$_3$—(O(CH$_2$)$_3$)$_7$—, —U—(CH$_2$)$_3$—(O(CH$_2$)$_3$)$_8$—, —U—(CH$_2$)$_3$—(O(CH$_2$)$_3$)$_9$—, —U—(CH$_2$)$_3$—(O(CH$_2$)$_3$)$_{10}$—, —U—CH$_2$—O—(CH$_2$)$_2$—O—(CH$_2$)$_3$—, —U—CH$_2$—(O(CH$_2$)$_2$)$_2$—(O(CH$_2$)$_3$)$_2$—, —U—CH$_2$—(O(CH$_2$)$_2$)$_3$—(O(CH$_2$)$_3$)$_3$—, —U—CH$_2$—(O(CH$_2$)$_2$)$_4$—(O(CH$_2$)$_3$)$_4$—, —U—CH$_2$—(O(CH$_2$)$_2$)$_5$—(O(CH$_2$)$_3$)$_5$—, —U—CH$_2$—(O(CH$_2$)$_2$)$_6$—(O(CH$_2$)$_3$)$_6$—, —U—(CH$_2$)$_2$—O—(CH$_2$)$_2$—O—(CH$_2$)$_3$—, —U—(CH$_2$)$_2$—(O(CH$_2$)$_2$)$_2$—(O(CH$_2$)$_3$)$_2$—, —U—(CH$_2$)$_2$—(O(CH$_2$)$_2$)$_3$—(O(CH$_2$)$_3$)$_3$—, —U—(CH$_2$)$_2$—(O(CH$_2$)$_2$)$_4$—(O(CH$_2$)$_3$)$_4$—(O(CH$_2$)$_3$)$_4$—, —U—(CH$_2$)$_2$—(O(CH$_2$)$_2$)$_5$—(O(CH$_2$)$_3$)$_5$—, —U—(CH$_2$)$_2$—(O(CH$_2$)$_2$)$_6$—(O(CH$_2$)$_3$)$_6$—, —U—(CH$_2$)$_3$—O—(CH$_2$)$_2$—O—(CH$_2$)$_3$—, —U—(CH$_2$)$_3$—(O(CH$_2$)$_2$)$_2$—(O(CH$_2$)$_3$)$_2$—, —U—(CH$_2$)$_3$—(O(CH$_2$)$_2$)$_3$—(O(CH$_2$)$_3$)$_3$—, —U—(CH$_2$)$_3$—(O(CH$_2$)$_2$)$_4$—(O(CH$_2$)$_3$)$_4$—, —U—(CH$_2$)$_3$—(O(CH$_2$)$_2$)$_5$—(O(CH$_2$)$_3$)$_5$—, —U—(CH$_2$)$_3$—(O(CH$_2$)$_2$)$_6$—(O(CH$_2$)$_3$)$_6$—, —U—CH$_2$—O—(CH$_2$)$_2$—O—CH$_2$—, —U—(CH$_2$)$_2$—O—(CH$_2$)$_2$—O—CH$_2$—, —U—(CH$_2$)$_2$—(O(CH$_2$)$_2$)$_2$—O—(CH$_2$)$_3$—, —U—(CH$_2$)$_2$—(O(CH$_2$)$_2$)$_3$—O—(CH$_2$)$_3$—, —U—(CH$_2$)$_2$—(O(CH$_2$)$_2$)$_4$—O—(CH$_2$)$_3$—, —U—(CH$_2$)$_5$—(O(CH$_2$)$_2$)$_2$—O—(CH$_2$)$_5$—, or —U—(CH$_2$)$_5$—(O(CH$_2$)$_2$)$_2$—O—(CH$_2$)$_6$—; wherein the group U represents CO or NH, or the group U is absent.

In an embodiment of the present disclosure, the compound of formula (I) is also the compound of formula (Ie-2):

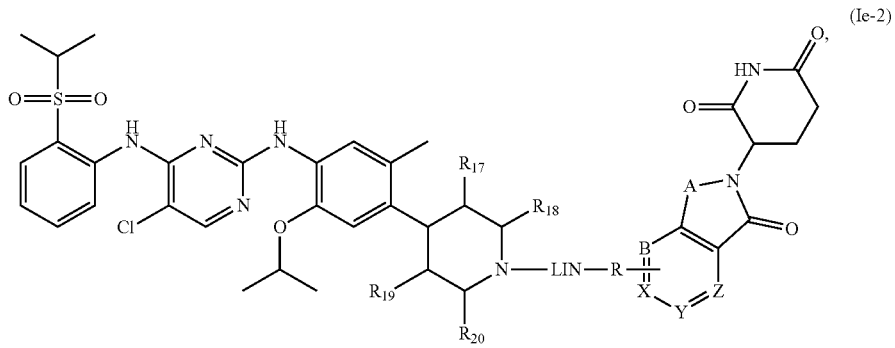

(Ie-2)

wherein, the groups LIN, R, A, B, X, Y and Z are as defined above, and the groups R$_{17}$, R$_{18}$, R$_{19}$ and R$_{20}$ are as defined above.

In an embodiment of the present disclosure, the compound of formula (I) is also the compound of formula (Ie-3):

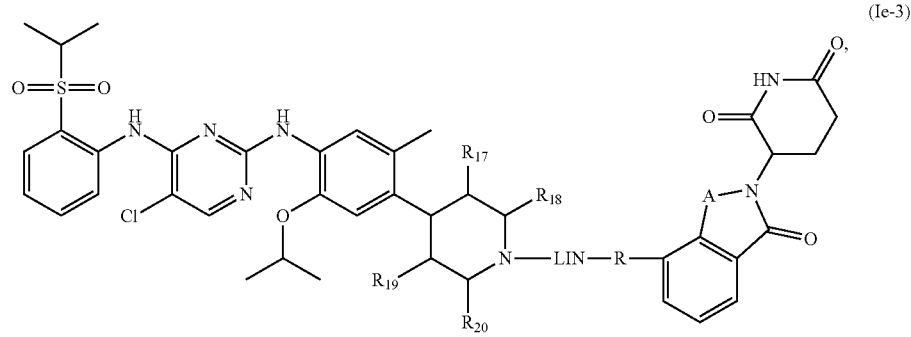

(Ie-3)

wherein, the groups LIN, R and A are as defined above, and the groups $R_{17}$, $R_{18}$, $R_{19}$ and $R_{20}$ are as defined above.

In a sub-embodiment of the compound of formula (Ie-3) of the present disclosure, the LIN represents —U—$C_{1-30}$ alkylene-; and the group U represents CO or NH, or the group U is absent. In a sub-embodiment of the compound of formula (Ie-3), the LIN represents: —U—$CH_2$—; —U—$(CH_2)_2$—; —U—$(CH_2)_3$—; —U—$(CH_2)_4$—; —U—$(CH_2)_5$—; —U—$(CH_2)_6$—; —U—$(CH_2)_7$—; —U—$(CH_2)_8$—; —U—$(CH_2)_9$—; —U—$(CH_2)_{10}$—; —U—$(CH_2)_{11}$—; —U—$(CH_2)_{12}$—; —U—$(CH_2)_{13}$—; —U—$(CH_2)_{14}$—; —U—$(CH_2)_{15}$—; —U—$(CH_2)_{16}$—; —U—$(CH_2)_{17}$—; —U—$(CH_2)_{18}$—; —U—$(CH_2)_{19}$—; —U—$(CH_2)_{20}$—; —U—$(CH_2)_{21}$—; —U—$(CH_2)_{22}$—; —U—$(CH_2)_{23}$—; —U—$(CH_2)_{24}$—; —U—$(CH_2)_{25}$—; —U—$(CH_2)_{26}$—; —U—$(CH_2)_{27}$—; —U—$(CH_2)_{28}$—; —U—$(CH_2)_{29}$—; or U—$(CH_2)_{30}$—; wherein the group U represents CO or NH, or the group U is absent.

In a sub-embodiment of the compound of formula (Ie-3) of the present disclosure, the LIN is preferably —U—$C_{2-40}$ alkylene-(preferably —U—$C_{2-30}$ alkylene-), wherein the alkylene chain is optionally interrupted one or more times by one or more of O, CONH, NHCO, NH, alkynylene, alkenylene, cycloalkylene, arylene, heterocyclylene or heteroarylene or any combination thereof, and the group U represents CO or NH, or the group U is absent. In a sub-embodiment of the compound of formula (Ie-3), the LIN preferably represents: —U—$(CH_2)_{n1}$—$(O(CH_2)_{n2})_{m1}$— or —U—$(CH_2)_{n1}$—$(O(CH_2)_{n2})_{m1}$—$(O(CH_2)_{n3})_{m2}$—, wherein n1, n2, n3, m1 and m2 each independently represent an integer of 1, 2, 3, 4, 5, 6, 7, 8, 9, 10, 11, 12, 13, 14, 15, 16, 17, 18, 19 or 20; and wherein the group U represents CO or NH, or the group U is absent. In a sub-embodiment of the compound of formula (Ie-3), the LIN preferably represents: —U—$CH_2$—O—$(CH_2)_2$—, —U—$CH_2$—$(O(CH_2)_2)_2$—, —U—$CH_2$—$(O(CH_2)_2)_3$—, —U—$CH_2$—$(O(CH_2)_2)_4$—, —U—$CH_2$—$(O(CH_2)_2)_5$—, —U—$CH_2$—$(O(CH_2)_2)_6$—, —U—$CH_2$—$(O(CH_2)_2)_7$—, —U—$CH_2$—$(O(CH_2)_2)_8$—, —U—$CH_2$—$(O(CH_2)_2)_9$—, —U—$CH_2$—$(O(CH_2)_2)_{10}$—, —U—$(CH_2)_2$—O—$(CH_2)_2$—, —U—$(CH_2)_2$—$(O(CH_2)_2)_2$—, —U—$(CH_2)_2$—$(O(CH_2)_2)_3$—, —U—$(CH_2)_2$—$(O(CH_2)_2)_4$—, —U—$(CH_2)_2$—$(O(CH_2)_2)_5$—, —U—$(CH_2)_2$—$(O(CH_2)_2)_6$—, —U—$(CH_2)_2$—$(O(CH_2)_2)_7$—, —U—$(CH_2)_2$—$(O(CH_2)_2)_8$—, —U—$(CH_2)_2$—$(O(CH_2)_2)_9$—, —U—$(CH_2)_2$—$(O(CH_2)_2)_{10}$—, —U—$(CH_2)_3$—O—$(CH_2)_2$—, —U—$(CH_2)_3$—$(O(CH_2)_2)_2$—, —U—$(CH_2)_3$—$(O(CH_2)_2)_3$—, —U—$(CH_2)_3$—$(O(CH_2)_2)_4$—, —U—$(CH_2)_3$—$(O(CH_2)_2)_5$—, —U—$(CH_2)_3$—$(O(CH_2)_2)_6$—, —U—$(CH_2)_3$—$(O(CH_2)_2)_7$—, —U—$(CH_2)_3$—$(O(CH_2)_2)_8$—, —U—$(CH_2)_3$—$(O(CH_2)_2)_9$—, —U—$(CH_2)_3$—$(O(CH_2)_2)_{10}$—, —U—$(CH_2)_4$—O—$(CH_2)_2$—, —U—$(CH_2)_4$—$(O(CH_2)_2)_2$—, —U—$(CH_2)_4$—$(O(CH_2)_2)_3$—, —U—$(CH_2)_4$—$(O(CH_2)_2)_4$—, —U—$(CH_2)_4$—$(O(CH_2)_2)_5$—, —U—$(CH_2)_4$—$(O(CH_2)_2)_6$—, —U—$(CH_2)_4$—$(O(CH_2)_2)_7$—, —U—$(CH_2)_4$—$(O(CH_2)_2)_8$—, —U—$(CH_2)_4$—$(O(CH_2)_2)_9$—, —U—$(CH_2)_4$—$(O(CH_2)_2)_{10}$—, —U—$CH_2$—O—$(CH_2)_3$—, —U—$CH_2$—$(O(CH_2)_3)_2$—, —U—$CH_2$—$(O(CH_2)_3)_3$—, —U—$CH_2$—$(O(CH_2)_3)_4$—, —U—$CH_2$—$(O(CH_2)_3)_5$—, —U—$CH_2$—$(O(CH_2)_3)_6$—, —U—$CH_2$—$(O(CH_2)_3)_7$—, —U—$CH_2$—$(O(CH_2)_3)_8$—, —U—$CH_2$—$(O(CH_2)_3)_9$—, —U—$CH_2$—$(O(CH_2)_3)_{10}$—, —U—$(CH_2)_2$—O—$(CH_2)_3$—, —U—$(CH_2)_2$—$(O(CH_2)_3)_2$—, —U—$(CH_2)_2$—$(O(CH_2)_3)_3$—, —U—$(CH_2)_2$—$(O(CH_2)_3)_4$—, —U—$(CH_2)_2$—$(O(CH_2)_3)_5$—, —U—$(CH_2)_2$—$(O(CH_2)_3)_6$—, —U—$(CH_2)_2$—$(O(CH_2)_3)_7$—, —U—$(CH_2)_2$—$(O(CH_2)_3)_8$—, —U—$(CH_2)_2$—$(O(CH_2)_3)_9$—, —U—$(CH_2)_2$—$(O(CH_2)_3)_{10}$—, —U—$(CH_2)_3$—O—$(CH_2)_3$—, —U—$(CH_2)_3$—$(O(CH_2)_3)_2$—, —U—$(CH_2)_3$—$(O(CH_2)_3)_3$—, —U—$(CH_2)_3$—$(O(CH_2)_3)_4$—, —U—$(CH_2)_3$—$(O(CH_2)_3)_5$—, —U—$(CH_2)_3$—$(O(CH_2)_3)_6$—, —U—$(CH_2)_3$—$(O(CH_2)_3)_7$—, —U—$(CH_2)_3$—$(O(CH_2)_3)_8$—, —U—$(CH_2)_3$—$(O(CH_2)_3)_9$—, —U—$(CH_2)_3$—$(O(CH_2)_3)_{10}$—, —U—$CH_2$—O—$(CH_2)_2$—O—$(CH_2)_3$—, —U—$CH_2$—$(O(CH_2)_2)_2$—$(O(CH_2)_3)_2$—, —U—$CH_2$—$(O(CH_2)_2)_3$—$(O(CH_2)_3)_3$—, —U—$CH_2$—$(O(CH_2)_2)_4$—$(O(CH_2)_3)_4$—, —U—$CH_2$—$(O(CH_2)_2)_5$—$(O(CH_2)_3)_5$—, —U—$CH_2$—$(O(CH_2)_2)_6$—$(O(CH_2)_3)_6$—, —U—$(CH_2)_2$—O—$(CH_2)_2$—O—$(CH_2)_3$—, —U—$(CH_2)_2$—$(O(CH_2)_2)_2$—$(O(CH_2)_3)_2$—, —U—$(CH_2)_2$—$(O(CH_2)_2)_3$—$(O(CH_2)_3)_3$—, —U—$(CH_2)_2$—$(O(CH_2)_2)_4$—$(O(CH_2)_3)_4$—, —U—$(CH_2)_2$—$(O(CH_2)_2)_5$—$(O(CH_2)_3)_5$—, —U—$(CH_2)_2$—$(O(CH_2)_2)_6$—$(O(CH_2)_3)_6$—, —U—$(CH_2)_3$—O—$(CH_2)_2$—O—$(CH_2)_3$—, —U—$(CH_2)_3$—$(O(CH_2)_2)_2$—$(O(CH_2)_3)_2$—, —U—$(CH_2)_3$—$(O(CH_2)_2)_3$—$(O(CH_2)_3)_3$—, —U—$(CH_2)_3$—$(O(CH_2)_2)_4$—$(O(CH_2)_3)_4$—, —U—$(CH_2)_3$—$(O(CH_2)_2)_5$—$(O(CH_2)_3)_5$—, —U—$(CH_2)_3$—$(O(CH_2)_2)_6$—$(O(CH_2)_3)_6$—, —U—$CH_2$—O—$(CH_2)_2$—O—$CH_2$—, —U—$(CH_2)_2$—O—$(CH_2)_2$—O—$CH_2$—, —U—$(CH_2)_2$—$(O(CH_2)_2)_2$—O—$(CH_2)_3$—, —U—$(CH_2)_2$—$(O(CH_2)_2)_3$—O—$(CH_2)_3$—, —U—$(CH_2)_2$—$(O(CH_2)_2)_4$—O—$(CH_2)_3$—, —U—$(CH_2)_5$—$(O(CH_2)_2)_2$—O—$(CH_2)_5$—, or —U—$(CH_2)_5$—$(O(CH_2)_2)_2$—O—$(CH_2)_6$—; wherein the group U represents CO or NH, or the group U is absent.

In an embodiment of the present disclosure, the compound of formula (I) is also the compound of formula (If-2):

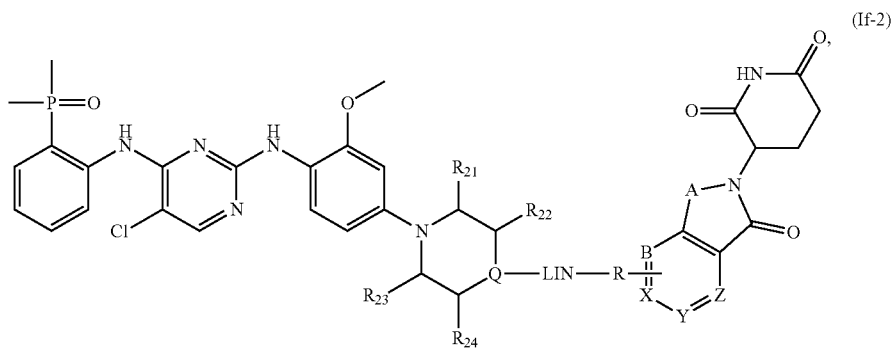

(If-2)

wherein, the groups LIN, R, A, B, X, Y and Z are as defined above, and the groups $R_{21}$, $R_{22}$, $R_{23}$ and $R_{24}$ are as defined above.

In an embodiment of the present disclosure, the compound of formula (I) is also the compound of formula (If-2-1):

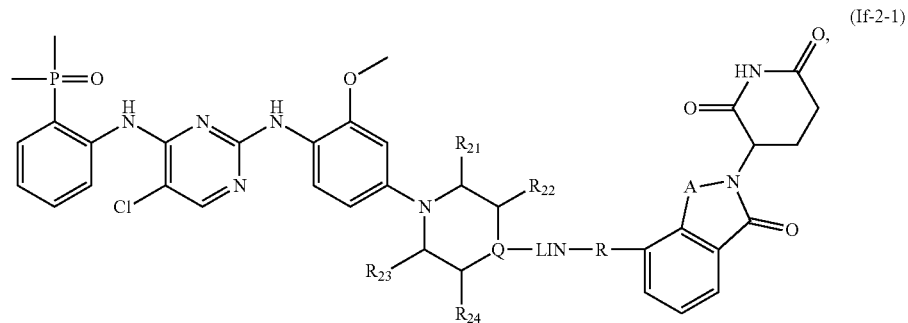

(If-2-1)

wherein, the groups LIN, R and A are as defined above, and the groups $R_{21}$, $R_{22}$, $R_{23}$ and $R_{24}$ are as defined above, and Q is N or CH, wherein CH is connected to the group LIN through NH or piperazinylene.

In an embodiment of the present disclosure, the compound of formula (I) is also the compound of formula (If-2-2):

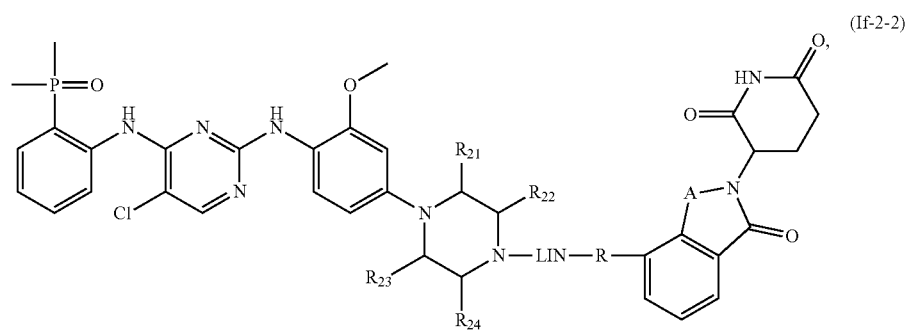

(If-2-2)

wherein, the groups LIN, R and A are as defined above, and the groups $R_{21}$, $R_{22}$, $R_{23}$ and $R_{24}$ are as defined above.

In an embodiment of the present disclosure, the compound of formula (I) is also the compound of formula (If-2-3):

(If-2-3)

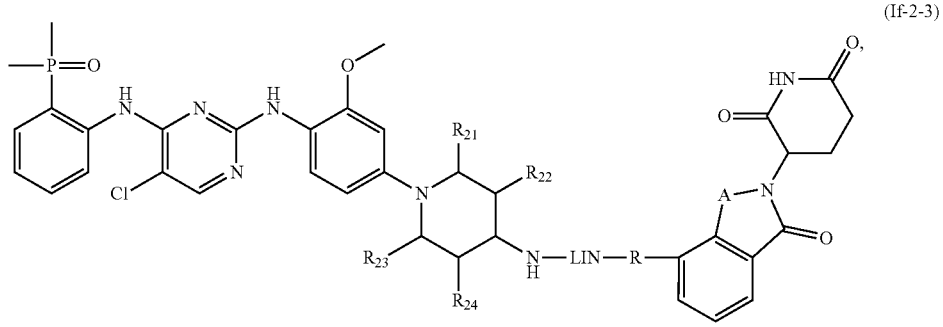

wherein, the groups LIN, R and A are as defined above, and the groups $R_{21}$, $R_{22}$, $R_{23}$ and $R_{24}$ are as defined above.

In an embodiment of the present disclosure, the compound of formula (I) is also the compound of formula (If-2-4):

(If-2-4)

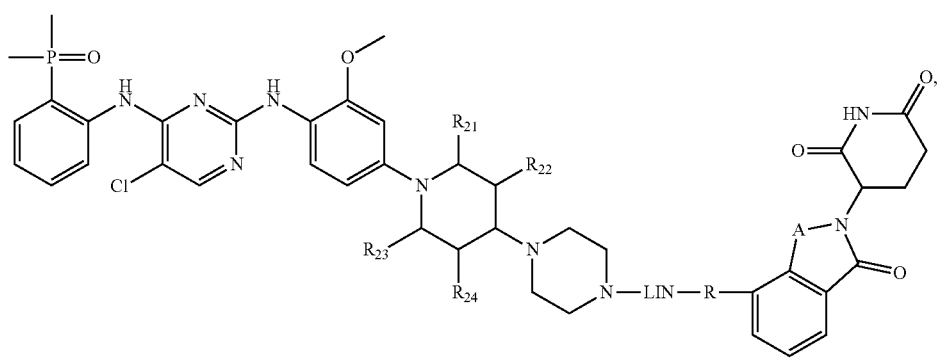

wherein, the groups LIN, R and A are as defined above, and the groups $R_{21}$, $R_{22}$, $R_{23}$ and $R_{24}$ are as defined above.

In a sub-embodiment of the compound of formula (If-2-1), (If-2-2), (If-2-3) or (If-2-4) in the present disclosure, the LIN represents —U—$C_{1-30}$ alkylene-; and the group U represents CO or NH, or the group U is absent. In a sub-embodiment of the compound of formula (If-2-1), (If-2-2), (If-2-3) or (If-2-4), the LIN represents: —U—$CH_2$—; —U—$(CH_2)_2$—; —U—$(CH_2)_3$—; —U—$(CH_2)_4$—; —U—$(CH_2)_5$—; —U—$(CH_2)_6$—; —U—$(CH_2)_7$—; —U—$(CH_2)_8$—; —U—$(CH_2)_9$—; —U—$(CH_2)_{10}$—; —U—$(CH_2)_{11}$—; —U—$(CH_2)_{12}$—; —U—$(CH_2)_{13}$—; —U—$(CH_2)_{14}$—; —U—$(CH_2)_{15}$—; —U—$(CH_2)_{16}$—; —U—$(CH_2)_{17}$—; —U—$(CH_2)_{18}$—; —U—$(CH_2)_{19}$—; —U—$(CH_2)_{20}$—; —U—$(CH_2)_{21}$—; —U—$(CH_2)_{22}$—; —U—$(CH_2)_{23}$—; —U—$(CH_2)_{24}$—; —U—$(CH_2)_{25}$—; —U—$(CH_2)_{26}$—; —U—$(CH_2)_{27}$—; —U—$(CH_2)_{28}$—; —U—$(CH_2)_{29}$—; or U—$(CH_2)_{30}$—; wherein the group U represents CO or NH, or the group U is absent.

In a sub-embodiment of the compound of formula (If-2-1), (If-2-2), (If-2-3) or (If-2-4) of the present disclosure, the LIN is preferably —U—$C_{2-40}$ alkylene-(preferably —U—$C_{2-30}$ alkylene-), wherein the alkylene chain is optionally interrupted one or more times by one or more of O, CONH, NHCO, NH, alkynylene, alkenylene, cycloalkylene, arylene, heterocyclylene or heteroarylene or any combination thereof, and the group U represents CO or NH, or the group U is absent. In a sub-embodiment of the compound of formula (If-2-1), (If-2-2), (If-2-3) or (If-2-4), the LIN preferably represents: —U—$(CH_2)_{n1}$—$(O(CH_2)_{n2})_{m1}$— or —U—$(CH_2)_{n1}$—$(O(CH_2)_{n2})_{m1}$—$(O(CH_2)_{n3})_{m2}$—, wherein n1, n2, n3, m1 and m2 each independently represent an integer of 1, 2, 3, 4, 5, 6, 7, 8, 9, 10, 11, 12, 13, 14, 15, 16, 17, 18, 19 or 20; and wherein the group U represents CO or NH, or the group U is absent. In a sub-embodiment of the compound of formula (If-2-1), (If-2-2), (If-2-3) or (If-2-4) of the present disclosure, the LIN preferably represents: —U—$CH_2$—O—$(CH_2)_2$—, —U—$CH_2$—$(O(CH_2)_2)_2$—, —U—$CH_2$—$(O(CH_2)_2)_3$—, —U—$CH_2$—$(O(CH_2)_2)_4$—, —U—$CH_2$—$(O(CH_2)_2)_5$—, —U—$CH_2$—$(O(CH_2)_2)_6$—, —U—$CH_2$—$(O(CH_2)_2)_7$—, —U—$CH_2$—$(O(CH_2)_2)_8$—, —U—$CH_2$—$(O(CH_2)_2)_9$—, —U—$CH_2$—$(O(CH_2)_2)_{10}$—, —U—$(CH_2)_2$—O—$(CH_2)_2$—, —U—$(CH_2)_2$—$(O(CH_2)_2)_2$—, —U—$(CH_2)_2$—$(O(CH_2)_2)_3$—, —U—$(CH_2)_2$—$(O(CH_2)_2)_4$—, —U—$(CH_2)_2$—$(O(CH_2)_2)_5$—, —U—$(CH_2)_2$—$(O(CH_2)_2)_6$—, —U—$(CH_2)_2$—$(O(CH_2)_2)_7$—, —U—$(CH_2)_2$—$(O(CH_2)_2)_8$—, —U—$(CH_2)_2$—$(O(CH_2)_2)_9$—, —U—$(CH_2)_2$—$(O(CH_2)_2)_{10}$—, —U—$(CH_2)_3$—O—$(CH_2)_2$—, —U—$(CH_2)_3$—$(O(CH_2)_2)_2$—, —U—$(CH_2)_3$—$(O(CH_2)_2)_3$—, —U—$(CH_2)_3$—$(O(CH_2)_2)_4$—, —U—$(CH_2)_3$—$(O(CH_2)_2)_5$—, —U—$(CH_2)_3$—$(O(CH_2)_2)_6$—, —U—$(CH_2)_3$—$(O(CH_2)_2)_7$—, —U—$(CH_2)_3$—$(O(CH_2)_2)_8$—, —U—$(CH_2)_3$—$(O(CH_2)_2)_9$—, —U—$(CH_2)_3$—$(O(CH_2)_2)_{10}$—, —U—$(CH_2)_4$—O—$(CH_2)_2$—, —U—$(CH_2)_4$—$(O(CH_2)_2)_2$—, —U—$(CH_2)_4$—$(O(CH_2)_2)_3$—, —U—$(CH_2)_4$—$(O(CH_2)_2)_4$—, —U—$(CH_2)_4$—$(O(CH_2)_2)_5$—, —U—$(CH_2)_4$—$(O(CH_2)_2)_6$—, —U—$(CH_2)_4$—$(O(CH_2)_2)_7$—, —U—$(CH_2)_4$—$(O(CH_2)_2)_8$—, —U—$(CH_2)_4$—$(O(CH_2)_2)_9$—, —U—$(CH_2)_4$—$(O(CH_2)_2)_{10}$—, —U—$CH_2$—O—$(CH_2)_3$—, —U—$CH_2$—$(O(CH_2)_3)_2$—, —U—CH$_2$—(O(CH$_2$)$_3$)$_3$—, —U—CH$_2$—(O(CH$_2$)$_3$)$_4$—, —U—CH$_2$—(O(CH$_2$)$_3$)$_5$—, —U—CH$_2$—(O(CH$_2$)$_3$)$_6$—, —U—CH$_2$—(O(CH$_2$)$_3$)$_7$—, —U—CH$_2$—(O(CH$_2$)$_3$)$_8$—, —U—CH$_2$—(O(CH$_2$)$_3$)$_9$—, —U—CH$_2$—(O(CH$_2$)$_3$)$_{10}$—, —U—(CH$_2$)$_2$—O—(CH$_2$)$_3$—, —U—(CH$_2$)$_2$—(O(CH$_2$)$_3$)$_2$—, —U—(CH$_2$)$_2$—(O(CH$_2$)$_3$)$_3$—, —U—(CH$_2$)$_2$—(O(CH$_2$)$_3$)$_4$—, —U—(CH$_2$)$_2$—(O(CH$_2$)$_3$)$_5$—, —U—(CH$_2$)$_2$—(O(CH$_2$)$_3$)$_6$—, —U—(CH$_2$)$_2$—(O(CH$_2$)$_3$)$_7$—, —U—(CH$_2$)$_2$—(O(CH$_2$)$_3$)$_8$—, —U—(CH$_2$)$_2$—(O(CH$_2$)$_3$)$_9$—, —U—(CH$_2$)$_2$—(O(CH$_2$)$_3$)$_{10}$—, —U—(CH$_2$)$_3$—O—(CH$_2$)$_3$—, —U—(CH$_2$)$_3$—(O(CH$_2$)$_3$)$_2$—, —U—(CH$_2$)$_3$—(O(CH$_2$)$_3$)$_3$—, —U—(CH$_2$)$_3$—(O(CH$_2$)$_3$)$_4$—, —U—(CH$_2$)$_3$—(O(CH$_2$)$_3$)$_5$—, —U—(CH$_2$)$_3$—(O(CH$_2$)$_3$)$_6$—, —U—(CH$_2$)$_3$—(O(CH$_2$)$_3$)$_7$—, —U—(CH$_2$)$_3$—(O(CH$_2$)$_3$)$_8$—, —U—(CH$_2$)$_3$—(O(CH$_2$)$_3$)$_9$—, —U—(CH$_2$)$_3$—(O(CH$_2$)$_3$)$_{10}$—, —U—CH$_2$—O—(CH$_2$)$_2$—O—(CH$_2$)$_3$—, —U—CH$_2$—(O(CH$_2$)$_2$)$_2$—(O(CH$_2$)$_3$)$_2$—, —U—CH$_2$—(O(CH$_2$)$_2$)$_3$—(O(CH$_2$)$_3$)$_3$—, —U—CH$_2$—(O(CH$_2$)$_2$)$_4$—(O(CH$_2$)$_3$)$_4$—, —U—CH$_2$—(O(CH$_2$)$_2$)$_5$—(O(CH$_2$)$_3$)$_5$—, —U—CH$_2$—(O(CH$_2$)$_2$)$_6$—(O(CH$_2$)$_3$)$_6$—, —U—(CH$_2$)$_2$—O—(CH$_2$)$_2$—O—(CH$_2$)$_3$—, —U—(CH$_2$)$_2$ —(O(CH$_2$)$_2$)$_2$—(O(CH$_2$)$_3$)$_2$—, —U—(CH$_2$)$_2$—(O(CH$_2$)$_2$)$_3$—(O(CH$_2$)$_3$)$_3$—, —U—(CH$_2$)$_2$—(O(CH$_2$)$_2$)$_4$—(O(CH$_2$)$_3$)$_4$—, —U—(CH$_2$)$_2$—(O(CH$_2$)$_2$)$_5$—(O(CH$_2$)$_3$)$_5$—, —U—(CH$_2$)$_2$—(O(CH$_2$)$_2$)$_6$—(O(CH$_2$)$_3$)$_6$—, —U—(CH$_2$)$_3$—O—(CH$_2$)$_2$—O—(CH$_2$)$_3$—, —U—(CH$_2$)$_3$—(O(CH$_2$)$_2$)$_2$—(O(CH$_2$)$_3$)$_2$—, —U—(CH$_2$)$_3$—(O(CH$_2$)$_2$)$_3$—(O(CH$_2$)$_3$)$_3$—, —U—(CH$_2$)$_3$—(O(CH$_2$)$_2$)$_4$—(O(CH$_2$)$_3$)$_4$—, —U—(CH$_2$)$_3$—(O(CH$_2$)$_2$)$_5$—(O(CH$_2$)$_3$)$_5$—, —U—(CH$_2$)$_3$—(O(CH$_2$)$_2$)$_6$—(O(CH$_2$)$_3$)$_6$—, —U—CH$_2$—O—(CH$_2$)$_2$—O—CH$_2$—, —U—(CH$_2$)$_2$—O—(CH$_2$)$_2$—O—CH$_2$—, —U—(CH$_2$)$_2$—(O(CH$_2$)$_2$)$_2$—O—(CH$_2$)$_3$—, —U—(CH$_2$)$_2$—(O(CH$_2$)$_2$)$_3$—O—(CH$_2$)$_3$—, —U—(CH$_2$)$_2$—(O(CH$_2$)$_2$)$_4$—O—(CH$_2$)$_3$—, —U—(CH$_2$)$_5$—(O(CH$_2$)$_2$)$_2$—O—(CH$_2$)$_5$—, or —U—(CH$_2$)$_5$—(O(CH$_2$)$_2$)$_2$—O—(CH$_2$)$_6$—; wherein the group U represents CO or NH, or the group U is absent.

In an embodiment of the present disclosure, the compound of formula (I) is also the compound of formula (If-3):

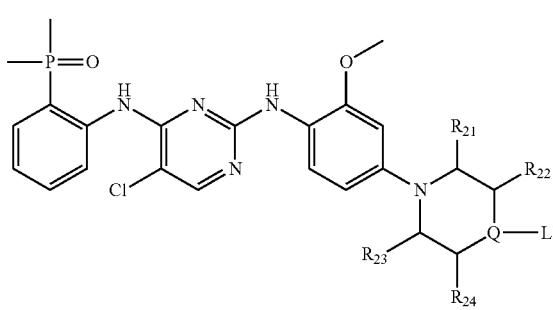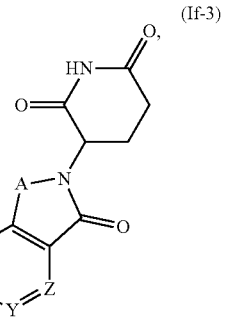

(If-3)

wherein, the groups LIN, R, A, B, X, Y and Z are as defined above, and the groups R$_{21}$, R$_{22}$, R$_{23}$ and R$_{24}$ are each independently H or methyl, and Q is CH, wherein CH is connected to the group LIN through N(CH$_3$).

In an embodiment of the present disclosure, the compound of formula (I) is also the compound of formula (If-3-1):

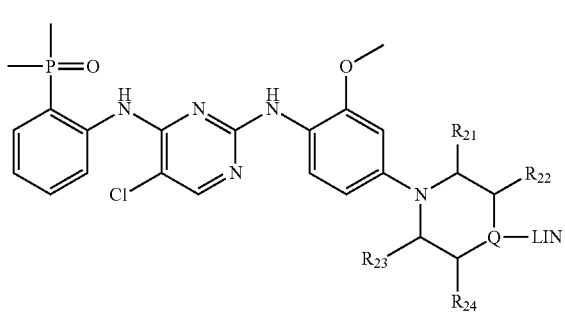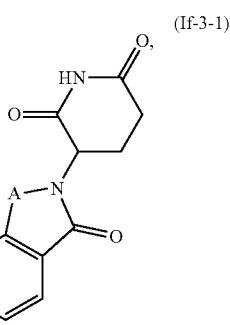

(If-3-1)

wherein, the groups LIN, R and A are as defined above, and the groups R$_{21}$, R$_{22}$, R$_{23}$ and R$_{24}$ are each independently H or methyl, and Q is CH, wherein CH is connected to the group LIN through N(CH$_3$).

In an embodiment of the present disclosure, the compound of formula (I) is also the compound of formula (If-3-2):

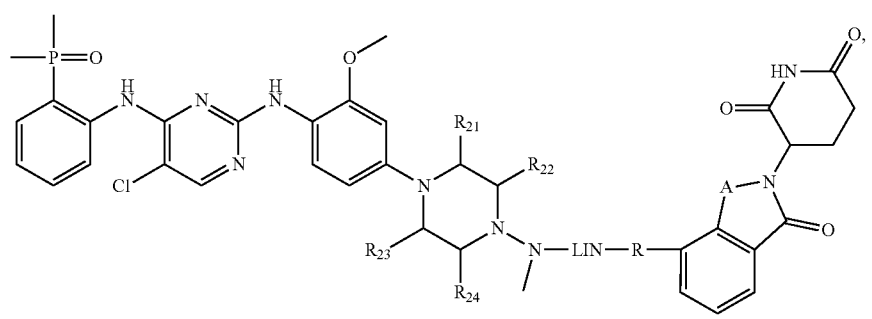

(If-3-2)

wherein, the groups LIN, R and A are as defined above, and the groups $R_{21}$, $R_{22}$, $R_{23}$ and $R_{24}$ are each independently H or methyl.

In a sub-embodiment of the compound of formula (If-3-1) or formula (If-3-2) of the present disclosure, the LIN represents —U—$C_{1-30}$ alkylene-; and the group U represents CO or NH, or the group U is absent. In a sub-embodiment of the compound of formula (If-3-1) or formula (If-3-2), the LIN represents: —U—$CH_2$—; —U—$(CH_2)_2$—; —U—$(CH_2)_3$—; —U—$(CH_2)_4$—; —U—$(CH_2)_5$—; —U—$(CH_2)_6$—; —U—$(CH_2)_7$—; —U—$(CH_2)_8$—; —U—$(CH_2)_9$—; —U—$(CH_2)_{10}$—; —U—$(CH_2)_{11}$—; —U—$(CH_2)_{12}$—; —U—$(CH_2)_{13}$—; —U—$(CH_2)_{14}$—; —U—$(CH_2)_{15}$—; —U—$(CH_2)_{16}$—; —U—$(CH_2)_{17}$—; —U—$(CH_2)_{18}$—; —U—$(CH_2)_{19}$—; —U—$(CH_2)_{20}$—; —U—$(CH_2)_{21}$—; —U—$(CH_2)_{22}$—; —U—$(CH_2)_{23}$—; —U—$(CH_2)_{24}$—; —U—$(CH_2)_{25}$—; —U—$(CH_2)_{26}$—; —U—$(CH_2)_{27}$—; —U—$(CH_2)_{28}$—; —U—$(CH_2)_{29}$—; or —U—$(CH_2)_{30}$—; wherein the group U represents CO or NH, or the group U is absent.

In a sub-embodiment of the compound of formula (If-3-1) or formula (If-3-2) of the present disclosure, the LIN is preferably —U—$C_{2-40}$ alkylene-(preferably —U—$C_{2-30}$ alkylene-), wherein the alkylene chain is optionally interrupted one or more times by one or more of O, CONH, NHCO, NH, alkynylene, alkenylene, cycloalkylene, arylene, heterocyclylene or heteroarylene or any combination thereof, and the group U represents CO or NH, or the group U is absent. In a sub-embodiment of the compound of formula (If-3-1) or formula (If-3-2), the LIN preferably represents: —U—$(CH_2)_{n1}$—$(O(CH_2)_{n2})_{m1}$— or —U—$(CH_2)_{n1}$—$(O(CH_2)_{n2})_{n1}$—$(O(CH_2)_{n3})_{m2}$—, wherein n1, n2, n3, m1 and m2 each independently represent an integer of 1, 2, 3, 4, 5, 6, 7, 8, 9, 10, 11, 12, 13, 14, 15, 16, 17, 18, 19 or 20; and wherein the group U represents CO or NH, or the group U is absent. In a sub-embodiment of the compound of formula (If-3-1) or formula (If-3-2), the LIN preferably represents: —U—$CH_2$—O—$(CH_2)_2$—, —U—$CH_2$—$(O(CH_2)_2)_2$—, —U—$CH_2$—$(O(CH_2)_2)_3$—, —U—$CH_2$—$(O(CH_2)_2)_4$—, —U—$CH_2$—$(O(CH_2)_2)_5$—, —U—$CH_2$—$(O(CH_2)_2)_6$—, —U—$CH_2$—$(O(CH_2)_2)_7$—, —U—$CH_2$—$(O(CH_2)_2)_8$—, —U—$CH_2$—$(O(CH_2)_2)_9$—, —U—$CH_2$—$(O(CH_2)_2)_{10}$—, —U—$(CH_2)_2$—O—$(CH_2)_2$—, —U—$(CH_2)_2$—$(O(CH_2)_2)_2$—, —U—$(CH_2)_2$—$(O(CH_2)_2)_3$—, —U—$(CH_2)_2$—$(O(CH_2)_2)_4$—, —U—$(CH_2)_2$—$(O(CH_2)_2)_5$—, —U—$(CH_2)_2$—$(O(CH_2)_2)_6$—, —U—$(CH_2)_2$—$(O(CH_2)_2)_7$—, —U—$(CH_2)_2$—$(O(CH_2)_2)_8$—, —U—$(CH_2)_2$—$(O(CH_2)_2)_9$—, —U—$(CH_2)_2$—$(O(CH_2)_2)_{10}$—, —U—$(CH_2)_3$—O—$(CH_2)_2$—, —U—$(CH_2)_3$—$(O(CH_2)_2)_2$—, —U—$(CH_2)_3$—$(O(CH_2)_2)_3$—, —U—$(CH_2)_3$—$(O(CH_2)_2)_4$—, —U—$(CH_2)_3$—$(O(CH_2)_2)_5$—, —U—$(CH_2)_3$—$(O(CH_2)_2)_6$—, —U—$(CH_2)_3$—$(O(CH_2)_2)_7$—, —U—$(CH_2)_3$—$(O(CH_2)_2)_8$—, —U—$(CH_2)_3$—$(O(CH_2)_2)_9$—, —U—$(CH_2)_3$—$(O(CH_2)_2)_{19}$—, —U—$(CH_2)_4$—O—$(CH_2)_2$—, —U—$(CH_2)_4$—$(O(CH_2)_2)_2$—, —U—$(CH_2)_4$—$(O(CH_2)_2)_3$—, —U—$(CH_2)_4$—$(O(CH_2)_2)_4$—, —U—$(CH_2)_4$—$(O(CH_2)_2)_5$—, —U—$(CH_2)_4$—$(O(CH_2)_2)_6$—, —U—$(CH_2)_4$—$(O(CH_2)_2)_7$—, —U—$(CH_2)_4$—$(O(CH_2)_2)_8$—, —U—$(CH_2)_4$—$(O(CH_2)_2)_9$—, —U—$(CH_2)_4$—$(O(CH_2)_2)_{10}$—, —U—$CH_2$—O—$(CH_2)_3$—, —U—$CH_2$—$(O(CH_2)_3)_2$—, —U—$CH_2$—$(O(CH_2)_3)_3$—, —U—$CH_2$—$(O(CH_2)_3)_4$—, —U—$CH_2$—$(O(CH_2)_3)_5$—, —U—$CH_2$—$(O(CH_2)_3)_6$—, —U—$CH_2$—$(O(CH_2)_3)_7$—, —U—$CH_2$—$(O(CH_2)_3)_8$—, —U—$CH_2$—$(O(CH_2)_3)_9$—, —U—$CH_2$—$(O(CH_2)_3)_{10}$—, —U—$(CH_2)_2$—O—$(CH_2)_3$—, —U—$(CH_2)_2$—$(O(CH_2)_3)_2$—, —U—$(CH_2)_2$—$(O(CH_2)_3)_3$—, —U—$(CH_2)_2$—$(O(CH_2)_3)_4$—, —U—$(CH_2)_2$—$(O(CH_2)_3)_5$—, —U—$(CH_2)_2$—$(O(CH_2)_3)_6$—, —U—$(CH_2)_2$—$(O(CH_2)_3)_7$—, —U—$(CH_2)_2$—$(O(CH_2)_3)_5$—, —U—$(CH_2)_2$—$(O(CH_2)_3)_9$—, —U—$(CH_2)_2$—$(O(CH_2)_3)_{10}$—, —U—$(CH_2)_3$—O—$(CH_2)_3$—, —U—$(CH_2)_3$—$(O(CH_2)_3)_2$—, —U—$(CH_2)_3$—$(O(CH_2)_3)_3$—, —U—$(CH_2)_3$—$(O(CH_2)_3)_4$—, —U—$(CH_2)_3$—$(O(CH_2)_3)_5$—, —U—$(CH_2)_3$—$(O(CH_2)_3)_6$—, —U—$(CH_2)_3$—$(O(CH_2)_3)_7$—, —U—$(CH_2)_3$—$(O(CH_2)_3)_8$—, —U—$(CH_2)_3$—$(O(CH_2)_3)_9$—, —U—$(CH_2)_3$—$(O(CH_2)_3)_{10}$—, —U—$CH_2$—O—$(CH_2)_2$—O—$(CH_2)_3$—, —U—$CH_2$—$(O(CH_2)_2)_2$—$(O(CH_2)_3)_2$—, —U—$CH_2$—$(O(CH_2)_2)_3$—$(O(CH_2)_3)_3$—, —U—$CH_2$—$(O(CH_2)_2)_4$—$(O(CH_2)_3)_4$—, —U—$CH_2$—$(O(CH_2)_2)_5$—$(O(CH_2)_3)_5$—, —U—$CH_2$—$(O(CH_2)_2)_6$—$(O(CH_2)_3)_6$—, —U—$(CH_2)_2$—O—$(CH_2)_2$—O—$(CH_2)_3$—, —U—$(CH_2)_2$—$(O(CH_2)_2)_2$—$(O(CH_2)_3)_2$—, —U—$(CH_2)_2$—$(O(CH_2)_2)_3$—$(O(CH_2)_3)_3$—, —U—$(CH_2)_2$—$(O(CH_2)_2)_4$—$(O(CH_2)_3)_4$—, —U—$(CH_2)_2$—$(O(CH_2)_2)_5$—$(O(CH_2)_3)_5$—, —U—$(CH_2)_2$—$(O(CH_2)_2)_6$—$(O(CH_2)_3)_6$—, —U—$(CH_2)_3$—O—$(CH_2)_2$—O—$(CH_2)_3$—, —U—$(CH_2)_3$—$(O(CH_2)_2)_2$—$(O(CH_2)_3)_2$—, —U—$(CH_2)_3$—$(O(CH_2)_2)_3$—$(O(CH_2)_3)_3$—, —U—$(CH_2)_3$—$(O(CH_2)_2)_4$—$(O(CH_2)_3)_4$—, —U—$(CH_2)_3$—$(O(CH_2)_2)_5$—$(O(CH_2)_3)_5$—, —U—$(CH_2)_3$—$(O(CH_2)_2)_6$—$(O(CH_2)_3)_6$—, —U—$CH_2$—O—$(CH_2)_3$—O—$(CH_2)_2$—, —U—$CH_2$—$(O(CH_2)_3)_2$—$(O(CH_2)_2)_2$—, —U—$CH_2$—$(O(CH_2)_3)_3$—$(O(CH_2)_2)_3$—, —U—$CH_2$—$(O(CH_2)_3)_4$—$(O(CH_2)_2)_4$—, —U—$CH_2$—$(O(CH_2)_3)_5$—$(O(CH_2)_2)_5$—, —U—$CH_2$—$(O(CH_2)_3)_6$—$(O(CH_2)_2)_6$—, —U—$(CH_2)_2$—O—$(CH_2)_3$—O—$(CH_2)_2$—, —U—$(CH_2)_2$—$(O(CH_2)_3)_2$—$(O(CH_2)_2)_2$—, —U—

$(CH_2)_2$—$(O(CH_2)_3)_3$—$(O(CH_2)_2)_3$—, —U—$(CH_2)_2$—$(O(CH_2)_3)_4$—$(O(CH_2)_2)_4$—, —U—$(CH_2)_2$—$(O(CH_2)_3)_5$—$(O(CH_2)_2)_5$—, —U—$(CH_2)_2$—$(O(CH_2)_3)_6$—$(O(CH_2)_2)_6$—, —U—$(CH_2)_3$—O—$(CH_2)_3$—O—$(CH_2)_2$—, —U—$(CH_2)_3$—$(O(CH_2)_3)_2$—$(O(CH_2)_2)_2$—, —U—$(CH_2)_3$—$(O(CH_2)_3)_2$—, —U—$(CH_2)_3$—$(O(CH_2)_3)_3$—$(O(CH_2)_2)_3$—, —U—$(CH_2)_3$—$(O(CH_2)_3)_4$—$(O(CH_2)_2)_4$—, —U—$(CH_2)_3$—$(O(CH_2)_3)_5$—$(O(CH_2)_2)_5$—, —U—$(CH_2)_3$—$(O(CH_2)_3)_6$—$(O(CH_2)_2)_6$—, —U—$CH_2$—O—$(CH_2)_2$—O—$CH_2$—, —U—$(CH_2)_2$—O—$(CH_2)_2$—O—$CH_2$—, —U—$(CH_2)_2$—$(O(CH_2)_2)_2$—O—$(CH_2)_3$—, —U—$(CH_2)_2$—$(O(CH_2)_2)_3$—O—$(CH_2)_3$—, —U—$(CH_2)_2$—$(O(CH_2)_2)_4$—O—$(CH_2)_3$—, —U—$(CH_2)_5$—$(O(CH_2)_2)_2$—O—$(CH_2)_5$—, or —U—$(CH_2)_5$—$(O(CH_2)_2)_2$—O—$(CH_2)_6$—; wherein the group U represents CO or NH, or the group U is absent.

In an embodiment of the present disclosure, the compound of formula (I) is also the compound of formula (Ig-2):

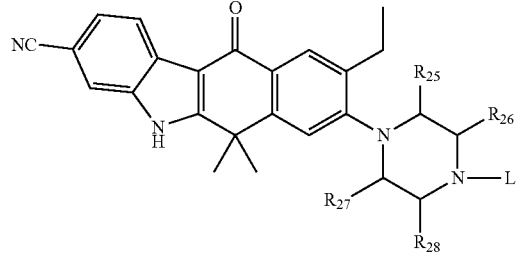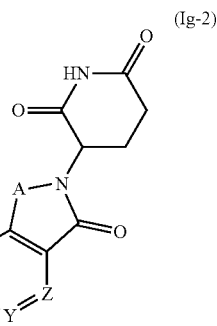

(Ig-2)

wherein, the groups LIN, R, A, B, X, Y and Z are as defined above, and the groups $R_{25}$, $R_{26}$, $R_{27}$ and $R_{28}$ are as defined above.

In an embodiment of the present disclosure, the compound of formula (I) is also the compound of formula (Ig-3):

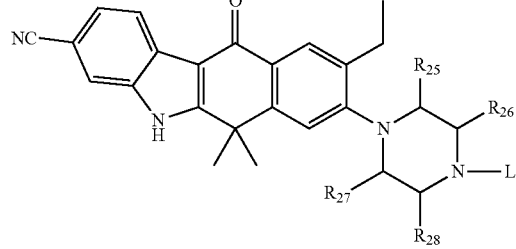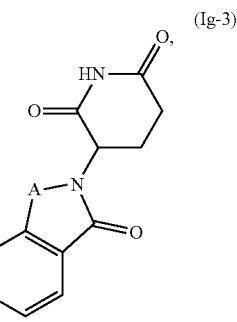

(Ig-3)

wherein, the groups LIN, R and A are as defined above, and the groups $R_{25}$, $R_{26}$, $R_{27}$ and $R_{28}$ are as defined above.

In a sub-embodiment of the compound of formula (Ig-3) of the present disclosure, the LIN represents —U—$C_{1-30}$ alkylene-; and the group U represents CO or NH, or the group U is absent. In a sub-embodiment of the compound of formula (Ig-3), the LIN represents: —U—$CH_2$—; —U—$(CH_2)_2$—; —U—$(CH_2)_3$—; —U—$(CH_2)_4$—; —U—$(CH_2)_5$—; —U—$(CH_2)_6$—; —U—$(CH_2)_7$—; —U—$(CH_2)_8$—; —U—$(CH_2)_9$—; —U—$(CH_2)_{10}$—; —U—$(CH_2)_{11}$—; —U—$(CH_2)_{12}$—; —U—$(CH_2)_{13}$—; —U—$(CH_2)_{14}$—; —U—$(CH_2)_{15}$—; —U—$(CH_2)_{16}$—; —U—$(CH_2)_{17}$—; —U—$(CH_2)_{18}$—; —U—$(CH_2)_{19}$—; —U—$(CH_2)_{20}$—; —U—$(CH_2)_{21}$—; —U—$(CH_2)_{22}$—; —U—$(CH_2)_{23}$—; —U—$(CH_2)_{24}$—; —U—$(CH_2)_{25}$—; —U—$(CH_2)_{26}$—; —U—$(CH_2)_{27}$—; —U—$(CH_2)_{28}$—; —U—$(CH_2)_{29}$—; or U—$(CH_2)_{30}$—; wherein the group U represents CO or NH, or the group U is absent.

In a sub-embodiment of the compound of formula (Ig-3) of the present disclosure, the LIN is preferably —U—$C_{2-40}$ alkylene-(preferably —U—$C_{2-30}$ alkylene-), wherein the alkylene chain is optionally interrupted one or more times by one or more of O, CONH, NHCO, NH, alkynylene, alkenylene, cycloalkylene, arylene, heterocyclylene or heteroarylene or any combination thereof, and the group U represents CO or NH, or the group U is absent. In a sub-embodiment of the compound of formula (Ig-3), the LIN preferably represents: —U—$(CH_2)_{n1}$—$(O(CH_2)_{n2})_{m1}$— or —U—$(CH_2)_{n1}$—$(O(CH_2)_{n2})_{m1}$—$(O(CH_2)_{n3})_{m2}$—, wherein n1, n2, n3, m1 and m2 each independently represent an integer of 1, 2, 3, 4, 5, 6, 7, 8, 9, 10, 11, 12, 13, 14, 15, 16, 17, 18, 19 or 20; and wherein the group U represents CO or NH, or the group U is absent. In a sub-embodiment of the compound of formula (Ig-3), the LIN preferably represents: —U—$CH_2$—O—$(CH_2)_2$—, —U—$CH_2$—$(O(CH_2)_2)_2$—, —U—$CH_2$—$(O(CH_2)_2)_3$—, —U—$CH_2$—$(O(CH_2)_2)_4$—, —U—$CH_2$—$(O(CH_2)_2)_5$—, —U—$CH_2$—$(O(CH_2)_2)_6$—, —U—$CH_2$—$(O(CH_2)_2)_7$—, —U—$CH_2$—$(O(CH_2)_2)_8$—, —U—$CH_2$—$(O(CH_2)_2)_9$—, —U—$CH_2$—$(O(CH_2)_2)_{10}$—, —U—$(CH_2)_2$—O—$(CH_2)_2$—, —U—$(CH_2)_2$—$(O(CH_2)_2)_2$—, —U—$(CH_2)_2$—$(O(CH_2)_2)_3$—, —U—$(CH_2)_2$—$(O(CH_2)_2)_4$—, —U—$(CH_2)_2$—$(O(CH_2)_2)_5$—, —U—$(CH_2)_2$—$(O(CH_2)_2)_6$—, —U—$(CH_2)_2$—$(O(CH_2)_2)_7$—, —U—$(CH_2)_2$—$(O(CH_2)_2)_8$—, —U—$(CH_2)_2$—$(O(CH_2)_2)_9$—, —U—$(CH_2)_2$—$(O(CH_2)_2)_{10}$—, —U—$(CH_2)_3$—O—$(CH_2)_2$—, —U—(CH₂)₃—(O(CH₂)₂)₂—, —U—(CH₂)₃—(O(CH₂)₂)₃—, —U—(CH₂)₃—(O(CH₂)₂)₄—, —U—(CH₂)₃—(O(CH₂)₂)₅—, —U—(CH₂)₃—(O(CH₂)₂)₆—, —U—(CH₂)₃—(O(CH₂)₂)₇—, —U—(CH₂)₃—(O(CH₂)₂)₈—, —U—(CH₂)₃—(O(CH₂)₂)₉—, —U—(CH₂)₃—(O(CH₂)₂)₁₀—, —U—(CH₂)₄—O—(CH₂)₂—, —U—(CH₂)₄—(O(CH₂)₂)₂—, —U—(CH₂)₄—(O(CH₂)₂)₃—, —U—(CH₂)₄—(O(CH₂)₂)₄—, —U—(CH₂)₄—(O(CH₂)₂)₅—, —U—(CH₂)₄—(O(CH₂)₂)₆—, —U—(CH₂)₄—(O(CH₂)₂)₇—, —U—(CH₂)₄—(O(CH₂)₂)₈—, —U—(CH₂)₄—(O(CH₂)₂)₉—, —U—(CH₂)₄—(O(CH₂)₂)₁₀—, —U—CH₂—O—(CH₂)₃—, —U—CH₂—(O(CH₂)₃)₂—, —U—CH₂—(O(CH₂)₃)₃—, —U—CH₂—(O(CH₂)₃)₄—, —U—CH₂—(O(CH₂)₃)₅—, —U—CH₂—(O(CH₂)₃)₆—, —U—CH₂—(O(CH₂)₃)₇—, —U—CH₂—(O(CH₂)₃)₈—, —U—CH₂—(O(CH₂)₃)₉—, —U—CH₂—(O(CH₂)₃)₁₀—, —U—(CH₂)₂—O—(CH₂)₃—, —U—(CH₂)₂—(O(CH₂)₃)₂—, —U—(CH₂)₂—(O(CH₂)₃)₃—, —U—(CH₂)₂—(O(CH₂)₃)₄—, —U—(CH₂)₂—(O(CH₂)₃)₅—, —U—(CH₂)₂—(O(CH₂)₃)₆—, —U—(CH₂)₂—(O(CH₂)₃)₇—, —U—(CH₂)₂—(O(CH₂)₃)₈—, —U—(CH₂)₂—(O(CH₂)₃)₉—, —U—(CH₂)₂—(O(CH₂)₃)₁₀—, —U—(CH₂)₃—O—(CH₂)₃—, —U—(CH₂)₃—(O(CH₂)₃)₂—, —U—(CH₂)₃—(O(CH₂)₃)₃—, —U—(CH₂)₃—(O(CH₂)₃)₄—, —U—(CH₂)₃—(O(CH₂)₃)₅—, —U—(CH₂)₃—(O(CH₂)₃)₆—, —U—(CH₂)₃—(O(CH₂)₃)₇—, —U—(CH₂)₃—(O(CH₂)₃)₈—, —U—(CH₂)₃—(O(CH₂)₃)₉—, —U—(CH₂)₃—(O(CH₂)₃)₁₀—, —U—CH₂—O—(CH₂)₂—O—(CH₂)₃—, —U—CH₂—(O(CH₂)₂)₂—(O(CH₂)₃)₂—, —U—CH₂—(O(CH₂)₂)₃—(O(CH₂)₃)₃—, —U—CH₂—(O(CH₂)₂)₄—(O(CH₂)₃)₄—, —U—CH₂—(O(CH₂)₂)₅—(O(CH₂)₃)₅—, —U—CH₂—(O(CH₂)₂)₆—(O(CH₂)₃)₆—, —U—(CH₂)₂—O—(CH₂)₂—O—(CH₂)₃—, —U—(CH₂)₂—(O(CH₂)₂)₂—(O(CH₂)₃)₂—, —U—(CH₂)₂—(O(CH₂)₂)₃—(O(CH₂)₃)₃—, —U—(CH₂)₂—(O(CH₂)₂)₄—(O(CH₂)₃)₄—, —U—(CH₂)₂—(O(CH₂)₂)₅—(O(CH₂)₃)₅—, —U—(CH₂)₂—(O(CH₂)₂)₆—(O(CH₂)₃)₆—, —U—(CH₂)₃—O—(CH₂)₂—O—(CH₂)₃—, —U—(CH₂)₃—(O(CH₂)₂)₂—(O(CH₂)₃)₂—, —U—(CH₂)₃—(O(CH₂)₂)₃—(O(CH₂)₃)₃—, —U—(CH₂)₃—(O(CH₂)₂)₄—(O(CH₂)₃)₄—, —U—(CH₂)₃—(O(CH₂)₂)₅—(O(CH₂)₃)₅—, —U—(CH₂)₃—(O(CH₂)₂)₆—(O(CH₂)₃)₆—, —U—CH₂—O—(CH₂)₃—O—(CH₂)₂—, —U—CH₂—(O(CH₂)₃)₂—(O(CH₂)₂)₂—, —U—CH₂—(O(CH₂)₃)₃—(O(CH₂)₂)₃—, —U—CH₂—(O(CH₂)₃)₄—(O(CH₂)₂)₄—, —U—CH₂—(O(CH₂)₃)₅—(O(CH₂)₂)₅—, —U—CH₂—(O(CH₂)₃)₆—(O(CH₂)₂)₆—, —U—(CH₂)₂—O—(CH₂)₃—O—(CH₂)₂—, —U—(CH₂)₂—(O(CH₂)₃)₂—(O(CH₂)₂)₂—, —U—(CH₂)₂—(O(CH₂)₃)₃—(O(CH₂)₂)₃—, —U—(CH₂)₂—(O(CH₂)₃)₄—(O(CH₂)₂)₄—, —U—(CH₂)₂—(O(CH₂)₃)₅—(O(CH₂)₂)₅—, —U—(CH₂)₂—(O(CH₂)₃)₆—(O(CH₂)₂)₆—, —U—(CH₂)₃—O—(CH₂)₃—O—(CH₂)₂—, —U—(CH₂)₃—(O(CH₂)₃)₂—(O(CH₂)₂)₂—, —U—(CH₂)₃—(O(CH₂)₃)₃—(O(CH₂)₂)₃—, —U—(CH₂)₃—(O(CH₂)₃)₄—(O(CH₂)₂)₄—, —U—(CH₂)₃—(O(CH₂)₃)₅—(O(CH₂)₂)₅—, —U—(CH₂)₃—(O(CH₂)₃)₆—(O(CH₂)₂)₆—, —U—CH₂—O—(CH₂)₂—O—CH₂—, —U—(CH₂)₂—O—(CH₂)₂—O—CH₂—, —U—(CH₂)₂—(O(CH₂)₂)₂—O—(CH₂)₃—, —U—(CH₂)₂—(O(CH₂)₂)₃—O—(CH₂)₃—, —U—(CH₂)₂—(O(CH₂)₂)₄—O—(CH₂)₃—, —U—(CH₂)₅—(O(CH₂)₂)₂—O—(CH₂)₅—, or —U—(CH₂)₅—(O(CH₂)₂)₂—O—(CH₂)₆—; wherein the group U represents CO or NH, or the group U is absent.

In an embodiment of the present disclosure, the compound of formula (I) is also the compound of formula (Ih-2):

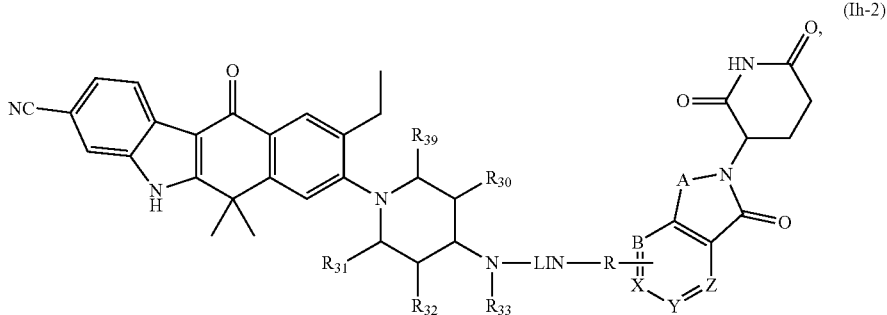

(Ih-2)

wherein, the groups LIN, R, A, B, X, Y and Z are as defined above, and the groups $R_{29}$, $R_{30}$, $R_{31}$, $R_{32}$ and $R_{33}$ are as defined above.

In an embodiment of the present disclosure, the compound of formula (I) is also the compound of formula (Ih-3):

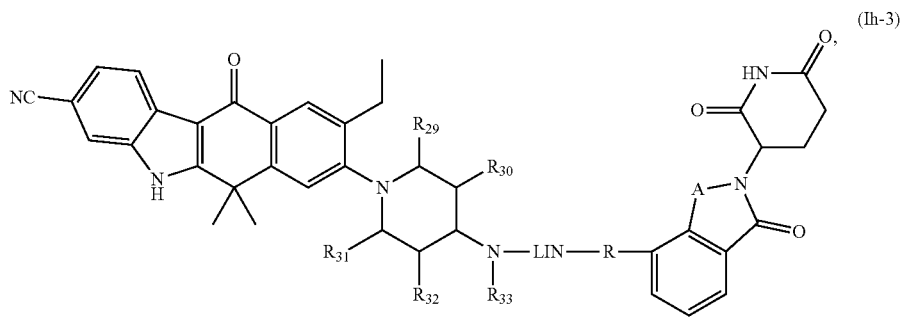

(Ih-3)

wherein, the groups LIN, R and A are as defined above, and the groups $R_{29}$, $R_{30}$, $R_{31}$, $R_{32}$ and $R_{33}$ are as defined above.

In a sub-embodiment of the compound of formula (Ih-3) of the present disclosure, the LIN represents —U—$C_{1-30}$ alkylene-; and the group U represents CO or NH, or the group U is absent. In a sub-embodiment of the compound of formula (Ih-3), the LIN represents: —U—$CH_2$—; —U—$(CH_2)_2$—; —U—$(CH_2)_3$—; —U—$(CH_2)_4$—; —U—$(CH_2)_5$—; —U—$(CH_2)_6$—; —U—$(CH_2)_7$—; —U—$(CH_2)_8$—; —U—$(CH_2)_9$—; —U—$(CH_2)_{10}$—; —U—$(CH_2)_{11}$—; —U—$(CH_2)_{12}$—; —U—$(CH_2)_{13}$—; —U—$(CH_2)_{14}$—; —U—$(CH_2)_{15}$—; —U—$(CH_2)_{16}$—; —U—$(CH_2)_{17}$—; —U—$(CH_2)_{18}$—; —U—$(CH_2)_{19}$—; —U—$(CH_2)_{20}$—; —U—$(CH_2)_{21}$—; —U—$(CH_2)_{22}$—; —U—$(CH_2)_{23}$—; —U—$(CH_2)_{24}$—; —U—$(CH_2)_{25}$—; —U—$(CH_2)_{26}$—; —U—$(CH_2)_{27}$—; —U—$(CH_2)_{28}$—; —U—$(CH_2)_{29}$—; or U—$(CH_2)_{30}$—; wherein the group U represents CO or NH, or the group U is absent.

In a sub-embodiment of the compound of formula (Ih-3) of the present disclosure, the LIN is preferably —U—$C_{2-40}$ alkylene-(preferably —U—$C_{2-30}$ alkylene-), wherein the alkylene chain is optionally interrupted one or more times by one or more of O, CONH, NHCO, NH, alkynylene, alkenylene, cycloalkylene, arylene, heterocyclylene or heteroarylene or any combination thereof, and the group U represents CO or NH, or the group U is absent. In a sub-embodiment of the compound of formula (Ih-3), the LIN preferably represents: —U—$(CH_2)_{n1}$—(O$(CH_2)_{n2})_{m1}$— or —U—$(CH_2)_{n1}$—(O$(CH_2)_{n2})_{m1}$—(O$(CH_2)_{n3})_{m2}$—, wherein n1, n2, n3, m1 and m2 each independently represent an integer of 1, 2, 3, 4, 5, 6, 7, 8, 9, 10, 11, 12, 13, 14, 15, 16, 17, 18, 19 or 20; and wherein the group U represents CO or NH, or the group U is absent. In a sub-embodiment of the compound of formula (Ih-3), the LIN preferably represents: —U—$CH_2$—O—$(CH_2)_2$—, —U—$CH_2$—(O$(CH_2)_2)_2$—, —U—$CH_2$—(O$(CH_2)_2)_3$—, —U—$CH_2$—(O$(CH_2)_2)_4$—, —U—$CH_2$—(O$(CH_2)_2)_5$—, —U—$CH_2$—(O$(CH_2)_2)_6$—, —U—$CH_2$—(O$(CH_2)_2)_7$—, —U—$CH_2$—(O$(CH_2)_2)_8$—, —U—$CH_2$—(O$(CH_2)_2)_9$—, —U—$CH_2$—(O$(CH_2)_2)_{10}$—, —U—$(CH_2)_2$—O—$(CH_2)_2$—, —U—$(CH_2)_2$—(O$(CH_2)_2)_2$—, —U—$(CH_2)_2$—(O$(CH_2)_2)_3$—, —U—$(CH_2)_2$—(O$(CH_2)_2)_4$—, —U—$(CH_2)_2$—(O$(CH_2)_2)_5$—, —U—$(CH_2)_2$—(O$(CH_2)_2)_6$—, —U—$(CH_2)_2$—(O$(CH_2)_2)_7$—, —U—$(CH_2)_2$—(O$(CH_2)_2)_8$—, —U—$(CH_2)_2$—(O$(CH_2)_2)_9$—, —U—$(CH_2)_2$—(O$(CH_2)_2)_{10}$—, —U—$(CH_2)_3$—O—$(CH_2)_2$—, —U—$(CH_2)_3$—(O$(CH_2)_2)_2$—, —U—$(CH_2)_3$—(O$(CH_2)_2)_3$—, —U—$(CH_2)_3$—(O$(CH_2)_2)_4$—, —U—$(CH_2)_3$—(O$(CH_2)_2)_5$—, —U—$(CH_2)_3$—(O$(CH_2)_2)_6$—, —U—$(CH_2)_3$—(O$(CH_2)_2)_7$—, —U—$(CH_2)_3$—(O$(CH_2)_2)_8$—, —U—$(CH_2)_3$—(O$(CH_2)_2)_9$—, —U—$(CH_2)_3$—(O$(CH_2)_2)_{10}$—, —U—$(CH_2)_4$—O—$(CH_2)_2$—, —U—$(CH_2)_4$—(O$(CH_2)_2)_2$—, —U—$(CH_2)_4$—(O$(CH_2)_2)_3$—, —U—$(CH_2)_4$—(O$(CH_2)_2)_4$—, —U—$(CH_2)_4$—(O$(CH_2)_2)_5$—, —U—$(CH_2)_4$—(O$(CH_2)_2)_6$—, —U—$(CH_2)_4$—(O$(CH_2)_2)_7$—, —U—$(CH_2)_4$—(O$(CH_2)_2)_8$—, —U—$(CH_2)_4$—(O$(CH_2)_2)_9$—, —U—$(CH_2)_4$—(O$(CH_2)_2)_{10}$—, —U—$CH_2$—O—$(CH_2)_3$—, —U—$CH_2$—(O$(CH_2)_3)_2$—, —U—$CH_2$—(O$(CH_2)_3)_3$—, —U—$CH_2$—(O$(CH_2)_3)_4$—, —U—$CH_2$—(O$(CH_2)_3)_5$—, —U—$CH_2$—(O$(CH_2)_3)_6$—, —U—$CH_2$—(O$(CH_2)_3)_7$—, —U—$CH_2$—(O$(CH_2)_3)_8$—, —U—$CH_2$—(O$(CH_2)_3)_9$—, —U—$(CH_2)_2$—O—$(CH_2)_3$—, —U—$(CH_2)_2$—(O$(CH_2)_3)_2$—, —U—$(CH_2)_2$—(O$(CH_2)_3)_3$—, —U—$(CH_2)_2$—(O$(CH_2)_3)_4$—, —U—$(CH_2)_2$—(O$(CH_2)_3)_5$—, —U—$(CH_2)_2$—(O$(CH_2)_3)_6$—, —U—$(CH_2)_2$—(O$(CH_2)_3)_7$—, —U—$(CH_2)_2$—(O$(CH_2)_3)_8$—, —U—$(CH_2)_2$—(O$(CH_2)_3)_9$—, —U—$(CH_2)_2$—(O$(CH_2)_3)_{10}$—, —U—$(CH_2)_3$—O—$(CH_2)_3$—, —U—$(CH_2)_3$—(O$(CH_2)_3)_2$—, —U—$(CH_2)_3$—(O$(CH_2)_3)_3$—, —U—$(CH_2)_3$—(O$(CH_2)_3)_4$—, —U—$(CH_2)_3$—(O$(CH_2)_3)_5$—, —U—$(CH_2)_3$—(O$(CH_2)_3)_6$—, —U—$(CH_2)_3$—(O$(CH_2)_3)_7$—, —U—$(CH_2)_3$—(O$(CH_2)_3)_8$—, —U—$(CH_2)_3$—(O$(CH_2)_3)_9$—, —U—$(CH_2)_3$—(O$(CH_2)_3)_{10}$—, —U—$CH_2$—O—$(CH_2)_2$—O—$(CH_2)_3$—, —U—$CH_2$—(O$(CH_2)_2)_2$—(O$(CH_2)_3)_2$—, —U—$CH_2$—(O$(CH_2)_2)_3$—(O$(CH_2)_3)_3$—, —U—$CH_2$—(O$(CH_2)_2)_4$—(O$(CH_2)_3)_4$—, —U—$CH_2$—(O$(CH_2)_2)_5$—(O$(CH_2)_3)_5$—, —U—$CH_2$—(O$(CH_2)_2)_6$—(O$(CH_2)_3)_6$—, —U—$(CH_2)_2$—O—$(CH_2)_2$—O—$(CH_2)_3$—, —U—$(CH_2)_2$—(O$(CH_2)_2)_2$—(O$(CH_2)_3)_2$—, —U—$(CH_2)_2$—(O$(CH_2)_2)_3$—(O$(CH_2)_3)_3$—, —U—$(CH_2)_2$—(O$(CH_2)_2)_4$—(O$(CH_2)_3)_4$—, —U—$(CH_2)_2$—(O$(CH_2)_2)_5$—(O$(CH_2)_3)_5$—, —U—$(CH_2)_2$—(O$(CH_2)_2)_6$—(O$(CH_2)_3)_6$—, —U—$(CH_2)_3$—O—$(CH_2)_2$—O—$(CH_2)_2$—O—$(CH_2)_3$—, —U—$(CH_2)_3$—(O$(CH_2)_2)_2$—(O$(CH_2)_3)_2$—, —U—$(CH_2)_3$—(O$(CH_2)_2)_3$—(O$(CH_2)_3)_3$—, —U—$(CH_2)_3$—(O$(CH_2)_2)_4$—(O$(CH_2)_3)_4$—, —U—$(CH_2)_3$—(O$(CH_2)_2)_5$—(O$(CH_2)_3)_5$—, —U—$(CH_2)_3$—(O$(CH_2)_2)_6$—(O$(CH_2)_3)_6$—, —U—$CH_2$—O—$(CH_2)_2$—O—$CH_2$—, —U—$(CH_2)_2$—O—$(CH_2)_3$—O—$(CH_2)_2$—, —U—$(CH_2)_2$—O—$(CH_2)_2$—O—$(CH_2)_3$—, —U—$(CH_2)_2$—(O$(CH_2)_2)_3$—O—$(CH_2)_3$—, —U—$(CH_2)_2$—(O$(CH_2)_2)_4$—O—$(CH_2)_3$—, —U—$(CH_2)_2$—O—$(CH_2)_5$—(O$(CH_2)_2)_2$—O—$(CH_2)_6$—; wherein the group U represents CO or NH, or the group U is absent.

In an embodiment of the present disclosure, the compound of formula (I) is also the compound of formula (Ii-2):

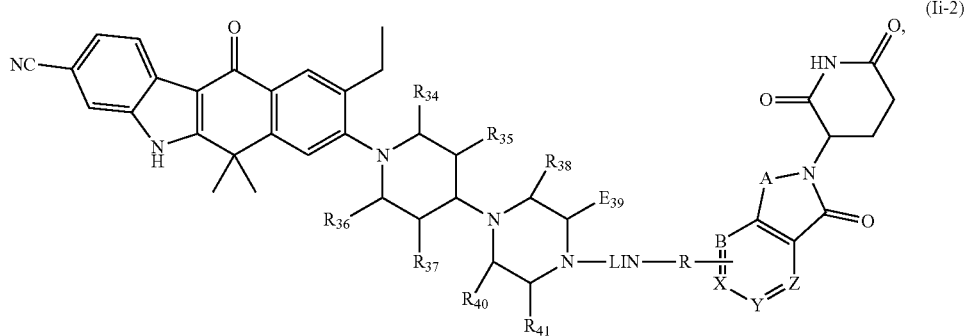

(Ii-2)

wherein, the groups LIN, R, A, B, X, Y and Z are as defined above, and the groups $R_{34}$, $R_{35}$, $R_{36}$, $R_{37}$, $R_{38}$, $R_{39}$, $R_{40}$ and $R_{41}$ are as defined above.

In an embodiment of the present disclosure, the compound of formula (I) is also the compound of formula (Ii-3):

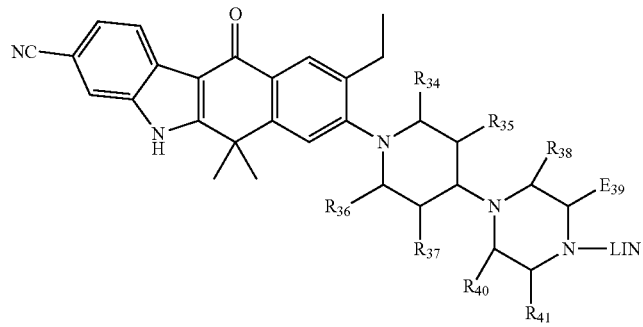
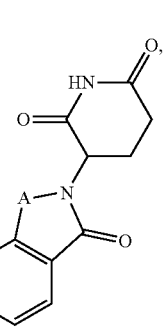

(Ii-3)

wherein, the groups LIN, R, A are as defined above, and the groups $R_{34}$, $R_{35}$, $R_{36}$, $R_{37}$, $R_{38}$, $R_{39}$, $R_{40}$ and $R_{41}$ are as defined above.

In a sub-embodiment of the compound of formula (Ii-3) of the present disclosure, the LIN represents —U—$C_{1-30}$ alkylene-; and the group U represents CO or NH, or the group U is absent. In a sub-embodiment of the compound of formula (Ii-3), the LIN represents: —U—$CH_2$—; —U—$(CH_2)_2$—; —U—$(CH_2)_3$—; —U—$(CH_2)_4$—; —U—$(CH_2)_5$—; —U—$(CH_2)_6$—; —U—$(CH_2)_7$—; —U—$(CH_2)_8$—; —U—$(CH_2)_9$—; —U—$(CH_2)_{10}$—; —U—$(CH_2)_{11}$—; —U—$(CH_2)_{12}$—; —U—$(CH_2)_{13}$—; —U—$(CH_2)_{14}$—; —U—$(CH_2)_{15}$—; —U—$(CH_2)_{16}$—; —U—$(CH_2)_{17}$—; —U—$(CH_2)_{18}$—; —U—$(CH_2)_{19}$—; —U—$(CH_2)_{20}$—; —U—$(CH_2)_{21}$—; —U—$(CH_2)_{22}$—; —U—$(CH_2)_{23}$—; —U—$(CH_2)_{24}$—; —U—$(CH_2)_{25}$—; —U—$(CH_2)_{26}$—; —U—$(CH_2)_{27}$—; —U—$(CH_2)_{28}$—; —U—$(CH_2)_{29}$—; or U—$(CH_2)_{30}$—; wherein the group U represents CO or NH, or the group U is absent.

In a sub-embodiment of the compound of formula (Ii-3) of the present disclosure, the LIN is preferably —U—$C_{2-40}$ alkylene-(preferably —U—$C_{2-30}$ alkylene-), wherein the alkylene chain is optionally interrupted one or more times by one or more of O, CONH, NHCO, NH, alkynylene, alkenylene, cycloalkylene, arylene, heterocyclylene or heteroarylene or any combination thereof, and the group U represents CO or NH, or the group U is absent. In a sub-embodiment of the compound of formula (Ii-3), the LIN preferably represents: —U—$(CH_2)_{n1}$—$(O(CH_2)_{n2})_{m1}$— or —U—$(CH_2)_{n1}$—$(O(CH_2)_{n2})_{m1}$—$(O(CH_2)_{n3})_{m2}$—, wherein n1, n2, n3, m1 and m2 each independently represent an integer of 1, 2, 3, 4, 5, 6, 7, 8, 9, 10, 11, 12, 13, 14, 15, 16, 17, 18, 19 or 20; and wherein the group U represents CO or NH, or the group U is absent. In a sub-embodiment of the compound of formula (Ii-3), the LIN preferably represents: —U—$CH_2$—O—$(CH_2)_2$—, —U—$CH_2$—$(O(CH_2)_2)_2$—, —U—$CH_2$—$(O(CH_2)_2)_3$—, —U—$CH_2$—$(O(CH_2)_2)_4$—, —U—$CH_2$—$(O(CH_2)_2)_5$—, —U—$CH_2$—$(O(CH_2)_2)_6$—, —U—$CH_2$—$(O(CH_2)_2)_7$—, —U—$CH_2$—$(O(CH_2)_2)_8$—, —U—$CH_2$—$(O(CH_2)_2)_9$—, —U—$CH_2$—$(O(CH_2)_2)_{10}$—, —U—$(CH_2)_2$—O—$(CH_2)_2$—, —U—$(CH_2)_2$—$(O(CH_2)_2)_2$—, —U—$(CH_2)_2$—$(O(CH_2)_2)_3$—, —U—$(CH_2)_2$—$(O(CH_2)_2)_4$—, —U—$(CH_2)_2$—$(O(CH_2)_2)_5$—, —U—$(CH_2)_2$—$(O(CH_2)_2)_6$—, —U—$(CH_2)_2$—$(O(CH_2)_2)_7$—, —U—$(CH_2)_2$—$(O(CH_2)_2)_8$—, —U—$(CH_2)_2$—$(O(CH_2)_2)_9$—, —U—$(CH_2)_2$—$(O(CH_2)_2)_{10}$—, —U—$(CH_2)_3$—O—$(CH_2)_2$—, —U—$(CH_2)_3$—$(O(CH_2)_2)_2$—, —U—$(CH_2)_3$—$(O(CH_2)_2)_3$—, —U—$(CH_2)_3$—$(O(CH_2)_2)_4$—, —U—$(CH_2)_3$—$(O(CH_2)_2)_5$—, —U—$(CH_2)_3$—$(O(CH_2)_2)_6$—, —U—$(CH_2)_3$—$(O(CH_2)_2)_7$—, —U—$(CH_2)_3$—$(O(CH_2)_2)_8$—, —U—$(CH_2)_3$—$(O(CH_2)_2)_9$—, —U—$(CH_2)_3$—$(O(CH_2)_2)_{10}$—, —U—$(CH_2)_4$—O—$(CH_2)_2$—, —U—$(CH_2)_4$—$(O(CH_2)_2)_2$—, —U—$(CH_2)_4$—$(O(CH_2)_2)_3$—, —U—$(CH_2)_4$—$(O(CH_2)_2)_4$—, —U—$(CH_2)_4$—$(O(CH_2)_2)_5$—, —U—$(CH_2)_4$—$(O(CH_2)_2)_6$—, —U—$(CH_2)_4$—$(O(CH_2)_2)_7$—, —U—$(CH_2)_4$—$(O(CH_2)_2)_8$—, —U—$(CH_2)_4$—$(O(CH_2)_2)_9$—, —U—$(CH_2)_4$—$(O(CH_2)_2)_{10}$—, —U—$CH_2$—O—$(CH_2)_3$—, —U—$CH_2$—$(O(CH_2)_3)_2$—, —U—$CH_2$—$(O(CH_2)_3)_3$—, —U—$CH_2$—$(O(CH_2)_3)_4$—, —U—$CH_2$—$(O(CH_2)_3)_5$—, —U—$CH_2$—$(O(CH_2)_3)_6$—, —U—$CH_2$—$(O(CH_2)_3)_7$—, —U—$CH_2$—$(O(CH_2)_3)_8$—, —U—$CH_2$—$(O(CH_2)_3)_9$—, —U—$CH_2$—$(O(CH_2)_3)_{10}$—, —U—$(CH_2)_2$—O—$(CH_2)_3$—, —U—$(CH_2)_2$—$(O(CH_2)_3)_2$—, —U—$(CH_2)_2$—$(O(CH_2)_3)_3$—, —U—$(CH_2)_2$—$(O(CH_2)_3)_4$—, —U—$(CH_2)_2$—$(O(CH_2)_3)_5$—, —U—$(CH_2)_2$—$(O(CH_2)_3)_6$—, —U—$(CH_2)_2$—$(O(CH_2)_3)_7$—, —U—$(CH_2)_2$—$(O(CH_2)_3)_8$—, —U—$(CH_2)_2$—$(O(CH_2)_3)_9$—, —U—$(CH_2)_2$—$(O(CH_2)_3)_{10}$—, —U—$(CH_2)_3$—O—$(CH_2)_3$—, —U—$(CH_2)_3$—$(O(CH_2)_3)_2$—, —U—$(CH_2)_3$—$(O(CH_2)_3)_3$—, —U—$(CH_2)_3$—$(O(CH_2)_3)_4$—, —U—$(CH_2)_3$—$(O(CH_2)_3)_5$—, —U—$(CH_2)_3$—$(O(CH_2)_3)_6$—, —U—$(CH_2)_3$—$(O(CH_2)_3)_7$—, —U—$(CH_2)_3$—$(O(CH_2)_3)_8$—, —U—$(CH_2)_3$—$(O(CH_2)_3)_9$—, —U—$(CH_2)_3$—$(O(CH_2)_3)_{10}$—, —U—$CH_2$—O—$(CH_2)_2$—O—$(CH_2)_3$—, —U—$CH_2$—$(O(CH_2)_2)_2$—$(O(CH_2)_3)_2$—, —U—$CH_2$—$(O(CH_2)_2)_3$—$(O(CH_2)_3)_3$—, —U—$CH_2$—$(O(CH_2)_2)_4$—$(O(CH_2)_3)_4$—, —U—$CH_2$—$(O(CH_2)_2)_5$—$(O(CH_2)_3)_5$—, —U—$CH_2$—$(O(CH_2)_2)_6$—$(O(CH_2)_3)_6$—, —U—$(CH_2)_2$—O—$(CH_2)_2$—O—$(CH_2)_3$—, —U—$(CH_2)_2$—$(O(CH_2)_2)_2$—$(O(CH_2)_3)_2$—, —U—$(CH_2)_2$—$(O(CH_2)_2)_3$—$(O(CH_2)_3)_3$—, —U—$(CH_2)_2$—$(O(CH_2)_2)_4$—$(O(CH_2)_3)_4$—, —U—$(CH_2)_2$—$(O(CH_2)_2)_5$—$(O(CH_2)_3)_5$—, —U—$(CH_2)_2$—$(O(CH_2)_2)_6$—$(O(CH_2)_3)_6$—, —U—$(CH_2)_3$—O—$(CH_2)_2$—O—$(CH_2)_3$—, —U—$(CH_2)_3$—$(O(CH_2)_2)_2$—$(O(CH_2)_3)_2$—, —U—$(CH_2)_3$—$(O(CH_2)_2)_3$—$(O(CH_2)_3)_3$—, —U—$(CH_2)_3$—$(O(CH_2)_2)_4$—$(O(CH_2)_3)_4$—, —U—$(CH_2)_3$—$(O(CH_2)_2)_5$—$(O(CH_2)_3)_5$—, —U—$(CH_2)_3$—$(O(CH_2)_2)_6$—$(O(CH_2)_3)_6$—, —U—$CH_2$—O—$(CH_2)_3$—O—$(CH_2)_2$—, —U—$CH_2$—$(O(CH_2)_3)_2$—$(O(CH_2)_2)_2$—, —U—$CH_2$—$(O(CH_2)_3)_3$—$(O(CH_2)_2)_3$—, —U—$CH_2$—$(O(CH_2)_3)_4$—$(O(CH_2)_2)_4$—, —U—$CH_2$—$(O(CH_2)_3)_5$—$(O(CH_2)_2)_5$—, —U—$CH_2$—$(O(CH_2)_3)_6$—$(O(CH_2)_2)_6$—, —U—$(CH_2)_2$—O—$(CH_2)_3$—O—$(CH_2)_2$—, —U—$(CH_2)_2$—$(O(CH_2)_3)_2$—$(O(CH_2)_2)_2$—, —U—$(CH_2)_2$—$(O(CH_2)_3)_3$—

$-(CH_2)_2)_3-$, $-U-(CH_2)_2-(O(CH_2)_3)_4-(O(CH_2)_2)_4-$, $-U-(CH_2)_2-(O(CH_2)_3)_5-(O(CH_2)_2)_5-$, $-U-(CH_2)_2-(O(CH_2)_3)_6-(O(CH_2)_2)_6-$, $-U-(CH_2)_3-O-(CH_2)_3-O-(CH_2)_2-$, $-U-(CH_2)_3-(O(CH_2)_3)_2-(O(CH_2)_2)_2-$, $-U-(CH_2)_3-(O(CH_2)_3)_3-(O(CH_2)_2)_3-$, $-U-(CH_2)_3-(O(CH_2)_3)_4-(O(CH_2)_2)_4-$, $-U-(CH_2)_3-(O(CH_2)_3)_5-(O(CH_2)_2)_5-$, $-U-(CH_2)_3-(O(CH_2)_3)_6-(O(CH_2)_2)_6-$, $-U-CH_2-O-(CH_2)_2-O-CH_2-$, $-U-(CH_2)_2-O-(CH_2)_2-O-CH_2-$, $-U-(CH_2)_2-(O(CH_2)_2)_2-O-(CH_2)_3-$, $-U-(CH_2)_2-(O(CH_2)_2)_3-O-(CH_2)_3-$, $-U-(CH_2)_2-(O(CH_2)_2)_4-O-(CH_2)_3-$, $-U-(CH_2)_5-(O(CH_2)_2)_2-O-(CH_2)_5-$, or $-U-(CH_2)_5-(O(CH_2)_2)_2-O-(CH_2)_6-$; wherein the group U represents CO or NH, or the group U is absent.

In an embodiment of the present disclosure, the compound of formula (I) is also the compound of formula (Ij-2):

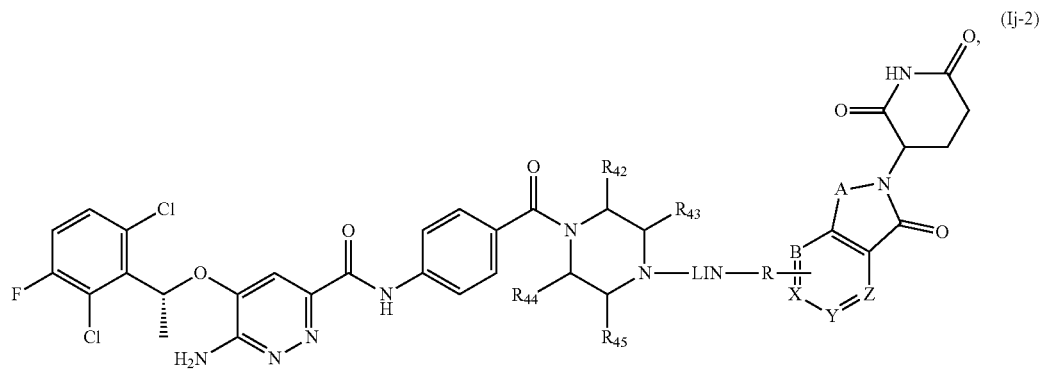

(Ij-2)

wherein, the groups LIN, R, A, B, X, Y and Z are as defined above, and the groups $R_{42}$, $R_{43}$, $R_{44}$ and $R_{45}$ are as defined above.

In an embodiment of the present disclosure, the compound of formula (I) is also the compound of formula (Ij-3):

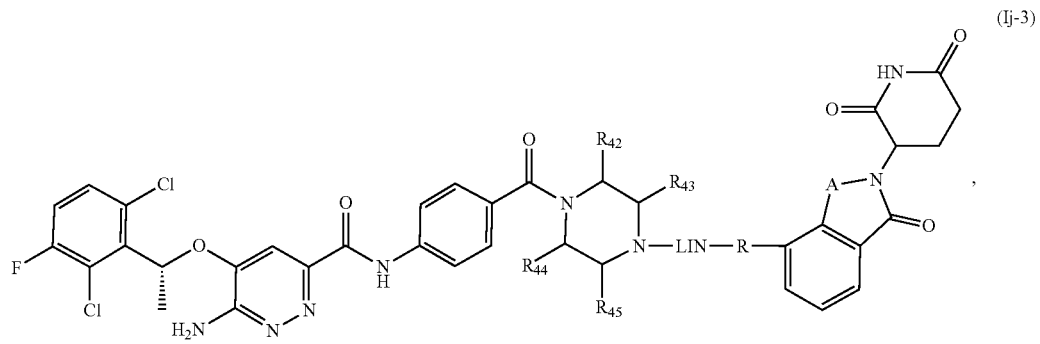

(Ij-3)

wherein, the groups LIN, R and A are as defined above, and the groups $R_{42}$, $R_{43}$, $R_{44}$ and $R_{45}$ are as defined above.

In a sub-embodiment of the compound of formula (Ij-3) of the present disclosure, the LIN represents $-U-C_{1-30}$ alkylene-; and the group U represents CO or NH, or the group U is absent. In a sub-embodiment of the compound of formula (Ij-3), the LIN represents: $-U-CH_2-$; $-U-(CH_2)_2-$; $-U-(CH_2)_3-$; $-U-(CH_2)_4-$; $-U-(CH_2)_5-$; $-U-(CH_2)_6-$; $-U-(CH_2)_7-$; $-U-(CH_2)_8-$; $-U-(CH_2)_9-$; $-U-(CH_2)_{10}-$; $-U-(CH_2)_{11}-$; $-U-(CH_2)_{12}-$; $-U-(CH_2)_{13}-$; $-U-(CH_2)_{14}-$; $-U-(CH_2)_{15}-$; $-U-(CH_2)_{16}-$; $-U-(CH_2)_{17}-$; $-U-(CH_2)_{18}-$; $-U-(CH_2)_{19}-$; $-U-(CH_2)_{20}-$; $-U-(CH_2)_{21}-$; $-U-(CH_2)_{22}-$; $-U-(CH_2)_{23}-$; $-U-(CH_2)_{24}-$; $-U-(CH_2)_{25}-$; $-U-(CH_2)_{26}-$; $-U-(CH_2)_{27}-$; $-U-(CH_2)_{28}-$; $-U-(CH_2)_{29}-$; or $-U-(CH_2)_{30}-$; wherein the group U represents CO or NH, or the group U is absent.

In a sub-embodiment of the compound of formula (Ij-3) of the present disclosure, the LIN is preferably $-U-C_{2-40}$ alkylene-(preferably $-U-C_{2-30}$ alkylene-), wherein the alkylene chain is optionally interrupted one or more times by one or more of O, CONH, NHCO, NH, alkynylene, alkenylene, cycloalkylene, arylene, heterocyclylene or heteroarylene or any combination thereof, and the group U represents CO or NH, or the group U is absent. In a sub-embodiment of the compound of formula (Ij-3), the LIN preferably represents: $-U-(CH_2)_{n1}-(O(CH_2)_{n2})_{m1}-$ or $-U-(CH_2)_{n1}-(O(CH_2)_{n2})_{m1}-(O(CH_2)_{n3})_{m2}-$, wherein n1, n2, n3, m1 and m2 each independently represent an integer of 1, 2, 3, 4, 5, 6, 7, 8, 9, 10, 11, 12, 13, 14, 15, 16, 17, 18, 19 or 20; and wherein the group U represents CO or NH, or the group U is absent. In a sub-embodiment of the compound of formula (Ij-3), the LIN preferably represents: $-U-CH_2-O-(CH_2)_2-$, $-U-CH_2-(O(CH_2)_2)_2-$, $-U-CH_2-(O(CH_2)_2)_3-$, $-U-CH_2-(O(CH_2)_2)_4-$, $-U-CH_2-(O(CH_2)_2)_5-$, $-U-CH_2-(O(CH_2)_2)_6-$, $-U-CH_2-(O(CH_2)_2)_7-$, $-U-CH_2-(O(CH_2)_2)_8-$, $-U-CH_2-(O(CH_2)_2)_9-$, $-U-CH_2-(O(CH_2)_2)_{10}-$, $-U-(CH_2)_2-O-(CH_2)_2-$, $-U-(CH_2)_2-(O(CH_2)_2)_2-$, $-U-(CH_2)_2-(O(CH_2)_2)_3-$, $-U-(CH_2)_2-(O(CH_2)_2)_4-$, $-U-(CH_2)_2-(O(CH_2)_2)_5-$, $-U-(CH_2)_2-(O(CH_2)_2)_6-$, $-U-(CH_2)_2-(O(CH_2)_2)_7-$, $-U-(CH_2)_2-(O(CH_2)_2)_8-$, $-U-(CH_2)_2-(O(CH_2)_2)_9-$, —U—(CH$_2$)$_2$—(O(CH$_2$)$_2$)$_{10}$—, —U—(CH$_2$)$_3$—O—(CH$_2$)$_2$—, —U—(CH$_2$)$_3$—(O(CH$_2$)$_2$)$_2$—, —U—(CH$_2$)$_3$—(O(CH$_2$)$_2$)$_3$—, —U—(CH$_2$)$_3$—(O(CH$_2$)$_2$)$_4$—, —U—(CH$_2$)$_3$—(O(CH$_2$)$_2$)$_5$—, —U—(CH$_2$)$_3$—(O(CH$_2$)$_2$)$_6$—, —U—(CH$_2$)$_3$—(O(CH$_2$)$_2$)$_7$—, —U—(CH$_2$)$_3$—(O(CH$_2$)$_2$)$_8$—, —U—(CH$_2$)$_3$—(O(CH$_2$)$_2$)$_9$—, —U—(CH$_2$)$_3$—(O(CH$_2$)$_2$)$_{10}$—, —U—(CH$_2$)$_4$—O—(CH$_2$)$_2$—, —U—(CH$_2$)$_4$—(O(CH$_2$)$_2$)$_2$—, —U—(CH$_2$)$_4$—(O(CH$_2$)$_2$)$_3$—, —U—(CH$_2$)$_4$—(O(CH$_2$)$_2$)$_4$—, —U—(CH$_2$)$_4$—(O(CH$_2$)$_2$)$_5$—, —U—(CH$_2$)$_4$—(O(CH$_2$)$_2$)$_6$—, —U—(CH$_2$)$_4$—(O(CH$_2$)$_2$)$_7$—, —U—(CH$_2$)$_4$—(O(CH$_2$)$_2$)$_8$—, —U—(CH$_2$)$_4$—(O(CH$_2$)$_2$)$_9$—, —U—(CH$_2$)$_4$—(O(CH$_2$)$_2$)$_{10}$—, —U—CH$_2$—O—(CH$_2$)$_3$—, —U—CH$_2$—(O(CH$_2$)$_3$)$_2$—, —U—CH$_2$—(O(CH$_2$)$_3$)$_3$—, —U—CH$_2$—(O(CH$_2$)$_3$)$_4$—, —U—CH$_2$—(O(CH$_2$)$_3$)$_5$—, —U—CH$_2$—(O(CH$_2$)$_3$)$_6$—, —U—CH$_2$—(O(CH$_2$)$_3$)$_7$—, —U—CH$_2$—(O(CH$_2$)$_3$)$_8$—, —U—CH$_2$—(O(CH$_2$)$_3$)$_9$—, —U—CH$_2$—(O(CH$_2$)$_3$)$_{10}$—, —U—(CH$_2$)$_2$—O—(CH$_2$)$_3$—, —U—(CH$_2$)$_2$—(O(CH$_2$)$_3$)$_2$—, —U—(CH$_2$)$_2$—(O(CH$_2$)$_3$)$_3$—, —U—(CH$_2$)$_2$—(O(CH$_2$)$_3$)$_4$—, —U—(CH$_2$)$_2$—(O(CH$_2$)$_3$)$_5$—, —U—(CH$_2$)$_2$—(O(CH$_2$)$_3$)$_6$—, —U—(CH$_2$)$_2$—(O(CH$_2$)$_3$)$_7$—, —U—(CH$_2$)$_2$—(O(CH$_2$)$_3$)$_8$—, —U—(CH$_2$)$_2$—(O(CH$_2$)$_3$)$_9$—, —U—(CH$_2$)$_2$—(O(CH$_2$)$_3$)$_{10}$—, —U—(CH$_2$)$_3$—O—(CH$_2$)$_3$—, —U—(CH$_2$)$_3$—(O(CH$_2$)$_3$)$_2$—, —U—(CH$_2$)$_3$—(O(CH$_2$)$_3$)$_3$—, —U—(CH$_2$)$_3$—(O(CH$_2$)$_3$)$_4$—, —U—(CH$_2$)$_3$—(O(CH$_2$)$_3$)$_5$—, —U—(CH$_2$)$_3$—(O(CH$_2$)$_3$)$_6$—, —U—(CH$_2$)$_3$—(O(CH$_2$)$_3$)$_7$—, —U—(CH$_2$)$_3$—(O(CH$_2$)$_3$)$_8$—, —U—(CH$_2$)$_3$—(O(CH$_2$)$_3$)$_9$—, —U—(CH$_2$)$_3$—(O(CH$_2$)$_3$)$_{10}$—, —U—CH$_2$—O—(CH$_2$)$_2$—O—(CH$_2$)$_3$—, —U—CH$_2$—(O(CH$_2$)$_2$)$_2$—(O(CH$_2$)$_3$)$_2$—, —U—CH$_2$—(O(CH$_2$)$_2$)$_3$—(O(CH$_2$)$_3$)$_3$—, —U—CH$_2$—(O(CH$_2$)$_2$)$_4$—(O(CH$_2$)$_3$)$_4$—, —U—CH$_2$—(O(CH$_2$)$_2$)$_5$—(O(CH$_2$)$_3$)$_5$—, —U—CH$_2$—(O(CH$_2$)$_2$)$_6$—(O(CH$_2$)$_3$)$_6$—, —U—(CH$_2$)$_2$—O—(CH$_2$)$_2$—O—(CH$_2$)$_3$—, —U—(CH$_2$)$_2$—(O(CH$_2$)$_2$)$_2$—(O(CH$_2$)$_3$)$_2$—, —U—(CH$_2$)$_2$—(O(CH$_2$)$_2$)$_3$—(O(CH$_2$)$_3$)$_3$—, —U—(CH$_2$)$_2$—(O(CH$_2$)$_2$)$_4$—(O(CH$_2$)$_3$)$_4$—, —U—(CH$_2$)$_2$—(O(CH$_2$)$_2$)$_5$—(O(CH$_2$)$_3$)$_5$—, —U—(CH$_2$)$_2$—(O(CH$_2$)$_2$)$_6$—(O(CH$_2$)$_3$)$_6$—, —U—(CH$_2$)$_2$—O—(CH$_2$)$_3$—O—(CH$_2$)$_2$—, —U—(CH$_2$)$_2$—(O(CH$_2$)$_3$)$_2$—(O(CH$_2$)$_2$)$_2$—, —U—(CH$_2$)$_2$—(O(CH$_2$)$_3$)$_3$—(O(CH$_2$)$_2$)$_3$—, —U—(CH$_2$)$_2$—(O(CH$_2$)$_3$)$_4$—(O(CH$_2$)$_2$)$_4$—, —U—(CH$_2$)$_2$—(O(CH$_2$)$_3$)$_5$—(O(CH$_2$)$_2$)$_5$—, —U—(CH$_2$)$_2$—(O(CH$_2$)$_3$)$_6$—(O(CH$_2$)$_2$)$_6$—, —U—(CH$_2$)$_3$—O—(CH$_2$)$_3$—O—(CH$_2$)$_2$—, —U—(CH$_2$)$_3$—(O(CH$_2$)$_3$)$_2$—(O(CH$_2$)$_2$)$_2$—, —U—(CH$_2$)$_3$—(O(CH$_2$)$_3$)$_3$—(O(CH$_2$)$_2$)$_3$—, —U—(CH$_2$)$_3$—(O(CH$_2$)$_3$)$_4$—(O(CH$_2$)$_2$)$_4$—, —U—(CH$_2$)$_3$—(O(CH$_2$)$_3$)$_5$—(O(CH$_2$)$_2$)$_5$—, —U—(CH$_2$)$_3$—(O(CH$_2$)$_3$)$_6$—(O(CH$_2$)$_2$)$_6$—, —U—(CH$_2$)$_2$—(O(CH$_2$)$_2$)$_4$—(O(CH$_2$)$_3$)$_4$—, —U—(CH$_2$)$_2$—(O(CH$_2$)$_2$)$_5$—(O(CH$_2$)$_3$)$_5$—, —U—(CH$_2$)$_2$—(O(CH$_2$)$_2$)$_6$—(O(CH$_2$)$_3$)$_6$—, —U—(CH$_2$)$_3$—O—(CH$_2$)$_2$—O—(CH$_2$)$_3$—, —U—(CH$_2$)$_3$—(O(CH$_2$)$_2$)$_2$—(O(CH$_2$)$_3$)$_2$—, —U—(CH$_2$)$_3$—(O(CH$_2$)$_2$)$_3$—(O(CH$_2$)$_3$)$_3$—, —U—(CH$_2$)$_3$—(O(CH$_2$)$_2$)$_4$—(O(CH$_2$)$_3$)$_4$—, —U—(CH$_2$)$_3$—(O(CH$_2$)$_2$)$_5$—(O(CH$_2$)$_3$)$_5$—, —U—(CH$_2$)$_3$—(O(CH$_2$)$_2$)$_6$—(O(CH$_2$)$_3$)$_6$—, —U—CH$_2$—O—(CH$_2$)$_2$—O—CH$_2$—, —U—(CH$_2$)$_2$—O—(CH$_2$)$_2$—O—CH$_2$—, —U—(CH$_2$)$_2$—(O(CH$_2$)$_2$)$_2$—O—(CH$_2$)$_3$—, —U—(CH$_2$)$_2$—(O(CH$_2$)$_2$)$_3$—O—(CH$_2$)$_3$—, —U—(CH$_2$)$_2$—(O(CH$_2$)$_2$)$_4$—O—(CH$_2$)$_3$—, —U—(CH$_2$)$_5$—(O(CH$_2$)$_2$)$_2$—O—(CH$_2$)$_5$—, or —U—(CH$_2$)$_5$—(O(CH$_2$)$_2$)$_2$—O—(CH$_2$)$_6$—; wherein the group U represents CO or NH, or the group U is absent.

In an embodiment of the present disclosure, the compound of formula (I) is also the compound of formula (II-2):

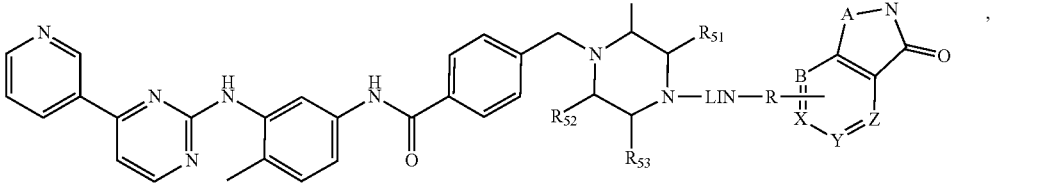

wherein, the groups LIN, R, A, B, X, Y and Z are as defined above, and the groups R$_{50}$, R$_{51}$, R$_{52}$ and R$_{53}$ are as defined above.

In an embodiment of the present disclosure, the compound of formula (I) is also the compound of formula (II-3):

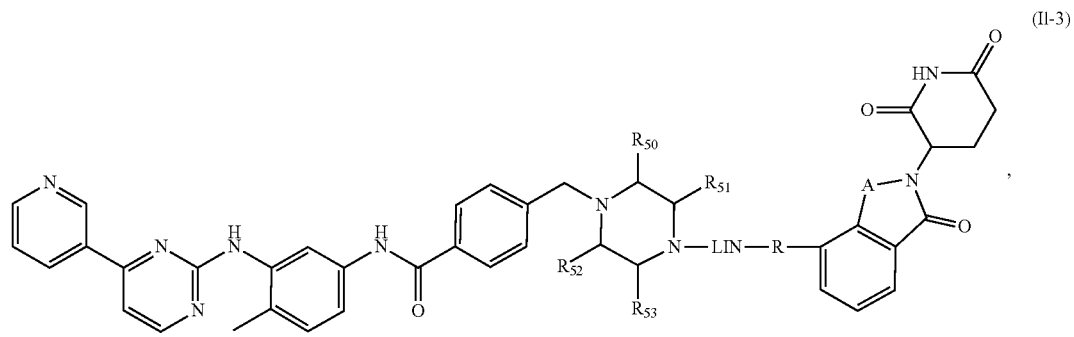

wherein, the groups LIN, R and A are as defined above, and the groups $R_{50}$, $R_{51}$, $R_{52}$ and $R_{53}$ are as defined above.

In a sub-embodiment of the compound of formula (Il-3) of the present disclosure, the LIN represents —U—$C_{1-30}$ alkylene-; and the group U represents CO or NH, or the group U is absent. In a sub-embodiment of the compound of formula (Il-3), the LIN represents: —U—$CH_2$—; —U—$(CH_2)_2$—; —U—$(CH_2)_3$—; —U—$(CH_2)_4$—; —U—$(CH_2)_5$—; —U—$(CH_2)_6$—; —U—$(CH_2)_7$—; —U—$(CH_2)_8$—; —U—$(CH_2)_9$—; —U—$(CH_2)_{10}$—; —U—$(CH_2)_{11}$—; —U—$(CH_2)_{12}$—; —U—$(CH_2)_{13}$—; —U—$(CH_2)_{14}$—; —U—$(CH_2)_{15}$—; —U—$(CH_2)_{16}$—; —U—$(CH_2)_{17}$—; —U—$(CH_2)_{18}$—; —U—$(CH_2)_{19}$—; —U—$(CH_2)_{20}$—; —U—$(CH_2)_{21}$—; —U—$(CH_2)_{22}$—; —U—$(CH_2)_{23}$—; —U—$(CH_2)_{24}$—; —U—$(CH_2)_{25}$—; —U—$(CH_2)_{26}$—; —U—$(CH_2)_{27}$—; —U—$(CH_2)_{28}$—; —U—$(CH_2)_{29}$—; or U—$(CH_2)_{30}$—; wherein the group U represents CO or NH, or the group U is absent.

In a sub-embodiment of the compound of formula (Il-3) of the present disclosure, the LIN is preferably —U—$C_{2-40}$ alkylene-(preferably —U—$C_{2-30}$ alkylene-), wherein the alkylene chain is optionally interrupted one or more times by one or more O, CONH, NHCO, NH, alkynylene, alkenylene, cycloalkylene, arylene, heterocyclylene or heteroarylene or any combination thereof, and the group U represents CO or NH, or the group U is absent. In a sub-embodiment of the compound of formula (Il-3), the LIN preferably represents: —U—$(CH_2)_{n1}$—$(O(CH_2)_{n2})_{m1}$— or —U—$(CH_2)_{n1}$—$(O(CH_2)_{n2})_{m1}$—$(O(CH_2)_{n3})_{m2}$—, wherein n1, n2, n3, m1 and m2 each independently represent an integer of 1, 2, 3, 4, 5, 6, 7, 8, 9, 10, 11, 12, 13, 14, 15, 16, 17, 18, 19 or 20; and wherein the group U represents CO or NH, or the group U is absent. In a sub-embodiment of the compound of formula (Il-3), the LIN preferably represents: —U—$CH_2$—O—$(CH_2)_2$—, —U—$CH_2$—$(O(CH_2)_2)_2$—, —U—$CH_2$—$(O(CH_2)_2)_3$—, —U—$CH_2$—$(O(CH_2)_2)_4$—, —U—$CH_2$—$(O(CH_2)_2)_5$—, —U—$CH_2$—$(O(CH_2)_2)_6$—, —U—$CH_2$—$(O(CH_2)_2)_7$—, —U—$CH_2$—$(O(CH_2)_2)_8$—, —U—$CH_2$—$(O(CH_2)_2)_9$—, —U—$CH_2$—$(O(CH_2)_2)_{10}$—, —U—$(CH_2)_2$—O—$(CH_2)_2$—, —U—$(CH_2)_2$—$(O(CH_2)_2)_2$—, —U—$(CH_2)_2$—$(O(CH_2)_2)_3$—, —U—$(CH_2)_2$—$(O(CH_2)_2)_4$—, —U—$(CH_2)_2$—$(O(CH_2)_2)_5$—, —U—$(CH_2)_2$—$(O(CH_2)_2)_6$—, —U—$(CH_2)_2$—$(O(CH_2)_2)_7$—, —U—$(CH_2)_2$—$(O(CH_2)_2)_8$—, —U—$(CH_2)_2$—$(O(CH_2)_2)_9$—, —U—$(CH_2)_2$—$(O(CH_2)_2)_{10}$—, —U—$(CH_2)_3$—O—$(CH_2)_2$—, —U—$(CH_2)_3$—$(O(CH_2)_2)_2$—, —U—$(CH_2)_3$—$(O(CH_2)_2)_3$—, —U—$(CH_2)_3$—$(O(CH_2)_2)_4$—, —U—$(CH_2)_3$—$(O(CH_2)_2)_5$—, —U—$(CH_2)_3$—$(O(CH_2)_2)_6$—, —U—$(CH_2)_3$—$(O(CH_2)_2)_7$—, —U—$(CH_2)_3$—$(O(CH_2)_2)_8$—, —U—$(CH_2)_3$—$(O(CH_2)_2)_9$—, —U—$(CH_2)_3$—$(O(CH_2)_2)_{10}$—, —U—$(CH_2)_4$—O—$(CH_2)_2$—, —U—$(CH_2)_4$—$(O(CH_2)_2)_2$—, —U—$(CH_2)_4$—$(O(CH_2)_2)_3$—, —U—$(CH_2)_4$—$(O(CH_2)_2)_4$—, —U—$(CH_2)_4$—$(O(CH_2)_2)_5$—, —U—$(CH_2)_4$—$(O(CH_2)_2)_6$—, —U—$(CH_2)_4$—$(O(CH_2)_2)_7$—, —U—$(CH_2)_4$—$(O(CH_2)_2)_8$—, —U—$(CH_2)_4$—$(O(CH_2)_2)_9$—, —U—$(CH_2)_4$—$(O(CH_2)_2)_{10}$—, —U—$CH_2$—O—$(CH_2)_3$—, —U—$CH_2$—$(O(CH_2)_3)_2$—, —U—$CH_2$—$(O(CH_2)_3)_3$—, —U—$CH_2$—$(O(CH_2)_3)_4$—, —U—$CH_2$—$(O(CH_2)_3)_5$—, —U—$CH_2$—$(O(CH_2)_3)_6$—, —U—$CH_2$—$(O(CH_2)_3)_7$—, —U—$CH_2$—$(O(CH_2)_3)_8$—, —U—$CH_2$—$(O(CH_2)_3)_9$—, —U—$CH_2$—$(O(CH_2)_3)_{10}$—, —U—$(CH_2)_2$—O—$(CH_2)_3$—, —U—$(CH_2)_2$—$(O(CH_2)_3)_2$—, —U—$(CH_2)_2$—$(O(CH_2)_3)_3$—, —U—$(CH_2)_2$—$(O(CH_2)_3)_4$—, —U—$(CH_2)_2$—$(O(CH_2)_3)_5$—, —U—$(CH_2)_2$—$(O(CH_2)_3)_6$—, —U—$(CH_2)_2$—$(O(CH_2)_3)_7$—, —U—$(CH_2)_2$—$(O(CH_2)_3)_8$—, —U—$(CH_2)_2$—$(O(CH_2)_3)_9$—, —U—$(CH_2)_2$—$(O(CH_2)_3)_{10}$—, —U—$(CH_2)_3$—O—$(CH_2)_3$—, —U—$(CH_2)_3$—$(O(CH_2)_3)_2$—, —U—$(CH_2)_3$—$(O(CH_2)_3)_3$—, —U—$(CH_2)_3$—$(O(CH_2)_3)_4$—, —U—$(CH_2)_3$—$(O(CH_2)_3)_5$—, —U—$(CH_2)_3$—$(O(CH_2)_3)_6$—, —U—$(CH_2)_3$—$(O(CH_2)_3)_7$—, —U—$(CH_2)_3$—$(O(CH_2)_3)_8$—, —U—$(CH_2)_3$—$(O(CH_2)_3)_9$—, —U—$(CH_2)_3$—$(O(CH_2)_3)_{10}$—, —U—$CH_2$—O—$(CH_2)_2$—O—$(CH_2)_3$—, —U—$CH_2$—$(O(CH_2)_2)_2$—$(O(CH_2)_3)_2$—, —U—$CH_2$—$(O(CH_2)_2)_3$—$(O(CH_2)_3)_3$—, —U—$CH_2$—$(O(CH_2)_2)_4$—$(O(CH_2)_3)_4$—, —U—$CH_2$—$(O(CH_2)_2)_5$—$(O(CH_2)_3)_5$—, —U—$CH_2$—$(O(CH_2)_2)_6$—$(O(CH_2)_3)_6$—, —U—$(CH_2)_2$—O—$(CH_2)_2$—O—$(CH_2)_3$—, —U—$(CH_2)_2$—$(O(CH_2)_2)_2$—$(O(CH_2)_3)_2$—, —U—$(CH_2)_2$—$(O(CH_2)_2)_3$—$(O(CH_2)_3)_3$—, —U—$(CH_2)_2$—$(O(CH_2)_2)_4$—$(O(CH_2)_3)_4$—, —U—$(CH_2)_2$—$(O(CH_2)_2)_5$—$(O(CH_2)_3)_5$—, —U—$(CH_2)_2$—$(O(CH_2)_2)_6$—$(O(CH_2)_3)_6$—, —U—$(CH_2)_3$—O—$(CH_2)_2$—O—$(CH_2)_3$—, —U—$(CH_2)_3$—$(O(CH_2)_2)_2$—$(O(CH_2)_3)_2$—, —U—$(CH_2)_3$—$(O(CH_2)_2)_3$—$(O(CH_2)_3)_3$—, —U—$(CH_2)_3$—$(O(CH_2)_2)_4$—$(O(CH_2)_3)_4$—, —U—$(CH_2)_3$—$(O(CH_2)_2)_5$—$(O(CH_2)_3)_5$—, —U—$(CH_2)_3$—$(O(CH_2)_2)_6$—$(O(CH_2)_3)_6$—, —U—$CH_2$—O—$(CH_2)_2$—O—$CH_2$—, —U—$(CH_2)_2$—O—$(CH_2)_2$—O—$CH_2$—, —U—$(CH_2)_2$—$(O(CH_2)_2)_2$—O—$(CH_2)_3$—, —U—$(CH_2)_2$—$(O(CH_2)_2)_3$—O—$(CH_2)_3$—, —U—$(CH_2)_2$—$(O(CH_2)_2)_4$—O—$(CH_2)_3$—, —U—$(CH_2)_5$—$(O(CH_2)_2)_2$—O—$(CH_2)_5$—, or —U—$(CH_2)_5$—$(O(CH_2)_2)_2$—O—$(CH_2)_6$—; wherein the group U represents CO or NH, or the group U is absent.

In an embodiment of the present disclosure, the compound of formula (I) is also the compound of formula (Im-2):

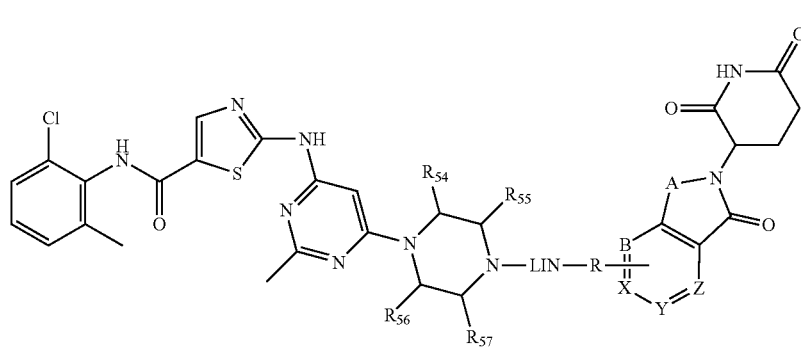

(Im-2)

wherein, the groups LIN, R, A, B, X, Y and Z are as defined above, and the groups $R_{54}$, $R_{55}$, $R_{56}$ and $R_{57}$ are as defined above.

In an embodiment of the present disclosure, the compound of formula (I) is also the compound of formula (Im-3):

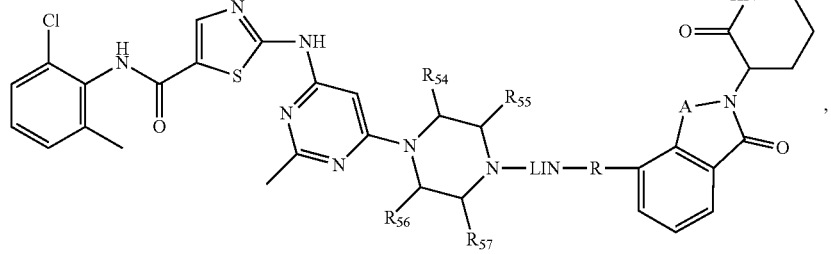

(Im-3)

wherein, the groups LIN, R and A are as defined above, and the groups $R_{54}$, $R_{55}$, $R_{56}$ and $R_{57}$ are as defined above.

In a sub-embodiment of the compound of formula (Im-3) of the present disclosure, the LIN represents —U—$C_{1-30}$ alkylene-; and the group U represents CO or NH, or the group U is absent. In a sub-embodiment of the compound of formula (Im-3), the LIN represents: —U—$CH_2$—; —U—$(CH_2)_2$—; —U—$(CH_2)_3$—; —U—$(CH_2)_4$—; —U—$(CH_2)_5$—; —U—$(CH_2)_6$—; —U—$(CH_2)_7$—; —U—$(CH_2)_8$—; —U—$(CH_2)_9$—; —U—$(CH_2)_{10}$—; —U—$(CH_2)_{11}$—; —U—$(CH_2)_{12}$—; —U—$(CH_2)_{13}$—; —U—$(CH_2)_{14}$—; —U—$(CH_2)_{15}$—; —U—$(CH_2)_{16}$—; —U—$(CH_2)_{17}$—; —U—$(CH_2)_{18}$—; —U—$(CH_2)_{19}$—; —U—$(CH_2)_{20}$—; —U—$(CH_2)_{21}$—; —U—$(CH_2)_{22}$—; —U—$(CH_2)_{23}$—; —U—$(CH_2)_{24}$—; —U—$(CH_2)_{25}$—; —U—$(CH_2)_{26}$—; —U—$(CH_2)_{27}$—; —U—$(CH_2)_{28}$—; —U—$(CH_2)_{29}$—; or U—$(CH_2)_{30}$—; wherein the group U represents CO or NH, or the group U is absent.

In a sub-embodiment of the compound of formula (Im-3) of the present disclosure, the LIN is preferably —U—$C_{2-40}$ alkylene-(preferably —U—$C_{2-30}$ alkylene-), wherein the alkylene chain is optionally interrupted one or more times by one or more of O, CONH, NHCO, NH, alkynylene, alkenylene, cycloalkylene, arylene, heterocyclylene or heteroarylene or any combination thereof, and the group U represents CO or NH, or the group U is absent. In a sub-embodiment of the compound of formula (Im-3), the LIN preferably represents: —U—$(CH_2)_{n1}$—(O$(CH_2)_{n2})_{m1}$— or —U—$(CH_2)_{n1}$—(O$(CH_2)_{n2})_{m1}$—(O$(CH_2)_{n3})_{m2}$—, wherein n1, n2, n3, m1 and m2 each independently represent an integer of 1, 2, 3, 4, 5, 6, 7, 8, 9, 10, 11, 12, 13, 14, 15, 16, 17, 18, 19 or 20; and wherein the group U represents CO or NH, or the group U is absent. In a sub-embodiment of the compound of formula (Im-3), the LIN preferably represents: —U—$CH_2$—O—$(CH_2)_2$—, —U—$CH_2$—(O$(CH_2)_2)_2$—, —U—$CH_2$—(O$(CH_2)_2)_3$—, —U—$CH_2$—(O$(CH_2)_2)_4$—, —U—$CH_2$—(O$(CH_2)_2)_5$—, —U—$CH_2$—(O$(CH_2)_2)_6$—, —U—$CH_2$—(O$(CH_2)_2)_7$—, —U—$CH_2$—(O$(CH_2)_2)_8$—, —U—$CH_2$—(O$(CH_2)_2)_9$—, —U—$CH_2$—(O$(CH_2)_2)_{10}$—, —U—$(CH_2)_2$—O—$(CH_2)_2$—, —U—$(CH_2)_2$—(O$(CH_2)_2)_2$—, —U—$(CH_2)_2$—(O$(CH_2)_2)_3$—, —U—$(CH_2)_2$—(O$(CH_2)_2)_4$—, —U—$(CH_2)_2$—(O$(CH_2)_2)_5$—, —U—$(CH_2)_2$—(O$(CH_2)_2)_6$—, —U—$(CH_2)_2$—(O$(CH_2)_2)_7$—, —U—$(CH_2)_2$—(O$(CH_2)_2)_8$—, —U—$(CH_2)_2$—(O$(CH_2)_2)_9$—, —U—$(CH_2)_2$—(O$(CH_2)_2)_{10}$—, —U—$(CH_2)_3$—O—$(CH_2)_2$—, —U—$(CH_2)_3$—(O$(CH_2)_2)_2$—, —U—$(CH_2)_3$—(O$(CH_2)_2)_3$—, —U—$(CH_2)_3$—(O$(CH_2)_2)_4$—, —U—$(CH_2)_3$—(O$(CH_2)_2)_5$—, —U—$(CH_2)_3$—(O$(CH_2)_2)_6$—, —U—$(CH_2)_3$—(O$(CH_2)_2)_7$—, —U—$(CH_2)_3$—(O$(CH_2)_2)_8$—, —U—$(CH_2)_3$—(O$(CH_2)_2)_9$—, —U—$(CH_2)_3$—(O$(CH_2)_2)_{10}$—, —U—$(CH_2)_4$—O—$(CH_2)_2$—, —U—$(CH_2)_4$—(O$(CH_2)_2)_2$—, —U—$(CH_2)_4$—(O$(CH_2)_2)_3$—, —U—$(CH_2)_4$—(O$(CH_2)_2)_4$—, —U—$(CH_2)_4$—(O$(CH_2)_2)_5$—, —U—$(CH_2)_4$—(O$(CH_2)_2)_6$—, —U—$(CH_2)_4$—(O$(CH_2)_2)_7$—, —U—$(CH_2)_4$—(O$(CH_2)_2)_8$—, —U—$(CH_2)_4$—(O$(CH_2)_2)_9$—, —U—$(CH_2)_4$—(O$(CH_2)_2)_{10}$—, —U—$CH_2$—O—$(CH_2)_3$—, —U—$CH_2$—(O$(CH_2)_3)_2$—, —U—$CH_2$—(O$(CH_2)_3)_3$—, —U—$CH_2$—(O$(CH_2)_3)_4$—, —U—$CH_2$—(O$(CH_2)_3)_5$—, —U—$CH_2$—(O$(CH_2)_3)_6$—, —U—$CH_2$—(O$(CH_2)_3)_7$—, —U—$CH_2$—(O$(CH_2)_3)_8$—, —U—$CH_2$—(O$(CH_2)_3)_9$—, —U—$CH_2$—(O$(CH_2)_3)_{10}$—, —U—$(CH_2)_2$ —O—(CH₂)₃—, —U—(CH₂)₂—(O(CH₂)₃)₂—, —U—(CH₂)₂—(O(CH₂)₃)₃—, —U—(CH₂)₂—(O(CH₂)₃)₄—, —U—(CH₂)₂—(O(CH₂)₃)₅—, —U—(CH₂)₂—(O(CH₂)₃)₆—, —U—(CH₂)₂—(O(CH₂)₃)₇—, —U—(CH₂)₂—(O(CH₂)₃)₈—, —U—(CH₂)₂—(O(CH₂)₃)₉—, —U—(CH₂)₂—(O(CH₂)₃)₁₀—, —U—(CH₂)₃—O—(CH₂)₃—, —U—(CH₂)₃—(O(CH₂)₃)₂—, —U—(CH₂)₃—(O(CH₂)₃)₃—, —U—(CH₂)₃—(O(CH₂)₃)₄—, —U—(CH₂)₃—(O(CH₂)₃)₅—, —U—(CH₂)₃—(O(CH₂)₃)₆—, —U—(CH₂)₃—(O(CH₂)₃)₇—, —U—(CH₂)₃—(O(CH₂)₃)₈—, —U—(CH₂)₃—(O(CH₂)₃)₉—, —U—(CH₂)₃—(O(CH₂)₃)₁₀—, —U—CH₂—O—(CH₂)₂—O—(CH₂)₃—, —U—CH₂—(O(CH₂)₂)₂—(O(CH₂)₃)₃—, —U—CH₂—(O(CH₂)₂)₃—(O(CH₂)₃)₃—, —U—CH₂—(O(CH₂)₂)₄—(O(CH₂)₃)₄—, —U—CH₂—(O(CH₂)₂)₅—(O(CH₂)₃)₅—, —U—CH₂—(O(CH₂)₂)₆—(O(CH₂)₃)₆—, —U—(CH₂)₂—O—(CH₂)₂—O—(CH₂)₃—, —U—(CH₂)₂—(O(CH₂)₂)₂—(O(CH₂)₃)₂—, —U—(CH₂)₂—(O(CH₂)₂)₃—(O(CH₂)₃)₃—, —U—(CH₂)₂—(O(CH₂)₂)₄—(O(CH₂)₃)₄—, —U—(CH₂)₂—(O(CH₂)₂)₅—(O(CH₂)₃)₅—, —U—(CH₂)₂—(O(CH₂)₂)₆—(O(CH₂)₃)₆—, —U—(CH₂)₃—O—(CH₂)₂—O—(CH₂)₃—, —U—(CH₂)₃—(O(CH₂)₂)₂—(O(CH₂)₃)₂—, —U—(CH₂)₃—(O(CH₂)₂)₃—(O(CH₂)₃)₃—, —U—(CH₂)₃—(O(CH₂)₂)₄—(O(CH₂)₃)₄—, —U—(CH₂)₃—(O(CH₂)₂)₅—(O(CH₂)₃)₅—, —U—(CH₂)₃—(O(CH₂)₂)₆—(O(CH₂)₃)₆—, —U—(CH₂)₃—(O(CH₂)₃)₂—(O(CH₂)₂)₂—, —U—CH₂—(O(CH₂)₃)₃—(O(CH₂)₂)₃—, —U—CH₂—(O(CH₂)₃)₄—(O(CH₂)₂)₄—, —U—CH₂—(O(CH₂)₃)₅—(O(CH₂)₂)₅—, —U—CH₂—(O(CH₂)₃)₆—(O(CH₂)₂)₆—, —U—(CH₂)₂—O—(CH₂)₃—O—(CH₂)₂—, —U—(CH₂)₂—(O(CH₂)₃)₂—(O(CH₂)₂)₂—, —U—(CH₂)₂—(O(CH₂)₃)₃—(O(CH₂)₂)₃—, —U—(CH₂)₂—(O(CH₂)₃)₄—(O(CH₂)₂)₄—, —U—(CH₂)₂—(O(CH₂)₃)₅—(O(CH₂)₂)₅—, —U—(CH₂)₂—(O(CH₂)₃)₆—(O(CH₂)₂)₆—, —U—(CH₂)₃—O—(CH₂)₃—O—(CH₂)₂—, —U—(CH₂)₃—(O(CH₂)₃)₂—(O(CH₂)₂)₂—, —U—(CH₂)₃—(O(CH₂)₃)₃—(O(CH₂)₂)₃—, —U—(CH₂)₃—(O(CH₂)₃)₄—(O(CH₂)₂)₄—, —U—(CH₂)₃—(O(CH₂)₃)₅—(O(CH₂)₂)₅—, —U—(CH₂)₃—(O(CH₂)₃)₆—(O(CH₂)₂)₆—, —U—CH₂—O—(CH₂)₂—O—CH₂—, —U—(CH₂)₂—O—(CH₂)₂—O—CH₂—, —U—(CH₂)₂—(O(CH₂)₂)₂—O—(CH₂)₃—, —U—(CH₂)₂—(O(CH₂)₂)₃—O—(CH₂)₃—, —U—(CH₂)₂—(O(CH₂)₂)₄—O—(CH₂)₃—, —U—(CH₂)₅—(O(CH₂)₂)₂—O—(CH₂)₅—; or —U—(CH₂)₅—(O(CH₂)₂)₂—O—(CH₂)₆—; wherein the group U represents CO or NH, or the group U is absent.

In an embodiment of the present disclosure, the compound of formula (I) is also the compound of formula (In-2):

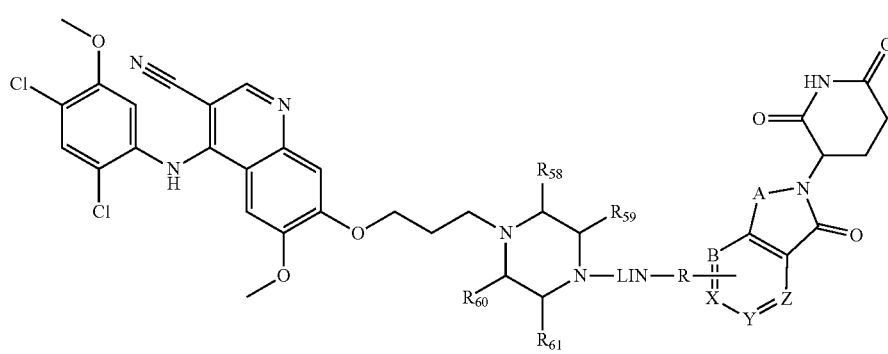

(In-2)

wherein, the groups LIN, R, A, B, X, Y and Z are as defined above, and the groups $R_{58}$, $R_{59}$, $R_{60}$ and $R_{61}$ are as defined above.

In an embodiment of the present disclosure, the compound of formula (I) is also the compound of formula (In-3):

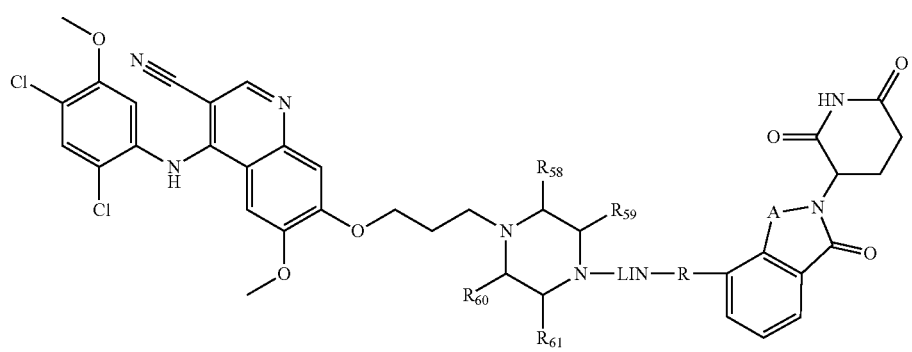

(In-3)

wherein, the groups LIN, R and A are as defined above, and the groups $R_{58}$, $R_{59}$, $R_{60}$ and $R_{61}$ are as defined above.

In a sub-embodiment of the compound of formula (In-3) of the present disclosure, the LIN represents —U—$C_{1-30}$ alkylene-; and the group U represents CO or NH, or the group U is absent. In a sub-embodiment of the compound of formula (In-3), the LIN represents: —U—$CH_2$—; —U—$(CH_2)_2$—; —U—$(CH_2)_3$—; —U—$(CH_2)_4$—; —U—$(CH_2)_5$—; —U—$(CH_2)_6$—; —U—$(CH_2)_7$—; —U—$(CH_2)_8$—; —U—$(CH_2)_9$—; —U—$(CH_2)_{10}$—; —U—$(CH_2)_{11}$—; —U—$(CH_2)_{12}$—; —U—$(CH_2)_{13}$—; —U—$(CH_2)_{14}$—; —U—$(CH_2)_{15}$—; —U—$(CH_2)_{16}$—; —U—$(CH_2)_{17}$—; —U—$(CH_2)_{18}$—; —U—$(CH_2)_{19}$—; —U—$(CH_2)_{20}$—; —U—$(CH_2)_{21}$—; —U—$(CH_2)_{22}$—; —U—$(CH_2)_{23}$—; —U—$(CH_2)_{24}$—; —U—$(CH_2)_{25}$—; —U—$(CH_2)_{26}$—; —U—$(CH_2)_{27}$—; —U—$(CH_2)_{28}$—; —U—$(CH_2)_{29}$—; or U—$(CH_2)_{30}$—; wherein the group U represents CO or NH, or the group U is absent.

In a sub-embodiment of the compound of formula (In-3) of the present disclosure, the LIN is preferably —U—$C_{2-40}$ alkylene-(preferably —U—$C_{2-30}$ alkylene-), wherein the alkylene chain is optionally interrupted one or more times by one or more of O, CONH, NHCO, NH, alkynylene, alkenylene, cycloalkylene, arylene, heterocyclylene or heteroarylene or any combination thereof, and the group U represents CO or NH, or the group U is absent. In a sub-embodiment of the compound of formula (In-3), the LIN preferably represents: —U—$(CH_2)_{n1}$—$(O(CH_2)_{n2})_{m1}$— or —U—$(CH_2)_{n1}$—$(O(CH_2)_{n2})_{m1}$—$(O(CH_2)_{n3})_{m2}$—, wherein n1, n2, n3, m1 and m2 each independently represent an integer of 1, 2, 3, 4, 5, 6, 7, 8, 9, 10, 11, 12, 13, 14, 15, 16, 17, 18, 19 or 20; and wherein the group U represents CO or NH, or the group U is absent. In a sub-embodiment of the compound of formula (In-3), the LIN preferably represents: —U—$CH_2$—O—$(CH_2)_2$—, —U—$CH_2$—$(O(CH_2)_2)_2$—, —U—$CH_2$—$(O(CH_2)_2)_3$—, —U—$CH_2$—$(O(CH_2)_2)_4$—, —U—$CH_2$—$(O(CH_2)_2)_5$—, —U—$CH_2$—$(O(CH_2)_2)_6$—, —U—$CH_2$—$(O(CH_2)_2)_7$—, —U—$CH_2$—$(O(CH_2)_2)_8$—, —U—$CH_2$—$(O(CH_2)_2)_9$—, —U—$CH_2$—$(O(CH_2)_2)_{10}$—, —U—$(CH_2)_2$—O—$(CH_2)_2$—, —U—$(CH_2)_2$—$(O(CH_2)_2)_2$—, —U—$(CH_2)_2$—$(O(CH_2)_2)_3$—, —U—$(CH_2)_2$—$(O(CH_2)_2)_4$—, —U—$(CH_2)_2$—$(O(CH_2)_2)_5$—, —U—$(CH_2)_2$—$(O(CH_2)_2)_6$—, —U—$(CH_2)_2$—$(O(CH_2)_2)_7$—, —U—$(CH_2)_2$—$(O(CH_2)_2)_5$—, —U—$(CH_2)_2$—$(O(CH_2)_2)_9$—, —U—$(CH_2)_2$—$(O(CH_2)_2)_{10}$—, —U—$(CH_2)_3$—O—$(CH_2)_2$—, —U—$(CH_2)_3$—$(O(CH_2)_2)_2$—, —U—$(CH_2)_3$—$(O(CH_2)_2)_3$—, —U—$(CH_2)_3$—$(O(CH_2)_2)_4$—, —U—$(CH_2)_3$—$(O(CH_2)_2)_5$—, —U—$(CH_2)_3$—$(O(CH_2)_2)_6$—, —U—$(CH_2)_3$—$(O(CH_2)_2)_7$—, —U—$(CH_2)_3$—$(O(CH_2)_2)_8$—, —U—$(CH_2)_3$—$(O(CH_2)_2)_9$—, —U—$(CH_2)_3$—$(O(CH_2)_2)_{10}$—, —U—$(CH_2)_4$—O—$(CH_2)_2$—, —U—$(CH_2)_4$—$(O(CH_2)_2)_2$—, —U—$(CH_2)_4$—$(O(CH_2)_2)_3$—, —U—$(CH_2)_4$—$(O(CH_2)_2)_4$—, —U—$(CH_2)_4$—$(O(CH_2)_2)_5$—, —U—$(CH_2)_4$—$(O(CH_2)_2)_6$—, —U—$(CH_2)_4$—$(O(CH_2)_2)_7$—, —U—$(CH_2)_4$—$(O(CH_2)_2)_8$—, —U—$(CH_2)_4$—$(O(CH_2)_2)_9$—, —U—$(CH_2)_4$—$(O(CH_2)_2)_{10}$—, —U—$CH_2$—O—$(CH_2)_3$—, —U—$CH_2$—$(O(CH_2)_3)_2$—, —U—$CH_2$—$(O(CH_2)_3)_3$—, —U—$CH_2$—$(O(CH_2)_3)_4$—, —U—$CH_2$—$(O(CH_2)_3)_5$—, —U—$CH_2$—$(O(CH_2)_3)_6$—, —U—$CH_2$—$(O(CH_2)_3)_7$—, —U—$CH_2$—$(O(CH_2)_3)_8$—, —U—$CH_2$—$(O(CH_2)_3)_9$—, —U—$CH_2$—$(O(CH_2)_3)_{10}$—, —U—$(CH_2)_2$—O—$(CH_2)_3$—, —U—$(CH_2)_2$—$(O(CH_2)_3)_2$—, —U—$(CH_2)_2$—$(O(CH_2)_3)_3$—, —U—$(CH_2)_2$—$(O(CH_2)_3)_4$—, —U—$(CH_2)_2$—$(O(CH_2)_3)_5$—, —U—$(CH_2)_2$—$(O(CH_2)_3)_6$—, —U—$(CH_2)_2$—$(O(CH_2)_3)_7$—, —U—$(CH_2)_2$—$(O(CH_2)_3)_8$—, —U—$(CH_2)_2$—$(O(CH_2)_3)_9$—, —U—$(CH_2)_2$—$(O(CH_2)_3)_{10}$—, —U—$(CH_2)_3$—O—$(CH_2)_3$—, —U—$(CH_2)_3$—$(O(CH_2)_3)_2$—, —U—$(CH_2)_3$—$(O(CH_2)_3)_3$—, —U—$(CH_2)_3$—$(O(CH_2)_3)_4$—, —U—$(CH_2)_3$—$(O(CH_2)_3)_5$—, —U—$(CH_2)_3$—$(O(CH_2)_3)_6$—, —U—$(CH_2)_3$—$(O(CH_2)_3)_7$—, —U—$(CH_2)_3$—$(O(CH_2)_3)_8$—, —U—$(CH_2)_3$—$(O(CH_2)_3)_9$—, —U—$(CH_2)_3$—$(O(CH_2)_3)_{10}$—, —U—$CH_2$—O—$(CH_2)_2$—O—$(CH_2)_3$—, —U—$CH_2$—$(O(CH_2)_2)_2$—$(O(CH_2)_3)_2$—, —U—$CH_2$—$(O(CH_2)_2)_3$—$(O(CH_2)_3)_3$—, —U—$CH_2$—$(O(CH_2)_2)_4$—$(O(CH_2)_3)_4$—, —U—$CH_2$—$(O(CH_2)_2)_5$—$(O(CH_2)_3)_5$—, —U—$CH_2$—$(O(CH_2)_2)_6$—$(O(CH_2)_3)_6$—, —U—$(CH_2)_2$—O—$(CH_2)_2$—O—$(CH_2)_3$—, —U—$(CH_2)_2$—$(O(CH_2)_2)_2$—$(O(CH_2)_2)_2$—, —U—$(CH_2)_2$—$(O(CH_2)_2)_3$—$(O(CH_2)_3)_3$—, —U—$(CH_2)_2$—$(O(CH_2)_2)_4$—$(O(CH_2)_3)_4$—, —U—$(CH_2)_2$—$(O(CH_2)_2)_5$—$(O(CH_2)_3)_5$—, —U—$(CH_2)_2$—$(O(CH_2)_2)_6$—$(O(CH_2)_3)_6$—, —U—$(CH_2)_3$—O—$(CH_2)_2$—O—$(CH_2)_3$—, —U—$(CH_2)_3$—$(O(CH_2)_2)_2$—$(O(CH_2)_3)_2$—, —U—$(CH_2)_3$—$(O(CH_2)_2)_3$—$(O(CH_2)_3)_3$—, —U—$(CH_2)_3$—$(O(CH_2)_2)_4$—$(O(CH_2)_3)_4$—, —U—$(CH_2)_3$—$(O(CH_2)_2)_5$—$(O(CH_2)_3)_5$—, —U—$(CH_2)_3$—$(O(CH_2)_2)_6$—$(O(CH_2)_3)_6$—, —U—$CH_2$—O—$(CH_2)_3$—O—$(CH_2)_2$—, —U—$CH_2$—$(O(CH_2)_3)_2$—$(O(CH_2)_2)_2$—, —U—$CH_2$—$(O(CH_2)_3)_3$—$(O(CH_2)_2)_3$—, —U—$CH_2$—$(O(CH_2)_3)_4$—$(O(CH_2)_2)_4$—, —U—$CH_2$—$(O(CH_2)_3)_5$—$(O(CH_2)_2)_5$—, —U—$CH_2$—$(O(CH_2)_3)_6$—$(O(CH_2)_2)_6$—, —U—$(CH_2)_2$—O—$(CH_2)_3$—O—$(CH_2)_2$—, —U—$(CH_2)_2$—$(O(CH_2)_3)_2$—$(O(CH_2)_2)_2$—, —U—$(CH_2)_2$—$(O(CH_2)_3)_3$—$(O(CH_2)_2)_3$—, —U—$(CH_2)_2$—$(O(CH_2)_3)_4$—$(O(CH_2)_2)_4$—, —U—$(CH_2)_2$—$(O(CH_2)_3)_5$—$(O(CH_2)_2)_5$—, —U—$(CH_2)_2$—$(O(CH_2)_3)_6$—$(O(CH_2)_2)_6$—, —U—$(CH_2)_3$—O—$(CH_2)_3$—O—$(CH_2)_2$—, —U—$(CH_2)_3$—$(O(CH_2)_3)_2$—$(O(CH_2)_2)_2$—, —U—$(CH_2)_3$—$(O(CH_2)_3)_3$—$(O(CH_2)_2)_3$—, —U—$(CH_2)_3$—$(O(CH_2)_3)_4$—$(O(CH_2)_2)_4$—, —U—$(CH_2)_3$—$(O(CH_2)_3)_5$—$(O(CH_2)_2)_5$—, —U—$(CH_2)_3$—$(O(CH_2)_3)_6$—$(O(CH_2)_2)_6$—, —U—$CH_2$—O—$(CH_2)_2$—O—$CH_2$—, —U—$(CH_2)_2$—O—$(CH_2)_2$—O—$CH_2$—, —U—$(CH_2)_2$—$(O(CH_2)_2)_2$—O—$(CH_2)_3$—, —U—$(CH_2)_2$—$(O(CH_2)_2)_3$—O—$(CH_2)_3$—, —U—$(CH_2)_2$—$(O(CH_2)_2)_4$—O—$(CH_2)_3$—, —U—$(CH_2)_5$—$(O(CH_2)_2)_2$—O—$(CH_2)_5$—, or —U—$(CH_2)_5$—$(O(CH_2)_2)_2$—O—$(CH_2)_6$—; wherein the group U represents CO or NH, or the group U is absent.

In an embodiment of the present disclosure, the compound of formula (I) is also the compound of formula (Io-2):

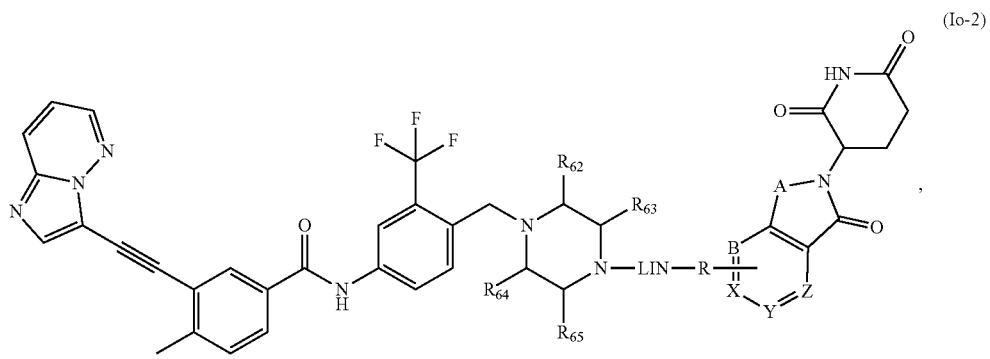

(Io-2)

wherein, the groups LIN, R, A, B, X, Y and Z are as defined above, and the groups $R_{62}$, $R_{63}$, $R_{64}$ and $R_{65}$ are as defined above.

In an embodiment of the present disclosure, the compound of formula (I) is also the compound of formula (Io-3):

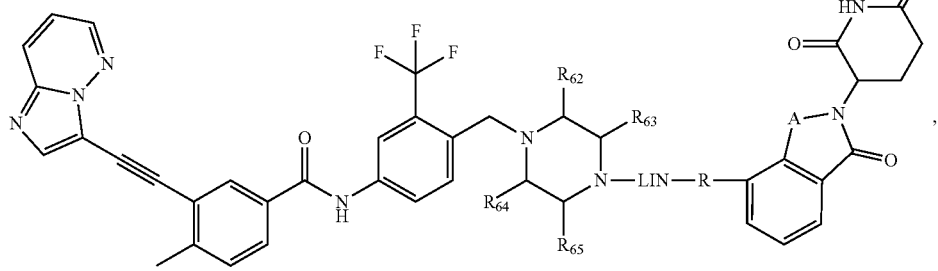

(Io-3)

wherein, the groups LIN, R and A are as defined above, and the groups $R_{62}$, $R_{63}$, $R_{64}$ and $R_{65}$ are as defined above.

In a sub-embodiment of the compound of formula (Io-3) of the present disclosure, the LIN represents —U—$C_{1-30}$ alkylene-; and the group U represents CO or NH, or the group U is absent. In a sub-embodiment of the compound of formula (Io-3), the LIN represents: —U—$CH_2$—; —U—$(CH_2)_2$—; —U—$(CH_2)_3$—; —U—$(CH_2)_4$—; —U—$(CH_2)_5$—; —U—$(CH_2)_6$—; —U—$(CH_2)_7$—; —U—$(CH_2)_8$—; —U—$(CH_2)_9$—; —U—$(CH_2)_{10}$—; —U—$(CH_2)_{11}$—; —U—$(CH_2)_{12}$—; —U—$(CH_2)_{13}$—; —U—$(CH_2)_{14}$—; —U—$(CH_2)_{15}$—; —U—$(CH_2)_{16}$—; —U—$(CH_2)_{17}$—; —U—$(CH_2)_{18}$—; —U—$(CH_2)_{19}$—; —U—$(CH_2)_{20}$—; —U—$(CH_2)_{21}$—; —U—$(CH_2)_{22}$—; —U—$(CH_2)_{23}$—; —U—$(CH_2)_{24}$—; —U—$(CH_2)_{25}$—; —U—$(CH_2)_{26}$—; —U—$(CH_2)_{27}$—; —U—$(CH_2)_{28}$—; —U—$(CH_2)_{29}$—; or U—$(CH_2)_{30}$—; wherein the group U represents CO or NH, or the group U is absent.

In a sub-embodiment of the compound of formula (Io-3) of the present disclosure, the LIN is preferably —U—$C_{2-40}$ alkylene-(preferably —U—$C_{2-30}$ alkylene-), wherein the alkylene chain is optionally interrupted one or more times by one or more of O, CONH, NHCO, NH, alkynylene, alkenylene, cycloalkylene, arylene, heterocyclylene or heteroarylene or any combination thereof, and the group U represents CO or NH, or the group U is absent. In a sub-embodiment of the compound of formula (Io-3), the LIN preferably represents: —U—$(CH_2)_{n1}$—(O$(CH_2)_{n2})_{m1}$— or —U—$(CH_2)_{n1}$—(O$(CH_2)_{n2})_{m1}$—(O$(CH_2)_{n3})_{m2}$—, wherein n1, n2, n3, m1 and m2 each independently represent an integer of 1, 2, 3, 4, 5, 6, 7, 8, 9, 10, 11, 12, 13, 14, 15, 16, 17, 18, 19 or 20; and wherein the group U represents CO or NH, or the group U is absent. In a sub-embodiment of the compound of formula (Io-3), the LIN preferably represents: —U—$CH_2$—O—$(CH_2)_2$—, —U—$CH_2$—$(O(CH_2)_2)_2$—, —U—$CH_2$—$(O(CH_2)_2)_3$—, —U—$CH_2$—$(O(CH_2)_2)_4$—, —U—$CH_2$—$(O(CH_2)_2)_5$—, —U—$CH_2$—$(O(CH_2)_2)_6$—, —U—$CH_2$—$(O(CH_2)_2)_7$—, —U—$CH_2$—$(O(CH_2)_2)_8$—, —U—$CH_2$—$(O(CH_2)_2)_9$—, —U—$CH_2$—$(O(CH_2)_2)_{10}$—, —U—$(CH_2)_2$—O—$(CH_2)_2$—, —U—$(CH_2)_2$—$(O(CH_2)_2)_2$—, —U—$(CH_2)_2$—$(O(CH_2)_2)_3$—, —U—$(CH_2)_2$—$(O(CH_2)_2)_4$—, —U—$(CH_2)_2$—$(O(CH_2)_2)_5$—, —U—$(CH_2)_2$—$(O(CH_2)_2)_6$—, —U—$(CH_2)_2$—$(O(CH_2)_2)_7$—, —U—$(CH_2)_2$—$(O(CH_2)_2)_8$—, —U—$(CH_2)_2$—$(O(CH_2)_2)_9$—, —U—$(CH_2)_2$—$(O(CH_2)_2)_{10}$—, —U—$(CH_2)_3$—O—$(CH_2)_2$—, —U—$(CH_2)_3$—$(O(CH_2)_2)_2$—, —U—$(CH_2)_3$—$(O(CH_2)_2)_3$—, —U—$(CH_2)_3$—$(O(CH_2)_2)_4$—, —U—$(CH_2)_3$—$(O(CH_2)_2)_5$—, —U—$(CH_2)_3$—$(O(CH_2)_2)_6$—, —U—$(CH_2)_3$—$(O(CH_2)_2)_7$—, —U—$(CH_2)_3$—$(O(CH_2)_2)_8$—, —U—$(CH_2)_3$—$(O(CH_2)_2)_9$—, —U—$(CH_2)_3$—$(O(CH_2)_2)_{10}$—, —U—$(CH_2)_4$—O—$(CH_2)_2$—, —U—$(CH_2)_4$—$(O(CH_2)_2)_2$—, —U—$(CH_2)_4$—$(O(CH_2)_2)_3$—, —U—$(CH_2)_4$—$(O(CH_2)_2)_4$—, —U—$(CH_2)_4$—$(O(CH_2)_2)_5$—, —U—$(CH_2)_4$—$(O(CH_2)_2)_6$—, —U—$(CH_2)_4$—$(O(CH_2)_2)_7$—, —U—$(CH_2)_4$—$(O(CH_2)_2)_8$—, —U—$(CH_2)_4$—$(O(CH_2)_2)_9$—, —U—$(CH_2)_4$—$(O(CH_2)_2)_{10}$—, —U—$CH_2$—O—$(CH_2)_3$—, —U—$CH_2$—$(O(CH_2)_3)_2$—, —U—$CH_2$—$(O(CH_2)_3)_3$—, —U—$CH_2$—$(O(CH_2)_3)_4$—, —U—$CH_2$—$(O(CH_2)_3)_5$—, —U—$CH_2$—$(O(CH_2)_3)_6$—, —U—$CH_2$—$(O(CH_2)_3)_7$—, —U—$CH_2$—$(O(CH_2)_3)_8$—, —U—$CH_2$—

(O(CH$_2$)$_3$)$_9$—, —U—CH$_2$—(O(CH$_2$)$_3$)$_{10}$—, —U—(CH$_2$)$_2$—O—(CH$_2$)$_3$—, —U—(CH$_2$)$_2$—(O(CH$_2$)$_3$)$_2$—, —U—(CH$_2$)$_2$—(O(CH$_2$)$_3$)$_3$—, —U—(CH$_2$)$_2$—(O(CH$_2$)$_3$)$_4$—, —U—(CH$_2$)$_2$—(O(CH$_2$)$_3$)$_5$—, —U—(CH$_2$)$_2$—(O(CH$_2$)$_3$)$_6$—, —U—(CH$_2$)$_2$—(O(CH$_2$)$_3$)$_7$—, —U—(CH$_2$)$_2$—(O(CH$_2$)$_3$)$_8$—, —U—(CH$_2$)$_2$—(O(CH$_2$)$_3$)$_9$—, —U—(CH$_2$)$_2$—(O(CH$_2$)$_3$)$_{10}$—, —U—(CH$_2$)$_3$—O—(CH$_2$)$_3$—, —U—(CH$_2$)$_3$—(O(CH$_2$)$_3$)$_2$—, —U—(CH$_2$)$_3$—(O(CH$_2$)$_3$)$_3$—, —U—(CH$_2$)$_3$—(O(CH$_2$)$_3$)$_4$—, —U—(CH$_2$)$_3$—(O(CH$_2$)$_3$)$_5$—, —U—(CH$_2$)$_3$—(O(CH$_2$)$_3$)$_6$—, —U—(CH$_2$)$_3$—(O(CH$_2$)$_3$)$_7$—, —U—(CH$_2$)$_3$—(O(CH$_2$)$_3$)$_8$—, —U—(CH$_2$)$_3$—(O(CH$_2$)$_3$)$_9$—, —U—(CH$_2$)$_3$—(O(CH$_2$)$_3$)$_{10}$—, —U—CH$_2$—O—(CH$_2$)$_2$—O—(CH$_2$)$_3$—, —U—CH$_2$—(O(CH$_2$)$_2$)$_2$—(O(CH$_2$)$_3$)$_2$—, —U—CH$_2$—(O(CH$_2$)$_2$)$_3$—(O(CH$_2$)$_3$)$_3$—, —U—CH$_2$—(O(CH$_2$)$_2$)$_4$—(O(CH$_2$)$_3$)$_4$—, —U—CH$_2$—(O(CH$_2$)$_2$)$_5$—(O(CH$_2$)$_3$)$_5$—, —U—CH$_2$—(O(CH$_2$)$_2$)$_6$—(O(CH$_2$)$_3$)$_6$—, —U—(CH$_2$)$_2$—O—(CH$_2$)$_2$—O—(CH$_2$)$_3$—, —U—(CH$_2$)$_2$—(O(CH$_2$)$_2$)$_2$—(O(CH$_2$)$_3$)$_2$—, —U—(CH$_2$)$_2$—(O(CH$_2$)$_2$)$_3$—(O(CH$_2$)$_3$)$_3$—, —U—(CH$_2$)$_2$—(O(CH$_2$)$_2$)$_4$—(O(CH$_2$)$_3$)$_4$—, —U—(CH$_2$)$_2$—(O(CH$_2$)$_2$)$_5$—(O(CH$_2$)$_3$)$_5$—, —U—(CH$_2$)$_2$—(O(CH$_2$)$_2$)$_6$—(O(CH$_2$)$_3$)$_6$—, —U—(CH$_2$)$_3$—O—(CH$_2$)$_2$—O—(CH$_2$)$_3$—, —U—(CH$_2$)$_3$—(O(CH$_2$)$_2$)$_2$—(O(CH$_2$)$_3$)$_2$—, —U—(CH$_2$)$_3$—(O(CH$_2$)$_2$)$_3$—(O(CH$_2$)$_3$)$_3$—, —U—(CH$_2$)$_3$—(O(CH$_2$)$_2$)$_4$—(O(CH$_2$)$_3$)$_4$—, —U—(CH$_2$)$_3$—(O(CH$_2$)$_2$)$_5$—(O(CH$_2$)$_3$)$_5$—, —U—(CH$_2$)$_3$—(O(CH$_2$)$_2$)$_6$—(O(CH$_2$)$_3$)$_6$—, —U—CH$_2$—O—(CH$_2$)$_3$—O—(CH$_2$)$_2$—, —U—CH$_2$—(O(CH$_2$)$_3$)$_2$—(O(CH$_2$)$_2$)$_2$—, —U—CH$_2$—(O(CH$_2$)$_3$)$_3$—(O(CH$_2$)$_2$)$_3$—, —U—CH$_2$—(O(CH$_2$)$_3$)$_4$—(O(CH$_2$)$_2$)$_4$—, —U—CH$_2$—(O(CH$_2$)$_3$)$_5$—(O(CH$_2$)$_2$)$_5$—, —U—CH$_2$—(O(CH$_2$)$_3$)$_6$—(O(CH$_2$)$_2$)$_6$—, —U—(CH$_2$)$_2$—O—(CH$_2$)$_3$—O—(CH$_2$)$_2$—, —U—(CH$_2$)$_2$—(O(CH$_2$)$_3$)$_2$—(O(CH$_2$)$_2$)$_2$—, —U—(CH$_2$)$_2$—(O(CH$_2$)$_3$)$_3$—(O(CH$_2$)$_2$)$_3$—, —U—(CH$_2$)$_2$—(O(CH$_2$)$_3$)$_4$—(O(CH$_2$)$_2$)$_4$—, —U—(CH$_2$)$_2$—(O(CH$_2$)$_3$)$_5$—(O(CH$_2$)$_2$)$_5$—, —U—(CH$_2$)$_2$—(O(CH$_2$)$_3$)$_6$—(O(CH$_2$)$_2$)$_6$—, —U—(CH$_2$)$_3$—O—(CH$_2$)$_3$—O—(CH$_2$)$_2$—, —U—(CH$_2$)$_3$—(O(CH$_2$)$_3$)$_2$—(O(CH$_2$)$_2$)$_2$—, —U—(CH$_2$)$_3$—(O(CH$_2$)$_3$)$_3$—(O(CH$_2$)$_2$)$_3$—, —U—(CH$_2$)$_3$—(O(CH$_2$)$_3$)$_4$—(O(CH$_2$)$_2$)$_4$—, —U—(CH$_2$)$_3$—(O(CH$_2$)$_3$)$_5$—(O(CH$_2$)$_2$)$_5$—, —U—(CH$_2$)$_3$—(O(CH$_2$)$_3$)$_6$—(O(CH$_2$)$_2$)$_6$—, —U—CH$_2$—O—(CH$_2$)$_2$—O—CH$_2$—, —U—(CH$_2$)$_2$—O—(CH$_2$)$_2$—O—CH$_2$—, —U—(CH$_2$)$_2$—(O(CH$_2$)$_2$)$_2$—O—(CH$_2$)$_3$—, —U—(CH$_2$)$_2$—(O(CH$_2$)$_2$)$_3$—O—(CH$_2$)$_3$—, —U—(CH$_2$)$_2$—(O(CH$_2$)$_2$)$_4$—O—(CH$_2$)$_3$—, —U—(CH$_2$)$_5$—(O(CH$_2$)$_2$)$_2$—O—(CH$_2$)$_5$—, or —U—(CH$_2$)$_5$—(O(CH$_2$)$_2$)$_2$—O—(CH$_2$)$_6$—; wherein the group U represents CO or NH, or the group U is absent.

In an embodiment of the present disclosure, the compound of formula (I) is also the compound of formula (Ip-2):

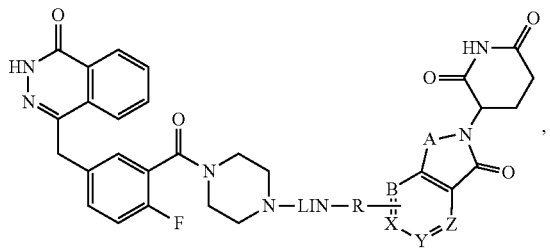

(Ip-2)

wherein, the groups LIN, R, A, B, X, Y and Z are as defined above.

In an embodiment of the present disclosure, the compound of formula (I) is also the compound of formula (Ip-3):

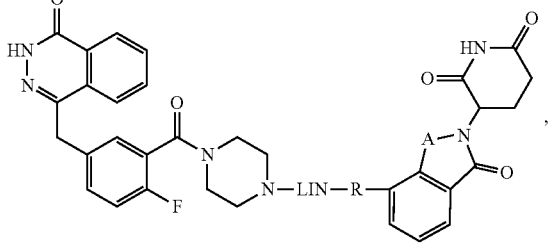

(Ip-3)

wherein, the groups LIN, R and A are as defined above.

In a sub-embodiment of the compound of formula (Ip-3) of the present disclosure, the LIN represents —U—C$_{1-30}$ alkylene-; and the group U represents CO or NH, or the group U is absent. In a sub-embodiment of the compound of formula (Ip-3), the LIN represents: —U—CH$_2$—; —U—(CH$_2$)$_2$—; —U—(CH$_2$)$_3$—; —U—(CH$_2$)$_4$—; —U—(CH$_2$)$_5$—; —U—(CH$_2$)$_6$—; —U—(CH$_2$)$_7$—; —U—(CH$_2$)$_8$—; —U—(CH$_2$)$_9$—; —U—(CH$_2$)$_{10}$—; —U—(CH$_2$)$_{11}$—; —U—(CH$_2$)$_{12}$—; —U—(CH$_2$)$_{13}$—; —U—(CH$_2$)$_{14}$—; —U—(CH$_2$)$_{15}$—; —U—(CH$_2$)$_{16}$—; —U—(CH$_2$)$_{17}$—; —U—(CH$_2$)$_{18}$—; —U—(CH$_2$)$_{19}$—; —U—(CH$_2$)$_{20}$—; —U—(CH$_2$)$_{21}$—; —U—(CH$_2$)$_{22}$—; —U—(CH$_2$)$_{23}$—; —U—(CH$_2$)$_{24}$—; —U—(CH$_2$)$_{25}$—; —U—(CH$_2$)$_{26}$—; —U—(CH$_2$)$_{27}$—; —U—(CH$_2$)$_{28}$—; —U—(CH$_2$)$_{29}$—; or U—(CH$_2$)$_{30}$—; wherein the group U represents CO or NH, or the group U is absent.

In a sub-embodiment of the compound of formula (Ip-3) of the present disclosure, the LIN is preferably —U—C$_{2-40}$ alkylene-(preferably —U—C$_{2-30}$ alkylene-), wherein the alkylene chain is optionally interrupted one or more times by one or more of O, CONH, NHCO, NH, alkynylene, alkenylene, cycloalkylene, arylene, heterocyclylene or heteroarylene or any combination thereof, and the group U represents CO or NH, or the group U is absent. In a sub-embodiment of the compound of formula (Ip-3), the LIN preferably represents: —U—(CH$_2$)$_{n1}$—(O(CH$_2$)$_{n2}$)$_{m1}$— or —U—(CH$_2$)$_{n1}$—(O(CH$_2$)$_{n2}$)$_{m1}$—(O(CH$_2$)$_{n3}$)$_{m2}$—, wherein n1, n2, n3, m1 and m2 each independently represent an integer of 1, 2, 3, 4, 5, 6, 7, 8, 9, 10, 11, 12, 13, 14, 15, 16, 17, 18, 19 or 20; and wherein the group U represents CO or NH, or the group U is absent. In a sub-embodiment of the compound of formula (Ip-3), the LIN preferably represents: —U—CH$_2$—O—(CH$_2$)$_2$—, —U—CH$_2$—(O(CH$_2$)$_2$)$_2$—, —U—CH$_2$—(O(CH$_2$)$_2$)$_3$—, —U—CH$_2$—(O(CH$_2$)$_2$)$_4$—, —U—CH$_2$—(O(CH$_2$)$_2$)$_5$—, —U—CH$_2$—(O(CH$_2$)$_2$)$_6$—, —U—CH$_2$—(O(CH$_2$)$_2$)$_7$—, —U—CH$_2$—(O(CH$_2$)$_2$)$_8$—, —U—CH$_2$—(O(CH$_2$)$_2$)$_9$—, —U—CH$_2$—(O(CH$_2$)$_2$)$_{10}$—, —U—(CH$_2$)$_2$—O—(CH$_2$)$_2$—, —U—(CH$_2$)$_2$—(O(CH$_2$)$_2$)$_2$—, —U—(CH$_2$)$_2$—(O(CH$_2$)$_2$)$_3$—, —U—(CH$_2$)$_2$—(O(CH$_2$)$_2$)$_4$—, —U—(CH$_2$)$_2$ —(O(CH$_2$)$_2$)$_5$—, —U—(CH$_2$)$_2$—(O(CH$_2$)$_2$)$_6$—, —U—(CH$_2$)$_2$—(O(CH$_2$)$_2$)$_7$—, —U—(CH$_2$)$_2$—(O(CH$_2$)$_2$)$_8$—, —U—(CH$_2$)$_2$—(O(CH$_2$)$_2$)$_9$—, —U—(CH$_2$)$_2$—(O(CH$_2$)$_2$)$_{10}$—, —U—(CH$_2$)$_3$—O—(CH$_2$)$_2$—, —U—(CH$_2$)$_3$—(O(CH$_2$)$_2$)$_2$—, —U—(CH$_2$)$_3$—(O(CH$_2$)$_2$)$_3$—, —U—(CH$_2$)$_3$—(O(CH$_2$)$_2$)$_4$—, —U—(CH$_2$)$_3$—(O(CH$_2$)$_2$)$_5$—, —U—(CH$_2$)$_3$—(O(CH$_2$)$_2$)$_6$—, —U—(CH$_2$)$_3$—(O(CH$_2$)$_2$)$_7$—, —U—(CH$_2$)$_3$—(O(CH$_2$)$_2$)$_8$—, —U—(CH$_2$)$_3$—(O(CH$_2$)$_2$)$_9$—, —U—(CH$_2$)$_3$—(O(CH$_2$)$_2$)$_{10}$—, —U—(CH$_2$)$_4$—O—(CH$_2$)$_2$—, —U—(CH$_2$)$_4$—(O(CH$_2$)$_2$)$_2$—, —U—(CH$_2$)$_4$—(O(CH$_2$)$_2$)$_3$—, —U—(CH$_2$)$_4$—(O(CH$_2$)$_2$)$_4$—, —U—(CH$_2$)$_4$—(O(CH$_2$)$_2$)$_5$—, —U—(CH$_2$)$_4$—(O(CH$_2$)$_2$)$_6$—, —U—(CH$_2$)$_4$—(O(CH$_2$)$_2$)$_7$—, —U—(CH$_2$)$_4$—(O(CH$_2$)$_2$)$_8$—, —U—(CH$_2$)$_4$—(O(CH$_2$)$_2$)$_9$—, —U—(CH$_2$)$_4$—(O(CH$_2$)$_2$)$_{10}$—, —U—CH$_2$—O—(CH$_2$)$_3$—, —U—CH$_2$—(O(CH$_2$)$_3$)$_2$—, —U—CH$_2$—(O(CH$_2$)$_3$)$_3$—, —U—CH$_2$—(O(CH$_2$)$_3$)$_4$—, —U—CH$_2$—(O(CH$_2$)$_3$)$_5$—, —U—CH$_2$—(O(CH$_2$)$_3$)$_6$—, —U—CH$_2$—(O(CH$_2$)$_3$)$_7$—, —U—CH$_2$—(O(CH$_2$)$_3$)$_8$—, —U—CH$_2$—(O(CH$_2$)$_3$)$_9$—, —U—CH$_2$—(O(CH$_2$)$_3$)$_{10}$—, —U—(CH$_2$)$_2$—O—(CH$_2$)$_3$—, —U—(CH$_2$)$_2$—(O(CH$_2$)$_3$)$_2$—, —U—(CH$_2$)$_2$—(O(CH$_2$)$_3$)$_3$—, —U—(CH$_2$)$_2$—(O(CH$_2$)$_3$)$_4$—, —U—(CH$_2$)$_2$—(O(CH$_2$)$_3$)$_5$—, —U—(CH$_2$)$_2$—(O(CH$_2$)$_3$)$_6$—, —U—(CH$_2$)$_2$—(O(CH$_2$)$_3$)$_7$—, —U—(CH$_2$)$_2$—(O(CH$_2$)$_3$)$_8$—, —U—(CH$_2$)$_2$—(O(CH$_2$)$_3$)$_9$—, —U—(CH$_2$)$_2$—(O(CH$_2$)$_3$)$_{10}$—, —U—(CH$_2$)$_3$—O—(CH$_2$)$_3$—, —U—(CH$_2$)$_3$—(O(CH$_2$)$_3$)$_2$—, —U—(CH$_2$)$_3$—(O(CH$_2$)$_3$)$_3$—, —U—(CH$_2$)$_3$—(O(CH$_2$)$_3$)$_4$—, —U—(CH$_2$)$_3$—(O(CH$_2$)$_3$)$_5$—, —U—(CH$_2$)$_3$—(O(CH$_2$)$_3$)$_6$—, —U—(CH$_2$)$_3$—(O(CH$_2$)$_3$)$_7$—, —U—(CH$_2$)$_3$—(O(CH$_2$)$_3$)$_8$—, —U—(CH$_2$)$_3$—(O(CH$_2$)$_3$)$_9$—, —U—(CH$_2$)$_3$—(O(CH$_2$)$_3$)$_{10}$—, —U—CH$_2$—O—(CH$_2$)$_2$—O—(CH$_2$)$_3$—, —U—CH$_2$—(O(CH$_2$)$_2$)$_2$—(O(CH$_2$)$_2$)$_2$—, —U—CH$_2$—(O(CH$_2$)$_2$)$_3$—(O(CH$_2$)$_3$)$_3$—, —U—CH$_2$—(O(CH$_2$)$_2$)$_4$—(O(CH$_2$)$_3$)$_4$—, —U—CH$_2$—(O(CH$_2$)$_2$)$_5$—(O(CH$_2$)$_3$)$_5$—, —U—CH$_2$—(O(CH$_2$)$_2$)$_6$—(O(CH$_2$)$_3$)$_6$—, —U—(CH$_2$)$_2$—O—(CH$_2$)$_2$—O—(CH$_2$)$_3$—, —U—(CH$_2$)$_2$—(O(CH$_2$)$_2$)$_2$—(O(CH$_2$)$_3$)$_2$—, —U—(CH$_2$)$_2$—(O(CH$_2$)$_2$)$_3$—(O(CH$_2$)$_3$)$_3$—, —U—(CH$_2$)$_2$—(O(CH$_2$)$_2$)$_4$—(O(CH$_2$)$_3$)$_4$—, —U—(CH$_2$)$_2$—(O(CH$_2$)$_2$)$_5$—(O(CH$_2$)$_3$)$_5$—, —U—(CH$_2$)$_2$—(O(CH$_2$)$_2$)$_6$—(O(CH$_2$)$_3$)$_6$—, —U—(CH$_2$)$_3$—O—(CH$_2$)$_2$—O—(CH$_2$)$_3$—, —U—(CH$_2$)$_3$—(O(CH$_2$)$_2$)$_2$—(O(CH$_2$)$_3$)$_2$—, —U—(CH$_2$)$_3$—(O(CH$_2$)$_2$)$_3$—(O(CH$_2$)$_3$)$_3$—, —U—(CH$_2$)$_3$—(O(CH$_2$)$_2$)$_4$—(O(CH$_2$)$_3$)$_4$—, —U—(CH$_2$)$_3$—(O(CH$_2$)$_2$)$_5$—(O(CH$_2$)$_3$)$_5$—, —U—(CH$_2$)$_3$—(O(CH$_2$)$_2$)$_6$—(O(CH$_2$)$_3$)$_6$—, —U—CH$_2$—O—(CH$_2$)$_3$—O—(CH$_2$)$_2$—, —U—CH$_2$—(O(CH$_2$)$_3$)$_2$—(O(CH$_2$)$_2$)$_2$—, —U—CH$_2$—(O(CH$_2$)$_3$)$_3$—(O(CH$_2$)$_2$)$_3$—, —U—CH$_2$—(O(CH$_2$)$_3$)$_4$—(O(CH$_2$)$_2$)$_4$—, —U—CH$_2$—(O(CH$_2$)$_3$)$_5$—(O(CH$_2$)$_2$)$_5$—, —U—CH$_2$—(O(CH$_2$)$_3$)$_6$—(O(CH$_2$)$_2$)$_6$—, —U—(CH$_2$)$_2$—O—(CH$_2$)$_3$—O—(CH$_2$)$_2$—, —U—(CH$_2$)$_2$—(O(CH$_2$)$_3$)$_2$—(O(CH$_2$)$_2$)$_2$—, —U—(CH$_2$)$_2$—(O(CH$_2$)$_3$)$_3$—(O(CH$_2$)$_2$)$_3$—, —U—(CH$_2$)$_2$—(O(CH$_2$)$_3$)$_4$—(O(CH$_2$)$_2$)$_4$—, —U—(CH$_2$)$_2$—(O(CH$_2$)$_3$)$_5$—(O(CH$_2$)$_2$)$_5$—, —U—(CH$_2$)$_2$—(O(CH$_2$)$_3$)$_6$—(O(CH$_2$)$_2$)$_6$—, —U—(CH$_2$)$_3$—O—(CH$_2$)$_3$—O—(CH$_2$)$_2$—, —U—(CH$_2$)$_3$—(O(CH$_2$)$_3$)$_2$—(O(CH$_2$)$_2$)$_2$—, —U—(CH$_2$)$_3$—(O(CH$_2$)$_3$)$_3$—(O(CH$_2$)$_2$)$_3$—, —U—(CH$_2$)$_3$—(O(CH$_2$)$_3$)$_4$—(O(CH$_2$)$_2$)$_4$—, —U—(CH$_2$)$_3$—(O(CH$_2$)$_3$)$_5$—(O(CH$_2$)$_2$)$_5$—, —U—(CH$_2$)$_3$—(O(CH$_2$)$_3$)$_6$—(O(CH$_2$)$_2$)$_6$—, —U—CH$_2$—O—(CH$_2$)$_2$—O—CH$_2$—, —U—(CH$_2$)$_2$—O—(CH$_2$)$_2$—O—CH$_2$—, —U—(CH$_2$)$_2$—(O(CH$_2$)$_2$)$_2$—O—(CH$_2$)$_3$—, —U—(CH$_2$)$_2$—(O(CH$_2$)$_2$)$_3$—O—(CH$_2$)$_3$—, —U—(CH$_2$)$_2$—(O(CH$_2$)$_2$)$_4$—O—(CH$_2$)$_3$—, —U—(CH$_2$)$_5$—(O(CH$_2$)$_2$)$_2$—O—(CH$_2$)$_5$—, or —U—(CH$_2$)$_5$—(O(CH$_2$)$_2$)$_2$—O—(CH$_2$)$_6$—; wherein the group U represents CO or NH, or the group U is absent.

In an embodiment of the present disclosure, the compound of formula (I) is also the compound of formula (Iq-2):

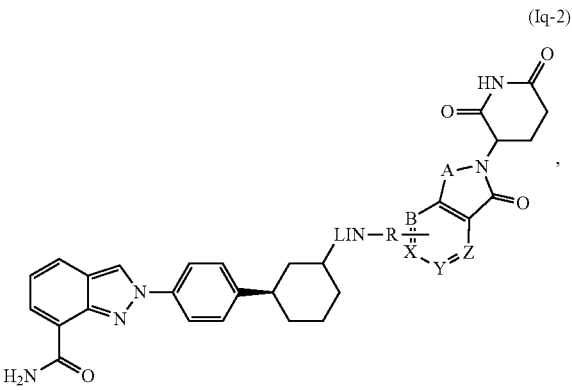

(Iq-2)

wherein, the groups LIN, R, A, B, X, Y and Z are as defined above.

In an embodiment of the present disclosure, the compound of formula (I) is also the compound of formula (Iq-3):

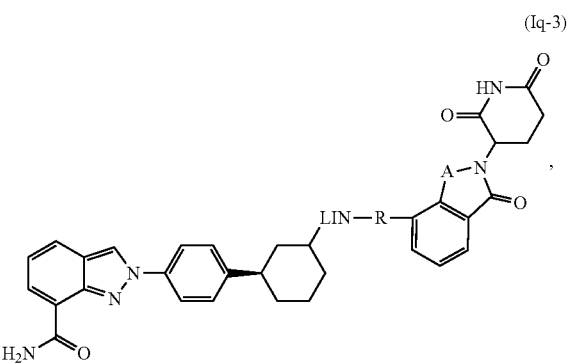

(Iq-3)

wherein, the groups LIN, R and A are as defined above.

In a sub-embodiment of the compound of formula (Iq-3) of the present disclosure, the LIN represents —U—C$_{1-30}$ alkylene-; and the group U represents CO or NH, or the group U is absent. In a sub-embodiment of the compound of formula (Iq-3), the LIN represents: —U—CH$_2$—; —U—(CH$_2$)$_2$—; —U—(CH$_2$)$_3$—; —U—(CH$_2$)$_4$—; —U—(CH$_2$)$_5$—; —U—(CH$_2$)$_6$—; —U—(CH$_2$)$_7$—; —U—(CH$_2$)$_8$—; —U—(CH$_2$)$_9$—; —U—(CH$_2$)$_{10}$—; —U—(CH$_2$)$_{11}$—; —U—(CH$_2$)$_{12}$—; —U—(CH$_2$)$_{13}$—; —U—(CH$_2$)$_{14}$—; —U—(CH$_2$)$_{15}$—; —U—(CH$_2$)$_{16}$—; —U—(CH$_2$)$_{17}$—; —U—(CH$_2$)$_{18}$—; —U—(CH$_2$)$_{19}$—; —U—(CH$_2$)$_{20}$—; —U—(CH$_2$)$_{21}$—; —U—(CH$_2$)$_{22}$—; —U—(CH$_2$)$_{23}$—; —U—(CH$_2$)$_{24}$—; —U—(CH$_2$)$_{25}$—; —U—(CH$_2$)$_{26}$—; —U—(CH$_2$)$_{27}$—; —U—(CH$_2$)$_{28}$—; —U—(CH$_2$)$_{29}$—; or U—(CH$_2$)$_{30}$—; wherein the group U represents CO or NH, or the group U is absent.

In a sub-embodiment of the compound of formula (Iq-3) of the present disclosure, the LIN is preferably —U—C$_{2-40}$ alkylene-(preferably —U—C$_{2-30}$ alkylene-), wherein the alkylene chain is optionally interrupted one or more times by one or more of O, CONH, NHCO, NH, alkynylene, alkenylene, cycloalkylene, arylene, heterocyclylene or heteroarylene or any combination thereof, and the group U represents CO or NH, or the group U is absent. In a sub-embodiment of the compound of formula (Iq-3), the LIN preferably represents: —U—(CH$_2$)$_{n1}$—(O(CH$_2$)$_{n2}$)$_{m1}$— or —U—(CH$_2$)$_{n1}$—(O(CH$_2$)$_{n2}$)$_{m1}$—(O(CH$_2$)$_{n3}$)$_{m2}$—, wherein n1, n2, n3, m1 and m2 each independently represent an integer of 1, 2, 3, 4, 5, 6, 7, 8, 9, 10, 11, 12, 13, 14, 15, 16, 17, 18, 19 or 20; and wherein the group U represents CO or NH, or the group U is absent. In a sub-embodiment of the compound of formula (Iq-3), the LIN preferably represents: —U—CH$_2$—O—(CH$_2$)$_2$—, —U—CH$_2$—(O(CH$_2$)$_2$)$_2$—, —U—CH$_2$—(O(CH$_2$)$_2$)$_3$—, —U—CH$_2$—(O(CH$_2$)$_2$)$_4$—, —U—CH$_2$—(O(CH$_2$)$_2$)$_5$—, —U—CH$_2$—(O(CH$_2$)$_2$)$_6$—, —U—CH$_2$—(O(CH$_2$)$_2$)$_7$—, —U—CH$_2$—(O(CH$_2$)$_2$)$_8$—, —U—CH$_2$—(O(CH$_2$)$_2$)$_9$—, —U—CH$_2$—(O(CH$_2$)$_2$)$_{10}$—, —U—(CH$_2$)$_2$—O—(CH$_2$)$_2$—, —U—(CH$_2$)$_2$—(O(CH$_2$)$_2$)$_2$—, —U—(CH$_2$)$_2$—(O(CH$_2$)$_2$)$_3$—, —U—(CH$_2$)$_2$—(O(CH$_2$)$_2$)$_4$—, —U—(CH$_2$)$_2$—(O(CH$_2$)$_2$)$_5$—, —U—(CH$_2$)$_2$—(O(CH$_2$)$_2$)$_6$—, —U—(CH$_2$)$_2$—(O(CH$_2$)$_2$)$_7$—, —U—(CH$_2$)$_2$—(O(CH$_2$)$_2$)$_8$—, —U—(CH$_2$)$_2$—(O(CH$_2$)$_2$)$_9$—, —U—(CH$_2$)$_2$—(O(CH$_2$)$_2$)$_{10}$—, —U—(CH$_2$)$_3$—O—(CH$_2$)$_2$—, —U—(CH$_2$)$_3$—(O(CH$_2$)$_2$)$_2$—, —U—(CH$_2$)$_3$—(O(CH$_2$)$_2$)$_3$—, —U—(CH$_2$)$_3$—(O(CH$_2$)$_2$)$_4$—, —U—(CH$_2$)$_3$—(O(CH$_2$)$_2$)$_5$—, —U—(CH$_2$)$_3$—(O(CH$_2$)$_2$)$_6$—, —U—(CH$_2$)$_3$—(O(CH$_2$)$_2$)$_7$—, —U—(CH$_2$)$_3$—(O(CH$_2$)$_2$)$_8$—, —U—(CH$_2$)$_3$—(O(CH$_2$)$_2$)$_9$—, —U—(CH$_2$)$_3$—(O(CH$_2$)$_2$)$_{10}$—, —U—(CH$_2$)$_4$—O—(CH$_2$)$_2$—, —U—(CH$_2$)$_4$—(O(CH$_2$)$_2$)$_2$—, —U—(CH$_2$)$_4$—(O(CH$_2$)$_2$)$_3$—, —U—(CH$_2$)$_4$—(O(CH$_2$)$_2$)$_4$—, —U—(CH$_2$)$_4$—(O(CH$_2$)$_2$)$_5$—, —U—(CH$_2$)$_4$—(O(CH$_2$)$_2$)$_6$—, —U—(CH$_2$)$_4$—(O(CH$_2$)$_2$)$_7$—, —U—(CH$_2$)$_4$—(O(CH$_2$)$_2$)$_8$—, —U—(CH$_2$)$_4$—(O(CH$_2$)$_2$)$_9$—, —U—(CH$_2$)$_4$—(O(CH$_2$)$_2$)$_{10}$—, —U—CH$_2$—O—(CH$_2$)$_3$—, —U—CH$_2$—(O(CH$_2$)$_3$)$_2$—, —U—CH$_2$—(O(CH$_2$)$_3$)$_3$—, —U—CH$_2$—(O(CH$_2$)$_3$)$_4$—, —U—CH$_2$—(O(CH$_2$)$_3$)$_5$—, —U—CH$_2$—(O(CH$_2$)$_3$)$_6$—, —U—CH$_2$—(O(CH$_2$)$_3$)$_7$—, —U—CH$_2$—(O(CH$_2$)$_3$)$_8$—, —U—CH$_2$—(O(CH$_2$)$_3$)$_9$—, —U—CH$_2$—(O(CH$_2$)$_3$)$_{10}$—, —U—(CH$_2$)$_2$—O—(CH$_2$)$_3$—, —U—(CH$_2$)$_2$—(O(CH$_2$)$_3$)$_2$—, —U—(CH$_2$)$_2$—(O(CH$_2$)$_3$)$_3$—, —U—(CH$_2$)$_2$—(O(CH$_2$)$_3$)$_4$—, —U—(CH$_2$)$_2$—(O(CH$_2$)$_3$)$_5$—, —U—(CH$_2$)$_2$—(O(CH$_2$)$_3$)$_6$—, —U—(CH$_2$)$_2$—(O(CH$_2$)$_3$)$_7$—, —U—(CH$_2$)$_2$—(O(CH$_2$)$_3$)$_8$—, —U—(CH$_2$)$_2$—(O(CH$_2$)$_3$)$_9$—, —U—(CH$_2$)$_2$—(O(CH$_2$)$_3$)$_{10}$—, —U—(CH$_2$)$_3$—O—(CH$_2$)$_3$—, —U—(CH$_2$)$_3$—(O(CH$_2$)$_3$)$_2$—, —U—(CH$_2$)$_3$—(O(CH$_2$)$_3$)$_3$—, —U—(CH$_2$)$_3$—(O(CH$_2$)$_3$)$_4$—, —U—(CH$_2$)$_3$—(O(CH$_2$)$_3$)$_5$—, —U—(CH$_2$)$_3$—(O(CH$_2$)$_3$)$_6$—, —U—(CH$_2$)$_3$—(O(CH$_2$)$_3$)$_7$—, —U—(CH$_2$)$_3$—(O(CH$_2$)$_3$)$_8$—, —U—(CH$_2$)$_3$—(O(CH$_2$)$_3$)$_9$—, —U—(CH$_2$)$_3$—(O(CH$_2$)$_3$)$_{10}$—, —U—CH$_2$—O—(CH$_2$)$_2$—O—(CH$_2$)$_3$—, —U—CH$_2$—(O(CH$_2$)$_2$)$_2$—(O(CH$_2$)$_3$)$_2$—, —U—CH$_2$—(O(CH$_2$)$_2$)$_3$—(O(CH$_2$)$_3$)$_3$—, —U—CH$_2$—(O(CH$_2$)$_2$)$_4$—(O(CH$_2$)$_3$)$_4$—, —U—CH$_2$—(O(CH$_2$)$_2$)$_5$—(O(CH$_2$)$_3$)$_5$—, —U—CH$_2$—(O(CH$_2$)$_2$)$_6$—(O(CH$_2$)$_3$)$_6$—, —U—(CH$_2$)$_2$—O—(CH$_2$)$_2$—O—(CH$_2$)$_3$—, —U—(CH$_2$)$_2$—(O(CH$_2$)$_2$)$_2$—(O(CH$_2$)$_3$)$_2$—, —U—(CH$_2$)$_2$—(O(CH$_2$)$_2$)$_3$—(O(CH$_2$)$_3$)$_3$—, —U—(CH$_2$)$_2$—(O(CH$_2$)$_2$)$_4$—(O(CH$_2$)$_3$)$_4$—, —U—(CH$_2$)$_2$—(O(CH$_2$)$_2$)$_5$—(O(CH$_2$)$_3$)$_5$—, —U—(CH$_2$)$_2$—(O(CH$_2$)$_3$)$_6$—(O(CH$_2$)$_2$)$_6$—, —U—(CH$_2$)$_3$—O—(CH$_2$)$_3$—O—(CH$_2$)$_2$—, —U—(CH$_2$)$_3$—(O(CH$_2$)$_3$)$_2$—(O(CH$_2$)$_2$)$_2$—, —U—(CH$_2$)$_3$—(O(CH$_2$)$_3$)$_3$—(O(CH$_2$)$_2$)$_3$—, —U—(CH$_2$)$_3$—(O(CH$_2$)$_3$)$_4$—(O(CH$_2$)$_2$)$_4$—, —U—(CH$_2$)$_3$—(O(CH$_2$)$_3$)$_5$—(O(CH$_2$)$_2$)$_5$—, —U—(CH$_2$)$_3$—(O(CH$_2$)$_3$)$_6$—(O(CH$_2$)$_2$)$_6$—, —U—CH$_2$—O—(CH$_2$)$_2$—O—CH$_2$—, —U—(CH$_2$)$_2$—O—(CH$_2$)$_2$—O—CH$_2$—, —U—(CH$_2$)$_2$—(O(CH$_2$)$_2$)$_2$—O—(CH$_2$)$_3$—, —U—(CH$_2$)$_2$—(O(CH$_2$)$_2$)$_3$—O—(CH$_2$)$_3$—, —U—(CH$_2$)$_2$—(O(CH$_2$)$_2$)$_4$—O—(CH$_2$)$_3$—, —U—(CH$_2$)$_5$—(O(CH$_2$)$_2$)$_2$—O—(CH$_2$)$_5$—, or —U—(CH$_2$)$_5$—(O(CH$_2$)$_2$)$_2$—O—(CH$_2$)$_6$—; wherein the group U represents CO or NH, or the group U is absent.

In an embodiment of the present disclosure, the compound of formula (I) is also the compound of formula (Ir-2):

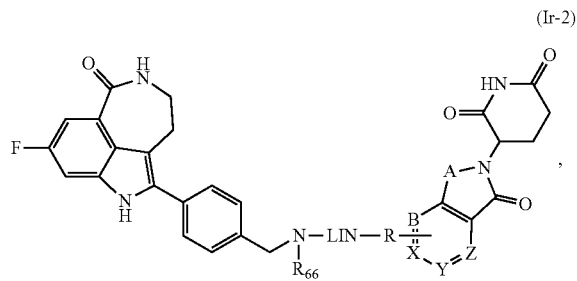

(Ir-2)

wherein, the groups LIN, R, A, B, X, Y and Z are as defined above, and the group R$_{66}$ is as defined above.

In an embodiment of the present disclosure, the compound of formula (I) is also the compound of formula (Ir-3):

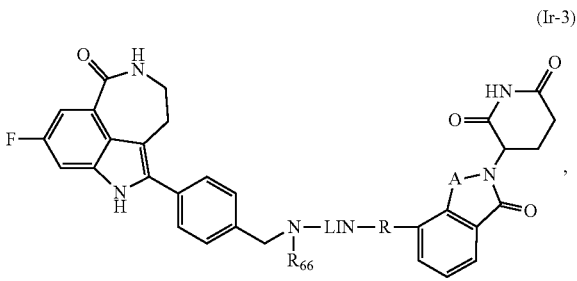

(Ir-3)

wherein, the groups LIN, R and A are as defined above, and the group R$_{66}$ is as defined above.

In a sub-embodiment of the compound of formula (Ir-3) of the present disclosure, the LIN represents —U—C$_{1-30}$ alkylene-; and the group U represents CO or NH, or the group U is absent. In a sub-embodiment of the compound of formula (Ir-3), the LIN represents: —U—CH$_2$—; —U—(CH$_2$)$_2$—; —U—(CH$_2$)$_3$—; —U—(CH$_2$)$_4$—; —U—(CH$_2$)$_5$—; —U—(CH$_2$)$_6$—; —U—(CH$_2$)$_7$—; —U—(CH$_2$)$_8$—; —U—(CH$_2$)$_9$—; —U—(CH$_2$)$_{10}$—; —U—(CH$_2$)$_{11}$—; —U—(CH$_2$)$_{12}$—; —U—(CH$_2$)$_{13}$—; —U—(CH$_2$)$_{14}$—; —U—(CH$_2$)$_{15}$—; —U—(CH$_2$)$_{16}$—; —U—(CH$_2$)$_{17}$—; —U—(CH$_2$)$_{18}$—; —U—(CH$_2$)$_{19}$—; —U—(CH$_2$)$_{20}$—; —U—(CH$_2$)$_{21}$—; —U—(CH$_2$)$_{22}$—; —U—(CH$_2$)$_{23}$—; —U—(CH$_2$)$_{24}$—; —U—(CH$_2$)$_{25}$—; —U—(CH$_2$)$_{26}$—; —U—(CH$_2$)$_{27}$—; —U—(CH$_2$)$_{28}$—; —U—(CH$_2$)$_{29}$—; or U—(CH$_2$)$_{30}$—; wherein the group U represents CO or NH, or the group U is absent.

In a sub-embodiment of the compound of formula (Ir-3) of the present disclosure, the LIN is preferably —U—C$_{2-40}$ alkylene-(preferably —U—C$_{2-30}$ alkylene-), wherein the alkylene chain is optionally interrupted one or more times by one or more of O, CONH, NHCO, NH, alkynylene, alkenylene, cycloalkylene, arylene, heterocyclylene or heteroarylene or any combination thereof, and the group U represents CO or NH, or the group U is absent. In a sub-embodiment of the compound of formula (Ir-3), the LIN preferably represents: —U—$(CH_2)_{n1}$—$(O(CH_2)_{n2})_{m1}$— or —U—$(CH_2)_{n1}$—$(O(CH_2)_{n2})_{m1}$—$(O(CH_2)_{n3})_{m2}$—, wherein n1, n2, n3, m1 and m2 each independently represent an integer of 1, 2, 3, 4, 5, 6, 7, 8, 9, 10, 11, 12, 13, 14, 15, 16, 17, 18, 19 or 20; and wherein the group U represents CO or NH, or the group U is absent. In a sub-embodiment of the compound of formula (Ir-3), the LIN preferably represents:
—U—$CH_2$—O—$(CH_2)_2$—, —U—$CH_2$—$(O(CH_2)_2)_2$—, —U—$CH_2$—$(O(CH_2)_2)_3$—, —U—$CH_2$—$(O(CH_2)_2)_4$—, —U—$CH_2$—$(O(CH_2)_2)_5$—, —U—$CH_2$—$(O(CH_2)_2)_6$—, —U—$CH_2$—$(O(CH_2)_2)_7$—, —U—$CH_2$—$(O(CH_2)_2)_8$—, —U—$CH_2$—$(O(CH_2)_2)_9$—, —U—$CH_2$—$(O(CH_2)_2)_{10}$—, —U—$(CH_2)_2$—O—$(CH_2)_2$—, —U—$(CH_2)_2$—$(O(CH_2)_2)_2$—, —U—$(CH_2)_2$—$(O(CH_2)_2)_3$—, —U—$(CH_2)_2$—$(O(CH_2)_2)_4$—, —U—$(CH_2)_2$—$(O(CH_2)_2)_5$—, —U—$(CH_2)_2$—$(O(CH_2)_2)_6$—, —U—$(CH_2)_2$—$(O(CH_2)_2)_7$—, —U—$(CH_2)_2$—$(O(CH_2)_2)_8$—, —U—$(CH_2)_2$—$(O(CH_2)_2)_9$—, —U—$(CH_2)_2$—$(O(CH_2)_2)_{10}$—, —U—$(CH_2)_3$—O—$(CH_2)_2$—, —U—$(CH_2)_3$—$(O(CH_2)_2)_2$—, —U—$(CH_2)_3$—$(O(CH_2)_2)_3$—, —U—$(CH_2)_3$—$(O(CH_2)_2)_4$—, —U—$(CH_2)_3$—$(O(CH_2)_2)_5$—, —U—$(CH_2)_3$—$(O(CH_2)_2)_6$—, —U—$(CH_2)_3$—$(O(CH_2)_2)_7$—, —U—$(CH_2)_3$—$(O(CH_2)_2)_8$—, —U—$(CH_2)_3$—$(O(CH_2)_2)_9$—, —U—$(CH_2)_3$—$(O(CH_2)_2)_{10}$—, —U—$(CH_2)_4$—O—$(CH_2)_2$—, —U—$(CH_2)_4$—$(O(CH_2)_2)_2$—, —U—$(CH_2)_4$—$(O(CH_2)_2)_3$—, —U—$(CH_2)_4$—$(O(CH_2)_2)_4$—, —U—$(CH_2)_4$—$(O(CH_2)_2)_5$—, —U—$(CH_2)_4$—$(O(CH_2)_2)_6$—, —U—$(CH_2)_4$—$(O(CH_2)_2)_7$—, —U—$(CH_2)_4$—$(O(CH_2)_2)_8$—, —U—$(CH_2)_4$—$(O(CH_2)_2)_9$—, —U—$(CH_2)_4$—$(O(CH_2)_2)_{10}$—, —U—$CH_2$—O—$(CH_2)_3$—, —U—$CH_2$—$(O(CH_2)_3)_2$—, —U—$CH_2$—$(O(CH_2)_3)_3$—, —U—$CH_2$—$(O(CH_2)_3)_4$—, —U—$CH_2$—$(O(CH_2)_3)_5$—, —U—$CH_2$—$(O(CH_2)_3)_6$—, —U—$CH_2$—$(O(CH_2)_3)_7$—, —U—$CH_2$—$(O(CH_2)_3)_8$—, —U—$CH_2$—$(O(CH_2)_3)_9$—, —U—$CH_2$—$(O(CH_2)_3)_{10}$—, —U—$(CH_2)_2$—O—$(CH_2)_3$—, —U—$(CH_2)_2$—$(O(CH_2)_3)_2$—, —U—$(CH_2)_2$—$(O(CH_2)_3)_3$—, —U—$(CH_2)_2$—$(O(CH_2)_3)_4$—, —U—$(CH_2)_2$—$(O(CH_2)_3)_5$—, —U—$(CH_2)_2$—$(O(CH_2)_3)_6$—, —U—$(CH_2)_2$—$(O(CH_2)_3)_7$—, —U—$(CH_2)_2$—$(O(CH_2)_3)_8$—, —U—$(CH_2)_2$—$(O(CH_2)_3)_9$—, —U—$(CH_2)_2$—$(O(CH_2)_3)_{10}$—, —U—$(CH_2)_3$—O—$(CH_2)_3$—, —U—$(CH_2)_3$—$(O(CH_2)_3)_2$—, —U—$(CH_2)_3$—$(O(CH_2)_3)_3$—, —U—$(CH_2)_3$—$(O(CH_2)_3)_4$—, —U—$(CH_2)_3$—$(O(CH_2)_3)_5$—, —U—$(CH_2)_3$—$(O(CH_2)_3)_6$—, —U—$(CH_2)_3$—$(O(CH_2)_3)_7$—, —U—$(CH_2)_3$—$(O(CH_2)_3)_8$—, —U—$(CH_2)_3$—$(O(CH_2)_3)_{10}$—, —U—$CH_2$—$(O(CH_2)_2)_2$—O—$(CH_2)_3$—, —U—$CH_2$—$(O(CH_2)_2)_3$—$(O(CH_2)_3)_3$—, —U—$CH_2$—$(O(CH_2)_2)_4$—$(O(CH_2)_3)_4$—, —U—$CH_2$—$(O(CH_2)_2)_5$—$(O(CH_2)_3)_5$—, —U—$CH_2$—$(O(CH_2)_2)_6$—$(O(CH_2)_3)_6$—, —U—$(CH_2)_3$—O—$(CH_2)_2$—O—$(CH_2)_3$—, —U—$(CH_2)_3$—$(O(CH_2)_2)_2$—$(O(CH_2)_3)_2$—, —U—$(CH_2)_3$—$(O(CH_2)_2)_3$—$(O(CH_2)_3)_3$—, —U—$(CH_2)_3$—$(O(CH_2)_2)_4$—$(O(CH_2)_3)_4$—, —U—$(CH_2)_3$—$(O(CH_2)_2)_5$—$(O(CH_2)_3)_5$—, —U—$(CH_2)_3$—$(O(CH_2)_2)_6$—$(O(CH_2)_3)_6$—, —U—$CH_2$—O—$(CH_2)_3$—O—$(CH_2)_2$—, —U—$CH_2$—$(O(CH_2)_3)_2$—$(O(CH_2)_2)_2$—, —U—$CH_2$—$(O(CH_2)_3)_3$—$(O(CH_2)_2)_3$—, —U—$CH_2$—$(O(CH_2)_3)_4$—$(O(CH_2)_2)_4$—, —U—$CH_2$—$(O(CH_2)_3)_5$—$(O(CH_2)_2)_5$—, —U—$CH_2$—$(O(CH_2)_3)_6$—$(O(CH_2)_2)_6$—, —U—$(CH_2)_2$—O—$(CH_2)_3$—O—$(CH_2)_2$—, —U—$(CH_2)_2$—$(O(CH_2)_3)_2$—$(O(CH_2)_2)_2$—, —U—$(CH_2)_2$—$(O(CH_2)_3)_3$—$(O(CH_2)_3)_3$—, —U—$(CH_2)_2$—$(O(CH_2)_3)_4$—$(O(CH_2)_2)_4$—, —U—$(CH_2)_2$—$(O(CH_2)_3)_5$—$(O(CH_2)_2)_5$—, —U—$(CH_2)_2$—$(O(CH_2)_3)_6$—$(O(CH_2)_3)_6$—, —U—$(CH_2)_3$—O—$(CH_2)_3$—O—$(CH_2)_2$—, —U—$(CH_2)_3$—$(O(CH_2)_3)_2$—$(O(CH_2)_2)_2$—, —U—$(CH_2)_3$—$(O(CH_2)_3)_3$—$(O(CH_2)_2)_3$—, —U—$(CH_2)_3$—$(O(CH_2)_3)_4$—$(O(CH_2)_2)_4$—, —U—$(CH_2)_3$—$(O(CH_2)_3)_5$—$(O(CH_2)_2)_5$—, —U—$(CH_2)_3$—$(O(CH_2)_3)_6$—$(O(CH_2)_2)_6$—, —U—$CH_2$—O—$(CH_2)_2$—O—$CH_2$—, —U—$(CH_2)_2$—O—$(CH_2)_2$—O—$CH_2$—, —U—$(CH_2)_2$—$(O(CH_2)_2)_2$—O—$(CH_2)_3$—, —U—$(CH_2)_2$—$(O(CH_2)_2)_3$—O—$(CH_2)_3$—, —U—$(CH_2)_2$—$(O(CH_2)_2)_4$—O—$(CH_2)_3$—, —U—$(CH_2)_5$—$(O(CH_2)_2)_2$—O—$(CH_2)_5$—, or —U—$(CH_2)_5$—$(O(CH_2)_2)_2$—O—$(CH_2)_6$—; wherein the group U represents CO or NH, or the group U is absent.

In an embodiment of the present disclosure, the compound of formula (I) is also the compound of formula (Is-2):

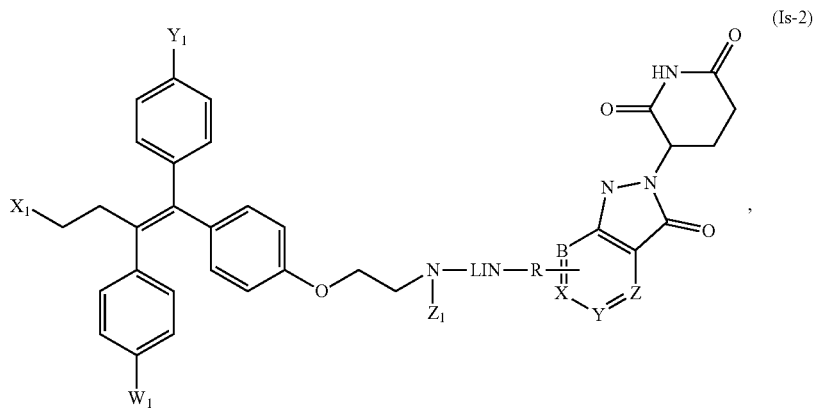

wherein, the groups LIN, R, A, B, X, Y and Z are as defined above, and the groups $X_1$, $Y_1$, $Z_1$ and $W_1$ are as defined above.

In an embodiment of the present disclosure, the compound of formula (I) is also the compound of formula (Is-3):

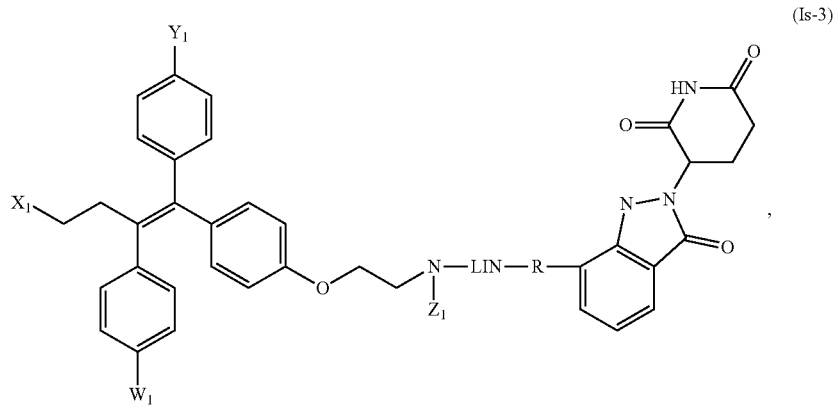

(Is-3)

wherein, the groups LIN, R and A are as defined above, and the groups $X_1$, $Y_1$, $Z_1$ and $W_1$ are as defined above.

In a sub-embodiment of the compound of formula (Is-3) of the present disclosure, the LIN represents —U—$C_{1-30}$ alkylene-; and the group U represents CO or NH, or the group U is absent. In a sub-embodiment of the compound of formula (Is-3), the LIN represents: —U—$CH_2$—; —U—$(CH_2)_2$—; —U—$(CH_2)_3$—; —U—$(CH_2)_4$—; —U—$(CH_2)_5$—; —U—$(CH_2)_6$—; —U—$(CH_2)_7$—; —U—$(CH_2)_8$—; —U—$(CH_2)_9$—; —U—$(CH_2)_{10}$—; —U—$(CH_2)_{11}$—; —U—$(CH_2)_{12}$—; —U—$(CH_2)_{13}$—; —U—$(CH_2)_{14}$—; —U—$(CH_2)_{15}$—; —U—$(CH_2)_{16}$—; —U—$(CH_2)_{17}$—; —U—$(CH_2)_{18}$—; —U—$(CH_2)_{19}$—; —U—$(CH_2)_{20}$—; —U—$(CH_2)_{21}$—; —U—$(CH_2)_{22}$—; —U—$(CH_2)_{23}$—; —U—$(CH_2)_{24}$—; —U—$(CH_2)_{25}$—; —U—$(CH_2)_{26}$—; —U—$(CH_2)_{27}$—; —U—$(CH_2)_{28}$—; —U—$(CH_2)_{29}$—; or U—$(CH_2)_{30}$—; wherein the group U represents CO or NH, or the group U is absent.

In a sub-embodiment of the compound of formula (Is-3) of the present disclosure, the LIN is preferably —U—$C_{2-40}$ alkylene-(preferably —U—$C_{2-30}$ alkylene-), wherein the alkylene chain is optionally interrupted one or more times by one or more of O, CONH, NHCO, NH, alkynylene, alkenylene, cycloalkylene, arylene, heterocyclylene or heteroarylene or any combination thereof, and the group U represents CO or NH, or the group U is absent. In a sub-embodiment of the compound of formula (Is-3), the LIN preferably represents: —U—$(CH_2)_{n1}$—$(O(CH_2)_{n2})_{m1}$— or —U—$(CH_2)_{n1}$—$(O(CH_2)_{n2})_{m1}$—$(O(CH_2)_{n3})_{m2}$—, wherein n1, n2, n3, m1 and m2 each independently represent an integer of 1, 2, 3, 4, 5, 6, 7, 8, 9, 10, 11, 12, 13, 14, 15, 16, 17, 18, 19 or 20; and wherein the group U represents CO or NH, or the group U is absent. In a sub-embodiment of the compound of formula (Is-3), the LIN preferably represents: —U—$CH_2$—O—$(CH_2)_2$—, —U—$CH_2$—$(O(CH_2)_2)_2$—, —U—$CH_2$—$(O(CH_2)_2)_3$—, —U—$CH_2$—$(O(CH_2)_2)_4$—, —U—$CH_2$—$(O(CH_2)_2)_5$—, —U—$CH_2$—$(O(CH_2)_2)_6$—, —U—$CH_2$—$(O(CH_2)_2)_7$—, —U—$CH_2$—$(O(CH_2)_2)_8$—, —U—$CH_2$—$(O(CH_2)_2)_9$—, —U—$CH_2$—$(O(CH_2)_2)_{10}$—, —U—$(CH_2)_2$—O—$(CH_2)_2$—, —U—$(CH_2)_2$—$(O(CH_2)_2)_2$—, —U—$(CH_2)_2$—$(O(CH_2)_2)_3$—, —U—$(CH_2)_2$—$(O(CH_2)_2)_4$—, —U—$(CH_2)_2$—$(O(CH_2)_2)_5$—, —U—$(CH_2)_2$—$(O(CH_2)_2)_6$—, —U—$(CH_2)_2$—$(O(CH_2)_2)_7$—, —U—$(CH_2)_2$—$(O(CH_2)_2)_8$—, —U—$(CH_2)_2$—$(O(CH_2)_2)_9$—, —U—$(CH_2)_2$—$(O(CH_2)_2)_{10}$—, —U—$(CH_2)_3$—O—$(CH_2)_2$—, —U—$(CH_2)_3$—$(O(CH_2)_2)_2$—, —U—$(CH_2)_3$—$(O(CH_2)_2)_3$—, —U—$(CH_2)_3$—$(O(CH_2)_2)_4$—, —U—$(CH_2)_3$—$(O(CH_2)_2)_5$—, —U—$(CH_2)_3$—$(O(CH_2)_2)_6$—, —U—$(CH_2)_3$—$(O(CH_2)_2)_7$—, —U—$(CH_2)_3$—$(O(CH_2)_2)_8$—, —U—$(CH_2)_3$—$(O(CH_2)_2)_9$—, —U—$(CH_2)_3$—$(O(CH_2)_2)_{10}$—, —U—$(CH_2)_4$—O—$(CH_2)_2$—, —U—$(CH_2)_4$—$(O(CH_2)_2)_2$—, —U—$(CH_2)_4$—$(O(CH_2)_2)_3$—, —U—$(CH_2)_4$—$(O(CH_2)_2)_4$—, —U—$(CH_2)_4$—$(O(CH_2)_2)_5$—, —U—$(CH_2)_4$—$(O(CH_2)_2)_6$—, —U—$(CH_2)_4$—$(O(CH_2)_2)_7$—, —U—$(CH_2)_4$—$(O(CH_2)_2)_8$—, —U—$(CH_2)_4$—$(O(CH_2)_2)_9$—, —U—$(CH_2)_4$—$(O(CH_2)_2)_{10}$—, —U—$CH_2$—O—$(CH_2)_3$—, —U—$CH_2$—$(O(CH_2)_3)_2$—, —U—$CH_2$—$(O(CH_2)_3)_3$—, —U—$CH_2$—$(O(CH_2)_3)_4$—, —U—$CH_2$—$(O(CH_2)_3)_5$—, —U—$CH_2$—$(O(CH_2)_3)_6$—, —U—$CH_2$—$(O(CH_2)_3)_7$—, —U—$CH_2$—$(O(CH_2)_3)_8$—, —U—$CH_2$—$(O(CH_2)_3)_9$—, —U—$CH_2$—$(O(CH_2)_3)_{10}$—, —U—$(CH_2)_2$—O—$(CH_2)_3$—, —U—$(CH_2)_2$—$(O(CH_2)_3)_2$—, —U—$(CH_2)_2$—$(O(CH_2)_3)_3$—, —U—$(CH_2)_2$—$(O(CH_2)_3)_4$—, —U—$(CH_2)_2$—$(O(CH_2)_3)_5$—, —U—$(CH_2)_2$—$(O(CH_2)_3)_6$—, —U—$(CH_2)_2$—$(O(CH_2)_3)_7$—, —U—$(CH_2)_2$—$(O(CH_2)_3)_8$—, —U—$(CH_2)_2$—$(O(CH_2)_3)_9$—, —U—$(CH_2)_2$—$(O(CH_2)_3)_{10}$—, —U—$(CH_2)_3$—O—$(CH_2)_3$—, —U—$(CH_2)_3$—$(O(CH_2)_3)_2$—, —U—$(CH_2)_3$—$(O(CH_2)_3)_3$—, —U—$(CH_2)_3$—$(O(CH_2)_3)_4$—, —U—$(CH_2)_3$—$(O(CH_2)_3)_5$—, —U—$(CH_2)_3$—$(O(CH_2)_3)_6$—, —U—$(CH_2)_3$—$(O(CH_2)_3)_7$—, —U—$(CH_2)_3$—$(O(CH_2)_3)_8$—, —U—$(CH_2)_3$—$(O(CH_2)_3)_9$—, —U—$(CH_2)_3$—$(O(CH_2)_3)_{10}$—, —U—$CH_2$—O—$(CH_2)_2$—O—$(CH_2)_3$—, —U—$CH_2$—$(O(CH_2)_2)_2$—$(O(CH_2)_3)_2$—, —U—$CH_2$—$(O(CH_2)_2)_3$—$(O(CH_2)_3)_3$—, —U—$CH_2$—$(O(CH_2)_2)_4$—$(O(CH_2)_3)_4$—, —U—$CH_2$—$(O(CH_2)_2)_5$—$(O(CH_2)_3)_5$—, —U—$CH_2$—$(O(CH_2)_2)_6$—$(O(CH_2)_3)_6$—, —U—$(CH_2)_2$—O—$(CH_2)_2$—O—$(CH_2)_3$—, —U—$(CH_2)_2$—$(O(CH_2)_2)_2$—$(O(CH_2)_3)_2$—, —U—$(CH_2)_2$—$(O(CH_2)_2)_3$—$(O(CH_2)_3)_3$—, —U—$(CH_2)_2$—$(O(CH_2)_2)_4$—$(O(CH_2)_3)_4$—, —U—$(CH_2)_2$—$(O(CH_2)_2)_5$—$(O(CH_2)_3)_5$—, —U—$(CH_2)_2$—$(O(CH_2)_2)_6$—$(O(CH_2)_3)_6$—, —U—$(CH_2)_3$—O—$(CH_2)_2$—O—$(CH_2)_3$—, —U—$(CH_2)_3$—$(O(CH_2)_2)_2$—$(O(CH_2)_3)_2$—, —U—$(CH_2)_3$—$(O(CH_2)_2)_3$—$(O(CH_2)_3)_3$—, —U—$(CH_2)_3$—$(O(CH_2)_2)_4$—$(O(CH_2)_3)_4$—, —U—$(CH_2)_3$—$(O(CH_2)_2)_5$—$(O(CH_2)_3)_5$—, —U—$(CH_2)_3$—$(O(CH_2)_2)_6$—$(O(CH_2)_3)_6$—, —U—$CH_2$—O—$(CH_2)_3$—O—$(CH_2)_2$—, —U—$CH_2$—$(O(CH_2)_3)_2$—$(O(CH_2)_2)_2$—, —U—$CH_2$—$(O(CH_2)_3)_3$—$(O(CH_2)_2)_3$—, —U—$CH_2$—$(O(CH_2)_3)_4$—$(O(CH_2)_2)_4$—, —U—$CH_2$—$(O(CH_2)_3)_5$—$(O(CH_2)_2)_5$—, —U—$(CH_2)_2$—O—$(CH_2)_3$—O—$(CH_2)_2$—, —U—$(CH_2)_2$—$(O(CH_2)_3)_2$—$(O(CH_2)_2)_2$—, —U—$(CH_2)_2$—$(O(CH_2)_3)_3$—$(O(CH_2)_2)_3$—, —U—$(CH_2)_2$—$(O(CH_2)_3)_4$—$(O(CH_2)_2)_4$—, —U—$(CH_2)_2$—$(O(CH_2)_3)_5$—$(O(CH_2)_2)_5$—, —U—

(CH$_2$)$_2$—(O(CH$_2$)$_3$)$_6$—(O(CH$_2$)$_2$)$_6$—, —U—(CH$_2$)$_3$—O—(CH$_2$)$_3$—O—(CH$_2$)$_2$—, —U—(CH$_2$)$_3$—(O(CH$_2$)$_3$)$_2$—(O(CH$_2$)$_2$)$_2$—, —U—(CH$_2$)$_3$—(O(CH$_2$)$_3$)$_3$—(O(CH$_2$)$_2$)$_3$—, —U—(CH$_2$)$_3$—(O(CH$_2$)$_3$)$_4$—(O(CH$_2$)$_2$)$_4$—, —U—(CH$_2$)$_3$—(O(CH$_2$)$_3$)$_5$—(O(CH$_2$)$_2$)$_5$—, —U—(CH$_2$)$_3$—(O(CH$_2$)$_3$)$_6$—(O(CH$_2$)$_2$)$_6$—, —U—CH$_2$—O—(CH$_2$)$_2$—O—CH$_2$—, —U—(CH$_2$)$_2$—O—(CH$_2$)$_2$—O—CH$_2$—, —U—(CH$_2$)$_2$—(O(CH$_2$)$_2$)$_2$—O—(CH$_2$)$_3$—, —U—(CH$_2$)$_2$—(O(CH$_2$)$_2$)$_3$—O—(CH$_2$)$_3$—, —U—(CH$_2$)$_2$—(O(CH$_2$)$_2$)$_4$—O—(CH$_2$)$_3$—, —U—(CH$_2$)$_5$—(O(CH$_2$)$_2$)$_2$—O—(CH$_2$)$_5$—, or —U—(CH$_2$)$_5$—(O(CH$_2$)$_2$)$_2$—O—(CH$_2$)$_6$—; wherein the group U represents CO or NH, or the group U is absent.

In an embodiment of the present disclosure, the compound of formula (I) is also the compound of formula (It-2):

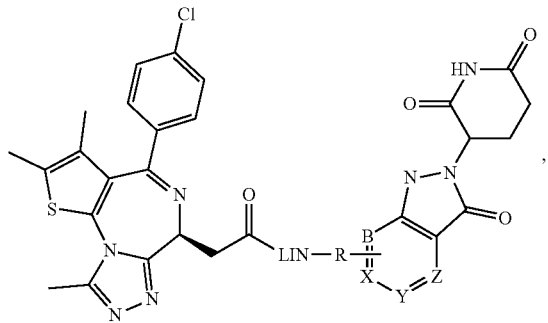

(It-2)

wherein, the groups LIN, R, A, B, X, Y and Z are as defined above.

In an embodiment of the present disclosure, the compound of formula (I) is also the compound of formula (It-2-1):

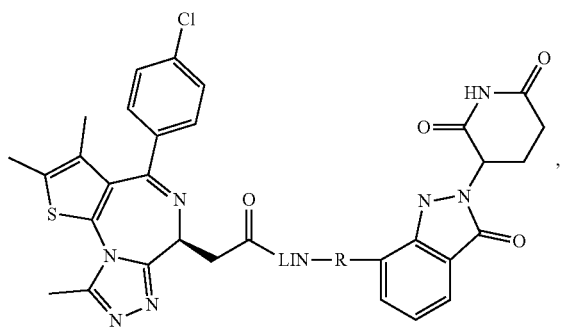

(It-2-1)

wherein, the groups LIN, R and A are as defined above.

In a sub-embodiment of the compound of formula (It-2-1) of the present disclosure, the LIN represents —U—C$_{1-30}$ alkylene-; and the group U represents CO or NH, or the group U is absent. In a sub-embodiment of the compound of formula (It-2-1), the LIN represents: —U—CH$_2$—; —U—(CH$_2$)$_2$—; —U—(CH$_2$)$_3$—; —U—(CH$_2$)$_4$—; —U—(CH$_2$)$_5$—; —U—(CH$_2$)$_6$—; —U—(CH$_2$)$_7$—; —U—(CH$_2$)$_8$—; —U—(CH$_2$)$_9$—; —U—(CH$_2$)$_{10}$—; —U—(CH$_2$)$_{11}$—; —U—(CH$_2$)$_{12}$—; —U—(CH$_2$)$_{13}$—; —U—(CH$_2$)$_{14}$—; —U—(CH$_2$)$_{15}$—; —U—(CH$_2$)$_{16}$—; —U—(CH$_2$)$_{17}$—; —U—(CH$_2$)$_{18}$—; —U—(CH$_2$)$_{19}$—; —U—(CH$_2$)$_{20}$—; —U—(CH$_2$)$_{21}$—; —U—(CH$_2$)$_{22}$—; —U—(CH$_2$)$_{23}$—; —U—(CH$_2$)$_{24}$—; —U—(CH$_2$)$_{25}$—; —U—(CH$_2$)$_{26}$—; —U—(CH$_2$)$_{27}$—; —U—(CH$_2$)$_{28}$—; —U—(CH$_2$)$_{29}$—; or U—(CH$_2$)$_{30}$—; wherein the group U represents CO or NH, or the group U is absent.

In a sub-embodiment of the compound of formula (It-2-1) of the present disclosure, the LIN is preferably —U—C$_{2-40}$ alkylene-(preferably —U—C$_{2-30}$ alkylene-), wherein the alkylene chain is optionally interrupted one or more times by one or more of O, CONH, NHCO, NH, alkynylene, alkenylene, cycloalkylene, arylene, heterocyclylene or heteroarylene or any combination thereof, and the group U represents CO or NH, or the group U is absent. In a sub-embodiment of the compound of formula (It-2-1), the LIN preferably represents: —U—(CH$_2$)$_{n1}$—(O(CH$_2$)$_{n2}$)$_{m1}$— or —U—(CH$_2$)$_{n1}$—(O(CH$_2$)$_{n2}$)$_{m1}$—(O(CH$_2$)$_{n3}$)$_{m2}$—, wherein n1, n2, n3, m1 and m2 each independently represent an integer of 1, 2, 3, 4, 5, 6, 7, 8, 9, 10, 11, 12, 13, 14, 15, 16, 17, 18, 19 or 20; and wherein the group U represents CO or NH, or the group U is absent. In a sub-embodiment of the compound of formula (It-2-1), the LIN preferably represents: —U—CH$_2$—O—(CH$_2$)$_2$—, —U—CH$_2$—(O(CH$_2$)$_2$)$_2$—, —U—CH$_2$—(O(CH$_2$)$_2$)$_3$—, —U—CH$_2$—(O(CH$_2$)$_2$)$_4$—, —U—CH$_2$—(O(CH$_2$)$_2$)$_5$—, —U—CH$_2$—(O(CH$_2$)$_2$)$_6$—, —U—CH$_2$—(O(CH$_2$)$_2$)$_7$—, —U—CH$_2$—(O(CH$_2$)$_2$)$_8$—, —U—CH$_2$—(O(CH$_2$)$_2$)$_9$—, —U—CH$_2$—(O(CH$_2$)$_2$)$_{10}$—, —U—(CH$_2$)$_2$—O—(CH$_2$)$_2$—, —U—(CH$_2$)$_2$—(O(CH$_2$)$_2$)$_2$—, —U—(CH$_2$)$_2$—(O(CH$_2$)$_2$)$_3$—, —U—(CH$_2$)$_2$—(O(CH$_2$)$_2$)$_4$—, —U—(CH$_2$)$_2$—(O(CH$_2$)$_2$)$_5$—, —U—(CH$_2$)$_2$—(O(CH$_2$)$_2$)$_6$—, —U—(CH$_2$)$_2$—(O(CH$_2$)$_2$)$_7$—, —U—(CH$_2$)$_2$—(O(CH$_2$)$_2$)$_8$—, —U—(CH$_2$)$_2$—(O(CH$_2$)$_2$)$_9$—, —U—(CH$_2$)$_2$—(O(CH$_2$)$_2$)$_{10}$—, —U—(CH$_2$)$_3$—O—(CH$_2$)$_2$—, —U—(CH$_2$)$_3$—(O(CH$_2$)$_2$)$_2$—, —U—(CH$_2$)$_3$—(O(CH$_2$)$_2$)$_3$—, —U—(CH$_2$)$_3$—(O(CH$_2$)$_2$)$_4$—, —U—(CH$_2$)$_3$—(O(CH$_2$)$_2$)$_5$—, —U—(CH$_2$)$_3$—(O(CH$_2$)$_2$)$_6$—, —U—(CH$_2$)$_3$—(O(CH$_2$)$_2$)$_7$—, —U—(CH$_2$)$_3$—(O(CH$_2$)$_2$)$_8$—, —U—(CH$_2$)$_3$—(O(CH$_2$)$_2$)$_9$—, —U—(CH$_2$)$_3$—(O(CH$_2$)$_2$)$_{10}$—, —U—(CH$_2$)$_4$—O—(CH$_2$)$_2$—, —U—(CH$_2$)$_4$—(O(CH$_2$)$_2$)$_2$—, —U—(CH$_2$)$_4$—(O(CH$_2$)$_2$)$_3$—, —U—(CH$_2$)$_4$—(O(CH$_2$)$_2$)$_4$—, —U—(CH$_2$)$_4$—(O(CH$_2$)$_2$)$_5$—, —U—(CH$_2$)$_4$—(O(CH$_2$)$_2$)$_6$—, —U—(CH$_2$)$_4$—(O(CH$_2$)$_2$)$_7$—, —U—(CH$_2$)$_4$—(O(CH$_2$)$_2$)$_8$—, —U—(CH$_2$)$_4$—(O(CH$_2$)$_2$)$_9$—, —U—(CH$_2$)$_4$—(O(CH$_2$)$_2$)$_{10}$—, —U—CH$_2$—O—(CH$_2$)$_3$—, —U—CH$_2$—(O(CH$_2$)$_3$)$_2$—, —U—CH$_2$—(O(CH$_2$)$_3$)$_3$—, —U—CH$_2$—(O(CH$_2$)$_3$)$_4$—, —U—CH$_2$—(O(CH$_2$)$_3$)$_5$—, —U—CH$_2$—(O(CH$_2$)$_3$)$_6$—, —U—CH$_2$—(O(CH$_2$)$_3$)$_7$—, —U—CH$_2$—(O(CH$_2$)$_3$)$_8$—, —U—CH$_2$—(O(CH$_2$)$_3$)$_9$—, —U—CH$_2$—(O(CH$_2$)$_3$)$_{10}$—, —U—(CH$_2$)$_2$—O—(CH$_2$)$_3$—, —U—(CH$_2$)$_2$—(O(CH$_2$)$_3$)$_2$—, —U—(CH$_2$)$_2$—(O(CH$_2$)$_3$)$_3$—, —U—(CH$_2$)$_2$—(O(CH$_2$)$_3$)$_4$—, —U—(CH$_2$)$_2$—(O(CH$_2$)$_3$)$_5$—, —U—(CH$_2$)$_2$—(O(CH$_2$)$_3$)$_6$—, —U—(CH$_2$)$_2$—(O(CH$_2$)$_3$)$_7$—, —U—(CH$_2$)$_2$—(O(CH$_2$)$_3$)$_8$—, —U—(CH$_2$)$_2$—(O(CH$_2$)$_3$)$_9$—, —U—(CH$_2$)$_2$—(O(CH$_2$)$_3$)$_{10}$—, —U—(CH$_2$)$_3$—O—(CH$_2$)$_3$—, —U—(CH$_2$)$_3$—(O(CH$_2$)$_3$)$_2$—, —U—(CH$_2$)$_3$—(O(CH$_2$)$_3$)$_3$—, —U—(CH$_2$)$_3$—(O(CH$_2$)$_3$)$_4$—, —U—(CH$_2$)$_3$—(O(CH$_2$)$_3$)$_5$—, —U—(CH$_2$)$_3$—(O(CH$_2$)$_3$)$_6$—, —U—(CH$_2$)$_3$—(O(CH$_2$)$_3$)$_7$—, —U—(CH$_2$)$_3$—(O(CH$_2$)$_3$)$_8$—, —U—(CH$_2$)$_3$—(O(CH$_2$)$_3$)$_9$—, —U—(CH$_2$)$_3$—(O(CH$_2$)$_3$)$_{10}$—, —U—CH$_2$—O—(CH$_2$)$_2$—O—(CH$_2$)$_3$—, —U—CH$_2$—(O(CH$_2$)$_2$)$_2$—(O(CH$_2$)$_3$)$_2$—, —U—CH$_2$—(O(CH$_2$)$_2$)$_3$—(O(CH$_2$)$_3$)$_3$—, —U—CH$_2$—(O(CH$_2$)$_2$)$_4$—(O(CH$_2$)$_3$)$_4$—, —U—CH$_2$—(O(CH$_2$)$_2$)$_5$—(O(CH$_2$)$_3$)$_5$—, —U—CH$_2$—(O(CH$_2$)$_2$)$_6$—(O(CH$_2$)$_3$)$_6$—, —U—(CH$_2$)$_2$—O—(CH$_2$)$_2$—O—(CH$_2$)$_3$—, —U—(CH$_2$)$_2$—(O(CH$_2$)$_2$)$_2$—(O(CH$_2$)$_3$)$_2$—, —U—(CH$_2$)$_2$—(O(CH$_2$)$_2$)$_3$—(O(CH$_2$)$_3$)$_3$—, —U—(CH$_2$)$_2$—(O(CH$_2$)$_2$)$_4$—(O(CH$_2$)$_3$)$_4$—, —U—(CH$_2$)$_2$—(O(CH$_2$)$_2$)$_5$—(O(CH$_2$)$_3$)$_5$—, —U—(CH$_2$)$_2$—(O(CH$_2$)$_2$)$_6$—(O(CH$_2$)$_3$)$_6$—, —U—(CH$_2$)$_3$—O—(CH$_2$)$_2$—O—(CH$_2$)$_3$—, —U—(CH$_2$)$_3$—(O(CH$_2$)$_2$)$_2$—(O(CH$_2$)$_3$)$_2$—, —U—(CH$_2$)$_3$—(O(CH$_2$)$_2$)$_3$—(O(CH$_2$)$_3$)$_3$—, —U—(CH₂)₃—(O(CH₂)₂)₄—(O(CH₂)₃)₄—, —U—(CH₂)₃—(O(CH₂)₂)₅—(O(CH₂)₃)₅—, —U—(CH₂)₃—(O(CH₂)₂)₆—(O(CH₂)₃)₆—, —U—CH₂—O—(CH₂)₃—O—(CH₂)₂—, —U—CH₂—(O(CH₂)₃)₂—(O(CH₂)₂)₂—, —U—CH₂—(O(CH₂)₃)₃—(O(CH₂)₂)₃—, —U—CH₂—(O(CH₂)₃)₄—(O(CH₂)₂)₄—, —U—CH₂—(O(CH₂)₃)₅—(O(CH₂)₂)₅—, —U—CH₂—(O(CH₂)₃)₆—(O(CH₂)₂)₆—, —U—(CH₂)₂—O—(CH₂)₃—O—(CH₂)₂—, —U—(CH₂)₂—(O(CH₂)₃)₂—(O(CH₂)₂)₂—, —U—(CH₂)₂—(O(CH₂)₃)₃—(O(CH₂)₂)₃—, —U—(CH₂)₂—(O(CH₂)₃)₄—(O(CH₂)₂)₄—, —U—(CH₂)₂—(O(CH₂)₃)₅—(O(CH₂)₂)₅—, —U—(CH₂)₂—(O(CH₂)₃)₆—(O(CH₂)₂)₆—, —U—(CH₂)₃—O—(CH₂)₃—O—(CH₂)₂—, —U—(CH₂)₃—(O(CH₂)₂)₂—, —U—(CH₂)₃—(O(CH₂)₃)₃—(O(CH₂)₂)₃—, —U—(CH₂)₃—(O(CH₂)₃)₄—(O(CH₂)₂)₄—, —U—(CH₂)₃—(O(CH₂)₃)₅—(O(CH₂)₂)₅—, —U—(CH₂)₃—(O(CH₂)₃)₆—(O(CH₂)₂)₆—, —U—CH₂—O—(CH₂)₂—O—CH₂—, —U—(CH₂)₂—O—(CH₂)₂—O—CH₂—, —U—(CH₂)₂—(O(CH₂)₂)₂—O—(CH₂)₃—, —U—(CH₂)₂—(O(CH₂)₂)₃—O—(CH₂)₃—, —U—(CH₂)₂—(O(CH₂)₂)₄—O—(CH₂)₃—, —U—(CH₂)₅—(O(CH₂)₂)₂—O—(CH₂)₅—, or —U—(CH₂)₅—(O(CH₂)₂)₂—O—(CH₂)₆—; wherein the group U represents CO or NH, or the group U is absent.

In an embodiment of the present disclosure, the compound of formula (I) is also the compound of formula (Iu-2):

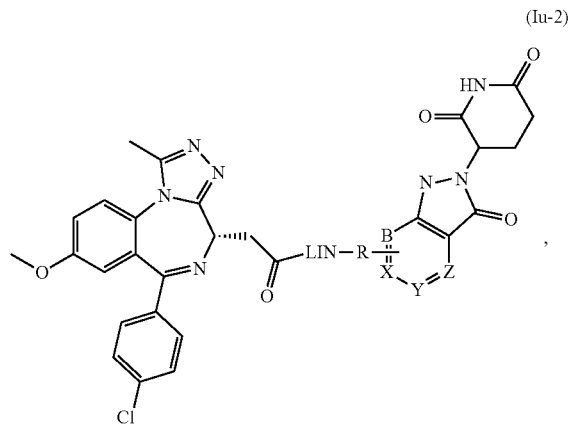

(Iu-2)

wherein, the groups LIN, R, A, B, X, Y and Z are as defined above.

In an embodiment of the present disclosure, the compound of formula (I) is also the compound of formula (Iu-3):

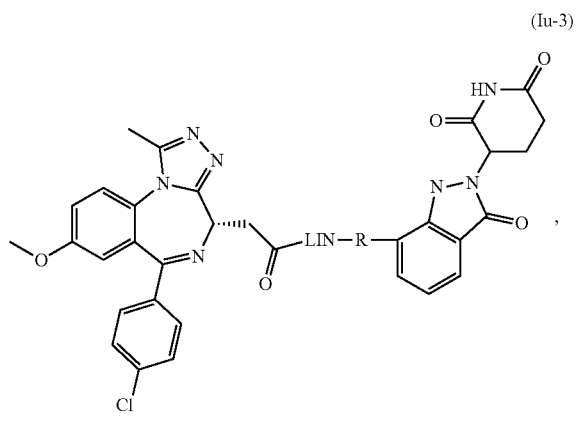

(Iu-3)

wherein, the groups LIN, R and A are as defined above.

In a sub-embodiment of the compound of formula (Iu-3) of the present disclosure, the LIN represents —U—C₁₋₃₀ alkylene-; and the group U represents CO or NH, or the group U is absent. In a sub-embodiment of the compound of formula (Iu-3), the LIN represents: —U—CH₂—; —U—(CH₂)₂—; —U—(CH₂)₃—; —U—(CH₂)₄—; —U—(CH₂)₅—; —U—(CH₂)₆—; —U—(CH₂)₇—; —U—(CH₂)₈—; —U—(CH₂)₉—; —U—(CH₂)₁₀—; —U—(CH₂)₁₁—; —U—(CH₂)₁₂—; —U—(CH₂)₁₃—; —U—(CH₂)₁₄—; —U—(CH₂)₁₅—; —U—(CH₂)₁₆—; —U—(CH₂)₁₇—; —U—(CH₂)₁₈—; —U—(CH₂)₁₉—; —U—(CH₂)₂₀—; —U—(CH₂)₂₁—; —U—(CH₂)₂₂—; —U—(CH₂)₂₃—; —U—(CH₂)₂₄—; —U—(CH₂)₂₅—; —U—(CH₂)₂₆—; —U—(CH₂)₂₇—; —U—(CH₂)₂₈—; —U—(CH₂)₂₉—; or U—(CH₂)₃₀—; wherein the group U represents CO or NH, or the group U is absent.

In a sub-embodiment of the compound of formula (Iu-3) of the present disclosure, the LIN is preferably —U—C₂₋₄₀ alkylene-(preferably —U—C₂₋₃₀ alkylene-), wherein the alkylene chain is optionally interrupted one or more times by one or more of O, CONH, NHCO, NH, alkynylene, alkenylene, cycloalkylene, arylene, heterocyclylene or heteroarylene or any combination thereof, and the group U represents CO or NH, or the group U is absent. In a sub-embodiment of the compound of formula (Iu-3), the LIN preferably represents: —U—(CH₂)ₙ₁—(O(CH₂)ₙ₂)ₘ₁— or —U—(CH₂)ₙ₁—(O(CH₂)ₙ₂)ₘ₁—(O(CH₂)ₙ₃)ₘ₂—, wherein n1, n2, n3, m1 and m2 each independently represent an integer of 1, 2, 3, 4, 5, 6, 7, 8, 9, 10, 11, 12, 13, 14, 15, 16, 17, 18, 19 or 20; and wherein the group U represents CO or NH, or the group U is absent. In a sub-embodiment of the compound of formula (Iu-3), the LIN preferably represents: —U—CH₂—O—(CH₂)₂—, —U—CH₂—(O(CH₂)₂)₂—, —U—CH₂—(O(CH₂)₂)₃—, —U—CH₂—(O(CH₂)₂)₄—, —U—CH₂—(O(CH₂)₂)₅—, —U—CH₂—(O(CH₂)₂)₆—, —U—CH₂—(O(CH₂)₂)₇—, —U—CH₂—(O(CH₂)₂)₈—, —U—CH₂—(O(CH₂)₂)₉—, —U—CH₂—(O(CH₂)₂)₁₀—, —U—(CH₂)₂—O—(CH₂)₂—, —U—(CH₂)₂—(O(CH₂)₂)₂—, —U—(CH₂)₂—(O(CH₂)₂)₃—, —U—(CH₂)₂—(O(CH₂)₂)₄—, —U—(CH₂)₂—(O(CH₂)₂)₅—, —U—(CH₂)₂—(O(CH₂)₂)₆—, —U—(CH₂)₂—(O(CH₂)₂)₇—, —U—(CH₂)₂—(O(CH₂)₂)₈—, —U—(CH₂)₂—(O(CH₂)₂)₉—, —U—(CH₂)₂—(O(CH₂)₂)₁₀—, —U—(CH₂)₃—O—(CH₂)₂—, —U—(CH₂)₃—(O(CH₂)₂)₂—, —U—(CH₂)₃—(O(CH₂)₂)₃—, —U—(CH₂)₃—(O(CH₂)₂)₄—, —U—(CH₂)₃—(O(CH₂)₂)₅—, —U—(CH₂)₃—(O(CH₂)₂)₆—, —U—(CH₂)₃—(O(CH₂)₂)₇—, —U—(CH₂)₃—(O(CH₂)₂)₈—, —U—(CH₂)₃—(O(CH₂)₂)₉—, —U—(CH₂)₃—(O(CH₂)₂)₁₀—, —U—(CH₂)₄—O—(CH₂)₂—, —U—(CH₂)₄—(O(CH₂)₂)₂—, —U—(CH₂)₄—(O(CH₂)₂)₃—, —U—(CH₂)₄—(O(CH₂)₂)₄—, —U—(CH₂)₄—(O(CH₂)₂)₅—, —U—(CH₂)₄—(O(CH₂)₂)₆—, —U—(CH₂)₄—(O(CH₂)₂)₇—, —U—(CH₂)₄—(O(CH₂)₂)₈—, —U—(CH₂)₄—(O(CH₂)₂)₉—, —U—(CH₂)₄—(O(CH₂)₂)₁₀—, —U—CH₂—O—(CH₂)₃—, —U—CH₂—(O(CH₂)₃)₂—, —U—CH₂—(O(CH₂)₃)₃—, —U—CH₂—(O(CH₂)₃)₄—, —U—CH₂—(O(CH₂)₃)₅—, —U—CH₂—(O(CH₂)₃)₆—, —U—CH₂—(O(CH₂)₃)₇—, —U—CH₂—(O(CH₂)₃)₈—, —U—CH₂—(O(CH₂)₃)₉—, —U—CH₂—(O(CH₂)₃)₁₀—, —U—(CH₂)₂—O—(CH₂)₃—, —U—(CH₂)₂—(O(CH₂)₃)₂—, —U—(CH₂)₂—(O(CH₂)₃)₃—, —U—(CH₂)₂—(O(CH₂)₃)₄—, —U—(CH₂)₂—(O(CH₂)₃)₅—, —U—(CH₂)₂—(O(CH₂)₃)₆—, —U—(CH₂)₂—(O(CH₂)₃)₇—, —U—(CH₂)₂—(O(CH₂)₃)₈—, —U—(CH₂)₂—(O(CH₂)₃)₉—, —U—(CH₂)₂—(O(CH₂)₃)₁₀—, —U—

(CH₂)₃—O—(CH₂)₃—, —U—(CH₂)₃—(O(CH₂)₃)₂—, —U—(CH₂)₃—(O(CH₂)₃)₃—, —U—(CH₂)₃—(O(CH₂)₃)₄—, —U—(CH₂)₃—(O(CH₂)₃)₅—, —U—(CH₂)₃—(O(CH₂)₃)₆—, —U—(CH₂)₃—(O(CH₂)₃)₇—, —U—(CH₂)₃—(O(CH₂)₃)₈—, —U—(CH₂)₃—(O(CH₂)₃)₉—, —U—(CH₂)₃—(O(CH₂)₃)₁₀—, —U—CH₂—O—(CH₂)₂—O—(CH₂)₃—, —U—CH₂—(O(CH₂)₂)₂—(O(CH₂)₃)₂—, —U—CH₂—(O(CH₂)₂)₃—(O(CH₂)₃)₃—, —U—CH₂—(O(CH₂)₂)₄—(O(CH₂)₃)₄—, —U—CH₂—(O(CH₂)₂)₅—(O(CH₂)₃)₅—, —U—CH₂—(O(CH₂)₂)₆—(O(CH₂)₃)₆—, —U—(CH₂)₂—O—(CH₂)₂—O—(CH₂)₃—, —U—(CH₂)₂—(O(CH₂)₂)₂—(O(CH₂)₃)₂—, —U—(CH₂)₂—(O(CH₂)₂)₃—(O(CH₂)₃)₃—, —U—(CH₂)₂—(O(CH₂)₂)₄—(O(CH₂)₃)₄—, —U—(CH₂)₂—(O(CH₂)₂)₅—(O(CH₂)₃)₅—, —U—(CH₂)₂—(O(CH₂)₂)₆—(O(CH₂)₃)₆—, —U—(CH₂)₃—O—(CH₂)₂—O—(CH₂)₃—, —U—(CH₂)₃—(O(CH₂)₂)₂—(O(CH₂)₃)₂—, —U—(CH₂)₃—(O(CH₂)₂)₃—(O(CH₂)₃)₃—, —U—(CH₂)₃—(O(CH₂)₂)₄—(O(CH₂)₃)₄—, —U—(CH₂)₃—(O(CH₂)₂)₅—(O(CH₂)₃)₅—, —U—(CH₂)₃—(O(CH₂)₂)₆—(O(CH₂)₃)₆—, —U—CH₂—O—(CH₂)₃—O—(CH₂)₂—, —U—CH₂—(O(CH₂)₃)₂—(O(CH₂)₂)₂—,

—U—CH₂—(O(CH₂)₃)₃—(O(CH₂)₂)₃—, —U—CH₂—(O(CH₂)₃)₄—(O(CH₂)₂)₄—, —U—CH₂—(O(CH₂)₃)₅—(O(CH₂)₂)₅—, —U—CH₂—(O(CH₂)₃)₆—(O(CH₂)₂)₆—, —U—(CH₂)₂—O—(CH₂)₃—O—(CH₂)₂—, —U—(CH₂)₂—(O(CH₂)₃)₂—(O(CH₂)₂)₂—, —U—(CH₂)₂—(O(CH₂)₃)₃—(O(CH₂)₂)₃—, —U—(CH₂)₂—(O(CH₂)₃)₄—(O(CH₂)₂)₄—, —U—(CH₂)₂—(O(CH₂)₃)₅—(O(CH₂)₂)₅—, —U—(CH₂)₂—(O(CH₂)₃)₆—(O(CH₂)₂)₆—, —U—(CH₂)₃—O—(CH₂)₃—O—(CH₂)₂—, —U—(CH₂)₃—(O(CH₂)₃)₂—(O(CH₂)₂)₂—, —U—(CH₂)₃—(O(CH₂)₃)₃—(O(CH₂)₂)₃—, —U—(CH₂)₃—(O(CH₂)₃)₄—(O(CH₂)₂)₄—, —U—(CH₂)₃—(O(CH₂)₃)₅—(O(CH₂)₂)₅—, —U—(CH₂)₃—(O(CH₂)₃)₆—(O(CH₂)₂)₆—, —U—CH₂—O—(CH₂)₂—O—CH₂—, —U—(CH₂)₂—(O(CH₂)₂)₂—O—(CH₂)₃—, —U—(CH₂)₂—(O(CH₂)₂)₃—O—(CH₂)₃—, —U—(CH₂)₂—(O(CH₂)₂)₄—O—(CH₂)₃—, —U—(CH₂)₅—(O(CH₂)₂)₂—O—(CH₂)₅—, or —U—(CH₂)₅—(O(CH₂)₂)₂—O—(CH₂)₆—;
wherein the group U represents CO or NH, or the group U is absent.

In an embodiment of the present disclosure, the compound of formula (I) is also the compound of formula (Iv-2):

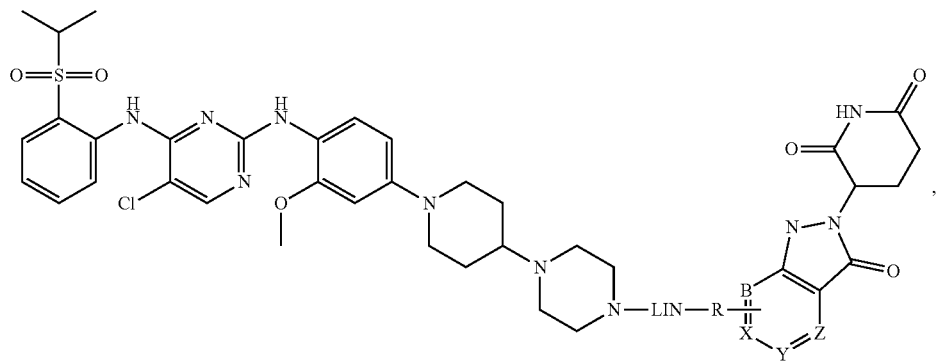

(Iv-2)

wherein, the groups LIN, R, A, B, X, Y and Z are as defined above.

In an embodiment of the present disclosure, the compound of formula (I) is also the compound of formula (Iv-3):

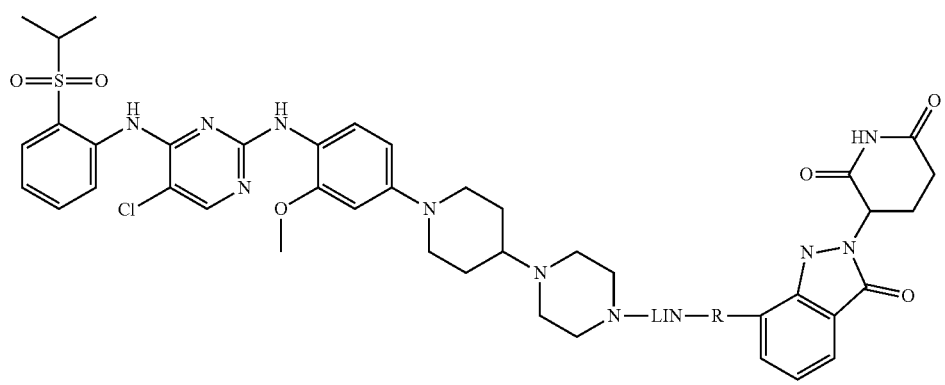

(Iv-3)

wherein, the groups LIN, R and A are as defined above.

In a sub-embodiment of the compound of formula (Iv-3) of the present disclosure, the LIN represents —U—$C_{1-30}$ alkylene-; and the group U represents CO or NH, or the group U is absent. In a sub-embodiment of the compound of formula (Iv-3), the LIN represents: —U—$CH_2$—; —U—$(CH_2)_2$—; —U—$(CH_2)_3$—; —U—$(CH_2)_4$—; —U—$(CH_2)_5$—; —U—$(CH_2)_6$—; —U—$(CH_2)_7$—; —U—$(CH_2)_8$—; —U—$(CH_2)_9$—; —U—$(CH_2)_{10}$—; —U—$(CH_2)_{11}$—; —U—$(CH_2)_{12}$—; —U—$(CH_2)_{13}$—; —U—$(CH_2)_{14}$—; —U—$(CH_2)_{15}$—; —U—$(CH_2)_{16}$—; —U—$(CH_2)_{17}$—; —U—$(CH_2)_{18}$—; —U—$(CH_2)_{19}$—; —U—$(CH_2)_{20}$—; —U—$(CH_2)_{21}$—; —U—$(CH_2)_{22}$—; —U—$(CH_2)_{23}$—; —U—$(CH_2)_{24}$—; —U—$(CH_2)_{25}$—; —U—$(CH_2)_{26}$—; —U—$(CH_2)_{27}$—; —U—$(CH_2)_{28}$—; —U—$(CH_2)_{29}$—; or U—$(CH_2)_{30}$—; wherein the group U represents CO or NH, or the group U is absent.

In a sub-embodiment of the compound of formula (Iv-3) of the present disclosure, the LIN is preferably —U—$C_{2-40}$ alkylene-(preferably —U—$C_{2-30}$ alkylene-), wherein the alkylene chain is optionally interrupted one or more times by one or more of O, CONH, NHCO, NH, alkynylene, alkenylene, cycloalkylene, arylene, heterocyclylene or heteroarylene or any combination thereof, and the group U represents CO or NH, or the group U is absent. In a sub-embodiment of the compound of formula (Iv-3), the LIN preferably represents: —U—$(CH_2)_{n1}$—(O$(CH_2)_{n2})_{m1}$— or —U—$(CH_2)_{n1}$—(O$(CH_2)_{n2})_{m1}$—(O$(CH_2)_{n3})_{m2}$—, wherein n1, n2, n3, m1 and m2 each independently represent an integer of 1, 2, 3, 4, 5, 6, 7, 8, 9, 10, 11, 12, 13, 14, 15, 16, 17, 18, 19 or 20; and wherein the group U represents CO or NH, or the group U is absent. In a sub-embodiment of the compound of formula (Iv-3), the LIN preferably represents: —U—$CH_2$—O—$(CH_2)_2$—, —U—$CH_2$—(O$(CH_2)_2)_2$—, —U—$CH_2$—(O$(CH_2)_2)_3$—, —U—$CH_2$—(O$(CH_2)_2)_4$—, —U—$CH_2$—(O$(CH_2)_2)_5$—, —U—$CH_2$—(O$(CH_2)_2)_6$—, —U—$CH_2$—(O$(CH_2)_2)_7$—, —U—$CH_2$—(O$(CH_2)_2)_8$—, —U—$CH_2$—(O$(CH_2)_2)_9$—, —U—$CH_2$—(O$(CH_2)_2)_{10}$—, —U—$(CH_2)_2$—O—$(CH_2)_2$—, —U—$(CH_2)_2$—(O$(CH_2)_2)_2$—, —U—$(CH_2)_2$—(O$(CH_2)_2)_3$—, —U—$(CH_2)_2$—(O$(CH_2)_2)_4$—, —U—$(CH_2)_2$—(O$(CH_2)_2)_5$—, —U—$(CH_2)_2$—(O$(CH_2)_2)_6$—, —U—$(CH_2)_2$—(O$(CH_2)_2)_7$—, —U—$(CH_2)_2$—(O$(CH_2)_2)_8$—, —U—$(CH_2)_2$—(O$(CH_2)_2)_9$—, —U—$(CH_2)_2$—(O$(CH_2)_2)_{10}$—, —U—$(CH_2)_3$—O—$(CH_2)_2$—, —U—$(CH_2)_3$—(O$(CH_2)_2)_2$—, —U—$(CH_2)_3$—(O$(CH_2)_2)_3$—, —U—$(CH_2)_3$—(O$(CH_2)_2)_4$—, —U—$(CH_2)_3$—(O$(CH_2)_2)_5$—, —U—$(CH_2)_3$—(O$(CH_2)_2)_6$—, —U—$(CH_2)_3$—(O$(CH_2)_2)_7$—, —U—$(CH_2)_3$—(O$(CH_2)_2)_8$—, —U—$(CH_2)_3$—(O$(CH_2)_2)_9$—, —U—$(CH_2)_3$—(O$(CH_2)_2)_{10}$—, —U—$(CH_2)_4$—O—$(CH_2)_2$—, —U—$(CH_2)_4$—(O$(CH_2)_2)_2$—, —U—$(CH_2)_4$—(O$(CH_2)_2)_3$—, —U—$(CH_2)_4$—(O$(CH_2)_2)_4$—, —U—$(CH_2)_4$—(O$(CH_2)_2)_5$—, —U—$(CH_2)_4$—(O$(CH_2)_2)_6$—, —U—$(CH_2)_4$—(O$(CH_2)_2)_7$—, —U—$(CH_2)_4$—(O$(CH_2)_2)_8$—, —U—$(CH_2)_4$—(O$(CH_2)_2)_9$—, —U—$(CH_2)_4$—(O$(CH_2)_2)_{10}$—, —U—$CH_2$—O—$(CH_2)_3$—, —U—$CH_2$—(O$(CH_2)_3)_2$—, —U—$CH_2$—(O$(CH_2)_3)_3$—, —U—$CH_2$—(O$(CH_2)_3)_4$—, —U—$CH_2$—(O$(CH_2)_3)_5$—, —U—$CH_2$—(O$(CH_2)_3)_6$—, —U—$CH_2$—(O$(CH_2)_3)_7$—, —U—$CH_2$—(O$(CH_2)_3)_8$—, —U—$CH_2$—(O$(CH_2)_3)_9$—, —U—$CH_2$—(O$(CH_2)_3)_{10}$—, —U—$(CH_2)_2$—O—$(CH_2)_3$—, —U—$(CH_2)_2$—(O$(CH_2)_3)_2$—, —U—$(CH_2)_2$—(O$(CH_2)_3)_3$—, —U—$(CH_2)_2$—(O$(CH_2)_3)_4$—, —U—$(CH_2)_2$—(O$(CH_2)_3)_5$—, —U—$(CH_2)_2$—(O$(CH_2)_3)_6$—, —U—$(CH_2)_2$—(O$(CH_2)_3)_7$—, —U—$(CH_2)_2$—(O$(CH_2)_3)_8$—, —U—$(CH_2)_2$—(O$(CH_2)_3)_9$—, —U—$(CH_2)_2$—(O$(CH_2)_3)_{10}$—, —U—$(CH_2)_3$—O—$(CH_2)_3$—, —U—$(CH_2)_3$—(O$(CH_2)_3)_2$—, —U—$(CH_2)_3$—(O$(CH_2)_3)_3$—, —U—$(CH_2)_3$—(O$(CH_2)_3)_4$—, —U—$(CH_2)_3$—(O$(CH_2)_3)_5$—, —U—$(CH_2)_3$—(O$(CH_2)_3)_6$—, —U—$(CH_2)_3$—(O$(CH_2)_3)_7$—, —U—$(CH_2)_3$—(O$(CH_2)_3)_8$—, —U—$(CH_2)_3$—(O$(CH_2)_3)_9$—, —U—$(CH_2)_3$—(O$(CH_2)_3)_{10}$—, —U—$CH_2$—O—$(CH_2)_2$—O—$(CH_2)_3$—, —U—$CH_2$—(O$(CH_2)_2)_2$—(O$(CH_2)_3)_2$—, —U—$CH_2$—(O$(CH_2)_2)_3$—(O$(CH_2)_3)_3$—, —U—$CH_2$—(O$(CH_2)_2)_4$—(O$(CH_2)_3)_4$—, —U—$CH_2$—(O$(CH_2)_2)_5$—(O$(CH_2)_3)_5$—, —U—$CH_2$—(O$(CH_2)_2)_6$—(O$(CH_2)_3)_6$—, —U—$(CH_2)_2$—O—$(CH_2)_2$—O—$(CH_2)_3$—, —U—$(CH_2)_2$—(O$(CH_2)_2)_2$—(O$(CH_2)_2)_2$—, —U—$(CH_2)_2$—(O$(CH_2)_2)_3$—(O$(CH_2)_2)_3$—, —U—$(CH_2)_2$—(O$(CH_2)_2)_4$—(O$(CH_2)_3)_4$—, —U—$(CH_2)_2$—(O$(CH_2)_2)_5$—(O$(CH_2)_3)_5$—, —U—$(CH_2)_2$—(O$(CH_2)_2)_6$—(O$(CH_2)_3)_6$—, —U—$(CH_2)_3$—O—$(CH_2)_2$—O—$(CH_2)_3$—, —U—$(CH_2)_3$—(O$(CH_2)_2)_2$—(O$(CH_2)_3)_2$—, —U—$(CH_2)_3$—(O$(CH_2)_2)_3$—(O$(CH_2)_3)_3$—, —U—$(CH_2)_3$—(O$(CH_2)_2)_4$—(O$(CH_2)_3)_4$—, —U—$(CH_2)_3$—(O$(CH_2)_2)_5$—(O$(CH_2)_3)_5$—, —U—$(CH_2)_3$—(O$(CH_2)_3)_6$—(O$(CH_2)_2)_6$—, —U—$CH_2$—O—$(CH_2)_2$—O—$CH_2$—, —U—$(CH_2)_2$—O—$(CH_2)_2$—O—$CH_2$—, —U—$(CH_2)_2$—(O$(CH_2)_2)_2$—O—$(CH_2)_3$—, —U—$(CH_2)_2$—(O$(CH_2)_2)_3$—O—$(CH_2)_3$—, —U—$(CH_2)_2$—(O$(CH_2)_2)_4$—O—$(CH_2)_3$—, —U—$(CH_2)_5$—(O$(CH_2)_2)_2$—O—$(CH_2)_5$—, or —U—$(CH_2)_5$—(O$(CH_2)_2)_2$—O—$(CH_2)_6$—; wherein the group U represents CO or NH, or the group U is absent.

In an embodiment of the present disclosure, the compound of formula (I) is also the compound of formula (Iw-2):

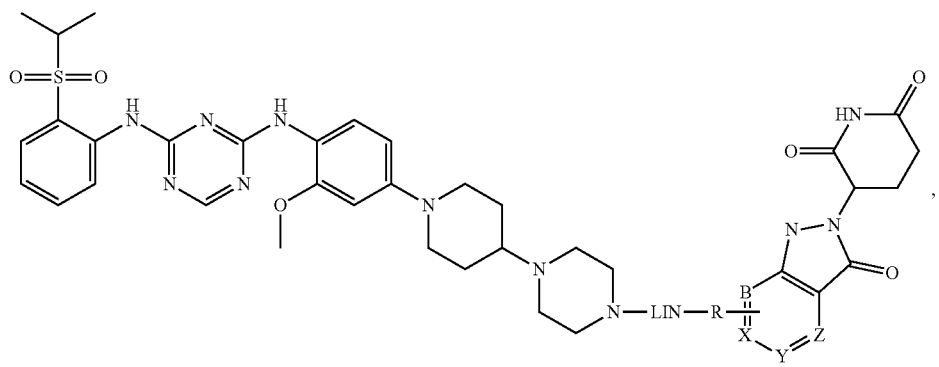

(Iw-2)

wherein, the groups LIN, R, A, B, X, Y and Z are as defined above.

In an embodiment of the present disclosure, the compound of formula (I) is also the compound of formula (Iw-3):

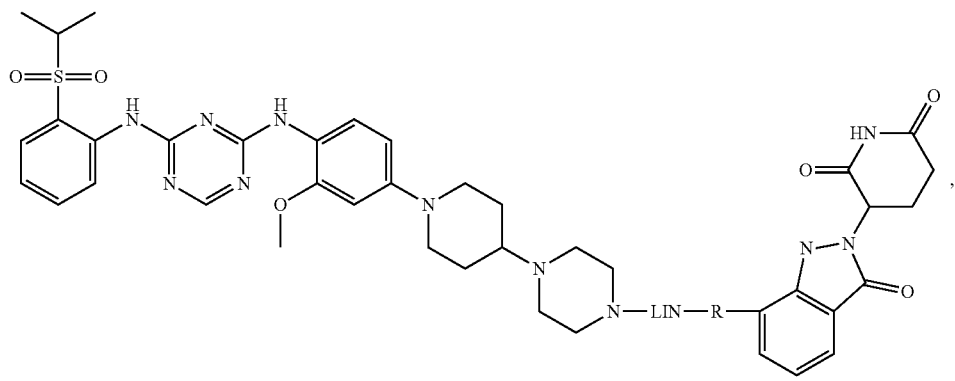

(Iw-3)

wherein, the groups LIN, R and A are as defined above.

In a sub-embodiment of the compound of formula (Iw-3) of the present disclosure, the LIN represents —U—$C_{1-30}$ alkylene-; and the group U represents CO or NH, or the group U is absent. In a sub-embodiment of the compound of formula (Iw-3), the LIN represents: —U—$CH_2$—; —U—$(CH_2)_2$—; —U—$(CH_2)_3$—; —U—$(CH_2)_4$—; —U—$(CH_2)_5$—; —U—$(CH_2)_6$—; —U—$(CH_2)_7$—; —U—$(CH_2)_8$—; —U—$(CH_2)_9$—; —U—$(CH_2)_{10}$—; —U—$(CH_2)_{11}$—; —U—$(CH_2)_{12}$—; —U—$(CH_2)_{13}$—; —U—$(CH_2)_{14}$—; —U—$(CH_2)_{15}$—; —U—$(CH_2)_{16}$—; —U—$(CH_2)_{17}$—; —U—$(CH_2)_{18}$—; —U—$(CH_2)_{19}$—; —U—$(CH_2)_{20}$—; —U—$(CH_2)_{21}$—; —U—$(CH_2)_{22}$—; —U—$(CH_2)_{23}$—; —U—$(CH_2)_{24}$—; —U—$(CH_2)_{25}$—; —U—$(CH_2)_{26}$—; —U—$(CH_2)_{27}$—; —U—$(CH_2)_{28}$—; —U—$(CH_2)_{29}$—; or U—$(CH_2)_{30}$—; wherein the group U represents CO or NH, or the group U is absent.

In a sub-embodiment of the compound of formula (Iw-3) of the present disclosure, the LIN is preferably —U—$C_{2-40}$ alkylene-(preferably —U—$C_{2-30}$ alkylene-), wherein the alkylene chain is optionally interrupted one or more times by one or more of O, CONH, NHCO, NH, alkynylene, alkenylene, cycloalkylene, arylene, heterocyclylene or heteroarylene or any combination thereof, and the group U represents CO or NH, or the group U is absent. In a sub-embodiment of the compound of formula (Iw-3), the LIN preferably represents: —U—$(CH_2)_{n1}$—(O$(CH_2)_{n2})_{m1}$— or —U—$(CH_2)_{n1}$—(O$(CH_2)_{n2})_{m1}$—(O$(CH_2)_{n3})_{m2}$—, wherein n1, n2, n3, m1 and m2 each independently represent an integer of 1, 2, 3, 4, 5, 6, 7, 8, 9, 10, 11, 12, 13, 14, 15, 16, 17, 18, 19 or 20; and wherein the group U represents CO or NH, or the group U is absent. In a sub-embodiment of the compound of formula (Iw-3), the LIN preferably represents: —U—$CH_2$—O—$(CH_2)_2$—, —U—$CH_2$—(O$(CH_2)_2)_2$—, —U—$CH_2$—(O$(CH_2)_2)_3$—, —U—$CH_2$—(O$(CH_2)_2)_4$—, —U—$CH_2$—(O$(CH_2)_2)_5$—, —U—$CH_2$—(O$(CH_2)_2)_6$—, —U—$CH_2$—(O$(CH_2)_2)_7$—, —U—$CH_2$—(O$(CH_2)_2)_8$—, —U—$CH_2$—(O$(CH_2)_2)_9$—, —U—$CH_2$—(O$(CH_2)_2)_{10}$—, —U—$(CH_2)_2$—O—$(CH_2)_2$—, —U—$(CH_2)_2$—(O$(CH_2)_2)_2$—, —U—$(CH_2)_2$—(O$(CH_2)_2)_3$—, —U—$(CH_2)_2$—(O$(CH_2)_2)_4$—, —U—$(CH_2)_2$—(O$(CH_2)_2)_5$—, —U—$(CH_2)_2$—(O$(CH_2)_2)_6$—, —U—$(CH_2)_2$—(O$(CH_2)_2)_7$—, —U—$(CH_2)_2$—(O$(CH_2)_2)_8$—, —U—$(CH_2)_2$—(O$(CH_2)_2)_9$—, —U—$(CH_2)_2$—(O$(CH_2)_2)_{10}$—, —U—$(CH_2)_3$—O—$(CH_2)_2$—, —U—$(CH_2)_3$—(O$(CH_2)_2)_2$—, —U—$(CH_2)_3$—(O$(CH_2)_2)_3$—, —U—$(CH_2)_3$—(O$(CH_2)_2)_4$—, —U—$(CH_2)_3$—(O$(CH_2)_2)_5$—, —U—$(CH_2)_3$—(O$(CH_2)_2)_6$—, —U—$(CH_2)_3$—(O$(CH_2)_2)_7$—, —U—$(CH_2)_3$—(O$(CH_2)_2)_8$—, —U—$(CH_2)_3$—(O$(CH_2)_2)_9$—, —U—$(CH_2)_3$—(O$(CH_2)_2)_{10}$—, —U—$(CH_2)_4$—O—$(CH_2)_2$—, —U—$(CH_2)_4$—(O$(CH_2)_2)_2$—, —U—$(CH_2)_4$—(O$(CH_2)_2)_3$—, —U—$(CH_2)_4$—(O$(CH_2)_2)_4$—, —U—$(CH_2)_4$—(O$(CH_2)_2)_5$—, —U—$(CH_2)_4$—(O$(CH_2)_2)_6$—, —U—$(CH_2)_4$—(O$(CH_2)_2)_7$—, —U—$(CH_2)_4$—(O$(CH_2)_2)_8$—, —U—$(CH_2)_4$—(O$(CH_2)_2)_9$—, —U—$(CH_2)_4$—(O$(CH_2)_2)_{10}$—, —U—$CH_2$—O—$(CH_2)_3$—, —U—$CH_2$—(O$(CH_2)_3)_2$—, —U—$CH_2$—(O$(CH_2)_3)_3$—, —U—$CH_2$—(O$(CH_2)_3)_4$—, —U—$CH_2$—(O$(CH_2)_3)_5$—, —U—$CH_2$—(O$(CH_2)_3)_6$—, —U—$CH_2$—(O$(CH_2)_3)_7$—, —U—CH₂—(O(CH₂)₃)₈—, —U—CH₂—(O(CH₂)₃)₉—, —U—CH₂—(O(CH₂)₃)₁₀—, —U—(CH₂)₂—O—(CH₂)₃—, —U—(CH₂)₂—(O(CH₂)₃)₂—, —U—(CH₂)₂—(O(CH₂)₃)₃—, —U—(CH₂)₂—(O(CH₂)₃)₄—, —U—(CH₂)₂—(O(CH₂)₃)₅—, —U—(CH₂)₂—(O(CH₂)₃)₆—, —U—(CH₂)₂—(O(CH₂)₃)₇—, —U—(CH₂)₂—(O(CH₂)₃)₈—, —U—(CH₂)₂—(O(CH₂)₃)₉—, —U—(CH₂)₂—(O(CH₂)₃)₁₀—, —U—(CH₂)₃—O—(CH₂)₃—, —U—(CH₂)₃—(O(CH₂)₃)₂—, —U—(CH₂)₃—(O(CH₂)₃)₃—, —U—(CH₂)₃—(O(CH₂)₃)₄—, —U—(CH₂)₃—(O(CH₂)₃)₅—, —U—(CH₂)₃—(O(CH₂)₃)₆—, —U—(CH₂)₃—(O(CH₂)₃)₇—, —U—(CH₂)₃—(O(CH₂)₃)₈—, —U—(CH₂)₃—(O(CH₂)₃)₉—, —U—(CH₂)₃—(O(CH₂)₃)₁₀—, —U—CH₂—O—(CH₂)₂—O—(CH₂)₃—, —U—CH₂—(O(CH₂)₂)₂—(O(CH₂)₃)₂—, —U—CH₂—(O(CH₂)₂)₃—(O(CH₂)₃)₃—, —U—CH₂—(O(CH₂)₂)₄—(O(CH₂)₃)₄—, —U—CH₂—(O(CH₂)₂)₅—(O(CH₂)₃)₅—, —U—CH₂—(O(CH₂)₂)₆—(O(CH₂)₃)₆—, —U—(CH₂)₂—O—(CH₂)₂—O—(CH₂)₃—, —U—(CH₂)₂—(O(CH₂)₂)₂—(O(CH₂)₃)₂—, —U—(CH₂)₂—(O(CH₂)₂)₃—(O(CH₂)₃)₃—, —U—(CH₂)₂—(O(CH₂)₂)₄—(O(CH₂)₃)₄—, —U—(CH₂)₂—(O(CH₂)₂)₅—(O(CH₂)₃)₅—, —U—(CH₂)₂—(O(CH₂)₂)₆—(O(CH₂)₃)₆—, —U—(CH₂)₃—O—(CH₂)₂—O—(CH₂)₃—, —U—(CH₂)₃—(O(CH₂)₂)₂—(O(CH₂)₃)₂—, —U—(CH₂)₃—(O(CH₂)₂)₃—(O(CH₂)₃)₃—, —U—(CH₂)₃—(O(CH₂)₂)₄—(O(CH₂)₃)₄—, —U—(CH₂)₃—(O(CH₂)₂)₅—(O(CH₂)₃)₅—, —U—(CH₂)₃—(O(CH₂)₂)₆—(O(CH₂)₃)₆—, —U—CH₂—O—(CH₂)₃—O—(CH₂)₂—, —U—CH₂—(O(CH₂)₃)₂—(O(CH₂)₂)₂—, —U—CH₂—(O(CH₂)₃)₃—(O(CH₂)₂)₃—, —U—CH₂—(O(CH₂)₃)₄—(O(CH₂)₂)₄—, —U—CH₂—(O(CH₂)₃)₅—(O(CH₂)₂)₅—, —U—CH₂—(O(CH₂)₃)₆—(O(CH₂)₂)₆—, —U—(CH₂)₂—O—(CH₂)₃—O—(CH₂)₂—, —U—(CH₂)₂—(O(CH₂)₃)₂—(O(CH₂)₂)₂—, —U—(CH₂)₂—(O(CH₂)₃)₃—(O(CH₂)₂)₃—, —U—(CH₂)₂—(O(CH₂)₃)₄—(O(CH₂)₂)₄—, —U—(CH₂)₂—(O(CH₂)₃)₅—(O(CH₂)₂)₅—, —U—(CH₂)₂—(O(CH₂)₃)₆—(O(CH₂)₂)₆—, —U—(CH₂)₃—O—(CH₂)₃—O—(CH₂)₂—, —U—(CH₂)₃—(O(CH₂)₃)₂—(O(CH₂)₂)₂—, —U—(CH₂)₃—(O(CH₂)₃)₃—(O(CH₂)₂)₃—, —U—(CH₂)₃—(O(CH₂)₃)₄—(O(CH₂)₂)₄—, —U—(CH₂)₃—(O(CH₂)₃)₅—(O(CH₂)₂)₅—, —U—(CH₂)₃—(O(CH₂)₃)₆—(O(CH₂)₂)₆—, —U—CH₂—O—(CH₂)₂—O—CH₂—, —U—(CH₂)₂—O—(CH₂)₂—O—CH₂—, —U—(CH₂)₂—(O(CH₂)₂)₂—O—(CH₂)₃—, —U—(CH₂)₂—(O(CH₂)₂)₃—O—(CH₂)₃—, —U—(CH₂)₂—(O(CH₂)₂)₄—O—(CH₂)₅—, —U—(CH₂)₅—(O(CH₂)₂)₂—O—(CH₂)₅—, or —U—(CH₂)₅—(O(CH₂)₂)₂—O—(CH₂)₆—; wherein the group U represents CO or NH, or the group U is absent.

In an embodiment of the present disclosure, the compound of formula (I) is also the compound of formula (Ix-2):

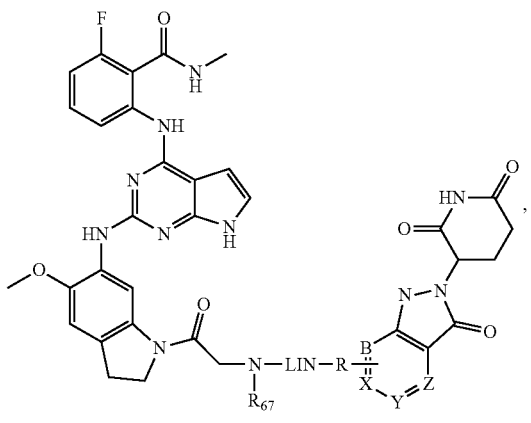

(Ix-2)

wherein, the groups LIN, R, A, B, X, Y and Z are as defined above, and the group R₆₇ is as defined above.

In an embodiment of the present disclosure, the compound of formula (I) is also the compound of formula (Ix-3):

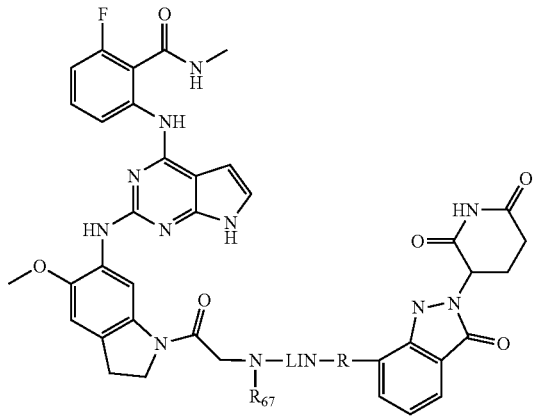

(Ix-3)

wherein, the groups LIN, R and A are as defined above, and the group R₆₇ is as defined above.

In a sub-embodiment of the compound of formula (Ix-3) of the present disclosure, the LIN represents —U—C₁₋₃₀ alkylene-; and the group U represents CO or NH, or the group U is absent. In a sub-embodiment of the compound of formula (Ix-3), the LIN represents: —U—CH₂—; —U—(CH₂)₂—; —U—(CH₂)₃—; —U—(CH₂)₄—; —U—(CH₂)₅—; —U—(CH₂)₆—; —U—(CH₂)₇—; —U—(CH₂)₈—; —U—(CH₂)₉—; —U—(CH₂)₁₀—; —U—(CH₂)₁₁—; —U—(CH₂)₁₂—; —U—(CH₂)₁₃—; —U—(CH₂)₁₄—; —U—(CH₂)₁₅—; —U—(CH₂)₁₆—; —U—(CH₂)₁₇—; —U—(CH₂)₁₈—; —U—(CH₂)₁₉—; —U—(CH₂)₂₀—; —U—(CH₂)₂₁—; —U—(CH₂)₂₂—; —U—(CH₂)₂₃—; —U—(CH₂)₂₄—; —U—(CH₂)₂₅—; —U—(CH₂)₂₆—; —U—(CH₂)₂₇—; —U—(CH₂)₂₈—; —U—(CH₂)₂₉—; or —U—(CH₂)₃₀—; wherein the group U represents CO or NH, or the group U is absent.

In a sub-embodiment of the compound of formula (Ix-3) of the present disclosure, the LIN is preferably —U—C₂₋₄₀ alkylene-(preferably —U—C₂₋₃₀ alkylene-), wherein the alkylene chain is optionally interrupted one or more times by one or more of O, CONH, NHCO, NH, alkynylene, alkenylene, cycloalkylene, arylene, heterocyclylene or heteroarylene or any combination thereof, and the group U represents CO or NH, or the group U is absent. In a sub-embodiment of the compound of formula (Ix-3), the LIN preferably represents: —U—(CH₂)ₙ₁—(O(CH₂)ₙ₂)ₘ₁— or —U—(CH₂)ₙ₁—(O(CH₂)ₙ₂)ₘ₁—(O(CH₂)ₙ₃)ₘ₂—, wherein n1, n2, n3, m1 and m2 each independently represent an integer of 1, 2, 3, 4, 5, 6, 7, 8, 9, 10, 11, 12, 13, 14, 15, 16, 17, 18, 19 or 20; and wherein the group U represents CO or NH, or the group U is absent. In a sub-embodiment of the compound of formula (Ix-3), the LIN preferably represents: —U—CH₂—O—(CH₂)₂—, —U—CH₂—(O(CH₂)₂)₂—, —U—CH₂—(O(CH₂)₂)₃—, —U—CH₂—(O(CH₂)₂)₄—, —U—CH₂—(O(CH₂)₂)₅—, —U—CH₂—(O(CH₂)₂)₆—, —U—CH₂—(O(CH₂)₂)₇—, —U—CH₂—(O(CH₂)₂)₈—, —U—CH₂—(O(CH₂)₂)₉—, —U—CH₂—(O(CH₂)₂)₁₀—, —U—(CH₂)₂—O—(CH₂)₂—, —U—(CH₂)₂—(O(CH₂)₂)₂—, —U—(CH₂)₂—(O(CH₂)₂)₃—, —U—(CH₂)₂—(O(CH₂)₂)₄—, —U—(CH₂)₂—(O(CH₂)₂)₅—, —U—(CH₂)₂—(O(CH₂)₂)₆—, —U—(CH₂)₂—(O(CH₂)₂)₇—, —U—(CH₂)₂—(O(CH₂)₂)₈—, —U—(CH₂)₂—(O(CH₂)₂)₉—, —U—(CH₂)₂—(O(CH₂)₂)₁₀—, —U—(CH₂)₃—O—

(CH₂)₂—, —U—(CH₂)₃—(O(CH₂)₂)₂—, —U—(CH₂)₃—(O(CH₂)₂)₃—, —U—(CH₂)₃—(O(CH₂)₂)₄—, —U—(CH₂)₃—(O(CH₂)₂)₅—, —U—(CH₂)₃—(O(CH₂)₂)₆—, —U—(CH₂)₃—(O(CH₂)₂)₇—, —U—(CH₂)₃—(O(CH₂)₂)₈—, —U—(CH₂)₃—(O(CH₂)₂)₉—, —U—(CH₂)₃—(O(CH₂)₂)₁₀—, —U—(CH₂)₄—O—(CH₂)₂—, —U—(CH₂)₄—(O(CH₂)₂)₂—, —U—(CH₂)₄—(O(CH₂)₂)₃—, —U—(CH₂)₄—(O(CH₂)₂)₄—, —U—(CH₂)₄—(O(CH₂)₂)₅—, —U—(CH₂)₄—(O(CH₂)₂)₆—, —U—(CH₂)₄—(O(CH₂)₂)₇—, —U—(CH₂)₄—(O(CH₂)₂)₈—, —U—(CH₂)₄—(O(CH₂)₂)₉—, —U—(CH₂)₄—(O(CH₂)₂)₁₀—, —U—CH₂—O—(CH₂)₃—, —U—CH₂—(O(CH₂)₃)₂—, —U—CH₂—(O(CH₂)₃)₃—, —U—CH₂—(O(CH₂)₃)₄—, —U—CH₂—(O(CH₂)₃)₅—, —U—CH₂—(O(CH₂)₃)₆—, —U—CH₂—(O(CH₂)₃)₇—, —U—CH₂—(O(CH₂)₃)₈—, —U—CH₂—(O(CH₂)₃)₉—, —U—CH₂—(O(CH₂)₃)₁₀—, —U—(CH₂)₂—O—(CH₂)₃—, —U—(CH₂)₂—(O(CH₂)₃)₂—, —U—(CH₂)₂—(O(CH₂)₃)₃—, —U—(CH₂)₂—(O(CH₂)₃)₄—, —U—(CH₂)₂—(O(CH₂)₃)₅—, —U—(CH₂)₂—(O(CH₂)₃)₆—, —U—(CH₂)₂—(O(CH₂)₃)₇—, —U—(CH₂)₂—(O(CH₂)₃)₈—, —U—(CH₂)₂—(O(CH₂)₃)₉—, —U—(CH₂)₂—(O(CH₂)₃)₁₀—, —U—(CH₂)₃—O—(CH₂)₃—, —U—(CH₂)₃—(O(CH₂)₃)₂—, —U—(CH₂)₃—(O(CH₂)₃)₃—, —U—(CH₂)₃—(O(CH₂)₃)₄—, —U—(CH₂)₃—(O(CH₂)₃)₅—, —U—(CH₂)₃—(O(CH₂)₃)₆—, —U—(CH₂)₃—(O(CH₂)₃)₇—, —U—(CH₂)₃—(O(CH₂)₃)₈—, —U—(CH₂)₃—(O(CH₂)₃)₉—, —U—(CH₂)₃—(O(CH₂)₃)₁₀—, —U—CH₂—O—(CH₂)₂—O—(CH₂)₃—, —U—CH₂—(O(CH₂)₂)₂—(O(CH₂)₃)₂—, —U—CH₂—(O(CH₂)₂)₃—(O(CH₂)₃)₃—, —U—CH₂—(O(CH₂)₂)₄—(O(CH₂)₃)₄—, —U—CH₂—(O(CH₂)₂)₅—(O(CH₂)₃)₅—, —U—CH₂—(O(CH₂)₂)₆—(O(CH₂)₃)₆—, —U—(CH₂)₂—O—(CH₂)₂—O—(CH₂)₃—, —U—(CH₂)₂—(O(CH₂)₂)₂—(O(CH₂)₃)₂—, —U—(CH₂)₂—(O(CH₂)₂)₃—(O(CH₂)₃)₃—, —U—(CH₂)₂—(O(CH₂)₂)₄—(O(CH₂)₃)₄—, —U—(CH₂)₂—(O(CH₂)₂)₅—(O(CH₂)₃)₅—, —U—(CH₂)₂—(O(CH₂)₂)₆—(O(CH₂)₃)₆—, —U—(CH₂)₃—O—(CH₂)₂—O—(CH₂)₃—, —U—(CH₂)₃—(O(CH₂)₂)₂—(O(CH₂)₃)₂—, —U—(CH₂)₃—(O(CH₂)₂)₃—(O(CH₂)₃)₃—, —U—(CH₂)₃—(O(CH₂)₂)₄—(O(CH₂)₃)₄—, —U—(CH₂)₃—(O(CH₂)₂)₅—(O(CH₂)₃)₅—, —U—(CH₂)₃—(O(CH₂)₂)₆—(O(CH₂)₃)₆—, —U—CH₂—O—(CH₂)₃—O—(CH₂)₂—, —U—CH₂—(O(CH₂)₃)₂—(O(CH₂)₂)₂—, —U—CH₂—(O(CH₂)₃)₃—(O(CH₂)₂)₃—, —U—CH₂—(O(CH₂)₃)₄—(O(CH₂)₂)₄—, —U—CH₂—(O(CH₂)₃)₅—(O(CH₂)₂)₅—, —U—CH₂—(O(CH₂)₃)₆—(O(CH₂)₂)₆—, —U—(CH₂)₂—O—(CH₂)₃—O—(CH₂)₂—, —U—(CH₂)₂—(O(CH₂)₃)₂—(O(CH₂)₂)₂—, —U—(CH₂)₂—(O(CH₂)₃)₃—(O(CH₂)₂)₃—, —U—(CH₂)₂—(O(CH₂)₃)₄—(O(CH₂)₂)₄—, —U—(CH₂)₂—(O(CH₂)₃)₅—(O(CH₂)₂)₅—, —U—(CH₂)₂—(O(CH₂)₃)₆—(O(CH₂)₂)₆—, —U—(CH₂)₃—O—(CH₂)₃—O—(CH₂)₂—, —U—(CH₂)₃—(O(CH₂)₃)₂—(O(CH₂)₂)₂—, —U—(CH₂)₃—(O(CH₂)₃)₃—(O(CH₂)₂)₃—, —U—(CH₂)₃—(O(CH₂)₃)₄—(O(CH₂)₂)₄—, —U—(CH₂)₃—(O(CH₂)₃)₅—(O(CH₂)₂)₅—, —U—(CH₂)₃—(O(CH₂)₃)₆—(O(CH₂)₂)₆—, —U—CH₂—O—(CH₂)₂—O—CH₂—, —U—(CH₂)₂—O—(CH₂)₂—O—CH₂—, —U—(CH₂)₂—(O(CH₂)₂)₂—O—(CH₂)₂—, —U—(CH₂)₂—(O(CH₂)₂)₃—O—(CH₂)₃—, —U—(CH₂)₂—(O(CH₂)₂)₄—O—(CH₂)₃—, —U—(CH₂)₅—(O(CH₂)₂)₂—O—(CH₂)₅—, or —U—(CH₂)₅—(O(CH₂)₂)₂—O—(CH₂)₆—; wherein the group U represents CO or NH, or the group U is absent.

In an embodiment of the present disclosure, the compound of formula (I) is also the compound of formula (Iy-2):

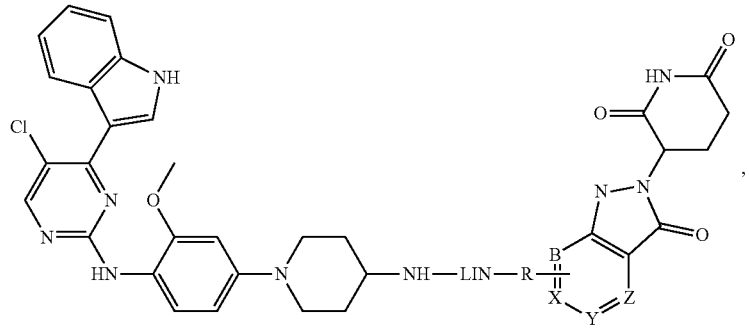

(Iy-2)

wherein, the groups LIN, R, A, B, X, Y and Z are as defined above.

In an embodiment of the present disclosure, the compound of formula (I) is also the compound of formula (Iy-3):

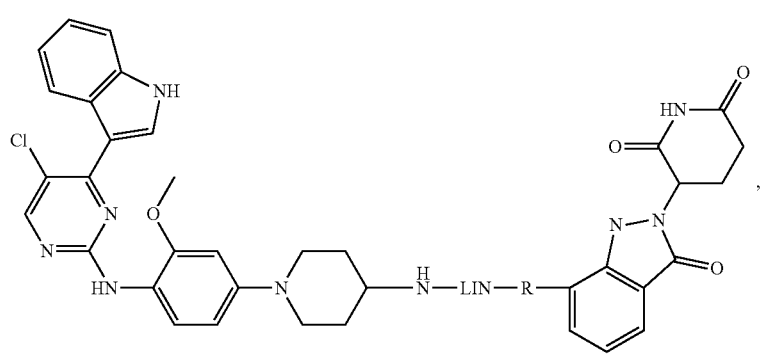

(Iy-3)

wherein, the groups LIN, R and A are as defined above.

In a sub-embodiment of the compound of formula (Iy-3) of the present disclosure, the LIN represents —U—$C_{1-30}$ alkylene-; and the group U represents CO or NH, or the group U is absent. In a sub-embodiment of the compound of formula (Iy-3), the LIN represents: —U—$CH_2$—; —U—$(CH_2)_2$—; —U—$(CH_2)_3$—; —U—$(CH_2)_4$—; —U—$(CH_2)_5$—; —U—$(CH_2)_6$—; —U—$(CH_2)_7$—; —U—$(CH_2)_8$—; —U—$(CH_2)_9$—; —U—$(CH_2)_{10}$—; —U—$(CH_2)_{11}$—; —U—$(CH_2)_{12}$—; —U—$(CH_2)_{13}$—; —U—$(CH_2)_{14}$—; —U—$(CH_2)_{15}$—; —U—$(CH_2)_{16}$—; —U—$(CH_2)_{17}$—; —U—$(CH_2)_{18}$—; —U—$(CH_2)_{19}$—; —U—$(CH_2)_{20}$—; —U—$(CH_2)_{21}$—; —U—$(CH_2)_{22}$—; —U—$(CH_2)_{23}$—; —U—$(CH_2)_{24}$—; —U—$(CH_2)_{25}$—; —U—$(CH_2)_{26}$—; —U—$(CH_2)_{27}$—; —U—$(CH_2)_{28}$—; —U—$(CH_2)_{29}$—; or U—$(CH_2)_{30}$—; wherein the group U represents CO or NH, or the group U is absent.

In a sub-embodiment of the compound of formula (Iy-3) of the present disclosure, the LIN is preferably —U—$C_{2-40}$ alkylene-(preferably —U—$C_{2-30}$ alkylene-), wherein the alkylene chain is optionally interrupted one or more times by one or more of O, CONH, NHCO, NH, alkynylene, alkenylene, cycloalkylene, arylene, heterocyclylene or heteroarylene or any combination thereof, and the group U represents CO or NH, or the group U is absent. In a sub-embodiment of the compound of formula (Iy-3), the LIN preferably represents: —U—$(CH_2)_{n1}$—$(O(CH_2)_{n2})_{m1}$— or —U—$(CH_2)_{n1}$—$(O(CH_2)_{n2})_{m1}$—$(O(CH_2)_{n3})_{m2}$—, wherein n1, n2, n3, m1 and m2 each independently represent an integer of 1, 2, 3, 4, 5, 6, 7, 8, 9, 10, 11, 12, 13, 14, 15, 16, 17, 18, 19 or 20; and wherein the group U represents CO or NH, or the group U is absent. In a sub-embodiment of the compound of formula (Iy-3), the LIN preferably represents: —U—$CH_2$—O—$(CH_2)_2$—, —U—$CH_2$—$(O(CH_2)_2)_2$—, —U—$CH_2$—$(O(CH_2)_2)_3$—, —U—$CH_2$—$(O(CH_2)_2)_4$—, —U—$CH_2$—$(O(CH_2)_2)_5$—, —U—$CH_2$—$(O(CH_2)_2)_6$—, —U—$CH_2$—$(O(CH_2)_2)_7$—, —U—$CH_2$—$(O(CH_2)_2)_8$—, —U—$CH_2$—$(O(CH_2)_2)_9$—, —U—$CH_2$—$(O(CH_2)_2)_{10}$—, —U—$(CH_2)_2$—O—$(CH_2)_2$—, —U—$(CH_2)_2$—$(O(CH_2)_2)_2$—, —U—$(CH_2)_2$—$(O(CH_2)_2)_3$—, —U—$(CH_2)_2$—$(O(CH_2)_2)_4$—, —U—$(CH_2)_2$—$(O(CH_2)_2)_5$—, —U—$(CH_2)_2$—$(O(CH_2)_2)_6$—, —U—$(CH_2)_2$—$(O(CH_2)_2)_7$—, —U—$(CH_2)_2$—$(O(CH_2)_2)_8$—, —U—$(CH_2)_2$—$(O(CH_2)_2)_9$—, —U—$(CH_2)_2$—$(O(CH_2)_2)_{10}$—, —U—$(CH_2)_3$—O—$(CH_2)_2$—, —U—$(CH_2)_3$—$(O(CH_2)_2)_2$—, —U—$(CH_2)_3$—$(O(CH_2)_2)_3$—, —U—$(CH_2)_3$—$(O(CH_2)_2)_4$—, —U—$(CH_2)_3$—$(O(CH_2)_2)_5$—, —U—$(CH_2)_3$—$(O(CH_2)_2)_6$—, —U—$(CH_2)_3$—$(O(CH_2)_2)_7$—, —U—$(CH_2)_3$—$(O(CH_2)_2)_8$—, —U—$(CH_2)_3$—$(O(CH_2)_2)_9$—, —U—$(CH_2)_3$—$(O(CH_2)_2)_{10}$—, —U—$(CH_2)_4$—O—$(CH_2)_2$—, —U—$(CH_2)_4$—$(O(CH_2)_2)_2$—, —U—$(CH_2)_4$—$(O(CH_2)_2)_3$—, —U—$(CH_2)_4$—$(O(CH_2)_2)_4$—, —U—$(CH_2)_4$—$(O(CH_2)_2)_5$—, —U—$(CH_2)_4$—$(O(CH_2)_2)_6$—, —U—$(CH_2)_4$—$(O(CH_2)_2)_7$—, —U—$(CH_2)_4$—$(O(CH_2)_2)_8$—, —U—$(CH_2)_4$—$(O(CH_2)_2)_9$—, —U—$(CH_2)_4$—$(O(CH_2)_2)_{10}$—, —U—$CH_2$—O—$(CH_2)_3$—, —U—$CH_2$—$(O(CH_2)_3)_2$—, —U—$CH_2$—$(O(CH_2)_3)_3$—, —U—$CH_2$—$(O(CH_2)_3)_4$—, —U—$CH_2$—$(O(CH_2)_3)_5$—, —U—$CH_2$—$(O(CH_2)_3)_6$—, —U—$CH_2$—$(O(CH_2)_3)_7$—, —U—$CH_2$—$(O(CH_2)_3)_8$—, —U—$CH_2$—$(O(CH_2)_3)_9$—, —U—$CH_2$—$(O(CH_2)_3)_{10}$—, —U—$(CH_2)_2$—O—$(CH_2)_3$—, —U—$(CH_2)_2$—$(O(CH_2)_3)_2$—, —U—$(CH_2)_2$—$(O(CH_2)_3)_3$—, —U—$(CH_2)_2$—$(O(CH_2)_3)_4$—, —U—$(CH_2)_2$—$(O(CH_2)_3)_5$—, —U—$(CH_2)_2$—$(O(CH_2)_3)_6$—, —U—$(CH_2)_2$—$(O(CH_2)_3)_7$—, —U—$(CH_2)_2$—$(O(CH_2)_3)_8$—, —U—$(CH_2)_2$—$(O(CH_2)_3)_9$—, —U—$(CH_2)_2$—$(O(CH_2)_3)_{10}$—, —U—$(CH_2)_3$—O—$(CH_2)_3$—, —U—$(CH_2)_3$—$(O(CH_2)_3)_2$—, —U—$(CH_2)_3$—$(O(CH_2)_3)_3$—, —U—$(CH_2)_3$—$(O(CH_2)_3)_4$—, —U—$(CH_2)_3$—$(O(CH_2)_3)_5$—, —U—$(CH_2)_3$—$(O(CH_2)_3)_6$—, —U—$(CH_2)_3$—$(O(CH_2)_3)_7$—, —U—$(CH_2)_3$—$(O(CH_2)_3)_8$—, —U—$(CH_2)_3$—$(O(CH_2)_3)_9$—, —U—$(CH_2)_3$—$(O(CH_2)_3)_{10}$—, —U—$CH_2$—O—$(CH_2)_2$—O—$(CH_2)_3$—, —U—$CH_2$—O—$(CH_2)_2$—O—$(CH_2)_2$—$(O(CH_2)_3)_2$—, —U—$CH_2$—$(O(CH_2)_2)_3$—$(O(CH_2)_3)_2$—, —U—$CH_2$—$(O(CH_2)_2)_2$—$(O(CH_2)_3)_3$—, —U—$CH_2$—$(O(CH_2)_2)_3$—$(O(CH_2)_3)_3$—, —U—$(CH_2)_2$—$(O(CH_2)_2)_4$—$(O(CH_2)_3)_4$—, —U—$(CH_2)_2$—$(O(CH_2)_2)_5$—$(O(CH_2)_3)_5$—, —U—$(CH_2)_2$—$(O(CH_2)_2)_6$—$(O(CH_2)_3)_6$—, —U—$(CH_2)_3$—O—$(CH_2)_2$—O—$(CH_2)_3$—, —U—$(CH_2)_3$—$(O(CH_2)_2)_2$—$(O(CH_2)_3)_2$—, —U—$(CH_2)_3$—$(O(CH_2)_2)_3$—$(O(CH_2)_3)_3$—, —U—$(CH_2)_3$—$(O(CH_2)_2)_4$—$(O(CH_2)_3)_4$—, —U—$(CH_2)_3$—$(O(CH_2)_2)_5$—$(O(CH_2)_3)_5$—, —U—$(CH_2)_3$—$(O(CH_2)_2)_6$—$(O(CH_2)_3)_6$—, —U—$CH_2$—O—$(CH_2)_3$—O—$(CH_2)_2$—, —U—$CH_2$—O—$(CH_2)_3)_2$—$(O(CH_2)_2)_2$—, —U—$CH_2$—$(O(CH_2)_3)_3$—$(O(CH_2)_2)_3$—, —U—$CH_2$—$(O(CH_2)_3)_4$—$(O(CH_2)_2)_4$—, —U—$CH_2$—$(O(CH_2)_3)_5$—$(O(CH_2)_2)_5$—, —U—$CH_2$—$(O(CH_2)_3)_6$—$(O(CH_2)_2)_6$—, —U—$(CH_2)_2$—O—$(CH_2)_3$—O—$(CH_2)_2$—, —U—$(CH_2)_2$—$(O(CH_2)_3)_2$—$(O(CH_2)_2)_2$—, —U—$(CH_2)_2$—$(O(CH_2)_3)_3$—$(O(CH_2)_2)_3$—, —U—$(CH_2)_2$—$(O(CH_2)_3)_4$—$(O(CH_2)_2)_4$—, —U—$(CH_2)_2$—$(O(CH_2)_3)_5$—$(O(CH_2)_2)_5$—, —U—$(CH_2)_2$—$(O(CH_2)_3)_6$—$(O(CH_2)_2)_6$—, —U—$(CH_2)_3$—O—$(CH_2)_3$—O—$(CH_2)_2$—, —U—$(CH_2)_3$—$(O(CH_2)_3)_2$—$(O(CH_2)_2)_2$—, —U—$(CH_2)_3$—$(O(CH_2)_3)_3$—$(O(CH_2)_2)_3$—, —U—$(CH_2)_3$—$(O(CH_2)_3)_4$—$(O(CH_2)_2)_4$—, —U—$(CH_2)_3$—$(O(CH_2)_3)_5$—$(O(CH_2)_2)_5$—, —U—$(CH_2)_3$—$(O(CH_2)_3)_6$—$(O(CH_2)_2)_6$—, —U—$CH_2$—O—$(CH_2)_2$—O—$CH_2$—, —U—$(CH_2)_2$—O—$(CH_2)_2$—O—$CH_2$—, —U—$(CH_2)_2$—$(O(CH_2)_2)_2$—O—$(CH_2)_3$—, —U—$(CH_2)_2$—$(O(CH_2)_2)_3$—O—$(CH_2)_3$—, —U—$(CH_2)_2$—$(O(CH_2)_2)_4$—O—$(CH_2)_3$—, —U—$(CH_2)_5$—$(O(CH_2)_2)_2$—O—$(CH_2)_5$—, or —U—$(CH_2)_5$—$(O(CH_2)_2)_2$—O—$(CH_2)_6$—; wherein the group U represents CO or NH, or the group U is absent.

In an embodiment of the present disclosure, the SMBP represents the fragment of formula (It-3):

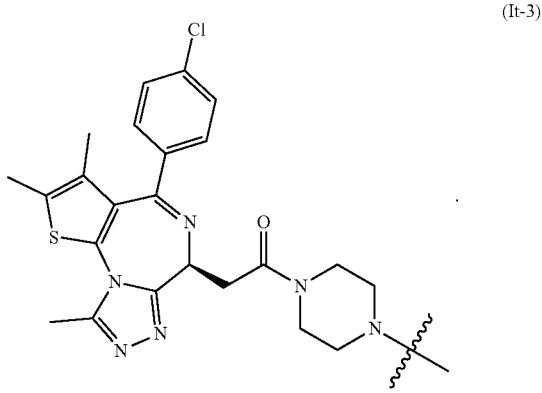 [SMILES: *N1CCN(C(=O)C[C@@H]2N=C(c3ccc(Cl)cc3)c3c(sc(C)c3C)-n3c(C)nnc32)CC1]

(It-3)

In an embodiment of the present disclosure, the compound of formula (I) is also the compound of formula (It-3-1):

(It-3-1)

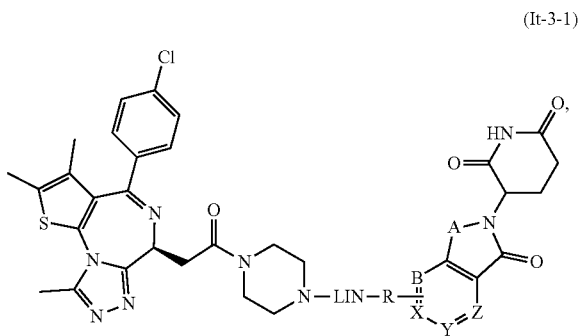

wherein, the groups LIN, R, A, B, X, Y and Z are as defined above.

In an embodiment of the present disclosure, the compound of formula (I) is also the compound of formula (It-3-2):

(It-3-2)

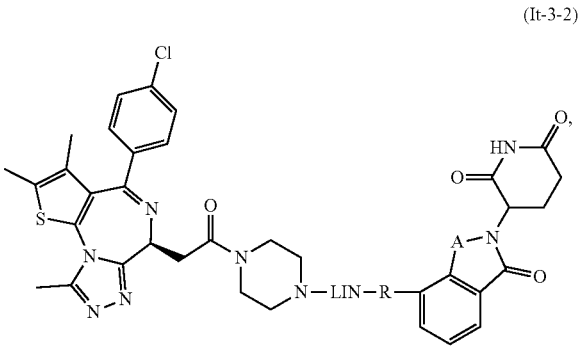

wherein, the groups LIN, R and A are as defined above.

In a sub-embodiment of the compound of formula (It-3-2) of the present disclosure, the LIN represents —U—$C_{1-30}$ alkylene-; and the group U represents CO or NH, or the group U is absent. In a sub-embodiment of the compound of formula (It-3-2), the LIN represents: —U—$CH_2$—; —U—$(CH_2)_2$—; —U—$(CH_2)_3$—; —U—$(CH_2)_4$—; —U—$(CH_2)_5$—; —U—$(CH_2)_6$—; —U—$(CH_2)_7$—; —U—$(CH_2)_8$—; —U—$(CH_2)_9$—; —U—$(CH_2)_{10}$—; —U—$(CH_2)_{11}$—; —U—$(CH_2)_{12}$—; —U—$(CH_2)_{13}$—; —U—$(CH_2)_{14}$—; —U—$(CH_2)_{15}$—; —U—$(CH_2)_{16}$—; —U—$(CH_2)_{17}$—; —U—$(CH_2)_{18}$—; —U—$(CH_2)_{19}$—; —U—$(CH_2)_{20}$—; —U—$(CH_2)_{21}$—; —U—$(CH_2)_{22}$—; —U—$(CH_2)_{23}$—; —U—$(CH_2)_{24}$—; —U—$(CH_2)_{25}$—; —U—$(CH_2)_{26}$—; —U—$(CH_2)_{27}$—; —U—$(CH_2)_{28}$—; —U—$(CH_2)_{29}$—; or —U—$(CH_2)_{30}$—; wherein the group U represents CO or NH, or the group U is absent.

In a sub-embodiment of the compound of formula (It-3-2) of the present disclosure, the LIN is preferably —U—$C_{2-40}$ alkylene-(preferably —U—$C_{2-30}$ alkylene-), wherein the alkylene chain is optionally interrupted one or more times by one or more of O, CONH, NHCO, NH, alkynylene, alkenylene, cycloalkylene, arylene, heterocyclylene or heteroarylene or any combination thereof, and the group U represents CO or NH, or the group U is absent. In a sub-embodiment of the compound of formula (It-3-2), the LIN preferably represents: —U—$(CH_2)_{n1}$—$(O(CH_2)_{n2})_{m1}$— or —U—$(CH_2)_{n1}$—$(O(CH_2)_{n2})_{m1}$—$(O(CH_2)_{n3})_{m2}$—, wherein n1, n2, n3, m1 and m2 each independently represent an integer of 1, 2, 3, 4, 5, 6, 7, 8, 9, 10, 11, 12, 13, 14, 15, 16, 17, 18, 19 or 20; and wherein the group U represents CO or NH, or the group U is absent. In a sub-embodiment of the compound of formula (It-3-2), the LIN preferably represents: —U—$CH_2$—O—$(CH_2)_2$—, —U—$CH_2$—(O$(CH_2)_2)_2$—, —U—$CH_2$—(O$(CH_2)_2)_3$—, —U—$CH_2$—(O$(CH_2)_2)_4$—, —U—$CH_2$—(O$(CH_2)_2)_5$—, —U—$CH_2$—(O$(CH_2)_2)_6$—, —U—$CH_2$—(O$(CH_2)_2)_7$—, —U—$CH_2$—(O$(CH_2)_2)_8$—, —U—$CH_2$—(O$(CH_2)_2)_9$—, —U—$CH_2$—(O$(CH_2)_2)_{10}$—, —U—$(CH_2)_2$—O—$(CH_2)_2$—, —U—$(CH_2)_2$—(O$(CH_2)_2)_2$—, —U—$(CH_2)_2$—(O$(CH_2)_2)_3$—, —U—$(CH_2)_2$—(O$(CH_2)_2)_4$—, —U—$(CH_2)_2$—(O$(CH_2)_2)_5$—, —U—$(CH_2)_2$—(O$(CH_2)_2)_6$—, —U—$(CH_2)_2$—(O$(CH_2)_2)_7$—, —U—$(CH_2)_2$—(O$(CH_2)_2)_5$—, —U—$(CH_2)_2$—(O$(CH_2)_2)_9$—, —U—$(CH_2)_2$—(O$(CH_2)_2)_{10}$—, —U—$(CH_2)_3$—O—$(CH_2)_2$—, —U—$(CH_2)_3$—(O$(CH_2)_2)_2$—, —U—$(CH_2)_3$—(O$(CH_2)_2)_3$—, —U—$(CH_2)_3$—(O$(CH_2)_2)_4$—, —U—$(CH_2)_3$—(O$(CH_2)_2)_5$—, —U—$(CH_2)_3$—(O$(CH_2)_2)_6$—, —U—$(CH_2)_3$—(O$(CH_2)_2)_7$—, —U—$(CH_2)_3$—(O$(CH_2)_2)_8$—, —U—$(CH_2)_3$—(O$(CH_2)_2)_9$—, —U—$(CH_2)_3$—(O$(CH_2)_2)_{10}$—, —U—$(CH_2)_4$—O—$(CH_2)_2$—, —U—$(CH_2)_4$—(O$(CH_2)_2)_2$—, —U—$(CH_2)_4$—(O$(CH_2)_2)_3$—, —U—$(CH_2)_4$—(O$(CH_2)_2)_4$—, —U—$(CH_2)_4$—(O$(CH_2)_2)_5$—, —U—$(CH_2)_4$—(O$(CH_2)_2)_6$—, —U—$(CH_2)_4$—(O$(CH_2)_2)_7$—, —U—$(CH_2)_4$—(O$(CH_2)_2)_8$—, —U—$(CH_2)_4$—(O$(CH_2)_2)_9$—, —U—$(CH_2)_4$—(O$(CH_2)_2)_{10}$—, —U—$CH_2$—O—$(CH_2)_3$—, —U—$CH_2$—(O$(CH_2)_3)_2$—, —U—$CH_2$—(O$(CH_2)_3)_3$—, —U—$CH_2$—(O$(CH_2)_3)_4$—, —U—$CH_2$—(O$(CH_2)_3)_5$—, —U—$CH_2$—(O$(CH_2)_3)_6$—, —U—$CH_2$—(O$(CH_2)_3)_7$—, —U—$CH_2$—(O$(CH_2)_3)_8$—, —U—$CH_2$—(O$(CH_2)_3)_9$—, —U—$CH_2$—(O$(CH_2)_3)_{10}$—, —U—$(CH_2)_2$—O—$(CH_2)_3$—, —U—$(CH_2)_2$—(O$(CH_2)_3)_2$—, —U—$(CH_2)_2$—(O$(CH_2)_3)_3$—, —U—$(CH_2)_2$—(O$(CH_2)_3)_4$—, —U—$(CH_2)_2$—(O$(CH_2)_3)_5$—, —U—$(CH_2)_2$—(O$(CH_2)_3)_6$—, —U—$(CH_2)_2$—(O$(CH_2)_3)_7$—, —U—$(CH_2)_2$—(O$(CH_2)_3)_8$—, —U—$(CH_2)_2$—(O$(CH_2)_3)_9$—, —U—$(CH_2)_2$—(O$(CH_2)_3)_{10}$—, —U—$(CH_2)_3$—O—$(CH_2)_3$—, —U—$(CH_2)_3$—(O$(CH_2)_3)_2$—, —U—$(CH_2)_3$—(O$(CH_2)_3)_3$—, —U—$(CH_2)_3$—(O$(CH_2)_3)_4$—, —U—$(CH_2)_3$—(O$(CH_2)_3)_5$—, —U—$(CH_2)_3$—(O$(CH_2)_3)_6$—, —U—$(CH_2)_3$—(O$(CH_2)_3)_7$—, —U—$(CH_2)_3$—(O$(CH_2)_3)_8$—, —U—$(CH_2)_3$—(O$(CH_2)_3)_9$—, —U—$(CH_2)_3$—(O$(CH_2)_3)_{10}$—, —U—$CH_2$—O—$(CH_2)_2$—O—$(CH_2)_3$—, —U—$CH_2$—(O$(CH_2)_2)_2$—(O$(CH_2)_3)_2$—, —U—$CH_2$—(O$(CH_2)_2)_3$—(O$(CH_2)_3)_3$—, —U—$CH_2$—(O$(CH_2)_2)_4$—(O$(CH_2)_3)_4$—, —U—$CH_2$—(O$(CH_2)_2)_5$—(O$(CH_2)_3)_5$—, —U—$CH_2$—(O$(CH_2)_2)_6$—(O$(CH_2)_3)_6$—, —U—$(CH_2)_2$—O—$(CH_2)_2$—O—$(CH_2)_3$—, —U—$(CH_2)_2$—(O$(CH_2)_2)_2$—(O$(CH_2)_3)_2$—, —U—$(CH_2)_2$—(O$(CH_2)_2)_3$—(O$(CH_2)_3)_3$—, —U—$(CH_2)_2$—(O$(CH_2)_2)_4$—(O$(CH_2)_3)_4$—, —U—$(CH_2)_2$—(O$(CH_2)_2)_5$—(O$(CH_2)_3)_5$—, —U—$(CH_2)_2$—(O$(CH_2)_2)_6$—(O$(CH_2)_3)_6$—, —U—$(CH_2)_3$—O—$(CH_2)_2$—O—$(CH_2)_3$—, —U—$(CH_2)_3$—(O$(CH_2)_2)_2$—(O$(CH_2)_3)_2$—, —U—$(CH_2)_3$—(O$(CH_2)_2)_3$—(O$(CH_2)_3)_3$—, —U—$(CH_2)_3$—(O$(CH_2)_2)_4$—(O$(CH_2)_3)_4$—, —U—$(CH_2)_3$—(O$(CH_2)_2)_5$—(O$(CH_2)_3)_5$—, —U—$(CH_2)_3$—(O$(CH_2)_2)_6$—(O$(CH_2)_3)_6$—, —U—$CH_2$—O—$(CH_2)_2$—O—$CH_2$—, —U—$(CH_2)_2$—O—$(CH_2)_2$—O—$CH_2$—, —U—$(CH_2)_2$—O—$(CH_2)_3$—, —U—$(CH_2)_2$—(O$(CH_2)_2)_3$—

O—(CH$_2$)$_3$—, —U—(CH$_2$)$_2$—(O(CH$_2$)$_2$)$_4$—O—(CH$_2$)$_3$—, —U—(CH$_2$)$_5$—(O(CH$_2$)$_2$)$_2$—O—(CH$_2$)$_5$—, or —U—(CH$_2$)$_5$—(O(CH$_2$)$_2$)$_2$—O—(CH$_2$)$_6$—; wherein the group U represents CO or NH, or the group U is absent.

In an embodiment of the present disclosure, the SMBP represents the fragment of formula (It-4):

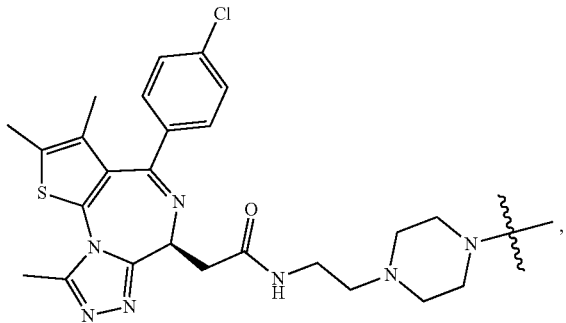

(It-4)

In an embodiment of the present disclosure, the compound of formula (I) is also the compound of formula (It-4-1):

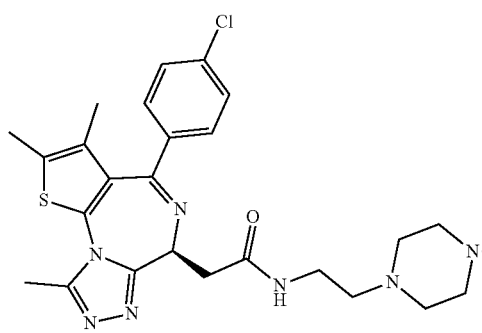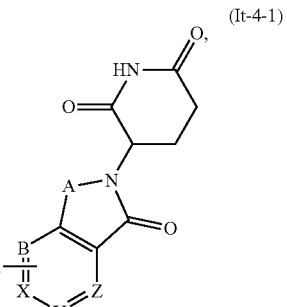

(It-4-1)

wherein, the groups LIN, R, A, B, X, Y and Z are as defined above.

In an embodiment of the present disclosure, the compound of formula (I) is also the compound of formula (It-4-2):

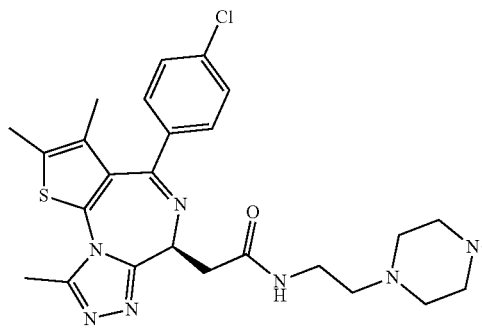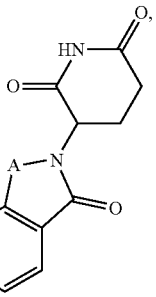

(It-4-2)

wherein, the groups LIN, R and A are as defined above.

In a sub-embodiment of the compound of formula (It-4-2) of the present disclosure, the LIN represents —U—C$_{1-30}$ alkylene-; and the group U represents CO or NH, or the group U is absent. In a sub-embodiment of the compound of formula (It-4-2), the LIN represents: —U—CH$_2$—; —U—(CH$_2$)$_2$—; —U—(CH$_2$)$_3$—; —U—(CH$_2$)$_4$—; —U—(CH$_2$)$_5$—; —U—(CH$_2$)$_6$—; —U—(CH$_2$)$_7$—; —U—(CH$_2$)$_8$—; —U—(CH$_2$)$_9$—; —U—(CH$_2$)$_{10}$—; —U—(CH$_2$)$_{11}$—; —U—(CH$_2$)$_{12}$—; —U—(CH$_2$)$_{13}$—; —U—(CH$_2$)$_{14}$—; —U—(CH$_2$)$_{15}$—; —U—(CH$_2$)$_{16}$—; —U—(CH$_2$)$_{17}$—; —U—(CH$_2$)$_{18}$—; —U—(CH$_2$)$_{19}$—; —U—(CH$_2$)$_{20}$—; —U—(CH$_2$)$_{21}$—; —U—(CH$_2$)$_{22}$—; —U—(CH$_2$)$_{23}$—; —U—(CH$_2$)$_{24}$—; —U—(CH$_2$)$_{25}$—; —U—(CH$_2$)$_{26}$—; —U—(CH$_2$)$_{27}$—; —U—(CH$_2$)$_{28}$—; —U—(CH$_2$)$_{29}$—; or U—(CH$_2$)$_{30}$—; wherein the group U represents CO or NH, or the group U is absent.

In a sub-embodiment of the compound of formula (It-4-2) of the present disclosure, the LIN is preferably —U—C$_{2-40}$ alkylene-(preferably —U—C$_{2-30}$ alkylene-), wherein the alkylene chain is optionally interrupted one or more times by one or more of O, CONH, NHCO, NH, alkynylene, alkenylene, cycloalkylene, arylene, heterocyclylene or heteroarylene or any combination thereof, and the group U represents CO or NH, or the group U is absent. In a sub-embodiment of the compound of formula (It-4-2), the LIN preferably represents: —U—(CH$_2$)$_{n1}$—(O(CH$_2$)$_{n2}$)$_{m1}$— or —U—(CH$_2$)$_{n1}$—(O(CH$_2$)$_{n2}$)$_{m1}$—(O(CH$_2$)$_{n3}$)$_{m2}$—, wherein n1, n2, n3, m1 and m2 each independently represent an integer of 1, 2, 3, 4, 5, 6, 7, 8, 9, 10, 11, 12, 13, 14, 15, 16, 17, 18, 19 or 20; and wherein the group U represents CO or NH, or the group U is absent. In a sub-embodiment of the compound of formula (It-4-2), the LIN preferably represents: —U—CH₂—O—(CH₂)₂—, —U—CH₂—(O(CH₂)₂)₂—, —U—CH₂—(O(CH₂)₂)₃—, —U—CH₂—(O(CH₂)₂)₄—, —U—CH₂—(O(CH₂)₂)₅—, —U—CH₂—(O(CH₂)₂)₆—, —U—CH₂—(O(CH₂)₂)₇—, —U—CH₂—(O(CH₂)₂)₈—, —U—CH₂—(O(CH₂)₂)₉—, —U—CH₂—(O(CH₂)₂)₁₀—, —U—(CH₂)₂—O—(CH₂)₂—, —U—(CH₂)₂—(O(CH₂)₂)₂—, —U—(CH₂)₂—(O(CH₂)₂)₃—, —U—(CH₂)₂—(O(CH₂)₂)₄—, —U—(CH₂)₂—(O(CH₂)₂)₅—, —U—(CH₂)₂—(O(CH₂)₂)₆—, —U—(CH₂)₂—(O(CH₂)₂)₇—, —U—(CH₂)₂—(O(CH₂)₂)₅—, —U—(CH₂)₂—(O(CH₂)₂)₉—, —U—(CH₂)₂—(O(CH₂)₂)₁₀—, —U—(CH₂)₃—O—(CH₂)₂—, —U—(CH₂)₃—(O(CH₂)₂)₂—, —U—(CH₂)₃—(O(CH₂)₂)₃—, —U—(CH₂)₃—(O(CH₂)₂)₄—, —U—(CH₂)₃—(O(CH₂)₂)₅—, —U—(CH₂)₃—(O(CH₂)₂)₆—, —U—(CH₂)₃—(O(CH₂)₂)₇—, —U—(CH₂)₃—(O(CH₂)₂)₈—, —U—(CH₂)₃—(O(CH₂)₂)₉—, —U—(CH₂)₃—(O(CH₂)₂)₁₀—, —U—(CH₂)₄—O—(CH₂)₂—, —U—(CH₂)₄—(O(CH₂)₂)₂—, —U—(CH₂)₄—(O(CH₂)₂)₃—, —U—(CH₂)₄—(O(CH₂)₂)₄—, —U—(CH₂)₄—(O(CH₂)₂)₅—, —U—(CH₂)₄—(O(CH₂)₂)₆—, —U—(CH₂)₄—(O(CH₂)₂)₇—, —U—(CH₂)₄—(O(CH₂)₂)₈—, —U—(CH₂)₄—(O(CH₂)₂)₉—, —U—(CH₂)₄—(O(CH₂)₂)₁₀—, —U—CH₂—O—(CH₂)₃—, —U—CH₂—(O(CH₂)₃)₂—, —U—CH₂—(O(CH₂)₃)₃—, —U—CH₂—(O(CH₂)₃)₄—, —U—CH₂—(O(CH₂)₃)₅—, —U—CH₂—(O(CH₂)₃)₆—, —U—CH₂—(O(CH₂)₃)₇—, —U—CH₂—(O(CH₂)₃)₈—, —U—CH₂—(O(CH₂)₃)₉—, —U—CH₂—(O(CH₂)₃)₁₀—, —U—(CH₂)₂—O—(CH₂)₃—, —U—(CH₂)₂—(O(CH₂)₃)₂—, —U—(CH₂)₂—(O(CH₂)₃)₃—, —U—(CH₂)₂—(O(CH₂)₃)₄—, —U—(CH₂)₂—(O(CH₂)₃)₅—, —U—(CH₂)₂—(O(CH₂)₃)₆—, —U—(CH₂)₂—(O(CH₂)₃)₇—, —U—(CH₂)₂—(O(CH₂)₃)₈—, —U—(CH₂)₂—(O(CH₂)₃)₉—, —U—(CH₂)₂—(O(CH₂)₃)₁₀—, —U—(CH₂)₃—O—(CH₂)₃—, —U—(CH₂)₃—(O(CH₂)₃)₂—, —U—(CH₂)₃—(O(CH₂)₃)₃—, —U—(CH₂)₃—(O(CH₂)₃)₄—, —U—(CH₂)₃—(O(CH₂)₃)₅—, —U—(CH₂)₃—(O(CH₂)₃)₆—, —U—(CH₂)₃—(O(CH₂)₃)₇—, —U—(CH₂)₃—(O(CH₂)₃)₈—, —U—(CH₂)₃—(O(CH₂)₃)₉—, —U—(CH₂)₃—(O(CH₂)₃)₁₀—, —U—CH₂—O—(CH₂)₂—O—(CH₂)₃—, —U—CH₂—(O(CH₂)₂)₂—(O(CH₂)₃)₂—, —U—CH₂—(O(CH₂)₂)₃—(O(CH₂)₃)₃—, —U—CH₂—(O(CH₂)₂)₄—(O(CH₂)₃)₄—, —U—CH₂—(O(CH₂)₂)₅—(O(CH₂)₃)₅—, —U—CH₂—(O(CH₂)₂)₆—(O(CH₂)₃)₆—, —U—(CH₂)₂—O—(CH₂)₃—O—(CH₂)₂—, —U—(CH₂)₂—(O(CH₂)₃)₂—(O(CH₂)₂)₂—, —U—(CH₂)₂—(O(CH₂)₃)₃—(O(CH₂)₂)₃—, —U—(CH₂)₂—(O(CH₂)₃)₄—(O(CH₂)₂)₄—, —U—(CH₂)₂—(O(CH₂)₃)₅—(O(CH₂)₂)₅—, —U—(CH₂)₂—(O(CH₂)₃)₆—(O(CH₂)₂)₆—, —U—(CH₂)₂—O—(CH₂)₃—O—(CH₂)₂—, —U—(CH₂)₂—(O(CH₂)₃)₂—(O(CH₂)₂)₂—, —U—(CH₂)₂—(O(CH₂)₃)₃—(O(CH₂)₂)₃—, —U—(CH₂)₂—(O(CH₂)₃)₄—(O(CH₂)₂)₄—, —U—(CH₂)₂—(O(CH₂)₃)₅—(O(CH₂)₂)₅—, —U—(CH₂)₂—(O(CH₂)₃)₆—(O(CH₂)₂)₆—, —U—(CH₂)₃—O—(CH₂)₃—O—(CH₂)₂—, —U—(CH₂)₃—(O(CH₂)₃)₂—(O(CH₂)₂)₂—, —U—(CH₂)₃—(O(CH₂)₃)₃—(O(CH₂)₂)₃—, —U—(CH₂)₃—(O(CH₂)₃)₄—(O(CH₂)₂)₄—, —U—(CH₂)₃—(O(CH₂)₃)₅—(O(CH₂)₂)₅—, —U—(CH₂)₃—(O(CH₂)₃)₆—(O(CH₂)₂)₆—, —U—CH₂—O—(CH₂)₂—O—CH₂—, —U—(CH₂)₂—O—(CH₂)₂—O—CH₂—, —U—(CH₂)₂—O—(CH₂)₂—O—(CH₂)₂—, —U—(CH₂)₂—O—(CH₂)₃—, —U—(CH₂)₂—(O(CH₂)₂)₃—O—(CH₂)₃—, —U—(CH₂)₂—(O(CH₂)₂)₄—O—(CH₂)₃—, —U—(CH₂)₅—(O(CH₂)₂)₂—O—(CH₂)₅—, or —U—(CH₂)₅—(O(CH₂)₂)₂—O—(CH₂)₆—; wherein the group U represents CO or NH, or the group U is absent.

In an embodiment of the present disclosure, the SMBP represents the fragment of formula (It-5):

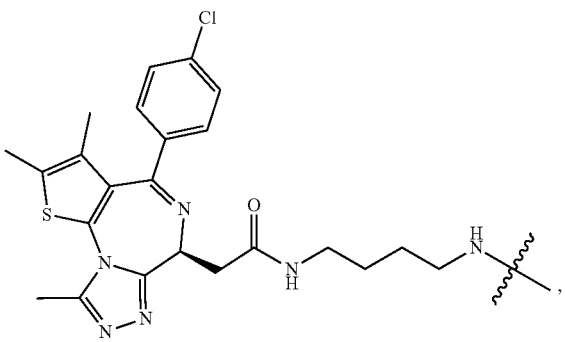

(It-5)

In an embodiment of the present disclosure, the compound of formula (I) is also the compound of formula (It-5-1):

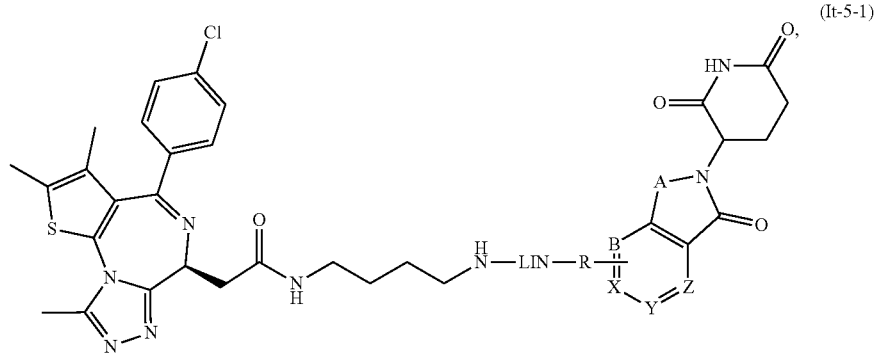

(It-5-1)

wherein, the groups LIN, R, A, B, X, Y and Z are as defined above.

In an embodiment of the present disclosure, the compound of formula (I) is also the compound of formula (It-5-2):

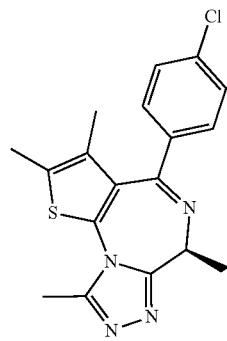

(It-5-2)

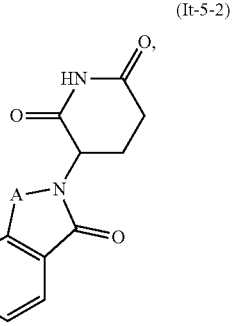

wherein, the groups LIN, R and A are as defined above.

In a sub-embodiment of the compound of formula (It-5-2) of the present disclosure, the LIN represents —U—$C_{1-30}$ alkylene-; and the group U represents CO or NH, or the group U is absent. In a sub-embodiment of the compound of formula (It-5-2), the LIN represents: —U—$CH_2$—; —U—$(CH_2)_2$—; —U—$(CH_2)_3$—; —U—$(CH_2)_4$—; —U—$(CH_2)_5$—; —U—$(CH_2)_6$—; —U—$(CH_2)_7$—; —U—$(CH_2)_8$—; —U—$(CH_2)_9$—; —U—$(CH_2)_{10}$—; —U—$(CH_2)_{11}$—; —U—$(CH_2)_{12}$—; —U—$(CH_2)_{13}$—; —U—$(CH_2)_{14}$—; —U—$(CH_2)_{15}$—; —U—$(CH_2)_{16}$—; —U—$(CH_2)_{17}$—; —U—$(CH_2)_{18}$—; —U—$(CH_2)_{19}$—; —U—$(CH_2)_{20}$—; —U—$(CH_2)_{21}$—; —U—$(CH_2)_{22}$—; —U—$(CH_2)_{23}$—; —U—$(CH_2)_{24}$—; —U—$(CH_2)_{25}$—; —U—$(CH_2)_{26}$—; —U—$(CH_2)_{27}$—; —U—$(CH_2)_{28}$—; —U—$(CH_2)_{29}$—; or —U—$(CH_2)_{30}$—; wherein the group U represents CO or NH, or the group U is absent.

In a sub-embodiment of the compound of formula (It-5-2) of the present disclosure, the LIN is preferably —U—$C_{2-40}$ alkylene-(preferably —U—$C_{2-30}$ alkylene-), wherein the alkylene chain is optionally interrupted one or more times by one or more of O, CONH, NHCO, NH, alkynylene, alkenylene, cycloalkylene, arylene, heterocyclylene or heteroarylene or any combination thereof, and the group U represents CO or NH, or the group U is absent. In a sub-embodiment of the compound of formula (It-5-2), the LIN preferably represents: —U—$(CH_2)_{n1}$—$(O(CH_2)_{n2})_{m1}$— or —U—$(CH_2)_{n1}$—$(O(CH_2)_{n2})_{m1}$—$(O(CH_2)_{n3})_{m2}$—, wherein n1, n2, n3, m1 and m2 each independently represent an integer of 1, 2, 3, 4, 5, 6, 7, 8, 9, 10, 11, 12, 13, 14, 15, 16, 17, 18, 19 or 20; and wherein the group U represents CO or NH, or the group U is absent. In a sub-embodiment of the compound of formula (It-5-2), the LIN preferably represents: —U—$CH_2$—O—$(CH_2)_2$—, —U—$CH_2$—$(O(CH_2)_2)_2$—, —U—$CH_2$—$(O(CH_2)_2)_3$—, —U—$CH_2$—$(O(CH_2)_2)_4$—, —U—$CH_2$—$(O(CH_2)_2)_5$—, —U—$CH_2$—$(O(CH_2)_2)_6$—, —U—$CH_2$—$(O(CH_2)_2)_7$—, —U—$CH_2$—$(O(CH_2)_2)_8$—, —U—$CH_2$—$(O(CH_2)_2)_9$—, —U—$CH_2$—$(O(CH_2)_2)_{10}$—, —U—$(CH_2)_2$—O—$(CH_2)_2$—, —U—$(CH_2)_2$—$(O(CH_2)_2)_2$—, —U—$(CH_2)_2$—$(O(CH_2)_2)_3$—, —U—$(CH_2)_2$—$(O(CH_2)_2)_4$—, —U—$(CH_2)_2$—$(O(CH_2)_2)_5$—, —U—$(CH_2)_2$—$(O(CH_2)_2)_6$—, —U—$(CH_2)_2$—$(O(CH_2)_2)_7$—, —U—$(CH_2)_2$—$(O(CH_2)_2)_5$—, —U—$(CH_2)_2$—$(O(CH_2)_2)_9$—, —U—$(CH_2)_2$—$(O(CH_2)_2)_{10}$—, —U—$(CH_2)_3$—O—$(CH_2)_2$—, —U—$(CH_2)_3$—$(O(CH_2)_2)_2$—, —U—$(CH_2)_3$—$(O(CH_2)_2)_3$—, —U—$(CH_2)_3$—$(O(CH_2)_2)_4$—, —U—$(CH_2)_3$—$(O(CH_2)_2)_5$—, —U—$(CH_2)_3$—$(O(CH_2)_2)_6$—, —U—$(CH_2)_3$—$(O(CH_2)_2)_7$—, —U—$(CH_2)_3$—$(O(CH_2)_2)_8$—, —U—$(CH_2)_3$—$(O(CH_2)_2)_9$—, —U—$(CH_2)_3$—$(O(CH_2)_2)_{10}$—, —U—$(CH_2)_4$—O—$(CH_2)_2$—, —U—$(CH_2)_4$—$(O(CH_2)_2)_2$—, —U—$(CH_2)_4$—$(O(CH_2)_2)_3$—, —U—$(CH_2)_4$—$(O(CH_2)_2)_4$—, —U—$(CH_2)_4$—$(O(CH_2)_2)_5$—, —U—$(CH_2)_4$—$(O(CH_2)_2)_6$—, —U—$(CH_2)_4$—$(O(CH_2)_2)_7$—, —U—$(CH_2)_4$—$(O(CH_2)_2)_8$—, —U—$(CH_2)_4$—$(O(CH_2)_2)_9$—, —U—$(CH_2)_4$—$(O(CH_2)_2)_{10}$—, —U—$CH_2$—O—$(CH_2)_3$—, —U—$CH_2$—$(O(CH_2)_3)_2$—, —U—$CH_2$—$(O(CH_2)_3)_3$—, —U—$CH_2$—$(O(CH_2)_3)_4$—, —U—$CH_2$—$(O(CH_2)_3)_5$—, —U—$CH_2$—$(O(CH_2)_3)_6$—, —U—$CH_2$—$(O(CH_2)_3)_7$—, —U—$CH_2$—$(O(CH_2)_3)_8$—, —U—$CH_2$—$(O(CH_2)_3)_9$—, —U—$CH_2$—$(O(CH_2)_3)_{10}$—, —U—$(CH_2)_2$—O—$(CH_2)_3$—, —U—$(CH_2)_2$—$(O(CH_2)_3)_2$—, —U—$(CH_2)_2$—$(O(CH_2)_3)_3$—, —U—$(CH_2)_2$—$(O(CH_2)_3)_4$—, —U—$(CH_2)_2$—$(O(CH_2)_3)_5$—, —U—$(CH_2)_2$—$(O(CH_2)_3)_6$—, —U—$(CH_2)_2$—$(O(CH_2)_3)_7$—, —U—$(CH_2)_2$—$(O(CH_2)_3)_8$—, —U—$(CH_2)_2$—$(O(CH_2)_3)_9$—, —U—$(CH_2)_2$—$(O(CH_2)_3)_{10}$—, —U—$(CH_2)_3$—O—$(CH_2)_3$—, —U—$(CH_2)_3$—$(O(CH_2)_3)_2$—, —U—$(CH_2)_3$—$(O(CH_2)_3)_3$—, —U—$(CH_2)_3$—$(O(CH_2)_3)_4$—, —U—$(CH_2)_3$—$(O(CH_2)_3)_5$—, —U—$(CH_2)_3$—$(O(CH_2)_3)_6$—, —U—$(CH_2)_3$—$(O(CH_2)_3)_7$—, —U—$(CH_2)_3$—$(O(CH_2)_3)_8$—, —U—$(CH_2)_3$—$(O(CH_2)_3)_9$—, —U—$(CH_2)_3$—$(O(CH_2)_3)_{10}$—, —U—$CH_2$—O—$(CH_2)_2$—O—$(CH_2)_3$—, —U—$CH_2$—$(O(CH_2)_2)_2$—$(O(CH_2)_3)_2$—, —U—$CH_2$—$(O(CH_2)_2)_3$—$(O(CH_2)_3)_3$—, —U—$CH_2$—$(O(CH_2)_2)_4$—$(O(CH_2)_3)_4$—, —U—$CH_2$—$(O(CH_2)_2)_5$—$(O(CH_2)_3)_5$—, —U—$CH_2$—$(O(CH_2)_2)_6$—$(O(CH_2)_3)_6$—, —U—$(CH_2)_2$—O—$(CH_2)_2$—O—$(CH_2)_3$—, —U—$(CH_2)_2$—$(O(CH_2)_2)_2$—$(O(CH_2)_3)_2$—, —U—$(CH_2)_2$—$(O(CH_2)_2)_3$—$(O(CH_2)_3)_3$—, —U—$(CH_2)_2$—$(O(CH_2)_2)_4$—$(O(CH_2)_3)_4$—, —U—$(CH_2)_2$—$(O(CH_2)_2)_5$—$(O(CH_2)_3)_5$—, —U—$(CH_2)_2$—$(O(CH_2)_3)_6$—$(O(CH_2)_2)_6$—, —U—$(CH_2)_3$—O—

(CH$_2$)$_3$—O—(CH$_2$)$_2$—, —U—(CH$_2$)$_3$—(O(CH$_2$)$_3$)$_2$—(O(CH$_2$)$_2$)$_2$—, —U—(CH$_2$)$_3$—(O(CH$_2$)$_3$)$_3$—(O(CH$_2$)$_2$)$_3$—, —U—(CH$_2$)$_3$—(O(CH$_2$)$_3$)$_4$—(O(CH$_2$)$_2$)$_4$—, —U—(CH$_2$)$_3$—(O(CH$_2$)$_3$)$_5$—(O(CH$_2$)$_2$)$_5$—, —U—(CH$_2$)$_3$—(O(CH$_2$)$_3$)$_6$—(O(CH$_2$)$_2$)$_6$—, —U—CH$_2$—O—(CH$_2$)$_2$—O—CH$_2$—, —U—(CH$_2$)$_2$—O—(CH$_2$)$_2$—O—CH$_2$—, —U—(CH$_2$)$_2$—(O(CH$_2$)$_2$)$_2$—O—(CH$_2$)$_3$—, —U—(CH$_2$)$_2$—(O(CH$_2$)$_2$)$_3$—O—(CH$_2$)$_3$—, —U—(CH$_2$)$_2$—(O(CH$_2$)$_2$)$_4$—O—(CH$_2$)$_3$—, —U—(CH$_2$)$_5$—(O(CH$_2$)$_2$)$_2$—O—(CH$_2$)$_5$—, or —U—(CH$_2$)$_5$—(O(CH$_2$)$_2$)$_2$—O—(CH$_2$)$_6$—; wherein the group U represents CO or NH, or the group U is absent.

Particularly preferred are the following compounds of formula (I) in Table 1 of the present disclosure and their salts (especially their pharmaceutically acceptable salts):

TABLE 1

The compounds of formula (I) of the present disclosure

| Compound ID | Name of the compound |
|---|---|
| SIAIS219100 | 7-cyclopentyl-2-((5-(4-(2-((2-(2,6-dioxopiperidin-3-yl)-1,3-dioxoisoindolin-4-yl)thio)acetyl)piperazin-1-yl)pyridin-2-yl)amino)-N,N-dimethyl-7H-pyrrolo[2,3-d]pyrimidine-6-carboxamide |
| SIAIS219101 | 7-cyclopentyl-2-((5-(4-(3-((2-(2,6-dioxopiperidin-3-yl)-1,3-dioxoisoindolin-4-yl)thio)propanoyl)piperazin-1-yl)pyridin-2-yl)amino)-N,N-dimethyl-7H-pyrrolo[2,3-d]pyrimidine-6-carboxamide |
| SIAIS219102 | 7-cyclopentyl-2-((5-(4-(4-((2-(2,6-dioxopiperidin-3-yl)-1,3-dioxoisoindolin-4-yl)thio)butanoyl)piperazin-1-yl)pyridin-2-yl)amino)-N,N-dimethyl-7H-pyrrolo[2,3-d]pyrimidine-6-carboxamide |
| SIAIS219103 | 7-cyclopentyl-2-((5-(4-(5-((2-(2,6-dioxopiperidin-3-yl)-1,3-dioxoisoindolin-4-yl)thio)pentanoyl)piperazin-1-yl)pyridin-2-yl)amino)-N,N-dimethyl-7H-pyrrolo[2,3-d]pyrimidine-6-carboxamide |
| SIAIS219104 | 7-cyclopentyl-2-((5-(4-(6-((2-(2,6-dioxopiperidin-3-yl)-1,3-dioxoisoindolin-4-yl)thio)hexanoyl)piperazin-1-yl)pyridin-2-yl)amino)-N,N-dimethyl-7H-pyrrolo[2,3-d]pyrimidine-6-carboxamide |
| | 7-cyclopentyl-2-((5-(4-(6-((2-(2,6-dioxopiperidin-3-yl)-1,3-dioxoisoindolin-4-yl)thio)hexyl)piperazin-1-yl)pyridin-2-yl)amino)-N,N-dimethyl-7H-pyrrolo[2,3-d]pyrimidine-6-carboxamide |
| SIAIS219105 | 7-cyclopentyl-2-((5-(4-(7-((2-(2,6-dioxopiperidin-3-yl)-1,3-dioxoisoindolin-4-yl)thio)heptanoyl)piperazin-1-yl)pyridin-2-yl)amino)-N,N-dimethyl-7H-pyrrolo[2,3-d]pyrimidine-6-carboxamide |
| | 7-cyclopentyl-2-((5-(4-(11-((2-(2,6-dioxopiperidin-3-yl)-1,3-dioxoisoindolin-4-yl)thio)undecanoyl)piperazin-1-yl)pyridin-2-yl)amino)-N,N-dimethyl-7H-pyrrolo[2,3-d]pyrimidine-6-carboxamide |
| SIAIS219086 | 7-cyclopentyl-2-((5-(4-(2-((2-(2,6-dioxopiperidin-3-yl)-1-oxoisoindolin-4-yl)thio)acetyl)piperazin-1-yl)pyridin-2-yl)amino)-N,N-dimethyl-7H-pyrrolo[2,3-d]pyrimidine-6-carboxamide |
| SIAIS219087 | 7-cyclopentyl-2-((5-(4-(3-((2-(2,6-dioxopiperidin-3-yl)-1-oxoisoindolin-4-yl)thio)propanoyl)piperazin-1-yl)pyridin-2-yl)amino)-N,N-dimethyl-7H-pyrrolo[2,3-d]pyrimidine-6-carboxamide |
| SIAIS219088 | 7-cyclopentyl-2-((5-(4-(4-((2-(2,6-dioxopiperidin-3-yl)-1-oxoisoindolin-4-yl)thio)butanoyl)piperazin-1-yl)pyridin-2-yl)amino)-N,N-dimethyl-7H-pyrrolo[2,3-d]pyrimidine-6-carboxamide |
| SIAIS219089 | 7-cyclopentyl-2-((5-(4-(5-((2-(2,6-dioxopiperidin-3-yl)-1-oxoisoindolin-4-yl)thio)pentanoyl)piperazin-1-yl)pyridin-2-yl)amino)-N,N-dimethyl-7H-pyrrolo[2,3-d]pyrimidine-6-carboxamide |
| SIAIS219090 | 7-cyclopentyl-2-((5-(4-(6-((2-(2,6-dioxopiperidin-3-yl)-1-oxoisoindolin-4-yl)thio)hexanoyl)piperazin-1-yl)pyridin-2-yl)amino)-N,N-dimethyl-7H-pyrrolo[2,3-d]pyrimidine-6-carboxamide |
| SIAIS219091 | 7-cyclopentyl-2-((5-(4-(7-((2-(2,6-dioxopiperidin-3-yl)-1-oxoisoindolin-4-yl)thio)heptanoyl)piperazin-1-yl)pyridin-2-yl)amino)-N,N-dimethyl-7H-pyrrolo[2,3-d]pyrimidine-6-carboxamide |
| SIAIS219111 | 7-cyclopentyl-2-((5-(4-(2-(2-((2-(2,6-dioxopiperidin-3-yl)-1,3-dioxoisoindolin-4-yl)thio)ethoxy)acetyl)piperazin-1-yl)pyridin-2-yl)amino)-N,N-dimethyl-7H-pyrrolo[2,3-d]pyrimidine-6-carboxamide |
| | 7-cyclopentyl-2-((5-(4-(3-(2-((2-(2,6-dioxopiperidin-3-yl)-1,3-dioxoisoindolin-4-yl)thio)ethoxy)propanoyl)piperazin-1-yl)pyridin-2-yl)amino)-N,N-dimethyl-7H-pyrrolo[2,3-d]pyrimidine-6-carboxamide |
| SIAIS219112 | 7-cyclopentyl-2-((5-(4-(2-(2-(2-((2-(2,6-dioxopiperidin-3-yl)-1,3-dioxoisoindolin-4-yl)thio)ethoxy)ethoxy)acetyl)piperazin-1-yl)pyridin-2-yl)amino)-N,N-dimethyl-7H-pyrrolo[2,3-d]pyrimidine-6-carboxamide |
| SIAIS219113 | 7-cyclopentyl-2-((5-(4-(2-(2-(2-(2-((2-(2,6-dioxopiperidin-3-yl)-1,3-dioxoisoindolin-4-yl)thio)ethoxy)ethoxy)ethoxy)acetyl)piperazin-1-yl)pyridin-2-yl)amino)-N,N-dimethyl-7H-pyrrolo[2,3-d]pyrimidine-6-carboxamide |
| | 7-cyclopentyl-2-((5-(4-(2-(2-(2-(2-((2-(2,6-dioxopiperidin-3-yl)-1,3-dioxoisoindolin-4-yl)thio)ethoxy)ethoxy)ethoxy)ethyl)piperazin-1-yl)pyridin-2-yl)amino)-N,N-dimethyl-7H-pyrrolo[2,3-d]pyrimidine-6-carboxamide |
| SIAIS219114 | 7-cyclopentyl-2-((5-(4-(14-((2-(2,6-dioxopiperidin-3-yl)-1,3-dioxoisoindolin-4-yl)thio)-3,6,9,12-tetraoxatetradecanoyl)piperazin-1-yl)pyridin-2-yl)amino)-N,N-dimethyl-7H-pyrrolo[2,3-d]pyrimidine-6-carboxamide |
| SIAIS219115 | 7-cyclopentyl-2-((5-(4-(17-((2-(2,6-dioxopiperidin-3-yl)-1,3-dioxoisoindolin-4-yl)thio)-3,6,9,12,15-pentaoxaheptadecanoyl)piperazin-1-yl)pyridin-2-yl)amino)-N,N-dimethyl-7H-pyrrolo[2,3-d]pyrimidine-6-carboxamide |
| SIAIS219106 | 7-cyclopentyl-2-((5-(4-(2-(2-((2-(2,6-dioxopiperidin-3-yl)-1-oxoisoindolin-4-yl)thio)ethoxy)acetyl)piperazin-1-yl)pyridin-2-yl)amino)-N,N-dimethyl-7H- |

TABLE 1-continued

The compounds of formula (I) of the present disclosure

| Compound ID | Name of the compound |
|---|---|
| | pyrrolo[2,3-d]pyrimidine-6-carboxamide |
| | 7-cyclopentyl-2-((5-(4-(3-(2-((2-(2,6-dioxopiperidin-3-yl)-1-oxoisoindolin-4-yl)thio)ethoxy)propanoyl)piperazin-1-yl)pyridin-2-yl)amino)-N,N-dimethyl-7H-pyrrolo[2,3-d]pyrimidine-6-carboxamide |
| SIAIS219107 | 7-cyclopentyl-2-((5-(4-(2-(2-((2-(2,6-dioxopiperidin-3-yl)-1-oxoisoindolin-4-yl)thio)ethoxy)ethoxy)acetyl)piperazin-1-yl)pyridin-2-yl)amino)-N,N-dimethyl-7H-pyrrolo[2,3-d]pyrimidine-6-carboxamide |
| SIAIS219108 | 7-cyclopentyl-2-((5-(4-(2-(2-(2-((2-(2,6-dioxopiperidin-3-yl)-1-oxoisoindolin-4-yl)thio)ethoxy)ethoxy)acetyl)piperazin-1-yl)pyridin-2-yl)amino)-N,N-dimethyl-7H-pyrrolo[2,3-d]pyrimidine-6-carboxamide |
| | 7-cyclopentyl-2-((5-(4-(2-(2-(2-((2-(2,6-dioxopiperidin-3-yl)-1-oxoisoindolin-4-yl)thio)ethoxy)ethoxy)ethyl)piperazin-1-yl)pyridin-2-yl)amino)-N,N-dimethyl-7H-pyrrolo[2,3-d]pyrimidine-6-carboxamide |
| SIAIS219109 | 7-cyclopentyl-2-((5-(4-(14-((2-(2,6-dioxopiperidin-3-yl)-1-oxoisoindolin-4-yl)thio)-3,6,9,12-tetraoxatetradecanoyl)piperazin-1-yl)pyridin-2-yl)amino)-N,N-dimethyl-7H-pyrrolo[2,3-d]pyrimidine-6-carboxamide |
| SIAIS219110 | 7-cyclopentyl-2-((5-(4-(17-((2-(2,6-dioxopiperidin-3-yl)-1-oxoisoindolin-4-yl)thio)-3,6,9,12,15-pentaoxaheptadecanoyl)piperazin-1-yl)pyridin-2-yl)amino)-N,N-dimethyl-7H-pyrrolo[2,3-d]pyrimidine-6-carboxamide |
| | 2-(2,6-dioxopiperidin-3-yl)-4-((2-(4-((6-((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)-2-oxoethyl)thio)isoindoline-1,3-dione |
| | 2-(2,6-dioxopiperidin-3-yl)-4-((3-(4-((6-((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)-3-oxopropyl)thio)isoindoline-1,3-dione |
| | 2-(2,6-dioxopiperidin-3-yl)-4-((4-(4-((6-((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)-4-oxobutyl)thio)isoindoline-1,3-dione |
| | 2-(2,6-dioxopiperidin-3-yl)-4-((5-(4-((6-((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)-5-oxopentyl)thio)isoindoline-1,3-dione |
| | 2-(2,6-dioxopiperidin-3-yl)-4-((6-(4-((6-((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)-6-oxohexyl)thio)isoindoline-1,3-dione |
| | 2-(2,6-dioxopiperidin-3-yl)-4-((7-(4-((6-((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)-7-oxoheptyl)thio)isoindoline-1,3-dione |
| | 2-(2,6-dioxopiperidin-3-yl)-4-((8-(4-((6-((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)-8-oxooctyl)thio)isoindoline-1,3-dione |
| | 2-(2,6-dioxopiperidin-3-yl)-4-((8-(4-((6-((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)octyl)thio)isoindoline-1,3-dione |
| | 2-(2,6-dioxopiperidin-3-yl)-4-((12-(4-((6-((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)-12-oxododecyl)thio)isoindoline-1,3-dione |
| SIAIS262164 | 3-(4-((2-(4-((6-((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)-2-oxoethyl)thio)-1-oxoisoindolin-2-yl)piperidine-2,6-dione |
| | 3-(4-((2-(4-((6-((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)ethyl)thio)-1-oxoisoindolin-2-yl)piperidine-2,6-dione |
| SIAIS262165 | 3-(4-((3-(4-((6-((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)-3-oxopropyl)thio)-1-oxoisoindolin-2-yl)piperidine-2,6-dione |
| SIAIS262166 | 3-(4-((4-(4-((6-((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)-4-oxobutyl)thio)-1-oxoisoindolin-2-yl)piperidine-2,6-dione |
| SIAIS262167 | 3-(4-(5-(4-((6-((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)-5-oxopentyl)thio)-1-oxoisoindolin-2-yl)piperidine-2,6-dione |
| SIAIS262168 | 3-(4-((6-(4-((6-((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)-6-oxohexyl)thio)-1-oxoisoindolin-2-yl)piperidine-2,6-dione |
| SIAIS262173 | 3-(4-((6-(4-((6-((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)hexyl)thio)-1-oxoisoindolin-2-yl)piperidine-2,6-dione |
| SIAIS262169 | 3-(4-((7-(4-((6-((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)-7-oxoheptyl)thio)-1-oxoisoindolin-2-yl)piperidine-2,6-dione |
| | 3-(4-((6-(4-((6-((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)hexyl)thio)-1-oxoisoindolin-2-yl)piperidine-2,6-dione |
| SIAIS262170 | 3-(4-((11-(4-((6-((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)-11-oxoundecyl)thio)-1- |

TABLE 1-continued

The compounds of formula (I) of the present disclosure

| Compound ID | Name of the compound |
|---|---|
| | oxoisoindolin-2-yl)piperidine-2,6-dione |
| | 2-(2,6-dioxopiperidin-3-yl)-4-((2-(2-(4-((6-((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)-2-oxoethoxy)ethyl)thio)isoindoline-1,3-dione |
| | 2-(2,6-dioxopiperidin-3-yl)-4-((2-(2-(2-(4-((6-((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)-2-oxoethoxy)ethoxy)ethyl)thio)isoindoline-1,3-dione |
| | 2-(2,6-dioxopiperidin-3-yl)-4-((2-(3-(3-(4-((6-((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)-3-oxopropoxy)propoxy)ethyl)thio)isoindoline-1,3-dione |
| | 2-(2,6-dioxopiperidin-3-yl)-4-((2-(3-(3-(4-((6-((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)propoxy)propoxy)ethyl)thio)isoindoline-1,3-dione |
| | 2-(2,6-dioxopiperidin-3-yl)-4-((2-(2-(2-(2-(4-((6-((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)-2-oxoethoxy)ethoxy)ethoxy)ethyl)thio)isoindoline-1,3-dione |
| | 2-(2,6-dioxopiperidin-3-yl)-4-((2-(2-(2-(3-(4-((6-((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)-3-oxopropoxy)ethoxy)ethoxy)ethyl)thio)isoindoline-1,3-dione |
| | 2-(2,6-dioxopiperidin-3-yl)-4-((14-(4-((6-((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)-14-oxo-3,6,9,12-tetraoxatetradecyl)thio)isoindoline-1,3-dione |
| | 2-(2,6-dioxopiperidin-3-yl)-4-((15-(4-((6-((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)-15-oxo-3,6,9,12-tetraoxapentadecyl)thio)isoindoline-1,3-dione |
| | 2-(2,6-dioxopiperidin-3-yl)-4-((17-(4-((6-((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)-17-oxo-3,6,9,12,15-pentaoxaheptadecyl)thio)isoindoline-1,3-dione |
| SIAIS262171 | 3-(4-((2-(2-(4-((6-((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)-2-oxoethoxy)ethyl)thio)-1-oxoisoindolin-2-yl)piperidine-2,6-dione |
| | 3-(4-((2-(2-(2-(4-((6-((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)-2-oxoethoxy)ethoxy)ethyl)thio)-1-oxoisoindolin-2-yl)piperidine-2,6-dione |
| | 3-(4-((2-(2-(2-(2-(4-((6-((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)-2-oxoethoxy)ethoxy)ethoxy)ethyl)thio)-1-oxoisoindolin-2-yl)piperidine-2,6-dione |
| | 3-(4-((2-(2-(2-(3-(4-((6-((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)-3-oxopropoxy)ethoxy)ethoxy)ethyl)thio)-1-oxoisoindolin-2-yl)piperidine-2,6-dione |
| | 3-(4-((2-(2-(2-(3-(4-((6-((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)propoxy)ethoxy)ethoxy)ethyl)thio)-1-oxoisoindolin-2-yl)piperidine-2,6-dione |
| | 3-(4-((14-(4-((6-((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)-14-oxo-3,6,9,12-tetraoxatetradecyl)thio)-1-oxoisoindolin-2-yl)piperidine-2,6-dione |
| | 3-(4-((17-(4-((6-((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)-17-oxo-3,6,9,12,15-pentaoxaheptadecyl)thio)-1-oxoisoindolin-2-yl)piperidine-2,6-dione |
| SIAIS151046 | 4-((2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-2-oxoethyl)thio)-2-(2,6-dioxopiperidin-3-yl)isoindoline-1,3-dione |
| SIAIS219063 | 4-((2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)ethyl)thio)-2-(2,6-dioxopiperidin-3-yl)isoindoline-1,3-dione |
| SIAIS151057 | 4-((2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-2-oxoethyl)sulfinyl)-2-(2,6-dioxopiperidin-3-yl)isoindoline-1,3-dione |
| | 4-((2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)ethyl)sulfinyl)-2-(2,6-dioxopiperidin-3-yl)isoindoline-1,3-dione |
| SIAIS151056 | 4-((2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-2-oxoethyl)sulfonyl)-2-(2,6-dioxopiperidin-3-yl)isoindoline-1,3-dione |
| | 4-((2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)ethyl)sulfonyl)-2-(2,6-dioxopiperidin-3-yl)isoindoline-1,3-dione |
| SIAIS184086 | 4-((3-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-3-oxopropyl)thio)-2-(2,6-dioxopiperidin-3-yl)isoindoline-1,3-dione |
| | 4-((3-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)propyl)thio)-2-(2,6-dioxopiperidin-3-yl)isoindoline-1,3-dione |

TABLE 1-continued

The compounds of formula (I) of the present disclosure

| Compound ID | Name of the compound |
| --- | --- |
| SIAIS184087 | 4-((4-(4-(6-(((6-acetyl-8-cyclopentyl-5-methyl-7-oxo-7,8-dihydropyrido[2,3-d]pyrimidin-2-yl)amino)pyridin-3-yl)piperazin-1-yl)-4-oxobutyl)thio)-2-(2,6-dioxopiperidin-3-yl)isoindoline-1,3-dione<br>4-((4-(4-(6-(((6-acetyl-8-cyclopentyl-5-methyl-7-oxo-7,8-dihydropyrido[2,3-d]pyrimidin-2-yl)amino)pyridin-3-yl)piperazin-1-yl)butyl)thio)-2-(2,6-dioxopiperidin-3-yl)isoindoline-1,3-dione |
| SIAIS184088 | 4-((5-(4-(6-(((6-acetyl-8-cyclopentyl-5-methyl-7-oxo-7,8-dihydropyrido[2,3-d]pyrimidin-2-yl)amino)pyridin-3-yl)piperazin-1-yl)-5-oxopentyl)thio)-2-(2,6-dioxopiperidin-3-yl)isoindoline-1,3-dione<br>4-((5-(4-(6-(((6-acetyl-8-cyclopentyl-5-methyl-7-oxo-7,8-dihydropyrido[2,3-d]pyrimidin-2-yl)amino)pyridin-3-yl)piperazin-1-yl)pentyl)thio)-2-(2,6-dioxopiperidin-3-yl)isoindoline-1,3-dione |
| SIAIS184089 | 4-((6-(4-(6-(((6-acetyl-8-cyclopentyl-5-methyl-7-oxo-7,8-dihydropyrido[2,3-d]pyrimidin-2-yl)amino)pyridin-3-yl)piperazin-1-yl)-6-oxohexyl)thio)-2-(2,6-dioxopiperidin-3-yl)isoindoline-1,3-dione<br>4-((6-(4-(6-(((6-acetyl-8-cyclopentyl-5-methyl-7-oxo-7,8-dihydropyrido[2,3-d]pyrimidin-2-yl)amino)pyridin-3-yl)piperazin-1-yl)hexyl)thio)-2-(2,6-dioxopiperidin-3-yl)isoindoline-1,3-dione |
| SIAIS184090 | 4-((7-(4-(6-(((6-acetyl-8-cyclopentyl-5-methyl-7-oxo-7,8-dihydropyrido[2,3-d]pyrimidin-2-yl)amino)pyridin-3-yl)piperazin-1-yl)-7-oxoheptyl)thio)-2-(2,6-dioxopiperidin-3-yl)isoindoline-1,3-dione<br>4-((7-(4-(6-(((6-acetyl-8-cyclopentyl-5-methyl-7-oxo-7,8-dihydropyrido[2,3-d]pyrimidin-2-yl)amino)pyridin-3-yl)piperazin-1-yl)heptyl)thio)-2-(2,6-dioxopiperidin-3-yl)isoindoline-1,3-dione |
| SIAIS219051 | 3-(4-((2-(4-(6-(((6-acetyl-8-cyclopentyl-5-methyl-7-oxo-7,8-dihydropyrido[2,3-d]pyrimidin-2-yl)amino)pyridin-3-yl)piperazin-1-yl)-2-oxoethyl)thio)-1-oxoisoindolin-2-yl)piperidine-2,6-dione<br>3-(4-((2-(4-(6-(((6-acetyl-8-cyclopentyl-5-methyl-7-oxo-7,8-dihydropyrido[2,3-d]pyrimidin-2-yl)amino)pyridin-3-yl)piperazin-1-yl)ethyl)thio)-1-oxoisoindolin-2-yl)piperidine-2,6-dione<br>3-(4-((2-(4-(6-(((6-acetyl-8-cyclopentyl-5-methyl-7-oxo-7,8-dihydropyrido[2,3-d]pyrimidin-2-yl)amino)pyridin-3-yl)piperazin-1-yl)ethyl)sulfonyl)-1-oxoisoindolin-2-yl)piperidine-2,6-dione |
| SIAIS219052 | 3-(4-((3-(4-(6-(((6-acetyl-8-cyclopentyl-5-methyl-7-oxo-7,8-dihydropyrido[2,3-d]pyrimidin-2-yl)amino)pyridin-3-yl)piperazin-1-yl)-3-oxopropyl)thio)-1-oxoisoindolin-2-yl)piperidine-2,6-dione<br>3-(4-((3-(4-(6-(((6-acetyl-8-cyclopentyl-5-methyl-7-oxo-7,8-dihydropyrido[2,3-d]pyrimidin-2-yl)amino)pyridin-3-yl)piperazin-1-yl)propyl)thio)-1-oxoisoindolin-2-yl)piperidine-2,6-dione |
| SIAIS219053 | 3-(4-((4-(4-(6-(((6-acetyl-8-cyclopentyl-5-methyl-7-oxo-7,8-dihydropyrido[2,3-d]pyrimidin-2-yl)amino)pyridin-3-yl)piperazin-1-yl)-4-oxobutyl)thio)-1-oxoisoindolin-2-yl)piperidine-2,6-dione |
| SIAIS184092 | 3-(4-((5-(4-(6-(((6-acetyl-8-cyclopentyl-5-methyl-7-oxo-7,8-dihydropyrido[2,3-d]pyrimidin-2-yl)amino)pyridin-3-yl)piperazin-1-yl)-5-oxopentyl)thio)-1-oxoisoindolin-2-yl)piperidine-2,6-dione<br>3-(4-((5-(4-(6-(((6-acetyl-8-cyclopentyl-5-methyl-7-oxo-7,8-dihydropyrido[2,3-d]pyrimidin-2-yl)amino)pyridin-3-yl)piperazin-1-yl)pentyl)thio)-1-oxoisoindolin-2-yl)piperidine-2,6-dione |
| SIAIS219054 | 3-(4-((6-(4-(6-(((6-acetyl-8-cyclopentyl-5-methyl-7-oxo-7,8-dihydropyrido[2,3-d]pyrimidin-2-yl)amino)pyridin-3-yl)piperazin-1-yl)-6-oxohexyl)thio)-1-oxoisoindolin-2-yl)piperidine-2,6-dione |
| SIAIS219055 | 3-(4-((7-(4-(6-(((6-acetyl-8-cyclopentyl-5-methyl-7-oxo-7,8-dihydropyrido[2,3-d]pyrimidin-2-yl)amino)pyridin-3-yl)piperazin-1-yl)-7-oxoheptyl)thio)-1-oxoisoindolin-2-yl)piperidine-2,6-dione |
| SIAIS184091 | 4-((2-(2-(4-(6-(((6-acetyl-8-cyclopentyl-5-methyl-7-oxo-7,8-dihydropyrido[2,3-d]pyrimidin-2-yl)amino)pyridin-3-yl)piperazin-1-yl)-2-oxoethoxy)ethyl)thio)-2-(2,6-dioxopiperidin-3-yl)isoindoline-1,3-dione<br>4-((2-(2-(4-(6-(((6-acetyl-8-cyclopentyl-5-methyl-7-oxo-7,8-dihydropyrido[2,3-d]pyrimidin-2-yl)amino)pyridin-3-yl)piperazin-1-yl)ethoxy)ethyl)thio)-2-(2,6-dioxopiperidin-3-yl)isoindoline-1,3-dione<br>4-((2-(3-(4-(6-(((6-acetyl-8-cyclopentyl-5-methyl-7-oxo-7,8-dihydropyrido[2,3-d]pyrimidin-2-yl)amino)pyridin-3-yl)piperazin-1-yl)-3-oxopropoxy)ethyl)thio)-2-(2,6-dioxopiperidin-3-yl)isoindoline-1,3-dione<br>4-((2-(3-(4-(6-(((6-acetyl-8-cyclopentyl-5-methyl-7-oxo-7,8-dihydropyrido[2,3-d]pyrimidin-2-yl)amino)pyridin-3-yl)piperazin-1-yl)propoxy)ethyl)thio)-2-(2,6-dioxopiperidin-3-yl)isoindoline-1,3-dione |
| SIAIS219059 | 4-((2-(2-(2-(4-(6-(((6-acetyl-8-cyclopentyl-5-methyl-7-oxo-7,8-dihydropyrido[2,3-d]pyrimidin-2-yl)amino)pyridin-3-yl)piperazin-1-yl)-2-oxoethoxy)ethoxy)ethyl)thio)-2-(2,6-dioxopiperidin-3-yl)isoindoline-1,3-dione<br>4-((2-(2-(3-(4-(6-(((6-acetyl-8-cyclopentyl-5-methyl-7-oxo-7,8-dihydropyrido[2,3-d]pyrimidin-2-yl)amino)pyridin-3-yl)piperazin-1-yl)-3-oxopropoxy)ethoxy)ethyl)thio)-2-(2,6-dioxopiperidin-3-yl)isoindoline-1,3-dione<br>4-((2-(2-(3-(4-(6-(((6-acetyl-8-cyclopentyl-5-methyl-7-oxo-7,8-dihydropyrido[2,3-d]pyrimidin-2-yl)amino)pyridin-3-yl)piperazin-1-yl)propoxy)ethoxy)ethyl)thio)-2-(2,6-dioxopiperidin-3-yl)isoindoline-1,3-dione |

TABLE 1-continued

The compounds of formula (I) of the present disclosure

| Compound ID | Name of the compound |
|---|---|
| SIAIS219060 | 4-((2-(2-(2-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-2-oxoethoxy)ethoxy)ethoxy)ethyl)thio)-2-(2,6-dioxopiperidin-3-yl)isoindoline-1,3-dione |
| | 4-((2-(2-(2-(3-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-3-oxopropoxy)ethoxy)ethoxy)ethyl)thio)-2-(2,6-dioxopiperidin-3-yl)isoindoline-1,3-dione |
| SIAIS219061 | 4-((14-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-14-oxo-3,6,9,12-tetraoxatetradecyl)thio)-2-(2,6-dioxopiperidin-3-yl)isoindoline-1,3-dione |
| | 4-((15-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-15-oxo-3,6,9,12-tetraoxapentadecyl)thio)-2-(2,6-dioxopiperidin-3-yl)isoindoline-1,3-dione |
| | 4-((15-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-3,6,9,12-tetraoxapentadecyl)thio)-2-(2,6-dioxopiperidin-3-yl)isoindoline-1,3-dione |
| SIAIS219062 | 4-((17-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-17-oxo-3,6,9,12,15-pentaoxaheptadecyl)thio)-2-(2,6-dioxopiperidin-3-yl)isoindoline-1,3-dione |
| | 4-((18-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-18-oxo-3,6,9,12,15-pentaoxaoctadecyl)thio)-2-(2,6-dioxopiperidin-3-yl)isoindoline-1,3-dione |
| | 4-((18-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-3,6,9,12,15-pentaoxaoctadecyl)thio)-2-(2,6-dioxopiperidin-3-yl)isoindoline-1,3-dione |
| | 3-(4-((2-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-2-oxoethoxy)ethyl)thio)-1-oxoisoindolin-2-yl)piperidine-2,6-dione |
| | 3-(4-((2-(3-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-3-oxopropoxy)ethyl)thio)-1-oxoisoindolin-2-yl)piperidine-2,6-dione |
| | 3-(4-((2-(2-(3-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-3-oxopropoxy)ethoxy)ethyl)thio)-1-oxoisoindolin-2-yl)piperidine-2,6-dione |
| | 3-(4-((2-(2-(2-(3-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-3-oxopropoxy)ethoxy)ethyl)thio)-1-oxoisoindolin-2-yl)piperidine-2,6-dione |
| | 3-(4-((18-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-18-oxo-3,6,9,12,15-pentaoxaoctadecyl)thio)-1-oxoisoindolin-2-yl)piperidine-2,6-dione |
| | 3-(4-((18-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-3,6,9,12,15-pentaoxaoctadecyl)thio)-1-oxoisoindolin-2-yl)piperidine-2,6-dione |
| | 4-((6-(4-(4-(6-amino-5-((R)-1-(2,6-dichloro-3-fluorophenyl)ethoxy)pyridin-3-yl)-1H-pyrazol-1-yl)piperidin-1-yl)-6-oxohexyl)thio)-2-(2,6-dioxopiperidin-3-yl)isoindoline-1,3-dione |
| | 4-((2-(3-(4-(4-(6-amino-5-((R)-1-(2,6-dichloro-3-fluorophenyl)ethoxy)pyridin-3-yl)-1H-pyrazol-1-yl)piperidin-1-yl)-3-oxopropoxy)ethyl)thio)-2-(2,6-dioxopiperidin-3-yl)isoindoline-1,3-dione |
| | 3-(4-((6-(4-(4-(6-amino-5-((R)-1-(2,6-dichloro-3-fluorophenyl)ethoxy)pyridin-3-yl)-1H-pyrazol-1-yl)piperidin-1-yl)-6-oxohexyl)thio)-1-oxoisoindolin-2-yl)piperidine-2,6-dione |
| | 3-(4-((2-(3-(4-(4-(6-amino-5-((R)-1-(2,6-dichloro-3-fluorophenyl)ethoxy)pyridin-3-yl)-1H-pyrazol-1-yl)piperidin-1-yl)-3-oxopropoxy)ethyl)thio)-1-oxoisoindolin-2-yl)piperidine-2,6-dione |
| | 4-((2-(3-(4-(4-(6-amino-5-((R)-1-(2,6-dichloro-3-fluorophenyl)ethoxy)pyridin-3-yl)-1H-pyrazol-1-yl)piperidin-1-yl)propoxy)ethyl)thio)-2-(2,6-dioxopiperidin-3-yl)isoindoline-1,3-dione |
| | 3-(4-((2-(3-(4-(4-(6-amino-5-((R)-1-(2,6-dichloro-3-fluorophenyl)ethoxy)pyridin-3-yl)-1H-pyrazol-1-yl)piperidin-1-yl)propoxy)ethyl)thio)-1-oxoisoindolin-2-yl)piperidine-2,6-dione |
| | 4-((6-(4-(4-((5-chloro-4-((2-(isopropylsulfonyl)phenyl)amino)pyrimidin-2-yl)amino)-5-isopropoxy-2-methylphenyl)piperidin-1-yl)-6-oxohexyl)thio)-2-(2,6-dioxopiperidin-3-yl)isoindoline-1,3-dione |
| | 4-((6-(4-(4-((5-chloro-4-((2-(isopropylsulfonyl)phenyl)amino)pyrimidin-2-yl)amino)-5-isopropoxy-2-methylphenyl)piperidin-1-yl)hexyl)thio)-2-(2,6-dioxopiperidin-3-yl)isoindoline-1,3-dione |
| | 3-(4-((6-(4-(4-((5-chloro-4-((2-(isopropylsulfonyl)phenyl)amino)pyrimidin-2-yl)amino)-5-isopropoxy-2-methylphenyl)piperidin-1-yl)-6-oxohexyl)thio)-1-oxoisoindolin-2-yl)piperidine-2,6-dione |
| | 3-(4-((6-(4-(4-((5-chloro-4-((2-(isopropylsulfonyl)phenyl)amino)pyrimidin-2-yl)amino)-5-isopropoxy-2-methylphenyl)piperidin-1-yl)hexyl)thio)-1-oxoisoindolin-2-yl)piperidine-2,6-dione |
| | 4-((2-(3-(4-(4-((5-chloro-4-((2-(isopropylsulfonyl)phenyl)amino)pyrimidin-2-yl)amino)-5-isopropoxy-2-methylphenyl)piperidin-1-yl)-3-oxopropoxy)ethyl)thio)-2- |

TABLE 1-continued

The compounds of formula (I) of the present disclosure

| Compound ID | Name of the compound |
|---|---|
| | (2,6-dioxopiperidin-3-yl)isoindoline-1,3-dione |
| | 4-((9-(4-(4-((5-chloro-4-((2-(isopropylsulfonyl)phenyl)amino)pyrimidin-2-yl)amino)-5-isopropoxy-2-methylphenyl)piperidin-1-yl)-9-oxononyl)thio)-2-(2,6-dioxopiperidin-3-yl)isoindoline-1,3-dione |
| | 4-((2-(2-(3-(4-(4-((5-chloro-4-((2-(isopropylsulfonyl)phenyl)amino)pyrimidin-2-yl)amino)-5-isopropoxy-2-methylphenyl)piperidin-1-yl)-3-oxopropoxy)ethoxy)ethyl)thio)-2-(2,6-dioxopiperidin-3-yl)isoindoline-1,3-dione |
| | 4-((2-(2-(3-(4-(4-((5-chloro-4-((2-(isopropylsulfonyl)phenyl)amino)pyrimidin-2-yl)amino)-5-isopropoxy-2-methylphenyl)piperidin-1-yl)propoxy)ethoxy)ethyl)thio)-2-(2,6-dioxopiperidin-3-yl)isoindoline-1,3-dione |
| | 3-(4-((2-(2-(3-(4-(4-((5-chloro-4-((2-(isopropylsulfonyl)phenyl)amino)pyrimidin-2-yl)amino)-5-isopropoxy-2-methylphenyl)piperidin-1-yl)-3-oxopropoxy)ethoxy)ethyl)thio)-1-oxoisoindolin-2-yl)piperidine-2,6-dione |
| | 4-((2-(2-(2-(3-(4-(4-((5-chloro-4-((2-(isopropylsulfonyl)phenyl)amino)pyrimidin-2-yl)amino)-5-isopropoxy-2-methylphenyl)piperidin-1-yl)-3-oxopropoxy)ethoxy)ethoxy)ethyl)thio)-2-(2,6-dioxopiperidin-3-yl)isoindoline-1,3-dione |
| | 3-(4-((2-(2-(2-(3-(4-(4-((5-chloro-4-((2-(isopropylsulfonyl)phenyl)amino)pyrimidin-2-yl)amino)-5-isopropoxy-2-methylphenyl)piperidin-1-yl)-3-oxopropoxy)ethoxy)ethoxy)ethyl)thio)-1-oxoisoindolin-2-yl)piperidine-2,6-dione |
| SIAIS1197113 | 4-((2-(4-(4-((5-chloro-4-((2-(dimethylphosphoryl)phenyl)amino)pyrimidin-2-yl)amino)-3-methoxyphenyl)piperazin-1-yl)-2-oxoethyl)thio)-2-(2,6-dioxopiperidin-3-yl)isoindoline-1,3-dione |
| SIAIS1197115 | 4-((3-(4-(4-((5-chloro-4-((2-(dimethylphosphoryl)phenyl)amino)pyrimidin-2-yl)amino)-3-methoxyphenyl)piperazin-1-yl)-3-oxopropyl)thio)-2-(2,6-dioxopiperidin-3-yl)isoindoline-1,3-dione |
| | 4-((3-(4-(4-((5-chloro-4-((2-(dimethylphosphoryl)phenyl)amino)pyrimidin-2-yl)amino)-3-methoxyphenyl)piperazin-1-yl)propyl)thio)-2-(2,6-dioxopiperidin-3-yl)isoindoline-1,3-dione |
| SIAIS1197117 | 4-((4-(4-(4-((5-chloro-4-((2-(dimethylphosphoryl)phenyl)amino)pyrimidin-2-yl)amino)-3-methoxyphenyl)piperazin-1-yl)-4-oxobutyl)thio)-2-(2,6-dioxopiperidin-3-yl)isoindoline-1,3-dione |
| SIAIS1197119 | 4-((5-(4-(4-((5-chloro-4-((2-(dimethylphosphoryl)phenyl)amino)pyrimidin-2-yl)amino)-3-methoxyphenyl)piperazin-1-yl)-5-oxopentyl)thio)-2-(2,6-dioxopiperidin-3-yl)isoindoline-1,3-dione |
| | 4-((5-(4-(4-((5-chloro-4-((2-(dimethylphosphoryl)phenyl)amino)pyrimidin-2-yl)amino)-3-methoxyphenyl)piperazin-1-yl)pentyl)thio)-2-(2,6-dioxopiperidin-3-yl)isoindoline-1,3-dione |
| SIAIS1197121 | 4-((6-(4-(4-((5-chloro-4-((2-(dimethylphosphoryl)phenyl)amino)pyrimidin-2-yl)amino)-3-methoxyphenyl)piperazin-1-yl)-6-oxohexyl)thio)-2-(2,6-dioxopiperidin-3-yl)isoindoline-1,3-dione |
| SIAIS1197159 | 4-((7-(4-(4-((5-chloro-4-((2-(dimethylphosphoryl)phenyl)amino)pyrimidin-2-yl)amino)-3-methoxyphenyl)piperazin-1-yl)-7-oxoheptyl)thio)-2-(2,6-dioxopiperidin-3-yl)isoindoline-1,3-dione |
| | 4-((7-(4-(4-((5-chloro-4-((2-(dimethylphosphoryl)phenyl)amino)pyrimidin-2-yl)amino)-3-methoxyphenyl)piperazin-1-yl)heptyl)thio)-2-(2,6-dioxopiperidin-3-yl)isoindoline-1,3-dione |
| | 4-((11-(4-(4-((5-chloro-4-((2-(dimethylphosphoryl)phenyl)amino)pyrimidin-2-yl)amino)-3-methoxyphenyl)piperazin-1-yl)-11-oxoundecyl)thio)-2-(2,6-dioxopiperidin-3-yl)isoindoline-1,3-dione |
| | 4-((11-(4-(4-((5-chloro-4-((2-(dimethylphosphoryl)phenyl)amino)pyrimidin-2-yl)amino)-3-methoxyphenyl)piperazin-1-yl)undecyl)thio)-2-(2,6-dioxopiperidin-3-yl)isoindoline-1,3-dione |
| | 3-(4-((2-(4-(4-((5-chloro-4-((2-(dimethylphosphoryl)phenyl)amino)pyrimidin-2-yl)amino)-3-methoxyphenyl)piperazin-1-yl)-2-oxoethyl)thio)-1-oxoisoindolin-2-yl)piperidine-2,6-dione |
| | 3-(4-((4-(4-(4-((5-chloro-4-((2-(dimethylphosphoryl)phenyl)amino)pyrimidin-2-yl)amino)-3-methoxyphenyl)piperazin-1-yl)-4-oxobutyl)thio)-1-oxoisoindolin-2-yl)piperidine-2,6-dione |
| | 3-(4-((6-(4-(4-((5-chloro-4-((2-(dimethylphosphoryl)phenyl)amino)pyrimidin-2-yl)amino)-3-methoxyphenyl)piperazin-1-yl)-6-oxohexyl)thio)-1-oxoisoindolin-2-yl)piperidine-2,6-dione |
| | 3-(4-((7-(4-(4-((5-chloro-4-((2-(dimethylphosphoryl)phenyl)amino)pyrimidin-2-yl)amino)-3-methoxyphenyl)piperazin-1-yl)heptyl)thio)-1-oxoisoindolin-2-yl)piperidine-2,6-dione |
| | 3-(4-((11-(4-(4-((5-chloro-4-((2-(dimethylphosphoryl)phenyl)amino)pyrimidin-2-yl)amino)-3-methoxyphenyl)piperazin-1-yl)-11-oxoundecyl)thio)-1-oxoisoindolin-2-yl)piperidine-2,6-dione |
| | 3-(4-((11-(4-(4-((5-chloro-4-((2-(dimethylphosphoryl)phenyl)amino)pyrimidin-2-yl)amino)-3-methoxyphenyl)piperazin-1-yl)undecyl)thio)-1-oxoisoindolin-2-yl)piperidine-2,6-dione |
| | 4-((2-(2-(2-(2-(4-(4-((5-chloro-4-((2-(dimethylphosphoryl)phenyl)amino)pyrimidin-2-yl)amino)-3-methoxyphenyl)piperazin-1-yl)-2-oxoethoxy)ethoxy)ethoxy)ethyl)thio)-2-(2,6-dioxopiperidin-3-yl)isoindoline-1,3-dione |
| | 4-((2-(2-(2-(2-(4-(4-((5-chloro-4-((2-(dimethylphosphoryl)phenyl)amino)pyrimidin-2- |

TABLE 1-continued

The compounds of formula (I) of the present disclosure

| Compound ID | Name of the compound |
|---|---|
| | yl)amino)-3-methoxyphenyl)piperazin-1-yl)ethoxy)ethoxy)ethoxy)ethyl)thio)-2-(2,6-dioxopiperidin-3-yl)isoindoline-1,3-dione |
| | 3-(4-((2-(2-(2-(2-(4-(4-((5-chloro-4-((2-(dimethylphosphoryl)phenyl)amino)pyrimidin-2-yl)amino)-3-methoxyphenyl)piperazin-1-yl)-2-oxoethoxy)ethoxy)ethoxy)ethyl)thio)-1-oxoisoindolin-2-yl)piperidine-2,6-dione |
| SIAIS164137 | N-(1-(4-((5-chloro-4-((2-(dimethylphosphoryl)phenyl)amino)pyrimidin-2-yl)amino)-3-methoxyphenyl)piperidin-4-yl)-2-((2-(2,6-dioxopiperidin-3-yl)-1,3-dioxoisoindolin-4-yl)thio)acetamide |
| SIAIS164138 | N-(1-(4-((5-chloro-4-((2-(dimethylphosphoryl)phenyl)amino)pyrimidin-2-yl)amino)-3-methoxyphenyl)piperidin-4-yl)-3-((2-(2,6-dioxopiperidin-3-yl)-1,3-dioxoisoindolin-4-yl)thio)propanamide |
| SIAIS164139 | N-(1-(4-((5-chloro-4-((2-(dimethylphosphoryl)phenyl)amino)pyrimidin-2-yl)amino)-3-methoxyphenyl)piperidin-4-yl)-4-((2-(2,6-dioxopiperidin-3-yl)-1,3-dioxoisoindolin-4-yl)thio)butanamide |
| SIAIS164140 | N-(1-(4-((5-chloro-4-((2-(dimethylphosphoryl)phenyl)amino)pyrimidin-2-yl)amino)-3-methoxyphenyl)piperidin-4-yl)-5-((2-(2,6-dioxopiperidin-3-yl)-1,3-dioxoisoindolin-4-yl)thio)pentanamide |
| SIAIS164141 | N-(1-(4-((5-chloro-4-((2-(dimethylphosphoryl)phenyl)amino)pyrimidin-2-yl)amino)-3-methoxyphenyl)piperidin-4-yl)-6-((2-(2,6-dioxopiperidin-3-yl)-1,3-dioxoisoindolin-4-yl)thio)hexanamide |
| SIAIS164142 | N-(1-(4-((5-chloro-4-((2-(dimethylphosphoryl)phenyl)amino)pyrimidin-2-yl)amino)-3-methoxyphenyl)piperidin-4-yl)-7-((2-(2,6-dioxopiperidin-3-yl)-1,3-dioxoisoindolin-4-yl)thio)heptanamide |
| | 4-((7-((1-(4-((5-chloro-4-((2-(dimethylphosphoryl)phenyl)amino)pyrimidin-2-yl)amino)-3-methoxyphenyl)piperidin-4-yl)amino)heptyl)thio)-2-(2,6-dioxopiperidin-3-yl)isoindoline-1,3-dione |
| SIAIS219133 | N-(1-(4-((5-chloro-4-((2-(dimethylphosphoryl)phenyl)amino)pyrimidin-2-yl)amino)-3-methoxyphenyl)piperidin-4-yl)-2-((2-(2,6-dioxopiperidin-3-yl)-1-oxoisoindolin-4-yl)thio)acetamide |
| SIAIS219134 | N-(1-(4-((5-chloro-4-((2-(dimethylphosphoryl)phenyl)amino)pyrimidin-2-yl)amino)-3-methoxyphenyl)piperidin-4-yl)-3-((2-(2,6-dioxopiperidin-3-yl)-1-oxoisoindolin-4-yl)thio)propanamide |
| SIAIS219135 | N-(1-(4-((5-chloro-4-((2-(dimethylphosphoryl)phenyl)amino)pyrimidin-2-yl)amino)-3-methoxyphenyl)piperidin-4-yl)-4-((2-(2,6-dioxopiperidin-3-yl)-1-oxoisoindolin-4-yl)thio)butanamide |
| SIAIS219136 | N-(1-(4-((5-chloro-4-((2-(dimethylphosphoryl)phenyl)amino)pyrimidin-2-yl)amino)-3-methoxyphenyl)piperidin-4-yl)-5-((2-(2,6-dioxopiperidin-3-yl)-1-oxoisoindolin-4-yl)thio)pentanamide |
| SIAIS219137 | N-(1-(4-((5-chloro-4-((2-(dimethylphosphoryl)phenyl)amino)pyrimidin-2-yl)amino)-3-methoxyphenyl)piperidin-4-yl)-6-((2-(2,6-dioxopiperidin-3-yl)-1-oxoisoindolin-4-yl)thio)hexanamide |
| SIAIS219138 | N-(1-(4-((5-chloro-4-((2-(dimethylphosphoryl)phenyl)amino)pyrimidin-2-yl)amino)-3-methoxyphenyl)piperidin-4-yl)-7-((2-(2,6-dioxopiperidin-3-yl)-1-oxoisoindolin-4-yl)thio)heptanamide |
| | 3-(4-((7-((1-(4-((5-chloro-4-((2-(dimethylphosphoryl)phenyl)amino)pyrimidin-2-yl)amino)-3-methoxyphenyl)piperidin-4-yl)amino)heptyl)thio)-1-oxoisoindolin-2-yl)piperidine-2,6-dione |
| | N-(1-(4-((5-chloro-4-((2-(dimethylphosphoryl)phenyl)amino)pyrimidin-2-yl)amino)-3-methoxyphenyl)piperidin-4-yl)-2-((2-(2,6-dioxopiperidin-3-yl)-1,3-dioxoisoindolin-4-yl)thio)-N-methylacetamide |
| | 4-((2-((1-(4-((5-chloro-4-((2-(dimethylphosphoryl)phenyl)amino)pyrimidin-2-yl)amino)-3-methoxyphenyl)piperidin-4-yl)(methyl)amino)ethyl)thio)-2-(2,6-dioxopiperidin-3-yl)isoindoline-1,3-dione |
| | N-(1-(4-((5-chloro-4-((2-(dimethylphosphoryl)phenyl)amino)pyrimidin-2-yl)amino)-3-methoxyphenyl)piperidin-4-yl)-3-((2-(2,6-dioxopiperidin-3-yl)-1,3-dioxoisoindolin-4-yl)thio)-N-methylpropanamide |
| | 4-((3-((1-(4-((5-chloro-4-((2-(dimethylphosphoryl)phenyl)amino)pyrimidin-2-yl)amino)-3-methoxyphenyl)piperidin-4-yl)(methyl)amino)propyl)thio)-2-(2,6-dioxopiperidin-3-yl)isoindoline-1,3-dione |
| | N-(1-(4-((5-chloro-4-((2-(dimethylphosphoryl)phenyl)amino)pyrimidin-2-yl)amino)-3-methoxyphenyl)piperidin-4-yl)-4-((2-(2,6-dioxopiperidin-3-yl)-1,3-dioxoisoindolin-4-yl)thio)-N-methylbutanamide |
| | N-(1-(4-((5-chloro-4-((2-(dimethylphosphoryl)phenyl)amino)pyrimidin-2-yl)amino)-3-methoxyphenyl)piperidin-4-yl)-5-((2-(2,6-dioxopiperidin-3-yl)-1,3-dioxoisoindolin-4-yl)thio)-N-methylpentanamide |
| | 4-((7-((1-(4-((5-chloro-4-((2-(dimethylphosphoryl)phenyl)amino)pyrimidin-2-yl)amino)-3-methoxyphenyl)piperidin-4-yl)(methyl)amino)heptyl)thio)-2-(2,6-dioxopiperidin-3-yl)isoindoline-1,3-dione |
| | N-(1-(4-((5-chloro-4-((2-(dimethylphosphoryl)phenyl)amino)pyrimidin-2-yl)amino)-3-methoxyphenyl)piperidin-4-yl)-3-((2-(2,6-dioxopiperidin-3-yl)-1-oxoisoindolin-4-yl)thio)-N-methylpropanamide |
| | 3-(4-((3-((1-(4-((5-chloro-4-((2-(dimethylphosphoryl)phenyl)amino)pyrimidin-2-yl)amino)-3-methoxyphenyl)piperidin-4-yl)(methyl)amino)propyl)thio)-1-oxoisoindolin-2-yl)piperidine-2,6-dione |
| | N-(1-(4-((5-chloro-4-((2-(dimethylphosphoryl)phenyl)amino)pyrimidin-2-yl)amino)-3- |

TABLE 1-continued

The compounds of formula (I) of the present disclosure

| Compound ID | Name of the compound |
|---|---|
| | methoxyphenyl)piperidin-4-yl)-4-((2-(2,6-dioxopiperidin-3-yl)-1-oxoisoindolin-4-yl)thio)-N-methylbutanamide |
| | 3-(4-((7-((1-(4-((5-chloro-4-((2-(dimethylphosphoryl)phenyl)amino)pyrimidin-2-yl)amino)-3-methoxyphenyl)piperidin-4-yl)(methyl)amino)heptyl)thio)-1-oxoisoindolin-2-yl)piperidine-2,6-dione |
| SIAIS219144 | N-(1-(4-((5-chloro-4-((2-(dimethylphosphoryl)phenyl)amino)pyrimidin-2-yl)amino)-3-methoxyphenyl)piperidin-4-yl)-2-(2-((2-(2,6-dioxopiperidin-3-yl)-1,3-dioxoisoindolin-4-yl)thio)ethoxy)acetamide |
| | 4-((3-(3-((1-(4-((5-chloro-4-((2-(dimethylphosphoryl)phenyl)amino)pyrimidin-2-yl)amino)-3-methoxyphenyl)piperidin-4-yl)amino)propoxy)propyl)thio)-2-(2,6-dioxopiperidin-3-yl)isoindoline-1,3-dione |
| SIAIS219139 | N-(1-(4-((5-chloro-4-((2-(dimethylphosphoryl)phenyl)amino)pyrimidin-2-yl)amino)-3-methoxyphenyl)piperidin-4-yl)-2-(2-((2-(2,6-dioxopiperidin-3-yl)-1-oxoisoindolin-4-yl)thio)ethoxy)acetamide |
| SIAIS219140 | N-(1-(4-((5-chloro-4-((2-(dimethylphosphoryl)phenyl)amino)pyrimidin-2-yl)amino)-3-methoxyphenyl)piperidin-4-yl)-2-(2-(2-((2-(2,6-dioxopiperidin-3-yl)-1-oxoisoindolin-4-yl)thio)ethoxy)ethoxy)acetamide |
| SIAIS219141 | N-(1-(4-((5-chloro-4-((2-(dimethylphosphoryl)phenyl)amino)pyrimidin-2-yl)amino)-3-methoxyphenyl)piperidin-4-yl)-2-(2-(2-(2-((2-(2,6-dioxopiperidin-3-yl)-1-oxoisoindolin-4-yl)thio)ethoxy)ethoxy)ethoxy)acetamide |
| SIAIS219142 | N-(1-(4-((5-chloro-4-((2-(dimethylphosphoryl)phenyl)amino)pyrimidin-2-yl)amino)-3-methoxyphenyl)piperidin-4-yl)-14-((2-(2,6-dioxopiperidin-3-yl)-1-oxoisoindolin-4-yl)thio)-3,6,9,12-tetraoxatetradecan-1-amide |
| SIAIS219143 | N-(1-(4-((5-chloro-4-((2-(dimethylphosphoryl)phenyl)amino)pyrimidin-2-yl)amino)-3-methoxyphenyl)piperidin-4-yl)-17-((2-(2,6-dioxopiperidin-3-yl)-1-oxoisoindolin-4-yl)thio)-3,6,9,12,15-pentaoxaheptadecan-1-amide |
| | 4-((3-(3-((1-(4-((5-chloro-4-((2-(dimethylphosphoryl)phenyl)amino)pyrimidin-2-yl)amino)-3-methoxyphenyl)piperidin-4-yl)(methyl)amino)propoxy)propyl)thio)-2-(2,6-dioxopiperidin-3-yl)isoindoline-1,3-dione |
| SIAIS164062 | 4-((2-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-2-oxoethyl)thio)-2-(2,6-dioxopiperidin-3-yl)isoindoline-1,3-dione |
| SIAIS164063 | 4-((3-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-3-oxopropyl)thio)-2-(2,6-dioxopiperidin-3-yl)isoindoline-1,3-dione |
| | 4-((3-(4-(1-(4-((5-chloro-4-((2-(dimethylphosphoryl)phenyl)amino)pyrimidin-2-yl)amino)-3-methoxyphenyl)piperidin-4-yl)piperazin-1-yl)propyl)thio)-2-(2,6-dioxopiperidin-3-yl)isoindoline-1,3-dione |
| SIAIS164064 | 4-((4-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-4-oxobutyl)thio)-2-(2,6-dioxopiperidin-3-yl)isoindoline-1,3-dione |
| | 3-(4-((4-(4-(1-(4-((5-chloro-4-((2-(dimethylphosphoryl)phenyl)amino)pyrimidin-2-yl)amino)-3-methoxyphenyl)piperidin-4-yl)piperazin-1-yl)butyl)thio)-1-oxoisoindolin-2-yl)piperidine-2,6-dione |
| SIAIS164066 | 4-((5-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-5-oxopentyl)thio)-2-(2,6-dioxopiperidin-3-yl)isoindoline-1,3-dione |
| | 4-((5-(4-(1-(4-((5-chloro-4-((2-(dimethylphosphoryl)phenyl)amino)pyrimidin-2-yl)amino)-3-methoxyphenyl)piperidin-4-yl)piperazin-1-yl)pentyl)thio)-2-(2,6-dioxopiperidin-3-yl)isoindoline-1,3-dione |
| SIAIS164065 | 4-((6-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-6-oxohexyl)thio)-2-(2,6-dioxopiperidin-3-yl)isoindoline-1,3-dione |
| SIAIS164067 | 4-((7-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-7-oxoheptyl)thio)-2-(2,6-dioxopiperidin-3-yl)isoindoline-1,3-dione |
| SIAIS219067 | 3-(4-((2-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-2-oxoethyl)thio)-1-oxoisoindolin-2-yl)piperidine-2,6-dione |
| SIAIS219068 | 3-(4-((3-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-3-oxopropyl)thio)-1-oxoisoindolin-2-yl)piperidine-2,6-dione |
| SIAIS219069 | 3-(4-((4-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-4-oxobutyl)thio)-1-oxoisoindolin-2-yl)piperidine-2,6-dione |
| SIAIS219070 | 3-(4-((5-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-5-oxopentyl)thio)-1-oxoisoindolin-2-yl)piperidine-2,6-dione |
| SIAIS219071 | 3-(4-((6-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-6-oxohexyl)thio)-1-oxoisoindolin-2-yl)piperidine-2,6-dione |
| SIAIS219098 | 3-(4-((6-(4-(1-(4-((5-chloro-4-((2-(dimethylphosphoryl)phenyl)amino)pyrimidin-2-yl)amino)-3-methoxyphenyl)piperidin-4-yl)piperazin-1-yl)hexyl)thio)-1-oxoisoindolin-2-yl)piperidine-2,6-dione |

TABLE 1-continued

The compounds of formula (I) of the present disclosure

| Compound ID | Name of the compound |
|---|---|
| SIAIS219072 | 3-(4-((7-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-7-oxoheptyl)thio)-1-oxoisoindolin-2-yl)piperidine-2,6-dione |
| | 4-((7-(4-(1-(4-((5-chloro-4-((2-(dimethylphosphoryl)phenyl)amino)pyrimidin-2-yl)amino)-3-methoxyphenyl)piperidin-4-yl)piperazin-1-yl)heptyl)thio)-2-(2,6-dioxopiperidin-3-yl)isoindoline-1,3-dione |
| | 4-((3-(3-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-3-oxopropoxy)propyl)thio)-2-(2,6-dioxopiperidin-3-yl)isoindoline-1,3-dione |
| | 4-((3-(3-(4-(1-(4-((5-chloro-4-((2-(dimethylphosphoryl)phenyl)amino)pyrimidin-2-yl)amino)-3-methoxyphenyl)piperidin-4-yl)piperazin-1-yl)propoxy)propyl)thio)-2-(2,6-dioxopiperidin-3-yl)isoindoline-1,3-dione |
| SIAIS219092 | 3-(4-((2-(2-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-2-oxoethoxy)ethyl)thio)-1-oxoisoindolin-2-yl)piperidine-2,6-dione |
| | 3-(4-((3-(3-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-3-oxopropoxy)propyl)thio)-1-oxoisoindolin-2-yl)piperidine-2,6-dione |
| SIAIS164068 | 8-(4-(2-((2-(2,6-dioxopiperidin-3-yl)-1,3-dioxoisoindolin-4-yl)thio)acetyl)piperazin-1-yl)-9-ethyl-6,6-dimethyl-11-oxo-6,11-dihydro-5H-benzo[b]carbazole-3-carbonitrile |
| SIAIS164069 | 8-(4-(3-((2-(2,6-dioxopiperidin-3-yl)-1,3-dioxoisoindolin-4-yl)thio)propanoyl)piperazin-1-yl)-9-ethyl-6,6-dimethyl-11-oxo-6,11-dihydro-5H-benzo[b]carbazole-3-carbonitrile |
| SIAIS164070 | 8-(4-(4-((2-(2,6-dioxopiperidin-3-yl)-1,3-dioxoisoindolin-4-yl)thio)butanoyl)piperazin-1-yl)-9-ethyl-6,6-dimethyl-11-oxo-6,11-dihydro-5H-benzo[b]carbazole-3-carbonitrile |
| SIAIS164072 | 8-(4-(5-((2-(2,6-dioxopiperidin-3-yl)-1,3-dioxoisoindolin-4-yl)thio)pentanoyl)piperazin-1-yl)-9-ethyl-6,6-dimethyl-11-oxo-6,11-dihydro-5H-benzo[b]carbazole-3-carbonitrile |
| SIAIS164071 | 8-(4-(6-((2-(2,6-dioxopiperidin-3-yl)-1,3-dioxoisoindolin-4-yl)thio)hexanoyl)piperazin-1-yl)-9-ethyl-6,6-dimethyl-11-oxo-6,11-dihydro-5H-benzo[b]carbazole-3-carbonitrile |
| SIAIS164073 | 8-(4-(7-((2-(2,6-dioxopiperidin-3-yl)-1,3-dioxoisoindolin-4-yl)thio)heptanoyl)piperazin-1-yl)-9-ethyl-6,6-dimethyl-11-oxo-6,11-dihydro-5H-benzo[b]carbazole-3-carbonitrile |
| | 8-(4-(6-((2-(2,6-dioxopiperidin-3-yl)-1-oxoisoindolin-4-yl)thio)hexanoyl)piperazin-1-yl)-9-ethyl-6,6-dimethyl-11-oxo-6,11-dihydro-5H-benzo[b]carbazole-3-carbonitrile |
| | 8-(4-(6-((2-(2,6-dioxopiperidin-3-yl)-1-oxoisoindolin-4-yl)thio)hexyl)piperazin-1-yl)-9-ethyl-6,6-dimethyl-11-oxo-6,11-dihydro-5H-benzo[b]carbazole-3-carbonitrile |
| | 8-(4-(3-(3-((2-(2,6-dioxopiperidin-3-yl)-1,3-dioxoisoindolin-4-yl)thio)propoxy)propanoyl)piperazin-1-yl)-9-ethyl-6,6-dimethyl-11-oxo-6,11-dihydro-5H-benzo[b]carbazole-3-carbonitrile |
| | 8-(4-(3-(3-((2-(2,6-dioxopiperidin-3-yl)-1,3-dioxoisoindolin-4-yl)thio)propoxy)propyl)piperazin-1-yl)-9-ethyl-6,6-dimethyl-11-oxo-6,11-dihydro-5H-benzo[b]carbazole-3-carbonitrile |
| SIAIS219012 | N-(1-(3-cyano-9-ethyl-6,6-dimethyl-11-oxo-6,11-dihydro-5H-benzo[b]carbazol-8-yl)piperidin-4-yl)-2-((2-(2,6-dioxopiperidin-3-yl)-1,3-dioxoisoindolin-4-yl)thio)acetamide |
| | 8-(4-((2-((2-(2,6-dioxopiperidin-3-yl)-1,3-dioxoisoindolin-4-yl)thio)ethyl)amino)piperidin-1-yl)-9-ethyl-6,6-dimethyl-11-oxo-6,11-dihydro-5H-benzo[b]carbazole-3-carbonitrile |
| | N-(1-(3-cyano-9-ethyl-6,6-dimethyl-11-oxo-6,11-dihydro-5H-benzo[b]carbazol-8-yl)piperidin-4-yl)-3-((2-(2,6-dioxopiperidin-3-yl)-1,3-dioxoisoindolin-4-yl)thio)propanamide |
| SIAIS219013 | N-(1-(3-cyano-9-ethyl-6,6-dimethyl-11-oxo-6,11-dihydro-5H-benzo[b]carbazol-8-yl)piperidin-4-yl)-4-((2-(2,6-dioxopiperidin-3-yl)-1,3-dioxoisoindolin-4-yl)thio)butanamid |
| | N-(1-(3-cyano-9-ethyl-6,6-dimethyl-11-oxo-6,11-dihydro-5H-benzo[b]carbazol-8-yl)piperidin-4-yl)-5-((2-(2,6-dioxopiperidin-3-yl)-1,3-dioxoisoindolin-4-yl)thio)pentanamide |
| SIAIS219014 | N-(1-(3-cyano-9-ethyl-6,6-dimethyl-11-oxo-6,11-dihydro-5H-benzo[b]carbazol-8-yl)piperidin-4-yl)-6-((2-(2,6-dioxopiperidin-3-yl)-1,3-dioxoisoindolin-4-yl)thio)hexanamide |
| | 8-(4-((6-((2-(2,6-dioxopiperidin-3-yl)-1,3-dioxoisoindolin-4-yl)thio)hexyl)amino)piperidin-1-yl)-9-ethyl-6,6-dimethyl-11-oxo-6,11-dihydro-5H-benzo[b]carbazole-3-carbonitrile |
| | N-(1-(3-cyano-9-ethyl-6,6-dimethyl-11-oxo-6,11-dihydro-5H-benzo[b]carbazol-8-yl)piperidin-4-yl)-7-((2-(2,6-dioxopiperidin-3-yl)-1,3-dioxoisoindolin-4-yl)thio)heptanamide |
| | N-(1-(3-cyano-9-ethyl-6,6-dimethyl-11-oxo-6,11-dihydro-5H-benzo[b]carbazol-8-yl)piperidin-4-yl)-10-((2-(2,6-dioxopiperidin-3-yl)-1,3-dioxoisoindolin-4-yl)thio)decanamide |
| SIAIS262161 | N-(1-(3-cyano-9-ethyl-6,6-dimethyl-11-oxo-6,11-dihydro-5H-benzo[b]carbazol-8-yl)piperidin-4-yl)-2-((2-(2,6-dioxopiperidin-3-yl)-1-oxoisoindolin-4-yl)thio)acetamide |
| | 8-(4-((2-((2-(2,6-dioxopiperidin-3-yl)-1-oxoisoindolin-4-yl)thio)ethyl)amino)piperidin-1-yl)-9-ethyl-6,6-dimethyl-11-oxo-6,11-dihydro-5H-benzo[b]carbazole-3-carbonitrile |

TABLE 1-continued

The compounds of formula (I) of the present disclosure

| Compound ID | Name of the compound |
|---|---|
| | N-(1-(3-cyano-9-ethyl-6,6-dimethyl-11-oxo-6,11-dihydro-5H-benzo[b]carbazol-8-yl)piperidin-4-yl)-3-((2-(2,6-dioxopiperidin-3-yl)-1-oxoisoindolin-4-yl)thio)propanamide |
| | N-(1-(3-cyano-9-ethyl-6,6-dimethyl-11-oxo-6,11-dihydro-5H-benzo[b]carbazol-8-yl)piperidin-4-yl)-4-((2-(2,6-dioxopiperidin-3-yl)-1-oxoisoindolin-4-yl)thio)butanamide |
| | N-(1-(3-cyano-9-ethyl-6,6-dimethyl-11-oxo-6,11-dihydro-5H-benzo[b]carbazol-8-yl)piperidin-4-yl)-5-((2-(2,6-dioxopiperidin-3-yl)-1-oxoisoindolin-4-yl)thio)pentanamide |
| SIAIS262162 | N-(1-(3-cyano-9-ethyl-6,6-dimethyl-11-oxo-6,11-dihydro-5H-benzo[b]carbazol-8-yl)piperidin-4-yl)-6-((2-(2,6-dioxopiperidin-3-yl)-1-oxoisoindolin-4-yl)thio)hexanamide |
| | 8-(4-((6-((2-(2,6-dioxopiperidin-3-yl)-1-oxoisoindolin-4-yl)thio)hexyl)amino)piperidin-1-yl)-9-ethyl-6,6-dimethyl-11-oxo-6,11-dihydro-5H-benzo[b]carbazole-3-carbonitrile |
| | N-(1-(3-cyano-9-ethyl-6,6-dimethyl-11-oxo-6,11-dihydro-5H-benzo[b]carbazol-8-yl)piperidin-4-yl)-7-((2-(2,6-dioxopiperidin-3-yl)-1-oxoisoindolin-4-yl)thio)heptanamide |
| | N-(1-(3-cyano-9-ethyl-6,6-dimethyl-11-oxo-6,11-dihydro-5H-benzo[b]carbazol-8-yl)piperidin-4-yl)-10-((2-(2,6-dioxopiperidin-3-yl)-1-oxoisoindolin-4-yl)thio)decanamide |
| | N-(1-(3-cyano-9-ethyl-6,6-dimethyl-11-oxo-6,11-dihydro-5H-benzo[b]carbazol-8-yl)piperidin-4-yl)-10-((2-(2,6-dioxopiperidin-3-yl)-1,3-dioxoisoindolin-4-yl)thio)-N-methyldecanamide |
| | N-(1-(3-cyano-9-ethyl-6,6-dimethyl-11-oxo-6,11-dihydro-5H-benzo[b]carbazol-8-yl)piperidin-4-yl)-2-(2-((2-(2,6-dioxopiperidin-3-yl)-1,3-dioxoisoindolin-4-yl)thio)ethoxy)acetamide |
| | 8-(4-((2-(2-((2-(2,6-dioxopiperidin-3-yl)-1,3-dioxoisoindolin-4-yl)thio)ethoxy)ethyl)amino)piperidin-1-yl)-9-ethyl-6,6-dimethyl-11-oxo-6,11-dihydro-5H-benzo[b]carbazole-3-carbonitrile |
| SIAIS219022 | N-(1-(3-cyano-9-ethyl-6,6-dimethyl-11-oxo-6,11-dihydro-5H-benzo[b]carbazol-8-yl)piperidin-4-yl)-2-(2-(2-((2-(2,6-dioxopiperidin-3-yl)-1,3-dioxoisoindolin-4-yl)thio)ethoxy)ethoxy)acetamide |
| | N-(1-(3-cyano-9-ethyl-6,6-dimethyl-11-oxo-6,11-dihydro-5H-benzo[b]carbazol-8-yl)piperidin-4-yl)-3-(2-(3-((2-(2,6-dioxopiperidin-3-yl)-1,3-dioxoisoindolin-4-yl)thio)propoxy)ethoxy)propanamide |
| | N-(1-(3-cyano-9-ethyl-6,6-dimethyl-11-oxo-6,11-dihydro-5H-benzo[b]carbazol-8-yl)piperidin-4-yl)-2-(2-(2-(2-((2-(2,6-dioxopiperidin-3-yl)-1,3-dioxoisoindolin-4-yl)thio)ethoxy)ethoxy)ethoxy)acetamide |
| | N-(1-(3-cyano-9-ethyl-6,6-dimethyl-11-oxo-6,11-dihydro-5H-benzo[b]carbazol-8-yl)piperidin-4-yl)-14-((2-(2,6-dioxopiperidin-3-yl)-1,3-dioxoisoindolin-4-yl)thio)-3,6,9,12-tetraoxatetradecanamide |
| | N-(1-(3-cyano-9-ethyl-6,6-dimethyl-11-oxo-6,11-dihydro-5H-benzo[b]carbazol-8-yl)piperidin-4-yl)-17-((2-(2,6-dioxopiperidin-3-yl)-1,3-dioxoisoindolin-4-yl)thio)-3,6,9,12,15-pentaoxaheptadecanamide |
| SIAIS262163 | N-(1-(3-cyano-9-ethyl-6,6-dimethyl-11-oxo-6,11-dihydro-5H-benzo[b]carbazol-8-yl)piperidin-4-yl)-2-(2-((2-(2,6-dioxopiperidin-3-yl)-1-oxoisoindolin-4-yl)thio)ethoxy)acetamide |
| | 8-(4-((2-(2-((2-(2,6-dioxopiperidin-3-yl)-1-oxoisoindolin-4-yl)thio)ethoxy)ethyl)amino)piperidin-1-yl)-9-ethyl-6,6-dimethyl-11-oxo-6,11-dihydro-5H-benzo[b]carbazole-3-carbonitrile |
| | N-(1-(3-cyano-9-ethyl-6,6-dimethyl-11-oxo-6,11-dihydro-5H-benzo[b]carbazol-8-yl)piperidin-4-yl)-2-(2-(2-((2-(2,6-dioxopiperidin-3-yl)-1-oxoisoindolin-4-yl)thio)ethoxy)ethoxy)acetamide |
| | N-(1-(3-cyano-9-ethyl-6,6-dimethyl-11-oxo-6,11-dihydro-5H-benzo[b]carbazol-8-yl)piperidin-4-yl)-3-(2-(3-((2-(2,6-dioxopiperidin-3-yl)-1-oxoisoindolin-4-yl)thio)propoxy)ethoxy)propanamide |
| | N-(1-(3-cyano-9-ethyl-6,6-dimethyl-11-oxo-6,11-dihydro-5H-benzo[b]carbazol-8-yl)piperidin-4-yl)-2-(2-(2-(2-((2-(2,6-dioxopiperidin-3-yl)-1-oxoisoindolin-4-yl)thio)ethoxy)ethoxy)ethoxy)acetamide |
| | N-(1-(3-cyano-9-ethyl-6,6-dimethyl-11-oxo-6,11-dihydro-5H-benzo[b]carbazol-8-yl)piperidin-4-yl)-14-((2-(2,6-dioxopiperidin-3-yl)-1-oxoisoindolin-4-yl)thio)-3,6,9,12-tetraoxatetradecanamide |
| | N-(1-(3-cyano-9-ethyl-6,6-dimethyl-11-oxo-6,11-dihydro-5H-benzo[b]carbazol-8-yl)piperidin-4-yl)-17-((2-(2,6-dioxopiperidin-3-yl)-1-oxoisoindolin-4-yl)thio)-3,6,9,12,15-pentaoxaheptadecanamide |
| | N-(1-(3-cyano-9-ethyl-6,6-dimethyl-11-oxo-6,11-dihydro-5H-benzo[b]carbazol-8-yl)piperidin-4-yl)-3-(2-(3-((2-(2,6-dioxopiperidin-3-yl)-1,3-dioxoisoindolin-4-yl)thio)propoxy)ethoxy)-N-methylpropanamide |
| SIAIS219005 | 8-(4-(1-(2-((2-(2,6-dioxopiperidin-3-yl)-1,3-dioxoisoindolin-4-yl)thio)acetyl)piperidin-4-yl)piperazin-1-yl)-9-ethyl-6,6-dimethyl-11-oxo-6,11-dihydro-5H-benzo[b]carbazole-3-carbonitrile |
| SIAIS219006 | 8-(4-(4-(4-((2-(2,6-dioxopiperidin-3-yl)-1,3-dioxoisoindolin-4-yl)thio)butanoyl)piperazin-1-yl)piperidin-1-yl)-9-ethyl-6,6-dimethyl-11-oxo-6,11-dihydro-5H-benzo[b]carbazole-3-carbonitrile |

TABLE 1-continued

The compounds of formula (I) of the present disclosure

| Compound ID | Name of the compound |
|---|---|
| SIAIS219007 | 8-(4-(4-(6-((2-(2,6-dioxopiperidin-3-yl)-1,3-dioxoisoindolin-4-yl)thio)hexanoyl)piperazin-1-yl)piperidin-1-yl)-9-ethyl-6,6-dimethyl-11-oxo-6,11-dihydro-5H-benzo[b]carbazole-3-carbonitrile |
| | 8-(4-(4-(9-((2-(2,6-dioxopiperidin-3-yl)-1,3-dioxoisoindolin-4-yl)thio)nonanoyl)piperazin-1-yl)piperidin-1-yl)-9-ethyl-6,6-dimethyl-11-oxo-6,11-dihydro-5H-benzo[b]carbazole-3-carbonitrile |
| | 8-(4-(4-(9-((2-(2,6-dioxopiperidin-3-yl)-1,3-dioxoisoindolin-4-yl)thio)nonyl)piperazin-1-yl)piperidin-1-yl)-9-ethyl-6,6-dimethyl-11-oxo-6,11-dihydro-5H-benzo[b]carbazole-3-carbonitrile |
| SIAIS262096 | 8-(4-(4-(2-((2-(2,6-dioxopiperidin-3-yl)-1-oxoisoindolin-4-yl)thio)acetyl)piperazin-1-yl)piperidin-1-yl)-9-ethyl-6,6-dimethyl-11-oxo-6,11-dihydro-5H-benzo[b]carbazole-3-carbonitrile |
| SIAIS262158 | 8-(4-(4-(2-((2-(2,6-dioxopiperidin-3-yl)-1,3-dioxoisoindolin-4-yl)thio)ethyl)piperazin-1-yl)piperidin-1-yl)-9-ethyl-6,6-dimethyl-11-oxo-6,11-dihydro-5H-benzo[b]carbazole-3-carbonitrile |
| SIAIS262097 | 8-(4-(4-(3-((2-(2,6-dioxopiperidin-3-yl)-1-oxoisoindolin-4-yl)thio)propanoyl)piperazin-1-yl)piperidin-1-yl)-9-ethyl-6,6-dimethyl-11-oxo-6,11-dihydro-5H-benzo[b]carbazole-3-carbonitrile |
| SIAIS262098 | 8-(4-(4-(4-((2-(2,6-dioxopiperidin-3-yl)-1-oxoisoindolin-4-yl)thio)butanoyl)piperazin-1-yl)piperidin-1-yl)-9-ethyl-6,6-dimethyl-11-oxo-6,11-dihydro-5H-benzo[b]carbazole-3-carbonitrile |
| SIAIS262099 | 8-(4-(4-(5-((2-(2,6-dioxopiperidin-3-yl)-1-oxoisoindolin-4-yl)thio)pentanoyl)piperazin-1-yl)piperidin-1-yl)-9-ethyl-6,6-dimethyl-11-oxo-6,11-dihydro-5H-benzo[b]carbazole-3-carbonitrile |
| SIAIS262100 | 8-(4-(4-(6-((2-(2,6-dioxopiperidin-3-yl)-1-oxoisoindolin-4-yl)thio)hexanoyl)piperazin-1-yl)piperidin-1-yl)-9-ethyl-6,6-dimethyl-11-oxo-6,11-dihydro-5H-benzo[b]carbazole-3-carbonitrile |
| SIAIS262159 | 8-(4-(4-(6-((2-(2,6-dioxopiperidin-3-yl)-1-oxoisoindolin-4-yl)thio)hexyl)piperazin-1-yl)piperidin-1-yl)-9-ethyl-6,6-dimethyl-11-oxo-6,11-dihydro-5H-benzo[b]carbazole-3-carbonitrile |
| SIAIS262101 | 8-(4-(4-(7-((2-(2,6-dioxopiperidin-3-yl)-1-oxoisoindolin-4-yl)thio)heptanoyl)piperazin-1-yl)piperidin-1-yl)-9-ethyl-6,6-dimethyl-11-oxo-6,11-dihydro-5H-benzo[b]carbazole-3-carbonitrile |
| | 8-(4-(4-(9-((2-(2,6-dioxopiperidin-3-yl)-1-oxoisoindolin-4-yl)thio)nonanoyl)piperazin-1-yl)piperidin-1-yl)-9-ethyl-6,6-dimethyl-11-oxo-6,11-dihydro-5H-benzo[b]carbazole-3-carbonitrile |
| | 8-(4-(4-(9-((2-(2,6-dioxopiperidin-3-yl)-1-oxoisoindolin-4-yl)thio)nonyl)piperazin-1-yl)piperidin-1-yl)-9-ethyl-6,6-dimethyl-11-oxo-6,11-dihydro-5H-benzo[b]carbazole-3-carbonitrile |
| | 8-(4-(4-(3-(2-(2-((2-(2,6-dioxopiperidin-3-yl)-1,3-dioxoisoindolin-4-yl)thio)ethoxy)ethoxy)propanoyl)piperazin-1-yl)piperidin-1-yl)-9-ethyl-6,6-dimethyl-11-oxo-6,11-dihydro-5H-benzo[b]carbazole-3-carbonitrile |
| | 8-(4-(4-(3-(2-(2-((2-(2,6-dioxopiperidin-3-yl)-1,3-dioxoisoindolin-4-yl)thio)ethoxy)ethoxy)propyl)piperazin-1-yl)piperidin-1-yl)-9-ethyl-6,6-dimethyl-11-oxo-6,11-dihydro-5H-benzo[b]carbazole-3-carbonitrile |
| SIAIS249066 | 8-(4-(4-(2-(2-((2-(2,6-dioxopiperidin-3-yl)-1-oxoisoindolin-4-yl)thio)ethoxy)acetyl)piperazin-1-yl)piperidin-1-yl)-9-ethyl-6,6-dimethyl-11-oxo-6,11-dihydro-5H-benzo[b]carbazole-3-carbonitrile |
| SIAIS249067 | 8-(4-(4-(2-(2-(2-((2-(2,6-dioxopiperidin-3-yl)-1-oxoisoindolin-4-yl)thio)ethoxy)ethoxy)acetyl)piperazin-1-yl)piperidin-1-yl)-9-ethyl-6,6-dimethyl-11-oxo-6,11-dihydro-5H-benzo[b]carbazole-3-carbonitrile |
| | 8-(4-(4-(3-(2-(2-((2-(2,6-dioxopiperidin-3-yl)-1-oxoisoindolin-4-yl)thio)ethoxy)ethoxy)propanoyl)piperazin-1-yl)piperidin-1-yl)-9-ethyl-6,6-dimethyl-11-oxo-6,11-dihydro-5H-benzo[b]carbazole-3-carbonitrile |
| | 8-(4-(4-(3-(2-(2-((2-(2,6-dioxopiperidin-3-yl)-1-oxoisoindolin-4-yl)thio)ethoxy)ethoxy)propyl)piperazin-1-yl)piperidin-1-yl)-9-ethyl-6,6-dimethyl-11-oxo-6,11-dihydro-5H-benzo[b]carbazole-3-carbonitrile |
| SIAIS249068 | 8-(4-(4-(2-(2-(2-(2-((2-(2,6-dioxopiperidin-3-yl)-1-oxoisoindolin-4-yl)thio)ethoxy)ethoxy)ethoxy)acetyl)piperazin-1-yl)piperidin-1-yl)-9-ethyl-6,6-dimethyl-11-oxo-6,11-dihydro-5H-benzo[b]carbazole-3-carbonitrile |
| SIAIS249069 | 8-(4-(4-(14-((2-(2,6-dioxopiperidin-3-yl)-1-oxoisoindolin-4-yl)thio)-3,6,9,12-tetraoxatetradecanoyl)piperazin-1-yl)piperidin-1-yl)-9-ethyl-6,6-dimethyl-11-oxo-6,11-dihydro-5H-benzo[b]carbazole-3-carbonitrile |
| SIAIS249070 | 8-(4-(4-(17-((2-(2,6-dioxopiperidin-3-yl)-1-oxoisoindolin-4-yl)thio)-3,6,9,12,15-pentaoxaheptadecanoyl)piperazin-1-yl)piperidin-1-yl)-9-ethyl-6,6-dimethyl-11-oxo-6,11-dihydro-5H-benzo[b]carbazole-3-carbonitrile |
| | 6-amino-5-((R)-1-(2,6-dichloro-3-fluorophenyl)ethoxy)-N-(4-((3R,5S)-4-(4-((2-(2,6-dioxopiperidin-3-yl)-1,3-dioxoisoindolin-4-yl)thio)butanoyl)-3,5-dimethylpiperazine-1-carbonyl)phenyl)pyridazine-3-carboxamide |
| | 6-amino-5-((R)-1-(2,6-dichloro-3-fluorophenyl)ethoxy)-N-(4-((3R,5S)-4-(6-((2-(2,6-dioxopiperidin-3-yl)-1,3-dioxoisoindolin-4-yl)thio)hexanoyl)-3,5-dimethylpiperazine-1-carbonyl)phenyl)pyridazine-3-carboxamide |
| | 6-amino-5-((R)-1-(2,6-dichloro-3-fluorophenyl)ethoxy)-N-(4-((3R,5S)-4-(6-((2-(2,6-dioxopiperidin-3-yl)-1,3-dioxoisoindolin-4-yl)thio)hexyl)-3,5-dimethylpiperazine-1-carbonyl)phenyl)pyridazine-3-carboxamide |

TABLE 1-continued

The compounds of formula (I) of the present disclosure

| Compound ID | Name of the compound |
|---|---|
| | 6-amino-5-((R)-1-(2,6-dichloro-3-fluorophenyl)ethoxy)-N-(4-((3R,5S)-4-(12-((2-(2,6-dioxopiperidin-3-yl)-1,3-dioxoisoindolin-4-yl)thio)dodecanoyl)-3,5-dimethylpiperazine-1-carbonyl)phenyl)pyridazine-3-carboxamide |
| | 6-amino-5-((R)-1-(2,6-dichloro-3-fluorophenyl)ethoxy)-N-(4-((3R,5S)-4-(6-((2-(2,6-dioxopiperidin-3-yl)-1-oxoisoindolin-4-yl)thio)hexanoyl)-3,5-dimethylpiperazine-1-carbonyl)phenyl)pyridazine-3-carboxamide |
| | 6-amino-5-((R)-1-(2,6-dichloro-3-fluorophenyl)ethoxy)-N-(4-((3R,5S)-4-(6-((2-(2,6-dioxopiperidin-3-yl)-1-oxoisoindolin-4-yl)thio)hexyl)-3,5-dimethylpiperazine-1-carbonyl)phenyl)pyridazine-3-carboxamide |
| | 6-amino-5-((R)-1-(2,6-dichloro-3-fluorophenyl)ethoxy)-N-(4-((3R,5S)-4-(3-(2-(2-(2-((2-(2,6-dioxopiperidin-3-yl)-1,3-dioxoisoindolin-4-yl)thio)ethoxy)ethoxy)ethoxy)propanoyl)-3,5-dimethylpiperazine-1-carbonyl)phenyl)pyridazine-3-carboxamide |
| | 6-amino-5-((R)-1-(2,6-dichloro-3-fluorophenyl)ethoxy)-N-(4-((3R,5S)-4-(3-(2-(2-(2-((2-(2,6-dioxopiperidin-3-yl)-1,3-dioxoisoindolin-4-yl)thio)ethoxy)ethoxy)ethoxy)propyl)-3,5-dimethylpiperazine-1-carbonyl)phenyl)pyridazine-3-carboxamide |
| | 6-amino-5-((R)-1-(2,6-dichloro-3-fluorophenyl)ethoxy)-N-(4-((3R,5S)-4-(3-(2-(2-(2-((2-(2,6-dioxopiperidin-3-yl)-1-oxoisoindolin-4-yl)thio)ethoxy)ethoxy)ethoxy)propanoyl)-3,5-dimethylpiperazine-1-carbonyl)phenyl)pyridazine-3-carboxamide |
| | 6-amino-5-((R)-1-(2,6-dichloro-3-fluorophenyl)ethoxy)-N-(4-((3R,5S)-4-(3-(2-(2-(2-((2-(2,6-dioxopiperidin-3-yl)-1-oxoisoindolin-4-yl)thio)ethoxy)ethoxy)ethoxy)propyl)-3,5-dimethylpiperazine-1-carbonyl)phenyl)pyridazine-3-carboxamide |
| SIAIS1197107 | 4-((4-(2-((2-(2,6-dioxopiperidin-3-yl)-1,3-dioxoisoindolin-4-yl)thio)acetyl)piperazin-1-yl)methyl)-N-(4-methyl-3-((4-(pyridin-3-yl)pyrimidin-2-yl)amino)phenyl)benzamide |
| SIAIS1197097 | 4-((4-(3-((2-(2,6-dioxopiperidin-3-yl)-1,3-dioxoisoindolin-4-yl)thio)propanoyl)piperazin-1-yl)methyl)-N-(4-methyl-3-((4-(pyridin-3-yl)pyrimidin-2-yl)amino)phenyl)benzamide |
| SIAIS1197099 | 4-((4-(4-((2-(2,6-dioxopiperidin-3-yl)-1,3-dioxoisoindolin-4-yl)thio)butanoyl)piperazin-1-yl)methyl)-N-(4-methyl-3-((4-(pyridin-3-yl)pyrimidin-2-yl)amino)phenyl)benzamide |
| SIAIS1197101 | 4-((4-(5-((2-(2,6-dioxopiperidin-3-yl)-1,3-dioxoisoindolin-4-yl)thio)pentanoyl)piperazin-1-yl)methyl)-N-(4-methyl-3-((4-(pyridin-3-yl)pyrimidin-2-yl)amino)phenyl)benzamide |
| SIAIS1197103 | 4-((4-(6-((2-(2,6-dioxopiperidin-3-yl)-1,3-dioxoisoindolin-4-yl)thio)hexanoyl)piperazin-1-yl)methyl)-N-(4-methyl-3-((4-(pyridin-3-yl)pyrimidin-2-yl)amino)phenyl)benzamide |
| SIAIS1197105 | 4-((4-(7-((2-(2,6-dioxopiperidin-3-yl)-1,3-dioxoisoindolin-4-yl)thio)heptanoyl)piperazin-1-yl)methyl)-N-(4-methyl-3-((4-(pyridin-3-yl)pyrimidin-2-yl)amino)phenyl)benzamide |
| SIAIS151110 | N-(2-chloro-6-methylphenyl)-2-((6-(4-(2-((2-(2,6-dioxopiperidin-3-yl)-1,3-dioxoisoindolin-4-yl)thio)acetyl)piperazin-1-yl)-2-methylpyrimidin-4-yl)amino)thiazole-5-carboxamide |
| SIAIS172056 | N-(2-chloro-6-methylphenyl)-2-((6-(4-(2-((2-(2,6-dioxopiperidin-3-yl)-1,3-dioxoisoindolin-4-yl)thio)ethyl)piperazin-1-yl)-2-methylpyrimidin-4-yl)amino)thiazole-5-carboxamide |
| SIAIS151109 | N-(2-chloro-6-methylphenyl)-2-((6-(4-(2-((2-(2,6-dioxopiperidin-3-yl)-1,3-dioxoisoindolin-4-yl)sulfinyl)acetyl)piperazin-1-yl)-2-methylpyrimidin-4-yl)amino)thiazole-5-carboxamide |
| SIAIS151108 | N-(2-chloro-6-methylphenyl)-2-((6-(4-(2-((2-(2,6-dioxopiperidin-3-yl)-1,3-dioxoisoindolin-4-yl)sulfonyl)acetyl)piperazin-1-yl)-2-methylpyrimidin-4-yl)amino)thiazole-5-carboxamide |
| SIAIS151152 | N-(2-chloro-6-methylphenyl)-2-((6-(4-(3-((2-(2,6-dioxopiperidin-3-yl)-1,3-dioxoisoindolin-4-yl)thio)propanoyl)piperazin-1-yl)-2-methylpyrimidin-4-yl)amino)thiazole-5-carboxamide |
| SIAIS172106 | N-(2-chloro-6-methylphenyl)-2-((6-(4-(3-((2-(2,6-dioxopiperidin-3-yl)-1,3-dioxoisoindolin-4-yl)thio)propyl)piperazin-1-yl)-2-methylpyrimidin-4-yl)amino)thiazole-5-carboxamide |
| SIAIS151153 | N-(2-chloro-6-methylphenyl)-2-((6-(4-(4-((2-(2,6-dioxopiperidin-3-yl)-1,3-dioxoisoindolin-4-yl)thio)butanoyl)piperazin-1-yl)-2-methylpyrimidin-4-yl)amino)thiazole-5-carboxamide |
| SIAIS151154 | N-(2-chloro-6-methylphenyl)-2-((6-(4-(5-((2-(2,6-dioxopiperidin-3-yl)-1,3-dioxoisoindolin-4-yl)thio)pentanoyl)piperazin-1-yl)-2-methylpyrimidin-4-yl)amino)thiazole-5-carboxamide |
| SIAIS151155 | N-(2-chloro-6-methylphenyl)-2-((6-(4-(6-((2-(2,6-dioxopiperidin-3-yl)-1,3-dioxoisoindolin-4-yl)thio)hexanoyl)piperazin-1-yl)-2-methylpyrimidin-4-yl)amino)thiazole-5-carboxamide |
| SIAIS151156 | N-(2-chloro-6-methylphenyl)-2-((6-(4-(7-((2-(2,6-dioxopiperidin-3-yl)-1,3-dioxoisoindolin-4-yl)thio)heptanoyl)piperazin-1-yl)-2-methylpyrimidin-4-yl)amino)thiazole-5-carboxamide |
| | N-(2-chloro-6-methylphenyl)-2-((6-(4-(7-((2-(2,6-dioxopiperidin-3-yl)-1,3-dioxoisoindolin-4-yl)thio)heptyl)piperazin-1-yl)-2-methylpyrimidin-4-yl)amino)thiazole-5-carboxamide |

TABLE 1-continued

The compounds of formula (I) of the present disclosure

| Compound ID | Name of the compound |
| --- | --- |
| SIAIS171105 | N-(2-chloro-6-methylphenyl)-2-((6-(4-(2-((2-(2,6-dioxopiperidin-3-yl)-1-oxoisoindolin-4-yl)thio)acetyl)piperazin-1-yl)-2-methylpyrimidin-4-yl)amino)thiazole-5-carboxamide |
| SIAIS171166 | N-(2-chloro-6-methylphenyl)-2-((6-(4-(2-((2-(2,6-dioxopiperidin-3-yl)-1-oxoisoindolin-4-yl)thio)ethyl)piperazin-1-yl)-2-methylpyrimidin-4-yl)amino)thiazole-5-carboxamide |
| SIAIS171106 | N-(2-chloro-6-methylphenyl)-2-((6-(4-(3-((2-(2,6-dioxopiperidin-3-yl)-1-oxoisoindolin-4-yl)thio)propanoyl)piperazin-1-yl)-2-methylpyrimidin-4-yl)amino)thiazole-5-carboxamide |
| SIAIS171181 | N-(2-chloro-6-methylphenyl)-2-((6-(4-(3-((2-(2,6-dioxopiperidin-3-yl)-1-oxoisoindolin-4-yl)thio)propyl)piperazin-1-yl)-2-methylpyrimidin-4-yl)amino)thiazole-5-carboxamide |
| SIAIS171107 | N-(2-chloro-6-methylphenyl)-2-((6-(4-(4-((2-(2,6-dioxopiperidin-3-yl)-1-oxoisoindolin-4-yl)thio)butanoyl)piperazin-1-yl)-2-methylpyrimidin-4-yl)amino)thiazole-5-carboxamide |
| SIAIS171108 | N-(2-chloro-6-methylphenyl)-2-((6-(4-(5-((2-(2,6-dioxopiperidin-3-yl)-1-oxoisoindolin-4-yl)thio)pentanoyl)piperazin-1-yl)-2-methylpyrimidin-4-yl)amino)thiazole-5-carboxamide |
| SIAIS171109 | N-(2-chloro-6-methylphenyl)-2-((6-(4-(6-((2-(2,6-dioxopiperidin-3-yl)-1-oxoisoindolin-4-yl)thio)hexanoyl)piperazin-1-yl)-2-methylpyrimidin-4-yl)amino)thiazole-5-carboxamide |
| | N-(2-chloro-6-methylphenyl)-2-((6-(4-(6-((2-(2,6-dioxopiperidin-3-yl)-1-oxoisoindolin-4-yl)thio)hexyl)piperazin-1-yl)-2-methylpyrimidin-4-yl)amino)thiazole-5-carboxamide |
| SIAIS171110 | N-(2-chloro-6-methylphenyl)-2-((6-(4-(7-((2-(2,6-dioxopiperidin-3-yl)-1-oxoisoindolin-4-yl)thio)heptanoyl)piperazin-1-yl)-2-methylpyrimidin-4-yl)amino)thiazole-5-carboxamide |
| | N-(2-chloro-6-methylphenyl)-2-((6-(4-(3-(2-((2-(2,6-dioxopiperidin-3-yl)-1-oxoisoindolin-4-yl)thio)ethoxy)propanoyl)piperazin-1-yl)-2-methylpyrimidin-4-yl)amino)thiazole-5-carboxamide |
| | N-(2-chloro-6-methylphenyl)-2-((6-(4-(3-(3-(2-((2-(2,6-dioxopiperidin-3-yl)-1-oxoisoindolin-4-yl)thio)ethoxy)propoxy)propanoyl)piperazin-1-yl)-2-methylpyrimidin-4-yl)amino)thiazole-5-carboxamide |
| SIAIS151168 | 4-((2,4-dichloro-5-methoxyphenyl)amino)-7-(3-(4-(2-((2-(2,6-dioxopiperidin-3-yl)-1,3-dioxoisoindolin-4-yl)thio)acetyl)piperazin-1-yl)propoxy)-6-methoxyquinoline-3-carbonitrile |
| SIAIS151169 | 4-((2,4-dichloro-5-methoxyphenyl)amino)-7-(3-(4-(3-((2-(2,6-dioxopiperidin-3-yl)-1,3-dioxoisoindolin-4-yl)thio)propanoyl)piperazin-1-yl)propoxy)-6-methoxyquinoline-3-carbonitrile |
| SIAIS151170 | 4-((2,4-dichloro-5-methoxyphenyl)amino)-7-(3-(4-(4-((2-(2,6-dioxopiperidin-3-yl)-1,3-dioxoisoindolin-4-yl)thio)butanoyl)piperazin-1-yl)propoxy)-6-methoxyquinoline-3-carbonitrile |
| SIAIS151171 | 4-((2,4-dichloro-5-methoxyphenyl)amino)-7-(3-(4-(5-((2-(2,6-dioxopiperidin-3-yl)-1,3-dioxoisoindolin-4-yl)thio)pentanoyl)piperazin-1-yl)propoxy)-6-methoxyquinoline-3-carbonitrile |
| SIAIS151172 | 4-((2,4-dichloro-5-methoxyphenyl)amino)-7-(3-(4-(6-((2-(2,6-dioxopiperidin-3-yl)-1,3-dioxoisoindolin-4-yl)thio)hexanoyl)piperazin-1-yl)propoxy)-6-methoxyquinoline-3-carbonitrile |
| SIAIS151173 | 4-((2,4-dichloro-5-methoxyphenyl)amino)-7-(3-(4-(7-((2-(2,6-dioxopiperidin-3-yl)-1,3-dioxoisoindolin-4-yl)thio)heptanoyl)piperazin-1-yl)propoxy)-6-methoxyquinoline-3-carbonitrile |
| | 4-((2,4-dichloro-5-methoxyphenyl)amino)-7-(3-(4-(2-((2-(2,6-dioxopiperidin-3-yl)-1-oxoisoindolin-4-yl)thio)acetyl)piperazin-1-yl)propoxy)-6-methoxyquinoline-3-carbonitrile |
| | 4-((2,4-dichloro-5-methoxyphenyl)amino)-7-(3-(4-(3-((2-(2,6-dioxopiperidin-3-yl)-1-oxoisoindolin-4-yl)thio)propanoyl)piperazin-1-yl)propoxy)-6-methoxyquinoline-3-carbonitrile |
| | 4-((2,4-dichloro-5-methoxyphenyl)amino)-7-(3-(4-(4-((2-(2,6-dioxopiperidin-3-yl)-1-oxoisoindolin-4-yl)thio)butanoyl)piperazin-1-yl)propoxy)-6-methoxyquinoline-3-carbonitrile |
| | 4-((2,4-dichloro-5-methoxyphenyl)amino)-7-(3-(4-(2-(2-((2-(2,6-dioxopiperidin-3-yl)-1,3-dioxoisoindolin-4-yl)thio)ethoxy)acetyl)piperazin-1-yl)propoxy)-6-methoxyquinoline-3-carbonitrile |
| | 4-((2,4-dichloro-5-methoxyphenyl)amino)-7-(3-(4-(3-(2-((2-(2,6-dioxopiperidin-3-yl)-1-oxoisoindolin-4-yl)thio)ethoxy)propanoyl)piperazin-1-yl)propoxy)-6-methoxyquinoline-3-carbonitrile |
| | 4-((2,4-dichloro-5-methoxyphenyl)amino)-7-(3-(4-(3-(3-((2-(2,6-dioxopiperidin-3-yl)-1,3-dioxoisoindolin-4-yl)thio)propoxy)propyl)piperazin-1-yl)propoxy)-6-methoxyquinoline-3-carbonitrile |
| | 4-((2,4-dichloro-5-methoxyphenyl)amino)-7-(3-(4-(3-(3-((2-(2,6-dioxopiperidin-3-yl)-1-oxoisoindolin-4-yl)thio)propoxy)propyl)piperazin-1-yl)propoxy)-6-methoxyquinoline-3-carbonitrile |
| SIAIS220046 | N-(4-((4-(3-((2-(2,6-dioxopiperidin-3-yl)-1,3-dioxoisoindolin-4-yl)thio)propanoyl)piperazin-1-yl)methyl)-3-(trifluoromethyl)phenyl)-3-(imidazo[1,2-b]pyridazin-3-ylethynyl)-4-methylbenzamide |

TABLE 1-continued

The compounds of formula (I) of the present disclosure

| Compound ID | Name of the compound |
|---|---|
| SIAIS220047 | N-(4-((4-(4-((2-(2,6-dioxopiperidin-3-yl)-1,3-dioxoisoindolin-4-yl)thio)butanoyl)piperazin-1-yl)methyl)-3-(trifluoromethyl)phenyl)-3-(imidazo[1,2-b]pyridazin-3-ylethynyl)-4-methylbenzamide |
| SIAIS220048 | N-(4-((4-(5-((2-(2,6-dioxopiperidin-3-yl)-1,3-dioxoisoindolin-4-yl)thio)pentanoyl)piperazin-1-yl)methyl)-3-(trifluoromethyl)phenyl)-3-(imidazo[1,2-b]pyridazin-3-ylethynyl)-4-methylbenzamide |
| | N-(4-((4-(5-((2-(2,6-dioxopiperidin-3-yl)-1,3-dioxoisoindolin-4-yl)thio)pentyl)piperazin-1-yl)methyl)-3-(trifluoromethyl)phenyl)-3-(imidazo[1,2-b]pyridazin-3-ylethynyl)-4-methylbenzamide |
| SIAIS220049 | N-(4-((4-(6-((2-(2,6-dioxopiperidin-3-yl)-1,3-dioxoisoindolin-4-yl)thio)hexanoyl)piperazin-1-yl)methyl)-3-(trifluoromethyl)phenyl)-3-(imidazo[1,2-b]pyridazin-3-ylethynyl)-4-methylbenzamide |
| SIAIS220050 | N-(4-((4-(7-((2-(2,6-dioxopiperidin-3-yl)-1,3-dioxoisoindolin-4-yl)thio)heptanoyl)piperazin-1-yl)methyl)-3-(trifluoromethyl)phenyl)-3-(imidazo[1,2-b]pyridazin-3-ylethynyl)-4-methylbenzamide |
| SIAIS220051 | N-(4-((4-(2-((2-(2,6-dioxopiperidin-3-yl)-1-oxoisoindolin-4-yl)thio)acetyl)piperazin-1-yl)methyl)-3-(trifluoromethyl)phenyl)-3-(imidazo[1,2-b]pyridazin-3-ylethynyl)-4-methylbenzamide |
| SIAIS220052 | N-(4-((4-(3-((2-(2,6-dioxopiperidin-3-yl)-1-oxoisoindolin-4-yl)thio)propanoyl)piperazin-1-yl)methyl)-3-(trifluoromethyl)phenyl)-3-(imidazo[1,2-b]pyridazin-3-ylethynyl)-4-methylbenzamide |
| SIAIS220053 | N-(4-((4-(4-((2-(2,6-dioxopiperidin-3-yl)-1-oxoisoindolin-4-yl)thio)butanoyl)piperazin-1-yl)methyl)-3-(trifluoromethyl)phenyl)-3-(imidazo[1,2-b]pyridazin-3-ylethynyl)-4-methylbenzamide |
| SIAIS220054 | N-(4-((4-(5-((2-(2,6-dioxopiperidin-3-yl)-1-oxoisoindolin-4-yl)thio)pentanoyl)piperazin-1-yl)methyl)-3-(trifluoromethyl)phenyl)-3-(imidazo[1,2-b]pyridazin-3-ylethynyl)-4-methylbenzamide |
| SIAIS220055 | N-(4-((4-(6-((2-(2,6-dioxopiperidin-3-yl)-1-oxoisoindolin-4-yl)thio)hexanoyl)piperazin-1-yl)methyl)-3-(trifluoromethyl)phenyl)-3-(imidazo[1,2-b]pyridazin-3-ylethynyl)-4-methylbenzamide |
| SIAIS220056 | N-(4-((4-(7-((2-(2,6-dioxopiperidin-3-yl)-1-oxoisoindolin-4-yl)thio)heptanoyl)piperazin-1-yl)methyl)-3-(trifluoromethyl)phenyl)-3-(imidazo[1,2-b]pyridazin-3-ylethynyl)-4-methylbenzamide |
| | N-(4-((4-(2-(2-((2-(2,6-dioxopiperidin-3-yl)-1,3-dioxoisoindolin-4-yl)thio)ethoxy)acetyl)piperazin-1-yl)methyl)-3-(trifluoromethyl)phenyl)-3-(imidazo[1,2-b]pyridazin-3-ylethynyl)-4-methylbenzamide |
| | N-(4-((4-(2-(2-(2-(2-((2-(2,6-dioxopiperidin-3-yl)-1,3-dioxoisoindolin-4-yl)thio)ethoxy)ethoxy)ethoxy)acetyl)piperazin-1-yl)methyl)-3-(trifluoromethyl)phenyl)-3-(imidazo[1,2-b]pyridazin-3-ylethynyl)-4-methylbenzamide |
| | N-(4-((4-(2-(2-(2-(2-((2-(2,6-dioxopiperidin-3-yl)-1,3-dioxoisoindolin-4-yl)thio)ethoxy)ethoxy)ethoxy)ethyl)piperazin-1-yl)methyl)-3-(trifluoromethyl)phenyl)-3-(imidazo[1,2-b]pyridazin-3-ylethynyl)-4-methylbenzamide |
| | N-(4-((4-(2-(2-(2-(2-((2-(2,6-dioxopiperidin-3-yl)-1-oxoisoindolin-4-yl)thio)ethoxy)ethoxy)ethoxy)acetyl)piperazin-1-yl)methyl)-3-(trifluoromethyl)phenyl)-3-(imidazo[1,2-b]pyridazin-3-ylethynyl)-4-methylbenzamide |
| | N-(4-((4-(2-(2-(2-(2-((2-(2,6-dioxopiperidin-3-yl)-1-oxoisoindolin-4-yl)thio)ethoxy)ethoxy)ethoxy)ethyl)piperazin-1-yl)methyl)-3-(trifluoromethyl)phenyl)-3-(imidazo[1,2-b]pyridazin-3-ylethynyl)-4-methylbenzamide |
| SIAIS180063 | 2-(2,6-dioxopiperidin-3-yl)-4-((2-(4-(2-fluoro-5-((4-oxo-3,4-dihydrophthalazin-1-yl)methyl)benzoyl)piperazin-1-yl)-2-oxoethyl)thio)isoindoline-1,3-dione |
| SIAIS180064 | 2-(2,6-dioxopiperidin-3-yl)-4-((3-(4-(2-fluoro-5-((4-oxo-3,4-dihydrophthalazin-1-yl)methyl)benzoyl)piperazin-1-yl)-3-oxopropyl)thio)isoindoline-1,3-dione |
| | 2-(2,6-dioxopiperidin-3-yl)-4-((3-(4-(2-fluoro-5-((4-oxo-3,4-dihydrophthalazin-1-yl)methyl)benzoyl)piperazin-1-yl)propyl)thio)isoindoline-1,3-dione |
| SIAIS180065 | 2-(2,6-dioxopiperidin-3-yl)-4-((4-(4-(2-fluoro-5-((4-oxo-3,4-dihydrophthalazin-1-yl)methyl)benzoyl)piperazin-1-yl)-4-oxobutyl)thio)isoindoline-1,3-dione |
| SIAIS180066 | 2-(2,6-dioxopiperidin-3-yl)-4-((5-(4-(2-fluoro-5-((4-oxo-3,4-dihydrophthalazin-1-yl)methyl)benzoyl)piperazin-1-yl)-5-oxopentyl)thio)isoindoline-1,3-dione |
| SIAIS180067 | 2-(2,6-dioxopiperidin-3-yl)-4-((6-(4-(2-fluoro-5-((4-oxo-3,4-dihydrophthalazin-1-yl)methyl)benzoyl)piperazin-1-yl)-6-oxohexyl)thio)isoindoline-1,3-dione |
| SIAIS180068 | 2-(2,6-dioxopiperidin-3-yl)-4-((7-(4-(2-fluoro-5-((4-oxo-3,4-dihydrophthalazin-1-yl)methyl)benzoyl)piperazin-1-yl)-7-oxoheptyl)thio)isoindoline-1,3-dione |
| | 3-(4-((4-(2-fluoro-5-((4-oxo-3,4-dihydrophthalazin-1-yl)methyl)benzoyl)piperazin-1-yl)-2-oxoethyl)thio)-1-oxoisoindolin-2-yl)piperidine-2,6-dione |
| | 3-(4-((4-(4-(2-fluoro-5-((4-oxo-3,4-dihydrophthalazin-1-yl)methyl)benzoyl)piperazin-1-yl)butyl)thio)-1-oxoisoindolin-2-yl)piperidine-2,6-dione |
| | 2-(2,6-dioxopiperidin-3-yl)-4-((2-(2-(4-(2-fluoro-5-((4-oxo-3,4-dihydrophthalazin-1-yl)methyl)benzoyl)piperazin-1-yl)-2-oxoethoxy)ethyl)thio)isoindoline-1,3-dione |
| | 2-(2,6-dioxopiperidin-3-yl)-4-((2-(2-(2-(4-(2-fluoro-5-((4-oxo-3,4-dihydrophthalazin-1-yl)methyl)benzoyl)piperazin-1-yl)-2-oxoethoxy)ethoxy)ethoxy)ethyl)thio)isoindoline-1,3-dione |
| | 3-(4-((2-(3-(4-(2-fluoro-5-((4-oxo-3,4-dihydrophthalazin-1-yl)methyl)benzoyl)piperazin-1-yl)-3-oxopropoxy)ethyl)thio)-1-oxoisoindolin-2-yl)piperidine-2,6-dione |

TABLE 1-continued

The compounds of formula (I) of the present disclosure

| Compound ID | Name of the compound |
| --- | --- |
| SIAIS164165 | 2-(4-((3S)-1-(2-((2-(2,6-dioxopiperidin-3-yl)-1,3-dioxoisoindolin-4-yl)thio)acetyl)piperidin-3-yl)phenyl)-2H-indazole-7-carboxamide |
| SIAIS164166 | 2-(4-((3S)-1-(3-((2-(2,6-dioxopiperidin-3-yl)-1,3-dioxoisoindolin-4-yl)thio)propanoyl)piperidin-3-yl)phenyl)-2H-indazole-7-carboxamide |
| | 2-(4-((3S)-1-(3-((2-(2,6-dioxopiperidin-3-yl)-1,3-dioxoisoindolin-4-yl)thio)propyl)piperidin-3-yl)phenyl)-2H-indazole-7-carboxamide |
| SIAIS164167 | 2-(4-((3S)-1-(4-((2-(2,6-dioxopiperidin-3-yl)-1,3-dioxoisoindolin-4-yl)thio)butanoyl)piperidin-3-yl)phenyl)-2H-indazole-7-carboxamide |
| SIAIS164168 | 2-(4-((3S)-1-(5-((2-(2,6-dioxopiperidin-3-yl)-1,3-dioxoisoindolin-4-yl)thio)pentanoyl)piperidin-3-yl)phenyl)-2H-indazole-7-carboxamide |
| SIAIS164169 | 2-(4-((3S)-1-(6-((2-(2,6-dioxopiperidin-3-yl)-1,3-dioxoisoindolin-4-yl)thio)hexanoyl)piperidin-3-yl)phenyl)-2H-indazole-7-carboxamide |
| SIAIS164170 | 2-(4-((3S)-1-(7-((2-(2,6-dioxopiperidin-3-yl)-1,3-dioxoisoindolin-4-yl)thio)heptanoyl)piperidin-3-yl)phenyl)-2H-indazole-7-carboxamide |
| | 2-(4-((3S)-1-(2-((2-(2,6-dioxopiperidin-3-yl)-1-oxoisoindolin-4-yl)thio)acetyl)piperidin-3-yl)phenyl)-2H-indazole-7-carboxamide |
| | 2-(4-((3S)-1-(4-((2-(2,6-dioxopiperidin-3-yl)-1-oxoisoindolin-4-yl)thio)butyl)piperidin-3-yl)phenyl)-2H-indazole-7-carboxamide |
| | 2-(4-((3S)-1-(2-(2-((2-(2,6-dioxopiperidin-3-yl)-1,3-dioxoisoindolin-4-yl)thio)ethoxy)acetyl)piperidin-3-yl)phenyl)-2H-indazole-7-carboxamide |
| | 2-(4-((3S)-1-(3-(2-((2-(2,6-dioxopiperidin-3-yl)-1,3-dioxoisoindolin-4-yl)thio)ethoxy)propyl)piperidin-3-yl)phenyl)-2H-indazole-7-carboxamide |
| | 2-(4-((3S)-1-(3-(3-((2-(2,6-dioxopiperidin-3-yl)-1,3-dioxoisoindolin-4-yl)thio)propoxy)propanoyl)piperidin-3-yl)phenyl)-2H-indazole-7-carboxamide |
| | 2-(4-((3S)-1-(3-(2-((2-(2,6-dioxopiperidin-3-yl)-1-oxoisoindolin-4-yl)thio)ethoxy)propyl)piperidin-3-yl)phenyl)-2H-indazole-7-carboxamide |
| SIAIS180043 | 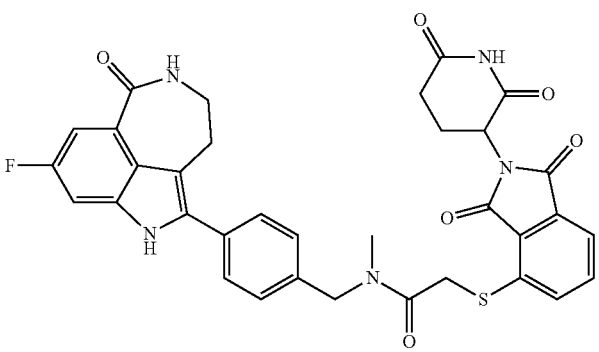 [SMILES: CN(Cc1ccc(-c2[nH]c3cc(F)cc4c3c2CCNC4=O)cc1)C(=O)CSc1cccc2c1C(=O)N(C1CCC(=O)NC1=O)C2=O] 2-((2-(2,6-dioxopiperidin-3-yl)-1,3-dioxoisoindolin-4-yl)thio)-N-(4-(8-fluoro-1-oxo-2,3,4,6-tetrahydro-1H-azepino[5,4,3-cd]indol-5-yl)benzyl)-N-methylacetamide |
| SIAIS180044 | 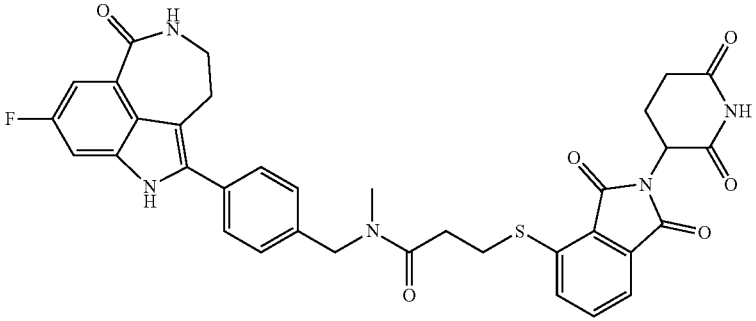 [SMILES: CN(Cc1ccc(-c2[nH]c3cc(F)cc4c3c2CCNC4=O)cc1)C(=O)CCSc1cccc2c1C(=O)N(C1CCC(=O)NC1=O)C2=O] 3-((2-(2,6-dioxopiperidin-3-yl)-1,3-dioxoisoindolin-4-yl)thio)-N-(4-(8-fluoro-1-oxo-2,3,4,6-tetrahydro-1H-azepino[5,4,3-cd]indol-5-yl)benzyl)-N-methylpropanamide |

TABLE 1-continued

The compounds of formula (I) of the present disclosure

| Compound ID | Name of the compound |
|---|---|
| SIAIS180045 | 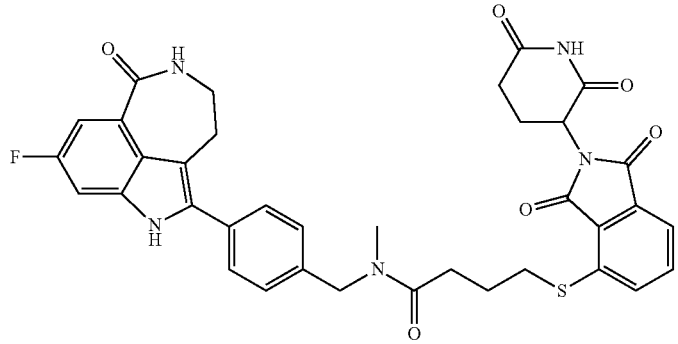 [SMILES: CN(Cc1ccc(-c2[nH]c3cc(F)cc4c3c2CCNC4=O)cc1)C(=O)CCCSc1cccc2c1C(=O)N(C1CCC(=O)NC1=O)C2=O] 4-((2-(2,6-dioxopiperidin-3-yl)-1,3-dioxoisoindolin-4-yl)thio)-N-(4-(8-fluoro-1-oxo-2,3,4,6-tetrahydro-1H-azepino[5,4,3-cd]indol-5-yl)benzyl)-N-methylbutanamide |
| SIAIS180046 | 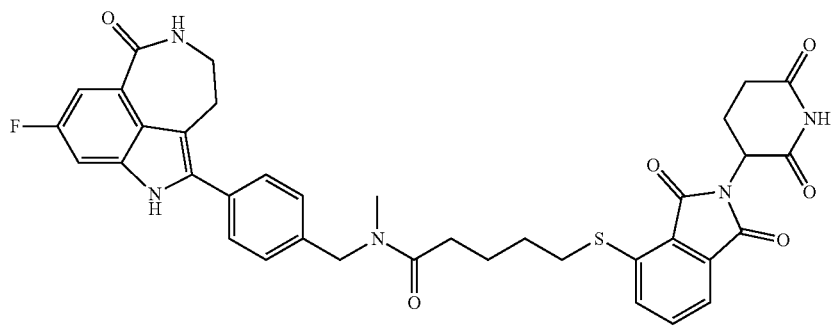 [SMILES: CN(Cc1ccc(-c2[nH]c3cc(F)cc4c3c2CCNC4=O)cc1)C(=O)CCCCSc1cccc2c1C(=O)N(C1CCC(=O)NC1=O)C2=O] 5-((2-(2,6-dioxopiperidin-3-yl)-1,3-dioxoisoindolin-4-yl)thio)-N-(4-(8-fluoro-1-oxo-2,3,4,6-tetrahydro-1H-azepino[5,4,3-cd]indol-5-yl)benzyl)-N-methylpentanamide |
| SIAIS180047 | 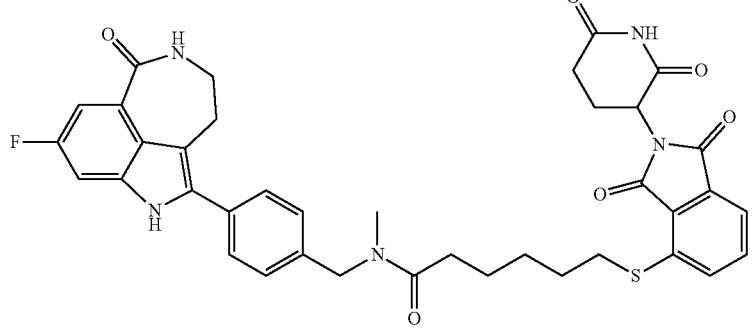 6-((2-(2,6-dioxopiperidin-3-yl)-1,3-dioxoisoindolin-4-yl)thio)-N-(4-(8-fluoro-1-oxo-2,3,4,6-tetrahydro-1H-azepino[5,4,3-cd]indol-5-yl)benzyl)-N-methylhexanamide |
| SIAIS180048 | 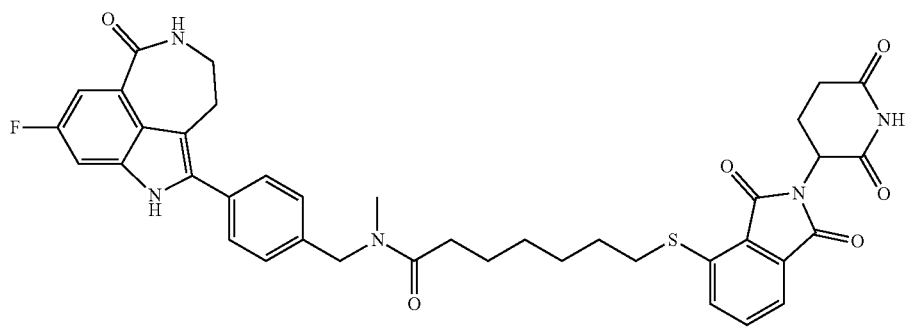 [SMILES: CN(Cc1ccc(-c2[nH]c3cc(F)cc4c3c2CCNC4=O)cc1)C(=O)CCCCCCSc1cccc2c1C(=O)N(C1CCC(=O)NC1=O)C2=O] |

TABLE 1-continued

The compounds of formula (I) of the present disclosure

| Compound ID | Name of the compound |
|---|---|

7-((2-(2,6-dioxopiperidin-3-yl)-1,3-dioxoisoindolin-4-yl)thio)-N-(4-(8-fluoro-1-oxo-2,3,4,6-tetrahydro-1H-azepino[5,4,3-cd]indol-5-yl)benzyl)-N-methylheptanamide

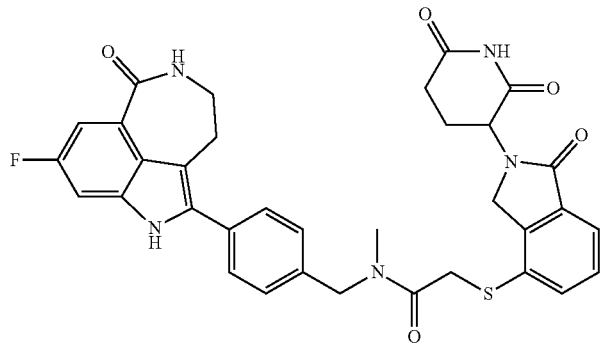 [SMILES: CN(Cc1ccc(-c2[nH]c3cc(F)cc4c3c2CCNC4=O)cc1)C(=O)CSc1cccc2c1CN(C1CCC(=O)NC1=O)C2=O]

2-((2-(2,6-dioxopiperidin-3-yl)-1-oxoisoindolin-4-yl)thio)-N-(4-(8-fluoro-1-oxo-2,3,4,6-tetrahydro-1H-azepino[5,4,3-cd]indol-5-yl)benzyl)-N-methylacetamide

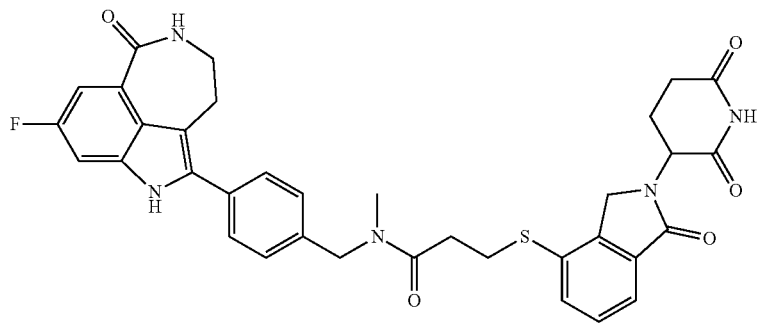 [SMILES: CN(Cc1ccc(-c2[nH]c3cc(F)cc4c3c2CCNC4=O)cc1)C(=O)CCSc1cccc2c1CN(C1CCC(=O)NC1=O)C2=O]

3-((2-(2,6-dioxopiperidin-3-yl)-1-oxoisoindolin-4-yl)thio)-N-(4-(8-fluoro-1-oxo-2,3,4,6-tetrahydro-1H-azepino[5,4,3-cd]indol-5-yl)benzyl)-N-methylpropanamide

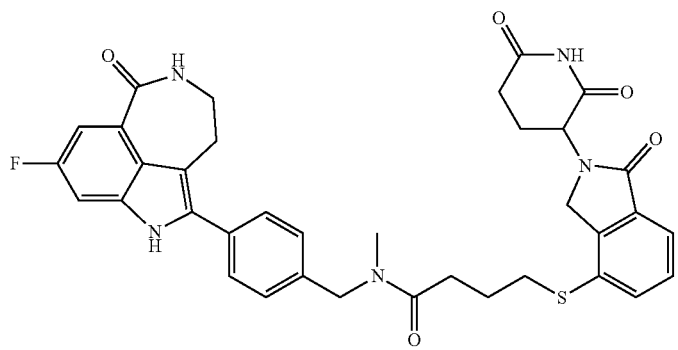 [SMILES: CN(Cc1ccc(-c2[nH]c3cc(F)cc4c3c2CCNC4=O)cc1)C(=O)CCCSc1cccc2c1CN(C1CCC(=O)NC1=O)C2=O]

4-((2-(2,6-dioxopiperidin-3-yl)-1-oxoisoindolin-4-yl)thio)-N-(4-(8-fluoro-1-oxo-2,3,4,6-tetrahydro-1H-azepino[5,4,3-cd]indol-5-yl)benzyl)-N-methylbutanamide TABLE 1-continued The compounds of formula (I) of the present disclosure Compound ID | Name of the compound

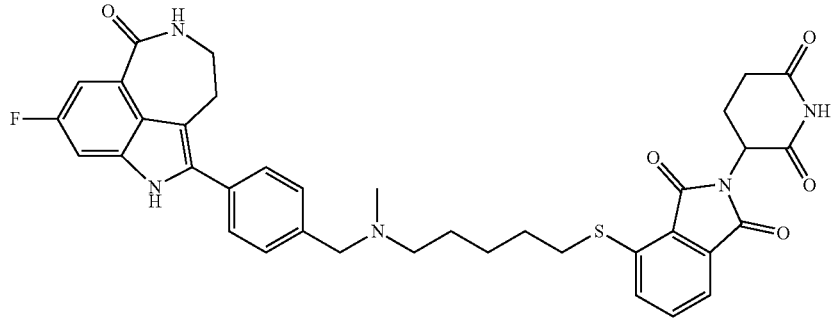 [SMILES: CN(CCCCCSc1cccc2c1C(=O)N(C1CCC(=O)NC1=O)C2=O)Cc1ccc(-c2[nH]c3cc(F)cc4c3c2CCNC4=O)cc1]

2-(2,6-dioxopiperidin-3-yl)-4-((5-((4-(8-fluoro-1-oxo-2,3,4,6-tetrahydro-1H-azepino[5,4,3-cd]indol-5-yl)benzyl)(methyl)amino)pentyl)thio)isoindoline-1,3-dione

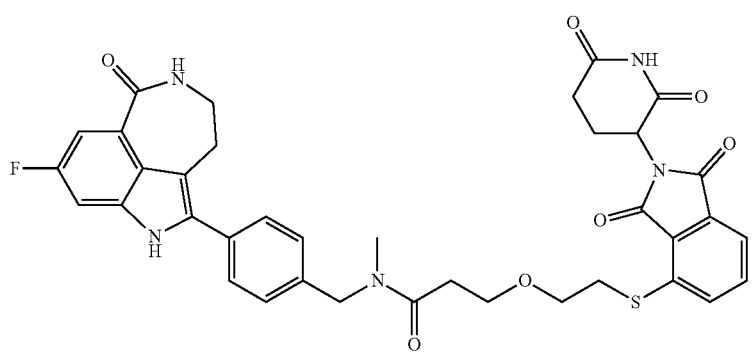

3-(2-((2-(2,6-dioxopiperidin-3-yl)-1,3-dioxoisoindolin-4-yl)thio)ethoxy)-N-(4-(8-fluoro-1-oxo-2,3,4,6-tetrahydro-1H-azepino[5,4,3-cd]indol-5-yl)benzyl)-N-methylpropanamide

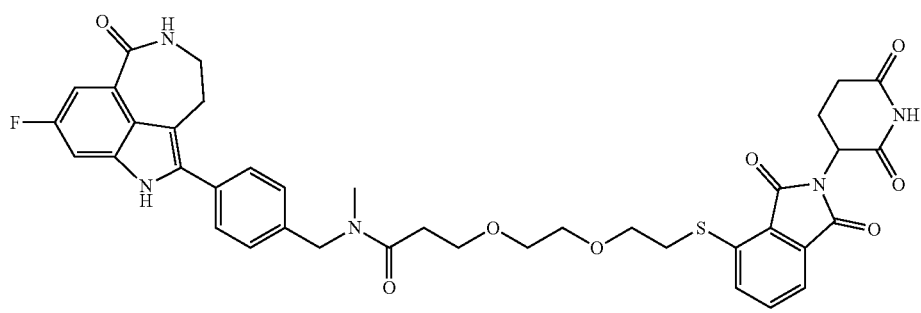 [SMILES: CN(Cc1ccc(-c2[nH]c3cc(F)cc4c3c2CCNC4=O)cc1)C(=O)CCOCCOCCSc1cccc2c1C(=O)N(C1CCC(=O)NC1=O)C2=O]

3-(2-(2-((2-(2,6-dioxopiperidin-3-yl)-1,3-dioxoisoindolin-4-yl)thio)ethoxy)ethoxy)-N-(4-(8-fluoro-1-oxo-2,3,4,6-tetrahydro-1H-azepino[5,4,3-cd]indol-5-yl)benzyl)-N-methylpropanamide

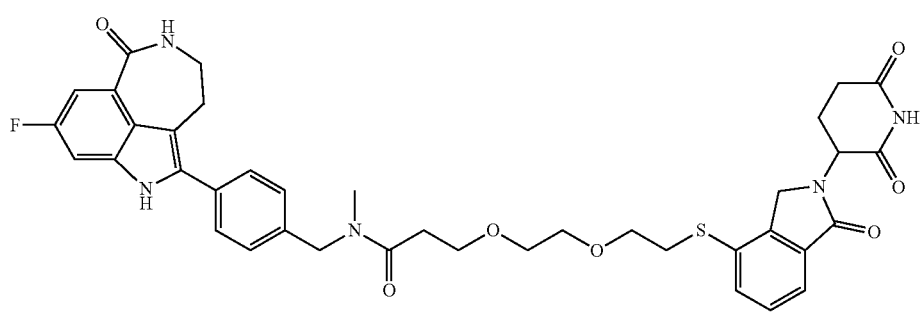 [SMILES: CN(Cc1ccc(-c2[nH]c3cc(F)cc4c3c2CCNC4=O)cc1)C(=O)CCOCCOCCSc1cccc2c1CN(C1CCC(=O)NC1=O)C2=O]

3-(2-(2-((2-(2,6-dioxopiperidin-3-yl)-1-oxoisoindolin-4-yl)thio)ethoxy)ethoxy)-N-(4-(8-fluoro-1-oxo-2,3,4,6-tetrahydro-1H-azepino[5,4,3-cd]indol-5-yl)benzyl)-N-methylpropanamide TABLE 1-continued The compounds of formula (I) of the present disclosure Compound ID | Name of the compound

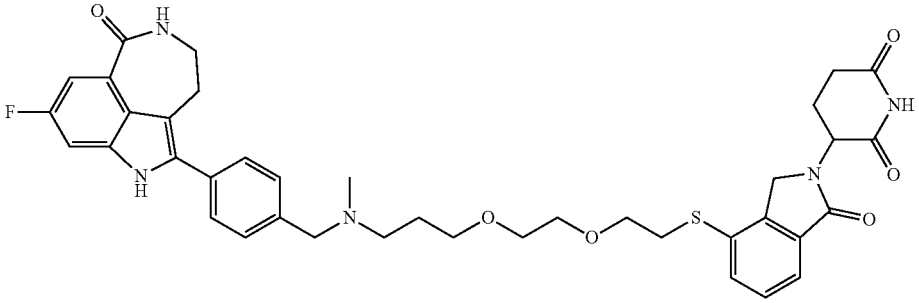 [SMILES: CN(CCCOCCOCCSc1cccc2c1CN(C1CCC(=O)NC1=O)C2=O)Cc1ccc(-c2[nH]c3cc(F)cc4c3c2CCNC4=O)cc1]

3-(4-((2-(2-(3-((4-(8-fluoro-1-oxo-2,3,4,6-tetrahydro-1H-azepino[5,4,3-cd]indol-5-yl)benzyl)(methyl)amino)propoxy)ethoxy)ethyl)thio)-1-oxoisoindolin-2-yl)piperidine-2,6-dione

| | |
|---|---|
| SIAIS180014 | (Z)-N-(2-(4-(4-chloro-1,2-diphenylbut-1-en-1-yl)phenoxy)ethyl)-2-((2-(2,6-dioxopiperidin-3-yl)-1,3-dioxoisoindolin-4-yl)thio)-N-methylacetamide |
| SIAIS180015 | (Z)-N-(2-(4-(4-chloro-1,2-diphenylbut-1-en-1-yl)phenoxy)ethyl)-3-((2-(2,6-dioxopiperidin-3-yl)-1,3-dioxoisoindolin-4-yl)thio)-N-methylpropanamide |
| SIAIS180016 | (Z)-N-(2-(4-(4-chloro-1,2-diphenylbut-1-en-1-yl)phenoxy)ethyl)-4-((2-(2,6-dioxopiperidin-3-yl)-1,3-dioxoisoindolin-4-yl)thio)-N-methylbutanamide |
| SIAIS180017 | (Z)-N-(2-(4-(4-chloro-1,2-diphenylbut-1-en-1-yl)phenoxy)ethyl)-5-((2-(2,6-dioxopiperidin-3-yl)-1,3-dioxoisoindolin-4-yl)thio)-N-methylpentanamide |
| SIAIS180018 | (Z)-N-(2-(4-(4-chloro-1,2-diphenylbut-1-en-1-yl)phenoxy)ethyl)-6-((2-(2,6-dioxopiperidin-3-yl)-1,3-dioxoisoindolin-4-yl)thio)-N-methylhexanamide |
| SIAIS180019 | (Z)-N-(2-(4-(4-chloro-1,2-diphenylbut-1-en-1-yl)phenoxy)ethyl)-7-((2-(2,6-dioxopiperidin-3-yl)-1,3-dioxoisoindolin-4-yl)thio)-N-methylheptanamide |
| | (Z)-N-(2-(4-(4-chloro-1,2-diphenylbut-1-en-1-yl)phenoxy)ethyl)-6-((2-(2,6-dioxopiperidin-3-yl)-1-oxoisoindolin-4-yl)thio)-N-methylhexanamide |
| | (Z)-N-(2-(4-(4-chloro-1,2-diphenylbut-1-en-1-yl)phenoxy)ethyl)-12-((2-(2,6-dioxopiperidin-3-yl)-1-oxoisoindolin-4-yl)thio)-N-methyldodecanamide |
| | (Z)-N-(2-(4-(4-chloro-1,2-diphenylbut-1-en-1-yl)phenoxy)ethyl)-3-(2-((2-(2,6-dioxopiperidin-3-yl)-1,3-dioxoisoindolin-4-yl)thio)ethoxy)-N-methylpropanamide |
| | (Z)-N-(2-(4-(4-chloro-1,2-diphenylbut-1-en-1-yl)phenoxy)ethyl)-3-(2-(2-((2-(2,6-dioxopiperidin-3-yl)-1,3-dioxoisoindolin-4-yl)thio)ethoxy)ethoxy)-N-methylpropanamide |
| | (Z)-N-(2-(4-(4-chloro-1,2-diphenylbut-1-en-1-yl)phenoxy)ethyl)-3-(2-(2-(2-((2-(2,6-dioxopiperidin-3-yl)-1,3-dioxoisoindolin-4-yl)thio)ethoxy)ethoxy)ethoxy)-N-methylpropanamide |
| | (Z)-N-(2-(4-(4-chloro-1,2-diphenylbut-1-en-1-yl)phenoxy)ethyl)-1-((2-(2,6-dioxopiperidin-3-yl)-1,3-dioxoisoindolin-4-yl)thio)-N-methyl-3,6,9,12-tetraoxapentadecan-15-amide |
| | (Z)-N-(2-(4-(4-chloro-1,2-diphenylbut-1-en-1-yl)phenoxy)ethyl)-1-((2-(2,6-dioxopiperidin-3-yl)-1,3-dioxoisoindolin-4-yl)thio)-N-methyl-3,6,9,12,15-pentaoxaoctadecan-18-amide |
| | (Z)-4-((21-(4-(4-chloro-1,2-diphenylbut-1-en-1-yl)phenoxy)-19-methyl-3,6,9,12,15-pentaoxa-19-azahenicosyl)thio)-2-(2,6-dioxopiperidin-3-yl)isoindoline-1,3-dione |
| | (Z)-N-(2-(4-(4-chloro-1,2-diphenylbut-1-en-1-yl)phenoxy)ethyl)-3-(2-(2-((2-(2,6-dioxopiperidin-3-yl)-1-oxoisoindolin-4-yl)thio)ethoxy)ethoxy)-N-methylpropanamide |
| | (Z)-N-(2-(4-(4-chloro-1,2-diphenylbut-1-en-1-yl)phenoxy)ethyl)-1-((2-(2,6-dioxopiperidin-3-yl)-1-oxoisoindolin-4-yl)thio)-N-methyl-3,6,9,12-tetraoxapentadecan-15-amide |
| | (Z)-3-(4-((21-(4-(4-chloro-1,2-diphenylbut-1-en-1-yl)phenoxy)-19-methyl-3,6,9,12,15-pentaoxa-19-azahenicosyl)thio)-1-oxoisoindolin-2-yl)piperidine-2,6-dione |
| | (Z)-6-((2-(2,6-dioxopiperidin-3-yl)-1,3-dioxoisoindolin-4-yl)thio)-N-(2-(4-(1,2-diphenylbut-1-en-1-yl)phenoxy)ethyl)-N-methylhexanamide |
| | (Z)-9-((2-(2,6-dioxopiperidin-3-yl)-1,3-dioxoisoindolin-4-yl)thio)-N-(2-(4-(1,2-diphenylbut-1-en-1-yl)phenoxy)ethyl)-N-methylnonanamide |
| | (Z)-6-((2-(2,6-dioxopiperidin-3-yl)-1-oxoisoindolin-4-yl)thio)-N-(2-(4-(1,2-diphenylbut-1-en-1-yl)phenoxy)ethyl)-N-methylhexanamide |
| | (Z)-9-((2-(2,6-dioxopiperidin-3-yl)-1-oxoisoindolin-4-yl)thio)-N-(2-(4-(1,2-diphenylbut-1-en-1-yl)phenoxy)ethyl)-N-methylnonanamide |
| | (Z)-3-(4-((18-((2-(4-(1,2-diphenylbut-1-en-1-yl)phenoxy)ethyl)(methyl)amino)octadecyl)thio)-1-oxoisoindolin-2-yl)piperidine-2,6-dione |
| | (Z)-3-(2-(2-(2-((2-(2,6-dioxopiperidin-3-yl)-1,3-dioxoisoindolin-4-yl)thio)ethoxy)ethoxy)ethoxy)-N-(2-(4-(1,2-diphenylbut-1-en-1-yl)phenoxy)ethyl)-N-methylpropanamide |
| | (Z)-1-((2-(2,6-dioxopiperidin-3-yl)-1,3-dioxoisoindolin-4-yl)thio)-N-(2-(4-(1,2-diphenylbut-1-en-1-yl)phenoxy)ethyl)-N-methyl-3,6,9,12-tetraoxapentadecan-15-amide |
| | (Z)-1-((2-(2,6-dioxopiperidin-3-yl)-1,3-dioxoisoindolin-4-yl)thio)-N-(2-(4-(1,2-diphenylbut-1-en-1-yl)phenoxy)ethyl)-N-methyl-3,6,9,12,15-pentaoxaoctadecan-18-amide |
| | (Z)-3-(2-(2-(2-((2-(2,6-dioxopiperidin-3-yl)-1-oxoisoindolin-4- |

TABLE 1-continued

The compounds of formula (I) of the present disclosure

| Compound ID | Name of the compound |
|---|---|
| | yl)thio)ethoxy)ethoxy)ethoxy)-N-(2-(4-(1,2-diphenylbut-1-en-1-yl)phenoxy)ethyl)-N-methylpropanamide |
| | (Z)-1-((2-(2,6-dioxopiperidin-3-yl)-1-oxoisoindolin-4-yl)thio)-N-(2-(4-(1,2-diphenylbut-1-en-1-yl)phenoxy)ethyl)-N-methyl-3,6,9,12-tetraoxapentadecan-15-amide |
| | (Z)-3-(4-((21-(4-(1,2-diphenylbut-1-en-1-yl)phenoxy)-19-methyl-3,6,9,12,15-pentaoxa-19-azahenicosyl)thio)-1-oxoisoindolin-2-yl)piperidine-2,6-dione |
| | (Z)-12-((2-(2,6-dioxopiperidin-3-yl)-1,3-dioxoisoindolin-4-yl)thio)-N-(2-(4-(1-(4-hydroxyphenyl)-2-phenylbut-1-en-1-yl)phenoxy)ethyl)-N-methyldodecanamide |
| | (Z)-2-(2,6-dioxopiperidin-3-yl)-4-((12-((2-(4-(1-(4-hydroxyphenyl)-2-phenylbut-1-en-1-yl)phenoxy)ethyl)(methyl)amino)dodecyl)thio)isoindoline-1,3-dione |
| | (Z)-15-((2-(2,6-dioxopiperidin-3-yl)-1,3-dioxoisoindolin-4-yl)thio)-N-(2-(4-(1-(4-hydroxyphenyl)-2-phenylbut-1-en-1-yl)phenoxy)ethyl)-N-methylpentadecanamide |
| | (Z)-9-((2-(2,6-dioxopiperidin-3-yl)-1-oxoisoindolin-4-yl)thio)-N-(2-(4-(1-(4-hydroxyphenyl)-2-phenylbut-1-en-1-yl)phenoxy)ethyl)-N-methylnonanamide |
| | (Z)-3-(4-((9-((2-(4-(1-(4-hydroxyphenyl)-2-phenylbut-1-en-1-yl)phenoxy)ethyl)(methyl)amino)nonyl)thio)-1-oxoisoindolin-2-yl)piperidine-2,6-dione |
| | (Z)-3-(2-((2-(2,6-dioxopiperidin-3-yl)-1,3-dioxoisoindolin-4-yl)thio)ethoxy)-N-(2-(4-(1-(4-hydroxyphenyl)-2-phenylbut-1-en-1-yl)phenoxy)ethyl)-N-methylpropanamide |
| | (Z)-3-(2-(2-((2-(2,6-dioxopiperidin-3-yl)-1,3-dioxoisoindolin-4-yl)thio)ethoxy)ethoxy)-N-(2-(4-(1-(4-hydroxyphenyl)-2-phenylbut-1-en-1-yl)phenoxy)ethyl)-N-methylpropanamide |
| | (Z)-3-(2-(2-(2-((2-(2,6-dioxopiperidin-3-yl)-1,3-dioxoisoindolin-4-yl)thio)ethoxy)ethoxy)ethoxy)-N-(2-(4-(1-(4-hydroxyphenyl)-2-phenylbut-1-en-1-yl)phenoxy)ethyl)-N-methylpropanamide |
| | (Z)-1-((2-(2,6-dioxopiperidin-3-yl)-1,3-dioxoisoindolin-4-yl)thio)-N-(2-(4-(1-(4-hydroxyphenyl)-2-phenylbut-1-en-1-yl)phenoxy)ethyl)-N-methyl-3,6,9,12-tetraoxapentadecan-15-amide |
| | (Z)-2-(2,6-dioxopiperidin-3-yl)-4-((21-(4-(1-(4-hydroxyphenyl)-2-phenylbut-1-en-1-yl)phenoxy)-19-methyl-3,6,9,12,15-pentaoxa-19-azahenicosyl)thio)isoindoline-1,3-dione |
| | (Z)-3-(2-((2-(2,6-dioxopiperidin-3-yl)-1-oxoisoindolin-4-yl)thio)ethoxy)-N-(2-(4-(1-(4-hydroxyphenyl)-2-phenylbut-1-en-1-yl)phenoxy)ethyl)-N-methylpropanamide |
| SIAIS208146 | N-(2-(4-(4-chloro-1-(4-hydroxyphenyl)-2-phenylbut-1-en-1-yl)phenoxy)ethyl)-2-((2-(2,6-dioxopiperidin-3-yl)-1,3-dioxoisoindolin-4-yl)thio)acetamide |
| SIAIS208147 | N-(2-(4-(4-chloro-1-(4-hydroxyphenyl)-2-phenylbut-1-en-1-yl)phenoxy)ethyl)-3-((2-(2,6-dioxopiperidin-3-yl)-1,3-dioxoisoindolin-4-yl)thio)propanamide |
| SIAIS208148 | N-(2-(4-(4-chloro-1-(4-hydroxyphenyl)-2-phenylbut-1-en-1-yl)phenoxy)ethyl)-4-((2-(2,6-dioxopiperidin-3-yl)-1,3-dioxoisoindolin-4-yl)thio)butanamide |
| SIAIS208152 | N-(2-(4-(4-chloro-1-(4-hydroxyphenyl)-2-phenylbut-1-en-1-yl)phenoxy)ethyl)-5-((2-(2,6-dioxopiperidin-3-yl)-1,3-dioxoisoindolin-4-yl)thio)pentanamide |
| SIAIS208153 | N-(2-(4-(4-chloro-1-(4-hydroxyphenyl)-2-phenylbut-1-en-1-yl)phenoxy)ethyl)-6-((2-(2,6-dioxopiperidin-3-yl)-1,3-dioxoisoindolin-4-yl)thio)hexanamide |
| SIAIS208154 | N-(2-(4-(4-chloro-1-(4-hydroxyphenyl)-2-phenylbut-1-en-1-yl)phenoxy)ethyl)-7-((2-(2,6-dioxopiperidin-3-yl)-1,3-dioxoisoindolin-4-yl)thio)heptanamide |
| SIAIS208155 | N-(2-(4-(4-chloro-1-(4-hydroxyphenyl)-2-phenylbut-1-en-1-yl)phenoxy)ethyl)-2-((2-(2,6-dioxopiperidin-3-yl)-1-oxoisoindolin-4-yl)thio)acetamide |
| SIAIS208156 | N-(2-(4-(4-chloro-1-(4-hydroxyphenyl)-2-phenylbut-1-en-1-yl)phenoxy)ethyl)-3-((2-(2,6-dioxopiperidin-3-yl)-1-oxoisoindolin-4-yl)thio)propanamide |
| SIAIS208157 | N-(2-(4-(4-chloro-1-(4-hydroxyphenyl)-2-phenylbut-1-en-1-yl)phenoxy)ethyl)-4-((2-(2,6-dioxopiperidin-3-yl)-1-oxoisoindolin-4-yl)thio)butanamide |
| SIAIS208158 | N-(2-(4-(4-chloro-1-(4-hydroxyphenyl)-2-phenylbut-1-en-1-yl)phenoxy)ethyl)-5-((2-(2,6-dioxopiperidin-3-yl)-1-oxoisoindolin-4-yl)thio)pentanamide |
| SIAIS208159 | N-(2-(4-(4-chloro-1-(4-hydroxyphenyl)-2-phenylbut-1-en-1-yl)phenoxy)ethyl)-6-((2-(2,6-dioxopiperidin-3-yl)-1-oxoisoindolin-4-yl)thio)hexanamide |
| SIAIS208160 | N-(2-(4-(4-chloro-1-(4-hydroxyphenyl)-2-phenylbut-1-en-1-yl)phenoxy)ethyl)-7-((2-(2,6-dioxopiperidin-3-yl)-1-oxoisoindolin-4-yl)thio)heptanamide |
| SIAIS251128 | N-(2-(4-(1,2-bis(4-hydroxyphenyl)but-1-en-1-yl)phenoxy)ethyl)-2-((2-(2,6-dioxopiperidin-3-yl)-1,3-dioxoisoindolin-4-yl)thio)acetamide |
| SIAIS251129 | N-(2-(4-(1,2-bis(4-hydroxyphenyl)but-1-en-1-yl)phenoxy)ethyl)-3-((2-(2,6-dioxopiperidin-3-yl)-1,3-dioxoisoindolin-4-yl)thio)propanamide |
| SIAIS251130 | N-(2-(4-(1,2-bis(4-hydroxyphenyl)but-1-en-1-yl)phenoxy)ethyl)-4-((2-(2,6-dioxopiperidin-3-yl)-1,3-dioxoisoindolin-4-yl)thio)butanamide |
| SIAIS251131 | N-(2-(4-(1,2-bis(4-hydroxyphenyl)but-1-en-1-yl)phenoxy)ethyl)-5-((2-(2,6-dioxopiperidin-3-yl)-1,3-dioxoisoindolin-4-yl)thio)pentanamide |
| SIAIS251132 | N-(2-(4-(1,2-bis(4-hydroxyphenyl)but-1-en-1-yl)phenoxy)ethyl)-6-((2-(2,6-dioxopiperidin-3-yl)-1,3-dioxoisoindolin-4-yl)thio)hexanamide |
| SIAIS208170 | N-(2-(4-(1,2-bis(4-hydroxyphenyl)but-1-en-1-yl)phenoxy)ethyl)-7-((2-(2,6-dioxopiperidin-3-yl)-1,3-dioxoisoindolin-4-yl)thio)heptanamide |
| SIAIS251133 | N-(2-(4-(1,2-bis(4-hydroxyphenyl)but-1-en-1-yl)phenoxy)ethyl)-2-((2-(2,6-dioxopiperidin-3-yl)-1-oxoisoindolin-4-yl)thio)acetamide |
| SIAIS251134 | N-(2-(4-(1,2-bis(4-hydroxyphenyl)but-1-en-1-yl)phenoxy)ethyl)-3-((2-(2,6-dioxopiperidin-3-yl)-1-oxoisoindolin-4-yl)thio)propanamide |
| SIAIS251135 | N-(2-(4-(1,2-bis(4-hydroxyphenyl)but-1-en-1-yl)phenoxy)ethyl)-4-((2-(2,6-dioxopiperidin-3-yl)-1-oxoisoindolin-4-yl)thio)butanamide |
| SIAIS251137 | N-(2-(4-(1,2-bis(4-hydroxyphenyl)but-1-en-1-yl)phenoxy)ethyl)-6-((2-(2,6-dioxopiperidin-3-yl)-1-oxoisoindolin-4-yl)thio)hexanamide |

TABLE 1-continued

The compounds of formula (I) of the present disclosure

| Compound ID | Name of the compound |
|---|---|
| SIAIS208171 | N-(2-(4-(1,2-bis(4-hydroxyphenyl)but-1-en-1-yl)phenoxy)ethyl)-7-((2-(2,6-dioxopiperidin-3-yl)-1-oxoisoindolin-4-yl)thio)heptanamide |
| | 2-((S)-6-(4-chlorophenyl)-8-methoxy-1-methyl-4H-benzo[f][1,2,4]triazolo[4,3-a][1,4]diazepin-4-yl)-N-(2-((2-(2,6-dioxopiperidin-3-yl)-1,3-dioxoisoindolin-4-yl)thio)ethyl)acetamide |
| | 2-((S)-6-(4-chlorophenyl)-8-methoxy-1-methyl-4H-benzo[f][1,2,4]triazolo[4,3-a][1,4]diazepin-4-yl)-N-(4-((2-(2,6-dioxopiperidin-3-yl)-1,3-dioxoisoindolin-4-yl)thio)butyl)acetamide |
| | 2-((S)-6-(4-chlorophenyl)-8-methoxy-1-methyl-4H-benzo[f][1,2,4]triazolo[4,3-a][1,4]diazepin-4-yl)-N-(10-((2-(2,6-dioxopiperidin-3-yl)-1,3-dioxoisoindolin-4-yl)thio)decyl)acetamide |
| | 2-((S)-6-(4-chlorophenyl)-8-methoxy-1-methyl-4H-benzo[f][1,2,4]triazolo[4,3-a][1,4]diazepin-4-yl)-N-(4-((2-(2,6-dioxopiperidin-3-yl)-1-oxoisoindolin-4-yl)thio)butyl)acetamide |
| | 2-((S)-6-(4-chlorophenyl)-8-methoxy-1-methyl-4H-benzo[f][1,2,4]triazolo[4,3-a][1,4]diazepin-4-yl)-N-(3-(2-(3-((2-(2,6-dioxopiperidin-3-yl)-1,3-dioxoisoindolin-4-yl)thio)propoxy)ethoxy)propyl)acetamide |
| | 2-((S)-6-(4-chlorophenyl)-8-methoxy-1-methyl-4H-benzo[f][1,2,4]triazolo[4,3-a][1,4]diazepin-4-yl)-N-(3-(2-(3-((2-(2,6-dioxopiperidin-3-yl)-1-oxoisoindolin-4-yl)thio)propoxy)ethoxy)propyl)acetamide |
| SIAIS171036 | 2-((S)-4-(4-chlorophenyl)-2,3,9-trimethyl-6H-thieno[3,2-f][1,2,4]triazolo[4,3-a][1,4]diazepin-6-yl)-N-(2-((2-(2,6-dioxopiperidin-3-yl)-1,3-dioxoisoindolin-4-yl)thio)ethyl)acetamide |
| SIAIS171013 | 2-((S)-4-(4-chlorophenyl)-2,3,9-trimethyl-6H-thieno[3,2-f][1,2,4]triazolo[4,3-a][1,4]diazepin-6-yl)-N-(3-((2-(2,6-dioxopiperidin-3-yl)-1,3-dioxoisoindolin-4-yl)thio)propyl)acetamide |
| SIAIS171037 | 2-((S)-4-(4-chlorophenyl)-2,3,9-trimethyl-6H-thieno[3,2-f][1,2,4]triazolo[4,3-a][1,4]diazepin-6-yl)-N-(4-((2-(2,6-dioxopiperidin-3-yl)-1,3-dioxoisoindolin-4-yl)thio)butyl)acetamide |
| SIAIS171038 | 2-((S)-4-(4-chlorophenyl)-2,3,9-trimethyl-6H-thieno[3,2-f][1,2,4]triazolo[4,3-a][1,4]diazepin-6-yl)-N-(5-((2-(2,6-dioxopiperidin-3-yl)-1,3-dioxoisoindolin-4-yl)thio)pentyl)acetamide |
| SIAIS171039 | 2-((S)-4-(4-chlorophenyl)-2,3,9-trimethyl-6H-thieno[3,2-f][1,2,4]triazolo[4,3-a][1,4]diazepin-6-yl)-N-(6-((2-(2,6-dioxopiperidin-3-yl)-1,3-dioxoisoindolin-4-yl)thio)hexyl)acetamide |
| SIAIS171040 | 2-((S)-4-(4-chlorophenyl)-2,3,9-trimethyl-6H-thieno[3,2-f][1,2,4]triazolo[4,3-a][1,4]diazepin-6-yl)-N-(7-((2-(2,6-dioxopiperidin-3-yl)-1,3-dioxoisoindolin-4-yl)thio)heptyl)acetamide |
| SIAIS171049 | 2-((S)-4-(4-chlorophenyl)-2,3,9-trimethyl-6H-thieno[3,2-f][1,2,4]triazolo[4,3-a][1,4]diazepin-6-yl)-N-(8-((2-(2,6-dioxopiperidin-3-yl)-1,3-dioxoisoindolin-4-yl)thio)octyl)acetamide |
| SIAIS171138 | 2-((S)-4-(4-chlorophenyl)-2,3,9-trimethyl-6H-thieno[3,2-f][1,2,4]triazolo[4,3-a][1,4]diazepin-6-yl)-N-(2-((2-(2,6-dioxopiperidin-3-yl)-1-oxoisoindolin-4-yl)thio)ethyl)acetamide |
| SIAIS171139 | 2-((S)-4-(4-chlorophenyl)-2,3,9-trimethyl-6H-thieno[3,2-f][1,2,4]triazolo[4,3-a][1,4]diazepin-6-yl)-N-(3-((2-(2,6-dioxopiperidin-3-yl)-1-oxoisoindolin-4-yl)thio)propyl)acetamide |
| SIAIS171141 | 2-((S)-4-(4-chlorophenyl)-2,3,9-trimethyl-6H-thieno[3,2-f][1,2,4]triazolo[4,3-a][1,4]diazepin-6-yl)-N-(4-((2-(2,6-dioxopiperidin-3-yl)-1-oxoisoindolin-4-yl)thio)butyl)acetamide |
| SIAIS171142 | 2-((S)-4-(4-chlorophenyl)-2,3,9-trimethyl-6H-thieno[3,2-f][1,2,4]triazolo[4,3-a][1,4]diazepin-6-yl)-N-(5-((2-(2,6-dioxopiperidin-3-yl)-1-oxoisoindolin-4-yl)thio)pentyl)acetamide |
| SIAIS171143 | 2-((S)-4-(4-chlorophenyl)-2,3,9-trimethyl-6H-thieno[3,2-f][1,2,4]triazolo[4,3-a][1,4]diazepin-6-yl)-N-(6-((2-(2,6-dioxopiperidin-3-yl)-1-oxoisoindolin-4-yl)thio)hexyl)acetamide |
| SIAIS171144 | 2-((S)-4-(4-chlorophenyl)-2,3,9-trimethyl-6H-thieno[3,2-f][1,2,4]triazolo[4,3-a][1,4]diazepin-6-yl)-N-(7-((2-(2,6-dioxopiperidin-3-yl)-1-oxoisoindolin-4-yl)thio)heptyl)acetamide |
| SIAIS171145 | 2-((S)-4-(4-chlorophenyl)-2,3,9-trimethyl-6H-thieno[3,2-f][1,2,4]triazolo[4,3-a][1,4]diazepin-6-yl)-N-(8-((2-(2,6-dioxopiperidin-3-yl)-1-oxoisoindolin-4-yl)thio)octyl)acetamide |
| | 2-((S)-4-(4-chlorophenyl)-2,3,9-trimethyl-6H-thieno[3,2-f][1,2,4]triazolo[4,3-a][1,4]diazepin-6-yl)-N-(2-(2-((2-(2,6-dioxopiperidin-3-yl)-1,3-dioxoisoindolin-4-yl)thio)ethoxy)ethyl)acetamide |
| SIAIS213070 | 2-((S)-4-(4-chlorophenyl)-2,3,9-trimethyl-6H-thieno[3,2-f][1,2,4]triazolo[4,3-a][1,4]diazepin-6-yl)-N-(2-(2-(2-((2-(2,6-dioxopiperidin-3-yl)-1,3-dioxoisoindolin-4-yl)thio)ethoxy)ethoxy)ethyl)acetamide |
| | 2-((S)-4-(4-chlorophenyl)-2,3,9-trimethyl-6H-thieno[3,2-f][1,2,4]triazolo[4,3-a][1,4]diazepin-6-yl)-N-(2-(2-(2-(2-((2-(2,6-dioxopiperidin-3-yl)-1,3-dioxoisoindolin-4-yl)thio)ethoxy)ethoxy)ethoxy)ethyl)acetamide |
| | 2-((S)-4-(4-chlorophenyl)-2,3,9-trimethyl-6H-thieno[3,2-f][1,2,4]triazolo[4,3-a][1,4]diazepin-6-yl)-N-(1-((2-(2,6-dioxopiperidin-3-yl)-1,3-dioxoisoindolin-4-yl)thio)-3,6,9,12-tetraoxapentadecan-15-yl)acetamide |
| | 2-((S)-4-(4-chlorophenyl)-2,3,9-trimethyl-6H-thieno[3,2-f][1,2,4]triazolo[4,3- |

TABLE 1-continued

The compounds of formula (I) of the present disclosure

| Compound ID | Name of the compound |
|---|---|
| | a][1,4]diazepin-6-yl)-N-(1-((2-(2,6-dioxopiperidin-3-yl)-1,3-dioxoisoindolin-4-yl)thio)-3,6,9,12,15,18-hexaoxahenicosan-21-yl)acetamide |
| SIAIS213100 | 2-((S)-4-(4-chlorophenyl)-2,3,9-trimethyl-6H-thieno[3,2-f][1,2,4]triazolo[4,3-a][1,4]diazepin-6-yl)-N-(2-(2-((2-(2,6-dioxopiperidin-3-yl)-1-oxoisoindolin-4-yl)thio)ethoxy)ethyl)acetamide |
| SIAIS213072 | 2-((S)-4-(4-chlorophenyl)-2,3,9-trimethyl-6H-thieno[3,2-f][1,2,4]triazolo[4,3-a][1,4]diazepin-6-yl)-N-(2-(2-(2-((2-(2,6-dioxopiperidin-3-yl)-1-oxoisoindolin-4-yl)thio)ethoxy)ethoxy)ethyl)acetamide |
| SIAIS213112 | 2-((S)-4-(4-chlorophenyl)-2,3,9-trimethyl-6H-thieno[3,2-f][1,2,4]triazolo[4,3-a][1,4]diazepin-6-yl)-N-(2-(2-(2-(2-((2-(2,6-dioxopiperidin-3-yl)-1-oxoisoindolin-4-yl)thio)ethoxy)ethoxy)ethoxy)ethyl)acetamide |
| | 2-((S)-4-(4-chlorophenyl)-2,3,9-trimethyl-6H-thieno[3,2-f][1,2,4]triazolo[4,3-a][1,4]diazepin-6-yl)-N-(1-((2-(2,6-dioxopiperidin-3-yl)-1-oxoisoindolin-4-yl)thio)-3,6,9,12-tetraoxapentadecan-15-yl)acetamide |
| | 2-((S)-4-(4-chlorophenyl)-2,3,9-trimethyl-6H-thieno[3,2-f][1,2,4]triazolo[4,3-a][1,4]diazepin-6-yl)-N-(1-((2-(2,6-dioxopiperidin-3-yl)-1-oxoisoindolin-4-yl)thio)-3,6,9,12,15,18-hexaoxahenicosan-21-yl)acetamide |
| SIAIS213075 | 2-((S)-4-(4-chlorophenyl)-2,3,9-trimethyl-6H-thieno[3,2-f][1,2,4]triazolo[4,3-a][1,4]diazepin-6-yl)-N-(4-(2-((2-(2,6-dioxopiperidin-3-yl)-1,3-dioxoisoindolin-4-yl)thio)acetamido)butyl)acetamide |
| SIAIS213094 | 2-((S)-4-(4-chlorophenyl)-2,3,9-trimethyl-6H-thieno[3,2-f][1,2,4]triazolo[4,3-a][1,4]diazepin-6-yl)-N-(4-(2-((2-(2,6-dioxopiperidin-3-yl)-1-oxoisoindolin-4-yl)thio)acetamido)butyl)acetamide |
| SIAIS213140 | 3-(4-((2-(4-(2-((S)-4-(4-chlorophenyl)-2,3,9-trimethyl-6H-thieno[3,2-f][1,2,4]triazolo[4,3-a][1,4]diazepin-6-yl)acetyl)piperazin-1-yl)ethyl)thio)-1-oxoisoindolin-2-yl)piperidine-2,6-dione |
| SIAIS213117 | 3-(4-((3-(4-(2-((S)-4-(4-chlorophenyl)-2,3,9-trimethyl-6H-thieno[3,2-f][1,2,4]triazolo[4,3-a][1,4]diazepin-6-yl)acetyl)piperazin-1-yl)propyl)thio)-1-oxoisoindolin-2-yl)piperidine-2,6-dione |
| SIAIS213138 | 3-(4-((4-(4-(2-((S)-4-(4-chlorophenyl)-2,3,9-trimethyl-6H-thieno[3,2-f][1,2,4]triazolo[4,3-a][1,4]diazepin-6-yl)acetyl)piperazin-1-yl)butyl)thio)-1-oxoisoindolin-2-yl)piperidine-2,6-dione |
| SIAIS213131 | 3-(4-((5-(4-(2-((S)-4-(4-chlorophenyl)-2,3,9-trimethyl-6H-thieno[3,2-f][1,2,4]triazolo[4,3-a][1,4]diazepin-6-yl)acetyl)piperazin-1-yl)pentyl)thio)-1-oxoisoindolin-2-yl)piperidine-2,6-dione |
| SIAIS213141 | 2-((S)-4-(4-chlorophenyl)-2,3,9-trimethyl-6H-thieno[3,2-f][1,2,4]triazolo[4,3-a][1,4]diazepin-6-yl)-N-(2-(4-(2-((2-(2,6-dioxopiperidin-3-yl)-1-oxoisoindolin-4-yl)thio)ethyl)piperazin-1-yl)ethyl)acetamide |
| SIAIS213136 | 2-((S)-4-(4-chlorophenyl)-2,3,9-trimethyl-6H-thieno[3,2-f][1,2,4]triazolo[4,3-a][1,4]diazepin-6-yl)-N-(2-(4-(3-((2-(2,6-dioxopiperidin-3-yl)-1-oxoisoindolin-4-yl)thio)propyl)piperazin-1-yl)ethyl)acetamide |
| SIAIS213139 | 2-((S)-4-(4-chlorophenyl)-2,3,9-trimethyl-6H-thieno[3,2-f][1,2,4]triazolo[4,3-a][1,4]diazepin-6-yl)-N-(2-(4-(4-((2-(2,6-dioxopiperidin-3-yl)-1-oxoisoindolin-4-yl)thio)butyl)piperazin-1-yl)ethyl)acetamide |
| SIAIS213133 | 2-((S)-4-(4-chlorophenyl)-2,3,9-trimethyl-6H-thieno[3,2-f][1,2,4]triazolo[4,3-a][1,4]diazepin-6-yl)-N-(2-(4-(5-((2-(2,6-dioxopiperidin-3-yl)-1-oxoisoindolin-4-yl)thio)pentyl)piperazin-1-yl)ethyl)acetamide |

In another aspect, the present disclosure also provides a pharmaceutical composition comprising, as an active ingredient, the compound of formula (I) according to the present disclosure or a pharmaceutically acceptable salt thereof, and a pharmaceutically acceptable carrier.

The pharmaceutical composition according to the present disclosure further includes at least one additional drug for treating or preventing a cancer.

In another aspect of the present disclosure, the compound of formula (I) according to the present disclosure, or a pharmaceutically acceptable salt thereof, is for use as a medicament.

In another aspect of the present disclosure, the compound of formula (I) according to the present disclosure, or a pharmaceutically acceptable salt thereof, is used for the prevention and/or treatment of a cancer.

In an embodiment, the cancer is selected from: tumors related to cyclin-dependent kinase (CDK4/6), including: breast cancer, advanced breast cancer, and metastatic breast cancer, and advanced breast cancer in postmenopausal women, and central nervous system tumors; tumors related to anaplastic lymphoma kinase (ALK), including: non-small cell lung cancer, ROS1-positive non-small cell lung cancer, anaplastic lymphoma kinase (ALK) positive non-small cell lung cancer, and metastatic non-small cell lung cancer; tumors related to the BCR-ABL target, including: myelodysplastic syndrome, bone marrow and external myeloproliferation, gastrointestinal stromal tumor, aggressive systemic mastocytosis, eosinophilia, dermatofibrosarcoma protuberans, chronic eosinophilic leukemia, acute lymphoblastic leukemia, and chronic myelogenous leukemia; tumors related to polyadenosine diphosphate-ribose polymerase (PARP), including: BRCA mutation/HER-2 negative metastasis breast cancer, primary peritoneal cancer, fallopian tube cancer, epithelial ovarian cancer, advanced ovarian cancer, BRCA-mutated advanced ovarian cancer, pancreatic cancer, and solid tumors; tumors related to estrogen receptor (ER), including: breast cancer, and metastatic breast cancer; and tumors related to BET bromodomain and extra-terminal protein (including BRD2 (bromodomain protein 2), BRD3 (bromodomain protein 3), BRD4 (bromodomain protein 4) and BRDT targets protein), including: recurrent gliomas, solid tumors, hematological malignancies, and breast cancer.

In another aspect of the present disclosure, the compound of formula (I) according to the present disclosure, or a pharmaceutically acceptable salt thereof, is used to prepare a medicament for preventing and/or treating a cancer. In a sub-embodiment, the cancer is selected from: tumors related to cyclin-dependent kinase (CDK4/6), including: advanced breast cancer, breast cancer, advanced breast cancer in postmenopausal women, metastatic breast cancer, and central nervous system tumors; tumors related to anaplastic lymphoma kinase (ALK), including: non-small cell lung cancer, ROS1-positive non-small cell lung cancer, anaplastic lymphoma kinase (ALK) positive non-small cell lung cancer, and metastatic non-small cell lung cancer; Tumors related to the BCR-ABL target, including: myelodysplastic syndrome, bone marrow and external myeloproliferation, gastrointestinal stromal tumor, aggressive systemic mastocytosis, eosinophilia, dermatofibrosarcoma protuberans, chronic eosinophilic leukemia, acute lymphoblastic leukemia, and chronic myelogenous leukemia; tumors related to polyadenosine diphosphate-ribose polymerase (PARP), including: BRCA mutation/HER-2 negative metastatic breast cancer, primary peritoneal cancer, fallopian tube cancer, epithelial ovarian cancer, advanced ovarian cancer, BRCA-mutated advanced ovarian cancer, pancreatic cancer, and solid tumors; tumors related to estrogen receptor (ER), including: breast cancer, and Metastatic breast cancer; and tumors related to BET bromodomain and extra-terminal protein (including BRD2 (bromodomain protein 2), BRD3 (bromodomain protein 3), BRD4 (bromodomain protein 4) and BRDT target protein) include: recurrent gliomas, solid tumors, hematological malignancies, and breast cancer.

In another aspect, the present disclosure also provides a method for treating or preventing a cancer, which comprises administering to a subject a therapeutically effective amount of the compound of formula (I) according to the present disclosure, or a pharmaceutically acceptable salt thereof, or the pharmaceutical composition comprising the compound of formula (I). In an embodiment, the cancer is selected from: tumors related to cyclin-dependent kinase (CDK4/6), including: advanced breast cancer, breast cancer, advanced breast cancer in postmenopausal women, and metastatic breast cancer; central nervous system; tumors related to anaplastic lymphoma kinase (ALK), including: non-small cell lung cancer, ROS1-positive non-small cell lung cancer, anaplastic lymphoma kinase (ALK) positive non-small cell lung cancer, and metastatic non-small cell lung cancer; tumors related to BCR-ABL targets, including: myelodysplastic syndrome, bone marrow and external myeloproliferation, gastrointestinal stromal tumor, aggressive systemic mastocytosis, eosinophilia, dermatofibrosarcoma protuberans, chronic eosinophilic leukemia, acute lymphoblastic leukemia, and chronic myelogenous leukemia; tumors related to polyadenosine diphosphate-ribose polymerase (PARP), including: BRCA mutation/HER-2 negative metastatic breast cancer, primary peritoneal cancer, fallopian tube cancer, epithelial ovarian cancer, advanced ovarian cancer, BRCA-mutated advanced ovarian cancer, pancreatic cancer, and solid tumors; tumors related to estrogen receptor (ER), including: breast cancer, and metastasis breast cancer; and tumors related to BET bromodomain and extra-terminal proteins (including BRD2 (bromodomain protein 2), BRD3 (bromodomain protein 3), BRD4 (bromodomain protein 4) and BRDT target proteins), including: recurrent gliomas, solid tumors, hematological malignancies, and breast cancer.

In the method for treating or preventing a cancer according to the present disclosure, the compound of formula (I) according to the present disclosure, or a pharmaceutically acceptable salt thereof, or the pharmaceutical composition comprising the compound of formula (I) is administered to the subject by at least one mode of administration selected from: nasal administration, inhalation administration, topical administration, oral administration, oral mucosal administration, rectal administration, pleural, peritoneal, vaginal, intramuscular, subcutaneous, transdermal, epidural, intrathecal, and intravenous administration.

In another aspect, the present disclosure provides a compound of formula (III):

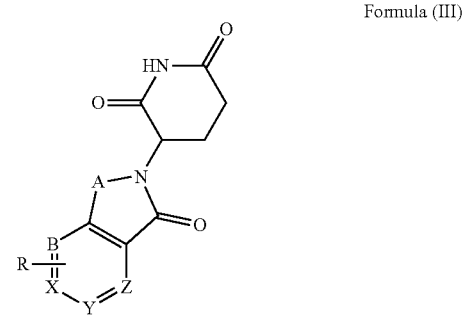

Formula (III)

wherein A represents $CH_2$ or CO, B, X, Y, and Z are the same or different and each independently represent CH or N, and R represents SH, S(O)-alkyl, $SO_2$-alkyl, or piperazinyl;

or salts, enantiomers, stereoisomers, solvates, or polymorphs thereof.

In the present disclosure, the compound of formula (III) is an intermediate compound for preparing the compound of formula (I).

In an embodiment of the present disclosure, the compound of formula (III) is also represented by any one of the following structural formulas:

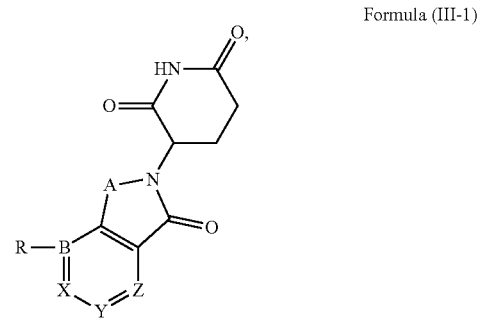

Formula (III-1)

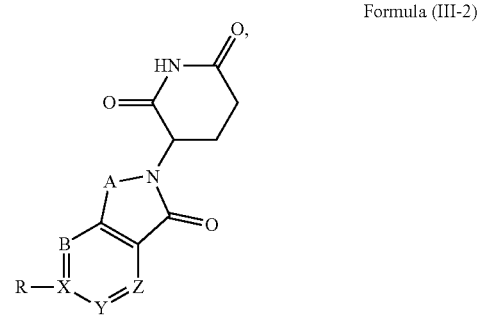

Formula (III-2)

-continued

Formula (III-3)

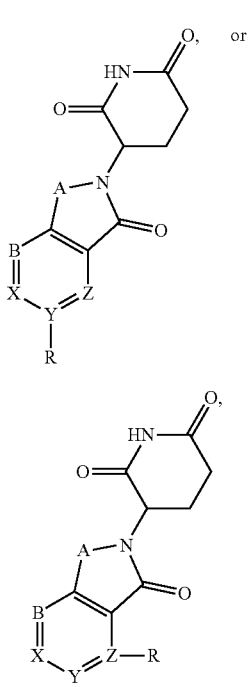

Formula (III-3)

wherein the group R, A, B, X, Y, and Z are as defined above.

In an embodiment of formula (III), A represents $CH_2$ or CO, B, X, Y, and Z are the same and all represent CH, and R represents SH, S(O)-alkyl, $SO_2$-alkyl, or piperazinyl.

In a sub-embodiment of the formula (III), A represents $CH_2$ or CO, B, X, Y, and Z are the same and all represent CH, and R represents SH. In a sub-embodiment of formula (III), A represents $CH_2$ or CO, B, X, Y, and Z are the same and all represent CH, and R represents S(O)-alkyl. In a sub-embodiment of formula (III), A represents $CH_2$ or CO, B, X, Y, and Z are the same and all represent CH, and R represents $SO_2$-alkyl. In a sub-embodiment of formula (III), A represents $CH_2$ or CO, B, X, Y, and Z are the same and all represent CH, and R represents piperazinyl.

In an embodiment, the S(O)-alkyl is S(O)—$C_{1-4}$ alkyl, for example S(O)—$C_{1-3}$ alkyl, S(O)—$C_{1-2}$ alkyl, S(O)—$C_{2-4}$ alkyl, or S(O)—$C_{2-3}$ alkyl. In an embodiment, the S(O)-alkyl group is S(O)—$CH_3$, S(O)-ethyl, S(O)-propyl, S(O)-butyl, S(O)-isobutyl, or S(O)-tert-butyl.

In an embodiment, the $SO_2$-alkyl is $SO_2$—$C_{1-4}$ alkyl, such as $SO_2$—$C_{1-3}$ alkyl, $SO_2$—$C_{1-2}$ alkyl, $SO_2$—$C_{2-4}$ alkyl, or $SO_2$—$C_{2-3}$ alkyl. In an embodiment, the $SO_2$-alkyl group is $SO_2$—$CH_3$, $SO_2$-ethyl, $SO_2$-propyl, $SO_2$-butyl, $SO_2$-isobutyl, or $SO_2$-tert-butyl.

Particularly preferred are the following compounds of formula (III) in Table 2 of the present disclosure and their salts:

TABLE 2

| The compounds of formula (III) of the present disclosure | |
|---|---|
| Compound ID | Name of the compound |
| SIAIS151014 | 2-(2,6-dioxopiperidin-3-yl)-4-mercaptoisoindoline-1,3-dione |
| SIAIS171095 | 3-(4-mercapto-1-oxoisoindolin-2-yl)piperidine-2,6-dione |
| SIAIS151024 | 2-(2,6-dioxopiperidin-3-yl)-4-(piperazin-1-yl)isoindoline-1,3-dione |
|  | 3-(1-oxo-4-(piperazin-1-yl)isoindolin-2-yl)piperidine-2,6-dione |
|  | 2-(2,6-dioxopiperidin-3-yl)-4-(methylsulfinyl)isoindoline-1,3-dione |
|  | 3-(4-(methylsulfinyl)-1-oxoisoindolin-2-yl)piperidine-2,6-dione |
|  | 2-(2,6-dioxopiperidin-3-yl)-4-(methylsulfonyl)isoindoline-1,3-dione |
|  | 3-(4-(methylsulfonyl)-1-oxoisoindolin-2-yl)piperidine-2,6-dione |

In another aspect, the present disclosure provides the use of a compound of formula (III) or a salt, enantiomer, stereoisomer, solvate, or polymorph thereof for preparing the compound of formula (I) as defined above.

In another aspect, the present disclosure provides a compound of formula (IV):

Formula (IV)

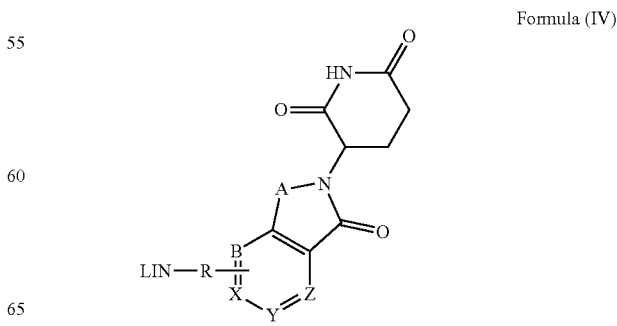

wherein A represents CH$_2$ or CO, B, X, Y, and Z are the same or different and each independently represent CH or N, and R represents S, S(O), SO$_2$ or piperazinylene; and LIN represents W-alkylene-, wherein the alkylene group is a linear or branched alkylene group optionally interrupted one or more times by one or more groups selected from the group consisting of O, CONH, NHCO, NH, alkynylene, alkenylene, cycloalkylene, arylene, heterocyclylene, heteroarylene, or any combination thereof, wherein the linear or branched alkylene group is optionally substituted with one or more substituents, and W represents hydrogen, a leaving group, CHO, COOH, or NH$_2$ (which can covalently link the LIN of the compound of formula (IV) to SMBP, a small molecule compound capable of binding proteins, through a reaction);

or its salts, enantiomers, stereoisomers, solvates, polymorphs.

In an embodiment of the present disclosure, in formula (IV), A represents CH$_2$ or CO, B, X, Y and Z are the same and all represent CH, and R represents S, SO, SO$_2$, or piperazinylene. In a sub-embodiment of the present disclosure, in formula (IV), A represents CH$_2$ or CO, B, X, Y and Z are the same and all represent CH, and R represents S. In a sub-embodiment of the present disclosure, in formula (IV), A represents CH$_2$ or CO, B, X, Y and Z are the same and all represent CH, and R represents SO. In a sub-embodiment of the present disclosure, in formula (IV), A represents CH$_2$ or CO, B, X, Y and Z are the same and all represent CH, and R represents SO$_2$. In a sub-embodiment of the present disclosure, in formula (IV), A represents CH$_2$ or CO, B, X, Y and Z are the same and all represent CH, and R represents a piperazinylene group.

In an embodiment of the present disclosure, the compound of formula (IV) is also represented by any one of the following structural formulas:

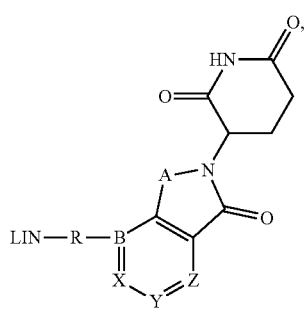

Formula (IV-1)

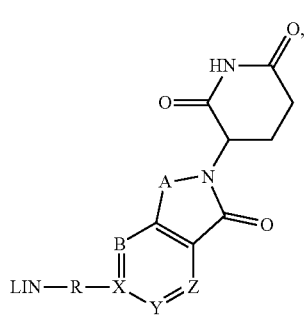

Formula (IV-2)

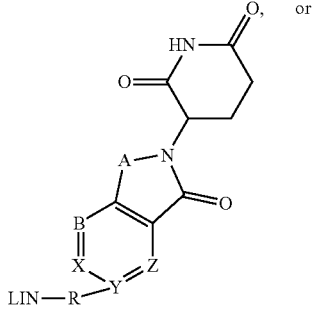

Formula (IV-3)

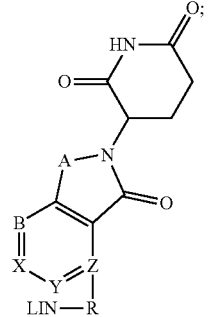

Formula (IV-4)

wherein the groups LIN, R, A, B, X, Y, and Z are as defined above.

In an embodiment of the present disclosure, formula (IV) is also the following structural formula:

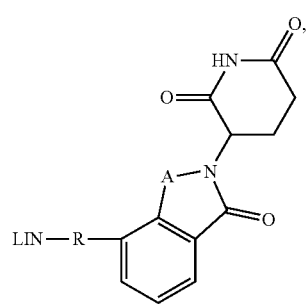

Formula (IV-5)

wherein the groups LIN, R and A are as defined above.

In an embodiment of the present disclosure, the SMBP is a small molecule drug that targets CDK4/6, ALK, Bcr-abl, PARP, ER, or BET.

In an embodiment of the present disclosure, preferably the small molecule compound SMBP capable of binding protein is: Ribociclib, Abemaciclib, Palbociclib, Crizotinib, Ceritinib, Brigatinib, Alectinib, Ensartinib, TAE684, ASP3026, GSK1838705A, AZD3463, Imatinib, Dasatinib, Bosutinib, Ponatinib, Olaparib, Niraparib, Rucaparib, Toremifene, Tamoxifen, 4-Hydroxyltamoxifen, JQ-1, I-BET762, or their derivatives.

In an embodiment of the present disclosure, the SMBP is a compound represented by any one of the following general formula or structural formula:

(Ia1)
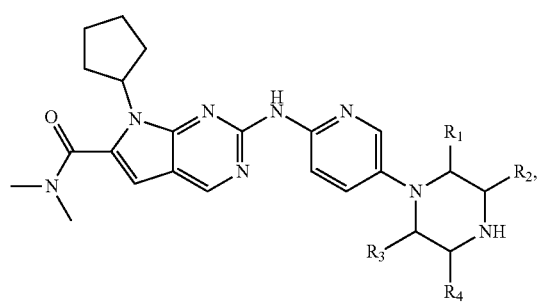
(Ib1)
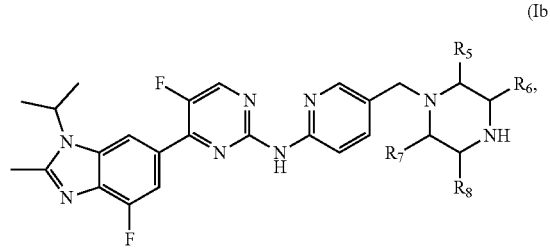
(Ic1)
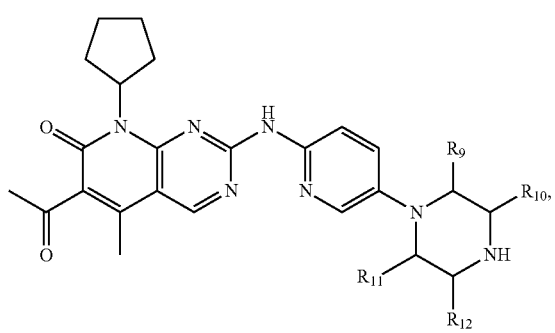
(Id1)
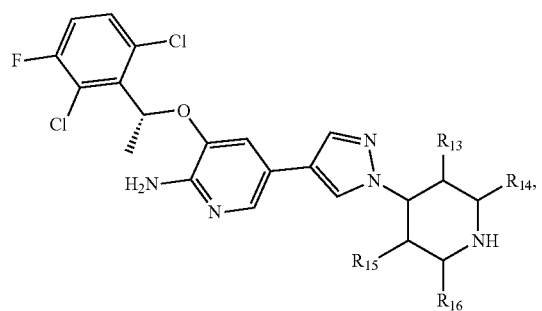
(Ie1)
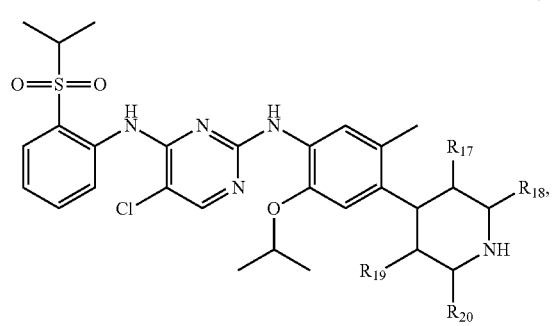
(If1)
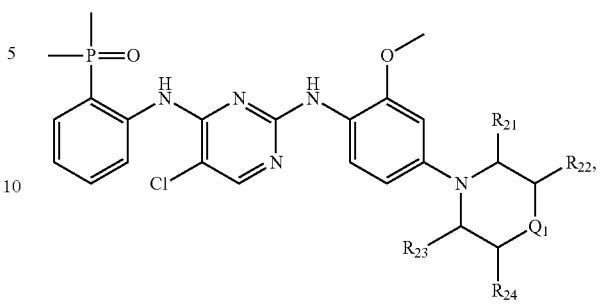
(Ig1)
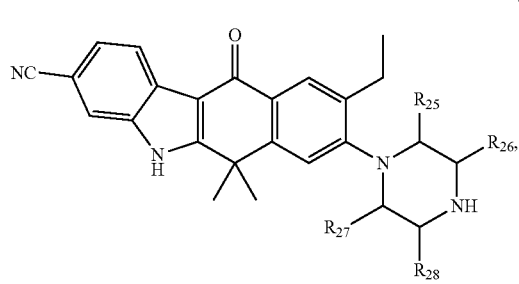
(Ih1)
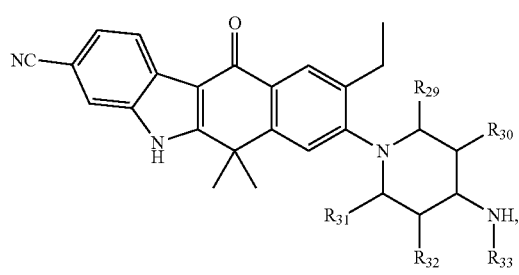
(Ii1)
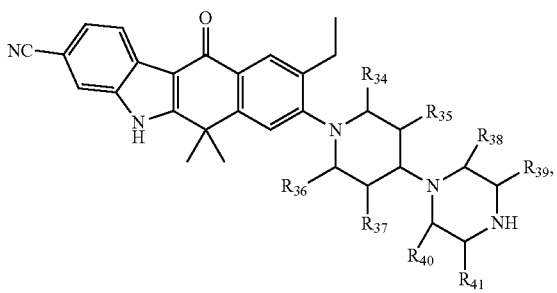
(Ij1)
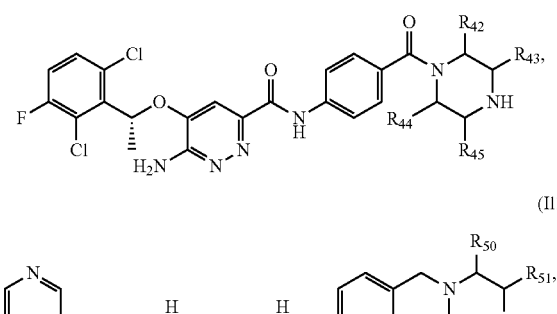
(Il1)
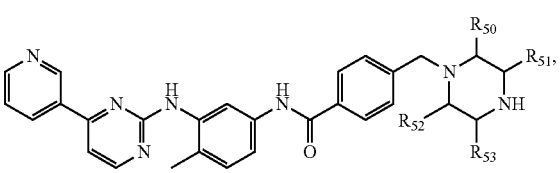

-continued
(Im1)
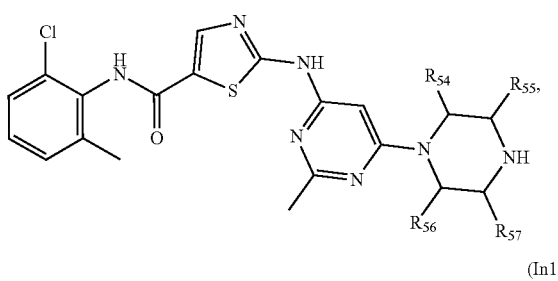
(In1)
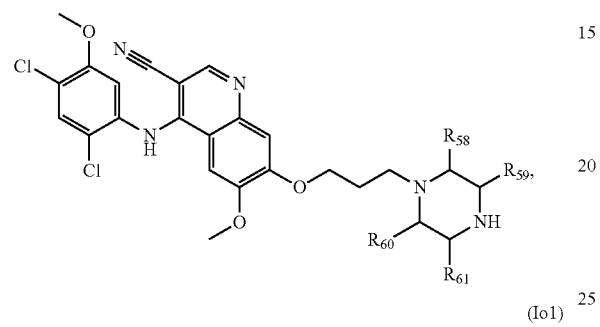
(Io1)
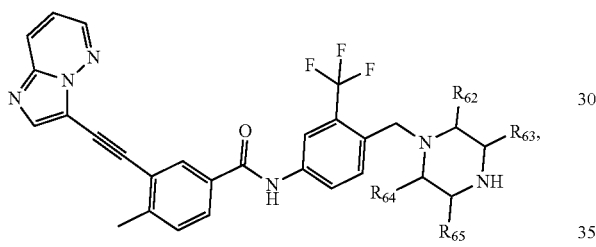
(Ip1)
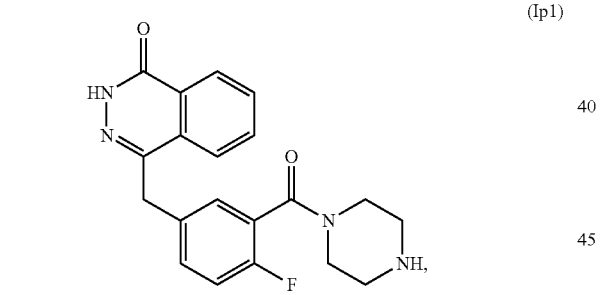
(Iq1)
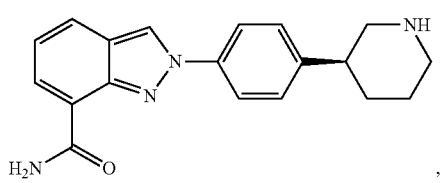
(Ir1)
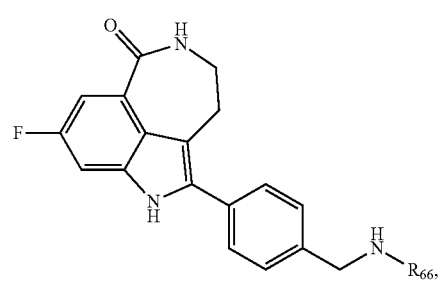
(Is1)
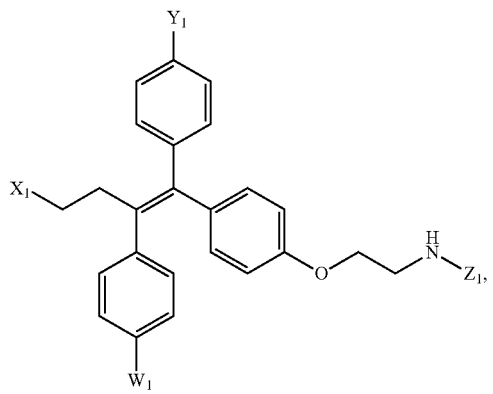
(It1)
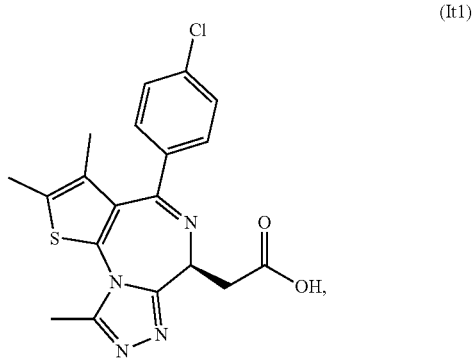
(Iu1)
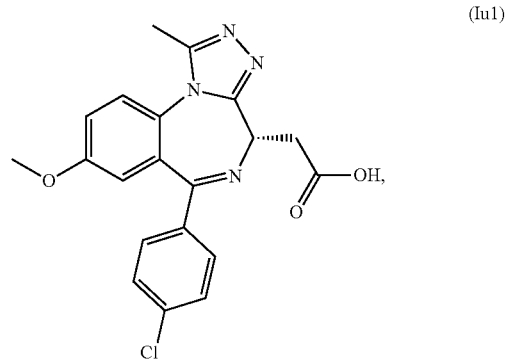
(Iv1)
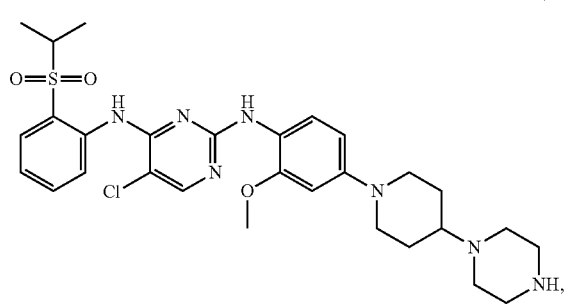

-continued (Iw1)
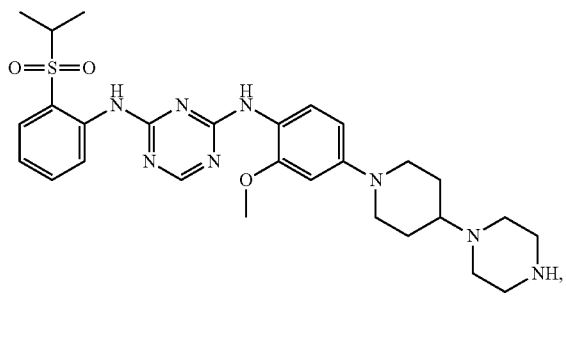

(It-31)
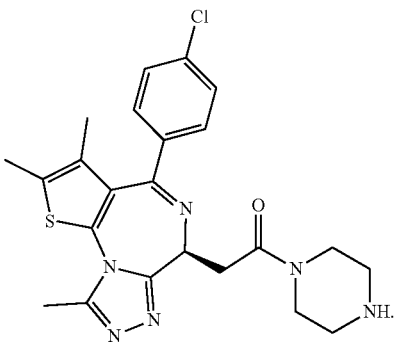

In an embodiment of the present disclosure, the SMBP is a compound represented by the following structural formula:

(Ix1)
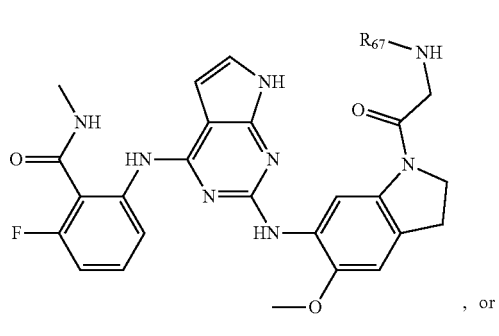, or (It-41)
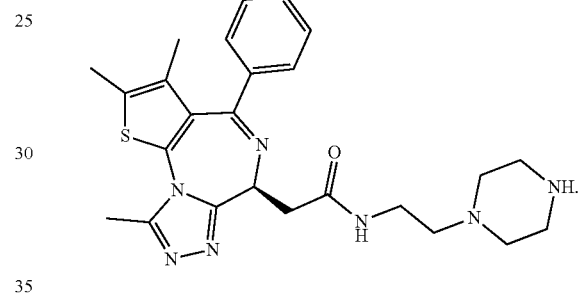

(Iy1)
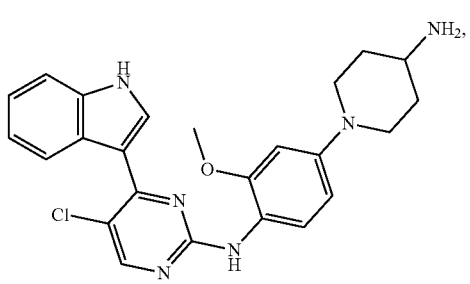

wherein, $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{34}$, $R_{35}$, $R_{36}$, $R_{37}$, $R_{38}$, $R_{39}$, $R_{40}$, $R_{41}$, $R_{42}$, $R_{43}$, $R_{44}$, $R_{45}$, $R_{50}$, $R_{51}$, $R_{52}$, $R_{53}$, $R_{54}$, $R_{55}$, $R_{56}$, $R_{57}$, $R_{58}$, $R_{59}$, $R_{60}$, $R_{61}$, $R_{62}$, $R_{63}$, $R_{64}$, $R_{65}$, $R_{66}$ are each independently H or methyl, and $R_{33}$ and $R_{67}$ each independently represent H, methyl or ethyl; and wherein in formula (If1), $Q_1$ is NH or CH, wherein CH is substituted by $NH_2$ or piperazinyl; and wherein in formula (Is1), $X_1$ is Cl or H, $Y_1$ is H or OH, $Z_1$ is H or methyl, and $W_1$ is H; or in an embodiment, $X_1$ is Cl or H, and $Y_1$ is H or OH, $Z_1$ is H or methyl, and $W_1$ is OH.

In an embodiment of the present disclosure, the SMBP is a compound represented by the following structural formula:

In an embodiment of the present disclosure, preferably, the W represents COOH, $NH_2$, $N_3$, CHO, halogen, methanesulfonyloxy, trifluoromethanesulfonyloxy, or p-toluenesulfonyloxy.

In an embodiment of formula (IV) of the present disclosure, preferably, the LIN represents: W—$C_{1-30}$ alkylene-, W—$(CH_2)_{n1}$—$(O(CH_2)_{n2})_{m1}$—, W—$(CH_2)_{n1}$—$(O(CH_2)_2)_{m1}$—$(O(CH_2))_3)_{m2}$—, W—$(CR_{a1}R_{a2})_{n1}$—$(O(CR_{a3}R_{a4})_{n2})_{m1}$—, W—$(CR_{a5}R_{a6})_{n1}$—$(O(CR_{a7}R_{a8})_{n2})_{m1}$—$(O(CR_{a9}R_{a10})_{n3})_{m2}$—, W—$(CH_2)_{n1}$—(CONH—$(CH_2)_{n2})_{m1}$—, W—$(CH_2)_{n1}$—(CONH—$(CH_2)_{n2})_{m1}$—$(O(CH_2)_{n3})_{m2}$—, W—$(CH_2)_{n1}$—$(O(CH_2)_{n2})_{m1}$—O—$(CH_2)_{n3}$—CONH—$(CH_2)_{n4}$—$(O(CH_2)_{n5})_{m2}$—O—$(CH_2)_{n6}$—, W—$(CR_{a11}R_{a12})_{n1}$—$(O(CR_{a13}R_{a14})_{n2})_{m1}$—O—$(CR_{a15}R_{a16})_{n3}$—CONH—$(CR_{a17}R_{a18})_{n4}$—$(O(CR_{a19}R_{a20})_{n5})_{m2}$—O—$(CR_{a21}R_{a22})_{n6}$—, W—$(CR_{a23}R_{a24})_{n1}$—CONH—$(O(CR_{a25}R_{a26})_{n2})_{m1}$—, W—$(CH_2)_{n1}$—(NHCO—$(CH_2)_{n2})_{m1}$—, W—$(CH_2)_{n1}$—(NHCO—$(CH_2)_{n2})_{m1}$—$(O(CH_2)_{n3})_{m2}$—, a straight or branched —W-alkylene-interrupted one or more times by one or more of alkynylene, alkenylene, cycloalkylene, arylene, heterocyclylene or heteroarylene or any combination thereof, or W—$(CH_2)_{n1}$—$(O(CH_2)_{n2})_{m1}$— whose backbone carbon chain is interrupted one or more times by one or more of arylene or heterocyclylene or heteroarylene or any combination thereof;

wherein $R_{a1}$, $R_{a2}$, $R_{a3}$, $R_{a4}$, $R_{a5}$, $R_{a6}$, $R_{a7}$, $R_{a8}$, $R_{a9}$, $R_{a10}$, $R_{a11}$, $R_{a12}$, $R_{a13}$, $R_{a14}$, $R_{a15}$, $R_{a16}$, $R_{a17}$, $R_{a18}$, $R_{a19}$, $R_{a20}$, $R_{a21}$, $R_{a22}$, $R_{a23}$, $R_{a24}$, $R_{a25}$, $R_{a26}$ each independently represent H, linear or branched $C_1$-$C_{10}$ alkyl or $C_3$-$C_{10}$ cycloalkyl, wherein in the same group LIN, $R_{a1}$, $R_{a2}$, $R_{a3}$, and $R_{a4}$ are not H at the same time, $R_{a5}$, $R_{a6}$, $R_{a7}$, $R_{a8}$, $R_{a9}$, and Rain are not H at the same time, Ran, $R_{a12}$, $R_{a13}$, $R_{a14}$, $R_{a15}$, $R_{a16}$, $R_{a17}$, $R_{a18}$, $R_{a19}$, $R_{a20}$, $R_{a21}$, and $R_{a22}$ are not H at the same time, or $R_{a23}$, $R_{a24}$, $R_{a25}$, and $R_{a26}$ are not H at the same time;

n1, n2, n3, n4, n5, n6, m1, m2 each independently represent an integer of 1, 2, 3, 4, 5, 6, 7, 8, 9, 10, 11, 12, 13, 14, 15, 16, 17, 18, 19, or 20; and W is as defined above.

In an embodiment of formula (IV) of the present disclosure, the LIN is preferably W—$C_{1-30}$ alkylene-. In an embodiment of the present disclosure, the LIN is preferably W-methylene or W—$C_{2-30}$ alkylene-, wherein the $C_{2-30}$ alkylene group is a linear or branched $C_{2-30}$ alkylene (preferably $C_2$-$C_{29}$ alkylene chain, $C_2$-$C_{28}$ alkylene chain, $C_2$-$C_{27}$ alkylene chain, $C_2$-$C_{26}$ alkylene chain, $C_2$-$C_{25}$ alkylene chain, $C_2$-$C_{24}$ alkylene chain, $C_2$-$C_{23}$ alkylene chain, $C_2$-$C_{22}$ alkylene chain, $C_2$-$C_{21}$ alkylene chain, $C_2$-$C_{20}$ alkylene chain, $C_2$-$C_{19}$ alkylene chain, $C_2$-$C_{18}$ alkylene chain Chain, $C_2$-$C_{17}$ alkylene chain, $C_2$-$C_{16}$ alkylene chain, $C_2$-$C_{15}$ alkylene chain, $C_2$-$C_{14}$ alkylene chain, $C_2$-$C_{13}$ alkylene chain, $C_2$-$C_{12}$ alkylene chain, $C_2$-$C_{11}$ alkylene chain, $C_2$-$C_{10}$ alkylene chain, $C_2$-$C_9$ alkylene chain, $C_2$-$C_8$ alkylene chain, $C_2$-$C_7$ alkylene chain, $C_2$-$C_6$ alkylene chain, $C_2$-$C_8$ alkylene chain, $C_2$-$C_4$ alkylene chain, or $C_2$-$C_3$ alkylene chain), and W is as defined above.

In an embodiment of formula (IV) of the present disclosure, the LIN preferably represents: W—$CH_2$—; W—$(CH_2)_2$—; W—$(CH_2)_3$—; W—$(CH_2)_4$—; W—$(CH_2)_5$—; W—$(CH_2)_6$—; W—$(CH_2)_7$—; W—$(CH_2)_8$—; W—$(CH_2)_9$—; W—$(CH_2)_{10}$—; W—$(CH_2)_{11}$—; W—$(CH_2)_{12}$—; W—$(CH_2)_{13}$—; W—$(CH_2)_{14}$—; W—$(CH_2)_{15}$—; W—$(CH_2)_{16}$—; W—$(CH_2)_{17}$—; W—$(CH_2)_{18}$—; W—$(CH_2)_{19}$—; W—$(CH_2)_{20}$—; W—$(CH_2)_{21}$—; W—$(CH_2)_{22}$—; W—$(CH_2)_{23}$—; W—$(CH_2)_{24}$—; W—$(CH_2)_{25}$—; W—$(CH_2)_{26}$—; W—$(CH_2)_{27}$—; W—$(CH_2)_{28}$—; W—$(CH_2)_{29}$—; or W—$(CH_2)_{30}$—, wherein W is as defined above.

In an embodiment of the present disclosure, the LIN is preferably W—$C_{2-40}$ alkylene-(preferably W—$C_{2-30}$ alkylene-), wherein the alkylene group is optionally interrupted one or more times by one or more of O, CONH, NHCO, NH, alkynylene, alkenylene, cycloalkylene, arylene, heterocyclylene, or heteroarylene or any combination thereof, and W is as defined above.

In an embodiment of formula (IV) of the present disclosure, the LIN preferably represents: W—$CH_2$—O—$(CH_2)_2$—, W—$CH_2$—$(O(CH_2)_2)_2$—, W—$CH_2$—$(O(CH_2)_2)_3$—, W—$CH_2$—$(O(CH_2)_2)_4$—, W—$CH_2$—$(O(CH_2)_2)_5$—, W—$CH_2$—$(O(CH_2)_2)_6$—, W—$CH_2$—$(O(CH_2)_2)_7$—, W—$CH_2$—$(O(CH_2)_2)_5$—, W—$CH_2$—$(O(CH_2)_2)_9$—, W—$CH_2$—$(O(CH_2)_2)_{10}$—, W—$(CH_2)_2$—O—$(CH_2)_2$—, W—$(CH_2)_2$—$(O(CH_2)_2)_2$—, W—$(CH_2)_2$—$(O(CH_2)_2)_3$—, W—$(CH_2)_2$—$(O(CH_2)_2)_4$—, W—$(CH_2)_2$—$(O(CH_2)_2)_5$—, W—$(CH_2)_2$—$(O(CH_2)_2)_6$—, W—$(CH_2)_2$—$(O(CH_2)_2)_7$—, W—$(CH_2)_2$—$(O(CH_2)_2)_5$—, W—$(CH_2)_2$—$(O(CH_2)_2)_9$—, W—$(CH_2)_2$—$(O(CH_2)_2)_{10}$—, W—$(CH_2)_3$—O—$(CH_2)_2$—, W—$(CH_2)_3$—$(O(CH_2)_2)_2$—, W—$(CH_2)_3$—$(O(CH_2)_2)_3$—, W—$(CH_2)_3$—$(O(CH_2)_2)_4$—, W—$(CH_2)_3$—$(O(CH_2)_2)_5$—, W—$(CH_2)_3$—$(O(CH_2)_2)_6$—, W—$(CH_2)_3$—$(O(CH_2)_2)_7$—, W—$(CH_2)_3$—$(O(CH_2)_2)_8$—, W—$(CH_2)_3$—$(O(CH_2)_2)_9$—, W—$(CH_2)_3$—$(O(CH_2)_2)_{10}$—, W—$(CH_2)_4$—O—$(CH_2)_2$—, W—$(CH_2)_4$—$(O(CH_2)_2)_2$—, W—$(CH_2)_4$—$(O(CH_2)_2)_3$—, W—$(CH_2)_4$—$(O(CH_2)_2)_4$—, W—$(CH_2)_4$—$(O(CH_2)_2)_5$—, W—$(CH_2)_4$—$(O(CH_2)_2)_6$—, W—$(CH_2)_4$—$(O(CH_2)_2)_7$—, W—$(CH_2)_4$—$(O(CH_2)_2)_8$—, W—$(CH_2)_4$—$(O(CH_2)_2)_9$—, W—$(CH_2)_4$—$(O(CH_2)_2)_{10}$—, W—$CH_2$—O—$(CH_2)_3$—, W—$CH_2$—$(O(CH_2)_3)_2$—, W—$CH_2$—$(O(CH_2)_3)_3$—, W—$CH_2$—$(O(CH_2)_3)_4$—, W—$CH_2$—$(O(CH_2)_3)_5$—, W—$CH_2$—$(O(CH_2)_3)_6$—, W—$CH_2$—$(O(CH_2)_3)_7$—, W—$CH_2$—$(O(CH_2)_3)_8$—, W—$CH_2$—$(O(CH_2)_3)_9$—, W—$CH_2$—$(O(CH_2)_3)_{10}$—, W—$(CH_2)_2$—O—$(CH_2)_3$—, W—$(CH_2)_2$—$(O(CH_2)_3)_2$—, W—$(CH_2)_2$—$(O(CH_2)_3)_3$—, W—$(CH_2)_2$—$(O(CH_2)_3)_4$—, W—$(CH_2)_2$—$(O(CH_2)_3)_5$—, W—$(CH_2)_2$—$(O(CH_2)_3)_6$—, W—$(CH_2)_2$—$(O(CH_2)_3)_7$—, W—$(CH_2)_2$—$(O(CH_2)_3)_8$—, W—$(CH_2)_2$—$(O(CH_2)_3)_9$—, W—$(CH_2)_2$—$(O(CH_2)_3)_{10}$—, W—$(CH_2)_3$—O—$(CH_2)_3$—, W—$(CH_2)_3$—$(O(CH_2)_3)_2$—, W—$(CH_2)_3$—$(O(CH_2)_3)_3$—, W—$(CH_2)_3$—$(O(CH_2)_3)_4$—, W—$(CH_2)_3$—$(O(CH_2)_3)_5$—, W—$(CH_2)_3$—$(O(CH_2)_3)_6$—, W—$(CH_2)_3$—$(O(CH_2)_3)_7$—, W—$(CH_2)_3$—$(O(CH_2)_3)_8$—, W—$(CH_2)_3$—$(O(CH_2)_3)_9$—, W—$(CH_2)_3$—$(O(CH_2)_3)_{10}$—, W—$CH_2$—O—$(CH_2)_2$—O—$(CH_2)_3$—, W—$CH_2$—$(O(CH_2)_2)_2$—$(O(CH_2)_3)_2$—, W—$CH_2$—$(O(CH_2)_2)_3$—$(O(CH_2)_3)_3$—, W—$CH_2$—$(O(CH_2)_2)_4$—$(O(CH_2)_3)_4$—, W—$CH_2$—$(O(CH_2)_2)_5$—$(O(CH_2)_3)_5$—, W—$CH_2$—$(O(CH_2)_2)_6$—$(O(CH_2)_3)_6$—, W—$(CH_2)_2$—O—$(CH_2)_2$—O—$(CH_2)_3$—, W—$(CH_2)_2$—$(O(CH_2)_2)_2$—$(O(CH_2)_3)_2$—, W—$(CH_2)_2$—$(O(CH_2)_2)_3$—$(O(CH_2)_3)_3$—, W—$(CH_2)_2$—$(O(CH_2)_2)_4$—$(O(CH_2)_3)_4$—, W—$(CH_2)_2$—$(O(CH_2)_2)_5$—$(O(CH_2)_3)_5$—, W—$(CH_2)_2$—$(O(CH_2)_2)_6$—$(O(CH_2)_3)_6$—, W—$(CH_2)_3$—O—$(CH_2)_2$—O—$(CH_2)_3$—, W—$(CH_2)_3$—$(O(CH_2)_2)_2$—$(O(CH_2)_3)_2$—, W—$(CH_2)_3$—$(O(CH_2)_2)_3$—$(O(CH_2)_3)_3$—, W—$(CH_2)_3$—$(O(CH_2)_2)_4$—$(O(CH_2)_3)_4$—, W—$(CH_2)_3$—$(O(CH_2)_2)_5$—$(O(CH_2)_3)_5$—, W—$(CH_2)_3$—$(O(CH_2)_2)_6$—$(O(CH_2)_3)_6$—, W—$CH_2$—O—$(CH_2)_3$—O—$(CH_2)_2$—, W—$CH_2$—$(O(CH_2)_3)_2$—$(O(CH_2)_2)_2$—, W—$CH_2$—$(O(CH_2)_3)_3$—$(O(CH_2)_2)_3$—, W—$CH_2$—$(O(CH_2)_3)_4$—$(O(CH_2)_2)_4$—, W—$CH_2$—$(O(CH_2)_3)_5$—$(O(CH_2)_2)_5$—, W—$CH_2$—$(O(CH_2)_3)_6$—$(O(CH_2)_2)_6$—, W—$(CH_2)_2$—O—$(CH_2)_3$—O—$(CH_2)_2$—, W—$(CH_2)_2$—$(O(CH_2)_3)_2$—$(O(CH_2)_2)_2$—, W—$(CH_2)_2$—$(O(CH_2)_3)_3$—$(O(CH_2)_2)_3$—, W—$(CH_2)_2$—$(O(CH_2)_3)_4$—$(O(CH_2)_2)_4$—, W—$(CH_2)_2$—$(O(CH_2)_3)_5$—$(O(CH_2)_2)_5$—, W—$(CH_2)_2$—$(O(CH_2)_3)_6$—$(O(CH_2)_2)_6$—, W—$(CH_2)_3$—O—$(CH_2)_3$—O—$(CH_2)_2$—, W—$(CH_2)_3$—$(O(CH_2)_3)_2$—$(O(CH_2)_2)_2$—, W—$(CH_2)_3$—$(O(CH_2)_3)_3$—$(O(CH_2)_2)_3$—, W—$(CH_2)_3$—$(O(CH_2)_3)_4$—$(O(CH_2)_2)_4$—, W—$(CH_2)_3$—$(O(CH_2)_3)_5$—$(O(CH_2)_2)_5$—, W—$(CH_2)_3$—$(O(CH_2)_3)_6$—$(O(CH_2)_2)_6$—, W—$CH_2$—O—$(CH_2)_2$—O—$CH_2$—, W—$(CH_2)_2$—O—$(CH_2)_2$—O—$CH_2$—, W—$(CH_2)_2$—$(O(CH_2)_2)_2$—O—$(CH_2)_3$—, W—$(CH_2)_2$—$(O(CH_2)_2)_3$—O—$(CH_2)_3$—, W—$(CH_2)_2$—$(O(CH_2)_2)_4$—O—$(CH_2)_3$—, W—$(CH_2)_5$—$(O(CH_2)_2)_2$—O—$(CH_2)_5$—, or W—$(CH_2)_5$—$(O(CH_2)_2)_2$—O—$(CH_2)_6$—; and W is as defined above.

In an embodiment of formula (IV) of the present disclosure, the LIN preferably represents: W-alkylene-, the alkylene (preferably a $C_{1-30}$ alkylene chain, particularly preferably a $C_2$-$C_{29}$ alkylene chain, $C_2$-$C_{28}$ alkylene chain, $C_2$-$C_{27}$ alkylene chain, $C_2$-$C_{26}$ alkylene chain, $C_2$-$C_{25}$ alkylene chain, $C_2$-$C_{24}$ alkylene chain, $C_2$-$C_{23}$ alkylene chain, $C_2$-$C_{22}$ alkylene chain, $C_2$-$C_{21}$ alkylene chain, $C_2$-$C_{20}$ alkylene chain, $C_2$-$C_{19}$ alkylene chain, $C_2$-$C_{18}$ alkylene chain, $C_2$-$C_{17}$ alkylene chain, $C_2$-$C_{16}$ alkylene chain, $C_2$-$C_{18}$ alkylene chain, $C_2$-$C_{14}$ alkylene chain, $C_2$-$C_{13}$ alkylene chain, $C_2$-$C_{12}$ alkylene chain, $C_2$-$C_{11}$ alkylene chain, $C_2$-$C_{10}$ alkylene chain, $C_2$-$C_9$ alkylene chain, $C_2$-$C_8$ alkylene chain, $C_2$-$C_7$ alkylene chain, $C_2$-$C_6$ alkylene chain, $C_2$-$C_5$ alkylene chain, $C_2$-$C_4$ alkylene chain, or $C_2$-$C_3$ alkylene chain) is a linear or branched alkylene chain substituted one or more times by one or more substituents selected from hydroxyl, amino, mercapto, halogen or a combination thereof; wherein the group W is as defined above.

In an embodiment of formula (IV) of the present disclosure, the LIN preferably represents: W—C$_{1-30}$ alkylene-, and the C$_{1-30}$ alkylene group is a linear or branched C$_1$-C$_{30}$ alkylene chain (preferably C$_1$-C$_{29}$ alkylene chain, C$_1$-C$_{28}$ alkylene chain, C$_1$-C$_{27}$ alkylene chain, C$_1$-C$_{26}$ alkylene chain, C$_1$-C$_{25}$ alkylene chain, C$_1$-C$_{24}$ alkylene chain, C$_1$-C$_{23}$ alkylene chain, C$_1$-C$_{22}$ alkylene chain, C$_1$-C$_{21}$ alkylene chain, C$_1$-C$_{20}$ alkylene chain, C$_1$-C$_{19}$ alkylene chain, C$_1$-C$_{18}$ alkylene chain, C$_1$-C$_{17}$ alkylene chain, C$_1$-C$_{16}$ alkylene chain, C$_1$-C$_{15}$ alkylene chain, C$_1$-C$_{14}$ alkylene chain, C$_1$-C$_{13}$ alkylene chain, C$_1$-C$_{12}$ alkylene chain, C$_1$-C$_{11}$ alkylene chain, C$_1$-C$_{10}$ alkylene chain, C$_1$-C$_9$ alkylene chain, C$_1$-C$_8$ alkylene chain, C$_1$-C$_7$ alkylene chain, C$_1$-C$_6$ alkylene chain, C$_1$-C$_5$ alkylene chain, C$_1$-C$_4$ alkylene chain, C$_1$-C$_3$ alkylene chain, or C$_1$-C$_2$ alkylene chain) substituted by one or more substituents selected from hydroxyl, amino, mercapto, halogen or a combination thereof, wherein the group W is as defined above. In a sub-embodiment of formula (IV) of the present disclosure, the number of the substituents can be, for example, 1-30, 1-25, 1-20, 1-15, 1-10, 1-9, 1-8, 1-7, 1-6, 1-5, 1-4, 1-3, or 1-2, or 20, 19, 18, 17, 16, 15, 14, 13, 12, 11, 10, 9, 8, 7, 6, 5, 4, 3, 2, or 1.

In an embodiment of formula (IV) of the present disclosure, the LIN represents: W—(CH$_2$)$_{n11}$-triazolylene-(CH$_2$)$_{n12}$—, W—(CH$_2$)$_{n11}$-triazolylene-(CH$_2$)$_{n12}$—(O(CH$_2$)$_{n13}$)$_{m11}$—, W—(CH$_2$)$_{n11}$—(O(CH$_2$)$_{n12}$)$_{m11}$—O—(CH$_2$)$_{n13}$-triazolylene-(CH$_2$)$_{n14}$—(O(CH$_2$)$_{n15}$)$_{m12}$—O—(CH$_2$)$_{n16}$—, W—(CH$_2$)$_{n11}$-triazolylene-(CH$_2$)$_{n12}$—(O(CH$_2$)$_{n13}$)$_{m11}$—O—(CH$_2$)$_{n14}$—, or W—(CH$_2$)$_{n11}$—(O(CH$_2$)$_{n12}$)$_{m11}$—O—(CH$_2$)$_{n13}$-triazolylidene-(CH$_2$)$_{n14}$—;

wherein n11, n12, n13, n14, n15, n16, m11, m12 each independently represent an integer of 1, 2, 3, 4, 5, 6, 7, 8, 9, 10, 11, 12, 13, 14, 15, 16, 17, 18, 19, or 20;

wherein the group W is as defined above.

In an embodiment of formula (IV) of the present disclosure, the LIN preferably represents: W—(CH$_2$)$_3$-triazolylene-(CH$_2$)$_5$—, W—(CH$_2$)$_2$-triazolylene-(CH$_2$)$_5$—, W—CH$_2$-triazolylene-(CH$_2$)$_5$—, W—(CH$_2$)$_2$-triazolylene-(CH$_2$)$_4$—, W—(CH$_2$)$_3$-triazolylene-(CH$_2$)$_2$—O(CH$_2$)$_2$—, W—(CH$_2$)$_2$-triazolylene-(CH$_2$)$_2$—O(CH$_2$)$_2$—, or W—CH$_2$-triazolylene-(CH$_2$)$_2$—O(CH$_2$)$_2$—, wherein the group W is as defined above.

In an embodiment of formula (IV) of the present disclosure, the LIN preferably represents:

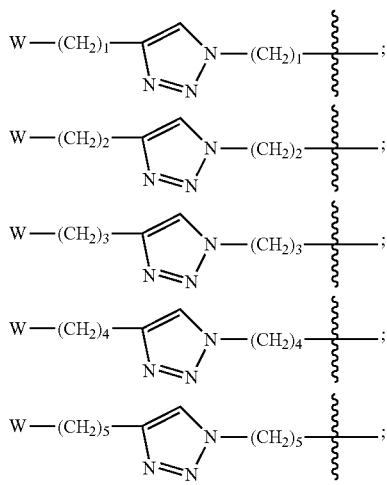

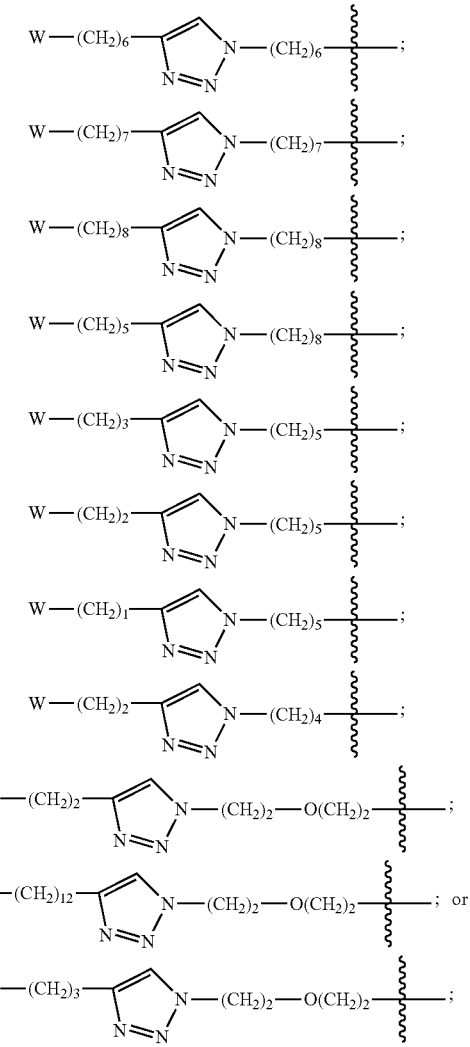

wherein the group W is as defined above.

In an embodiment of formula (IV) of the present disclosure, the LIN preferably represents: W—CH$_2$CONHCH$_2$—, W—(CH$_2$)$_2$CONH(CH$_2$)$_2$—, W—(CH$_2$)$_3$CONH(CH$_2$)$_3$—, W—(CH$_2$)$_3$CONH(CH$_2$)$_4$—, W—(CH$_2$)$_4$CONH(CH$_2$)$_4$—, W—(CH$_2$)$_5$CONH(CH$_2$)$_5$—, W—(CH$_2$)$_6$CONH(CH$_2$)$_7$—, W—(CH$_2$)$_6$CONH(CH$_2$)$_6$—, W—(CH$_2$)$_7$CONH(CH$_2$)$_7$—, W—(CH$_2$)$_8$CONH(CH$_2$)$_8$, W—(CH$_2$)$_9$CONH(CH$_2$)$_9$—, W—(CH$_2$)$_{10}$CONH(CH$_2$)$_{10}$—, W—(CH$_2$)$_2$CONH(CH$_2$)$_5$—, W—(CH$_2$)$_2$CONH(CH$_2$)$_3$—, W—(CH$_2$)$_2$CONH(CH$_2$)$_4$—, or W—(CH$_2$)$_2$CONH(CH$_2$)$_2$—O—(CH$_2$)$_2$—, wherein the group W is as defined above.

In an embodiment of formula (IV) of the present disclosure, the LIN preferably represents: W—CH$_2$NHCOCH$_2$—, W—(CH$_2$)$_2$NHCO(CH$_2$)$_2$—, W—(CH$_2$)$_3$NHCO(CH$_2$)$_3$—, W—(CH$_2$)$_3$NHCO(CH$_2$)$_4$—, W—(CH$_2$)$_4$NHCO(CH$_2$)$_4$—, W—(CH$_2$)$_5$NHCO(CH$_2$)$_5$—, W—(CH$_2$)$_6$NHCO(CH$_2$)$_7$—, W—(CH$_2$)$_6$NHCO(CH$_2$)$_6$—, W—(CH$_2$)$_7$NHCO(CH$_2$)$_7$—, W—(CH$_2$)$_8$NHCO(CH$_2$)$_8$, W—(CH$_2$)$_9$NHCO(CH$_2$)$_9$—, W—(CH$_2$)$_{10}$NHCO(CH$_2$)$_{10}$—, W—(CH$_2$)$_2$NHCO(CH$_2$)$_5$—, W—(CH$_2$)$_2$NHCO(CH$_2$)$_3$—, W—(CH$_2$)$_2$NHCO(CH$_2$)$_4$—, W—(CH$_2$)$_4$NHCO(CH$_2$)$_8$—, or W—(CH$_2$)$_2$NHCO(CH$_2$)$_2$—O—(CH$_2$)$_2$—, wherein the group W is as defined above.

In an embodiment of the formula (IV) of the present disclosure, the LIN represents: W—(CH$_2$)$_4$NHCOCH$_2$—, W—(CH$_2$)$_2$—O—CH$_2$-phenylene-CH$_2$—O—(CH$_2$)$_2$—, W—CH$_2$-phenylene-CH$_2$—, W—(CH$_2$)$_3$-phenylene-(CH$_2$)$_3$—, W—(CH$_2$)$_2$—O—CH$_2$-piperazinylene-CH$_2$—O—(CH$_2$)$_2$—, or W—(CH$_2$)$_3$-piperazinylene-(CH$_2$)$_3$—.

In one embodiment of the present disclosure, when the LIN in the compound of formula (I) is represented by —U-alkylene- in which the alkylene of —U-alkylene- is connected to SMBP, and the group U is connected to ULM, the corresponding group LIN in the compound of formula (IV) as an intermediate correspondingly represents alkyl-W$_2$—, wherein the group W$_2$ corresponds to the group U of the compound of formula (I) and is connected to the group R in the formula (IV), wherein the alkyl group corresponds to the monovalent group derived from the alkylene group in the —U-alkylene group, and has the definition of the corresponding monovalent group derived from the alkylene group as defined above, that is, the alkyl is a linear or branched alkyl group optionally interrupted one or more times by one or more groups selected from: O, CONH, NHCO, NH, alkynylene, alkenylene, cycloalkylene, arylene, heterocyclylene, heteroarylene, or any combination thereof, wherein the linear or branched alkyl group is optionally substituted with one or more substituents, and W$_2$ corresponds to the group U, and represents CO or NH, or W$_2$ is absent.

Herein, when the LIN in the compound of formula (IV) represents alkyl-W$_2$—, the group W$_2$ is connected to the group R in the formula (IV), and the alkyl group may further connect with the aforementioned small molecule compound SMBP capable of binding proteins by conventional methods well known to those skilled in the art to form the compounds of formula (I) as defined above.

Particularly preferred are the following compounds of formula (IV) in Table 3 of the present disclosure and their salts:

TABLE 3

The compounds of formula (IV) of the present disclosure

| Compound ID | Name of the compound |
| --- | --- |
| SIAIS1204137 | 2-(2-((2-(2,6-dioxopiperidin-3-yl)-1,3-dioxoisoindolin-4-yl)thio)ethoxy)acetic acid |
| | 3-(2-((2-(2,6-dioxopiperidin-3-yl)-1,3-dioxoisoindolin-4-yl)thio)ethoxy)propanoic acid |
| SIAIS1204139 | 2-(2-(2-((2-(2,6-dioxopiperidin-3-yl)-1,3-dioxoisoindolin-4-yl)thio)ethoxy)ethoxy)acetic acid |
| | 3-(2-(2-((2-(2,6-dioxopiperidin-3-yl)-1,3-dioxoisoindolin-4-yl)thio)ethoxy)ethoxy)propanoic acid |
| SIAIS1204141 | 2-(2-(2-(2-((2-(2,6-dioxopiperidin-3-yl)-1,3-dioxoisoindolin-4-yl)thio)ethoxy)ethoxy)ethoxy)acetic acid |
| | 3-(2-(2-(2-((2-(2,6-dioxopiperidin-3-yl)-1,3-dioxoisoindolin-4-yl)thio)ethoxy)ethoxy)ethoxy)propanoic acid |
| SIAIS1204147 | 14-((2-(2,6-dioxopiperidin-3-yl)-1,3-dioxoisoindolin-4-yl)thio)-3,6,9,12-tetraoxatetradecanoic acid |
| | 1-((2-(2,6-dioxopiperidin-3-yl)-1,3-dioxoisoindolin-4-yl)thio)-3,6,9,12-tetraoxapentadecan-15-oic acid |
| SIAIS1204149 | 17-((2-(2,6-dioxopiperidin-3-yl)-1,3-dioxoisoindolin-4-yl)thio)-3,6,9,12,15-pentaoxaheptadecanoic acid |
| | 1-((2-(2,6-dioxopiperidin-3-yl)-1,3-dioxoisoindolin-4-yl)thio)-3,6,9,12,15-pentaoxaoctadecan-18-oic acid |
| | 3-(3-((2-(2,6-dioxopiperidin-3-yl)-1,3-dioxoisoindolin-4-yl)thio)propoxy)propanoic acid |
| | 3-(3-(2-((2-(2,6-dioxopiperidin-3-yl)-1,3-dioxoisoindolin-4-yl)thio)ethoxy)propoxy)propanoic acid |
| | 3-(2-(3-((2-(2,6-dioxopiperidin-3-yl)-1,3-dioxoisoindolin-4-yl)thio)propoxy)ethoxy)propanoic acid |
| | 3-(3-(2-((2-(2,6-dioxopiperidin-3-yl)-1,3-dioxoisoindolin-4-yl)thio)ethoxy)propanamido)propanoic acid |
| SIAIS151045 | 2-((2-(2,6-dioxopiperidin-3-yl)-1,3-dioxoisoindolin-4-yl)thio)acetic acid |
| SIAIS151138B | 3-((2-(2,6-dioxopiperidin-3-yl)-1,3-dioxoisoindolin-4-yl)thio)propanoic acid |
| SIAIS151139B | 4-((2-(2,6-dioxopiperidin-3-yl)-1,3-dioxoisoindolin-4-yl)thio)butanoic acid |
| SIAIS151140B | 5-((2-(2,6-dioxopiperidin-3-yl)-1,3-dioxoisoindolin-4-yl)thio)pentanoic acid |
| SIAIS151141B | 6-((2-(2,6-dioxopiperidin-3-yl)-1,3-dioxoisoindolin-4-yl)thio)hexanoic acid |
| SIAIS151142B | 7-((2-(2,6-dioxopiperidin-3-yl)-1,3-dioxoisoindolin-4-yl)thio)heptanoic acid |
| | 8-((2-(2,6-dioxopiperidin-3-yl)-1,3-dioxoisoindolin-4-yl)thio)octanoic acid |
| | 9-((2-(2,6-dioxopiperidin-3-yl)-1,3-dioxoisoindolin-4-yl)thio)nonanoic acid |
| | 10-((2-(2,6-dioxopiperidin-3-yl)-1,3-dioxoisoindolin-4-yl)thio)decanoic acid |
| | 11-((2-(2,6-dioxopiperidin-3-yl)-1,3-dioxoisoindolin-4-yl)thio)undecanoic acid |
| | 12-((2-(2,6-dioxopiperidin-3-yl)-1,3-dioxoisoindolin-4-yl)thio)dodecanoic acid |
| | 13-((2-(2,6-dioxopiperidin-3-yl)-1,3-dioxoisoindolin-4-yl)thio)tridecanoic acid |
| | 14-((2-(2,6-dioxopiperidin-3-yl)-1,3-dioxoisoindolin-4-yl)thio)tetradecanoic acid |
| | 15-((2-(2,6-dioxopiperidin-3-yl)-1,3-dioxoisoindolin-4-yl)thio)pentadecanoic acid |
| | 3-(6-((2-(2,6-dioxopiperidin-3-yl)-1,3-dioxoisoindolin-4-yl)thio)hexanamido)propanoic acid |
| | 4-((2-(2-aminoethoxy)ethyl)thio)-2-(2,6-dioxopiperidin-3-yl)isoindoline-1,3-dione |
| SIAIS213066 | 4-((2-(2-(2-aminoethoxy)ethoxy)ethyl)thio)-2-(2,6-dioxopiperidin-3-yl)isoindoline-1,3-dione |
| SIAIS213073 | N-(4-aminobutyl)-2-((2-(2,6-dioxopiperidin-3-yl)-1,3-dioxoisoindolin-4-yl)thio)acetamide |
| SIAIS213092 | N-(4-aminobutyl)-2-((2-(2,6-dioxopiperidin-3-yl)-1-oxoisoindolin-4-yl)thio)acetamide |
| | 4-((3-(2-(3-aminopropoxy)ethoxy)propyl)thio)-2-(2,6-dioxopiperidin-3-yl)isoindoline-1,3-dione |

TABLE 3-continued

The compounds of formula (IV) of the present disclosure

| Compound ID | Name of the compound |
|---|---|
| | 4-((2-(2-(2-(2-aminoethoxy)ethoxy)ethoxy)ethyl)thio)-2-(2,6-dioxopiperidin-3-yl)isoindoline-1,3-dione |
| | 4-((14-amino-3,6,9,12-tetraoxatetradecyl)thio)-2-(2,6-dioxopiperidin-3-yl)isoindoline-1,3-dione |
| | 4-((17-amino-3,6,9,12,15-pentaoxaheptadecyl)thio)-2-(2,6-dioxopiperidin-3-yl)isoindoline-1,3-dione |
| | 4-((2-(2-((2-(2,6-dioxopiperidin-3-yl)-1,3-dioxoisoindolin-4-yl)thio)ethoxy)ethyl)amino)-4-oxobutanoic acid |
| SIAIS171026 | 4-((2-aminoethyl)thio)-2-(2,6-dioxopiperidin-3-yl)isoindoline-1,3-dione |
| SIAIS171025 | 4-((3-aminopropyl)thio)-2-(2,6-dioxopiperidin-3-yl)isoindoline-1,3-dione |
| SIAIS171023 | 4-((4-aminobutyl)thio)-2-(2,6-dioxopiperidin-3-yl)isoindoline-1,3-dione |
| SIAIS171027 | 4-((5-aminopentyl)thio)-2-(2,6-dioxopiperidin-3-yl)isoindoline-1,3-dione |
| SIAIS171028 | 4-((6-aminohexyl)thio)-2-(2,6-dioxopiperidin-3-yl)isoindoline-1,3-dione |
| SIAIS171033 | 4-((7-aminoheptyl)thio)-2-(2,6-dioxopiperidin-3-yl)isoindoline-1,3-dione |
| SIAIS171047 | 4-((8-aminooctyl)thio)-2-(2,6-dioxopiperidin-3-yl)isoindoline-1,3-dione |
| | 4-((5-((2-(2,6-dioxopiperidin-3-yl)-1,3-dioxoisoindolin-4-yl)thio)pentyl)amino)-4-oxobutanoic acid |
| | 4-((2-(2-azidoethoxy)ethyl)thio)-2-(2,6-dioxopiperidin-3-yl)isoindoline-1,3-dione |
| | 4-((2-(2-(2-azidoethoxy)ethoxy)ethyl)thio)-2-(2,6-dioxopiperidin-3-yl)isoindoline-1,3-dione |
| | 4-((2-(2-(2-(2-azidoethoxy)ethoxy)ethoxy)ethyl)thio)-2-(2,6-dioxopiperidin-3-yl)isoindoline-1,3-dione |
| | 4-((14-azido-3,6,9,12-tetraoxatetradecyl)thio)-2-(2,6-dioxopiperidin-3-yl)isoindoline-1,3-dione |
| | 4-((17-azido-3,6,9,12,15-pentaoxaheptadecyl)thio)-2-(2,6-dioxopiperidin-3-yl)isoindoline-1,3-dione |
| | 4-(1-(2-(2-((2-(2,6-dioxopiperidin-3-yl)-1,3-dioxoisoindolin-4-yl)thio)ethoxy)ethyl)-1H-1,2,3-triazol-4-yl)butanoic acid |
| SIAIS213163 | 4-((2-azidoethyl)thio)-2-(2,6-dioxopiperidin-3-yl)isoindoline-1,3-dione |
| SIAIS213161 | 4-((3-azidopropyl)thio)-2-(2,6-dioxopiperidin-3-yl)isoindoline-1,3-dione |
| | 4-((4-azidobutyl)thio)-2-(2,6-dioxopiperidin-3-yl)isoindoline-1,3-dione |
| | 4-((5-azidopentyl)thio)-2-(2,6-dioxopiperidin-3-yl)isoindoline-1,3-dione |
| | 4-((6-azidohexyl)thio)-2-(2,6-dioxopiperidin-3-yl)isoindoline-1,3-dione |
| | 4-((7-azidoheptyl)thio)-2-(2,6-dioxopiperidin-3-yl)isoindoline-1,3-dione |
| | 4-(1-(5-((2-(2,6-dioxopiperidin-3-yl)-1,3-dioxoisoindolin-4-yl)thio)pentyl)-1H-1,2,3-triazol-4-yl)butanoic acid |
| | 2-(2,6-dioxopiperidin-3-yl)-4-(2-(2-iodoethoxy)ethylthio)isoindoline-1,3-dione |
| | 2-(2,6-dioxopiperidin-3-yl)-4-(2-(2-(2-iodoethoxy)ethoxy)ethylthio)isoindoline-1,3-dione |
| | 2-(2,6-dioxopiperidin-3-yl)-4-(2-(2-(2-(2-iodoethoxy)ethoxy)ethoxy)ethylthio)isoindoline-1,3-dione |
| | 2-(2,6-dioxopiperidin-3-yl)-4-(2-(2-(2-(2-(2-iodoethoxy)ethoxy)ethoxy)ethoxy)ethylthio)isoindoline-1,3-dione |
| | 2-(2,6-dioxopiperidin-3-yl)-4-(2-(2-(2-(2-(2-(2-iodoethoxy)ethoxy)ethoxy)ethoxy)ethoxy)ethylthio)isoindoline-1,3-dione |
| | 2-(2,6-dioxopiperidin-3-yl)-4-(3-(3-iodopropoxy)propylthio)isoindoline-1,3-dione |
| | 2-(2,6-dioxopiperidin-3-yl)-4-(2-(3-(3-iodopropoxy)propoxy)ethylthio)isoindoline-1,3-dione |
| | 2-(2,6-dioxopiperidin-3-yl)-4-(2-iodoethylthio)isoindoline-1,3-dione |
| | 2-(2,6-dioxopiperidin-3-yl)-4-(3-iodopropylthio)isoindoline-1,3-dione |
| | 2-(2,6-dioxopiperidin-3-yl)-4-(4-iodobutylthio)isoindoline-1,3-dione |
| | 2-(2,6-dioxopiperidin-3-yl)-4-(5-iodopentylthio)isoindoline-1,3-dione |
| | 2-(2,6-dioxopiperidin-3-yl)-4-(6-iodohexylthio)isoindoline-1,3-dione |
| | 2-(2,6-dioxopiperidin-3-yl)-4-(7-iodoheptylthio)isoindoline-1,3-dione |
| | 4-(2-(2-bromoethoxy)ethylthio)-2-(2,6-dioxopiperidin-3-yl)isoindoline-1,3-dione |
| | 4-(2-(2-(2-bromoethoxy)ethoxy)ethylthio)-2-(2,6-dioxopiperidin-3-yl)isoindoline-1,3-dione |
| | 4-(2-(2-(2-(2-bromoethoxy)ethoxy)ethoxy)ethylthio)-2-(2,6-dioxopiperidin-3-yl)isoindoline-1,3-dione |
| | 4-(2-(2-(2-(2-(2-bromoethoxy)ethoxy)ethoxy)ethoxy)ethylthio)-2-(2,6-dioxopiperidin-3-yl)isoindoline-1,3-dione |
| | 4-(2-(2-(2-(2-(2-(2-bromoethoxy)ethoxy)ethoxy)ethoxy)ethoxy)ethylthio)-2-(2,6-dioxopiperidin-3-yl)isoindoline-1,3-dione |
| | 4-(3-(3-bromopropoxy)propylthio)-2-(2,6-dioxopiperidin-3-yl)isoindoline-1,3-dione |
| | 4-(2-(3-(3-bromopropoxy)propoxy)ethylthio)-2-(2,6-dioxopiperidin-3-yl)isoindoline-1,3-dione |
| SIAIS213162 | 4-(2-bromoethylthio)-2-(2,6-dioxopiperidin-3-yl)isoindoline-1,3-dione |
| SIAIS213159 | 4-(3-bromopropylthio)-2-(2,6-dioxopiperidin-3-yl)isoindoline-1,3-dione |
| SIAIS213165 | 4-(4-bromobutylthio)-2-(2,6-dioxopiperidin-3-yl)isoindoline-1,3-dione |
| SIAIS213166 | 4-(5-bromopentylthio)-2-(2,6-dioxopiperidin-3-yl)isoindoline-1,3-dione |
| | 4-(6-bromohexylthio)-2-(2,6-dioxopiperidin-3-yl)isoindoline-1,3-dione |
| | 4-(7-bromoheptylthio)-2-(2,6-dioxopiperidin-3-yl)isoindoline-1,3-dione |
| | 2-(2-(2-(2,6-dioxopiperidin-3-yl)-1,3-dioxoisoindolin-4-ylthio)ethoxy)ethyl 4-methylbenzenesulfonate |
| | 2-(2-(2-(2-(2,6-dioxopiperidin-3-yl)-1,3-dioxoisoindolin-4-ylthio)ethoxy)ethoxy)ethyl 4-methylbenzenesulfonate |

TABLE 3-continued

The compounds of formula (IV) of the present disclosure

| Compound ID | Name of the compound |
| --- | --- |
| | 2-(2-(2-(2-(2-(2,6-dioxopiperidin-3-yl)-1,3-dioxoisoindolin-4-ylthio)ethoxy)ethoxy)ethoxy)ethyl 4-methylbenzenesulfonate |
| | 2-(2-(2-(2-(2-(2-(2,6-dioxopiperidin-3-yl)-1,3-dioxoisoindolin-4-ylthio)ethoxy)ethoxy)ethoxy)ethoxy)ethyl 4-methylbenzenesulfonate |
| | 2-(2-(2-(2-(2-(2-(2-(2,6-dioxopiperidin-3-yl)-1,3-dioxoisoindolin-4-ylthio)ethoxy)ethoxy)ethoxy)ethoxy)ethoxy)ethyl 4-methylbenzenesulfonate |
| | 3-(3-(2-(2,6-dioxopiperidin-3-yl)-1,3-dioxoisoindolin-4-ylthio)propoxy)propyl 4-methylbenzenesulfonate |
| | 3-(3-(2-(2,6-dioxopiperidin-3-yl)-1,3-dioxoisoindolin-4-ylthio)ethoxy)propoxy)propyl 4-methylbenzenesulfonate |
| | 2-(2-(2,6-dioxopiperidin-3-yl)-1,3-dioxoisoindolin-4-ylthio)ethyl 4-methylbenzenesulfonate |
| | 3-(2-(2,6-dioxopiperidin-3-yl)-1,3-dioxoisoindolin-4-ylthio)propyl 4-methylbenzenesulfonate |
| | 4-(2-(2,6-dioxopiperidin-3-yl)-1,3-dioxoisoindolin-4-ylthio)butyl 4-methylbenzenesulfonate |
| | 5-(2-(2,6-dioxopiperidin-3-yl)-1,3-dioxoisoindolin-4-ylthio)pentyl 4-methylbenzenesulfonate |
| | 6-(2-(2,6-dioxopiperidin-3-yl)-1,3-dioxoisoindolin-4-ylthio)hexyl 4-methylbenzenesulfonate |
| | 7-(2-(2,6-dioxopiperidin-3-yl)-1,3-dioxoisoindolin-4-ylthio)heptyl 4-methylbenzenesulfonate |
| | 2-(2-((2-(2,6-dioxopiperidin-3-yl)-1,3-dioxoisoindolin-4-yl)sulfinyl)ethoxy)acetic acid |
| | 3-(2-((2-(2,6-dioxopiperidin-3-yl)-1,3-dioxoisoindolin-4-yl)sulfinyl)ethoxy)propanoic acid |
| | 2-(2-(2-((2-(2,6-dioxopiperidin-3-yl)-1,3-dioxoisoindolin-4-yl)sulfinyl)ethoxy)ethoxy)acetic acid |
| | 3-(2-(2-((2-(2,6-dioxopiperidin-3-yl)-1,3-dioxoisoindolin-4-yl)sulfinyl)ethoxy)ethoxy)propanoic acid |
| | 2-(2-(2-(2-((2-(2,6-dioxopiperidin-3-yl)-1,3-dioxoisoindolin-4-yl)sulfinyl)ethoxy)ethoxy)ethoxy)acetic acid |
| | 3-(2-(2-(2-((2-(2,6-dioxopiperidin-3-yl)-1,3-dioxoisoindolin-4-yl)sulfinyl)ethoxy)ethoxy)ethoxy)propanoic acid |
| | 14-((2-(2,6-dioxopiperidin-3-yl)-1,3-dioxoisoindolin-4-yl)sulfinyl)-3,6,9,12-tetraoxatetradecanoic acid |
| | 1-((2-(2,6-dioxopiperidin-3-yl)-1,3-dioxoisoindolin-4-yl)sulfinyl)-3,6,9,12-tetraoxapentadecan-15-oic acid |
| | 17-((2-(2,6-dioxopiperidin-3-yl)-1,3-dioxoisoindolin-4-yl)sulfinyl)-3,6,9,12,15-pentaoxaheptadecanoic acid |
| | 1-((2-(2,6-dioxopiperidin-3-yl)-1,3-dioxoisoindolin-4-yl)sulfinyl)-3,6,9,12,15-pentaoxaoctadecan-18-oic acid |
| | 3-(3-(2-((2-(2,6-dioxopiperidin-3-yl)-1,3-dioxoisoindolin-4-yl)sulfinyl)ethoxy)propanamido)propanoic acid |
| SIAIS151107 | 2-((2-(2,6-dioxopiperidin-3-yl)-1,3-dioxoisoindolin-4-yl)sulfinyl)acetic acid |
| | 3-((2-(2,6-dioxopiperidin-3-yl)-1,3-dioxoisoindolin-4-yl)sulfinyl)propanoic acid |
| | 4-((2-(2,6-dioxopiperidin-3-yl)-1,3-dioxoisoindolin-4-yl)sulfinyl)butanoic acid |
| | 5-((2-(2,6-dioxopiperidin-3-yl)-1,3-dioxoisoindolin-4-yl)sulfinyl)pentanoic acid |
| | 6-((2-(2,6-dioxopiperidin-3-yl)-1,3-dioxoisoindolin-4-yl)sulfinyl)hexanoic acid |
| | 7-((2-(2,6-dioxopiperidin-3-yl)-1,3-dioxoisoindolin-4-yl)sulfinyl)heptanoic acid |
| | 8-((2-(2,6-dioxopiperidin-3-yl)-1,3-dioxoisoindolin-4-yl)sulfinyl)octanoic acid |
| | 9-((2-(2,6-dioxopiperidin-3-yl)-1,3-dioxoisoindolin-4-yl)sulfinyl)nonanoic acid |
| | 10-((2-(2,6-dioxopiperidin-3-yl)-1,3-dioxoisoindolin-4-yl)sulfinyl)decanoic acid |
| | 11-((2-(2,6-dioxopiperidin-3-yl)-1,3-dioxoisoindolin-4-yl)sulfinyl)undecanoic acid |
| | 12-((2-(2,6-dioxopiperidin-3-yl)-1,3-dioxoisoindolin-4-yl)sulfinyl)dodecanoic acid |
| | 13-((2-(2,6-dioxopiperidin-3-yl)-1,3-dioxoisoindolin-4-yl)sulfinyl)tridecanoic acid |
| | 14-((2-(2,6-dioxopiperidin-3-yl)-1,3-dioxoisoindolin-4-yl)sulfinyl)tetradecanoic acid |
| | 15-((2-(2,6-dioxopiperidin-3-yl)-1,3-dioxoisoindolin-4-yl)sulfinyl)pentadecanoic acid |
| | 3-(6-((2-(2,6-dioxopiperidin-3-yl)-1,3-dioxoisoindolin-4-yl)sulfinyl)hexanamido)propanoic acid |
| | 4-((2-(2-aminoethoxy)ethyl)sulfinyl)-2-(2,6-dioxopiperidin-3-yl)isoindoline-1,3-dione |
| | 4-((2-(2-(2-aminoethoxy)ethoxy)ethyl)sulfinyl)-2-(2,6-dioxopiperidin-3-yl)isoindoline-1,3-dione |
| | 4-((2-(2-(2-(2-aminoethoxy)ethoxy)ethoxy)ethyl)sulfinyl)-2-(2,6-dioxopiperidin-3-yl)isoindoline-1,3-dione |
| | 4-((14-amino-3,6,9,12-tetraoxatetradecyl)sulfinyl)-2-(2,6-dioxopiperidin-3-yl)isoindoline-1,3-dione |
| | 4-((17-amino-3,6,9,12,15-pentaoxaheptadecyl)sulfinyl)-2-(2,6-dioxopiperidin-3-yl)isoindoline-1,3-dione |
| | 4-((2-(2-((2-(2,6-dioxopiperidin-3-yl)-1,3-dioxoisoindolin-4-yl)sulfinyl)ethoxy)ethyl)amino)-4-oxobutanoic acid |
| | 4-((2-aminoethyl)sulfinyl)-2-(2,6-dioxopiperidin-3-yl)isoindoline-1,3-dione |
| | 4-((3-aminopropyl)sulfinyl)-2-(2,6-dioxopiperidin-3-yl)isoindoline-1,3-dione |
| | 4-((4-aminobutyl)sulfinyl)-2-(2,6-dioxopiperidin-3-yl)isoindoline-1,3-dione |

TABLE 3-continued

The compounds of formula (IV) of the present disclosure

| Compound ID | Name of the compound |
|---|---|
| | 4-((5-aminopentyl)sulfinyl)-2-(2,6-dioxopiperidin-3-yl)isoindoline-1,3-dione |
| | 4-((6-aminohexyl)sulfinyl)-2-(2,6-dioxopiperidin-3-yl)isoindoline-1,3-dione |
| | 4-((7-aminoheptyl)sulfinyl)-2-(2,6-dioxopiperidin-3-yl)isoindoline-1,3-dione |
| | 4-((8-aminooctyl)sulfinyl)-2-(2,6-dioxopiperidin-3-yl)isoindoline-1,3-dione |
| | 4-((5-((2-(2,6-dioxopiperidin-3-yl)-1,3-dioxoisoindolin-4-yl)sulfinyl)pentyl)amino)-4-oxobutanoic acid |
| | 4-((2-(2-azidoethoxy)ethyl)sulfinyl)-2-(2,6-dioxopiperidin-3-yl)isoindoline-1,3-dione |
| | 4-((2-(2-(2-azidoethoxy)ethoxy)ethyl)sulfinyl)-2-(2,6-dioxopiperidin-3-yl)isoindoline-1,3-dione |
| | 4-((2-(2-(2-(2-azidoethoxy)ethoxy)ethoxy)ethyl)sulfinyl)-2-(2,6-dioxopiperidin-3-yl)isoindoline-1,3-dione |
| | 4-((14-azido-3,6,9,12-tetraoxatetradecyl)sulfinyl)-2-(2,6-dioxopiperidin-3-yl)isoindoline-1,3-dione |
| | 4-((17-azido-3,6,9,12,15-pentaoxaheptadecyl)sulfinyl)-2-(2,6-dioxopiperidin-3-yl)isoindoline-1,3-dione |
| | 4-(1-(2-(2-((2-(2,6-dioxopiperidin-3-yl)-1,3-dioxoisoindolin-4-yl)sulfinyl)ethoxy)ethyl)-1H-1,2,3-triazol-4-yl)butanoic acid |
| | 4-((2-azidoethyl)sulfinyl)-2-(2,6-dioxopiperidin-3-yl)isoindoline-1,3-dione |
| | 4-((3-azidopropyl)sulfinyl)-2-(2,6-dioxopiperidin-3-yl)isoindoline-1,3-dione |
| | 4-((4-azidobutyl)sulfinyl)-2-(2,6-dioxopiperidin-3-yl)isoindoline-1,3-dione |
| | 4-((5-azidopentyl)sulfinyl)-2-(2,6-dioxopiperidin-3-yl)isoindoline-1,3-dione |
| | 4-((6-azidohexyl)sulfinyl)-2-(2,6-dioxopiperidin-3-yl)isoindoline-1,3-dione |
| | 4-((7-azidoheptyl)sulfinyl)-2-(2,6-dioxopiperidin-3-yl)isoindoline-1,3-dione |
| | 4-(1-(5-((2-(2,6-dioxopiperidin-3-yl)-1,3-dioxoisoindolin-4-yl)sulfinyl)pentyl)-1H-1,2,3-triazol-4-yl)butanoic acid |
| | 2-(2,6-dioxopiperidin-3-yl)-4-(2-(2-iodoethoxy)ethylsulfinyl)isoindoline-1,3-dione |
| | 2-(2,6-dioxopiperidin-3-yl)-4-(2-(2-(2-iodoethoxy)ethoxy)ethylsulfinyl)isoindoline-1,3-dione |
| | 2-(2,6-dioxopiperidin-3-yl)-4-(2-(2-(2-(2-iodoethoxy)ethoxy)ethoxy)ethylsulfinyl)isoindoline-1,3-dione |
| | 2-(2,6-dioxopiperidin-3-yl)-4-(2-(2-(2-(2-(2-iodoethoxy)ethoxy)ethoxy)ethoxy)ethylsulfinyl)isoindoline-1,3-dione |
| | 2-(2,6-dioxopiperidin-3-yl)-4-(2-(2-(2-(2-(2-(2-iodoethoxy)ethoxy)ethoxy)ethoxy)ethoxy)ethylsulfinyl)isoindoline-1,3-dione |
| | 2-(2,6-dioxopiperidin-3-yl)-4-(2-iodoethylsulfinyl)isoindoline-1,3-dione |
| | 2-(2,6-dioxopiperidin-3-yl)-4-(3-iodopropylsulfinyl)isoindoline-1,3-dione |
| | 2-(2,6-dioxopiperidin-3-yl)-4-(4-iodobutylsulfinyl)isoindoline-1,3-dione |
| | 2-(2,6-dioxopiperidin-3-yl)-4-(5-iodopentylsulfinyl)isoindoline-1,3-dione |
| | 2-(2,6-dioxopiperidin-3-yl)-4-(6-iodohexylsulfinyl)isoindoline-1,3-dione |
| | 2-(2,6-dioxopiperidin-3-yl)-4-(7-iodoheptylsulfinyl)isoindoline-1,3-dione |
| | 4-(2-(2-bromoethoxy)ethylsulfinyl)-2-(2,6-dioxopiperidin-3-yl)isoindoline-1,3-dione |
| | 4-(2-(2-(2-bromoethoxy)ethoxy)ethylsulfinyl)-2-(2,6-dioxopiperidin-3-yl)isoindoline-1,3-dione |
| | 4-(2-(2-(2-(2-bromoethoxy)ethoxy)ethoxy)ethylsulfinyl)-2-(2,6-dioxopiperidin-3-yl)isoindoline-1,3-dione |
| | 4-(2-(2-(2-(2-(2-bromoethoxy)ethoxy)ethoxy)ethoxy)ethylsulfinyl)-2-(2,6-dioxopiperidin-3-yl)isoindoline-1,3-dione |
| | 4-(2-(2-(2-(2-(2-(2-bromoethoxy)ethoxy)ethoxy)ethoxy)ethoxy)ethylsulfinyl)-2-(2,6-dioxopiperidin-3-yl)isoindoline-1,3-dione |
| | 4-(bromoethylsulfinyl)-2-(2,6-dioxopiperidin-3-yl)isoindoline-1,3-dione |
| | 4-(3-bromopropylsulfinyl)-2-(2,6-dioxopiperidin-3-yl)isoindoline-1,3-dione |
| | 4-(4-bromobutylsulfinyl)-2-(2,6-dioxopiperidin-3-yl)isoindoline-1,3-dione |
| | 4-(5-bromopentylsulfinyl)-2-(2,6-dioxopiperidin-3-yl)isoindoline-1,3-dione |
| | 4-(6-bromohexylsulfinyl)-2-(2,6-dioxopiperidin-3-yl)isoindoline-1,3-dione |
| | 4-(7-bromoheptylsulfinyl)-2-(2,6-dioxopiperidin-3-yl)isoindoline-1,3-dione |
| | 2-(2-(2-(2,6-dioxopiperidin-3-yl)-1,3-dioxoisoindolin-4-ylsulfinyl)ethoxy)ethyl 4-methylbenzenesulfonate |
| | 2-(2-(2-(2-(2,6-dioxopiperidin-3-yl)-1,3-dioxoisoindolin-4-ylsulfinyl)ethoxy)ethoxy)ethyl 4-methylbenzenesulfonate |
| | 2-(2-(2-(2-(2-(2,6-dioxopiperidin-3-yl)-1,3-dioxoisoindolin-4-ylsulfinyl)ethoxy)ethoxy)ethoxy)ethyl 4-methylbenzenesulfonate |
| | 2-(2-(2-(2-(2-(2-(2,6-dioxopiperidin-3-yl)-1,3-dioxoisoindolin-4-ylsulfinyl)ethoxy)ethoxy)ethoxy)ethoxy)ethyl 4-methylbenzenesulfonate |
| | 2-(2-(2-(2-(2-(2-(2-(2,6-dioxopiperidin-3-yl)-1,3-dioxoisoindolin-4-ylsulfinyl)ethoxy)ethoxy)ethoxy)ethoxy)ethoxy)ethyl 4-methylbenzenesulfonate |
| | 2-(2-(2,6-dioxopiperidin-3-yl)-1,3-dioxoisoindolin-4-ylsulfinyl)ethyl 4-methylbenzenesulfonate |
| | 3-(2-(2,6-dioxopiperidin-3-yl)-1,3-dioxoisoindolin-4-ylsulfinyl)propyl 4-methylbenzenesulfonate |
| | 4-(2-(2,6-dioxopiperidin-3-yl)-1,3-dioxoisoindolin-4-ylsulfinyl)butyl 4-methylbenzenesulfonate |
| | 5-(2-(2,6-dioxopiperidin-3-yl)-1,3-dioxoisoindolin-4-ylsulfinyl)pentyl 4-methylbenzenesulfonate |
| | 6-(2-(2,6-dioxopiperidin-3-yl)-1,3-dioxoisoindolin-4-ylsulfinyl)hexyl 4-methylbenzenesulfonate |

TABLE 3-continued

The compounds of formula (IV) of the present disclosure

| Compound ID | Name of the compound |
|---|---|
| | 7-(2-(2,6-dioxopiperidin-3-yl)-1,3-dioxoisoindolin-4-ylsulfinyl)heptyl 4-methylbenzenesulfonate |
| | 2-(2-((2-(2,6-dioxopiperidin-3-yl)-1,3-dioxoisoindolin-4-yl)sulfonyl)ethoxy)acetic acid |
| | 3-(2-((2-(2,6-dioxopiperidin-3-yl)-1,3-dioxoisoindolin-4-yl)sulfonyl)ethoxy)propanoic acid |
| | 2-(2-(2-((2-(2,6-dioxopiperidin-3-yl)-1,3-dioxoisoindolin-4-yl)sulfonyl)ethoxy)ethoxy)acetic acid |
| | 3-(2-(2-((2-(2,6-dioxopiperidin-3-yl)-1,3-dioxoisoindolin-4-yl)sulfonyl)ethoxy)ethoxy)propanoic acid |
| | 2-(2-(2-(2-((2-(2,6-dioxopiperidin-3-yl)-1,3-dioxoisoindolin-4-yl)sulfonyl)ethoxy)ethoxy)ethoxy)acetic acid |
| | 3-(2-(2-(2-((2-(2,6-dioxopiperidin-3-yl)-1,3-dioxoisoindolin-4-yl)sulfonyl)ethoxy)ethoxy)ethoxy)propanoic acid |
| | 14-((2-(2,6-dioxopiperidin-3-yl)-1,3-dioxoisoindolin-4-yl)sulfonyl)-3,6,9,12-tetraoxatetradecanoic acid |
| | 1-((2-(2,6-dioxopiperidin-3-yl)-1,3-dioxoisoindolin-4-yl)sulfonyl)-3,6,9,12-tetraoxapentadecan-15-oic acid |
| | 17-((2-(2,6-dioxopiperidin-3-yl)-1,3-dioxoisoindolin-4-yl)sulfonyl)-3,6,9,12,15-pentaoxaheptadecanoic acid |
| | 1-((2-(2,6-dioxopiperidin-3-yl)-1,3-dioxoisoindolin-4-yl)sulfonyl)-3,6,9,12,15-pentaoxaoctadecan-18-oic acid |
| | 3-(3-(2-((2-(2,6-dioxopiperidin-3-yl)-1,3-dioxoisoindolin-4-yl)sulfonyl)ethoxy)propanamido)propanoic acid |
| SIAIS151106 | 2-((2-(2,6-dioxopiperidin-3-yl)-1,3-dioxoisoindolin-4-yl)sulfonyl)acetic acid |
| | 3-((2-(2,6-dioxopiperidin-3-yl)-1,3-dioxoisoindolin-4-yl)sulfonyl)propanoic acid |
| | 4-((2-(2,6-dioxopiperidin-3-yl)-1,3-dioxoisoindolin-4-yl)sulfonyl)butanoic acid |
| | 5-((2-(2,6-dioxopiperidin-3-yl)-1,3-dioxoisoindolin-4-yl)sulfonyl)pentanoic acid |
| | 6-((2-(2,6-dioxopiperidin-3-yl)-1,3-dioxoisoindolin-4-yl)sulfonyl)hexanoic acid |
| | 7-((2-(2,6-dioxopiperidin-3-yl)-1,3-dioxoisoindolin-4-yl)sulfonyl)heptanoic acid |
| | 8-((2-(2,6-dioxopiperidin-3-yl)-1,3-dioxoisoindolin-4-yl)sulfonyl)octanoic acid |
| | 9-((2-(2,6-dioxopiperidin-3-yl)-1,3-dioxoisoindolin-4-yl)sulfonyl)nonanoic acid |
| | 10-((2-(2,6-dioxopiperidin-3-yl)-1,3-dioxoisoindolin-4-yl)sulfonyl)decanoic acid |
| | 11-((2-(2,6-dioxopiperidin-3-yl)-1,3-dioxoisoindolin-4-yl)sulfonyl)undecanoic acid |
| | 12-((2-(2,6-dioxopiperidin-3-yl)-1,3-dioxoisoindolin-4-yl)sulfonyl)dodecanoic acid |
| | 13-((2-(2,6-dioxopiperidin-3-yl)-1,3-dioxoisoindolin-4-yl)sulfonyl)tridecanoic acid |
| | 14-((2-(2,6-dioxopiperidin-3-yl)-1,3-dioxoisoindolin-4-yl)sulfonyl)tetradecanoic acid |
| | 15-((2-(2,6-dioxopiperidin-3-yl)-1,3-dioxoisoindolin-4-yl)sulfonyl)pentadecanoic acid |
| | 3-(6-((2-(2,6-dioxopiperidin-3-yl)-1,3-dioxoisoindolin-4-yl)sulfonyl)hexanamido)propanoic acid |
| | 4-((2-(2-aminoethoxy)ethyl)sulfonyl)-2-(2,6-dioxopiperidin-3-yl)isoindoline-1,3-dione |
| | 4-((2-(2-(2-aminoethoxy)ethoxy)ethyl)sulfonyl)-2-(2,6-dioxopiperidin-3-yl)isoindoline-1,3-dione |
| | 4-((2-(2-(2-(2-aminoethoxy)ethoxy)ethoxy)ethyl)sulfonyl)-2-(2,6-dioxopiperidin-3-yl)isoindoline-1,3-dione |
| | 4-((14-amino-3,6,9,12-tetraoxatetradecyl)sulfonyl)-2-(2,6-dioxopiperidin-3-yl)isoindoline-1,3-dione |
| | 4-((17-amino-3,6,9,12,15-pentaoxaheptadecyl)sulfonyl)-2-(2,6-dioxopiperidin-3-yl)isoindoline-1,3-dione |
| | 4-((2-(2-((2-(2,6-dioxopiperidin-3-yl)-1,3-dioxoisoindolin-4-yl)sulfonyl)ethoxy)ethyl)amino)-4-oxobutanoic acid |
| | 4-((2-aminoethyl)sulfonyl)-2-(2,6-dioxopiperidin-3-yl)isoindoline-1,3-dione |
| | 4-((3-aminopropyl)sulfonyl)-2-(2,6-dioxopiperidin-3-yl)isoindoline-1,3-dione |
| | 4-((4-aminobutyl)sulfonyl)-2-(2,6-dioxopiperidin-3-yl)isoindoline-1,3-dione |
| | 4-((5-aminopentyl)sulfonyl)-2-(2,6-dioxopiperidin-3-yl)isoindoline-1,3-dione |
| | 4-((6-aminohexyl)sulfonyl)-2-(2,6-dioxopiperidin-3-yl)isoindoline-1,3-dione |
| | 4-((7-aminoheptyl)sulfonyl)-2-(2,6-dioxopiperidin-3-yl)isoindoline-1,3-dione |
| | 4-((8-aminooctyl)sulfonyl)-2-(2,6-dioxopiperidin-3-yl)isoindoline-1,3-dione |
| | 4-((5-((2-(2,6-dioxopiperidin-3-yl)-1,3-dioxoisoindolin-4-yl)sulfonyl)pentyl)amino)-4-oxobutanoic acid |
| | 4-((2-(2-azidoethoxy)ethyl)sulfonyl)-2-(2,6-dioxopiperidin-3-yl)isoindoline-1,3-dione |
| | 4-((2-(2-(2-azidoethoxy)ethoxy)ethyl)sulfonyl)-2-(2,6-dioxopiperidin-3-yl)isoindoline-1,3-dione |
| | 4-((2-(2-(2-(2-azidoethoxy)ethoxy)ethoxy)ethyl)sulfonyl)-2-(2,6-dioxopiperidin-3-yl)isoindoline-1,3-dione |
| | 4-((14-azido-3,6,9,12-tetraoxatetradecyl)sulfonyl)-2-(2,6-dioxopiperidin-3-yl)isoindoline-1,3-dione |
| | 4-((17-azido-3,6,9,12,15-pentaoxaheptadecyl)sulfonyl)-2-(2,6-dioxopiperidin-3-yl)isoindoline-1,3-dione |
| | 4-(1-(2-(2-((2-(2,6-dioxopiperidin-3-yl)-1,3-dioxoisoindolin-4-yl)sulfonyl)ethoxy)ethyl)-1H-1,2,3-triazol-4-yl)butanoic acid |
| | 4-((2-azidoethyl)sulfonyl)-2-(2,6-dioxopiperidin-3-yl)isoindoline-1,3-dione |
| | 4-((3-azidopropyl)sulfonyl)-2-(2,6-dioxopiperidin-3-yl)isoindoline-1,3-dione |

TABLE 3-continued

The compounds of formula (IV) of the present disclosure

| Compound ID | Name of the compound |
|---|---|
| | 4-((4-azidobutyl)sulfonyl)-2-(2,6-dioxopiperidin-3-yl)isoindoline-1,3-dione |
| | 4-((5-azidopentyl)sulfonyl)-2-(2,6-dioxopiperidin-3-yl)isoindoline-1,3-dione |
| | 4-((6-azidohexyl)sulfonyl)-2-(2,6-dioxopiperidin-3-yl)isoindoline-1,3-dione |
| | 4-((7-azidoheptyl)sulfonyl)-2-(2,6-dioxopiperidin-3-yl)isoindoline-1,3-dione |
| | 4-(1-(5-((2-(2,6-dioxopiperidin-3-yl)-1,3-dioxoisoindolin-4-yl)sulfonyl)pentyl)-1H-1,2,3-triazol-4-yl)butanoic acid |
| | 2-(2,6-dioxopiperidin-3-yl)-4-(2-(2-iodoethoxy)ethylsulfonyl)isoindoline-1,3-dione |
| | 2-(2,6-dioxopiperidin-3-yl)-4-(2-(2-(2-iodoethoxy)ethoxy)ethylsulfonyl)isoindoline-1,3-dione |
| | 2-(2,6-dioxopiperidin-3-yl)-4-(2-(2-(2-(2-iodoethoxy)ethoxy)ethoxy)ethylsulfonyl)isoindoline-1,3-dione |
| | 2-(2,6-dioxopiperidin-3-yl)-4-(2-(2-(2-(2-(2-iodoethoxy)ethoxy)ethoxy)ethoxy)ethylsulfonyl)isoindoline-1,3-dione |
| | 2-(2,6-dioxopiperidin-3-yl)-4-(2-(2-(2-(2-(2-(2-iodoethoxy)ethoxy)ethoxy)ethoxy)ethoxy)ethylsulfonyl)isoindoline-1,3-dione |
| | 2-(2,6-dioxopiperidin-3-yl)-4-(2-iodoethylsulfonyl)isoindoline-1,3-dione |
| | 2-(2,6-dioxopiperidin-3-yl)-4-(3-iodopropylsulfonyl)isoindoline-1,3-dione |
| | 2-(2,6-dioxopiperidin-3-yl)-4-(4-iodobutylsulfonyl)isoindoline-1,3-dione |
| | 2-(2,6-dioxopiperidin-3-yl)-4-(5-iodopentylsulfonyl)isoindoline-1,3-dione |
| | 2-(2,6-dioxopiperidin-3-yl)-4-(6-iodohexylsulfonyl)isoindoline-1,3-dione |
| | 2-(2,6-dioxopiperidin-3-yl)-4-(7-iodoheptylsulfonyl)isoindoline-1,3-dione |
| | 4-(2-(2-bromoethoxy)ethylsulfonyl)-2-(2,6-dioxopiperidin-3-yl)isoindoline-1,3-dione |
| | 4-(2-(2-(2-bromoethoxy)ethoxy)ethylsulfonyl)-2-(2,6-dioxopiperidin-3-yl)isoindoline-1,3-dione |
| | 4-(2-(2-(2-(2-bromoethoxy)ethoxy)ethoxy)ethylsulfonyl)-2-(2,6-dioxopiperidin-3-yl)isoindoline-1,3-dione |
| | 4-(2-(2-(2-(2-(2-bromoethoxy)ethoxy)ethoxy)ethoxy)ethylsulfonyl)-2-(2,6-dioxopiperidin-3-yl)isoindoline-1,3-dione |
| | 4-(2-(2-(2-(2-(2-(2-bromoethoxy)ethoxy)ethoxy)ethoxy)ethoxy)ethylsulfonyl)-2-(2,6-dioxopiperidin-3-yl)isoindoline-1,3-dione |
| | 4-(2-bromoethylsulfonyl)-2-(2,6-dioxopiperidin-3-yl)isoindoline-1,3-dione |
| | 4-(3-bromopropylsulfonyl)-2-(2,6-dioxopiperidin-3-yl)isoindoline-1,3-dione |
| | 4-(4-bromobutylsulfonyl)-2-(2,6-dioxopiperidin-3-yl)isoindoline-1,3-dione |
| | 4-(5-bromopentylsulfonyl)-2-(2,6-dioxopiperidin-3-yl)isoindoline-1,3-dione |
| | 4-(6-bromohexylsulfonyl)-2-(2,6-dioxopiperidin-3-yl)isoindoline-1,3-dione |
| | 4-(7-bromoheptylsulfonyl)-2-(2,6-dioxopiperidin-3-yl)isoindoline-1,3-dione |
| | 2-(2-(2-(2,6-dioxopiperidin-3-yl)-1,3-dioxoisoindolin-4-ylsulfonyl)ethoxy)ethyl 4-methylbenzenesulfonate |
| | 2-(2-(2-(2-(2,6-dioxopiperidin-3-yl)-1,3-dioxoisoindolin-4-ylsulfonyl)ethoxy)ethoxy)ethyl 4-methylbenzenesulfonate |
| | 2-(2-(2-(2-(2-(2,6-dioxopiperidin-3-yl)-1,3-dioxoisoindolin-4-ylsulfonyl)ethoxy)ethoxy)ethoxy)ethyl 4-methylbenzenesulfonate |
| | 2-(2-(2-(2-(2-(2-(2,6-dioxopiperidin-3-yl)-1,3-dioxoisoindolin-4-ylsulfonyl)ethoxy)ethoxy)ethoxy)ethoxy)ethyl 4-methylbenzenesulfonate |
| | 2-(2-(2-(2-(2-(2-(2-(2,6-dioxopiperidin-3-yl)-1,3-dioxoisoindolin-4-ylsulfonyl)ethoxy)ethoxy)ethoxy)ethoxy)ethoxy)ethyl 4-methylbenzenesulfonate |
| | 2-(2-(2,6-dioxopiperidin-3-yl)-1,3-dioxoisoindolin-4-ylsulfonyl)ethyl 4-methylbenzenesulfonate |
| | 3-(2-(2,6-dioxopiperidin-3-yl)-1,3-dioxoisoindolin-4-ylsulfonyl)propyl 4-methylbenzenesulfonate |
| | 4-(2-(2,6-dioxopiperidin-3-yl)-1,3-dioxoisoindolin-4-ylsulfonyl)butyl 4-methylbenzenesulfonate |
| | 5-(2-(2,6-dioxopiperidin-3-yl)-1,3-dioxoisoindolin-4-ylsulfonyl)pentyl 4-methylbenzenesulfonate |
| | 6-(2-(2,6-dioxopiperidin-3-yl)-1,3-dioxoisoindolin-4-ylsulfonyl)hexyl 4-methylbenzenesulfonate |
| | 7-(2-(2,6-dioxopiperidin-3-yl)-1,3-dioxoisoindolin-4-ylsulfonyl)heptyl 4-methylbenzenesulfonate |
| SIAIS1213129 | 2-(2-((2-(2,6-dioxopiperidin-3-yl)-1-oxoisoindolin-4-yl)thio)ethoxy)acetic acid |
| | 3-(2-((2-(2,6-dioxopiperidin-3-yl)-1-oxoisoindolin-4-yl)thio)ethoxy)propanoic acid |
| SIAIS1213131 | 2-(2-(2-((2-(2,6-dioxopiperidin-3-yl)-1-oxoisoindolin-4-yl)thio)ethoxy)ethoxy)acetic acid |
| | 3-(2-(2-((2-(2,6-dioxopiperidin-3-yl)-1-oxoisoindolin-4-yl)thio)ethoxy)ethoxy)propanoic acid |
| SIAIS1213133 | 2-(2-(2-(2-((2-(2,6-dioxopiperidin-3-yl)-1-oxoisoindolin-4-yl)thio)ethoxy)ethoxy)ethoxy)acetic acid |
| | 3-(2-(2-(2-((2-(2,6-dioxopiperidin-3-yl)-1-oxoisoindolin-4-yl)thio)ethoxy)ethoxy)ethoxy)propanoic acid |
| SIAIS1213135 | 14-((2-(2,6-dioxopiperidin-3-yl)-1-oxoisoindolin-4-yl)thio)-3,6,9,12-tetraoxatetradecanoic acid |
| | 1-((2-(2,6-dioxopiperidin-3-yl)-1-oxoisoindolin-4-yl)thio)-3,6,9,12-tetraoxapentadecan-15-oic acid |
| SIAIS1213137 | 17-((2-(2,6-dioxopiperidin-3-yl)-1-oxoisoindolin-4-yl)thio)-3,6,9,12,15-pentaoxaheptadecanoic acid |
| | 1-((2-(2,6-dioxopiperidin-3-yl)-1-oxoisoindolin-4-yl)thio)-3,6,9,12,15- |

TABLE 3-continued

The compounds of formula (IV) of the present disclosure

| Compound ID | Name of the compound |
|---|---|
| | pentaoxaoctadecan-18-oic acid |
| | 3-((4-((2-((2-(2,6-dioxopiperidin-3-yl)-1-oxoisoindolin-4-yl)thio)ethoxy)methyl)benzyl)oxy)propanoic acid |
| | 3-((4-((2-((2-(2,6-dioxopiperidin-3-yl)-1-oxoisoindolin-4-yl)thio)ethoxy)methyl)piperazin-1-yl)methoxy)propanoic acid |
| | 3-(3-((2-(2,6-dioxopiperidin-3-yl)-1-oxoisoindolin-4-yl)thio)propoxy)propanoic acid |
| | 3-(3-(2-((2-(2,6-dioxopiperidin-3-yl)-1-oxoisoindolin-4-yl)thio)ethoxy)propanamido)propanoic acid |
| SIAIS171090 | 2-((2-(2,6-dioxopiperidin-3-yl)-1-oxoisoindolin-4-yl)thio)acetic acid |
| SIAIS171086 | 3-((2-(2,6-dioxopiperidin-3-yl)-1-oxoisoindolin-4-yl)thio)propanoic acid |
| SIAIS171089 | 4-((2-(2,6-dioxopiperidin-3-yl)-1-oxoisoindolin-4-yl)thio)butanoic acid |
| SIAIS171079 | 5-((2-(2,6-dioxopiperidin-3-yl)-1-oxoisoindolin-4-yl)thio)pentanoic acid |
| SIAIS171091 | 6-((2-(2,6-dioxopiperidin-3-yl)-1-oxoisoindolin-4-yl)thio)hexanoic acid |
| SIAIS171092 | 7-((2-(2,6-dioxopiperidin-3-yl)-1-oxoisoindolin-4-yl)thio)heptanoic acid |
| | 8-((2-(2,6-dioxopiperidin-3-yl)-1-oxoisoindolin-4-yl)thio)octanoic acid |
| | 9-((2-(2,6-dioxopiperidin-3-yl)-1-oxoisoindolin-4-yl)thio)nonanoic acid |
| | 10-((2-(2,6-dioxopiperidin-3-yl)-1-oxoisoindolin-4-yl)thio)decanoic acid |
| SIAIS1220099 | 11-((2-(2,6-dioxopiperidin-3-yl)-1-oxoisoindolin-4-yl)thio)undecanoic acid |
| | 12-((2-(2,6-dioxopiperidin-3-yl)-1-oxoisoindolin-4-yl)thio)dodecanoic acid |
| | 13-((2-(2,6-dioxopiperidin-3-yl)-1-oxoisoindolin-4-yl)thio)tridecanoic acid |
| | 14-((2-(2,6-dioxopiperidin-3-yl)-1-oxoisoindolin-4-yl)thio)tetradecanoic acid |
| | 15-((2-(2,6-dioxopiperidin-3-yl)-1-oxoisoindolin-4-yl)thio)pentadecanoic acid |
| | 3-(6-((2-(2,6-dioxopiperidin-3-yl)-1-oxoisoindolin-4-yl)thio)hexanamido)propanoic acid |
| | 4-(4-(3-((2-(2,6-dioxopiperidin-3-yl)-1-oxoisoindolin-4-yl)thio)propyl)phenyl)butanoic acid |
| | 4-(4-(3-((2-(2,6-dioxopiperidin-3-yl)-1-oxoisoindolin-4-yl)thio)propyl)piperazin-1-yl)butanoic acid |
| SIAIS213096 | 3-(4-((2-(2-aminoethoxy)ethyl)thio)-1-oxoisoindolin-2-yl)piperidine-2,6-dione |
| SIAIS213068 | 3-(4-((2-(2-(2-aminoethoxy)ethoxy)ethyl)thio)-1-oxoisoindolin-2-yl)piperidine-2,6-dione |
| | 3-(4-((3-(2-(3-aminopropoxy)ethoxy)propyl)thio)-1-oxoisoindolin-2-yl)piperidine-2,6-dione |
| SIAIS213111 | 3-(4-((2-(2-(2-(2-aminoethoxy)ethoxy)ethoxy)ethyl)thio)-1-oxoisoindolin-2-yl)piperidine-2,6-dione |
| | 3-(4-((14-amino-3,6,9,12-tetraoxatetradecyl)thio)-1-oxoisoindolin-2-yl)piperidine-2,6-dione |
| | 3-(4-((17-amino-3,6,9,12,15-pentaoxaheptadecyl)thio)-1-oxoisoindolin-2-yl)piperidine-2,6-dione |
| | 3-(4-((2-((4-((2-aminoethoxy)methyl)benzyl)oxy)ethyl)thio)-1-oxoisoindolin-2-yl)piperidine-2,6-dione |
| | 3-(4-((2-((4-((2-aminoethoxy)methyl)piperazin-1-yl)methoxy)ethyl)thio)-1-oxoisoindolin-2-yl)piperidine-2,6-dione |
| | 4-((2-(2-((2-(2,6-dioxopiperidin-3-yl)-1-oxoisoindolin-4-yl)thio)ethoxy)ethyl)amino)-4-oxobutanoic acid |
| SIAIS171123 | 3-(4-((2-aminoethyl)thio)-1-oxoisoindolin-2-yl)piperidine-2,6-dione |
| SIAIS171124 | 3-(4-((3-aminopropyl)thio)-1-oxoisoindolin-2-yl)piperidine-2,6-dione |
| SIAIS171131 | 3-(4-((4-aminobutyl)thio)-1-oxoisoindolin-2-yl)piperidine-2,6-dione |
| SIAIS171132 | 3-(4-((5-aminopentyl)thio)-1-oxoisoindolin-2-yl)piperidine-2,6-dione |
| SIAIS171134 | 3-(4-((6-aminohexyl)thio)-1-oxoisoindolin-2-yl)piperidine-2,6-dione |
| SIAIS171135 | 3-(4-((7-aminoheptyl)thio)-1-oxoisoindolin-2-yl)piperidine-2,6-dione |
| SIAIS171136 | 3-(4-((8-aminooctyl)thio)-1-oxoisoindolin-2-yl)piperidine-2,6-dione |
| | 3-(4-((3-(4-(3-aminopropyl)phenyl)propyl)thio)-1-oxoisoindolin-2-yl)piperidine-2,6-dione |
| | 3-(4-((3-(4-(3-aminopropyl)piperazin-1-yl)propyl)thio)-1-oxoisoindolin-2-yl)piperidine-2,6-dione |
| | 4-((5-((2-(2,6-dioxopiperidin-3-yl)-1-oxoisoindolin-4-yl)thio)pentyl)amino)-4-oxobutanoic acid |
| | 3-(4-((2-(2-azidoethoxy)ethyl)thio)-1-oxoisoindolin-2-yl)piperidine-2,6-dione |
| | 3-(4-((2-(2-(2-azidoethoxy)ethoxy)ethyl)thio)-1-oxoisoindolin-2-yl)piperidine-2,6-dione |
| | 3-(4-((2-(2-(2-(2-azidoethoxy)ethoxy)ethoxy)ethyl)thio)-1-oxoisoindolin-2-yl)piperidine-2,6-dione |
| | 3-(4-((14-azido-3,6,9,12-tetraoxatetradecyl)thio)-1-oxoisoindolin-2-yl)piperidine-2,6-dione |
| | 3-(4-((17-azido-3,6,9,12,15-pentaoxaheptadecyl)thio)-1-oxoisoindolin-2-yl)piperidine-2,6-dione |
| | 3-(4-((2-((4-((2-azidoethoxy)methyl)benzyl)oxy)ethyl)thio)-1-oxoisoindolin-2-yl)piperidine-2,6-dione |
| | 3-(4-((2-((4-((2-azidoethoxy)methyl)piperazin-1-yl)methoxy)ethyl)thio)-1-oxoisoindolin-2-yl)piperidine-2,6-dione |
| | 4-(1-(2-(2-((2-(2,6-dioxopiperidin-3-yl)-1-oxoisoindolin-4-yl)thio)ethoxy)ethyl)-1H-1,2,3-triazol-4-yl)butanoic acid |
| | 3-(4-((2-azidoethyl)thio)-1-oxoisoindolin-2-yl)piperidine-2,6-dione |
| SIAIS287035 | 3-(4-((3-azidopropyl)thio)-1-oxoisoindolin-2-yl)piperidine-2,6-dione |
| SIAIS287036 | 3-(4-((4-azidobutyl)thio)-1-oxoisoindolin-2-yl)piperidine-2,6-dione |

TABLE 3-continued

The compounds of formula (IV) of the present disclosure

| Compound ID | Name of the compound |
|---|---|
| SIAIS287037 | 3-(4-((5-azidopentyl)thio)-1-oxoisoindolin-2-yl)piperidine-2,6-dione |
| | 3-(4-((6-azidohexyl)thio)-1-oxoisoindolin-2-yl)piperidine-2,6-dione |
| SIAIS287038 | 3-(4-((8-azidooctyl)thio)-1-oxoisoindolin-2-yl)piperidine-2,6-dione |
| SIAIS287039 | 3-(4-((9-azidononyl)thio)-1-oxoisoindolin-2-yl)piperidine-2,6-dione |
| SIAIS287040 | 3-(4-((10-azidodecyl)thio)-1-oxoisoindolin-2-yl)piperidine-2,6-dione |
| SIAIS287041 | 3-(4-((11-azidoundecyl)thio)-1-oxoisoindolin-2-yl)piperidine-2,6-dione |
| SIAIS287042 | 3-(4-((12-azidododecyl)thio)-1-oxoisoindolin-2-yl)piperidine-2,6-dione |
| | 3-(4-((3-(4-(3-azidopropyl)phenyl)propyl)thio)-1-oxoisoindolin-2-yl)piperidine-2,6-dione |
| | 3-(4-((3-(4-(3-azidopropyl)piperazin-1-yl)propyl)thio)-1-oxoisoindolin-2-yl)piperidine-2,6-dione |
| | 4-(1-(5-((2-(2,6-dioxopiperidin-3-yl)-1-oxoisoindolin-4-yl)thio)pentyl)-1H-1,2,3-triazol-4-yl)butanoic acid |
| | 3-(4-(2-(2-iodoethoxy)ethylthio)-1-oxoisoindolin-2-yl)piperidine-2,6-dione |
| | 3-(4-(3-(3-iodopropoxy)propylthio)-1-oxoisoindolin-2-yl)piperidine-2,6-dione |
| | 3-(4-(2-(2-(2-iodoethoxy)ethoxy)ethylthio)-1-oxoisoindolin-2-yl)piperidine-2,6-dione |
| | 3-(4-(2-(2-(2-(2-iodoethoxy)ethoxy)ethoxy)ethylthio)-1-oxoisoindolin-2-yl)piperidine-2,6-dione |
| | 3-(4-(2-(2-(2-(2-(2-iodoethoxy)ethoxy)ethoxy)ethoxy)ethylthio)-1-oxoisoindolin-2-yl)piperidine-2,6-dione |
| | 3-(4-(2-(2-(2-(2-(2-(2-iodoethoxy)ethoxy)ethoxy)ethoxy)ethoxy)ethylthio)-1-oxoisoindolin-2-yl)piperidine-2,6-dione |
| | 3-(4-((2-((4-((2-iodoethoxy)methyl)benzyl)oxy)ethyl)thio)-1-oxoisoindolin-2-yl)piperidine-2,6-dione |
| | 3-(4-((2-((4-((2-iodoethoxy)methyl)piperazin-1-yl)methoxy)ethyl)thio)-1-oxoisoindolin-2-yl)piperidine-2,6-dione |
| | 3-(4-(2-iodoethylthio)-1-oxoisoindolin-2-yl)piperidine-2,6-dione |
| | 3-(4-(3-iodopropylthio)-1-oxoisoindolin-2-yl)piperidine-2,6-dione |
| | 3-(4-(4-iodobutylthio)-1-oxoisoindolin-2-yl)piperidine-2,6-dione |
| | 3-(4-(5-iodopentylthio)-1-oxoisoindolin-2-yl)piperidine-2,6-dione |
| | 3-(4-(6-iodohexylthio)-1-oxoisoindolin-2-yl)piperidine-2,6-dione |
| | 3-(4-(7-iodoheptylthio)-1-oxoisoindolin-2-yl)piperidine-2,6-dione |
| | 3-(4-((3-(4-(3-iodopropyl)phenyl)propyl)thio)-1-oxoisoindolin-2-yl)piperidine-2,6-dione |
| | 3-(4-((3-(4-(3-iodopropyl)piperazin-1-yl)propyl)thio)-1-oxoisoindolin-2-yl)piperidine-2,6-dione |
| | 3-(4-(2-(2-bromoethoxy)ethylthio)-1-oxoisoindolin-2-yl)piperidine-2,6-dione |
| | 3-(4-(3-(3-bromopropoxy)propylthio)-1-oxoisoindolin-2-yl)piperidine-2,6-dione |
| | 3-(4-(2-(2-(2-bromoethoxy)ethoxy)ethylthio)-1-oxoisoindolin-2-yl)piperidine-2,6-dione |
| | 3-(4-(2-(2-(2-(2-bromoethoxy)ethoxy)ethoxy)ethylthio)-1-oxoisoindolin-2-yl)piperidine-2,6-dione |
| | 3-(4-(2-(2-(2-(2-(2-bromoethoxy)ethoxy)ethoxy)ethoxy)ethylthio)-1-oxoisoindolin-2-yl)piperidine-2,6-dione |
| | 3-(4-(2-(2-(2-(2-(2-(2-bromoethoxy)ethoxy)ethoxy)ethoxy)ethoxy)ethylthio)-1-oxoisoindolin-2-yl)piperidine-2,6-dione |
| | 3-(4-((2-((4-((2-bromoethoxy)methyl)benzyl)oxy)ethyl)thio)-1-oxoisoindolin-2-yl)piperidine-2,6-dione |
| | 3-(4-((2-((4-((2-bromoethoxy)methyl)piperazin-1-yl)methoxy)ethyl)thio)-1-oxoisoindolin-2-yl)piperidine-2,6-dione |
| SIAIS213137 | 3-(4-(2-bromoethylthio)-1-oxoisoindolin-2-yl)piperidine-2,6-dione |
| SIAIS213132 | 3-(4-(3-bromopropylthio)-1-oxoisoindolin-2-yl)piperidine-2,6-dione |
| SIAIS213134 | 3-(4-(4-bromobutylthio)-1-oxoisoindolin-2-yl)piperidine-2,6-dione |
| SIAIS213135 | 3-(4-(5-bromopentylthio)-1-oxoisoindolin-2-yl)piperidine-2,6-dione |
| SIAIS1216133 | 3-(4-(6-bromohexylthio)-1-oxoisoindolin-2-yl)piperidine-2,6-dione |
| SIAIS1216135 | 3-(4-(7-bromoheptylthio)-1-oxoisoindolin-2-yl)piperidine-2,6-dione |
| SIAIS1216137 | 3-(4-((8-bromooctyl)thio)-1-oxoisoindolin-2-yl)piperidine-2,6-dione |
| SIAIS1220059 | 3-(4-((9-bromononyl)thio)-1-oxoisoindolin-2-yl)piperidine-2,6-dione |
| SIAIS1220013 | 3-(4-((10-bromodecyl)thio)-1-oxoisoindolin-2-yl)piperidine-2,6-dione |
| SIAIS1220015 | 3-(4-((11-bromoundecyl)thio)-1-oxoisoindolin-2-yl)piperidine-2,6-dione |
| SIAIS264005 | 3-(4-((12-bromododecyl)thio)-1-oxoisoindolin-2-yl)piperidine-2,6-dione |
| SIAIS1220141 | 3-(4-((4-(bromomethyl)benzyl)thio)-1-oxoisoindolin-2-yl)piperidine-2,6-dione |
| | 3-(4-((3-(4-(3-bromopropyl)phenyl)propyl)thio)-1-oxoisoindolin-2-yl)piperidine-2,6-dione |
| | 3-(4-((3-(4-(3-bromopropyl)piperazin-1-yl)propyl)thio)-1-oxoisoindolin-2-yl)piperidine-2,6-dione |
| | 2-(2-(2-(2,6-dioxopiperidin-3-yl)-1-oxoisoindolin-4-ylthio)ethoxy)ethyl 4-methylbenzenesulfonate |
| | 3-(3-(2-(2,6-dioxopiperidin-3-yl)-1-oxoisoindolin-4-ylthio)propoxy)propyl 4-methylbenzenesulfonate |
| | 2-(2-(2-(2-(2,6-dioxopiperidin-3-yl)-1-oxoisoindolin-4-ylthio)ethoxy)ethoxy)ethyl 4-methylbenzenesulfonate |
| | 2-(2-(2-(2-(2-(2,6-dioxopiperidin-3-yl)-1-oxoisoindolin-4-ylthio)ethoxy)ethoxy)ethoxy)ethyl 4-methylbenzenesulfonate |
| | 2-(2-(2-(2-(2-(2-(2,6-dioxopiperidin-3-yl)-1-oxoisoindolin-4- |

TABLE 3-continued

The compounds of formula (IV) of the present disclosure

| Compound ID | Name of the compound |
|---|---|
| | ylthio)ethoxy)ethoxy)ethoxy)ethoxy)ethyl 4-methylbenzenesulfonate |
| | 2-(2-(2-(2-(2-(2-(2-(2,6-dioxopiperidin-3-yl)-1-oxoisoindolin-4-ylthio)ethoxy)ethoxy)ethoxy)ethoxy)ethoxy)ethyl 4-methylbenzenesulfonate |
| | 2-((4-((2-((2-(2,6-dioxopiperidin-3-yl)-1-oxoisoindolin-4-yl)thio)ethoxy)methyl)benzyl)oxy)ethyl 4-methylbenzenesulfonate |
| | 2-((4-((2-((2-(2,6-dioxopiperidin-3-yl)-1-oxoisoindolin-4-yl)thio)ethoxy)methyl)piperazin-1-yl)methoxy)ethyl 4-methylbenzenesulfonate |
| | 2-(2-(2,6-dioxopiperidin-3-yl)-1-oxoisoindolin-4-ylthio)ethyl 4-methylbenzenesulfonate |
| | 3-(2-(2,6-dioxopiperidin-3-yl)-1-oxoisoindolin-4-ylthio)propyl 4-methylbenzenesulfonate |
| | 4-(2-(2,6-dioxopiperidin-3-yl)-1-oxoisoindolin-4-ylthio)butyl 4-methylbenzenesulfonate |
| | 5-(2-(2,6-dioxopiperidin-3-yl)-1-oxoisoindolin-4-ylthio)pentyl 4-methylbenzenesulfonate |
| | 6-(2-(2,6-dioxopiperidin-3-yl)-1-oxoisoindolin-4-ylthio)hexyl 4-methylbenzenesulfonate |
| | 7-(2-(2,6-dioxopiperidin-3-yl)-1-oxoisoindolin-4-ylthio)heptyl 4-methylbenzenesulfonate |
| | 3-(4-(3-((2-(2,6-dioxopiperidin-3-yl)-1-oxoisoindolin-4-yl)thio)propyl)phenyl)propyl 4-methylbenzenesulfonate |
| | 3-(4-(3-((2-(2,6-dioxopiperidin-3-yl)-1-oxoisoindolin-4-yl)thio)propyl)piperazin-1-yl)propyl 4-methylbenzenesulfonate |
| | 2-(2-((2-(2,6-dioxopiperidin-3-yl)-1-oxoisoindolin-4-yl)sulfinyl)ethoxy)acetic acid |
| | 3-(2-((2-(2,6-dioxopiperidin-3-yl)-1-oxoisoindolin-4-yl)sulfinyl)ethoxy)propanoic acid |
| | 2-(2-(2-((2-(2,6-dioxopiperidin-3-yl)-1-oxoisoindolin-4-yl)sulfinyl)ethoxy)ethoxy)acetic acid |
| | 3-(2-(2-((2-(2,6-dioxopiperidin-3-yl)-1-oxoisoindolin-4-yl)sulfinyl)ethoxy)ethoxy)propanoic acid |
| | 2-(2-(2-(2-((2-(2,6-dioxopiperidin-3-yl)-1-oxoisoindolin-4-yl)sulfinyl)ethoxy)ethoxy)ethoxy)acetic acid |
| | 3-(2-(2-(2-((2-(2,6-dioxopiperidin-3-yl)-1-oxoisoindolin-4-yl)sulfinyl)ethoxy)ethoxy)ethoxy)propanoic acid |
| | 14-((2-(2,6-dioxopiperidin-3-yl)-1-oxoisoindolin-4-yl)sulfinyl)-3,6,9,12-tetraoxatetradecanoic acid |
| | 1-((2-(2,6-dioxopiperidin-3-yl)-1-oxoisoindolin-4-yl)sulfinyl)-3,6,9,12-tetraoxapentadecan-15-oic acid |
| | 17-((2-(2,6-dioxopiperidin-3-yl)-1-oxoisoindolin-4-yl)sulfinyl)-3,6,9,12,15-pentaoxaheptadecanoic acid |
| | 1-((2-(2,6-dioxopiperidin-3-yl)-1-oxoisoindolin-4-yl)sulfinyl)-3,6,9,12,15-pentaoxaoctadecan-18-oic acid |
| | 3-(3-(2-((2-(2,6-dioxopiperidin-3-yl)-1-oxoisoindolin-4-yl)sulfinyl)ethoxy)propanamido)propanoic acid |
| | 2-((2-(2,6-dioxopiperidin-3-yl)-1-oxoisoindolin-4-yl)sulfinyl)acetic acid |
| | 3-((2-(2,6-dioxopiperidin-3-yl)-1-oxoisoindolin-4-yl)sulfinyl)propanoic acid |
| | 4-((2-(2,6-dioxopiperidin-3-yl)-1-oxoisoindolin-4-yl)sulfinyl)butanoic acid |
| | 5-((2-(2,6-dioxopiperidin-3-yl)-1-oxoisoindolin-4-yl)sulfinyl)pentanoic acid |
| | 6-((2-(2,6-dioxopiperidin-3-yl)-1-oxoisoindolin-4-yl)sulfinyl)hexanoic acid |
| | 7-((2-(2,6-dioxopiperidin-3-yl)-1-oxoisoindolin-4-yl)sulfinyl)heptanoic acid |
| | 8-((2-(2,6-dioxopiperidin-3-yl)-1-oxoisoindolin-4-yl)sulfinyl)octanoic acid |
| | 9-((2-(2,6-dioxopiperidin-3-yl)-1-oxoisoindolin-4-yl)sulfinyl)nonanoic acid |
| | 10-((2-(2,6-dioxopiperidin-3-yl)-1-oxoisoindolin-4-yl)sulfinyl)decanoic acid |
| | 11-((2-(2,6-dioxopiperidin-3-yl)-1-oxoisoindolin-4-yl)sulfinyl)undecanoic acid |
| | 12-((2-(2,6-dioxopiperidin-3-yl)-1-oxoisoindolin-4-yl)sulfinyl)dodecanoic acid |
| | 13-((2-(2,6-dioxopiperidin-3-yl)-1-oxoisoindolin-4-yl)sulfinyl)tridecanoic acid |
| | 14-((2-(2,6-dioxopiperidin-3-yl)-1-oxoisoindolin-4-yl)sulfinyl)tetradecanoic acid |
| | 15-((2-(2,6-dioxopiperidin-3-yl)-1-oxoisoindolin-4-yl)sulfinyl)pentadecanoic acid |
| | 3-(6-((2-(2,6-dioxopiperidin-3-yl)-1-oxoisoindolin-4-yl)sulfinyl)hexanamido)propanoic acid |
| | 3-(4-((2-(2-aminoethoxy)ethyl)sulfinyl)-1-oxoisoindolin-2-yl)piperidine-2,6-dione |
| | 3-(4-((2-(2-(2-aminoethoxy)ethoxy)ethyl)sulfinyl)-1-oxoisoindolin-2-yl)piperidine-2,6-dione |
| | 3-(4-((2-(2-(2-(2-aminoethoxy)ethoxy)ethoxy)ethyl)sulfinyl)-1-oxoisoindolin-2-yl)piperidine-2,6-dione |
| | 3-(4-((14-amino-3,6,9,12-tetraoxatetradecyl)sulfinyl)-1-oxoisoindolin-2-yl)piperidine-2,6-dione |
| | 3-(4-((17-amino-3,6,9,12,15-pentaoxaheptadecyl)sulfinyl)-1-oxoisoindolin-2-yl)piperidine-2,6-dione |
| | 4-((2-(2-((2-(2,6-dioxopiperidin-3-yl)-1-oxoisoindolin-4-yl)sulfinyl)ethoxy)ethyl)amino)-4-oxobutanoic acid |
| | 3-(4-((2-aminoethyl)sulfinyl)-1-oxoisoindolin-2-yl)piperidine-2,6-dione |
| | 3-(4-((3-aminopropyl)sulfinyl)-1-oxoisoindolin-2-yl)piperidine-2,6-dione |
| | 3-(4-((4-aminobutyl)sulfinyl)-1-oxoisoindolin-2-yl)piperidine-2,6-dione |
| | 3-(4-((5-aminopentyl)sulfinyl)-1-oxoisoindolin-2-yl)piperidine-2,6-dione |
| | 3-(4-((6-aminohexyl)sulfinyl)-1-oxoisoindolin-2-yl)piperidine-2,6-dione |

TABLE 3-continued

The compounds of formula (IV) of the present disclosure

| Compound ID | Name of the compound |
|---|---|
| | 3-(4-((7-aminoheptyl)sulfinyl)-1-oxoisoindolin-2-yl)piperidine-2,6-dione |
| | 3-(4-((8-aminooctyl)sulfinyl)-1-oxoisoindolin-2-yl)piperidine-2,6-dione |
| | 4-((5-((2-(2,6-dioxopiperidin-3-yl)-1-oxoisoindolin-4-yl)sulfinyl)pentyl)amino)-4-oxobutanoic acid |
| | 3-(4-((2-(2-azidoethoxy)ethyl)sulfinyl)-1-oxoisoindolin-2-yl)piperidine-2,6-dione |
| | 3-(4-((2-(2-(2-azidoethoxy)ethoxy)ethyl)sulfinyl)-1-oxoisoindolin-2-yl)piperidine-2,6-dione |
| | 3-(4-((2-(2-(2-(2-azidoethoxy)ethoxy)ethoxy)ethyl)sulfinyl)-1-oxoisoindolin-2-yl)piperidine-2,6-dione |
| | 3-(4-((14-azido-3,6,9,12-tetraoxatetradecyl)sulfinyl)-1-oxoisoindolin-2-yl)piperidine-2,6-dione |
| | 3-(4-((17-azido-3,6,9,12,15-pentaoxaheptadecyl)sulfinyl)-1-oxoisoindolin-2-yl)piperidine-2,6-dione |
| | 4-(1-(2-(2-((2-(2,6-dioxopiperidin-3-yl)-1-oxoisoindolin-4-yl)sulfinyl)ethoxy)ethyl)-1H-1,2,3-triazol-4-yl)butanoic acid |
| | 3-(4-((2-azidoethyl)sulfinyl)-1-oxoisoindolin-2-yl)piperidine-2,6-dione |
| | 3-(4-((3-azidopropyl)sulfinyl)-1-oxoisoindolin-2-yl)piperidine-2,6-dione |
| | 3-(4-((4-azidobutyl)sulfinyl)-1-oxoisoindolin-2-yl)piperidine-2,6-dione |
| | 3-(4-((5-azidopentyl)sulfinyl)-1-oxoisoindolin-2-yl)piperidine-2,6-dione |
| | 3-(4-((6-azidohexyl)sulfinyl)-1-oxoisoindolin-2-yl)piperidine-2,6-dione |
| | 3-(4-((7-azidoheptyl)sulfinyl)-1-oxoisoindolin-2-yl)piperidine-2,6-dione |
| | 4-(1-(5-((2-(2,6-dioxopiperidin-3-yl)-1-oxoisoindolin-4-yl)sulfinyl)pentyl)-1H-1,2,3-triazol-4-yl)butanoic acid |
| | 3-(4-(2-(2-iodoethoxy)ethylsulfinyl)-1-oxoisoindolin-2-yl)piperidine-2,6-dione |
| | 3-(4-(2-(2-(2-iodoethoxy)ethoxy)ethylsulfinyl)-1-oxoisoindolin-2-yl)piperidine-2,6-dione |
| | 3-(4-(2-(2-(2-(2-iodoethoxy)ethoxy)ethoxy)ethylsulfinyl)-1-oxoisoindolin-2-yl)piperidine-2,6-dione |
| | 3-(4-(2-(2-(2-(2-(2-iodoethoxy)ethoxy)ethoxy)ethoxy)ethylsulfinyl)-1-oxoisoindolin-2-yl)piperidine-2,6-dione |
| | 3-(4-(2-(2-(2-(2-(2-(2-iodoethoxy)ethoxy)ethoxy)ethoxy)ethoxy)ethylsulfinyl)-1-oxoisoindolin-2-yl)piperidine-2,6-dione |
| | 3-(4-(2-iodoethylsulfinyl)-1-oxoisoindolin-2-yl)piperidine-2,6-dione |
| | 3-(4-(3-iodopropylsulfinyl)-1-oxoisoindolin-2-yl)piperidine-2,6-dione |
| | 3-(4-(4-iodobutylsulfinyl)-1-oxoisoindolin-2-yl)piperidine-2,6-dione |
| | 3-(4-(5-iodopentylsulfinyl)-1-oxoisoindolin-2-yl)piperidine-2,6-dione |
| | 3-(4-(6-iodohexylsulfinyl)-1-oxoisoindolin-2-yl)piperidine-2,6-dione |
| | 3-(4-(7-iodoheptylsulfinyl)-1-oxoisoindolin-2-yl)piperidine-2,6-dione |
| | 3-(4-(2-(2-bromoethoxy)ethylsulfinyl)-1-oxoisoindolin-2-yl)piperidine-2,6-dione |
| | 3-(4-(2-(2-(2-bromoethoxy)ethoxy)ethylsulfinyl)-1-oxoisoindolin-2-yl)piperidine-2,6-dione |
| | 3-(4-(2-(2-(2-(2-bromoethoxy)ethoxy)ethoxy)ethylsulfinyl)-1-oxoisoindolin-2-yl)piperidine-2,6-dione |
| | 3-(4-(2-(2-(2-(2-(2-bromoethoxy)ethoxy)ethoxy)ethoxy)ethylsulfinyl)-1-oxoisoindolin-2-yl)piperidine-2,6-dione |
| | 3-(4-(2-(2-(2-(2-(2-(2-bromoethoxy)ethoxy)ethoxy)ethoxy)ethoxy)ethylsulfinyl)-1-oxoisoindolin-2-yl)piperidine-2,6-dione |
| | 3-(4-(2-bromoethylsulfinyl)-1-oxoisoindolin-2-yl)piperidine-2,6-dione |
| | 3-(4-(3-bromopropylsulfinyl)-1-oxoisoindolin-2-yl)piperidine-2,6-dione |
| | 3-(4-(4-bromobutylsulfinyl)-1-oxoisoindolin-2-yl)piperidine-2,6-dione |
| | 3-(4-(5-bromopentylsulfinyl)-1-oxoisoindolin-2-yl)piperidine-2,6-dione |
| | 3-(4-(6-bromohexylsulfinyl)-1-oxoisoindolin-2-yl)piperidine-2,6-dione |
| | 3-(4-(7-bromoheptylsulfinyl)-1-oxoisoindolin-2-yl)piperidine-2,6-dione |
| | 2-(2-(2-(2,6-dioxopiperidin-3-yl)-1-oxoisoindolin-4-ylsulfinyl)ethoxy)ethyl 4-methylbenzenesulfonate |
| | 2-(2-(2-(2-(2,6-dioxopiperidin-3-yl)-1-oxoisoindolin-4-ylsulfinyl)ethoxy)ethoxy)ethyl 4-methylbenzenesulfonate |
| | 2-(2-(2-(2-(2-(2,6-dioxopiperidin-3-yl)-1-oxoisoindolin-4-ylsulfinyl)ethoxy)ethoxy)ethoxy)ethyl 4-methylbenzenesulfonate |
| | 2-(2-(2-(2-(2-(2-(2,6-dioxopiperidin-3-yl)-1-oxoisoindolin-4-ylsulfinyl)ethoxy)ethoxy)ethoxy)ethoxy)ethyl 4-methylbenzenesulfonate |
| | 2-(2-(2-(2-(2-(2-(2-(2,6-dioxopiperidin-3-yl)-1-oxoisoindolin-4-ylsulfinyl)ethoxy)ethoxy)ethoxy)ethoxy)ethoxy)ethyl 4-methylbenzenesulfonate |
| | 2-(2-(2,6-dioxopiperidin-3-yl)-1-oxoisoindolin-4-ylsulfinyl)ethyl 4-methylbenzenesulfonate |
| | 3-(2-(2,6-dioxopiperidin-3-yl)-1-oxoisoindolin-4-ylsulfinyl)propyl 4-methylbenzenesulfonate |
| | 4-(2-(2,6-dioxopiperidin-3-yl)-1-oxoisoindolin-4-ylsulfinyl)butyl 4-methylbenzenesulfonate |
| | 5-(2-(2,6-dioxopiperidin-3-yl)-1-oxoisoindolin-4-ylsulfinyl)pentyl 4-methylbenzenesulfonate |
| | 6-(2-(2,6-dioxopiperidin-3-yl)-1-oxoisoindolin-4-ylsulfinyl)hexyl 4-methylbenzenesulfonate |
| | 7-(2-(2,6-dioxopiperidin-3-yl)-1-oxoisoindolin-4-ylsulfinyl)heptyl 4-methylbenzenesulfonate |
| | 2-(2-((2-(2,6-dioxopiperidin-3-yl)-1-oxoisoindolin-4-yl)sulfonyl)ethoxy)acetic acid |

TABLE 3-continued

The compounds of formula (IV) of the present disclosure

| Compound ID | Name of the compound |
|---|---|
| | 3-(2-((2-(2,6-dioxopiperidin-3-yl)-1-oxoisoindolin-4-yl)sulfonyl)ethoxy)propanoic acid |
| | 2-(2-(2-((2-(2,6-dioxopiperidin-3-yl)-1-oxoisoindolin-4-yl)sulfonyl)ethoxy)ethoxy)acetic acid |
| | 3-(2-(2-((2-(2,6-dioxopiperidin-3-yl)-1-oxoisoindolin-4-yl)sulfonyl)ethoxy)ethoxy)propanoic acid |
| | 2-(2-(2-(2-((2-(2,6-dioxopiperidin-3-yl)-1-oxoisoindolin-4-yl)sulfonyl)ethoxy)ethoxy)ethoxy)acetic acid |
| | 3-(2-(2-(2-((2-(2,6-dioxopiperidin-3-yl)-1-oxoisoindolin-4-yl)sulfonyl)ethoxy)ethoxy)ethoxy)propanoic acid |
| | 14-((2-(2,6-dioxopiperidin-3-yl)-1-oxoisoindolin-4-yl)sulfonyl)-3,6,9,12-tetraoxatetradecanoic acid |
| | 1-((2-(2,6-dioxopiperidin-3-yl)-1-oxoisoindolin-4-yl)sulfonyl)-3,6,9,12-tetraoxapentadecan-15-oic acid |
| | 17-((2-(2,6-dioxopiperidin-3-yl)-1-oxoisoindolin-4-yl)sulfonyl)-3,6,9,12,15-pentaoxaheptadecanoic acid |
| | 1-((2-(2,6-dioxopiperidin-3-yl)-1-oxoisoindolin-4-yl)sulfonyl)-3,6,9,12,15-pentaoxaoctadecan-18-oic acid |
| | 3-(3-(2-((2-(2,6-dioxopiperidin-3-yl)-1-oxoisoindolin-4-yl)sulfonyl)ethoxy)propanamido)propanoic acid |
| | 2-((2-(2,6-dioxopiperidin-3-yl)-1-oxoisoindolin-4-yl)sulfonyl)acetic acid |
| | 3-((2-(2,6-dioxopiperidin-3-yl)-1-oxoisoindolin-4-yl)sulfonyl)propanoic acid |
| | 4-((2-(2,6-dioxopiperidin-3-yl)-1-oxoisoindolin-4-yl)sulfonyl)butanoic acid |
| | 5-((2-(2,6-dioxopiperidin-3-yl)-1-oxoisoindolin-4-yl)sulfonyl)pentanoic acid |
| | 6-((2-(2,6-dioxopiperidin-3-yl)-1-oxoisoindolin-4-yl)sulfonyl)hexanoic acid |
| | 7-((2-(2,6-dioxopiperidin-3-yl)-1-oxoisoindolin-4-yl)sulfonyl)heptanoic acid |
| | 8-((2-(2,6-dioxopiperidin-3-yl)-1-oxoisoindolin-4-yl)sulfonyl)octanoic acid |
| | 9-((2-(2,6-dioxopiperidin-3-yl)-1-oxoisoindolin-4-yl)sulfonyl)nonanoic acid |
| | 10-((2-(2,6-dioxopiperidin-3-yl)-1-oxoisoindolin-4-yl)sulfonyl)decanoic acid |
| | 11-((2-(2,6-dioxopiperidin-3-yl)-1-oxoisoindolin-4-yl)sulfonyl)undecanoic acid |
| | 12-((2-(2,6-dioxopiperidin-3-yl)-1-oxoisoindolin-4-yl)sulfonyl)dodecanoic acid |
| | 13-((2-(2,6-dioxopiperidin-3-yl)-1-oxoisoindolin-4-yl)sulfonyl)tridecanoic acid |
| | 14-((2-(2,6-dioxopiperidin-3-yl)-1-oxoisoindolin-4-yl)sulfonyl)tetradecanoic acid |
| | 15-((2-(2,6-dioxopiperidin-3-yl)-1-oxoisoindolin-4-yl)sulfonyl)pentadecanoic acid |
| | 3-(6-((2-(2,6-dioxopiperidin-3-yl)-1-oxoisoindolin-4-yl)sulfonyl)hexanamido)propanoic acid |
| | 3-(4-((2-(2-aminoethoxy)ethyl)sulfonyl)-1-oxoisoindolin-2-yl)piperidine-2,6-dione |
| | 3-(4-((2-(2-(2-aminoethoxy)ethoxy)ethyl)sulfonyl)-1-oxoisoindolin-2-yl)piperidine-2,6-dione |
| | 3-(4-((2-(2-(2-(2-aminoethoxy)ethoxy)ethoxy)ethyl)sulfonyl)-1-oxoisoindolin-2-yl)piperidine-2,6-dione |
| | 3-(4-((14-amino-3,6,9,12-tetraoxatetradecyl)sulfonyl)-1-oxoisoindolin-2-yl)piperidine-2,6-dione |
| | 3-(4-((17-amino-3,6,9,12,15-pentaoxaheptadecyl)sulfonyl)-1-oxoisoindolin-2-yl)piperidine-2,6-dione |
| | 4-((2-(2-((2-(2,6-dioxopiperidin-3-yl)-1-oxoisoindolin-4-yl)sulfonyl)ethoxy)ethyl)amino)-4-oxobutanoic acid |
| | 3-(4-((2-aminoethyl)sulfonyl)-1-oxoisoindolin-2-yl)piperidine-2,6-dione |
| | 3-(4-((3-aminopropyl)sulfonyl)-1-oxoisoindolin-2-yl)piperidine-2,6-dione |
| | 3-(4-((4-aminobutyl)sulfonyl)-1-oxoisoindolin-2-yl)piperidine-2,6-dione |
| | 3-(4-((5-aminopentyl)sulfonyl)-1-oxoisoindolin-2-yl)piperidine-2,6-dione |
| | 3-(4-((6-aminohexyl)sulfonyl)-1-oxoisoindolin-2-yl)piperidine-2,6-dione |
| | 3-(4-((7-aminoheptyl)sulfonyl)-1-oxoisoindolin-2-yl)piperidine-2,6-dione |
| | 3-(4-((8-aminooctyl)sulfonyl)-1-oxoisoindolin-2-yl)piperidine-2,6-dione |
| | 4-((5-((2-(2,6-dioxopiperidin-3-yl)-1-oxoisoindolin-4-yl)sulfonyl)pentyl)amino)-4-oxobutanoic acid |
| | 3-(4-((2-(2-azidoethoxy)ethyl)sulfonyl)-1-oxoisoindolin-2-yl)piperidine-2,6-dione |
| | 3-(4-((2-(2-(2-azidoethoxy)ethoxy)ethyl)sulfonyl)-1-oxoisoindolin-2-yl)piperidine-2,6-dione |
| | 3-(4-((2-(2-(2-(2-azidoethoxy)ethoxy)ethoxy)ethyl)sulfonyl)-1-oxoisoindolin-2-yl)piperidine-2,6-dione |
| | 3-(4-((14-azido-3,6,9,12-tetraoxatetradecyl)sulfonyl)-1-oxoisoindolin-2-yl)piperidine-2,6-dione |
| | 3-(4-((17-azido-3,6,9,12,15-pentaoxaheptadecyl)sulfonyl)-1-oxoisoindolin-2-yl)piperidine-2,6-dione |
| | 4-(1-(2-(2-((2-(2,6-dioxopiperidin-3-yl)-1-oxoisoindolin-4-yl)sulfonyl)ethoxy)ethyl)-1H-1,2,3-triazol-4-yl)butanoic acid |
| | 3-(4-((2-azidoethyl)sulfonyl)-1-oxoisoindolin-2-yl)piperidine-2,6-dione |
| | 3-(4-((3-azidopropyl)sulfonyl)-1-oxoisoindolin-2-yl)piperidine-2,6-dione |
| | 3-(4-((4-azidobutyl)sulfonyl)-1-oxoisoindolin-2-yl)piperidine-2,6-dione |
| | 3-(4-((5-azidopentyl)sulfonyl)-1-oxoisoindolin-2-yl)piperidine-2,6-dione |
| | 3-(4-((6-azidohexyl)sulfonyl)-1-oxoisoindolin-2-yl)piperidine-2,6-dione |
| | 3-(4-((6-azidohexyl)sulfonyl)-1-oxoisoindolin-2-yl)piperidine-2,6-dione) |
| | 3-(4-((7-azidoheptyl)sulfonyl)-1-oxoisoindolin-2-yl)piperidine-2,6-dione |
| | 4-(1-(5-((2-(2,6-dioxopiperidin-3-yl)-1-oxoisoindolin-4-yl)sulfonyl)pentyl)-1H-1,2,3-triazol-4-yl)butanoic acid |

TABLE 3-continued

The compounds of formula (IV) of the present disclosure

| Compound ID | Name of the compound |
|---|---|
| | 3-(4-(2-(2-iodoethoxy)ethylsulfonyl)-1-oxoisoindolin-2-yl)piperidine-2,6-dione |
| | 3-(4-(2-(2-(2-iodoethoxy)ethoxy)ethylsulfonyl)-1-oxoisoindolin-2-yl)piperidine-2,6-dione |
| | 3-(4-(2-(2-(2-(2-iodoethoxy)ethoxy)ethoxy)ethylsulfonyl)-1-oxoisoindolin-2-yl)piperidine-2,6-dione |
| | 3-(4-(2-(2-(2-(2-(2-iodoethoxy)ethoxy)ethoxy)ethoxy)ethylsulfonyl)-1-oxoisoindolin-2-yl)piperidine-2,6-dione |
| | 3-(4-(2-(2-(2-(2-(2-(2-iodoethoxy)ethoxy)ethoxy)ethoxy)ethoxy)ethylsulfonyl)-1-oxoisoindolin-2-yl)piperidine-2,6-dione |
| | 3-(4-(2-iodoethylsulfonyl)-1-oxoisoindolin-2-yl)piperidine-2,6-dione |
| | 3-(4-(3-iodopropylsulfonyl)-1-oxoisoindolin-2-yl)piperidine-2,6-dione |
| | 3-(4-(4-iodobutylsulfonyl)-1-oxoisoindolin-2-yl)piperidine-2,6-dione |
| | 3-(4-(5-iodopentylsulfonyl)-1-oxoisoindolin-2-yl)piperidine-2,6-dione |
| | 3-(4-(6-iodohexylsulfonyl)-1-oxoisoindolin-2-yl)piperidine-2,6-dione |
| | 3-(4-(7-iodoheptylsulfonyl)-1-oxoisoindolin-2-yl)piperidine-2,6-dione |
| | 3-(4-(2-(2-bromoethoxy)ethylsulfonyl)-1-oxoisoindolin-2-yl)piperidine-2,6-dione |
| | 3-(4-(2-(2-(2-bromoethoxy)ethoxy)ethylsulfonyl)-1-oxoisoindolin-2-yl)piperidine-2,6-dione |
| | 3-(4-(2-(2-(2-(2-bromoethoxy)ethoxy)ethoxy)ethylsulfonyl)-1-oxoisoindolin-2-yl)piperidine-2,6-dione |
| | 3-(4-(2-(2-(2-(2-(2-bromoethoxy)ethoxy)ethoxy)ethoxy)ethylsulfonyl)-1-oxoisoindolin-2-yl)piperidine-2,6-dione |
| | 3-(4-(2-(2-(2-(2-(2-(2-bromoethoxy)ethoxy)ethoxy)ethoxy)ethoxy)ethylsulfonyl)-1-oxoisoindolin-2-yl)piperidine-2,6-dione) |
| | 3-(4-(2-bromoethylsulfonyl)-1-oxoisoindolin-2-yl)piperidine-2,6-dione |
| | 3-(4-(3-bromopropylsulfonyl)-1-oxoisoindolin-2-yl)piperidine-2,6-dione |
| | 3-(4-(4-bromobutylsulfonyl)-1-oxoisoindolin-2-yl)piperidine-2,6-dione |
| | 3-(4-(5-bromopentylsulfonyl)-1-oxoisoindolin-2-yl)piperidine-2,6-dione |
| | 3-(4-(6-bromohexylsulfonyl)-1-oxoisoindolin-2-yl)piperidine-2,6-dione |
| | 3-(4-(7-bromoheptylsulfonyl)-1-oxoisoindolin-2-yl)piperidine-2,6-dione |
| | 2-(2-(2-(2,6-dioxopiperidin-3-yl)-1-oxoisoindolin-4-ylsulfonyl)ethoxy)ethyl 4-methylbenzenesulfonate |
| | 2-(2-(2-(2-(2,6-dioxopiperidin-3-yl)-1-oxoisoindolin-4-ylsulfonyl)ethoxy)ethoxy)ethyl 4-methylbenzenesulfonate |
| | 2-(2-(2-(2-(2,6-dioxopiperidin-3-yl)-1-oxoisoindolin-4-ylsulfonyl)ethoxy)ethoxy)ethoxy)ethyl 4-methylbenzenesulfonate |
| | 2-(2-(2-(2-(2-(2,6-dioxopiperidin-3-yl)-1-oxoisoindolin-4-ylsulfonyl)ethoxy)ethoxy)ethoxy)ethoxy)ethyl 4-methylbenzenesulfonate |
| | 2-(2-(2-(2-(2-(2-(2,6-dioxopiperidin-3-yl)-1-oxoisoindolin-4-ylsulfonyl)ethoxy)ethoxy)ethoxy)ethoxy)ethoxy)ethyl 4-methylbenzenesulfonate |
| | 2-(2-(2,6-dioxopiperidin-3-yl)-1-oxoisoindolin-4-ylsulfonyl)ethyl 4-methylbenzenesulfonate |
| | 3-(2-(2,6-dioxopiperidin-3-yl)-1-oxoisoindolin-4-ylsulfonyl)propyl 4-methylbenzenesulfonate |
| | 4-(2-(2,6-dioxopiperidin-3-yl)-1-oxoisoindolin-4-ylsulfonyl)butyl 4-methylbenzenesulfonate |
| | 5-(2-(2,6-dioxopiperidin-3-yl)-1-oxoisoindolin-4-ylsulfonyl)pentyl 4-methylbenzenesulfonate |
| | 6-(2-(2,6-dioxopiperidin-3-yl)-1-oxoisoindolin-4-ylsulfonyl)hexyl 4-methylbenzenesulfonate |
| | 7-(2-(2,6-dioxopiperidin-3-yl)-1-oxoisoindolin-4-ylsulfonyl)heptyl 4-methylbenzenesulfonate |

In another aspect, the present disclosure also provides the use of the compound of formula (IV) or a salt, enantiomer, stereoisomer, solvate, or polymorph thereof for preparing the compound of the formula (I) as claimed in claim 1.

In another aspect, the present disclosure also provides a pharmaceutical composition comprising, as an active ingredient, the compound of formula (IV) according to the present disclosure or a pharmaceutically acceptable salt thereof, and a pharmaceutically acceptable carrier.

The pharmaceutical composition of the present disclosure above further includes at least one additional medicine for treating or preventing a cancer.

In another aspect of the present disclosure, the compound of formula (IV) according to the present disclosure, or a pharmaceutically acceptable salt thereof, is for use as a medicament.

In another aspect of the present disclosure, the compound of formula (IV) according to the present disclosure, or a pharmaceutically acceptable salt thereof, is used for preventing and/or treating a cancer. In an embodiment, the cancer is selected from: multiple myeloma, myelodysplastic syndrome (MDS), previously treated myelodysplastic syndrome, plasma cell myeloma, transplantation-related cancer, myelofibrosis, plasma cell myeloma, bone marrow disease, neutropenia, leukemia, acute myelogenous leukemia, anemia, chronic granulocytic leukemia, B-cell chronic lymphocytic leukemia, acute myeloid leukemia (AML), CD20 positive, primary lymphoma, B-cell lymphoma, recurrent B-cell non-Hodgkin's lymphoma, recurrent diffuse large B-cell lymphoma, recurrent/primary mediastinal (thymus) large B-cell lymphoma, relapsed transformed non-Hodgkin's lymphoma, refractory B-cell non-Hodgkin's lymphoma, refractory diffuse large B-cell lymphoma, refractory primary mediastinal (thymus) large B-cell lymphoma, refractory transformed non-Hodgkin's lymphoma, smoldering myeloma, smoldering multiple myeloma, and Unverricht Syndrome.

Another aspect of the present disclosure provides the use of the compound of formula (IV) according to the present disclosure, or a pharmaceutically acceptable salt thereof, for the preparation of a medicament for the prevention and/or treatment of a cancer. In an embodiment, the cancer is selected from: multiple myeloma, myelodysplastic syndrome (MDS), previously treated myelodysplastic syndrome, plasma cell myeloma, transplantation-related cancer, myelofibrosis, plasma cell myeloma, bone marrow disease, neutropenia, leukemia, acute myelogenous leukemia, anemia, chronic myelogenous leukemia, B-cell chronic lymphocytic leukemia, acute myeloid leukemia (AML), CD20 positive, primary lymphoma, B-cell lymphoma, recurrent B-cell non-Hodgkin's lymphoma, recurrent diffuse large B-cell lymphoma, recurrent/primary mediastinal (thymus) large B-cell lymphoma, relapsed transformed non-Hodgkin's lymphoma, refractory B-cell non-Hodgkin's lymphoma, refractory diffuse large B-cell lymphoma, refractory primary mediastinal (thymus) large B-cell lymphoma, refractory transformed non-Hodgkin's lymphoma, smoldering myeloma, smoldering multiple myeloma, and Unverricht Syndrome.

A further aspect of the present disclosure also provides a method for treating or preventing a cancer, which comprises administering to a subject a therapeutically effective amount of the compound of formula (IV) according to the present disclosure, or a pharmaceutically acceptable salt thereof, or the pharmaceutical composition comprising the compound of formula (IV). In an embodiment, the cancer is selected from: multiple myeloma, myelodysplastic syndrome (MDS), previously treated myelodysplastic syndrome, plasma cell myeloma, transplantation-related cancer, myelofibrosis, plasma cell myeloma, bone marrow disease, neutropenia, leukemia, acute myelogenous leukemia, anemia, chronic myelogenous leukemia, B-cell chronic lymphocytic leukemia, acute myeloid leukemia (AML), CD20 positive, primary lymphoma, B-cell lymphoma, recurrent B-cell non-Hodgkin's lymphoma, recurrent diffuse large B-cell lymphoma, recurrent/primary mediastinal (thymus) large B-cell lymphoma, relapsed transformed non-Hodgkin's lymphoma, refractory B-cell non-Hodgkin's lymphoma, refractory diffuse large B-cell lymphoma, refractory primary mediastinal (thymus) large B-cell lymphoma, refractory transformed non-Hodgkin's lymphoma, smoldering myeloma, smoldering multiple myeloma, and Unverricht Syndrome.

In the method for treating or preventing a cancer according to the present disclosure, the compound of formula (IV) according to the present disclosure, or a pharmaceutically acceptable salt thereof, or the pharmaceutical composition comprising the compound of formula (IV) is administered to the subject by at least one mode of administration selected from: nasal administration, inhalation administration, topical administration, oral administration, oral mucosal administration, rectal administration, pleural, peritoneal, vaginal, intramuscular, subcutaneous, transdermal, epidural, intrathecal, and intravenous administration.

Definition

Herein, the compound of formula (I) of the present disclosure is also referred to as a degrader (or degradation agent), proteolysis targeting drug PROTAD, or PROTAD small molecule (PROTAD compound), which can be used interchangeably.

Herein, the compound fragment represented by formula (Ia) and the compound of formula (Ia1):

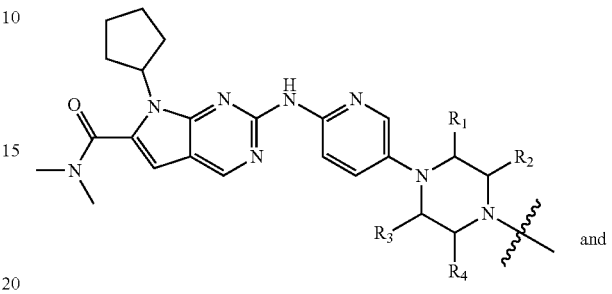

(Ia)

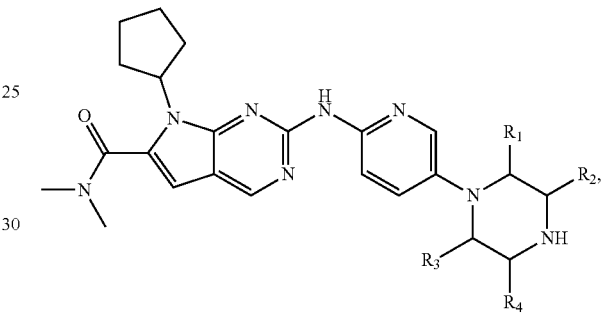

(Ia1)

are both structures derived from Ribociclib by modifying the piperazinyl of Ribociclib, wherein $R_1$, $R_2$, $R_3$, and $R_4$ are each independently H or methyl.

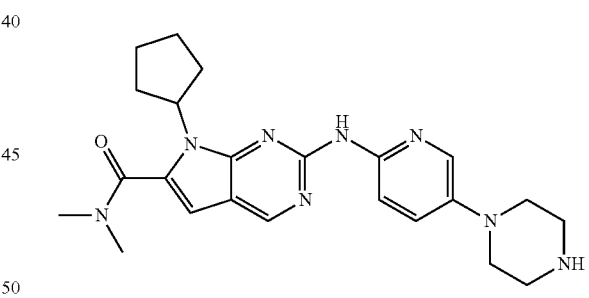

Ribociclib

Herein, the compound fragment represented by formula (Ib) and the compound of formula (Ib1):

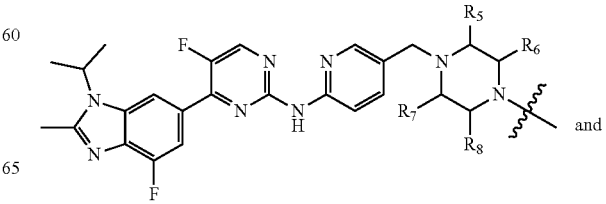

(Ib)

(Ib1)

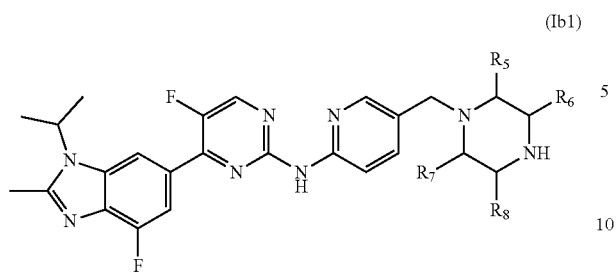

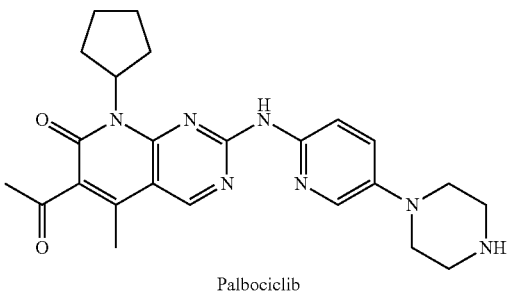 [SMILES: CC(=O)c1c(C)c2cnc(Nc3ccc(N4CCNCC4)cn3)nc2n(C2CCCC2)c1=O]

Palbociclib are both structures derived from Abemaciclib by removing the ethyl group on the nitrogen of piperazinyl, wherein $R_5$, $R_6$, $R_7$, and $R_8$ are each independently H or methyl.

Herein, the compound fragment represented by formula (Id) and the compound of formula (Id1):

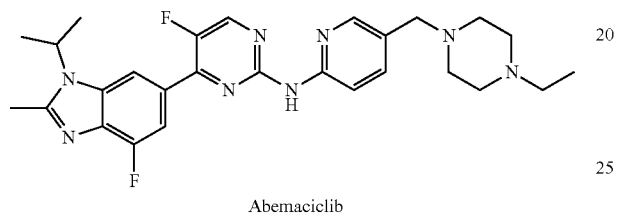

Abemaciclib (Id)

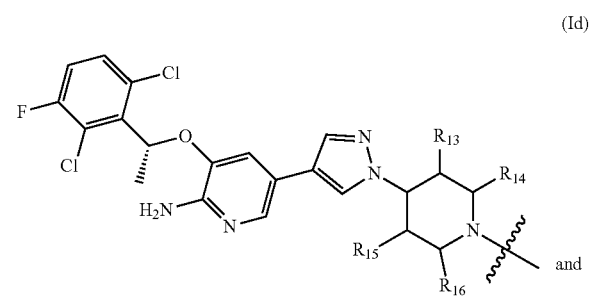

and

Herein, the compound fragment represented by formula (Ic) and the compound of formula (Ic1):

(Ic)

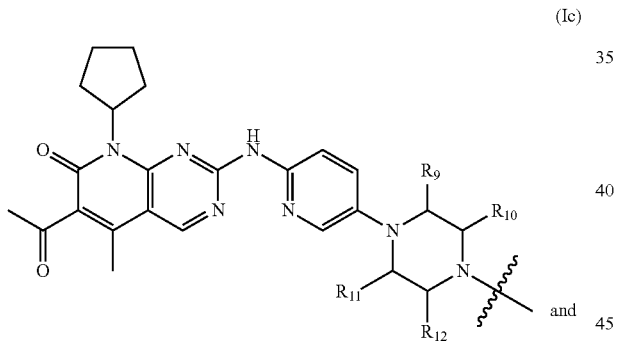

and (Id1)

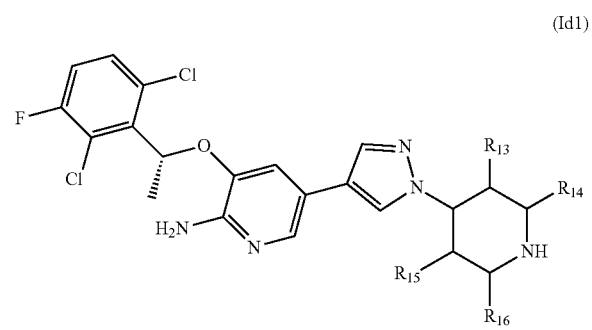

are both structures derived from Crizotinib by modifying the piperidinyl of Crizotinib, wherein $R_{13}$, $R_{14}$, $R_{15}$, and $R_{16}$ are each independently H or methyl.

(Ic1)

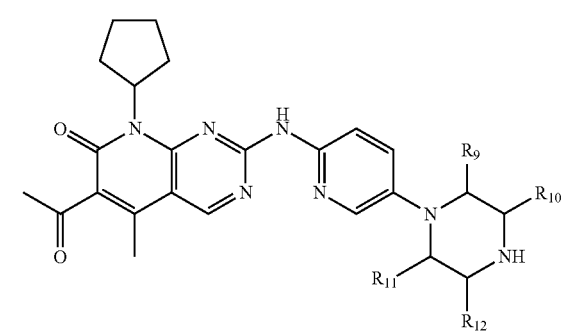

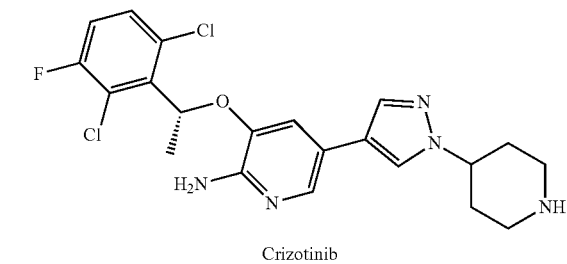 [SMILES: C[C@@H](Oc1cc(-c2cnn(C3CCNCC3)c2)cnc1N)c1c(Cl)ccc(F)c1Cl]

Crizotinib are both structures derived from Palbociclib by modifying the piperazinyl of Palbociclib, wherein $R_9$, $R_{10}$, $R_{11}$, and $R_{12}$ are each independently H or methyl.

Herein, the compound fragment represented by formula (Ie) and the compound of formula (Ie1):

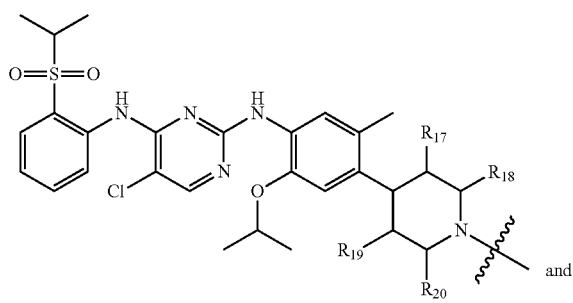

(Ie)

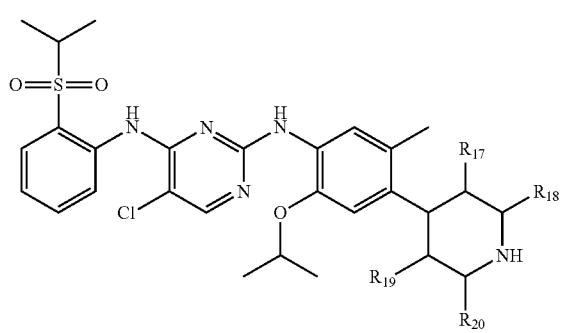

(Ie1)

are both structures derived from Ceritinib by modifying the piperidinyl of Ceritinib, wherein $R_{17}$, $R_{18}$, $R_{19}$, and $R_{20}$ are each independently H or methyl.

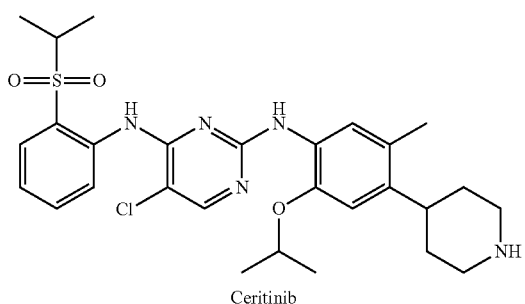 [SMILES: Cc1cc(Nc2ncc(Cl)c(Nc3ccccc3S(=O)(=O)C(C)C)n2)c(OC(C)C)cc1C1CCNCC1]

Ceritinib

Herein, the compound fragment represented by formula (If) and the compound of formula (If1):

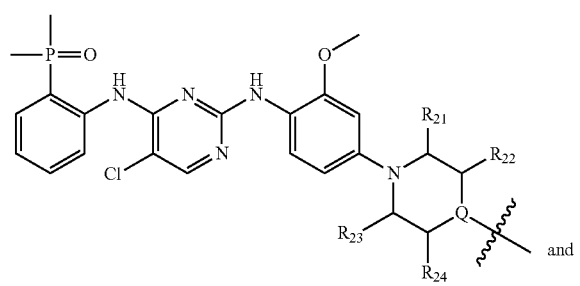

(If)

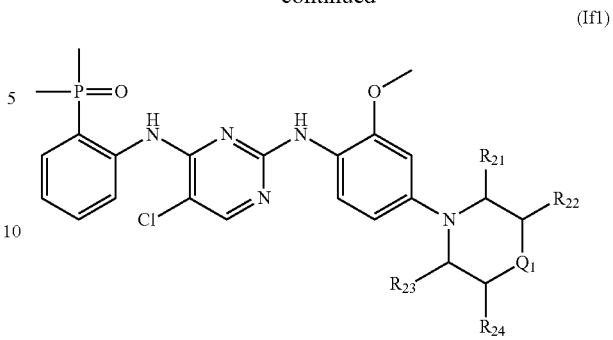

(If1)

are both structures derived from Brigatinib by modifying the piperidine-piperazine group of Brigatinib, wherein $R_{21}$, $R_{22}$, $R_{23}$, and $R_{24}$ are each independently H or methyl, and Q is N or CH, wherein CH is connected to the group LIN through NH or piperazinylene, or Q is CH, wherein CH is connected to the group LIN through $N(CH_3)$, and $Q_1$ is NH or CH, wherein CH is substituted by $NH_2$ or piperazinyl.

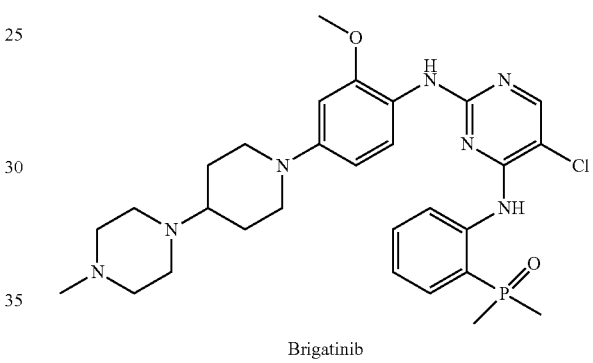

Brigatinib

Herein, the compound fragments represented by formulas (Ig), (Ih), and (Ii) and the compounds of formulas (Ig1), (Ih1), and (Ii1):

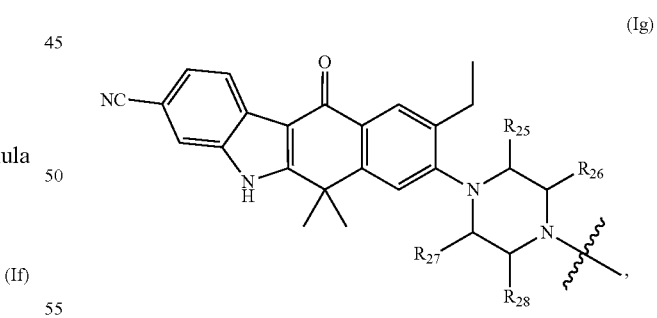

(Ig)

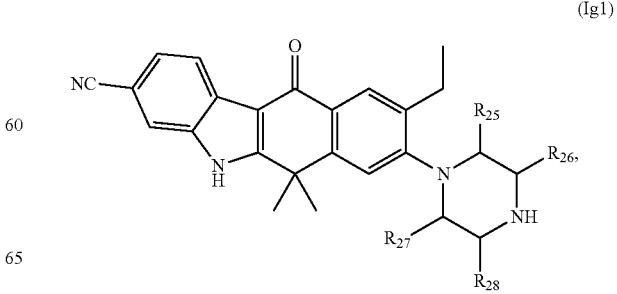

(Ig1)

-continued (Ih)

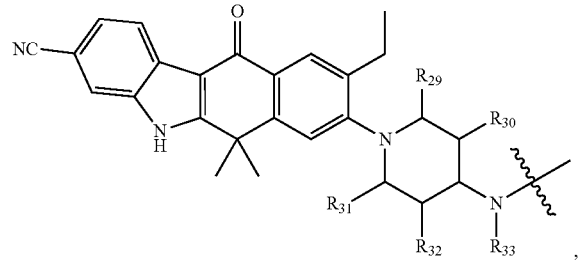

(Ih1)

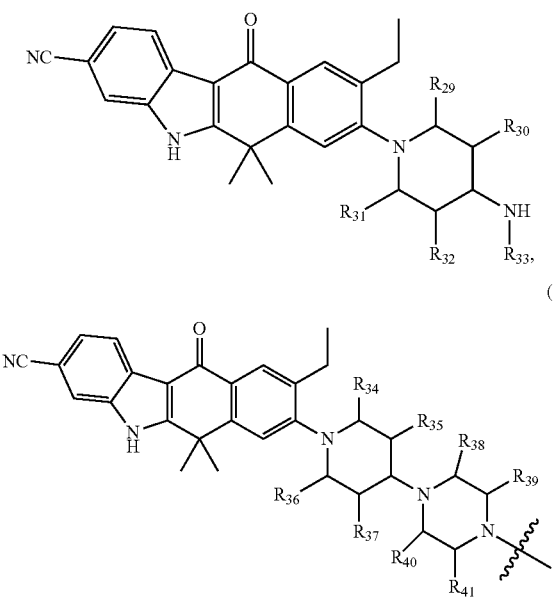

(Ii)

(Ii1)

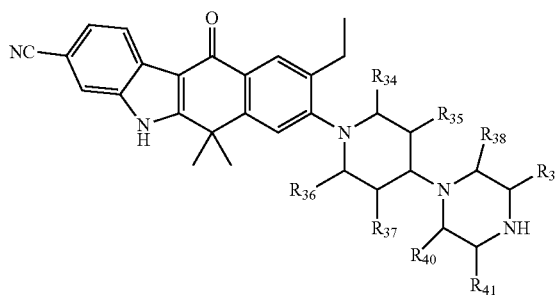

are all structures derived from Alectinib by modifying the piperidine-morpholine group of Alectinib, wherein $R_{25}$, $R_{26}$, $R_{27}$, $R_{28}$, $R_{29}$, $R_{30}$, $R_{31}$, $R_{32}$, $R_{34}$, $R_{35}$, $R_{36}$, $R_{37}$, $R_{38}$, $R_{39}$, $R_{40}$, $R_{41}$ are each independently H or methyl, and $R_{33}$ represents H, methyl or ethyl.

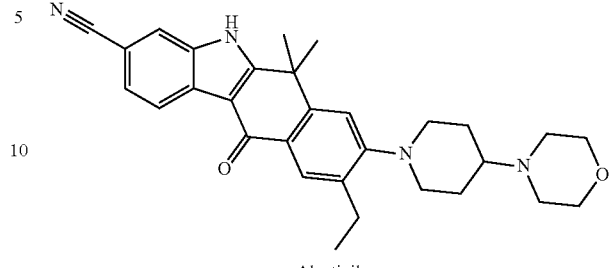

Alectinib

Herein, the compound fragment represented by formula (Ij) and the compound of formula (Ij1):

(Ij)

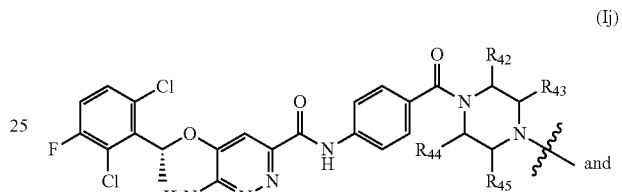

and (Ij1)

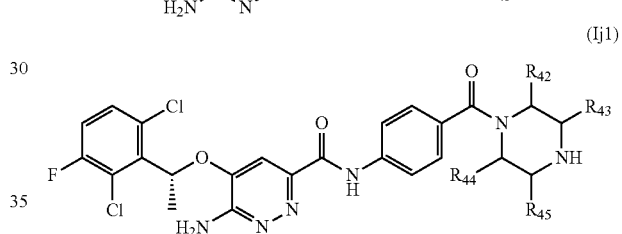

are both structures derived from Ensartinib by removing the methyl group on the nitrogen of piperazinyl, wherein $R_{42}$, $R_{43}$, $R_{44}$, and $R_{45}$ are each independently H or methyl.

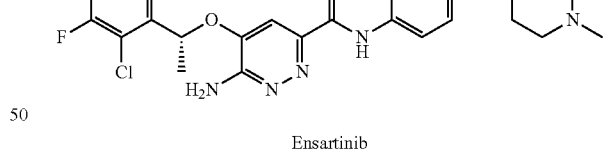

Ensartinib

Herein, the compound fragment represented by formula (Il) and the compound of formula (Il1):

(Il)

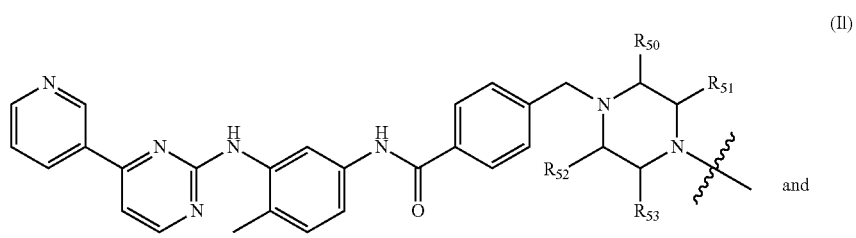

and

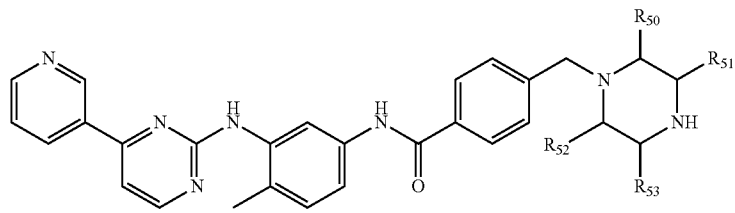

are both structures derived from Imatinib by removing the methyl group on the nitrogen of piperazinyl, wherein $R_{50}$, $R_{51}$, $R_{52}$, and $R_{53}$ are each independently H or methyl.

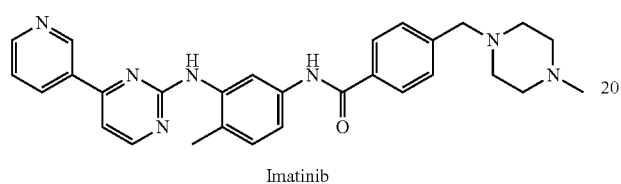

Imatinib

Herein, the compound fragment represented by formula (Im) and the compound of formula (Im1):

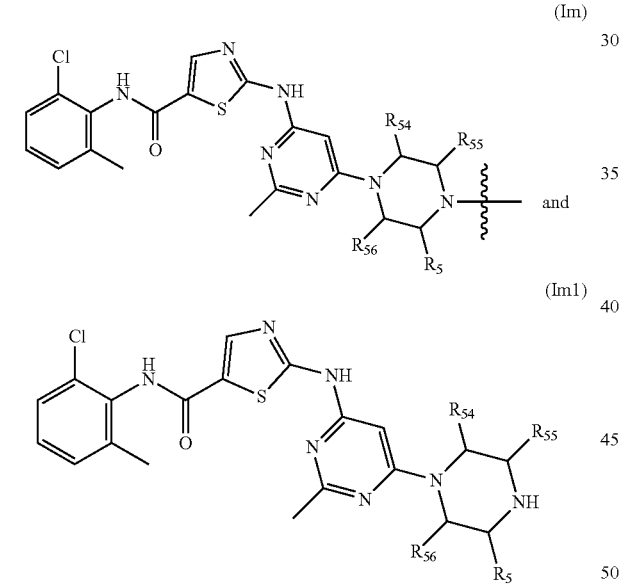

are both structures derived from Dasatinib by removing the hydroxyethyl group on the nitrogen of piperazinyl, wherein $R_{54}$, $R_{55}$, $R_{56}$, and $R_{57}$ are each independently H or methyl.

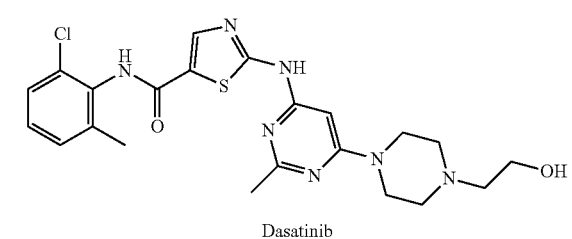 [SMILES: Cc1nc(Nc2ncc(C(=O)Nc3c(C)cccc3Cl)s2)cc(N2CCN(CCO)CC2)n1]

Dasatinib

Herein, the compound fragment represented by formula (In) and the compound of formula (In1):

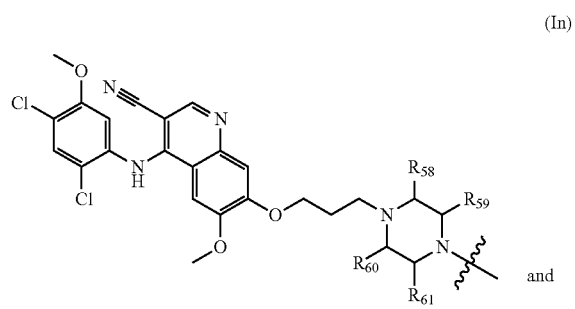

and

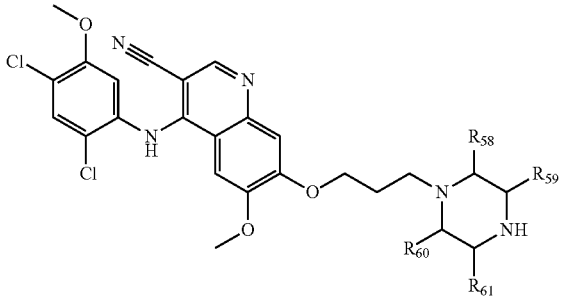

are both structures derived from Bosutinib by removing the methyl group on the nitrogen of piperazinyl, wherein $R_{58}$, $R_{59}$, $R_{60}$, and $R_{61}$ are each independently H or methyl.

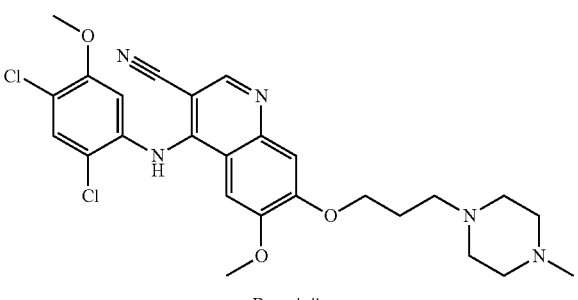

Bosutinib

Herein, the compound fragment represented by formula (Io) and the compound of formula (Io1):

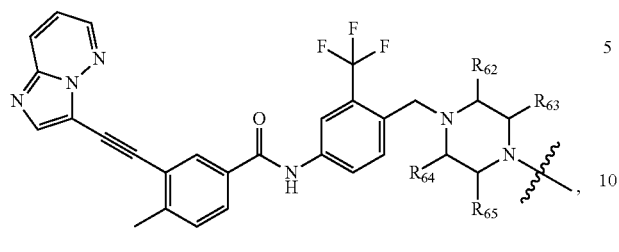
(Io)

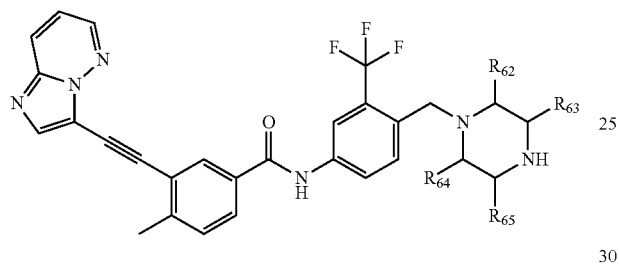
(Io1)

are both structures derived from Ponatinib by removing the methyl group on the nitrogen of piperazinyl, wherein $R_{62}$, $R_{63}$, $R_{64}$, and $R_{65}$ are each independently H or methyl.

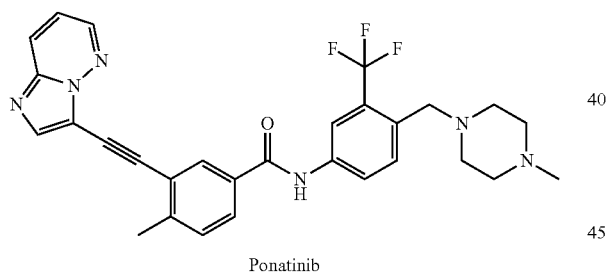
Ponatinib

Herein, the compound fragment represented by formula (Ip) and the compound of formula (Ip1):

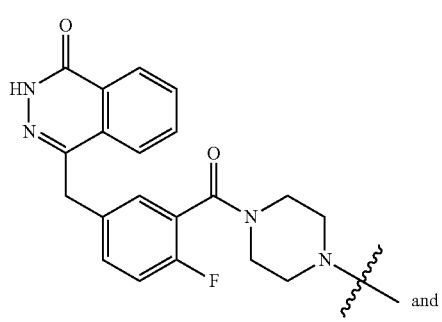
(Ip) and

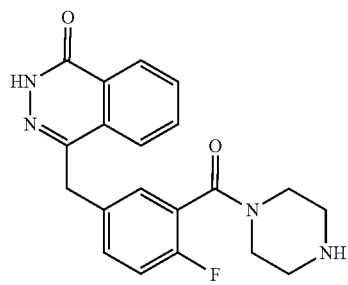
(Ip1)

are both structures derived from Olaparib by removing the cyclopropylformyl group on the nitrogen of piperazinyl.

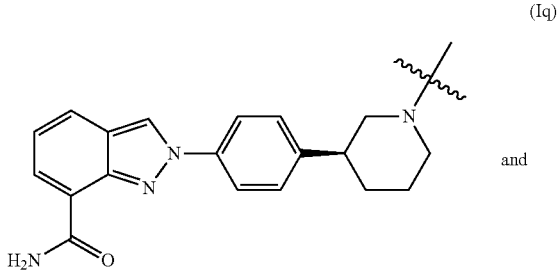
Olaparib

Herein, the compound fragment represented by formula (Iq) and the compound of formula (Iq1):

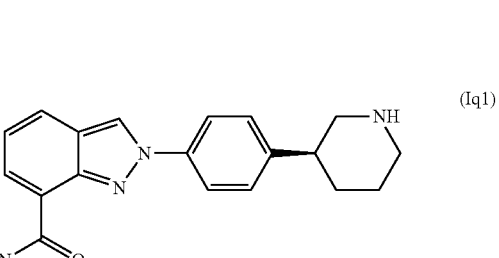
(Iq) and (Iq1)

are both structures derived from Niraparib by modifying the piperidinyl of Niraparib.

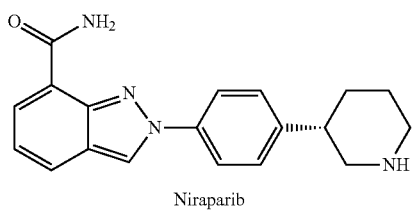 [SMILES: NC(=O)c1cccc2cn(-c3ccc([C@@H]4CCCNC4)cc3)nc12]

Niraparib

Herein, the compound fragment represented by formula (Ir) and the compound of formula (Ir1):

(Ir)

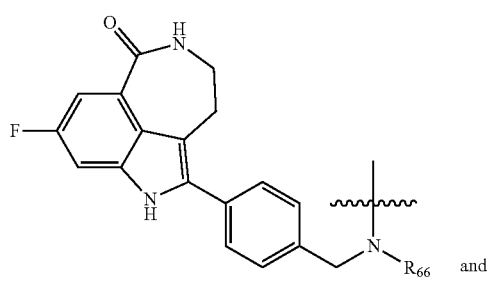

and (Ir1)

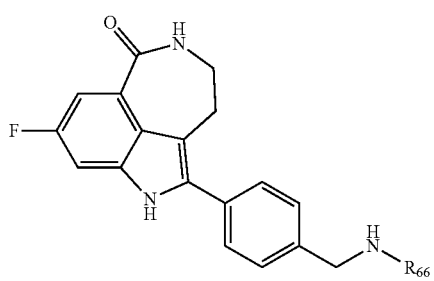

are both structures derived from Rucaparib by modifying the methylamino group of Rucaparib, wherein $R_{66}$ is H or methyl.

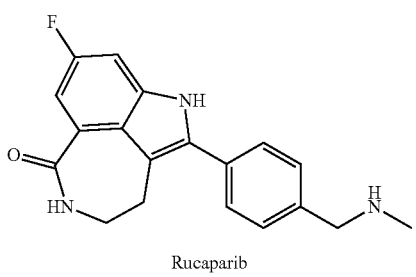 [SMILES: CNCc1ccc(-c2[nH]c3cc(F)cc4c3c2CCNC4=O)cc1]

Rucaparib

Herein, the compound fragment represented by formula (Is) and the compound of formula (Is1):

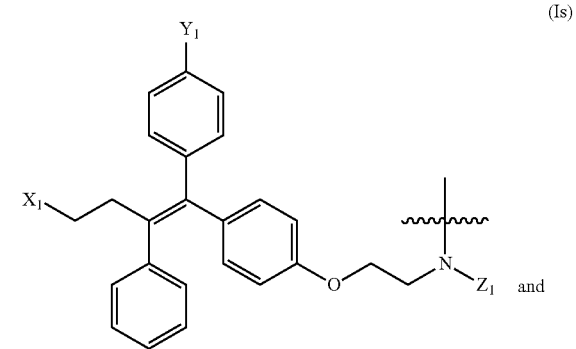

are both structures derived from Toremifene, Tamoxifen, 4-Hydroxyltamoxifen or 4-Hydroxyltoremifene by modifying the amino of Toremifene, Tamoxifen, 4-Hydroxyltamoxifen or 4-Hydroxyltoremifene, respectively, wherein:

when formula (Is) or (Is1) represents a derivative or fragment of toremifene, $X_1$ is Cl, $Y_1$ is H, $Z_1$ is H or methyl, and $W_1$ is H;

when formula (Is) or (Is1) represents a derivative or fragment of 4-hydroxytoremifene, $X_1$ is Cl, $Y_1$ is OH, $Z_1$ is H or methyl, and $W_1$ is H;

when formula (Is) or (Is1) represents a derivative of tamoxifen or a fragment thereof, $X_1$ is H, $Y_1$ is H, $Z_1$ is H or methyl, and $W_1$ is H;

when formula (Is) or (Is1) represents a derivative or fragment of 4-hydroxytamoxifen, $X_1$ is H, $Y_1$ is OH, $Z_1$ is H or methyl, and $W_1$ is H;

when formula (Is) or (Is1) represents a derivative or fragment of 4,4'-dihydroxytamoxifen, $X_1$ is H, $Y_1$ is OH, $Z_1$ is H or methyl, and $W_1$ is OH.

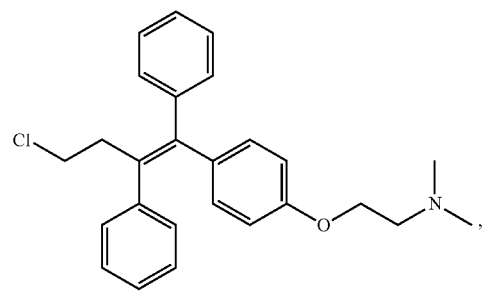

Toremifene

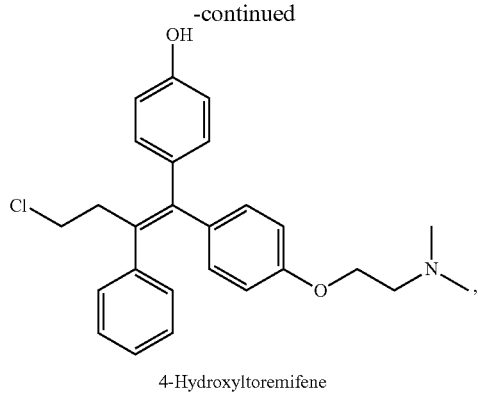
4-Hydroxytoremifene
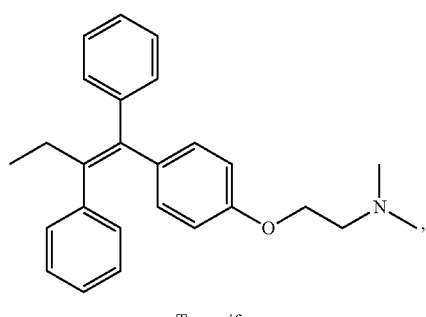
Tamoxifen
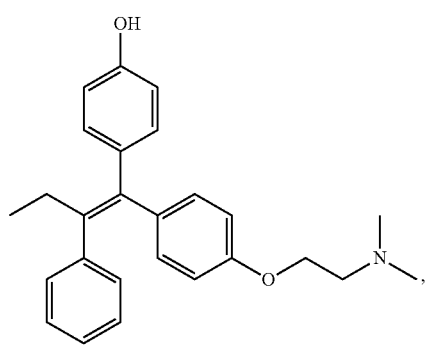
4-Hydroxytamoxifen
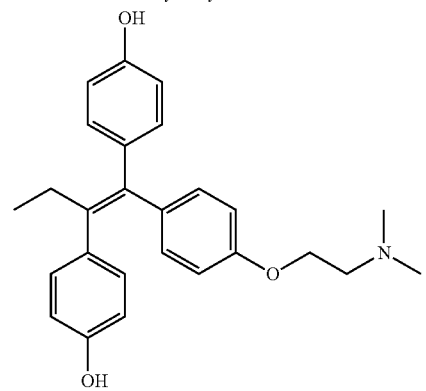
4,4'-dihydroxytamoxifen
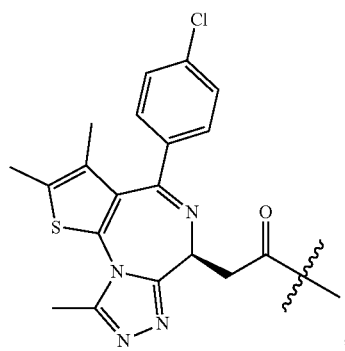
(It)
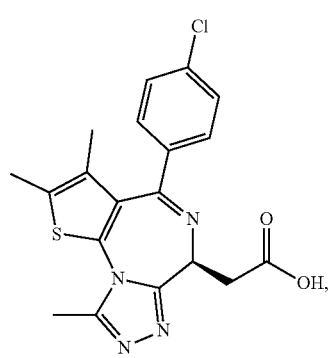
(It1)
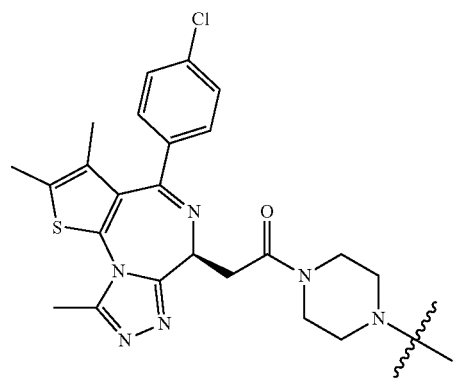
(It-3)
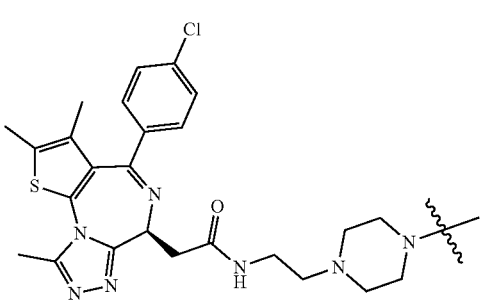
(It-4)
, and
Herein, the compound fragment represented by formula (It), the compound of formula (It1), the compound fragments represented by formulas (It-3), (It-4) and (It-5):

-continued (It-5)

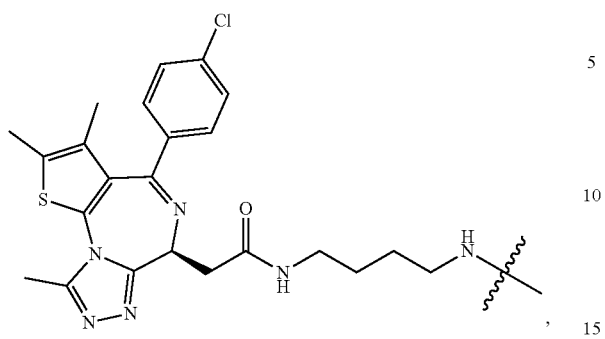

are all structures derived from the hydrolysis product of JQ-1 tert-butyl ester.

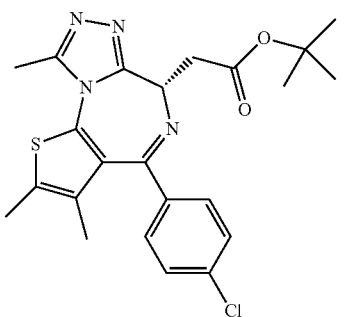

JQ-1

Herein, the compound fragment represented by formula (Iu) and the compound of formula (Iu1):

(Iu)

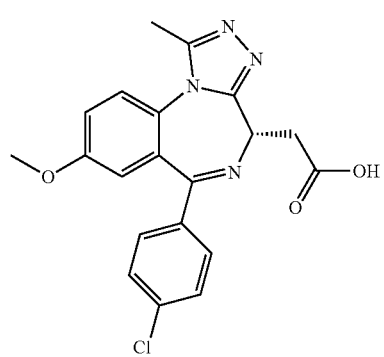

and (Iu1)

are both structures derived from I-BET762 by removing the ethyl group on nitrogen.

I-BET762

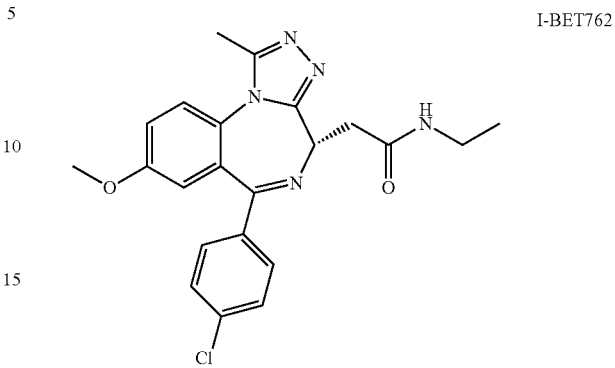

Herein, the compound fragment represented by formula (Iv) and the compound of formula (Iv1):

(IV)

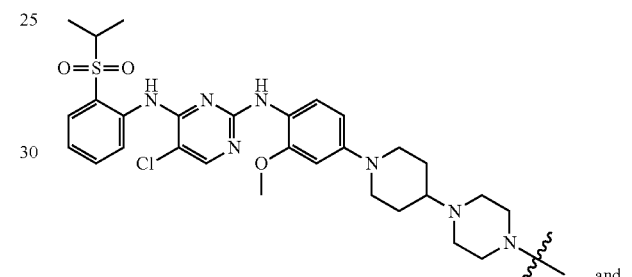

and (Iv1)

are both structures derived from TAE684 by removing the methyl group on piperazinyl.

TAE684

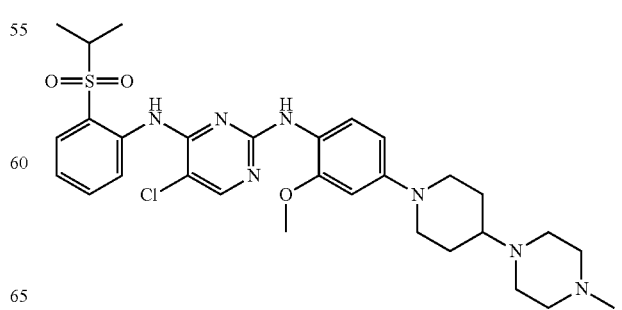

Herein, the compound fragment represented by formula (Iw) and the compound of formula (Iw1):

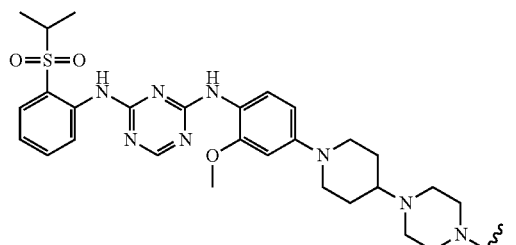
(Iw)

and

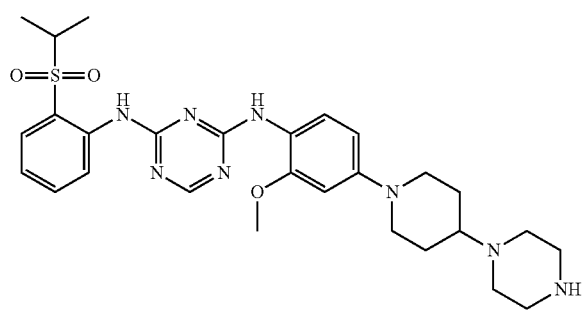
(Iw1)

are both structures derived from ASP3026 by removing the methyl group on piperazinyl.

ASP3026

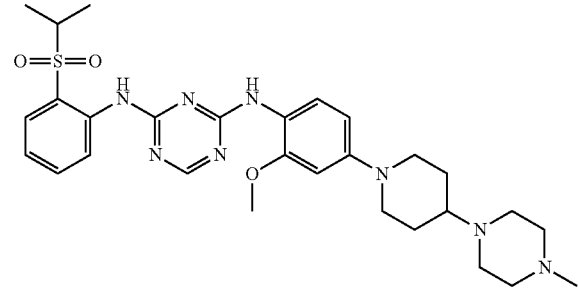

Herein, the compound fragment represented by formula (Ix) and the compound of formula (Ix1):

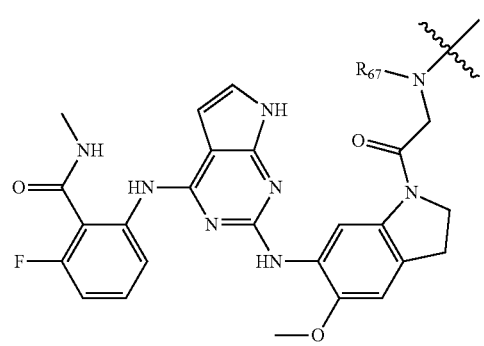
(Ix)

and

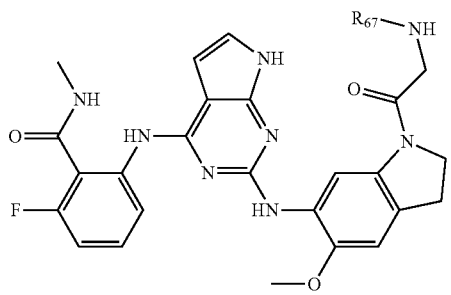
(Ix1)

are both structures derived from GSK1838705A by removing the methyl group on the dimethylamino group, wherein $R_{67}$ is H, methyl or ethyl.

GSK1838705A

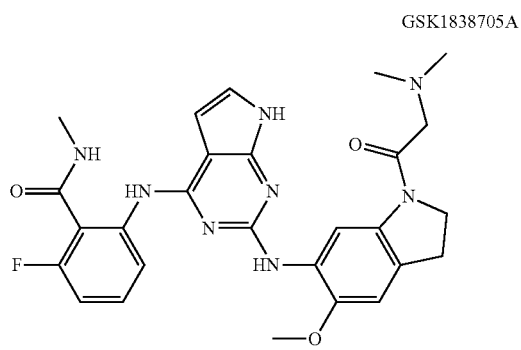 [SMILES: CNC(=O)c1c(F)cccc1Nc1nc(Nc2cc3c(cc2OC)CCN3C(=O)CN(C)C)nc2[nH]ccc12]

Herein, the compound fragment represented by formula (Iy) and the compound of formula (Iy1):

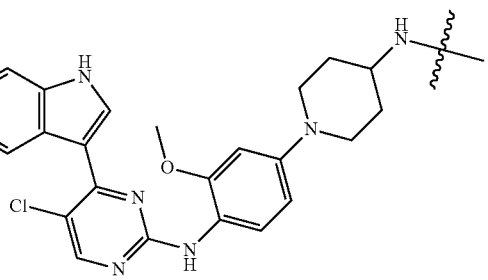
(Iy)

and

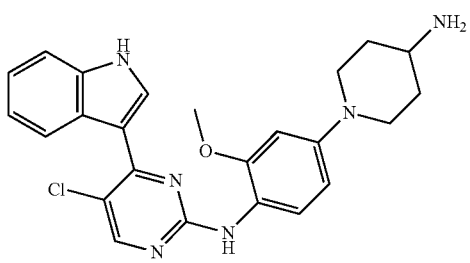
(Iy1)

are both structures derived from AZD3463 by modifying the primary amino group.

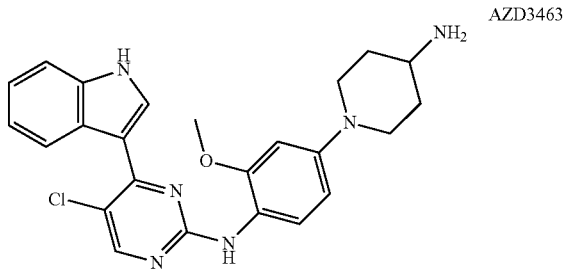

AZD3463

Herein, a bond interrupted by a wavy line shows the point of attachment of the radical depicted. For example, the group depicted below

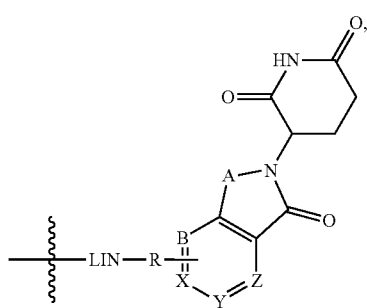

(II)

represents the chemical fragment represented by formula (II), which is connected to the SMBP part of the compound of formula (I) through the linking group LIN.

As used herein, the ULM in the compound of formula (I) represents a monovalent group obtained by removing one hydrogen from the R group of the following formula (III) structure:

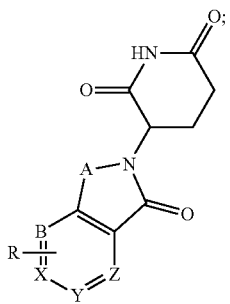

formula (III)

in formula (III), A represents —CH$_2$— or —CO—, B, X, Y, and Z are the same or different and each independently represent —CH$_2$— or —N—, R represents —SH, —S(O)-alkyl (preferably-S(O)—CH$_3$), —SO$_2$-alkyl (preferably —SO$_2$—CH$_3$) or piperazinyl.

As used herein, the terms "LIN" and "linker" are used interchangeably and both refers to a linking group in a compound of formula (I).

As used herein, the term "halogen atom" or "halogen" used alone or in combination refers to fluorine, chlorine, bromine or iodine, and is preferably F, Cl or Br.

As used herein, the term "alkyl" used alone or in combination refers to a linear or branched alkyl group. The term "(Cx-Cy) alkyl" or "Cx-y alkyl" (x and y are each an integer) refers to a linear or branched chain alkyl group containing from x to y carbon atoms. The term "$C_{1-10}$ alkyl" used alone or in combination in the present disclosure refers to a linear or branched chain alkyl group containing from 1 to 10 carbon atoms. The $C_{1-10}$ alkyl group of the present disclosure includes, but are not limited to, a $C_{1-9}$ alkyl group, more preferably $C_{1-8}$ alkyl group, still more preferably $C_{2-8}$ alkyl group, more preferably $C_{1-7}$ alkyl group, even more preferably $C_{1-6}$ alkyl, $C_{1-5}$ alkyl, or $C_{1-4}$ alkyl. Representative examples include, methyl, ethyl, n-propyl, isopropyl, n-butyl, isobutyl, sec-butyl, tert-butyl, pentyl, isopentyl, neopentyl, tert-pentyl, hexyl, heptyl, octyl, nonyl and decyl. The term "$C_{1-3}$ alkyl group" in the present disclosure refers to an alkyl group containing from 1 to 3 carbon atoms, and its representative examples include methyl, ethyl, n-propyl, and isopropyl.

As used herein, the "alkyl" is optionally substituted, and the substituent can be one or more selected from halogen, cyano, $C_{1-3}$ alkyl, $C_{1-3}$ alkoxy, trifluoromethyl, heterocyclyl, or any combination thereof.

As used herein, the term "alkylene" (which is used interchangeably with "alkylene chain") used alone or in combination refers to a linear or branched divalent saturated hydrocarbon group composed of carbon and hydrogen atoms. The term "$C_x$-$C_y$ alkylene" or "$C_{x-y}$ alkylene" (x and y are each an integer) refers to a linear or branched alkylene group containing from x to y carbon atoms. The $C_1$-$C_{30}$ alkylene group in the present disclosure includes $C_1$-$C_{29}$ alkylene, $C_1$-$C_{28}$ alkylene, $C_1$-$C_{27}$ alkylene, $C_1$-$C_{26}$ alkylene, $C_1$-$C_{25}$ alkylene, $C_1$-$C_{24}$ alkylene, $C_1$-$C_{23}$ alkylene, $C_1$-$C_{22}$ alkylene, $C_1$-$C_{21}$ alkylene, $C_1$-$C_{20}$ alkylene, $C_1$-$C_{19}$ alkylene, $C_1$-$C_{15}$ alkylene, $C_1$-$C_{17}$ alkylene, $C_1$-$C_{16}$ alkylene, $C_1$-$C_{15}$ alkylene, $C_1$-$C_{14}$ alkylene, $C_1$-$C_{13}$ alkylene, $C_1$-$C_{12}$ alkylene, $C_1$-$C_{11}$ alkylene, $C_1$-$C_{10}$ alkylene, $C_1$-$C_9$ alkylene, $C_1$-$C_8$ alkylene, $C_1$-$C_7$ alkylene, $C_1$-$C_6$ alkylene, $C_1$-$C_5$ alkylene, $C_1$-$C_4$ alkylene, $C_1$-$C_3$ alkylene, or $C_1$-$C_2$ alkylene. Representative examples include, but are not limited to, methylene, ethylene, propylene, isopropylidene, butylene, isobutylene, sec-butylene, tert-butylene, n-pentylene, isopentylene, neopentylene, tert-pentylene, hexylene, heptylene, octylene, nonylene, decylene, undecylene, dodecylene, tridecylene, tetradecylene, pentadecylene, hexadecylene, heptadecylene, octadecylene, nonadecylene, eicosylene, heneicosylene, docosylene, tricosylene, tetracosylene, pentacosylene, hexacosylene, peptacosylene, octacosylene, nonacosylene, and triacontylene.

As used herein, the "alkylene" is optionally substituted, and the substituent can be one or more selected from halogen, cyano, $C_{1-3}$ alkyl, $C_{1-3}$ alkoxy, trifluoromethyl, heterocyclyl, or any combination thereof.

As used herein, the term "arylene" used alone or in combination refers to a divalent aromatic hydrocarbon group containing from 5 to 14 carbon atoms and optionally one or more fused rings, such as phenylene group, naphthylene group or fluorenylene group. In the present disclosure, the "arylene" is an optionally substituted arylene. A substituted arylene group refers to an arylene group optionally substituted 1-3 times with a substituent(s), wherein the substituent is optionally selected from $C_{1-3}$ alkyl, $C_{1-3}$ alkoxy, trifluoromethyl, mercapto, cyano, halogen, amino, and hydroxyl.

As used herein, the term "$C_{1-3}$ alkoxy group" used alone or in combination refers to a linear or branched alkoxy group containing from 1 to 3 carbon atoms. Representative examples of $C_{1-3}$ alkoxy include, but are not limited to, methoxy, ethoxy, n-propoxy, and isopropoxy. Preferred are methoxy and ethoxy.

As used herein, the term "cycloalkyl" used alone or in combination refers to a saturated or partially unsaturated (i.e., containing one or more double bonds, but not having a completely conjugated π-electron system) monocyclic or bicyclic cyclic hydrocarbon group, having from 3 to 12 carbon atoms. The term "$C_3$-$C_{10}$ cycloalkyl" refers to a saturated or partially unsaturated (i.e., containing one or more double bonds, but not having a completely conjugated π-electron system) monocyclic or bicyclic cyclic hydrocarbon group, having from 3 to 10 carbon atoms. Representative examples of "cycloalkyl" include, but are not limited to, cyclopropyl, cyclobutyl, cyclopentyl, cyclopentenyl, cyclohexyl, cyclohexenyl, cycloheptyl, cyclooctyl, decalinyl, octahydropentalenyl, octahydro-1H-indenyl, and Spiro-cycloalkyl. As used herein, the cycloalkyl group is optionally substituted, and the substituent can be one or more selected from trifluoromethyl, mercapto, hydroxyl, amino, halogen, cyano, $C_{1-3}$ alkyl, $C_{1-3}$ alkoxy, heterocyclyl, or any combination thereof.

As used herein, the term "cycloalkylene", used alone or in combination, refers to a saturated and partially unsaturated (ie, containing one or more double bonds, but not having a completely conjugated 7π-electron system) divalent monocyclic or bicyclic cyclic hydrocarbon group, having from 3 to 12 carbon atoms. Representative examples of "cycloalkylene" include, but are not limited to, cyclopropylene, cyclobutylene, cyclopentylene, cyclopentenylene, cyclohexylene, cyclohexenylene, cycloheptylene, cyclooctylene, decalinylene, octahydropentalenylene, octahydro-1H-indenylene, and Spiro-cycloalkylene. The cycloalkylene group may be unsubstituted or substituted, according to a clear definition. In the present disclosure, the substituent(s) of the substituted "cycloalkylene" is preferably one or more selected from halogen, mercapto, hydroxy, amino, cyano, $C_{1-3}$ alkyl, $C_{1-3}$ alkoxy, trifluoromethyl, heterocyclyl or a combination thereof.

As used herein, the term "heteroarylene" used alone or in combination refers to a 5- to 10-membered monocyclic or bicyclic divalent aromatic ring group containing one or more (eg., from 1 to 6, or from 1 to 5, or from 1 to 4, or from 1 to 3) heteroatoms independently selected from the group consisting of oxygen, nitrogen, and sulfur. Representative examples of such heteroarylene group include, but are not limited to, furanylene, oxazolylene, isoxazolylene, oxadiazolylene, thienylene, thiazolylene, isothiazolylene, thiadiazolylene, pyrrolylene, imidazolylene, triazolylene, pyridylene, pyrimidinylene, pyridazinylene, pyrazinylene, indolylene, isoindolylene, benzofuranylene, isobenzofuranylene, benzothienylene, indazolylene, benzimidazolylene, benzoxazolylene, benzoisoxazolylene, benzothiazolylene, benzoisothiazolylene, benzotriazolylene, benzo[2,1,3]oxadiazolylene, benzo[2,1,3]thiadiazolylene, benzo[1,2,3]thiadiazolylene, quinolylene, isoquinolylene, naphthyridinylene, cinnolinylene, quinazolinylene, quinoxalinylene, phthalazinylene, pyrazolo[1,5-a]pyridinylene, pyrazolo[1,5-a]pyrimidinylene, imidazo[1,2-a]pyridinylene, 1H-pyrrolo[3,2-b]pyridinylene, 1H-pyrrolo[2,3-b]pyridinylene, 4H-fluoro[3,2-b]pyrrolylene, pyrrolo[2,1-b]thiazolylene, and imidazo[2,1-b]thiazolylene. According to a clear definition, the heteroarylene group may be unsubstituted or substituted. A substituted heteroarylene group refers to a heteroarylene group optionally substituted 1-3 times by a substituent(s), wherein the substituent(s) is/are selected from $C_{1-3}$ alkyl, $C_{1-3}$ alkoxy, cyano, trifluoromethyl, heterocyclyl, halogen, amino, or hydroxyl.

As used herein, the term "heterocyclylene" used alone or in combination refers to a 4- to 6-membered saturated or partially unsaturated (i.e., having one or more double bonds, but not having a completely conjugated π-electron system) monocyclic bivalent group, containing one or more heteroatoms independently selected from the group consisting of sulfur, oxygen, and nitrogen. Representative examples of the heterocyclylene group include, but are not limited to, azetidinylene, oxetanylene, pyrrolidinylene, imidazolidylene, pyrazolidylene, triazolylend, tetrahydrofuranylene, tetrahydrothienylene, tetrahydrothiopyranylene, oxazolidinylene, thiazolidinylene, piperidinylene, piperazinylene, morpholinylene, thiomorpholinylene, and dioxanylene. The heterocyclylene group may be unsubstituted or substituted as explicitly defined. The substituent(s) of the substituted heterocyclylene is/are preferably one or more substituents selected from $C_{1-3}$ alkyl, $C_{1-3}$ alkoxy, cyano, trifluoromethyl, heterocyclyl, halogen, amino or hydroxyl.

As used herein, the term "alkynylene" used alone or in combination refers to a linear or branched divalent hydrocarbon group containing one or more carbon-carbon triple bonds and containing from 2 to 10 (preferably from 2 to 6, more preferably from 2 to 4) carbon atoms. Preferred examples of the alkynylene group include, but are not limited to, ethynylene, 1-propynylene, 1-butynylene, and 1,3-diynylene.

As used herein, the term "alkenylene" used alone or in combination refers to a linear or branched divalent hydrocarbon group containing one or more carbon-carbon double bonds and containing from 2 to 10 (preferably from 2 to 6, more preferably from 2 to 4) carbon atoms. Preferred examples of the alkenylene group include, but are not limited to, vinylidene (e.g., —CH=CH—), 1-propenylene, and 1-butenylene.

In the present disclosure, the term "leaving group" used alone or in combination is a term well known to those skilled in the art, which is a leaving molecular fragment (ion or neutral molecule) that carries a pair of electrons from a reactant in chemical reactions, as is a term used in nucleophilic substitution and elimination reactions. Common ionic leaving groups include Cl⁻, Br⁻, I⁻ and sulfonate (such as p-toluenesulfonate, TsO⁻), and neutral molecular leaving groups include water, ammonia and alcohol. In this disclosure, those skilled in the art can select an appropriate leaving group as needed, such as but not limited to —N₃, halogen, methanesulfonyloxy, trifluoromethanesulfonyloxy or p-toluenesulfonyloxy, etc.

Salts or pharmaceutically acceptable salts, enantiomers, stereoisomers, solvates, polymorphs of the compounds of formula I according to the present disclosure are also encompassed within the scope of the present invention.

In all embodiments of the present disclosure, the salt or pharmaceutically acceptable salt of the compound of formula I refers to a non-toxic inorganic or organic acid and/or base addition salt. Examples include, but are not limited to, sulfate, hydrochloride, citrate, maleate, sulfonate, or p-toluenesulfonate etc.

Salts or pharmaceutically acceptable salts, enantiomers, stereoisomers, solvates, polymorphs of the compounds of formula IV according to the present disclosure are also encompassed within the scope of the present invention.

In all embodiments of the present disclosure, the salt or pharmaceutically acceptable salt of the compound of formula IV refers to a non-toxic inorganic or organic acid and/or base addition salt. Examples include, but are not limited to, sulfate, hydrochloride, citrate, maleate, sulfonate, or p-toluenesulfonate etc.

"Pharmaceutically acceptable carrier" refers to a pharmaceutically acceptable material, such as a filler, stabilizer, dispersant, suspending agent, diluent, excipient, thickener, solvent, or encapsulating material, with which the useful compounds according to the present disclosure are carried or transported into or administered to a patient so that they can perform their intended function. Generally, such constructs are carried or transported from one organ or part of the body to another organ or part of the body. The carrier is compatible with the other ingredients of the formulation, including the compounds useful in the present disclosure, and is not harmful to the patient, and the carrier must be "acceptable." Some examples of materials that can be used as pharmaceutically acceptable carriers include, but are not limited to, sugars such as lactose, glucose, and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository wax; oils such as peanut oil, cottonseed oil, safflower oil, sesame oil, olive oil, corn oil and soybean oil; glycols such as propylene glycol; polyols such as glycerol, sorbitol, mannitol, and polyethylene glycol; esters such as ethyl oleate and ethyl laurate; agar; buffers such as magnesium hydroxide and aluminum hydroxide; surfactant; phosphate buffer solution; and other common non-toxic compatible substances used in pharmaceutical preparations.

The term "treatment" or "treating" refers to the administration of the compound of formula I or the compound of formula IV or a pharmaceutically acceptable salt thereof according to the present invention, or the pharmaceutical composition containing the compound of formula I or formula IV or a pharmaceutically acceptable salt thereof as an active ingredient, to a subject to mitigate (alleviate) undesirable diseases or conditions, such as the development of cancer or tumors. The beneficial or desired clinical results of the present invention include, but are not limited to: alleviating symptoms, reducing the severity of the disease, stabilizing the state of the disease, slowing down or delaying the progression of the disease, improving or alleviating the condition, and alleviating the disease.

A "therapeutically effective amount" of a compound of the present disclosure depends on the age, sex, and weight of the patient, the patient's current medical condition, and the cancer progression of the patient being treated. Those skilled in the art will be able to determine a suitable dosage based on these and other factors.

The term "room temperature" used herein refers to the ambient temperature, such as a temperature of 20-30° C.

The compounds developed by the present invention belongs to a specific protein-degrading agent, which is composed of three parts: a small molecule compound (SMBP, Small Molecules Binding Protein) capable of binding protein, an E3 ligase ligand with ubiquitination function, and link unit (linker or LIN). The present disclosure selects small molecule compounds (SMBP) capable of binding proteins as anchoring elements, and an E3 ligase ligand is combined with SMBP through a linker to develop a degrader targeting a specific protein. Through the specific recognition of target proteins by SMBP, the activity of the target protein is inhibited, and at the same time, E3 ligase specifically ubiquitinates target protein to achieve degradation and elimination of the target protein, and finally can remove the target protein from tumor cells. The compounds developed by the present invention can not only inhibit tumorigenesis and progression, but also potentially overcome resistance to targeted drugs. The E3 ligase ligand with a novel structure designed and developed in the present disclosure has been successfully applied to a degrading agent that targets specific proteins, providing a new treatment strategy for tumor patients in the context of precision medicine.

EXAMPLES

In the following description, many specific details are set forth in order to provide a thorough understanding of the present disclosure. The present disclosure may be implemented without some or all of these specific details. In other cases, in order not to cause unnecessary confusion to the present disclosure, well-known process operations are not described in detail. Although the present disclosure will be described in conjunction with specific embodiments, it should be understood that this is not intended to limit the present disclosure to these embodiments.

The following abbreviations are used throughout the specification and examples:

Boc Tert-Butoxycarbonyl
n-BuOH n-Butanol
Bipy Bipyridine
'BuOH tert-Butanol
Con. Concentration
m-CPBA m-Chloroperoxybenzoic acid
DME 1,2-dimethoxyethane
DMF N,N-Dimethylformamide
DMSO Dimethyl sulfoxide
DIPEA N,N-Diisopropylethylamine
EDCI 1-(3-Dimethylaminopropyl)-3-ethylcarbodiimide hydrochloride
ESI Electrospray ionization
equiv Equivalent
EtOH Ethanol
HOAT 1-Hydroxy-7-azabenzotriazole
HPLC High performance liquid chromatography
HRMS High resolution mass spectrometry
LC-MS Liquid chromatography-mass spectrometry
LRMS Low resolution mass spectrometry
LC Liquid chromatography
Me Methyl
MeCN Acetonitrile
MeOH Methanol
MS Mass spectrometry
MW Microwave
NMM N-methylmorpholine
NMP N-methylpyrrolidone
$^1$H NMR Proton nuclear magnetic resonance spectroscopy
rt Room temperature
TFA Trifluoroacetate
THF Tetrahydrofuran
TLC Thin layer chromatography
TMS Trimethylsilyl
TBHP Tert-butyl hydroperoxide
Xantphos 4,5-Bisdiphenylphosphine-9,9-dimethylxanthene
LIN-ULM Intermediate formed by covalent connection of linking group and ULM (Ubiquitin Ligase binding Moiety)
PROTAD Proteolysis Targeting Drug In the examples, the $^1$H NMR spectrum was measured with a Bruker-500 MHz nuclear magnetic resonance instrument, and CD$_3$OD containing 0.1% TMS was used as the solvent, and the ¹H NMR spectrum used CD₃OD (δ=3.31 ppm) as an internal standard; or 0.1% TMS CDCl₃ is used as the solvent, in which the ¹H NMR spectrum uses CDCl₃ (δ=7.26 ppm) as the internal standard; or the DMSO-d6 containing 0.03% TMS is used as the solvent, and the ¹H NMR spectrum uses DMSO-d6 (δ=2.50 ppm) as internal standard. LRMS spectrum was measured on AB Triple 4600 mass spectrometer. HPLC preparation was measured on SHIMADZU LC-20AP instrument, and HPLC purity was measured on SHIMADZU LC-30AP or Waters 1525 instrument. All reactions were carried out under air atmosphere without special instructions; the reactions were followed by TLC or LC-MS.

Solvents and reagents are processed as follows:

the solvents used in the reaction, anhydrous dichloromethane, N,N-dimethylformamide, N-methylpyrrolidone, anhydrous ethanol, anhydrous methanol, etc., were all purchased from Chinese Sinopharm Group;

HPLC preparation uses preparative grade CH₃CN and deionized water;

The selected targeted protein inhibitors SMBP are: demethylated imatinib, palbociclib, derivatives of Abemaciclib, Ribocicib, Rucaparib, Alectinib derivative A, Alectinib derivative B, Alectinib derivative C, Olaparib derivative without cyclopropionyl, Niraparib, Toremifene Derivative A, and Tamoxifen Derivative A, which were all commercially available; Dasatinib Derivatives (SIAIS151055), Bosutinib Derivatives (SIAIS151151), JQ-1 derivative A (SIAIS171018), JQ-1 derivative B (SIAIS213113), JQ-1 derivative C (SIAIS213130), Brigatinib derivative A (SIAIS1197135), Brigatinib derivative Substance B (SIAIS151101), Brigatinib derivative C (SIAIS164005), ponatinib derivative (SIAIS151190B), toremifen derivative B (SIAIS208164) were synthesized by the laboratory through the method described below. LIN-ULM (LIN: Linker; ULM: Ubiquitin Ligase binding Moiety) Other reagents and medicines were purchased from commercial channels and used directly without special instructions.

General Method for Preparing Thio-Substituted Pomalidomide/Lenalidomide PEG Chain Series of HO₂C-LIN-ULM Scheme 1

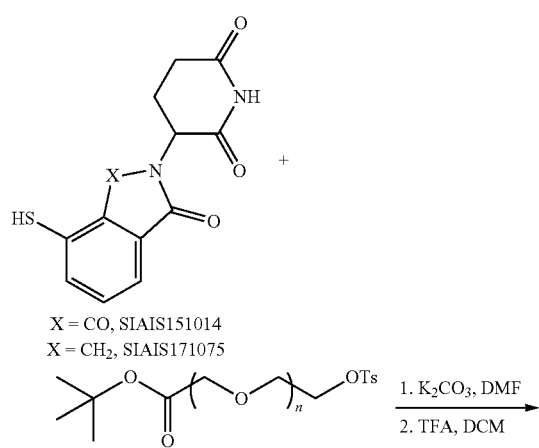

X = CO, SIAIS151014
X = CH₂, SIAIS171075

1. K₂CO₃, DMF
2. TFA, DCM

-continued

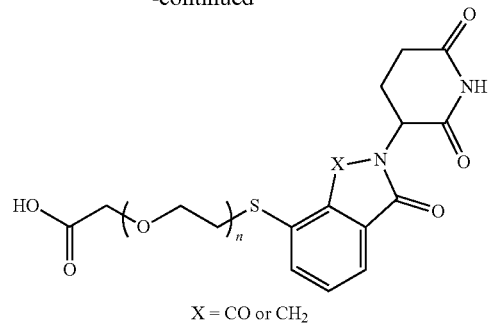

X = CO or CH₂

A 50 mL egg-shaped flask was charged with the corresponding intermediate compound thiophenol SIAIS151014 or SIAIS171075 (0.724 mmol, 1 equiv), and then anhydrous N,N-dimethylformamide (10 mL) and anhydrous Potassium carbonate (1.448 mmol, 2 equiv), followed by slow dropwise addition of the corresponding p-toluenesulfonate substrate (0.869 mmol, 1.2 equiv) as a linker under stirring at room temperature. After adding, the reaction mixture was stirred at room temperature for 0.5 h. After the starting materials were completely consumed, the reaction mixture was filtered to remove the insoluble substances, and the filtrate was directly loaded on a C18 reversed phase column (eluent: 10%-100% (v1:v2) acetonitrile:water) for separation and purifycation. The solvent was removed under reduced pressure to obtain the corresponding tert-butanol ester intermediate product. The corresponding tert-butanol ester intermediate compound was then added to a 25 mL egg-shaped flask, followed by addition of dichloromethane (1 mL) and trifluoroacetic acid (3 mL). The mixture was stirred at room temperature for 1 h. The solvent was evaporated under reduced pressure and the residue was treated by addition of water, and lyophilized to obtain the corresponding HO₂C-LIN-ULM containing thio-substituted lenalidomide and PEG chain.

Intermediate Preparation Example 1: Preparation of 2-(2-((2-(2,6-dioxopiperidin-3-yl)-1,3-dioxoisoindolin-4-yl)thio)ethoxy)acetic acid (SIAIS1204137)

According to the method of Scheme 1, the compound SIAIS1204137 was prepared under appropriate conditions that will be recognized by one skilled in the art, except that tert-butyl 2-(2-(p-toluenesulfonyloxy)ethoxy)acetate was used as the brominated substrate of the linker, and the thiophenol substrate SIAIS151014 was used. The target compound SIAIS1204137 was obtained as light yellow solid (185 mg, yield 69%), ¹H NMR (500 MHz, DMSO) δ 11.12 (s, 1H), 7.83-7.73 (m, 2H), 7.64 (d, J=6.6 Hz, 1H), 5.12 (dd, J=12.8, 5.4 Hz, 1H), 4.08 (s, 2H), 3.77 (t, J=6.4 Hz, 2H), 3.14-3.07 (m, 2H), 2.94-2.82 (m, 1H), 2.66-2.55 (m, 2H), 2.09-2.01 (m, 1H). HRMS (ESI) m/z: calcd for, C₁₇H₁₇N₂O₇S⁺ [M+H]⁺, 393.0751; found, 393.0763.

Intermediate Preparation Example 2: Preparation of 2-(2-(2-((2-(2,6-dioxopiperidin-3-yl)-1,3-dioxoisoindolin-4-yl)thio)ethoxy)ethoxy)acetic acid (SIAIS1204139)

According to the method of Scheme 1, the compound SIAIS1204139 was prepared under appropriate conditions that will be recognized by one skilled in the art, except that tert-butyl 2-(2-(2-(p-toluenesulfonyloxy)ethoxy)ethoxy)acetate was used as the brominated substrate of the linker and the thiophenol substrate SIAIS151014 was used. The target compound SIAIS1204139 was obtained as light yellow solid (190 mg, yield 63%), $^1$H NMR (500 MHz, DMSO) δ 11.12 (s, 1H), 7.83-7.76 (m, 2H), 7.63 (dd, J=6.4, 1.3 Hz, 1H), 5.12 (dd, J=12.9, 5.4 Hz, 1H), 4.02 (s, 2H), 3.72 (t, J=6.3 Hz, 2H), 3.59 (s, 4H), 3.39-3.30 (m, 2H), 3.13-3.06 (m, 1H), 2.64-2.52 (m, 2H), 2.09-2.02 (m, 1H). HRMS (ESI) m/z: calcd for, $C_{19}H_{21}BN_2O_8S^+$ [M+H]$^+$, 437.1013; found, 437.1032.

Intermediate Preparation Example 3: Preparation of 2-(2-(2-(2-((2-(2,6-dioxopiperidin-3-yl)-1,3-dioxoisoindolin-4-yl)thio)ethoxy)ethoxy)ethoxy)acetic acid (SIAIS1204141)

The compound SIAIS1204141 was prepared according to the method of Scheme 1 under appropriate conditions that will be recognized by one skilled in the art, except that tert-butyl 2-(2-(2-(2-(p-toluenesulfonyloxy)ethoxy)ethoxy)ethoxy)acetate was used as the brominated substrate of linker and the thiophenol substrate SIAIS151014 was used. The target compound SIAIS1204141 was obtained as light yellow solid (246 mg, yield 74%), $^1$H NMR (500 MHz, DMSO) δ 11.12 (s, 1H), 7.85-7.73 (m, 2H), 7.63 (dd, J=6.1, 1.9 Hz, 1H), 5.12 (dd, J=12.9, 5.4 Hz, 1H), 4.02 (s, 2H), 3.71 (t, J=6.3 Hz, 2H), 3.62-3.48 (m, 8H), 3.35 (t, J=6.3 Hz, 2H), 2.94-2.84 (m, 1H), 2.63-2.52 (m, 2H), 2.11-1.99 (m, 1H). HRMS (ESI) m/z: calcd for, $C_{21}H_{25}N_2O_9S^+$ [M+H]$^+$, 481.1275; found, 481.1273.

Intermediate Preparation Example 4: Preparation of 14-((2-(2,6-dioxopiperidin-3-yl)-1,3-dioxoisoindolin-4-yl)thio)-3,6,9,12-tetraoxatetradecanoic acid (SIAIS1204147)

The compound SIAIS1204147 was prepared according to the method of Scheme 1 and under appropriate conditions that will be recognized by one skilled in the art, except that tert-butyl 14-(p-toluenesulfonyloxy)-3,6,9,12-tetraoxatetradecanoate was used as the brominated substrate of the linker and the thiophenol substrate SIAIS151014 was used. The target compound SIAIS1204147 was obtained as light yellow solid (228 mg, yield 63%), $^1$H NMR (500 MHz, DMSO) δ 11.12 (s, 1H), 7.83-7.73 (m, 2H), 7.63 (dd, J=6.2, 1.7 Hz, 1H), 5.12 (dd, J=12.9, 5.4 Hz, 1H), 4.01 (s, 2H), 3.71 (t, J=6.3 Hz, 2H), 3.59-3.54 (m, 4H), 3.54-3.49 (m, 8H), 3.35 (t, J=6.3 Hz, 2H), 2.94-2.84 (m, 1H), 2.64-2.56 (m, 1H), 2.55-2.51 (m, 1H), 2.08-2.02 (m, 1H). HRMS (ESI) m/z: calcd for, $C_{23}H_{29}N_2O_{10}S^+$ [M+H]$^+$, 525.1537; Found, 525.1536.

Intermediate Preparation Example 5: Preparation of 17-((2-(2,6-dioxopiperidin-3-yl)-1,3-dioxoisoindolin-4-yl)thio)-3,6,9,12,15-pentaoxaheptadecanoic acid (SIAIS1204149)

The compound SIAIS1204149 was prepared according to the method of Scheme 1 and under appropriate conditions that will be recognized by one skilled in the art, except that tert-butyl 17-(p-toluenesulfonyloxy)-3,6,9,12,15-pentaoxaheptadecanoate was used as the brominated substrate of the linker and the thiophenol substrate SIAIS151014 were used. The target compound SIAIS1204149 was obtained as light yellow solid (259 mg, yield 66%), $^1$H NMR (500 MHz, DMSO) δ 11.12 (s, 1H), 7.83-7.74 (m, 2H), 7.63 (dd, J=6.2, 1.8 Hz, 1H), 5.12 (dd, J=12.9, 5.4 Hz, 1H), 4.01 (s, 2H), 3.71 (t, J=6.3 Hz, 2H), 3.60-3.55 (m, 4H), 3.55-3.47 (m, 12H), 3.35 (t, J=6.3 Hz, 2H), 2.93-2.84 (m, 1H), 2.64-2.56 (m, 1H), 2.55-2.51 (m, 1H), 2.08-2.02 (m, 1H). HRMS (ESI) m/z: calcd for, $C_{25}H_{33}N_2O_{11}S^+$ [M+H]$^+$, 569.1800; found, 569.1814.

Intermediate Preparation Example 6: Preparation of 2-(2-((2-(2,6-dioxopiperidin-3-yl)-1-oxoisoindolin-4-yl)thio)ethoxy)acetic acid (SIAIS1213129)

According to the method of Scheme 1, the compound SIAIS1213129 was prepared under appropriate conditions that will be recognized by one skilled in the art, except that tert-butyl 2-(2-(p-toluenesulfonyloxy)ethoxy)acetate was used as the brominated substrate of the linker and the thiophenol substrate SIAIS171075 was used. The target compound SIAIS1213129 was obtained as light yellow solid (148 mg, yield 54%), $^1$H NMR (500 MHz, CDCl$_3$) δ 8.90 (s, 1H), 7.81 (d, J=7.5 Hz, 1H), 7.68 (d, J=7.7 Hz, 1H), 7.54 (t, J=7.7 Hz, 1H), 5.33 (dd, J=13.4, 5.1 Hz, 1H), 4.60 (d, J=17.2 Hz, 1H), 4.47 (d, J=17.2 Hz, 1H), 4.11 (s, 2H), 3.78-3.73 (m, 1H), 3.72-3.66 (m, 1H), 3.22 (t, J=6.2 Hz, 2H), 2.98-2.93 (m, 1H), 2.90-2.82 (m, 1H), 2.53-2.43 (m, 1H), 2.32-2.25 (m, 1H). HRMS (ESI) m/z: calcd for, $C_{17}H_{19}N_2O_6S^+$ [M+H]$^+$, 379.0958; found, 379.0963.

Intermediate Preparation Example 7: Preparation of 2-(2-(2-((2-(2,6-dioxopiperidin-3-yl)-1-oxoisoindolin-4-yl)thio)ethoxy)ethoxy)acetic acid (SIAIS1213131)

According to the method of Scheme 1, the compound SIAIS1213131 was prepared under appropriate conditions that will be recognized by one skilled in the art, except that tert-butyl 2-(2-(2-(p-toluenesulfonyloxy)ethoxy)ethoxy)acetate was used as the brominated substrate of the linker and the thiophenol substrate SIAIS171075 was used. The target compound SIAIS1213131 was obtained as light yellow oil (158 mg, yield 52%), $^1$H NMR (500 MHz, CDCl3) δ 8.77 (s, 1H), 7.68 (d, J=7.5 Hz, 1H), 7.53 (d, J=7.7 Hz, 1H), 7.42 (t, J=7.7 Hz, 1H), 5.21 (dd, J=13.4, 5.1 Hz, 1H), 4.41 (d, J=17.1 Hz, 1H), 4.32 (d, J=17.1 Hz, 1H), 4.06 (s, 2H), 3.65-3.59 (m, 4H), 3.54 (t, J=4.1 Hz, 2H), 3.11 (t, J=6.1 Hz, 2H), 2.88-2.83 (m, 1H), 2.81-2.76 (m, 1H), 2.42-2.34 (m, 1H), 2.20-2.14 (m, 1H). HRMS (ESI) m/z: calcd for, $C_{19}H_{23}N_2O_7S^+$ [M+H]$^+$, 423.1200; found, 423.1205.

Intermediate Preparation Example 8: Preparation of 2-(2-(2-(2-((2-(2,6-dioxopiperidin-3-yl)-1-oxoisoindolin-4-yl)thio)ethoxy)ethoxy)ethoxy)acetic acid (SIAIS1213133)

According to the method of Scheme 1, the compound SIAIS1213133 was prepared under appropriate conditions that will be recognized by one skilled in the art, except that tert-butyl 2-(2-(2-(2-(p-toluenesulfonyloxy)ethoxy)ethoxy)ethoxy)acetate was used as the brominated substrate of the linker and the thiophenol substrate SIAIS171075 was used. The target compound SIAIS1213133 was obtained as light yellow oil (149 mg, yield 44%), $^1$H NMR (500 MHz, CDCl$_3$) δ 8.91 (s, 1H), 7.75 (d, J=7.5 Hz, 1H), 7.61 (d, J=7.6 Hz, 1H), 7.50 (t, J=7.7 Hz, 1H), 5.29 (dd, J=13.4, 5.1 Hz, 1H), 4.49 (d, J=17.0 Hz, 1H), 4.39 (d, J=17.1 Hz, 1H), 4.17-4.15 (m, 2H), 3.72-3.63 (m, 10H), 3.20 (t, J=6.3 Hz, 2H), 2.96-2.90 (m, 1H), 2.90-2.82 (m, 1H), 2.50-2.44 (m, 1H), 2.28-2.22 (m, 1H). HRMS (ESI) m/z: calcd for, $C_{21}H_{27}N_2O_8S^+$ [M+H]$^+$, 467.1483; found, 467.1467.

Intermediate Preparation Example 9: Preparation of 14-((2-(2,6-dioxopiperidin-3-yl)-1-oxoisoindolin-4-yl)thio)-3,6,9,12-tetraoxatetradecanoic acid (SIAIS1213135)

According to the method of Scheme 1, the compound SIAIS1213135 was prepared under appropriate conditions that will be recognized by one skilled in the art, except that tert-butyl 14-(p-toluenesulfonyloxy)-3,6,9,12-tetraoxatetradecanoate was used as the brominated substrate of the linker and the thiophenol substrate SIAIS171075 was used. The target compound SIAIS1213135 was obtained as light yellow oil (181 mg, yield 49%), $^1$H NMR (500 MHz, CDCl$_3$) δ 8.61 (s, 1H), 7.78 (dd, J=7.6, 0.7 Hz, 1H), 7.63 (dd, J=7.8, 0.8 Hz, 1H), 7.50 (t, J=7.0 Hz, 1H), 5.29 (dd, J=13.3, 5.1 Hz, 1H), 4.50 (d, J=17.0 Hz, 1H), 4.40 (d, J=16.9 Hz, 1H), 4.15 (s, 2H), 3.72-3.66 (m, 14H), 3.19 (t, J=6.6 Hz, 2H), 2.95-2.93 (m, 1H), 2.91-2.86 (m, 1H), 2.52-2.46 (m, 1H), 2.28-2.24 (m, 1H). HRMS (ESI) m/z: calcd for, $C_{23}H_{31}N_2O_9S^+$ [M+H]$^+$, 511.1745; found, 511.1749.

Intermediate Preparation Example 10: Preparation of 17-((2-(2,6-dioxopiperidin-3-yl)-1-oxoisoindolin-4-yl)thio)-3,6,9,12,15-pentaoxaheptadecanoic acid (SIAIS1213137)

According to the method of Scheme 1, the compound SIAIS1213137 was prepared under appropriate conditions that will be recognized by one skilled in the art, except that tert-butyl 17-(p-toluenesulfonyloxy)-3,6,9,12,15-pentaoxaheptadecanoate was used as the brominated substrate of the linker and the thiophenol substrate SIAIS171075 was used. The target compound SIAIS1213137 was obtained as light yellow oil (209 mg, yield 52%), $^1$H NMR (500 MHz, CDCl$_3$) δ 8.71 (s, 1H), 7.77 (d, J=7.0 Hz, 1H), 7.64 (dd, J=7.7, 0.7 Hz, 1H), 7.54-7.49 (m, 1H), 5.31 (dd, J=13.4, 5.1 Hz, 1H), 4.50 (d, J=17.0 Hz, 1H), 4.40 (d, J=17.0 Hz, 1H), 4.17 (s, 2H), 3.76-3.74 (m, 2H), 3.70-3.66 (m, 12H), 3.64-3.61 (m, 4H), 3.20 (t, J=6.5 Hz, 2H), 2.98-2.94 (m, 1H), 2.90-2.85 (m, 1H), 2.53-2.43 (m, 1H), 2.30-2.25 (m, 1H). HRMS (ESI) m/z: calcd for, $C_{25}H_{35}N_2O_{10}S^+$ [M+H]$^+$, 569.1800; found, 569.1814.

General Method for Preparing Thio-Substituted Pomalidomide Carbon Chain Series of HO$_2$C-LIN-ULM:

Scheme 2

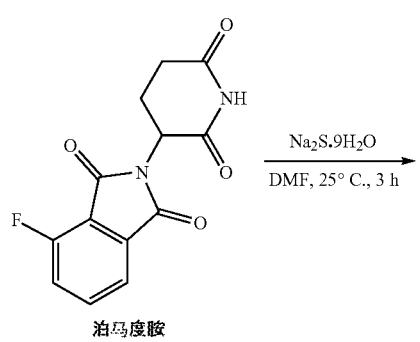

泊马度胺

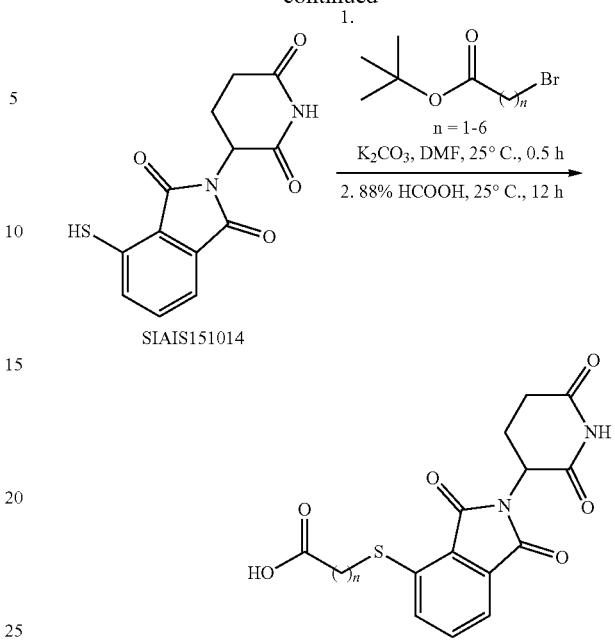

Step 1: Preparation of 2-(2,6-dioxopiperidin-3-yl)-4-mercaptoisoindoline-1,3-dione (SIAIS151014) according to Scheme 2: a 250 mL egg-shaped flask was charged with compound 2-(2,6-dioxopiperidin-3-yl)-4-fluoroisoindoline-1,3-dione (20 g, 72.4 mmol), and then anhydrous N,N-dimethylformamide (150 mL), followed by addition of sodium sulfide nonahydrate (28 g, 108.6 mmol) in batches under stirring at room temperature. The reaction mixture was stirred at room temperature for 6 h after completion of addition. Then the reaction solution was slowly poured into 400 mL of ice-water mixture, and the pH of the reaction solution was slowly adjusted to 2-3 with 6N hydrochloric acid aqueous solution under stirring. The color of the solution changes from blood red to pale yellow gradually, and a lot of off-white solids were precipitate out. The mixture was stirred at room temperature for 0.5 h, suction filtered, and the filter cake was washed 3 times with water, and then slurried with 100 mL of anhydrous acetone, and suction filtered. The obtained filter cake was washed with acetone 3 times, and dried under reduced pressure to obtain the intermediate compound (SIAIS151014) (Off-white solid, 14 g, yield 67%). $^1$H NMR (500 MHz, DMSO) δ 11.16 (s, 1H), 7.79 (d, J=7.8 Hz, 1H), 7.69 (t, J=7.6 Hz, 1H), 7.64 (d, J=7.1 Hz, 1H), 6.30 (s, 1H), 5.14 (dd, J=12.9, 5.4 Hz, 1H), 2.93-2.84 (m, 1H), 2.62-2.52 (m, 2H), 2.09-2.02 (m, 1H). HRMS (ESI) m/z: calcd for, $C_{13}H_{11}N_2O_4S^+$ [M+H]$^+$, 291.0434; found, 291.0119.

Step 2: General method for preparing thio-substituted pomalidomide carbon chain series of HO$_2$C-LIN-ULM from compound SIAIS151014 according to scheme 2

A 100 mL egg-shaped flask was charged with the intermediate compound SIAIS151014 (3.4 mmol, 1 equiv), and then anhydrous N,N-dimethylformamide (10 mL) and anhydrous potassium carbonate (6.8 mmol, 2 equiv), followed by slow dropwise addition of the corresponding brominated substrate (4.1 mmol, 1.2 equiv) as the linker under stirring at room temperature. After adding, the resulting reaction mixture was stirred at room temperature for 0.5 h. After the raw materials were completely consumed, 50 mL of water was poured into the reaction mixture, and the resulting mixture was extracted with ethyl acetate (2×50 mL). The organic phases were combined, washed with water (3×20 mL) and saturated brine (50 mL), dried over anhydrous $Na_2SO_4$, and then concentrated to remove the solvent under reduced pressure. The residue was purified by column chromatography (eluent (v/v): dichloromethane/ethyl acetate=20:1) and rotary-evaporated to dryness to obtain the corresponding tert-butanol ester intermediate product. The corresponding tert-butanol ester intermediate compound was then added to a 25 mL egg-shaped flask, followed by addition of 88% formic acid (10 mL), and stirred at room temperature for 12 h. The solvent was evaporated under reduced pressure and the residue was treated by addition of water, and lyophilized to obtain the corresponding thio-substituted pomalidomamine alkyl carbon chain series of $HO_2C$-LIN-ULM.

Intermediate Preparation Example 11: Preparation of 2-((2-(2,6-dioxopiperidin-3-yl)-1,3-dioxoisoindo-lin-4-yl)thio)acetic acid (SIAIS151045)

The compound SIAIS151045 was prepared according to the method of Scheme 2 and under appropriate conditions that will be recognized by one skilled in the art, except that the brominated substrate used as the linker was tert-butyl 2-bromoacetate. The target compound SIAIS151045 was obtained as light yellow solid (0.69 g, yield 80%). $^1$H NMR (500 MHz, DMSO) δ 13.06 (s, 1H), 11.15 (s, 1H), 7.80 (dd, J=8.1, 7.3 Hz, 1H), 7.66 (t, J=7.9 Hz, 2H), 5.13 (dd, J=12.9, 5.4 Hz, 1H), 4.09 (s, 2H), 2.92-2.85 (m, 1H), 2.66-2.51 (m, 2H), 2.08-2.03 (m, 1H). HRMS (ESI) m/z: calcd for, $C_{15}H_{13}N_2O_6S^+$ [M+H]$^+$, 349.0489; found, 349.0297.

Intermediate Preparation Example 12: Preparation of 3-((2-(2,6-dioxopiperidin-3-yl)-1,3-dioxoisoindo-lin-4-yl)thio)propanoic acid (SIAIS151138B)

The compound SIAIS151138B was prepared according to the method of Scheme 2 and under appropriate conditions that will be recognized by one skilled in the art, except that the brominated substrate used as the linker was tert-butyl 3-bromopropionate. The target compound SIAIS151138B was obtained as light yellow solid (0.64 g, yield 74%). $^1$H NMR (500 MHz, DMSO) δ 11.12 (s, 1H), 7.81-7.76 (m, 2H), 7.64 (d, J=6.7 Hz, 1H), 5.11 (dd, J=12.9, 5.4 Hz, 1H), 3.32 (t, J=7.0 Hz, 2H), 2.92-2.84 (m, 1H), 2.66 (t, J=7.0 Hz, 2H), 2.62-2.51 (m, 2H), 2.07-2.00 (m, 1H). HRMS (ESI) m/z: calcd for, $C_{16}H_{15}N_2O_6S^+$ [M+H]$^+$, 363.0645; found, 363.0802.

Intermediate Preparation Example 13: Preparation of 4-((2-(2,6-dioxopiperidin-3-yl)-1,3-dioxoisoindo-lin-4-yl)thio)butanoic acid (SIAIS151139B)

The compound SIAIS151139B was prepared according to the method of Scheme 2 under appropriate conditions that will be recognized by one skilled in the art, except that the brominated substrate used as the linker was tert-butyl 4-bromobutyrate. The target compound SIAIS151139B was obtained as light yellow solid (0.71 g, yield 82%). $^1$H NMR (500 MHz, DMSO) δ 12.24 (s, 1H), 11.12 (s, 1H), 7.86-7.74 (m, 2H), 7.63 (d, J=6.2 Hz, 1H), 5.11 (dd, J=12.9, 5.4 Hz, 1H), 3.15 (t, J=7.2 Hz, 2H), 2.92-2.84 (m, 1H), 2.64-2.51 (m, 2H), 2.42 (t, J=7.2 Hz, 2H), 2.09-2.02 (m, 1H), 1.93-1.83 (m, 2H). HRMS (ESI) m/z: calcd for, $C_{17}H_{17}N_2O_6S^+$ [M+H]$^+$, 377.0802; found, 377.0962.

Intermediate Preparation Example 14: Preparation of 5-((2-(2,6-dioxopiperidin-3-yl)-1,3-dioxoisoindo-lin-4-yl)thio)pentanoic acid (SIAIS151140B)

The compound SIAIS151140B was prepared according to the method of Scheme 2 and under appropriate conditions that will be recognized by one skilled in the art, except that the brominated substrate used as the linker was tert-butyl 5-bromopentanoate. The target compound SIAIS151140B was obtained as light yellow solid (0.9 g, yield 74%). $^1$H NMR (500 MHz, DMSO) δ 11.12 (s, 1H), 7.83-7.71 (m, 2H), 7.62 (d, J=6.9 Hz, 1H), 5.11 (dd, J=12.9, 5.4 Hz, 1H), 3.13 (t, J=6.6 Hz, 2H), 2.92-2.85 (m, 1H), 2.64-2.52 (m, 2H), 2.28 (t, J=6.6 Hz, 2H), 2.08-2.02 (m, 1H), 1.72-1.65 (m, 4H). HRMS (ESI) m/z: calcd for, $C_{18}H_{19}N_2O_6S^+$ [M+H]$^+$, 391.0958; found, 391.1109.

Intermediate Preparation Example 15: Preparation of 6-((2-(2,6-dioxopiperidin-3-yl)-1,3-dioxoisoindo-lin-4-yl)thio)hexanoic acid (SIAIS151141B)

The compound SIAIS151141B was prepared according to the method of Scheme 2 and under appropriate conditions that will be recognized by one skilled in the art, except that the brominated substrate used as the linker was tert-butyl 6-bromohexanoate. The target compound SIAIS151141B was obtained as light yellow solid (0.71 g, yield 74%). $^1$H NMR (500 MHz, DMSO) δ 12.01 (s, 1H), 11.12 (s, 1H), 7.82-7.70 (m, 2H), 7.62 (d, J=7.1 Hz, 1H), 5.11 (dd, J=12.9, 5.4 Hz, 1H), 3.12 (t, J=7.2 Hz, 2H), 2.92-2.85 (m, 1H), 2.62-2.48 (m, 2H), 2.22 (t, J=7.2 Hz, 2H), 2.08-2.03 (m, 1H), 1.71-1.63 (m, 2H), 1.59-1.51 (m, 2H), 1.49-1.40 (m, 2H). HRMS (ESI) m/z: calcd for, $C_{19}H_{21}N_2O_6S^+$ [M+H]$^+$, 405.1115; found, 405.1268.

Intermediate Preparation Example 16: Preparation of 7-((2-(2,6-dioxopiperidin-3-yl)-1,3-dioxoisoindo-lin-4-yl)thio)heptanoic acid (SIAIS151142B)

The compound SIAIS151142B was prepared according to the method of Scheme 2 and under appropriate conditions that will be recognized by one skilled in the art, except that the brominated substrate used as the linker was tert-butyl 7-bromoheptanoate. The target compound SIAIS151142B was obtained as light yellow solid (0.7 g, yield 80%). $^1$H NMR (500 MHz, DMSO) δ 11.12 (s, 1H), 7.80-7.71 (m, 2H), 7.62 (d, J=6.9 Hz, 1H), 5.11 (dd, J=12.9, 5.4 Hz, 1H), 3.12 (t, J=7.3 Hz, 2H), 2.92-2.85 (m, 1H), 2.62-2.52 (m, 2H), 2.20 (t, J=7.3 Hz, 2H), 2.07-2.00 (m, 1H), 1.69-1.62 (m, 2H), 1.53-1.47 (m, 2H), 1.46-1.41 (m, 2H), 1.36-1.27 (m, 2H). HRMS (ESI) m/z: calcd for, $C_{20}H_{23}N_2O_6S^+$ [M+H]$^+$, 419.1271; found value, 419.1432.

General Method for Preparing Thio-Substituted Pomalidomide Carbon Chain Series of $NH_2$-LIN-ULM:

Scheme 3

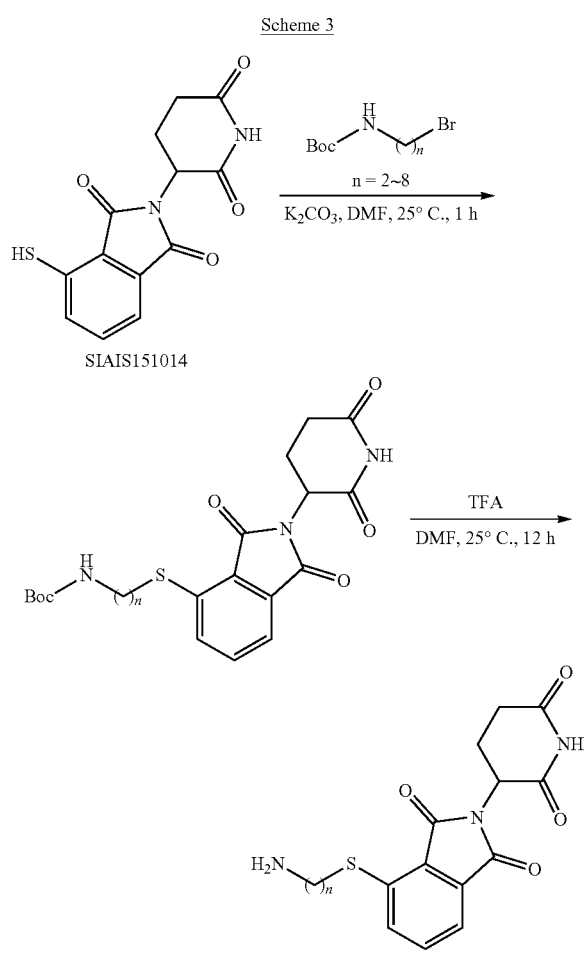

A 100 mL egg-shaped flask was charged with the compound SIAIS151014 (2.8 mmol, 1 equiv), and then anhydrous N,N-dimethylformamide (20 mL) and anhydrous potassium carbonate (5.6 mmol, 2 equiv), followed by slow dropwise addition of the corresponding bromide substrate (3.4 mmol, 1.2 equiv) with stirring at room temperature. After completion of adding, the reaction mixture was stirred at room temperature for 1 h. After the raw materials were completely consumed, 50 mL of water was poured into the reaction mixture, and the resulting mixture was extracted with ethyl acetate (3×50 mL). The organic phases were combined, washed with water (3×20 mL) and saturated brine (50 mL), dried over anhydrous $Na_2SO_4$, and concentrated to remove the solvent under reduced pressure. The residue was purified by a reversed phase C18 column with eluent (v/v): acetonitrile/(water+0.05% TFA)=10%-100%, concentrated to remove the solvent under reduced pressure, and freeze-dried to obtain the corresponding Boc protected alkylated product. The obtained alkylated product was then added into a 25 mL egg-shaped bottle, and then anhydrous dichloromethane (5 mL) and trifluoroacetic acid (0.5 mL) were added. The resulting mixture was stirred at room temperature for 12 h, and concentrated to remove the solvent under reduced pressure. The crude product was purified by a reversed phase C18 column (eluent (v/v): acetonitrile/(water+0.05% TFA)=10%-100%). The solvent was evaporated under reduced pressure, and the residue was freeze-dried to obtain the corresponding carbon chain series of $NH_2$-LIN-ULM.

Intermediate Preparation Example 17: Preparation of 4-((2-aminoethyl)thio)-2-(2,6-dioxopiperidin-3-yl)isoindoline-1,3-dione (SIAIS171026)

According to the method of Scheme 3, the compound SIAIS171026 was prepared under appropriate conditions that will be recognized by one skilled in the art, except that the brominated substrate used as the linker was tert-butyl (2-bromoethyl)carbamate. The target compound SIAIS171026 was obtained as light yellow solid (200 mg, yield 58%). $^1$H NMR (500 MHz, DMSO) δ 11.14 (s, 1H), 7.92 (br.s, 3H), 7.88-7.79 (m, 2H), 7.71 (d, J=6.6 Hz, 1H), 5.14 (dd, J=12.9, 5.4 Hz, 1H), 3.35-3.30 (m, 2H), 3.15-3.06 (m, 2H), 2.94-2.85 (m, 1H), 2.67-2.54 (m, 2H), 2.10-2.01 (m, 1H). HRMS (ESI) m/z: calcd for, $C_{15}H_{16}N_3O_4S^+$ $[M+H]^+$, 334.0856; found, 334.0858.

Intermediate Preparation Example 18: Preparation of 4-((3-aminopropyl)thio)-2-(2,6-dioxopiperidin-3-yl)isoindoline-1,3-dione (SIAIS171025)

According to the method of Scheme 3, the compound SIAIS171025 was prepared under appropriate conditions that will be recognized by one skilled in the art, except that the brominated substrate used as the linker was tert-butyl (3-bromopropyl)carbamate. The target compound SIAIS171025 was obtained as light yellow solid (300 mg, yield 77%). $^1$H NMR (500 MHz, DMSO) δ 11.13 (s, 1H), 7.93 (br.s, 3H), 7.83-7.75 (m, 2H), 7.69-7.62 (m, 1H), 5.12 (dd, J=12.9, 5.4 Hz, 1H), 3.23 (t, J=7.2 Hz, 2H), 3.00-2.97 (m, 2H), 2.92-2.85 (m, 1H), 2.64-2.51 (m, 2H), 2.13-2.03 (m, 1H), 1.99-1.91 (m, 2H). HRMS (ESI) m/z: calcd for, $C_{16}H_{18}N_3O_4S^+$ $[M+H]^+$, 348.1013; found, 348.1029.

Intermediate Preparation Example 19: Preparation of 4-((4-aminobutyl)thio)-2-(2,6-dioxopiperidin-3-yl)isoindoline-1,3-dione (SIAIS171023)

According to the method of Scheme 3, the compound SIAIS171023 was prepared under appropriate conditions that will be recognized by one skilled in the art, except that the brominated substrate used as the linker is tert-butyl (4-bromobutyl) carbamate. The target compound SIAIS171023 was obtained as light yellow solid (310 mg, yield 79%). $^1$H NMR (500 MHz, DMSO) δ 11.13 (s, 1H), 7.92 (br.s, 3H), 7.82-7.73 (m, 2H), 7.67-7.59 (m, 1H), 5.12 (dd, J=12.9, 5.4 Hz, 1H), 3.15-3.10 (m, 2H), 2.90-2.85 (m, 3H), 2.70-2.51 (m, 2H), 2.10-2.05 (m, 1H), 1.79-1.67 (m, 4H). HRMS (ESI) m/z: calcd for, $C_{17}H_{20}N_3O_4S^+$ $[M+H]^+$, 362.1169; found, 362.1441.

Intermediate Preparation Example 20: Preparation of 4-((5-aminopentyl)thio)-2-(2,6-dioxopiperidin-3-yl)isoindoline-1,3-dione (SIAIS171027)

According to the method of Scheme 3, the compound SIAIS171027 was prepared under appropriate conditions that will be recognized by one skilled in the art, except that the brominated substrate used as the linker is tert-butyl (5-bromopentyl)carbamate. The target compound SIAIS171027 was obtained as light yellow solid (210 mg, yield 53%). $^1$H NMR (500 MHz, DMSO) δ 11.13 (s, 1H), 7.83-7.72 (m, 5H), 7.72-7.61 (m, 1H), 5.12 (dd, J=12.9, 5.4 Hz, 1H), 3.15-3.10 (m, 2H), 2.91-2.79 (m, 3H), 2.63-2.53 (m, 2H), 2.30-2.17 (m, 1H), 1.55-1.46 (m, 6H). HRMS (ESI) m/z: Calcd for, $C_{18}H_{22}N_3O_4S^+$ $[M+H]^+$, 376.1326; found, 376.0869.

Intermediate Preparation Example 21: Preparation of 4-((6-aminohexyl)thio)-2-(2,6-dioxopiperidin-3-yl)isoindoline-1,3-dione (SIAIS171028)

The compound SIAIS171028 was prepared according to the method described in Scheme 3 under appropriate conditions that will be recognized by one skilled in the art, except that the brominated substrate used as the linker was tert-butyl (6-bromohexyl)carbamate. The target compound SIAIS171028 was obtained as light yellow solid (330 mg, yield 83%). $^1$H NMR (500 MHz, DMSO) δ 11.13 (s, 1H), 7.79-7.75 (m, 2H), 7.72-7.56 (m, 4H), 5.12 (dd, J=12.9, 5.4 Hz, 1H), 3.14 (t, J=7.2 Hz, 2H), 2.90-2.88 (m, 1H), 2.83-2.77 (m, 2H), 2.68-2.52 (m, 2H), 2.10-2.06 (m, 1H), 1.72-1.65 (m, 2H), 1.55-1.52 (m, 2H), 1.49-1.41 (m, 2H), 1.35-1.31 (m, 2H). HRMS (ESI) m/z: calcd for, $C_{19}H_{24}N_3O_4S^+$ [M+H]$^+$, 390.1482; found, 390.1477.

Intermediate Preparation Example 22: Preparation of 4-((7-aminoheptyl)thio)-2-(2,6-dioxopiperidin-3-yl)isoindoline-1,3-dione (SIAIS171033)

According to the method of Scheme 3, the compound SIAIS171033 was prepared under appropriate conditions that will be recognized by one skilled in the art, except that the brominated substrate used as the linker was tert-butyl (7-bromoheptyl)carbamate. The target compound SIAIS171033 was obtained as light yellow solid (400 mg, yield 71%). $^1$H NMR (500 MHz, DMSO) δ 11.13 (s, 1H), 7.81-7.60 (m, 6H), 5.11 (dd, J=12.8, 5.4 Hz, 1H), 3.14 (t, J=7.2 Hz, 2H), 2.95-2.84 (m, 1H), 2.80-2.74 (m, 2H), 2.65-2.52 (m, 2H), 2.10-1.99 (m, 1H), 1.72-1.68 (m, 2H), 1.55-1.45 (m, 4H), 1.40-1.35 (m, 4H). HRMS (ESI) m/z: calcd for, $C_{20}H_{26}N_3O_4S^+$ [M+H]$^+$, 404.5045; found, 404.1484.

Intermediate Preparation Example 23: Preparation of 4-((8-aminooctyl)thio)-2-(2,6-dioxopiperidin-3-yl)isoindoline-1,3-dione (SIAIS171047)

According to the method of Scheme 3, the compound SIAIS171047 was prepared under appropriate conditions that will be recognized by one skilled in the art, except that the brominated substrate used as the linker was tert-butyl (8-bromooctyl)carbamate. The target compound SIAIS171047 was obtained as light yellow solid (600 mg, yield 83%). $^1$H NMR (500 MHz, DMSO) δ 11.13 (s, 1H), 7.79-7.59 (m, 6H), 5.12 (dd, J=12.9, 5.4 Hz, 1H), 3.13 (t, J=7.2 Hz, 2H), 2.95-2.85 (m, 1H), 2.78-2.74 (m, 2H), 2.67-2.52 (m, 2H), 2.10-2.04 (m, 1H), 1.73-1.64 (m, 2H), 1.52-1.50 (m, 2H), 1.47-1.41 (m, 2H), 1.35-1.30 (m, 6H). HRMS (ESI) m/z: calcd for, $C_{21}H_{28}N_3O_4S^+$ [M+H]$^+$, 418.1795; found, 418.0408.

General Method for Preparing Thio-Substituted Lenalidomide Carbon Chain Series of COOH-LIN-ULM:

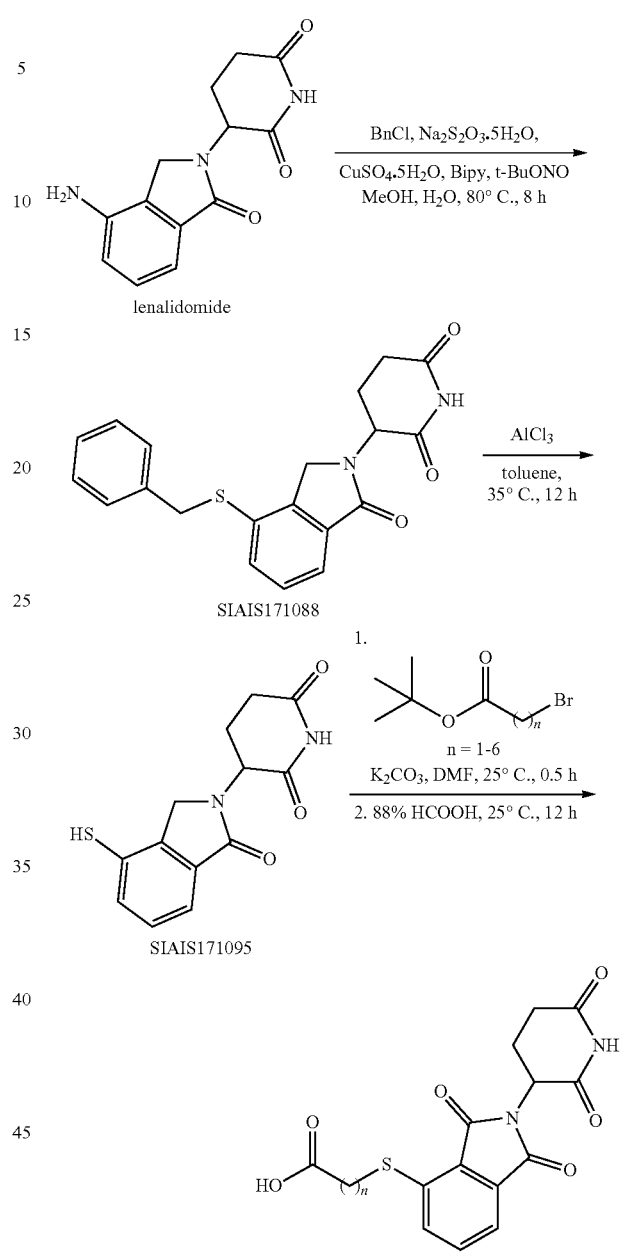

Scheme 4

Step 1: Preparation of 3-(4-(benzylthio)-1-oxoisoindolin-2-yl)piperidine-2,6-dione (SIAIS171088) According to Scheme 4

To a 500 mL egg-shaped flask containing methanol (120 mL) and water (120 mL) was charged with sodium thiosulfate pentahydrate (53.7 g, 216.3 mmol), benzyl chloride (27.4 g, 216.3 mmol), copper sulfate pentahydrate (77.4 mg, 0.31 mmol) and bipyridine (0.72 g, 4.6 mmol). The mixture was heated slowly to 80° C. and stirred for 2 hours. Then the reaction solution was cooled to room temperature, and 3-(4-amino-1-oxoisoindolin-2-yl)piperidine-2,6-dione (namely lenalidomide) (8.0 g, 30.9 mmol) was added, and finally tert-butyl nitrite (4.78 g, 46.4 mmol) was slowly added dropwise. After completion of the dropping, the mixture was heated to 80° C. again and stirred for 8 h. After the reaction, the reaction solution was cooled to room temperature, and water (200 mL) was added. The solution was then extracted with ethyl acetate (2×200 mL), and the organic phases were combined, washed with water (2×50 mL) and saturated brine (50 mL), dried over anhydrous $Na_2SO_4$, and concentrated to remove the solvent under reduced pressure. The crude product was purified by column chromatography (eluent (v/v): petroleum ether/ethyl acetate=1:2) to obtain the target compound (SIAIS171088) (white solid, 6.8 g, yield 60%). $^1$H NMR (500 MHz, CDCl$_3$) δ 8.07 (s, 1H), 7.75 (t, J=7.3 Hz, 1H), 7.55 (dd, J=7.4, 6.8 Hz, 1H), 7.49-7.41 (m, 1H), 7.27-7.17 (m, 5H), 5.20-5.17 (m, 1H), 4.22 (d, J=16.5 Hz, 1H), 4.15-4.04 (m, 2H), 3.92 (d, J=16.5 Hz, 1H), 2.95-2.74 (m, 2H), 2.32-2.22 (m, 1H), 2.17-2.11 (m, 1H). HRMS (ESI) m/z: calcd for, $C_{20}H_{19}N_2O_3S^+$ [M+H]$^+$, 367.1111; found, 367.1402.

Step 2: Preparation of 3-(4-mercapto-1-oxoisoindolin-2-yl)piperidine-2,6-dione (SIAIS171095) According to Scheme 4

A 250 mL egg-shaped flask was charged with anhydrous aluminum trichloride (2.61 g, 19.6 mmol) and anhydrous toluene (70 mL), followed by slow addition of the compound (SIAIS171088) (1.8 g, 4.9 mmol) with stirring. After addition, the reaction mixture was stirred overnight at 35° C. After the reaction, a 20% aqueous solution of citric acid was slowly added under stirring, and a large amount of solids were precipitated out. After suction filtering, the filter cake was washed with water and ethyl acetate, and dried to obtain the target compound (SIAIS171095) (white solid, 1.15 g, yield 85%). $^1$H NMR (500 MHz, DMSO) δ 11.01 (s, 1H), 7.82-7.39 (m, 3H), 5.73 (s, 1H), 5.21-5.04 (m, 1H), 4.40-4.20 (m, 2H), 2.99-2.85 (m, 1H), 2.67-2.56 (m, 1H), 2.47-2.30 (m, 1H), 2.05-1.95 (m, 1H) HRMS (ESI) m/z: calcd for, $C_{13}H_{13}N_2O_3S^+$ [M+H]$^+$, 277.0641; found, 276.8348.

Step 3: Preparation of the Thio-Substituted Lenalidomide Carbon Chain Series of COOH-LIN-ULM from Compound SIAIS171095 According to Scheme 4

A 10 mL egg-shaped flask was charged with the compound SIAIS171095 (0.36 mmol, 1 equiv), the corresponding brominated substrate (0.43 mmol, 1.2 equiv) and anhydrous potassium carbonate (0.72 mmol, 2 equiv), and then anhydrous N,N-dimethylformamide (2 mL). The reaction mixture was stirred at room temperature for 2 h. After the reaction, 50 mL of water was poured into the reaction mixture, and the mixture was then extracted with ethyl acetate (2×50 mL). The organic phases were combined, washed with water (2×30 mL) and saturated brine (50 mL), dried with anhydrous sodium sulfate, and concentrated to remove the solvent under reduced pressure. The crude product was separated by a reversed-phase C18 column (eluent (v/v): acetonitrile/(water+0.05% TFA)=10%-100%) to obtain the corresponding tert-butanol ester intermediate product. The corresponding tert-butanol ester intermediate product was then added to a 10 mL egg-shaped flask, followed by addition of 88% formic acid (3 mL), and the resulting reaction mixture was stirred at room temperature for 12 h. The reaction solvent was evaporated under reduced pressure, and the residue was treated by addition of water and freeze-dried to obtain the corresponding target compound.

Intermediate Preparation Example 24: Preparation of 2-((2-(2,6-dioxopiperidin-3-yl)-1-oxoisoindolin-4-yl)thio)acetic acid (SIAIS171090)

According to the method of Scheme 4, the compound SIAIS171090 was prepared under appropriate conditions that will be recognized by one skilled in the art, except that the brominated substrate used as the linker was tert-butyl 2-bromoacetate. The target compound SIAIS171090 was obtained as white solid (77 mg, step 3 total yield 64%). $^1$H NMR (500 MHz, DMSO) δ 12.88 (s, 1H), 11.00 (s, 1H), 7.68-7.45 (m, 3H), 5.15-5.13 (m, 1H), 4.32 (dd, J=56.2, 17.3 Hz, 2H), 3.94 (s, 2H), 2.95-2.91 (m, 1H), 2.63-2.59 (m, 1H), 2.49-2.39 (m, 1H), 2.08-1.92 (m, 1H). HRMS (ESI) m/z: calcd for, $C_{15}H_{15}N_2O_5S^+$ [M+H]$^+$, 335.0696; found, 334.8134.

Intermediate Preparation Example 25: Preparation of 3-((2-(2,6-dioxopiperidin-3-yl)-1-oxoisoindolin-4-yl)thio)propionic acid (SIAIS171086)

According to the method of Scheme 4, compound SIAIS171086 was prepared under appropriate conditions that will be recognized by one skilled in the art, except that the brominated substrate used as the linker was tert-butyl 3-bromopropionate. The target compound SIAIS171086 was obtained as white solid (40 mg, the total yield of step 3 was 32%). $^1$H NMR (500 MHz, DMSO) δ 10.99 (s, 1H), 7.70-7.55 (m, 3H), 5.13 (dd, J=13.3, 5.1 Hz, 1H), 4.40-4.18 (m, 2H), 3.24 (t, J=7.0 Hz, 2H), 2.95-2.87 (m, 1H), 2.63-2.53 (m, 3H), 2.47-2.34 (m, 1H), 2.05-1.95 (m, 1H). HRMS (ESI) m/z: calcd for, $C_{16}H_{17}N_2O_5S^+$ [M+H]$^+$, 349.0853; found, 348.8166.

Intermediate Preparation Example 26: Preparation of 4-((2-(2,6-dioxopiperidin-3-yl)-1-oxoisoindolin-4-yl)thio)butanoic acid (SIAIS171089)

According to the method of Scheme 4, the compound SIAIS171089 was prepared under appropriate conditions that will be recognized by one skilled in the art, except that the brominated substrate used as the linker was tert-butyl 4-bromobutyrate. The target compound SIAIS171089 was obtained as white solid (50 mg, step 3 total yield 38%). H NMR (500 MHz, DMSO) δ 12.15 (s, 1H), 10.99 (s, 1H), 7.71-7.49 (m, 3H), 5.13 (dd, J=13.3, 5.1 Hz, 1H), 4.41-4.18 (m, 2H), 3.10 (t, J=7.3 Hz, 2H), 2.92-2.88 (m, 1H), 2.61-2.59 (m, 1H), 2.49-2.42 (m, 1H), 2.38 (t, J=7.2 Hz, 2H), 2.05-1.96 (m, 1H), 1.84-1.74 (m, 2H). HRMS (ESI) m/z: calcd for, $C_{17}H_{19}N_2O_5S^+$ [M+H]$^+$, 363.1009; found, 362.8160.

Intermediate Preparation Example 27: Preparation of 5-((2-(2,6-dioxopiperidin-3-yl)-1-oxoisoindolin-4-yl)thio)pentanoic acid (SIAIS171079)

According to the method of Scheme 4, the compound SIAIS171079 was prepared under appropriate conditions that will be recognized by one skilled in the art, except that the brominated substrate used as the linker was tert-butyl 5-bromopentanoate. The target compound SIAIS171079 was obtained as white solid (30 mg, step 3 total yield 22%). $^1$H NMR (500 MHz, DMSO) δ 12.01 (s, 1H), 10.98 (s, 1H), 7.66-7.55 (m, 3H), 5.12 (dd, J=13.3, 5.1 Hz, 1H), 4.37-4.18 (m, 2H), 3.10-3.05 (m, 2H), 2.95-2.84 (m, 1H), 2.65-2.61 (m, 1H), 2.48-2.38 (m, 1H), 2.27-2.20 (m, 3H), 1.63-1.59

(m, 4H). HRMS (ESI) m/z: calcd for, $C_{18}H_{21}N_2O_5S^+$ [M+H]$^+$, 377.1166; found, 376.8981.

Intermediate Preparation Example 28: Preparation of 6-((2-(2,6-dioxopiperidin-3-yl)-1-oxoisoindolin-4-yl)thio)hexanoic acid (SIAIS171091)

The compound SIAIS171091 was prepared according to the method of Scheme 4 and under appropriate conditions that will be recognized by one skilled in the art, except that the brominated substrate used as the linker was tert-butyl 6-bromohexanoate. The target compound SIAIS171091 was obtained as white solid (75 mg, step 3 total yield 53%). $^1$H NMR (500 MHz, DMSO) δ 11.98 (s, 1H), 10.98 (s, 1H), 7.59-7.52 (m, 3H), 5.12 (dd, J=13.4, 5.1 Hz, 1H), 4.26 (dd, J=40.9, 20.5 Hz, 2H), 3.07 (t, J=7.3 Hz, 2H), 2.96-2.84 (m, 1H), 2.64-2.60 (m, 1H), 2.48-2.39 (m, 1H), 2.19-2.15 (m, 2H), 2.02-2.00 (m, 1H), 1.70-1.35 (m, 6H). HRMS (ESI) m/z: calcd for, $C_{19}H_{23}N_2O_5S^+$ [M+H]$^+$, 391.1322; found, 390.8150.

Intermediate Preparation Example 29: Preparation of 7-((2-(2,6-dioxopiperidin-3-yl)-1-oxoisoindolin-4-yl)thio)heptanoic acid (SIAIS171092)

According to the method of Scheme 4, the compound SIAIS171092 was prepared under appropriate conditions that will be recognized by one skilled in the art, except that the brominated substrate used as the linker was tert-butyl 7-bromoheptanoate. The target compound SIAIS171092 was obtained as white solid (79 mg, step 3 total yield 54%). $^1$H NMR (500 MHz, DMSO) δ 11.99 (s, 1H), 10.98 (s, 1H), 7.66-7.45 (m, 3H), 5.12 (dd, J=13.3, 5.1 Hz, 1H), 4.26 (dd, J=40.9, 20.5 Hz, 2H), 3.07 (t, J=7.3 Hz, 2H), 2.97-2.83 (m, 1H), 2.63-2.60 (m, 1H), 2.47-2.35 (m, 1H), 2.18 (t, J=7.3 Hz, 2H), 2.06-1.93 (m, 1H), 1.65-1.20 (m, 8H). HRMS (ESI) m/z: calcd for, $C_{20}H_{25}N_2O_5S^+$ [M+H]$^+$, 405.1479; actual measurement Value, 404.8155.

Intermediate Preparation Example 30: Preparation of 11-((2-(2,6-dioxopiperidin-3-yl)-1-oxoisoindolin-4-yl)thio)undecanoic acid (SIAIS1220099)

According to the method of Scheme 4, the compound SIAIS1220099 was prepared under appropriate conditions that will be recognized by one skilled in the art, except that the brominated substrate used as the linker was tert-butyl 11-bromoundecanoate. The target compound SIAIS1220099 was obtained as white solid (593 mg, yield 64%). $^1$H NMR (500 MHz, DMSO) δ 11.97 (s, 1H), 10.98 (s, 1H), 7.62 (d, J=7.4 Hz, 1H), 7.56 (d, J=6.6 Hz, 1H), 7.52 (t, J=7.5 Hz, 1H), 5.12 (dd, J=13.3, 5.1 Hz, 1H), 4.35 (d, J=17.4 Hz, 1H), 4.21 (d, J=17.4 Hz, 1H), 3.07 (t, J=7.2 Hz, 2H), 2.95-2.86 (m, 1H), 2.59 (d, J=17.5 Hz, 1H), 2.49-2.41 (m, 1H), 2.17 (t, J=7.4 Hz, 2H), 2.03-1.97 (m, 1H), 1.62-1.55 (m, 2H), 1.49-1.44 (m, 2H), 1.43-1.35 (m, 2H), 1.26-1.22 (m, 10H). HRMS (ESI) m/z: calcd for, $C_{24}H_{33}N_2O_5S^+$ [M+H]$^+$, 461.2105; found, 461.2103.

General method for preparing thio-substituted lenalidomide carbon chain series of NH$_2$-LIN-ULM:

Scheme 5

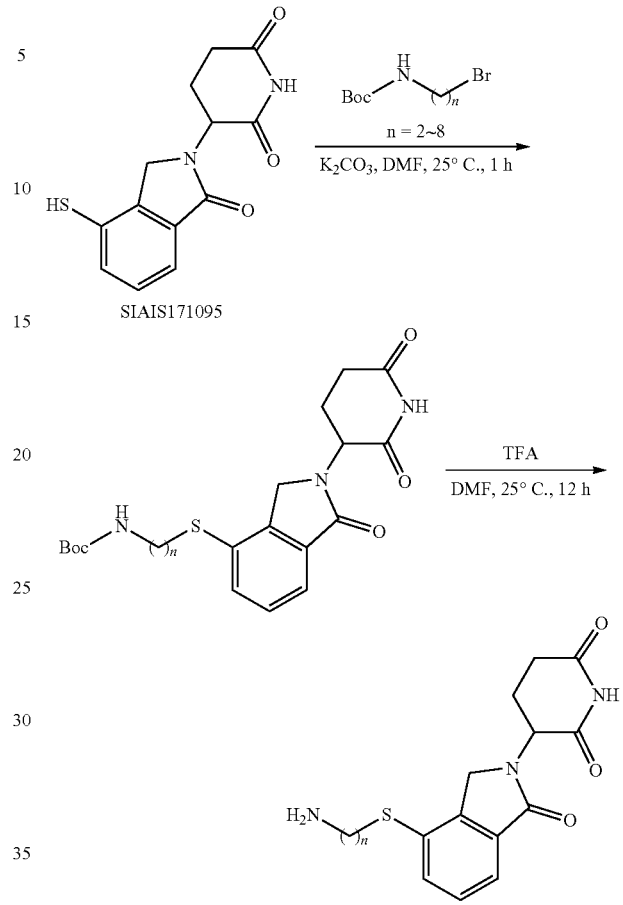

A 10 mL reaction flask was charged with the compound SIAIS171095 (0.36 mmol, 1 equiv), and then anhydrous N,N-dimethylformamide (2 mL) and anhydrous potassium carbonate (0.72 mmol, 2 equiv), followed by slowly addition of the corresponding bromide (0.43 mmol, 1.2 equiv) under stirring at room temperature. After completion of dropping, the reaction mixture was stirred at room temperature for 1 h. After the raw materials were completely consumed, the crude product was separated by reversed-phase C18 column (eluent (v/v): acetonitrile/(water+0.05% TFA)=10%-100%). The solvent was evaporated under reduced pressure, and the residue was lyophilized to obtain Boc protected alkylation intermediate product.

The Boc protected alkylation intermediate product obtained in step 1 was added in a 10 mL reaction flask, followed by addition of anhydrous dichloromethane (2 mL) and trifluoroacetic acid (2 mL). The resulting mixture was stirred at room temperature for 12 h, and concentrated to remove the solvent under reduced pressure. The crude product was purified by a reversed phase C18 column (eluent (v/v): acetonitrile/(water+0.05% TFA)=10%-100%). The solvent was evaporated under reduced pressure, and the residue was freeze-dried to obtain the corresponding target compound.

Intermediate Preparation Example 31: Preparation of 3-(4-((2-aminoethyl)thio)-1-oxoisoindolin-2-yl)piperidine-2,6-dione (SIAIS171123)

According to the method of Scheme 5, the compound SIAIS171123 was prepared under appropriate conditions that will be recognized by one skilled in the art, except that the brominated substrate used as the linker was tert-butyl (2-bromoethyl)carbamate. The target compound SIAIS171123 was obtained as white solid (68 mg, total yield of two steps 59%). $^1$H NMR (500 MHz, DMSO) δ 11.02 (s, 1H), 7.88 (s, 3H), 7.73 (dd, J=7.7, 0.8 Hz, 1H), 7.66 (dd, J=7.5, 0.7 Hz, 1H), 7.59 (t, J=7.6 Hz, 1H), 5.15 (dd, J=13.3, 5.1 Hz, 1H), 4.45-4.25 (m, 2H), 3.32-3.26 (m, 2H), 3.05-3.00 (m, 2H), 2.96-2.87 (m, 1H), 2.64-2.60 (m, 1H), 2.48-2.41 (m, 1H), 2.05-2.00 (m, 1H) HRMS (ESI) m/z: calcd for, $C_{15}H_{18}N_3O_3S^+$ [M+H]$^+$, 320.1063; found, 320.1082.

Intermediate Preparation Example 32: Preparation of 3-(4-((3-aminopropyl)thio)-1-oxoisoindolin-2-yl) piperidine-2,6-dione (SIAIS171124)

According to the method of Scheme 5, the compound SIAIS171124 was prepared under appropriate conditions that will be recognized by one skilled in the art, except that the brominated substrate used as the linker was tert-butyl (3-bromopropyl) carbamate. The target compound SIAIS171124 was obtained as white solid (68 mg, total yield of two steps 56%). $^1$H NMR (500 MHz, DMSO) δ 11.00 (s, 1H), 7.75-7.67 (m, 4H), 7.63-7.49 (m, 2H), 5.14 (dd, J=13.3, 5.1 Hz, 1H), 4.43-4.16 (m, 2H), 3.22-3.11 (m, 2H), 2.97-2.85 (m, 3H), 2.67-2.56 (m, 1H), 2.48-2.40 (m, 1H), 2.05-1.95 (m, 1H), 1.91-1.77 (m, 2H). HRMS (ESI) m/z: calcd for, $C_{16}H_{20}N_3O_3S^+$ [M+H]$^+$, 334.1220; found, 334.1213.

Intermediate Preparation Example 33: Preparation of 3-(4-((4-aminobutyl)thio)-1-oxoisoindolin-2-yl) piperidine-2,6-dione (SIAIS171131)

According to the method of Scheme 5, the compound SIAIS171131 was prepared under appropriate conditions that will be recognized by one skilled in the art, except that the brominated substrate used as the linker was tert-butyl (4-bromobutyl)carbamate. The target compound SIAIS171131 was obtained as light yellow solid (76 mg, total yield of two steps 60%). $^1$H NMR (500 MHz, DMSO) δ 10.99 (s, 1H), 7.81-7.47 (m, 6H), 5.13 (dd, J=13.3, 5.1 Hz, 1H), 4.25 (dd, J=31.3, 15.7 Hz, 2H), 3.20-3.03 (m, 2H), 2.96-2.85 (m, 1H), 2.85-2.80 (m, 2H), 2.63-2.60 (m, 1H), 2.46-2.30 (m, 1H), 2.06-1.94 (m, 1H), 1.71-1.56 (m, 4H). HRMS (ESI) m/z: calcd for, $C_{17}H_{22}N_3O_3S^+$ [M+H]$^+$, 348.1376; found, 348.1381.

Intermediate Preparation Example 34: Preparation of 3-(4-((5-aminopentyl)thio)-1-oxoisoindolin-2-yl) piperidine-2,6-dione (SIAIS171132)

According to the method of Scheme 5, the compound SIAIS171132 was prepared under appropriate conditions that will be recognized by one skilled in the art, except that the brominated substrate used as the linker was tert-butyl (5-bromopentyl)carbamate. The target compound SIAIS171132 was obtained as light yellow solid (95 mg, total yield of two steps 73%). $^1$H NMR (500 MHz, DMSO) δ 11.00 (s, 1H), 7.85-7.45 (m, 6H), 5.21-5.07 (m, 1H), 4.42-4.16 (m, 2H), 3.16-3.05 (m, 2H), 2.92-2.85 (m, 1H), 2.84-2.71 (m, 2H), 2.64-2.60 (m, 1H), 2.45-2.40 (m, 1H), 2.07-1.93 (m, 1H), 1.66-1.58 (m, 2H), 1.54-1.50 (m, 2H), 1.49-1.44 (m, 2H). HRMS (ESI) m/z: calcd for, $C_{18}H_{24}N_3O_3S^+$ [M+H]$^+$, 362.1533; found, 362.1537.

Intermediate Preparation Example 35: Preparation of 3-(4-((6-aminohexyl)thio)-1-oxoisoindolin-2-yl) piperidine-2,6-dione (SIAIS171134)

According to the method of Scheme 5, the compound SIAIS171134 was prepared under appropriate conditions that will be recognized by one skilled in the art, except that the brominated substrate used as the linker wail tert-butyl (6-bromohexyl)carbamate. The target compound SIAIS171134 was obtained as light yellow solid (78 mg, total yield of two steps 57%). $^1$H NMR (500 MHz, DMSO) δ 11.00 (s, 1H), 7.84-7.43 (m, 6H), 5.16-5.13 (m, 1H), 4.30-4.15 (m, 2H), 3.14-3.03 (m, 2H), 2.97-2.88 (m, 1H), 2.82-2.72 (m, 2H), 2.62 (t, J=14.7 Hz, 1H), 2.49-2.39 (m, 1H), 2.06-1.96 (m, 1H), 1.68-1.56 (m, 2H), 1.51-1.46 (m, 2H), 1.45-1.37 (m, 2H), 1.36-1.28 (m, 2H). HRMS (ESI) m/z: calcd for, $C_{19}H_{26}N_3O_3S^+$ [M+H]$^+$, 376.1689; Found, 376.1702.

Intermediate Preparation Example 36: Preparation of 3-(4-((7-aminoheptyl)thio)-1-oxoisoindolin-2-yl) piperidine-2,6-dione (SIAIS171135)

According to the method of Scheme 5, the compound SIAIS171135 was prepared under appropriate conditions that will be recognized by one skilled in the art, except that the brominated substrate used as the linker was tert-butyl (7-bromoheptyl)carbamate. The target compound SIAIS171135 was obtained as white solid (100 mg, total yield of two steps 71%). $^1$H NMR (500 MHz, DMSO) δ 10.99 (s, 1H), 7.84-7.42 (m, 6H), 5.13 (dd, J=13.3, 5.1 Hz, 1H), 4.37-4.18 (m, 2H), 3.15-3.02 (m, 2H), 2.92-2.88 (m, 1H), 2.81-2.71 (m, 2H), 2.61 (t, J=14.8 Hz, 1H), 2.48-2.40 (m, 1H), 2.05-1.98 (m, 1H), 1.65-1.56 (m, 2H), 1.54-1.46 (m, 2H), 1.44-1.36 (m, 2H), 1.33-1.23 (m, 4H). HRMS (ESI) m/z: calculation Value $C_{20}H_{28}N_3O_3S^+$ [M+H]$^+$, 390.1846; found, 390.1846.

Intermediate Preparation Example 37: Preparation of 3-(4-((8-aminooctyl)thio)-1-oxoisoindolin-2-yl) piperidine-2,6-dione (SIAIS171136)

According to the method of Scheme 5, compound SIAIS171136 was prepared under appropriate conditions that will be recognized by one skilled in the art, except that the brominated substrate used as the linker was tert-butyl (8-bromooctyl)carbamate. The target compound SIAIS171136 was obtained as white solid (100 mg, total yield of two steps 68%). $^1$H NMR (500 MHz, DMSO) δ 10.99 (s, 1H), 7.75-7.47 (m, 6H), 5.13 (dd, J=13.3, 5.1 Hz, 1H), 4.28 (dd, J=70.1, 17.4 Hz, 2H), 3.13-3.00 (m, 2H), 2.98-2.84 (m, 1H), 2.78-2.74 (m, 2H), 2.64-2.59 (m, 1H), 2.47-2.38 (m, 1H), 2.06-1.93 (m, 1H), 1.68-1.54 (m, 2H), 1.52-1.48 (m, 2H), 1.45-1.34 (m, 2H), 1.30-1.20 (m, 6H). HRMS (ESI) m/z: Calcd for, $C_{21}H_{30}N_3O_3S^+$ [M+H]$^+$, 404.2002; found, 404.1996.

General Method for Preparing Thio-Substituted Lenalidomide PEG Chain Series of NH$_2$-LIN-ULM:

Scheme 6

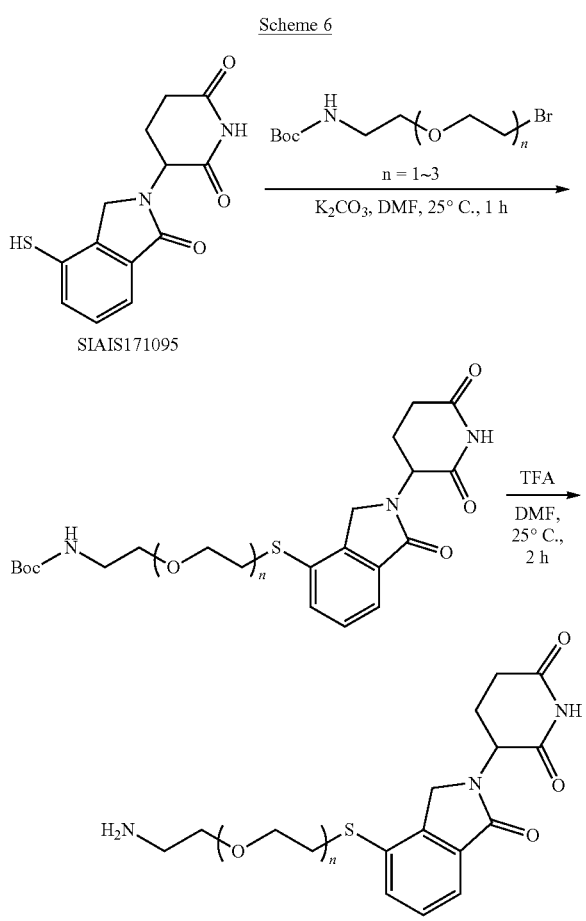

A 10 mL reaction flask was charged with the compound SIAIS171095 (0.36 mmol, 1 equiv), and then anhydrous N,N-dimethylformamide (3 mL) and anhydrous potassium carbonate (0.72 mmol, 2 equiv), followed by slow addition of the corresponding brominated substrate (0.43 mmol, 1.2 equiv) under stirring at room temperature. After completion of dropping, the reaction mixture was stirred at room temperature for 1 h. After the raw materials were completely consumed, the reaction mixture was quenched by adding water, extracted with ethyl acetate, and concentrated. The crude product was separated on a reversed-phase C18 column (eluent (v/v): acetonitrile/water=10%-100%). The solvent was evaporated under reduced pressure and the residue was lyophilized to obtain the corresponding intermediate compound. The obtained intermediate compound was added into a 10 mL reaction flask, then anhydrous dichloromethane (4 mL) and trifluoroacetic acid (1 mL) were added. The mixture was stirred at room temperature for 2 h, and concentrated to remove the reaction solvent under reduced pressure. The residue was treated by addition of water, and lyophilized to obtain the target compound.

Intermediate Preparation Example 38: Preparation of 3-(4-((2-(2-aminoethoxy)ethyl)thio)-1-oxoisoindolin-2-yl)piperidine-2,6-dione (SIAIS213096)

The compound SIAIS213096 was prepared according to the method of Scheme 6 under appropriate conditions that will be recognized by one skilled in the art, except that the brominated substrate used as the linker was tert-butyl (2-(2-Bromoethoxy)ethyl)carbamate. The target compound SIAIS213096 was obtained as white solid (41 mg, two-step yield 62.4%). $^1$H NMR (500 MHz, MeOD) δ 7.69 (ddd, J=17.2, 10.0, 2.9 Hz, 2H), 7.54 (t, J=7.7 Hz, 1H), 5.17 (dd, J=13.4, 5.2 Hz, 1H), 4.52-4.39 (m, 2H), 3.79-3.69 (m, 2H), 3.63 (ddd, J=5.0, 2.6, 1.0 Hz, 2H), 3.30-3.21 (m, 2H), 3.10-3.03 (m, 2H), 2.95-2.86 (m, 1H), 2.79 (ddd, J=17.6, 4.6, 2.3 Hz, 1H), 2.52 (qd, J=13.3, 4.6 Hz, 1H), 2.25-2.11 (m, 1H). LCMS (ESI) m/z: calcd for, $C_{17}H_{22}N_3O_4S^+$ $[M+H]^+$, 364.1326; found, 364.3.

Intermediate Preparation Example 39: Preparation of 3-(4-((2-(2-(2-aminoethoxy)ethoxy)ethyl)thio)-1-oxoisoindolin-2-yl)piperidine-2,6-dione (SIAIS213068)

The compound SIAIS213068 was prepared according to the method described in Scheme 6 under appropriate conditions that will be recognized by one skilled in the art, except that the brominated substrate used as the linker was tert-butyl (2-(2-(2-bromoethoxy)ethoxy)ethyl)carbamate. The target compound SIAIS213068 was obtained as light yellow solid (120 mg, two-step yield 40.7%). $^1$H NMR (500 MHz, DMSO) δ 11.03 (s, 1H), 7.86 (s, 3H), 7.69 (dt, J=7.7, 3.9 Hz, 1H), 7.63-7.50 (m, 2H), 5.15 (dd, J=13.3, 5.1 Hz, 1H), 4.31 (dd, J=70.7, 17.4 Hz, 2H), 3.67-3.46 (m, 8H), 3.32-3.23 (m, 2H), 3.01-2.83 (m, 3H), 2.61 (d, J=16.6 Hz, 1H), 2.49-2.40 (m, 1H), 2.09-1.95 (m, 1H).

Intermediate Preparation Example 40: Preparation of 3-(4-((2-(2-(2-(2-aminoethoxy)ethoxy)ethoxy)ethyl)thio)-1-oxoisoindolin-2-yl)piperidine-2,6-dione (SIAIS213111)

According to the method of Scheme 4, the compound SIAIS213111 was prepared under appropriate conditions that will be recognized by one skilled in the art, except that the brominated substrate used as the linker was tert-butyl (2-(2-(2-(2-bromoethoxy)ethoxy)ethoxy)ethyl)carbamate. The target compound SIAIS213111 was obtained as colorless oily liquid (140 mg, two-step yield 85.6%). $^1$H NMR (500 MHz, DMSO) δ 11.00 (s, 1H), 7.82 (s, 3H), 7.69 (dd, J=7.7, 0.8 Hz, 1H), 7.59 (dt, J=11.3, 5.6 Hz, 1H), 7.54 (t, J=7.6 Hz, 1H), 5.14 (dd, J=13.3, 5.1 Hz, 1H), 4.44-4.14 (m, 2H), 3.62 (t, J=6.4 Hz, 2H), 3.60-3.56 (m, 4H), 3.55-3.51 (m, 6H), 3.31-3.20 (m, 2H), 2.99-2.87 (m, 3H), 2.60 (d, J=17.5 Hz, 1H), 2.49-2.37 (m, 1H), 2.06-1.94 (m, 1H). LCMS (ESI) m/z: calcd for, $C_{21}H_{30}N_3O_6S^+$ $[M+H]^+$, 452.1850; found, 452.35.

General Method for Preparing Thio-Substituted Lenalidomide Carbon Chain Series of Br-LIN-ULM:

Scheme 7

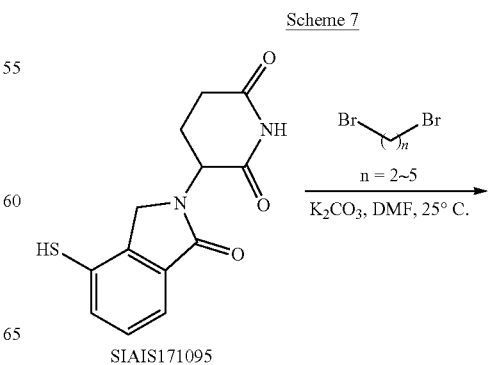

SIAIS171095

-continued

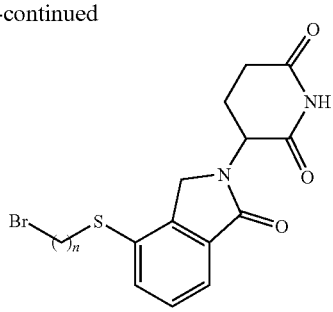

A 25 mL reaction flask was charged with the compound SIAIS171095 (1 equiv), and then anhydrous N,N-dimethylformamide (10 mL) and anhydrous potassium carbonate (2 equiv), followed by slow addition of the corresponding dibromide substrate (1.2 equiv) under stirring at room temperature. After completion of dropping, the reaction mixture was stirred at room temperature for 1 h. After the raw materials were completely consumed, the reaction mixture was quenched by adding water, extracted with ethyl acetate, and the organic phase was concentrated. The crude product was separated by a reversed phase C18 column (eluent (v/v): acetonitrile/water=10%-100%). The solvent was evaporated under reduced pressure and the residue was lyophilized to obtain the target compound.

Intermediate Preparation Example 41: Preparation of 3-(4-(2-bromoethylthio)-1-oxoisoindolin-2-yl) piperidine-2,6-dione (SIAIS213137)

The compound SIAIS213137 was prepared according to the method of Scheme 7 under appropriate conditions that will be recognized by one skilled in the art, except that the brominated substrate used as the linker was 1,2-dibromoethane. The target compound SIAIS213137 was obtained as light yellow solid (78 mg, yield 18.7%). $^1$H NMR (500 MHz, CDCl$_3$) δ 8.00 (s, 1H), 7.83-7.76 (m, 1H), 7.57 (t, J=7.1 Hz, 1H), 7.50 (dd, J=17.4, 9.8 Hz, 1H), 5.23 (dt, J=15.9, 7.9 Hz, 1H), 4.46 (d, J=16.5 Hz, 1H), 4.37-4.27 (m, 1H), 3.51-3.43 (m, 2H), 3.41-3.33 (m, 2H), 2.94 (d, J=15.1 Hz, 1H), 2.90-2.78 (m, 1H), 2.46-2.35 (m, 1H), 2.29-2.20 (m, 1H). LCMS (ESI) m/z: Calcd for, $C_{15}H_{16}BrN_2O_3S^+$ [M+H]$^+$, 383.0060\385.0039; found, 383.11 \385.12.

Intermediate Preparation Example 42: Preparation of 3-(4-(3-bromopropylthio)-1-oxoisoindolin-2-yl) piperidine-2,6-dione (SIAIS213132)

The compound SIAIS213132 was prepared according to the method of Scheme 7 under appropriate conditions that will be recognized by one skilled in the art, except that the brominated substrate used as the linker was 1,3-dibromopropane. The target compound SIAIS213132 was obtained as light yellow solid (130 mg, yield 30.1%). $^1$H NMR (500 MHz, CDCl$_3$) δ 8.01 (s, 1H), 7.76 (t, J=11.2 Hz, 1H), 7.57-7.43 (m, 2H), 5.28-5.18 (m, 1H), 4.46-4.25 (m, 2H), 3.62-3.50 (m, 2H), 3.16 (t, J=7.0 Hz, 2H), 2.98-2.77 (m, 2H), 2.46-2.33 (m, 1H), 2.28-2.13 (m, 3H). LCMS (ESI) m/z: calcd for, $C_{16}H_{18}BrN_2O_3S^+$ [M+H]$^+$, 397.0216\399.0196; found, 397.15\399.11.

Intermediate Preparation Example 43: Preparation of 3-(4-(4-bromobutylthio)-1-oxoisoindolin-2-yl) piperidine-2,6-dione (SIAIS213134)

The compound SIAIS213134 was prepared according to the method of Scheme 7 under appropriate conditions that will be recognized by one skilled in the art, except that the brominated substrate used as the linker was 1,4-dibromobutane. The target compound SIAIS213134 was obtained as light yellow solid (170 mg, yield 38.1%). $^1$H NMR (500 MHz, CDCl$_3$) δ 8.00 (s, 1H), 7.74 (t, J=8.7 Hz, 1H), 7.55-7.44 (m, 2H), 5.23 (dt, J=20.5, 10.3 Hz, 1H), 4.33 (ddd, J=33.1, 25.9, 11.5 Hz, 2H), 3.48-3.35 (m, 2H), 3.01 (dd, J=20.7, 13.5 Hz, 2H), 2.97-2.81 (m, 2H), 2.41 (ddd, J=26.6, 13.3, 4.8 Hz, 1H), 2.28-2.19 (m, 1H), 2.09-1.96 (m, 2H), 1.89-1.86 (m, 2H). LCMS (ESI) m/z: Calcd for, $C_{17}H_{20}BrN_2O_3S^+$ [M+H]$^+$, 411.0373\413.0352; found, 411.10\413.11.

Intermediate Preparation Example 44: Preparation of 3-(4-(5-bromopentylthio)-1-oxoisoindolin-2-yl) piperidine-2,6-dione (SIAIS213135)

The compound SIAIS213135 was prepared according to the method of Scheme 7 under appropriate conditions that will be recognized by one skilled in the art, except that the brominated substrate used as the linker was 1,5-dibromopentane. The target compound SIAIS213135 was obtained as light yellow solid (190 mg, yield 41.1%). $^1$H NMR (500 MHz, CDCl$_3$) δ 8.05 (d, J=28.3 Hz, 1H), 7.76-7.69 (m, 1H), 7.52-7.41 (m, 2H), 5.26-5.18 (m, 1H), 4.47-4.24 (m, 2H), 3.41 (t, J=6.6 Hz, 2H), 2.99 (dd, J=17.3, 10.1 Hz, 2H), 2.95-2.79 (m, 2H), 2.39 (tdd, J=22.4, 15.4, 7.4 Hz, 1H), 2.31-2.19 (m, 1H), 1.93-1.84 (m, 2H), 1.73-1.70 (m, 2H), 1.69-1.63 (m, 2H). LCMS (ESI) m/z: Calcd for, $C_{18}H_{22}BrN_2O_3S^+$ [M+H]$^+$, 425.0529\427.0509; found, 425.10\427.10.

Intermediate Preparation Example 45: Preparation of 3-(4-(6-bromohexylthio)-1-oxoisoindolin-2-yl) piperidine-2,6-dione (SIAIS1216133)

The compound SIAIS1216133 was prepared according to the method of Scheme 7 under appropriate conditions that will be recognized by one skilled in the art, except that the brominated substrate used as the linker was 1,6-dibromohexane. The target compound SIAIS1216133 was obtained as white solid (339 mg, yield 38%). $^1$H NMR (500 MHz, DMSO) δ 11.01 (s, 1H), 7.63 (dd, J=7.5, 1.2 Hz, 1H), 7.58-7.51 (m, 2H), 5.13 (dd, J=13.3, 5.1 Hz, 1H), 4.35 (d, J=17.4 Hz, 1H), 4.21 (d, J=17.4 Hz, 1H), 3.52 (t, J=6.7 Hz, 2H), 3.08 (t, J=7.2 Hz, 2H), 2.96-2.87 (m, 1H), 2.59 (d, J=17.4 Hz, 1H), 2.49-2.41 (m, 1H), 2.04-1.97 (m, 1H), 1.82-1.74 (m, 2H), 1.63-1.56 (m, 2H), 1.46-1.36 (m, 4H). HRMS (ESI) m/z: calcd for, $C_{19}H_{24}BrN_2O_3S^+$ [M+H]$^+$, 439.0686; found, 439.0680.

Intermediate Preparation Example 46: Preparation of 3-(4-(7-bromoheptylthio)-1-oxoisoindolin-2-yl) piperidine-2,6-dione (SIAIS1216135)

The compound SIAIS1216135 was prepared according to the method of Scheme 7 under appropriate conditions that will be recognized by one skilled in the art, except that the brominated substrate used as the linker was 1,7-dibromoheptane. The target compound SIAIS1216135 was obtained as white solid (212 mg, yield 23%). $^1$H NMR (500 MHz, DMSO) δ 11.02 (s, 1H), 7.63 (dd, J=7.5, 0.9 Hz, 1H), 7.58-7.51 (m, 2H), 5.13 (dd, J=13.3, 5.1 Hz, 1H), 4.35 (d, J=17.4 Hz, 1H), 4.21 (d, J=17.4 Hz, 1H), 3.52 (t, J=6.7 Hz, 2H), 3.08 (t, J=7.2 Hz, 2H), 2.96-2.87 (m, 1H), 2.63-2.56 (m, 1H), 2.49-2.40 (m, 1H), 2.04-1.97 (m, 1H), 1.82-1.73

(m, 2H), 1.63-1.56 (m, 2H), 1.44-1.27 (m, 6H). HRMS (ESI) m/z: calcd for, $C_{20}H_{26}BrN_2O_3S^+$ [M+H]$^+$, 453.0842; found, 453.0840.

Intermediate Preparation Example 47: Preparation of 3-(4-((8-bromooctyl)thio)-1-oxoisoindolin-2-yl)piperidine-2,6-dione (SIAIS1216137)

The compound SIAIS1216137 was prepared according to the method of Scheme 7 under appropriate conditions that will be recognized by one skilled in the art, except that the brominated substrate used as the linker was 1,8-dibromooctane. The target compound SIAIS1216137 was obtained as white solid (351 mg, yield 38%). $^1$H NMR (500 MHz, DMSO) δ 11.01 (s, 1H), 7.63 (dd, J=7.5, 1.1 Hz, 1H), 7.57-7.51 (m, 2H), 5.13 (dd, J=13.3, 5.1 Hz, 1H), 4.35 (d, J=17.4 Hz, 1H), 4.20 (d, J=17.4 Hz, 1H), 3.51 (t, J=6.7 Hz, 2H), 3.08 (t, J=7.3 Hz, 2H), 2.95-2.87 (m, 1H), 2.63-2.55 (m, 1H), 2.49-2.41 (m, 1H), 2.03-1.97 (m, 1H), 1.81-1.73 (m, 2H), 1.64-1.55 (m, 2H), 1.44-1.32 (m, 4H), 1.31-1.23 (m, 4H). HRMS (ESI) m/z: calcd for, $C_{21}H_{28}BrN_2O_3S^+$ [M+H]$^+$, 467.0999; found, 467.0996.

Intermediate Preparation Example 48: Preparation of 3-(4-((9-bromononyl)thio)-1-oxoisoindolin-2-yl)piperidine-2,6-dione (SIAIS1220059)

The compound SIAIS1220059 was prepared according to the method of Scheme 7 and under appropriate conditions that will be recognized by one skilled in the art, except that the brominated substrate used as the linker was 1,9-dibromononane. The target compound SIAIS1220059 was obtained as white solid (400 mg, yield 42%). $^1$H NMR (500 MHz, DMSO) δ 11.00 (s, 1H), 7.62 (dd, J=7.5, 0.9 Hz, 1H), 7.59-7.50 (m, 2H), 5.13 (dd, J=13.3, 5.1 Hz, 1H), 4.35 (d, J=17.4 Hz, 1H), 4.21 (d, J=17.4 Hz, 1H), 3.51 (t, J=6.7 Hz, 2H), 3.07 (t, J=7.2 Hz, 2H), 2.95-2.86 (m, 1H), 2.59 (d, J=17.4 Hz, 1H), 2.49-2.40 (m, 1H), 2.04-1.97 (m, 1H), 1.81-1.72 (m, 2H), 1.63-1.56 (m, 2H), 1.42-1.31 (m, 4H), 1.28-1.22 (m, 6H). HRMS (ESI) m/z: calcd for, $C_{22}H_{30}BrN_2O_3S^+$ [M+H]$^+$, 481.1155; found, 481.1152.

Intermediate Preparation Example 49: Preparation of 3-(4-((10-bromodecyl)thio)-1-oxoisoindolin-2-yl)piperidine-2,6-dione (SIAIS1220013)

The compound SIAIS1220013 was prepared according to the method of Scheme 7 under appropriate conditions that will be recognized by one skilled in the art, except that the brominated substrate used as the linker was 1,10-dibromodecane. The target compound SIAIS1220013 was obtained as light yellow solid (329 mg, yield 33%). $^1$H NMR (500 MHz, DMSO) δ 11.01 (s, 1H), 7.62 (d, J=7.5 Hz, 1H), 7.58-7.51 (m, 2H), 5.13 (dd, J=13.3, 5.1 Hz, 1H), 4.35 (d, J=17.4 Hz, 1H), 4.20 (d, J=17.4 Hz, 1H), 3.52 (t, J=6.7 Hz, 2H), 3.08 (t, J=7.2 Hz, 2H), 2.95-2.87 (m, 1H), 2.62-2.56 (m, 1H), 2.49-2.42 (m, 1H), 2.03-1.97 (m, 1H), 1.81-1.73 (m, 2H), 1.62-1.55 (m, 2H), 1.43-1.32 (m, 4H), 1.24 (s, 8H) HRMS (ESI) m/z: calcd for, $C_{23}H_{32}BrN_2O_3S^+$ [M+H]$^+$, 495.1312; found, 495.1310.

Intermediate Preparation Example 50: Preparation of 3-(4-((11-bromoundecyl)thio)-1-oxoisoindolin-2-yl)piperidine-2,6-dione (SIAIS1220015)

The compound SIAIS1220015 was prepared according to the method of Scheme 7 under appropriate conditions that will be recognized by one skilled in the art, except that the brominated substrate used as the linker was 1,11-dibromoundecane. The target compound SIAIS1220015 was obtained as white solid (276 mg, yield 27%) was obtained. $^1$H NMR (500 MHz, DMSO) δ 11.01 (s, 1H), 7.64-7.60 (m, 1H), 7.58-7.51 (m, 2H), 5.13 (dd, J=13.3, 5.1 Hz, 1H), 4.35 (d, J=17.4 Hz, 1H), 4.20 (d, J=17.4 Hz, 1H), 3.52 (t, J=6.7 Hz, 2H), 3.08 (t, J=7.2 Hz, 2H), 2.96-2.86 (m, 1H), 2.63-2.56 (m, 1H), 2.49-2.40 (m, 1H), 2.03-1.96 (m, 1H), 1.82-1.73 (m, 2H), 1.62-1.54 (m, 2H), 1.42-1.32 (m, 4H), 1.24 (s, 10H). HRMS (ESI) m/z: calcd for, $C_{24}H_{34}BrN_2O_3S^+$ [M+H]$^+$, 509.1468; found, 509.1466.

Intermediate Preparation Example 51: Preparation of 3-(4-((12-bromododecyl)thio)-1-oxoisoindolin-2-yl)piperidine-2,6-dione (SIAIS264005)

The compound SIAIS264005 was prepared according to the method of Scheme 7 under appropriate conditions that will be recognized by one skilled in the art, except that the brominated substrate used as the linker was 1,12-dibromododecane. The target compound SIAIS264005 was obtained as white solid (310 mg, yield 34%). HRMS (ESI) m/z: calcd for, $C_{25}H_{36}BrN_2O_3S^+$ [M+H]$^+$, 523.1625; found, 523.1624.

Intermediate Preparation Example 52: Preparation of 3-(4-((4-(bromomethyl)benzyl)thio)-1-oxoisoindolin-2-yl)piperidine-2,6-dione (SIAIS1220141)

The compound SIAIS1220141 was prepared according to the method of Scheme 7 under appropriate conditions that will be recognized by one skilled in the art, except that the brominated substrate used as the linker was 1,11-dibromoundecane. The target compound SIAIS1220141 was obtained as light yellow solid (247 mg, yield 27%). $^1$H NMR (500 MHz, DMSO) δ 11.00 (s, 1H), 7.67 (dd, J=7.7, 0.7 Hz, 1H), 7.58 (d, J=6.9 Hz, 1H), 7.50 (t, J=7.6 Hz, 1H), 7.43-7.31 (m, 4H), 5.10 (dd, J=13.3, 5.1 Hz, 1H), 4.67 (s, 2H), 4.34 (s, 2H), 4.24 (d, J=17.4 Hz, 1H), 4.13 (d, J=17.4 Hz, 1H), 2.95-2.86 (m, 1H), 2.58 (d, J=16.6 Hz, 1H), 2.45-2.35 (m, 1H), 2.00-1.94 (m, 1H). HRMS (ESI) m/z: calcd for, $C_{21}H_{20}BrN_2O_3S^+$ [M+H]$^+$, 459.0373; found, 459.0370.

General Method for Preparing Thio-Substituted Pomalidomide Carbon Chain Series of Br-LIN-ULM:

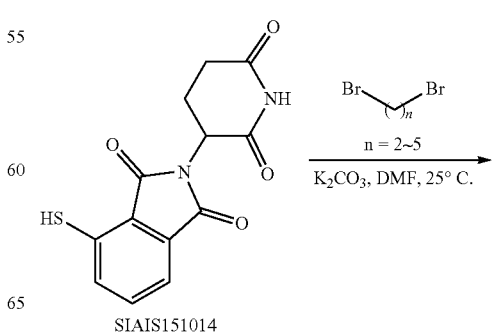

Scheme 8

SIAIS151014

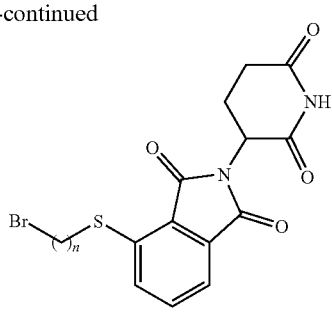

A 25 mL reaction flask was charged with the compound SIAIS151014 (1 equiv), and then anhydrous N, N-dimethylformamide (10 mL) and anhydrous potassium carbonate (2 equiv), followed by slow addition of the corresponding dibrominated substrate (1.2 equiv) under stirring at room temperature. After completion of dropping, the reaction mixture was stirred at room temperature for 1 h. After the raw materials were completely consumed, the reaction mixture was quenched with water, extracted with ethyl acetate, and the organic phase was concentrated. The crude product was separated by a reverse phase C18 column (eluent (v/v): acetonitrile/water=10%-100%). The solvent was evaporated under reduced pressure, and the residue was lyophilized to obtain the target compound.

Intermediate Preparation Example 53: Preparation of 4-(2-bromoethylthio)-2-(2,6-dioxopiperidin-3-yl)isoindoline-1,3-dione (SIAIS213162)

The compound SIAIS213162 was prepared according to the method of Scheme 8 under appropriate conditions that will be recognized by one skilled in the art, except that the brominated substrate used as the linker was 1,2-dibromoethane. The target compound SIAIS213162 was obtained as light yellow solid (310 mg, yield 45.3%), $^1$H NMR (500 MHz, CDCl$_3$) δ 8.00 (s, 1H), 7.74-7.65 (m, 2H), 7.55 (d, J=7.5 Hz, 1H), 4.97 (dd, J=12.4, 5.3 Hz, 1H), 3.61-3.46 (m, 4H), 2.93-2.73 (m, 3H), 2.19-2.09 (m, 1H). LCMS (ESI) m/z: calcd for, $C_{15}H_{14}BrN_2O_4S^+$ [M+H]$^+$, 396.9852\398.9832; found, 397.01\399.00.

Intermediate Preparation Example 54: Preparation of 4-(3-bromopropylthio)-2-(2,6-dioxopiperidin-3-yl)isoindoline-1,3-dione (SIAIS213159)

The compound SIAIS213159 was prepared according to the method of Scheme 8 under appropriate conditions that will be recognized by one skilled in the art, except that the brominated substrate used as the linker was 1,3-dibromopropane. The target compound SIAIS213159 was obtained as light yellow solid (260 mg, yield 36.7%), $^1$H NMR (500 MHz, CDCl$_3$) δ 8.05 (s, 1H), 7.67 (td, J=16.9, 8.0 Hz, 2H), 7.58 (d, J=7.8 Hz, 1H), 4.98 (dd, J=12.4, 5.3 Hz, 1H), 3.58 (t, J=6.2 Hz, 2H), 3.25 (t, J=7.1 Hz, 2H), 2.96-2.69 (m, 3H), 2.34-2.25 (m, 2H), 2.20-2.11 (m, 1H). LCMS (ESI) m/z: calcd for, $C_{16}H_{16}BrN_2O_4S^+$ [M+H]$^+$, 411.0009\412.9988; found, 411.01\413.06.

Intermediate Preparation Example 55: Preparation of 4-((4-bromobutyl)thio)-2-(2,6-dioxopiperidin-3-yl)isoindoline-1,3-dione (SIAIS213165)

The compound SIAIS213165 was prepared according to the method of Scheme 8 under appropriate conditions that will be recognized by one skilled in the art, except that the brominated substrate used as the linker was 1,4-dibromobutane. The target compound SIAIS213165 was obtained as light yellow solid (520 mg, yield 35.4%), $^1$H NMR (500 MHz, CDCl$_3$) δ 8.01 (s, 1H), 7.71-7.57 (m, 2H), 7.51 (t, J=15.9 Hz, 1H), 4.98 (dd, J=12.3, 5.3 Hz, 1H), 3.46 (t, J=6.4 Hz, 2H), 3.10 (t, J=7.1 Hz, 2H), 2.98-2.69 (m, 3H), 2.20-2.12 (m, 1H), 2.11-2.02 (m, 2H), 2.00-1.88 (m, 2H). LCMS (ESI) m/z: calcd for, $C_{17}H_{18}BrN_2O_4S^+$ [M+H]$^+$, 425.0165\427.0145; Found, 425.00\427.01.

Intermediate Preparation Example 56: Preparation of 4-(5-bromopentylthio)-2-(2,6-dioxopiperidin-3-yl)isoindoline-1,3-dione (SIAIS213166)

The compound SIAIS213166 was prepared according to the method of Scheme 8 under appropriate conditions that will be recognized by one skilled in the art, except that the brominated substrate used as the linker was 1,5-dibromopentane. The target compound SIAIS213166 was obtained as light yellow solid (540 mg, yield 35.8%), $^1$H NMR (500 MHz, CDCl$_3$) δ 8.01 (s, 1H), 7.68-7.58 (m, 2H), 7.50 (dt, J=15.0, 7.5 Hz, 1H), 4.97 (dd, J=12.4, 5.3 Hz, 1H), 3.43 (t, J=6.7 Hz, 2H), 3.08 (t, J=7.3 Hz, 2H), 2.97-2.65 (m, 3H), 2.20-2.09 (m, 1H), 1.97-1.87 (m, 2H), 1.81 (dt, J=15.0, 7.4 Hz, 2H), 1.67 (ddd, J=15.7, 9.1, 6.1 Hz, 2H). LCMS (ESI) m/z: calcd for, $C_{18}H_{20}BrN_2O_4S^+$ [M+H]$^+$, 439.0322\441.0301; found, 439.05\440.96.

General Method for Preparing Thio-Substituted Pomalidomide/Lenalidomide Carbon Chain Series of N$_3$-LIN-ULM:

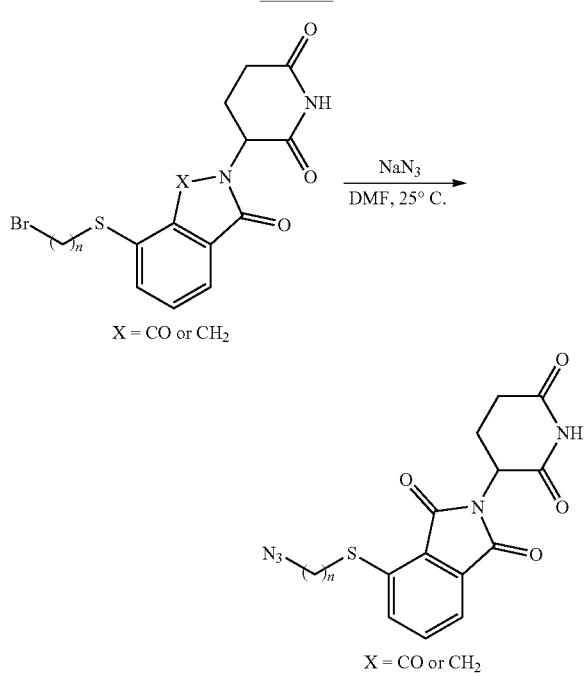

consumed, the reaction mixture were quenched with water, extracted with ethyl acetate, and the organic phase was washed twice with water, washed with saturated brine, dried over anhydrous sodium sulfate, filtered and concentrated to obtain the crude target compound.

Intermediate Preparation Example 57: Preparation of 4-((2-azidoethyl)thio)-2-(2,6-dioxopiperidin-3-yl)isoindoline-1,3-dione (SIAIS213163)

The compound SIAIS213163 was prepared according to the method of Scheme 9 under appropriate conditions that will be recognized by one skilled in the art, except that the brominated substrate used as the linker was SIAIS213162. The target compound SIAIS213163 was obtained as light yellow solid (65 mg, yield 89.8%), $^1$H NMR (500 MHz, CDCl$_3$) δ 8.05 (s, 1H), 7.67 (t, J=5.5 Hz, 2H), 7.60-7.53 (m, 1H), 5.03-4.93 (m, 1H), 3.62 (t, J=7.0 Hz, 2H), 3.28 (t, J=7.0 Hz, 2H), 2.87-2.68 (m, 3H), 2.18-2.09 (m, 1H). LCMS (ESI) m/z: calcd for, $C_{15}H_{14}N_5O_4S^+$ [M+H]$^+$, 360.0761; found, 332.22.

Intermediate Preparation Example 58: Preparation of 4-((3-azidopropyl)thio)-2-(2,6-dioxopiperidin-3-yl)isoindoline-1,3-dione (SIAIS213161)

The compound SIAIS213161 was prepared according to the method of Scheme 9 under appropriate conditions that will be recognized by one skilled in the art, except that the brominated substrate used as the linker was SIAIS213159. The target compound SIAIS213161 was obtained as light yellow solid (80 mg, yield 73.4%), 1 $^1$H NMR (500 MHz, CDCl$_3$) δ 8.02 (s, 1H), 7.72-7.59 (m, 2H), 7.54 (d, J=7.8 Hz, 1H), 4.97 (dd, J=12.4, 5.4 Hz, 1H), 3.52 (t, J=6.3 Hz, 2H), 3.16 (t, J=7.2 Hz, 2H), 2.92-2.70 (m, 3H), 2.22-2.09 (m, 1H), 2.07-1.96 (m, 2H) LCMS (ESI) m/z: calcd for, $C_{16}H_{16}N_5O_4S^+$ [M+H]$^+$, 374.0918; found, 346.06.

Intermediate Preparation Example 59: Preparation of 3-(4-((3-azidopropyl)thio)-1-oxoisoindolin-2-yl)piperidine-2,6-dione (SIAIS287035)

The compound SIAIS287035 was prepared according to the method of Scheme 9 under appropriate conditions that will be recognized by one skilled in the art, except that the brominated substrate used as the linker was SIAIS213132. The target compound SIAIS287035 was obtained as white solid (21 mg, yield 23%), $^1$H NMR (500 MHz, Chloroform-d) δ 8.21 (s, 1H), 7.74 (dd, J=1.5, 7.0 Hz, 1H), 7.47-7.54 (m, 2H), 5.22-5.25 (m, 1H), 4.43 (d, J=16.5 Hz, 1H), 4.29 (d, J=16.5 Hz, 1H), 3.47 (t, J=6.0 Hz, 2H), 3.08 (t, J=6.0 Hz, 2H), 2.91-2.93 (m, 1H), 2.79-2.87 (m, 1H), 2.36-2.45 (m, 1H), 2.21-2.26 (m, 1H), 1.89-1.95 (m, 2H). HRMS: calcd for, HRMS (ESI) calcd for, $C_{16}H_{17}N_5O_3S^+$ [M+H]$^+$ 360.1052, found 360.1154.

Intermediate Preparation Example 60: Preparation of 3-(4-((4-azidobutyl)thio)-1-oxoisoindolin-2-yl)piperidine-2,6-dione (SIAIS287036)

The compound SIAIS287036 was prepared according to the method of Scheme 9 under appropriate conditions that will be recognized by one skilled in the art, except that the brominated substrate used as the linker was SIAIS213134. The target compound SIAIS287036 was obtained as white solid (43 mg, yield 47%), $^1$H NMR (500 MHz, Chloroform-d) δ 8.07 (s, 1H), 7.73 (dd, J=1.5, 7.0 Hz, 1H), 7.46-7.52 (m, 2H), 5.22-5.26 (m, 1H), 4.42 (d, J=16.5 Hz, 1H), 4.29 (d, J=16.5 Hz, 1H), 3.29-3.35 (m, 2H), 3.00-3.04 (m, 2H), 2.91-2.93 (m, 1H), 2.80-2.88 (m, 1H), 2.36-2.45 (m, 1H), 2.19-2.26 (m, 1H), 1.71-1.78 (m, 4H). HRMS (ESI) calcd for, $C_{17}H_{19}N_5O_3S^+$ [M+H]$^+$ 374.1209, found 374.1282.

Intermediate Preparation Example 61: Preparation of 3-(4-((5-azidopentyl)thio)-1-oxoisoindolin-2-yl)piperidine-2,6-dione (SIAIS287037)

The compound SIAIS287037 was prepared according to the method of Scheme 9 under appropriate conditions that will be recognized by one skilled in the art, except that the brominated substrate used as the linker was SIAIS213135. The target compound SIAIS287037 was obtained as white solid (70 mg, yield 77%), $^1$H NMR (500 MHz, Chloroform-d) δ 8.27 (s, 1H), 7.72 (dd, J=1.5, 7.0 Hz, 1H), 7.45-7.51 (m, 2H), 5.21-5.25 (m, 1H), 4.42 (d, J=16.5 Hz, 1H), 4.28 (d, J=16.5 Hz, 1H), 3.28 (t, J=6.5 Hz, 2H), 3.00 (t, J=6.5 Hz, 2H), 2.930-2.93 (m, 1H), 2.79-2.87 (m, 1H), 2.36-2.45 (m, 1H), 2.21-2.26 (m, 1H), 1.65-1.73 (m, 2H), 1.58-1.64 (m, 2H), 1.50-1.57 (m, 2H). HRMS (ESI) calcd for, $C_{18}H_{21}N_5O_3S^+$ [M+H]$^+$ 388.1365, found 388.1443.

Intermediate Preparation Example 62: Preparation of 3-(4-((8-azidooctyl)thio)-1-oxoisoindolin-2-yl)piperidine-2,6-dione (SIAIS287038)

The compound SIAIS287038 was prepared according to the method of Scheme 9 under appropriate conditions that will be recognized by one skilled in the art, except that the brominated substrate used as the linker was SIAIS1216137. The target compound SIAIS287038 was obtained as white solid (65 mg, yield 71%), $^1$H NMR (500 MHz, Chloroform-d) δ 8.06 (s, 1H), 7.71 (dd, J=1.5, 7.0 Hz, 1H), 7.45-7.50 (m, 2H), 5.22-5.25 (m, 1H), 4.41 (d, J=16.5 Hz, 1H), 4.27 (d, J=16.5 Hz, 1H), 3.26 (t, J=6.5 Hz, 2H), 2.99 (t, J=6.5 Hz, 2H), 2.91-2.92 (m, 1H), 2.86-2.88 (m, 1H), 2.35-2.43 (m, 1H), 2.20-2.25 (m, 1H), 1.64-1.70 (m, 2H), 1.56-1.59 (m, 2H), 1.42-1.46 (m, 2H), 1.31-1.38 (m, 6H). HRMS (ESI) calcd for, $C_{21}H_{27}N_5O_3S^+$ [M+H]$^+$ 430.1835, found 430.1909.

Intermediate Preparation Example 63: Preparation of 3-(4-((9-azidononyl)thio)-1-oxoisoindolin-2-yl)piperidine-2,6-dione (SIAIS287039)

The compound SIAIS287039 was prepared according to the method of Scheme 9 under appropriate conditions that will be recognized by one skilled in the art, except that the brominated substrate used as the linker was SIAIS1220059. The target compound SIAIS287039 was obtained as light yellow solid (80 mg, yield 73.4%), $^1$H NMR (500 MHz, Chloroform-d) δ 8.17 (s, 1H), 7.71 (dd, J=1.5, 7.0 Hz, 1H), 7.44-7.50 (m, 2H), 5.22-5.25 (m, 1H), 4.41 (d, J=16.5 Hz, 1H), 4.27 (d, J=16.5 Hz, 1H), 3.26 (t, J=6.5 Hz, 2H), 2.98 (t, J=6.5 Hz, 2H), 2.90-2.93 (m, 1H), 2.80-2.87 (m, 1H), 2.35-2.44 (m, 1H), 2.20-2.25 (m, 12H), 1.63-1.67 (m, 2H), 1.54-1.62 (m, 2H), 1.41-1.45 (m, 2H), 1.29-1.39 (m, 8H). HRMS (ESI) calcd for, $C_{22}H_{29}N_5O_3S^+$ [M+H]$^+$ 444.1991, found 444.2063.

Intermediate Preparation Example 64: Preparation of 3-(4-((10-azidodecyl)thio)-1-oxoisoindolin-2-yl)piperidine-2,6-dione (SIAIS287040)

The compound SIAIS287040 was prepared according to the method of Scheme 9 and under appropriate conditions that will be recognized by one skilled in the art, except that the brominated substrate used as the linker was SIAIS1220013. The target compound SIAIS287040 was obtained as white solid (66 mg, yield 72%), $^1$H NMR (500 MHz, Chloroform-d) δ 8.05 (s, 1H), 7.71 (dd, J=1.5, 7.0 Hz, 1H), 7.44-7.50 (m, 2H), 5.21-5.25 (m, 1H), 4.41 (d, J=16.5 Hz, 1H), 4.27 (d, J=16.5 Hz, 1H), 3.26 (t, J=6.5 Hz, 2H), 2.98 (t, J=6.5 Hz, 2H), 2.90-2.93 (m, 1H), 2.84-2.88 (m, 1H), 2.35-2.44 (m, 1H), 2.21-2.25 (m, 1H), 1.62-1.68 (m, 2H), 1.54-1.61 (m, 2H), 1.41-1.47 (m, 2H), 1.28-1.38 (m, 10H). HRMS (ESI) calcd for, $C_{23}H_{31}N_5O_3S$ [M+H]$^+$ 458.2148, found 458.2239.

Intermediate Preparation Example 65: Preparation of 3-(4-((11-azidoundecyl)thio)-1-oxoisoindolin-2-yl)piperidine-2,6-dione (SIAIS287041)

The compound SIAIS287041 was prepared according to the method of Scheme 9 and under appropriate conditions that will be recognized by one skilled in the art, except that the brominated substrate used as the linker was SIAIS1220015. The target compound SIAIS287041 was obtained as white solid (60 mg, yield 65%), $^1$H NMR (500 MHz, Chloroform-d) δ 9.09 (s, 1H), 7.69 (dd, J=1.5, 7.0 Hz, 1H), 7.44-7.50 (m, 2H), 5.21-5.25 (m, 1H), 4.42 (d, J=16.5 Hz, 1H), 4.28 (d, J=16.5 Hz, 1H), 3.26 (t, J=6.5 Hz, 2H), 2.99 (d, J=6.5 Hz, 2H), 2.98-3.02 (m, 1H), 2.79-2.86 (m, 1H), 2.35-2.44 (m, 1H), 2.20-2.23 (m, 1H), 1.64-1.70 (m, 2H), 1.56-1.62 (m, 2H), 1.41-1.45 (m, 2H), 1.26-1.38 (m, 12H). HRMS (ESI) calcd for, $C_{24}H_{33}N_5O_3S$ [M+H]$^+$ 472.2304, found 472.2388.

Intermediate Preparation Example 66: Preparation of 3-(4-((12-azidododecyl)thio)-1-oxoisoindolin-2-yl)piperidine-2,6-dione (SIAIS287042)

The compound SIAIS287042 was prepared according to the method of Scheme 9 under appropriate conditions that will be recognized by one skilled in the art, except that the brominated substrate used as the linker was SIAIS264005. The target compound SIAIS287042 was obtained as white solid (60 mg, yield 65%), $^1$H NMR (500 MHz, Chloroform-d) δ 7.97 (s, 1H), 7.71 (dd, J=1.5, 6.0 Hz, 1H), 7.44-7.50 (m, 2H), 5.21-5.25 (m, 1H), 4.41 (d, J=16.5 Hz, 1H), 4.27 (d, J=16.5 Hz, 1H), 3.25 (t, J=6.5 Hz, 2H), 2.98 (t, J=6.5 Hz, 2H), 2.90-2.96 (m, 1H), 2.80-2.88 (m, 1H), 2.35-2.44 (m, 1H), 2.20-2.25 (m, 1H), 1.64-1.68 (m, 2H), 1.56-1.59 (m, 2H), 1.41-1.44 (m, 2H), 1.26-1.39 (m, 14H). HRMS(ESI) calcd for, $C_{25}H_{35}N_5O_3S$ [M+H]$^+$ 486.2461, found 486.2543.

General Methods for Preparing Some Special Intermediates LIN-ULM:

Scheme 10

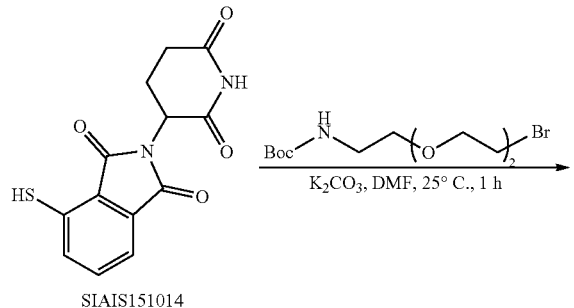

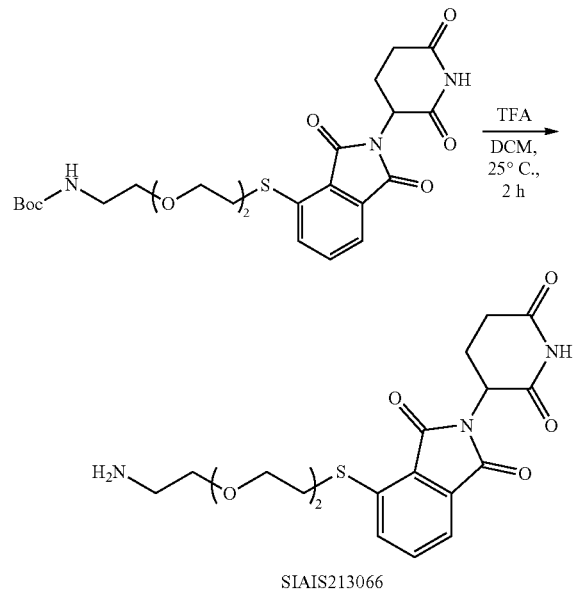

A 25 mL reaction flask was charged with the compound SIAIS151014 (0.69 mmol, 1 equiv), and then anhydrous N,N-dimethylformamide (6 mL) and anhydrous potassium carbonate (1.38 mmol, 2 equiv), followed by slow addition of the brominated substrate (0.83 mmol, 1.2 equiv) under stirring at room temperature. After completion of dropping, the reaction mixture was stirred at room temperature for 1 h. After the raw materials were completely consumed, the reaction mixture was quenched by adding water, extracted with ethyl acetate, and concentrated. The crude product was separated on a reversed-phase C18 column (eluent (v/v): acetonitrile/water=10%-100%), the solvent was evaporated under reduced pressure, and the residue was lyophilized to obtain the intermediate compound. The intermediate compound obtained was added to a 10 mL reaction flask, followed by adding anhydrous dichloromethane (4 mL) and trifluoroacetic acid (1 mL). The mixture was stirred at room temperature for 2 h. The reaction solvent was evaporated under reduced pressure, and the residue was treated by addition of water, and lyophilized to obtain the target compound (SIAIS213066).

Intermediate Preparation Example 67: Preparation of 4-((2-(2-(2-aminoethoxy)ethoxy)ethyl)thio)-2-(2,6-dioxopiperidin-3-yl)isoindoline-1,3-dione (SIAIS213066)

According to the method of Scheme 10, compound SIAIS213066 was prepared under appropriate conditions that will be recognized by one skilled in the art, and the brominated substrate used as the linker was tert-butyl (2-(2-(2-Bromoethoxy)ethoxy)ethyl)carbamate. The target compound SIAIS213066 was obtained as pale yellow solid (120 mg, two-step yield 41.3%). $^1$H NMR (500 MHz, DMSO) δ 11.16 (d, J=7.7 Hz, 1H), 7.89 (ddd, J=21.0, 10.5, 3.6 Hz, 3H), 7.82-7.74 (m, 2H), 7.65 (p, J=4.9 Hz, 1H), 5.18-5.05 (m, 1H), 3.78-3.68 (m, 2H), 3.63-3.58 (m, 6H), 3.36 (t, J=6.2 Hz, 2H), 3.04-2.94 (m, 2H), 2.90 (ddd, J=17.2, 13.9, 5.4 Hz, 1H), 2.68-2.53 (m, 2H), 2.13-2.00 (m, 1H).

Scheme 11

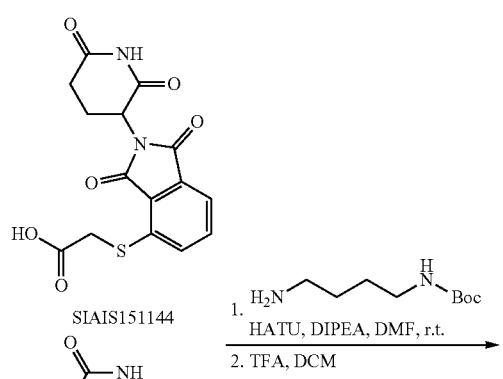

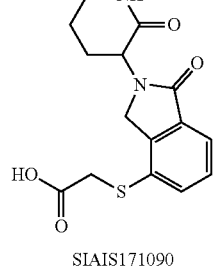

At room temperature, a reaction flask was charged with SIAIS151144 or SIAIS171090 (1 equiv), tert-butyl (4-aminobutyl)carbamate (1 equiv), anhydrous N,N-dimethylformamide (2 mL), HATU (1.5 equiv), and DIPEA (3 equiv). The reaction mixture was stirred overnight at room temperature. After the completion of reaction was detected by LC-MS, the crude product was separated by reversed-phase C18 column (eluent (v/v): acetonitrile/(water+0.05% TFA)= 10%-100%). The solvent was evaporated under reduced pressure, and the residue was lyophilized to obtain the corresponding intermediate compound. The obtained intermediate compound was then added to a 10 mL reaction flask, followed by addition of anhydrous dichloromethane (4 mL) and trifluoroacetic acid (1 mL). The mixture was stirred at room temperature for 3 h. The reaction solvent was evaporated under reduced pressure, and the residue was treated by addition of water water, and lyophilized to obtain the corresponding target compound (SIAIS213073; or SIAIS213092).

Intermediate Preparation Example 68: Preparation of N-(4-aminobutyl)-2-((2-(2,6-dioxopiperidin-3-yl)-1,3-dioxoisoindolin-4-yl)thio)acetamide (SIAIS213073)

According to the method of Scheme 11, the compound SIAIS213073 was prepared under appropriate conditions that will be recognized by one skilled in the art, except that the acid substrate used was SIAIS151144. The target compound SIAIS213073 was obtained as light yellow solid (45 mg, total yield of two steps 75.1%). $^1$H NMR (500 MHz, DMSO) δ 11.13 (s, 1H), 8.34 (t, J=5.7 Hz, 1H), 7.74 (ddd, J=50.2, 19.3, 7.5 Hz, 6H), 5.13 (dd, J=12.9, 5.4 Hz, 1H), 3.87 (s, 2H), 3.10 (q, J=6.5 Hz, 2H), 2.89 (ddd, J=17.2, 14.0, 5.4 Hz, 1H), 2.77 (dt, J=12.8, 6.2 Hz, 2H), 2.66-2.51 (m, 2H), 2.14-1.97 (m, 1H), 1.54-1.42 (m, 4H). LCMS (ESI) m/z: calcd for, $C_{19}H_{23}N_4O_5S^+$ [M+H]$^+$, 419.1384; found, 419.35.

Intermediate Preparation Example 69: Preparation of N-(4-aminobutyl)-2-((2-(2,6-dioxopiperidin-3-yl)-1-oxoisoindoline-4-yl)thio)acetamide (SIAIS213092)

According to the method of Scheme 11, compound SIAIS213092 was prepared under appropriate conditions that will be recognized by one skilled in the art, except that the acid substrate used was SIAIS171090. The target compound SIAIS213092 was obtained as light yellow solid (60 mg, two steps yield 99.1%). $^1$H NMR (500 MHz, MeOD) δ 7.72 (d, J=7.7 Hz, 2H), 7.55 (t, J=7.7 Hz, 1H), 5.17 (dd, J=13.4, 5.2 Hz, 1H), 4.51 (q, J=17.4 Hz, 2H), 3.73-3.63 (m, 2H), 3.19-3.10 (m, 2H), 2.93-2.76 (m, 4H), 2.53 (qd, J=13.3, 4.7 Hz, 1H), 2.19 (dtd, J=12.8, 5.3, 2.4 Hz, 1H), 1.54-1.38 (m, 4H). LCMS (ESI) m/z: calcd for, $C_{19}H_{25}N_4O_4S^+$ [M+H]$^+$, 405.1591; found, 405.34.

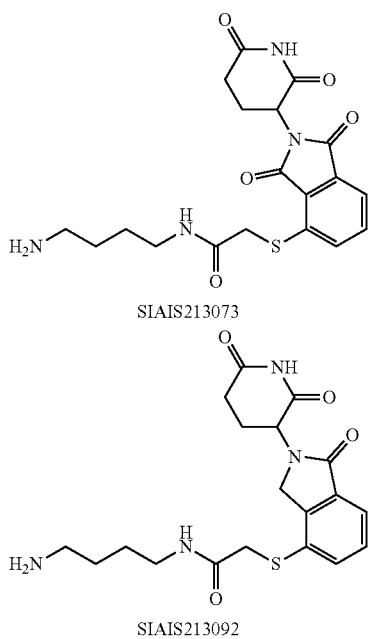

Scheme 12

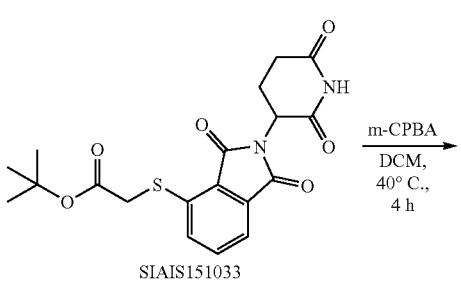

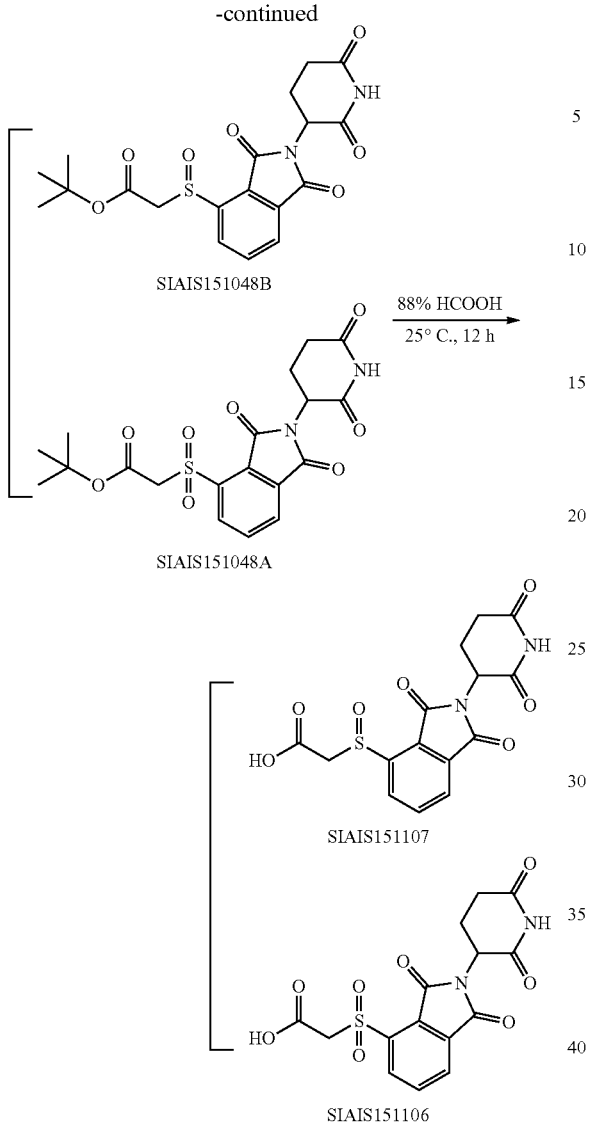

Step 1: A 100 mL egg-shaped flask was charged with the compound (SIAIS151033) (1.1 mmol, 1 equiv), and then anhydrous dichloromethane (20 mL), followed by slow addition of m-chloroperoxybenzoic acid (4.4 mmol, 4 equiv) under stirring at room temperature. After completion of dropping, the reaction mixture was slowly heated to 40° C. and stirred for 4 h. After completion of the reaction, the reaction mixture was cooled to room temperature, adjusted to pH 8-9 with 10% sodium bicarbonate aqueous solution, extracted with dichloromethane (2×30 mL). The organic phases were combined, and washed with water (2×20 mL) and saturated brine (50 mL), dried with anhydrous sodium sulfate, evaporated under reduced pressure to remove the solvent. The crude product was purified (eluent (v/v): petroleum ether/ethyl acetate=1:1) to obtain the oxidation product sulfoxide or sulfone compounds (SIAIS151048A; SIAIS151048B).

Step 2: A 25 mL egg-shaped flask was charged with the sulfoxide or sulfone compound, and then 88% formic acid (5 mL). The reaction mixture was stirred at room temperature for 12 h. The reaction solvent was evaporated under reduced pressure, and the residue was treated by adding water and lyophilized to obtain the hydrolysis product (SIAIS151107; SIAIS151106) after removing tert-butyl.

Intermediate Preparation Example 70: Preparation of tert-butyl 2-((2-(2,6-dioxopiperidin-3-yl)-1,3-dioxoisoindolin-4-yl)sulfinyl)acetate (SIAIS151048B)

The compound SIAIS151048B was prepared according to the method of Scheme 12 and under appropriate conditions that will be recognized by one skilled in the art, except that the brominated substrate used as the linker was tert-butyl 2-bromoacetate. The target compound SIAIS151048B was obtained as light yellow solid (0.2 g, yield 39%). $^1$H NMR (500 MHz, CDCl$_3$) δ 8.40-8.35 (m, 1H), 8.17 (s, 1H), 8.06-8.00 (m, 2H), 5.00-4.96 (m, 1H), 4.09 (d, J=13.8 Hz, 1H), 3.78 (dd, J=14.6, 14.0 Hz, 1H), 2.96-2.89 (m, 1H), 2.88-2.71 (m, 2H), 2.23-2.13 (m, 1H), 1.41 (d, J=4.4 Hz, 9H). HRMS (ESI) m/z: calcd for, $C_{19}H_{21}N_2O_7S^+$ [M-56+H]+, 365.0438; found, 365.0295.

Intermediate Preparation Example 71: Preparation of tert-butyl 2-((2-(2,6-dioxopiperidin-3-yl)-1,3-dioxoisoindolin-4-yl)sulfonyl)acetate (SIAIS151048A)

According to the method of Scheme 12, the compound SIAIS151048A was prepared under appropriate conditions that will be recognized by one skilled in the art, except that the brominated substrate used as the linker was tert-butyl 2-bromoacetate. The target compound SIAIS151048A was obtained as light yellow solid (0.3 g, yield 59%). $^1$H NMR (500 MHz, CDCl$_3$) δ 8.42 (dd, J=7.9, 0.9 Hz, 1H), 8.19 (dd, J=7.5, 0.9 Hz, 1H), 8.12 (s, 1H), 8.00 (t, J=7.7 Hz, 1H), 5.03 (dd, J=12.6, 5.4 Hz, 1H), 4.72-4.64 (m, 2H), 2.96-2.72 (m, 3H), 2.26-2.17 (m, 1H), 1.30 (s, 9H). HRMS (ESI) m/z: calcd for, $C_{19}H_{21}N_2O_8S^+$ [M-56+H]$^+$, 381.0387; found, 381.0241.

Intermediate Preparation Example 72: Preparation of 2-((2-(2,6-dioxopiperidin-3-yl)-1,3-dioxoisoindolin-4-yl)sulfinyl)acetic acid (SIAIS151107)

According to the method of Scheme 12, the compound SIAIS151107 was prepared under appropriate conditions that will be recognized by one skilled in the art, except that the brominated substrate used as the linker is tert-butyl 2-bromoacetate. The target compound SIAIS151107 was obtained as light yellow solid (0.16 g, yield 92%). $^1$H NMR (500 MHz, DMSO) δ 11.18 (s, 1H), 8.24-8.20 (m, 1H), 8.13 (t, J=7.6 Hz, 1H), 8.10-8.08 (m, 1H), 5.17 (dd, J=12.9, 5.4 Hz, 1H), 4.22 (dd, J=28.5, 14.9 Hz, 1H), 3.75 (d, J=14.9 Hz, 1H), 2.92-2.84 (m, 1H), 2.63-2.59 (m, 1H), 2.48-2.44 (m, 1H), 2.11-2.00 (m, 1H). HRMS (ESI) m/z: calcd for, $C_{15}H_{13}N_2O_7S^+$ [M+H]$^+$, 365.0438; found, 365.0498.

Intermediate Preparation Example 73: Preparation of 2-((2-(2,6-dioxopiperidin-3-yl)-1,3-dioxoisoindolin-4-yl)sulfonyl)acetic acid (SIAIS151106)

According to the method of Scheme 12, the compound SIAIS151106 was prepared under appropriate conditions that will be recognized by one skilled in the art, except that the brominated substrate used as the linker was tert-butyl 2-bromoacetate. The target compound SIAIS151106 was obtained as light yellow solid (0.25 g, yield 96%). $^1$H NMR (500 MHz, DMSO) δ 11.20 (s, 1H), 8.35-8.25 (m, 2H), 8.14

(t, J=7.7 Hz, 1H), 5.23 (dd, J=12.9, 5.4 Hz, 1H), 4.96-4.73 (m, 2H), 2.93-2.86 (m, 1H), 2.66-2.51 (m, 2H), 2.13-2.08 (m, 1H). HRMS (ESI) m/z: calcd for, $C_{15}H_{13}N_2O_8S^+$ [M+H]$^+$, 381.0387; found, 381.0452.

Intermediate Preparation Example 74: Preparation of 2-(2,6-dioxopiperidin-3-yl)-4-(piperazin-1-yl) isoindoline-1,3-dione (SIAIS151024)

Scheme 13

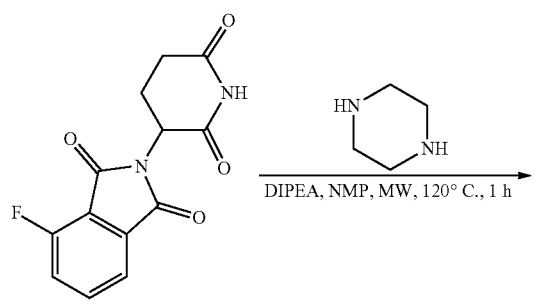

Scheme 14

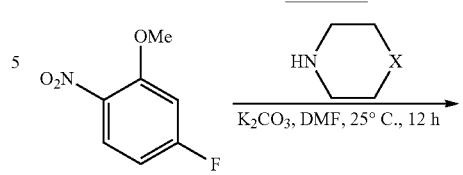

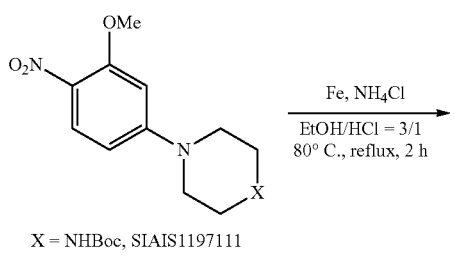

X = NHBoc, SIAIS1197111

X = CHNHBoc, SIAIS151054

X = CHpiperazineBoc, SIAIS151059

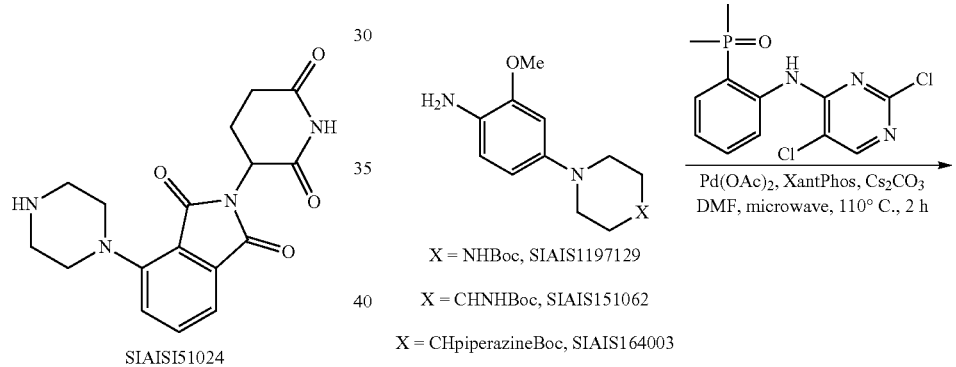

X = NHBoc, SIAIS1197129

X = CHNHBoc, SIAIS151062

X = CHpiperazineBoc, SIAIS164003

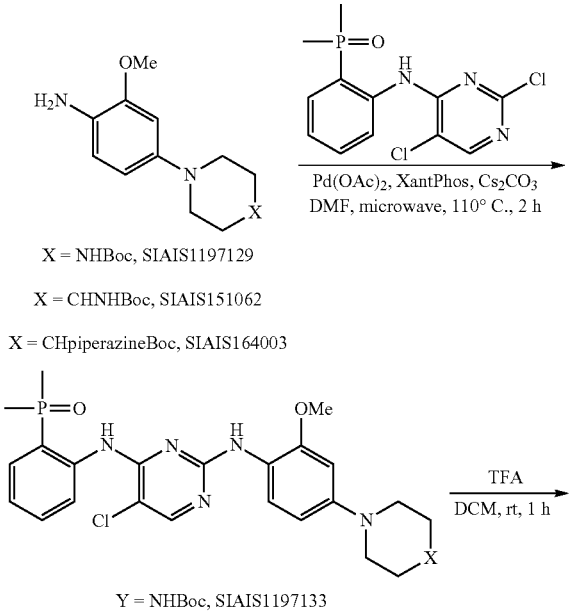

Y = NHBoc, SIAIS1197133

Y = NH, SIAIS1197135, Brigatinib derivative A

Y = CHNH$_2$, SIAIS151101, Brigatinib derivative B

Y = CHpiperazine, SIAIS164005, Brigatinib derivative C

SIAIS151024

A 10 mL microwave reaction tube was charged with 2-(2,6-dioxopiperidin-3-yl)-4-fluoroisoindoline-1,3-dione (200 mg, 0.72 mmol), anhydrous piperazine (93.6 mg, 1.08 mmol), N,N-diisopropylethylamine (467.6 mg, 3.60 mmol) and anhydrous N-methylpyrrolidone (3 mL), followed by slowly bubbling Argon gas to the microwave tube. After sealing, the reaction tube was put into a microwave reactor, raised to 120° C. and stirred for 1 h. After the completion of the reaction detected by LC-MS, the reaction solution was separated and purified by preparative HPLC (eluent (v/v): acetonitrile/(water+0.05% HCl)=10%-100%). The acetonitrile was removed by rotary evaporation, and the residue was lyophilization to give the target compound (SIAIS151024) as yellow solid (0.11 g, yield 36%). $^1$H NMR (500 MHz, DMSO) δ 11.10 (s, 1H), 9.01 (s, 1H), 7.76 (dd, J=8.3, 7.3 Hz, 1H), 7.45 (d, J=7.0 Hz, 1H), 7.42 (d, J=8.0 Hz, 1H), 5.11 (dd, J=12.9, 5.4 Hz, 1H), 3.52-3.46 (m, 4H), 3.29-3.25 (m, 4H), 2.92-2.85 (m, 1H), 2.65-2.54 (m, 2H), 2.05-1.99 (m, 1H). HRMS (ESI) m/z: calcd for, $C_{17}H_{19}N_4O_4^+$ [M+H]$^+$, 343.1401; found, 343.1450.

General Preparation Method of Brigatinib Derivatives a, B, and C:

Intermediate Preparation Example 75: Preparation of Brigatinib Derivative A (SIAIS1197135) According to Scheme 14

Step 1: Preparation of tert-butyl 4-(3-methoxy-4-nitrophenyl)piperazine-1-carboxylate (SIAIS1197111) According to Scheme 14

Under open conditions, to a solution of 5-fluoro-2-nitroanisole (7 g, 40.9 mmol) in N,N-dimethylformamide (60 mL) were added potassium carbonate (8.4 g, 60.8 mmol) and N-tert-butoxycarbonylpiperazine (9.1 g, 48.9 mmol). The mixture was stirred at room temperature overnight. After the reaction is complete, the reaction mixture was quenched with water, extracted with ethyl acetate, and the organic phase was washed with water and saturated brine, dried with anhydrous sodium sulfate, concentrated to remove the solvent, slurried with mixed solvent of petroleum ether and ethyl acetate (5:1), and filtered with sand core to obtain the compound (SIAIS1197111) (yellow solid, 11.1 g, yield 80%). $^1$H NMR (500 MHz, DMSO) δ 7.89 (d, J=9.3 Hz, 1H), 6.57 (d, J=9.5 Hz, 1H), 6.52 (s, 1H), 3.90 (s, 3H), 3.46 (s, 8H), 1.42 (s, 9H). HRMS (ESI) calcd for, $C_{16}H_{24}N_3O_5^+$ [M+H]$^+$, 338.1710; found, 338.1610.

Step 2: Preparation of tert-butyl 4-(4-amino-3-methoxyphenyl)piperazine-1-carboxylate (SIAIS1197129) According to Scheme 14

Under open conditions at room temperature, in an egg-shaped flask were sequentially added compound SIAIS1197111 (10 g, 29.6 mmol), ethanol (90 mL), water (30 mL), ammonium chloride (6.3 g, 118.6 mmol), and Iron powder (8.3 g, 148.2 mmol), followed by evacuation and refilling with argon gas, the reaction mixture was refluxed at 80° C. for 2 h. After completion of the reaction was detected by TLC, the reaction mixture was filtered through the silica gel, concentrated and evaporated to remove ethanol, extracted with dichloromethane, dried over anhydrous sodium sulfate, and evaporated to dryness to obtain the compound (SIAIS1197129) (gray blue solid, 7.7 g, yield 85%). $^1$H NMR (500 MHz, MeOD) δ 6.72 (d, J=8.3 Hz, 1H), 6.63 (d, J=2.2 Hz, 1H), 6.47 (d, J=7.0 Hz, 1H), 3.86 (s, 3H), 3.57 (s, 4H), 2.99 (s, 4H), 1.50 (s, 9H). HRMS (ESI) calcd for, $C_{16}H_{26}N_3O_3^+$ [M+H]$^+$, 308.1969; found, 308.1882.

Step 3: Preparation of Compound (SIAIS1197133) According to Scheme 14

At room temperature, in a standard microwave reaction tube were sequentially added (2-((2,5-dichloropyrimidin-4-yl)amino)phenyl)dimethylphosphine oxide (2 g, 6.3 mmol), Compound SIAIS1197129 (2.4 g, 7.8 mmol), palladium acetate (176 mg, 0.78 mmol), Xantphos (810 mg, 1.4 mmol), Cesium carbonate (6.4 g, 19.6 mmol), and anhydrous N,N-dimethylformamide (30 mL), followed by evacuation and refilled with argon gas, and reacting in microwave at 110° C. for 1.5 h. After completion of the reaction was detected by TLC, the reaction mixture was filtered through silica gel, quenched with water, extracted with ethyl acetate, washed with water, dried with anhydrous sodium sulfate, separated by reversed-phase C18 column using methanol and water as the eluent to obtain the compound (SIAIS1197133) (red-brown solid, 900 mg).

Step 4: Preparation of (2-((5-Chloro-2-((2-methoxy-4-(piperazin-1-yl)phenyl)amino)pyrimidin-4-yl)amino)phenyl)dimethylphosphine oxide (SIAIS1197135) According to Scheme 14

Under open conditions at room temperature, in an egg-shaped flask were sequentially added the compound SIAIS1197133 (900 mg), dichloromethane (6 mL), and trifluoroacetic acid (20 mL), followed by reacting at room temperature for 2 h. After completion of the reaction is detected by LC-MS, the trifluoroacetic acid was removed by rotary evaporation under reduced pressure, and saturated sodium bicarbonate solution was added to adjust the pH value of the solution to alkaline. The solution was extracted with dichloromethane, dried with anhydrous sodium sulfate, rotary evaporated to dryness, separated by reversed-phase C18 column using methanol and water as eluent to obtain the target compound (SIAIS1197135) (red-brown solid, 701 mg, the total yield of steps 3 and 4 is 23%). $^1$H NMR (500 MHz, MeOD) δ 8.32 (dd, J=8.2, 4.4 Hz, 1H), 8.04 (s, 1H), 7.70 (d, J=8.7 Hz, 1H), 7.61 (dd, J=14.1, 7.7 Hz, 1H), 7.52 (t, J=7.9 Hz, 1H), 7.26 (t, J=7.5 Hz, 1H), 6.67 (d, J=2.5 Hz, 1H), 6.45 (dd, J=8.8, 2.5 Hz, 1H), 3.86 (s, 3H), 3.24-3.17 (m, 4H), 3.17-3.11 (m, 4H), 1.83 (d, J=13.5 Hz, 6H). HRMS (ESI) calcd for, $C_{23}H_{29}ClN_6O_2P^+$ [M+H]$^+$, 487.1773; found, 487.1773.

Intermediate Preparation Example 76: Preparation of Brigatinib Derivative B (SIAIS151101) According to Scheme 14

Step 1: Preparation of tert-butyl (1-(3-methoxy-4-nitrophenyl)piperidin-4-yl) carbamate (SIAIS151054) According to Scheme 14

According to the step 1 of the scheme 14 of the intermediate preparation example 75, the compound SIAIS151054 was prepared under appropriate conditions that will be recognized by one skilled in the art, except that the amine used as the substrate was tert-butyl piperidin-4-ylcarbamate. Compound SIAIS151054 was obtained as yellow solid (1.81 g, yield 88%). $^1$H NMR (500 MHz, CDCl$_3$) δ 7.99 (t, J=8.9 Hz, 1H), 6.41 (dd, J=9.4, 2.5 Hz, 1H), 6.30 (d, J=2.5 Hz, 1H), 4.49 (s, 1H), 3.94 (s, 3H), 3.86-3.82 (m, 2H), 3.71 (s, 1H), 3.09-3.00 (m, 2H), 2.11-2.03 (m, 2H), 1.89-1.75 (m, 2H), 1.45 (s, 9H).

Step 2: Preparation of tert-butyl (1-(4-amino-3-methoxyphenyl)piperidin-4-yl)carbamate (SIAIS151062) According to Scheme 14

According to the step 2 of the scheme 14 of the intermediate preparation example 75, the compound SIAIS151062 was prepared from the product SIAIS151054 obtained in step 1 under the appropriate conditions that will be recognized by one skilled in the art. The compound SIAIS151062 was obtained as gray purple solid (411.6 mg, yield 90%). $^1$H NMR (500 MHz, DMSO) δ 6.82 (d, J=7.6 Hz, 1H), 6.50 (d, J=8.5 Hz, 1H), 6.48 (d, J=2.5 Hz, 1H), 6.28 (dd, J=8.4, 2.4 Hz, 1H), 4.20 (s, 2H), 3.73 (s, 3H), 3.33-3.26 (m, 3H), 2.56-2.50 (m, 2H), 1.77 (d, J=11.4 Hz, 2H), 1.53-1.45 (m, 2H), 1.39 (s, 9H).

Step 3: Preparation of (2-((2-((4-(4-aminopiperidin-1-yl)-2-methoxyphenyl)amino)-5-chloropyrimidin-4-yl)amino)phenyl)dimethylphosphine oxide (SIAIS151101) According to Scheme 14

According to steps 3 and 4 of the method of Scheme 14, the target compound SIAIS151101 was prepared from the product SIAIS151062 obtained in step 2 under appropriate conditions that will be recognized by one skilled in the art. The target compound SIAIS151101 was obtained as yellow solid (330 mg, the total yield of steps 3 and 4, 33%). $^1$H NMR (500 MHz, DMSO) δ 8.49 (s, 1H), 8.08 (s, 1H), 8.06 (s, 1H), 7.53 (ddd, J=14.0, 7.7, 1.3 Hz, 1H), 7.38-7.32 (m, 2H), 7.10 (t, J=7.1 Hz, 1H), 6.62 (d, J=2.5 Hz, 1H), 6.46 (dd, J=8.7, 2.5 Hz, 1H), 3.75 (s, 3H), 3.65-3.61 (m, 2H), 2.78-2.67 (m, 3H), 1.82-1.79 (m, 2H), 1.78 (s, 3H), 1.75 (s, 3H), 1.42-1.34 (m, 2H). HRMS (ESI) calcd for, $C_{24}H_{31}ClN_6O_2P$ [M+H]$^+$: 501.1913, found 501.1900.

Intermediate Preparation Example 77: Preparation of Brigatinib Derivative C (SIAIS164005) According to Scheme 14

Step 1: Preparation of tert-butyl 4-(1-(3-methoxy-4-nitrophenyl)piperidin-4-yl)piperazine-1-carboxylate (SIAIS151059) According to Scheme 14

According to the step 1 of the scheme 14 of the intermediate preparation example 75, the compound SIAIS151059 was prepared under appropriate conditions that will be recognized by one skilled in the art, except that the amine used as the substrate was tert-butyl 4-(pyridin-4-yl)piperazine-1-carboxylate. The target compound SIAIS151059 was obtained as yellow solid (1.02 g, yield 83%). $^1$H NMR (500 MHz, MeOD) δ 7.93 (d, J=9.4 Hz, 1H), 6.55 (dt, J=13.4, 6.7 Hz, 1H), 6.50 (d, J=2.5 Hz, 1H), 4.10 (s, 1H), 4.07 (s, 1H), 3.94 (d, J=6.6 Hz, 3H), 3.43 (s, 4H), 3.02-2.93 (m, 2H), 2.60-2.55 (m, 5H), 2.02-1.95 (m, 2H), 1.57 (qd, J=12.4, 4.0 Hz, 2H), 1.46 (s, 9H). HRMS (ESI) calcd for, $C_{21}H_{33}N_4O_5$ [M+H]$^+$: 421.2445, found 421.2442.

Step 2: Preparation of tert-butyl 4-(1-(4-amino-3-methoxyphenyl)piperidin-4-yl)piperazine-1-carboxylate (SIAIS164003) According to Scheme 14

According to the step 2 of the method of the scheme 14 of the intermediate preparation example 75, the compound SIAIS164003 was prepared from the product SIAIS151059 obtained in step 1 under appropriate conditions that will be recognized by one skilled in the art. The compound SIAIS164003 was obtained as off-white solid (745 mg, yield 79%). $^1$H NMR (500 MHz, MeOD) δ 6.59 (t, J=56.8 Hz, 3H), 3.78 (s, 3H), 3.46 (s, 6H), 2.62 (d, J=4.3 Hz, 6H), 2.42 (s, 1H), 1.98 (s, 2H), 1.69 (d, J=9.7 Hz, 2H), 1.46 (s, 9H). HRMS (ESI) calcd for, $C_{21}H_{35}N_4O_3$ [M+H]$^+$: 391.2704, found 391.3048.

Step 3: Preparation of (2-((5-chloro-2-((2-methoxy-4-(4-(piperazin-1-yl)piperidin-1-yl)phenyl)amino)pyrimidin-4-yl) amino)phenyl)dimethylphosphine oxide (SIAIS164005) According to Scheme 14

According to steps 3 and 4 of the Scheme 14 method of intermediate preparation Example 66, the target compound SIAIS164005 was prepared from the product SIAIS164003 obtained in step 2 under appropriate conditions that will be recognized by one skilled in the art. The target compound SIAIS164005 was obtained as yellow solid (350 mg, the total yield of the two steps is 37%). $^1$H NMR (500 MHz, MeOD) δ 8.33 (dd, J=8.2, 4.4 Hz, 1H), 8.03 (s, 1H), 7.69-7.64 (m, 1H), 7.60 (ddd, J=14.0, 7.7, 1.4 Hz, 1H), 7.51 (t, J=7.9 Hz, 1H), 7.26 (td, J=7.6, 1.2 Hz, 1H), 6.66 (d, J=2.4 Hz, 1H), 6.45 (dd, J=8.8, 2.5 Hz, 1H), 3.85 (s, 3H), 3.73-3.63 (m, 2H), 3.11-3.02 (m, 4H), 2.79-2.66 (m, 6H), 2.48-2.43 (m, 1H), 1.99 (d, J=12.5 Hz, 2H), 1.84 (d, J=13.5 Hz, 6H), 1.72-1.63 (m, 2H). HRMS (ESI) calcd for, $C_{24}H_{38}ClN_7O_2P$ [M+H]$^+$: 570.2508, found 570.2498.

Intermediate Preparation Example 78: Preparation of Intermediate Dasatinib Derivative (SIAIS151055)

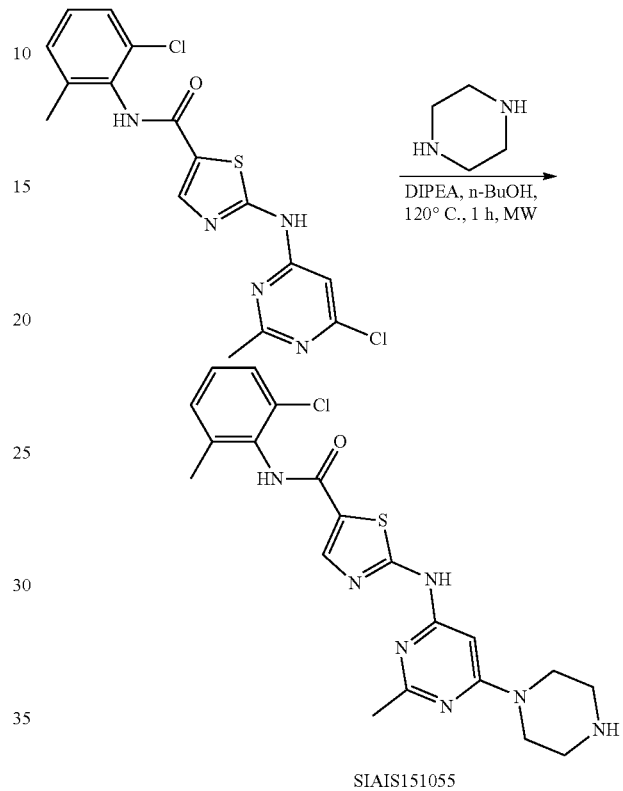

Scheme 15

SIAIS151055

Preparation of N-(2-chloro-6-methylphenyl)-2-((2-methyl-6-(piperazin-1-yl)pyrimidin-4-yl)amino)thiazole-5-carboxamide (SIAIS151055) According to Scheme 15

A 30 mL microwave reaction tube was charged with N-(2-chloro-6-methylphenyl)-2-[(6-chloro-2-methyl-4-pyrimidinyl)amino]-5-thiazolecarboxamide (1.0 g, 2.54 mmol), anhydrous piperazine (1.31 g, 15.21 mmol), N,N-diisopropylethylamine (4.9 g, 38.0 mmol) and anhydrous n-butanol (8 mL), and the mixture was stirred at room temperature for 10 minutes, and then argon gas was slowly bubbled into the microwave tube. After sealing, the reaction tube was put in the microwave reactor, slowly raised to 120° C., and stirred for 1 h. The reaction solution was cooled to room temperature and left overnight. A large amount of white solid were precipitate out. The mixture was filtered, and the filter cake was washed twice with anhydrous n-butanol. The solvent was removed under reduced pressure to obtain the target compound (SIAIS151055) (white solid, 0.9 g, yield 80%). $^1$H NMR (500 MHz, DMSO) δ 9.88 (s, 1H), 8.23 (s, 1H), 7.43-7.38 (m, 1H), 7.31-7.24 (m, 2H), 6.04 (s, 1H), 3.45 (d, J=4.6 Hz, 4H), 2.79-2.71 (m, 4H), 2.44-2.37 (m, 3H), 2.25 (s, 3H). HRMS (ESI) $C_{20}H_{23}ClN_7OS^+$ [M+H]$^+$, calcd for, 444.1368; found, 444.1301.

Intermediate Preparation Example 79: Preparation of Intermediate Bosutinib Derivative (SIAIS151151)

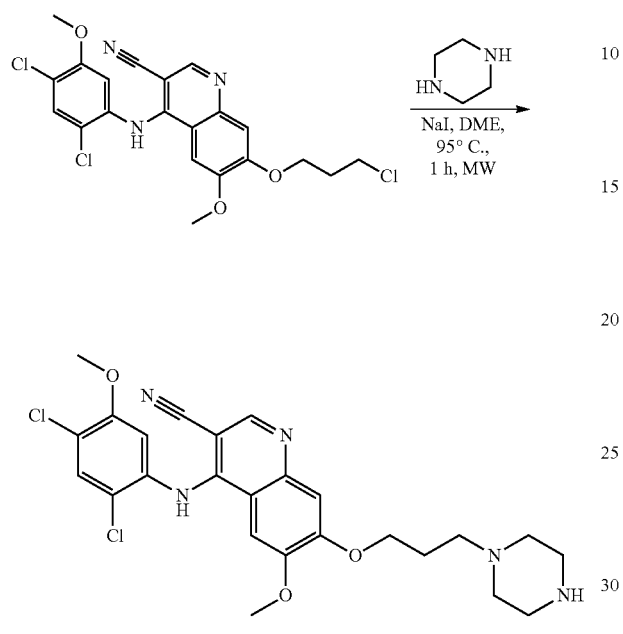

Preparation of 4-((2,4-dichloro-5-methoxyphenyl)amino)-6-methoxy-7-(3-(piperazin-1-yl)propoxy)quinoline-3-carbonitrile (SIAIS151151) According to Scheme 16

A 30 mL microwave reaction tub was charged with 7-(3-chloropropoxy)-4-[(2,4-dichloro-5-methoxyphenyl)amino]-6-methoxy-3-cyanoquinoline (1.0 g, 2.14 mmol), anhydrous piperazine (0.93 g, 10.7 mmol), sodium iodide (0.4 g, 2.14 mmol) and ethylene glycol dimethyl ether (8 mL), the mixture was stirred at room temperature for 10 min, and then argon gas was slowly bubbled into the microwave tube. The reaction tube was placed in the microwave reactor, raised to 120° C. and stirred for 1 h. The reaction solution was cooled to room temperature, evaporated to remove the reaction solvent under reduced pressure, and then 20 mL of saturated sodium bicarbonate solution was added. The mixture was extracted with ethyl acetate (4×50 mL), and the combined organic phases were washed with saturated brine (20 mL), dried over anhydrous $Na_2SO_4$, and concentrated to remove the solvent under reduced pressure, the crude product was separated and purified by column chromatography (eluent (v/v): dichloromethane/methanol=10:1) to obtain the target compound (SIAIS151151) (light brown solid, 0.55 g), yield 50%). $^1H$ NMR (500 MHz, DMSO) δ 8.39 (s, 1H), 7.82 (s, 1H), 7.72 (s, 1H), 7.30 (s, 1H), 7.28 (s, 1H), 5.75 (s, 1H), 4.19 (t, J=6.4 Hz, 2H), 3.94 (s, 3H), 3.85 (s, 3H), 2.76 (t, J=4.8 Hz, 4H), 2.43 (t, J=7.1 Hz, 2H), 2.39-2.32 (m, 4H), 1.99-1.91 (m, 2H). HRMS (ESI): calcd for, $C_{25}H_{28}Cl_2N_5O_3^+$ $[M+H]^+$, 516.1564; found, 516.1699.

Intermediate Preparation Example 80: Preparation Method of Intermediate Ponatinib Derivative (SIAIS151190B)

-continued

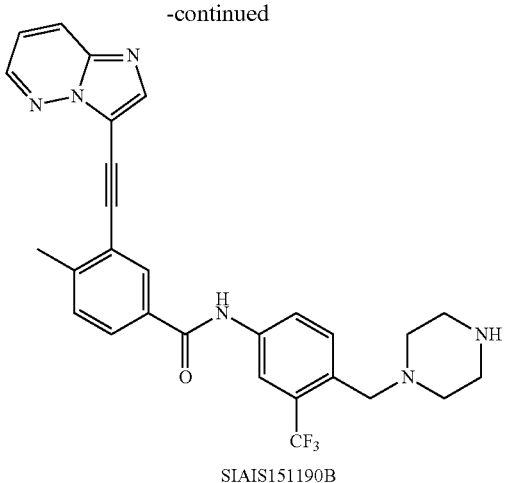

SIAIS151190B

Preparation of 1-(bromomethyl)-4-nitro-2-(trifluoromethyl)benzene (SIAIS151182) According to Scheme 17

A 100 mL egg-shaped flask was charged with the compound 1-methyl-4-nitro-2-(trifluoromethyl)benzene (2.0 g, 9.75 mmol), followed by anhydrous 1,2-bis Chloroethane (20 mL), N-bromosuccinimide (1.74 g, 9.75 mmol) and azobisisobutyronitrile (160 mg, 0.98 mmol). After the addition, the reaction mixture was slowly heated to reflux state and stirred overnight. The reaction mixture was then cooled to room temperature, poured into water (100 mL), extracted with ethyl acetate (2×50 mL). The combined organic phases were washed with water (50 mL) and saturated brine, dried over anhydrous sodium sulfate, and concentrated to remove the solvent under reduced pressure. The residue was purified by column chromatography (eluent (v/v): petroleum ether/ethyl acetate=20:1), and rotary-evaporated to dryness to give the target product SIAIS151182 (yellow solid, 1.8 g, yield 65%). $^1$HNMR (500 MHz, CDCl$_3$) δ 8.54 (d, J=2.2 Hz, 1H), 8.42 (dd, J=8.5, 2.3 Hz, 1H), 7.84 (d, J=8.5 Hz, 1H), 4.67 (s, 2H).

Preparation of tert-butyl 4-(4-nitro-2-(trifluoromethyl)benzyl)piperazine-1-carboxylate (SIAIS151186) According to Scheme 17

A 100 mL egg-shaped flask was charged with the compound SIAIS151182 (1.8 g, 6.33 mmol), followed by anhydrous dichloromethane (30 mL), 1-Boc-piperazine (1.8 g, 7.59 mmol) and triethyl amine (1.28 g, 12.66 mmol). After the addition, the mixture was stirred at room temperature for 3 h. After the raw materials were completely consumed, 50 mL of water was poured into the reaction mixture, which was then extracted with ethyl acetate (2×50 mL). The combined organic phases were washed with water (30 mL) and saturated brine (50 mL), and dried with anhydrous sodium sulfate, concentrated to remove the solvent under reduced pressure. The crude product was purified by column chromatography (eluent (v/v): petroleum ether/ethyl acetate=5:1), and rotary-evaporated to dryness to give the target product SIAIS151186 (yellow solid, 2.0 g, yield 81%), $^1$H NMR (500 MHz, CDCl$_3$) δ 8.51 (s, 1H), 8.45-8.36 (m, 1H), 8.11 (d, J=8.6 Hz, 1H), 3.75 (s, 2H), 3.47 (s, 4H), 2.45 (s, 4H), 1.46 (s, 9H).

Preparation of tert-butyl 4-(4-amino-2-(trifluoromethyl)benzyl)piperazine-1-carboxylate (SIAIS151189) according to Scheme 17

At room temperature, an egg-shaped bottle were sequentially charged with SIAIS151186 (1.0 g, 2.57 mmol), ethanol (15 mL), water (5 mL), ammonium chloride (0.55 g, 10.28 mmol), and iron powder (0.72 g, 12.85 mmol), followed by slowly heating to reflux under nitrogen protection and stirring for 1 h. After completion of the reaction was detected by TLC, the reaction mixture was filtered while hot, evaporated to remove the ethanol, after which water (50 mL) was added, and the mixture was extracted with dichloromethane (3×50 mL), washed with saturated brine, dried with anhydrous sodium sulfate, and evaporated to remove the solvent under reduced pressure. The crude product was purified by column chromatography (eluent (v/v): dichloromethane/methanol=20:1) and rotary-evaporated to dryness to obtain the target compound SIAIS151189 (light yellow solid, 0.9 g, yield 97%), $^1$H NMR (500 MHz, CDCl$_3$) δ 7.47 (d, J=8.3 Hz, 1H), 6.91 (d, J=2.2 Hz, 1H), 6.85-6.72 (m, 1H), 3.78 (s, 2H), 3.52 (s, 2H), 3.41 (s, 4H), 2.38 (s, 4H), 1.45 (s, 9H).

Preparation of tert-butyl 4-(4-(3-(imidazo[1,2-b]pyridazin-3-ylethynyl)-4-methylbenzamido)-2-(trifluoromethyl)benzyl)piperazine-1-carboxylate (SIAIS151190A) According to Scheme 17

At room temperature, a reaction flask was charged with 3-(imidazo[1,2-b]pyridazin-3-ylethynyl)-4-methylbenzoic acid (300 mg, 1.08 mmol), SIAIS151189 (420 mg, 1.19 mmol), 1-hydroxy-7-azabenzotriazole (73.5 mg, 0.54 mmol), 1-(3-dimethylaminopropyl)-3-ethylcarbodiimide hydrochloride (414 mg, 2.16 mmol), anhydrous N,N-dimethylformamide (10 mL), and N-methylmorpholine (329 mg, 3.24 mmol). After addition, the mixture was stirred overnight at 35° C. After the completion of the reaction was detected by LC-MS, 50 mL of water was poured into the reaction mixture, and the resulting mixture was extracted with ethyl acetate (3×50 mL). The organic phases were combined, washed with water (2×20 mL, and saturated brine (20 mL), dried over anhydrous Na$_2$SO$_4$ and concentrated to remove the solvent under reduced pressure. The crude product was purified by column chromatography (eluent (v/v): petroleum ether/ethyl acetate=1:3), and rotary-evaporated to dryness to obtain the target product SIAIS151190A (yellow solid, 450 mg, 67% yield), $^1$H NMR (500 MHz, CDCl$_3$) δ 8.56-8.46 (m, 1H), 8.29 (s, 1H), 8.07 (d, J=15.2 Hz, 2H), 8.02-7.90 (m, 3H), 7.88-7.77 (m, 2H), 7.39 (d, J=8.0 Hz, 1H), 7.13 (dd, J=9.2, 4.4 Hz, 1H), 3.64 (s, 2H), 3.45 (s, 4H), 2.64 (s, 3H), 2.43 (s, 4H), 1.46 (s, 9H). HRMS (ESI) m/z: calcd for, $C_{33}H_{34}F_3N_6O_3^+$ [M+H]$^+$, 619.2639; found, 619.3310.

Preparation of 3-(imidazo[1,2-b]pyridazin-3-ylethynyl)-4-methyl-N-(4-(piperazin-1-ylmethyl)-3-(trifluoromethyl)phenyl)benzamide (SIAIS151190B) According to Scheme 17

A 50 mL egg-shaped flask was charged with the compound (SIAIS151190A), followed by anhydrous dichloromethane (15 mL) and trifluoroacetic acid (5 mL). The mixture was stirred at room temperature for 3 h, and concentrated to remove the solvent under reduced pressure, after which dichloromethane/methanol (volume ratio: 10:1) (22 mL) was added, and then saturated sodium bicarbonate aqueous solution was slowly added under stirring to adjust the pH of the solution to 8-9. The reaction solution was extracted with 10% dichloromethane/methanol (3×30 mL), and the organic phases were combined, washed with saturated brine (10 mL), dried with anhydrous sodium sulfate, and concentrated to remove the solvent under reduced pressure to obtain the target compound SIAIS151190B. The crude product was used directly in the next step without further purification. (Yellow Solid, 300 mg, 80% yield), $^1$H NMR (500 MHz, DMSO) δ 10.63 (s, 1H), 8.80 (s, 1H), 8.74 (dd, J=4.4, 1.5 Hz, 1H), 8.27 (dd, J=9.2, 1.5 Hz, 1H), 8.26-8.24 (m, 2H), 8.22 (d, J=1.8 Hz, 1H), 8.14 (dd, J=8.5, 1.8 Hz, 1H), 7.96 (dd, J=8.0, 1.8 Hz, 1H), 7.75 (d, J=8.6 Hz, 1H), 7.56 (d, J=8.2 Hz, 1H), 7.41 (dd, J=9.2, 4.4 Hz, 1H), 3.80 (s, 2H), 3.17 (s, 4H), 2.74 (s, 4H), 2.61 (s, 3H). HRMS (ESI) m/z: calcd for, $C_{28}H_{26}F_3N_6O^+$ [M+H]$^+$, 519.2115; found, 519.2119.

Intermediate Preparation Example 81: Preparation of Intermediate Toremifene Derivative B

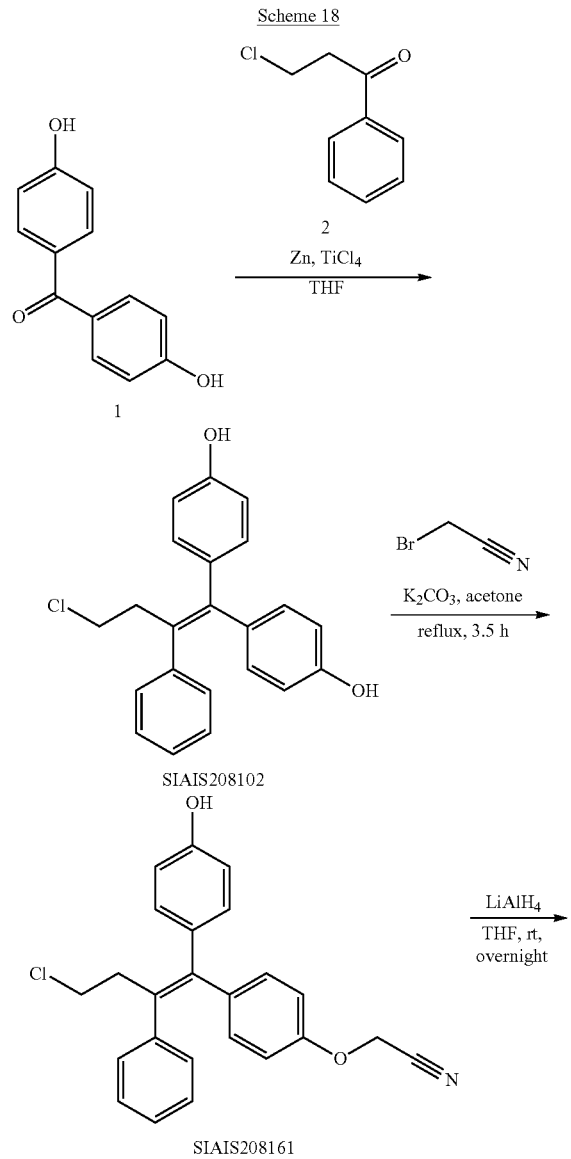

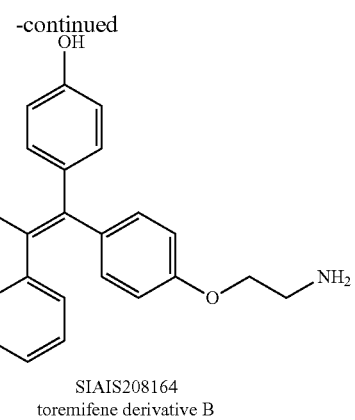

SIAIS208164
toremifene derivative B

Step 1: Preparation of 4,4'-(4-chloro-2-phenylbut-1-ene-1,1-diyl)biphenol (SIAIS208102) According to Scheme 18

A dry three-necked flask equipped with a reflux device was charged with Zinc powder (6.5 g, 100 mmol), evacuated and refilled with the air three times, and then THF (80 mL) was added under Ar gas, and followed by dropping TiCl$_4$ (9.5 g, 50 mmol) at 0° C. After removing the ice bath, the reaction mixture was warmed to room temperature and heated to reflux for 2 h. After cooling to room temperature, solutions of compounds 1 (2.14 g, 10 mmol) and 2 (5.1 g, 30 mmol) in THF (80 mL) were added, and refluxed for 3 h in the dark. After the reaction is complete, the reaction mixture was cooled and rotary-evaporated to remove most of the solvent, quenched with saturated ammonium chloride solution, and extracted with ethyl acetate. The organic phases were combined, washed with water and saturated brine, dried with anhydrous sodium sulfate, rotary-evaporated to dryness, and separated by silica gel column chromatography (eluent: petroleum ether:ethyl acetate=2:1) to obtain 3 g of yellow solid product with a yield of 86%. $^1$H NMR (500 MHz, CDCl$_3$) δ 7.21-7.10 (m, 7H), 6.84-6.81 (m, 2H), 6.75-6.72 (m, 2H), 6.49-6.46 (m, 2H), 4.99 (s, 1H), 4.73 (s, 1H), 3.45-3.36 (m, 2H), 2.99-2.91 (m, 2H). HRMS (ESI) m/z: calcd for, $C_{22}H_{20}ClO_2^+$ [M+H]$^+$, 351.1146; found, 351.1138.

Step 2: Preparation of 2-(4-(4-chloro-1-(4-hydroxyphenyl)-2-phenylbut-1-en-1-yl)phenoxy)acetonitrile (SIAIS208161) According to Scheme 18

A single-mouth bottle was sequentially charged with SIAIS208102 (1.5 g, 4.28 mmol), acetone (15 mL), K$_2$CO$_3$ (592 mg, 4.28 mmol), and bromoacetonitrile (257 mg, 2.14 mmol), evacuated and refilled with the air three times, and then heated to reflux for 3.5 h under Ar gas. After completion of the reaction, the reaction mixture was cooled to room temperature, concentrated to remove the solvent, and the residue was separated by silica gel column chromatography (pure dichloromethane as eluent) to obtain 782 mg of light yellow liquid product with a yield of 94%. $^1$H NMR (500 MHz, CDCl$_3$) δ 7.31-7.27 (m, 1H), 7.21-7.18 (m, 2H), 7.17-7.14 (m, 2H), 7.13-7.10 (m, 2H), 7.00-6.97 (m, 1H), 6.86-6.83 (m, 2H), 6.75-6.70 (m, 1H), 6.65-6.61 (m, 1H), 6.51-6.47 (m, 1H), 4.95-4.70 (m, 1H), 4.81 (s, 1H), 4.70 (s, 1H), 4.64 (s, 1H), 3.45-3.39 (m, 2H), 2.97-2.91 (m, 2H). HRMS (ESI) m/z: calcd for, $C_{24}H_{21}ClNO_2^+$ [M+H]$^+$, 390.1255; found, 390.1263.

Step 3: Preparation of 4-(1-(4-(2-aminoethoxy)phenyl)-4-chloro-2-phenylbut-1-en-1-yl)phenol (SIAIS208164) According to Scheme 18

A single-necked flask was charged with SIAIS208161 (782 mg, 2 mmol), THF (25 mL), followed by adding LiAlH$_4$ (228 mg, 6 mmol) in batches at 0° C., and evacuation and refilling with the air three times, and the reaction was carried out at room temperature under Ar gas overnight. After completion of the reaction, the reaction mixture was quenched by adding saturated ammonium chloride, concentrated to dryness, filtered, washed with methanol, and the filtrate was concentrated and separated by C18 reversed-phase column chromatography [eluent was water (containing 0.05% HCl) and acetonitrile] to obtain 473 mg light yellow solid product with a yield of 60%. $^1$H NMR (500 MHz, DMSO) δ 9.68-9.17 (m, 1H), 8.12 (d, J=41.4 Hz, 3H), 7.24-7.18 (m, 3H), 7.16-7.12 (m, 3H), 7.06 (d, J=8.5 Hz, 1H), 7.00 (d, J=8.7 Hz, 1H), 6.77 (t, J=8.4 Hz, 2H), 6.65 (d, J=8.8 Hz, 1H), 6.61 (d, J=8.6 Hz, 1H), 6.42 (d, J=8.6 Hz, 1H), 4.20 (t, J=4.9 Hz, 1H), 4.03 (t, J=4.9 Hz, 1H), 3.43 (t, J=7.3 Hz, 2H), 3.23 (s, 1H), 3.12 (s, 1H), 2.93-2.83 (m, 2H). HRMS (ESI) m/z: calcd for, $C_{24}H_{25}ClNO_2^+$ [M+H]$^+$, 394.1568; found, 394.1561.

Intermediate Preparation Example 82: Preparation of Intermediate JQ-1 Derivative A (SIAIS171018)

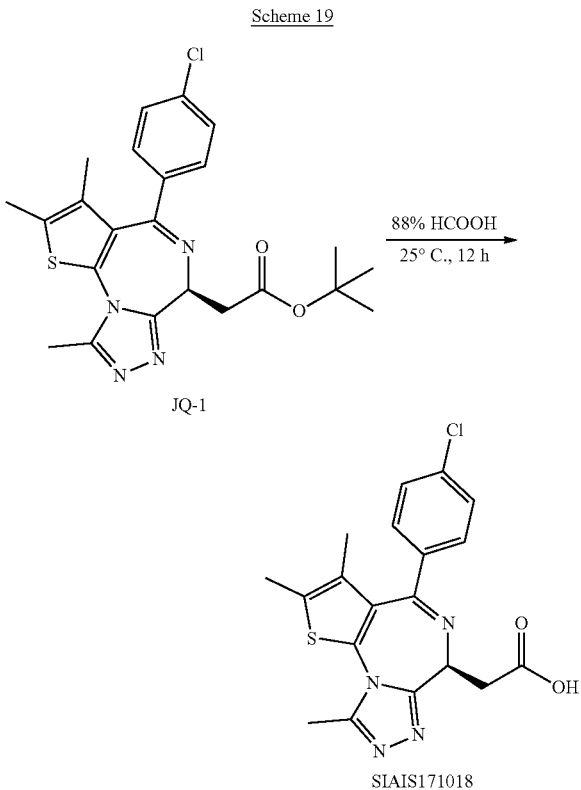

Preparation of (S)-2-(4-(4-chlorophenyl)-2,3,9-trimethyl-6H-thieno[3,2-f][1,2,4]triazolo[4,3-a][1,4]diazepin-6-yl)acetic acid (SIAIS171018) According to Scheme 19

A 10 mL egg-shaped flask was charged with Compound JQ-1 (1.0 g, 2.14 mmol), followed by 88% formic acid (5 mL), the reaction mixture was stirred at room temperature for 12 h. After completion of the reaction was detected by LC-MS, the solvent was evaporated under reduced pressure, and the residue was treated by adding water and lyophilized to give the target compound (SISIS171018) (white solid, 840 mg, yield 96%). $^1$H NMR (500 MHz, DMSO) δ 12.46 (s, 1H), 7.50 (d, J=8.6 Hz, 2H), 7.44 (d, J=8.5 Hz, 2H), 4.45 (t, J=7.1 Hz, 1H), 3.43 (dd, J=16.7, 6.8 Hz, 2H), 2.61 (d, J=12.4 Hz, 3H), 2.41 (s, 3H), 1.63 (s, 3H). HRMS (ESI): calcd for, $C_{19}H_{18}ClN_4O_2S^+$ [M+H]$^+$, 401.0834; found, 401.1217.

Intermediate Preparation Example 83: Preparation of Intermediate JQ-1 Derivative B (SIAIS213113)

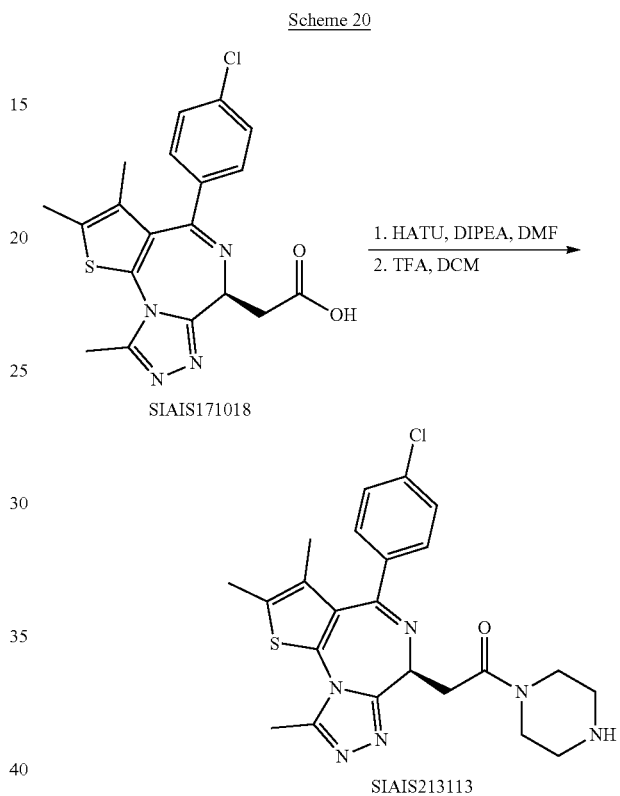

Preparation of (S)-2-(4-(4-chlorophenyl)-2,3,9-trimethyl-6H-thieno[3,2-f][1,2,4]triazolo[4,3-a][1,4]diazepin-6-yl)-1-(piperazin-1-yl)ethan-1-one (SIAIS213113) According to Scheme 20

At room temperature, a reaction flask was charged with SIAIS171018 (200 mg, 0.5 mmol), tert-butyl piperazine-1-carboxylate (102 mg, 0.55 mmol), HATU (285 mg, 0.75 mmol), DIPEA (193.5 mg, 1.5 mmol), and anhydrous N,N-dimethylformamide (10 mL). The reaction mixture was stirred overnight at room temperature. After completion of the reaction is detected by LC-MS, the reaction mixture was subjected to reverse-phase column (eluent (v/v): acetonitrile/(water+0.05% HCl)=10%-100%) for separation, concentrated to remove the acetonitrile, and lyophilized to obtain the Boc protection intermediate. The intermediate (270 mg, 0.47 mmol) was dissolved in dichloromethane (15 mL), and then trifluoroacetic acid (2 mL) was added, followed by stirring for 2 hours at room temperature. The mixture was concentrated, treated by adding water and lyophilized to give the target compound (SIAIS213113). (Yellow solid, 200 mg, two-step total yield 89.9%), $^1$H NMR (500 MHz, MeOD) δ 7.54-7.40 (m, 4H), 4.78-4.72 (m, 1H), 4.11 (dt, J=6.6, 4.8 Hz, 1H), 4.03-3.91 (m, 2H), 3.85-3.77 (m, 1H), 3.73 (dd, J=16.6, 7.0 Hz, 1H), 3.67-3.59 (m, 1H), 3.43 (ddt, J=18.9, 12.4, 9.2 Hz, 2H), 3.32-3.15 (m, 2H), 2.77 (s, 3H), 2.48 (s, 3H), 1.72 (s, 3H). HRMS (ESI): calcd for, $C_{23}H_{26}ClN_6OS^+$ [M+H]$^+$, 469.1572; found, 469.1572.

Intermediate Preparation Example 84: Preparation of Intermediate JQ-1 Derivative C (SIAIS213130)

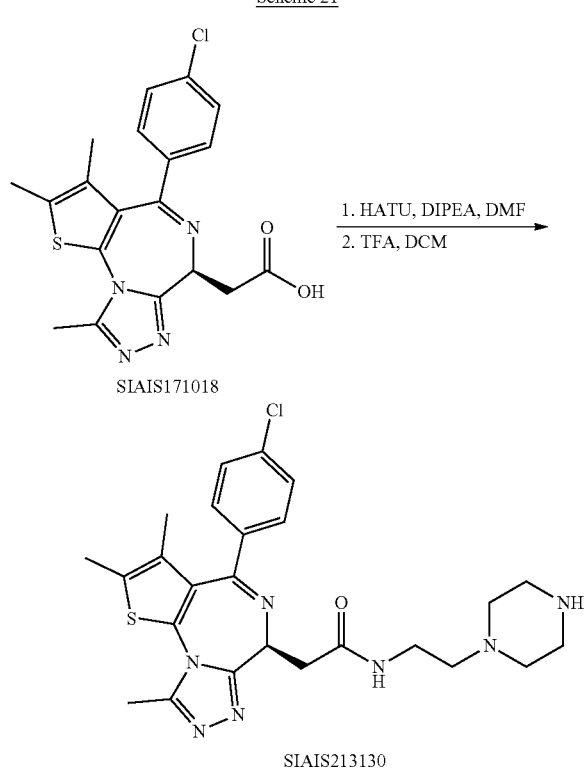

Scheme 21

SIAIS171018

1. HATU, DIPEA, DMF
2. TFA, DCM

SIAIS213130

Preparation of (S)-2-(4-(4-chlorophenyl)-2,3,9-trimethyl-6H-thieno[3,2-f][1,2,4]triazolo[4,3-a][1,4]diazepin-6-yl)-N-(2-(piperazin-1-yl)ethyl)acetamide (SIAIS213130) According to Scheme 21

At room temperature, a reaction flask was charged with SIAIS171018 (100 mg, 0.25 mmol), tert-butyl 4-(2-aminoethyl)piperazine-1-carboxylate (69 mg, 0.3 mmol), HATU (142.5 mg, 0.375 mmol), DIPEA (97 mg, 0.75 mmol), and anhydrous N,N-dimethylformamide (3 mL), and the reaction mixture was stirred overnight at room temperature. After completion of the reaction was detected by LC-MS, the reaction mixture was subjected to reverse-phase column (eluent (v/v): acetonitrile/(water+0.05% HCl)=10%-100%) for separation, concentrated to remove the acetonitrile, and lyophilized to obtain the Boc protection intermediate. The intermediate (120 mg, 0.20 mmol) was dissolved in dichloromethane (6 mL), and then trifluoroacetic acid (2 mL) was added, followed by stirring for 3 hours at room temperature. The mixture was concentrated, treated by adding water and lyophilized to give the target compound (SIAIS213130). (Light Yellow oily liquid, 100 mg, two-step total yield 99%), $^1$H NMR (500 MHz, MeOD) δ 7.46 (dd, J=20.9, 8.6 Hz, 4H), 4.67 (t, J=7.1 Hz, 1H), 3.78 (dt, J=14.9, 6.1 Hz, 1H), 3.55-3.37 (m, 11H), 3.19 (dd, J=13.2, 7.2 Hz, 2H), 2.74 (s, 3H), 2.46 (s, 3H), 1.71 (s, 3H). HRMS (ESI): calcd for, $C_{25}H_{31}ClN_7OS^+$ [M+H]$^+$, 512.1994; found, 512.1994.

Degradation Agents Preparation Examples

General Method for Preparing a Series of Degradation Agents of CDK4/6 Target:

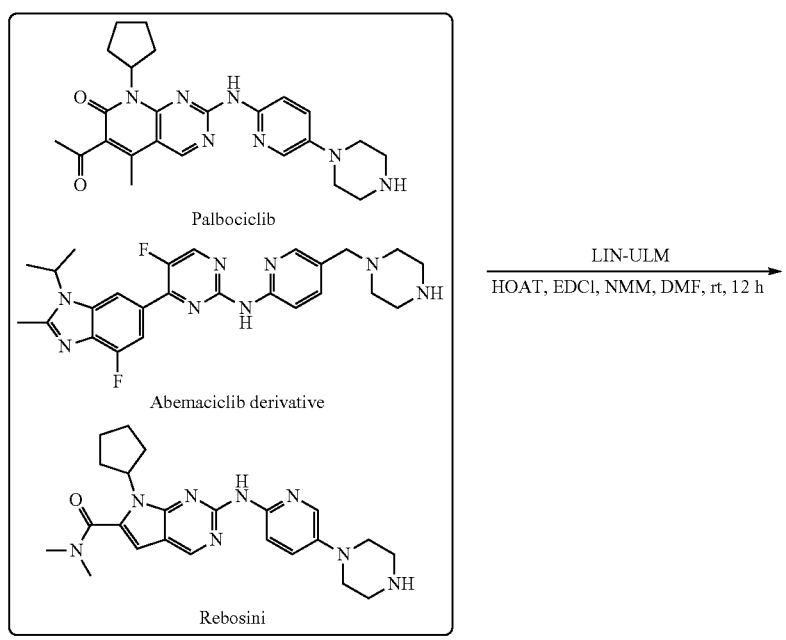

Scheme 22

Palbociclib

Abemaciclib derivative

Rebosini

CDK4/6 inhibitor

LIN-ULM
HOAT, EDCl, NMM, DMF, rt, 12 h

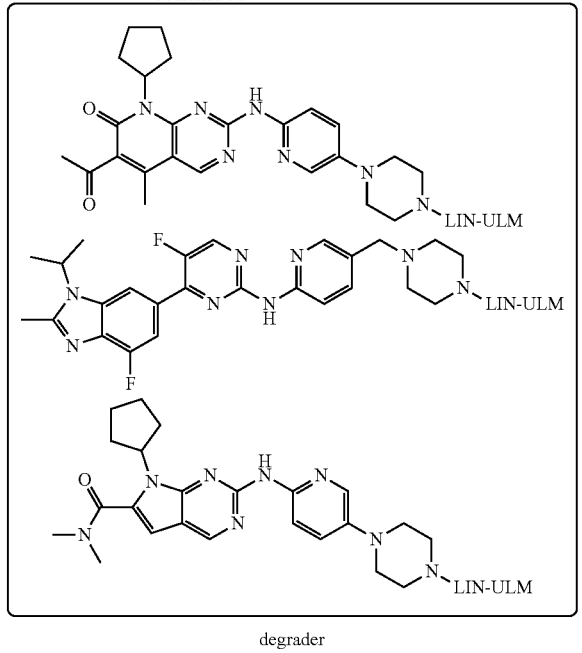

degrader

According to Scheme 22, at room temperature, a reaction flask was charged with Palbociclib inhibitor (1 equiv), the corresponding LIN-ULM (1 equiv), 1-hydroxy-7-azabenzotriazole (2 equiv), 1-(3-dimethylaminopropyl)-3-ethylcarbodiimide hydrochloride (2 equiv), anhydrous N,N-dimethylformamide (2 mL), and N-methylmorpholine (5 equiv), and the reaction mixture was stirred at room temperature overnight. After the completion of the reaction detected by LC-MS, the reaction mixture was subjected to preparative HPLC (eluent (v/v): acetonitrile/(water+0.05% HCl)=10%-100%) for separation and purification. The acetonitrile was removed by rotary evaporation, and the residue was lyophilized to give the corresponding final degradation agent compound.

Example 1: Preparation of 7-cyclopentyl-2-((5-(4-(2-((2-(2,6-dioxopiperidin-3-yl)-1,3-dioxoisoindolin-4-yl)thio)acetyl)piperazin-1-yl)pyridin-2-yl)amino)-N,N-dimethyl-7H-pyrrolo[2,3-d]pyrimidine-6-carboxamide (SIAIS219100)

According to the general method described in Scheme 22, the target compound (SIAIS219100) was prepared by using Rebosini inhibitor and LIN-ULM (SIAIS151045) under appropriate conditions that will be recognized by one skilled in the art. (yellow solid, 6.9 mg, yield, 39%) $^1$H NMR (500 MHz, DMSO) δ 11.13 (s, 1H), 8.96 (s, 1H), 8.03 (s, 1H), 7.92 (s, 1H), 7.85 (d, J=8.2 Hz, 1H), 7.82-7.77 (m, 1H), 7.65 (d, J=7.1 Hz, 2H), 6.80 (s, 1H), 5.13 (dd, J=12.8, 5.5 Hz, 1H), 4.84-4.74 (m, 1H), 4.35 (s, 2H), 3.80 (s, 2H), 3.68 (s, 2H), 3.28 (s, 4H), 3.18 (s, 2H), 3.06 (s, 6H), 2.89-2.85 (m, 1H), 2.64-2.55 (m, 1H), 2.54 (d, J=4.6 Hz, 1H), 2.35 (d, J=16.1 Hz, 2H), 2.08-2.03 (m, 5H), 1.65 (d, J=6.2 Hz, 2H). HRMS (ESI) m/z: calcd for, $C_{38}H_{41}N_{10}O_6S^+$ [M+H]$^+$, 765.2926; found, 765.2922.

Example 2: Preparation of 7-cyclopentyl-2-((5-(4-(3-((2-(2,6-dioxopiperidin-3-yl)-1,3-dioxoisoindolin-4-yl)thio)propanoyl)piperazin-1-yl)pyridin-2-yl)amino)-N,N-dimethyl-7H-pyrrolo[2,3-d]pyrimidine-6-carboxamide (SIAIS219101)

According to the general method described in Scheme 22, the target compound (SIAIS219101) was prepared by using the Rebosini inhibitor and LIN-ULM (SIAIS151138B) under appropriate conditions that will be recognized by one skilled in the art. (yellow solid, 7.1 mg, yield 40%) $^1$H NMR (500 MHz, DMSO) δ 11.33 (s, 1H), 11.12 (s, 1H), 8.97 (s, 1H), 8.04 (s, 1H), 7.89 (d, J=2.4 Hz, 1H), 7.83-7.77 (m, 2H), 7.68-7.59 (m, 2H), 6.81 (s, 1H), 5.11 (dd, J=12.9, 5.4 Hz, 1H), 4.80 (p, J=8.7 Hz, 1H), 3.68-3.59 (m, 4H), 3.21-3.12 (m, 4H), 3.06 (s, 6H), 2.92-2.83 (m, 3H), 2.64-2.54 (m, 1H), 2.54-2.51 (m, 1H), 2.38-2.32 (m, 2H), 2.07-1.92 (m, 5H), 1.69-1.60 (m, 2H). HRMS (ESI) m/z: calcd for, $C_{39}H_{43}N_{10}O_6S^+$ [M+H]$^+$, 779.3082; found, 779.3077.

Example 3: Preparation of 7-cyclopentyl-2-((5-(4-(4-((2-(2,6-dioxopiperidin-3-yl)-1,3-dioxoisoindolin-4-yl)thio)butanoyl)piperazin-1-yl)pyridin-2-yl)amino)-N,N-dimethyl-7H-pyrrolo[2,3-d]pyrimidine-6-carboxamide (SIAIS219102)

According to the general method described in Scheme 22, the target compound (SIAIS219102) was prepared by using Rebosini inhibitor and LIN-ULM (SIAIS151139B) under appropriate conditions that will be recognized by one skilled in the art. (yellow solid, 8.0 mg, yield 44%) $^1$H NMR (500 MHz, DMSO) δ 11.38 (s, 1H), 11.12 (s, 1H), 8.98 (s, 1H), 8.06 (s, 1H), 7.92-7.84 (m, 2H), 7.84-7.76 (m, 1H), 7.62 (dd, J=18.1, 8.2 Hz, 2H), 6.82 (s, 1H), 5.11 (dd, J=12.8, 5.4 Hz, 1H), 4.81 (p, J=8.8 Hz, 1H), 3.65 (s, 4H), 3.21-3.15 (m, 6H), 3.06 (s, 6H), 2.91-2.87 (m, 1H), 2.59-2.55 (m, 3H), 2.54-2.51 (m, 1H), 2.32 (d, J=11.8 Hz, 2H), 2.07-1.91 (m, 7H), 1.70-1.62 (m, 2H). HRMS (ESI) m/z: calcd for, $C_{40}H_{45}N_{10}O_6S^+$ [M+H]$^+$, 793.3239; found, 793.3231.

Example 4: Preparation of 7-cyclopentyl-2-((5-(4-(5-((2-(2,6-dioxopiperidin-3-yl)-1,3-dioxoisoindolin-4-yl)thio)pentanoyl)piperazin-1-yl)pyridin-2-yl)amino)-N,N-dimethyl-7H-pyrrolo[2,3-d]pyrimidine-6-carboxamide (SIAIS219103)

According to the general method described in Scheme 22, the target compound (SIAIS219103) was prepared by using Rebosini inhibitor and LIN-ULM (SIAIS151140B) under appropriate conditions that will be recognized by one skilled in the art. (yellow solid, 8.3 mg, yield 45%) $^1$H NMR (500 MHz, DMSO) δ 11.12 (s, 1H), 8.97 (s, 1H), 8.02 (s, 1H), 7.89 (s, 1H), 7.81-7.74 (m, 2H), 7.67-7.58 (m, 2H), 6.80 (s, 1H), 5.11 (dd, J=12.8, 5.4 Hz, 1H), 4.85-4.75 (m, 1H), 3.64 (s, 4H), 3.15 (s, 3H), 3.14 (s, 3H), 3.06 (s, 6H), 2.92-2.84 (m, 1H), 2.64-2.57 (m, 1H), 2.45 (s, 1H), 2.32 (s, 2H), 2.05-1.98 (m, 5H), 1.69-1.65 (m, 6H). HRMS (ESI) m/z: calcd for, $C_{41}H_{47}N_{10}O_6S^+$ [M+H]$^+$, 807.3395; found, 807.3392.

Example 5: Preparation of 7-cyclopentyl-2-((5-(4-(6-((2-(2,6-dioxopiperidin-3-yl)-1,3-dioxoisoindolin-4-yl)thio)hexanoyl)piperazin-1-yl)pyridin-2-yl)amino)-N,N-dimethyl-7H-pyrrolo[2,3-d]pyrimidine-6-carboxamide (SIAIS219104)

According to the general method described in Scheme 22, the target compound (SIAIS219104) was prepared by using Rebosini inhibitor and LIN-ULM (SIAIS151141B) under appropriate conditions that will be recognized by one skilled in the art. (yellow solid, 8.2 mg, yield 43%) $^1$H NMR (500 MHz, DMSO) δ 11.26 (s, 1H), 11.12 (s, 1H), 8.97 (s, 1H), 8.03 (s, 1H), 7.88 (d, J=2.5 Hz, 1H), 7.79-7.75 (m, 2H), 7.62 (d, J=6.6 Hz, 2H), 6.81 (s, 1H), 5.11 (dd, J=12.9, 5.4 Hz, 1H), 4.79-4.76 (m, 1H), 3.67-3.60 (m, 4H), 3.17-3.12 (m, 6H), 3.06 (s, 6H), 2.93-2.84 (m, 1H), 2.64-2.55 (m, 1H), 2.38-2.34 (m, 3H), 2.04-1.97 (m, 5H), 1.74-1.64-1.58 (m, 4H), 1.58 (m, 2H), 1.51-1.46 (m, 2H). HRMS (ESI) m/z: calcd for, $C_{42}H_{49}N_{10}O_6S^+$ [M+H]$^+$, 821.3552; found, 821.3548.

Example 6: Preparation of 7-cyclopentyl-2-((5-(4-(7-((2-(2,6-dioxopiperidin-3-yl)-1,3-dioxoisoindolin-4-yl)thio)heptanoyl)piperazin-1-yl)pyridin-2-yl)amino)-N,N-dimethyl-7H-pyrrolo[2,3-d]pyrimidine-6-carboxamide (SIAIS219105)

According to the general method described in Scheme 22, the target compound (SIAIS219105) was prepared by using Rebosini inhibitor and LIN-ULM (SIAIS151142B) under appropriate conditions that will be recognized by one skilled in the art. (yellow solid, 8.5 mg, yield 44%) $^1$H NMR (500 MHz, DMSO) δ 11.12 (s, 1H), 8.97 (s, 1H), 8.04 (s, 1H), 7.89 (s, 1H), 7.82-7.71 (m, 2H), 7.62 (d, J=6.9 Hz, 2H), 6.81 (s, 1H), 5.11 (dd, J=12.9, 5.4 Hz, 1H), 4.86-4.75 (m, 1H), 3.63 (d, J=5.4 Hz, 4H), 3.17-3.11 (m, 6H), 3.06 (s, 6H), 2.93-2.84 (m, 1H), 2.64-2.56 (m, 1H), 2.37 (d, J=6.6 Hz, 1H), 2.32 (s, 2H), 2.05-2.00 (m, 5H), 1.72-1.61 (m, 4H), 1.51-1.47 (m, 4H), 1.40-1.32 (m, 2H). HRMS (ESI) m/z: calcd for, $C_{43}H_{51}N_{10}O_6S^+$ [M+H]$^+$, 835.3708; found, 835.3701.

Example 7: Preparation of 7-cyclopentyl-2-((5-(4-(2-((2-(2,6-dioxopiperidin-3-yl)-1-oxoisoindolin-4-yl)thio)acetyl)piperazin-1-yl)pyridin-2-yl)amino)-N,N-dimethyl-7H-pyrrolo[2,3-d]pyrimidine-6-carboxamide (SIAIS219086)

According to the general method described in Scheme 22, the target compound (SIAIS219086) was prepared by using Rebosini inhibitor and LIN-ULM (SIAIS171090) under appropriate conditions that will be recognized by one skilled in the art. (yellow solid, 7.1 mg, yield 41%) $^1$H NMR (500 MHz, DMSO) δ 11.36 (s, 1H), 10.99 (s, 1H), 8.98 (s, 1H), 8.06 (s, 1H), 7.90 (d, J=2.6 Hz, 1H), 7.75 (d, J=7.1 Hz, 1H), 7.61 (d, J=7.1 Hz, 2H), 7.54 (t, J=7.6 Hz, 1H), 6.82 (s, 1H), 5.14 (dd, J=13.3, 5.1 Hz, 1H), 4.82-4.77 (m, 1H), 4.37 (d, J=17.4 Hz, 1H), 4.23 (d, J=17.4 Hz, 1H), 4.22 (s, 2H), 3.67-3.64 (m, 4H), 3.19-3.16 (m, 4H), 3.06 (s, 6H), 2.95-2.87 (m, 1H), 2.63-2.61 (m, 1H), 2.48-2.40 (m, 1H), 2.36-2.32 (m, 2H), 2.08-1.92 (m, 5H), 1.70-1.62 (m, 2H). HRMS (ESI) m/z: calcd for, $C_{38}H_{43}N_{10}O_5S^+$ [M+H]$^+$, 751.3133; found, 751.3122.

Example 8: Preparation of 7-cyclopentyl-2-((5-(4-(3-((2-(2,6-dioxopiperidin-3-yl)-1-oxoisoindolin-4-yl)thio)propanoyl)piperazin-1-yl)pyridin-2-yl)amino)-N,N-dimethyl-7H-pyrrolo[2,3-d]pyrimidine-6-carboxamide (SIAIS219087)

According to the general method described in Scheme 22, the target compound (SIAIS219087) was prepared by using Rebosini inhibitor and LIN-ULM (SIAIS171086) under appropriate conditions that will be recognized by one skilled in the art. (yellow solid, 7.3 mg, yield 41%) $^1$H NMR (500 MHz, DMSO) δ 11.32 (s, 1H), 10.99 (s, 1H), 8.97 (s, 1H), 8.02 (s, 1H), 7.88 (d, J=2.7 Hz, 1H), 7.68 (dd, J=7.5, 1.0 Hz, 1H), 7.62-7.51 (m, 3H), 6.81 (s, 1H), 5.13 (dd, J=13.3, 5.1 Hz, 1H), 4.80 (p, J=8.9 Hz, 1H), 4.36 (d, J=17.4 Hz, 1H), 4.22 (d, J=17.4 Hz, 1H), 3.63-3.58 (m, 4H), 3.28 (s, 2H), 3.14 (d, J=4.4 Hz, 4H), 3.06 (s, 6H), 2.95-2.86 (m, 1H), 2.77 (t, J=7.0 Hz, 2H), 2.65-2.54 (m, 1H), 2.48-2.40 (m, 1H), 2.34 (d, J=21.5 Hz, 2H), 2.07-1.91 (m, 5H), 1.70-1.60 (m, 2H). HRMS (ESI) m/z: calcd for, $C_{39}H_{45}N_{10}O_5S^+$ [M+H]$^+$, 765.3290; found, 765.3282.

Example 9: Preparation of 7-cyclopentyl-2-((5-(4-(4-((2-(2,6-dioxopiperidin-3-yl)-1-oxoisoindolin-4-yl)thio)butanoyl)piperazin-1-yl)pyridin-2-yl)amino)-N,N-dimethyl-7H-pyrrolo[2,3-d]pyrimidine-6-carboxamide (SIAIS219088)

According to the general method described in Scheme 22, the target compound (SIAIS219088) was prepared by using Rebosini inhibitor and LIN-ULM (SIAIS171089) under appropriate conditions that will be recognized by one skilled in the art. (yellow solid, 8.0 mg, yield 45%) $^1$H NMR (500 MHz, DMSO) δ 11.50 (s, 1H), 10.99 (d, J=5.5 Hz, 1H), 9.00 (s, 1H), 8.08 (d, J=7.3 Hz, 1H), 7.89 (d, J=2.7 Hz, 1H), 7.71-7.66 (m, 1H), 7.67-7.59 (m, 1H), 7.59-7.52 (m, 2H), 6.82 (s, 1H), 5.13 (dd, J=10.2, 5.1 Hz, 1H), 4.81-4.78 (m, 1H), 4.40-4.35 (m, 1H), 4.23 (d, J=17.4 Hz, 1H), 3.64-3.61 (m, 4H), 3.16-3.12 (m, 6H), 3.06 (s, 6H), 2.94-2.90 (m, 1H), 2.62-2.52 (m, 3H), 2.48-2.43 (m, 1H), 2.33-2.29 (m, 2H), 2.05-1.93 (m, 5H), 1.89-1.82 (m, 2H), 1.70-1.60 (m, 2H). HRMS (ESI) m/z: calcd for, $C_{40}H_{47}N_{10}O_5S^+$ [M+H]$^+$, 779.3446; found, 779.3442.

Example 10: Preparation of 7-cyclopentyl-2-((5-(4-(5-((2-(2,6-dioxopiperidin-3-yl)-1-oxoisoindolin-4-yl)thio)pentanoyl)piperazin-1-yl)pyridin-2-yl)amino)-N,N-dimethyl-7H-pyrrolo[2,3-d]pyrimidine-6-carboxamide (SIAIS219089)

According to the general method described in Scheme 22, the target compound (SIAIS219089) was prepared by using Rebosini inhibitor and LIN-ULM (SIAIS171079) under appropriate conditions that will be recognized by one skilled in the art. (yellow solid, 7.8 mg, yield 43%) $^1$H NMR (500 MHz, DMSO) δ 11.50 (s, 1H), 10.99 (s, 1H), 9.00 (s, 1H), 8.09 (d, J=7.4 Hz, 1H), 7.88 (d, J=2.7 Hz, 1H), 7.64 (dt, J=7.5, 3.8 Hz, 1H), 7.61-7.49 (m, 3H), 6.83 (s, 1H), 5.12 (dd, J=13.3, 5.1 Hz, 1H), 4.82-477 (m, 1H), 4.36 (d, J=17.4 Hz, 1H), 4.22 (d, J=17.4 Hz, 1H), 3.65-3.60 (m, 4H), 3.18-3.10 (m, 6H), 3.06 (s, 6H), 2.92-2.87 (m, 1H), 2.59-2.56 (m, 1H), 2.48-2.44 (m, 1H), 2.41 (t, J=6.8 Hz, 2H), 2.32 (d, J=12.3 Hz, 2H), 2.07-1.92 (m, 5H), 1.65 (d, J=4.3 Hz, 6H). HRMS (ESI) m/z: calcd for, $C_{41}H_{49}N_{10}O_5S^+$ [M+H]$^+$, 793.3603; found, 793.3601.

Example 11: Preparation of 7-cyclopentyl-2-((5-(4-(6-((2-(2,6-dioxopiperidin-3-yl)-1-oxoisoindolin-4-yl)thio)hexanoyl)piperazin-1-yl)pyridin-2-yl)amino)-N,N-dimethyl-7H-pyrrolo[2,3-d]pyrimidine-6-carboxamide (SIAIS219090)

According to the general method described in Scheme 22, the target compound (SIAIS219090) was prepared by using Rebosini inhibitor and LIN-ULM (SIAIS171091) under appropriate conditions that will be recognized by one skilled in the art. (yellow solid, 5.8 mg, yield 31%) $^1$H NMR (500 MHz, DMSO) δ 11.32 (s, 1H), 10.99 (s, 1H), 8.98 (s, 1H), 8.03 (s, 1H), 7.88 (d, J=2.7 Hz, 1H), 7.63 (dd, J=7.4, 1.1 Hz, 2H), 7.53 (dd, J=15.1, 7.6 Hz, 2H), 6.81 (s, 1H), 5.13 (dd, J=13.3, 5.1 Hz, 1H), 4.80 (p, J=8.8 Hz, 1H), 4.36 (d, J=17.4 Hz, 1H), 4.22 (d, J=17.4 Hz, 1H), 3.62 (d, J=4.1 Hz, 4H), 3.18-3.12 (m, 4H), 3.06 (s, 6H), 2.94-2.87 (m, 1H), 2.62-2.60 (m, 1H), 2.48-2.42 (m, 1H), 2.36-2.31 (m, 4H), 2.04-1.93 (m, 5H), 1.68-1.58 (m, 4H), 1.55-1.51 (m, 2H), 1.45-1.42 (m, 2H). HRMS (ESI) m/z: calcd for, $C_{42}H_{51}N_{10}O_5S^+$ [M+H]$^+$, 807.3759; found, 807.3749.

Example 12: Preparation of 7-cyclopentyl-2-((5-(4-(7-((2-(2,6-dioxopiperidin-3-yl)-1-oxoisoindolin-4-yl)thio)heptanoyl)piperazin-1-yl)pyridin-2-yl)amino)-N,N-dimethyl-7H-pyrrolo[2,3-d]pyrimidine-6-carboxamide (SIAIS219091)

According to the general method described in Scheme 22, the target compound (SIAIS219091) was prepared by using Rebosini inhibitor and LIN-ULM (SIAIS171092) under appropriate conditions that will be recognized by one skilled in the art. (yellow solid, 7.8 mg, yield 41%) $^1$H NMR (500 MHz, DMSO) δ 11.42 (s, 1H), 10.99 (s, 1H), 8.99 (s, 1H), 8.07 (d, J=8.7 Hz, 1H), 7.89 (d, J=2.6 Hz, 1H), 7.64-7.58 (m, 2H), 7.58-7.50 (m, 2H), 6.82 (s, 1H), 5.12 (dd, J=13.3, 5.1 Hz, 1H), 4.83-4.78 (m, 1H), 4.35 (d, J=17.4 Hz, 1H), 4.21 (d, J=17.4 Hz, 1H), 3.62 (s, 4H), 3.17-3.13 (m, 4H), 3.06 (d, J=5.0 Hz, 6H), 2.95-2.89 (m, 1H), 2.61-2.56 (m, 1H), 2.47-2.43 (m, 1H), 2.36-2.32 (m, 4H), 2.07-1.94 (m, 5H), 1.64-1.59 (m, 4H), 1.52-1.47 (m, 2H), 1.44-1.39 (m, 2H), 1.33-1.28 (m, 2H). HRMS (ESI) m/z: calcd for, $C_3H_{53}N_{10}O_5S^+$ [M+H]$^+$, 821.3916; found, 821.3916.

Example 13: Preparation of 7-cyclopentyl-2-((5-(4-(2-(2-((2-(2,6-dioxopiperidin-3-yl)-1,3-dioxoisoindolin-4-yl)thio)ethoxy)acetyl)piperazin-1-yl)pyridin-2-yl)amino)-N,N-dimethyl-7H-pyrrolo[2,3-d]pyrimidine-6-carboxamide (SIAIS219111)

According to the general method described in Scheme 22, the target compound (SIAIS219111) was prepared by using Rebosini inhibitor and LIN-ULM (SIAIS1204137) under appropriate conditions that will be recognized by one skilled in the art. (Yellow Solid, 8.2 mg, yield Rate 44%). $^1$H NMR (500 MHz, DMSO) δ 11.55 (s, 1H), 11.11 (s, 1H), 9.57 (s, 1H), 9.01 (d, J=8.1 Hz, 1H), 8.08 (td, J=9.3, 2.6 Hz, 1H), 7.84-7.74 (m, 2H), 7.68-7.57 (m, 2H), 6.83 (d, J=2.0 Hz, 1H), 5.11 (dd, J=12.7, 5.3 Hz, 1H), 4.81 (p, J=8.8 Hz, 1H), 3.79-3.75 (m, 2H), 3.60 (d, J=12.8 Hz, 4H), 3.39-3.34 (m, 4H), 3.27-3.14 (m, 4H), 3.06 (s, 6H), 2.92-2.83 (m, 1H), 2.59-2.56 (m, 1H), 2.54-2.51 (m, 1H), 2.37-2.25 (m, 2H), 2.05-1.98 (m, 5H), 1.70-1.60 (m, 2H). HRMS (ESI) m/z: calcd for, $C_{40}H_{45}N_{10}O_7S^+$ [M+H]$^+$, 809.3188; found, 809.3181.

Example 14: Preparation of 7-cyclopentyl-2-((5-(4-(2-(2-(2-((2-(2,6-dioxopiperidin-3-yl)-1,3-dioxoisoindolin-4-yl)thio)ethoxy)ethoxy)acetyl)piperazin-1-yl)pyridin-2-yl)amino)-N,N-dimethyl-7H-pyrrolo[2,3-d]pyrimidine-6-carboxamide (SIAIS219112)

According to the general method described in Scheme 22, the target compound (SIAIS219112) was prepared by using Rebosini inhibitor and LIN-ULM (SIAIS1204139) under appropriate conditions that will be recognized by one skilled in the art. (yellow solid, 9.2 mg, yield 47%) $^1$H NMR (500 MHz, DMSO) δ 11.48 (s, 1H), 11.12 (s, 1H), 9.48 (s, 1H), 8.99 (d, J=11.7 Hz, 1H), 8.02 (dd, J=39.3, 4.8 Hz, 1H), 7.83-7.71 (m, 2H), 7.69-7.53 (m, 2H), 6.83 (s, 1H), 5.11 (dd, J=13.1, 5.5 Hz, 1H), 4.85-4.76 (m, 1H), 3.74-3.70 (m, 2H), 3.62-3.58 (m, 6H), 3.45 (s, 4H), 3.29-3.14 (m, 6H), 3.06 (s, 6H), 2.89-2.85 (m, 1H), 2.59 (d, J=15.7 Hz, 1H), 2.54-2.51 (m, 1H), 2.32 (d, J=9.0 Hz, 2H), 2.08-1.93 (m, 5H), 1.70-1.59 (m, 2H). HRMS (ESI) m/z: calcd for, $C_{42}H_{49}N_{10}O_8S^+$ [M+H]$^+$, 853.3450; found, 853.3440.

Example 15: Preparation of 7-cyclopentyl-2-((5-(4-(2-(2-(2-(2-((2-(2,6-dioxopiperidin-3-yl)-1,3-dioxoisoindolin-4-yl)thio)ethoxy)ethoxy)ethoxy)acetyl)piperazin-1-yl)pyridin-2-yl)amino)-N,N-dimethyl-7H-pyrrolo[2,3-d]pyrimidine-6-carboxamide (SIAIS219113)

According to the general method described in Scheme 22, under appropriate conditions that will be recognized by one skilled in the art, the target compound (SIAIS219113) was prepared by using Rebosini inhibitor and LIN-ULM (SIAIS1204147). (yellow solid, 9.2 mg, yield 45%) $^1$H NMR (500 MHz, DMSO) δ 11.34 (s, 1H), 11.12 (s, 1H), 8.97 (s, 1H), 8.00 (d, J=23.0 Hz, 1H), 7.87 (d, J=2.6 Hz, 1H), 7.81-7.72 (m, 2H), 7.64-7.55 (m, 2H), 6.80 (d, J=5.7 Hz, 1H), 5.10 (dd, J=12.9, 5.5 Hz, 1H), 4.79 (dd, J=17.6, 8.8 Hz, 1H), 4.20 (s, 2H), 3.71 (t, J=6.3 Hz, 2H), 3.64-3.55 (m, 10H), 3.41 (s, 4H), 3.19-3.15 (m, 4H), 3.06 (s, 6H), 2.92-2.84 (m, 1H), 2.65-2.53 (m, 2H), 2.31 (s, 2H), 2.07-1.94 (m, 5H), 1.72-1.60 (m, 2H). HRMS (ESI) m/z: calcd for, $C_{44}H_{53}N_{10}O_9S^+$ [M+H]$^+$, 897.3712; found, 897.3701.

Example 16: Preparation of 7-cyclopentyl-2-((5-(4-(14-((2-(2,6-dioxopiperidin-3-yl)-1,3-dioxoisoindolin-4-yl)thio)-3,6,9,12-tetraoxatetradecanoyl)piperazin-1-yl)pyridin-2-yl)amino)-N,N-dimethyl-7H-pyrrolo[2,3-d]pyrimidine-6-carboxamide (SIAIS219114)

According to the general method described in Scheme 22, the target compound (SIAIS219114) was prepared by using Rebosini inhibitor and LIN-ULM (SIAIS1204147) under appropriate conditions that will be recognized by one skilled in the art. (yellow solid, 9.7 mg, yield 45%) $^1$H NMR (500

MHz, DMSO) δ 11.41 (s, 1H), 11.12 (s, 1H), 9.39 (s, 1H), 9.02-8.95 (m, 1H), 8.11-7.99 (m, 1H), 7.81-7.73 (m, 2H), 7.64-7.61 (m, 2H), 6.82 (d, J=7.7 Hz, 1H), 5.11 (dd, J=12.9, 4.9 Hz, 1H), 4.80 (p, J=8.7 Hz, 1H), 3.70 (q, J=6.2 Hz, 2H), 3.64-3.47 (m, 18H), 3.28-3.13 (m, 6H), 2.93-2.84 (m, 1H), 2.59 (d, J=17.0 Hz, 1H), 2.53 (dd, J=11.7, 6.6 Hz, 1H), 2.34-2.31 (m, 2H), 2.07-1.95 (m, 5H), 1.65 (d, J=5.4 Hz, 2H). HRMS (ESI) m/z: calcd for, $C_{46}H_{57}N_{10}O_{10}S^+$ [M+H]$^+$, 941.3974; found, 941.3966.

Example 17: Preparation of 7-cyclopentyl-2-((5-(4-(17-((2-(2,6-dioxopiperidin-3-yl)-1,3-dioxoisoindolin-4-yl)thio)-3,6,9,12,15-pentaoxaheptadecanoyl)piperazin-1-yl)pyridin-2-yl)amino)-N,N-dimethyl-7H-pyrrolo[2,3-d]pyrimidine-6-carboxamide (SIAIS219115)

According to the general method described in Scheme 22, the target compound (SIAIS219115) was prepared by using the Rebosini inhibitor and LIN-ULM (SIAIS1204149) under appropriate conditions that will be recognized by one skilled in the art. (Yellow solid, 10.1 mg, yield 45%) $^1$H NMR (500 MHz, DMSO) δ 11.27 (s, 1H), 11.12 (s, 1H), 9.24 (s, 1H), 8.96 (d, J=5.1 Hz, 1H), 8.05-7.99 (m, 1H), 7.79-7.74 (m, 2H), 7.68-7.58 (m, 2H), 6.79 (d, J=7.4 Hz, 1H), 5.17-5.05 (m, 1H), 4.86-4.74 (m, 1H), 3.69 (t, J=6.7 Hz, 2H), 3.59-3.48 (m, 22H), 3.19-3.15 (m, 6H), 2.94-2.83 (m, 1H), 2.64-2.52 (m, 2H), 2.36-2.33 (m, 2H), 2.09-1.91 (m, 5H), 1.65 (d, J=5.7 Hz, 2H). HRMS (ESI) m/z: calcd for, $C_{48}H_{61}N_{10}O_{11}S^+$ [M+H]$^+$, 985.4236; found, 985.4231.

Example 18: Preparation of 7-cyclopentyl-2-((5-(4-(2-(2-((2-(2,6-dioxopiperidin-3-yl)-1-oxoisoindolin-4-yl)thio)ethoxy)acetyl)piperazin-1-yl)pyridin-2-yl)amino)-N,N-dimethyl-7H-pyrrolo[2,3-d]pyrimidine-6-carboxamide (SIAIS219106)

According to the general method described in Scheme 22, the target compound (SIAIS219106) was prepared by using Rebosini inhibitor and LIN-ULM (SIAIS1213129) under appropriate conditions that will be recognized by one skilled in the art. (yellow solid, 7.8 mg, yield 43%). $^1$H NMR (500 MHz, DMSO) δ 10.99 (s, 1H), 8.81 (s, 1H), 8.03 (s, 1H), 7.97 (s, 1H), 7.70 (d, J=7.0 Hz, 1H), 7.57 (d, J=6.8 Hz, 1H), 7.52 (t, J=7.6 Hz, 1H), 6.65 (s, 1H), 6.52 (s, 1H), 5.12 (dd, J=13.3, 5.1 Hz, 1H), 4.79-4.69 (m, 1H), 4.38 (d, J=17.4 Hz, 1H), 4.25 (d, J=15.3 Hz, 3H), 3.69 (t, J=6.4 Hz, 2H), 3.59-3.55 (m, 4H), 3.17-3.03 (m, 10H), 2.95-2.85 (m, 1H), 2.58 (d, J=16.6 Hz, 1H), 2.48-2.37 (m, 3H), 1.99-1.93 (m, 5H), 1.64 (d, J=5.7 Hz, 2H), 1.27-1.24 (m, 2H). HRMS (ESI) m/z: calcd for, $C_{40}H_{47}N_{10}O_6S^+$ [M+H]$^+$, 795.3395; found, 795.3391.

Example 19: Preparation of 7-cyclopentyl-2-((5-(4-(2-(2-(2-((2-(2,6-dioxopiperidin-3-yl)-1-oxoisoindolin-4-yl)thio)ethoxy)ethoxy)acetyl)piperazin-1-yl)pyridin-2-yl)amino)-N,N-dimethyl-7H-pyrrolo[2,3-d]pyrimidine-6-carboxamide (SIAIS219107)

According to the general method described in Scheme 22, the target compound (SIAIS219107) was prepared by using Rebosini inhibitor and LIN-ULM (SIAIS1213131) under appropriate conditions that will be recognized by one skilled in the art. (yellow solid, 7.5 mg, yield 39%). $^1$H NMR (500 MHz, DMSO) δ 10.99 (s, 1H), 9.70 (s, 1H), 8.81 (s, 1H), 8.03 (s, 1H), 7.98 (d, J=2.7 Hz, 1H), 7.67 (dd, J=7.7, 0.9 Hz, 1H), 7.60-7.54 (m, 2H), 7.51 (t, J=7.6 Hz, 1H), 6.64 (s, 1H), 5.11 (dd, J=13.3, 5.1 Hz, 1H), 4.74 (dd, J=17.5, 8.7 Hz, 1H), 4.36 (d, J=17.4 Hz, 1H), 4.23 (d, J=17.4 Hz, 1H), 4.19 (s, 2H), 3.66-3.59 (m, 4H), 3.56 (s, 6H), 3.25 (t, J=6.3 Hz, 2H), 3.15-3.09 (m, 4H), 3.05 (s, 4H), 2.95-2.85 (m, 1H), 2.58 (d, J=17.4 Hz, 1H), 2.47-2.35 (m, 3H), 1.99-1.95 (m, 5H), 1.68-1.58 (m, 2H), 1.26 (dt, J=7.4, 5.3 Hz, 2H). HRMS (ESI) m/z: calcd for, $C_{42}H_{51}N_{10}O_7S+$ [M+H]$^+$, 839.3657; found, 839.3651.

Example 20: Preparation of 7-cyclopentyl-2-((5-(4-(2-(2-(2-(2-((2-(2,6-dioxopiperidin-3-yl)-1-oxoisoindolin-4-yl)thio)ethoxy)ethoxy)ethoxy)acetyl)piperazin-1-yl)pyridin-2-yl)amino)-N,N-dimethyl-7H-pyrrolo[2,3-d]pyrimidine-6-carboxamide (SIAIS219108)

According to the general method described in Scheme 22, the target compound (SIAIS219108) was prepared by using Rebosini inhibitor and LIN-ULM (SIAIS1213133) under appropriate conditions that will be recognized by one skilled in the art. (yellow solid, 9.1 mg, yield, 45%). $^1$H NMR (500 MHz, DMSO) δ 10.99 (s, 1H), 8.88 (s, 1H), 7.92 (s, 1H), 7.81 (s, 1H), 7.65 (d, J=7.0 Hz, 1H), 7.55 (d, J=6.8 Hz, 1H), 7.50 (t, J=7.6 Hz, 1H), 6.72 (s, 1H), 5.11 (dd, J=13.2, 5.1 Hz, 1H), 4.78-4.73 (m, 1H), 4.35 (d, J=17.4 Hz, 1H), 4.22 (d, J=19.7 Hz, 3H), 3.61-3.51 (m, 12H), 3.23 (d, J=6.4 Hz, 2H), 3.16-3.12 (m, 4H), 3.06 (s, 6H), 2.92-2.88 (m, 1H), 2.58 (d, J=16.9 Hz, 1H), 2.45 (m, 1H), 2.36 (s, 2H), 2.05-1.93 (m, 5H), 1.64 (d, J=5.9 Hz, 2H), 1.26 (dd, J=7.0, 3.4 Hz, 2H). HRMS (ESI) m/z: calcd for, $C_{44}H_{55}N_{10}O_8S^+$ [M+H]$^+$, 883.3920; found, 883.3912.

Example 21: Preparation of 7-cyclopentyl-2-((5-(4-(14-((2-(2,6-dioxopiperidin-3-yl)-1-oxoisoindolin-4-yl)thio)-3,6,9,12-tetraoxatetradecanoyl)piperazin-1-yl)pyridin-2-yl)amino)-N,N-dimethyl-7H-pyrrolo[2,3-d]pyrimidine-6-carboxamide (SIAIS219109)

According to the general method described in Scheme 22, the target compound (SIAIS219109) was prepared by using Rebosini inhibitor and LIN-ULM (SIAIS1213135) under appropriate conditions that will be recognized by one skilled in the art. (yellow solid, 9.3 mg, yield 44%). $^1$H NMR (500 MHz, DMSO) δ 10.99 (s, 1H), 9.70 (s, 1H), 8.80 (s, 1H), 8.06 (s, 1H), 7.99 (d, J=2.8 Hz, 1H), 7.65 (dd, J=7.7, 0.7 Hz, 1H), 7.56 (d, J=6.9 Hz, 1H), 7.51 (td, J=7.5, 3.2 Hz, 1H), 6.63 (s, 1H), 5.12 (dd, J=13.3, 5.1 Hz, 1H), 4.74 (p, J=8.8 Hz, 1H), 4.39-4.33 (m, 1H), 4.26-4.17 (m, 3H), 3.62-3.55 (m, 8H), 3.49 (d, J=6.6 Hz, 6H), 3.16-3.03 (m, 10H), 2.94-2.85 (m, 1H), 2.58 (d, J=17.4 Hz, 1H), 2.48-2.37 (m, 3H), 2.00-1.95 (m, 5H), 1.64 (d, J=5.5 Hz, 2H), 1.26 (dd, J=7.0, 3.7 Hz, 2H). HRMS (ESI) m/z: calcd for, $C_{46}H_{59}N_{10}O_9S^+$ [M+H]$^+$, 927.4182; found, 927.4185.

Example 22: Preparation of 7-cyclopentyl-2-((5-(4-(17-((2-(2,6-dioxopiperidin-3-yl)-1-oxoisoindolin-4-yl)thio)-3,6,9,12,15-pentaoxaheptadecanoyl)piperazin-1-yl)pyridin-2-yl)amino)-N,N-dimethyl-7H-pyrrolo[2,3-d]pyrimidine-6-carboxamide (SIAIS219110)

According to the general method described in Scheme 22, under appropriate conditions that will be recognized by one skilled in the art, the target compound (SIAIS219110) was prepared by using Rebosini inhibitor and LIN-ULM (SIAIS1213137). (yellow solid, 9.5 mg, yield, 43%). $^1$H NMR (500 MHz, DMSO) δ 11.01 (s, 1H), 9.71 (s, 1H), 8.81

(s, 1H), 8.08 (s, 1H), 7.99 (d, J=2.8 Hz, 1H), 7.67 (dd, J=7.7, 0.7 Hz, 1H), 7.58 (d, J=6.9 Hz, 2H), 7.55-7.50 (m, 1H), 6.65 (s, 1H), 5.13 (dd, J=13.3, 5.1 Hz, 1H), 4.76 (p, J=8.8 Hz, 1H), 4.41-4.33 (m, 1H), 4.28-4.19 (m, 3H), 3.65-3.56 (m, 12H), 3.49 (d, J=6.6 Hz, 6H), 3.18-3.03 (m, 10H), 2.96-2.87 (m, 1H), 2.59 (d, J=17.4 Hz, 1H), 2.49-2.38 (m, 3H), 2.01-1.97 (m, 5H), 1.66 (d, J=5.5 Hz, 2H), 1.27 (dd, J=7.0, 3.7 Hz, 2H). HRMS (ESI) m/z: calcd for, $C_{48}H_{63}N_{10}O_{10}S^+$ $[M+H]^+$, 971.4444; found, 971.4438.

Example 23: Preparation of 3-(4-((2-(4-(((6-((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)-2-oxoethyl)thio)-1-oxoisoindolin-2-yl)piperidine-2,6-dione (SIAIS262164)

According to the general method described in Scheme 22, the target compound (SIAIS262164) was prepared by using Abemaciclib derivatives and LIN-ULM (SIAIS171090) under appropriate conditions that will be recognized by one skilled in the art. (yellow solid, 7.2 mg, yield 43%) $^1$H NMR (500 MHz, MeOD) δ 8.88 (s, 1H), 8.56 (s, 2H), 8.39 (d, J=9.3 Hz, 1H), 8.16 (d, J=11.2 Hz, 1H), 7.81 (d, J=7.8 Hz, 1H), 7.74 (dt, J=27.9, 14.2 Hz, 2H), 7.57 (t, J=7.7 Hz, 1H), 5.15 (ddd, J=20.2, 13.2, 5.6 Hz, 2H), 4.56 (d, J=17.5 Hz, 1H), 4.50 (d, J=13.9 Hz, 1H), 4.47 (d, J=7.6 Hz, 2H), 3.99 (dt, J=18.8, 9.3 Hz, 2H), 3.30 (s, 8H), 2.95 (s, 3H), 2.93-2.87 (m, 1H), 2.80 (dd, J=15.4, 2.2 Hz, 1H), 2.56 (ddd, J=25.9, 13.2, 4.5 Hz, 1H), 2.24-2.15 (m, 1H), 1.81 (d, J=6.9 Hz, 6H). HRMS (ESI) m/z: calcd for, $C_{40}H_{41}F_2N_{10}O_4S^+$ $[M+H]^+$, 795.2996; found, 795.3002.

Example 24: Preparation of 3-(4-(((3-(4-(((6-((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)-3-oxopropyl)thio)-1-oxoisoindolin-2-yl)piperidine-2,6-dione (SIAIS262165)

According to the general method described in Scheme 22, the target compound (SIAIS262165) was prepared by using Abemaciclib derivatives and LIN-ULM (SIAIS171086) under appropriate conditions that will be recognized by one skilled in the art. (yellow solid, 6.9 mg, yield 41%) $^1$H NMR (500 MHz, MeOD) δ 8.88 (d, J=3.1 Hz, 1H), 8.57 (s, 2H), 8.41 (d, J=9.6 Hz, 1H), 8.17 (d, J=11.2 Hz, 1H), 7.77 (d, J=9.0 Hz, 1H), 7.70 (dd, J=16.5, 7.4 Hz, 2H), 7.56 (t, J=7.7 Hz, 1H), 5.21-5.11 (m, 2H), 4.53-4.39 (m, 4H), 3.40-3.32 (m, 6H), 3.30-3.23 (m, 4H), 2.96 (s, 3H), 2.93-2.87 (m, 1H), 2.83-2.75 (m, 3H), 2.57-2.53 (m, 1H), 2.24-2.14 (m, 1H), 1.81 (d, J=6.9 Hz, 6H). HRMS (ESI) m/z: calcd for, $C_{41}H_{43}F_2N_{10}O_4S^+$ $[M+H]^+$, 809.3152; found, 809.3134.

Example 25: Preparation of 3-(4-((4-(4-(((6-((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)-4-oxobutyl)thio)-1-oxoisoindolin-2-yl)piperidine-2,6-dione (SIAIS262166)

According to the general method described in Scheme 22, the target compound (SIAIS262166) was prepared by using Abemaciclib derivatives and LIN-ULM (SIAIS171089) under appropriate conditions that will be recognized by one skilled in the art. (yellow solid, 7.4 mg, yield 43%) $^1$H NMR (500 MHz, MeOD) δ 8.89 (s, 1H), 8.57 (s, 2H), 8.40 (s, 1H), 8.17 (d, J=10.9 Hz, 1H), 7.81 (s, 1H), 7.72 (d, J=7.7 Hz, 1H), 7.67 (d, J=7.4 Hz, 1H), 7.55 (t, J=7.7 Hz, 1H), 5.14 (dd, J=11.6, 4.7 Hz, 2H), 4.45 (dt, J=17.4, 15.0 Hz, 4H), 3.67-3.33 (m, 4H), 3.30-3.01 (m, 6H), 2.95 (s, 3H), 2.92-2.86 (m, 1H), 2.79 (d, J=17.8 Hz, 1H), 2.62-2.50 (m, 3H), 2.25-2.17 (m, 1H), 2.00-1.92 (m, 2H), 1.81 (d, J=6.9 Hz, 6H). HRMS (ESI) m/z: calcd for, $C_{42}H_{45}F_2N_{10}O_4S^+$ $[M+H]^+$, 823.3309; found, 823.3294.

Example 26: Preparation of 3-(4-((5-(4-(((6-((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)-5-oxopentyl)thio)-1-oxoisoindolin-2-yl)piperidine-2,6-dione (SIAIS262167)

According to the general method described in Scheme 22, the target compound (SIAIS262167) was prepared by using Abemaciclib derivatives and LIN-ULM (SIAIS171079) under appropriate conditions that will be recognized by one skilled in the art. (yellow solid, 7.8 mg, yield 44%) $^1$H NMR (500 MHz, MeOD) δ 8.91 (d, J=3.1 Hz, 1H), 8.64 (d, J=1.7 Hz, 1H), 8.59 (s, 1H), 8.49 (dd, J=9.1, 1.9 Hz, 1H), 8.19 (d, J=11.2 Hz, 1H), 7.74 (d, J=9.1 Hz, 1H), 7.66 (t, J=8.0 Hz, 2H), 7.57-7.50 (m, 1H), 5.21-5.13 (m, 2H), 4.52 (s, 2H), 4.48 (d, J=17.3 Hz, 1H), 4.41 (d, J=17.4 Hz, 1H), 3.32 (s, 6H), 3.22-3.05 (m, 4H), 2.97 (s, 3H), 2.94-2.86 (m, 1H), 2.82-2.76 (m, 1H), 2.59-2.53 (m, 1H), 2.45 (t, J=7.1 Hz, 2H), 2.22-2.16 (m, 1H), 1.82 (d, J=6.9 Hz, 6H), 1.76-1.73 (m, 4H). HRMS (ESI) m/z: calcd for, $C_{43}H_{47}F_2N_{10}O_4S^+$ $[M+H]^+$, 837.3465; found, 837.3450.

Example 27: Preparation of 3-(4-((6-(4-(((6-((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)-6-oxohexyl)thio)-1-oxoisoindolin-2-yl)piperidine-2,6-dione (SIAIS262168)

According to the general method described in Scheme 22, the target compound (SIAIS262168) was prepared by using Abemaciclib derivatives and LIN-ULM (SIAIS171091) under appropriate conditions that will be recognized by one skilled in the art. (yellow solid, 8.4 mg, yield 47%) $^1$H NMR (500 MHz, MeOD) δ 8.88 (d, J=2.7 Hz, 1H), 8.62 (s, 1H), 8.57 (s, 1H), 8.45 (d, J=8.6 Hz, 1H), 8.16 (d, J=11.2 Hz, 1H), 7.82 (d, J=8.7 Hz, 1H), 7.66 (dd, J=7.7, 4.6 Hz, 2H), 7.53 (t, J=7.6 Hz, 1H), 5.20-5.11 (m, 2H), 4.45 (dd, J=29.1, 17.4 Hz, 4H), 3.73-3.32 (m, 6H), 3.23-3.02 (m, 4H), 2.94 (d, J=6.2 Hz, 3H), 2.93-2.86 (m, 1H), 2.82-2.75 (m, 1H), 2.58-2.53 (m, 1H), 2.39 (t, J=7.3 Hz, 2H), 2.25-2.17 (m, 1H), 1.81 (d, J=6.9 Hz, 6H), 1.69-1.65 (m, 2H), 1.64-1.61 (m, 2H), 1.56-1.48 (m, 2H). HRMS (ESI) m/z: calcd for, $C_{44}H_{49}F_2N_{10}O_4S^+$ $[M+H]^+$, 851.3622; found, 851.3614.

Example 28: Preparation of 3-(4-((7-(4-(((6-((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)-7-oxoheptyl)thio)-1-oxoisoindolin-2-yl)piperidine-2,6-dione (SIAIS262169)

According to the general method described in Scheme 22, the target compound (SIAIS262169) was prepared by using Abemaciclib derivatives and LIN-ULM (SIAIS171092) under appropriate conditions that will be recognized by one skilled in the art. (yellow solid, 8.3 mg, yield 46%) $^1$H NMR (500 MHz, MeOD) δ 8.91 (d, J=3.1 Hz, 1H), 8.66 (s, 1H), 8.59 (s, 1H), 8.50 (d, J=9.2 Hz, 1H), 8.19 (d, J=10.9 Hz, 1H), 7.77 (d, J=9.1 Hz, 1H), 7.65 (dd, J=6.5, 3.1 Hz, 1H), 7.54 (d, J=7.7 Hz, 1H), 7.32 (d, J=4.9 Hz, 1H), 5.19-5.14 (m, 2H), 4.53 (s, 2H), 4.47 (d, J=17.3 Hz, 1H), 4.40 (d, J=17.3 Hz, 1H), 3.63-3.35 (m, 4H), 3.19 (d, J=22.9 Hz, 4H), 3.09-3.05 (m, 2H), 2.97 (s, 3H), 2.93-2.86 (m, 2H), 2.82-2.77 (m, 1H), 2.54 (dd, J=13.1, 4.7 Hz, 1H), 2.41 (s, 1H), 2.22-2.17 (m, 1H), 1.82 (d, J=6.9 Hz, 6H), 1.71-1.67 (m, 2H), 1.59-1.55 (m, 2H), 1.51-1.47 (m, 2H), 1.39-1.35 (m, 2H). HRMS (ESI) m/z: calcd. for, $C_{45}H_{51}F_2N_{10}O_4S^+$ [M+H]$^+$, 865.3778; found, 865.3769.

Example 29: Preparation of 3-(4-((11-(4-((6-((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)-11-oxoundecyl)thio)-1-oxoisoindolin-2-yl)piperidine-2,6-dione (SIAIS262170)

According to the general method described in Scheme 22, the target compound (SIAIS262170) was prepared by using Abemaciclib derivatives and LIN-ULM (SIAIS1220099) under appropriate conditions that will be recognized by one skilled in the art. (yellow solid, 10.2 mg, yield 53%) $^1$H NMR (500 MHz, MeOD) δ 8.83 (d, J=3.2 Hz, 1H), 8.55 (d, J=9.9 Hz, 2H), 8.33 (d, J=7.2 Hz, 1H), 8.13 (d, J=11.2 Hz, 1H), 7.93 (s, 1H), 7.62 (d, J=8.0 Hz, 2H), 7.52 (t, J=7.7 Hz, 1H), 5.18-5.09 (m, 2H), 4.46-4.41 (m, 4H), 3.40 (d, J=49.0 Hz, 4H), 3.22 (s, 4H), 3.05 (t, J=6.9 Hz, 2H), 2.96-2.88 (m, 4H), 2.80 (dd, J=10.1, 7.8 Hz, 1H), 2.56-2.52 (m, 1H), 2.42 (t, J=7.5 Hz, 2H), 2.19-2.16 (m, 1H), 1.80 (d, J=6.9 Hz, 6H), 1.69-1.55 (m, 4H), 1.46-1.41 (m, 2H), 1.30 (s, 10H). HRMS (ESI) m/z: calcd for, $C_{49}H_{59}F_2N_{10}O_4S^+$ [M+H]$^+$, 921.4404; found, 921.4411.

Example 30: Preparation of 3-(4-((2-(2-(4-((6-((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)-2-oxoethoxy)ethyl)thio)-1-oxoisoindolin-2-yl)piperidine-2,6-dione (SIAIS262171)

According to the general method described in Scheme 22, the target compound (SIAIS262171) was prepared by using Abemaciclib derivatives and LIN-ULM (SIAIS1213129) under appropriate conditions that will be recognized by one skilled in the art. (yellow solid, 8.4 mg, yield 48%) $^1$H NMR (500 MHz, MeOD) δ 8.85 (s, 1H), 8.55 (s, 2H), 8.36 (s, 1H), 8.15 (d, J=10.9 Hz, 1H), 7.83 (s, 1H), 7.73 (d, J=7.7 Hz, 1H), 7.69-7.65 (m, 1H), 7.54 (t, J=7.6 Hz, 1H), 5.15 (dd, J=18.3, 5.3 Hz, 2H), 4.49-4.46 (m, 4H), 3.81-3.68 (m, 4H), 3.50-3.34 (m, 4H), 3.30-3.15 (m, 4H), 2.98-2.85 (m, 6H), 2.79-2.76 (m, 1H), 2.60-2.51 (m, 1H), 2.20 (dd, J=9.0, 4.2 Hz, 1H), 1.81 (d, J=6.9 Hz, 6H). HRMS (ESI) m/z: calcd. for, $C_{42}H_{45}F_2N_{10}O_5S^+$ [M+H]$^+$, 839.3258; found, 839.3257.

Example 31: Preparation of 4-((2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-2-oxoethyl)thio)-2-(2,6-dioxopiperidin-3-yl)isoindoline-1,3-dione (SIAIS151046)

According to the general method described in Scheme 22, under appropriate conditions that will be recognized by one skilled in the art, the target compound (SIAIS151046) was prepared with Palbociclib inhibitor and LIN-ULM (SIAIS151045). (yellow solid, 20 mg, yield 59%) $^1$H NMR (500 MHz, MeOD) δ 9.09 (s, 1H), 8.16 (dd, J=9.6, 2.7 Hz, 1H), 7.90-7.86 (m, 2H), 7.75 (t, J=7.7 Hz, 1H), 7.67 (d, J=7.3 Hz, 1H), 7.56 (d, J=9.6 Hz, 1H), 6.04-5.98 (m, 1H), 5.12 (dd, J=12.5, 5.4 Hz, 1H), 4.21 (s, 2H), 3.92-3.76 (m, 4H), 3.43-3.38 (m, 2H), 3.28-3.26 (m, 2H), 2.89-2.83 (m, 1H), 2.79-2.64 (m, 2H), 2.50 (s, 3H), 2.43 (s, 3H), 2.38-2.26 (m, 2H), 2.15-2.07 (m, 3H), 1.96-1.86 (m, 2H), 1.72-1.68 (m, 2H). HRMS (ESI) calcd for, $C_{39}H_{40}N_9O_7S^+$ [M+H]$^+$, 778.2766; found, 778.2209.

Example 32: Preparation of 4-((2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-2-oxoethyl)sulfinyl)-2-(2,6-dioxopiperidin-3-yl)isoindoline-1,3-dione (SIAIS151057)

According to the general method described in Scheme 22, under appropriate conditions that will be recognized by one skilled in the art, the target compound (SIAIS151057) was prepared by using Palbociclib inhibitor and LIN-ULM (SIAIS151107). (yellow solid, 26.5 mg, yield 72%) $^1$H NMR (500 MHz, MeOD) δ 9.10 (d, J=2.3 Hz, 1H), 8.31 (dt, J=7.6, 1.1 Hz, 1H), 8.17 (d, J=9.6 Hz, 1H), 8.14-8.07 (m, 2H), 7.88 (d, J=2.9 Hz, 1H), 7.57 (dd, J=9.6, 1.9 Hz, 1H), 6.04-5.98 (m, 1H), 5.21-5.16 (m, 1H), 4.59 (dd, J=19.3, 14.5 Hz, 1H), 4.10 (d, J=14.5 Hz, 1H), 3.93-3.86 (m, 2H), 3.78-3.68 (m, 2H), 3.46-3.23 (m, 4H), 2.92-2.85 (m, 1H), 2.80-2.68 (m, 2H), 2.50 (s, 3H), 2.43 (s, 3H), 2.36-2.28 (m, 2H), 2.21-2.15 (m, 1H), 2.13-2.06 (m, 2H), 1.94-1.88 (m, 2H), 1.74-1.68 (m, 2H). HRMS (ESI) calcd for, $C_{39}H_{40}N_9O_8S^+$ [M+H]$^+$, 794.2715; found, 794.2978.

Example 33: Preparation of 4-((2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-2-oxoethyl)sulfonyl)-2-(2,6-dioxopiperidin-3-yl)isoindoline-1,3-dione (SIAIS151056)

According to the general method described in Scheme 22, and under appropriate conditions that will be recognized by one skilled in the art, the target compound (SIAIS151056) was prepared by using Palbociclib inhibitor and LIN-ULM (SIAIS151106). (yellow solid, 22.7 mg, yield 63%) $^1$H NMR (500 MHz, MeOD) δ 9.10 (s, 1H), 8.37 (d, J=7.9 Hz, 1H), 8.25 (d, J=7.5 Hz, 1H), 8.20 (dd, J=9.6, 2.8 Hz, 1H), 8.09 (t, J=7.7 Hz, 1H), 7.87 (d, J=2.8 Hz, 1H), 7.55 (d, J=9.6 Hz, 1H), 6.04-5.98 (m, 1H), 5.24 (dd, J=12.4, 5.5 Hz, 1H), 5.06 (s, 2H), 4.21 (s, 2H), 4.01-3.96 (m, 2H), 3.46-3.42 (m, 2H), 3.30-3.26 (m, 2H), 2.93-2.86 (m, 1H), 2.80-2.70 (m, 2H), 2.50 (s, 3H), 2.43 (s, 3H), 2.35-2.28 (m, 2H), 2.23-2.17 (m, 3H), 1.94-1.87 (m, 2H), 1.72-1.68 (m, 2H). HRMS (ESI) calcd. for, $C_{39}H_{40}N_9O_9S^+$ [M+H]$^+$, 810.2664; found, 810.2929.

Example 34: Preparation of 4-((3-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-3-oxopropyl)thio)-2-(2,6-dioxopiperidin-3-yl)isoindoline-1,3-dione (SIAIS184086)

According to the general method described in Scheme 22, under appropriate conditions that will be recognized by one skilled in the art, the target compound (SIAIS184086) was prepared by using Palbociclib inhibitor and LIN-ULM (SIAIS151138B). (yellow solid, 11.1 mg, yield 42%) $^1$H NMR (500 MHz, MeOD) δ 9.11 (s, 1H), 8.18 (dd, J=9.7, 2.9

Hz, 1H), 7.84 (d, J=2.9 Hz, 1H), 7.82-7.74 (m, 2H), 7.63 (dd, J=6.7, 1.4 Hz, 1H), 7.53 (d, J=9.6 Hz, 1H), 6.01 (dd, J=17.7, 8.8 Hz, 1H), 5.10 (dd, J=12.7, 5.5 Hz, 1H), 3.80 (d, J=5.1 Hz, 2H), 3.77-3.70 (m, 2H), 3.46 (t, J=6.8 Hz, 2H), 3.30-3.23 (m, 6H), 2.93 (t, J=6.9 Hz, 2H), 2.89-2.84 (m, 1H), 2.78-2.69 (m, 1H), 2.51 (s, 3H), 2.44 (s, 3H), 2.35-2.28 (m, 2H), 2.16-2.05 (m, 3H), 1.95-1.88 (m, 2H), 1.73-1.66 (m, 2H). HRMS (ESI) m/z: calcd for, $C_{40}H_{42}N_9O_7S^+$ $[M+H]^+$, 792.2922; found, 792.2925.

Example 35: Preparation of 4-((4-(4-(6-((6-acetyl-8-cyclopentyl-5-methyl-7-oxo-7,8-dihydropyrido [2,3-d]pyrimidin-2-yl)amino)pyridin-3-yl)piperazin-1-yl)-4-oxobutyl)thio)-2-(2,6-dioxo Piperidin-3-yl) isoindoline-1,3-dione (SIAIS184087)

According to the general method described in Scheme 22, under appropriate conditions that will be recognized by one skilled in the art, the target compound (SIAIS184087) was prepared by using Palbociclib inhibitor and LIN-ULM (SIAIS151139B). (yellow solid, 11.5 mg, yield 43%) $^1$H NMR (500 MHz, MeOD) δ 9.11 (s, 1H), 8.18 (dd, J=9.7, 2.9 Hz, 1H), 7.86-7.79 (m, 2H), 7.77-7.71 (m, 1H), 7.59 (d, J=7.2 Hz, 1H), 7.52 (d, J=9.6 Hz, 1H), 6.09-5.98 (m, 1H), 5.14-5.10 (m, 1H), 3.82-3.76 (m, 4H), 3.29-3.21 (m, 6H), 2.92-2.82 (m, 1H), 2.79-2.66 (m, 4H), 2.51 (s, 3H), 2.44 (s, 3H), 2.33 (s, 2H), 2.16-2.07 (m, 5H), 1.93 (d, J=7.8 Hz, 2H), 1.70 (d, J=5.1 Hz, 2H). HRMS (ESI) m/z: calcd for, $C_{41}H_{44}N_9O_7S^+$ $[M+H]^+$, 806.3079; found, 806.3082.

Example 36: Preparation of 4-((5-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-5-oxopentyl)thio)-2-(2,6-dioxopiperidin-3-yl) isoindoline-1,3-dione (SIAIS184088)

According to the general method described in Scheme 22, under appropriate conditions that will be recognized by one skilled in the art, the target compound (SIAIS184088) was prepared by using Palbociclib inhibitor and LIN-ULM (SIAIS151140B). (yellow solid, 10.8 mg, yield 39%) $^1$H NMR (500 MHz, MeOD) δ 9.10 (s, 1H), 8.17 (dd, J=9.6, 2.9 Hz, 1H), 7.83 (d, J=2.9 Hz, 1H), 7.72 (dd, J=6.7, 6.0 Hz, 2H), 7.57-7.52 (m, 2H), 6.02 (p, J=8.8 Hz, 1H), 5.08 (dd, J=12.7, 5.5 Hz, 1H), 3.80-3.75 (m, 4H), 3.29-3.18 (m, 6H), 2.87-2.82 (m, 1H), 2.77-2.66 (m, 2H), 2.55 (t, J=6.7 Hz, 2H), 2.51 (s, 3H), 2.44 (s, 3H), 2.35-2.31 (m, 2H), 2.14-2.07 (m, 3H), 1.95-1.83 (m, 6H), 1.73-1.67 (m, 2H). HRMS (ESI) m/z: calcd for, $C_{42}H_{46}N_9O_7S^+$ $[M+H]^+$, 820.3235; found, 820.3239.

Example 37: Preparation of 4-((6-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-6-oxohexyl)thio)-2-(2,6-dioxopiperidin-3-yl) isoindoline-1,3-dione (SIAIS184089)

According to the general method described in Scheme 22, under appropriate conditions that will be recognized by one skilled in the art, the target compound (SIAIS184089) was prepared by using Palbociclib inhibitor and LIN-ULM (SIAIS151141B). (yellow solid, 11.6 mg, yield 42%) $^1$H NMR (500 MHz, MeOD) δ 9.09 (s, 1H), 8.09 (t, J=9.1 Hz, 1H), 7.82 (d, J=2.8 Hz, 1H), 7.76-7.67 (m, 1H), 7.57-7.45 (m, 2H), 6.01 (p, J=8.8 Hz, 1H), 5.10 (dd, J=12.8, 5.5 Hz, 1H), 3.83-3.72 (m, 4H), 3.30-3.23 (m, 4H), 3.15 (t, J=7.1 Hz, 2H), 2.89-2.83 (m, 1H), 2.79-2.65 (m, 2H), 2.53-2.48 (m, 5H), 2.44 (s, 3H), 2.37-2.29 (m, 2H), 2.17-2.07 (m, 3H), 1.95-1.90 (m, 2H), 1.86-1.79 (m, 2H), 1.76-1.68 (m, 4H), 1.62-1.56 (m, 2H). HRMS (ESI) m/z: calcd for, $C_{43}H_{48}N_9O_7S^+$ $[M+H]^+$, 834.3392; found, 834.3386.

Example 38: Preparation of 4-((7-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-7-oxoheptyl)thio)-2-(2,6-dioxopiperidin-3-yl) isoindoline-1,3-dione (SIAIS184090)

According to the general method described in Scheme 22, under appropriate conditions that will be recognized by one skilled in the art, the target compound (SIAIS184090) was prepared by using Palbociclib inhibitor and LIN-ULM (SIAIS151142B). (yellow solid, 12.1 mg, yield 43%) $^1$H NMR (500 MHz, MeOD) δ 9.10 (s, 1H), 8.19 (dd, J=9.7, 3.0 Hz, 1H), 7.83 (d, J=2.9 Hz, 1H), 7.74-7.67 (m, 2H), 7.60-7.50 (m, 2H), 6.02 (p, J=8.8 Hz, 1H), 5.10 (dd, J=12.7, 5.5 Hz, 1H), 3.77 (d, J=10.4 Hz, 4H), 3.26 (t, J=11.8 Hz, 2H), 3.13 (t, J=7.1 Hz, 2H), 2.89-2.83 (m, 1H), 2.77-2.67 (m, 2H), 2.53-2.46 (m, 5H), 2.44 (s, 3H), 2.34-2.31 (m, 2H), 2.16-2.08 (m, 3H), 1.95-1.90 (m, 2H), 1.83-1.76 (m, 2H), 1.75-1.65 (m, 4H), 1.62-1.53 (m, 2H), 1.48-1.42 (m, 2H). HRMS (ESI) m/z: calcd for, $C_{44}H_{50}N_9O_7S^+$ $[M+H]^+$, 848.3548; found, 848.3540.

Example 39: Preparation of 3-(4-((2-(4-(6-((6-acetyl-8-cyclopentyl-5-methyl-7-oxo-7,8-dihydro-pyrido[2,3-d]pyrimidin-2-yl)amino)pyridin-3-yl) piperazin-1-yl)-2-oxoethyl)thio)-1-oxoisoindolin-2-yl)piperidine-2,6-dione (SIAIS219051)

According to the general method described in Scheme 22, under appropriate conditions that will be recognized by one skilled in the art, the target compound (SIAIS219051) was prepared by using Palbociclib inhibitor and LIN-ULM (SIAIS171090). (yellow solid, 9.8 mg, yield 38%) $^1$H NMR (500 MHz, MeOD) δ 9.12 (s, 1H), 8.17 (dd, J=9.6, 2.9 Hz, 1H), 7.83 (dd, J=8.5, 1.5 Hz, 2H), 7.73 (d, J=7.5 Hz, 1H), 7.56 (t, J=7.7 Hz, 1H), 7.53 (d, J=9.6 Hz, 1H), 6.02 (p, J=8.8 Hz, 1H), 5.17 (dd, J=13.4, 5.2 Hz, 1H), 4.58 (d, J=17.4 Hz, 1H), 4.51 (d, J=17.4 Hz, 1H), 4.06-3.97 (m, 2H), 3.79-3.70 (m, 4H), 3.27-3.14 (m, 4H), 2.95-2.87 (m, 1H), 2.81-2.76 (m, 1H), 2.57-2.53 (m, 1H), 2.50 (d, J=3.4 Hz, 4H), 2.44 (s, 3H), 2.35-2.30 (m, 2H), 2.23-2.16 (m, 1H), 2.10 (s, 2H), 1.94-1.88 (m, 2H), 1.76-1.67 (m, 2H), 1.31 (d, J=23.7 Hz, 2H). HRMS (ESI) m/z: calcd for, $C_{39}H_{42}N_9O_6S^+$ $[M+H]^+$, 764.2973; found, 764.2970.

Example 40: Preparation of 3-(4-((3-(4-(6-((6-acetyl-8-cyclopentyl-5-methyl-7-oxo-7,8-dihydro-pyrido[2,3-d]pyrimidin-2-yl)amino)pyridin-3-yl) piperazin-1-yl)-3-oxopropyl)thio)-1-oxoisoindolin-2-yl)piperidine-2,6-dione (SIAIS219052)

According to the general method described in Scheme 22, under appropriate conditions that will be recognized by one skilled in the art, the target compound (SIAIS219052) was prepared by using Palbociclib inhibitor and LIN-ULM (SIAIS171086). (yellow solid, 10.2 mg, yield 39%). $^1$H NMR (500 MHz, MeOD) δ 9.10 (s, 1H), 8.11 (d, J=7.4 Hz, 1H), 7.82 (d, J=2.7 Hz, 1H), 7.77-7.70 (m, 1H), 7.65 (d, J=6.9 Hz, 1H), 7.55 (t, J=7.7 Hz, 2H), 6.01 (p, J=8.9 Hz, 1H), 5.15 (dd, J=13.4, 5.2 Hz, 1H), 4.48 (d, J=17.3 Hz, 1H), 4.42 (d, J=17.3 Hz, 1H), 3.75 (s, 2H), 3.65 (s, 2H), 3.45-3.38 (m, 1H), 3.36-3.32 (m, 2H), 3.25-3.13 (m, 4H), 2.93-2.88

(m, 1H), 2.86-2.76 (m, 3H), 2.58-2.48 (m, 4H), 2.43 (s, 3H), 2.34-2.28 (m, 2H), 2.19-2.14 (m, 1H), 2.10 (s, 2H), 1.95-1.87 (m, 2H), 1.74-1.68 (m, 2H). HRMS (ESI) m/z: calcd for, $C_{40}H_{44}N_9O_6S^+$ [M+H]$^+$, 778.3130; found, 778.3127.

Example 41: Preparation of 3-(4-((4-(4-(6-((6-acetyl-8-cyclopentyl-5-methyl-7-oxo-7,8-dihydro-pyrido[2,3-d]pyrimidin-2-yl)amino)pyridin-3-yl)piperazin-1-yl)-4-oxobutyl)thio)-1-oxoisoindolin-2-yl)piperidine-2,6-dione (SIAIS219053)

According to the general method described in Scheme 22, under appropriate conditions that will be recognized by one skilled in the art, the target compound (SIAIS219053) was prepared by using Palbociclib inhibitor and LIN-ULM (SIAIS171089). (yellow solid, 11.2 mg, yield 42%) $^1$H NMR (500 MHz, MeOD) δ 9.11 (s, 1H), 8.10 (s, 1H), 7.80 (s, 1H), 7.70 (dd, J=7.7, 0.9 Hz, 1H), 7.55 (dt, J=15.2, 7.2 Hz, 3H), 6.01 (dd, J=17.7, 8.9 Hz, 1H), 5.16 (dd, J=13.3, 5.2 Hz, 1H), 4.50 (d, J=17.4 Hz, 1H), 4.44 (d, J=17.4 Hz, 1H), 3.80-3.69 (m, 2H), 3.66-3.63 (m, 2H), 3.24-3.12 (m, 5H), 3.09-3.05 (m, 1H), 2.96-2.88 (m, 1H), 2.83-2.79 (m, 1H), 2.68-2.53 (m, 3H), 2.51 (s, 3H), 2.44 (s, 3H), 2.35-2.30 (m, 2H), 2.25-2.16 (m, 1H), 2.10 (s, 2H), 2.02-1.97 (m, 2H), 1.96-1.89 (m, 2H), 1.76-1.67 (m, 2H). HRMS (ESI) m/z: calcd for, $C_{41}H_{48}N_9O_6S^+$ [M+H]$^+$, 792.3286; found, 792.3281.

Example 42: Preparation of 3-(4-((5-(4-(6-((6-acetyl-8-cyclopentyl-5-methyl-7-oxo-7,8-dihydro-pyrido[2,3-d]pyrimidin-2-yl)amino)pyridin-3-yl)piperazin-1-yl)-5-oxopentyl)thio)-1-oxoisoindolin-2-yl)piperidine-2,6-dione (SIAIS184092)

According to the general method described in Scheme 22, under appropriate conditions that will be recognized by one skilled in the art, the target compound (SIAIS184092) was prepared by using Palbociclib inhibitor and LIN-ULM (SIAIS171079). (yellow solid, 11.2 mg, yield 41%) $^1$H NMR (500 MHz, MeOD) δ 9.11 (d, J=4.3 Hz, 1H), 8.14 (dd, J=9.7, 2.9 Hz, 1H), 7.77 (d, J=2.9 Hz, 1H), 7.65 (dd, J=7.3, 1.3 Hz, 1H), 7.59-7.41 (m, 3H), 6.02 (p, J=8.8 Hz, 1H), 5.11 (dd, J=13.4, 5.2 Hz, 1H), 4.46 (d, J=17.3 Hz, 1H), 4.40 (d, J=17.3 Hz, 1H), 3.88-3.63 (m, 4H), 3.21-3.17 (m, 3H), 3.13-3.00 (m, 3H), 2.92-2.86 (m, 1H), 2.81-2.77 (m, 1H), 2.56-2.48 (m, 5H), 2.44 (s, 3H), 2.35-2.31 (m, 2H), 2.19-2.08 (m, 3H), 1.97-1.88 (m, 2H), 1.87-1.65 (m, 6H). HRMS (ESI) m/z: calcd for, $C_{42}H_{50}N_9O_6S^+$ [M+H]$^+$, 806.3443; found, 806.3433.

Example 43: Preparation of 3-(4-((6-(4-(6-((6-acetyl-8-cyclopentyl-5-methyl-7-oxo-7,8-dihydro-pyrido[2,3-d]pyrimidin-2-yl)amino)pyridin-3-yl)piperazin-1-yl)-6-oxohexyl)thio)-1-oxoisoindolin-2-yl)piperidine-2,6-dione (SIAIS219054)

According to the general method described in Scheme 22, under appropriate conditions that will be recognized by one skilled in the art, the target compound (SIAIS219054) was prepared by using Palbociclib inhibitor and LIN-ULM (SIAIS171091). (yellow solid, 11.5 mg, yield 42%) $^1$H NMR (500 MHz, MeOD) δ 9.12 (s, 1H), 8.16 (dd, J=9.7, 3.0 Hz, 1H), 7.79 (d, J=2.9 Hz, 1H), 7.62 (dd, J=7.6, 0.9 Hz, 1H), 7.57-7.47 (m, 3H), 6.02 (p, J=8.9 Hz, 1H), 5.14 (dd, J=13.3, 5.2 Hz, 1H), 4.45 (d, J=17.3 Hz, 1H), 4.40 (d, J=17.3 Hz, 1H), 3.80-3.66 (m, 4H), 3.23 (d, J=4.6 Hz, 2H), 3.15-3.07 (m, 2H), 2.95-2.88 (m, 1H), 2.81-2.76 (m, 1H), 2.58- 2.49 (m, 4H), 2.47-2.41 (m, 5H), 2.35-2.31 (m, 2H), 2.21-2.16 (m, 1H), 2.11 (s, 2H), 1.96-1.91 (m, 2H), 1.74-1.65 (m, 6H), 1.59-1.49 (m, 2H). HRMS (ESI) m/z: calcd for, $C_{43}H_{52}N_9O_6S^+$ [M+H]$^+$, 820.3599; found, 820.3591.

Example 44: Preparation of 3-(4-((7-(4-(6-((6-acetyl-8-cyclopentyl-5-methyl-7-oxo-7,8-dihydro-pyrido[2,3-d]pyrimidin-2-yl)amino)pyridin-3-yl)piperazin-1-yl)-7-oxoheptyl)thio)-1-oxoisoindolin-2-yl)piperidine-2,6-dione (SIAIS219055)

According to the general method described in Scheme 22, under appropriate conditions that will be recognized by one skilled in the art, the target compound (SIAIS219055) was prepared by using Palbociclib inhibitor and LIN-ULM (SIAIS171092). (yellow solid, 12.1 mg, yield 43%) $^1$H NMR (500 MHz, MeOD) δ 9.12 (s, 1H), 8.19 (dd, J=9.7, 2.9 Hz, 1H), 7.84 (d, J=2.8 Hz, 1H), 7.66-7.57 (m, 2H), 7.57-7.46 (m, 2H), 6.02 (p, J=8.8 Hz, 1H), 5.14 (dd, J=13.3, 5.2 Hz, 1H), 4.45 (d, J=17.3 Hz, 1H), 4.39 (d, J=17.3 Hz, 1H), 3.81-3.70 (m, 4H), 3.28-3.22 (m, 4H), 3.10-3.03 (m, 2H), 2.93-2.88 (m, 1H), 2.81-2.77 (m, 1H), 2.60-2.48 (m, 4H), 2.48-2.42 (m, 5H), 2.36-2.29 (m, 2H), 2.18 (m, 1H), 2.14-2.08 (m, 2H), 1.94-1.90 (m, 2H), 1.74-1.66 (m, 4H), 1.66-1.59 (m, 2H), 1.55-1.48 (m, 2H), 1.41 (dd, J=14.7, 7.4 Hz, 2H). HRMS (ESI) m/z: calcd for, $C_{44}H_{54}N_9O_6S^+$ [M+H]$^+$, 834.3756; found, 834.3750.

Example 45: Preparation of 4-((2-(2-(4-(6-((6-acetyl-8-cyclopentyl-5-methyl-7-oxo-7,8-dihydro-pyrido[2,3-d]pyrimidin-2-yl)amino)pyridin-3-yl)piperazin-1-yl)-2-oxoethoxy)ethyl)thio)-2-(2,6-dioxopiperidin-3-yl)isoindoline-1,3-dione (SIAIS184091)

According to the general method described in Scheme 22, under appropriate conditions that will be recognized by one skilled in the art, the target compound (SIAIS184091) was prepared by using Palbociclib inhibitor and LIN-ULM (SIAIS1204137). (yellow solid, 11.6 mg, yield 42%) $^1$H NMR (500 MHz, MeOD) δ 9.09 (d, J=8.7 Hz, 1H), 8.13 (d, J=9.4 Hz, 1H), 7.80 (d, J=7.6 Hz, 1H), 7.75-7.69 (m, 1H), 7.54 (dd, J=12.6, 8.4 Hz, 1H), 6.09-5.99 (m, 1H), 5.07 (dd, J=12.7, 5.5 Hz, 1H), 4.32-4.25 (m, 1H), 3.88 (t, J=5.7 Hz, 2H), 3.74 (d, J=3.9 Hz, 3H), 3.52-3.37 (m, 4H), 3.23 (d, J=23.4 Hz, 2H), 2.86-2.81 (m, 1H), 2.78-2.63 (m, 2H), 2.51 (d, J=1.7 Hz, 3H), 2.44 (d, J=1.2 Hz, 3H), 2.31 (d, J=8.0 Hz, 2H), 2.16-2.07 (m, 3H), 1.93 (d, J=9.2 Hz, 2H), 1.78-1.64 (m, 2H). HRMS (ESI) m/z: calcd for, $C_{41}H_{44}N_9O_8S^+$ [M+H]$^+$, 822.3028; found, 822.3022.

Example 46: Preparation of 4-((2-(2-(2-(4-(6-((6-acetyl-8-cyclopentyl-5-methyl-7-oxo-7,8-dihydro-pyrido[2,3-d]pyrimidin-2-yl)amino)pyridin-3-yl)piperazin-1-yl)-2-oxoethoxy)ethoxy)ethyl)thio)-2-(2,6-dioxopiperidin-3-yl)isoindoline-1,3-dione (SIAIS219059)

According to the general method described in Scheme 22, the target compound (SIAIS219059) was prepared by using Palbociclib inhibitor and LIN-ULM (SIAIS1204139). (yellow solid, 9.1 mg, yield 47%) $^1$H NMR (500 MHz, MeOD) δ 9.03 (s, 1H), 8.13 (dd, J=9.7, 3.0 Hz, 1H), 7.73 (d, J=2.9 Hz, 1H), 7.69-7.58 (m, 2H), 7.46-7.35 (m, 2H), 6.00 (p, J=9.1 Hz, 1H), 5.11 (dd, J=12.7, 5.5 Hz, 1H), 4.29 (s, 2H), 3.88-3.75 (m, 7H), 3.70-3.64 (m, 9H), 3.37 (d, J=5.3 Hz, 2H), 2.93-2.81 (m, 1H), 2.80-2.65 (m, 2H), 2.52 (s, 3H), 2.44 (s, 3H), 2.33 (dd, J=11.7, 7.7 Hz, 2H), 2.17-2.09 (m, 3H), 1.94 (s, 2H), 1.75-1.68 (m, 2H). HRMS (ESI) m/z: calcd for, $C_{43}H_{48}N_9O_9S^+$ [M+H]$^+$, 866.3290; found, 866.3281.

Example 47: Preparation of 4-((2-(2-(2-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-2-oxoethoxy)ethoxy)ethoxy)ethyl)thio)-2-(2,6-dioxopiperidin-3-yl)isoindoline-1,3-dione (SIAIS219060)

According to the general method described in Scheme 22, under appropriate conditions that will be recognized by one skilled in the art, the target compound (SIAIS219060) was prepared by using Palbociclib inhibitor and LIN-ULM (SIAIS1204141). (yellow solid, 9.1 mg, yield 45%). $^1$H NMR (500 MHz, MeOD) δ 9.02 (s, 1H), 8.08 (dd, J=9.7, 3.0 Hz, 1H), 7.69 (d, J=2.9 Hz, 1H), 7.67-7.59 (m, 2H), 7.39-7.28 (m, 2H), 6.02 (p, J=9.0 Hz, 1H), 5.12 (dd, J=12.7, 5.5 Hz, 1H), 4.29 (s, 2H), 3.89-3.76 (m, 6H), 3.70 (s, 4H), 3.45 (d, J=4.7 Hz, 2H), 2.96-2.82 (m, 1H), 2.78-2.64 (m, 2H), 2.51 (d, J=4.4 Hz, 3H), 2.45 (s, 3H), 2.35-2.32 (m, 2H), 2.11 (d, J=10.3 Hz, 3H), 1.94 (s, 2H), 1.76-1.69 (m, 2H). HRMS (ESI) m/z: calcd for, $C_{45}H_{52}N_9O_{10}S^+$ [M+H]$^+$, 910.3552; found, 910.3545.

Example 48: Preparation of 4-((14-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-14-oxo-3,6,9,12-tetraoxatetradecyl)thio)-2-(2,6-dioxopiperidin-3-yl)isoindoline-1,3-dione (SIAIS219061)

According to the general method described in Scheme 22, under appropriate conditions that will be recognized by one skilled in the art, the target compound (SIAIS219061) was prepared by using Palbociclib inhibitor and LIN-ULM (SIAIS1204147). (yellow solid, 9.3 mg, yield 44%) $^1$H NMR (500 MHz, MeOD) δ 9.05 (s, 1H), 8.17 (d, J=9.6 Hz, 1H), 7.80 (s, 1H), 7.68-7.63 (m, 2H), 7.45 (dd, J=9.2, 3.9 Hz, 2H), 5.98 (dd, J=17.7, 8.8 Hz, 1H), 5.11 (dd, J=12.7, 5.5 Hz, 1H), 4.31 (s, 2H), 3.81 (dd, J=16.9, 10.9 Hz, 6H), 3.72-3.61 (m, 14H), 3.37 (s, 2H), 2.93-2.82 (m, 1H), 2.79-2.63 (m, 2H), 2.51 (s, 3H), 2.43 (s, 3H), 2.36-2.28 (m, 2H), 2.14-2.09 (m, 3H), 1.93 (d, J=11.7 Hz, 2H), 1.75-1.66 (m, 2H). HRMS (ESI) m/z: calcd for, $C_{47}H_{56}N_9O_{11}S^+$ [M+H]$^+$, 954.3815; found, 954.3820.

Example 49: Preparation of 4-((17-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-17-oxo-3,6,9,12,15-pentaoxaheptadecyl)thio)-2-(2,6-dioxopiperidin-3-yl)isoindoline-1,3-dione (SIAIS219062)

According to the general method described in Scheme 22, under appropriate conditions that will be recognized by one skilled in the art, the target compound (SIAIS219062) was prepared by using Palbociclib inhibitor and LIN-ULM (SIAIS1204149). (yellow solid, 10.2 mg, yield 46%) $^1$H NMR (500 MHz, MeOD) δ 9.04 (s, 1H), 8.20 (dd, J=9.6, 2.9 Hz, 1H), 7.81 (d, J=2.9 Hz, 1H), 7.73-7.60 (m, 2H), 7.51-7.41 (m, 2H), 5.99 (p, J=9.0 Hz, 1H), 5.12 (dd, J=12.8, 5.5 Hz, 1H), 4.31 (s, 2H), 3.85-3.75 (m, 7H), 3.72-3.60 (m, 19H), 3.38 (s, 2H), 2.92-2.82 (m, 1H), 2.79-2.63 (m, 2H), 2.51 (s, 3H), 2.43 (s, 3H), 2.31 (d, J=7.6 Hz, 2H), 2.18-2.06 (m, 3H), 1.93 (d, J=16.4 Hz, 2H), 1.76-1.66 (m, 2H). HRMS (ESI) m/z: calcd for, $C_{49}H_{60}N_9O_{12}S^+$ [M+H]$^+$, 998.4077; found, 998.4071.

Example 50: Synthesis of the Special Degradation Agent SIAIS219063 for CDK4/6 Target

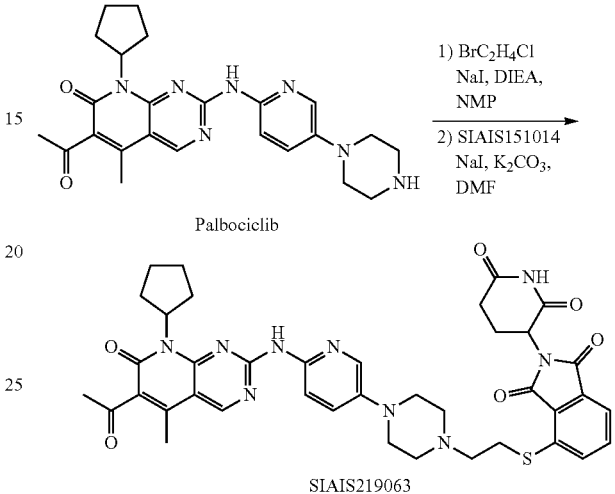

Preparation of 4-((2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)ethyl)thio)-2-(2,6-dioxopiperidin-3-yl)isoindoline-1,3-dione (SIAIS219063)

A 15 mL sample bottle was charged with Palbociclib (50 mg, 0.11 mmol) and NMP (2 mL), and then 1-bromo-2-chloroethane (48.2 mg, 0.33 mmol), Sodium iodide (16.8 mg, 0.11 mmol), and diisopropylamine (43.4 mg, 0.33 mmol), and was heated at 90° C. for 2 h. After membrane filtration, the reaction mixture was subjected to preparative HPLC (eluent (v/v): acetonitrile/(water+0.05% HCl)=10%-100%) for separation. The acetonitrile was removed by rotary evaporation, and the residue was lyophilized to give the intermediate (30 mg) to be used in the next step directly. The obtained intermediate (10.2 mg, 0.02 mmol) and DMF (2 mL) were added to a 15 mL sample bottle, followed by addition of SIAIS151014 (11.6 mg, 0.04 mmol), potassium carbonate (8.3 mg, 0.06 mmol), and sodium iodide (6 mg, 0.04 mmol). The reaction mixture was heated at 50° C. for 2 h, and subjected to membrane filtration, and preparative HPLC (eluent (v/v): acetonitrile/(water+0.05% HCl)=10%-100%) for separation. The acetonitrile was removed by rotary evaporation, and the residue was lyophilized to obtain the target product (5.2 mg, the total yield of the two steps is 18%). $^1$H NMR (500 MHz, MeOD) δ 9.12 (s, 1H), 8.19 (dd, J=9.7, 2.9 Hz, 1H), 7.85 (d, J=2.9 Hz, 1H), 7.84-7.75 (m, 2H), 7.65 (dd, J=6.7, 1.4 Hz, 1H), 7.54 (d, J=9.6 Hz, 1H), 6.05-5.98 (m, 1H), 5.12 (dd, J=12.7, 5.5 Hz, 1H), 3.81 (d, J=5.1 Hz, 2H), 3.79-3.70 (m, 2H), 3.47 (t, J=6.8 Hz, 2H), 3.31-3.23 (m, 6H), 2.95 (t, J=6.9 Hz, 2H), 2.89-2.85 (m, 1H), 2.79-2.69 (m, 2H), 2.52 (s, 3H), 2.44 (s, 3H), 2.36-2.31 (m, 2H), 2.13-2.08 (m, 3H), 1.93 (dd, J=12.0, 7.0 Hz, 2H), 1.75-1.68 (m, 2H). HRMS (ESI) m/z: calcd for, $C_{39}H_{42}N_9O_6S^+$ [M+H]$^+$, 764.2973; found, 764.2971.

Example 51: Synthesis of the Special Degradation Agent SIAIS262173 for CDK4/6 Target

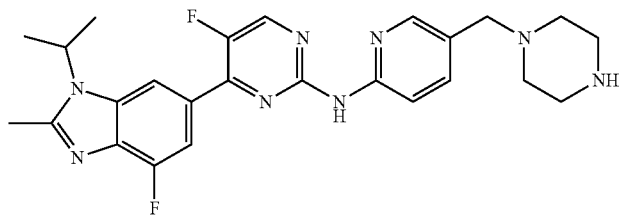

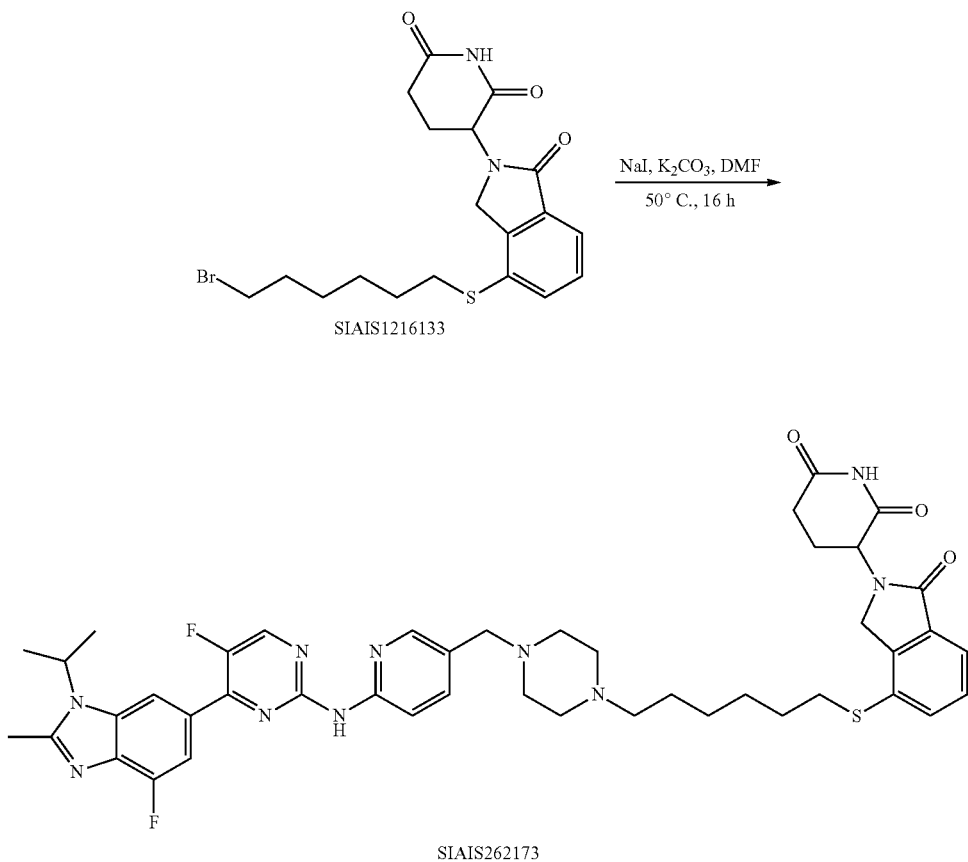

Preparation of 3-(4-((6-(4-((6-(((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)hexyl)thio)-1-oxoisoindolin-2-yl)piperidine-2,6-dione (SIAIS262173)

A 15 mL sample bottle was sequentially charged with Abemaciclib derivative (9.6 mg, 0.02 mmol) and DMF (2 mL), and SIAIS1216133 (17.6 mg, 0.04 mmol) and potassium carbonate (8.3 mg, 0.06 mmol), sodium iodide (6 mg, 0.04 mmol) with stirring. The reaction mixture was heated at 50° C. for 16 h, and subjected to membrane filtration, and preparative HPLC (eluent (v/v): acetonitrile/(water+0.05% HCl)=10%-100%) for separation. The acetonitrile was removed by rotary evaporation, and the residue was lyophilizated to obtain the target product (yellow solid, 8.9 mg, yield 34%). $^1$H NMR (500 MHz, MeOD) δ 8.92 (d, J=3.1 Hz, 1H), 8.60 (s, 1H), 8.56-8.45 (m, 2H), 8.21 (d, J=11.2 Hz, 1H), 7.65 (dd, J=8.9, 5.5 Hz, 3H), 7.53 (t, J=7.6 Hz, 1H), 5.15 (dd, J=13.8, 5.7 Hz, 2H), 4.44 (q, J=17.3 Hz, 2H), 4.15 (s, 2H), 3.66 (s, 2H), 3.38 (d, J=59.2 Hz, 4H), 3.11-3.08 (m, 6H), 2.98 (s, 3H), 2.92-2.88 (m, 1H), 2.79-2.75 (m, 1H), 2.56-2.52 (m, 1H), 2.25-2.16 (m, 1H), 1.82 (d, J=6.9 Hz, 6H), 1.77-1.65 (m, 4H), 1.56-1.50 (m, 2H), 1.43-1.38 (m, 2H). HRMS (ESI) m/z: calcd for, $C_{44}H_{51}F_2N_{10}O_3S^+$ [M+H]$^+$, 837.3829; found, 837.3821.

A General Synthesis Method for a Series of Degradation Agents of ALK Target:

Scheme 25
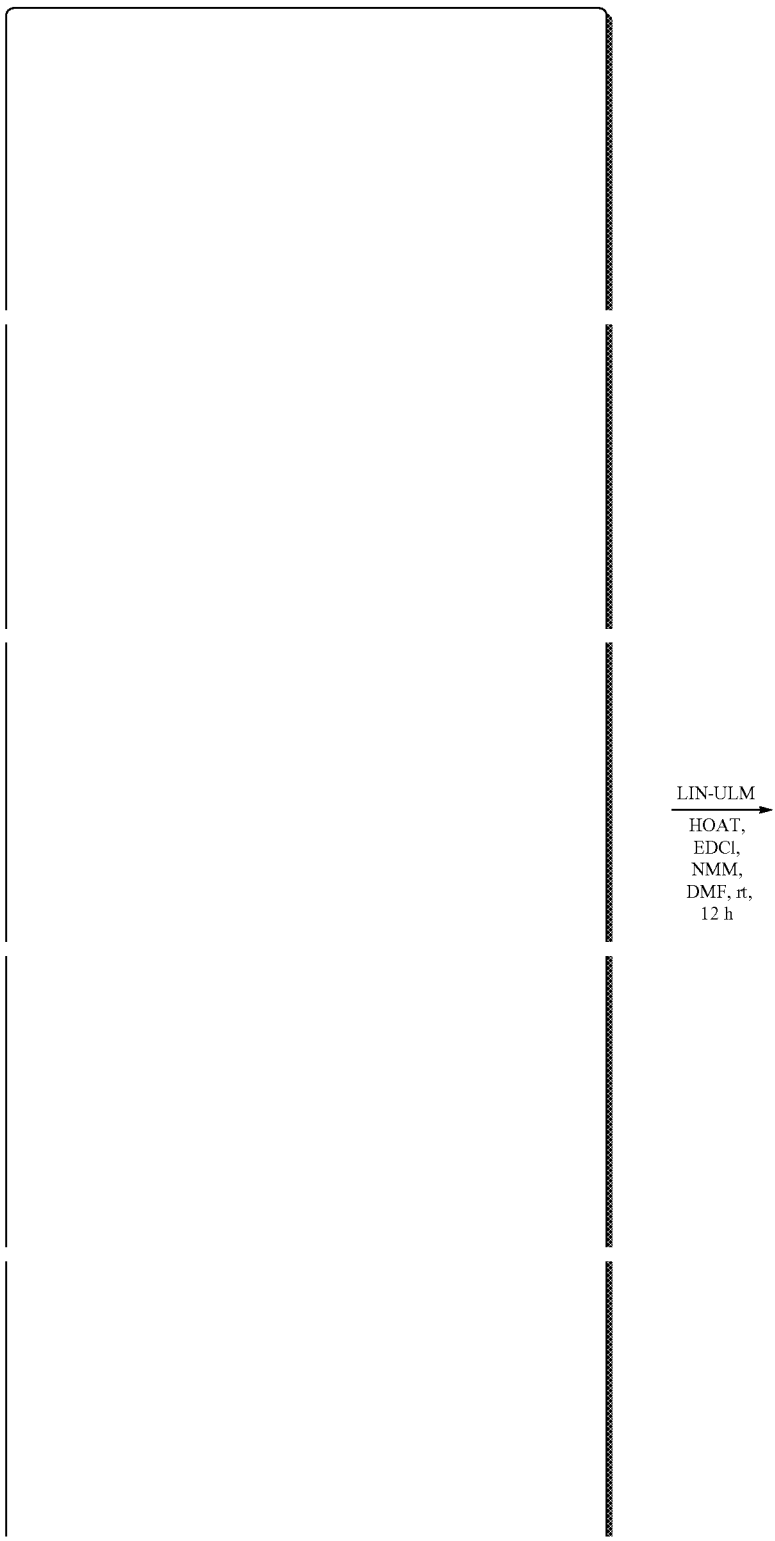

-continued
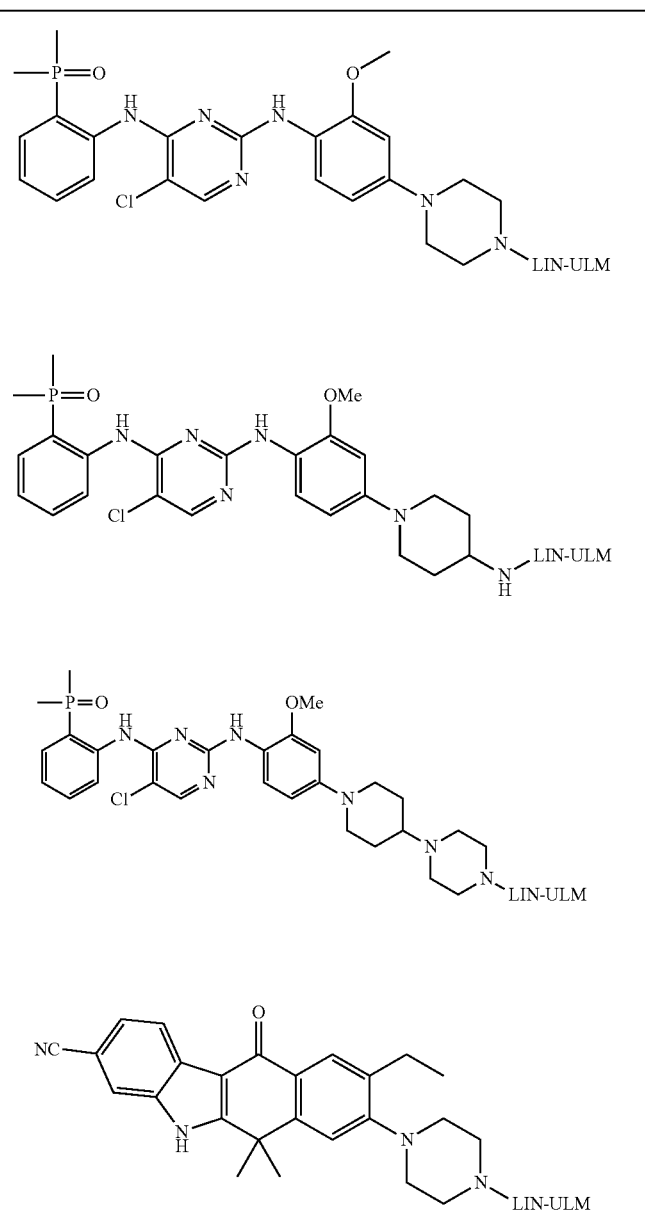
ALK inhibitor

-continued

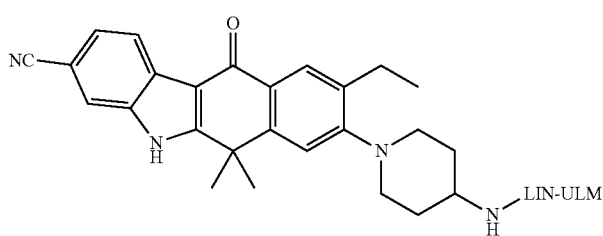

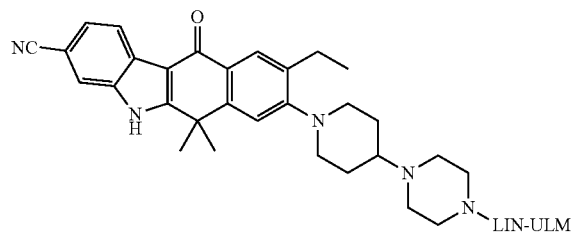

degrader

According to Scheme 25, at room temperature, a reaction flask was charged with the corresponding ALK inhibitor (1 equiv), the corresponding LIN-ULM (1 equiv), 1-hydroxy-7-azabenzotriazole (2 equiv), 1-(3-dimethylaminopropyl)-3-ethylcarbodiimide hydrochloride (2 equiv), anhydrous N,N-dimethylformamide (2 mL), and N-methylmorpholine (5 equiv). The reaction mixture was stirred overnight at room temperature. After the completion of the reaction was detected by LC-MS, the reaction mixture was separated by preparative HPLC (eluent (v/v): acetonitrile/(water+0.05% HCl)=10%-100%). The acetonitrile is removed by rotary evaporation, and the residue was lyophilizated to obtain the corresponding final degradation agent compound.

Example 52: Preparation of 4-((2-(4-(4-((5-chloro-4-((2-(dimethylphosphoryl)phenyl)amino)pyrimidin-2-yl)amino)-3-methoxyphenyl)piperazin-1-yl)-2-oxoethyl)thio)-2-(2,6-dioxopiperidin-3-yl)isoindoline-1,3-dione (SIAIS1197113)

According to the general method described in Scheme 25, under appropriate conditions that will be recognized by one skilled in the art, the target compound (SIAIS1197113) was prepared by using Brigatinib derivative A (SIAIS1197135) and LIN-ULM (SIAIS151045). (yellow solid, 13.4 mg, yield 49%) $^1$H NMR (500 MHz, DMSO) δ 11.13 (s, 1H), 8.44 (s, 1H), 8.19 (s, 1H), 7.85 (d, J=8.2 Hz, 1H), 7.80 (t, J=8.7 Hz, 1H), 7.65 (d, J=7.1 Hz, 1H), 7.60 (s, 1H), 7.40 (s, 2H), 7.19 (s, 1H), 6.76 (s, 1H), 6.59 (s, 1H), 5.13 (dd, J=12.9, 5.4 Hz, 1H), 4.35 (s, 2H), 3.80 (s, 3H), 3.67 (s, 4H), 3.30 (s, 2H), 3.21 (s, 2H), 2.94-2.83 (m, 1H), 2.66-2.56 (m, 2H), 2.06 (s, 1H), 1.79 (d, J=13.6 Hz, 6H). HRMS (ESI) calcd for, $C_{38}H_{39}ClN_8O_7PS^+$ [M+H]$^+$, 817.2083; found, 817.1844.

Example 53: Preparation of 4-((3-(4-(4-((5-chloro-4-((2-(dimethylphosphoryl)phenyl)amino)pyrimidin-2-yl)amino)-3-methoxyphenyl)piperazin-1-yl)-3-oxopropyl)thio)-2-(2,6-dioxopiperidin-3-yl)isoindoline-1,3-dione (SIAIS1197115)

According to the general method described in Scheme 25, under appropriate conditions that will be recognized by one skilled in the art, the target compound (SIAIS1197115) was prepared by using Brigatinib derivative A (SIAIS1197135) and LIN-ULM (SIAIS151138B). (yellow solid, 13.3 mg, yield 49%). $^1$H NMR (500 MHz, MeOD) δ 8.35 (s, 1H), 8.07 (s, 1H), 7.81-7.74 (m, 2H), 7.67 (dd, J=13.7, 8.5 Hz, 1H), 7.64 (dd, J=6.6, 1.3 Hz, 1H), 7.56 (s, 1H), 7.39 (t, J=7.0 Hz, 1H), 7.32 (s, 1H), 6.81 (s, 1H), 6.65 (dd, J=8.7, 2.2 Hz, 1H), 5.08 (dd, J=12.8, 5.4 Hz, 1H), 3.86 (s, 3H), 3.82 (s, 2H), 3.74 (s, 2H), 3.46 (t, J=6.9 Hz, 2H), 3.32 (s, 4H), 2.93 (t, J=7.0 Hz, 2H), 2.87-2.78 (m, 1H), 2.74-2.60 (m, 2H), 2.07 (s, 1H), 1.88 (d, J=13.6 Hz, 6H). HRMS (ESI) calcd for, $C_{39}H_{41}ClN_8O_7PS^+$ [M+H]$^+$, 831.2240; found, 831.2001.

Example 54: Preparation of 4-((4-(4-(4-((5-chloro-4-((2-(dimethylphosphoryl)phenyl)amino)pyrimidin-2-yl)amino)-3-methoxyphenyl)piperazin-1-yl)-4-oxobutyl)thio)-2-(2,6-dioxopiperidin-3-yl)isoindoline-1,3-dione (SIAIS1197117)

According to the general method described in Scheme 25, under appropriate conditions that will be recognized by one skilled in the art, the target compound (SIAIS1197117) was prepared with Brigatinib derivative A (SIAIS1197135) and LIN-ULM (SIAIS151139B). (yellow solid, 14.6 mg, yield 54%). $^1$H NMR (500 MHz, MeOD) δ 8.28 (s, 1H), 8.13 (s, 1H), 7.83 (d, J=7.9 Hz, 1H), 7.78-7.72 (m, 1H), 7.70 (dd, J=14.1, 7.9 Hz, 1H), 7.63-7.58 (m, 2H), 7.42 (t, J=8.0 Hz, 2H), 7.00 (s, 1H), 6.81 (d, J=7.9 Hz, 1H), 5.13-5.06 (m, 1H), 3.90 (s, 3H), 3.86 (s, 4H), 3.48-3.38 (m, 4H), 3.24 (t, J=7.0 Hz, 2H), 2.89-2.79 (m, 1H), 2.79-2.65 (m, 2H), 2.69 (t, J=6.8 Hz, 2H), 2.12-2.08 (m, 2H), 2.06-1.97 (m, 1H), 1.88 (d, J=13.6 Hz, 6H). HRMS (ESI) calcd for, $C_{40}H_{43}ClN_8O_7PS^+$ [M+H]$^+$, 845.2396; found, 845.2171.

Example 55: Preparation of 4-((5-(4-(4-((5-chloro-4-((2-(dimethylphosphoryl)phenyl)amino)pyrimidin-2-yl)amino)-3-methoxyphenyl)piperazin-1-yl)-5-oxopentyl)thio)-2-(2,6-dioxopiperidin-3-yl)isoindoline-1,3-dione (SIAIS1197119)

According to the general method described in Scheme 25, under appropriate conditions that will be recognized by one skilled in the art, the target compound (SIAIS1197119) was prepared by using Brigatinib derivative A (SIAIS1197135) and LIN-ULM (SIAIS151140B). (yellow solid, 4.2 mg, yield 52%). $^1$H NMR (500 MHz, MeOD) δ 8.32 (s, 1H), 8.10 (s, 1H), 7.76-7.69 (m, 2H), 7.68 (dd, J=13.3, 8.0 Hz, 1H), 7.61-7.56 (m, 2H), 7.44-7.33 (m, 2H), 6.90 (s, 1H), 6.72 (d, J=8.6 Hz, 1H), 5.07 (dd, J=12.6, 5.5 Hz, 1H), 3.88 (s, 3H), 3.82 (s, 4H), 3.38 (s, 2H), 3.33 (s, 2H), 3.19 (t, J=6.5 Hz, 2H), 2.88-2.78 (m, 1H), 2.78-2.62 (m, 2H), 2.55 (t, J=6.7 Hz, 2H), 2.16-2.05 (m, 1H), 1.88 (d, J=13.6 Hz, 6H), 1.87-1.83 (m, 2H), 1.83-1.77 (m, 2H). HRMS (ESI) calcd for, $C_{41}H_{45}ClN_8O_7PS^+$ [M+H]$^+$, 859.2553; found, 859.2326.

Example 56: Preparation of 4-((6-(4-(4-((5-chloro-4-((2-(dimethylphosphoryl)phenyl)amino)pyrimidin-2-yl)amino)-3-methoxyphenyl)piperazin-1-yl)-6-oxohexyl)thio)-2-(2,6-dioxopiperidin-3-yl)isoindoline-1,3-dione (SIAIS1197121)

According to the general method described in Scheme 25, under appropriate conditions that will be recognized by one skilled in the art, the target compound (SIAIS1197121) was prepared by using Brigatinib derivative A (SIAIS1197135) and LIN-ULM (SIAIS151141B). (yellow solid, 13.8 mg, yield 51%). $^1$H NMR (500 MHz, MeOD) δ 8.22 (s, 1H), 8.18 (s, 1H), 7.75-7.66 (m, 3H), 7.62 (t, J=7.8 Hz, 1H), 7.58 (dd, J=6.0, 2.0 Hz, 1H), 7.57-7.50 (m, 1H), 7.45 (t, J=6.9 Hz, 1H), 7.18 (s, 1H), 6.95 (dd, J=8.5, 1.9 Hz, 1H), 5.09 (dd, J=12.7, 5.5 Hz, 1H), 3.95 (s, 4H), 3.92 (s, 3H), 3.55 (s, 2H), 3.51 (s, 2H), 3.16 (t, J=7.1 Hz, 2H), 2.90-2.80 (m, 1H), 2.77-2.64 (m, 2H), 2.52 (t, J=7.3 Hz, 2H), 2.15-2.07 (m, 1H), 1.87 (d, J=13.6 Hz, 6H), 1.84-1.76 (m, 2H), 1.75-1.65 (m, 2H), 1.64-1.56 (m, 2H). HRMS (ESI) calcd for, $C_{42}H_{47}ClN_8O_7PS^+$ [M+H]$^+$, 873.2709; found, 873.0905.

Example 57: Preparation of 4-((7-(4-(4-((5-chloro-4-((2-(dimethylphosphoryl)phenyl)amino)pyrimidin-2-yl)amino)-3-methoxyphenyl)piperazin-1-yl)-7-oxoheptyl)thio)-2-(2,6-dioxopiperidin-3-yl)isoindoline-1,3-dione (SIAIS1197159)

According to the general method described in Scheme 25, under appropriate conditions that will be recognized by one skilled in the art, the target compound (SIAIS1197159) was prepared by using Brigatinib derivative A (SIAIS1197135) and LIN-ULM (SIAIS151142B). (yellow solid, 12.5 mg, yield 46%). $^1$H NMR (500 MHz, MeOD) δ 8.30 (s, 1H), 8.10 (s, 1H), 7.73-7.66 (m, 3H), 7.58 (dd, J=6.3, 1.6 Hz, 2H), 7.45-7.35 (m, 2H), 6.92 (s, 1H), 6.74 (dd, J=8.9, 1.8 Hz, 1H), 5.09 (dd, J=12.6, 5.5 Hz, 1H), 3.88 (s, 3H), 3.84 (s, 4H), 3.40 (s, 2H), 3.35 (s, 2H), 3.13 (t, J=7.1 Hz, 2H), 2.90-2.78 (m, 1H), 2.76-2.64 (m, 2H), 2.49 (t, J=7.4 Hz, 2H), 2.11 (dd, J=8.8, 3.7 Hz, 1H), 1.88 (d, J=13.6 Hz, 6H), 1.82-1.73 (m, 2H), 1.72-1.62 (m, 2H), 1.61-1.53 (m, 2H), 1.50-1.40 (m, 2H). HRMS (ESI) calcd for, $C_{43}H_{49}ClN_8O_7PS^+$ [M+H]$^+$, 887.2866; found, 887.1081.

Example 58: Preparation of N-(1-(4-((5-chloro-4-((2-(dimethylphosphoryl)phenyl)amino)pyrimidin-2-yl)amino)-3-methoxyphenyl)piperidin-4-yl)-2-((2-(2,6-dioxopiperidin-3-yl)-1,3-dioxoisoindolin-4-yl)thio)acetamide (SIAIS164137)

According to the general method described in Scheme 25, under appropriate conditions that will be recognized by one skilled in the art, the target compound (SIAIS164137) was prepared by using Brigatinib derivative B (SIAIS151101) and LIN-ULM (SIAIS151045). (yellow solid, 13.0 mg, yield 78%). $^1$H NMR (500 MHz, MeOD) δ 8.20 (s, 2H), 7.82 (d, J=8.0 Hz, 1H), 7.78-7.70 (m, 3H), 7.68-7.63 (m, 2H), 7.46 (t, J=7.0 Hz, 1H), 7.33 (s, 1H), 7.08 (s, 1H), 5.14 (dd, J=12.7, 5.5 Hz, 1H), 4.13-4.05 (m, 1H), 3.96 (s, 3H), 3.92 (s, 2H), 3.76-3.73 (m, 2H), 3.68-3.51 (m, 2H), 2.91-2.83 (m, 1H), 2.77-2.67 (m, 2H), 2.22-2.11 (m, 3H), 2.07-2.02 (m, 2H), 1.88 (s, 3H), 1.85 (s, 3H). HRMS (ESI) calcd for, $C_{39}H_{41}ClN_8O_7PS^+$ [M+H]$^+$: 831.2240, found 831.1913.

Example 59: Preparation of N-(1-(4-((5-chloro-4-((2-(dimethylphosphoryl)phenyl)amino)pyrimidin-2-yl)amino)-3-methoxyphenyl)piperidin-4-yl)-3-((2-(2,6-dioxopiperidin-3-yl)-1,3-dioxoisoindolin-4-yl)thio)propanamide (SIAIS164138)

According to the general method described in Scheme 25, under appropriate conditions that will be recognized by one skilled in the art, the target compound (SIAIS164138) was prepared by using Brigatinib derivative B (SIAIS151101) and LIN-ULM (SIAIS15138B). (yellow solid, 11.8 mg, yield 70%). $^1$H NMR (500 MHz, MeOD) δ 8.23 (s, 1H), 8.17 (s, 1H), 7.81-7.70 (m, 4H), 7.68-7.62 (m, 2H), 7.47 (t, J=7.6 Hz, 1H), 7.41 (s, 1H), 7.14 (d, J=7.7 Hz, 1H), 5.09 (dd, J=12.8, 5.3 Hz, 1H), 4.15-4.10 (m, 1H), 3.98 (s, 3H), 3.83-3.73 (m, 2H), 3.71-3.58 (m, 2H), 3.44 (t, J=6.8 Hz, 2H), 2.88-2.81 (m, 1H), 2.75-2.62 (m, 4H), 2.26-2.23 (m, 2H), 2.14-2.02 (m, 3H), 1.88 (s, 3H), 1.85 (s, 3H). HRMS (ESI) calcd for, $C_{40}H_{43}ClN_8O_7PS^+$ [M+H]$^+$: 845.2396, found 845.2034.

Example 60: Preparation of N-(1-(4-((5-chloro-4-((2-(dimethylphosphoryl)phenyl)amino)pyrimidin-2-yl)amino)-3-methoxyphenyl)piperidin-4-yl)-4-((2-(2,6-dioxopiperidin-3-yl)-1,3-dioxoisoindolin-4-yl)thio)butanamide (SIAIS164139)

According to the general method described in Scheme 25, the target compound (SIAIS164139) was obtained by using Brigatinib derivative B (SIAIS151139B) and LIN-ULM (SIAIS164139B) under appropriate conditions that will be recognized by one skilled in the art. (yellow solid, 12.0 mg, yield 70%). $^1$H NMR (500 MHz, MeOD) δ 8.24 (s, 1H), 8.16 (s, 1H), 7.80-7.71 (m, 4H), 7.66 (t, J=7.9 Hz, 1H), 7.61 (dd, J=6.3, 1.7 Hz, 1H), 7.49-7.44 (m, 2H), 7.17 (d, J=8.1 Hz, 1H), 5.11 (dd, J=12.7, 5.5 Hz, 1H), 4.16-4.09 (m, 1H), 3.98 (s, 3H), 3.79-3.65 (m, 4H), 3.19 (t, J=7.1 Hz, 2H), 2.90-2.83 (m, 1H), 2.77-2.65 (m, 2H), 2.47 (t, J=7.1 Hz, 2H), 2.28-2.24 (m, 2H), 2.16-2.04 (m, 5H), 1.88 (s, 3H), 1.85 (s, 3H). HRMS (ESI) calcd for, $C_{41}H_{45}ClN_8O_7PS^+$ [M+H]$^+$: 859.2553, found 859.2198.

Example 61: Preparation of N-(1-(4-((5-chloro-4-((2-(dimethylphosphoryl)phenyl)amino)pyrimidin-2-yl)amino)-3-methoxyphenyl)piperidin-4-yl)-5-((2-(2,6-dioxopiperidin-3-yl)-1,3-dioxoisoindolin-4-yl)thio)pentanamide (SIAIS164140)

According to the general method described in Scheme 25, under appropriate conditions that will be recognized by one skilled in the art, t The target compound (SIAIS164140) was prepared with Brigatinib derivative B (SIAIS151101) and LIN-ULM (SIAIS151140B). (yellow solid, 12.7 mg, yield 73%). $^1$H NMR (500 MHz, MeOD) δ 8.24 (s, 1H), 8.15 (s, 1H), 7.78-7.65 (m, 5H), 7.60 (d, J=6.4 Hz, 1H), 7.53-7.44 (m, 2H), 7.18 (d, J=8.2 Hz, 1H), 5.11 (dd, J=12.7, 5.3 Hz, 1H), 4.14-4.08 (m, 1H), 3.99 (s, 3H), 3.80-3.66 (m, 4H), 3.16 (t, J=6.9 Hz, 2H), 2.90-2.83 (m, 1H), 2.78-2.66 (m, 2H), 2.34-2.31 (m, 2H), 2.24-2.22 (m, 2H), 2.15-2.04 (m, 3H), 1.88 (s, 3H), 1.86 (s, 3H), 1.82-1.79 (m, 4H). HRMS (ESI) calcd for, $C_{42}H_{47}ClN_8O_7PS^+$ [M+H]$^+$: 873.2709, found 873.2339.

Example 62: Preparation of N-(1-(4-((5-chloro-4-((2-(dimethylphosphoryl)phenyl)amino)pyrimidin-2-yl)amino)-3-methoxyphenyl)piperidin-4-yl)-6-((2-(2,6-dioxopiperidin-3-yl)-1,3-dioxoisoindolin-4-yl)thio)hexanamide (SIAIS164141)

According to the general method described in Scheme 25, under appropriate conditions that will be recognized by one skilled in the art, the target compound (SIAIS164141) was prepared by using Brigatinib derivative B (SIAIS151101) and LIN-ULM (SIAIS151141B). (yellow solid, 13.5 mg, yield 76%). $^1$H NMR (500 MHz, MeOD) δ 8.26 (s, 1H), 8.14 (s, 1H), 7.79-7.66 (m, 5H), 7.59 (dd, J=6.8, 1.0 Hz, 1H), 7.54-7.46 (m, 2H), 7.22 (dd, J=8.8, 2.1 Hz, 1H), 5.07 (dd, J=12.5, 5.5 Hz, 1H), 4.17-4.11 (m, 1H), 3.99 (s, 3H), 3.81-3.70 (m, 4H), 3.15 (t, J=7.0 Hz, 2H), 2.85-2.76 (m, 1H), 2.73-2.62 (m, 2H), 2.29 (t, J=7.1 Hz, 4H), 2.18-2.06 (m, 3H), 1.89 (s, 3H), 1.86 (s, 3H), 1.84-1.78 (m, 2H), 1.75-1.69 (m, 2H), 1.60-1.54 (m, 2H). HRMS (ESI) calcd for, $C_{43}H_{49}ClN_8O_7PS^+$ [M+H]$^+$: 887.2866, found 887.2421.

Example 63: Preparation of N-(1-(4-((5-chloro-4-((2-(dimethylphosphoryl)phenyl)amino)pyrimidin-2-yl)amino)-3-methoxyphenyl)piperidin-4-yl)-7-((2-(2,6-dioxopiperidin-3-yl)-1,3-dioxoisoindolin-4-yl)thio)heptanamide (SIAIS164142)

According to the general method described in Scheme 25, under appropriate conditions that will be recognized by one skilled in the art, the target compound (SIAIS164142) was prepared by using Brigatinib derivative B (SIAIS151101) and LIN-ULM (SIAIS151142B) (yellow solid, 13.0 mg, yield 72%). $^1$H NMR (500 MHz, MeOD) δ 8.24 (s, 1H), 8.16 (s, 1H), 7.78-7.69 (m, 4H), 7.66 (t, J=7.9 Hz, 1H), 7.61-7.58 (m, 1H), 7.50-7.44 (m, 2H), 7.16 (d, J=8.3 Hz, 1H), 5.10 (dd, J=12.6, 5.5 Hz, 1H), 4.15-4.08 (m, 1H), 3.98 (s, 3H), 3.78-3.64 (m, 4H), 3.14 (t, J=7.1 Hz, 2H), 2.88-2.81 (m, 1H), 2.75-2.68 (m, 2H), 2.29-2.21 (m, 4H), 2.14-2.04 (m, 3H), 1.88 (s, 3H), 1.85 (s, 3H), 1.81-1.75 (m, 2H), 1.71-1.64 (m, 2H), 1.59-1.53 (m, 2H), 1.45-1.40 (m, 2H). HRMS (ESI) calcd for, $C_{44}H_{51}ClN_8O_7PS^+$ [M+H]$^+$: 901.3022, found 901.2544.

Example 64: Preparation of N-(1-(4-((5-chloro-4-((2-(dimethylphosphoryl)phenyl)amino)pyrimidin-2-yl)amino)-3-methoxyphenyl)piperidin-4-yl)-2-((2-(2,6-dioxopiperidin-3-yl)-1-oxoisoindolin-4-yl)thio)acetamide (SIAIS219133)

According to the general method described in Scheme 25, under the appropriate conditions that will be recognized by one skilled in the art, the target compound (SIAIS219133) was prepared by using Brigatinib derivative B (SIAIS151101) and LIN-ULM (SIAIS171090). (yellow solid, SIAIS219133, 7.2 mg, yield 44%). $^1$H NMR (500 MHz, MeOD) δ 8.26 (s, 1H), 8.09 (s, 1H), 7.85-7.79 (m, 1H), 7.75 (dd, J=14.3, 5.4 Hz, 3H), 7.67 (t, J=7.7 Hz, 1H), 7.59-7.48 (m, 3H), 7.23 (d, J=8.5 Hz, 1H), 5.16 (d, J=11.3 Hz, 1H), 4.59 (d, J=17.4 Hz, 1H), 4.51 (d, J=17.5 Hz, 1H), 4.06 (s, 1H), 3.98 (s, 3H), 3.77-3.67 (m, 6H), 2.92 (t, J=15.4 Hz, 1H), 2.80 (d, J=17.4 Hz, 1H), 2.56 (q, J=12.9 Hz, 1H), 2.22-1.97 (m, 5H), 1.87 (dd, J=13.5, 2.4 Hz, 6H). HRMS (ESI) m/z: calcd for, $C_{39}H_{43}ClN_8O_6PS^+$ [M+H]$^+$, 817.2447; found, 817.2443.

Example 65: Preparation of N-(1-(4-((5-chloro-4-((2-(dimethylphosphoryl)phenyl)amino)pyrimidin-2-yl)amino)-3-methoxyphenyl)piperidin-4-yl)-3-((2-(2,6-dioxopiperidin-3-yl)-1-oxoisoindolin-4-yl)thio)propanamide (SIAIS219134)

According to the general method described in Scheme 25, under appropriate conditions that will be recognized by one skilled in the art, the target compound (SIAIS219134) was prepared by using Brigatinib derivative B (SIAIS151101) and LIN-ULM (SIAIS171086). (yellow solid, 7.5 mg, yield 45%). $^1$H NMR (500 MHz, MeOD) δ 8.22 (s, 1H), 8.07 (s, 1H), 7.74-7.69 (m, 3H), 7.63 (t, J=6.7 Hz, 2H), 7.54-7.45 (m, 3H), 7.20 (dd, J=8.7, 2.3 Hz, 1H), 5.13 (dd, J=13.3, 5.2 Hz, 1H), 4.46 (d, J=17.3 Hz, 1H), 4.39 (d, J=17.3 Hz, 1H), 4.10-4.00 (m, 1H), 3.95 (s, 3H), 3.72 (d, J=5.4 Hz, 4H), 3.36-3.33 (m, 2H), 2.92-2.84 (m, 1H), 2.78-2.73 (m, 1H), 2.60-2.45 (m, 3H), 2.19-2.15 (m, 3H), 2.11-2.02 (m, 2H), 1.83 (d, J=13.5 Hz, 6H). HRMS (ESI) m/z: calcd for, $C_{40}H_{45}ClN_8O_6PS^+$ Example 66: Preparation of N-(1-(4-((5-chloro-4-((2-(dimethylphosphoryl)phenyl)amino)pyrimidin-2-yl)amino)-3-methoxyphenyl)piperidin-4-yl)-4-((2-(2,6-dioxopiperidin-3-yl)-1-oxoisoindolin-4-yl)thio)butanamide (SIAIS219135)

According to the general method described in Scheme 25, under appropriate conditions that will be recognized by one skilled in the art, the target compound (SIAIS219135) was prepared by using Brigatinib derivative B (SIAIS151101) and LIN-ULM (SIAIS171089). (yellow solid, 8.1 mg, yield 48%). $^1$H NMR (500 MHz, MeOD) δ 8.26 (s, 1H), 8.11 (s, 1H), 7.78-7.72 (m, 2H), 7.71-7.63 (m, 3H), 7.57-7.49 (m, 3H), 7.25 (d, J=8.6 Hz, 1H), 5.17 (dd, J=13.3, 5.1 Hz, 1H), 4.49 (d, J=17.3 Hz, 1H), 4.43 (d, J=17.3 Hz, 1H), 4.17-4.09 (m, 1H), 3.99 (s, 3H), 3.77 (s, 4H), 3.11 (t, J=7.3 Hz, 2H), 2.96-2.87 (m, 1H), 2.83-2.76 (m, 1H), 2.61-2.50 (m, 1H), 2.43 (t, J=7.2 Hz, 2H), 2.28-2.11 (m, 5H), 2.02-1.95 (m, 2H), 1.87 (d, J=13.5 Hz, 6H). HRMS (ESI) m/z: calcd for, $C_{41}H_{47}ClN_8O_6PS^+$ [M+H]$^+$, 845.2760; found, 845.2755.

Example 67: Preparation of N-(1-(4-((5-chloro-4-((2-(dimethylphosphoryl)phenyl)amino)pyrimidin-2-yl)amino)-3-methoxyphenyl)piperidin-4-yl)-5-((2-(2,6-dioxopiperidin-3-yl)-1-oxoisoindolin-4-yl)thio)pentanamide (SIAIS219136)

According to the general method described in Scheme 25, under appropriate conditions that will be recognized by one skilled in the art, the target compound (SIAIS219136) was prepared by using Brigatinib derivative B (SIAIS151101) and LIN-ULM (SIAIS171079). (yellow solid, 8.4 mg, yield 49%). $^1$H NMR (500 MHz, MeOD) δ 8.20 (d, J=11.3 Hz, 2H), 7.79-7.71 (m, 2H), 7.66 (dd, J=17.5, 7.6 Hz, 3H), 7.54 (t, J=7.6 Hz, 1H), 7.47 (t, J=7.4 Hz, 1H), 7.32 (s, 1H), 7.07 (d, J=8.0 Hz, 1H), 5.15 (dd, J=13.3, 5.2 Hz, 1H), 4.51 (d, J=17.3 Hz, 1H), 4.44 (d, J=17.4 Hz, 1H), 4.02-3.98 (m, 4H), 3.66 (t, J=24.9 Hz, 4H), 3.11-3.07 (m, 2H), 2.99-2.87 (m, 1H), 2.85-2.77 (m, 1H), 2.58-2.54 (m, 1H), 2.25-2.22 (m, 3H), 2.03 (d, J=12.1 Hz, 2H), 1.96-1.92 (m, 2H), 1.87 (d, J=13.5 Hz, 6H), 1.84-1.77 (m, 2H), 1.69-1.61 (m, 2H). HRMS (ESI) m/z: calcd for, $C_{42}H_{49}ClN_8O_6PS^+$ [M+H]$^+$, 859.2916; found, 859.2912.

Example 68: Preparation of N-(1-(4-((5-chloro-4-((2-(dimethylphosphoryl)phenyl)amino)pyrimidin-2-yl)amino)-3-methoxyphenyl)piperidin-4-yl)-6-((2-(2,6-dioxopiperidin-3-yl)-1-oxoisoindolin-4-yl)thio)hexanamide (SIAIS219137)

According to the general method described in Scheme 25, under appropriate conditions that will be recognized by one skilled in the art, the target compound (SIAIS219137) was prepared by using Brigatinib derivative B (SIAIS151101) and LIN-ULM (SIAIS171091). (yellow solid, 7.9 mg, yield 45%). $^1$H NMR (500 MHz, MeOD) δ 8.24 (s, 1H), 8.14 (s, 1H), 7.79-7.71 (m, 2H), 7.70-7.62 (m, 3H), 7.53 (t, J=7.7 Hz, 1H), 7.47 (dd, J=25.4, 12.1 Hz, 2H), 7.17 (s, 1H), 5.16 (dd, J=13.3, 5.2 Hz, 1H), 4.47 (d, J=17.3 Hz, 1H), 4.41 (d, J=17.3 Hz, 1H), 4.08 (s, 1H), 3.99 (s, 3H), 3.73 (s, 4H), 3.13-3.04 (m, 2H), 2.95-2.87 (m, 1H), 2.81-2.76 (m, 1H), 2.61-2.50 (m, 1H), 2.29-2.16 (m, 5H), 2.05 (s, 2H), 1.87 (d, J=13.6 Hz, 6H), 1.72-1.63 (m, 4H), 1.54-1.49 (m, 2H). HRMS (ESI) m/z: calcd for, $C_{43}H_{51}ClN_8O_6PS^+$ [M+H]$^+$, 873.3073; found, 873.3066.

Example 69: Preparation of N-(1-(4-((5-chloro-4-((2-(dimethylphosphoryl)phenyl)amino)pyrimidin-2-yl)amino)-3-methoxyphenyl)piperidin-4-yl)-7-((2-(2,6-dioxopiperidin-3-yl)-1-oxoisoindolin-4-yl)thio)heptanamide (SIAIS219138)

According to the general method described in Scheme 25, under appropriate conditions that will be recognized by one skilled in the art, Using Brigatinib derivative B (SIAIS151101) and LIN-ULM (SIAIS171092) to prepare the target compound (SIAIS219138). (yellow solid, 8.3 mg, yield 47%). $^1$H NMR (500 MHz, MeOD) δ 8.19 (s, 1H), 7.72 (dd, J=13.8, 7.8 Hz, 2H), 7.67-7.61 (m, 4H), 7.53 (t, J=7.6 Hz, 1H), 7.45 (t, J=7.6 Hz, 1H), 7.27 (s, 1H), 7.03 (s, 1H), 5.16 (dd, J=13.4, 5.2 Hz, 1H), 4.46 (d, J=17.3 Hz, 1H), 4.40 (d, J=17.3 Hz, 1H), 4.04 (s, 1H), 3.96 (s, 3H), 3.71 (s, 2H), 3.56 (s, 2H), 3.07 (t, J=7.0 Hz, 2H), 2.91-2.87 (m, 1H), 2.82-2.78 (m, 1H), 2.60-2.49 (m, 1H), 2.23-2.15 (m, 5H), 1.97-1.94 (m, 2H), 1.87 (d, J=13.5 Hz, 6H), 1.72-1.66 (m, 2H), 1.65-1.60 (m, 2H), 1.54-1.48 (m, 2H), 1.38-1.33 (m, 2H). HRMS (ESI) m/z: calcd for, $C_{44}H_{53}ClN_8O_6PS^+$ [M+H]$^+$, 887.3229; found, 887.3223.

Example 70: Preparation of N-(1-(4-((5-chloro-4-((2-(dimethylphosphoryl)phenyl)amino)pyrimidin-2-yl)amino)-3-methoxyphenyl)piperidin-4-yl)-2-(2-42-(2,6-dioxopiperidin-3-yl)-1,3-dioxoisoindolin-4-yl)thio)ethoxy)acetamide (SIAIS219144)

According to the general method described in Scheme 25, under appropriate conditions that will be recognized by one skilled in the art, the target compound (SIAIS219144) was prepared by using Brigatinib derivative B (SIAIS151101) and LIN-ULM (SIAIS1204137). (yellow solid, 9.2 mg, yield 53%). $^1$H NMR (500 MHz, MeOD) δ 8.27 (s, 1H), 8.12 (s, 1H), 7.83-7.74 (m, 4H), 7.72-7.62 (m, 2H), 7.56-7.48 (m, 2H), 7.25 (d, J=8.7 Hz, 1H), 5.11 (dd, J=12.8, 5.4 Hz, 1H), 4.24-4.18 (m, 1H), 4.07 (s, 2H), 3.99 (s, 3H), 3.89 (t, J=6.0 Hz, 2H), 3.84-3.73 (m, 4H), 3.44 (t, J=6.0 Hz, 2H), 2.93-2.80 (m, 1H), 2.78-2.62 (m, 2H), 2.23 (t, J=7.2 Hz, 4H), 2.17-2.08 (m, 1H), 1.87 (d, J=13.5 Hz, 6H). HRMS (ESI) m/z: calcd for, $C_{41}H_{45}ClN_8O_8PS^+$ [M+H]$^+$, 875.2502; found, 875.2501.

Example 71: Preparation of N-(1-(4-((5-chloro-4-((2-(dimethylphosphoryl)phenyl)amino)pyrimidin-2-yl)amino)-3-methoxyphenyl)piperidin-4-yl)-2-(2-((2-(2,6-dioxopiperidin-3-yl)-1-oxoisoindolin-4-yl)thio)ethoxy)acetamide (SIAIS219139)

According to the general method described in Scheme 25, under appropriate conditions that will be recognized by one skilled in the art, the target compound (SIAIS219139) was prepared by using Brigatinib derivative B (SIAIS151101) and LIN-ULM (SIAIS1213129). (yellow solid, 8.5 mg, yield 49%). $^1$H NMR (500 MHz, MeOD) δ 8.24 (s, 1H), 8.15 (s, 1H), 7.74 (dd, J=13.8, 7.2 Hz, 3H), 7.67 (t, J=7.5 Hz, 2H), 7.56 (t, J=7.6 Hz, 1H), 7.50 (t, J=7.3 Hz, 1H), 7.43 (s, 1H), 7.15 (d, J=8.6 Hz, 1H), 5.18 (dd, J=13.3, 5.2 Hz, 1H), 4.54 (d, J=17.4 Hz, 1H), 4.48 (d, J=17.4 Hz, 1H), 4.15-4.07 (m, 1H), 3.98 (d, J=4.6 Hz, 5H), 3.79 (t, J=6.1 Hz, 2H), 3.70 (s, 4H), 3.36-3.31 (m, 2H), 2.96-2.87 (m, 1H), 2.79 (d, J=15.5 Hz, 1H), 2.61-2.51 (m, 1H), 2.25-2.17 (m, 1H), 2.11 (s, 4H), 1.87 (d, J=13.5 Hz, 6H). HRMS (ESI) m/z: calcd for, $C_{41}H_{47}ClN_8O_7PS^+$ [M+H]$^+$, 861.2709; found, 861.2701.

Example 72: Preparation of N-(1-(4-((5-chloro-4-((2-(dimethylphosphoryl)phenyl)amino)pyrimidin-2-yl)amino)-3-methoxyphenyl)piperidin-4-yl)-2-(2-(2-((2-(2,6-dioxopiperidin-3-yl)-1-oxoisoindolin-4-yl)thio)ethoxy)ethoxy)acetamide (SIAIS219140)

According to the general method described in Scheme 25, under appropriate conditions that will be recognized by one skilled in the art, the target compound (SIAIS219140) was prepared by using Brigatinib derivative B (SIAIS151101) and LIN-ULM (SIAIS1213131). (yellow solid, 9.1 mg, yield 50%). $^1$H NMR (500 MHz, MeOD) δ 8.26 (s, 1H), 8.12 (s, 1H), 7.78-7.71 (m, 3H), 7.68 (t, J=7.9 Hz, 1H), 7.63 (d, J=7.5 Hz, 1H), 7.56-7.49 (m, 3H), 7.25 (dd, J=8.8, 2.1 Hz, 1H), 5.16 (dd, J=13.3, 5.2 Hz, 1H), 4.51 (d, J=17.4 Hz, 1H), 4.45 (d, J=17.4 Hz, 1H), 4.22-4.15 (m, 1H), 4.04 (s, 2H), 3.99 (s, 3H), 3.76 (t, J=6.1 Hz, 4H), 3.68 (d, J=4.3 Hz, 6H), 3.31-3.28 (m, 2H), 2.95-2.88 (m, 1H), 2.82-2.77 (m, 1H), 2.62-2.50 (m, 1H), 2.29-2.10 (m, 5H), 1.87 (d, J=13.5 Hz, 6H). HRMS (ESI) m/z: calcd for, $C_{43}H_{51}ClN_8O_8PS^+$ [M+H]$^+$, 905.2971; found, 905.2965.

Example 73: Preparation of N-(1-(4-((5-chloro-4-((2-(dimethylphosphoryl)phenyl)amino)pyrimidin-2-yl)amino)-3-methoxyphenyl)piperidin-4-yl)-2-(2-(2-(2-((2-(2,6-dioxopiperidin-3-yl)-1-oxoisoindolin-4-yl)thio)ethoxy)ethoxy)ethoxy)acetamide (SIAIS219141)

According to the general method described in Scheme 25, under appropriate conditions that will be recognized by one skilled in the art, the target compound (SIAIS219141) was prepared by using Brigatinib derivative B (SIAIS151101) and LIN-ULM (SIAIS1213133). (yellow solid, 9.0 mg, yield 47%). $^1$H NMR (500 MHz, MeOD) δ 8.24 (s, 1H), 8.15 (s, 1H), 7.76-7.69 (m, 3H), 7.68-7.61 (m, 2H), 7.50 (dd, J=14.5, 6.9 Hz, 2H), 7.42 (s, 1H), 7.14 (s, 1H), 5.16 (dd, J=13.3, 5.2 Hz, 1H), 4.48 (d, J=17.4 Hz, 1H), 4.42 (d, J=17.4 Hz, 1H), 4.15 (s, 1H), 4.03 (s, 2H), 3.98 (s, 3H), 3.75-3.63 (m, 12H), 3.25 (dd, J=11.5, 6.2 Hz, 4H), 2.96-2.86 (m, 1H), 2.81-2.79 (m, 1H), 2.59-2.50 (m, 1H), 2.20-2.17 (m, 5H), 1.87 (d, Example 74: Preparation of N-(1-(4-((5-chloro-4-((2-(dimethylphosphoryl)phenyl)amino)pyrimidin-2-yl)amino)-3-methoxyphenyl)piperidin-4-yl)-14-((2-(2,6-dioxopiperidin-3-yl)-1-oxoisoindolin-4-yl)thio)-3,6,9,12-tetraoxatetradecan-1-amide (SIAIS219142)

According to the general method described in Scheme 25, under appropriate conditions that will be recognized by one skilled in the art, the target compound (SIAIS219142) was prepared by using Brigatinib derivative B (SIAIS151101) and LIN-ULM (SIAIS1213135). (yellow solid, 10.1 mg, yield 51%). $^1$H NMR (500 MHz, MeOD) δ 8.26 (s, 1H), 8.12 (s, 1H), 7.75 (dd, J=14.2, 8.6 Hz, 2H), 7.71-7.61 (m, 3H), 7.54-7.48 (m, 3H), 7.23 (dd, J=8.7, 2.2 Hz, 1H), 5.16 (dd, J=13.3, 5.1 Hz, 1H), 4.48 (d, J=17.4 Hz, 1H), 4.42 (d, J=17.4 Hz, 1H), 4.23-4.16 (m, 1H), 4.04 (s, 2H), 3.99 (s, 3H), 3.80-3.60 (m, 18H), 3.24-3.21 (m, 2H), 2.95-2.87 (m, 1H), 2.82-2.76 (m, 1H), 2.59-2.48 (m, 1H), 2.26-2.21 (m, 5H), 1.87 (d, J=13.5 Hz, 6H). HRMS (ESI) m/z: calcd for, $C_{47}H_{59}ClN_8O_{10}PS^+$ [M+H]$^+$, 993.3496; found, 993.3491.

Example 75: Preparation of N-(1-(4-((5-chloro-4-((2-(dimethylphosphoryl)phenyl)amino)pyrimidin-2-yl)amino)-3-methoxyphenyl)piperidin-4-yl)-17-((2-(2,6-dioxopiperidin-3-yl)-1-oxoisoindolin-4-yl)thio)-3,6,9,12,15-pentaoxaheptadecan-1-amide (SIAIS219143)

According to the general method described in Scheme 25, under the appropriate conditions that will be recognized by one skilled in the art, the target compound (SIAIS219143) was prepared by using Brigatinib derivative B (SIAIS151101) and LIN-ULM (SIAIS1213137). (yellow solid, 9.9 mg, yield 48%). $^1$H NMR (500 MHz, MeOD) δ 8.25 (s, 1H), 8.14 (s, 1H), 7.84-7.61 (m, 5H), 7.50 (dd, J=16.6, 8.4 Hz, 3H), 7.20 (s, 1H), 5.16 (dd, J=13.4, 5.0 Hz, 1H), 4.48 (d, J=17.4 Hz, 1H), 4.42 (d, J=17.3 Hz, 1H), 4.23-4.14 (m, 1H), 4.03 (s, 2H), 3.99 (s, 3H), 3.85-3.52 (m, 22H), 3.21 (t, J=6.3 Hz, 2H), 2.97-2.85 (m, 1H), 2.79 (d, J=16.3 Hz, 1H), 2.58-2.50 (m, 1H), 2.33-2.13 (m, 5H), 1.87 (d, J=13.5 Hz, 6H). HRMS (ESI) m/z: calcd for, $C_{49}H_{63}ClN_8O_{11}PS^+$ [M+H]$^+$, 1037.3758; found, 1037.3751.

Example 76: Preparation of 4-((2-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-2-oxoethyl)thio)-2-(2,6-dioxopiperidin-3-yl)isoindoline-1,3-dione (SIAIS164062)

According to the general method described in Scheme 25, under the appropriate conditions that will be recognized by one skilled in the art, the target compound (SIAIS164062) was prepared by using Brigatinib derivative C (SIAIS164005) and LIN-ULM (SIAIS151045). (yellow solid, 11.9 mg, yield 76%). $^1$H NMR (500 MHz, MeOD) δ 8.37 (s, 1H), 8.05 (s, 1H), 7.89 (s, 1H), 7.82-7.62 (m, 3H), 7.56 (s, 1H), 7.38 (s, 2H), 6.75 (s, 1H), 6.60 (s, 1H), 5.15 (dd, J=13.5, 7.3 Hz, 1H), 4.23-4.14 (m, 3H), 3.95 (d, J=10.9 Hz, 2H), 3.86 (s, 3H), 3.63-3.38 (m, 6H), 2.87 (d, J=11.8 Hz, 4H), 2.78-2.74 (m, 3H), 2.26 (s, 2H), 2.15 (s, 1H), 1.94-1.87 (m, 8H). HRMS (ESI) calcd for, $C_{43}H_{48}ClN_9O_7PS^+$ [M+H]$^+$: 900.2818, found 900.3216.

Example 77: Preparation of 4-((3-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-3-oxopropyl)thio)-2-(2,6-dioxopiperidin-3-yl)isoindoline-1,3-dione (SIAIS164063)

According to the general method described in Scheme 25, under the appropriate conditions that will be recognized by one skilled in the art, the target compound (SIAIS164063) was prepared by using Brigatinib derivative C (SIAIS164005) and LIN-ULM (SIAIS151138B). (yellow solid, 9.6 mg, yield 60%). $^1$H NMR (500 MHz, MeOD) δ 8.38 (s, 1H), 8.06 (s, 1H), 7.79-7.78 (m, 2H), 7.71-7.64 (m, 2H), 7.56 (s, 1H), 7.36 (dd, J=15.4, 8.0 Hz, 2H), 6.73 (s, 1H), 6.59 (d, J=8.3 Hz, 1H), 5.11 (dd, J=12.3, 5.4 Hz, 1H), 3.94 (s, 2H), 3.86 (s, 3H), 3.65-3.32 (m, 10H), 2.97-2.65 (m, 8H), 2.23 (s, 2H), 2.17-2.09 (m, 1H), 1.89-1.87 (m, 8H). HRMS (ESI) calcd for, $C_{44}H_{50}ClN_9O_7PS^+$ [M+H]$^+$: 914.2975, found 914.3368.

Example 78: Preparation of 4-((4-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-4-oxobutyl)thio)-2-(2,6-dioxopiperidin-3-yl)isoindoline-1,3-dione (SIAIS164064)

According to the general method described in Scheme 25, under appropriate conditions that will be recognized by one skilled in the art, the target compound (SIAIS164064) was prepared by using Brigatinib derivative C (SIAIS164005) and LIN-ULM (SIAIS151139B). (yellow solid, 8 mg, yield 49%). $^1$H NMR (500 MHz, MeOD) δ 8.30 (s, 1H), 8.12 (s, 1H), 7.83 (d, J=8.1 Hz, 1H), 7.78-7.74 (m, 1H), 7.71 (dd, J=13.6, 8.2 Hz, 1H), 7.64 (d, J=7.2 Hz, 1H), 7.61 (s, 1H), 7.44 (t, J=7.1 Hz, 2H), 7.03 (s, 1H), 6.83 (s, 1H), 5.14 (dd, J=12.5, 5.5 Hz, 1H), 4.29 (s, 1H), 3.95 (d, J=11.9 Hz, 2H), 3.91 (s, 3H), 3.62 (s, 4H), 3.31-3.17 (m, 7H), 2.92-2.84 (m, 1H), 2.76-2.67 (m, 5H), 2.36 (s, 2H), 2.24-2.03 (m, 5H), 1.88 (d, J=13.6 Hz, 6H). HRMS (ESI) calcd for, $C_{45}H_{52}ClN_9O_7PS^+$ [M+H]$^+$: 928.3131, found 928.0598.

Example 79: Preparation of 4-((5-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-5-oxopentyl)thio)-2-(2,6-dioxopiperidin-3-yl)isoindoline-1,3-dione (SIAIS164066)

According to the general method described in Scheme 25, under appropriate conditions that will be recognized by one skilled in the art, the target compound (SIAIS164066) was prepared by using Brigatinib derivative C (SIAIS164005) and LIN-ULM (SIAIS151140B). (yellow solid, 8.2 mg, yield 50%). $^1$H NMR (500 MHz, MeOD) δ 8.28 (s, 1H), 8.14 (s, 1H), 7.80-7.67 (m, 3H), 7.62 (s, 2H), 7.45 (s, 2H), 7.13 (s, 1H), 6.91 (s, 1H), 5.13 (dd, J=12.4, 5.4 Hz, 1H), 4.28 (s, 1H), 3.96-3.91 (m, 5H), 3.67 (s, 4H), 3.31-3.25 (m, 8H), 2.84 (d, J=17.8 Hz, 1H), 2.80-2.66 (m, 2H), 2.54 (s, 2H), 2.41 (s, 2H), 2.21-2.12 (m, 3H), 1.98-1.74 (m, 10H). HRMS (ESI) calcd for, $C_{46}H_{54}ClN_9O_7PS^+$ [M+H]$^+$: 942.3288, found 942.0592.

Example 80: Preparation of 4-((6-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-6-oxohexyl)thio)-2-(2,6-dioxopiperidin-3-yl)isoindoline-1,3-dione (SIAIS164065)

According to the general method described in Scheme 25, under appropriate conditions that will be recognized by one skilled in the art, the target compound (SIAIS164065) was prepared by using Brigatinib derivative C (SIAIS164005) and LIN-ULM (SIAIS151141B). (yellow solid, 11.2 mg, 67% yield). $^1$H NMR (500 MHz, MeOD) δ 8.38 (s, 1H), 8.05 (s, 1H), 7.76-7.70 (m, 2H), 7.67 (dd, J=14.4, 8.1 Hz, 1H), 7.61 (d, J=6.7 Hz, 1H), 7.58-7.55 (m, 1H), 7.37 (t, J=7.2 Hz, 1H), 7.33 (d, J=8.4 Hz, 1H), 6.73 (d, J=2.3 Hz, 1H), 6.58 (d, J=9.4 Hz, 1H), 5.11 (dd, J=12.5, 5.5 Hz, 1H), 3.94 (d, J=12.1 Hz, 2H), 3.85 (s, 3H), 3.60-3.31 (m, 8H), 3.16 (t, J=7.0 Hz, 3H), 2.89-2.83 (m, 3H), 2.76-2.66 (m, 2H), 2.49 (t, J=7.1 Hz, 2H), 2.26 (d, J=12.1 Hz, 2H), 2.17-2.08 (m, 1H), 1.97-1.83 (m, 8H), 1.84-1.78 (m, 2H), 1.71-1.57 (m, 2H), 1.61-1.57 (m, 2H). HRMS (ESI) calcd for, $C_{47}H_{56}ClN_9O_7PS^+$ [M+H]$^+$: 956.3444, found 956.3885.

Example 81: Preparation of 4-((7-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-7-oxoheptyl)thio)-2-(2,6-dioxopiperidin-3-yl)isoindoline-1,3-dione (SIAIS164067)

According to the general method described in Scheme 25, under appropriate conditions that will be recognized by one skilled in the art, the target compound (SIAIS164067) was prepared by using Brigatinib derivative C (SIAIS164005) and LIN-ULM (SIAIS151142B). (yellow solid, 6.8 mg, yield 40%). $^1$H NMR (500 MHz, MeOD) δ 8.30 (s, 1H), 8.12 (s, 1H), 7.76-7.68 (m, 3H), 7.63-7.60 (m, 2H), 7.44 (t, J=7.0 Hz, 2H), 7.05 (s, 1H), 6.84 (s, 1H), 5.12 (dd, J=12.5, 5.5 Hz, 1H), 4.27 (s, 1H), 3.96 (d, J=14.0 Hz, 2H), 3.91 (s, 3H), 3.69-3.62 (m, 5H), 3.24 (s, 3H), 3.15 (t, J=7.1 Hz, 4H), 2.91-2.83 (m, 1H), 2.79-2.66 (m, 2H), 2.48 (t, J=7.3 Hz, 2H), 2.39 (d, J=10.6 Hz, 2H), 2.22-2.08 (m, 3H), 1.88 (d, J=13.6 Hz, 6H), 1.82-1.75 (m, 2H), 1.69-1.63 (m, 2H), 1.61-1.53 (m, 2H), 1.48-1.43 (m, 2H). HRMS (ESI) calcd for, $C_{48}H_{58}ClN_9O_7PS^+$ [M+H]$^+$: 970.3601, found 970.0767.

Example 82: Preparation of 3-(4-((2-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-2-oxoethyl)thio)-1-oxoisoindolin-2-yl)piperidine-2,6-dione (SIAIS219067)

According to the general method described in Scheme 25, under appropriate conditions that will be recognized by one skilled in the art, using Brigatinib derivative C (SIAIS164005) and LIN-ULM (SIAIS171090) to prepare the target compound (SIAIS219067). (yellow solid, 6.1 mg, yield 39%). $^1$H NMR (500 MHz, MeOD) δ 8.25 (s, 1H), 8.15 (s, 1H), 7.85 (d, J=7.7 Hz, 1H), 7.79 (d, J=7.6 Hz, 1H), 7.74-7.70 (m, 1H), 7.65-7.58 (m, 2H), 7.47 (t, J=7.5 Hz, 2H), 7.14 (s, 1H), 6.91 (d, J=7.2 Hz, 1H), 5.19 (dd, J=13.7, 4.9 Hz, 1H), 4.59 (d, J=17.5 Hz, 1H), 4.50 (d, J=15.8 Hz, 1H), 4.06 (s, 2H), 3.95 (s, 3H), 3.93 (s, 3H), 3.68-3.60 (m, 4H), 3.35 (s, 2H), 2.97-2.77 (m, 3H), 2.62-2.51 (m, 1H), 2.36 (d, J=11.7 Hz, 2H), 2.25-2.14 (m, 4H), 1.93-1.90 (m, 1H), 1.89 (s, 3H), 1.86 (s, 3H). HRMS (ESI) m/z: calcd for, $C_{43}H_{50}ClN_9O_6PS^+$ [M+H]$^+$, 886.3025; found, 886.3021.

Example 83: Preparation of 3-(4-((3-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-3-oxopropyl)thio)-1-oxoisoindolin-2-yl)piperidine-2,6-dione (SIAIS219068)

According to the general method described in Scheme 25, under appropriate conditions that will be recognized by one skilled in the art, the target compound (SIAIS219068) was prepared by using Brigatinib derivative C (SIAIS164005) and LIN-ULM (SIAIS171086). (yellow solid, 5.4 mg, yield 34%). $^1$H NMR (500 MHz, MeOD) δ 8.20 (s, 2H), 7.76-7.69 (m, 3H), 7.66 (t, J=7.9 Hz, 1H), 7.59-7.55 (m, 2H), 7.49 (t, J=7.5 Hz, 1H), 7.34 (s, 1H), 7.07 (d, J=6.4 Hz, 1H), 5.18 (dd, J=13.4, 5.2 Hz, 1H), 4.50 (d, J=17.4 Hz, 1H), 4.46-4.42 (m, 1H), 3.96 (s, 3H), 3.91 (d, J=12.3 Hz, 2H), 3.72 (s, 2H), 3.60 (s, 4H), 3.42-3.33 (m, 3H), 3.28 (d, J=6.9 Hz, 1H), 3.17 (s, 2H), 2.95-2.89 (m, 2H), 2.86-2.77 (m, 3H), 2.60-2.51 (m, 1H), 2.46 (d, J=10.9 Hz, 2H), 2.35 (s, 2H), 2.24-2.17 (m, 1H), 1.89 (s, 3H), 1.86 (s, 3H). HRMS (ESI) m/z: calcd for, $C_{44}H_{52}ClN_9O_6PS^+$ [M+H]$^+$, 900.3182; found, 900.3176.

Example 84: Preparation of 3-(4-((4-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-4-oxobutyl)thio)-1-oxoisoindolin-2-yl)piperidine-2,6-dione (SIAIS219069)

According to the general method described in Scheme 25, under appropriate conditions that will be recognized by one skilled in the art, the target compound (SIAIS219069) was prepared by using Brigatinib derivative C (SIAIS164005) and LIN-ULM (SIAIS171089). (yellow solid, 5.1 mg, yield 32%). $^1$H NMR (500 MHz, MeOD) δ 8.25 (s, 1H), 8.15 (s, 1H), 7.75-7.71 (m, 2H), 7.68 (d, J=7.5 Hz, 1H), 7.63 (t, J=7.5 Hz, 1H), 7.56 (t, J=7.6 Hz, 1H), 7.50 (s, 1H), 7.47 (t, J=7.1 Hz, 1H), 7.16 (s, 1H), 6.93 (d, J=8.1 Hz, 1H), 5.17 (dd, J=13.4, 5.2 Hz, 1H), 4.51 (d, J=17.4 Hz, 1H), 4.44 (d, J=17.3 Hz, 1H), 3.94 (s, 2H), 3.93 (s, 3H), 3.68-3.64 (m, 4H), 3.38 (s, 2H), 3.19-3.15 (m, 4H), 2.96-2.89 (m, 1H), 2.84-2.80 (m, 1H), 2.59-2.53 (m, 4H), 2.40 (d, J=11.6 Hz, 2H), 2.27-2.17 (m, 4H), 2.01-1.96 (m, J=6.9 Hz, 3H), 1.89 (s, 3H), 1.86 (s, 3H). HRMS (ESI) m/z: calcd for, $C_{45}H_{54}ClN_9O_6PS^+$ [M+H]$^+$, 914.3338; found, 914.3334.

Example 85: Preparation of 3-(4-((5-(4-(1-(4-((5-chloro-4-((2-(dimethylphosphoryl)phenyl)amino)pyrimidin-2-yl)amino)-3-methoxyphenyl)piperidin-4-yl)piperazin-1-yl)-5-oxopentyl)thio)-1-oxoisoindolin-2-yl)piperidine-2,6-dione (SIAIS219070)

According to the general method described in Scheme 25, under appropriate conditions that will be recognized by one skilled in the art, the target compound (SIAIS219070) was prepared by using Brigatinib derivative C (SIAIS164005) and LIN-ULM (SIAIS171079). (yellow solid, 5.0 mg, yield 31%). $^1$H NMR (500 MHz, MeOD) δ 8.19 (s, 2H), 7.73 (dd, J=12.6, 6.6 Hz, 1H), 7.67 (t, J=7.8 Hz, 3H), 7.59 (s, 1H), 7.54 (t, J=7.8 Hz, 1H), 7.49 (t, J=7.3 Hz, 1H), 7.32 (s, 1H), 7.06 (d, J=8.6 Hz, 1H), 5.18-5.15 (m, 1H), 4.49 (d, J=17.4 Hz, 1H), 4.43 (d, J=17.4 Hz, 1H), 3.95 (s, 3H), 3.91 (s, 2H), 3.71 (s, 4H), 3.59 (s, 4H), 3.13-3.07 (m, 4H), 2.95-2.87 (m, 1H), 2.79 (d, J=16.8 Hz, 1H), 2.59-2.46 (m, 5H), 2.38-2.33 (m, 3H), 2.24-2.17 (m, 1H), 1.89 (s, 3H), 1.86 (s, 3H), 1.80-1.71 (m, 4H). HRMS (ESI) m/z: calcd for, $C_{46}H_{56}ClN_9O_6PS^+$ [M+H]$^+$, 928.3495; found, 928.3491.

Example 86: Preparation of 3-(4-((6-(4-(1-(4-((5-chloro-4-((2-(dimethylphosphoryl)phenyl)amino) pyrimidin-2-yl)amino)-3-methoxyphenyl)piperidin-4-yl)piperazin-1-yl)-6-oxohexyl)thio)-1-oxoisoindolin-2-yl)piperidine-2,6-dione (SIAIS219071)

According to the general method described in Scheme 25, under appropriate conditions that will be recognized by one skilled in the art, the target compound (SIAIS219071) was prepared by using Brigatinib derivative C (SIAIS164005) and LIN-ULM (SIAIS171091). (yellow solid, 6.2 mg, yield 38%). $^1$H NMR (500 MHz, MeOD) δ 8.23 (s, 1H), 8.16 (s, 1H), 7.72 (dd, J=13.8, 7.8 Hz, 1H), 7.68-7.63 (m, 3H), 7.54 (t, J=7.7 Hz, 2H), 7.47 (t, J=7.4 Hz, 1H), 7.19 (s, 1H), 6.95 (d, J=7.6 Hz, 1H), 5.17 (dd, J=13.1, 4.8 Hz, 1H), 4.48 (d, J=17.4 Hz, 1H), 4.44-4.40 (m, 1H), 3.93 (s, 3H), 3.93-3.89 (m, 2H), 3.69 (s, 4H), 3.43-3.40 (m, 4H), 3.13-3.08 (m, 4H), 2.96-2.88 (m, 1H), 2.84-2.77 (m, 1H), 2.59-2.53 (m, 1H), 2.42 (t, J=11.5 Hz, 4H), 2.33-2.16 (m, 4H), 1.89 (s, 3H), 1.86 (s, 3H), 1.71-1.61 (m, 4H), 1.57-1.50 (m, 2H). HRMS (ESI) m/z: calcd for, $C_{47}H_{58}ClN_9O_6PS^+$ [M+H]$^+$, 942.3651; found, 942.3644.

Example 87: Preparation of 3-(4-((7-(4-(1-(4-((5-chloro-4-((2-(dimethylphosphoryl)phenyl)amino) pyrimidin-2-yl)amino)-3-methoxyphenyl)piperidin-4-yl)piperazin-1-yl)-7-oxoheptyl)thio)-1-oxoisoindolin-2-yl)piperidine-2,6-dione (SIAIS219072)

According to the general method described in Scheme 25, under appropriate conditions that will be recognized by one skilled in the art, the target compound (SIAIS219072) was prepared by using Brigatinib derivative C (SIAIS164005) and LIN-ULM (SIAIS171092). (yellow solid, 6.3 mg, yield 38%). $^1$H NMR (500 MHz, MeOD) δ 8.31 (s, 1H), 8.11 (s, 1H), 7.71 (dd, J=14.0, 7.7 Hz, 1H), 7.65 (dd, J=7.6, 2.0 Hz, 2H), 7.60 (s, 1H), 7.54 (t, J=7.7 Hz, 1H), 7.43 (t, J=7.6 Hz, 2H), 6.97 (s, 1H), 6.78 (d, J=8.1 Hz, 1H), 5.17 (dd, J=13.3, 5.2 Hz, 1H), 4.47 (d, J=17.4 Hz, 1H), 4.41 (d, J=17.3 Hz, 1H), 3.96 (d, J=12.6 Hz, 2H), 3.90 (s, 3H), 3.68-3.60 (m, 4H), 3.36-3.32 (m, 2H), 3.25-3.02 (m, 7H), 2.97-2.87 (m, 1H), 2.81-2.77 (m, 1H), 2.60-2.50 (m, 1H), 2.42 (t, J=7.5 Hz, 2H), 2.36 (d, J=11.4 Hz, 2H), 2.21-2.17 (m, 1H), 2.08 (d, J=12.1 Hz, 2H), 1.89 (d, J=8.4 Hz, 3H), 1.87 (s, 3H), 1.71-1.65 (m, 2H), 1.62-1.56 (m, 2H), 1.54-1.47 (m, 2H), 1.41-1.35 (m, 2H). HRMS (ESI) m/z: calcd for, $C_{48}H_{60}ClN_9O_6PS^+$ [M+H]$^+$, 956.3808; found, 956.3805.

Example 88: Preparation of 3-(4-((2-(2-(4-(1-(4-((5-chloro-4-((2-(dimethylphosphoryl)phenyl)amino) pyrimidin-2-yl)amino)-3-methoxyphenyl)piperidin-4-yl)piperazin-1-yl)-2-oxoethoxy)ethyl)thio)-1-oxoisoindolin-2-yl)piperidine-2,6-dione (SIAIS219092)

According to the general method described in Scheme 25, under the appropriate conditions that will be recognized by one skilled in the art, the target compound (SIAIS219092) was prepared by using Brigatinib derivative C (SIAIS164005) and LIN-ULM (SIAIS1213129). (yellow solid, 6.7 mg, yield 41%). $^1$H NMR (500 MHz, MeOD) δ 8.32 (d, J=18.7 Hz, 1H), 8.13 (s, 1H), 7.71 (ddd, J=21.8, 14.5, 7.9 Hz, 4H), 7.62 (t, J=7.5 Hz, 1H), 7.55 (dd, J=14.4, 6.9 Hz, 1H), 7.45 (t, J=6.9 Hz, 2H), 7.05 (s, 1H), 6.85 (d, J=7.3 Hz, 1H), 5.17 (dd, J=13.3, 5.0 Hz, 1H), 4.53 (d, J=17.4 Hz, 1H), 4.48 (d, J=14.5 Hz, 1H), 4.25 (s, 2H), 3.93 (d, J=12.7 Hz, 7H), 3.76 (d, J=13.8 Hz, 2H), 3.69-3.52 (m, 4H), 3.29-2.99 (m, 6H), 2.92-2.88 (m, 1H), 2.82-2.76 (m, 1H), 2.58-2.54 (m, 1H), 2.32 (s, 2H), 2.23-2.18 (m, 1H), 2.12 (s, 2H), 1.89-1.85 (m, 6H). HRMS (ESI) m/z: calcd for, $C_{45}H_{54}ClN_9O_7PS^+$ [M+H]$^+$, 930.3288; found, 930.3282.

Example 89: Preparation of 8-(4-(2-((2-(2,6-di-oxopiperidin-3-yl)-1,3-dioxoisoindolin-4-yl)thio) acetyl)piperazin-1-yl)-9-ethyl-6,6-dimethyl-11-oxo-6,11-dihydro-5H-benzo[b]carbazole-3-carbonitrile (SIAIS164068)

According to the general method described in Scheme 25, under appropriate conditions that will be recognized by one skilled in the art, the target compound (SIAIS164068) was prepared by using Alectinib derivative A and LIN-ULM (SIAIS151045). (yellow solid, 11.7 mg, yield 47%). $^1$H NMR (500 MHz, DMSO) δ 12.71 (s, 1H), 11.13 (s, 1H), 8.32 (d, J=8.2 Hz, 1H), 8.08 (s, 1H), 8.00 (s, 1H), 7.86 (d, J=8.1 Hz, 1H), 7.83-7.78 (m, 1H), 7.66 (d, J=7.1 Hz, 1H), 7.61 (dd, J=8.1, 1.4 Hz, 1H), 7.41 (s, 1H), 5.14 (dd, J=12.8, 5.4 Hz, 1H), 4.35 (s, 2H), 3.75 (d, J=54.1 Hz, 4H), 3.02 (d, J=31.7 Hz, 4H), 2.96-2.83 (m, 1H), 2.77 (q, J=7.4 Hz, 2H), 2.66-2.53 (m, 2H), 2.09-2.04 (m, 1H), 1.76 (s, 6H), 1.30 (t, J=7.5 Hz, 3H). HRMS (ESI) calcd for, $C_{40}H_{37}N_6O_6S^+$ [M+H]$^+$: 729.2490, found 729.2846.

Example 90: Preparation of 8-(4-(3-((2-(2,6-di-oxopiperidin-3-yl)-1,3-dioxoisoindolin-4-yl)thio) propanoyl)piperazin-1-yl)-9-ethyl-6,6-dimethyl-11-oxo-6,11-dihydro-5H-benzo[b]carbazole-3-carbonitrile (SIAIS164069)

According to the general method described in Scheme 25, under appropriate conditions that will be recognized by one skilled in the art, the target compound (SIAIS164069) was prepared by using Alectinib derivative A and LIN-ULM (SIAIS151138B). (yellow solid, 13.6 mg, yield 53%). $^1$H NMR (500 MHz, DMSO) δ 12.70 (s, 1H), 11.12 (s, 1H), 8.32 (d, J=8.1 Hz, 1H), 8.06 (s, 1H), 8.00 (s, 1H), 7.87-7.76 (m, 2H), 7.65 (d, J=6.0 Hz, 1H), 7.61 (d, J=9.1 Hz, 1H), 7.39 (s, 1H), 5.12 (dd, J=12.9, 5.4 Hz, 1H), 3.69 (s, 2H), 3.62 (s, 2H), 3.40-3.36 (m, 2H), 2.94 (s, 4H), 2.87-2.85 (m, 3H), 2.75 (q, J=7.4 Hz, 2H), 2.61-2.58 (m, 2H), 2.07-2.04 (m, 1H), 1.75 (s, 6H), 1.28 (t, J=7.5 Hz, 3H). HRMS (ESI) calcd for, $C_{41}H_{39}N_6O_6S^+$ [M+H]$^+$: 743.2646, found 743.3002.

Example 91: Preparation of 8-(4-(4-((2-(2,6-di-oxopiperidin-3-yl)-1,3-dioxoisoindolin-4-yl)thio) butanoyl)piperazin-1-yl)-9-ethyl-6,6-dimethyl-11-oxo-6,11-dihydro-5H-benzo[b]carbazole-3-carbonitrile (SIAIS164070)

According to the general method described in Scheme 25, the target compound (SIAIS164070) was prepared by using Alectinib derivative A and LIN-ULM (SIAIS151139B) under appropriate conditions that will be recognized by one skilled in the art. (yellow solid, 13.6 mg, yield 75%). $^1$H NMR (500 MHz, DMSO) δ 12.71 (s, 1H), 11.12 (s, 1H), 8.32 (d, J=8.1 Hz, 1H), 8.07 (s, 1H), 8.00 (s, 1H), 7.90 (d, J=8.3 Hz, 1H), 7.84-7.78 (m, 1H), 7.64 (d, J=7.2 Hz, 1H), 7.61 (dd, J=8.1, 1.3 Hz, 1H), 7.39 (s, 1H), 5.12 (dd, J=12.8, 5.4 Hz, 1H), 3.66 (d, J=10.5 Hz, 2H), 3.64 (s, 2H), 3.20 (t, J=7.4 Hz, 2H), 2.98 (s, 2H), 2.93 (s, 2H), 2.91-2.83 (m, 1H), 2.76 (q, J=7.5 Hz, 2H), 2.66-2.52 (m, 4H), 2.06 (dd, J=10.2, 4.9 Hz, 1H), 2.00-1.90 (m, 2H), 1.75 (s, 6H), 1.29 (t, J=7.5 Hz, 3H). HRMS (ESI) calcd for, $C_{42}H_{41}N_6O_6S^+$ [M+H]$^+$: 757.2803, found 757.3013.

Example 92: Preparation of 8-(4-(5-((2-(2,6-di-oxopiperidin-3-yl)-1,3-dioxoisoindolin-4-yl)thio) pentanoyl)piperazin-1-yl)-9-ethyl-6,6-dimethyl-11-oxo-6,11-dihydro-5H-benzo[b]carbazole-3-carbonitrile (SIAIS164072)

According to the general method described in Scheme 25, under appropriate conditions that will be recognized by one skilled in the art, the target compound (SIAIS164072). (yellow solid, 16.6 mg, Alectinib derivative A and LIN-ULM (SIAIS151140B)) yield 62%). $^1$H NMR (500 MHz, DMSO) δ 12.70 (s, 1H), 11.12 (s, 1H), 8.32 (d, J=8.2 Hz, 1H), 8.07 (s, 1H), 8.00 (s, 1H), 7.82-7.76 (m, 2H), 7.63 (d, J=4.6 Hz, 1H), 7.62-7.59 (m, 1H), 7.39 (s, 1H), 5.11 (dd, J=12.9, 5.4 Hz, 1H), 3.65 (s, 4H), 3.18 (s, 2H), 2.98 (s, 2H), 2.93 (s, 2H), 2.90-2.84 (m, 1H), 2.75 (q, J=7.4 Hz, 2H), 2.66-2.55 (m, 2H), 2.45 (s, 2H), 2.04 (s, 1H), 1.75 (s, 10H), 1.28 (t, J=7.5 Hz, 3H). HRMS (ESI) calcd for, $C_{43}H_{43}N_6O_6S^+$ [M+H]$^+$: 771.2959, found 771.3153.

Example 93: Preparation of 8-(4-(6-((2-(2,6-di-oxopiperidin-3-yl)-1,3-dioxoisoindolin-4-yl)thio) hexanoyl)piperazin-1-yl)-9-ethyl-6,6-dimethyl-11-oxo-6,11-dihydro-5H-benzo[b]carbazole-3-carbonitrile (SIAIS164071)

According to the general method described in Scheme 25, the target compound (SIAIS164071) was prepared by using Alectinib derivative A and LIN-ULM (SIAIS151141B) under appropriate conditions that will be recognized by one skilled in the art. (yellow solid, 20.7 mg, yield 75%). $^1$H NMR (500 MHz, DMSO) δ 12.70 (s, 1H), 11.12 (s, 1H), 8.32 (d, J=8.1 Hz, 1H), 8.07 (s, 1H), 8.00 (s, 1H), 7.82-7.73 (m, 2H), 7.63 (d, J=6.9 Hz, 1H), 7.61 (dd, J=8.2, 1.3 Hz, 1H), 7.39 (s, 1H), 5.11 (dd, J=12.9, 5.4 Hz, 1H), 3.64 (s, 4H), 3.15 (t, J=7.3 Hz, 2H), 2.97 (s, 2H), 2.93 (s, 2H), 2.90-2.84 (m, 1H), 2.75 (q, J=7.5 Hz, 2H), 2.66-2.55 (m, 2H), 2.41-2.36 (m, 2H), 2.07-2.04 (m, 1H), 1.75 (s, 6H), 1.72-1.70 (m, 2H), 1.64-1.55 (m, 2H), 1.51-1.50 (m, 2H), 1.29 (t, J=7.5 Hz, 3H). HRMS (ESI) calcd for, $C_{44}H_{45}N_6O_6S^+$ [M+H]$^+$: 785.3116, found 785.3486.

Example 94: Preparation of 8-(4-(7-((2-(2,6-di-oxopiperidin-3-yl)-1,3-dioxoisoindolin-4-yl)thio) heptanoyl)piperazin-1-yl)-9-ethyl-6,6-dimethyl-11-oxo-6,11-dihydro-5H-benzo[b]carbazole-3-carbonitrile (SIAIS164073)

According to the general method described in Scheme 25, under appropriate conditions that will be recognized by one skilled in the art, the target compound (SIAIS164073) was prepared by using Alectinib derivative A and LIN-ULM (SIAIS151142B). (yellow solid, 19.7 mg, yield 71%). $^1$H NMR (500 MHz, DMSO) δ 12.71 (s, 1H), 11.12 (s, 1H), 8.32 (d, J=8.2 Hz, 1H), 8.06 (s, 1H), 8.00 (s, 1H), 7.82-7.73 (m, 2H), 7.61 (t, J=8.4 Hz, 1H), 7.39 (s, 1H), 5.10 (s, 1H), 3.64 (s, 4H), 3.14 (s, 2H), 2.97 (s, 2H), 2.93 (s, 2H), 2.89-2.84 (m, 1H), 2.75 (d, J=7.7 Hz, 2H), 2.61 (s, 2H), 2.37 (s, 2H), 2.07-2.03 (m, 1H), 1.75 (s, 6H), 1.69 (s, 2H), 1.55 (s, 2H), 1.48 (s, 2H), 1.37 (s, 2H), 1.28 (t, J=7.4 Hz, 3H). HRMS (ESI) calcd for, $C_{45}H_{47}N_6O_6S^+$ [M+H]$^+$: 799.3272, found 799.3473.

Example 95: Preparation of N-(1-(3-cyano-9-ethyl-6,6-dimethyl-11-oxo-6,11-dihydro-5H-benzo[b]car-bazol-8-yl)piperidin-4-yl)-2-((2-(2,6-dioxopiperidin-3-yl)-1,3-dioxoisoindolin-4-yl)thio)acetamide (SIAIS219012)

According to the general method described in Scheme 25, t under appropriate conditions that will be recognized by one skilled in the art, the target compound (SIAIS219012) was prepared by using Alectinib derivative B and LIN-ULM (SIAIS151045). (yellow solid, 6.7 mg, yield 37%). $^1$H NMR (500 MHz, DMSO) δ 12.76 (s, 1H), 11.13 (s, 1H), 8.38 (d, J=7.6 Hz, 1H), 8.32 (d, J=8.2 Hz, 1H), 8.02 (d, J=21.8 Hz, 2H), 7.90-7.76 (m, 2H), 7.73-7.55 (m, 2H), 7.36 (s, 1H), 5.14 (dd, J=12.8, 5.4 Hz, 1H), 3.90 (s, 2H), 3.79 (s, 1H), 3.44 (s, 4H), 3.16 (d, J=11.6 Hz, 2H), 2.89-2.85 (m, 3H), 2.71 (q, J=7.5 Hz, 2H), 2.61 (d, J=19.0 Hz, 2H), 2.11-2.02 (m, 1H), 1.90 (d, J=10.2 Hz, 2H), 1.75 (s, 6H), 1.68-1.61 (m, 2H), 1.28 (t, J=7.5 Hz, 3H). HRMS (ESI) m/z: calcd for, $C_{41}H_{39}N_6O_6S^+$ [M+H]$^+$, 743.2646; found, 743.2674.

Example 96: Preparation of N-(1-(3-cyano-9-ethyl-6,6-dimethyl-11-oxo-6,11-dihydro-5H-benzo[b]car-bazol-8-yl)piperidin-4-yl)-4-((2-(2,6-dioxopiperidin-3-yl)-1,3-dioxoisoindolin-4-yl)thio)butanamide (SIAIS219013)

According to the general method described in Scheme 25, under appropriate conditions that will be recognized by one skilled in the art, the target compound (SIAIS219013) was prepared using Alectinib derivative B and LIN-ULM (SIAIS151139B). (yellow solid, 9.2 mg, yield 49%). $^1$H NMR (500 MHz, DMSO) δ 12.71 (s, 1H), 11.12 (s, 1H), 8.32 (d, J=8.2 Hz, 1H), 8.02 (d, J=19.9 Hz, 2H), 7.95 (d, J=7.7 Hz, 1H), 7.81 (dd, J=7.1, 5.0 Hz, 2H), 7.64-7.61 (m, 2H), 7.36 (s, 1H), 5.12 (dd, J=12.9, 5.4 Hz, 1H), 3.78 (s, 1H), 3.22-3.11 (m, 4H), 2.87-2.82 (m, 3H), 2.70 (q, J=7.5 Hz, 2H), 2.66-2.56 (m, 2H), 2.30 (t, J=7.1 Hz, 2H), 2.10-2.00 (m, 1H), 1.93-1.90 (m, 4H), 1.75 (s, 6H), 1.59 (d, J=9.3 Hz, 2H), 1.28 (d, J=7.5 Hz, 3H). HRMS (ESI) m/z: calcd for, $C_{43}H_{43}N_6O_6S^+$ [M+H]$^+$, 771.2959; found, 771.2979.

Example 97: Preparation of N-(1-(3-cyano-9-ethyl-6,6-dimethyl-11-oxo-6,11-dihydro-5H-benzo[b]car-bazol-8-yl)piperidin-4-yl)-6-((2-(2,6-dioxopiperidin-3-yl)-1,3-dioxoisoindolin-4-yl)thio)hexanamide (SIAIS219014)

According to the general method described in Scheme 25, under appropriate conditions that will be recognized by one skilled in the art, the target compound (SIAIS219014). (yellow solid, 9.3 mg, yield 48%) was prepared by using Alectinib derivative B and LIN-ULM (SIAIS151141B). $^1$H NMR (500 MHz, DMSO) δ 12.71 (s, 1H), 11.12 (s, 1H), 8.32 (d, J=8.1 Hz, 1H), 8.03-7.98 (m, 2H), 7.78 (dd, J=15.1, 8.1 Hz, 2H), 7.64-7.59 (m, 2H), 7.36 (s, 1H), 5.11 (dd, J=12.8, 5.5 Hz, 1H), 3.75 (s, 1H), 3.15 (d, J=7.5 Hz, 4H), 2.83 (t, J=10.9 Hz, 3H), 2.70 (q, J=7.6 Hz, 2H), 2.62 (d, J=18.3 Hz, 1H), 2.11-2.08 (m, 3H), 1.87 (d, J=10.1 Hz, 2H), 1.75 (s, 6H), 1.72-1.67 (m, 2H), 1.59-1.55 (m, 4H), 1.45 (d, J=6.4 Hz, 2H), 1.27 (t, J=7.5 Hz, 3H). HRMS (ESI) m/z: calcd for, $C_{45}H_{47}N_6O_6S^+$ [M+H]$^+$, 799.3272; found, 799.3274.

Example 98: Preparation of N-(1-(3-cyano-9-ethyl-6,6-dimethyl-11-oxo-6,11-dihydro-5H-benzo[b]carbazol-8-yl)piperidin-4-yl)-2-((2-(2,6-dioxopiperidin-3-yl)-1-oxoisoindolin-4-yl)thio)acetamide (SIAIS262161)

According to the general method described in Scheme 25, the target compound (SIAIS262161) was prepared by using Alectinib derivative B and LIN-ULM (SIAIS171090). (yellow solid, 7.5 mg, yield 43%) $^1$H NMR (500 MHz, DMSO) δ 12.72 (s, 1H), 11.00 (s, 1H), 8.32 (d, J=8.2 Hz, 1H), 8.20 (d, J=7.7 Hz, 1H), 8.04 (s, 1H), 8.00 (s, 1H), 7.70 (d, J=7.6 Hz, 1H), 7.60 (dd, J=7.3, 2.0 Hz, 2H), 7.55 (t, J=7.6 Hz, 1H), 7.34 (s, 1H), 5.14 (dd, J=13.3, 5.1 Hz, 1H), 4.42 (d, J=17.4 Hz, 1H), 4.28 (d, J=17.4 Hz, 1H), 3.74 (d, J=14.8 Hz, 3H), 3.13 (d, J=12.0 Hz, 2H), 2.95-2.87 (m, 1H), 2.83 (s, 1H), 2.69 (q, J=7.5 Hz, 2H), 2.60 (d, J=16.9 Hz, 1H), 2.44 (dd, J=13.4, 4.4 Hz, 1H), 2.00 (dd, J=16.4, 8.8 Hz, 2H), 1.84 (d, J=12.4 Hz, 2H), 1.75 (s, 6H), 1.56 (d, J=12.0 Hz, 2H), 1.27 (t, J=7.4 Hz, 3H). HRMS (ESI) m/z: calcd for, $C_{41}H_{41}N_6O_5S^+$ [M+H]$^+$, 729.2854; found, 729.2839.

Example 99: Preparation of N-(1-(3-cyano-9-ethyl-6,6-dimethyl-11-oxo-6,11-dihydro-5H-benzo[b]carbazol-8-yl)piperidin-4-yl)-6-((2-(2,6-dioxopiperidin-3-yl)-1-oxoisoindolin-4-yl)thio)hexanamide (SIAIS262162)

According to the general method described in Scheme 25, the target compound (SIAIS262162) was prepared by using Alectinib derivative B and LIN-ULM (SIAIS171091)) under appropriate conditions that will be recognized by one skilled in the art. (yellow solid, 9.2 mg, yield 48%). $^1$H NMR (500 MHz, DMSO) δ 12.72 (s, 1H), 10.99 (s, 1H), 8.32 (d, J=8.2 Hz, 1H), 8.04 (s, 1H), 8.00 (s, 1H), 7.80 (d, J=7.6 Hz, 1H), 7.62 (dd, J=16.8, 7.9 Hz, 2H), 7.59-7.51 (m, 2H), 7.36 (s, 1H), 5.13 (dd, J=13.3, 5.2 Hz, 1H), 4.36 (d, J=17.5 Hz, 1H), 4.22 (d, J=17.4 Hz, 1H), 3.73 (s, 1H), 3.14 (d, J=12.1 Hz, 2H), 3.09 (t, J=7.2 Hz, 2H), 2.94-2.80 (m, 3H), 2.70 (q, J=7.5 Hz, 2H), 2.62 (d, J=18.9 Hz, 1H), 2.45 (d, J=4.4 Hz, 1H), 2.10-2.05 (m, 2H), 2.04-1.97 (m, 1H), 1.86 (d, J=9.8 Hz, 2H), 1.75 (s, 6H), 1.65-1.52 (m, 6H), 1.41 (d, J=7.0 Hz, 2H), 1.27 (t, J=7.5 Hz, 3H). HRMS (ESI) m/z: calcd for, $C_{45}H_{49}N_6O_5S^+$ [M+H]$^+$, 785.3480; found, 785.3470.

Example 100: Preparation of N-(1-(3-cyano-9-ethyl-6,6-dimethyl-11-oxo-6,11-dihydro-5H-benzo[b]carbazol-8-yl)piperidin-4-yl)-2-(2-(2-((2-(2,6-dioxopiperidin-3-yl)-1,3-dioxoisoindolin-4-yl)thio)ethoxy)ethoxy)acetamide (SIAIS219022)

According to the general method described in Scheme 25, under appropriate conditions that will be recognized by one skilled in the art, the target compound (SIAIS219022) was prepared by using Alectinib derivative B and LIN-ULM (SIAIS1204139). (yellow solid, 9.7 mg, yield 48%) $^1$H NMR (500 MHz, DMSO) δ 12.72 (s, 1H), 11.13 (s, 1H), 8.33 (d, J=8.1 Hz, 1H), 8.04-8.01 (m, 2H), 7.79 (dd, J=15.1, 8.1 Hz, 2H), 7.65-7.59 (m, 2H), 7.37 (s, 1H), 5.12 (dd, J=12.8, 5.5 Hz, 1H), 3.88-3.81 (m, 6H), 3.77 (s, 1H), 3.16 (d, J=7.5 Hz, 4H), 2.84 (t, J=10.9 Hz, 3H), 2.71 (q, J=7.6 Hz, 2H), 2.63 (d, J=18.3 Hz, 1H), 2.09-2.04 (m, 3H), 1.89 (d, J=10.1 Hz, 2H), 1.76 (s, 6H), 1.73-1.67 (m, 2H), 1.46 (d, J=6.4 Hz, 2H), 1.29 (t, J=7.5 Hz, 3H). HRMS (ESI) m/z: calcd for, $C_{45}H_{47}N_6O_8S^+$ [M+H]$^+$, 831.3171; found, 831.3170.

Example 101: Preparation of N-(1-(3-cyano-9-ethyl-6,6-dimethyl-11-oxo-6,11-dihydro-5H-benzo[b]carbazol-8-yl)piperidin-4-yl)-2-(2-((2-(2,6-dioxopiperidin-3-yl)-1-oxoisoindolin-4-yl)thio)ethoxy)acetamide (SIAIS262163)

According to the general method described in Scheme 25, under appropriate conditions that will be recognized by one skilled in the art, the target compound (SIAIS262163) was prepared by using Alectinib derivative B and LIN-ULM (SIAIS1213129). (yellow solid, 8.9 mg, yield 48%). $^1$H NMR (500 MHz, DMSO) δ 12.72 (s, 1H), 10.99 (s, 1H), 8.32 (d, J=8.2 Hz, 1H), 8.04 (s, 1H), 8.00 (s, 1H), 7.73 (d, J=7.4 Hz, 1H), 7.65 (d, J=8.1 Hz, 1H), 7.62-7.58 (m, 2H), 7.55 (t, J=7.6 Hz, 1H), 7.36 (s, 1H), 5.13 (dd, J=13.3, 5.1 Hz, 1H), 4.39 (d, J=17.5 Hz, 1H), 4.25 (d, J=17.4 Hz, 1H), 3.91 (s, 2H), 3.81 (s, 1H), 3.69 (t, J=6.5 Hz, 2H), 3.15 (d, J=11.6 Hz, 2H), 2.88 (ddd, J=30.9, 21.8, 8.6 Hz, 3H), 2.71 (q, J=7.5 Hz, 2H), 2.57 (d, J=17.1 Hz, 1H), 2.49-2.40 (m, 2H), 2.04-1.94 (m, 2H), 1.81 (s, 2H), 1.75 (s, 6H), 1.68 (d, J=11.6 Hz, 2H), 1.28 (t, J=7.5 Hz, 3H). HRMS (ESI) m/z: calcd for, $C_{43}H_{45}N_6O_6S^+$ [M+H]$^+$, 773.3116; found, 773.3105.

Example 102: Preparation of 8-(4-(1-(2-((2-(2,6-dioxopiperidin-3-yl)-1,3-dioxoisoindolin-4-yl)thio)acetyl)piperidin-4-yl)piperazin-1-yl)-9-ethyl-6,6-dimethyl-11-oxo-6,11-dihydro-5H-benzo[b]carbazole-3-carbonitrile (SIAIS219005)

According to the general method described in Scheme 25, the target compound (SIAIS219005) was prepared by using Alectinib derivative C and LIN-ULM (SIAIS151045)) under appropriate conditions that will be recognized by one skilled in the art. (yellow solid, 6.8 mg, yield 40%). $^1$H NMR (500 MHz, DMSO) δ 12.70 (s, 1H), 11.13 (s, 1H), 8.32 (d, J=8.3 Hz, 1H), 8.02 (d, J=22.0 Hz, 2H), 7.82-7.76 (m, 2H), 7.65-7.61 (m, 2H), 7.34 (s, 1H), 5.13 (dd, J=12.9, 5.4 Hz, 1H), 4.28 (s, 2H), 3.58-3.54 (m, 6H), 3.24 (s, 2H), 2.88 (d, J=12.0 Hz, 1H), 2.78 (s, 2H), 2.74-2.69 (m, 2H), 2.61 (d, J=20.0 Hz, 4H), 2.06 (s, 1H), 2.00 (d, J=7.5 Hz, 1H), 1.89 (s, 1H), 1.75 (s, 6H), 1.65 (s, 1H), 1.27 (d, J=7.4 Hz, 3H). HRMS (ESI) m/z: calcd for, $C_{45}H_{46}N_7O_6S^+$ [M+H]$^+$, 812.3225; found, 812.3222.

Example 103: Preparation of 8-(4-(4-(4-((2-(2,6-dioxopiperidin-3-yl)-1,3-dioxoisoindolin-4-yl)thio)butanoyl)piperazin-1-yl)piperidin-1-yl)-9-ethyl-6,6-dimethyl-11-oxo-6,11-dihydro-5H-benzo[b]carbazole-3-carbonitrile (SIAIS219006)

According to the general method described in Scheme 25, under appropriate conditions that will be recognized by one skilled in the art, the target compound (SIAIS219006) was prepared using Alectinib derivative C and LIN-ULM (SIAIS151139B). (yellow solid, 7.5 mg, yield 43%). $^1$H NMR (500 MHz, DMSO) δ 12.71 (s, 1H), 11.14 (s, 1H), 8.32 (d, J=8.3 Hz, 1H), 8.05-8.01 (m, 2H), 7.82-7.79 (m, 2H), 7.66-7.62 (m, 2H), 7.35 (s, 1H), 5.12 (dd, J=12.9, 5.4 Hz, 1H), 4.29 (s, 2H), 3.59-3.54 (m, 6H), 3.24 (s, 2H), 2.89 (d, J=12.0 Hz, 1H), 2.78 (s, 2H), 2.76-2.69 (m, 2H), 2.65-2.60 (m, 6H), 2.07 (s, 1H), 2.01 (d, J=7.5 Hz, 1H), 1.89-1.81

(m, 3H), 1.76 (s, 1H), 1.67 (s, 1H), 1.28 (d, J=7.4 Hz, 3H). HRMS (ESI) m/z: calcd for, $C_{47}H_{50}N_7O_6S^+$ [M+H]$^+$, 840.3538; found, 840.3550.

Example 104: Preparation of 8-(4-(4-(6-((2-(2,6-dioxopiperidin-3-yl)-1,3-dioxoisoindolin-4-yl)thio)hexanoyl)piperazin-1-yl)piperidin-1-yl)-9-ethyl-6,6-dimethyl-11-oxo-6,11-dihydro-5H-benzo[b]carbazole-3-carbonitrile (SIAIS219007)

According to the general method described in Scheme 25, the target compound (SIAIS219007) was prepared using Alectinib derivative C and LIN-ULM (SIAIS151141B) under appropriate conditions that will be recognized by one skilled in the art. (yellow solid, 6.9 mg, yield 38%). $^1$H NMR (500 MHz, DMSO) δ 12.84 (s, 1H), 11.14 (s, 1H), 8.31 (d, J=8.2 Hz, 1H), 8.06 (s, 1H), 8.01 (s, 1H), 7.86-7.72 (m, 2H), 7.70-7.59 (m, 2H), 7.36 (s, 1H), 5.12 (dd, J=12.9, 5.4 Hz, 1H), 4.51 (d, J=13.1 Hz, 1H), 4.10 (d, J=13.5 Hz, 1H), 3.59-3.54 (m, 4H), 3.31 (d, J=11.3 Hz, 4H), 3.21-3.06 (m, 4H), 2.94-2.78 (m, 3H), 2.71 (q, J=7.4 Hz, 2H), 2.63-2.56 (m, 1H), 2.39-2.33 (m, 2H), 2.21 (d, J=10.7 Hz, 2H), 2.07-2.03 (m, 1H), 1.92 (t, J=19.9 Hz, 2H), 1.76 (s, 6H), 1.73-1.68 (m, 2H), 1.59-1.54 (m, 2H), 1.50-1.45 (m, 2H), 1.28 (t, J=7.2 Hz, 3H). HRMS (ESI) m/z: calcd for, $C_{49}H_{54}N_7O_6S^+$ [M+H]$^+$, 868.3851; found, 868.3856.

Example 105: Preparation of 8-(4-(4-(2-((2-(2,6-dioxopiperidin-3-yl)-1-oxoisoindolin-4-yl)thio)acetyl)piperazin-1-yl)piperidin-1-yl)-9-ethyl-6,6-dimethyl-11-oxo-6,11-dihydro-5H-benzo[b]carbazole-3-carbonitrile (SIAIS262096)

According to the general method described in Scheme 25, under appropriate conditions that will be recognized by one skilled in the art, the target compound (SIAIS262096) was prepared by using Alectinib derivative C and LIN-ULM (SIAIS171090). (yellow solid, 10.4 mg, yield 42%). $^1$H NMR (500 MHz, DMSO) δ 12.83 (s, 1H), 11.03 (s, 1H), 8.31 (d, J=8.2 Hz, 1H), 8.04 (d, J=23.8 Hz, 2H), 7.72 (d, J=7.2 Hz, 1H), 7.63-7.60 (m, 2H), 7.59-7.52 (m, 1H), 7.36 (s, 1H), 5.15 (dd, J=13.3, 5.1 Hz, 1H), 4.49-4.40 (m, 2H), 4.32-4.19 (m, 4H), 3.67-3.52 (m, 4H), 3.32 (d, J=11.1 Hz, 6H), 3.17 (t, J=12.3 Hz, 2H), 2.98-2.89 (m, 1H), 2.82 (d, J=5.2 Hz, 2H), 2.71 (q, J=7.4 Hz, 2H), 2.62-2.55 (m, 1H), 2.22 (s, 2H), 2.05-1.99 (m, 1H), 1.76 (s, 6H), 1.29 (t, J=7.5 Hz, 3H). HRMS (ESI) m/z: calcd for, $C_{45}H_{48}N_7O_5S^+$ [M+H]$^+$, 798.3432; found, 798.2945.

Example 106: Preparation of 8-(4-(4-(3-((2-(2,6-dioxopiperidin-3-yl)-1-oxoisoindolin-4-yl)thio)propanoyl)piperazin-1-yl)piperidin-1-yl)-9-ethyl-6,6-dimethyl-11-oxo-6,11-dihydro-5H-benzo[b]carbazole-3-carbonitrile (SIAIS262097)

According to the general method described in Scheme 25, under appropriate conditions that will be recognized by one skilled in the art, the target compound (SIAIS219007) was prepared by using Alectinib derivative C and LIN-ULM (SIAIS171086). (yellow solid, 9.8 mg, yield 39%). $^1$H NMR (500 MHz, DMSO) δ 12.83 (s, 1H), 11.02 (d, J=7.3 Hz, 1H), 8.31 (d, J=8.2 Hz, 1H), 8.06 (s, 1H), 8.01 (s, 1H), 7.68 (d, J=6.8 Hz, 1H), 7.64-7.53 (m, 3H), 7.36 (s, 1H), 5.15 (dd, J=13.3, 5.2 Hz, 1H), 4.51 (d, J=13.6 Hz, 1H), 4.40-4.34 (m, 1H), 4.24-4.21 (m, 1H), 4.03 (d, J=13.1 Hz, 1H), 3.37-3.23 (m, 6H), 3.11 (s, 2H), 3.04-2.87 (m, 3H), 2.79 (t, J=7.1 Hz, 4H), 2.71 (q, J=7.4 Hz, 2H), 2.63-2.56 (m, 1H), 2.19 (s, 2H), 2.03-1.99 (m, 1H), 1.90 (d, J=10.4 Hz, 2H), 1.76 (s, 6H), 1.28 (t, J=7.5 Hz, 3H). HRMS (ESI) m/z: calcd for, $C_{46}H_{50}N_7O_5S^+$ [M+H]$^+$, 812.3589; found, 8123110.

Example 107: Preparation of 8-(4-(4-(4-((2-(2,6-dioxopiperidin-3-yl)-1-oxoisoindolin-4-yl)thio)butanoyl)piperazin-1-yl)piperidin-1-yl)-9-ethyl-6,6-dimethyl-11-oxo-6,11-dihydro-5H-benzo[b]carbazole-3-carbonitrile (SIAIS262098)

According to the general method described in Scheme 25, the target compound (SIAIS262098) was prepared by using Alectinib derivative C and LIN-ULM (SIAIS171089) under appropriate conditions that will be recognized by one skilled in the art. (yellow solid, 10.9 mg, yield 43%). $^1$H NMR (500 MHz, DMSO) δ 12.83 (s, 1H), 11.02 (s, 1H), 8.31 (d, J=8.2 Hz, 1H), 8.06 (s, 1H), 8.01 (s, 1H), 7.70 (dd, J=7.4, 1.2 Hz, 1H), 7.65-7.51 (m, 3H), 7.36 (s, 1H), 5.14 (dd, J=13.3, 5.1 Hz, 1H), 4.51 (d, J=12.6 Hz, 1H), 4.37 (d, J=17.4 Hz, 1H), 4.22 (d, J=17.4 Hz, 1H), 4.06 (d, J=13.5 Hz, 1H), 3.58-3.55 (m, 4H), 3.43-3.27 (m, 5H), 3.14-3.05 (m, 4H), 3.01-2.88 (m, 2H), 2.81 (s, 2H), 2.71 (q, J=7.4 Hz, 2H), 2.59-2.55 (m, 2H), 2.49-2.44 (m, 1H), 2.19 (s, 2H), 2.04-1.99 (m, 1H), 1.93-1.81 (m, 4H), 1.76 (s, 6H), 1.28 (t, J=7.5 Hz, 3H). HRMS (ESI) m/z: calcd for, $C_{47}H_{52}N_7O_5S^+$ [M+H]$^+$, 826.3745; found, 826.3243.

Example 108: Preparation of 8-(4-(4-(5-((2-(2,6-dioxopiperidin-3-yl)-1-oxoisoindolin-4-yl)thio)pentanoyl)piperazin-1-yl)piperidin-1-yl)-9-ethyl-6,6-dimethyl-11-oxo-6,11-dihydro-5H-benzo[b]carbazole-3-carbonitrile (SIAIS262099)

According to the general method described in Scheme 25, the target compound (SIAIS262099) was prepared by using Alectinib derivative C and LIN-ULM (SIAIS171079) under appropriate conditions that will be recognized by one skilled in the art. (yellow solid, 11.3 mg, yield 43%). $^1$H NMR (500 MHz, DMSO) δ 12.89 (s, 1H), 11.01 (s, 1H), 8.31 (d, J=8.2 Hz, 1H), 8.05 (s, 1H), 8.01 (s, 1H), 7.67-7.52 (m, 4H), 7.36 (s, 1H), 5.14 (dd, J=13.3, 5.1 Hz, 1H), 4.50 (d, J=13.0 Hz, 1H), 4.37 (d, J=17.4 Hz, 1H), 4.22 (d, J=17.4 Hz, 1H), 4.08 (d, J=13.3 Hz, 1H), 3.61-3.49 (m, 4H), 3.31 (d, J=11.3 Hz, 4H), 3.14 (d, J=21.2 Hz, 4H), 2.93-2.91 (m, 2H), 2.81 (s, 2H), 2.71 (q, J=7.4 Hz, 2H), 2.61 (t, J=15.4 Hz, 1H), 2.47-2.40 (m, 2H), 2.22 (d, J=10.0 Hz, 2H), 2.01 (dd, J=9.0, 3.6 Hz), 1.91 (d, J=11.9 Hz, 2H), 1.76 (s, 6H), 1.64 (s, 4H), 1.28 (t, J=7.5 Hz, 3H). HRMS (ESI) m/z: calcd for, $C_{48}H_{54}N_7O_5S^+$ [M+H]$^+$, 840.3902; found, 840.3387.

Example 109: Preparation of 8-(4-(4-(6-((2-(2,6-dioxopiperidin-3-yl)-1-oxoisoindolin-4-yl)thio)hexanoyl)piperazin-1-yl)piperidin-1-yl)-9-ethyl-6,6-dimethyl-11-oxo-6,11-dihydro-5H-benzo[b]carbazole-3-carbonitrile (SIAIS262100)

According to the general method described in Scheme 25, under appropriate conditions that will be recognized by one skilled in the art, the target compound (SIAIS262100) was prepared by using Alectinib derivative C and LIN-ULM (SIAIS171091) (yellow solid, 11.8 mg, yield 45%). $^1$H NMR (500 MHz, DMSO) δ 12.86 (s, 1H), 11.01 (s, 1H), 8.31 (d, J=8.1 Hz, 1H), 8.06 (s, 1H), 8.01 (s, 1H), 7.68-7.51 (m, 4H), 7.36 (s, 1H), 5.14 (dd, J=13.3, 5.1 Hz, 1H), 4.50 (d, J=13.1 Hz, 1H), 4.36 (d, J=17.4 Hz, 1H), 4.22 (d, J=17.4 Hz, 1H), 4.07 (d, J=13.1 Hz, 1H), 3.56 (t, J=21.2 Hz, 4H), 3.31 (d, J=11.2 Hz, 4H), 3.16-3.05 (m, 4H), 3.02-2.87 (m, 2H), 2.82 (s, 2H), 2.71 (q, J=7.4 Hz, 2H), 2.59 (d, J=17.1 Hz, 1H), 2.46-2.41 (m, 1H), 2.36 (t, J=7.1 Hz, 2H), 2.22 (d, J=9.9 Hz, 2H), 2.06-1.98 (m, 1H), 1.90 (d, J=11.3 Hz, 2H), 1.76 (s, 6H), 1.65-1.60 (m, 2H), 1.51 (d, J=5.2 Hz, 2H), 1.46-1.42 (m, 2H), 1.28 (t, J=7.5 Hz, 3H). HRMS (ESI) m/z: calcd for, $C_{49}H_{56}N_7O_5S^+$ [M+H]$^+$, 854.4058; found, 854.3545.

Example 110: Preparation of 8-(4-(4-(7-((2-(2,6-dioxopiperidin-3-yl)-1-oxoisoindolin-4-yl)thio)heptanoyl)piperazin-1-yl)piperidin-1-yl)-9-ethyl-6,6-dimethyl-11-oxo-6,11-dihydro-5H-benzo[b]carbazole-3-carbonitrile (SIAIS262101)

According to the general method described in Scheme 25, the target compound (SIAIS262101) was prepared under appropriate conditions that will be recognized by one skilled in the art, using Alectinib derivative C and LIN-ULM (SIAIS171092). (yellow solid, 11.2 mg, yield 42%). $^1$H NMR (500 MHz, DMSO) δ 12.89 (s, 1H), 11.01 (s, 1H), 8.31 (d, J=8.2 Hz, 1H), 8.06 (s, 1H), 8.01 (s, 1H), 7.59-7.53 (m, 4H), 7.36 (s, 1H), 5.14 (dd, J=13.3, 5.1 Hz, 1H), 4.50 (d, J=13.3 Hz, 1H), 4.36 (d, J=17.4 Hz, 1H), 4.21 (d, J=17.4 Hz, 1H), 4.07 (d, J=13.3 Hz, 1H), 3.41-3.26 (m, 4H), 3.13-3.08 (m, 4H), 3.03-2.86 (m, 2H), 2.86-2.78 (m, 2H), 2.71 (q, J=7.4 Hz, 2H), 2.59 (d, J=17.6 Hz, 1H), 2.49-2.42 (m, 1H), 2.35 (t, J=7.3 Hz, 2H), 2.22 (d, J=10.8 Hz, 2H), 2.02-1.98 (m, 1H), 1.96-1.85 (m, 2H), 1.76 (s, 6H), 1.66-1.56 (m, 2H), 1.51-1.41 (m, 4H), 1.33-1.27 (m, 5H). HRMS (ESI) m/z: calcd for, $C_{50}H_{58}N_7O_5S^+$ [M+H]$^+$, 868.4215; found, 868.3679.

Example 111: Preparation of 8-(4-(4-(2-(2-((2-(2,6-dioxopiperidin-3-yl)-1-oxoisoindolin-4-yl)thio)ethoxy)acetyl)piperazin-1-yl)piperidin-1-yl)-9-ethyl-6,6-dimethyl-11-oxo-6,11-dihydro-5H-benzo[b]carbazole-3-carbonitrile (SIAIS249066)

According to the general method described in Scheme 25, the target compound (SIAIS249066) was prepared by using Alectinib derivative C and LIN-ULM (SIAIS1213129) under appropriate conditions that will be recognized by one skilled in the art. (yellow solid, 11.8 mg, yield 45%). $^1$H NMR (500 MHz, DMSO) δ 12.87 (s, 1H), 11.02 (s, 1H), 8.31 (d, J=8.2 Hz, 1H), 8.05 (s, 1H), 8.01 (s, 1H), 7.71 (d, J=7.0 Hz, 1H), 7.63-7.50 (m, 3H), 7.36 (s, 1H), 5.14 (dd, J=13.3, 5.1 Hz, 1H), 4.47-4.35 (m, 2H), 4.25 (t, J=8.7 Hz, 3H), 3.97 (d, J=13.2 Hz, 1H), 3.77-3.65 (m, 3H), 3.32 (d, J=6.0 Hz, 6H), 3.17-3.11 (m, 2H), 3.04-2.88 (m, 2H), 2.80 (s, 2H), 2.70 (q, J=7.4 Hz, 2H), 2.59-2.55 (m, 1H), 2.47-2.44 (m, 1H), 2.20 (s, 2H), 2.02-1.98 (m, 1H), 1.90 (d, J=8.9 Hz, 2H), 1.76 (s, 6H), 1.28 (t, J=6.6 Hz, 3H). HRMS (ESI) m/z: calcd for, $C_{47}H_{52}N_7O_6S^+$ [M+H]$^+$, 842.3694; found, 842.3691.

Example 112: Preparation of 8-(4-(4-(2-(2-(2-((2-(2,6-dioxopiperidin-3-yl)-1-oxoisoindolin-4-yl)thio)ethoxy)ethoxy)acetyl)piperazin-1-yl)piperidin-1-yl)-9-ethyl-6,6-dimethyl-11-oxo-6,11-dihydro-5H-benzo[b]carbazole-3-carbonitrile (SIAIS249067)

According to the general method described in Scheme 25, under appropriate conditions that will be recognized by one skilled in the art, the target compound (SIAIS249067) was prepared, using Alectinib derivative C and LIN-ULM (SIAIS1213131). (yellow solid, 12.2 mg, yield 44%). $^1$H NMR (500 MHz, DMSO) δ 12.89 (s, 1H), 11.01 (s, 1H), 8.31 (d, J=8.2 Hz, 1H), 8.05 (s, 1H), 8.01 (s, 1H), 7.70 (d, J=7.6 Hz, 1H), 7.59-7.54 (m, 3H), 7.35 (s, 1H), 5.14 (dd, J=13.3, 5.1 Hz, 1H), 4.44 (d, J=12.4 Hz, 1H), 4.39 (d, J=17.6 Hz, 1H), 4.25 (d, J=17.6 Hz, 1H), 4.01 (d, J=12.8 Hz, 1H), 3.81-3.62 (m, 8H), 3.39-3.25 (m, 6H), 3.14-2.97 (m, 2H), 2.94-2.86 (m, 1H), 2.79 (s, 2H), 2.70 (q, J=7.5 Hz, 2H), 2.59 (d, J=17.7 Hz, 1H), 2.21 (d, J=8.6 Hz, 2H), 2.03-1.96 (m, 2H), 1.93 (d, J=26.9 Hz, 2H), 1.76 (s, 6H), 1.28 (d, J=7.5 Hz, 3H). HRMS (ESI) m/z: calcd for, $C_{49}H_{56}N_7O_7S^+$ [M+H]$^+$, 886.3956; found, 886.3952.

Example 113: Preparation of 8-(4-(4-(2-(2-(2-(2-((2-(2,6-dioxopiperidin-3-yl)-1-oxoisoindolin-4-yl)thio)ethoxy)ethoxy)ethoxy)acetyl)piperazin-1-yl)piperidin-1-yl)-9-ethyl-6,6-dimethyl-11-oxo-6,11-dihydro-5H-benzo[b]carbazole-3-carbonitrile (SIAIS249068)

According to the general method described in Scheme 25, under appropriate conditions that will be recognized by one skilled in the art, the target compound (SIAIS249068) was prepared, using Alectinib derivative C and LIN-ULM (SIAIS1213133). (yellow solid, 12.5 mg, yield 43%). $^1$H NMR (500 MHz, DMSO) δ 12.89 (s, 1H), 11.01 (s, 1H), 8.31 (d, J=8.1 Hz, 1H), 8.05 (s, 1H), 8.01 (s, 1H), 7.69 (d, J=7.3 Hz, 1H), 7.62-7.49 (m, 3H), 7.36 (s, 1H), 5.13 (dd, J=13.3, 5.1 Hz, 1H), 4.44 (d, J=13.7 Hz, 1H), 4.38 (d, J=17.5 Hz, 1H), 4.24-4.21 (m, 2H), 4.02 (d, J=13.2 Hz, 1H), 3.65-3.61 (m, 8H), 3.44-3.23 (m, 8H), 3.12-3.07 (m, 3H), 2.89-2.84 (m, 4H), 2.70 (q, J=7.4 Hz, 2H), 2.59 (d, J=17.5 Hz, 1H), 2.21 (s, 2H), 2.03-1.96 (m, 2H), 1.91 (s, 2H), 1.76 (s, 6H), 1.27 (d, J=7.5 Hz, 3H). HRMS (ESI) m/z: calcd for, $C_{51}H_{60}N_7O_8S^+$ [M+H]$^+$, 930.4219; found, 930.4214.

Example 114: Preparation of 8-(4-(4-(14-((2-(2,6-dioxopiperidin-3-yl)-1-oxoisoindolin-4-yl)thio)-3,6,9,12-tetraoxatetradecanoyl)piperazin-1-yl)piperidin-1-yl)-9-ethyl-6,6-dimethyl-11-oxo-6,11-dihydro-5H-benzo[b]carbazole-3-carbonitrile (SIAIS249069)

According to the general method described in Scheme 25, under appropriate conditions that will be recognized by one skilled in the art, the target compound (SIAIS249069) was prepared, using Alectinib derivative C and LIN-ULM (SIAIS1213135). (yellow solid, 12.4 mg, yield 41%). $^1$H NMR (500 MHz, DMSO) δ 12.89 (s, 1H), 11.01 (s, 1H), 8.31 (d, J=8.1 Hz, 1H), 8.06 (s, 1H), 8.01 (s, 1H), 7.69 (d, J=6.8 Hz, 1H), 7.65-7.50 (m, 3H), 7.36 (s, 1H), 5.13 (dd, J=13.3, 5.0 Hz, 1H), 4.45 (d, J=14.0 Hz, 1H), 4.37 (d, J=17.4 Hz, 1H), 4.24-4.18 (m, 2H), 4.03 (d, J=17.0 Hz, 1H), 3.65-3.58 (m, 8H), 3.39-3.22 (m, 8H), 3.14-3.11 (m, 4H), 2.96-2.86 (m, 1H), 2.81 (t, J=11.0 Hz, 2H), 2.77-2.69 (m, 2H), 2.59 (d, J=16.8 Hz, 1H), 2.47-2.41 (m, 1H), 2.21 (s, 2H), 2.02-1.98 (m, 2H), 1.95-1.91 (m, 2H), 1.76 (s, 6H), 1.27 (d, J=7.5 Hz, 3H). HRMS (ESI) m/z: calcd for, $C_{53}H_{64}N_7O_9S^+$ [M+H]$^+$, 974.4481; found, 974.4477.

Example 115: Preparation of 8-(4-(4-(17-((2-(2,6-dioxopiperidin-3-yl)-1-oxoisoindolin-4-yl)thio)-3,6,9,12,15-pentaoxaheptadecanoyl)piperazin-1-yl)piperidin-1-yl)-9-ethyl-6,6-dimethyl-11-oxo-6,11-dihydro-5H-benzo[b]carbazole-3-carbonitrile (SIAIS249070)

According to the general method described in Scheme 25, under appropriate conditions that will be recognized by one skilled in the art, the target compound (SIAIS249070) was prepared by using Alectinib derivative C and LIN-ULM (SIAIS1213137). (yellow solid, 14.3 mg, yield 45%). $^1$H NMR (500 MHz, DMSO) δ 12.97 (s, 1H), 11.01 (s, 1H), 8.31 (d, J=8.2 Hz, 1H), 8.05 (s, 1H), 8.01 (s, 1H), 7.67 (dt, J=9.0, 4.5 Hz, 1H), 7.63-7.49 (m, 3H), 7.36 (d, J=8.7 Hz, 1H), 5.13 (dd, J=13.3, 5.1 Hz, 1H), 4.44 (d, J=12.8 Hz, 1H), 4.37 (d, J=17.4 Hz, 1H), 4.27-4.19 (m, 2H), 4.05-4.01 (m, 1H), 3.60-3.48 (m, 22H), 3.40-3.20 (m, 7H), 3.15-2.98 (m, 2H), 2.92-2.88 (m, 1H), 2.82 (t, J=11.5 Hz, 2H), 2.70 (q, J=7.4 Hz, 2H), 2.59 (d, J=16.9 Hz, 1H), 2.49-2.41 (m, 2H), 2.23 (d, J=9.8 Hz, 2H), 2.04-1.88 (m, 4H), 1.76 (s, 6H), 1.28 (t, J=6.7 Hz, 3H). HRMS (ESI) m/z: calcd for, $C_{55}H_{68}N_7O_{10}S^+$ [M+H]$^+$, 1018.4743; found, 1018.4733.

Example 116: Synthesis Method of the Special Degradation Agent SIAIS219098 for ALK Target Scheme 26

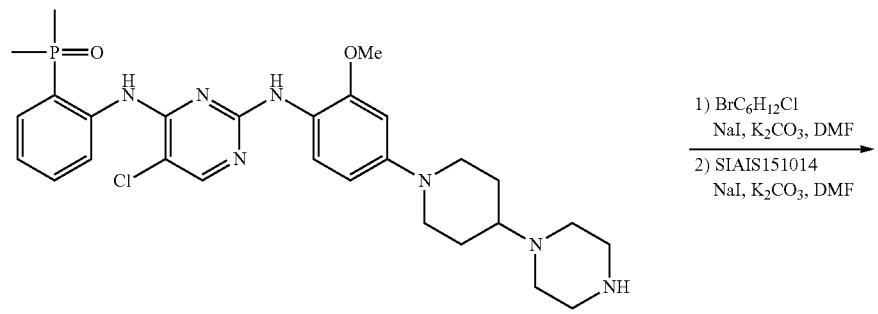

Brigatinib derivative C

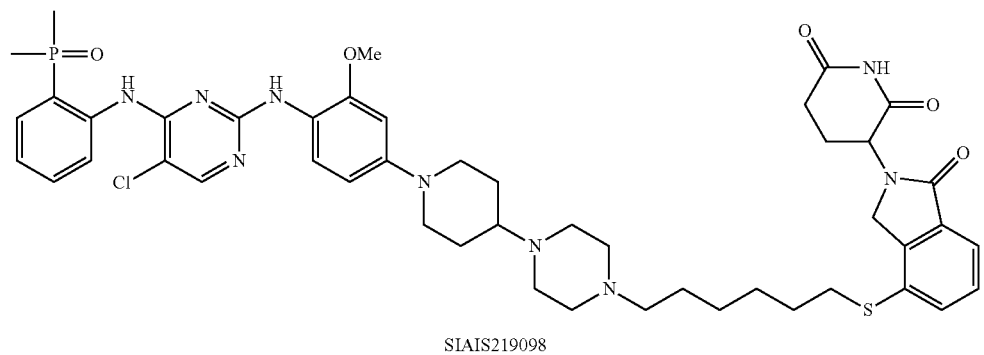

SIAIS219098

Preparation of 3-(4-((6-(4-(1-(4-((5-chloro-4-((2-(dimethylphosphoryl)phenyl)amino)pyrimidin-2-yl)amino)-3-methoxyphenyl)piperidin-4-yl)piperazin-1-yl)hexyl)thio)-1-oxoisoindolin-2-yl)piperidine-2,6-dione (SIAIS219098)

A 15 mL sample bottle was sequentially charged with the Brigatinib derivative C (20 mg, 0.035 mmol) and DMF (2 mL), and 1-bromo-6-chlorohexane (20.9 mg, 0.105 mmol), sodium iodide (5.2 mg, 0.035 mmol) and potassium carbonate (9.7 mg, 0.07 mmol) under stirring. The mixture was heated at 45° C. for 6 h. After membrane filtration, the reaction mixture was subjected to preparative HPLC (eluent (v/v): acetonitrile/(water+0.05% HCl)=10%-100%) for separation. The acetonitrile was removed by rotary evaporation, and the residue was lyophilized to obtain 18 mg of the intermediate, to be used in the next step directly. The obtained intermediate (10 mg, 0.0145 mmol) and DMF (2 mL) were added to a 15 mL sample bottle, followed by addition of SIAIS151014 (9.6 mg, 0.0348 mmol), potassium carbonate (6 mg, 0.0435 mmol), and sodium iodide (4.3 mg, 0.029 mmol). The reaction mixture was heated at 50° C. for 12 h, and subjected to membrane filtration, and preparative HPLC (Eluent (v/v): acetonitrile/(water+0.05% HCl)=10%-100%) for separation. The acetonitrile was removed by rotary evaporation, and the residue was lyophilized to obtain the target product (5.8 mg, yellow solid, the total yield of the two steps is 35%). $^1$H NMR (500 MHz, MeOD) δ 8.24 (s, 1H), 8.17 (s, 1H), 7.73 (dd, J=13.8, 7.8 Hz, 1H), 7.69-7.63 (m, 3H), 7.55 (t, J=7.7 Hz, 2H), 7.48 (t, J=7.4 Hz, 1H), 7.19 (s, 1H), 6.96 (d, J=7.6 Hz, 1H), 5.18 (dd, J=13.1, 4.8 Hz, 1H), 4.49 (d, J=17.4 Hz, 1H), 4.45-4.40 (m, 1H), 3.95 (s, 3H), 3.95-3.89 (m, 4H), 3.71 (s, 4H), 3.44-3.40 (m, 4H), 3.15-3.08 (m, 4H), 2.98-2.89 (m, 1H), 2.85-2.77 (m, 1H), 2.59-2.53 (m, 1H), 2.43 (t, J=11.5 Hz, 4H), 2.35-2.16 (m, 4H), 1.91 (s, 3H), 1.87 (s, 3H), 1.72-1.61 (m, 4H), 1.58-1.50 (m, 2H). HRMS (ESI) m/z: calcd for, $C_{47}H_{60}ClN_9O_5PS^+$ [M+H]$^+$, 928.3859; found, 928.3851.

Example 117: Synthesis Method of the Special Degradation Agents SIAIS262158 and SIAIS262159 of ALK Target

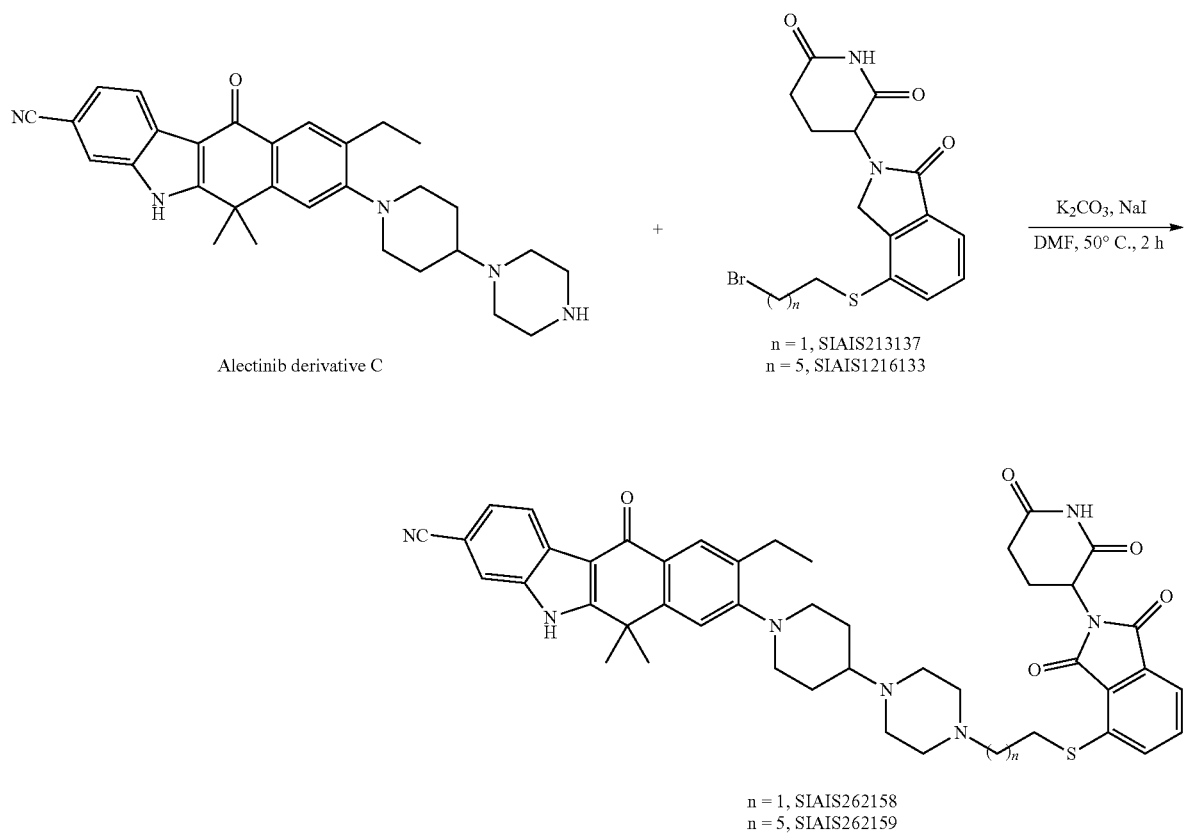

Preparation of 8-(4-(4-(2-((2-(2,6-dioxopiperidin-3-yl)-1,3-dioxoisoindolin-4-yl)thio)ethyl)piperazin-1-yl)piperidin-1-yl)-9-ethyl-6,6-dimethyl-11-oxo-6,11-dihydro-5H-benzo[b]carbazole-3-carbonitrile (SIAIS262158)

A 15 mL sample bottle was sequentially charged with Alectinib derivative C (20 mg, 0.042 mmol) and DMF (2 mL), and SIAIS213137 (48.3 mg, 0.126 mmol), sodium iodide (6.3 mg, 0.042 mmol), and potassium carbonate (11.6 mg, 0.084 mmol). The reaction mixture was heated at 50° C. for 2 h. After membrane filtration, the reaction mixture was subjected to preparative HPLC (eluent (v/v): acetonitrile/(water+0.05% HCl)=10%-100%) for separation. The acetonitrile was removed by rotary evaporation, and the residue was lyophilizated to obtain the target product (12.4 mg, yellow solid, yield 37%). $^1$H NMR (500 MHz, DMSO) δ 12.83 (s, 1H), 11.14 (s, 1H), 8.32 (d, J=8.2 Hz, 1H), 8.07 (s, 1H), 8.01 (s, 1H), 7.90 (s, 1H), 7.83 (t, J=7.7 Hz, 1H), 7.69 (d, J=7.3 Hz, 1H), 7.64-7.57 (m, 1H), 7.37 (s, 1H), 5.13 (dd, J=12.8, 5.5 Hz, 1H), 3.66 (d, J=58.3 Hz, 4H), 3.32 (d, J=11.2 Hz, 8H), 3.19-3.08 (m, 2H), 2.89-2.84 (m, 4H), 2.72 (q, J=7.4 Hz, 2H), 2.61 (d, J=17.4 Hz, 1H), 2.57-2.52 (m, 1H), 2.23 (s, 2H), 2.10-2.04 (m, 1H), 1.91 (s, 2H), 1.77 (s, 6H), 1.29 (t, J=7.5 Hz, 3H). HRMS (ESI) m/z: calcd for, $C_{45}H_{48}N_7O_5S^+$ [M+H]$^+$, 798.3432; found, 798.3435.

Example 118: Preparation of 8-(4-(4-(6-((2-(2,6-dioxopiperidin-3-yl)-1-oxoisoindolin-4-yl)thio)hexyl)piperazin-1-yl)piperidin-1-yl)-9-ethyl-6,6-dimethyl-11-oxo-6,11-dihydro-5H-benzo[b]carbazole-3-carbonitrile (SIAIS262159)

According to the general method described in Scheme 27, under appropriate conditions that will be recognized by one skilled in the art, the target compound (SIAIS262159) was prepared by using Alectinib derivative C and LIN-ULM (SIAIS1216133). (yellow solid, 7.3 mg, yield 29%). $^1$H NMR (500 MHz, MeOD) δ 8.41 (d, J=8.1 Hz, 1H), 8.21 (s, 1H), 7.87 (s, 1H), 7.67 (dd, J=7.5, 3.7 Hz, 2H), 7.57-7.54 (m, 2H), 7.43 (s, 1H), 5.18 (dd, J=13.4, 5.2 Hz, 1H), 4.48 (d, J=17.3 Hz, 1H), 4.45-4.40 (m, 1H), 3.93 (s, 4H), 3.59 (s, 2H), 3.43 (d, J=12.7 Hz, 2H), 3.29-3.23 (m, 2H), 3.14-3.05 (m, 2H), 3.00-2.91 (m, 3H), 2.82 (q, J=7.7 Hz, 3H), 2.59-2.51 (m, 1H), 2.35 (s, 1H), 2.23-2.16 (m, 1H), 2.10-2.02 (m, 2H), 1.80 (d, J=13.6 Hz, 8H), 1.77-1.64 (m, 4H), 1.63-1.49 (m, 4H), 1.47-1.41 (m, 2H), 1.35 (d, J=6.6 Hz, 3H). HRMS (ESI) m/z: calcd for, $C_{49}H_{58}N_7O_4S^+$ [M+H]$^+$, 840.4266; found, 840.4261.

A General Synthesis Method for a Series of Degradation Agents of BCR-ABL Target
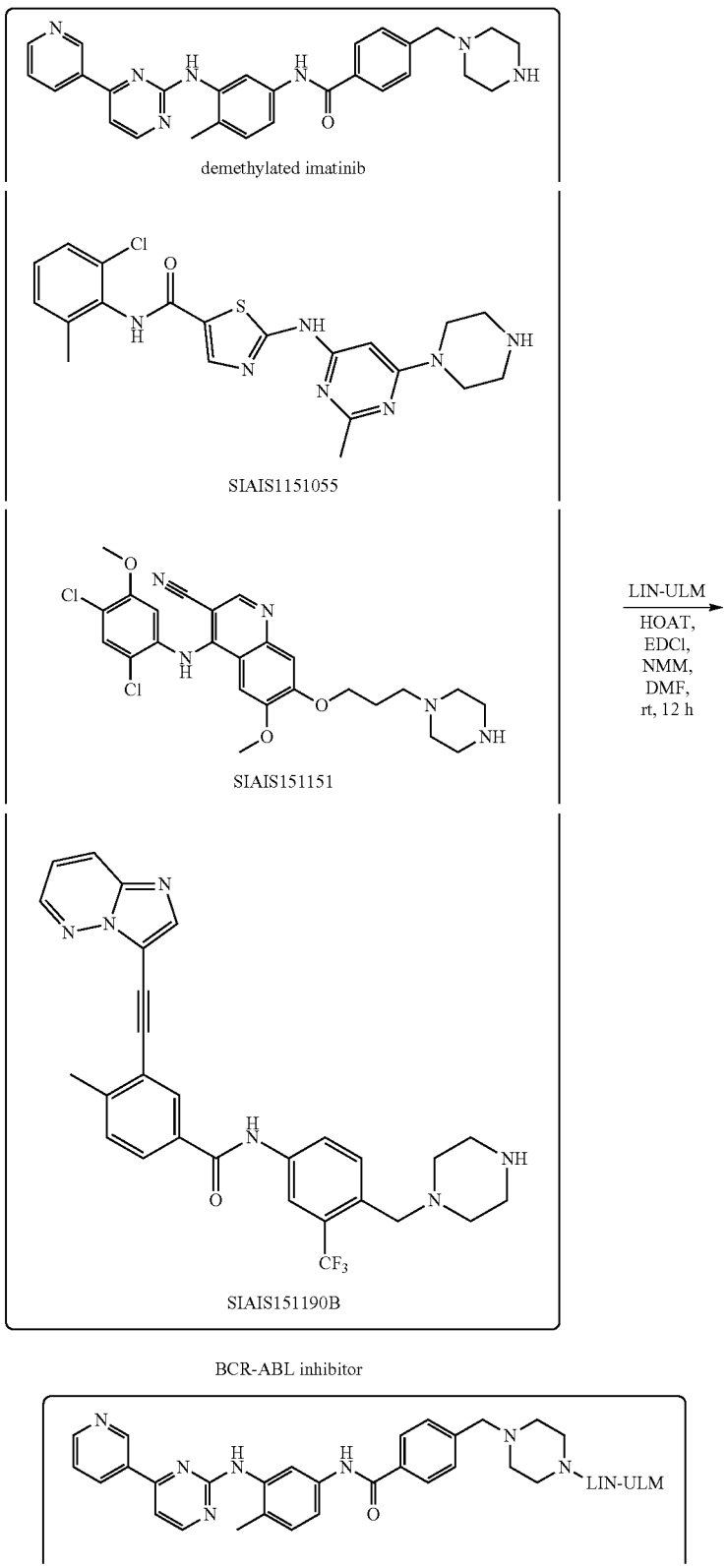

-continued

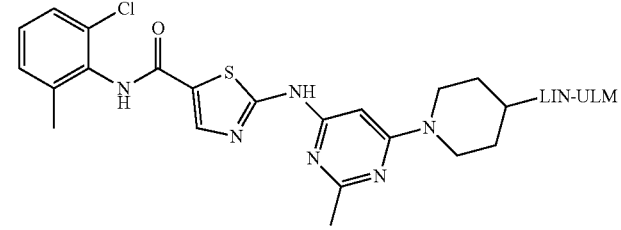

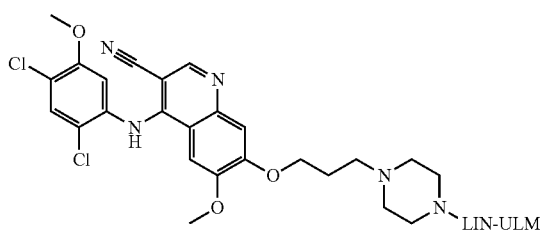

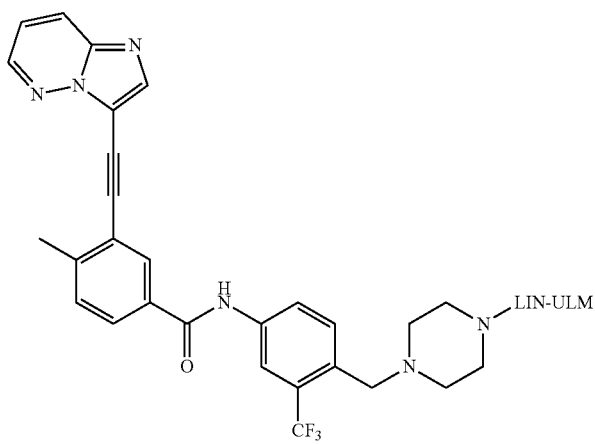

degradation agent

According to Scheme 28, at room temperature, a reaction flask was charged with the corresponding BCR-ABL inhibitor (1 equiv), the corresponding LIN-ULM (1 equiv), 1-hydroxy-7-azabenzotriazole (2 equiv), 1-(3-dimethylaminopropyl)-3-ethylcarbodiimide hydrochloride (2 equiv), anhydrous N,N-dimethylformamide (2 mL), and N-methylmorpholine (5 equiv), and the reaction mixture was stirred at room temperature overnight. After the completion of the reaction was detected by LC-MS, the reaction mixture was subjected to preparative HPLC (eluent (v/v): acetonitrile/(water+0.05% HCl)=10%-100%) for separation and purification. The acetonitrile wars removed by rotary evaporation, and the residue was lyophilized to give the corresponding final degradation agent compound.

Example 119: Preparation of 4-((4-(2-((2-(2,6-dioxopiperidin-3-yl)-1,3-dioxoisoindolin-4-yl)thio)acetyl)piperazin-1-yl)methyl)-N-(4-methyl-3-((4-(pyridin-3-yl)pyrimidin-2-yl)amino)phenyl)benzamide (SIAIS1197107)

According to the general method described in Scheme 28, the target compound (SIAIS1197107) was prepared by using demethylated imatinib and LIN-ULM (SIAIS151045) under appropriate conditions that will be recognized by one skilled in the art. (yellow solid, 7.3 mg, yield 29%). $^1$H NMR (500 MHz, DMSO) δ 11.13 (s, 1H), 10.30 (s, 1H), 9.33 (s, 1H), 9.05 (s, 1H), 8.75 (d, J=4.5 Hz, 1H), 8.62 (s, 1H), 8.55 (d, J=5.1 Hz, 1H), 8.11 (s, 1H), 8.06 (d, J=8.1 Hz, 2H), 7.79 (d, J=3.1 Hz, 2H), 7.74 (d, J=8.0 Hz, 2H), 7.68-7.62 (m, 2H), 7.48 (t, J=5.5 Hz, 2H), 7.23 (d, J=8.4 Hz, 1H), 5.13 (dd, J=12.9, 5.4 Hz, 1H), 4.50-4.22 (m, 6H), 3.3-3.30 (m, 2H), 3.20-2.95 (m, 4H), 2.95-2.84 (m, 1H), 2.64 (s, 1H), 2.36 (s, 1H), 2.23 (s, 3H), 2.10-2.02 (m, 1H). HRMS (ESI) m/z: calcd for, $C_{43}H_{40}N_9O_6S^+$ [M+H]$^+$, 810.2817; found, 810.2351.

Example 120: Preparation of 4-((4-(3-((2-(2,6-dioxopiperidin-3-yl)-1,3-dioxoisoindolin-4-yl)thio)propanoyl)piperazin-1-yl)methyl)-N-(4-methyl-3-((4-(pyridin-3-yl)pyrimidin-2-yl)amino)phenyl)benzamide (SIAIS1197097)

According to the general method described in Scheme 28 and under appropriate conditions that will be recognized by one skilled in the art, the target compound (SIAIS1197097) was prepared by using demethylated imatinib and LIN-ULM (SIAIS151138B). (yellow solid, 6.1 mg, yield 23%). $^1$H NMR (500 MHz, DMSO) δ 11.12 (s, 1H), 10.30 (s, 1H), 9.34 (s, 1H), 9.06 (s, 1H), 8.77 (s, 1H), 8.67 (s, 1H), 8.55 (s, 1H), 8.11 (s, 1H), 8.05 (d, J=8.1 Hz, 2H), 7.83-7.61 (m, 6H), 7.48 (d, J=6.4 Hz, 2H), 7.23 (d, J=8.5 Hz, 1H), 5.12 (dd, J=12.9, 5.2 Hz, 1H), 4.52-4.38 (m, 2H), 4.41 (s, 2H), 4.10-3.98 (m, 2H), 3.33 (s, 2H), 3.14-2.90 (m, 4H), 2.94-2.87 (m 1H), 2.87-2.78 (m, 2H), 2.65-2.60 (m, 1H), 2.36 (s, 1H), 2.23 (s, 3H), 2.08-2.01 (m, 1H). HRMS (ESI) m/z: calcd for, $C_{44}H_{42}N_9O_6S^+$ [M+H]$^+$, 824.2973; found, 824.2485.

Example 121: Preparation of 4-((4-(4-((2-(2,6-dioxopiperidin-3-yl)-1,3-dioxoisoindolin-4-yl)thio)butanoyl)piperazin-1-yl)methyl)-N-(4-methyl-3-((4-(pyridin-3-yl)pyrimidin-2-yl)amino)phenyl)benzamide (SIAIS1197099)

According to the general method described in Scheme 28, under appropriate conditions that will be recognized by one skilled in the art, the target compound (SIAIS1197099) was prepared by using demethylated imatinib and LIN-ULM (SIAIS151139B). (yellow solid, 7.4 mg, yield 29%). 1H NMR (500 MHz, DMSO) δ 11.12 (s, 1H), 10.31 (s, 1H), 9.37 (s, 1H), 9.09 (s, 1H), 8.80 (s, 1H), 8.74 (s, 1H), 8.57 (d, J=5.1 Hz, 1H), 8.12 (s, 1H), 8.05 (d, J=8.2 Hz, 2H), 7.85 (d, J=8.3 Hz, 1H), 7.83-7.70 (m, 4H), 7.64 (d, J=6.9 Hz, 1H), 7.52-7.45 (m, 2H), 7.23 (d, J=8.4 Hz, 1H), 5.12 (dd, J=12.8, 5.4 Hz, 1H), 4.52-4.40 (m, 2H), 4.41 (s, 2H), 4.10-4.00 (m, 2H), 3.31 (s, 2H), 3.19-3.13 (m, 2H), 3.12-2.88 (m, 4H), 2.93-2.84 (m, 1H), 2.63-2.56 (m, 1H), 2.46-2.40 (m, 1H), 2.23 (s, 3H), 2.09-2.01 (m, 1H), 1.95-1.84 (m, 2H)). HRMS (ESI) m/z: calcd for, C45H44N9O6S+ [M+H]+, 838.3130; found, 838.2631.

Example 122: Preparation of 4-((4-(5-((2-(2,6-dioxopiperidin-3-yl)-1,3-dioxoisoindolin-4-yl)thio)pentanoyl)piperazin-1-yl)methyl)-N-(4-methyl-3-((4-(pyridin-3-yl)pyrimidin-2-yl)amino)phenyl)benzamide (SIAIS1197101)

According to the general method described in Scheme 28, under appropriate conditions that will be recognized by one skilled in the art, the target compound (SIAIS1197101) was prepared by using demethylated imatinib and LIN-ULM (SIAIS151140B). (yellow solid, 7.8 mg, yield 29%). $^1$H NMR (500 MHz, DMSO) δ 11.12 (s, 1H), 10.32 (s, 1H), 9.40 (s, 1H), 9.12 (s, 1H), 8.83 (dd, J=12.5, 6.7 Hz, 2H), 8.58 (d, J=5.1 Hz, 1H), 8.13 (s, 1H), 8.05 (d, J=8.2 Hz, 2H), 7.87-7.71 (m, 5H), 7.63 (d, J=6.8 Hz, 1H), 7.52 (d, J=5.2 Hz, 1H), 7.48 (dd, J=8.2, 1.8 Hz, 1H), 7.23 (d, J=8.5 Hz, 1H), 5.11 (dd, J=12.8, 5.4 Hz, 1H), 4.50-4.35 (m, 4H), 4.11-3.99 (m, 2H), 3.30 (s, 2H), 3.16 (s, 2H), 3.12-2.88 (m, 4H), 2.92-2.83 (m, 1H), 2.63-2.56 (m, 1H), 2.42 (d, J=7.1 Hz, 1H), 2.21 (s, 3H), 2.09-2.00 (m, 1H), 1.68 (s, 4H). HRMS (ESI) m/z: calcd for, $C_{46}H_{46}N_9O_6S^+$ [M+H]$^+$, 852.3286; found, 852.2785.

Example 123: Preparation of 4-((4-(6-((2-(2,6-dioxopiperidin-3-yl)-1,3-dioxoisoindolin-4-yl)thio)hexanoyl)piperazin-1-yl)methyl)-N-(4-methyl-3-((4-(pyridin-3-yl)pyrimidin-2-yl)amino)phenyl)benzamide (SIAIS1197103)

According to the general method described in Scheme 28, under appropriate conditions that will be recognized by one skilled in the art, the target compound (SIAIS1197103) was prepared with demethylated imatinib and LIN-ULM (SIAIS151141B). (yellow solid, 6.6 mg, yield 26%). $^1$H NMR (500 MHz, DMSO) δ 11.12 (s, 1H), 10.34 (s, 1H), 9.38 (s, 1H), 9.10 (s, 1H), 8.79 (d, J=27.6 Hz, 2H), 8.57 (d, J=5.0 Hz, 1H), 8.13 (s, 1H), 8.05 (d, J=8.2 Hz, 2H), 7.86-7.70 (m, 5H), 7.63 (d, J=7.1 Hz, 1H), 7.53-7.45 (m, 2H), 7.23 (d, J=8.5 Hz, 1H), 5.11 (dd, J=12.9, 5.4 Hz, 1H), 4.40 (s, 4H), 4.04 (s, 2H), 3.58 (s, 2H), 3.27 (s, 2H), 3.13 (t, J=7.1 Hz, 2H), 3.12-2.96 (m, 2H), 2.93-2.83 (m, 1H), 2.63-2.56 (m, 1H), 2.36 (s, 1H), 2.23 (s, 3H), 2.09-2.01 (m, 1H), 1.72-1.64 (m, 2H), 1.58-1.50 (m, 2H), 1.50-1.41 (m, 2H). HRMS (ESI) m/z: calcd for, $C_{47}H_{48}N_9O_6S^+$ [M+H]$^+$, 866.3443; found, 866.2928.

Example 124: Preparation of 4-((4-(7-((2-(2,6-dioxopiperidin-3-yl)-1,3-dioxoisoindolin-4-yl)thio)heptanoyl)piperazin-1-yl)methyl)-N-(4-methyl-3-((4-(pyridin-3-yl)pyrimidin-2-yl)amino)phenyl)benzamide (SIAIS1197105)

According to the general method described in Scheme 28, the target compound (SIAIS1197105) was prepared by using demethylated imatinib and LIN-ULM (SIAIS151142B) under appropriate conditions that will be recognized by one skilled in the art. (yellow solid, 6.0 mg, yield 23%). $^1$H NMR (500 MHz, DMSO) δ 11.12 (s, 1H), 10.32 (s, 1H), 9.37 (s, 1H), 9.09 (s, 1H), 8.84-8.74 (m, 2H), 8.57 (d, J=5.1 Hz, 1H), 8.12 (s, 1H), 8.05 (d, J=8.3 Hz, 2H), 7.77 (dt, J=19.6, 7.8 Hz, 5H), 7.66-7.64 (m, 1H), 7.53-7.45 (m, 2H), 7.23 (d, J=8.5 Hz, 1H), 5.11 (dd, J=12.9, 5.4 Hz, 1H), 4.41 (s, 4H), 4.05 (s, 2H), 3.30 (d, J=10.6 Hz, 2H), 3.13 (t, J=7.3 Hz, 2H), 3.08-2.83 (m, 5H), 2.63 (d, J=11.9 Hz, 1H), 2.37 (s, 1H), 2.23 (s, 3H), 2.09-2.00 (m, 1H), 1.73-1.64 (m, 2H), 1.60-1.50 (m, 2H), 1.50-1.42 (m, 2H), 1.42-1.30 (m, 2H). HRMS (ESI) m/z: calcd for, $C_{48}H_{50}N_9O_6S^+$ [M+H]$^+$, 880.3599; found, 880.3105.

Example 125: Preparation of N-(2-chloro-6-methylphenyl)-2-((6-(4-(2-((2-(2,6-dioxopiperidin-3-yl)-1,3-dioxoisoindolin-4-yl)thio)acetyl)piperazin-1-yl)-2-methylpyrimidin-4-yl)amino)thiazole-5-carboxamide (SIAIS151110)

According to the general method described in Scheme 28, the target compound (SIAIS151110) was prepared by using Dasatinib derivatives (SIAIS151055) and LIN-ULM (SIAIS151045) under appropriate conditions that will be recognized by one skilled in the art. (yellow solid, 26.6 mg, yield 56%). $^1$H NMR (500 MHz, DMSO) δ 11.56 (s, 1H), 11.15 (s, 1H), 9.91 (s, 1H), 8.23 (s, 1H), 7.85-7.75 (m, 2H), 7.64 (d, J=6.4 Hz, 1H), 7.40 (d, J=7.2 Hz, 1H), 7.34-7.21 (m, 2H), 6.09 (s, 1H), 5.13 (dd, J=12.9, 5.4 Hz, 1H), 4.34 (s, 2H), 3.75-3.59 (m, 8H), 2.94-2.84 (m, 1H), 2.64-2.53 (m, 2H), 2.44 (s, 3H), 2.24 (s, 3H), 2.10-2.02 (m, 1H). HRMS (ESI) m/z: calcd for, $C_{35}H_{33}ClN_9O_6S_2^+$ [M+H]$^+$, 774.1678; found, 774.1688.

Example 126: Preparation of N-(2-chloro-6-methylphenyl)-2-((6-(4-(3-((2-(2,6-dioxopiperidin-3-yl)-1,3-dioxoisoindolin-4-yl)thio)propanoyl)piperazin-1-yl)-2-methylpyrimidin-4-yl)amino)thiazole-5-carboxamide (SIAIS151152)

According to the general method described in Scheme 28, the target compound (SIAIS151152) was prepared by using Dasatinib derivative (SIAIS151055) and LIN-ULM (SIAIS151138B) under appropriate conditions that will be recognized by one skilled in the art. (yellow solid, 15.2 mg, yield 43%). $^1$H NMR (500 MHz, DMSO) δ 11.55 (s, 1H), 11.12 (s, 1H), 9.92 (s, 1H), 8.24 (s, 1H), 7.83-7.78 (m, 2H), 7.64 (d, J=6.3 Hz, 1H), 7.40 (d, J=7.2 Hz, 1H), 7.32-7.23 (m, 2H), 6.08 (s, 1H), 5.12 (dd, J=12.8, 5.4 Hz, 1H), 3.63-3.47 (m, 8H), 3.36 (t, J=6.9 Hz, 2H), 2.92-2.86 (m, 1H), 2.84 (t, J=7.5 Hz, 2H), 2.66-2.53 (m, 2H), 2.43 (s, 3H), 2.24 (s, 3H), 2.07-2.01 (m, 1H). HRMS (ESI) m/z: calcd for, $C_{36}H_{35}N_9O_6S_2^+$ [M+H]$^+$, 788.1835; found, 788.2066.

Example 127: Preparation of N-(2-chloro-6-methylphenyl)-2-((6-(4-(4-((2-(2,6-dioxopiperidin-3-yl)-1,3-dioxoisoindolin-4-yl)thio)butanoyl)piperazin-1-yl)-2-methylpyrimidin-4-yl)amino)thiazole-5-carboxamide (SIAIS151153)

According to the general method described in Scheme 28, the target compound (SIAIS151153) was prepared by using Dasatinib derivatives (SIAIS151055) and LIN-ULM (SIAIS151139B) under appropriate conditions that will be recognized by one skilled in the art. (yellow solid, 14.5 mg, yield 40%). $^1$H NMR (500 MHz, DMSO) δ 11.53 (s, 1H), 11.12 (s, 1H), 9.89 (s, 1H), 8.23 (s, 1H), 7.88 (d, J=8.2 Hz, 1H), 7.80 (t, J=7.7 Hz, 1H), 7.63 (d, J=7.2 Hz, 1H), 7.40 (d, J=7.1 Hz, 1H), 7.33-7.22 (m, 2H), 6.08 (s, 1H), 5.12 (dd, J=12.8, 5.4 Hz, 1H), 3.56 (s, 8H), 3.21-3.15 (m, 2H), 2.93-2.84 (m, 1H), 2.63-2.53 (m, 4H), 2.42 (s, 3H), 2.24 (s, 3H), 2.09-2.01 (m, 1H), 1.95-1.88 (m, 2H). HRMS (ESI) m/z: calcd for, $C_{37}H_{37}N_9O_6S_2^+$ [M+H]$^+$, 802.1991; found, 802.2222.

Example 128: Preparation of N-(2-chloro-6-methylphenyl)-2-((6-(4-(5-((2-(2,6-dioxopiperidin-3-yl)-1,3-dioxoisoindolin-4-yl)thio)pentanoyl)piperazin-1-yl)-2-methylpyrimidin-4-yl)amino)thiazole-5-carboxamide (SIAIS151154)

According to the general method described in Scheme 28, the target compound (SIAIS151154) was prepared by using Dasatinib derivatives (SIAIS151055) and LIN-ULM (SIAIS151140B) under appropriate conditions that will be recognized by one skilled in the art. (yellow solid, 17.3 mg, yield 47%). $^1$H NMR (500 MHz, DMSO) δ 11.53 (s, 1H), 11.12 (s, 1H), 9.90 (s, 1H), 8.23 (s, 1H), 7.81-7.73 (m, 2H), 7.63 (d, J=6.5 Hz, 1H), 7.40 (d, J=6.8 Hz, 1H), 7.32-7.22 (m, 2H), 6.08 (s, 1H), 5.11 (dd, J=12.8, 5.4 Hz, 1H), 3.54-3.42 (m, 8H), 3.17 (t, J=7.5 Hz, 2H), 2.92-2.84 (m, 1H), 2.65-2.52 (m, 2H), 2.43 (s, 3H), 2.48-2.36 (m, 2H), 2.24 (s, 3H), 2.08-2.01 (m, 1H), 1.75-1.66 (m, 4H). HRMS (ESI) m/z: calcd for, $C_{38}H_{39}N_9O_6S_2^+$ [M+H]$^+$, 816.2148; found, 816.2373.

Example 129: Preparation of N-(2-chloro-6-methylphenyl)-2-((6-(4-(6-((2-(2,6-dioxopiperidin-3-yl)-1,3-dioxoisoindolin-4-yl)thio)hexanoyl)piperazin-1-yl)-2-methylpyrimidin-4-yl)amino)thiazole-5-carboxamide (SIAIS151155)

According to the general method described in Scheme 28, the target compound (SIAIS151155) was prepared by using Dasatinib derivatives (SIAIS151055) and LIN-ULM (SIAIS151141B) under appropriate conditions that will be recognized by one skilled in the art. (yellow solid, 13.7 mg, yield 37%). $^1$H NMR (500 MHz, DMSO) δ 11.55 (s, 1H), 11.12 (s, 1H), 9.90 (s, 1H), 8.23 (s, 1H), 7.80-7.74 (m, 2H), 7.62 (d, J=6.9 Hz, 1H), 7.40 (d, J=6.7 Hz, 1H), 7.34-7.23 (m, 2H), 6.08 (s, 1H), 5.11 (dd, J=12.8, 5.4 Hz, 1H), 3.57 (s, 8H), 3.14 (t, J=7.2 Hz, 2H), 2.92-2.84 (m, 1H), 2.63-2.52 (m, 2H), 2.43 (s, 3H), 2.37 (t, J=7.2 Hz, 2H), 2.24 (s, 3H), 2.08-2.02 (m, 1H), 1.73-1.66 (m, 2H), 1.60-1.54 (m, 2H), 1.52-1.44 (m, 2H). HRMS (ESI) m/z: calcd for, $C_{39}H_{41}N_9O_6S_2^+$ [M+H]$^+$, 830.2304; found, 830.2543.

Example 130: Preparation of N-(2-chloro-6-methylphenyl)-2-((6-(4-(7-((2-(2,6-dioxopiperidin-3-yl)-1,3-dioxoisoindolin-4-yl)thio)heptanoyl)piperazin-1-yl)-2-methylpyrimidin-4-yl)amino)thiazole-5-carboxamide (SIAIS151156)

According to the general method described in Scheme 28, the target compound (SIAIS151156) was prepared by using Dasatinib derivative (SIAIS151055) and LIN-ULM (SIAIS151142B) under appropriate conditions that will be recognized by one skilled in the art. (yellow solid, 10.6 mg, yield 28%). $^1$H NMR (500 MHz, MeOD) δ 8.21 (s, 1H), 7.73-7.66 (m, 2H), 7.57 (d, J=6.7 Hz, 1H), 7.35 (d, J=7.4 Hz, 1H), 7.29-7.22 (m, 2H), 6.29 (s, 1H), 5.09 (dd, J=12.5, 5.4 Hz, 1H), 3.91-3.70 (m, 8H), 3.12 (t, J=7.1 Hz, 2H), 2.90-2.80 (m, 1H), 2.77-2.67 (m, 2H), 2.61 (s, 3H), 2.46 (t, J=7.4 Hz, 2H), 2.31 (s, 3H), 2.16-2.08 (m, 1H), 1.82-1.73 (m, 2H), 1.69-1.62 (m, 2H), 1.58-1.52 (m, 2H), 1.47-1.39 (m, 2H). HRMS (ESI) m/z: calcd for, $C_{40}H_{43}N_9O_6S_2^+$ [M+H]$^+$, 844.2461; found, 844.2696.

Example 131: Preparation of N-(2-chloro-6-methylphenyl)-2-((6-(4-(2-((2-(2,6-dioxopiperidin-3-yl)-1-oxoisoindolin-4-yl)thio)acetyl)piperazin-1-yl)-2-methylpyrimidin-4-yl)amino)thiazole-5-carboxamide (SIAIS171105)

According to the general method described in Scheme 28 and under appropriate conditions that will be recognized by one skilled in the art, the target compound (SIAIS171105) was prepared by using Dasatinib derivatives (SIAIS151055) and LIN-ULM (SIAIS171090). (white solid, 10 mg, yield 39%). $^1$H NMR (500 MHz, DMSO) δ 11.55 (s, 1H), 10.99 (s, 1H), 9.90 (s, 1H), 8.23 (s, 1H), 7.76-7.71 (m, 1H), 7.60 (d, J=6.8 Hz, 1H), 7.53 (t, J=7.6 Hz, 1H), 7.40 (d, J=6.4 Hz, 1H), 7.32-7.18 (m, 2H), 6.09 (s, 1H), 5.13 (dd, J=13.3, 5.1 Hz, 1H), 4.42 (d, J=17.4 Hz, 1H), 4.28 (d, J=17.4 Hz, 1H), 4.20 (s, 2H), 3.58-3.32 (m, 8H), 2.95-2.85 (m, 1H), 2.64-2.57 (m, 1H), 2.52-2.42 (m, 4H), 2.43 (s, 3H), 2.04-1.94 (m, 1H). HRMS (ESI) m/z: calcd for, $C_{35}H_{35}ClN_9O_5S_2^+$ [M+H]$^+$, 760.1886; found, 760.1930.

Example 132: Preparation of N-(2-chloro-6-methylphenyl)-2-((6-(4-(3-((2-(2,6-dioxopiperidin-3-yl)-1-oxoisoindolin-4-yl)thio)propanoyl)piperazin-1-yl)-2-methylpyrimidin-4-yl)amino)thiazole-5-carboxamide (SIAIS171106)

According to the general method described in Scheme 28, the target compound (SIAIS171106) was prepared by using Dasatinib derivatives (SIAIS151055) and LIN-ULM (SIAIS171086) under appropriate conditions that will be recognized by one skilled in the art. (white solid, 9 mg, yield 34%). $^1$H NMR (500 MHz, DMSO) δ 11.58 (s, 1H), 11.00 (s, 1H), 9.92 (s, 1H), 8.25 (s, 1H), 7.69 (dd, J=7.5, 1.0 Hz, 1H), 7.62-7.53 (m, 2H), 7.40 (d, J=7.7 Hz, 1H), 7.33-7.23 (m, 2H), 6.09 (s, 1H), 5.13 (dd, J=13.3, 5.1 Hz, 1H), 4.37 (d, J=17.4 Hz, 1H), 4.23 (d, J=17.4 Hz, 1H), 3.60-3.54 (m, 8H), 3.30 (t, J=7.1 Hz, 2H), 2.95-2.86 (m, 1H), 2.76 (t, J=7.0 Hz, 2H), 2.65-2.58 (m, 1H), 2.49-2.46 (m, 1H), 2.44 (s, 3H), 2.24 (s, 3H), 2.05-1.97 (m, 1H). HRMS (ESI) m/z: calcd for, $C_{36}H_{37}ClN_9O_5S_2^+$ [M+H]$^+$, 774.2024; found, 774.2075.

Example 133: Preparation of N-(2-chloro-6-methylphenyl)-2-((6-(4-(4-((2-(2,6-dioxopiperidin-3-yl)-1-oxoisoindolin-4-yl)thio)butanoyl)piperazin-1-yl)-2-methylpyrimidin-4-yl)amino)thiazole-5-carboxamide (SIAIS171107)

According to the general method described in Scheme 28, the target compound (SIAIS171107) was prepared by using Dasatinib derivatives (SIAIS151055) and LIN-ULM (SIAIS171089) under appropriate conditions that will be recognized by one skilled in the art. (white solid, 11 mg, yield 42%). $^1$H NMR (500 MHz, DMSO) δ 11.58 (s, 1H), 11.00 (s, 1H), 9.92 (s, 1H), 8.25 (s, 1H), 7.70 (dd, J=7.4, 1.2 Hz, 1H), 7.59-7.53 (m, 2H), 7.41 (d, J=7.4 Hz, 1H), 7.35-7.23 (m, 2H), 6.10 (s, 1H), 5.14 (dd, J=13.3, 5.1 Hz, 1H), 4.38 (d, J=17.4 Hz, 1H), 4.24 (d, J=17.4 Hz, 1H), 3.58-3.54 (m, 8H), 3.14 (t, J=7.3 Hz, 2H), 2.96-2.88 (m, 1H), 2.66-2.53 (m, 4H), 2.45 (s, 3H), 2.25 (s, 3H), 2.05-1.98 (m, 1H), 1.89-1.83 (m, 2H). HRMS (ESI) m/z: calcd for, $C_{37}H_{39}ClN_9O_5S_2^+$ [M+H]$^+$, 788.2199; found, 788.2216.

Example 134: Preparation of N-(2-chloro-6-methylphenyl)-2-((6-(4-(5-((2-(2,6-dioxopiperidin-3-yl)-1-oxoisoindolin-4-yl)thio)pentanoyl)piperazin-1-yl)-2-methylpyrimidin-4-yl)amino)thiazole-5-carboxamide (SIAIS171108)

According to the general method described in Scheme 28, the target compound (SIAIS171108) was prepared by using Dasatinib derivatives (SIAIS151055) and LIN-ULM (SIAIS171079) under appropriate conditions that will be recognized by one skilled in the art. (white solid, 10 mg, yield 37%). $^1$H NMR (500 MHz, DMSO) δ 11.58 (s, 1H), 10.99 (s, 1H), 9.92 (s, 1H), 8.25 (s, 1H), 7.64 (dd, J=12.9, 6.7 Hz, 1H), 7.55-7.45 (m, 2H), 7.41 (d, J=7.5 Hz, 1H), 7.32-7.25 (m, 2H), 6.10 (s, 1H), 5.13 (dd, J=13.3, 5.0 Hz, 1H), 4.43-4.17 (m, 2H), 3.57-3.52 (m, 8H), 3.15-3.11 (m, 2H), 2.96-2.85 (m, 1H), 2.66-2.57 (m, 1H), 2.47-2.36 (m, 6H), 2.22 (s, 3H), 2.06-1.96 (m, 1H), 1.69-1.58 (m, 4H). HRMS (ESI) m/z: calcd for, $C_{38}H_{41}ClN_9O_5S_2^+$ [M+H]$^+$, 802.2355; found, 802.2364.

Example 135: Preparation of N-(2-chloro-6-methylphenyl)-2-((6-(4-(6-((2-(2,6-dioxopiperidin-3-yl)-1-oxoisoindolin-4-yl)thio)hexanoyl)piperazin-1-yl)-2-methylpyrimidin-4-yl)amino)thiazole-5-carboxamide (SIAIS171109)

According to the general method described in Scheme 28, the target compound (SIAIS171109) was prepared by using Dasatinib derivatives (SIAIS151055) and LIN-ULM (SIAIS171091) under appropriate conditions that will be recognized by one skilled in the art. (white solid, 10 mg, yield 36%). $^1$H NMR (500 MHz, DMSO) δ 11.59 (s, 1H), 11.00 (s, 1H), 9.92 (s, 1H), 8.25 (s, 1H), 7.64 (dd, J=7-0.5, 1.1 Hz, 1H), 7.57-7.54 (m, 2H), 7.41 (d, J=7.7 Hz, 1H), 7.34-7.23 (m, 2H), 6.10 (s, 1H), 5.14 (dd, J=13.3, 5.1 Hz, 1H), 4.30 (dd, J=68.7, 17.4 Hz, 2H), 3.57-3.53 (m, 8H), 3.09 (t, J=7.2 Hz, 2H), 2.92-2.88 (m, 1H), 2.66-2.57 (m, 1H), 2.49-2.44 (m, 4H), 2.34 (t, J=7.2 Hz, 2H), 2.25 (s, 3H), 2.04-1.99 (m, 1H), 1.67-1.62 (m, 2H), 1.60-1.50 (m, 2H), 1.48-1.41 (m, 2H). HRMS (ESI) m/z: calcd for, $C_{39}H_{43}ClN_9O_5S_2^+$ [M+H]$^+$, 816.2512; found, 816.2520.

Example 136: Preparation of N-(2-chloro-6-methylphenyl)-2-((6-(4-(7-((2-(2,6-dioxopiperidin-3-yl)-1-oxoisoindolin-4-yl)thio)heptanoyl)piperazin-1-yl)-2-methylpyrimidin-4-yl)amino)thiazole-5-carboxamide (SIAIS171110)

According to the general method described in Scheme 28, the target compound (SIAIS171110) was prepared by using Dasatinib derivatives (SIAIS151055) and LIN-ULM (SIAIS171092) under appropriate conditions that will be recognized by one skilled in the art. (white solid, 10 mg, yield 37%). $^1$H NMR (500 MHz, DMSO) δ 11.56 (s, 1H), 10.99 (s, 1H), 9.91 (s, 1H), 8.24 (s, 1H), 7.64 (dd, J=7.5, 1.2 Hz, 1H), 7.58-7.53 (m, 2H), 7.41 (d, J=7.8 Hz, 1H), 7.32-7.23 (m, 2H), 6.09 (s, 1H), 5.13 (dd, J=13.3, 5.1 Hz, 1H), 4.29 (dd, J=69.8, 17.4 Hz, 2H), 3.58-3.53 (m, 8H), 3.09 (t, J=7.2 Hz, 2H), 2.95-2.86 (m, 1H), 2.65-2.58 (m, 1H), 2.47-2.44 (m, 4H), 2.34 (t, J=7.4 Hz, 2H), 2.25 (s, 3H), 2.05-1.98 (m, 1H), 1.67-1.63 (m, 2H), 1.61-1.58 (m, 2H), 1.55-1.52 (m, 2H), 1.50-1.30 (m, 2H). HRMS (ESI) m/z: calcd for, $C_{40}H_{45}ClN_9O_5S_2^+$ [M+H]$^+$, 830.2668; found, 830.2665.

Example 137: Preparation of N-(2-chloro-6-methylphenyl)-2-((6-(4-(2-((2-(2,6-dioxopiperidin-3-yl)-1,3-dioxoisoindolin-4-yl)sulfinyl)acetyl)piperazin-1-yl)-2-methylpyrimidin-4-yl)amino)thiazole-5-carboxamide (SIAIS151109)

According to the general method described in Scheme 28, under appropriate conditions that will be recognized by one skilled in the art, the target compound (SIAIS151109) was prepared by Dasatinib derivative (SIAIS151055) and LIN-ULM (SIAIS151107). (yellow solid, 17.2 mg, yield 48%). $^1$H NMR (500 MHz, MeOD) δ 8.32 (dd, J=7.6, 1.1 Hz, 1H), 8.20 (s, 1H), 8.13-8.06 (m, 2H), 7.41-7.33 (m, 1H), 7.29-7.22 (m, 2H), 6.24 (s, 1H), 5.21-5.16 (m, 1H), 4.59 (dd, J=22.9, 14.6 Hz, 1H), 4.10 (dd, J=14.6, 7.6 Hz, 1H), 3.95-3.77 (m, 5H), 3.74-3.62 (m, 3H), 2.93-2.84 (m, 1H), 2.79-2.68 (m, 2H), 2.57 (s, 3H), 2.32 (s, 3H), 2.20-2.13 (m, 1H). HRMS (ESI) m/z: calcd for, $C_{35}H_{33}ClN_9O_7S_2^+$ [M+H]$^+$, 790.1672; found, 790.1645.

Example 138: Preparation of N-(2-chloro-6-methylphenyl)-2-((6-(4-(2-((2-(2,6-dioxopiperidin-3-yl)-1,3-dioxoisoindolin-4-yl)sulfonyl)acetyl)piperazin-1-yl)-2-methylpyrimidin-4-yl)amino)thiazole-5-carboxamide (SIAIS151108)

According to the general method described in Scheme 28, the target compound (SIAIS151108) was prepared by using Dasatinib derivatives (SIAIS151055) and LIN-ULM (SIAIS151106) under appropriate conditions that will be recognized by one skilled in the art. (yellow solid, 25.2 mg, yield 69%). $^1$H NMR (500 MHz, MeOD) δ 8.38 (dd, J=7.9, 0.9 Hz, 1H), 8.25 (dd, J=7.5, 0.9 Hz, 1H), 8.20 (s, 1H), 8.09 (t, J=7.7 Hz, 1H), 7.37 (dd, J=7.4, 1.8 Hz, 1H), 7.31-7.19 (m, 2H), 6.24 (s, 1H), 5.25 (dd, J=12.6, 5.5 Hz, 1H), 5.06 (dd, J=22.0, 14.0 Hz, 2H), 3.95-3.86 (m, 4H), 3.80-3.66 (m, 4H), 2.94-2.85 (m, 1H), 2.82-2.70 (m, 2H), 2.58 (s, 3H), 2.32 (s, 3H), 2.25-2.16 (m, 1H). HRMS (ESI) m/z: calcd for, $C_{35}H_{33}ClN_9O_8S_2^+$ [M+H]$^+$, 806.1577; found, 806.1602.

Example 139: Preparation of 4-((2,4-dichloro-5-methoxyphenyl)amino)-7-(3-(4-(2-((2-(2,6-dioxopiperidin-3-yl)-1,3-dioxoisoindolin-4-yl)thio)acetyl)piperazin-1-yl)propoxy)-6-methoxyquinoline-3-carbonitrile (SIAIS151168)

According to the general method described in Scheme 28, under appropriate conditions that will be recognized by one skilled in the art, the target compound (SIAIS151168) was prepared by using Bosutinib derivatives (SIAIS151151) and LIN-ULM (SIAIS151045). (yellow solid, 9.3 mg, yield 38%). $^1$H NMR (500 MHz, DMSO) δ 11.30 (s, 1H), 11.13 (s, 1H), 8.85 (s, 1H), 8.18 (s, 1H), 7.85-7.77 (m, 3H), 7.65 (d, J=6.6 Hz, 1H), 7.52 (s, 1H), 7.47 (s, 1H), 5.13 (dd, J=12.9, 5.4 Hz, 1H), 4.45 (d, J=13.2 Hz, 1H), 4.37 (s, 2H), 4.35-4.28 (m, 3H), 4.01 (s, 3H), 3.88 (s, 3H), 3.71-3.57 (m, 4H), 3.25-3.15 (m, 3H), 3.08-2.98 (m, 1H), 2.94-2.83 (m, 1H), 2.67-2.52 (m, 2H), 2.40-2.33 (s, 2H), 2.11-2.00 (m, 1H). HRMS (ESI) m/z: calcd for, $C_{40}H_{38}Cl_2N_7O_8S^+$ [M+H]$^+$, 846.1874; found, 846.1415.

Example 140: Preparation of 4-((2,4-dichloro-5-methoxyphenyl)amino)-7-(3-(4-(3-((2-(2,6-dioxopiperidin-3-yl)-1,3-dioxoisoindolin-4-yl)thio)propanoyl)piperazin-1-yl)propoxy)-6-methoxyquinoline-3-carbonitrile (SIAIS151169)

According to the general method described in Scheme 28, the target compound (SIAIS151169) was prepared by using Bosutinib derivatives (SIAIS151151) and LIN-ULM (SIAIS151138B) under appropriate conditions that will be recognized by one skilled in the art. (yellow solid, 10.5 mg, yield 42%). $^1$H NMR (500 MHz, DMSO) δ 11.12 (s, 2H), 8.87 (s, 1H), 8.17 (s, 1H), 7.85-7.75 (m, 3H), 7.65 (d, J=6.3 Hz, 1H), 7.51 (s, 1H), 7.48 (s, 1H), 5.16-5.07 (m, 1H), 4.49 (d, J=13.6 Hz, 1H), 4.35-4.28 (m, 2H), 4.10-4.03 (s, 1H), 4.00 (s, 3H), 3.88 (s, 3H), 3.43-3.24 (m, 5H), 3.20-3.03 (m, 3H), 3.01-2.81 (m, 5H), 2.66-2.55 (m, 2H), 2.38-2.30 (m, 2H), 2.08-2.02 (m, 1H). HRMS (ESI) m/z: calcd for, $C_{41}H_{40}Cl_2N_7O_8S^+$ [M+H]$^+$, 860.2031; found, 860.1564.

Example 141: Preparation of 4-((2,4-dichloro-5-methoxyphenyl)amino)-7-(3-(4-(4-((2-(2,6-dioxopiperidin-3-yl)-1,3-dioxoisoindolin-4-yl)thio)butanoyl)piperazin-1-yl)propoxy)-6-methoxyquinoline-3-carbonitrile (SIAIS151170)

According to the general method described in Scheme 28, under appropriate conditions that will be recognized by one skilled in the art, the target compound (SIAIS151170) was prepared by using Bosutinib derivatives (SIAIS151151) and LIN-ULM (SIAIS151139B). (yellow solid, 12.3 mg, yield 48%). $^1$H NMR (500 MHz, MeOD) δ 8.84 (s, 1H), 8.00 (s, 1H), 7.81 (d, J=8.1 Hz, 1H), 7.74 (t, 2H), 7.66 (s, 1H), 7.61 (d, J=7.2 Hz, 1H), 7.40 (d, J=2.2 Hz, 2H), 5.12 (dd, J=12.7, 5.5 Hz, 1H), 4.79-4.63 (m, 1H), 4.45 (t, J=5.5 Hz, 2H), 4.39-4.16 (m, 1H), 4.08 (s, 3H), 3.94 (s, 3H), 3.87-3.54 (m, 3H), 3.49 (t, J=7.3 Hz, 2H), 3.25-3.06 (m, 4H), 2.90-2.81 (m, 1H), 2.75-2.58 (m, 4H), 2.52-2.44 (m, 2H), 2.18-2.05 (m, 3H). HRMS (ESI) m/z: calcd for, $C_{42}H_{42}Cl_2N_7O_8S^+$ [M+H]$^+$, 874.2187; found, 874.1729.

Example 142: Preparation of 4-((2,4-dichloro-5-methoxyphenyl)amino)-7-(3-(4-(5-((2-(2,6-dioxopiperidin-3-yl)-1,3-dioxoisoindolin-4-yl)thio)pentanoyl)piperazin-1-yl)propoxy)-6-methoxyquinoline-3-carbonitrile (SIAIS151171)

According to the general method described in Scheme 28, the target compound (SIAIS151171) was prepared by using Bosutinib derivatives (SIAIS151151) and LIN-ULM (SIAIS151140B) under appropriate conditions that will be recognized by one skilled in the art. (yellow solid, 10.6 mg, yield 42%). $^1$H NMR (500 MHz, MeOD) δ 8.86 (s, 1H), 8.01 (s, 1H), 7.75-7.69 (m, 2H), 7.66 (s, 1H), 7.59 (d, J=6.3 Hz, 1H), 7.41 (s, 2H), 5.11 (dd, J=12.5, 5.4 Hz, 1H), 4.74-4.61 (m, 1H), 4.46 (t, J=5.4 Hz, 2H), 4.33-4.17 (m, 1H), 4.08 (s, 3H), 3.94 (s, 3H), 3.85-3.57 (m, 3H), 3.49 (t, J=7.0 Hz, 2H), 3.25-3.00 (m, 5H), 2.89-2.81 (m, 1H), 2.76-2.65 (m, 2H), 2.55 (s, 2H), 2.50-2.43 (m, 2H), 2.17-2.09 (m, 1H), 1.87-1.79 (m, 4H). HRMS (ESI) m/z: calcd for, $C_{43}H_{44}Cl_2N_7O_8S^+$ [M+H]$^+$, 888.2344; found, 888.1851.

Example 143: Preparation of 4-((2,4-dichloro-5-methoxyphenyl)amino)-7-(3-(4-(6-((2-(2,6-dioxopiperidin-3-yl)-1,3-dioxoisoindolin-4-yl)thio)hexanoyl)piperazin-1-yl)propoxy)-6-methoxyquinoline-3-carbonitrile (SIAIS151172)

According to the general method described in Scheme 28, the target compound (SIAIS151172) was prepared by using Bosutinib derivatives (SIAIS151151) and LIN-ULM (SIAIS151141B) under appropriate conditions that will be recognized by one skilled in the art. (yellow solid, 11.3 mg, yield 43%). $^1$H NMR (500 MHz, MeOD) δ 8.84 (s, 1H), 7.99 (s, 1H), 7.74-7.68 (m, 2H), 7.66 (s, 1H), 7.58 (d, J=6.5 Hz, 1H), 7.40 (d, J=1.7 Hz, 2H), 5.11 (dd, J=12.7, 5.5 Hz, 1H), 4.78-4.61 (m, 1H), 4.45 (t, J=5.5 Hz, 2H), 4.35-4.16 (m, 1H), 4.08 (s, 3H), 3.94 (s, 3H), 3.86-3.56 (m, 3H), 3.49 (t, J=7.2 Hz, 2H), 3.25-2.95 (m, 3H), 3.13 (t, J=7.5 Hz, 2H), 2.91-2.81 (m, 1H), 2.78-2.65 (m, 2H), 2.53-2.43 (m, 4H), 2.18-2.10 (m, 1H), 1.83-1.77 (m, 2H), 1.74-1.66 (m, 2H), 1.62-1.55 (m, 2H). HRMS (ESI) m/z: calcd for, $C_{44}H_{46}Cl_2N_7O_8S^+$ [M+H]$^+$, 902.2500; found, 902.1993.

Example 144: Preparation of 4-((2,4-dichloro-5-methoxyphenyl)amino)-7-(3-(4-(7-((2-(2,6-dioxopiperidin-3-yl)-1,3-dioxoisoindolin-4-yl)thio)heptanoyl)piperazin-1-yl)propoxy)-6-methoxyquinoline-3-carbonitrile (SIAIS151173)

According to the general method described in Scheme 28, the target compound (SIAIS151173) was prepared by using Bosutinib derivatives (SIAIS151151) and LIN-ULM (SIAIS151142B) under appropriate conditions that will be recognized by one skilled in the art. (yellow solid, 14.0 mg, yield 52%). $^1$H NMR (500 MHz, MeOD) δ 8.83 (s, 1H), 7.99 (s, 1H), 7.75-7.68 (m, 2H), 7.66 (s, 1H), 7.59 (d, J=6.3 Hz, 1H), 7.40 (d, J=3.6 Hz, 2H), 5.11 (dd, J=12.6, 5.5 Hz, 1H), 4.78-4.61 (m, 1H), 4.45 (t, J=5.5 Hz, 2H), 4.33-4.16 (m, 1H), 4.08 (s, 3H), 3.94 (s, 3H), 3.85-3.56 (m, 3H), 3.49 (t, J=7.2 Hz, 2H), 3.26-2.97 (m, 3H), 3.14 (t, J=7.5 Hz, 2H), 2.90-2.83 (m, 1H), 2.79-2.65 (m, 2H), 2.53-2.42 (m, 4H), 2.16-2.10 (m, 1H), 1.81-1.75 (m, 2H), 1.71-1.62 (m, 2H), 1.59-1.53 (m, 2H), 1.50-1.41 (m, 2H). HRMS (ESI) m/z: calcd for, $C_{45}H_{48}Cl_2N_7O_8S^+$ [M+H]$^+$, 916.2657; found, 916.2110.

Example 145: Preparation of N-(4-((4-(3-((2-(2,6-dioxopiperidin-3-yl)-1,3-dioxoisoindolin-4-yl)thio) propanoyl)piperazin-1-yl)methyl)-3-(trifluoromethyl)phenyl)-3-(imidazo[1,2-b]pyridazin-3-ylethynyl)-4-methylbenzamide (SIAIS220046)

According to the general method described in Scheme 28, under appropriate conditions that will be recognized by one skilled in the art, the target compound (SIAIS220046) was prepared by using Ponatinib derivatives (SIAIS151190B) and LIN-ULM (SIAIS151138B). (light yellow solid, 9.2 mg, yield 55%), $^1$H NMR (500 MHz, DMSO) δ 11.12 (s, 1H), 10.82 (s, 1H), 8.76 (dd, J=4.4, 1.4 Hz, 1H), 8.38 (d, J=1.9 Hz, 1H), 8.33 (d, J=8.4 Hz, 1H), 8.31-8.26 (m, 2H), 8.22 (d, J=8.6 Hz, 2H), 7.99 (dd, J=8.0, 1.8 Hz, 1H), 7.83-7.75 (m, 2H), 7.64 (d, J=6.8 Hz, 1H), 7.57 (d, J=8.3 Hz, 1H), 7.43 (dd, J=9.2, 4.4 Hz, 1H), 5.11 (dd, J=12.9, 5.4 Hz, 1H), 4.48-4.40 (m, 2H), 4.09-3.97 (m, 1H), 3.75-3.64 (m, 4H), 3.34 (t, J=6.9 Hz, 2H), 3.28-3.16 (m, 2H), 3.12-2.99 (m, 1H), 2.93-2.80 (m, 3H), 2.62 (s, 3H), 2.61-2.51 (m, 2H), 2.08-2.02 (m, 1H). HRMS (ESI) m/z: calcd for, $C_{44}H_{38}F_3N_8O_6S^+$ [M+H]$^+$, 863.2582; found, 863.2589.

Example 146: Preparation of N-(4-((4-(4-((2-(2,6-dioxopiperidin-3-yl)-1,3-dioxoisoindolin-4-yl)thio) butanoyl)piperazin-1-yl)methyl)-3-(trifluoromethyl)phenyl)-3-(imidazo[1,2-b]pyridazin-3-ylethynyl)-4-methylbenzamide (SIAIS220047)

According to the general method described in Scheme 28, under appropriate conditions that will be recognized by one skilled in the art, the target compound (SIAIS220047) was prepared by using Ponatinib derivatives (SIAIS151190B) and LIN-ULM (SIAIS151139B). (light yellow solid, 8.6 mg, yield 51%), $^1$H NMR (500 MHz, DMSO) δ 11.12 (s, 1H), 10.80 (s, 1H), 8.75 (dd, J=4.4, 1.5 Hz, 1H), 8.37 (s, 1H), 8.30-8.22 (m, 4H), 7.99 (dd, J=8.0, 1.8 Hz, 1H), 7.86 (d, J=8.1 Hz, 1H), 7.82-7.77 (m, 1H), 7.63 (d, J=7.1 Hz, 1H), 7.58 (d, J=8.2 Hz, 1H), 7.42 (dd, J=9.2, 4.4 Hz, 1H), 5.11 (dd, J=12.9, 5.4 Hz, 1H), 4.50-4.40 (m, 2H), 3.76-3.66 (m, 4H), 3.31-3.13 (m, 4H), 3.08-3.02 (m, 2H), 2.91-2.85 (m, 1H), 2.63-2.55 (m, 5H), 2.11-2.01 (m, 1H), 1.94-1.86 (m, 2H). 'HRMS (ESI) m/z: calcd for, $C_{45}H_{40}F_3N_8O_6S^+$ [M+H]$^+$, 877.2738; found, 877.2733.

Example 147: Preparation of N-(4-((4-(5-((2-(2,6-dioxopiperidin-3-yl)-1,3-dioxoisoindolin-4-yl)thio) pentanoyl)piperazin-1-yl)methyl)-3-(trifluoromethyl)phenyl)-3-(imidazo[1,2-b]pyridazin-3-ylethynyl)-4-methylbenzamide (SIAIS220048)

According to the general method described in Scheme 28, under appropriate conditions that will be recognized by one skilled in the art, the target compound (SIAIS220048) was prepared by using Ponatinib derivatives (SIAIS151190B) and LIN-ULM (SIAIS151140B). (light yellow solid, 7.9 mg, yield 46%), $^1$H NMR (500 MHz, DMSO) δ 11.12 (s, 1H), 10.82 (s, 1H), 8.77 (dd, J=4.4, 1.4 Hz, 1H), 8.38 (t, J=5.4 Hz, 1H), 8.35 (d, J=8.7 Hz, 1H), 8.30 (dd, J=9.2, 1.5 Hz, 2H), 8.22 (dd, J=10.2, 1.7 Hz, 2H), 8.00 (dd, J=8.0, 1.8 Hz, 1H), 7.82-7.74 (m, 2H), 7.63 (d, J=6.8 Hz, 1H), 7.57 (d, J=8.3 Hz, 1H), 7.45 (dd, J=9.2, 4.5 Hz, 1H), 5.11 (dd, J=12.9, 5.4 Hz, 1H), 4.46 (d, J=14.8 Hz, 2H), 4.07-4.02 (m, 4H), 3.74-3.62 (m, 1H), 3.38-3.32 (m, 1H), 3.24-3.19 (m, 1H), 3.16 (t, J=6.3 Hz, 2H), 3.07-2.97 (m, 1H), 2.93-2.85 (m, 1H), 2.62 (s, 3H), 2.60-2.50 (m, 2H), 2.42 (t, J=6.3 Hz, 2H), 2.08-2.02 (m, 1H), 1.74-1.64 (m, 1H). HRMS (ESI) m/z: calcd for, $C_{46}H_{42}F_3N_8O_6S^+$ [M+H]$^+$, 891.2895; found, 891.2889.

Example 148: Preparation of N-(4-((4-(6-((2-(2,6-dioxopiperidin-3-yl)-1,3-dioxoisoindolin-4-yl)thio) hexanoyl)piperazin-1-yl)methyl)-3-(trifluoromethyl)phenyl)-3-(imidazo[1,2-b]pyridazin-3-ylethynyl)-4-methylbenzamide (SIAIS220049)

According to the general method described in Scheme 28, under appropriate conditions that will be recognized by one skilled in the art, the target compound (SIAIS220049) was prepared by using Ponatinib derivatives (SIAIS151190B) and LIN-ULM (SIAIS151141B). (light yellow solid, 8.2 mg, yield 47%), $^1$H NMR (500 MHz, DMSO) δ 11.12 (s, 1H), 10.81 (s, 1H), 8.75 (dd, J=4.4, 1.4 Hz, 1H), 8.38 (s, 1H), 8.36-8.26 (m, 3H), 8.23 (t, J=4.8 Hz, 2H), 7.99 (dd, J=8.0, 1.7 Hz, 1H), 7.83-7.71 (m, 2H), 7.63 (d, J=6.8 Hz, 1H), 7.58 (d, J=8.3 Hz, 1H), 7.43 (dd, J=9.2, 4.4 Hz, 1H), 5.11 (dd, J=12.9, 5.4 Hz, 1H), 4.50-4.40 (m, 2H), 4.12-3.98 (m, 1H), 3.68-3.56 (m, 4H), 3.38-3.30 (m, 1H), 3.16-3.09 (m, 4H), 2.94-2.84 (m, 1H), 2.62 (s, 3H), 2.61-2.51 (m, 2H), 2.37 (t, J=7.1 Hz, 2H), 2.08-2.02 (m, 1H), 1.72-1.66 (m, 2H), 1.59-1.42 (m, 4H). HRMS (ESI) m/z: calcd for, $C_{47}H_{44}F_3N_8O_6S^+$ [M+H]$^+$, 905.3051; found, 905.3058.

Example 149: Preparation of N-(4-((4-(7-((2-(2,6-dioxopiperidin-3-yl)-1,3-dioxoisoindolin-4-yl)thio) heptanoyl)piperazin-1-yl)methyl)-3-(trifluoromethyl)phenyl)-3-(imidazo[1,2-b]pyridazin-3-ylethynyl)-4-methylbenzamide (SIAIS220050)

According to the general method described in Scheme 28, under appropriate conditions that will be recognized by one skilled in the art, the target compound (SIAIS220050) was prepared by using Ponatinib derivatives (SIAIS151190B) and LIN-ULM (SIAIS15142B). (light yellow solid, 10.2 mg, yield 57%), $^1$H NMR (500 MHz, DMSO) δ 11.12 (s, 1H), 10.79 (s, 1H), 8.75 (dd, J=4.4, 1.5 Hz, 1H), 8.37 (s, 1H), 8.29 (dd, J=9.2, 1.6 Hz, 1H), 8.27 (s, 1H), 8.23 (d, J=1.8 Hz, 2H), 7.98 (dd, J=8.0, 1.9 Hz, 1H), 7.81-7.76 (m, 2H), 7.74 (d, J=7.5 Hz, 2H), 7.62 (s, 1H), 7.58 (d, J=8.2 Hz, 1H), 7.43 (dd, J=9.2, 4.4 Hz, 1H), 5.11 (dd, J=12.9, 5.4 Hz, 2H), 4.50-4.40 (m, 2H), 3.72-3.60 (m, 4H), 3.40-3.30 (m, 2H), 3.26-3.16 (m, 1H), 3.16-3.12 (t, J=7.0 Hz, 2H), 3.10-3.00 (m, 1H), 2.92-2.84 (m, 1H), 2.62 (s, 3H), 2.56-2.51 (m, 2H), 2.38-2.32 (m, 2H), 2.29 (t, J=7.4 Hz, 2H), 2.08-2.02 (m, 2H), 1.71-1.63 (m, 2H), 1.54-1.42 (m, 4H), 1.36-1.29 (m, 2H). HRMS (ESI) m/z: calcd for, $C_{48}H_{46}F_3N_8O_6S^+$ [M+H]$^+$, 919.3208; found, 919.3209.

Example 150: Preparation of N-(4-((4-(2-((2-(2,6-dioxopiperidin-3-yl)-1-oxoisoindolin-4-yl)thio) acetyl)piperazin-1-yl)methyl)-3-(trifluoromethyl)phenyl)-3-(imidazo[1,2-b]pyridazin-3-ylethynyl)-4-methylbenzamide (SIAIS220051)

According to the general method described in Scheme 28, under appropriate conditions that will be recognized by one skilled in the art, the target compound (SIAIS220051) was prepared by using Ponatinib derivatives (SIAIS151190B) and LIN-ULM (SIAIS171090). (light yellow solid, 10.3 mg, yield 64%), $^1$H NMR (500 MHz, DMSO) δ 11.00 (s, 1H), 10.79 (s, 1H), 8.74 (dd, J=4.4, 1.5 Hz, 1H), 8.37 (s, 1H), 8.28

(dd, J=9.2, 1.6 Hz, 1H), 8.26 (s, 1H), 8.23 (d, J=1.8 Hz, 2H), 7.98 (dd, J=8.0, 1.9 Hz, 1H), 7.70 (d, J=7.2 Hz, 1H), 7.59 (dd, J=11.7, 7.5 Hz, 2H), 7.53 (t, J=7.6 Hz, 1H), 7.42 (dd, J=9.2, 4.4 Hz, 1H), 5.14 (dd, J=13.3, 5.1 Hz, 1H), 4.44 (s, 2H), 4.40 (s, 1H), 4.27 (d, J=17.4 Hz, 1H), 4.23 (s, 2H), 3.57-3.05 (m, 8H), 2.97-2.87 (m, 1H), 2.62 (s, 3H), 2.49-2.42 (m, 2H), 2.07-1.98 (m, 1H). HRMS (ESI) m/z: calcd for, $C_{43}H_{38}F_3N_8O_5S^+$ [M+H]$^+$, 835.2632; found, 835.2635.

Example 151: Preparation of N-(4-((4-(3-((2-(2,6-dioxopiperidin-3-yl)-1-oxoisoindolin-4-yl)thio)propanoyl)piperazin-1-yl)methyl)-3-(trifluoromethyl)phenyl)-3-(imidazo[1,2-b]pyridazin-3-ylethynyl)-4-methylbenzamide (SIAIS220052)

According to the general method described in Scheme 28, under appropriate conditions that will be recognized by one skilled in the art, the target compound (SIAIS220052) was prepared by using Ponatinib derivatives (SIAIS151190B) and LIN-ULM (SIAIS171086). (light yellow solid, 9.1 mg, yield 55%), $^1$H NMR (500 MHz, DMSO) δ 10.99 (s, 1H), 10.79 (s, 1H), 8.75 (dd, J=4.4, 1.5 Hz, 1H), 8.37 (s, 1H), 8.28 (dd, J=9.2, 1.6 Hz, 1H), 8.27 (s, 1H), 8.23 (t, J=4.4 Hz, 2H), 7.98 (dd, J=8.0, 1.8 Hz, 1H), 7.66 (dd, J=7.6, 1.1 Hz, 1H), 7.60-7.52 (m, 3H), 7.43 (dd, J=9.2, 4.4 Hz, 1H), 5.13 (dd, J=13.3, 5.1 Hz, 1H), 4.50-4.40 (m, 2H), 4.35 (d, J=17.4 Hz, 1H), 4.22 (d, J=17.4 Hz, 1H), 3.73-3.55 (m, 4H), 3.37-3.31 (m, 1H), 3.28 (dd, J=15.2, 6.8 Hz, 2H), 3.22-3.00 (m, 3H), 2.96-2.86 (m, 1H), 2.76 (t, J=6.4 Hz, 2H), 2.62 (s, 3H), 2.49-2.41 (m, 2H), 2.04-1.97 (m, 1H). HRMS (ESI) m/z: calcd for, $C_{44}H_{40}F_3N_8O_5S^+$ [M+H]$^+$, 849.2789; found, 849.2783.

Example 152: Preparation of N-(4-((4-(4-((2-(2,6-dioxopiperidin-3-yl)-1-oxoisoindolin-4-yl)thio)butanoyl)piperazin-1-yl)methyl)-3-(trifluoromethyl)phenyl)-3-(imidazo[1,2-b]pyridazin-3-ylethynyl)-4-methylbenzamide (SIAIS220053)

According to the general method described in Scheme 28, under appropriate conditions that will be recognized by one skilled in the art, the target compound (SIAIS220053) was prepared by using Ponatinib derivatives (SIAIS151190B) and LIN-ULM (SIAIS171089) under appropriate conditions that will be recognized by one skilled in the art. (light yellow solid, 7.2 mg, yield 43%), $^1$H NMR (500 MHz, DMSO) δ 11.00 (s, 1H), 10.82 (s, 1H), 8.76 (d, J=3.1 Hz, 1H), 8.39 (d, J=1.5 Hz, 1H), 8.34 (d, J=7.9 Hz, 1H), 8.31-8.28 (m, 2H), 8.23 (d, J=8.4 Hz, 2H), 8.00 (dd, J=8.0, 1.5 Hz, 1H), 7.69 (d, J=6.7 Hz, 1H), 7.60-7.52 (m, 3H), 7.44 (dd, J=9.2, 4.4 Hz, 1H), 5.14 (dd, J=13.3, 5.0 Hz, 1H), 4.50-4.42 (m, 2H), 4.37 (d, J=17.4 Hz, 1H), 4.23 (d, J=17.4 Hz, 1H), 4.12-3.92 (d, J=37.5 Hz, 4H), 3.39-3.31 (m, 1H), 3.20-3.00 (m, 5H), 2.97-2.86 (m, 1H), 2.62 (s, 3H), 2.50-2.42 (m, 2H), 2.05-1.97 (m, 1H), 1.89-1.79 (m, 2H). HRMS (ESI) m/z: calcd for, $C_{45}H_{42}F_3N_8O_5S^+$ [M+H]$^+$, 863.2945; found, 863.2952.

Example 153: Preparation of N-(4-((4-(5-((2-(2,6-dioxopiperidin-3-yl)-1-oxoisoindolin-4-yl)thio)pentanoyl)piperazin-1-yl)methyl)-3-(trifluoromethyl)phenyl)-3-(imidazo[1,2-b]pyridazin-3-ylethynyl)-4-methylbenzamide (SIAIS220054)

According to the general method described in Scheme 28, under appropriate conditions that will be recognized by one skilled in the art, the target compound (SIAIS220054) was prepared by using Ponatinib derivatives (SIAIS151190B) and LIN-ULM (SIAIS171079). (light yellow solid, 7.5 mg, yield 44%), $^1$H NMR (500 MHz, DMSO) δ 10.99 (s, 1H), 10.79 (s, 1H), 8.75 (dd, J=4.4, 1.5 Hz, 1H), 8.37 (s, 1H), 8.28 (dd, J=9.2, 1.5 Hz, 1H), 8.26 (s, 1H), 8.23 (d, J=1.7 Hz, 2H), 7.98 (dd, J=8.0, 1.8 Hz, 1H), 7.64 (dd, J=7.5, 1.1 Hz, 1H), 7.59-7.56 (m, 2H), 7.53 (t, J=7.5 Hz, 1H), 7.42 (dd, J=9.2, 4.4 Hz, 1H), 5.13 (dd, J=13.3, 5.1 Hz, 1H), 4.44 (s, 2H), 4.36 (d, J=17.4 Hz, 1H), 4.22 (d, J=17.4 Hz, 1H), 3.67-3.58 (m, 4H), 3.38-3.32 (m, 1H), 3.20-2.98 (m, 5H), 2.95-2.87 (m, 1H), 2.62 (s, 3H), 2.49-2.45 (m, 2H), 2.39 (s, 2H), 2.04-1.97 (m, 1H), 1.69-1.57 (m, 4H). HRMS (ESI) m/z: calcd for, $C_{46}H_{44}F_3N_8O_5S^+$ [M+H]$^+$, 877.3102; found, 877.3110.

Example 154: Preparation of N-(4-((4-(6-((2-(2,6-dioxopiperidin-3-yl)-1-oxoisoindolin-4-yl)thio)hexanoyl)piperazin-1-yl)methyl)-3-(trifluoromethyl)phenyl)-3-(imidazo[1,2-b]pyridazin-3-ylethynyl)-4-methylbenzamide (SIAIS220055)

According to the general method described in Scheme 28, under appropriate conditions that will be recognized by one skilled in the art, the target compound (SIAIS220055) was prepared by using Ponatinib derivative (SIAIS151190B) and LIN-ULM (SIAIS171091). (light yellow solid, 8.2 mg, yield 48%), $^1$H NMR (500 MHz, DMSO) δ 10.99 (s, 1H), 10.80 (s, 1H), 8.75 (dd, J=4.4, 1.5 Hz, 1H), 8.37 (s, 1H), 8.28 (dd, J=9.2, 1.5 Hz, 1H), 8.27 (s, 1H), 8.25-8.21 (m, 2H), 7.98 (dd, J=8.0, 1.9 Hz, 1H), 7.63 (dd, J=7.5, 1.1 Hz, 1H), 7.59-7.55 (m, 2H), 7.53 (t, J=7.5 Hz, 1H), 7.42 (dd, J=9.2, 4.4 Hz, 1H), 5.13 (dd, J=13.3, 5.1 Hz, 1H), 4.49-4.41 (m, 2H), 4.35 (d, J=17.4 Hz, 1H), 4.22 (d, J=17.4 Hz, 1H), 4.07-3.97 (m, 1H), 3.68-3.57 (m, 4H), 3.36-3.32 (m, 1H), 3.23-3.11 (m, 2H), 3.08 (t, J=7.2 Hz, 2H), 2.95-2.85 (m, 1H), 2.62 (s, 3H), 2.49-2.41 (m, 2H), 2.33 (t, J=7.0 Hz, 2H), 2.04-1.97 (m, 1H), 1.65-1.58 (m, 2H), 1.54-1.48 (m, 2H), 1.45-1.39 (m, 2H). HRMS (ESI) m/z: calcd for, $C_{47}H_{46}F_3N_8O_5S^+$ [M+H]$^+$, 891.3258; found, 891.3255.

Example 155: Preparation of N-(4-((4-(7-((2-(2,6-dioxopiperidin-3-yl)-1-oxoisoindolin-4-yl)thio)heptanoyl)piperazin-1-yl)methyl)-3-(trifluoromethyl)phenyl)-3-(imidazo[1,2-b]pyridazin-3-ylethynyl)-4-methylbenzamide (SIAIS220056)

According to the general method described in Scheme 28, under appropriate conditions that will be recognized by one skilled in the art, the target compound (SIAIS220056) was prepared by using Ponatinib derivatives (SIAIS151190B) and LIN-ULM (SIAIS171092). (light yellow solid, 9.2 mg, yield 52%), $^1$H NMR (500 MHz, DMSO) δ 10.99 (s, 1H), 10.80 (s, 1H), 8.75 (dd, J=4.4, 1.5 Hz, 1H), 8.37 (d, J=1.8 Hz, 1H), 8.29 (dd, J=9.2, 1.6 Hz, 1H), 8.27 (s, 1H), 8.23 (t, J=4.0 Hz, 2H), 7.99 (dd, J=8.0, 1.9 Hz, 1H), 7.62 (dd, J=7.5, 1.2 Hz, 1H), 7.59-7.55 (m, 2H), 7.53 (t, J=7.5 Hz, 1H), 7.43 (dd, J=9.2, 4.4 Hz, 1H), 5.13 (dd, J=13.3, 5.1 Hz, 1H), 4.49-4.41 (m, 2H), 4.35 (d, J=17.4 Hz, 1H), 4.21 (d, J=17.4 Hz, 1H), 4.08-3.96 (m, 1H), 3.73-3.57 (m, 4H), 3.37-3.33 (m, 1H), 3.23-3.11 (m, 2H), 3.08 (t, J=7.2 Hz, 2H), 2.95-2.87 (m, 1H), 2.62 (s, 3H), 2.49-2.41 (m, 2H), 2.32 (t, J=7.3 Hz, 2H), 2.04-1.97 (m, 1H), 1.65-1.56 (m, 2H), 1.51-1.39 (m, 4H), 1.32-1.26 (m, 2H). HRMS (ESI) m/z: calcd for, $C_{48}H_{48}F_3N_8O_5S^+$ [M+H]$^+$, 905.3415; found, 905.3421.

General Synthesis Method of the Special Degradation Agents SIAIS172056 and SIAIS172106 of BCR-ABL Target:

Scheme 29
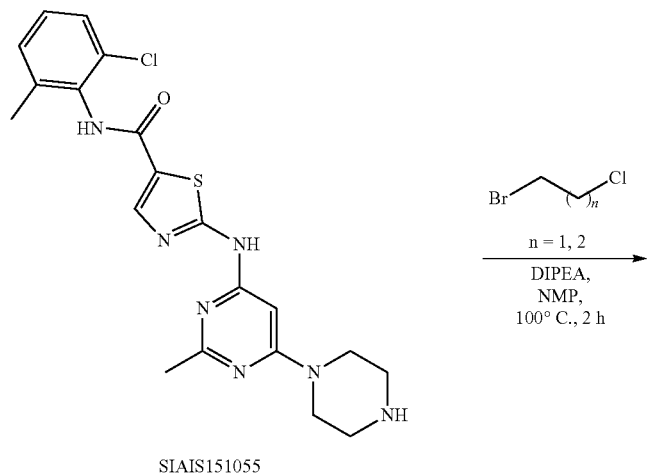
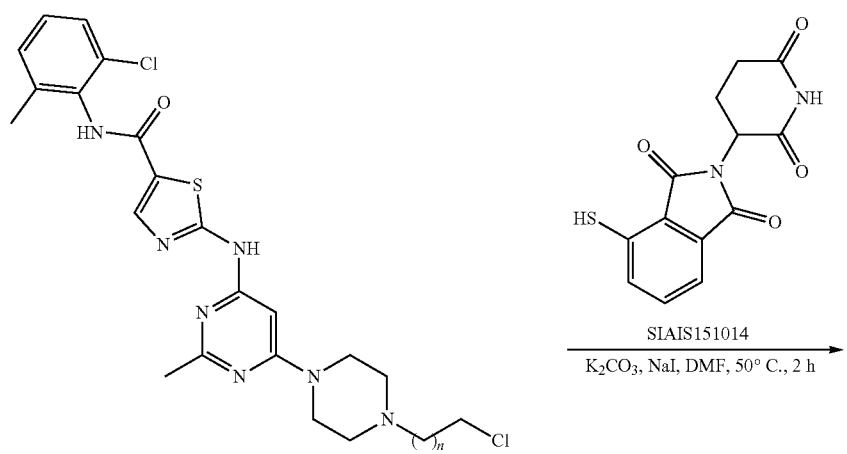
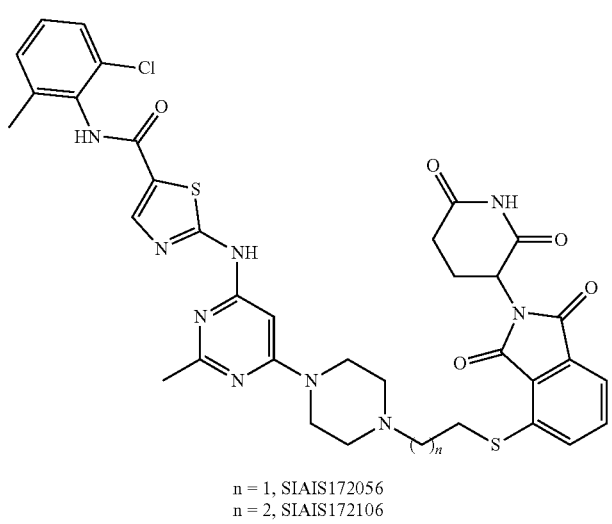

Preparation of N-(2-chloro-6-methylphenyl)-2-((6-(4-(2-chloroethyl)piperazin-1-yl)-2-methylpyrimidin-4-yl)amino)thiazole-5-carboxamide (SIAIS172051) According to Scheme 29

SIAIS151055 (1000 mg, 2.25 mmol), 1-bromo-2-chloroethane (968 mg, 6.75 mmol), N,N-diisopropylethylamine (1450 mg, 11.25 mmol) and N-methylpyrrolidone (15 mL) were added to a 100 mL egg-shaped flask, and then slowly heated to 100° C., and stirred for 2 h. After the reaction is complete, the reaction mixture was cooled to room temperature. Water (100 mL) was added to the reaction solution. The reaction solution was then extracted with ethyl acetate (3×50 mL), and the combined organic phases were washed with water (30 mL) and saturated brine, dried over anhydrous Na$_2$SO$_4$, and then concentrated to remove the solvent under reduced pressure. The residue was mixed with silica gel, and subjected to column chromatography (eluent gradient: 0-3% MeOH/DCM) and rotary-evaporated to dryness to obtain the target compound SIAIS172051. (yellow solid, 650 mg, yield 57%), $^1$H NMR (500 MHz, DMSO) δ 11.47 (s, 1H), 9.87 (s, 1H), 8.22 (s, 1H), 7.40 (d, J=6.6 Hz, 1H), 7.30-7.23 (m, 2H), 6.06 (s, 1H), 3.72 (t, J=6.4 Hz, 2H), 3.57-3.47 (m, 4H), 2.69 (t, J=6.3 Hz, 2H), 2.51-2.55 (m, 4H), 2.41 (s, 3H), 2.24 (s, 3H). HRMS (ESI) m/z: calcd for, C$_{22}$H$_{26}$Cl$_2$N$_7$OS$^+$ [M+H]$^+$, 506.1291; found, 505.7968.

Example 156: Preparation of N-(2-chloro-6-methylphenyl)-2-((6-(4-(2-((2-(2,6-dioxopiperidin-3-yl)-1,3-dioxoisoindolin-4-yl)thio)ethyl)piperazin-1-yl)-2-methylpyrimidin-4-yl)amino)thiazole-5-carboxamide (SIAIS172056)

A 10 mL egg-shaped flask was charged with Compound SIAIS172051 (20 mg, 0.04 mmol), SIAIS151014 (13 mg, 0.044 mmol), anhydrous potassium carbonate (27.6 mg, 0.2 mmol) and sodium iodide (30 mg, 0.2 mmol), followed by addition of anhydrous N,N-dimethylformamide (3 mL). The reaction mixture was slowly heated to 50° C. and stirred for 2 h. After the completion of the reaction was detected by the LC-MS, the reaction mixture was filtered, and the filtrate was separated by preparative HPLC (eluent (v/v): Acetonitrile/(water+0.05% HCl)=10%-100%) to obtain the target compound (SIAIS172056). (Light yellow solid, 20.2 mg, yield 68%), $^1$H NMR (500 MHz, DMSO) δ 11.50 (s, 1H), 11.13 (s, 1H), 9.93 (s, 1H), 8.26 (s, 1H), 7.97 (d, J=8.3 Hz, 1H), 7.84 (t, J=7.7 Hz, 1H), 7.71 (d, J=7.3 Hz, 1H), 7.40 (d, J=7.6 Hz, 1H), 7.32-7.23 (m, 2H), 6.18 (s, 1H), 5.13 (dd, J=12.9, 5.4 Hz, 1H), 4.39-4.37 (m, 2H), 3.73-3.66 (m, 4H), 3.44-3.35 (m, 4H), 3.18-3.07 (m, 2H), 2.93-2.85 (m, 1H), 2.64-2.52 (m, 2H), 2.46 (s, 3H), 2.24 (s, 3H), 2.08-2.01 (m, 1H). HRMS (ESI) m/z: calcd, for, C$_{35}$H$_{35}$ClN$_9$O$_5$S$_2$$^+$ [M+H]$^+$, 760.1886; found, 760.1882.

Preparation of N-(2-chloro-6-methylphenyl)-2-((6-(4-(3-chloropropyl)piperazin-1-yl)-2-methylpyrimidin-4-yl)amino)thiazole-5-carboxamide (SIAIS172104) According to Scheme 29

According to the general method described in Scheme 29, the target compound (SIAIS172104) was prepared by using 1-bromo-3-chloropropane. (yellow solid, 50 mg, yield 76%) $^1$H NMR (500 MHz, DMSO) δ 11.64 (s, 1H), 10.83 (d, J=43.8 Hz, 1H), 9.93 (s, 1H), 8.25 (s, 1H), 7.40 (d, J=7.4 Hz, 1H), 7.31-7.23 (m, 2H), 6.16 (s, 1H), 4.35 (d, J=10.8 Hz, 2H), 3.76 (t, J=6.3 Hz, 2H), 3.62-3.56 (m, 2H), 3.34 (d, J=12.7 Hz, 2H), 3.26-3.18 (m, 2H), 3.13-3.01 (m, 2H), 2.45 (s, 3H), 2.24 (s, 3H), 2.23-2.18 (m, 2H). HRMS (ESI) m/z: calcd, for, C$_{23}$H$_{28}$Cl$_2$N$_7$OS$^+$ [M+H]$^+$, 520.1448; found, 520.1443.

Example 157: Preparation of N-(2-chloro-6-methylphenyl)-2-((6-(4-(3-((2-(2,6-dioxopiperidin-3-yl)-1,3-dioxoisoindolin-4-yl)thio)propyl)piperazin-1-yl)-2-methylpyrimidin-4-yl)amino)thiazole-5-carboxamide (SIAIS172106)

According to the general method described in Scheme 29, the target compound (SIAIS172106) was prepared by using SIAIS172104 and SIAIS151014. (light yellow solid, 18.6 mg, yield 66%) $^1$H NMR (500 MHz, DMSO) δ 11.63 (s, 1H), 11.13 (s, 1H), 9.92 (s, 1H), 8.25 (s, 1H), 7.85-7.80 (m, 2H), 7.67 (dd, J=5.0, 3.0 Hz, 1H), 7.40 (d, J=7.8 Hz, 1H), 7.33-7.23 (m, 2H), 6.15 (s, 1H), 5.12 (dd, J=12.9, 5.4 Hz, 1H), 4.34 (d, J=12.3 Hz, 2H), 3.59 (d, J=11.4 Hz, 2H), 3.31-3.25 (m, 6H), 3.12-3.02 (m, 2H), 2.93-2.84 (m, 1H), 2.65-2.52 (m, 2H), 2.44 (s, 3H), 2.24 (s, 3H), 2.18-2.10 (m, 2H), 2.08-2.03 (m, 1H). HRMS (ESI) m/z: calcd for, C$_{36}$H$_{39}$ClN$_9$O$_5$S$_2$$^+$ [M+H]$^+$, 774.2042; found, 774.2042.

General Synthesis Method of the Special Degradation Agent SIAIS171166 and SIAIS171181 of Bcr-Abl Target:

Scheme 30

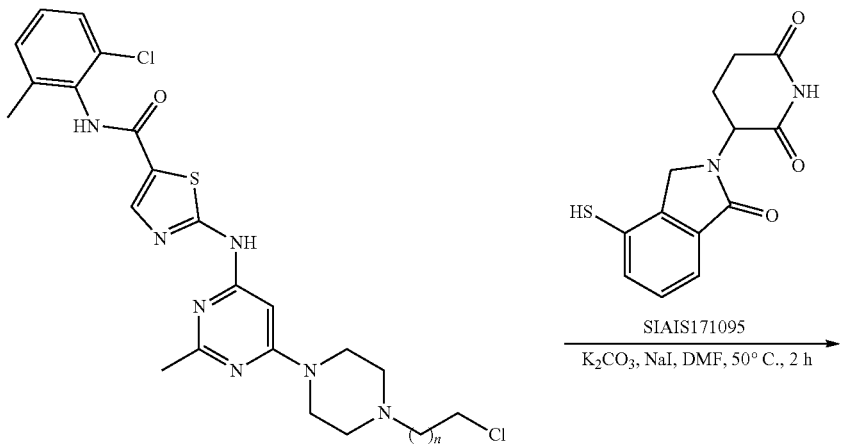

n = 1, SIAIS172051
n = 2, SIAIS172104

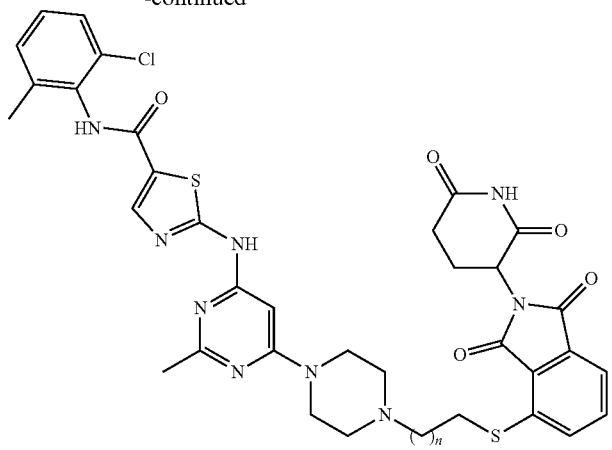

n = 1, SIAIS171166
n = 2, SIAIS171181

Example 158: Preparation of N-(2-chloro-6-methylphenyl)-2-((6-(4-(2-((2-(2,6-dioxopiperidin-3-yl)-1-oxoisoindolin-4-yl)thio)ethyl)piperazin-1-yl)-2-methylpyrimidin-4-yl)amino)thiazole-5-carboxamide (SIAIS171166) According to Scheme 30

A 10 mL egg-shaped flask was charged with Compound SIAIS172051 (15 mg, 0.03 mmol), SIAIS171095 (8.2 mg, 0.03 mmol), anhydrous potassium carbonate (8.2 mg, 0.06 mmol) and sodium iodide (9.0 mg, 0.06 mmol), followed by addition of anhydrous N,N-dimethylformamide (2 mL). The reaction mixture was slowly heated to 50° C. and stir for 2 h. After the completion of the reaction was detected by the LC-MS, the reaction mixture was filtered, and the filtrate was separated by preparative HPLC (eluent (v/v): Acetonitrile/(water+0.05% HCl)=10%-100%) to obtain the target compound (SIAIS171166). (White solid, 6.0 mg, yield 27%), $^1$H NMR (500 MHz, MeOD) δ 8.22 (s, 1H), 7.79 (ddd, J=24.9, 11.2, 3.9 Hz, 2H), 7.60 (dd, J=17.9, 10.2 Hz, 1H), 7.36 (dd, J=7.2, 2.0 Hz, 1H), 7.32-7.15 (m, 2H), 6.42 (d, J=29.7 Hz, 1H), 5.18 (dd, J=13.3, 5.2 Hz, 1H), 4.58-4.46 (m, 2H), 4.18-3.31 (m, 12H), 2.95-2.88 (m, 1H), 2.79 (ddd, J=17.5, 4.5, 2.3 Hz, 1H), 2.64-2.46 (m, 4H), 2.31 (s, 3H), 2.19 (ddd, J=10.4, 5.2, 2.6 Hz, 1H). HRMS (ESI) m/z: calcd for, $C_{35}H_{37}ClN_9O_4S_2^+$ [M+H]$^+$, 746.2093; found, 746.2660.

Example 159: Preparation of N-(2-chloro-6-methylphenyl)-2-((6-(4-(3-((2-(2,6-dioxopiperidin-3-yl)-1-oxoisoindolin-4-yl)thio)propyl)piperazin-1-yl)-2-methylpyrimidin-4-yl)amino)thiazole-5-carboxamide (SIAIS171181) According to Scheme 30

According to the general method described in Scheme 30, the target compound (SIAIS171181) was prepared by using SIAIS172104 and SIAIS171095. (White solid, 10.0 mg, yield 34%), $^1$H NMR (500 MHz, MeOD) δ 8.24 (s, 1H), 7.79-7.66 (m, 2H), 7.58 (t, J=7.7 Hz, 1H), 7.36 (dt, J=9.2, 4.5 Hz, 1H), 7.31-7.20 (m, 2H), 6.50 (d, J=11.0 Hz, 1H), 5.19 (dd, J=13.4, 5.2 Hz, 1H), 4.49 (q, J=17.4 Hz, 2H), 3.84-3.35 (m, 8H), 3.19 (ddt, J=36.4, 13.9, 7.0 Hz, 4H), 2.91 (ddd, J=18.8, 13.6, 5.4 Hz, 1H), 2.81-2.75 (m, 1H), 2.67-2.60 (m, 3H), 2.58-2.48 (m, 1H), 2.33 (d, J=19.5 Hz, 4H), 2.19-2.10 (m, 2H). HRMS (ESI) m/z: calcd for, $C_{36}H_{39}ClN_9O_4S_2^+$ [M+H]$^+$, 760.2249; found, 746.2399.

A General Synthesis Method for a Series of Degradation Agents of PARP Target

Scheme 31

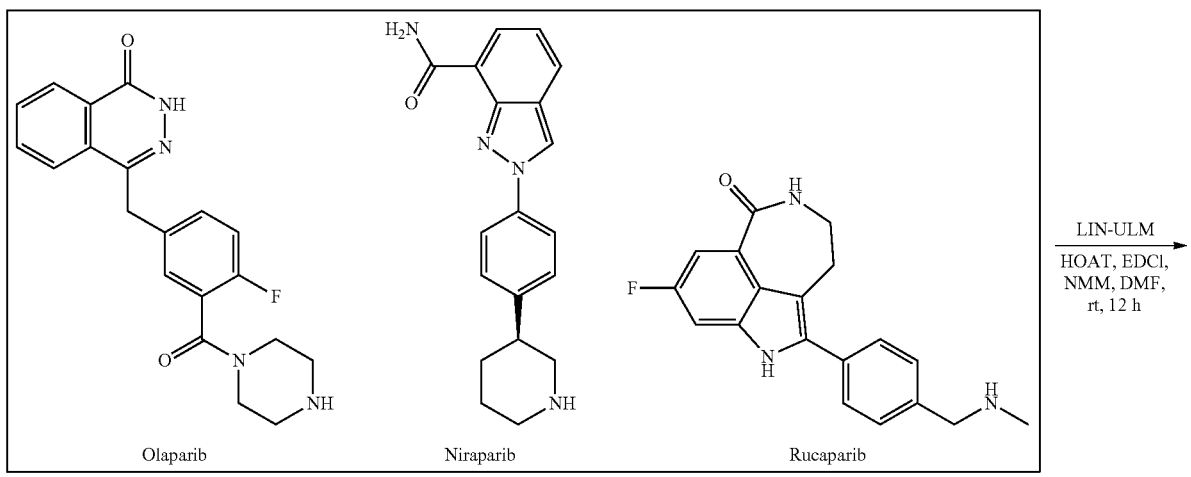

PARP inhibitor

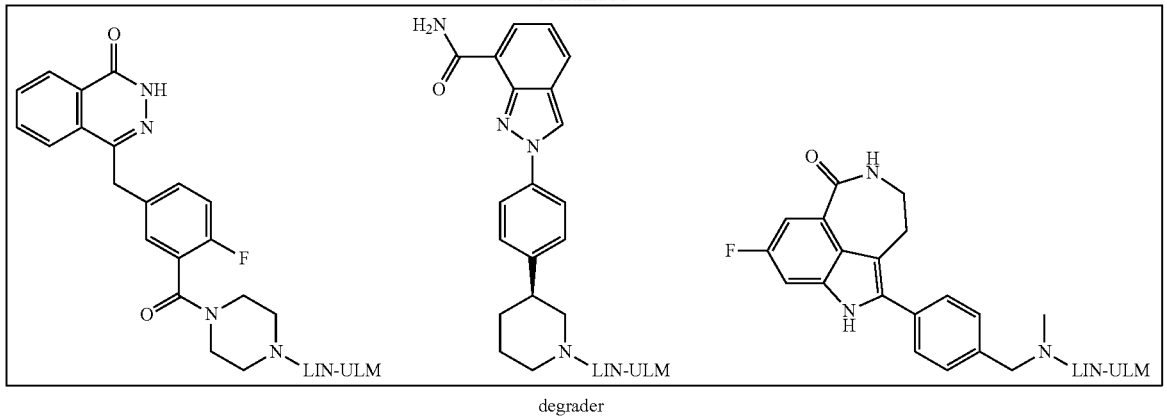

degrader

According to Scheme 31, at room temperature, a reaction flask was charged with the corresponding PARP inhibitor (1 equiv), the corresponding LIN-ULM (1 equiv), 1-hydroxy-7-azabenzotriazole (2 equiv), 1-(3-dimethylaminopropyl)-3-ethylcarbodiimide hydrochloride (2 equiv), anhydrous N,N-dimethylformamide (2 mL), and N-methylmorpholine (5 equiv). The reaction mixture was stirred overnight at room temperature. After the completion of the reaction was detected by LC-MS, the reaction mixture was subjected to preparative HPLC (eluent (v/v): acetonitrile/(water+0.05% HCl)=10%-100%) for separation. The acetonitrile is removed by rotary evaporation, and the residue was lyophilized to obtain the corresponding final degradation agent compound.

Example 160: Preparation of 2-(2,6-dioxopiperidin-3-yl)-4-((2-(4-(2-fluoro-5-((4-oxo-3,4-dihydrophthalazin-1-yl)methyl)benzoyl)piperazin-1-yl)-2-oxo-ethyl)thio)isoindoline-1,3-dione (SIAIS180063)

According to the general method described in Scheme 31, the target compound (SIAIS180063) was prepared by using an Olaparib inhibitor and LIN-ULM (SIAIS151045) under appropriate conditions that will be recognized by one skilled in the art. (yellow solid, 10.5 mg, yield 55%). $^1$H NMR (500 MHz, DMSO) δ 12.59 (s, 1H), 11.13 (s, 1H), 8.26 (dd, J=7.7, 2.3 Hz, 1H), 7.97 (t, J=7.6 Hz, 1H), 7.90 (dd, J=15.8, 8.0 Hz, 1H), 7.83 (t, J=7.8 Hz, 1H), 7.79-7.76 (m, 2H), 7.64 (d, J=6.8 Hz, 1H), 7.47-7.43 (m, 1H), 7.39 (dd, J=20.3, 6.3 Hz, 1H), 7.27-7.22 (m, 1H), 5.13 (dd, J=12.8, 5.3 Hz, 1H), 4.33 (s, 3H), 4.26 (s, 1H), 3.71-3.69 (m, 2H), 3.62 (s, 1H), 3.59-3.51 (m, 2H), 3.42 (s, 1H), 3.27 (s, 1H), 3.19 (s, 1H), 2.95-2.83 (m, 1H), 2.66-2.53 (m, 2H), 2.10-2.02 (m, 1H). HRMS (ESI) m/z: calcd for, $C_{35}H_{30}FN_6O_7S^+$ [M+H]$^+$, 697.1875; found, 696.9606.

Example 161: Preparation of 2-(2,6-dioxopiperidin-3-yl)-4-((3-(4-(2-fluoro-5-((4-oxo-3,4-dihydrophthalazin-1-yl)methyl)benzoyl)piperazin-1-yl)-3-oxopropyl)thio)isoindoline-1,3-dione (SIAIS180064)

According to the general method described in Scheme 31, the target compound (SIAIS180064) was prepared by using Olaparib inhibitor and LIN-ULM (SIAIS151138B) under appropriate conditions that will be recognized by one skilled in the art. (yellow solid, 9.9 mg, yield, 51%). $^1$H NMR (500 MHz, DMSO) δ 12.59 (d, J=4.4 Hz, 1H), 11.12 (s, 1H), 8.30-8.22 (m, 1H), 7.96 (d, J=7.5 Hz, 1H), 7.89 (t, J=7.5 Hz, 1H), 7.85-7.74 (m, 3H), 7.63 (dd, J=6.7, 2.7 Hz, 1H), 7.45-7.42 (m, 1H), 7.37-7.35 (m, 1H), 7.23 (t, J=8.8 Hz, 1H), 5.11 (dd, J=12.7, 3.3 Hz, 1H), 4.33 (s, 2H), 3.63-3.50 (m, 4H), 3.40 (s, 1H), 3.34 (s, 2H), 3.18-3.16 (m, 2H), 2.92-2.81 (m, 2H), 2.75 (t, J=6.8 Hz, 1H), 2.65-2.51 (m, 3H), 2.07-2.03 (m, 1H). HRMS (ESI) m/z: calcd for, $C_{36}H_{32}FN_6O_7S^+$ [M+H]$^+$, 711.2032; found, 710.9738.

Example 162: Preparation of 2-(2,6-dioxopiperidin-3-yl)-4-((4-(4-(2-fluoro-5-((4-oxo-3,4-dihydrophthalazin-1-yl)methyl)benzoyl)piperazin-1-yl)-4-oxobutyl)thio)isoindoline-1,3-dione (SIAIS180065)

According to the general method described in Scheme 31, the target compound (SIAIS180065) was prepared by using Olaparib inhibitor and LIN-ULM (SIAIS151139B) under appropriate conditions that will be recognized by one skilled in the art. (yellow solid, 9.7 mg, yield 49%). $^1$H NMR (500 MHz, DMSO) δ 12.59 (s, 1H), 11.12 (s, 1H), 8.26 (d, J=7.9 Hz, 1H), 7.96 (d, J=7.8 Hz, 1H), 7.93-7.76 (m, 4H), 7.63 (d, J=7.1 Hz, 1H), 7.46-7.43 (m, 1H), 7.37-7.35 (m, 1H), 7.24 (t, J=8.9 Hz, 1H), 5.11 (dd, J=12.1, 4.6 Hz, 1H), 4.33 (s, 2H), 3.69-3.48 (m, 4H), 3.40-3.33 (m, 3H), 3.19-3.15 (m, 4H), 2.95-2.82 (m, 1H), 2.66-2.53 (m, 3H), 2.06-2.03 (m, 1H), 1.96-1.85 (m, 2H). HRMS (ESI) m/z: calcd for, $C_{37}H_{34}FN_6O_7S^+$ [M+H]$^+$, 725.2188; found, 724.9790.

Example 163: Preparation of 2-(2,6-dioxopiperidin-3-yl)-4-((5-(4-(2-fluoro-5-((4-oxo-3,4-dihydrophthalazin-1-yl)methyl)benzoyl)piperazin-1-yl)-5-oxopentyl)thio)isoindoline-1,3-dione (SIAIS180066)

According to the general method described in Scheme 31, the target compound (SIAIS180066) (yellow solid, 9.1 mg, yield) was prepared by using an Olaparib inhibitor and LIN-ULM (SIAIS151140B) under appropriate conditions that will be recognized by one skilled in the art. (yellow solid, 9.1 mg, yield 45%). $^1$H NMR (500 MHz, DMSO) δ 12.59 (s, 1H), 11.12 (s, 1H), 8.26 (dd, J=7.9, 1.0 Hz, 1H), 7.96 (d, J=8.0 Hz, 1H), 7.89 (t, J=7.2 Hz, 1H), 7.83 (t, J=7.5 Hz, 1H), 7.80-7.72 (m, 2H), 7.62 (d, J=6.7 Hz, 1H), 7.45-7.43 (m, 1H), 7.37-7.35 (m, 1H), 7.23 (t, J=9.0 Hz, 1H), 5.11 (dd, J=12.7, 5.4 Hz, 1H), 4.33 (s, 2H), 3.67-3.49 (m, 4H), 3.36 (s, 2H), 3.17-3.14 (m, 4H), 2.92-2.85 (m, 1H), 2.68-2.52 (m, 2H), 2.43-2.42 (m, 1H), 2.36 (d, J=5.6 Hz, 1H), 2.07-1.99 (m, 1H), 1.68 (s, 4H). HRMS (ESI) m/z: calcd for, $C_{38}H_{36}FN_6O_7S^+$ [M+H]$^+$, 739.2345; found, 738.9875.

Example 164: Preparation of 2-(2,6-dioxopiperidin-3-yl)-4-((6-(4-(2-fluoro-5-((4-oxo-3,4-dihydrophthalazin-1-yl)methyl)benzoyl)piperazin-1-yl)-6-oxohexyl)thio)isoindoline-1,3-dione (SIAIS180067)

According to the general method described in Scheme 31, the target compound (SIAIS180067) was prepared by using Olaparib inhibitor and LIN-ULM (SIAIS151141B) under appropriate conditions that will be recognized by one skilled in the art. (yellow solid, 10.4 mg, yield, 51%). $^1$H NMR (500 MHz, DMSO) δ 12.59 (s, 1H), 11.12 (s, 1H), 8.26 (d, J=7.3 Hz, 1H), 7.96 (d, J=8.0 Hz, 1H), 7.89 (t, J=7.6 Hz, 1H), 7.83 (t, J=7.5 Hz, 1H), 7.80-7.71 (m, 2H), 7.63-7.61 (m, 1H), 7.45-7.44 (m, 1H), 7.36-7.35 (m, 1H), 7.23 (t, J=9.0 Hz, 1H), 5.11 (dd, J=12.8, 5.4 Hz, 1H), 4.33 (s, 2H), 3.68-3.47 (m, 4H), 3.36 (s, 2H), 3.22-3.08 (m, 4H), 2.92-2.85 (m, 1H), 2.65-2.51 (m, 2H), 2.37-2.34 (m, 1H), 2.29 (t, J=6.8 Hz, 1H), 2.07-1.99 (m, 1H), 1.70-1.66 (m, 2H), 1.56-1.52 (m, 2H), 1.47-1.43 (m, 2H). HRMS (ESI) m/z: calcd for, $C_{39}H_{38}FN_6O_7S^+$ [M+H]$^+$, 753.2501; found, 752.9993.

Example 165: Preparation of 2-(2,6-dioxopiperidin-3-yl)-4-((7-(4-(2-fluoro-5-((4-oxo-3,4-dihydrophthalazin-1-yl)methyl)benzoyl)piperazin-1-yl)-7-oxoheptyl)thio)isoindoline-1,3-dione (SIAIS180068)

According to the general method described in Scheme 31, the target compound (SIAIS180068) was prepared by using Olaparib inhibitor and LIN-ULM (SIAIS151142B) under appropriate conditions that will be recognized by one skilled in the art. (yellow solid, 10.1 mg, yield 48%). $^1$H NMR (500 MHz, DMSO) δ 12.59 (s, 1H), 11.12 (s, 1H), 8.26 (dd, J=7.9, 1.0 Hz, 1H), 7.96 (d, J=7.9 Hz, 1H), 7.89 (t, J=7.4 Hz, 1H), 7.83 (t, J=7.2 Hz, 1H), 7.81-7.72 (m, 2H), 7.62 (d, J=6.6 Hz, 1H), 7.45-7.43 (m, 1H), 7.37-7.35 (m, 1H), 7.23 (t, J=9.0 Hz, 1H), 5.11 (dd, J=12.9, 5.4 Hz, 1H), 4.33 (s, 2H), 3.67-3.46 (m, 4H), 3.37 (s, 1H), 3.17-3.12 (m, 4H), 2.92-2.85 (m, 1H), 2.66-2.51 (m, 3H), 2.34 (t, J=7.2 Hz, 1H), 2.27 (t, J=7.3 Hz, 1H), 2.07-1.98 (m, 1H), 1.66 (s, 2H), 1.56-1.39 (m, 4H), 1.34-1.31 (m, 2H). HRMS (ESI) m/z: calcd for, $C_{40}H_{40}FN_6O_7S^+$ [M+H]$^+$, 767.2658; found, 767.0053.

Example 166: Preparation of 2-(4-((3S)-1-(2-((2-(2,6-dioxopiperidin-3-yl)-1,3-dioxoisoindolin-4-yl)thio)acetyl)piperidin-3-yl)phenyl)-2H-indazole-7-carboxamide (SIAIS164165)

According to the general method described in Scheme 31, under appropriate conditions that will be recognized by one skilled in the art, the target compound (SIAIS164165) was prepared by using Niraparib inhibitor and LIN-ULM (SIAIS151045). (light yellow solid, 12.6 mg, yield 62%). $^1$H NMR (500 MHz, DMSO) δ 11.13 (s, 1H), 9.30 (d, J=5.0 Hz, 1H), 8.57 (s, 1H), 8.16-7.99 (m, 4H), 7.91-7.73 (m, 3H), 7.63 (dd, J=14.1, 7.2 Hz, 2H), 7.54 (d, J=8.5 Hz, 1H), 7.31-7.23 (m, 1H), 5.13 (dd, J=12.8, 5.4 Hz, 1H), 4.52-4.24 (m, 3H), 4.11 (d, J=13.4 Hz, 1H), 3.28-3.19 (m, 1H), 2.95-2.84 (m, 2H), 2.79-2.53 (m, 3H), 2.12-2.03 (m, 1H), 2.01-1.97 (m, 1H), 1.90-1.75 (m, 2H), 1.74-1.37 (m, 1H). HRMS (ESI) m/z: calcd for, $C_{34}H_{31}N_6O_6S^+$ [M+H]$^+$, 651.2020; found, 651.1876.

Example 167: Preparation of 2-(4-((3S)-1-(3-((2-(2,6-dioxopiperidin-3-yl)-1,3-dioxoisoindolin-4-yl)thio)propanoyl)piperidin-3-yl)phenyl)-2H-indazole-7-carboxamide (SIAIS164166)

According to the general method described in Scheme 31, the target compound (SIAIS164166) was prepared, using Niraparib inhibitor and LIN-ULM (SIAIS151138B) under appropriate conditions that will be recognized by one skilled in the art. (light yellow solid, 13.3 mg, yield 64%). $^1$H NMR (500 MHz, DMSO) δ 11.12 (d, J=5.6 Hz, 1H), 9.28 (d, J=9.3 Hz, 1H), 8.57 (s, 1H), 8.12-8.05 (m, 3H), 8.02 (d, J=8.4 Hz, 1H), 7.88 (s, 1H), 7.83-7.77 (m, 2H), 7.67-7.58 (m, 1H), 7.54-7.51 (m, 2H), 7.27 (dd, J=8.2, 7.2 Hz, 1H), 5.12 (dt, J=12.5, 6.2 Hz, 1H), 4.50 (d, J=11.8 Hz, 1H), 3.88 (t, J=12.5 Hz, 1H), 3.11 (dt, J=37.9, 12.0 Hz, 1H), 2.96-2.52 (m, 9H), 2.10-2.00 (m, 1H), 1.96 (d, J=9.5 Hz, 1H), 1.80-1.72 (m, 2H), 1.58-1.43 (m, 1H). HRMS (ESI) m/z: calcd for, $C_{35}H_{33}N_6O_6S^+$ [M+H]$^+$, 665.2177; found, 665.2068.

Example 168: Preparation of 2-(4-((3S)-1-(4-((2-(2,6-dioxopiperidin-3-yl)-1,3-dioxoisoindolin-4-yl)thio)butanoyl)piperidin-3-yl)phenyl)-2H-indazole-7-carboxamide (SIAIS164167)

According to the general method described in Scheme 31, under appropriate conditions that will be recognized by one skilled in the art, the target compound (SIAIS164167) was prepared by using Niraparib inhibitor and LIN-ULM (SIAIS151139B). (Light yellow solid, 13.1 mg, yield 62%). $^1$H NMR (500 MHz, DMSO) δ 11.12 (d, J=6.0 Hz, 1H), 9.29 (s, 1H), 8.57 (s, 1H), 8.08 (dd, J=16.8, 7.6 Hz, 3H), 8.10-8.05 (m, 1H), 7.93-7.85 (m, 2H), 7.81-7.76 (m, 1H), 7.62 (t, J=6.9 Hz, 1H), 7.53 (t, J=9.0 Hz, 2H), 7.32-7.23 (m, 1H), 5.11 (dt, J=12.7, 6.5 Hz, 1H), 4.50 (d, J=10.3 Hz, 1H), 3.91 (d, J=11.9 Hz, 1H), 3.24-3.03 (m, 3H), 2.96-2.66 (m, 3H), 2.66-2.52 (m, 4H), 2.12-2.00 (m, 1H), 1.97-1.90 (m, 3H), 1.78-1.76 (m, 2H), 1.61-1.38 (m, 1H). HRMS (ESI) m/z: calcd for, $C_{36}H_{35}N_6O_6S^+$ [M+H]$^+$ 679.2333; found, 679.2221.

Example 169: Preparation of 2-(4-((3S)-1-(5-((2-(2,6-dioxopiperidin-3-yl)-1,3-dioxoisoindolin-4-yl)thio)pentanoyl)piperidin-3-yl)phenyl)-2H-indazole-7-carboxamide (SIAIS164168)

According to the general method described in Scheme 31, under appropriate conditions that will be recognized by one skilled in the art, the target compound (SIAIS164168) was prepared by using Niraparib inhibitor and LIN-ULM (SIAIS151140B). (light yellow solid, 15.1 mg, yield 70%). $^1$H NMR (500 MHz, DMSO) δ 11.12 (d, J=5.0 Hz, 1H), 9.29 (d, J=5.0 Hz, 1H), 8.57 (s, 1H), 8.13-8.04 (m, 3H), 8.02 (d, J=8.2 Hz, 1H), 7.88 (s, 1H), 7.82-7.73 (m, 2H), 7.62 (dd, J=9.2, 6.6 Hz, 1H), 7.56 (d, J=8.2 Hz, 1H), 7.51 (d, J=8.4 Hz, 1H), 7.30-7.24 (m, 1H), 5.11 (dt, J=12.7, 6.5 Hz, 1H), 4.47 (d, J=8.0 Hz, 1H), 3.93 (d, J=12.3 Hz, 1H), 3.23-3.03 (m, 3H), 2.96-2.52 (m, 5H), 2.47-2.31 (m, 2H), 2.07-2.01 (m, 1H), 1.95 (d, J=11.6 Hz, 1H), 1.77-1.71 (m, 6H), 1.60-1.32 (m, 1H). HRMS (ESI) m/z: calcd for, $C_{37}H_{37}N_6O_6S^+$ [M+H]$^+$, 693.2490; found, 693.2381.

Example 170: Preparation of 2-(4-((3S)-1-(6-((2-(2,6-dioxopiperidin-3-yl)-1,3-dioxoisoindolin-4-yl)thio)hexanoyl)piperidin-3-yl)phenyl)-2H-indazole-7-carboxamide (SIAIS164169)

According to the general method described in Scheme 31, under appropriate conditions that will be recognized by one skilled in the art, the target compound (SIAIS164169) was prepared by using Niraparib inhibitor and LIN-ULM (SIAIS151141B). (light yellow solid, 15.0 mg, yield 68%). $^1$H NMR (500 MHz, DMSO) δ 11.11 (d, J=5.1 Hz, 1H), 9.29 (d, J=2.9 Hz, 1H), 8.56 (s, 1H), 8.10-8.05 (m, 3H), 8.02 (d, J=8.4 Hz, 1H), 7.88 (s, 1H), 7.82-7.71 (m, 2H), 7.63-7.59 (m, 1H), 7.58-7.49 (m, 2H), 7.27 (t, J=7.7 Hz, 1H), 5.10 (dt, J=12.5, 6.2 Hz, 1H), 4.48 (d, J=11.5 Hz, 1H), 3.94-3.89 (m, 1H), 3.19-3.03 (m, 3H), 2.96-2.52 (m, 5H), 2.42-2.33 (m, 2H), 2.06-1.99 (m, 1H), 1.96 (d, J=11.1 Hz, 1H), 1.84-1.64 (m, 4H), 1.62-1.37 (m, 5H). HRMS (ESI) m/z: calcd for, $C_{38}H_{39}N_6O_6S^+$ [M+H]$^+$, 707.2646; found, 707.2537.

Example 171: Preparation of 2-(4-((3S)-1-(7-((2-(2, 6-dioxopiperidin-3-yl)-1,3-dioxoisoindolin-4-yl) thio)heptanoyl)piperidin-3-yl)phenyl)-2H-indazole-7-carboxamide (SIAIS164170)

According to the general method described in Scheme 31, the target compound (SIAIS164170) was prepared by using Niraparib inhibitor and LIN-ULM (SIAIS151142B) under appropriate conditions that will be recognized by one skilled in the art. (light yellow solid, 12.9 mg, yield 57%). $^1$H NMR (500 MHz, DMSO) δ 11.11 (d, J=4.1 Hz, 1H), 9.29 (d, J=5.6 Hz, 1H), 8.57 (s, 1H), 8.14-8.04 (m, 3H), 8.02 (dd, J=8.4, 1.0 Hz, 1H), 7.80-7.71 (m, 1H), 7.80-7.71 (m, 2H), 7.61 (dd, J=13.0, 7.0 Hz, 1H), 7.56 (d, J=8.5 Hz, 1H), 7.51 (d, J=8.5 Hz, 1H), 7.30-7.24 (m, 1H), 5.11 (dt, J=12.4, 6.2 Hz, 1H), 4.47 (d, J=10.5 Hz, 1H), 3.92-3.88 (s, 1H), 3.21-3.02 (m, 3H), 2.96-2.53 (m, 5H), 2.41-2.26 (m, 2H), 2.07-2.02 (m, 1H), 1.96 (d, J=10.4 Hz, 1H), 1.79-1.75 (m, 2H), 1.70-1.65 (m, 2H), 1.59-1.40 (m, 5H), 1.40-1.29 (m, 2H). HRMS (ESI) m/z: calcd for, $C_{39}H_{41}N_6O_6S^+$ [M+H]$^+$, 721.2803; found, 721.2695.

Example 172: Preparation of 2-((2-(2,6-dioxopiperidin-3-yl)-1,3-dioxoisoindolin-4-yl)thio)-N-(4-(8-fluoro-1-oxo-2,3,4,6-tetrahydro-1H-azepino[5,4,3-cd]indol-5-yl)benzyl)-N-methylacetamide (SIAIS180043)

According to the general method described in Scheme 31, under appropriate conditions that will be recognized by one skilled in the art, the target compound (SIAIS180043) was prepared by using Rucaparib inhibitor and LIN-ULM (SIAIS151045). (light yellow solid, 9.7 mg, yield 48%) $^1$H NMR (500 MHz, DMSO) δ 11.75-11.67 (m, 1H), 11.13 (s, 1H), 8.25 (t, J=5.7 Hz, 1H), 7.82-7.73 (m, 2H), 7.68-7.57 (m, 3H), 7.47-7.30 (m, 4H), 5.16-5.10 (m, 1H), 4.71 (d, J=104.0 Hz, 2H), 4.38 (d, J=19.0 Hz, 2H), 3.43-3.37 (m, 2H), 3.13 (s, 2H), 3.06-3.00 (m, 2H), 2.93-2.84 (m, 1H), 2.87 (s, 1H), 2.65-2.51 (m, 2H), 2.08-2.02 (m, 1H). HRMS (ESI) m/z: calcd for, $C_{34}H_{29}FN_5O_6S^+$ [M+H]$^+$, 654.1817; found, 654.0244.

Example 173: Preparation of 3-((2-(2,6-dioxopiperidin-3-yl)-1,3-dioxoisoindolin-4-yl)thio)-N-(4-(8-fluoro-1-oxo-2,3,4,6-tetrahydro-1H-azepino[5,4,3-cd]indol-5-yl)benzyl)-N-methylpropanamide (SIAIS180044)

According to the general method described in Scheme 31, under appropriate conditions that will be recognized by one skilled in the art, the target compound (SIAIS180044) was prepared by using Rucaparib inhibitor and LIN-ULM (SIAIS151138B). (light yellow solid, 8.5 mg, yield 41%). $^1$H NMR (500 MHz, DMSO) δ 11.66 (d, J=11.5 Hz, 1H), 11.12 (d, J=3.3 Hz, 1H), 8.24 (t, J=5.7 Hz, 1H), 7.82-7.70 (m, 2H), 7.67-7.55 (m, 3H), 7.44-7.30 (m, 4H), 5.14-5.08 (m, 1H), 4.62 (d, J=14.3 Hz, 2H), 3.42-3.36 (m, 4H), 3.06-2.98 (m, 2H), 2.95 (s, 2H), 2.90 (s, 1H), 2.91-2.82 (m, 3H), 2.63-2.52 (m, 2H), 2.06-1.98 (m, 1H). HRMS (ESI) m/z: calcd for, $C_{35}H_{31}FN_5O_6S^+$ [M+H]$^+$, 668.1974; found, 668.0385.

Example 174: Preparation of 4-((2-(2,6-dioxopiperidin-3-yl)-1,3-dioxoisoindolin-4-yl)thio)-N-(4-(8-fluoro-1-oxo-2,3,4,6-tetrahydro-1H-azepino[5,4,3-cd]indol-5-yl)benzyl)-N-methylbutanamide (SIAIS180045)

According to the general method described in Scheme 31, under appropriate conditions that will be recognized by one skilled in the art, the target compound (SIAIS180045) was prepared by using Rucaparib inhibitor and LIN-ULM (SIAIS151139B). (light yellow solid, 10.0 mg, yield 48%). $^1$H NMR (500 MHz, DMSO) δ 11.68 (d, J=11.9 Hz, 1H), 11.11 (d, J=5.1 Hz, 1H), 8.24 (t, J=5.6 Hz, 1H), 7.88 (t, J=8.7 Hz, 1H), 7.81-7.76 (m, 1H), 7.65-7.57 (m, 3H), 7.43-7.41 (m, 1H), 7.38-7.35 (m, 2H), 7.33-7.31 (m, 1H), 5.14-5.08 (m, 1H), 4.62 (d, J=30.7 Hz, 2H), 3.41-3.36 (m, 2H), 3.22-3.13 (m, 2H), 3.06-3.00 (m, 2H), 2.97 (s, 2H), 2.87 (s, 1H), 2.90-2.83 (m, 1H), 2.66-2.52 (m, 4H), 2.09-2.01 (m, 1H), 1.97-1.91 (m, 2H). HRMS (ESI) m/z: calcd for, $C_{36}H_{33}FN_5O_6S^+$ [M+H]$^+$, 682.2130; found, 682.0486.

Example 175: Preparation of 5-((2-(2,6-dioxopiperidin-3-yl)-1,3-dioxoisoindolin-4-yl)thio)-N-(4-(8-fluoro-1-oxo-2,3,4,6-tetrahydro-1H-azepino[5,4,3-cd]indol-5-yl)benzyl)-N-methylpentanamide (SIAIS180046)

According to the general method described in Scheme 31, under appropriate conditions that will be recognized by one skilled in the art, the target compound (SIAIS180046) was prepared by using Rucaparib inhibitor and LIN-ULM (SIAIS151140B). (light yellow solid, 9.3 mg, yield 43%). $^1$H NMR (500 MHz, DMSO) δ 11.67 (d, J=7.1 Hz, 1H), 11.12 (s, 1H), 8.24 (t, J=5.7 Hz, 1H), 7.80-7.71 (m, 2H), 7.65-7.57 (m, 3H), 7.42 (dd, J=11.0, 2.3 Hz, 1H), 7.37-7.30 (m, 3H), 5.13-5.09 (m, 1H), 4.61 (d, J=42.5 Hz, 2H), 3.41-3.35 (m, 2H), 3.20-3.09 (m, 2H), 3.06-3.00 (m, 2H), 2.96 (s, 2H), 2.93-2.86 (m, 1H), 2.85 (s, 1H), 2.65-2.52 (m, 2H), 2.49-2.42 (m, 2H), 2.07-2.01 (m, 1H), 1.77-1.67 (m, 4H). HRMS (ESI) m/z: calcd for, $C_{37}H_{35}FN_5O_6S^+$ [M+H]$^+$, 696.2287; found, 696.0577.

Example 176: Preparation of 6-((2-(2,6-dioxopiperidin-3-yl)-1,3-dioxoisoindolin-4-yl)thio)-N-(4-(8-fluoro-1-oxo-2,3,4,6-tetrahydro-1H-azepino[5,4,3-cd]indol-5-yl)benzyl)-N-methylhexanamide (SIAIS180047)

According to the general method described in Scheme 31, under appropriate conditions that will be recognized by one skilled in the art, the target compound (SIAIS180047) was prepared by using Rucaparib inhibitor and LIN-ULM (SIAIS151141B). (light yellow solid, 10.5 mg, yield 48%). $^1$H NMR (500 MHz, DMSO) δ 11.67 (d, J=9.0 Hz, 1H), 11.12 (s, 1H), 8.24 (t, J=5.8 Hz, 1H), 7.80-7.69 (m, 2H), 7.65-7.57 (m, 3H), 7.42 (dd, J=11.0, 2.4 Hz, 1H), 7.37-7.29 (m, 3H), 5.12-5.08 (m, 1H), 4.60 (d, J=41.2 Hz, 2H), 3.42-3.35 (m, 2H), 3.17-3.07 (m, 2H), 3.03 (s, 2H), 2.96 (s, 2H), 2.86 (s, 1H), 2.92-2.83 (m, 1H), 2.62-2.51 (m, 2H), 2.44-2.35 (m, 2H), 2.06-2.00 (m, 1H), 1.73-1.42 (m, 6H). HRMS (ESI) m/z: calcd for, $C_{38}H_{37}FN_5O_6S^+$ [M+H]$^+$, 710.2443; found, 710.0702.

Example 177: Preparation of 7-((2-(2,6-dioxopiperidin-3-yl)-1,3-dioxoisoindolin-4-yl)thio)-N-(4-(8-fluoro-1-oxo-2,3,4,6-tetrahydro-1H-azepino[5,4,3-cd]indol-5-yl)benzyl)-N-methylheptanamide (SIAIS180048)

According to the general method described in Scheme 31, under appropriate conditions that will be recognized by one skilled in the art, the target compound (SIAIS180048) was prepared by using Rucaparib inhibitor and LIN-ULM (SIAIS151142B). (light yellow solid, 10.2 mg, yield 45%). $^1$H NMR (500 MHz, DMSO) δ 11.67 (d, J=9.3 Hz, 1H), 11.12 (s, 1H), 8.24 (t, J=5.7 Hz, 1H), 7.80-7.68 (m, 2H), 7.65-7.57 (m, 3H), 7.43-7.40 (m, 1H), 7.32 (ddd, J=9.9, 9.1, 5.5 Hz, 3H), 5.13-5.08 (m, 1H), 4.60 (d, J=40.3 Hz, 2H), 3.41-3.35 (m, 2H), 3.14-3.06 (m, 2H), 3.06-3.00 (m, 2H), 2.96 (s, 2H), 2.92-2.87 (m, 1H), 2.85 (s, 1H), 2.63-2.51 (m, 2H), 2.42-2.34 (m, 2H), 2.07-2.01 (m, 1H), 1.72-1.34 (m, 8H). HRMS (ESI) m/z: calcd for, $C_{39}H_{39}FN_5O_6S^+$ [M+H]$^+$, 724.2600; found, 724.0825.

A General Synthetic Method for a Series of Degradation Agents for ER Target

Scheme 32

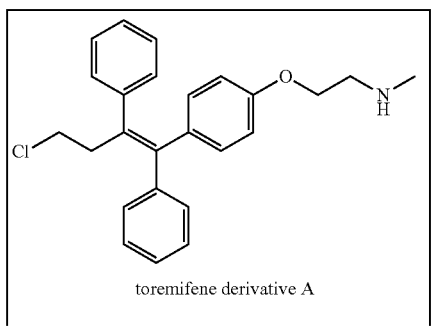

toremifene derivative A

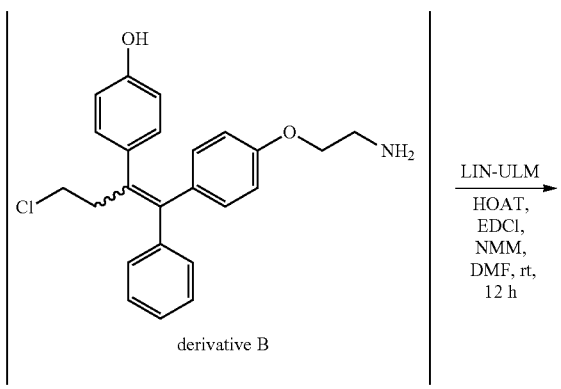

derivative B

LIN-ULM
HOAT,
EDCl,
NMM,
DMF, rt,
12 h

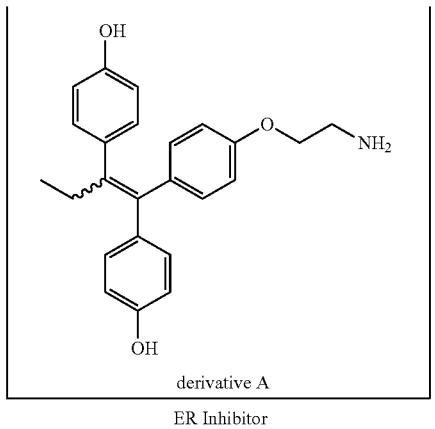

derivative A

ER Inhibitor

-continued

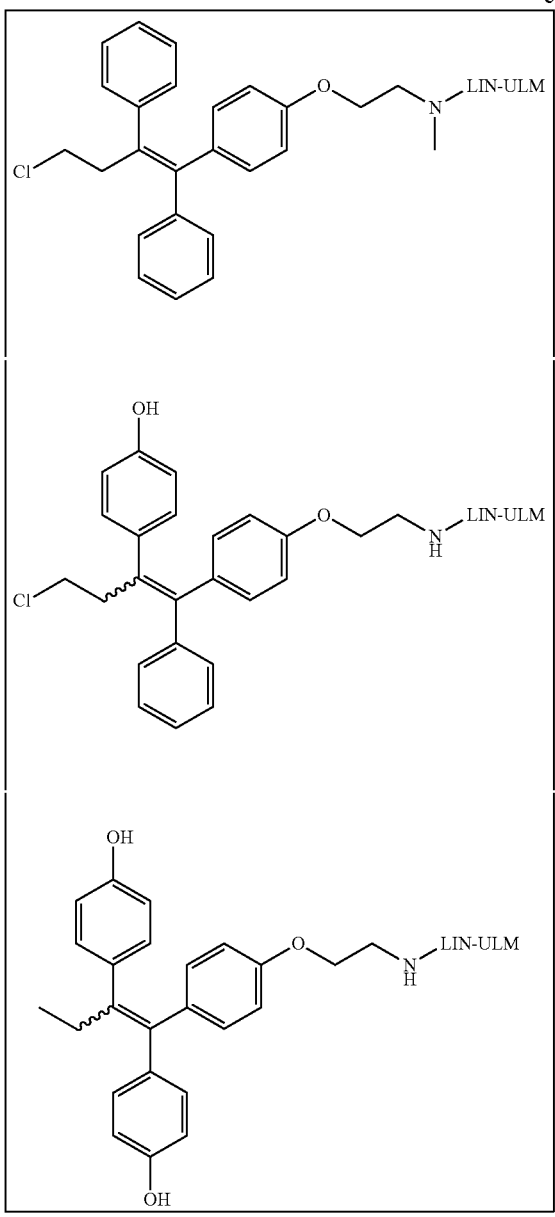

degrader

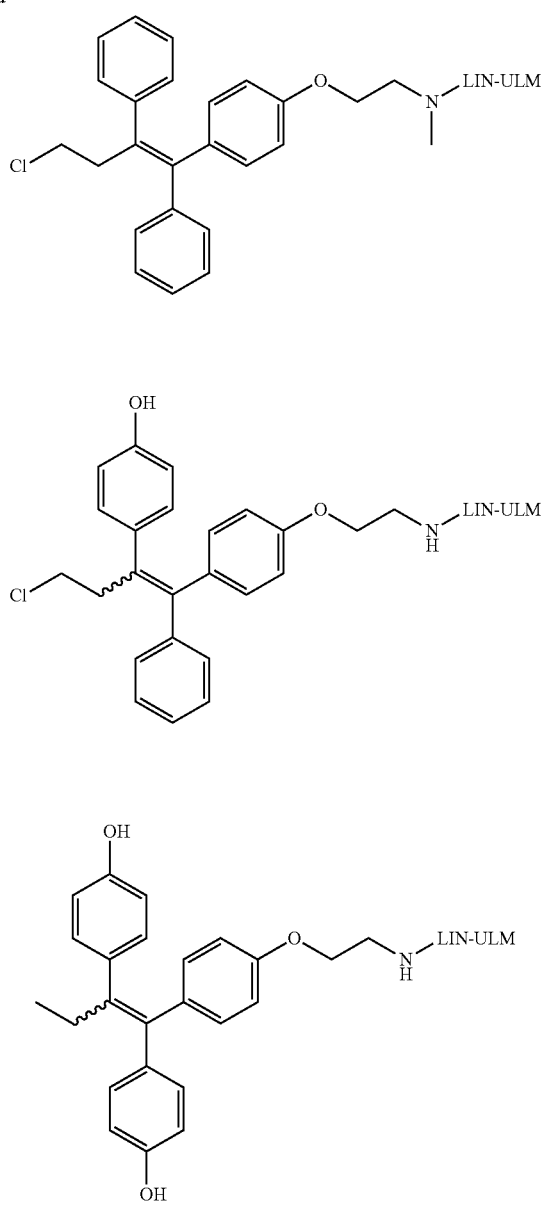

degrader

According to Scheme 32, at room temperature, a reaction flask was charged with the corresponding estrogen receptor modulator (1 equiv), the corresponding LIN-ULM (1 equiv), 1-hydroxy-7-azabenzotriazole (2 equiv), 1-(3-dimethylaminopropyl)-3-ethylcarbodiimide hydrochloride (2 equiv), anhydrous N,N-dimethylformamide (2 mL), and N-methylmorpholine (5 equiv). The reaction mixture was stirred at room temperature overnight. After the completion of the reaction was detected by LC-MS, the reaction mixture was subjected to preparative HPLC (eluent (v/v): acetonitrile/ (water+0.05% HCl)=10%-100%) for separation. The acetonitrile was removed by rotary evaporation, and the residue was lyophilized to obtain the corresponding final degradation agent compound.

Example 178: Preparation of (Z)—N-(2-(4-(4-chloro-1,2-diphenylbut-1-en-1-yl)phenoxy)ethyl)-2-((2-(2,6-dioxopiperidin-3-yl)-1,3-dioxoisoindolin-4-yl)thio)-N-methylacetamide (SIAIS180014)

According to the general method described in Scheme 32, the target compound (SIAIS180014) was prepared by using toremifene derivative A and LIN-ULM (SIAIS151045) under appropriate conditions that will be recognized by one skilled in the art. (light yellow solid, 16.9 mg, yield 50%) $^1$H NMR (500 MHz, DMSO) δ 11.13 (s, 1H), 7.74-7.63 (m, 2H), 7.63-7.57 (m, 1H), 7.40 (dt, J=7.6, 3.7 Hz, 2H), 7.32-7.27 (m, 3H), 7.25-7.20 (m, 2H), 7.19-7.13 (m, 3H), 6.79-6.73 (m, 2H), 6.63 (dd, J=13.3, 8.8 Hz, 2H), 5.12 (dd, J=12.8, 5.4 Hz, 1H), 4.30 (s, 1H), 4.24 (s, 1H), 4.08 (t, J=5.2 Hz, 1H), 3.93 (t, J=5.5 Hz, 1H), 3.79 (t, J=5.1 Hz, 1H), 3.60 (t, J=5.6 Hz, 1H), 3.43 (t, J=7.2 Hz, 2H), 3.15 (s, 1.5H, N—CH$_3$), 2.97-2.80 (m, 4.5H), 2.65-2.51 (m, 2H), 2.07-1.99 (m, 1H). HRMS (ESI) m/z: calcd for, C$_{40}$H$_{37}$ClN$_3$O$_6$S$^+$ [M+H]$^+$, 722.2086; found, 722.1727.

Example 179: Preparation of (Z)—N-(2-(4-(4-chloro-1,2-diphenylbut-1-en-1-yl)phenoxy)ethyl)-3-((2-(2,6-dioxopiperidin-3-yl)-1,3-dioxoisoindolin-4-yl)thio)-N-methylpropanamide (SIAIS180015)

According to the general method described in Scheme 32 and under appropriate conditions that will be recognized by one skilled in the art, the target compound (SIAIS180015) was prepared by using toremifene derivative A and LIN-ULM (SIAIS151138B). (yellow solid, 15.7 mg, yield 46%) $^1$H NMR (500 MHz, DMSO) δ 11.12 (d, J=5.6 Hz, 1H), 7.79-7.70 (m, 2H), 7.60 (dd, J=19.5, 6.7 Hz, 1H), 7.40 (t, J=6.9 Hz, 2H), 7.32-7.26 (m, 3H), 7.23-7.20 (m, 2H), 7.18-7.13 (m, 3H), 6.77-6.73 (m, 1H), 6.70 (d, J=8.7 Hz, 1H), 6.63-6.61 (m, 1H), 6.51 (d, J=8.8 Hz, 1H), 5.13-5.09 (m, 1H), 3.94 (dd, J=10.3, 5.1 Hz, 2H), 3.64-3.48 (m, 2H), 3.43 (t, J=7.2 Hz, 2H), 3.31-3.25 (m, 2H), 2.95 (s, 1.5H, N—CH$_3$), 2.92-2.80 (m, 5.5H), 2.71 (t, J=7.1 Hz, 1H), 2.65-2.52 (m, 2H), 2.05-2.01 (m, 1H). HRMS (ESI) m/z: calcd for, C$_{41}$H$_{39}$ClN$_3$O$_6$S$^+$ [M+H]$^+$, 736.2243; found, 736.1855.

Example 180: Preparation of (Z)—N-(2-(4-(4-chloro-1,2-diphenylbut-1-en-1-yl)phenoxy)ethyl)-4-((2-(2,6-dioxopiperidin-3-yl)-1,3-dioxoisoindolin-4-yl)thio)-N-methylbutanamide (SIAIS180016)

According to the general method described in Scheme 32 and under appropriate conditions that will be recognized by one skilled in the art, the target compound (SIAIS180016) was prepared by using toremifene derivative A and LIN-ULM (SIAIS151139B). (yellow solid, 17.3 mg, yield 49%) $^1$H NMR (500 MHz, DMSO) δ 11.12 (d, J=5.5 Hz, 1H), 7.84 (dd, J=8.2, 2.6 Hz, 1H), 7.75 (td, J=7.7, 4.8 Hz, 1H), 7.61 (d, J=7.4 Hz, 1H), 7.39 (dt, J=7.7, 3.7 Hz, 2H), 7.34-7.25 (m, 3H), 7.22 (t, J=7.7 Hz, 2H), 7.18-7.12 (m, 3H), 6.74 (d, J=8.7 Hz, 2H), 6.62 (dd, J=8.7, 5.0 Hz, 2H), 5.11 (dd, J=12.8, 5.4 Hz, 1H), 3.98 (t, J=5.2 Hz, 1H), 3.93 (t, J=5.7 Hz, 1H), 3.62 (t, J=5.2 Hz, 1H), 3.56 (t, J=5.7 Hz, 1H), 3.43 (t, J=7.1 Hz, 2H), 3.16-3.05 (m, 2H), 2.98 (s, 1.5H, N—CH$_3$), 2.94-2.80 (m, 4.5H), 2.65-2.52 (m, 3H), 2.45 (t, J=6.9 Hz, 2H), 2.07-1.98 (m, 1H), 1.88-1.84 (m, 2H). HRMS (ESI) m/z: calcd for, C$_{42}$H$_{41}$ClN$_3$O$_6$S$^+$ [M+H]$^+$, 750.2399; found, 750.2025.

Example 181: Preparation of (Z)—N-(2-(4-(4-chloro-1,2-diphenylbut-1-en-1-yl)phenoxy)ethyl)-5-((2-(2,6-dioxopiperidin-3-yl)-1,3-dioxoisoindolin-4-yl)thio)-N-methylpentanamide (SIAIS180017)

According to the general method described in Scheme 32, the target compound (SIAIS180017) was prepared by using toremifene derivative A and LIN-ULM (SIAIS151140B) under appropriate conditions that will be recognized by one skilled in the art. (yellow solid, 11.5 mg, yield 32%) $^1$H NMR (500 MHz, DMSO) δ 11.12 (s, 1H), 7.79-7.69 (m, 2H), 7.63-7.58 (m, 1H), 7.39 (td, J=7.5, 1.4 Hz, 2H), 7.33-7.25 (m, 3H), 7.23-7.19 (m, 2H), 7.18-7.11 (m, 3H), 6.75-6.72 (m, 2H), 6.65-6.56 (m, 2H), 5.11 (dd, J=12.8, 5.4 Hz, 1H), 3.98 (t, J=5.2 Hz, 1H), 3.90 (t, J=5.7 Hz, 1H), 3.60 (t, J=5.2 Hz, 1H), 3.54 (t, J=5.7 Hz, 1H), 3.46-3.37 (m, 2H), 3.18-3.07 (m, 2H), 2.97 (s, 1.5H, N—CH$_3$), 2.93-2.75 (m, 4.5H), 2.65-2.52 (m, 2H), 2.39-2.36 (m, 1H), 2.31 (t, J=6.8 Hz, 1H), 2.07-1.99 (m, 1H), 1.69-1.64 (m, 4H). HRMS (ESI) m/z: calcd for, C$_{43}$H$_{43}$ClN$_3$O$_6$S$^+$ [M+H]$^+$, 764.2556; found, 764.2167.

Example 182: Preparation of (Z)—N-(2-(4-(4-chloro-1,2-diphenylbut-1-en-1-yl)phenoxy)ethyl)-6-((2-(2,6-dioxopiperidin-3-yl)-1,3-dioxoisoindolin-4-yl)thio)-N-methylhexanamide (SIAIS180018)

According to the general method described in Scheme 32, under appropriate conditions that will be recognized by one skilled in the art, the target compound (SIAIS180018) was prepared by using toremifene derivative A and LIN-ULM (SIAIS151141B). (yellow solid, 21.7 mg, yield 60%). $^1$H NMR (500 MHz, DMSO) δ 11.12 (s, 1H), 7.75 (dt, J=22.5, 7.9 Hz, 2H), 7.62 (d, J=7.2 Hz, 1H), 7.39 (t, J=7.5 Hz, 2H), 7.31-7.27 (m, 3H), 7.25-7.18 (m, 2H), 7.18-7.11 (m, 3H), 6.74 (dd, J=8.7, 5.1 Hz, 2H), 6.61 (d, J=8.7 Hz, 2H), 5.18-5.04 (m, 1H), 3.97 (t, J=5.2 Hz, 1H), 3.91 (t, J=5.7 Hz, 1H), 3.60 (t, J=5.2 Hz, 1H), 3.53 (t, J=5.7 Hz, 1H), 3.42 (t, J=7.2 Hz, 2H), 3.15-3.05 (m, 2H), 2.97 (s, 1.5H, N—CH$_3$), 2.93-2.77 (m, 4.5H), 2.66-2.51 (m, 2H), 2.32 (t, J=7.2 Hz, 1H), 2.25 (t, J=7.2 Hz, 1H), 2.06-1.99 (m, 1H), 1.69-1.62 (m, 2H), 1.57-1.47 (m, 2H), 1.45-1.39 (m, 2H). HRMS (ESI) m/z: calcd for, C$_{44}$H$_{45}$ClN$_3$O$_6$S$^+$ [M+H]$^+$, 778.2712; found, 778.2304.

Example 183: Preparation of (Z)—N-(2-(4-(4-chloro-1,2-diphenylbut-1-en-1-yl)phenoxy)ethyl)-7-((2-(2,6-dioxopiperidin-3-yl)-1,3-dioxoisoindolin-4-yl)thio)-N-methylheptanamide (SIAIS180019)

According to the general method described in Scheme 32, under appropriate conditions that will be recognized by one skilled in the art, the target compound (SIAIS180019) was prepared by using toremifene derivative A and LIN-ULM (SIAIS151142B). (yellow solid, 21.7 mg, yield 59%). $^1$H NMR (500 MHz, DMSO) δ 11.12 (s, 1H), 7.81-7.69 (m, 2H), 7.62 (dd, J=6.9, 3.0 Hz, 1H), 7.39 (t, J=7.1 Hz, 2H), 7.33-7.25 (m, 3H), 7.25-7.18 (m, 2H), 7.18-7.12 (m, 3H), 6.74 (dd, J=8.5, 5.7 Hz, 2H), 6.61 (d, J=8.5 Hz, 2H), 5.11 (dd, J=12.8, 5.4 Hz, 1H), 3.97 (t, J=5.2 Hz, 1H), 3.90 (t, J=5.8 Hz, 1H), 3.59 (t, J=5.2 Hz, 1H), 3.53 (t, J=5.7 Hz, 1H), 3.42 (t, J=7.2 Hz, 2H), 3.11-3.06 (m, 2H), 2.96 (s, 1.5H, N—CH$_3$), 2.93-2.75 (m, 4.5H), 2.66-2.51 (m, 2H), 2.30 (t, J=7.3 Hz, 1H), 2.23 (t, J=7.3 Hz, 1H), 2.07-2.00 (m, 1H), 1.71-1.57 (m, 2H), 1.52-1.41 (m, 4H), 1.35-1.20 (m, 2H). HRMS (ESI) m/z: calcd for, C$_{45}$H$_{47}$ClN$_3$O$_6$S$^+$ [M+H]$^+$, 792.2869; found, 792.2457.

Example 184: Preparation of N-(2-(4-(4-chloro-1-(4-hydroxyphenyl)-2-phenylbut-1-en-1-yl)phenoxy)ethyl)-2-((2-(2,6-dioxopiperidin-3-yl)-1,3-dioxoisoindolin-4-yl)thio)acetamide (SIAIS208146)

According to the general method described in Scheme 32, and under appropriate conditions that will be recognized by one skilled in the art, the target compound (SIAIS208146) was prepared by using toremifene derivative B and LIN-ULM (SIAIS151045). (light yellow solid, 10.8 mg, yield 59%). $^1$H NMR (500 MHz, DMSO) δ 11.11 (d, J=17.0 Hz, 1H), 9.44 (d, J=113.9, 1H), 8.60-8.45 (m, 1H), 7.73-7.51 (m, 3H), 7.23-7.16 (m, 3H), 7.15-7.10 (m, 3H), 7.06 (d, J=8.5 Hz, 1H), 6.91 (d, J=8.7 Hz, 1H), 6.77 (d, J=8.5 Hz, 1H), 6.71 (d, J=8.8 Hz, 1H), 6.62-6.59 (m, 1H), 6.55 (d, J=8.8 Hz, 1H), 6.43-6.37 (m, 1H), 5.14-5.04 (m, 1H), 3.98 (t, J=5.3 Hz, 1H), 3.88 (d, J=25.7 Hz, 2H), 3.81 (t, J=5.3 Hz, 1H), 3.48-3.45 (m, 1H), 3.42-3.35 (m, 3H), 2.89-2.81 (m, 3H), 2.64-2.51 (m, 2H), 2.04-2.02 (m, 1H). HRMS (ESI) m/z: calcd for, $C_{39}H_{35}ClN_3O_7S^+$ [M+H]$^+$, 724.1879; found, 724.1871.

Example 185: Preparation of N-(2-(4-(4-chloro-1-(4-hydroxyphenyl)-2-phenylbut-1-en-1-yl)phenoxy)ethyl)-3-((2-(2,6-dioxopiperidin-3-yl)-1,3-dioxoisoindolin-4-yl)thio)propanamide (SIAIS208147)

According to the general method described in Scheme 32 and under appropriate conditions that will be recognized by one skilled in the art, the target compound (SIAIS208147) was prepared by using toremifene derivative B and LIN-ULM (SIAIS151138B). (light yellow solid, 9.8 mg, yield 52%). $^1$H NMR (500 MHz, DMSO) δ 11.12 (s, 1H), 9.41 (d, J=111.3 Hz, 1H), 8.33-8.18 (m, 1H), 7.82-7.70 (m, 2H), 7.65-7.58 (m, 1H), 7.23-7.09 (m, 6H), 7.07-7.02 (m, 1H), 6.94 (d, J=8.7 Hz, 1H), 6.78-6.74 (m, 1H), 6.71 (d, J=8.8 Hz, 1H), 6.62-6.55 (m, 2H), 6.42-6.37 (m, 1H), 5.15-5.04 (m, 1H), 4.00 (t, J=5.5 Hz, 1H), 3.83 (t, J=5.5 Hz, 1H), 3.47-3.39 (m, 4H), 3.36-3.27 (m, 4H), 2.92-2.80 (m, 3H), 2.62-2.54 (m, 2H), 2.08-1.98 (m, 1H). HRMS (ESI) m/z: calcd for, $C_{40}H37ClN_3O_7S^+$ [M+H]$^+$, 738.2035; found, 738.2031.

Example 186: Preparation of N-(2-(4-(4-chloro-1-(4-hydroxyphenyl)-2-phenylbut-1-en-1-yl)phenoxy)ethyl)-4-((2-(2,6-dioxopiperidin-3-yl)-1,3-dioxoisoindolin-4-yl)thio)butanamide (SIAIS208148)

According to the general method described in Scheme 32, the target compound (SIAIS208148) was prepared by using toremifene derivative B and LIN-ULM (SIAIS151139B) under appropriate conditions that will be recognized by one skilled in the art. (light yellow solid, 9.1 mg, yield 48%) $^1$H NMR (500 MHz, DMSO) δ 11.12 (s, 1H), 9.33 (d, J=126.8 Hz, 1H), 8.24-8.02 (m, 1H), 7.81-7.72 (m, 2H), 7.61 (d, J=6.6 Hz, 1H), 7.24-7.10 (m, 6H), 7.05 (d, J=8.5 Hz, 1H), 6.94 (d, J=8.7 Hz, 1H), 6.76 (d, J=8.6 Hz, 1H), 6.71 (d, J=8.8 Hz, 1H), 6.60 (dd, J=8.7, 5.7 Hz, 2H), 6.40 (d, J=8.7 Hz, 1H), 5.11 (dd, J=12.8, 5.4 Hz, 1H), 4.02 (t, J=5.6 Hz, 1H), 3.84 (t, J=5.6 Hz, 1H), 3.43 (dd, J=12.6, 6.4 Hz, 3H), 3.35 (s, 1H), 3.17-3.05 (m, 2H), 2.93-2.82 (m, 3H), 2.63-2.57 (m, 2H), 2.31 (t, J=7.2 Hz, 1H), 2.26 (t, J=7.1 Hz, 1H), 2.07-2.03 (m, 1H), 1.94-1.82 (m, 2H). HRMS (ESI) m/z: calcd for, $C_{41}H_{39}ClN_3O_7S^+$ [M+H]$^+$, 752.2192; found, 752.2197.

Example 187: Preparation of N-(2-(4-(4-chloro-1-(4-hydroxyphenyl)-2-phenylbut-1-en-1-yl)phenoxy)ethyl)-5-((2-(2,6-dioxopiperidin-3-yl)-1,3-dioxoisoindolin-4-yl)thio)pentanamide (SIAIS208152)

According to the general method described in Scheme 32, the target compound (SIAIS208152) was prepared by using toremifene derivative B and LIN-ULM (SIAIS151140B) under appropriate conditions that will be recognized by one skilled in the art. (light yellow solid, 10.6 mg, yield 54%) $^1$H NMR (500 MHz, DMSO) δ 11.12 (s, 1H), 9.52-9.18 (m, 1H), 8.04 (dd, J=36.1, 5.4 Hz, 1H), 7.81-7.68 (m, 2H), 7.61 (dd, J=6.6, 3.0 Hz, 1H), 7.24-7.08 (m, 6H), 7.05 (d, J=8.5 Hz, 1H), 6.94 (d, J=8.7 Hz, 1H), 6.76 (d, J=8.5 Hz, 1H), 6.72 (d, J=8.8 Hz, 1H), 6.60 (dd, J=8.7, 5.2 Hz, 2H), 6.40 (d, J=8.6 Hz, 1H), 5.11 (dd, J=12.9, 5.5 Hz, 1H), 4.00 (t, J=5.6 Hz, 1H), 3.82 (t, J=5.6 Hz, 1H), 3.43 (dd, J=9.0, 5.9 Hz, 3H), 3.12 (dd, J=13.7, 7.0 Hz, 2H), 2.93-2.80 (m, 3H), 2.63-2.51 (m, 3H), 2.16 (d, J=6.7 Hz, 1H), 2.11 (d, J=6.7 Hz, 1H), 2.08-2.01 (m, 1H), 1.65 (d, J=13.2 Hz, 4H). HRMS (ESI) m/z: calcd for, $C_{42}H_{41}ClN_3O_7S^+$ [M+H]$^+$, 766.2348; found, 766.2341.

Example 188: Preparation of N-(2-(4-(4-chloro-1-(4-hydroxyphenyl)-2-phenylbut-1-en-1-yl)phenoxy)ethyl)-6-((2-(2,6-dioxopiperidin-3-yl)-1,3-dioxoisoindolin-4-yl)thio)hexanamide (SIAIS208153)

According to the general method described in Scheme 32, the target compound (SIAIS208153) was prepared by using toremifene derivative B and LIN-ULM (SIAIS151141B) under appropriate conditions that will be recognized by one skilled in the art. (light yellow solid, 9.6 mg, yield 48%) $^1$H NMR (500 MHz, DMSO) δ 11.12 (s, 1H), 9.33 (d, J=126.6 Hz, 1H), 8.02 (d, J=41.0 Hz, 1H), 7.79-7.74 (m, 1H), 7.73-7.69 (m, 1H), 7.62 (d, J=7.0 Hz, 1H), 7.15 (ddd, J=45.8, 24.1, 18.2 Hz, 6H), 7.05 (d, J=8.6 Hz, 1H), 6.95 (d, J=8.7 Hz, 1H), 6.76 (d, J=8.5 Hz, 1H), 6.71 (d, J=8.8 Hz, 1H), 6.59 (dd, J=8.7, 2.0 Hz, 2H), 6.40 (d, J=8.7 Hz, 1H), 5.11 (dd, J=12.8, 5.3 Hz, 1H), 4.00 (t, J=5.7 Hz, 1H), 3.82 (t, J=5.6 Hz, 1H), 3.42 (d, J=3.1 Hz, 3H), 3.08 (dd, J=17.7, 7.7 Hz, 2H), 2.87 (dd, J=12.8, 6.3 Hz, 3H), 2.56 (dd, J=31.2, 14.1 Hz, 3H), 2.18 (t, J=8.1 Hz, 1H), 2.11 (t, J=7.3 Hz, 1H), 2.05 (d, J=7.2 Hz, 1H), 1.65 (d, J=6.4 Hz, 2H), 1.52 (d, J=12.9 Hz, 2H), 1.42 (s, 2H). HRMS (ESI) m/z: calcd for, $C_{43}H_{43}ClN_3O_7S^+$ [M+H]$^+$, 780.2505; found, 780.2501.

Example 189: Preparation of N-(2-(4-(4-chloro-1-(4-hydroxyphenyl)-2-phenylbut-1-en-1-yl)phenoxy)ethyl)-7-((2-(2,6-dioxopiperidin-3-yl)-1,3-dioxoisoindolin-4-yl)thio)heptanamide (SIAIS208154)

According to the general method described in Scheme 32, the target compound (SIAIS208154) was prepared by using toremifene derivative B and LIN-ULM (SIAIS151142B) under appropriate conditions that will be recognized by one skilled in the art. (light yellow solid, 10.2 mg, yield 51%) $^1$H NMR (500 MHz, DMSO) δ 11.12 (s, 1H), 9.49-9.18 (m, 1H), 8.08-7.92 (m, 1H), 7.80-7.69 (m, 2H), 7.62 (d, J=6.9 Hz, 1H), 7.25-7.07 (m, 6H), 7.05 (d, J=8.6 Hz, 1H), 6.94 (d, J=8.7 Hz, 1H), 6.76 (d, J=8.6 Hz, 1H), 6.71 (d, J=8.8 Hz, 1H), 6.62-6.57 (m, 2H), 6.42-6.38 (m, 1H), 5.11 (dd, J=12.9, 5.4 Hz, 1H), 3.99 (t, J=5.6 Hz, 1H), 3.82 (t, J=5.6 Hz, 1H), 3.42 (t, J=6.0 Hz, 3H), 3.09 (dd, J=14.5, 7.2 Hz, 2H), 2.93-2.82 (m, 3H), 2.62-2.52 (m, 3H), 2.10 (t, J=7.4 Hz, 1H), 2.05 (t, J=7.4 Hz, 2H), 1.69-1.58 (m, 2H), 1.55-1.37 (m, 4H), 1.33-1.21 (m, 2H). HRMS (ESI) m/z: calcd for, $C_{44}H_{45}ClN_3O_7S$+[M+H]$^+$, 794.2661; found, 794.2667.

Example 190: Preparation of N-(2-(4-(4-chloro-1-(4-hydroxyphenyl)-2-phenylbut-1-en-1-yl)phenoxy)ethyl)-2-((2-(2,6-dioxopiperidin-3-yl)-1-oxoisoindolin-4-yl)thio)acetamide (SIAIS208155)

According to the general method described in Scheme 32, the target compound (SIAIS208155) was prepared by using toremifene derivative B and LIN-ULM (SIAIS171090) under appropriate conditions that will be recognized by one skilled in the art. (light yellow solid, 7.0 mg, yield 39%) $^1$H NMR (500 MHz, DMSO) δ 10.99 (s, 1H), 9.34 (d, J=125.8 Hz, 2H), 8.40 (d, J=41.7 Hz, 1H), 7.57 (ddd, J=20.3, 19.2, 7.0 Hz, 2H), 7.38 (dt, J=26.5, 7.6 Hz, 1H), 7.24-7.10 (m, 6H), 7.07 (d, J=8.5 Hz, 1H), 6.93 (d, J=8.8 Hz, 1H), 6.77 (d, J=8.6 Hz, 1H), 6.73 (d, J=8.8 Hz, 1H), 6.62 (d, J=8.6 Hz, 1H), 6.58 (d, J=8.9 Hz, 1H), 6.41 (d, J=8.7 Hz, 1H), 5.17-5.08 (m, 1H), 4.39 (dd, J=17.5, 12.0 Hz, 1H), 4.25 (dd, J=17.5, 12.1 Hz, 1H), 3.95 (d, J=5.2 Hz, 1H), 3.79 (s, 2H), 3.74 (s, 1H), 3.44 (t, J=7.4 Hz, 3H), 3.30-3.24 (m, 2H), 2.88 (dd, J=16.5, 7.4 Hz, 3H), 2.59 (d, J=18.2 Hz, 1H), 1.98 (s, 1H). HRMS (ESI) m/z: calcd for, $C_{39}H_{37}ClN_3O_6S^+$ [M+H]$^+$, 710.2086; found, 710.2082.

Example 191: Preparation of N-(2-(4-(4-chloro-1-(4-hydroxyphenyl)-2-phenylbut-1-en-1-yl)phenoxy)ethyl)-3-((2-(2,6-dioxopiperidin-3-yl)-1-oxoisoindolin-4-yl)thio) propanamide (SIAIS208156)

According to the general method described in Scheme 32, the target compound (SIAIS208156) was prepared by using toremifene derivative B and LIN-ULM (SIAIS171086) under appropriate conditions that will be recognized by one skilled in the art. (light yellow solid, 7.3 mg, yield 40%) $^1$H NMR (500 MHz, DMSO) δ 10.98 (s, 1H), 9.34 (d, J=126.0 Hz, 2H), 8.17 (d, J=42.5 Hz, 1H), 7.68-7.49 (m, 3H), 7.16 (ddd, J=11.6, 10.0, 5.9 Hz, 6H), 7.05 (d, J=8.5 Hz, 1H), 6.94 (d, J=8.7 Hz, 1H), 6.76 (d, J=8.5 Hz, 1H), 6.72 (d, J=8.8 Hz, 1H), 6.59 (dd, J=8.7, 6.4 Hz, 2H), 6.40 (d, J=8.7 Hz, 1H), 5.11 (d, J=13.4 Hz, 1H), 4.34 (dd, J=17.4, 11.0 Hz, 1H), 4.21 (dd, J=17.5, 10.5 Hz, 1H), 3.99 (s, 1H), 3.82 (s, 1H), 3.42 (s, 3H), 3.24 (dd, J=19.7, 6.9 Hz, 4H), 2.93-2.82 (m, 3H), 2.56 (d, J=25.5 Hz, 3H), 1.99 (s, 1H). HRMS (ESI) m/z: calcd for, $C_{40}H_{39}ClN_3O_6S^+$ [M+H]$^+$, 724.2243; found, 724.2242.

Example 192: Preparation of N-(2-(4-(4-chloro-1-(4-hydroxyphenyl)-2-phenylbut-1-en-1-yl)phenoxy)ethyl)-4-((2-(2,6-dioxopiperidin-3-yl)-1-oxoisoindolin-4-yl)thio)butanamide (SIAIS208157)

According to the general method described in Scheme 32, the target compound (SIAIS208157) was prepared by using toremifene derivative B and LIN-ULM (SIAIS171089) under appropriate conditions that will be recognized by one skilled in the art. (light yellow solid, 8.4 mg, yield 45%) $^1$H NMR (500 MHz, DMSO) δ 10.99 (s, 1H), 9.33 (d, J=126.5 Hz, 2H), 8.08 (d, J=42.4 Hz, 1H), 7.56 (ddt, J=36.6, 16.5, 7.7 Hz, 3H), 7.25-7.08 (m, 6H), 7.06 (d, J=8.5 Hz, 1H), 6.94 (d, J=8.7 Hz, 1H), 6.76 (d, J=8.6 Hz, 1H), 6.71 (d, J=8.8 Hz, 1H), 6.59 (t, J=8.8 Hz, 2H), 6.40 (d, J=8.7 Hz, 1H), 5.12 (dd, J=13.1, 5.6 Hz, 1H), 4.35 (dd, J=17.5, 6.3 Hz, 1H), 4.21 (dd, J=17.4, 6.4 Hz, 1H), 4.00 (t, J=5.5 Hz, 1H), 3.83 (t, J=5.6 Hz, 1H), 3.46-3.39 (m, 3H), 3.10-3.01 (m, 2H), 2.95-2.82 (m, 3H), 2.58 (d, J=17.0 Hz, 1H), 2.44 (s, 2H), 2.27 (t, J=7.2 Hz, 1H), 2.22 (t, J=7.2 Hz, 1H), 1.99 (s, 1H), 1.87-1.74 (m, 2H). HRMS (ESI) m/z: calcd for, $C_1R_1ClN_3O_6S^+$ [M+H]$^+$, 738.2399; found, 738.2389.

Example 193: Preparation of N-(2-(4-(4-chloro-1-(4-hydroxyphenyl)-2-phenylbut-1-en-1-yl)phenoxy)ethyl)-5-((2-(2,6-dioxopiperidin-3-yl)-1-oxoisoindolin-4-yl)thio)pentanamide (SIAIS208158)

According to the general method described in Scheme 32, the target compound (SIAIS208158) was prepared by using toremifene derivative B and LIN-ULM (SIAIS171079) under appropriate conditions that will be recognized by one skilled in the art. (light yellow solid, 7.6 mg, yield 40%) $^1$H NMR (500 MHz, DMSO) δ 10.98 (s, 1H), 9.34 (d, J=126.4 Hz, 2H), 8.02 (d, J=41.5 Hz, 1H), 7.64-7.47 (m, 3H), 7.17 (ddd, J=18.7, 10.8, 5.7 Hz, 6H), 7.06 (d, J=8.5 Hz, 1H), 6.94 (d, J=8.7 Hz, 1H), 6.76 (d, J=8.5 Hz, 1H), 6.72 (d, J=8.8 Hz, 1H), 6.59 (t, J=8.9 Hz, 2H), 6.40 (d, J=8.7 Hz, 1H), 5.12 (dd, J=13.3, 5.1 Hz, 1H), 4.35 (dd, J=17.6, 4.9 Hz, 1H), 4.21 (dd, J=17.5, 4.8 Hz, 1H), 3.98 (t, J=5.6 Hz, 1H), 3.81 (t, J=5.6 Hz, 1H), 3.45-3.38 (m, 3H), 3.06 (dt, J=13.8, 7.0 Hz, 2H), 2.88 (dt, J=13.1, 12.2 Hz, 3H), 2.58 (d, J=18.7 Hz, 1H), 2.45 (s, 2H), 2.13 (t, J=7.1 Hz, 1H), 2.08 (t, J=7.2 Hz, 1H), 2.01 (s, 1H), 1.70-1.50 (m, 4H). HRMS (ESI) m/z: calcd for, $C_{42}H_{43}ClN_3O_6S^+$ [M+H]$^+$, 752.2556; found, 752.2566.

Example 194: Preparation of N-(2-(4-(4-chloro-1-(4-hydroxyphenyl)-2-phenylbut-1-en-1-yl)phenoxy)ethyl)-6-((2-(2,6-dioxopiperidin-3-yl)-1-oxoisoindolin-4-yl)thio)hexanamide (SIAIS208159)

According to the general method described in Scheme 32, under appropriate conditions that will be recognized by one skilled in the art, the target compound (SIAIS208159) was prepared by using toremifene derivative B and LIN-ULM (SIAIS171091). (light yellow solid, 8.7 mg, yield 45%). $^1$H NMR (500 MHz, DMSO) δ 10.98 (s, 1H), 9.33 (d, J=126.4 Hz, 1H), 8.02 (dd, J=26.4, 20.6 Hz, 1H), 7.63-7.47 (m, 3H), 7.24-7.07 (m, 6H), 7.05 (d, J=8.5 Hz, 1H), 6.94 (d, J=8.7 Hz, 1H), 6.76 (d, J=8.6 Hz, 1H), 6.71 (d, J=8.8 Hz, 1H), 6.59 (dd, J=8.7, 5.5 Hz, 2H), 6.40 (d, J=8.7 Hz, 1H), 5.12 (dd, J=13.4, 5.1 Hz, 1H), 4.34 (dd, J=17.4, 3.6 Hz, 1H), 4.20 (dd, J=17.5, 3.6 Hz, 1H), 3.99 (t, J=5.5 Hz, 1H), 3.82 (t, J=5.7 Hz, 1H), 3.42 (dd, J=11.3, 7.1 Hz, 3H), 3.04 (dd, J=17.1, 7.3 Hz, 2H), 2.94-2.81 (m, 3H), 2.58 (d, J=16.9 Hz, 1H), 2.49-2.39 (m, 2H), 2.09 (t, J=7.2 Hz, 1H), 2.06-1.96 (m, 2H), 1.62-1.43 (m, 4H), 1.37 (dd, J=16.9, 8.4 Hz, 2H). HRMS (ESI) m/z: calcd, for, $C_{43}H_{45}ClN_3O_6S^+$ [M+H]$^+$, 766.2712; found, 766.2712.

Example 195: Preparation of N-(2-(4-(4-chloro-1-(4-hydroxyphenyl)-2-phenylbut-1-en-1-yl)phenoxy)ethyl)-7-((2-(2,6-dioxopiperidin-3-yl)-1-oxoisoindolin-4-yl)thio)heptanamide (SIAIS208160)

According to the general method described in Scheme 32, the target compound (SIAIS208160) was prepared by using toremifene derivative B and LIN-ULM (SIAIS171092) under appropriate conditions that will be recognized by one skilled in the art. (light yellow solid, 9.3 mg, yield 47%) $^1$H NMR (500 MHz, DMSO) δ 10.98 (s, 1H), 9.48-9.18 (m, 1H), 7.98 (dt, J=41.9, 5.5 Hz, 1H), 7.63-7.48 (m, 3H), 7.24-7.08 (m, 6H), 7.05 (d, J=8.5 Hz, 1H), 6.94 (d, J=8.7 Hz, 1H), 6.76 (d, J=8.6 Hz, 1H), 6.71 (d, J=8.8 Hz, 1H), 6.59 (t, J=8.5 Hz, 2H), 6.42-6.38 (m, 1H), 5.12 (dd, J=13.3, 5.1 Hz, 1H), 4.34 (d, J=17.4 Hz, 1H), 4.21 (d, J=17.2 Hz, 1H), 3.99 (t, J=5.6 Hz, 1H), 3.81 (t, J=5.6 Hz, 1H), 3.47-3.38 (m, 3H), 3.04 (dd, J=14.4, 7.2 Hz, 2H), 2.95-2.81 (m, 3H), 2.58 (d, J=18.3 Hz, 1H), 2.49-2.39 (m, 2H), 2.08 (t, J=7.4 Hz, 1H), 2.05-1.97 (m, 2H), 1.62-1.52 (m, 2H), 1.51-1.42 (m, 2H), 1.37 (dt, J=14.7, 7.8 Hz, 2H), 1.29-1.17 (m, 2H). HRMS (ESI) m/z: calcd for, $C_{44}H_{47}ClN_3O_6S^+$ [M+H]$^+$, 780.2869; found, 780.2869.

Example 196: Preparation of N-(2-(4-(1,2-bis(4-hydroxyphenyl)but-1-en-1-yl)phenoxy)ethyl)-2-((2-(2,6-dioxopiperidin-3-yl)-1,3-dioxoisoindolin-4-yl)thio)acetamide (SIAIS251128)

According to the general method described in Scheme 32, the target compound (SIAIS251128) was prepared by using tamoxifen derivative A and LIN-ULM (SIAIS151045) under appropriate conditions that will be recognized by one skilled in the art. (light yellow solid, 8.7 mg, yield 46%) $^1$H NMR (500 MHz, DMSO) δ 11.12 (s, 1H), 9.36-9.13 (m, 2H), 8.22 (dt, J=34.2, 5.4 Hz, 1H), 7.83-7.72 (m, 2H), 7.68-7.60 (m, 1H), 7.05 (d, J=8.6 Hz, 1H), 6.92 (dd, J=11.3, 8.6 Hz, 2H), 6.87 (dd, J=8.4, 1.4 Hz, 2H), 6.71 (dd, J=11.8, 8.7 Hz, 2H), 6.63-6.52 (m, 4H), 6.41 (d, J=8.6 Hz, 1H), 5.11 (ddd, J=12.8, 5.4, 2.2 Hz, 1H), 3.99 (t, J=5.5 Hz, 1H), 3.85 (t, J=5.5 Hz, 1H), 3.44 (dt, J=16.1, 7.9 Hz, 1H), 2.94-2.82 (m, 1H), 2.64-2.53 (m, 4H), 2.33 (td, J=14.3, 6.9 Hz, 2H), 2.04 (dd, J=14.8, 9.3 Hz, 1H), 0.83 (td, J=7.3, 3.0 Hz, 3H). HRMS (ESI) m/z: calcd for, $C_{39}H_{36}N_3O_8S^+$ [M+H]$^+$, 706.2218; found, 706.2216.

Example 197: Preparation of N-(2-(4-(1,2-bis(4-hydroxyphenyl)but-1-en-1-yl)phenoxy)ethyl)-3-((2-(2,6-dioxopiperidin-3-yl)-1,3-dioxoisoindolin-4-yl)thio)propanamide (SIAIS251129)

According to the general method described in Scheme 32, the target compound (SIAIS251129) was prepared by using tamoxifen derivative A and LIN-ULM (SIAIS151138B) under appropriate conditions that will be recognized by one skilled in the art. (light yellow solid, 9.0 mg, yield 47%) $^1$H NMR (500 MHz, DMSO) δ 11.12 (s, 1H), 9.37-9.13 (m, 2H), 8.51 (dt, J=35.6, 5.5 Hz, 1H), 7.76-7.60 (m, 2H), 7.57 (dd, J=6.9, 3.3 Hz, 1H), 7.05 (d, J=8.6 Hz, 1H), 6.94 (d, J=8.5 Hz, 1H), 6.89 (t, J=8.3 Hz, 3H), 6.72 (dd, J=12.2, 8.7 Hz, 2H), 6.63-6.53 (m, 4H), 6.44-6.39 (m, 1H), 5.12 (ddd, J=12.8, 5.4, 2.0 Hz, 1H), 3.99 (t, J=5.3 Hz, 1H), 3.90 (d, J=17.5 Hz, 2H), 3.85 (t, J=5.3 Hz, 1H), 3.47 (dd, J=10.6, 5.2 Hz, 1H), 3.42-3.36 (m, 2H), 2.96-2.83 (m, 1H), 2.66-2.51 (m, 3H), 2.41-2.29 (m, 2H), 2.05 (dd, J=13.7, 6.6 Hz, 1H), 0.92-0.79 (m, 3H). HRMS (ESI) m/z: calcd for, $C_{40}H_{38}N_3O_8S^+$ [M+H]$^+$, 720.2374; found, 720.2371.

Example 198: Preparation of N-(2-(4-(1,2-bis(4-hydroxyphenyl)but-1-en-1-yl)phenoxy)ethyl)-4-((2-(2,6-dioxopiperidin-3-yl)-1,3-dioxoisoindolin-4-yl)thio)butanamide (SIAIS251130)

According to the general method described in Scheme 32, the target compound (SIAIS251130) was prepared by using tamoxifen derivative A and LIN-ULM (SIAIS151139B) under appropriate conditions that will be recognized by one skilled in the art. (light yellow solid, 8.9 mg, yield 46%) $^1$H NMR (500 MHz, DMSO) δ 11.12 (s, 1H), 9.36-9.13 (m, 2H), 8.13 (dt, J=36.3, 5.4 Hz, 1H), 7.80-7.71 (m, 2H), 7.61 (d, J=6.5 Hz, 1H), 7.04 (d, J=8.5 Hz, 1H), 6.96-6.84 (m, 4H), 6.71 (dd, J=15.5, 8.6 Hz, 2H), 6.61-6.52 (m, 4H), 6.41 (d, J=8.6 Hz, 1H), 5.12 (dd, J=12.8, 5.4 Hz, 1H), 4.00 (t, J=5.5 Hz, 1H), 3.85 (t, J=5.5 Hz, 1H), 3.44 (dd, J=10.8, 5.4 Hz, 1H), 3.17-3.05 (m, 2H), 2.93-2.85 (m, 1H), 2.65-2.51 (m, 3H), 2.39-2.23 (m, 4H), 2.05 (dd, J=13.6, 8.1 Hz, 1H), 1.95-1.82 (m, 2H), 0.85-0.81 (m, 3H). HRMS (ESI) m/z: calcd for, $C_{41}H_{40}N_3O_8S^+$ [M+H]$^+$, 734.2531; found, 734.2535.

Example 199: Preparation of N-(2-(4-(1,2-bis(4-hydroxyphenyl)but-1-en-1-yl)phenoxy)ethyl)-5-((2-(2,6-dioxopiperidin-3-yl)-1,3-dioxoisoindolin-4-yl)thio)pentanamide (SIAIS251131)

According to the general method described in Scheme 32, the target compound (SIAIS251131) was prepared by using tamoxifen derivative A and LIN-ULM (SIAIS151140B) under appropriate conditions that will be recognized by one skilled in the art. (light yellow solid, 9.8 mg, yield 49%) $^1$H NMR (500 MHz, DMSO) δ 11.12 (s, 1H), 9.36-9.13 (m, 2H), 8.04 (dt, J=35.4, 5.5 Hz, 1H), 7.79-7.69 (m, 2H), 7.61 (dd, J=6.9, 2.2 Hz, 1H), 7.04 (d, J=8.5 Hz, 1H), 6.96-6.84 (m, 4H), 6.71 (dd, J=12.4, 8.6 Hz, 2H), 6.60-6.54 (m, 4H), 6.40 (d, J=8.5 Hz, 1H), 5.11 (dd, J=12.8, 5.4 Hz, 1H), 3.98 (t, J=5.5 Hz, 1H), 3.83 (t, J=5.6 Hz, 1H), 3.42 (dd, J=11.0, 5.5 Hz, 1H), 3.17-3.06 (m, 2H), 2.94-2.82 (m, 1H), 2.65-2.51 (m, 3H), 2.36-2.30 (m, 2H), 2.14 (dt, J=17.9, 6.7 Hz, 2H), 2.05 (dd, J=14.9, 7.8 Hz, 1H), 1.73-1.58 (m, 4H), 0.85-0.81 (m, 3H). HRMS (ESI) m/z: calcd for, $C_{42}H_{42}N_3O_8S^+$ [M+H]$^+$, 748.2687; found, 748.2690.

Example 200: Preparation of N-(2-(4-(1,2-bis(4-hydroxyphenyl)but-1-en-1-yl)phenoxy)ethyl)-6-((2-(2,6-dioxopiperidin-3-yl)-1,3-dioxoisoindolin-4-yl)thio)hexanamide (SIAIS251132)

According to the general method described in Scheme 32, the target compound (SIAIS251132) was prepared by using tamoxifen derivative A and LIN-ULM (SIAIS151141B) under appropriate conditions that will be recognized by one skilled in the art. (light yellow solid, 10.5 mg, yield 52%) $^1$H NMR (500 MHz, DMSO) δ 11.12 (s, 1H), 9.36-9.13 (m, 2H), 8.02 (dt, J=34.7, 5.5 Hz, 1H), 7.80-7.74 (m, 1H), 7.71 (dd, J=7.7, 4.4 Hz, 1H), 7.61 (d, J=7.2 Hz, 1H), 7.03 (d, J=8.7 Hz, 1H), 6.91 (dd, J=10.4, 8.6 Hz, 2H), 6.86 (d, J=8.5 Hz, 2H), 6.75-6.66 (m, 2H), 6.60-6.53 (m, 4H), 6.43-6.38 (m, 1H), 5.11 (dd, J=12.8, 5.4 Hz, 1H), 3.98 (t, J=5.5 Hz, 1H), 3.83 (t, J=5.6 Hz, 1H), 3.41 (dd, J=11.1, 5.6 Hz, 1H), 3.08 (dd, J=14.3, 7.0 Hz, 2H), 2.94-2.82 (m, 1H), 2.66-2.51 (m, 3H), 2.33 (td, J=14.2, 6.9 Hz, 2H), 2.12-2.02 (m, 3H), 1.71-1.60 (m, 2H), 1.58-1.49 (m, 2H), 1.46-1.35 (m, 2H), 0.85-0.81 (m, 3H). HRMS (ESI) m/z: calcd for, $C_{43}H_{44}N_3O_8S^+$ [M+H]$^+$, 762.2844; found, 762.2843.

Example 201: Preparation of N-(2-(4-(1,2-bis(4-hydroxyphenyl)but-1-en-1-yl)phenoxy)ethyl)-7-((2-(2,6-dioxopiperidin-3-yl)-1,3-dioxoisoindolin-4-yl)thio)heptanamide (SIAIS208170)

According to the general method described in Scheme 32, the target compound (SIAIS208170) was prepared by using Tamoxifen derivative A and LIN-ULM (SIAIS151142B) under appropriate conditions that will be recognized by one skilled in the art. (light yellow solid, 10.1 mg, yield 49%) $^1$H NMR (500 MHz, DMSO) δ 11.12 (s, 1H), 9.36-9.12 (m, 2H), 8.00 (dt, J=35.5, 5.5 Hz, 1H), 7.80-7.74 (m, 1H), 7.72 (dd, J=7.8, 3.0 Hz, 1H), 7.61 (d, J=7.0 Hz, 1H), 7.04 (d, J=8.6 Hz, 1H), 6.96-6.89 (m, 2H), 6.86 (d, J=8.5 Hz, 2H), 6.75-6.66 (m, 2H), 6.62-6.52 (m, 4H), 6.43-6.38 (m, 1H), 5.11 (dd, J=12.8, 5.4 Hz, 1H), 3.97 (t, J=5.6 Hz, 1H), 3.83 (t, J=5.6 Hz, 1H), 3.44-3.40 (m, 1H), 3.31 (d, J=5.6 Hz, 1H), 3.09 (dd, J=11.9, 7.2 Hz, 2H), 2.95-2.80 (m, 1H), 2.63-2.55 (m, 1H), 2.53-2.51 (m, 1H), 2.38-2.27 (m, 2H), 2.14-1.99 (m, 3H), 1.67-1.60 (m, 2H), 1.55-1.37 (m, 4H), 1.31-1.24 (m, 2H), 0.83 (td, J=7.4, 3.9 Hz, 3H). HRMS (ESI) m/z: calcd for, $C_{44}H_{46}N_3O_8S^+$ [M+H]$^+$, 776.3000; found, 776.3003.

Example 202: Preparation of N-(2-(4-(1,2-bis(4-hydroxyphenyl)but-1-en-1-yl)phenoxy)ethyl)-2-((2-(2,6-dioxopiperidin-3-yl)-1-oxoisoindolin-4-yl)thio)acetamide (SIAIS251133)

According to the general method described in Scheme 32, the target compound (SIAIS251133) was prepared by using tamoxifen derivative A and LIN-ULM (SIAIS171090) under appropriate conditions that will be recognized by one skilled in the art. (light yellow solid, 7.8 mg, yield 42%) $^1$H NMR (500 MHz, DMSO) δ 10.99 (s, 1H), 9.37-9.14 (m, 2H), 8.40 (dt, J=35.2, 5.4 Hz, 1H), 7.61 (dd, J=19.5, 7.8 Hz, 1H), 7.53

(dd, J=7.5, 3.3 Hz, 1H), 7.38 (dt, J=18.5, 7.7 Hz, 1H), 7.06 (d, J=8.5 Hz, 1H), 6.95 (d, J=8.3 Hz, 1H), 6.88 (dd, J=8.6, 2.2 Hz, 3H), 6.76-6.69 (m, 2H), 6.62-6.52 (m, 4H), 6.41 (d, J=8.5 Hz, 1H), 5.12 (ddd, J=13.3, 4.9, 2.6 Hz, 1H), 4.39 (dd, J=17.4, 8.1 Hz, 1H), 4.25 (dd, J=17.4, 8.7 Hz, 1H), 3.94 (t, J=5.3 Hz, 1H), 3.84-3.72 (m, 3H), 3.44 (dd, J=10.7, 5.3 Hz, 1H), 3.36 (dd, J=10.4, 4.9 Hz, 1H), 2.95-2.85 (m, 1H), 2.59 (d, J=17.4 Hz, 1H), 2.48-2.39 (m, 1H), 2.39-2.29 (m, 2H), 2.00-1.98 (m, 1H), 0.84 (t, J=7.3 Hz, 3H). HRMS (ESI) m/z: calcd for, $C_{39}H_{38}N_3O_7S^+$ $[M+H]^+$, 692.2425; found, 692.2424.

Example 203: Preparation of N-(2-(4-(1,2-bis(4-hydroxyphenyl)but-1-en-1-yl)phenoxy)ethyl)-3-((2-(2,6-dioxopiperidin-3-yl)-1-oxoisoindolin-4-yl)thio)propanamide (SIAIS251134)

According to the general method described in Scheme 32, the target compound (SIAIS251134) was prepared by using tamoxifen derivative A and LIN-ULM (SIAIS171086) under appropriate conditions that will be recognized by one skilled in the art. (light yellow solid, 9.0 mg, yield 48%) $^1$H NMR (500 MHz, DMSO) δ 10.98 (s, 1H), 9.36-9.13 (m, 2H), 8.17 (dt, J=34.8, 5.3 Hz, 1H), 7.65 (dd, J=10.4, 7.7 Hz, 1H), 7.58 (dd, J=7.4, 3.9 Hz, 1H), 7.52 (dd, J=15.2, 7.6 Hz, 1H), 7.04 (d, J=8.6 Hz, 1H), 6.94-6.86 (m, 4H), 6.71 (dd, J=12.9, 8.7 Hz, 2H), 6.62-6.51 (m, 4H), 6.41 (d, J=8.6 Hz, 1H), 5.21-4.99 (m, 1H), 4.34 (dd, J=17.4, 6.6 Hz, 1H), 4.21 (dd, J=17.4, 7.2 Hz, 1H), 3.97 (t, J=5.4 Hz, 1H), 3.83 (t, J=5.4 Hz, 1H), 3.47-3.39 (m, 1H), 3.25 (dt, J=14.5, 7.1 Hz, 2H), 2.96-2.84 (m, 1H), 2.58 (d, J=17.5 Hz, 1H), 2.45 (dt, J=18.3, 7.2 Hz, 4H), 2.38-2.28 (m, 2H), 2.00-1.98 (m, 1H), 0.83 (td, J=7.3, 3.0 Hz, 3H). HRMS (ESI) m/z: calcd for, $C_{40}H_{40}N_3O_7S^+$ $[M+H]^+$, 706.2581; found, 706.2581.

Example 204: Preparation of N-(2-(4-(1,2-bis(4-hydroxyphenyl)but-1-en-1-yl)phenoxy)ethyl)-4-((2-(2,6-dioxopiperidin-3-yl)-1-oxoisoindolin-4-yl)thio)butanamide (SIAIS251135)

According to the general method described in Scheme 32, the target compound (SIAIS251135) was prepared by using tamoxifen derivative A and LIN-ULM (SIAIS171089) under appropriate conditions that will be recognized by one skilled in the art. (light yellow solid, 8.6 mg, yield 45%) $^1$H NMR (500 MHz, DMSO) δ 10.99 (s, 1H), 9.36-9.13 (m, 2H), 8.08 (dt, J=36.1, 5.5 Hz, 1H), 7.62 (td, J=7.6, 0.9 Hz, 1H), 7.55 (dd, J=6.3, 1.3 Hz, 1H), 7.50 (dd, J=14.4, 7.4 Hz, 1H), 7.08-7.01 (m, 1H), 6.96-6.84 (m, 4H), 6.75-6.67 (m, 2H), 6.61-6.57 (m, 2H), 6.56-6.52 (m, 2H), 6.44-6.37 (m, 1H), 5.12 (dd, J=13.3, 5.0 Hz, 1H), 4.35 (dd, J=17.4, 4.1 Hz, 1H), 4.21 (dd, J=17.4, 4.4 Hz, 1H), 3.98 (t, J=5.6 Hz, 1H), 3.84 (t, J=5.6 Hz, 1H), 3.42 (q, J=5.5 Hz, 1H), 3.10-3.01 (m, 2H), 2.96-2.84 (m, 1H), 2.58 (d, J=17.7 Hz, 1H), 2.48-2.40 (m, 1H), 2.38-2.30 (m, 2H), 2.25 (dt, J=18.3, 7.2 Hz, 2H), 2.05-1.94 (m, 1H), 1.88-1.72 (m, 2H), 0.83 (td, J=7.4, 3.0 Hz, 3H). HRMS (ESI) m/z: calcd for, $C_{41}H_{42}N_3O_7S^+$ $[M+H]^+$, 720.2738; found, 720.2735.

Example 205: Preparation of N-(2-(4-(1,2-bis(4-hydroxyphenyl)but-1-en-1-yl)phenoxy)ethyl)-6-((2-(2,6-dioxopiperidin-3-yl)-1-oxoisoindolin-4-yl)thio)hexanamide (SIAIS251137)

According to the general method described in Scheme 32, the target compound (SIAIS251137) was prepared by using tamoxifen derivative A and LIN-ULM (SIAIS171091) under appropriate conditions that will be recognized by one skilled in the art. (light yellow solid, 9.9 mg, yield 50%) $^1$H NMR (500 MHz, DMSO) δ 10.98 (s, 1H), 9.40-9.08 (m, 2H), 8.00 (dt, J=35.1, 5.5 Hz, 1H), 7.60 (ddd, J=7.6, 3.4, 1.0 Hz, 1H), 7.56 (d, J=6.7 Hz, 1H), 7.51 (td, J=7.5, 1.8 Hz, 1H), 7.04 (d, J=8.7 Hz, 1H), 6.91 (dd, J=13.7, 8.6 Hz, 2H), 6.86 (dd, J=8.5, 1.4 Hz, 2H), 6.71 (dd, J=15.8, 8.7 Hz, 2H), 6.62-6.52 (m, 4H), 6.43-6.37 (m, 1H), 5.12 (dd, J=13.3, 5.1 Hz, 1H), 4.34 (dd, J=17.4, 1.5 Hz, 1H), 4.20 (dd, J=17.4, 2.0 Hz, 1H), 3.97 (t, J=5.6 Hz, 1H), 3.83 (t, J=5.6 Hz, 1H), 3.40 (q, J=5.6 Hz, 1H), 3.04 (dd, J=14.0, 6.9 Hz, 2H), 2.96-2.84 (m, 1H), 2.64-2.53 (m, 1H), 2.48-2.39 (m, 1H), 2.36-2.29 (m, 2H), 2.13-2.02 (m, 2H), 2.02-1.94 (m, 1H), 1.61-1.45 (m, 4H), 1.41-1.32 (m, 2H), 0.83 (td, J=7.4, 4.5 Hz, 3H). HRMS (ESI) m/z: calcd for, $C_{43}H_{46}N_3O_7S^+$ $[M+H]^+$, 748.3051; found, 748.3050.

Example 206: Preparation of N-(2-(4-(1,2-bis(4-hydroxyphenyl)but-1-en-1-yl)phenoxy)ethyl)-7-((2-(2,6-dioxopiperidin-3-yl)-1-oxoisoindolin-4-yl)thio)heptanamide (SIAIS208171)

According to the general method described in Scheme 32, the target compound (SIAIS208171) was prepared by using tamoxifen derivative A and LIN-ULM (SIAIS171092) under appropriate conditions that will be recognized by one skilled in the art. (light yellow solid, 8.9 mg, yield 44%) $^1$H NMR (500 MHz, DMSO) δ 10.98 (s, 1H), 9.36-9.13 (m, 2H), 7.98 (dt, J=35.4, 5.4 Hz, 1H), 7.63-7.58 (m, 1H), 7.55 (d, J=6.6 Hz, 1H), 7.51 (dt, J=8.9, 4.4 Hz, 1H), 7.04 (d, J=8.6 Hz, 1H), 6.96-6.84 (m, 4H), 6.76-6.67 (m, 2H), 6.59-6.54 (m, 4H), 6.41 (d, J=8.6 Hz, 1H), 5.12 (dd, J=13.3, 5.1 Hz, 1H), 4.34 (d, J=17.4 Hz, 1H), 4.21 (d, J=17.4 Hz, 1H), 3.97 (t, J=5.5 Hz, 1H), 3.83 (t, J=5.6 Hz, 1H), 3.40 (dd, J=11.1, 5.5 Hz, 1H), 3.04 (dd, J=11.8, 7.2 Hz, 2H), 2.97-2.83 (m, 1H), 2.58 (d, J=17.5 Hz, 1H), 2.48-2.39 (m, 1H), 2.36-2.30 (m, 2H), 2.12-1.95 (m, 3H), 1.62-1.52 (m, 2H), 1.52-1.32 (m, 4H), 1.28-1.21 (m, 2H), 0.83 (td, J=7.3, 3.5 Hz, 3H). HRMS (ESI) m/z: calcd for, $C_{44}H_{48}N_3O_7S^+$ $[M+H]^+$, 762.3207; found, 762.3202.

General Synthesis Method of a Series of Degradation Agents for BRD4 Protein:

Scheme 33

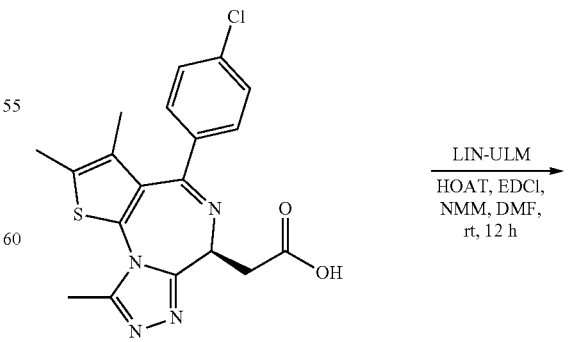

JQ-1 derivative A
SIAIS171018

LIN-ULM
HOAT, EDCl,
NMM, DMF,
rt, 12 h

-continued

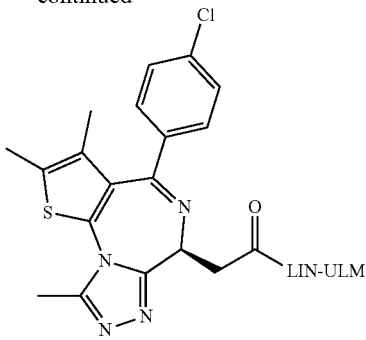

According to Scheme 33, at room temperature, a reaction flask was charged with the corresponding JQ-1 derivative A (1 equiv), the corresponding LIN-ULM (1 equiv), 1-hydroxy-7-azabenzotriazole (2 equiv), 1-(3-dimethylaminopropyl)-3-ethylcarbodiimide hydrochloride (2 equiv), anhydrous N,N-dimethylformamide (2 mL), and N-methylmorpholine (5 equiv). The reaction mixture was stirred at room temperature overnight. After the completion of the reaction was detected by LC-MS, the resulting mixture was subjected to preparative HPLC (eluent (v/v): acetonitrile/(water+0.05% HCl)=10%-100%) for separation. The acetonitrile is removed by rotary evaporation, and the residue was lyophilized to give the corresponding final degradation agent compound.

Example 207: Preparation of 2-((S)-4-(4-chlorophenyl)-2,3,9-trimethyl-6H-thieno[3,2-f][1,2,4]triazolo[4,3-a][1,4]diazepin-6-yl)-N-(2-((2-(2,6-dioxopiperidin-3-yl)-1,3-dioxoisoindolin-4-yl)thio)ethyl)acetamide (SIAIS171036)

According to the general method described in Scheme 33, under suitable conditions that will be recognized by one skilled in the art, JQ-1 derivative A (SIAIS171018) and LIN-ULM (SIAIS171026) were used to prepare the title compound (SIAIS171036) (pale yellow solid, 11.0 mg, yield 41%). $^1$H NMR (500 MHz, MeOD) δ 7.82 (d, J=8.1 Hz, 1H), 7.73 (t, J=7.7 Hz, 1H), 7.62 (d, J=7.2 Hz, 1H), 7.53 (dd, J=8.4, 5.0 Hz, 2H), 7.41 (d, J=8.7 Hz, 2H), 5.14-5.03 (m, 1H), 4.88-4.86 (m, 1H), 3.61 (t, J=6.5 Hz, 2H), 3.45-3.40 (m, 1H), 3.38-3.35 (m, 1H), 3.33 (t, J=6.4 Hz, 2H), 2.92 (s, 3H), 2.88-2.80 (m, 1H), 2.78-2.59 (m, 2H), 2.46 (s, 3H), 2.13-2.06 (m, 1H), 1.73 (s, 3H). HRMS (ESI) m/z: calcd for, $C_{34}H_{31}ClN_7O_5S_2^+$ [M+H]$^+$, 716.1511; found, 716.1228.

Example 208: Preparation of 2-((S)-4-(4-chlorophenyl)-2,3,9-trimethyl-6H-thieno[3,2-f][1,2,4]triazolo[4,3-a][1,4]diazepin-6-yl)-N-(3-((2-(2,6-dioxopiperidin-3-yl)-1,3-dioxoisoindolin-4-yl)thio)propyl)acetamide (SIAIS171013)

According to the general method described in Scheme 33, under appropriate conditions that will be recognized by one skilled in the art, the target compound (SIAIS171013) was prepared by using JQ-1 derivative A (SIAIS171018) and LIN-ULM (SIAIS171025). (light yellow solid, 5.2 mg, yield 25%) $^1$H NMR (500 MHz, MeOD) δ 7.71-7.66 (m, 2H), 7.62-7.56 (m, 1H), 7.47 (d, J=8.4 Hz, 2H), 7.40 (dd, J=8.8, 2.3 Hz, 2H), 5.13-5.08 (m, 1H), 4.82-4.78 (m, 1H), 3.51-3.40 (m, 3H), 3.38-3.34 (m, 1H), 3.21-3.18 (m, 2H), 2.91-2.83 (m, 1H), 2.81 (s, 3H), 2.78-2.67 (m, 2H), 2.47 (s, 3H), 2.16-2.08 (m, 1H), 2.05-1.96 (m, 2H), 1.69 (s, 3H). HRMS (ESI) m/z: calcd for, $C_{35}H_{33}ClN_7O_5S_2^+$ [M+H]$^+$, 730.1668; found, 730.2598.

Example 209: Preparation of 2-((S)-4-(4-chlorophenyl)-2,3,9-trimethyl-6H-thieno[3,2-f][1,2,4]triazolo[4,3-a][1,4]diazepin-6-yl)-N-(4-((2-(2,6-dioxopiperidin-3-yl)-1,3-dioxoisoindolin-4-yl)thio)butyl)acetamide (SIAIS171037)

According to the general method described in Scheme 33, under appropriate conditions that will be recognized by one skilled in the art, the target compound (SIAIS171037) was prepared by using JQ-1 derivative A (SIAIS171018) and LIN-ULM (SIAIS171023). v $^1$H NMR (500 MHz, MeOD) δ 7.74-7.66 (m, 2H), 7.62-7.55 (m, 1H), 7.51 (d, J=8.2 Hz, 2H), 7.45 (d, J=8.7 Hz, 2H), 5.12-5.08 (m, 1H), 4.93-4.90 (m, 1H), 3.46 (dd, J=15.3, 8.7 Hz, 1H), 3.40-3.32 (m, 3H), 3.15 (t, J=6.9 Hz, 2H), 2.91-2.81 (m, 4H), 2.78-2.64 (m, 2H), 2.48 (s, 3H), 2.17-2.06 (m, 1H), 1.85-1.75 (m, 4H), 1.70 (s, 3H). HRMS (ESI) m/z: calcd for, $C_{36}H_{35}ClN_7O_5S_2^+$ [M+H]$^+$, 744.1824; found, 744.1507.

Example 210: Preparation of 2-((S)-4-(4-chlorophenyl)-2,3,9-trimethyl-6H-thieno[3,2-f][1,2,4]triazolo[4,3-a][1,4]diazepin-6-yl)-N-(5-((2-(2,6-dioxopiperidin-3-yl)-1,3-dioxoisoindolin-4-yl)thio)pentyl)acetamide (SIAIS171038)

According to the general method described in Scheme 33, under appropriate conditions that will be recognized by one skilled in the art, the target compound (SIAIS171038) was prepared by using JQ-1 derivative A (SIAIS171018) and LIN-ULM (SIAIS171027). (pale yellow solid, 5.3 mg, yield 19%) $^1$H NMR (500 MHz, MeOD) δ 7.72-7.68 (m, 2H), 7.58 (d, J=7.0 Hz, 1H), 7.51-7.45 (m, 4H), 5.11-5.03 (m, 1H), 4.82-4.80 (m, 1H), 3.48-3.41 (m, 1H), 3.36-3.31 (m, 3H), 3.14-3.09 (m, 2H), 2.86-2.82 (m, 4H), 2.77-2.62 (m, 2H), 2.47 (s, 3H), 2.15-2.08 (m, 1H), 1.85-1.78 (m, 2H), 1.70 (s, 3H), 1.67-1.54 (m, 4H). HRMS (ESI) m/z: calcd for, $C_{37}H_{37}ClN_7O_5S_2^+$ [M+H]$^+$, 758.1981; found, 758.1658.

Example 211: Preparation of 2-((S)-4-(4-chlorophenyl)-2,3,9-trimethyl-6H-thieno[3,2-f][1,2,4]triazolo[4,3-a][1,4]diazepin-6-yl)-N-(6-((2-(2,6-dioxopiperidin-3-yl)-1,3-dioxoisoindolin-4-yl)thio)hexyl)acetamide (SIAIS171039)

According to the general method described in Scheme 33, under appropriate conditions that will be recognized by one skilled in the art, the target compound (SIAIS171039) was prepared by using JQ-1 derivative A (SIAIS171018) and LIN-ULM (SIAIS171028). (light yellow solid, 9.0 mg, yield 31%) $^1$H NMR (500 MHz, MeOD) δ 7.71-7.61 (m, 2H), 7.57 (d, J=7.0 Hz, 1H), 7.43 (dd, J=24.3, 8.6 Hz, 4H), 5.13-5.08 (m, 1H), 4.70-4.68 (m, 1H), 3.45-3.38 (m, 1H), 3.30-3.25 (m, 3H), 3.09 (t, J=7.3 Hz, 2H), 2.88-2.82 (m, 1H), 2.79-2.65 (m, 5H), 2.44 (s, 3H), 2.15-2.08 (m, 1H), 1.78-1.67 (m, 5H), 1.62-1.55 (m, 4H), 1.48-1.40 (m, 2H). HRMS (ESI) m/z: calcd for, $C_{38}H_{39}ClN_7O_5S_2^+$ [M+H]$^+$, 772.2137; found, 772.1789.

Example 212: Preparation of 2-((S)-4-(4-chlorophenyl)-2,3,9-trimethyl-6H-thieno[3,2-f][1,2,4]triazolo[4,3-a][1,4]diazepin-6-yl)-N-(7-((2-(2,6-dioxopiperidin-3-yl)-1,3-dioxoisoindolin-4-yl)thio)heptyl)acetamide (SIAIS171040)

According to the general method described in Scheme 33, under appropriate conditions that will be recognized by one skilled in the art, the target compound (SIAIS171040) was prepared by using JQ-1 derivative A (SIAIS171018) and LIN-ULM (SIAIS171033). (light yellow solid, 15.0 mg, yield 51%) $^1$H NMR (500 MHz, MeOD) δ 7.75-7.63 (m, 2H), 7.58 (d, J=6.8 Hz, 1H), 7.51-7.45 (m, 4H), 5.13-5.06 (m, 1H), 4.92-4.90 (m, 1H), 3.49-3.41 (m, 1H), 3.38-3.33 (m, 1H), 3.30-3.24 (m, 2H), 3.09 (t, J=7.1 Hz, 2H), 2.96-2.80 (m, 4H), 2.78-2.64 (m, 2H), 2.47 (s, 3H), 2.13-2.10 (m, 1H), 1.80-1.68 (m, 5H), 1.60-1.48 (m, 4H), 1.45-1.35 (m, 4H). HRMS (ESI) m/z: calcd for, $C_{39}H_{41}ClN_7O_5S_2^+$ [M+H]$^+$, 786.2294; found, 786.1950.

Example 213: Preparation of 2-((S)-4-(4-chlorophenyl)-2,3,9-trimethyl-6H-thieno[3,2-f][1,2,4]triazolo[4,3-a][1,4]diazepin-6-yl)-N-(8-((2-(2,6-dioxopiperidin-3-yl)-1,3-dioxoisoindolin-4-yl)thio)octyl)acetamide (SIAIS171049)

According to the general method described in Scheme 33, under appropriate conditions that will be recognized by one skilled in the art, the target compound (SIAIS171049) was prepared by using JQ-1 derivative A (SIAIS171018) and LIN-ULM (SIAIS171047). (pale yellow solid, 10.0 mg, yield 33%) $^1$H NMR (500 MHz, MeOD) δ 7.73-7.63 (m, 2H), 7.58-7.54 (m, 1H), 7.46-7.38 (m, 4H), 5.14-5.08 (m, 1H), 4.65-4.62 (m, 1H), 3.45-3.37 (m, 1H), 3.29-3.18 (m, 3H), 3.09 (t, J=7.3 Hz, 2H), 2.90-2.81 (m, 1H), 2.78-2.66 (m, 5H), 2.43 (s, 3H), 2.16-2.08 (m, 1H), 1.77-1.65 (m, 5H), 1.55-1.45 (m, 4H), 1.40-1.32 (m, 6H). HRMS (ESI) m/z: calcd for, $C_{40}H_{43}ClN_7O_5S_2^+$ [M+H]$^+$, 800.2450; found, 800.0319.

Example 214: Preparation of 2-((S)-4-(4-chlorophenyl)-2,3,9-trimethyl-6H-thieno[3,2-f][1,2,4]triazolo[4,3-a][1,4]diazepin-6-yl)-N-(2-((2-(2,6-dioxopiperidin-3-yl)-1-oxoisoindolin-4-yl)thio)ethyl)acetamide (SIAIS171138)

According to the general method described in Scheme 33, under appropriate conditions that will be recognized by one skilled in the art, the target compound (SIAIS171138) was prepared by using JQ-1 derivative A (SIAIS171018) and LIN-ULM (SIAIS171123). (light yellow solid, 10.0 mg, yield 38%) $^1$H NMR (500 MHz, MeOD) δ 7.78-7.76 (m, 1H), 7.66 (dd, J=7.7, 7.0 Hz, 1H), 7.55-7.52 (m, 3H), 7.44 (dd, J=8.9, 5.12 (m, 1H), 4.83-4.80 (m, 1H), 4.44 (q, J=17.3 Hz, 2H), 3.57-3.49 (m, 2H), 3.45-3.33 (m, 2H), 3.29-3.20 (m, 2H), 2.94-2.83 (m, 4H), 2.79-2.71 (m, 1H), 2.54-2.38 (m, 4H), 2.20-2.09 (m, 1H), 1.72 (s, 3H). HRMS (ESI) m/z: calcd for, $C_{34}H_{33}ClN_7O_4S_2^+$ [M+H]$^+$, 702.1718; found, 701.9827.

Example 215: Preparation of 2-((S)-4-(4-chlorophenyl)-2,3,9-trimethyl-6H-thieno[3,2-f][1,2,4]triazolo[4,3-a][1,4]diazepin-6-yl)-N-(3-((2-(2,6-dioxopiperidin-3-yl)-1-oxoisoindolin-4-yl)thio)propyl)acetamide (SIAIS171139)

According to the general method described in Scheme 33, under appropriate conditions that will be recognized by one skilled in the art, the target compound (SIAIS171139) was prepared by using JQ-1 derivative A (SIAIS171018) and LIN-ULM (SIAIS171124). (light yellow solid, 8.0 mg, yield 30%) $^1$H NMR (500 MHz, MeOD) δ 7.69-7.61 (m, 2H), 7.54-7.38 (m, 5H), 5.16-5.13 (m, 1H), 4.82-4.77 (m, 1H), 4.44-4.40 (m, 2H), 3.77-3.64 (m, 1H), 3.49-3.37 (m, 3H), 3.18-3.08 (m, 2H), 2.91-2.81 (m, 4H), 2.79-2.68 (m, 1H), 2.56-2.42 (m, 4H), 2.17-2.13 (m, 1H), 1.97-1.85 (m, 2H), 1.71 (s, 3H). HRMS (ESI) m/z: calcd for, $C_{35}H_{35}ClN_7O_4S_2^+$ [M+H]$^+$, 716.1875; found, 715.9937.

Example 216: Preparation of 2-((S)-4-(4-chlorophenyl)-2,3,9-trimethyl-6H-thieno[3,2-f][1,2,4]triazolo[4,3-a][1,4]diazepin-6-yl)-N-(4-((2-(2,6-dioxopiperidin-3-yl)-1-oxoisoindolin-4-yl)thio)butyl)acetamide (SIAIS171141)

According to the general method described in Scheme 33, under appropriate conditions that will be recognized by one skilled in the art, the target compound (SIAIS171141) was prepared by using JQ-1 derivative A (SIAIS171018) and LIN-ULM (SIAIS171131). (light yellow solid, 10.0 mg, yield 37%) $^1$H NMR (500 MHz, MeOD) δ 7.72-7.60 (m, 2H), 7.52-7.46 (m, 5H), 5.17-5.04 (m, 1H), 4.81-4.75 (m, 1H), 4.42-4.36 (m, 2H), 3.73-3.69 (m, 1H), 3.47-3.34 (m, 1H), 3.26-3.22 (m, 2H), 3.17-3.02 (m, 2H), 2.91-2.82 (m, 4H), 2.78-2.68 (m, 1H), 2.52-2.40 (m, 4H), 2.20-2.09 (m, 1H), 1.73-1.71 (m, 7H). HRMS (ESI) m/z: calcd for, $C_{36}H_{37}ClN_7O_4S_2^+$ [M+H]$^+$, 730.2031; found, 730.1548.

Example 217: Preparation of 2-((S)-4-(4-chlorophenyl)-2,3,9-trimethyl-6H-thieno[3,2-f][1,2,4]triazolo[4,3-a][1,4]diazepin-6-yl)-N-(5-((2-(2,6-dioxopiperidin-3-yl)-1-oxoisoindolin-4-yl)thio)pentyl)acetamide (SIAIS171142)

According to the general method described in Scheme 33, under appropriate conditions that will be recognized by one skilled in the art, the target compound (SIAIS171142) was prepared by using JQ-1 derivative A (SIAIS171018) and LIN-ULM (SIAIS171132). (light yellow solid, 14.0 mg, yield 50%) $^1$H NMR (500 MHz, MeOD) δ 7.61 (dd, J=7.8, 3.9 Hz, 2H), 7.48-7.42 (m, 5H), 5.15-5.11 (m, 1H), 4.76-4.72 (m, 1H), 4.42-4.38 (m, 2H), 3.46-3.34 (m, 2H), 3.28-3.21 (m, 2H), 3.07 (t, J=7.1 Hz, 2H), 2.91-2.87 (m, 1H), 2.79-2.62 (m, 4H), 2.50-2.42 (m, 4H), 2.18-2.10 (m, 1H), 1.72-1.65 (m, 5H), 1.60-1.51 (m, 4H). HRMS (ESI) m/z: calcd for, $C_{37}H_{39}ClN_7O_4S_2^+$ [M+H]$^+$, 744.2188; found, 744.1699.

Example 218: Preparation of 2-((S)-4-(4-chlorophenyl)-2,3,9-trimethyl-6H-thieno[3,2-f][1,2,4]triazolo[4,3-a][1,4]diazepin-6-yl)-N-(6-((2-(2,6-dioxopiperidin-3-yl)-1-oxoisoindolin-4-yl)thio)hexyl)acetamide (SIAIS171143)

According to the general method described in Scheme 33, under appropriate conditions that will be recognized by one skilled in the art, the target compound (SIAIS171143) was prepared by using JQ-1 derivative A (SIAIS171018) and LIN-ULM (SIAIS171134). (light yellow solid, 16.0 mg, yield 56%) $^1$H NMR (500 MHz, MeOD) δ 7.61 (dd, J=6.9, 5.7 Hz, 2H), 7.53-7.42 (m, 5H), 5.14 (dd, J=13.2, 5.2 Hz, 1H), 4.74 (dd, J=8.3, 5.0 Hz, 1H), 4.40 (qd, J=17.2, 4.0 Hz, 2H), 3.47-3.37 (m, 1H), 3.29-3.17 (m, 3H), 3.05 (t, J=7.2 Hz, 2H), 2.92-2.83 (m, 1H), 2.80-2.72 (m, 4H), 2.54-2.42 (m, 4H), 2.20-2.10 (m, 1H), 1.72-1.64 (m, 5H), 1.60-1.49 (m, 4H), 1.44-1.38 (m, 2H). HRMS (ESI) m/z: calcd for, $C_{38}H_{41}ClN_7O_4S_2^+$ [M+H]$^+$, 758.2344; found, 758.2989.

Example 219: Preparation of 2-((S)-4-(4-chlorophenyl)-2,3,9-trimethyl-6H-thieno[3,2-f][1,2,4]triazolo[4,3-a][1,4]diazepin-6-yl)-N-(7-((2-(2,6-dioxopiperidin-3-yl)-1-oxoisoindolin-4-yl)thio)heptyl)acetamide (SIAIS171144)

According to the general method described in Scheme 33, under appropriate conditions that will be recognized by one skilled in the art, the target compound (SIAIS171144) was prepared by using JQ-1 derivative A (SIAIS171018) and LIN-ULM (SIAIS171135). (light yellow solid, 15.0 mg, yield 52%) $^1$H NMR (500 MHz, MeOD) δ 7.65-7.58 (m, 2H), 7.56-7.42 (m, 5H), 5.17-5.11 (m, 1H), 4.80-4.78 (m, 1H), 4.39 (qd, J=17.2, 7.2 Hz, 2H), 3.49-3.41 (m, 1H), 3.29-3.18 (m, 3H), 3.04 (td, J=7.2, 3.5 Hz, 2H), 2.93-2.81 (m, 4H), 2.80-2.70 (m, 1H), 2.55-2.43 (m, 4H), 2.20-2.10 (m, 1H), 1.75-1.62 (m, 5H), 1.60-1.52 (m, 2H), 1.50-1.46 (m, 2H), 1.44-1.35 (m, 4H). HRMS (ESI) m/z: calcd for, $C_{39}H_{43}ClN_7O_4S_2^+$ [M+H]$^+$, 772.2501; found, 772.3154.

Example 220: Preparation of 2-((S)-4-(4-chlorophenyl)-2,3,9-trimethyl-6H-thieno[3,2-f][1,2,4]triazolo[4,3-a][1,4]diazepin-6-yl)-N-(8-((2-(2,6-dioxopiperidin-3-yl)-1-oxoisoindolin-4-yl)thio)octyl)acetamide (SIAIS171145)

According to the general method described in Scheme 33, under appropriate conditions that will be recognized by one skilled in the art, the target compound (SIAIS171145) was prepared by using JQ-1 derivative A (SIAIS171018) and LIN-ULM (SIAIS171136). (light yellow solid, 15.0 mg, yield 51%) $^1$H NMR (500 MHz, MeOD) δ 7.62 (t, J=7.2 Hz, 2H), 7.50-7.44 (m, 5H), 5.14 (dd, J=13.3, 5.1 Hz, 1H), 4.75 (dd, J=8.9, 5.3 Hz, 1H), 4.40 (qd, J=17.3, 3.4 Hz, 2H), 3.44 (dd, J=15.2, 8.9 Hz, 1H), 3.27-3.22 (m, 3H), 3.03 (t, J=7.2 Hz, 2H), 2.93-2.84 (m, 1H), 2.81-2.70 (m, 4H), 2.56-2.43 (m, 4H), 2.20-2.15 (m, 1H), 1.72-1.60 (m, 5H), 1.56-1.51 (m, 2H), 1.49-1.42 (m, 2H), 1.40-1.30 (m, 6H). HRMS (ESI) m/z: calcd for, $C_{40}H_{45}ClN_7O_4S_2^+$ [M+H]$^+$, 786.2657; found, 786.3335.

Example 221: Preparation of 2-((S)-4-(4-chlorophenyl)-2,3,9-trimethyl-6H-thieno[3,2-f][1,2,4]triazolo[4,3-a][1,4]diazepin-6-yl)-N-(2-(2-(2-((2-(2,6-dioxopiperidin-3-yl)-1,3-dioxoisoindolin-4-yl)thio)ethoxy)ethoxy)ethyl)acetamide (SIAIS213070)

According to the general method described in Scheme 33, the target compound (SIAIS213070) was prepared by using JQ-1 derivative A (SIAIS171018) and LIN-ULM (SIAIS213066) under appropriate conditions that will be recognized by one skilled in the art. (white solid, 8.0. mg, yield 39.8%) $^1$H NMR (500 MHz, MeOD) δ 7.69 (tdd, J=15.0, 7.7, 2.0 Hz, 2H), 7.55 (d, J=6.9 Hz, 1H), 7.44 (ddd, J=14.5, 8.7, 4.9 Hz, 4H), 5.12-4.95 (m, 1H), 4.71 (ddd, J=8.9, 5.2, 1.3 Hz, 1H), 3.87-3.75 (m, 2H), 3.72-3.57 (m, 6H), 3.53-3.39 (m, 3H), 3.33 (dd, J=9.8, 6.5 Hz, 3H), 2.87-2.61 (m, 6H), 2.46 (d, J=8.9 Hz, 3H), 2.14-2.01 (m, 1H), 1.69 (s, 3H). HRMS (ESI) m/z: calcd for, $C_{38}H_{39}ClN_7O_7S_2^+$ [M+H]$^+$, 804.2035; found, 804.2036.

Example 222: Preparation of 2-((S)-4-(4-chlorophenyl)-2,3,9-trimethyl-6H-thieno[3,2-f][1,2,4]triazolo[4,3-a][1,4]diazepin-6-yl)-N-(2-(2-((2-(2,6-dioxopiperidin-3-yl)-1-oxoisoindolin-4-yl)thio)ethoxy)ethyl)acetamide (SIAIS213100)

According to the general method described in Scheme 33, under appropriate conditions that will be recognized by one skilled in the art, the target compound (SIAIS213100) was prepared by using JQ-1 derivative A (SIAIS171018) and LIN-ULM (SIAIS213096). (light yellow solid, 12.0 mg, yield 64.2%), $^1$H NMR (500 MHz, MeOD) δ 7.69 (d, J=7.8 Hz, 1H), 7.61 (t, J=8.8 Hz, 1H), 7.53-7.37 (m, 5H), 5.06 (ddd, J=24.5, 13.3, 5.2 Hz, 1H), 4.74-4.66 (m, 1H), 4.46-4.27 (m, 2H), 3.78-3.68 (m, 2H), 3.62-3.54 (m, 2H), 3.50-3.35 (m, 3H), 3.29-3.20 (m, 3H), 2.85 (ddt, J=19.1, 13.5, 5.6 Hz, 1H), 2.79-2.68 (m, 4H), 2.51-2.35 (m, 4H), 2.15-2.13 (m, 1H), 1.68 (s, 3H). HRMS (ESI) m/z: calcd for, $C_{36}H_{37}ClN_7O_5S_2^+$ [M+H]$^+$, 746.1981; found, 746.1984.

Example 223: Preparation of 2-((S)-4-(4-chlorophenyl)-2,3,9-trimethyl-6H-thieno[3,2-f][1,2,4]triazolo[4,3-a][1,4]diazepin-6-yl)-N-(2-(2-(2-((2-(2,6-dioxopiperidin-3-yl)-1-oxoisoindolin-4-yl)thio)ethoxy)ethoxy)ethyl)acetamide (SIAIS213072)

According to the general method described in Scheme 33, under appropriate conditions that will be recognized by one skilled in the art, the target compound (SIAIS213072) was prepared by using JQ-1 derivative A (SIAIS171018) and LIN-ULM (SIAIS213068). (light yellow solid, 5.0 mg, yield 25.3%) $^1$H NMR (500 MHz, MeOD) δ 7.72-7.68 (m, 1H), 7.64 (dd, J=6.8, 5.3 Hz, 1H), 7.55-7.48 (m, 5H), 5.11 (dd, J=13.4, 5.2 Hz, 1H), 4.99 (dd, J=13.3, 5.2 Hz, 1H), 4.49-4.27 (m, 2H), 3.74-3.69 (m, 2H), 3.63-3.57 (m, 6H), 3.51-3.41 (m, 3H), 3.36 (dd, J=10.5, 5.3 Hz, 1H), 3.27-3.19 (m, 2H), 2.90-2.79 (m, 4H), 2.73 (ddd, J=15.0, 4.6, 2.3 Hz, 1H), 2.53-2.43 (m, 4H), 2.16-2.13 (m, 1H), 1.72 (s, 3H). HRMS (ESI) m/z: calcd for, $C_{38}H_{41}ClN_7O_6S_2^+$ [M+H]$^+$, 790.2243; found, 790.2238.

Example 224: Preparation of 2-((S)-4-(4-chlorophenyl)-2,3,9-trimethyl-6H-thieno[3,2-f][1,2,4]triazolo[4,3-a][1,4]diazepin-6-yl)-N-(2-(2-(2-(2-((2-(2,6-dioxopiperidin-3-yl)-1-oxoisoindolin-4-yl)thio)ethoxy)ethoxy)ethoxy)ethyl)acetamide (SIAIS213112)

According to the general method described in Scheme 33, under appropriate conditions that will be recognized by one skilled in the art, the target compound (SIAIS213112) was prepared with JQ-1 derivative A (SIAIS171018) and LIN-ULM (SIAIS213111). (light yellow solid, 12.0 mg, yield 57.5%). $^1$H NMR (500 MHz, MeOD) δ 7.72 (t, J=7.0 Hz, 1H), 7.65 (dt, J=14.7, 7.4 Hz, 1H), 7.52 (ddd, J=22.6, 20.6, 8.7 Hz, 5H), 5.21-5.03 (m, 1H), 4.77 (s, 1H), 4.44 (qd, J=17.3, 9.1 Hz, 2H), 3.70 (dd, J=13.2, 6.9 Hz, 2H), 3.63 (dt, J=6.6, 3.5 Hz, 10H), 3.57-3.40 (m, 4H), 3.25 (dd, J=11.6, 5.4 Hz, 2H), 2.94-2.85 (m, 4H), 2.81-2.74 (m, 1H), 2.55-2.46 (m, 4H), 2.20-2.16 (m, 1H), 1.73 (s, 3H). HRMS (ESI) m/z: calcd for, $C_{40}H_{45}ClN_7O_7S_2^+$ [M+H]$^+$, 834.2505; found, 834.2507.

Example 225: Preparation of 2-((S)-4-(4-chlorophenyl)-2,3,9-trimethyl-6H-thieno[3,2-f][1,2,4]triazolo[4,3-a][1,4]diazepin-6-yl)-N-(4-(2-((2-(2,6-dioxopiperidin-3-yl)-1,3-dioxoisoindolin-4-yl)thio)acetamido)butyl)acetamide (SIAIS213075)

According to the general method described in Scheme 33, under appropriate conditions that will be recognized by one skilled in the art, using JQ-1 derivative A (SIAIS171018) and LIN-ULM (SIAIS213073) to prepare the target compound (SIAIS213075). (light yellow solid, 14.0 mg, yield 70.0%), $^1$H NMR (500 MHz, MeOD) δ 7.75-7.67 (m, 2H), 7.64-7.59 (m, 1H), 7.48 (q, J=8.8 Hz, 4H), 5.07 (ddd, J=24.4, 12.7, 5.4 Hz, 1H), 4.81 (ddd, J=8.7, 5.9, 3.1 Hz, 1H), 3.85 (d, J=1.5 Hz, 2H), 3.45-3.34 (m, 2H), 3.26-3.15 (m, 4H), 2.89-2.78 (m, 4H), 2.69 (dddd, J=17.6, 12.8, 6.2, 3.3 Hz, 2H), 2.47 (s, 3H), 2.11 (ddd, J=13.1, 5.8, 2.6 Hz, 1H), 1.71 (s, 3H), 1.53-1.50 (m, 4H). HRMS (ESI) m/z: calcd for, $C_{34}H_{38}ClN_8O_6S_2^+$ [M+H]$^+$, 801.2039; found, 801.2037.

Example 226: Preparation of 2-((S)-4-(4-chlorophenyl)-2,3,9-trimethyl-6H-thieno[3,2-f][1,2,4]triazolo[4,3-a][1,4]diazepin-6-yl)-N-(4-(2-((2-(2,6-dioxopiperidin-3-yl)-1-oxoisoindolin-4-yl)thio)acetamido)butyl)acetamide (SIAIS213094)

According to the general method described in Scheme 33, under appropriate conditions that will be recognized by one skilled in the art, the target compound (SIAIS213094) was prepared by using JQ-1 derivative A (SIAIS171018) and LIN-ULM (SIAIS213092). (light yellow solid, 9.0 mg, yield 45.9%), $^1$H NMR (500 MHz, MeOD) δ 7.70 (dd, J=7.6, 6.6 Hz, 2H), 7.59-7.38 (m, 5H), 5.17-5.06 (m, 1H), 4.84-4.79 (m, 1H), 4.48 (qd, J=17.3, 7.1 Hz, 2H), 3.68-3.63 (m, 2H), 3.45-3.40 (m, 1H), 3.37 (d, J=5.9 Hz, 1H), 3.26-3.10 (m, 4H), 2.93-2.81 (m, 4H), 2.77 (ddd, J=20.0, 10.0, 7.6 Hz, 1H), 2.56-2.43 (m, 4H), 2.23-2.11 (m, 1H), 1.71 (s, 3H), 1.45-1.31 (m, 4H). HRMS (ESI) m/z: calcd for, $C_{38}H_{40}ClN_8O_5S_2^+$ [M+H]$^+$, 787.2246; found, 787.2249.

General Synthesis Methods of Some Special Degradation Agents for BRD4 Target:

Scheme 34

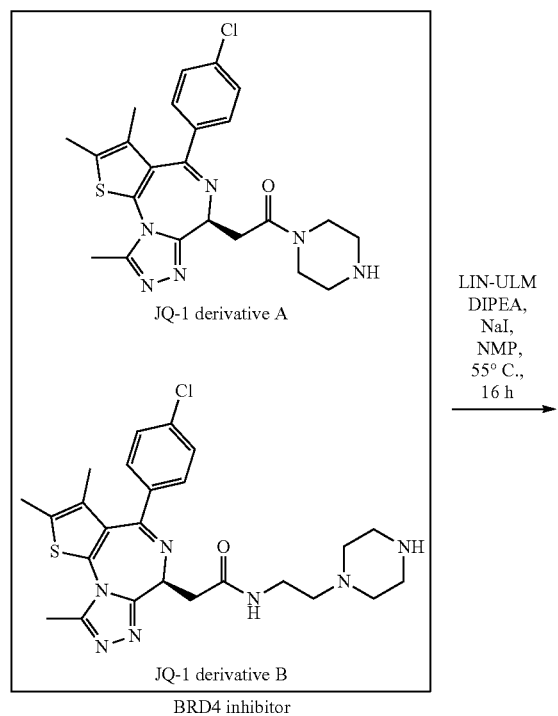

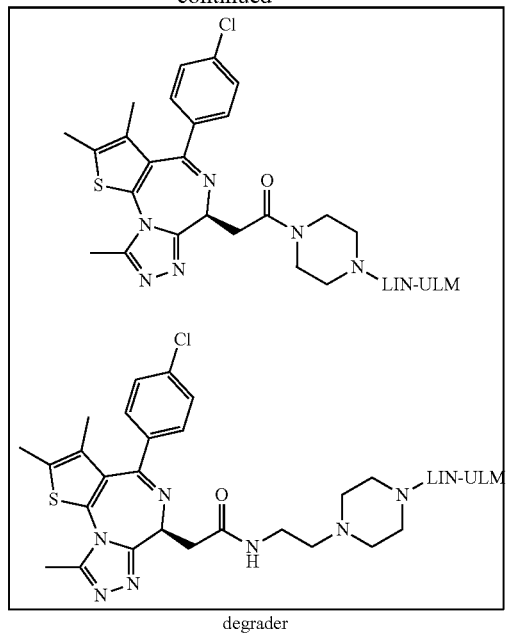

According to Scheme 34, at room temperature, a reaction flask was charged with JQ-1 derivative B (SIAIS213113) or JQ-1 derivative C (SIAIS213130) (1 equiv), LIN-ULM (1 equiv), N,N-Diisopropylethylamine (3 equiv), sodium iodide (1 equiv), and NMP (1.5 mL). The reaction mixture was stirred at 55° C. overnight. After completion of the reaction was detected by LC-MS, the reaction mixture was subjected to preparative HPLC (eluent (v/v): acetonitrile/(water+0.05% HCl)=10%-100%) for separation, The acetonitrile was removed by rotary evaporation, and the residue was lyophilizated to give the final compound.

Example 227: Preparation of 3-(4-((2-(4-(2-((S)-4-(4-chlorophenyl)-2,3,9-trimethyl-6H-thieno[3,2-f][1,2,4]triazolo[4,3-a][1,4]diazepin-6-yl)acetyl)piperazin-1-yl)ethyl)thio)-1-oxoisoindolin-2-yl)piperidine-2,6-dione (SIAIS213140)

According to the general method described in Scheme 34, under appropriate conditions that will be recognized by one skilled in the art, the target compound (SIAIS213140) was prepared by using JQ-1 derivative B (SIAIS213113) and LIN-ULM (SIAIS213137). (light yellow solid, 7.0 mg, yield 42.7%), $^1$H NMR (500 MHz, MeOD) δ 7.85-7.72 (m, 2H), 7.67-7.59 (m, 1H), 7.49 (q, J=8.8 Hz, 4H), 5.24-5.14 (m, 1H), 4.80 (s, 1H), 4.59-4.48 (m, 2H), 3.80-3.32 (m, 14H), 2.95-2.86 (m, 1H), 2.86-2.75 (m, 4H), 2.56-2.46 (m, 4H), 2.25-2.15 (m, 1H), 1.71 (s, 3H). HRMS (ESI) m/z: calcd for, $C_{38}H_{40}ClN_8O_4S_2^+$ [M+H]$^+$, 771.2297; found, 771.2298.

Example 228: Preparation of 3-(4-((3-(4-(2-((S)-4-(4-chlorophenyl)-2,3,9-trimethyl-6H-thieno[3,2-f][1,2,4]triazolo[4,3-a][1,4]diazepin-6-yl)acetyl)piperazin-1-yl)propyl)thio)-1-oxoisoindolin-2-yl)piperidine-2,6-dione (SIAIS213117)

According to the general method described in Scheme 34, under appropriate conditions that will be recognized by one skilled in the art, the target compound (SIAIS213117) was prepared by using JQ-1 derivative B (SIAIS213113) and LIN-ULM (SIAIS213132). (light yellow solid, 1.5 mg, yield 13.0%), $^1$H NMR (500 MHz, MeOD) δ 7.82-7.78 (m, 1H), 7.75 (dd, J=7.4, 1.8 Hz, 1H), 7.62 (t, J=7.7 Hz, 1H), 7.58-7.42 (m, 4H), 5.45-5.31 (m, 1H), 5.20 (dd, J=13.4, 4.9 Hz, 1H), 4.57-4.46 (m, 2H), 3.64 (d, J=23.4 Hz, 4H), 3.42-3.35 (m, 2H), 3.27-3.08 (m, 4H), 2.95-2.87 (m, 1H), 2.79 (d, J=18.7 Hz, 4H), 2.59-2.46 (m, 4H), 2.27-2.17 (m, 2H), 2.09 (d, J=36.9 Hz, 3H), 1.73 (s, 3H), 1.37-1.35 (s, 2H). HRMS (ESI) m/z: calcd for, $C_{39}H_{42}ClN_8O_4S_2^+$ [M+H]$^+$, 785.2453; found, 785.2457.

Example 229: Preparation of 3-(4-((4-(4-(2-((S)-4-(4-chlorophenyl)-2,3,9-trimethyl-6H-thieno[3,2-f][1,2,4]triazolo[4,3-a][1,4]diazepin-6-yl)acetyl)piperazin-1-yl)butyl)thio)-1-oxoisoindolin-2-yl)piperidine-2,6-dione (SIAIS213138)

According to the general method described in Scheme 34, under appropriate conditions that will be recognized by one skilled in the art, using JQ-1 derivative B (SIAIS213113) and LIN-ULM (SIAIS213134) to prepare the target compound (SIAIS213138). (light yellow solid, 7.0 mg, yield 41.2%). $^1$H NMR (500 MHz, MeOD) δ 7.70 (dd, J=15.2, 7.7 Hz, 2H), 7.58-7.47 (m, 5H), 5.18 (d, J=8.6 Hz, 1H), 4.84-4.58 (m, 2H), 4.47 (q, J=17.4 Hz, 3H), 3.70 (d, J=55.4 Hz, 6H), 3.26-3.09 (m, 6H), 2.93-2.76 (m, 5H), 2.56-2.44 (m, 4H), 2.19 (dd, J=9.0, 3.7 Hz, 1H), 2.00-1.89 (m, 2H), 1.78-1.73 (m, 5H). HRMS (ESI) m/z: calcd for, $C_{40}H_{44}ClN_8O_4S_2^+$ [M+H]$^+$, 799.2610; found, 799.2616.

Example 230: Preparation of 3-(4-((5-(4-(2-((S)-4-(4-chlorophenyl)-2,3,9-trimethyl-6H-thieno[3,2-f][1,2,4]triazolo[4,3-a][1,4]diazepin-6-yl)acetyl)piperazin-1-yl)pentyl)thio)-1-oxoisoindolin-2-yl)piperidine-2,6-dione (SIAIS213131)

According to the general method described in Scheme 34, under appropriate conditions that will be recognized by one skilled in the art, the target compound (SIAIS213131) was prepared by using JQ-1 derivative B (SIAIS213113) and LIN-ULM (SIAIS213129). (light yellow solid, 6.0 mg, yield 34.7%) $^1$H NMR (500 MHz, MeOD) δ 7.68-7.64 (m, 2H), 7.62-7.50 (m, 5H), 5.16 (dt, J=13.0, 6.5 Hz, 1H), 4.95 (d, J=15.9 Hz, 1H), 4.68 (d, J=14.2 Hz, 1H), 4.45 (q, J=17.3 Hz, 3H), 3.87-3.59 (m, 5H), 3.29-3.00 (m, 7H), 2.94-2.85 (m, 4H), 2.80 (dd, J=18.6, 16.5 Hz, 1H), 2.59-2.47 (m, 4H), 2.22-2.15 (m, 1H), 1.88-1.79 (m, 2H), 1.77-1.66 (m, 5H), 1.57-1.51 (m, 2H). HRMS (ESI) m/z: calcd for, $C_{41}H_{46}ClN_8O_4S_2^+$ [M+H]$^+$, 813.2766; found, 813.2767.

Example 231: Preparation of 2-((S)-4-(4-chlorophenyl)-2,3,9-trimethyl-6H-thieno[3,2-f][1,2,4]triazolo[4,3-a][1,4]diazepin-6-yl)-N-(2-(4-(2-((2-(2,6-dioxopiperidin-3-yl)-1-oxoisoindolin-4-yl)thio)ethyl)piperazin-1-yl)ethyl)acetamide (SIAIS213141)

According to the general method described in Scheme 34, the target compound (SIAIS213141) was prepared by using JQ-1 derivative C (SIAIS213130) and LIN-ULM (SIAIS213137) under appropriate conditions that will be recognized by one skilled in the art. (white solid, 5.0 mg, yield 31.4%) $^1$H NMR (500 MHz, MeOD) δ 7.67 (dt, J=21.4, 10.7 Hz, 2H), 7.53 (t, J=7.5 Hz, 1H), 7.49-7.35 (m, 4H), 5.16 (dd, J=13.3, 5.0 Hz, 1H), 4.63-4.55 (m, 2H), 4.46 (qd, J=17.6, 4.5 Hz, 2H), 3.62 (dd, J=32.0, 17.1 Hz, 2H), 3.46-3.34 (m, 4H), 3.16 (dd, J=17.7, 16.0 Hz, 4H), 2.96-2.83 (m, 1H), 2.83-2.73 (m, 1H), 2.68 (s, 3H), 2.62 (s, 2H), 2.52 (dd, J=15.9, 6.5 Hz, 6H), 2.44 (s, 3H), 2.19 (s, 1H), 1.69 (s, 3H). HRMS (ESI) m/z: calcd for, $C_{40}H_{45}ClN_9O_4S_2^+$ [M+H]$^+$, 814.2719; found, 814.2716.

Example 232: Preparation of 2-((S)-4-(4-chlorophenyl)-2,3,9-trimethyl-6H-thieno[3,2-f][1,2,4]triazolo[4,3-a][1,4]diazepin-6-yl)-N-(2-(4-(3-((2-(2,6-dioxopiperidin-3-yl)-1-oxoisoindolin-4-yl)thio)propyl)piperazin-1-yl)ethyl)acetamide (SIAIS213136)

According to the general method described in Scheme 34, under appropriate conditions that will be recognized by one skilled in the art, the target compound (SIAIS213136)) was prepared by using JQ-1 derivative C (SIAIS213130) and LIN-ULM (SIAIS213132). (light yellow solid, 6.0 mg, yield 37.0% $^1$H NMR (500 MHz, MeOD) δ 7.77 (d, J=7.8 Hz, 1H), 7.72 (d, J=8.3 Hz, 1H), 7.62-7.46 (m, 5H), 5.16 (dd, J=13.4, 5.1 Hz, 1H), 4.83-4.78 (m, 1H), 4.49 (q, J=17.5 Hz, 2H), 3.87-3.49 (m, 12H), 3.40 (dt, J=17.7, 5.9 Hz, 4H), 3.24-3.07 (m, 2H), 2.97-2.70 (m, 5H), 2.60-2.43 (m, 4H), 2.18 (dd, J=8.8, 3.9 Hz, 1H), 2.04 (dd, J=33.1, 25.9 Hz, 2H), 1.71 (s, 3H). HRMS (ESI) m/z: calcd for, $C_{41}H_{47}ClN_9O_4S_2^+$ [M+H]$^+$, 828.2875; found, 828.2874.

Example 233: Preparation of 2-((S)-4-(4-chlorophenyl)-2,3,9-trimethyl-6H-thieno[3,2-f][1,2,4]triazolo[4,3-a][1,4]diazepin-6-yl)-N-(2-(4-(4-((2-(2,6-dioxopiperidin-3-yl)-1-oxoisoindolin-4-yl)thio)butyl)piperazin-1-yl)ethyl)acetamide (SIAIS213139)

According to the general method described in Scheme 34, under appropriate conditions that will be recognized by one skilled in the art, the target compound (SIAIS213139) was prepared by using JQ-1 derivative C (SIAIS213130) and LIN-ULM (SIAIS213134). (light yellow solid, 5.0 mg, yield 30.3%), $^1$H NMR (500 MHz, MeOD) δ 7.78-7.65 (m, 2H), 7.61-7.44 (m, 5H), 5.16 (ddd, J=22.9, 13.4, 5.1 Hz, 1H), 4.84-4.79 (m, 1H), 4.54-4.39 (m, 2H), 3.96-3.44 (m, 12H), 3.39 (t, J=5.3 Hz, 2H), 3.19 (ddd, J=8.5, 4.9, 3.0 Hz, 3H), 3.09 (ddd, J=17.5, 13.7, 7.0 Hz, 1H), 2.94-2.71 (m, 5H), 2.59-2.42 (m, 4H), 2.17 (dd, J=7.5, 5.3 Hz, 1H), 2.06-1.88 (m, 2H), 1.80-1.53 (m, 5H). HRMS (ESI) m/z: calcd for, $C_{42}H_{49}ClN_9O_4S_2^+$ [M+H]$^+$, 842.3032; found, 842.3036.

Example 234: Preparation of 2-((S)-4-(4-chlorophenyl)-2,3,9-trimethyl-6H-thieno[3,2-f][1,2,4]triazolo[4,3-a][1,4]diazepin-6-yl)-N-(2-(4-(5-((2-(2,6-dioxopiperidin-3-yl)-1-oxoisoindolin-4-yl)thio)pentyl)piperazin-1-yl)ethyl)acetamide (SIAIS213133)

According to the general method described in Scheme 34, the target compound (SIAIS213133) was prepared by using JQ-1 derivative C (SIAIS213130) and LIN-ULM (SIAIS213129) under appropriate conditions that will be recognized by one skilled in the art. (white solid, 5.0 mg, yield 29.9%) $^1$H NMR (500 MHz, MeOD) δ 7.65 (dd, J=7.7, 1.2 Hz, 2H), 7.53 (t, J=7.6 Hz, 1H), 7.48-7.37 (m, 4H), 5.16 (dd, J=13.3, 5.1 Hz, 1H), 4.63 (t, J=7.1 Hz, 1H), 4.58 (s, 1H), 4.43 (q, J=17.3 Hz, 2H), 3.53-3.43 (m, 1H), 3.41-3.32 (m, 4H), 3.17-2.70 (m, 12H), 2.69 (s, 3H), 2.63 (t, J=6.3 Hz, 2H), 2.52 (dt, J=12.2, 7.8 Hz, 1H), 2.44 (s, 3H), 2.20-2.14 (m, 1H), 1.75-1.67 (m, 5H), 1.63 (dd, J=15.8, 7.7 Hz, 2H), 1.56-1.46 (m, 2H). HRMS (ESI) m/z: calcd for, $C_{43}H_{51}ClN_9O_4S_2^+$ [M+H]$^+$, 856.3188; found, 856.3189.

Comparative Example 1: Preparation of N-(2-chloro-6-methylphenyl)-2-((6-(4-((2-(2,6-dioxopiperidin-3-yl)-1,3-dioxoisoindolin-4-yl)aminoacetyl)piperazin-1-yl)-2-methylpyrimidin-4-yl)amino)thiazole-5-carboxamide (Reference Compound SIAIS151072)

At room temperature, a reaction flask was sequentially charged with N-(2-chloro-6-methylphenyl)-2-((2-methyl-6-(piperazin-1-yl)pyrimidine-4-yl)amino)thiazole-5-carboxamide (ie., Dasatinib derivative SIAIS151055; 1 equiv), (2-(2,6-dioxopiperidin-3-yl)-1,3-dioxoisoindolin-4-yl)aminoacetic acid (ie., HO$_2$C-LIN-ULM intermediate SIAIS151025; 1 equiv), HOAt (2 equiv), EDCI (2 equiv), anhydrous DMF (2 mL), and NMM (5 equiv). The reaction mixture was stirred overnight at room temperature. After the completion of the reaction was detected by LC-MS, the reaction mixture was subjected to preparative HPLC (eluent (v/v): acetonitrile/(water+0.05% HCl)=10%-100%) for separation. The acetonitrile was removed by rotary evaporation, and the residue was lyophilization to give the target compound (SIAIS151072), as a yellow solid, 19.1 mg, yield 56%, $^1$H NMR (500 MHz, MeOD) δ 8.11 (s, 1H), 7.51-7.46 (m, 1H), 7.27 (d, J=7.9 Hz, 1H), 7.19-7.12 (m, 2H), 7.01 (d, J=7.0 Hz, 1H), 6.94 (d, J=8.5 Hz, 1H), 6.19 (s, 1H), 4.98 (dd, J=12.6, 5.3 Hz, 1H), 4.19 (s, 2H), 3.83-3.63 (m, 8H), 2.82-2.73 (m, 1H), 2.69-2.61 (m, 2H), 2.50 (s, 3H), 2.22 (s, 3H), 2.06-1.99 (m, 1H). HRMS (ESI) m/z: calcd for, $C_{35}H_{34}ClN_{10}O_6S^+$ [M+H]$^+$, 757.2067; found, 757.1286.

Comparative Example 2: Preparation of 2-((S)-4-(4-chlorophenyl)-2,3,9-trimethyl-6H-thieno[3,2-f][1,2,4]triazolo[4,3-a][1,4]diazepin-6-yl)-N-(5-((2-(2,6-dioxopiperidin-3-yl)-1-oxoisoindolin-4-yl)amino)pentyl)acetamide (Reference Compound SIAIS213110)

At room temperature, a reaction flask was charged with (S)-2-(4-(4-chlorophenyl)-2,3,9-trimethyl-6H-thieno[3,2-f][1,2,4]triazolo[4,3-a][1,4]diazepin-6-yl)acetic acid (ie., JQ-1 derivative A: SIAIS171018; 1 equiv), 3-(4-((5-aminopentyl)amino)-1-oxoisoindolin-2-yl)piperidine-2,6-dione (ie., HO$_2$C-LIN-ULM intermediate SIAIS1204075; 1 equiv), HOAt (2 equiv), EDCI (2 equiv), anhydrous DMF (2 mL), and NMM (5 equiv). The reaction mixture was stirred overnight at room temperature. After the completion of the reaction was detected by LC-MS, the reaction mixture was subjected to preparative HPLC (eluent (v/v): acetonitrile/(water+0.05% HCl)=10%-100%) for separation. The acetonitrile was removed by rotary evaporation, and the residue was lyophilization to give the target compound (SIAIS213110), as a yellow solid, 21.4 mg, yield 59%, $^1$H NMR (500 MHz, MeOD) δ 7.45-7.27 (m, 5H), 7.06 (dd, J=7.4, 3.0 Hz, 1H), 6.79 (dd, J=8.0, 5.0 Hz, 1H), 5.07 (ddd, J=30.3, 13.3, 5.2 Hz, 1H), 4.67-4.59 (m, 1H), 4.31-4.19 (m, 2H), 3.45-3.32 (m, 2H), 3.29-3.23 (m, 2H), 3.18 (dt, J=6.7, 5.3 Hz, 2H), 2.86 (dtd, J=18.9, 13.6, 5.4 Hz, 1H), 2.75-2.64 (m, 4H), 2.45-2.33 (m, 4H), 2.09 (ddtd, J=18.1, 12.7, 5.2, 2.3 Hz, 1H), 1.72 (ddd, J=21.0, 13.9, 6.7 Hz, 2H), 1.62 (t, J=11.2 Hz, 5H), 1.56-1.47 (m, 2H). HRMS (ESI) m/z: calcd for, $C_{37}H_{40}ClN_8O_4S^+$ [M+H]$^+$, 727.2576; found, 727.2573.

Comparative Example 3: Preparation of 2-((S)-4-(4-chlorophenyl)-2,3,9-trimethyl-6H-thieno[3,2-f][1,2,4]triazolo[4,3-a][1,4]diazepin-6-yl)-N-(5-((2-(2,6-dioxopiperidin-3-yl)-1-oxoisoindolin-4-yl)oxy)pentyl)acetamide (Reference Compound SIAIS271066)

At room temperature, a reaction flask was charged with (S)-2-(4-(4-chlorophenyl)-2,3,9-trimethyl-6H-thieno[3,2-f][1,2,4]triazolo[4,3-a][1,4]diazepin-6-yl)acetic acid (ie., JQ-1 derivative A: SIAIS171018; 1 equiv), 3-(4-((5-aminopentyl)oxy)-1-oxoisoindolin-2-yl)piperidine-2,6-dione (ie., HO$_2$C-LIN-ULM intermediate SIAIS271064; 1 equiv), HOAt (2 equiv), EDCI (2 equiv), anhydrous DMF (2 mL), and NMM (5 equiv). The reaction mixture was stirred overnight at room temperature. After the completion of the reaction was detected by LC-MS, the reaction mixture was subjected to preparative HPLC (eluent (v/v): acetonitrile/(water+0.05% HCl)=10%-100%) for separation. The acetonitrile was removed by rotary evaporation, and the residue was lyophilization to give the target compound (SIAIS271066), as a pale yellow solid, 9.0 mg, yield 50%, $^1$H NMR (500 MHz, DMSO) δ 10.94 (d, J=14.8 Hz, 1H), 8.22 (s, 1H), 7.53-7.36 (m, 5H), 7.33-7.25 (m, 1H), 7.25-7.17 (m, 1H), 5.08 (dt, J=13.3, 4.8 Hz, 1H), 4.58-4.48 (m, 1H), 4.36 (dd, J=17.4, 9.7 Hz, 1H), 4.23-4.13 (m, 1H), 4.10 (dd, J=10.3, 6.1 Hz, 2H), 3.17 (qdd, J=18.8, 13.9, 7.3 Hz, 4H), 2.95-2.80 (m, 1H), 2.59 (t, J=9.6 Hz, 3H), 2.50-2.35 (m, 5H), 2.01-1.89 (m, 1H), 1.76 (d, J=5.1 Hz, 2H), 1.64-1.56 (m, 3H), 1.55-1.42 (m, 4H). HRMS (ESI) m/z: calcd for, $C_{37}H_{39}ClN_7O_5S^+$ [M+H]$^+$, 728.2416; found, 728.2411.

Biological Activity Assay

Evaluation of Biological Activities of Pomalidomide/Lenalidomide Based Thio-Substituted Compounds of Formula (IV)

Experimental Reagents

| Reagents and antibodies | manufacturer |
| --- | --- |
| RPMI1640 | Gibico |
| FBS | Gibico |
| Penicillin-Streptomycin | Gibico |
| DMSO | Sigma-Aldrich |
| Cell counting Kit-8 (CCK-8) | Dojindo |
| Lenalidomide | Selleck |
| Pomalidomide | Selleck |

Cell Lines

The multiple myeloma cell line used was: MM1S (myeloma (immunoglobulin A lambda), B lymphoblasts), purchased from American Type Culture Collection (ATCC). The medium is RPMI1640 supplemented with 10% FBS and 1% Penicillin-Streptomycin (penicillin and streptomycin). The cells used were identified as correct cells by STR cells, and were negative for mycoplasma through routine inspections.

Methods

Cell Culture

The cells used in this present disclosure were cultured in a 37° C. incubator containing 5% $CO_2$. The complete cell culture medium was RPMI 1640 medium with 10% fetal bovine serum, and the final concentrations of penicillin and streptomycin were 100 U/mL, respectively.

Determination of Half Inhibitory Concentration ($IC_{50}$) of Compounds of the Present Disclosure on Tumor Cells MM1S cells were seeded in 100 μL RPMI1640 complete medium at a density of 15000 cells/well. 100 μL of the inoculated cells were treated with 0.5 μL diluted thio-substituted compound of formula (IV) to be tested of the present disclosure at 10 successively decreasing concentrations (starting at the highest concentration of 10 μM/1 μM; 5-fold serial dilutions). After 72 hours of treatment, the cell viability was determined according to the CCK-8 reagent operating instructions. The negative control was DMSO, and the positive control was a commercial inhibitor. After CCK-8 treatment for 2 h, the value of O.D.450 was measured using a microplate reader. The formula for calculating the growth inhibition rate of the thio-substituted compound of formula (IV) of the present disclosure is cell inhibition rate %=(control group O.D. value−experimental group O.D. value)/control group O.D. value*100%, and further the inhibition curve was plotted by Prism Graphpad software and $IC_{50}$ values of the compounds of the present disclosure were calculated.

The results showed that the designed pomalidomide/lenalidomide-based thio-substituted compounds of formula (IV) of the present disclosure can inhibit the proliferation of multiple myeloma cells MM1S. It is worth mentioning that the $IC_{50}$ of the parent drug Pomalidomide (Pomalidomide) is 9.38 nM, and the $IC_{50}$ of Lenalidomide (Lenalidomide) is 19.59 nM. The $IC_{50}$ of the thio-substituted compound of formula (IV) we designed and synthesized has a minimum $IC_{50}$ of 1.98 nM, indicating that the thio-substituted compounds of formula (IV) have the better effect of inhibiting tumor cell growth than the parent drugs.

TABLE 4

$IC_{50}$ values of the thio-substituted compounds of formula (IV) of the present disclosure on MM1S cell proliferation inhibitory activity

| Compounds | $IC_{50}$(nM)/MM1S cell line |
|---|---|
| Pomalidomide | 9.38 ± 1.33 |
| Lenalidomide | 19.59 ± 3.30 |
| SIAIS171075 | 18.51 ± 0.64 |
| SIAIS1216049 | 1.27 ± 0.62 |
| SIAIS1216133 | 1.27 ± 0.13 |
| SIAIS1216135 | 1.23 ± 0.42 |
| SIAIS1216137 | 1.58 ± 0.71 |
| SIAIS1220013 | 1.98 |
| SIAIS1220015 | 3.45 |
| SIAIS171123 | 71.43 |
| SIAIS171124 | 56.93 |
| SIAIS171131 | 6.61 |
| SIAIS171132 | 8.27 |
| SIAIS171134 | 4.77 |
| SIAIS171135 | 4.31 |
| SIAIS171136 | 4.22 |
| SIAIS1210065 | 63.87 |
| SIAIS1210067 | 39.47 |
| SIAIS1210069 | 57.97 |
| SIAIS1216107 | 327.8 |
| SIAIS1210079 | 388 |
| SIAIS1210077 | 71.85 |

Evaluation of Biological Activities of CDK4/6 Target Compounds
Reagents

| Reagents and antibodies | manufacturer |
|---|---|
| RPMI1640 | Gibico |
| FBS | Gibico |
| Penicillin-Streptomycin | Gibico |
| DMSO | Sigma-Aldrich |
| Insulin | meilunbio |
| Cell counting Kit-8 (CCK-8) | Dojindo |
| Ribociclib | Selleck |
| Palbociclib | Selleck |
| Pierce Detergent Compatible Bradford Assay Kit (#23246) | Thermo Scientific |
| Western Blot Blocking Buffer (Fish Gelatin) | Takara |
| Immobilon western chemilum HRP substrate | Merck Millipore |
| CDK4 (#12790S) CDK6(#13331S) | Cell Signaling Technology |
| β-Actin (13E5) (#5125S) | |
| Anti-rabbit IgG HRP-linked (#7074S) | |

Cell Lines

CDK4/6 positive cells, T-47D cells (human breast cancer cells) were purchased from the Cell Bank of the Chinese Academy of Sciences; Jurkat (T cell leukemia) cells were purchased from the American Type Culture Collection (ATCC).

Methods

Cell Culture

The cells used in this present disclosure were cultured in a 37° C. incubator containing 5% $CO_2$. The complete cell culture medium was RPMI 1640 medium with 10% fetal bovine serum, and the final concentrations of penicillin and streptomycin were 100 U/mL, respectively. All cells were tested negative for mycoplasma with mycoplasma detection kit before the experiment.

Western-Blot Determination of PROTAD Compounds (1) Cell seeding plate: T-47D cells were added to a 24-well plate at the density of $1.5\times10^5$/mL, and the total volume of 1 mL. The PROTAD compounds of the examples of the present disclosure were tested at the concentrations of 1 nM, 10 nM, 500 nM, 100 nM, 500 nM, respectively, or 5 concentration gradients of 0.04 nM, 0.2 nM, 1 nM, 10 nM, 50 nM, and DMSO and commercial parent inhibitor groups (Ribociclib, Palbociclib) were set as negative control and positive control. After drug treatment for 24 h, the cells were washed with PBS twice, and lyzed by adding 50 μL SDS lysate to each well for lysis on ice for 5 min Lysate was collected in 1.5 mL EP tube, heated at 100° C. in metal bath for 8 mM, then placed on ice for 5 min, centrifuged at 10000 rpm for 5 min. The supernatant was aspirated as the total cell protein extracts. The protein concentrations were determined by the Bradford method. After each sample was at the same concentration, bromophenol blue was added as a loading indicator;

(2) Electrophoresis: the starting voltage of the Bio Rad electrophoresis instrument was 80V for electrophoresis, and when the dye entered the separation gel, the voltage was adjusted to 120V;

(3) Transferring membrane: the filter paper and nitrocellulose membrane (NC membrane) of corresponding size were prepared; both the filter paper and NC membrane were soaked in the transfer electrophoresis buffer. Following the sequence of "filter paper-gel-NC membrane-filter paper" they were put into the electrophoresis tank to transfer the membrane; constant current 400 mA, 1 h; then the antibody incubation and development were carried out according to the antibody instructions of Cell Signaling Technology.

The results showed that all the designed PROTAD compounds of the present disclosure can degrade CDK4/6 protein (as shown in Table 5). Western-blot was used to detect the expression of CDK4/6 protein in T-47D cells 24 h after treatment with PROTAD compound of the present disclosure. Immunoblotting experiments showed that the PROTAD compound (ie., the degrading agent) of the present disclosure can promote the degradation of CDK4/6 protein in a dose-dependent manner.

TABLE 5

CDK4/6 protein degradation results of PROTAD compounds examples for the CDK4/6 target of the present disclosure

| Compounds | $DC_{50}$(nM)/T-47D cell line | $DC_{50}$(nM)/Jurkat cell line |
|---|---|---|
| SIAIS151046 | 1~10 | 1~10 |
| SIAIS219063 | <1 | |
| SIAIS184086 | >500 | |
| SIAIS184087 | 1~10 | |
| SIAIS184088 | 1~10 | |
| SIAIS184089 | 1~10 | |
| SIAIS184090 | 1~10 | 1~10 |
| SIAIS151056 | 100~500 | |
| SIAIS151057 | 100~500 | |
| SIAIS184091 | 1~10 | 1~10 |
| SIAIS219059 | 10~50 | |
| SIAIS219060 | 1~10 | |
| SIAIS219061 | 1~10 | |
| SIAIS219062 | 1~10 | |
| SIAIS219051 | <1 | |
| SIAIS219052 | <1 | |
| SIAIS219053 | <1 | |
| SIAIS184092 | <0.1 | <1 |
| SIAIS219054 | <1 | |
| SIAIS219055 | <1 | |
| SIAIS219100 | <0.04 | |
| SIAIS219101 | <100 | |
| SIAIS219102 | 1~10 | |
| SIAIS219103 | <1 | |
| SIAIS219104 | 1~10 | |
| SIAIS219105 | 0.04~0.2 | |
| SIAIS219111 | <1 | |
| SIAIS219112 | 0.04~0.2 | |
| SIAIS219113 | <1 | |
| SIAIS219114 | 1~10 | |
| SIAIS219115 | | |
| SIAIS219086 | <1 | |
| SIAIS219087 | <1 | |
| SIAIS219088 | 1~10 | |
| SIAIS219089 | 1~10 | |
| SIAIS219090 | 0.2~1 | |
| SIAIS219091 | <1 | |
| SIAIS219106 | 0.04~0.2 | |
| SIAIS219107 | 0.04~0.2 | |
| SIAIS219108 | 0.04~0.2 | |
| SIAIS219109 | 1~10 | |
| SIAIS219110 | 0.04~0.2 | |
| SIAIS262164 | 0.5~5 | |
| SIAIS262165 | 5 | |
| SIAIS262166 | 0.5~5 | |
| SIAIS262167 | 0.5~5 | |
| SIAIS262168 | 0.05~0.5 | |
| SIAIS262173 | 0.05~0.5 | |
| SIAIS262169 | 5 | |
| SIAIS262170 | 50 | |
| SIAIS262171 | 0.5 | |

Evaluation of Biological Activities of ALK Target Compounds

Reagents

| Reagents and antibodies | manufactuer |
|---|---|
| RPMI1640 | Gibico |
| FBS | Gibico |
| Penicillin-Streptomycin | Gibico |
| DMSO | Sigma-Aldrich |
| Brigatinib | Selleck |
| Alectinib | Selleck |
| Cell counting Kit-8 (CCK-8) | Dojindo |
| MG-132 | Merck Millipore |
| Carfilzomib (PR-171) | Selleck |

-continued

| Reagents and antibodies | manufactuer |
|---|---|
| Pierce Detergent Compatible Bradford Assay Kit (#23246) | Thermo Scientific |
| Western Blot Blocking Buffer (Fish Gelatin) | Takara |
| Immobilon western chemilum HRP substrate | Merck Millipore |
| ALK (#3633S) | Cell Signaling Technology |
| phospho-ALK(#69625) | |
| AKT(#4691S) | |
| phospho-AKT(#4060S) | |
| MAPK(#9160S) | |
| phospho-MAPK (#4370S) | |
| STAT3( #12640S) | |
| phospho-STAT3 ( #9145S) | |
| β-Actin (13E5) (#5125S) | |
| Anti-rabbit IgG HRP-linked (#7074S) | |

Cell Lines

ALK-positive SR cells (human large cell immunoblastic lymphoma) were purchased from the American Type Culture Collection (ATCC); H3122 cells (human non-small cell lung cancer) were from the Shanghai University of Science and Technology Lin Haifan's research group.

Methods

Cell Culture

The cells used in this present disclosure were cultured in a 37° C. incubator containing 5% $CO_2$. The complete cell culture medium was RPMI 1640 medium with 10% fetal bovine serum, and the final concentrations of penicillin and streptomycin were 100 U/mL, respectively. All cells were tested negative for mycoplasma with mycoplasma detection kit before the experiment.

Determination of Half Inhibitory Concentration ($IC_{50}$) of PROTAD Compounds of the Present Disclosure on Tumor Cells SR cells were seeded in 100 μL RPMI1640 complete medium at a density of 10,000 cells/well. 100 μL of the inoculated cells were treated with 0.5 μL diluted PROTAD compound of the present disclosure to be tested at 10 successively decreasing concentrations (starting at the highest concentration of 10 μM; 5-fold serial dilutions) After the cells were treated with the drug for 72 h, cell viability was determined according to the CCK-8 reagent operating instructions. The negative control was DMSO, and the positive control was a commercial inhibitor. After CCK-8 treatment for 2 h, the value of O.D.450 was measured using a microplate reader. The formula for calculating the growth inhibition rate of the PROTAD compound of the present disclosure on cells is cell inhibition rate %=(control group O.D. value-experimental group O.D. value)/control group O.D. value*100%, and further the inhibition curve was plotted by Prism Graphpad software and the $IC_{50}$ values of the compound were calculated.

The results showed that the designed PROTAD compounds of the present disclosure can inhibit the proliferation of ALK-positive cells SR (as shown in Table 6). The $IC_{50}$ of all the example compounds were lower than 150 nM. It is worth mentioning that the $IC_{50}$ of the parent inhibitor Brigatinib (Brigatinib) is 10.6 nM, while the $IC_{50}$ of our designed and synthesized PROTAD compound is as low as 0.17 nM, which is more effective in inhibiting tumor cell growth than the parent drug Brigatinib by more than 60 times.

Western-Blot Determination of Half Degradation Concentration ($DC_{50}$) of PROTAD Compounds to Target Proteins (1) Seeding cells on plate: SR cells or H3122 cells were added to a 24-well plate, with a cell density of $3\times10^5$/mL/ $1.5\times10^5$/mL, and the total volume of 1 mL. The PROTAD compounds of the present disclosure and the reference compound SIAIS151072 were tested at the concentrations of 1 nM, 10 nM, 50 nM, 100 nM, 500 nM, respectively, or 5 concentration gradients of 0.01 nM, 0.1 nM, 1 nM, 10 nM, 50 nM, and DMSO and commercial parent inhibitor groups (Brigatinib, Alectinib) were set as a negative control and a positive control. The cells were collected in a 1.5 mL EP tube after 24 hours of drug treatment, centrifuged at 3000 rpm for 3 minutes, and the cell pellets were collected, suspended by adding 30 μL of PBS, and then lyzed by adding 30 μL of 2×SDS lysis solution, heated in metal bath at 100° C. for 8 minutes, then placed on ice for 5 minutes, centrifuged at 10000 rpm for 5 minutes. The supernatant was aspirated as the extracted total cell protein. The protein concentrations were determined by the Bradford method. After each sample was at the same concentration, bromophenol blue was added as a loading indicator;

(2) Electrophoresis: the starting voltage of the Bio Rad electrophoresis instrument was 80V for electrophoresis, and when the dye entered the separation gel, the voltage was adjusted to 120V;

(3) Transferring membrane: the filter paper and nitrocellulose membrane (NC membrane) of corresponding size were prepared; both the filter paper and NC membrane were soaked in the transfer electrophoresis buffer. Following the sequence of "filter paper-gel-NC membrane-filter paper" they were put into the electrophoresis tank to transfer the membrane; constant current 400 mA, 1 h; then the antibody incubation and development were carried out according to the antibody instructions of Cell Signaling Technology.

$DC_{50}$ (drug concentration corresponding to protein degradation to 50%) calculation: according to the gray value of the corresponding Western blotting band after drug treatment, fitting the relationship curve between drug concentration and gray value to calculate the drug concentration range corresponding to half of the gray value. The results were shown in Table 6.

TABLE 6

The $IC_{50}$ values and the ALK protein degradation result ($DC_{50}$ values) of the PROTAD compounds examples for the ALK target of the present disclosure on the proliferation inhibitory activity of ALK positive tumor cells

| Compounds | $IC_{50}$ (nM)/ SR cell line | $DC_{50}$ (nM)/ SR cell line | $DC_{50}$ (nM)/ H3122 cell line |
|---|---|---|---|
| Brigatinib | 2.1 ± 1.2 | 500 | 48.41 |
| Alectinib | 10.6 | | >500 |
| SIAIS1197113 | 23.6 ± 19.4 | | 100 |
| SIAIS1197115 | 42.0 ± 29.3 | | 500 |
| SIAIS1197117 | 16.9 ± 12.0 | | 500 |
| SIAIS1197119 | 13.2 ± 2.6 | | 500 |
| SIAIS1197121 | 7.4 ± 4.8 | 50-500 | 500 |
| SIAIS1197159 | 10.0 ± 5.7 | | 500 |
| SIAIS164137 | 16.8 ± 5.7 | | 500 |
| SIAIS164138 | 24.1 ± 17.5 | | 100 |
| SIAIS164139 | 11.6 ± 6.0 | | 500 |
| SIAIS164140 | 8.7 ± 4.9 | | 500 |
| SIAIS164141 | 3.2 ± 2.4 | 1~50 | 50 |
| SIAIS164142 | 6.4 ± 4.0 | | 50 |
| SIAIS219133 | 2.9 ± 0.1 | | |
| SIAIS219134 | 2.7 ± 0.8 | | |
| SIAIS219135 | 0.33 ± 0.02 | | |
| SIAIS219136 | 0.43 ± 0.09 | | |
| SIAIS219137 | 0.48 ± 0.05 | | |
| SIAIS219138 | 0.29 ± 0.01 | | |
| SIAIS219139 | 1.08 ± 0.1 | | |
| SIAIS219140 | 5.08 ± 0.62 | | |

TABLE 6-continued

The $IC_{50}$ values and the ALK protein degradation result ($DC_{50}$ values) of the PROTAD compounds examples for the ALK target of the present disclosure on the proliferation inhibitory activity of ALK positive tumor cells

| Compounds | $IC_{50}$ (nM)/ SR cell line | $DC_{50}$ (nM)/ SR cell line | $DC_{50}$ (nM)/ H3122 cell line |
|---|---|---|---|
| SIAIS219141 | 5 ± 0.71 | | |
| SIAIS219142 | 7 ± 1 | | |
| SIAIS219143 | 5.53 ± 1.28 | | |
| SIAIS164062 | 11.6 ± 6.2 | 6 | 13 |
| SIAIS164063 | 15.7 ± 9.8 | 500 | 500 |
| SIAIS164064 | 4.4 ± 2.5 | 1.1 | 49 |
| SIAIS164066 | 4.2 ± 2.9 | 5.6 | 11 |
| SIAIS164065 | 2.9 ± 2.7 | 5.2 | 173 |
| SIAIS164067 | 5.7 ± 3.9 | 4.1 | 11 |
| SIAIS219067 | 2.4 ± 1.4 | 0.1~10 | |
| SIAIS219068 | 1.7 ± 0.8 | 1~10 | |
| SIAIS219069 | 0.7 ± 0.3 | 0.1~10 | |
| SIAIS219070 | 0.5 ± 0.3 | 0.1~10 | |
| SIAIS219071 | 0.6 ± 0.4 | 0.01~10 | |
| SIAIS219072 | 0.8 ± 0.5 | 0.1~10 | |
| SIAIS164068 | | | 104.1 |
| SIAIS164069 | | | 100~500 |
| SIAIS164070 | | | 100~500 |
| SIAIS164072 | | | 63 |
| SIAIS164071 | | | 204.5 |
| SIAIS164073 | | | 100~500 |
| SIAIS219012 | 146.5 | | |
| SIAIS219013 | 143.1 | | |
| SIAIS219014 | 100.9 | | |
| SIAIS262161 | 1.86 | | |
| SIAIS262162 | 11.3 | | |
| SIAIS219022 | 80.5 | | |
| SIAIS262163 | 1.6 | | |
| SIAIS219005 | 8.7 | | |
| SIAIS219006 | 16.4 | | |
| SIAIS219007 | 50.1 | | |
| SIAIS262096 | 0.22 ± 0.11 | | |
| SIAIS262158 | 2.9 | | |
| SIAIS262097 | 3.89 ± 0.78 | | |
| SIAIS262098 | 0.29 ± 0.21 | | |
| SIAIS262099 | 0.93 ± 1.11 | | |
| SIAIS262100 | 0.52 ± 0.48 | | |
| SIAIS262159 | 1.0 | | |
| SIAIS262101 | 2.94 ± 3.7 | | |
| SIAIS249066 | 0.17 ± 0.14 | | |
| SIAIS249067 | 0.38 ± 0.18 | | |
| SIAIS249068 | 0.33 ± 0.06 | | |
| SIAIS249069 | 0.81 ± 0.28 | | |
| SIAIS249070 | 0.43 ± 0.11 | | |
| SIAIS219098 | 0.7 ± 0.2 | 0.1-1 | |

Evaluation of Biological Activities of BCR-ABL Target Compounds

Reagents

| Reagents and antibodies | manufactuer |
|---|---|
| RPMI1640 | Gibico |
| FBS | Gibico |
| Penicillin-Streptomycin | Gibico |
| DMSO | Sigma-Aldrich |
| Dasatinib | Selleck |
| Cell counting Kit-8 (CCK-8) | Dojindo |
| MG-132 | Merck Millipore |
| Carfilzomib (PR-171) | Selleck |
| Pierce Detergent Compatible Bradford Assay Kit (#23246) | Thermo Scientific |
| Western Blot Blocking Buffer (Fish Gelatin) | Takara |
| Immobilon western chemilum HRP substrate | Merck Millipore |
| c-Abl (#2862S) | Cell Signaling Technology |
| phospho-c-Abl (Y245) (#2861S) | |
| CRKL (#3182S) | |
| phospho-CRKL(#31815) | |
| C-Kit(#30745) | |
| phospho-CRKL (Y207) (#3181S) | |

| Reagents and antibodies | manufactuer |
|---|---|
| STAT5 ( #9363S) | |
| phospho-STAT5 (Y694) ( #4322S) | |
| β-Actin (13E5) (#5125S) | |
| Anti-rabbit IgG HRP-linked (#7074S) | |

Cell Lines

BCR-ABL positive cells K562 cells (human chronic myeloid leukemia cells) were purchased from the American Type Culture Collection (ATCC);

BCR-ABL Negative Cells:

U937 cells (human monocytic leukemia cell line) were purchased from American Type Culture Collection (ATCC);

HEK293 cells (human embryonic kidney cells) were purchased from American Type Culture Collection (ATCC).

Methods

Cell Culture

The cells used in this present disclosure were cultured in a 37° C. incubator containing 5% $CO_2$. The complete cell culture medium was RPMI 1640 medium with 10% fetal bovine serum, and the final concentrations of penicillin and streptomycin were 100 U/mL, respectively. All cells were tested negative for mycoplasma with mycoplasma detection kit before the experiment.

Determination of Half Inhibitory Concentration ($IC_{50}$) of PROTAD Compounds on Tumor Cells K562 cells were seeded in 100 μL of RPMI1640 complete medium at a density of 20,000 cells/well. 100 μL of the inoculated cells were treated with 100 μL diluted PROTAD compound of the present disclosure to be tested at 9 successively decreasing concentrations (starting at the highest concentration of 10 μM; 3-fold serial dilutions). After the cells were treated with the tested drugs for 48 hours, the cell viability determination was performed in accordance with CCK-8 reagent operating instructions. The negative control was DMSO, and positive control was a commercial inhibitor. After CCK-8 treatment for 2 h, the value of O.D.450 was measured using a microplate reader. The formula for calculating the growth inhibition rate of the PROTAD compound of the present disclosure on cells is cell inhibition rate %=(control group O.D. value−experimental group O.D. value)/control group O.D. value*100%, and further the inhibition curve was plotted by Prism Graphpad software and the $IC_{50}$ values of the compounds were calculated.

The results showed that the designed PROTAD compounds of the present disclosure can inhibit the proliferation of BCR-ABL positive cells K562 (as shown in Table 6). It is worth mentioning that the inhibitor Dasatinib has an $IC_{50}$ of 0.9 nM, while the PROTAD compound we designed and synthesized has a minimum $IC_{50}$ of 0.09 nM, which is 10 times more effective in inhibiting tumor cell growth than the parent drug Dasatinib. Moreover, these PROTAD small molecules of the present disclosure only have a strong proliferation inhibitory effect on BCR-ABL-positive cell lines such as K562, and have no proliferation inhibitory effect on other non-BCR-ABL-positive cell lines, such as U937 cells or HEK293 cells, indicating that PROTAD compounds of the present disclosure are indeed selective.

Western-Blot Determination of Half-Degradation Concentration ($DC_{50}$) of PROTAD Compounds to Target Proteins (1) Cell seeding plate: K562 cells were added to a 24-well plate at the cell density was $3 \times 10^5$/mL, and the total volume of 1.5 mL. The PROTAD compounds of the present disclosure and the reference compound SIAIS151072 were tested at 5 concentration gradients of 1 nM, 10 nM, 100 nM, 1 μM and 10 μM, and DMSO and commercial maternal inhibitor groups (Dasatinib, Bosutinib, Ponatinib) were set as negative control and positive control at the same time. After 24 hours of drug treatment, cells were collected in 1.5 mL EP tube, centrifuged at 3000 rpm for 3 min, and cell pellets were collected, suspended by adding 30 μL PBS, and then lyzed by adding 30 μL of 2×SDS lysate, heated in metal bath at 100° C. for 8 mM, then placed on ice for 5 minutes, centrifuged at 10,000 rpm for 5 minutes. The supernatant was aspirated as the extracted total cell protein. The protein concentrations were determined by the Bradford method. After each sample was at the same concentration, bromophenol blue was added as a loading indicator;

(2) Electrophoresis: the starting voltage of the Bio Rad electrophoresis apparatus was 80V for electrophoresis, and the dye entered the separation gel, the voltage was adjusted to 120V;

(3) Transferring membrane: the filter paper and nitrocellulose membrane (NC membrane) of corresponding size were prepared; both the filter paper and NC membrane were soaked in the transfer electrophoresis buffer. Following the sequence of "filter paper-gel-NC membrane-filter paper" they were put into the electrophoresis tank to transfer the membrane; constant pressure 100V, 1.5 h; then the antibody incubation and development were carried out according to the antibody instruction of Cell Signaling Technology.

The results were shown in Table 7, FIGS. 1 to 15b. Western-blot was used to detect the expression of BCR-ABL and c-ABL proteins in K562 cells 24 h after treatment with PROTAD compound of the present disclosure. Immunoblotting experiments showed that the PROTAD compound of the present disclosure (that is, the degrading agent) can promote degradation of BCR-ABL and c-ABL proteins in a dose-dependent manner, and can degrade more than 90% of the proteins at a concentration of 100 nM. However, the commercial parent inhibitor Dasatinib only inhibited the tyrosine kinase activity of BCR-ABL at a concentration of 100 nM, and did not degrade the target protein BCR-ABL like the degradation agents of the present disclosure. FIGS. 1, 2, 4, 5, 6, 13, 15a, 15b showed that the experiment used (Bio-Rad) Bole TGX precast gel (4-15% gradient separation gel), FIGS. 3, 7, 8, 9, 10, 11, 12, and 14 showed that the experiment used (Bio-Rad) Bole TGX precast gel (10% separation gel), in which the BCR-ABL band targeted by Dasatinib in FIG. 1 was slightly different from that in FIGS. 3, 7, 8, 9, 10, 11 and 12, which was caused by the different gradients of the two SDS-PAGE gel used in the electrophoresis experiment, which does not affect the test results.

Figure 15A:
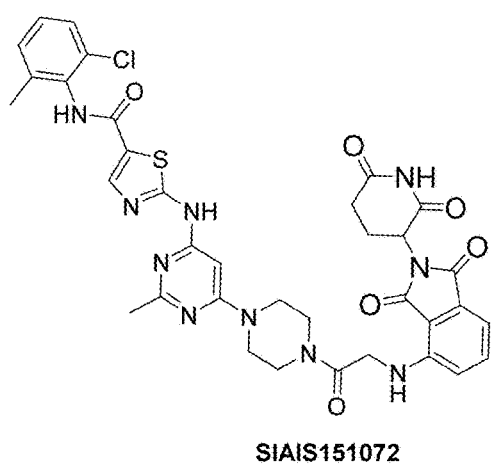
FIGS. 15a and 15b show the Western-blot analysis of the series of the newly designed PROTAD compounds containing the E3 ligase ligands according to the present disclosure. Compared to the comparative PROTAD compound (SIAIS151072) in which the E3 ligase ligand is covalently bound through carbon-nitrogen bond, the PROTAD compound based on carbon-sulfur bond of the present disclosure can effectively degrade BCR-ABL and c-ABL proteins, while the comparative PROTAD compound based on carbon-nitrogen bond has significantly weaker ability to degrade BCR-ABL and c-ABL proteins, which indicates the PROTAD compounds based on carbon-sulfur bond according to the present disclosure have more advantages.
Figure 15A:
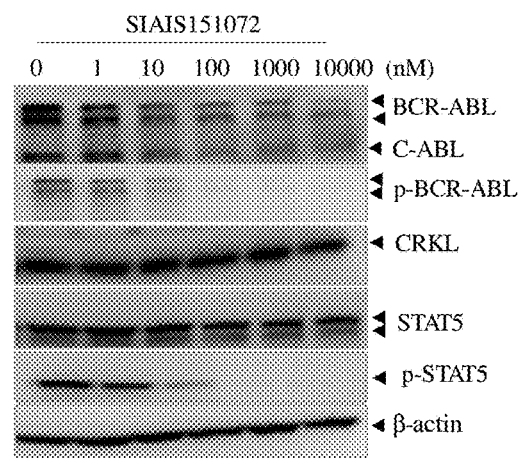
Figure 15B:
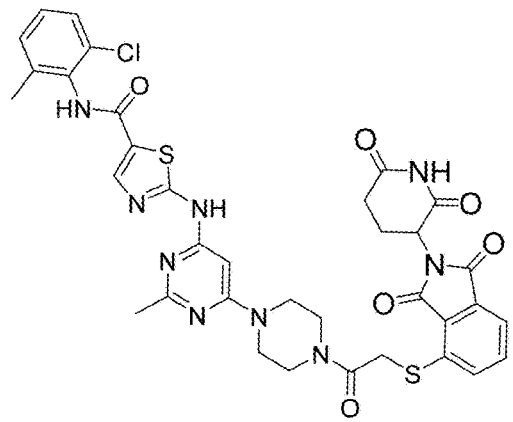
Figure 15B:
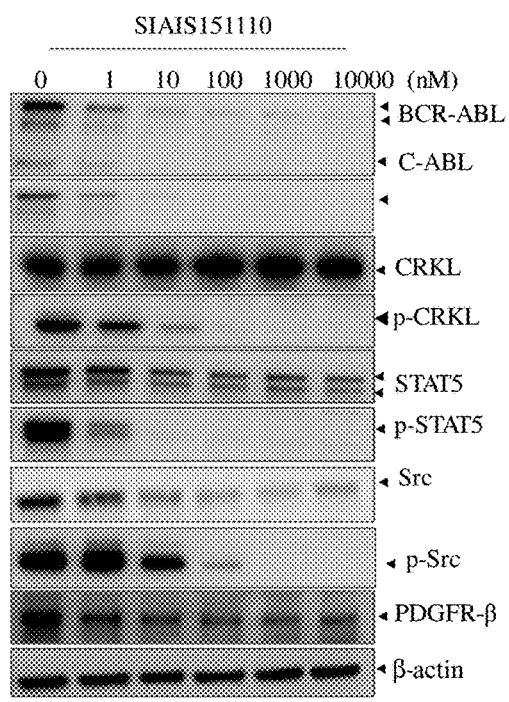

FIGS. 15a and 15b showed the Western-blot analysis of the series of PROTAD compounds of the present disclosure. Compared with the reference PROTAD compound (SIAIS151072) in which the E3 ligase ligand is covalently bound through carbon-nitrogen bond, the carbon-sulfur bonds based PROTAD compound of the present disclosure can effectively degrade BCR-ABL and c-ABL proteins, while the carbon-nitrogen bond based reference PROTAD compound has significantly weaker ability to degrade BCR-ABL and c-ABL proteins, which indicates that carbon-sulfur bond based PROTAD compounds have more advantages.

TABLE 7

The $IC_{50}$ values and the BCR-ABL protein degradation result of the PROTAD compounds examples for the BCR-ABL target of the present disclosure on the proliferation inhibitory activity of BCR-ABL positive tumor cells

| Compounds | $IC_{50}$ (nM)/ K562 cell line | $DC_{50}$ (nM)/ K562 cell line | $IC_{50}$ (nM)/ U937 cell line | $IC_{50}$ (nM)/ HEK293 cell line |
|---|---|---|---|---|
| Dasatinib | 0.9 ± 0.4 | | NA | NA |
| SIAIS151110 | 3.2 | <1 | NA | NA |
| SIAIS172056 | 0.49 | <1 | NA | NA |
| SIAIS151152 | 11.08 | <1 | | |
| SIAIS172106 | 0.83 | <3 | | |
| SIAIS151153 | 15 | 20.7 | | |
| SIAIS151154 | 5.74 | 2 | | |
| SIAIS151155 | 8.66 | 0.8 | | |
| SIAIS151156 | 6.63 | 2.9 | | |
| SIAIS151108 | 206 | 245.1 | NA | NA |
| SIAIS151109 | 148 | 482.9 | NA | NA |
| SIAIS171105 | 5.71 | 56.7 | NA | NA |
| SIAIS171166 | 0.51 | <1 | | |
| SIAIS171106 | 1.74 | 10.3 | NA | NA |
| SIAIS171181 | 0.09 | | | |
| SIAIS171107 | 1.4 | 5.2 | NA | NA |
| SIAIS171108 | 0.54 | <1 | NA | NA |
| SIAIS 171109 | 0.53 | 1~10 | NA | NA |
| SIAIS171110 | 1.33 | 1~10 | NA | NA |
| Bosutinib | 92.63 | | NA | NA |
| SIAIS151168 | | 1~100 | | |
| SIAIS151169 | | 100~1000 | | |
| SIAIS151170 | 400.2 | 1~100 | | |
| SIAIS151171 | 1536 | 1~100 | | |
| SIAIS151172 | 1366 | 1~100 | | |
| SIAIS151173 | 8260 | 1~100 | | |
| Ponatinib | 1.41 | | | |
| SIAIS220046 | 2.97 | | | |
| SIAIS220047 | 3.23 | | | |
| SIAIS220048 | 4.06 | | | |
| SIAIS220049 | 5.75 | | | |
| SIAIS220050 | 12.80 | | | |
| SIAIS220051 | 1.78 | | | |
| SIAIS220052 | 2.62 | | | |
| SIAIS220053 | 4.06 | | | |
| SIAIS220054 | 2.68 | | | |
| SIAIS220055 | 5.58 | | | |
| SIAIS220056 | 5.98 | | | |

Note:
NA: the highest concentration of 10 μM does not show significant proliferation inhibitory.

Evaluation of Biological Activities of PARP Target Compounds

Reagents

| Reagents and antibodies | manufactuer |
|---|---|
| DMEM | Gibico |
| FBS | Gibico |
| Penicillin-Streptomycin | Gibico |
| DMSO | Sigma-Aldrich |
| Olaparib | Selleck |
| Rucaparib | Selleck |
| Niraparib | Selleck |
| Cell counting Kit-8 (CCK-8) | Dojindo |
| Pierce Detergent Compatible Bradford Assay Kit (#23246) | Thermo Scientific |
| Western Blot Blocking Buffer (Fish Gelatin) | Takara |
| Immobilon western chemilum HRP substrate | Merck Millipore |
| PARP (#9542S) | Cell Signaling Technology |
| β-Actin (13E5) (#5125S) | |
| Anti-rabbit IgG HRP-linked (#7074S) | |

Cell Lines

PARP-positive cells MDA-MB-436 cells (human breast cancer cells) were purchased from the American Type Culture Collection (ATCC).

Methods

Cell Culture

The cells used in this present disclosure were cultured in a 37° C. incubator containing 5% $CO_2$. The complete cell culture medium was DMEM medium with 10% fetal bovine serum, and the final concentrations of penicillin and streptomycin were 100 U/mL, respectively. All cells were tested negative for mycoplasma with mycoplasma detection kit before the experiment.

Determination of Half Inhibitory Concentration ($IC_{50}$) of PROTAD Compounds on Tumor Cells MDA-MB-436 cells were seeded in 100 μL DMEM complete medium at a density of 3500 cells/well. 100 μL of the inoculated cells were treated with 0.5 μL diluted PROTAD compounds of the present disclosure to be tested at 10 successively decreasing concentrations (starting at the highest concentration of 50 μM; 3-fold serial dilutions). After the cells were treated with the tested drugs for 72 hours, cell viability was determined according to the CCK-8 reagent operating instructions. The negative control was DMSO, and the positive control was a commercial inhibitor. After CCK-8 treatment for 2 h, the value of O.D.450 was measured using a microplate reader. The formula for calculating the growth inhibition rate of the PROTAD compound of the present disclosure on cells is cell inhibition rate %=(control group O.D. value−experimental group O.D. value)/control group O.D. value*100%, and further the inhibition curve was plotted by Prism Graphpad software and the $IC_{50}$ values of the compounds were calculated.

The results showed that the designed PROTAD compounds of the present disclosure can inhibit the proliferation of PARP-positive cells MDA-MB-436 (as shown in Table 8). It is worth mentioning that the inhibitor Olaparib has an $IC_{50}$ of 2.31 μM, while the PROTAD compound we designed and synthesized has a minimum $IC_{50}$ of 2.09 μM, which is comparable to the parent drug Olaparib in inhibiting tumor cell growth.

TABLE 8

The $IC_{50}$ values of PROTAD compounds examples for the PARP target of the present disclosure on the proliferation inhibitory activity of PARP positive tumor cells

| Compounds | $IC_{50}$ (μM)/MDA-MB-436 cell line |
|---|---|
| Olaparib | 2.31 |
| Rucaparib | 1.12 |
| Niraparib | 1.0 |
| SIAIS180063 | 6.45 |
| SIAIS180064 | 5.78 |
| SIAIS180065 | 3.82 |
| SIAIS180066 | 3.57 |
| SIAIS180067 | 2.90 |
| SIAIS180068 | 2.09 |

Evaluation of Biological Activities of ER Target Compounds
Reagents

| reagents and antibdies | manufactuer |
|---|---|
| RPMI1640 | Gibico |
| FBS | Gibico |
| Penicillin-Streptomycin | Gibico |
| DMSO | Sigma-Aldrich |
| Insulin | meilunbio |
| Tamoxifen | Selleck |
| Toremifene | Selleck |
| Cell counting Kit-8 (CCK-8) | Dojindo |
| Pierce Detergent Compatible Bradford Assay Kit (#23246) | Thermo Scientific |
| Western Blot Blocking Buffer (Fish Gelatin) | Takara |
| Immobilon western chemilum HRP substrate | Merck Millipore |
| ER (#8644S) | Cell Signaling Technology |
| β-Actin (13E5) (#5125S) | |
| Anti-rabbit IgG HRP-linked (#7074S) | |

Cell Lines

ER positive cells T-47D cells (human breast cancer cells) were purchased from the Cell Bank of the Chinese Academy of Sciences;

Methods

Cell Culture

The cells used in this present disclosure were cultured in a 37° C. incubator containing 5% $CO_2$. The complete cell culture medium was RPMI 1640 medium with 10% fetal bovine serum, and the final concentrations of penicillin and streptomycin were 100 U/mL, respectively. All cells were tested negative for mycoplasma with mycoplasma detection kit before the experiment.

Western Blot Determination of the Half Degradation Concentration ($DC_{50}$) of the PROTAD Compounds on Target Proteins (1) Cell seeding plate: T-47D cells were added to a 24-well plate at the cell density of $1.5×10^5$/mL, and the total volume of 1 mL. The PROTAD compounds of the present disclosure were tested at 5 concentration of 1 nM, 10 nM, 50 nM, 100 nM, 500 nM, respectively, or 5 concentration gradients of 0.04 nM, 0.2 nM, 1 nM, 10 nM, 50 nM, and DMSO and commercial parent inhibitor groups (tamoxifen, toremifene) were set as negative and positive controls at the same time. After the drug treatment for 24 h, cells were washed twice with PBS, and lyzed by adding 50 μL of SDS lysate to each well for lysis on ice for 5 min. The lysate was collected in a 1.5 mL EP tube, heated at 100° C. in a metal bath for 8 mM, then placed on ice for 5 min, centrifuged at 10000 rpm for 5 min. The supernatant was aspirated as the extracted total cell protein. The protein concentrations were determined by the Bradford method. After each sample was at the same concentration, bromophenol blue was added as a loading indicator;

(2) Electrophoresis: the starting voltage of the Bio Rad electrophoresis apparatus I was 80V for electrophoresis, and when the dye entered the separation gel, the voltage was adjusted to 120V;

(3) Transferring membrane: the filter paper and nitrocellulose membrane (NC membrane) of corresponding size were prepared; both the filter paper and NC membrane were soaked in the transfer electrophoresis buffer. Following the sequence of "filter paper-gel-NC membrane-filter paper" they were put into the electrophoresis tank to transfer the membrane; constant current 400 mA, 1 h; then the antibody incubation and development were carried out in accordance with the antibody instructions of Cell Signaling Technology.

The results showed that the designed PROTAD compounds of the present disclosure can degrade ER protein (as shown in Table 9). Western-blot was used to detect the expression of ER protein in T-47D cells 24 h after treatment with PROTAD compounds of the present disclosure. Immunoblotting experiments showed that some PROTAD compounds of the present disclosure (that is, the degradation agent) can promote the degradation of ER protein in a dose-dependent manner.

TABLE 9

Degradation results of PROTAD compounds for ER target of the present disclosure on ER protein

| Compounds | $DC_{50}$ (nM)/T-47D cell line |
|---|---|
| SIAIS251132 | 50~100 |
| SIAIS208170 | 10 |
| SIAIS208171 | 10 |

Evaluation of Biological Activities of BET Target Compounds
Reagents

| reagents and antibodies | manufactuer |
|---|---|
| RPMI1640 | Gibico |
| DMEM | Gibico |
| IMDM | Gibico |
| FBS | Gibico |
| Penicillin-Streptomycin | Gibico |
| DMSO | Sigma-Aldrich |
| JQ-1 | Selleck |
| Cell counting Kit-8 (CCK-8) | Dojindo |
| Pierce Detergent Compatible Bradford Assay Kit (#23246) | Thermo Scientific |
| Western Blot Blocking Buffer (Fish Gelatin) | Takara |
| Immobilon western chemilum HRP substrate | Merck Millipore |

-continued

| reagents and antibodies | manufactuer |
|---|---|
| BRD2 (#5848S) | Cell Signaling Technology |
| BRD4 (#13440S) | |
| β-Actin (13E5) (#5125S) | |
| Anti-rabbit IgG HRP-linked (#7074S) | |

Cell Lines

BET-expressing cells MV-4-11 cells (human B granulocytic leukemia cells), MDA-MB-231 cells (human breast cancer cells), MDA-MB-468 cells (human breast cancer cells), MDA-MB-453 Cells (human breast cancer cells), MM1S cells (myeloma (immunoglobulin A lambda), B lymphoblasts) and SR cells (human large cell immunoblast lymphoma) were purchased from the American Type Culture Collection (ATCC).

Methods

Cell Culture

The cells used in this present disclosure were cultured in a 37° C. incubator containing 5% $CO_2$. The complete cell culture medium was RPMI 1640/IMDM/DMEM medium with 10% fetal bovine serum, and the final concentrations of penicillin and streptomycin were 100 U/mL, respectively. All cells were tested negative for mycoplasma with mycoplasma detection kit before the experiment.

Determination of the Half Inhibitory Concentration ($IC_{50}$) of PROTAD Compounds on Tumor Cells MV-411 cells, MM1S cells and SR cells were seeded in 100 μL IMDM/RPMI1640/DMEM complete medium at a density of 15000/10000 cells/well; MDA-MB-231 cells, MDA-MB-468 cells, and MDA-MB453 cells were seeded in 100 μL IMDM/RPMI1640/DMEM complete medium at a density of 3000/5000 cells/well, respectively. 100 μL of the inoculated cells were treated with 0.5 μL diluted PROTAD compounds of the present disclosure to be tested at 10 successively decreasing concentrations (starting at the highest concentration of 10 μM; 5-fold serial dilutions). After the cells were treated with the tested drugs 48/72 h, the cell viability was determined according to the CCK-8 reagent manual. The negative control was DMSO, and the positive control was a commercial inhibitor. After CCK-8 treatment for 2 h, the value of O.D.450 was measured using a microplate reader. The formula for calculating the growth inhibition rate of the PROTAD compounds of the present disclosure on cells is cell inhibition rate %=(control group O.D. value−experimental group O.D. value)/control group O.D. value*100%, and further the inhibition curve was plotted by Prism Graphpad software and The $IC_{50}$ of the compounds were calculated.

The results showed that the designed PROTAD compounds of the present disclosure can inhibit the proliferation of cells expressing BET (as shown in Tables 10 and 11). It is worth mentioning that the $IC_{50}$ of the inhibitor JQ-1 in the MV-4-11 cell line is 9.0 nM, while the $IC_{50}$ of the PROTAD compound we designed and synthesized is as low as 0.08 nM, which is more effective in inhibiting tumor cell growth than the drug JQ-1 by more than 100 times.

Western-Blot Determination of the Half-Degradation Concentration ($DC_{50}$) of the PROTAD Compounds on the Target Proteins (1) Cell seeding plate: MV-4-11 cells were added to a 24-well plate at the cell density of $3\times10^5$/mL, and the total volume of 1 mL. The PROTAD compounds of the present disclosure were tested at the concentrations of 1 nM, 10 nM, 50 nM, 100 nM, 500 nM, or 5 concentration gradients of 0.001 nM, 0.05 nM, 0.1 nM, 1 nM, 20 nM, and DMSO and commercial parent inhibitor group JQ-1 were set as negative control and positive control at the same time. Cells were collected in 1.5 mL EP after 24 hours of drug treatment, centrifuged at 3000 rpm for 3 min in the tube, and the cell pellets were collected, suspended by adding 30 μL of PBS, and then lyzed by adding 30 μL of 2×SDS lysate, heated in a metal bath at 100° C. for 8 min, then placed on ice for 5 min, centrifuged at 10,000 rpm for 5 min. The supernatant was aspirated as total cell protein extracted. The protein concentrations were determined by the Bradford method. After each sample was at the same concentration, bromophenol blue was added as a loading indicator;

(2) Electrophoresis: the starting voltage of the Bio Rad electrophoresis apparatus was 80V for electrophoresis, and when the dye entered the separation gel, the voltage was adjusted to 120V;

(3) Transferring membrane: the filter paper and nitrocellulose membrane (NC membrane) of corresponding size were prepared; both the filter paper and NC membrane were soaked in the transfer electrophoresis buffer. Following the sequence of "filter paper-gel-NC membrane-filter paper" they were put into the electrophoresis tank to transfer the membrane; constant pressure 100V, 1.5 h; then the antibody incubation and development were carried out according to the antibody instruction of Cell Signaling Technology. The results are shown in Table 11.

Figure 16A:
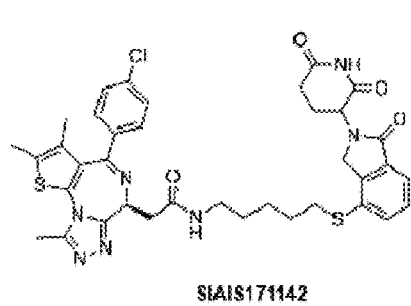
FIGS. 16a-c show the Western-blot detection of the series of the newly designed PROTAD compounds containing the E3 ligase ligands according to the present disclosure. Compared to the comparative PROTAD compounds in which the E3 ligase ligand is covalently bound by carbon nitrogen bond or carbon oxygen bond (SIAIS213110, SIAIS271066), the PROTAD compounds based on carbon-sulfur bonds according to the present disclosure can effectively degrade BRD2 and BRD4 proteins, while the comparative PROTAD compounds based on carbon-nitrogen bond or carbon-oxygen bond have significantly weaker ability to degrade BRD2 and BRD4 proteins, indicating that the PROTAD compounds based on carbon-sulfur bond according to the present disclosure have more advantages.
Figure 16A:
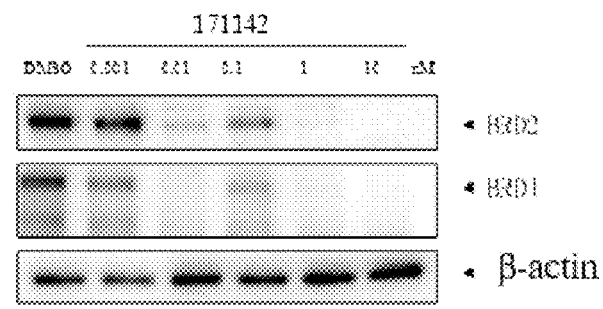
Figure 16B:
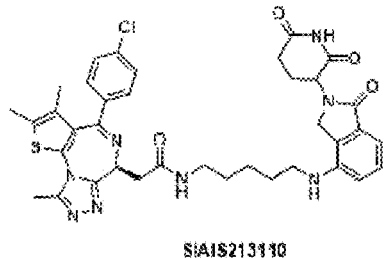
Figure 16B:
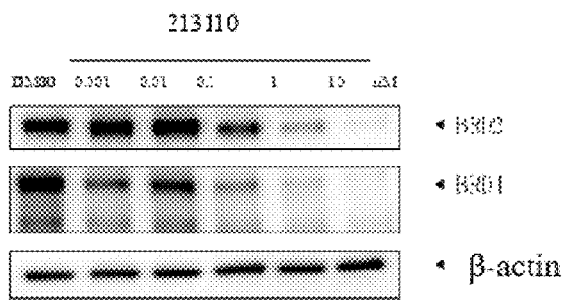
Figure 16C:
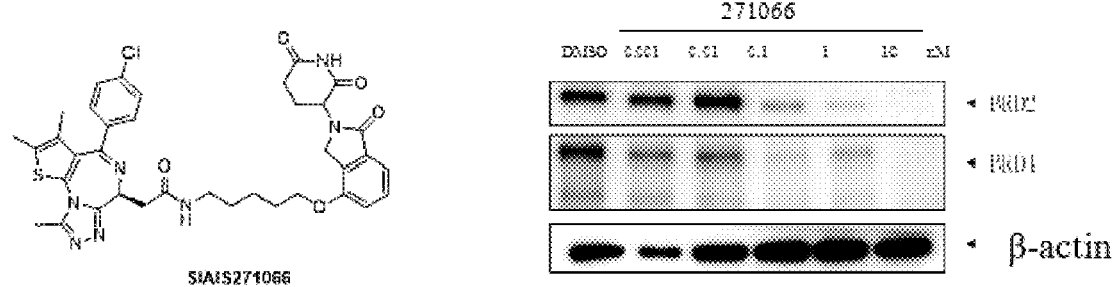

FIGS. 16a-c showed the Western-blot analysis of the series of PROTAD compounds of the present disclosure. Compared to the carbon-nitrogen bonds or carbon-oxygen bonds based reference PROTAD compound (SIAIS213110, SIAIS271066), the carbon-sulfur bond based PROTAD compound of the present disclosure can effectively degrade BRD2 and BRD4 proteins, while the carbon-nitrogen bond or carbon-oxygen bond based reference PROTAD compounds have significantly weaker ability to degrade BRD2 and BRD4 proteins, and indicating that the carbon-sulfur bond based PROTAD compounds have more advantageous.

TABLE 10

The $IC_{50}$ values of PROTAD compounds for the BET target of the present disclosure on the proliferation inhibitory activity of BET-expressing tumor cells

| Compounds | $IC_{50}$ (nM)/MV-4-11 cell line | $IC_{50}$ (nM)/MDA-MB-231 cell line | $IC_{50}$ (nM)/MDA-MB-468 cell line | $IC_{50}$ (nM)/MDA-MB-453 cell line | $IC_{50}$ (nM)/MM1S cell line |
|---|---|---|---|---|---|
| JQ-1 | 67.7 ± 16.7 | | | | |
| SIAIS213113 | 21.56/12.9 | | | | |
| SIAIS213130 | 29.77/17.72 | | | | |
| SIAIS213070 | 2.0 ± 0.4 | | | | 12.8 |
| SIAIS213075 | 6.5 ± 2.5 | | | | 96.12 |
| SIAIS171036 | 4.5 ± 3.2 | 242 ± 65 | 100 ± 21 | 162.6/214 | 8.60 |

TABLE 10-continued

The IC$_{50}$ values of PROTAD compounds for the BET target of the present disclosure on the proliferation inhibitory activity of BET-expressing tumor cells

| Compounds | IC$_{50}$ (nM)/MV-4-11 cell line | IC$_{50}$ (nM)/MDA-MB-231 cell line | IC$_{50}$ (nM)/MDA-MB-468 cell line | IC$_{50}$ (nM)/MDA-MB-453 cell line | IC$_{50}$ (nM)/MM1S cell line |
|---|---|---|---|---|---|
| SIAIS171013 | 8.6 ± 8.7 | >2824 | >300 | 1087 | 22.57 |
| SIAIS171037 | 6.2 ± 4.1 | 88 ± 38 | 52.5 ± 24 | 153.8/225.7 | 5.36 |
| SIAIS171038 | 6.2 ± 3.0 | 182 ± 89 | 61 ± 8 | 135.1/229.9 | 7.77 |
| SIAIS171039 | 2.7 ± 2.5 | 98 ± 82 | 92 ± 43 | 166.9/161.8 | 0.82 |
| SIAIS171040 | 2.2 ± 2.0 | 69 ± 38 | 46 ± 12 | 85/75.7 | 2.78 |
| SIAIS171049 | 7.2 ± 9.2 | 645 ± 249 | 1729 ± 1650 | 165.5/237.2 | 3.06 |
| SIAIS213100 | 0.5 ± 0.1 | | | | |
| SIAIS213072 | 0.5 ± 0.1 | | | | 3.03 |
| SIAIS213112 | | | | | |
| SIAIS171138 | 8.6 ± 9.1 | >10000 | >1735 | 2629/2804 | 3.10 |
| SIAIS171139 | 1.1 ± 0.6 | >10000 | >10000 | 451.6 | 2.03 |
| SIAIS171141 | 0.25 ± 0.2 | 19.9 ± 9.2 | 10 ± 2 | 111.9/98.01 | 0.24 |
| SIAIS171142 | 0.08 ± 0.03 | 17.7 ± 7.6 | 6.1 ± 0.4 | 37.43/37.07 | 0.31 |
| SIAIS171143 | 0.3 ± 0.0 | 313 ± 309 | 376 ± 55 | 215.5/94.22 | 0.32 |
| SIAIS171144 | 0.9 ± 0.8 | 55 ± 31 | 9.6 ± 2.9 | 52.34/63.89 | 0.70 |
| SIAIS171145 | 2.0 ± 1.8 | 537 ± 148 | 948 ± 241 | 135.4/222.3 | 1.2 |
| SIAIS213094 | 4.9 ± 0.8 | | | | 42.52 |
| SIAIS213117 | 0.063/0.041 | | | | |
| SIAIS213138 | 0.084/0.051 | | | | |
| SIAIS213131 | 0.10/0.027 | | | | |
| SIAIS213141 | 0.031/0.014 | | | | |
| SIAIS213136 | 0.068/0.040 | | | | |
| SIAIS213139 | 0.027 ± 0.006 | | | | |
| SIAIS213133 | 0.036 ± 0.045 | | | | |

TABLE 11

The IC$_{50}$ value and the BET protein degradation results (DC$_{50}$ values) of the PROTAD compounds for the BET target of the present disclosure on the proliferation inhibitory activity of tumor cells expressing BET

| Compunds | IC$_{50}$ (nM)/SR cell line | DC$_{50}$ (nM)/MV-4-11 cell line BRD2 degradation |
|---|---|---|
| JQ-1 | | |
| SIAIS213070 | | 0.1~1 |
| SIAIS213075 | | |
| SIAIS171036 | | 2~10 |
| SIAIS171013 | | 2~10 |
| SIAIS171037 | | <0.4 |
| SIAIS171038 | | <0.4 |
| SIAIS171039 | | 0.4~2 |
| SIAIS171040 | | 0.0001 |
| SIAIS171049 | | 2~10 |
| SIAIS213100 | | |
| SIAIS213072 | | 0.0001~0.005 |
| SIAIS213112 | | |
| SIAIS171138 | | 0.4~2 |
| SIAIS171139 | | 0.4~2 |
| SIAIS171141 | 3.91 | <0.0001 |
| SIAIS171142 | 2.42 | <0.0001 |
| SIAIS171143 | 1.48 | <0.0001 |
| SIAIS171144 | | 0.0001 |
| SIAIS171145 | | 0.04~2 |
| SIAIS213094 | | |

The present invention is not limited by the embodiments shown and described above, but can be changed within the scope of the claims.

The invention claimed is:

1. A compound of formula (IV):

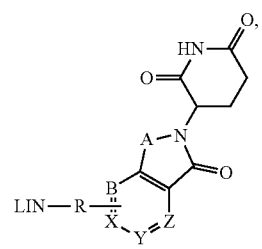

Formula (IV)

wherein,
A represents CH$_2$ or CO,
B, X, Y, and Z represent CH,
R represents S, SO, or SO$_2$, and
LIN is a linking group and represents W-alkylene-,
wherein -alkylene- is an alkylene group that is a linear or branched alkylene group optionally interrupted one or more times by one or more groups selected from the group consisting of O, CONH, NHCO, NH, or any combination thereof,
wherein the linear or branched alkylene group is optionally substituted with one or more substituents substituents selected from hydroxyl, amino, mercapto and halogen, or
the LIN represents: W—(CH$_2$)$_{n11}$—triazolylene—(CH$_2$)$_{n12}$—, W—(CH$_2$)$_{n11}$—triazolylene—(CH$_2$) $_{n12}$—(O(CH$_2$)$_{n13}$)$_{m11}$—, W—(CH$_2$) n11—(O (CH$_2$) n12) m11—O—(CH$_2$) n13—triazolylene—(CH$_2$) n14—(O(CH$_2$) n15) m12—O—(CH$_2$) n16—, W—(CH$_2$) n11-triazolylene—(CH$_2$) n12—(O(CH$_2$) n13) m11—O—(CH$_2$)$_{n14}$—, or W—(CH$_2$)$_{n11}$—(O (CH$_2$)$_{n12}$)$_{m11}$—O—(CH$_2$)$_{n13}$—triazolylene—

$(CH_2)_{n14}$—; and wherein n11, n12, n13, n14, n15, n16, m11, m12 each independently represent an integer of 1, 2, 3, 4, 5, 6, 7, 8, 9, 10, 11, 12, 13, 14, 15, 16, 17, 18, 19, or 20; or the LIN represents: W—$(CH_2)_2$—O—$CH_2$—phenylene—$CH_2$—O—$(CH_2)_2$—, W—$CH_2$—phenylene—$CH_2$—, W—$(CH_2)_3$—phenylene—$(CH_2)_3$—, W—$(CH_2)_2$—O—$CH_2$—piperazinylene—$CH_2$—O—$(CH_2)_2$—, or W—$(CH_2)_3$—piperazinylene—$(CH_2)_3$—;

wherein W— represents $N_3$, CHO, COOH, $NH_2$, halogen, methanesulfonyloxy, trifluoromethanesulfonyloxy, or p-toluenesulfonyloxy;

or a salt, enantiomer, stereoisomer, or solvate thereof.

2. The compound of formula (IV) or a salt, enantiomer, stereoisomer, or solvate thereof according to claim 1, wherein the LIN represents: W—$C_{1-30}$ alkylene-, W—$(CH_2)_{n1}$—$(O(CH_2)_{n2})_{m1}$—, W—$(CH_2)_{n1}$—$(O(CH_2)_{n2})_{m1}$—$(O(CH_2)_{n3})_{m2}$—, W—$(CR_{a1}R_{a2})_{n1}$—$(O(CR_{a3}R_{a4})_{n2})_{m1}$—, W—$(CR_{a5}R_{a6})_{n1}$—$(O(CR_{a7}R_{a8})_{n2})_{m1}$—$(O(CR_{a9}R_{a10})_{n3})_{m2}$—, W—$(CH_2)_{n1}$—$(CONH—(CH_2)_{n2})_{m1}$—, W—$(CH_2)_{n1}$—$(CONH—(CH_2)_{n2})_{m1}$—$(O(CH_2)_{n3})_{m2}$—, W—$(CH_2)_{n1}$—$(O(CH_2)_{n2})_{m1}$—O—$(CH_2)_{n3}$—CONH—$(CH_2)_{n4}$—$(O(CH_2)_{n5})_{m2}$—O—$(CH_2)_{n6}$—, W—$(CR_{a11}R_{a12})_{n1}$—$(O(CR_{a13}R_{a14})_{n2})_{m1}$—O—$(CR_{a15}R_{a16})_{n3}$—CONH—$(CR_{a17}R_{a18})_{n4}$—$(O(CR_{a19}R_{a20})_{n5})_{m2}$—O—$(CR_{a21}R_{a22})_{n6}$—, W—$(CR_{a23}R_{a24})_{n1}$—CONH—$(O(CR_{a25}R_{a26})_{n2})_{m1}$—, W—$(CH_2)_{n1}$—$(NHCO—(CH_2)_{n2})_{m1}$—, W—$(CH_2)_{n1}$—$(NHCO—(CH_2)_{n2})_{m1}$—$(O(CH_2)_{n3})_{m2}$;

wherein $R_{a1}$, $R_{a2}$, $R_{a3}$, $R_{a4}$, $R_{a5}$, $R_{a6}$, $R_{a7}$, $R_{a8}$, $R_{a9}$, $R_{a10}$, $R_{a11}$, $R_{a12}$, $R_{a13}$, $R_{a14}$, $R_{a15}$, $R_{a16}$, $R_{a17}$, $R_{a18}$, $R_{a19}$, $R_{a20}$, $R_{a21}$, $R_{a22}$, $R_{a23}$, $R_{a24}$, $R_{a25}$, $R_{a26}$ each independently represent H, linear or branched $C_1$-$C_{10}$ alkyl or $C_3$-$C_{10}$ cycloalkyl, wherein in the same group LIN, $R_{a1}$, $R_{a2}$, $R_{a3}$, and $R_{a4}$ are not H at the same time, $R_{a5}$, $R_{a6}$, $R_{a7}$, $R_{a8}$, $R_{a9}$, and $R_{a10}$ are not H at the same time, $R_{a11}$, $R_{a12}$, $R_{a13}$, $R_{a14}$, $R_{a15}$, $R_{a16}$, $R_{a17}$, $R_{a18}$, $R_{a19}$, $R_{a20}$, $R_{a21}$, and $R_{a22}$ are not H at the same time, or $R_{a23}$, $R_{a24}$, $R_{a25}$, and $R_{a26}$ are not H at the same time; and wherein n1, n2, n3, n4, n5, n6, m1, m2 each independently represent an integer of 1, 2, 3, 4, 5, 6, 7, 8, 9, 10, 11, 12, 13, 14, 15, 16, 17, 18, 19, or 20.

3. The compound of formula (IV) or a salt, enantiomer, stereoisomer, or solvate thereof according to claim 2, wherein the LIN represents:

W—$CH_2$—; W—$(CH_2)_2$—; W—$(CH_2)_3$—; W—$(CH_2)_4$—; W—$(CH_2)_5$—; W—$(CH_2)_6$—; W—$(CH_2)_7$—; W—$(CH_2)_8$—; W—$(CH_2)_9$—; W—$(CH_2)_{10}$—; W—$(CH_2)_{11}$—; W—$(CH_2)_{12}$—; W—$(CH_2)_{13}$—; W—$(CH_2)_{14}$—; W—$(CH_2)_{15}$—; W—$(CH_2)_{16}$—; W—$(CH_2)_{17}$—; W—$(CH_2)_{18}$—; W—$(CH_2)_{19}$—; W—$(CH_2)_{20}$—; W—$(CH_2)_{21}$—; W—$(CH_2)_{22}$—; W—$(CH_2)_{23}$—; W—$(CH_2)_{24}$—; W—$(CH_2)_{25}$—; W—$(CH_2)_{26}$—; W—$(CH_2)_{27}$—; W—$(CH_2)_{28}$—; W—$(CH_2)_{29}$—; or W—$(CH_2)_{30}$—.

4. The compound of formula (IV) or a salt, enantiomer, stereoisomer, or solvate thereof according to claim 2, wherein the LIN represents: W—$CH_2$—O—$(CH_2)_2$—, W—$CH_2$—$(O(CH_2)_2)_2$—, W—$CH_2$—$(O(CH_2)_2)_3$—, W—$CH_2$—$(O(CH_2)_2)_4$—, W—$CH_2$—$(O(CH_2)_2)_5$—, W—$CH_2$—$(O(CH_2)_2)_6$—, W—$CH_2$—$(O(CH_2)_2)_7$—, W—$CH_2$—$(O(CH_2)_2)_8$—, W—$CH_2$—$(O(CH_2)_2)_9$—, W—$CH_2$—$(O(CH_2)_2)_{10}$—, W—$(CH_2)_2$—O—$(CH_2)_2$—, W—$(CH_2)_2$—$(O(CH_2)_2)_2$—, W—$(CH_2)_2$—$(O(CH_2)_2)_3$—, W—$(CH_2)_2$—$(O(CH_2)_2)_4$—, W—$(CH_2)_2$—$(O(CH_2)_2)_5$—, W—$(CH_2)_2$—$(O(CH_2)_2)_6$—, W—$(CH_2)_2$—$(O(CH_2)_2)7$—, W—$(CH_2)_2$—$(O(CH_2)_2)_8$—, W—$(CH_2)_2$—$(O(CH_2)2)9$—, W—$(CH_2)_2$—$(O(CH_2)_2)_{10}$—, W—$(CH_2)_3$—O—$(CH_2)_2$—, W—$(CH_2)_3$—$(O(CH_2)_2)_2$—, W—$(CH_2)3$—$(O(CH_2)_2)_3$—, W—$(CH_2)_2$—$(O(CH_2)_2)_4$—, W—$(CH_2)_3$—$(O(CH_2)_2)5$—, W—$(CH_2)_3$—$(O(CH_2)_2)_6$—, W—$(CH_2)_3$—$(O(CH_2)_2)_7$—, W—$(CH_2)_2$—$(O(CH_2)_2)_8$—, W—$(CH_2)_3$—$(O(CH_2)_2)9$—, W—$(CH_2)_3$—$(O(CH_2)_2)_{10}$—, W—$(CH_2)_4$—O—$(CH_2)_2$—, W—$(CH_2)4$—$(O(CH_2)_2)_2$—, W—$(CH_2)_4$—$(O(CH_2)_2)3$—, W—$(CH_2)_4$—$(O(CH_2)_2)_4$—, W—$(CH_2)_4$—$(O(CH_2)_2)_5$—, W—$(CH_2)_4$—$(O(CH_2)_2)_6$—, W—$(CH_2)_4$—$(O(CH_2)_2)7$—, W—$(CH_2)_4$—$(O(CH_2)_2)_8$—, W—$(CH_2)_4$—$(O(CH_2)_2)_9$—, W—$(CH_2)_4$—$(O(CH_2)_2)_{10}$—, W—$CH_2$—O—$(CH_2)3$—, W—$CH2$—$(O(CH_2)_3)_2$—, W—$CH_2$—$(O(CH_2)_3)_3$—, W—$CH_2$—$(O(CH_2)_3)_4$—, W—$CH_2$—$(O(CH_2)_3)_5$—, W—$CH_2$—$(O(CH_2)_3)_6$—, W—$CH_2$—$(O(CH_2)_3)_7$—, W—$CH_2$—$(O(CH_2)3)8$—, W—$CH_2$—$(O(CH_2)_3)_9$—, W—$CH_2$—$(O(CH_2)_3)_{10}$—, W—$(CH_2)_2$—O—$(CH_2)_3$—, W—$(CH_2)_2$—$(O(CH_2)_3)_2$—, W—$(CH_2)_2$—$(O(CH_2)_3)_3$—, W—$(CH_2)_2$—$(O(CH_2)_3)_4$—, W—$(CH_2)_2$—$(O(CH_2)_3)_5$—, W—$(CH_2)_2$—$(O(CH_2)_3)_6$—, W—$(CH_2)_2$—$(O(CH_2)_3)_7$—, W—$(CH_2)_2$—$(O(CH_2)_3)_8$—, W—$(CH_2)_2$—$(O(CH_2)_3)_9$—, W—$(CH_2)_2$—$(O(CH_2)_3)_{10}$—, W—$(CH_2)_3$—O—$(CH_2)_3$—, W—$(CH_2)_{33}$—$(O(CH_2)_3)_2$—, W—$(CH_2)_3$—$(O(CH_2)_3)_3$—, W—$(CH_2)_3$—$(O(CH_2)_3)_4$—, W—$(CH_2)_3$—$(O(CH_2)_3)_5$—, W—$(CH_2)_{33}$—$(O(CH_2)_3)_6$—, W—$(CH_2)_3$—$(O(CH_2)_3)_7$—, W—$(CH_2)_3$—$(O(CH_2)_3)_8$—, W—$(CH_2)_3$—$(O(CH_2)_3)_9$—, W—$(CH_2)_3$—$(O(CH_2)_3)_{10}$—, W—$CH_2$—O—$(CH_2)_2$—O—$(CH_2)_3$—, W—$CH_2$—$(O(CH_2)_2)_2$—$(O(CH_2)_3)_2$—, W—$CH_2$—$(O(CH_2)_2)_3$—$(O(CH_2)_3)_3$—, W—$CH_2$—$(O(CH_2)_2)_4$—$(O(CH_2)_3)_4$—, W—$CH_2$—$(O(CH_2)_2)_5$—$(O(CH_2)_3)_5$—, W—$CH_2$—$(O(CH_2)_2)_6$—$(O(CH_2)_3)_6$—, W—$(CH_2)_2$—O—$(CH_2)_2$—O—$(CH_2)_3$—, W—$(CH_2)_2$—$(O(CH_2)_2)_2$—$(O(CH_2)_3)_2$—, W—$(CH_2)_2$—$(O(CH_2)_2)_3$—$(O(CH_2)_3)_3$—, W—$(CH_2)_2$—$(O(CH_2)_2)_4$—$(O(CH_2)_3)_4$—, W—$(CH_2)_2$—$(O(CH_2)_2)5$—$(O(CH_2)_3)_5$—, W—$(CH_2)_2$—$(O(CH_2)_2)_6$—$(O(CH_2)_3)_6$—, W—$(CH_2)_3$—O—$(CH_2)_2$—O—$(CH_2)_3$—, W—$(CH_2)3$—$(O(CH_2)_2)_2$—$(O(CH_2)_3)_2$—, W—$(CH_2)_3$—$(O(CH_2)_2)_3$—$(O(CH_2)_3)_3$—, W—$(CH_2)_3$—$(O(CH_2)_2)_4$—$(O(CH_2)_3)_4$—, W—$(CH_2)_3$—$(O(CH_2)_2)_5$—$(O(CH_2)_3)_5$—, W—$(CH_2)_3$—$(O(CH_2)_2)_6$—$(O(CH_2)_3)_6$—, W—$CH_2$—O—$(CH_2)_3$—O—$(CH_2)_2$—, W—$CH_2$—$(O(CH_2)_3)_2$—$(O(CH_2)_2)_2$—, W—$CH_2$—$(O(CH_2)_3)_3$—$(O(CH_2)_2)_3$—, W—$CH_2$—$(O(CH_2)_3)4$—$(O(CH_2)_2)4$—, W—$CH_2$—$(O(CH_2)_3)_5$—$(O(CH_2)_2)_5$—, W—$CH_2$—$(O(CH_2)_3)_6$—$(O(CH_2)_2)_6$—, W—$(CH_2)_2$—O—$(CH_2)_3$—O—$(CH_2)_2$—, W—$(CH_2)_2$—$(O(CH_2)_3)_2$—$(O(CH_2)_2)_2$—, W—$(CH_2)_2$—$(O(CH_2)_3)_3$—$(O(CH_2)_2)_3$—, W—$(CH_2)_2$—$(O(CH_2)_3)_4$—$(O(CH_2)_2)_4$—, W—$(CH_2)_2$—$(O(CH_2)_3)_5$—$(O(CH_2)_2)_5$—, W—$(CH_2)_2$—$(O(CH_2)_3)_6$—$(O(CH_2)_2)_6$—, W—$(CH_2)_3$—O—$(CH_2)_3$—O—$(CH_2)_2$—, W—$(CH_2)_3$—$(O(CH_2)_3)_2$—$(O(CH_2)_2)_2$—, W—$(CH_2)_3$—$(O(CH_2)_3)_3$—$(O(CH_2)_2)_3$—, W—$(CH_2)_3$—$(O(CH_2)_3)_4$—$(O(CH_2)_2)_4$—, W—$(CH_2)_3$—$(O(CH_2)_3)_5$—$(O(CH_2)_2)_5$—, W—$(CH_2)_3$—$(O(CH_2)_3)_6$—$(O(CH_2)_2)_6$—, W—$CH_2$—O—$(CH_2)_2$—O—$CH_2$—, W—$(CH_2)_2$—O—$(CH_2)_2$—O—$CH_2$—, W—$(CH_2)_2$—$(O(CH_2)_2)_2$—O—$(CH_2)_3$—, W—$(CH_2)_2$—$(O(CH_2)_2)_3$—O—$(CH_2)_3$—, W—$(CH_2)_2$—$(O(CH_2)_2)_4$—O—$(CH_22)_3$—, W—$(CH_2)_5$—$(O(CH_2)_2)_2$—O—$(CH_2)_5$—, or W—$(CH_2)_5$—$(O(CH_2)_2)_2$—O—$(CH_2)_6$—.

5. The compound of formula (IV) or a salt, enantiomer, stereoisomer, or solvate thereof according to claim 2, wherein the LIN represents: W—$CH_2CONHCH_2$—, W—$(CH_2)_2CONH(CH_2)_2$—, W—$(CH_2)_3CONH(CH2)3$—, W—$(CH_2)_3CONH(CH_2)_4$—, W—$(CH_2)_4CONH(CH_2)_4$—, W—$(CH_2)_5CONH(CH_2)_5$—, W—$(CH_2)_6CONH(CH_2)_7$—, W—$(CH_2)_6CONH(CH_2)_6$—, W—$(CH_2)_7CONH(CH_2)_7$—, W—(CH₂)₈CONH(CH₂)₈—, W—(CH₂)₉CONH(CH₂)₉—, W—(CH₂)₁₀CONH(CH2)₁₀—, W—(CH₂)₂CONH(CH₂)₅—, W—(CH₂)₂CONH(CH₂)₃—, W—(CH₂)₂CONH(CH₂)₄—, or W—(CH₂)₂CONH(CH₂)₂—O—(CH₂)₂—.

6. The compound of formula (IV) or a salt, enantiomer, stereoisomer, or solvate thereof according to claim 2, wherein the LIN represents:

W—CH₂NHCOCH₂—, W—(CH₂)₂NHCO(CH₂)₂—, W—(CH₂)₃NHCO(CH₂)3—, W—(CH₂)₃NHCO(CH₂)₄—, W—(CH₂)₄NHCO(CH₂)₄—, W—(CH₂)₅NHCO(CH₂)₅—, W—(CH₂)₆NHCO(CH₂)₇—, W—(CH₂)₆NHCO(CH₂)₆—, W—(CH₂)₇NHCO(CH₂)₇—, W—(CH₂)₃NHCO(CH₂)₈—, W—(CH₂)₉NHCO(CH₂)₉—, W—(CH₂)₁₀NHCO(CH₂)₁₀—, W—(CH₂)2NHCO(CH₂)₅—, W—(CH₂)₂NHCO(CH₂)₃—, W—(CH₂)₂NHCO(CH₂)₄—, W—(CH₂)4NHCO(CH₂)₈—, or W—(CH₂)₂NHCO(CH₂)₂—O—(CH₂)₂—.

7. The compound of formula (IV) or a salt, enantiomer, stereoisomer, or solvate thereof according to claim 2, wherein the LIN represents: W—(CH₂)₄NHCOCH₂—.

8. The compound of formula (IV) or a salt, enantiomer, stereoisomer, or solvate thereof according to claim 1, wherein the LIN represents W—$C_{1-30}$ alkylene, wherein the $C_{1-30}$ alkylene is a straight or branched $C_{1-30}$ alkylene chain substituted by one or more substituents selected from hydroxyl, amino, mercapto, halogen, or a combination thereof.

9. The compound of formula (IV) or a salt, enantiomer, stereoisomer, or solvate thereof according to claim 1, wherein the LIN represents: W—(CH₂)₃—triazolylene—(CH₂)₅—, W—(CH₂)₂—triazolylene—(CH₂)₅—, W—CH₂—triazolylene—(CH₂)₅—, W—(CH₂)₂—triazolylene—(CH₂)₄—, W—(CH₂)₃—triazolylene—(CH₂)₂—O (CH₂)₂—, W—(CH₂)₂—triazolylene—(CH₂)₂—O (CH₂)₂—, or W—CH₂—triazolylene-(CH₂)₂—O (CH₂)₂—.

10. The compound of formula (IV), or a salt, enantiomer, stereoisomer, or solvate thereof according to claim 1, which is selected from:

2-(2-((2-(2,6-dioxopiperidin-3-yl)-1,3-dioxoisoindolin-4-yl)thio)ethoxy)acetic acid;
3-(2-((2-(2,6-dioxopiperidin-3-yl)-1,3-dioxoisoindolin-4-yl)thio)ethoxy)propanoic acid;
2-(2-(2-((2-(2,6-dioxopiperidin-3-yl)-1,3-dioxoisoindolin-4-yl)thio)ethoxy)ethoxy)acetic acid;
3-(2-(2-((2-(2,6-dioxopiperidin-3-yl)-1,3-dioxoisoindolin-4-yl)thio)ethoxy)ethoxy)propanoic acid;
2-(2-(2-(2-((2-(2,6-dioxopiperidin-3-yl)-1,3-dioxoisoindolin-4-yl)thio)ethoxy)ethoxy)ethoxy)acetic acid;
3-(2-(2-(2-((2-(2,6-dioxopiperidin-3-yl)-1,3-dioxoisoindolin-4-yl)thio)ethoxy)ethoxy)ethoxy)propanoic acid;
14-((2-(2,6-dioxopiperidin-3-yl)-1,3-dioxoisoindolin-4-yl)thio)-3,6,9,12-tetraoxatetradecanoic acid;
1-((2-(2,6-dioxopiperidin-3-yl)-1,3-dioxoisoindolin-4-yl)thio)-3,6,9,12-tetraoxapentadecan-15-oic acid;
17-((2-(2,6-dioxopiperidin-3-yl)-1,3-dioxoisoindolin-4-yl)thio)-3,6,9,12,15-pentaoxaheptadecanoic acid;
1-((2-(2,6-dioxopiperidin-3-yl)-1,3-dioxoisoindolin-4-yl)thio)-3,6,9,12,15-pentaoxaoctadecan-18-oic acid;
3-(3-((2-(2,6-dioxopiperidin-3-yl)-1,3-dioxoisoindolin-4-yl)thio)propoxy)propanoic acid;
3-(3-(2-((2-(2,6-dioxopiperidin-3-yl)-1,3-dioxoisoindolin-4-yl)thio)ethoxy)propoxy)propanoic acid;
3-(2-(3-((2-(2,6-dioxopiperidin-3-yl)-1,3-dioxoisoindolin-4-yl)thio)propoxy)ethoxy)propanoic acid;
3-(3-(2-((2-(2,6-dioxopiperidin-3-yl)-1,3-dioxoisoindolin-4-yl)thio)ethoxy)propanamido)propanoic acid;
2-((2-(2,6-dioxopiperidin-3-yl)-1,3-dioxoisoindolin-4-yl)thio)acetic acid;
3-((2-(2,6-dioxopiperidin-3-yl)-1,3-dioxoisoindolin-4-yl)thio)propanoic acid;
4-((2-(2,6-dioxopiperidin-3-yl)-1,3-dioxoisoindolin-4-yl)thio)butanoic acid;
5-((2-(2,6-dioxopiperidin-3-yl)-1,3-dioxoisoindolin-4-yl)thio)pentanoic acid;
6-((2-(2,6-dioxopiperidin-3-yl)-1,3-dioxoisoindolin-4-yl)thio)hexanoic acid;
7-((2-(2,6-dioxopiperidin-3-yl)-1,3-dioxoisoindolin-4-yl)thio)heptanoic acid;
8-((2-(2,6-dioxopiperidin-3-yl)-1,3-dioxoisoindolin-4-yl)thio)octanoic acid;
9-((2-(2,6-dioxopiperidin-3-yl)-1,3-dioxoisoindolin-4-yl)thio)nonanoic acid;
10-((2-(2,6-dioxopiperidin-3-yl)-1,3-dioxoisoindolin-4-yl)thio)decanoic acid;
11-((2-(2,6-dioxopiperidin-3-yl)-1,3-dioxoisoindolin-4-yl)thio)undecanoic acid;
12-((2-(2,6-dioxopiperidin-3-yl)-1,3-dioxoisoindolin-4-yl)thio)dodecanoic acid;
13-((2-(2,6-dioxopiperidin-3-yl)-1,3-dioxoisoindolin-4-yl)thio)tridecanoic acid;
14-((2-(2,6-dioxopiperidin-3-yl)-1,3-dioxoisoindolin-4-yl)thio)tetradecanoic acid;
15-((2-(2,6-dioxopiperidin-3-yl)-1,3-dioxoisoindolin-4-yl)thio)pentadecanoic acid;
3-(6-((2-(2,6-dioxopiperidin-3-yl)-1,3-dioxoisoindolin-4-yl)thio)hexanamido)propanoic acid;
4-((2-(2-aminoethoxy)ethyl)thio)-2-(2,6-dioxopiperidin-3-yl)isoindoline-1,3-dione;
4-((2-(2-(2-aminoethoxy)ethoxy)ethyl)thio)-2-(2,6-dioxopiperidin-3-yl)isoindoline-1,3-dione;
4-((3-(2-(3-aminopropoxy)ethoxy)propyl)thio)-2-(2,6-dioxopiperidin-3-yl)isoindoline-1,3-dione;
4-((2-(2-(2-(2-aminoethoxy)ethoxy)ethoxy)ethyl)thio)-2-(2,6-dioxopiperidin-3-yl)isoindoline-1,3-dione;
4-((14-amino-3,6,9,12-tetraoxatetradecyl)thio)-2-(2,6-dioxopiperidin-3-yl)isoindoline-1,3-dione;
4-((17-amino-3,6,9,12,15-pentaoxaheptadecyl)thio)-2-(2,6-dioxopiperidin-3-yl)isoindoline-1,3-dione;
4-(2-(2-((2-(2,6-dioxopiperidin-3-yl)-1,3-dioxoisoindolin-4-yl)thio)ethoxy)ethyl)amino)-4-oxobutanoic acid;
4-((2-aminoethyl)thio)-2-(2,6-dioxopiperidin-3-yl)isoindoline-1,3-dione;
4-((3-aminopropyl)thio)-2-(2,6-dioxopiperidin-3-yl)isoindoline-1,3-dione;
4-((4-aminobutyl)thio)-2-(2,6-dioxopiperidin-3-yl)isoindoline-1,3-dione;
4-((5-aminopentyl)thio)-2-(2,6-dioxopiperidin-3-yl)isoindoline-1,3-dione;
4-((6-aminohexyl)thio)-2-(2,6-dioxopiperidin-3-yl)isoindoline-1,3-dione;
4-((7-aminoheptyl)thio)-2-(2,6-dioxopiperidin-3-yl)isoindoline-1,3-dione;
4-((8-aminooctyl)thio)-2-(2,6-dioxopiperidin-3-yl)isoindoline-1,3-dione;
4-((5-((2-(2,6-dioxopiperidin-3-yl)-1,3-dioxoisoindolin-4-yl)thio)pentyl)amino)-4-oxobutanoic acid;
4-((2-(2-azidoethoxy)ethyl)thio)-2-(2,6-dioxopiperidin-3-yl)isoindoline-1,3-dione;
4-((2-(2-(2-azidoethoxy)ethoxy)ethyl)thio)-2-(2,6-dioxopiperidin-3-yl)isoindoline-1,3-dione;
4-((2-(2-(2-(2-azidoethoxy)ethoxy)ethoxy)ethyl)thio)-2-(2,6-dioxopiperidin-3-yl)isoindoline-1,3-dione;

4-((14-azido-3,6,9,12-tetraoxatetradecyl)thio)-2-(2,6-dioxopiperidin-3-yl)isoindoline-1,3-dione;
4-((17-azido-3,6,9,12,15-pentaoxaheptadecyl)thio)-2-(2,6-dioxopiperidin-3-yl)isoindoline-1,3-dione;
4-(1-(2-(2-((2-(2,6-dioxopiperidin-3-yl)-1,3-dioxoisoindolin-4-yl)thio)ethoxy)ethyl)-1H-1,2,3-triazol-4-yl)butanoic acid;
4-((2-azidoethyl)thio)-2-(2,6-dioxopiperidin-3-yl)isoindoline-1,3-dione;
4-((3-azidopropyl)thio)-2-(2,6-dioxopiperidin-3-yl)isoindoline-1,3-dione;
4-((4-azidobutyl)thio)-2-(2,6-dioxopiperidin-3-yl)isoindoline-1,3-dione;
4-((5-azidopentyl)thio)-2-(2,6-dioxopiperidin-3-yl)isoindoline-1,3-dione;
4-((6-azidohexyl)thio)-2-(2,6-dioxopiperidin-3-yl)isoindoline-1,3-dione;
4-((7-azidoheptyl)thio)-2-(2,6-dioxopiperidin-3-yl)isoindoline-1,3-dione;
4-(1-(5-((2-(2,6-dioxopiperidin-3-yl)-1,3-dioxoisoindolin-4-yl)thio)pentyl)-1H-1,2,3-triazol-4-yl)butanoic acid;
2-(2,6-dioxopiperidin-3-yl)-4-(2-(2-iodoethoxy)ethylthio)isoindoline-1,3-dione;
4-(2-(2-bromoethoxy)ethylthio)-2-(2,6-dioxopiperidin-3-yl)isoindoline-1,3-dione;
2-(2-(2-(2,6-dioxopiperidin-3-yl)-1,3-dioxoisoindolin-4-ylthio)ethoxy)ethyl 4-methylbenzenesulfonate;
2-(2,6-dioxopiperidin-3-yl)-4-(2-(2-(2-iodoethoxy)ethoxy)ethylthio)isoindoline-1,3-dione;
4-(2-(2-(2-bromoethoxy)ethoxy)ethylthio)-2-(2,6-dioxopiperidin-3-yl)isoindoline-1,3-dione;
2-(2-(2-(2-(2,6-dioxopiperidin-3-yl)-1,3-dioxoisoindolin-4-ylthio)ethoxy)ethoxy)ethyl 4-methylbenzenesulfonate;
2-(2,6-dioxopiperidin-3-yl)-4-(2-(2-(2-(2-iodoethoxy)ethoxy)ethoxy)ethylthio)isoindoline-1,3-dione;
4-(2-(2-(2-(2-bromoethoxy)ethoxy)ethoxy)ethylthio)-2-(2,6-dioxopiperidin-3-yl)isoindoline-1,3-dione;
2-(2-(2-(2-(2-(2,6-dioxopiperidin-3-yl)-1,3-dioxoisoindolin-4-ylthio)ethoxy)ethoxy)ethoxy)ethyl 4-methylbenzenesulfonate;
2-(2,6-dioxopiperidin-3-yl)-4-(2-(2-(2-(2-(2-iodoethoxy)ethoxy)ethoxy)ethoxy)ethylthio)isoindoline-1,3-dione;
4-(2-(2-(2-(2-(2-bromoethoxy)ethoxy)ethoxy)ethoxy)ethylthio)-2-(2,6-dioxopiperidin-3-yl)isoindoline-1,3-dione;
2-(2-(2-(2-(2-(2-(2,6-dioxopiperidin-3-yl)-1,3-dioxoisoindolin-4-ylthio)ethoxy)ethoxy)ethoxy)ethoxy)ethyl 4-methylbenzenesulfonate;
2-(2,6-dioxopiperidin-3-yl)-4-(3-(3-iodopropoxy)propylthio)isoindoline-1,3-dione;
4-(3-(3-bromopropoxy)propylthio)-2-(2,6-dioxopiperidin-3-yl)isoindoline-1,3-dione;
3-(2-(2,6-dioxopiperidin-3-yl)-1,3-dioxoisoindolin-4-ylthio)propoxy)propyl 4-methylbenzenesulfonate;
2-(2,6-dioxopiperidin-3-yl)-4-(3-(3-iodopropoxy)propoxy)ethylthio)isoindoline-1,3-dione;
4-(2-(3-(3-bromopropoxy)propoxy)ethylthio)-2-(2,6-dioxopiperidin-3-yl)isoindoline-1,3-dione;
3-(3-(2-(2-(2,6-dioxopiperidin-3-yl)-1,3-dioxoisoindolin-4-ylthio)ethoxy)propoxy)propyl 4-methylbenzenesulfonate;
2-(2,6-dioxopiperidin-3-yl)-4-(2-iodoethylthio)isoindoline-1,3-dione;
4-(2-bromoethylthio)-2-(2,6-dioxopiperidin-3-yl)isoindoline-1,3-dione;
2-(2-(2,6-dioxopiperidin-3-yl)-1,3-dioxoisoindolin-4-ylthio)ethyl 4-methylbenzenesulfonate;
2-(2,6-dioxopiperidin-3-yl)-4-(3-iodopropylthio)isoindoline-1,3-dione;
4-(3-bromopropylthio)-2-(2,6-dioxopiperidin-3-yl)isoindoline-1,3-dione;
3-(2-(2,6-dioxopiperidin-3-yl)-1,3-dioxoisoindolin-4-ylthio)propyl 4-methylbenzenesulfonate;
2-(2,6-dioxopiperidin-3-yl)-4-(4-iodobutylthio)isoindoline-1,3-dione;
4-(4-bromobutylthio)-2-(2,6-dioxopiperidin-3-yl)isoindoline-1,3-dione;
4-(2-(2,6-dioxopiperidin-3-yl)-1,3-dioxoisoindolin-4-ylthio)butyl 4-methylbenzenesulfonate;
2-(2,6-dioxopiperidin-3-yl)-4-(5-iodopentylthio)isoindoline-1,3-dione;
4-(5-bromopentylthio)-2-(2,6-dioxopiperidin-3-yl)isoindoline-1,3-dione;
5-(2-(2,6-dioxopiperidin-3-yl)-1,3-dioxoisoindolin-4-ylthio)pentyl 4-methylbenzenesulfonate;
2-(2,6-dioxopiperidin-3-yl)-4-(6-iodohexylthio)isoindoline-1,3-dione;
4-(6-bromohexylthio)-2-(2,6-dioxopiperidin-3-yl)isoindoline-1,3-dione;
6-(2-(2,6-dioxopiperidin-3-yl)-1,3-dioxoisoindolin-4-ylthio)hexyl 4-methylbenzenesulfonate;
2-(2,6-dioxopiperidin-3-yl)-4-(7-iodoheptylthio)isoindoline-1,3-dione;
4-(7-bromoheptylthio)-2-(2,6-dioxopiperidin-3-yl)isoindoline-1,3-dione;
7-(2-(2,6-dioxopiperidin-3-yl)-1,3-dioxoisoindolin-4-ylthio)heptyl 4-methylbenzenesulfonate;
2-(2-((2-(2,6-dioxopiperidin-3-yl)-1,3-dioxoisoindolin-4-yl)sulfinyl)ethoxy)acetic acid;
3-(2-((2-(2,6-dioxopiperidin-3-yl)-1,3-dioxoisoindolin-4-yl)sulfinyl)ethoxy)propanoic acid;
2-(2-(2-((2-(2,6-dioxopiperidin-3-yl)-1,3-dioxoisoindolin-4-yl)sulfinyl)ethoxy)ethoxy)acetic acid;
3-(2-(2-((2-(2,6-dioxopiperidin-3-yl)-1,3-dioxoisoindolin-4-yl)sulfinyl)ethoxy)ethoxy)propanoic acid;
2-(2-(2-(2-((2-(2,6-dioxopiperidin-3-yl)-1,3-dioxoisoindolin-4-yl)sulfinyl)ethoxy)ethoxy)ethoxy)acetic acid;
3-(2-(2-(2-((2-(2,6-dioxopiperidin-3-yl)-1,3-dioxoisoindolin-4-yl)sulfinyl)ethoxy)ethoxy)ethoxy)propanoic acid;
14-((2-(2,6-dioxopiperidin-3-yl)-1,3-dioxoisoindolin-4-yl)sulfinyl)-3,6,9,12-tetraoxatetradecanoic acid;
1-((2-(2,6-dioxopiperidin-3-yl)-1,3-dioxoisoindolin-4-yl)sulfinyl)-3,6,9,12-tetraoxapentadecan-15-oic acid;
17-((2-(2,6-dioxopiperidin-3-yl)-1,3-dioxoisoindolin-4-yl)sulfinyl)-3,6,9,12,15-pentaoxaheptadecanoic acid;
1-((2-(2,6-dioxopiperidin-3-yl)-1,3-dioxoisoindolin-4-yl)sulfinyl)-3,6,9,12,15-pentaoxaoctadecan-18-oic acid;
3-(3-(2-((2-(2,6-dioxopiperidin-3-yl)-1,3-dioxoisoindolin-4-yl)sulfinyl)ethoxy)propanamido)propanoic acid;
2-((2-(2,6-dioxopiperidin-3-yl)-1,3-dioxoisoindolin-4-yl)sulfinyl)acetic acid;

3-((2-(2,6-dioxopiperidin-3-yl)-1,3-dioxoisoindolin-4-yl)sulfinyl)propanoic acid;
4-((2-(2,6-dioxopiperidin-3-yl)-1,3-dioxoisoindolin-4-yl)sulfinyl)butanoic acid;
5-((2-(2,6-dioxopiperidin-3-yl)-1,3-dioxoisoindolin-4-yl)sulfinyl)pentanoic acid;
6-((2-(2,6-dioxopiperidin-3-yl)-1,3-dioxoisoindolin-4-yl)sulfinyl)hexanoic acid;
7-((2-(2,6-dioxopiperidin-3-yl)-1,3-dioxoisoindolin-4-yl)sulfinyl)heptanoic acid;
8-((2-(2,6-dioxopiperidin-3-yl)-1,3-dioxoisoindolin-4-yl)sulfinyl)octanoic acid;
9-((2-(2,6-dioxopiperidin-3-yl)-1,3-dioxoisoindolin-4-yl)sulfinyl)nonanoic acid;
10-((2-(2,6-dioxopiperidin-3-yl)-1,3-dioxoisoindolin-4-yl)sulfinyl)decanoic acid;
11-((2-(2,6-dioxopiperidin-3-yl)-1,3-dioxoisoindolin-4-yl)sulfinyl)undecanoic acid;
12-((2-(2,6-dioxopiperidin-3-yl)-1,3-dioxoisoindolin-4-yl)sulfinyl)dodecanoic acid;
13-((2-(2,6-dioxopiperidin-3-yl)-1,3-dioxoisoindolin-4-yl)sulfinyl)tridecanoic acid;
14-((2-(2,6-dioxopiperidin-3-yl)-1,3-dioxoisoindolin-4-yl)sulfinyl)tetradecanoic acid;
15-((2-(2,6-dioxopiperidin-3-yl)-1,3-dioxoisoindolin-4-yl)sulfinyl)pentadecanoic acid;
3-(6-((2-(2,6-dioxopiperidin-3-yl)-1,3-dioxoisoindolin-4-yl)sulfinyl)hexanamido)propanoic acid;
4-((2-(2-aminoethoxy)ethyl)sulfinyl)-2-(2,6-dioxopiperidin-3-yl)isoindoline-1,3-dione;
4-((2-(2-(2-aminoethoxy)ethoxy)ethyl)sulfinyl)-2-(2,6-dioxopiperidin-3-yl)isoindoline-1,3-dione;
4-((2-(2-(2-(2-aminoethoxy)ethoxy)ethoxy)ethyl)sulfinyl)-2-(2,6-dioxopiperidin-3-yl)isoindoline-1,3-dione;
4-((14-amino-3,6,9,12-tetraoxatetradecyl)sulfinyl)-2-(2,6-dioxopiperidin-3-yl)isoindoline-1,3-dione;
4-((17-amino-3,6,9,12,15-pentaoxaheptadecyl)sulfinyl)-2-(2,6-dioxopiperidin-3-yl)isoindoline-1,3-dione;
4-((2-(2-((2-(2,6-dioxopiperidin-3-yl)-1,3-dioxoisoindolin-4-yl)sulfinyl)ethoxy)ethyl)amino)-4-oxobutanoic acid;
4-((2-aminoethyl)sulfinyl)-2-(2,6-dioxopiperidin-3-yl)isoindoline-1,3-dione;
4-((3-aminopropyl)sulfinyl)-2-(2,6-dioxopiperidin-3-yl)isoindoline-1,3-dione;
4-((4-aminobutyl)sulfinyl)-2-(2,6-dioxopiperidin-3-yl)isoindoline-1,3-dione;
4-((5-aminopentyl)sulfinyl)-2-(2,6-dioxopiperidin-3-yl)isoindoline-1,3-dione;
4-((6-aminohexyl)sulfinyl)-2-(2,6-dioxopiperidin-3-yl)isoindoline-1,3-dione;
4-((7-aminoheptyl)sulfinyl)-2-(2,6-dioxopiperidin-3-yl)isoindoline-1,3-dione;
4-((8-aminooctyl)sulfinyl)-2-(2,6-dioxopiperidin-3-yl)isoindoline-1,3-dione;
4-((5-((2-(2,6-dioxopiperidin-3-yl)-1,3-dioxoisoindolin-4-yl)sulfinyl)pentyl)amino)-4-oxobutanoic acid;
4-((2-(2-azidoethoxy)ethyl)sulfinyl)-2-(2,6-dioxopiperidin-3-yl)isoindoline-1,3-dione;
4-((2-(2-(2-azidoethoxy)ethoxy)ethyl)sulfinyl)-2-(2,6-dioxopiperidin-3-yl)isoindoline-1,3-dione;
4-((2-(2-(2-(2-azidoethoxy)ethoxy)ethoxy)ethyl)sulfinyl)-2-(2,6-dioxopiperidin-3-yl)isoindoline-1,3-dione;
4-((14-azido-3,6,9,12-tetraoxatetradecyl)sulfinyl)-2-(2,6-dioxopiperidin-3-yl)isoindoline-1,3-dione;
4-((17-azido-3,6,9,12,15-pentaoxaheptadecyl)sulfinyl)-2-(2,6-dioxopiperidin-3-yl)isoindoline-1,3-dione;
4-(1-(2-(2-((2-(2,6-dioxopiperidin-3-yl)-1,3-dioxoisoindolin-4-yl)sulfinyl)ethoxy)ethyl)-1H-1,2,3-triazol-4-yl)butanoic acid;
4-((2-azidoethyl)sulfinyl)-2-(2,6-dioxopiperidin-3-yl)isoindoline-1,3-dione;
4-((3-azidopropyl)sulfinyl)-2-(2,6-dioxopiperidin-3-yl)isoindoline-1,3-dione;
4-((4-azidobutyl)sulfinyl)-2-(2,6-dioxopiperidin-3-yl)isoindoline-1,3-dione;
4-((5-azidopentyl)sulfinyl)-2-(2,6-dioxopiperidin-3-yl)isoindoline-1,3-dione;
4-((6-azidohexyl)sulfinyl)-2-(2,6-dioxopiperidin-3-yl)isoindoline-1,3-dione;
4-((7-azidoheptyl)sulfinyl)-2-(2,6-dioxopiperidin-3-yl)isoindoline-1,3-dione;
4-(1-(5-((2-(2,6-dioxopiperidin-3-yl)-1,3-dioxoisoindolin-4-yl)sulfinyl)pentyl)-1H-1,2,3-triazol-4-yl)butanoic acid;
2-(2,6-dioxopiperidin-3-yl)-4-(2-(2-iodoethoxy)ethylsulfinyl)isoindoline-1,3-dione;
4-(2-(2-bromoethoxy)ethylsulfinyl)-2-(2,6-dioxopiperidin-3-yl)isoindoline-1,3-dione;
2-(2-(2-(2,6-dioxopiperidin-3-yl)-1,3-dioxoisoindolin-4-ylsulfinyl)ethoxy)ethyl 4-methylbenzenesulfonate;
2-(2,6-dioxopiperidin-3-yl)-4-(2-(2-(2-iodoethoxy)ethoxy)ethylsulfinyl)isoindoline-1,3-dione;
4-(2-(2-(2-bromoethoxy)ethoxy)ethylsulfinyl)-2-(2,6-dioxopiperidin-3-yl)isoindoline-1,3-dione;
2-(2-(2-(2-(2,6-dioxopiperidin-3-yl)-1,3-dioxoisoindolin-4-ylsulfinyl)ethoxy)ethoxy)ethyl 4-methylbenzenesulfonate;
2-(2,6-dioxopiperidin-3-yl)-4-(2-(2-(2-(2-iodoethoxy)ethoxy)ethoxy)ethylsulfinyl)isoindoline-1,3-dione;
4-(2-(2-(2-(2-bromoethoxy)ethoxy)ethoxy)ethylsulfinyl)-2-(2,6-dioxopiperidin-3-yl)isoindoline-1,3-dione;
2-(2-(2-(2-(2-(2,6-dioxopiperidin-3-yl)-1,3-dioxoisoindolin-4-ylsulfinyl)ethoxy)ethoxy)ethoxy)ethyl 4-methylbenzenesulfonate;
2-(2,6-dioxopiperidin-3-yl)-4-(2-(2-(2-(2-(2-iodoethoxy)ethoxy)ethoxy)ethoxy)ethylsulfinyl)isoindoline-1,3-dione;
4-(2-(2-(2-(2-(2-bromoethoxy)ethoxy)ethoxy)ethoxy)ethylsulfinyl)-2-(2,6-dioxopiperidin-3-yl)isoindoline-1,3-dione;
2-(2-(2-(2-(2-(2-(2,6-dioxopiperidin-3-yl)-1,3-dioxoisoindolin-4-ylsulfinyl)ethoxy)ethoxy)ethoxy)ethoxy)ethyl 4-methylbenzenesulfonate;
2-(2,6-dioxopiperidin-3-yl)-4-(2-iodoethylsulfinyl)isoindoline-1,3-dione;
4-(2-bromoethylsulfinyl)-2-(2,6-dioxopiperidin-3-yl)isoindoline-1,3-dione;
2-(2-(2,6-dioxopiperidin-3-yl)-1,3-dioxoisoindolin-4-ylsulfinyl)ethyl 4-methylbenzenesulfonate;
2-(2,6-dioxopiperidin-3-yl)-4-(3-iodopropylsulfinyl)isoindoline-1,3-dione;
4-(3-bromopropylsulfinyl)-2-(2,6-dioxopiperidin-3-yl)isoindoline-1,3-dione;

3-(2-(2,6-dioxopiperidin-3-yl)-1,3-dioxoisoindolin-4-ylsulfinyl)propyl 4-methylbenzenesulfonate;
2-(2,6-dioxopiperidin-3-yl)-4-(4-iodobutylsulfinyl)isoindoline-1,3-dione;
4-(4-bromobutylsulfinyl)-2-(2,6-dioxopiperidin-3-yl) isoindoline-1,3-dione;
4-(2-(2,6-dioxopiperidin-3-yl)-1,3-dioxoisoindolin-4-ylsulfinyl)butyl 4-methylbenzenesulfonate;
2-(2,6-dioxopiperidin-3-yl)-4-(5-iodopentylsulfinyl) isoindoline-1,3-dione;
4-(5-bromopentylsulfinyl)-2-(2,6-dioxopiperidin-3-yl) isoindoline-1,3-dione;
5-(2-(2,6-dioxopiperidin-3-yl)-1,3-dioxoisoindolin-4-ylsulfinyl)pentyl 4-methylbenzenesulfonate;
2-(2,6-dioxopiperidin-3-yl)-4-(6-iodohexylsulfinyl)isoindoline-1,3-dione;
4-(6-bromohexylsulfinyl)-2-(2,6-dioxopiperidin-3-yl) isoindoline-1,3-dione;
6-(2-(2,6-dioxopiperidin-3-yl)-1,3-dioxoisoindolin-4-ylsulfinyl)hexyl 4-methylbenzenesulfonate;
2-(2,6-dioxopiperidin-3-yl)-4-(7-iodoheptylsulfinyl) isoindoline-1,3-dione;
4-(7-bromoheptylsulfinyl)-2-(2,6-dioxopiperidin-3-yl) isoindoline-1,3-dione;
7-(2-(2,6-dioxopiperidin-3-yl)-1,3-dioxoisoindolin-4-ylsulfinyl)heptyl 4-methylbenzenesulfonate;
2-(2-((2-(2,6-dioxopiperidin-3-yl)-1,3-dioxoisoindolin-4-yl)sulfonyl)ethoxy)acetic acid;
3-(2-((2-(2,6-dioxopiperidin-3-yl)-1,3-dioxoisoindolin-4-yl)sulfonyl)ethoxy)propanoic acid;
2-(2-(2-((2-(2,6-dioxopiperidin-3-yl)-1,3-dioxoisoindolin-4-yl)sulfonyl)ethoxy)ethoxy)acetic acid;
3-(2-(2-((2-(2,6-dioxopiperidin-3-yl)-1,3-dioxoisoindolin-4-yl)sulfonyl)ethoxy)ethoxy)propanoic acid;
2-(2-(2-(2-((2-(2,6-dioxopiperidin-3-yl)-1,3-dioxoisoindolin-4-yl)sulfonyl)ethoxy)ethoxy)ethoxy)acetic acid;
3-(2-(2-(2-((2-(2,6-dioxopiperidin-3-yl)-1,3-dioxoisoindolin-4-yl)sulfonyl)ethoxy)ethoxy)ethoxy)propanoic acid;
14-((2-(2,6-dioxopiperidin-3-yl)-1,3-dioxoisoindolin-4-yl)sulfonyl)-3,6,9,12-tetraoxatetradecanoic acid;
1-((2-(2,6-dioxopiperidin-3-yl)-1,3-dioxoisoindolin-4-yl) sulfonyl)-3,6,9,12-tetraoxapentadecan-15-oic acid;
17-((2-(2,6-dioxopiperidin-3-yl)-1,3-dioxoisoindolin-4-yl)sulfonyl)-3,6,9,12,15-pentaoxaheptadecanoic acid;
1-((2-(2,6-dioxopiperidin-3-yl)-1,3-dioxoisoindolin-4-yl) sulfonyl)-3,6,9,12,15-pentaoxaoctadecan-18-oic acid;
3-(3-(2-((2-(2,6-dioxopiperidin-3-yl)-1,3-dioxoisoindolin-4-yl)sulfonyl)ethoxy)propanamido)propanoic acid;
2-((2-(2,6-dioxopiperidin-3-yl)-1,3-dioxoisoindolin-4-yl) sulfonyl)acetic acid;
3-((2-(2,6-dioxopiperidin-3-yl)-1,3-dioxoisoindolin-4-yl) sulfonyl)propanoic acid;
4-((2-(2,6-dioxopiperidin-3-yl)-1,3-dioxoisoindolin-4-yl) sulfonyl)butanoic acid;
5-((2-(2,6-dioxopiperidin-3-yl)-1,3-dioxoisoindolin-4-yl) sulfonyl)pentanoic acid;
6-((2-(2,6-dioxopiperidin-3-yl)-1,3-dioxoisoindolin-4-yl) sulfonyl)hexanoic acid;
7-((2-(2,6-dioxopiperidin-3-yl)-1,3-dioxoisoindolin-4-yl) sulfonyl)heptanoic acid;
8-((2-(2,6-dioxopiperidin-3-yl)-1,3-dioxoisoindolin-4-yl) sulfonyl)octanoic acid;
9-((2-(2,6-dioxopiperidin-3-yl)-1,3-dioxoisoindolin-4-yl) sulfonyl)nonanoic acid;
10-((2-(2,6-dioxopiperidin-3-yl)-1,3-dioxoisoindolin-4-yl)sulfonyl)decanoic acid;
11-((2-(2,6-dioxopiperidin-3-yl)-1,3-dioxoisoindolin-4-yl)sulfonyl)undecanoic acid;
12-((2-(2,6-dioxopiperidin-3-yl)-1,3-dioxoisoindolin-4-yl)sulfonyl)dodecanoic acid;
13-((2-(2,6-dioxopiperidin-3-yl)-1,3-dioxoisoindolin-4-yl)sulfonyl)tridecanoic acid;
14-((2-(2,6-dioxopiperidin-3-yl)-1,3-dioxoisoindolin-4-yl)sulfonyl)tetradecanoic acid;
15-((2-(2,6-dioxopiperidin-3-yl)-1,3-dioxoisoindolin-4-yl)sulfonyl)pentadecanoic acid;
3-(6-((2-(2,6-dioxopiperidin-3-yl)-1,3-dioxoisoindolin-4-yl)sulfonyl)hexanamido)propanoic acid;
4-((2-(2-aminoethoxy)ethyl)sulfonyl)-2-(2,6-dioxopiperidin-3-yl)isoindoline-1,3-dione;
4-((2-(2-(2-aminoethoxy)ethoxy)ethyl)sulfonyl)-2-(2,6-dioxopiperidin-3-yl)isoindoline-1,3-dione;
4-((2-(2-(2-(2-aminoethoxy)ethoxy)ethoxy)ethyl)sulfonyl)-2-(2,6-dioxopiperidin-3-yl)isoindoline-1,3-dione;
4-((14-amino-3,6,9,12-tetraoxatetradecyl)sulfonyl)-2-(2,6-dioxopiperidin-3-yl)isoindoline-1,3-dione;
4-((17-amino-3,6,9,12,15-pentaoxaheptadecyl)sulfonyl)-2-(2,6-dioxopiperidin-3-yl)isoindoline-1,3-dione;
4-((2-(2-((2-(2,6-dioxopiperidin-3-yl)-1,3-dioxoisoindolin-4-yl)sulfonyl)ethoxy)ethyl)amino)-4-oxobutanoic acid;
4-((2-aminoethyl)sulfonyl)-2-(2,6-dioxopiperidin-3-yl) isoindoline-1,3-dione;
4-((3-aminopropyl)sulfonyl)-2-(2,6-dioxopiperidin-3-yl) isoindoline-1,3-dione;
4-((4-aminobutyl)sulfonyl)-2-(2,6-dioxopiperidin-3-yl) isoindoline-1,3-dione;
4-((5-aminopentyl)sulfonyl)-2-(2,6-dioxopiperidin-3-yl) isoindoline-1,3-dione;
4-((6-aminohexyl)sulfonyl)-2-(2,6-dioxopiperidin-3-yl) isoindoline-1,3-dione;
4-((7-aminoheptyl)sulfonyl)-2-(2,6-dioxopiperidin-3-yl) isoindoline-1,3-dione;
4-((8-aminooctyl)sulfonyl)-2-(2,6-dioxopiperidin-3-yl) isoindoline-1,3-dione;
4-((5-((2-(2,6-dioxopiperidin-3-yl)-1,3-dioxoisoindolin-4-yl)sulfonyl)pentyl)amino)-4-oxobutanoic acid;
4-((2-(2-azidoethoxy)ethyl)sulfonyl)-2-(2,6-dioxopiperidin-3-yl)isoindoline-1,3-dione;
4-((2-(2-(2-azidoethoxy)ethoxy)ethyl)sulfonyl)-2-(2,6-dioxopiperidin-3-yl)isoindoline-1,3-dione;
4-((2-(2-(2-(2-azidoethoxy)ethoxy)ethoxy)ethyl)sulfonyl)-2-(2,6-dioxopiperidin-3-yl)isoindoline-1,3-dione;
4-((14-azido-3,6,9,12-tetraoxatetradecyl)sulfonyl)-2-(2,6-dioxopiperidin-3-yl)isoindoline-1,3-dione;
4-((17-azido-3,6,9,12,15-pentaoxaheptadecyl)sulfonyl)-2-(2,6-dioxopiperidin-3-yl)isoindoline-1,3-dione;
4-(1-(2-(2-((2-(2,6-dioxopiperidin-3-yl)-1,3-dioxoisoindolin-4-yl)sulfonyl)ethoxy)ethyl)-1H-1,2,3-triazol-4-yl)butanoic acid;
4-((2-azidoethyl)sulfonyl)-2-(2,6-dioxopiperidin-3-yl) isoindoline-1,3-dione;
4-((3-azidopropyl)sulfonyl)-2-(2,6-dioxopiperidin-3-yl) isoindoline-1,3-dione;
4-((4-azidobutyl)sulfonyl)-2-(2,6-dioxopiperidin-3-yl) isoindoline-1,3-dione;
4-((5-azidopentyl)sulfonyl)-2-(2,6-dioxopiperidin-3-yl) isoindoline-1,3-dione;
4-((6-azidohexyl)sulfonyl)-2-(2,6-dioxopiperidin-3-yl) isoindoline-1,3-dione;
4-((7-azidoheptyl)sulfonyl)-2-(2,6-dioxopiperidin-3-yl) isoindoline-1,3-dione;

4-(1-(5-((2-(2,6-dioxopiperidin-3-yl)-1,3-dioxoisoindolin-4-yl)sulfonyl)pentyl)-1H-1,2,3-triazol-4-yl)butanoic acid;
2-(2,6-dioxopiperidin-3-yl)-4-(2-(2-iodoethoxy)ethylsulfonyl)isoindoline-1,3-dione;
4-(2-(2-bromoethoxy)ethylsulfonyl)-2-(2,6-dioxopiperidin-3-yl)isoindoline-1,3-dione;
2-(2-(2-(2,6-dioxopiperidin-3-yl)-1,3-dioxoisoindolin-4-ylsulfonyl)ethoxy)ethyl 4-methylbenzenesulfonate;
2-(2,6-dioxopiperidin-3-yl)-4-(2-(2-(2-iodoethoxy)ethoxy)ethylsulfonyl)isoindoline-1,3-dione;
4-(2-(2-(2-bromoethoxy)ethoxy)ethylsulfonyl)-2-(2,6-dioxopiperidin-3-yl)isoindoline-1,3-dione;
2-(2-(2-(2-(2,6-dioxopiperidin-3-yl)-1,3-dioxoisoindolin-4-ylsulfonyl)ethoxy)ethoxy)ethyl 4-methylbenzenesulfonate;
2-(2,6-dioxopiperidin-3-yl)-4-(2-(2-(2-(2-iodoethoxy)ethoxy)ethoxy)ethylsulfonyl)isoindoline-1,3-dione;
4-(2-(2-(2-(2-bromoethoxy)ethoxy)ethoxy)ethylsulfonyl)-2-(2,6-dioxopiperidin-3-yl)isoindoline-1,3-dione;
2-(2-(2-(2-(2-(2,6-dioxopiperidin-3-yl)-1,3-dioxoisoindolin-4-ylsulfonyl)ethoxy)ethoxy)ethoxy)ethyl 4-methylbenzenesulfonate;
2-(2,6-dioxopiperidin-3-yl)-4-(2-(2-(2-(2-(2-iodoethoxy)ethoxy)ethoxy)ethoxy)ethylsulfonyl)isoindoline-1,3-dione;
4-(2-(2-(2-(2-(2-bromoethoxy)ethoxy)ethoxy)ethoxy)ethylsulfonyl)-2-(2,6-dioxopiperidin-3-yl)isoindoline-1,3-dione;
2-(2-(2-(2-(2-(2-(2,6-dioxopiperidin-3-yl)-1,3-dioxoisoindolin-4-ylsulfonyl)ethoxy)ethoxy)ethoxy)ethoxy)ethyl 4-methylbenzenesulfonate;
2-(2,6-dioxopiperidin-3-yl)-4-(2-iodoethylsulfonyl)isoindoline-1,3-dione;
4-(2-bromoethylsulfonyl)-2-(2,6-dioxopiperidin-3-yl)isoindoline-1,3-dione;
2-(2-(2,6-dioxopiperidin-3-yl)-1,3-dioxoisoindolin-4-ylsulfonyl)ethyl 4-methylbenzenesulfonate;
2-(2,6-dioxopiperidin-3-yl)-4-(3-iodopropylsulfonyl)isoindoline-1,3-dione;
4-(3-bromopropylsulfonyl)-2-(2,6-dioxopiperidin-3-yl)isoindoline-1,3-dione;
3-(2-(2,6-dioxopiperidin-3-yl)-1,3-dioxoisoindolin-4-ylsulfonyl)propyl 4-methylbenzenesulfonate;
2-(2,6-dioxopiperidin-3-yl)-4-(4-iodobutylsulfonyl)isoindoline-1,3-dione;
4-(4-bromobutylsulfonyl)-2-(2,6-dioxopiperidin-3-yl)isoindoline-1,3-dione;
4-(2-(2,6-dioxopiperidin-3-yl)-1,3-dioxoisoindolin-4-ylsulfonyl)butyl 4-methylbenzenesulfonate;
2-(2,6-dioxopiperidin-3-yl)-4-(5-iodopentylsulfonyl)isoindoline-1,3-dione;
4-(5-bromopentylsulfonyl)-2-(2,6-dioxopiperidin-3-yl)isoindoline-1,3-dione;
5-(2-(2,6-dioxopiperidin-3-yl)-1,3-dioxoisoindolin-4-ylsulfonyl)pentyl 4-methylbenzenesulfonate;
2-(2,6-dioxopiperidin-3-yl)-4-(6-iodohexylsulfonyl)isoindoline-1,3-dione;
4-(6-bromohexylsulfonyl)-2-(2,6-dioxopiperidin-3-yl)isoindoline-1,3-dione;
6-(2-(2,6-dioxopiperidin-3-yl)-1,3-dioxoisoindolin-4-ylsulfonyl)hexyl 4-methylbenzenesulfonate;
2-(2,6-dioxopiperidin-3-yl)-4-(7-iodoheptylsulfonyl)isoindoline-1,3-dione;
4-(7-bromoheptylsulfonyl)-2-(2,6-dioxopiperidin-3-yl)isoindoline-1,3-dione;
7-(2-(2,6-dioxopiperidin-3-yl)-1,3-dioxoisoindolin-4-ylsulfonyl)heptyl 4-methylbenzenesulfonate;
2-(2-((2-(2,6-dioxopiperidin-3-yl)-1-oxoisoindolin-4-yl)thio)ethoxy)acetic acid;
3-(2-((2-(2,6-dioxopiperidin-3-yl)-1-oxoisoindolin-4-yl)thio)ethoxy)propanoic acid;
2-(2-(2-((2-(2,6-dioxopiperidin-3-yl)-1-oxoisoindolin-4-yl)thio)ethoxy)ethoxy)acetic acid;
3-(2-(2-((2-(2,6-dioxopiperidin-3-yl)-1-oxoisoindolin-4-yl)thio)ethoxy)ethoxy)propanoic acid;
2-(2-(2-(2-((2-(2,6-dioxopiperidin-3-yl)-1-oxoisoindolin-4-yl)thio)ethoxy)ethoxy)ethoxy)acetic acid;
3-(2-(2-(2-((2-(2,6-dioxopiperidin-3-yl)-1-oxoisoindolin-4-yl)thio)ethoxy)ethoxy)ethoxy)propanoic acid;
14-((2-(2,6-dioxopiperidin-3-yl)-1-oxoisoindolin-4-yl)thio)-3,6,9,12-tetraoxatetradecanoic acid;
1-((2-(2,6-dioxopiperidin-3-yl)-1-oxoisoindolin-4-yl)thio)-3,6,9,12-tetraoxapentadecan-15-oic acid;
17-((2-(2,6-dioxopiperidin-3-yl)-1-oxoisoindolin-4-yl)thio)-3,6,9,12,15-pentaoxaheptadecanoic acid;
1-((2-(2,6-dioxopiperidin-3-yl)-1-oxoisoindolin-4-yl)thio)-3,6,9,12,15-pentaoxaoctadecan-18-oic acid;
3-(3-((2-(2,6-dioxopiperidin-3-yl)-1-oxoisoindolin-4-yl)thio)propoxy)propanoic acid;
3-(3-(2-((2-(2,6-dioxopiperidin-3-yl)-1-oxoisoindolin-4-yl)thio)ethoxy)propanamido)propanoic acid;
2-((2-(2,6-dioxopiperidin-3-yl)-1-oxoisoindolin-4-yl)thio)acetic acid;
3-((2-(2,6-dioxopiperidin-3-yl)-1-oxoisoindolin-4-yl)thio)propanoic acid;
4-((2-(2,6-dioxopiperidin-3-yl)-1-oxoisoindolin-4-yl)thio)butanoic acid;
5-((2-(2,6-dioxopiperidin-3-yl)-1-oxoisoindolin-4-yl)thio)pentanoic acid;
6-((2-(2,6-dioxopiperidin-3-yl)-1-oxoisoindolin-4-yl)thio)hexanoic acid;
7-((2-(2,6-dioxopiperidin-3-yl)-1-oxoisoindolin-4-yl)thio)heptanoic acid;
8-((2-(2,6-dioxopiperidin-3-yl)-1-oxoisoindolin-4-yl)thio)octanoic acid;
9-((2-(2,6-dioxopiperidin-3-yl)-1-oxoisoindolin-4-yl)thio)nonanoic acid;
10-((2-(2,6-dioxopiperidin-3-yl)-1-oxoisoindolin-4-yl)thio)decanoic acid;
11-((2-(2,6-dioxopiperidin-3-yl)-1-oxoisoindolin-4-yl)thio)undecanoic acid;
12-((2-(2,6-dioxopiperidin-3-yl)-1-oxoisoindolin-4-yl)thio)dodecanoic acid;
13-((2-(2,6-dioxopiperidin-3-yl)-1-oxoisoindolin-4-yl)thio)tridecanoic acid;
14-((2-(2,6-dioxopiperidin-3-yl)-1-oxoisoindolin-4-yl)thio)tetradecanoic acid;
15-((2-(2,6-dioxopiperidin-3-yl)-1-oxoisoindolin-4-yl)thio)pentadecanoic acid;
3-(6-((2-(2,6-dioxopiperidin-3-yl)-1-oxoisoindolin-4-yl)thio)hexanamido)propanoic acid;
3-(4-((2-(2-aminoethoxy)ethyl)thio)-1-oxoisoindolin-2-yl)piperidine-2,6-dione;

3-(4-((2-(2-(2-aminoethoxy)ethoxy)ethyl)thio)-1-oxoisoindolin-2-yl)piperidine-2,6-dione;
3-(4-((3-(2-(3-aminopropoxy)ethoxy)propyl)thio)-1-oxoisoindolin-2-yl)piperidine-2,6-dione;
3-(4-((2-(2-(2-aminoethoxy)ethoxy)ethoxy)ethyl)thio)-1-oxoisoindolin-2-yl)piperidine-2,6-dione;
3-(4-((14-amino-3,6,9,12-tetraoxatetradecyl)thio)-1-oxoisoindolin-2-yl)piperidine-2,6-dione;
3-(4-((17-amino-3,6,9,12,15-pentaoxaheptadecyl)thio)-1-oxoisoindolin-2-yl)piperidine-2,6-dione;
4-((2-(2-((2-(2,6-dioxopiperidin-3-yl)-1-oxoisoindolin-4-yl)thio)ethoxy)ethyl)amino)-4-oxobutanoic acid;
3-(4-((2-aminoethyl)thio)-1-oxoisoindolin-2-yl)piperidine-2,6-dione;
3-(4-((3-aminopropyl)thio)-1-oxoisoindolin-2-yl)piperidine-2,6-dione;
3-(4-((4-aminobutyl)thio)-1-oxoisoindolin-2-yl)piperidine-2,6-dione;
3-(4-((5-aminopentyl)thio)-1-oxoisoindolin-2-yl)piperidine-2,6-dione;
3-(4-((6-aminohexyl)thio)-1-oxoisoindolin-2-yl)piperidine-2,6-dione;
3-(4-((7-aminoheptyl)thio)-1-oxoisoindolin-2-yl)piperidine-2,6-dione;
3-(4-((8-aminooctyl)thio)-1-oxoisoindolin-2-yl)piperidine-2,6-dione;
4-((5-((2-(2,6-dioxopiperidin-3-yl)-1-oxoisoindolin-4-yl)thio)pentyl)amino)-4-oxobutanoic acid;
3-(4-((2-(2-azidoethoxy)ethyl)thio)-1-oxoisoindolin-2-yl)piperidine-2,6-dione;
3-(4-((2-(2-(2-azidoethoxy)ethoxy)ethyl)thio)-1-oxoisoindolin-2-yl)piperidine-2,6-dione;
3-(4-((2-(2-(2-(2-azidoethoxy)ethoxy)ethoxy)ethyl)thio)-1-oxoisoindolin-2-yl)piperidine-2,6-dione;
3-(4-((14-azido-3,6,9,12-tetraoxatetradecyl)thio)-1-oxoisoindolin-2-yl)piperidine-2,6-dione;
3-(4-((17-azido-3,6,9,12,15-pentaoxaheptadecyl)thio)-1-oxoisoindolin-2-yl)piperidine-2,6-dione;
4-(1-(2-(2-((2-(2,6-dioxopiperidin-3-yl)-1-oxoisoindolin-4-yl)thio)ethoxy)ethyl)-1H-1,2,3-triazol-4-yl)butanoic acid;
3-(4-((2-azidoethyl)thio)-1-oxoisoindolin-2-yl)piperidine-2,6-dione;
3-(4-((3-azidopropyl)thio)-1-oxoisoindolin-2-yl)piperidine-2,6-dione;
3-(4-((4-azidobutyl)thio)-1-oxoisoindolin-2-yl)piperidine-2,6-dione;
3-(4-((5-azidopentyl)thio)-1-oxoisoindolin-2-yl)piperidine-2,6-dione;
3-(4-((6-azidohexyl)thio)-1-oxoisoindolin-2-yl)piperidine-2,6-dione;
3-(4-((8-azidooctyl)thio)-1-oxoisoindolin-2-yl)piperidine-2,6-dione;
4-(1-(5-((2-(2,6-dioxopiperidin-3-yl)-1-oxoisoindolin-4-yl)thio)pentyl)-1H-1,2,3-triazol-4-yl)butanoic acid;
3-(4-(2-(2-iodoethoxy)ethylthio)-1-oxoisoindolin-2-yl)piperidine-2,6-dione;
3-(4-(2-(2-bromoethoxy)ethylthio)-1-oxoisoindolin-2-yl)piperidine-2,6-dione;
2-(2-(2-(2,6-dioxopiperidin-3-yl)-1-oxoisoindolin-4-ylthio)ethoxy)ethyl 4-methylbenzenesulfonate;
3-(4-(3-(3-iodopropoxy)propylthio)-1-oxoisoindolin-2-yl)piperidine-2,6-dione;
3-(4-(3-(3-bromopropoxy)propylthio)-1-oxoisoindolin-2-yl)piperidine-2,6-dione;
3-(3-(2-(2,6-dioxopiperidin-3-yl)-1-oxoisoindolin-4-ylthio)propoxy)propyl 4-methylbenzenesulfonate;
3-(4-(2-(2-(2-iodoethoxy)ethoxy)ethylthio)-1-oxoisoindolin-2-yl)piperidine-2,6-dione;
3-(4-(2-(2-(2-bromoethoxy)ethoxy)ethylthio)-1-oxoisoindolin-2-yl)piperidine-2,6-dione;
2-(2-(2-(2-(2,6-dioxopiperidin-3-yl)-1-oxoisoindolin-4-ylthio)ethoxy)ethoxy)ethyl 4-methylbenzenesulfonate;
3-(4-(2-(2-(2-(2-iodoethoxy)ethoxy)ethoxy)ethylthio)-1-oxoisoindolin-2-yl)piperidine-2,6-dione;
3-(4-(2-(2-(2-(2-bromoethoxy)ethoxy)ethoxy)ethylthio)-1-oxoisoindolin-2-yl)piperidine-2,6-dione;
2-(2-(2-(2-(2-(2,6-dioxopiperidin-3-yl)-1-oxoisoindolin-4-ylthio)ethoxy)ethoxy)ethoxy)ethyl 4-methylbenzenesulfonate;
3-(4-(2-(2-(2-(2-(2-iodoethoxy)ethoxy)ethoxy)ethoxy)ethylthio)-1-oxoisoindolin-2-yl)piperidine-2,6-dione;
3-(4-(2-(2-(2-(2-(2-bromoethoxy)ethoxy)ethoxy)ethoxy)ethylthio)-1-oxoisoindolin-2-yl)piperidine-2,6-dione;
2-(2-(2-(2-(2-(2-(2,6-dioxopiperidin-3-yl)-1-oxoisoindolin-4-ylthio)ethoxy)ethoxy)ethoxy)ethoxy)ethyl 4-methylbenzenesulfonate;
3-(4-(2-iodoethylthio)-1-oxoisoindolin-2-yl)piperidine-2,6-dione;
3-(4-(2-bromoethylthio)-1-oxoisoindolin-2-yl)piperidine-2,6-dione;
2-(2-(2,6-dioxopiperidin-3-yl)-1-oxoisoindolin-4-ylthio)ethyl 4-methylbenzenesulfonate;
3-(4-(3-iodopropylthio)-1-oxoisoindolin-2-yl)piperidine-2,6-dione;
3-(4-(3-bromopropylthio)-1-oxoisoindolin-2-yl)piperidine-2,6-dione;
3-(2-(2,6-dioxopiperidin-3-yl)-1-oxoisoindolin-4-ylthio)propyl 4-methylbenzenesulfonate;
3-(4-(4-iodobutylthio)-1-oxoisoindolin-2-yl)piperidine-2,6-dione;
3-(4-(4-bromobutylthio)-1-oxoisoindolin-2-yl)piperidine-2,6-dione;
4-(2-(2,6-dioxopiperidin-3-yl)-1-oxoisoindolin-4-ylthio)butyl 4-methylbenzenesulfonate;
3-(4-(5-iodopentylthio)-1-oxoisoindolin-2-yl)piperidine-2,6-dione;
3-(4-(5-bromopentylthio)-1-oxoisoindolin-2-yl)piperidine-2,6-dione;
5-(2-(2,6-dioxopiperidin-3-yl)-1-oxoisoindolin-4-ylthio)pentyl 4-methylbenzenesulfonate;
3-(4-(6-iodohexylthio)-1-oxoisoindolin-2-yl)piperidine-2,6-dione;
3-(4-(6-bromohexylthio)-1-oxoisoindolin-2-yl)piperidine-2,6-dione;
6-(2-(2,6-dioxopiperidin-3-yl)-1-oxoisoindolin-4-ylthio)hexyl 4-methylbenzenesulfonate;
3-(4-(7-iodoheptylthio)-1-oxoisoindolin-2-yl)piperidine-2,6-dione;
3-(4-(7-bromoheptylthio)-1-oxoisoindolin-2-yl)piperidine-2,6-dione;
7-(2-(2,6-dioxopiperidin-3-yl)-1-oxoisoindolin-4-ylthio)heptyl 4-methylbenzenesulfonate;
2-(2-((2-(2,6-dioxopiperidin-3-yl)-1-oxoisoindolin-4-yl)sulfinyl)ethoxy)acetic acid;

3-(2-((2-(2,6-dioxopiperidin-3-yl)-1-oxoisoindolin-4-yl)sulfinyl)ethoxy)propanoic acid;

2-(2-(2-((2-(2,6-dioxopiperidin-3-yl)-1-oxoisoindolin-4-yl)sulfinyl)ethoxy)ethoxy)acetic acid;

3-(2-(2-((2-(2,6-dioxopiperidin-3-yl)-1-oxoisoindolin-4-yl)sulfinyl)ethoxy)ethoxy)propanoic acid;

2-(2-(2-(2-((2-(2,6-dioxopiperidin-3-yl)-1-oxoisoindolin-4-yl)sulfinyl)ethoxy)ethoxy)ethoxy)acetic acid;

3-(2-(2-(2-((2-(2,6-dioxopiperidin-3-yl)-1-oxoisoindolin-4-yl)sulfinyl)ethoxy)ethoxy)ethoxy)propanoic acid;

14-((2-(2,6-dioxopiperidin-3-yl)-1-oxoisoindolin-4-yl)sulfinyl)-3,6,9,12-tetraoxatetradecanoic acid;

1-((2-(2,6-dioxopiperidin-3-yl)-1-oxoisoindolin-4-yl)sulfinyl)-3,6,9,12-tetraoxapentadecan-15-oic acid;

17-((2-(2,6-dioxopiperidin-3-yl)-1-oxoisoindolin-4-yl)sulfinyl)-3,6,9,12,15-pentaoxaheptadecanoic acid;

1-((2-(2,6-dioxopiperidin-3-yl)-1-oxoisoindolin-4-yl)sulfinyl)-3,6,9,12,15-pentaoxaoctadecan-18-oic acid;

3-(3-(2-((2-(2,6-dioxopiperidin-3-yl)-1-oxoisoindolin-4-yl)sulfinyl)ethoxy)propanamido)propanoic acid;

2-((2-(2,6-dioxopiperidin-3-yl)-1-oxoisoindolin-4-yl)sulfinyl)acetic acid;

3-((2-(2,6-dioxopiperidin-3-yl)-1-oxoisoindolin-4-yl)sulfinyl)propanoic acid;

4-((2-(2,6-dioxopiperidin-3-yl)-1-oxoisoindolin-4-yl)sulfinyl)butanoic acid;

5-((2-(2,6-dioxopiperidin-3-yl)-1-oxoisoindolin-4-yl)sulfinyl)pentanoic acid;

6-((2-(2,6-dioxopiperidin-3-yl)-1-oxoisoindolin-4-yl)sulfinyl)hexanoic acid;

7-((2-(2,6-dioxopiperidin-3-yl)-1-oxoisoindolin-4-yl)sulfinyl)heptanoic acid;

8-((2-(2,6-dioxopiperidin-3-yl)-1-oxoisoindolin-4-yl)sulfinyl)octanoic acid;

9-((2-(2,6-dioxopiperidin-3-yl)-1-oxoisoindolin-4-yl)sulfinyl)nonanoic acid;

10-((2-(2,6-dioxopiperidin-3-yl)-1-oxoisoindolin-4-yl)sulfinyl)decanoic acid;

11-((2-(2,6-dioxopiperidin-3-yl)-1-oxoisoindolin-4-yl)sulfinyl)undecanoic acid;

12-((2-(2,6-dioxopiperidin-3-yl)-1-oxoisoindolin-4-yl)sulfinyl)dodecanoic acid;

13-((2-(2,6-dioxopiperidin-3-yl)-1-oxoisoindolin-4-yl)sulfinyl)tridecanoic acid;

14-((2-(2,6-dioxopiperidin-3-yl)-1-oxoisoindolin-4-yl)sulfinyl)tetradecanoic acid;

15-((2-(2,6-dioxopiperidin-3-yl)-1-oxoisoindolin-4-yl)sulfinyl)pentadecanoic acid;

3-(6-((2-(2,6-dioxopiperidin-3-yl)-1-oxoisoindolin-4-yl)sulfinyl)hexanamido)propanoic acid;

3-(4-((2-(2-aminoethoxy)ethyl)sulfinyl)-1-oxoisoindolin-2-yl)piperidine-2,6-dione;

3-(4-((2-(2-(2-aminoethoxy)ethoxy)ethyl)sulfinyl)-1-oxoisoindolin-2-yl)piperidine-2,6-dione;

3-(4-((2-(2-(2-(2-aminoethoxy)ethoxy)ethoxy)ethyl)sulfinyl)-1-oxoisoindolin-2-yl)piperidine-2,6-dione;

3-(4-((14-amino-3,6,9,12-tetraoxatetradecyl)sulfinyl)-1-oxoisoindolin-2-yl)piperidine-2,6-dione;

3-(4-((17-amino-3,6,9,12,15-pentaoxaheptadecyl)sulfinyl)-1-oxoisoindolin-2-yl)piperidine-2,6-dione;

4-((2-(2-((2-(2,6-dioxopiperidin-3-yl)-1-oxoisoindolin-4-yl)sulfinyl)ethoxy)ethyl)amino)-4-oxobutanoic acid;

3-(4-((2-aminoethyl)sulfinyl)-1-oxoisoindolin-2-yl)piperidine-2,6-dione;

3-(4-((3-aminopropyl)sulfinyl)-1-oxoisoindolin-2-yl)piperidine-2,6-dione;

3-(4-((4-aminobutyl)sulfinyl)-1-oxoisoindolin-2-yl)piperidine-2,6-dione;

3-(4-((5-aminopentyl)sulfinyl)-1-oxoisoindolin-2-yl)piperidine-2,6-dione;

3-(4-((6-aminohexyl)sulfinyl)-1-oxoisoindolin-2-yl)piperidine-2,6-dione;

3-(4-((7-aminoheptyl)sulfinyl)-1-oxoisoindolin-2-yl)piperidine-2,6-dione;

3-(4-((8-aminooctyl)sulfinyl)-1-oxoisoindolin-2-yl)piperidine-2,6-dione;

4-((5-((2-(2,6-dioxopiperidin-3-yl)-1-oxoisoindolin-4-yl)sulfinyl)pentyl)amino)-4-oxobutanoic acid;

3-(4-((2-(2-azidoethoxy)ethyl)sulfinyl)-1-oxoisoindolin-2-yl)piperidine-2,6-dione;

3-(4-((2-(2-(2-azidoethoxy)ethoxy)ethyl)sulfinyl)-1-oxoisoindolin-2-yl)piperidine-2,6-dione;

3-(4-((2-(2-(2-(2-azidoethoxy)ethoxy)ethoxy)ethyl)sulfinyl)-1-oxoisoindolin-2-yl)piperidine-2,6-dione;

3-(4-((14-azido-3,6,9,12-tetraoxatetradecyl)sulfinyl)-1-oxoisoindolin-2-yl)piperidine-2,6-dione;

3-(4-((17-azido-3,6,9,12,15-pentaoxaheptadecyl)sulfinyl)-1-oxoisoindolin-2-yl)piperidine-2,6-dione;

4-(1-(2-(2-((2-(2,6-dioxopiperidin-3-yl)-1-oxoisoindolin-4-yl)sulfinyl)ethoxy)ethyl)-1H-1,2,3-triazol-4-yl)butanoic acid;

3-(4-((2-azidoethyl)sulfinyl)-1-oxoisoindolin-2-yl)piperidine-2,6-dione;

3-(4-((3-azidopropyl)sulfinyl)-1-oxoisoindolin-2-yl)piperidine-2,6-dione;

3-(4-((4-azidobutyl)sulfinyl)-1-oxoisoindolin-2-yl)piperidine-2,6-dione;

3-(4-((5-azidopentyl)sulfinyl)-1-oxoisoindolin-2-yl)piperidine-2,6-dione;

3-(4-((6-azidohexyl)sulfinyl)-1-oxoisoindolin-2-yl)piperidine-2,6-dione;

3-(4-((7-azidoheptyl)sulfinyl)-1-oxoisoindolin-2-yl)piperidine-2,6-dione;

4-(1-(5-((2-(2,6-dioxopiperidin-3-yl)-1-oxoisoindolin-4-yl)sulfinyl)pentyl)-1H-1,2,3-triazol-4-yl)butanoic acid;

3-(4-(2-(2-iodoethoxy)ethylsulfinyl)-1-oxoisoindolin-2-yl)piperidine-2,6-dione;

3-(4-(2-(2-bromoethoxy)ethylsulfinyl)-1-oxoisoindolin-2-yl)piperidine-2,6-dione;

2-(2-(2-(2,6-dioxopiperidin-3-yl)-1-oxoisoindolin-4-ylsulfinyl)ethoxy)ethyl 4-methylbenzenesulfonate;

3-(4-(2-(2-(2-iodoethoxy)ethoxy)ethylsulfinyl)-1-oxoisoindolin-2-yl)piperidine-2,6-dione;

3-(4-(2-(2-(2-bromoethoxy)ethoxy)ethylsulfinyl)-1-oxoisoindolin-2-yl)piperidine-2,6-dione;

2-(2-(2-(2-(2,6-dioxopiperidin-3-yl)-1-oxoisoindolin-4-ylsulfinyl)ethoxy)ethoxy)ethyl 4-methylbenzenesulfonate;

3-(4-(2-(2-(2-(2-iodoethoxy)ethoxy)ethoxy)ethylsulfinyl)-1-oxoisoindolin-2-yl)piperidine-2,6-dione;

3-(4-(2-(2-(2-(2-bromoethoxy)ethoxy)ethoxy)ethylsulfinyl)-1-oxoisoindolin-2-yl)piperidine-2,6-dione;

2-(2-(2-(2-(2-(2,6-dioxopiperidin-3-yl)-1-oxoisoindolin-4-ylsulfinyl)ethoxy)ethoxy)ethoxy)ethyl 4-methylbenzenesulfonate;

3-(4-(2-(2-(2-(2-(2-iodoethoxy)ethoxy)ethoxy)ethoxy)ethylsulfinyl)-1-oxoisoindolin-2-yl)piperidine-2,6-dione;

3-(4-(2-(2-(2-(2-(2-bromoethoxy)ethoxy)ethoxy)ethoxy)ethylsulfinyl)-1-oxoisoindolin-2-yl)piperidine-2,6-dione;

2-(2-(2-(2-(2-(2-(2,6-dioxopiperidin-3-yl)-1-oxoisoindo-lin-4-ylsulfinyl)ethoxy)ethoxy)ethoxy)ethyl 4-methylbenzenesulfonate;
3-(4-(2-(2-(2-(2-(2-iodoethoxy)ethoxy)ethoxy)ethoxy)ethylsulfinyl)-1-oxoisoindolin-2-yl)piperidine-2,6-dione;
3-(4-(2-(2-(2-(2-(2-bromoethoxy)ethoxy)ethoxy)ethoxy)ethylsulfinyl)-1-oxoisoindolin-2-yl)piperidine-2,6-dione;
2-(2-(2-(2-(2-(2-(2,6-dioxopiperidin-3-yl)-1-oxoisoindolin-4-ylsulfinyl)ethoxy)ethoxy)ethoxy)ethoxy)ethyl 4-methylbenzenesulfonate;
3-(4-(2-iodoethylsulfinyl)-1-oxoisoindolin-2-yl)piperidine-2,6-dione;
3-(4-(2-bromoethylsulfinyl)-1-oxoisoindolin-2-yl)piperidine-2,6-dione;
2-(2-(2,6-dioxopiperidin-3-yl)-1-oxoisoindolin-4-ylsulfinyl)ethyl 4-methylbenzenesulfonate;
3-(4-(3-iodopropylsulfinyl)-1-oxoisoindolin-2-yl)piperidine-2,6-dione;
3-(4-(3-bromopropylsulfinyl)-1-oxoisoindolin-2-yl)piperidine-2,6-dione;
3-(2-(2,6-dioxopiperidin-3-yl)-1-oxoisoindolin-4-ylsulfinyl)propyl 4-methylbenzenesulfonate;
3-(4-(4-iodobutylsulfinyl)-1-oxoisoindolin-2-yl)piperidine-2,6-dione;
3-(4-(4-bromobutylsulfinyl)-1-oxoisoindolin-2-yl)piperidine-2,6-dione;
4-(2-(2,6-dioxopiperidin-3-yl)-1-oxoisoindolin-4-ylsulfinyl)butyl 4-methylbenzenesulfonate;
3-(4-(5-iodopentylsulfinyl)-1-oxoisoindolin-2-yl)piperidine-2,6-dione;
3-(4-(5-bromopentylsulfinyl)-1-oxoisoindolin-2-yl)piperidine-2,6-dione;
5-(2-(2,6-dioxopiperidin-3-yl)-1-oxoisoindolin-4-ylsulfinyl)pentyl 4-methylbenzenesulfonate;
3-(4-(6-iodohexylsulfinyl)-1-oxoisoindolin-2-yl)piperidine-2,6-dione;
3-(4-(6-bromohexylsulfinyl)-1-oxoisoindolin-2-yl)piperidine-2,6-dione;
6-(2-(2,6-dioxopiperidin-3-yl)-1-oxoisoindolin-4-ylsulfinyl)hexyl 4-methylbenzenesulfonate;
3-(4-(7-iodoheptylsulfinyl)-1-oxoisoindolin-2-yl)piperidine-2,6-dione;
3-(4-(7-bromoheptylsulfinyl)-1-oxoisoindolin-2-yl)piperidine-2,6-dione;
7-(2-(2,6-dioxopiperidin-3-yl)-1-oxoisoindolin-4-ylsulfinyl)heptyl 4-methylbenzenesulfonate;
2-(2-((2-(2,6-dioxopiperidin-3-yl)-1-oxoisoindolin-4-yl)sulfonyl)ethoxy)acetic acid;
3-(2-((2-(2,6-dioxopiperidin-3-yl)-1-oxoisoindolin-4-yl)sulfonyl)ethoxy)propanoic acid;
2-(2-(2-((2-(2,6-dioxopiperidin-3-yl)-1-oxoisoindolin-4-yl)sulfonyl)ethoxy)ethoxy)acetic acid;
3-(2-(2-((2-(2,6-dioxopiperidin-3-yl)-1-oxoisoindolin-4-yl)sulfonyl)ethoxy)ethoxy)propanoic acid;
2-(2-(2-(2-((2-(2,6-dioxopiperidin-3-yl)-1-oxoisoindolin-4-yl)sulfonyl)ethoxy)ethoxy)ethoxy)acetic acid;
3-(2-(2-(2-((2-(2,6-dioxopiperidin-3-yl)-1-oxoisoindolin-4-yl)sulfonyl)ethoxy)ethoxy)ethoxy)propanoic acid;
14-((2-(2,6-dioxopiperidin-3-yl)-1-oxoisoindolin-4-yl)sulfonyl)-3,6,9,12-tetraoxatetradecanoic acid;
1-((2-(2,6-dioxopiperidin-3-yl)-1-oxoisoindolin-4-yl)sulfonyl)-3,6,9,12-tetraoxapentadecan-15-oic acid;
17-((2-(2,6-dioxopiperidin-3-yl)-1-oxoisoindolin-4-yl)sulfonyl)-3,6,9,12,15-pentaoxaheptadecanoic acid;
1-((2-(2,6-dioxopiperidin-3-yl)-1-oxoisoindolin-4-yl)sulfonyl)-3,6,9,12,15-pentaoxaoctadecan-18-oic acid;
3-(3-(2-((2-(2,6-dioxopiperidin-3-yl)-1-oxoisoindolin-4-yl)sulfonyl)ethoxy)propanamido)propanoic acid;
2-((2-(2,6-dioxopiperidin-3-yl)-1-oxoisoindolin-4-yl)sulfonyl)acetic acid;
3-((2-(2,6-dioxopiperidin-3-yl)-1-oxoisoindolin-4-yl)sulfonyl)propanoic acid;
4-((2-(2,6-dioxopiperidin-3-yl)-1-oxoisoindolin-4-yl)sulfonyl)butanoic acid;
5-((2-(2,6-dioxopiperidin-3-yl)-1-oxoisoindolin-4-yl)sulfonyl)pentanoic acid;
6-((2-(2,6-dioxopiperidin-3-yl)-1-oxoisoindolin-4-yl)sulfonyl)hexanoic acid;
7-((2-(2,6-dioxopiperidin-3-yl)-1-oxoisoindolin-4-yl)sulfonyl)heptanoic acid;
8-((2-(2,6-dioxopiperidin-3-yl)-1-oxoisoindolin-4-yl)sulfonyl)octanoic acid;
9-((2-(2,6-dioxopiperidin-3-yl)-1-oxoisoindolin-4-yl)sulfonyl)nonanoic acid;
10-((2-(2,6-dioxopiperidin-3-yl)-1-oxoisoindolin-4-yl)sulfonyl)decanoic acid;
11-((2-(2,6-dioxopiperidin-3-yl)-1-oxoisoindolin-4-yl)sulfonyl)undecanoic acid;
12-((2-(2,6-dioxopiperidin-3-yl)-1-oxoisoindolin-4-yl)sulfonyl)dodecanoic acid;
13-((2-(2,6-dioxopiperidin-3-yl)-1-oxoisoindolin-4-yl)sulfonyl)tridecanoic acid;
14-((2-(2,6-dioxopiperidin-3-yl)-1-oxoisoindolin-4-yl)sulfonyl)tetradecanoic acid;
15-((2-(2,6-dioxopiperidin-3-yl)-1-oxoisoindolin-4-yl)sulfonyl)pentadecanoic acid;
3-(6-((2-(2,6-dioxopiperidin-3-yl)-1-oxoisoindolin-4-yl)sulfonyl)hexanamido)propanoic acid;
3-(4-((2-(2-aminoethoxy)ethyl)sulfonyl)-1-oxoisoindolin-2-yl)piperidine-2,6-dione;
3-(4-((2-(2-(2-aminoethoxy)ethoxy)ethyl)sulfonyl)-1-oxoisoindolin-2-yl)piperidine-2,6-dione;
3-(4-((2-(2-(2-(2-aminoethoxy)ethoxy)ethoxy)ethyl)sulfonyl)-1-oxoisoindolin-2-yl)piperidine-2,6-dione;
3-(4-((14-amino-3,6,9,12-tetraoxatetradecyl)sulfonyl)-1-oxoisoindolin-2-yl)piperidine-2,6-dione;
3-(4-((17-amino-3,6,9,12,15-pentaoxaheptadecyl)sulfonyl)-1-oxoisoindolin-2-yl)piperidine-2,6-dione;
4-((2-(2-((2-(2,6-dioxopiperidin-3-yl)-1-oxoisoindolin-4-yl)sulfonyl)ethoxy)ethyl)amino)-4-oxobutanoic acid;
3-(4-((2-aminoethyl)sulfonyl)-1-oxoisoindolin-2-yl)piperidine-2,6-dione;
3-(4-((3-aminopropyl)sulfonyl)-1-oxoisoindolin-2-yl)piperidine-2,6-dione;
3-(4-((4-aminobutyl)sulfonyl)-1-oxoisoindolin-2-yl)piperidine-2,6-dione;
3-(4-((5-aminopentyl)sulfonyl)-1-oxoisoindolin-2-yl)piperidine-2,6-dione;
3-(4-((6-aminohexyl)sulfonyl)-1-oxoisoindolin-2-yl)piperidine-2,6-dione;
3-(4-((7-aminoheptyl)sulfonyl)-1-oxoisoindolin-2-yl)piperidine-2,6-dione;
3-(4-((8-aminooctyl)sulfonyl)-1-oxoisoindolin-2-yl)piperidine-2,6-dione;
4-((5-((2-(2,6-dioxopiperidin-3-yl)-1-oxoisoindolin-4-yl)sulfonyl)pentyl)amino)-4-oxobutanoic acid;
3-(4-((2-(2-azidoethoxy)ethyl)sulfonyl)-1-oxoisoindolin-2-yl)piperidine-2,6-dione;
3-(4-((2-(2-(2-azidoethoxy)ethoxy)ethyl)sulfonyl)-1-oxoisoindolin-2-yl)piperidine-2,6-dione;

3-(4-((2-(2-(2-(2-azidoethoxy)ethoxy)ethoxy)ethyl)sulfonyl)-1-oxoisoindolin-2-yl)piperidine-2,6-dione;
3-(4-(((14-azido-3,6,9,12-tetraoxatetradecyl)sulfonyl)-1-oxoisoindolin-2-yl)piperidine-2,6-dione;
3-(4-(((17-azido-3,6,9,12,15-pentaoxaheptadecyl)sulfonyl)-1-oxoisoindolin-2-yl)piperidine-2,6-dione;
4-(1-(2-(2-((2-(2,6-dioxopiperidin-3-yl)-1-oxoisoindolin-4-yl)sulfonyl)ethoxy)ethyl)-1H-1,2,3-triazol-4-yl)butanoic acid;
3-(4-((2-azidoethyl)sulfonyl)-1-oxoisoindolin-2-yl)piperidine-2,6-dione;
3-(4-((3-azidopropyl)sulfonyl)-1-oxoisoindolin-2-yl)piperidine-2,6-dione;
3-(4-((4-azidobutyl)sulfonyl)-1-oxoisoindolin-2-yl)piperidine-2,6-dione;
3-(4-((5-azidopentyl)sulfonyl)-1-oxoisoindolin-2-yl)piperidine-2,6-dione;
3-(4-((6-azidohexyl)sulfonyl)-1-oxoisoindolin-2-yl)piperidine-2,6-dione;
3-(4-((7-azidoheptyl)sulfonyl)-1-oxoisoindolin-2-yl)piperidine-2,6-dione;
4-(1-(5-((2-(2,6-dioxopiperidin-3-yl)-1-oxoisoindolin-4-yl)sulfonyl)pentyl)-1H-1,2,3-triazol-4-yl)butanoic acid;
3-(4-(2-(2-iodoethoxy)ethylsulfonyl)-1-oxoisoindolin-2-yl)piperidine-2,6-dione;
3-(4-(2-(2-bromoethoxy)ethylsulfonyl)-1-oxoisoindolin-2-yl)piperidine-2,6-dione;
2-(2-(2-(2,6-dioxopiperidin-3-yl)-1-oxoisoindolin-4-ylsulfonyl)ethoxy)ethyl 4-methylbenzenesulfonate;
3-(4-(2-(2-(2-iodoethoxy)ethoxy)ethylsulfonyl)-1-oxoisoindolin-2-yl)piperidine-2,6-dione;
3-(4-(2-(2-(2-bromoethoxy)ethoxy)ethylsulfonyl)-1-oxoisoindolin-2-yl)piperidine-2,6-dione;
2-(2-(2-(2-(2,6-dioxopiperidin-3-yl)-1-oxoisoindolin-4-ylsulfonyl)ethoxy)ethoxy)ethyl 4-methylbenzenesulfonate;
3-(4-(2-(2-(2-(2-iodoethoxy)ethoxy)ethoxy)ethylsulfonyl)-1-oxoisoindolin-2-yl)piperidine-2,6-dione;
3-(4-(2-(2-(2-(2-bromoethoxy)ethoxy)ethoxy)ethylsulfonyl)-1-oxoisoindolin-2-yl)piperidine-2,6-dione;
2-(2-(2-(2-(2-(2,6-dioxopiperidin-3-yl)-1-oxoisoindolin-4-ylsulfonyl)ethoxy)ethoxy)ethoxy)ethyl 4-methylbenzenesulfonate;
3-(4-(2-(2-(2-(2-(2-iodoethoxy)ethoxy)ethoxy)ethoxy)ethylsulfonyl)-1-oxoisoindolin-2-yl)piperidine-2,6-dione;
3-(4-(2-(2-(2-(2-(2-bromoethoxy)ethoxy)ethoxy)ethoxy)ethylsulfonyl)-1-oxoisoindolin-2-yl)piperidine-2,6-dione;
2-(2-(2-(2-(2-(2-(2,6-dioxopiperidin-3-yl)-1-oxoisoindolin-4-ylsulfonyl)ethoxy)ethoxy)ethoxy)ethoxy)ethyl 4-methylbenzenesulfonate;
3-(4-(2-iodoethylsulfonyl)-1-oxoisoindolin-2-yl)piperidine-2,6-dione;
3-(4-(2-bromoethylsulfonyl)-1-oxoisoindolin-2-yl)piperidine-2,6-dione;
2-(2-(2,6-dioxopiperidin-3-yl)-1-oxoisoindolin-4-ylsulfonyl)ethyl 4-methylbenzenesulfonate;
3-(4-(3-iodopropylsulfonyl)-1-oxoisoindolin-2-yl)piperidine-2,6-dione;
3-(4-(3-bromopropylsulfonyl)-1-oxoisoindolin-2-yl)piperidine-2,6-dione;
3-(2-(2,6-dioxopiperidin-3-yl)-1-oxoisoindolin-4-ylsulfonyl)propyl 4-methylbenzenesulfonate;
3-(4-(4-iodobutylsulfonyl)-1-oxoisoindolin-2-yl)piperidine-2,6-dione;
3-(4-(4-bromobutylsulfonyl)-1-oxoisoindolin-2-yl)piperidine-2,6-dione;
4-(2-(2,6-dioxopiperidin-3-yl)-1-oxoisoindolin-4-ylsulfonyl)butyl 4-methylbenzenesulfonate;
3-(4-(5-iodopentylsulfonyl)-1-oxoisoindolin-2-yl)piperidine-2,6-dione;
3-(4-(5-bromopentylsulfonyl)-1-oxoisoindolin-2-yl)piperidine-2,6-dione;
3-(4-((2-((4-((2-azidoethoxy)methyl)piperazin-1-yl)methoxy)ethyl)thio)-l-oxoisoindolin-2-yl)piperidine-2,6-dione;
3-(4-((3-(4-(3-azidopropyl)phenyl)propyl)thio)-1-oxoisoindolin-2-yl)piperidine-2,6-dione;
3-(4-((3-(4-(3-azidopropyl)piperazin-1-yl)propyl)thio)-1-oxoisoindolin-2-yl)piperidine-2,6-dione;
3-(4-((2-((4-((2-iodoethoxy)methyl)benzyl)oxy)ethyl)thio)-1-oxoisoindolin-2-yl)piperidine-2,6-dione;
3-(4-((2-((4-((2-iodoethoxy)methyl)piperazin-1-yl)methoxy)ethyl)thio)-1-oxoisoindolin-2-yl) piperidine-2,6-dione;
3-(4-((3-(4-(3-iodopropyl)phenyl)propyl)thio)-1-oxoisoindolin-2-yl)piperidine-2,6-dione;
3-(4-((3-(4-(3-iodopropyl)piperazin-1-yl)propyl)thio)-1-oxoisoindolin-2-yl)piperidine-2,6-dione;
3-(4-((2-((4-((2-bromoethoxy)methyl)benzyl)oxy)ethyl)thio)-1-oxoisoindolin-2-yl)piperidine-2,6-dione;
3-(4-((2-((4-((2-bromoethoxy)methyl)piperazin-1-yl)methoxy)ethyl)thio)-l-oxoisoindolin-2-yl)piperidine-2,6-dione;
3-(4-((12-bromododecyl)thio)-1-oxoisoindolin-2-yl)piperidine-2,6-dione;
3-(4-((4-(bromomethyl)benzyl)thio)-1-oxoisoindolin-2-yl)piperidine-2,6-dione;
3-(4-((3-(4-(3-bromopropyl)phenyl)propyl)thio)-1-oxoisoindolin-2-yl)piperidine-2,6-dione;
3-(4-((3-(4-(3-bromopropyl)piperazin-1-yl)propyl)thio)-1-oxoisoindolin-2-yl)piperidine-2,6-dione;
2-((4-((2-((2-(2,6-dioxopiperidin-3-yl)-1-oxoisoindolin-4-yl)thio)ethoxy)methyl)benzyl)oxy)ethyl 4-methylbenzenesulfonate;
5-(2-(2,6-dioxopiperidin-3-yl)-1-oxoisoindolin-4-ylsulfonyl)pentyl 4-methylbenzenesulfonate;
3-(4-(6-iodohexylsulfonyl)-1-oxoisoindolin-2-yl)piperidine-2,6-dione;
3-(4-(6-bromohexylsulfonyl)-1-oxoisoindolin-2-yl)piperidine-2,6-dione;
6-(2-(2,6-dioxopiperidin-3-yl)-1-oxoisoindolin-4-ylsulfonyl)hexyl 4-methylbenzenesulfonate;
3-(4-(7-iodoheptylsulfonyl)-1-oxoisoindolin-2-yl)piperidine-2,6-dione;
3-(4-(7-bromoheptylsulfonyl)-1-oxoisoindolin-2-yl)piperidine-2,6-dione; or
7-(2-(2,6-dioxopiperidin-3-yl)-1-oxoisoindolin-4-ylsulfonyl)heptyl 4-methylbenzenesulfonate.

11. The compound of formula (IV), or a salt, enantiomer, stereoisomer, or solvate thereof according to claim 1, which is selected from:

N-(4-aminobutyl)-2-((2-(2,6-dioxopiperidin-3-yl)-1,3-dioxoisoindolin-4-yl)thio)acetamide;
N-(4-aminobutyl)-2-((2-(2,6-dioxopiperidin-3-yl)-1-oxoisoindolin-4-yl)thio)acetamide;
3-((4-((2-((2-(2,6-dioxopiperidin-3-yl)-1-oxoisoindolin-4-yl)thio)ethoxy)methyl)benzyl)oxy)propanoic acid;
3-((4-((2-((2-(2,6-dioxopiperidin-3-yl)-1-oxoisoindolin-4-yl)thio)ethoxy)methyl)piperazin-1-yl)methoxy)propanoic acid;
4-(4-(3-((2-(2,6-dioxopiperidin-3-yl)-1-oxoisoindolin-4-yl)thio)propyl)phenyl)butanoic acid;
4-(4-(3-((2-(2,6-dioxopiperidin-3-yl)-1-oxoisoindolin-4-yl)thio)propyl)piperazin-1-yl)butanoic acid;
3-(4-((2-((4-((2-aminoethoxy)methyl)benzyl)oxy)ethyl)thio)-1-oxoisoindolin-2-yl)piperidine-2,6-dione;
3-(4-((2-((4-((2-aminoethoxy)methyl)piperazin-1-yl)methoxy)ethyl)thio)-1-oxoisoindolin-2-yl)piperidine-2,6-dione;
3-(4-((3-(4-(3-aminopropyl)phenyl)propyl)thio)-1-oxoisoindolin-2-yl)piperidine-2,6-dione;
3-(4-((3-(4-(3-aminopropyl)piperazin-1-yl)propyl)thio)-1-oxoisoindolin-2-yl)piperidine-2,6-dione;
3-(4-((2-((4-((2-azidoethoxy)methyl)benzyl)oxy)ethyl)thio)-1-oxoisoindolin-2-yl)piperidine-2,6-dione;
3-(4-((2-((4-((2-azidoethoxy)methyl)piperazin-1-yl)methoxy)ethyl)thio)-1-oxoisoindolin-2-yl)piperidine-2,6-dione;
3-(4-((3-(4-(3-azidopropyl)phenyl)propyl)thio)-1-oxoisoindolin-2-yl)piperidine-2,6-dione;
3-(4-((3-(4-(3-azidopropyl)piperazin-1-yl)propyl)thio)-1-oxoisoindolin-2-yl)piperidine-2,6-dione;
3-(4-((2-((4-((2-iodoethoxy)methyl)benzyl)oxy)ethyl)thio)-1-oxoisoindolin-2-yl)piperidine-2,6-dione;
3-(4-((2-((4-((2-iodoethoxy)methyl)piperazin-1-yl)methoxy)ethyl)thio)-1-oxoisoindolin-2-yl)piperidine-2,6-dione;
3-(4-((3-(4-(3-iodopropyl)phenyl)propyl)thio)-1-oxoisoindolin-2-yl)piperidine-2,6-dione;
3-(4-((3-(4-(3-iodopropyl)piperazin-1-yl)propyl)thio)-1-oxoisoindolin-2-yl)piperidine-2,6-dione;
3-(4-((2-((4-((2-bromoethoxy)methyl)benzyl)oxy)ethyl)thio)-1-oxoisoindolin-2-yl)piperidine-2,6-dione;
3-(4-((2-((4-((2-bromoethoxy)methyl)piperazin-1-yl)methoxy)ethyl)thio)-1-oxoisoindolin-2-yl)piperidine-2,6-dione;
3-(4-((8-bromooctyl)thio)-1-oxoisoindolin-2-yl)piperidine-2,6-dione;
3-(4-((9-bromononyl)thio)-1-oxoisoindolin-2-yl)piperidine-2,6-dione;
3-(4-((10-bromodecyl)thio)-1-oxoisoindolin-2-yl)piperidine-2,6-dione;
3-(4-((11-bromoundecyl)thio)-1-oxoisoindolin-2-yl)piperidine-2,6-dione;
3-(4-((12-bromododecyl)thio)-1-oxoisoindolin-2-yl)piperidine-2,6-dione;
3-(4-((4-(bromomethyl)benzyl)thio)-1-oxoisoindolin-2-yl)piperidine-2,6-dione;
3-(4-((3-(4-(3-bromopropyl)phenyl)propyl)thio)-1-oxoisoindolin-2-yl)piperidine-2,6-dione;
3-(4-(3-(4-(3-bromopropyl)piperazin-1-yl)propyl)thio)-1-oxoisoindolin-2-yl)piperidine-2,6-dione;
2-((4-((2-((2-(2,6-dioxopiperidin-3-yl)-1-oxoisoindolin-4-yl)thio)ethoxy)methyl)benzyl)oxy)ethyl 4-methylbenzenesulfonate;
2-((4-((2-((2-(2,6-dioxopiperidin-3-yl)-1-oxoisoindolin-4-yl)thio)ethoxy)methyl)piperazin-1-yl)methoxy)ethyl 4-methylbenzenesulfonate;
3-(4-(3-((2-(2,6-dioxopiperidin-3-yl)-1-oxoisoindolin-4-yl)thio)propyl)phenyl)propyl 4-methylbenzenesulfonate;
3-(4-(3-((2-(2,6-dioxopiperidin-3-yl)-1-oxoisoindolin-4-yl)thio)propyl)piperazin-1-yl)propyl 4-methylbenzenesulfonate;
3-(4-((9-azidononyl)thio)-1-oxoisoindolin-2-yl)piperidine-2,6-dione;
3-(4-((10-azidodecyl)thio)-1-oxoisoindolin-2-yl)piperidine-2,6-dione;
3-(4-((11-azidoundecyl)thio)-1-oxoisoindolin-2-yl)piperidine-2,6-dione; or
3-(4-((12-azidododecyl)thio)-1-oxoisoindolin-2-yl)piperidine-2,6-dione.

12. A pharmaceutical composition comprising the compound of formula (IV) according to claim 1 or a pharmaceutically acceptable salt thereof, and at least one pharmaceutically acceptable carrier.

13. The pharmaceutical composition according to claim 7, further comprising at least one additional therapeutic agent.

14. The pharmaceutical composition according to claim 7, further comprising at least one additional therapeutic agent, wherein the at least one additional therapeutic agent is a cancer treatment agent.

15. A method, comprising: preparing the compound of formula (I) from a compound of formula (IV):
wherein formula (I) is:

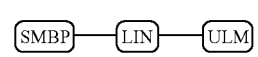

Formula (I)

wherein SMBP is covalently bonded to ULM through a linking group LIN;
wherein SMBP represents a small molecule compound or its derivative capable of binding protein; and
wherein LIN-ULM represents the chemical structure of the following formula (II):

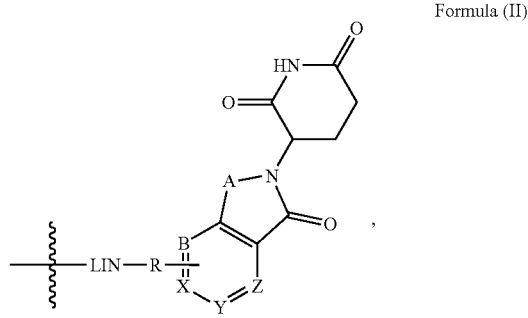

Formula (II)

wherein
A represents $CH_2$ or CO,
B, X, Y, and Z represent CH,
R represents S, SO, or $SO_2$, and
LIN is a linking group and represents —U-alkylene-, wherein -alkylene- is an alkylene group that is a linear or branched alkylene group optionally interrupted one or more times by one or more groups selected from the group consisting of O, CONH, NHCO, NH, alkynylene, alkenylene, cycloalkylene, arylene, heterocyclylene, heteroarylene, or any combination thereof,
wherein the linear or branched alkylene group is optionally substituted with one or more substituents, and
wherein —U— is a group that represents CO or NH, or the group —U— is absent;
or a salt, enantiomer, stereoisomer, or solvate thereof; and wherein formula (IV) is:

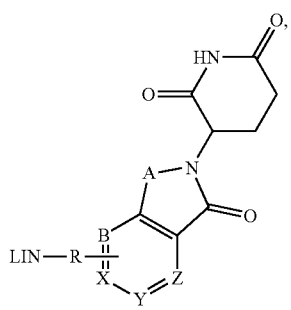

Formula (IV)

wherein,
A represents $CH_2$ or CO,
B, X, Y, and Z represent CH, R represents S, SO, or $SO_2$, and
LIN is a linking group and represents —W-alkylene-,
wherein -alkylene- is an alkylene group that is a linear or branched alkylene group optionally interrupted one or more times by one or more groups selected from the group consisting of O, CONH, NHCO, NH, or any combination thereof,
wherein the linear or branched alkylene group is optionally substituted with one or more substituents selected from hydroxyl, amino, mercapto and halogen, or
the LIN represents: W—$(CH_2)_{n11}$-triazolylene-$(CH_2)_{n12}$—, W—$(CH_2)_{n11}$—triazolylene-$(CH_2)_{n12}$—$(O(CH_2)_{n13})_{m11}$—, W—$(CH_2)_{n11}$—(O$(CH_2)_{n12})_{m11}$—O—$(CH_2)_{n13}$-triazolylene-$(CH_2)_{n14}$—$(O(CH_2)_{n15})_{m12}$—O—$(CH_2)_{n16}$—, W—$(CH_2)_{n11}$-triazolylene-$(CH_2)_{n12}$—(O$(CH_2)_{n13})_{m11}$-O—$(CH_2)_{n14}$—, or W—$(CH_2)_{n11}$—(O$(CH_2)_{n12})_{m11}$—O—$(CH_2)_{n13}$-triazolylene-$(CH_2)_{n14}$—; and
wherein n11, n12, n13, n14, n15, n16, m11, m12 each independently represent an integer of 1, 2, 3, 4, 5, 6, 7, 8, 9, 10, 11, 12, 13, 14, 15, 16, 17, 18, 19, or 20; or
the LIN represents: W—$(CH_2)_2$—O—$CH_2$-phenylene-$CH_2$—O—$(CH_2)_2$—, W—$CH_2$- phenylene-$CH_2$—, W—$(CH_2)_3$-phenylene-$(CH_2)_3$—, W—$(CH_2)_2$—O—$CH_2$—piperazinylene-$CH_2$—O—$(CH_2)_2$—, or W—$(CH_2)_3$-piperazinylene-$(CH_2)_3$—;
wherein —W— represents, $N_3$, CHO, COOH $NH_2$, halogen, methanesulfonyloxy, trifluoromethanesulfonyloxy, or p-toluenesulfonyloxy;
or a salt, enantiomer, stereoisomer, or solvate thereof.

16. A method of treating a cancer in a subject, comprising administering to the subject a therapeutically effective amount of a compound of formula (IV) or a pharmaceutically acceptable salt thereof, or a pharmaceutical composition according to claim 12,
wherein the compound of formula (IV) is:

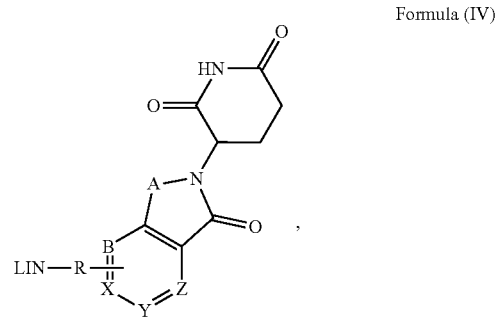

Formula (IV)

wherein,
A represents CH2 or CO,
B, X, Y, and Z represent CH,
R represents S, SO, or $SO_2$, and
LIN is a linking group and represents-W-alkylene-,
wherein-alkylene-is an alkylene group that is a linear or branched alkylene group optionally interrupted one or more times by one or more groups selected from the group consisting of O, CONH, NHCO, NH, or any combination thereof,
wherein the linear or branched alkylene group is optionally substituted with one or more substituents selected from hydroxyl, amino, mercapto and halogen, or
the LIN represents: W—$(CH_2)_{n11}$-triazolylene-$(CH_2)_{n12}$—, W—$(CH_2)_{n11}$—triazolylene-$(CH_2)_{n12}$—$(O(CH_2)_{n13})_{m11}$—, W—$(CH_2)_{n11}$—(O$(CH_2)_{n12})_{m11}$—O—$(CH_2)_{n13}$-triazolylene-$(CH_2)_{n14}$—$(O(CH_2)_{n15})_{m12}$—O—$(CH_2)_{n16}$—, W—$(CH_2)_{n11}$-triazolylene-$(CH_2)_{n12}$—(O$(CH_2)_{n13})_{m11}$-O—$(CH_2)_{n14}$—, or W—$(CH_2)_{n11}$—(O$(CH_2)_{n12})_{m11}$—O—$(CH_2)_{n13}$-triazolylene-$(CH_2)_{n14}$—; and
wherein n11, n12, n13, n14, n15, n16, m11, m12 each independently represent an integer of 1, 2, 3, 4, 5, 6, 7, 8, 9, 10, 11, 12, 13, 14, 15, 16, 17, 18, 19, or 20; or
the LIN represents: W—$(CH_2)_2$—O—$CH_2$-phenylene-$CH_2$—O—$(CH_2)_2$—, W—$CH_2$- phenylene-$CH_2$—, W—$(CH_2)_3$-phenylene-$(CH_2)_3$—, W—$(CH_2)$2—O—$CH_2$—piperazinylene-$CH_2$—O—$(CH_2)_2$—, or W—$(CH_2)_3$-piperazinylene-$(CH_2)_3$—;
wherein —U— is a group that represents CO or NH, or the group —U— is
wherein -W- represents, $N_3$, CHO, COOH, $NH_2$, halogen, methanesulfonyloxy, trifluoromethanesulfonyloxy, or p-toluenesulfonyloxy.

17. The method according to claim 16, wherein the administering to the subject is carried out through at least one mode of administration selected from nasal administration, inhalation administration, topical administration, oral administration, oral mucosal administration, rectal administration, pleural administration, peritoneal administration, vaginal administration, intramuscular administration, subcutaneous administration, transdermal administration, epidural administration, intrathecal administration and intravenous administration.

* * * * *